United States Patent
Haketa et al.

(10) Patent No.: US 10,424,740 B2
(45) Date of Patent: Sep. 24, 2019

(54) COMPOUND, MATERIAL FOR ORGANIC ELECTROLUMINESCENCE DEVICES, ORGANIC ELECTROLUMINESCENCE DEVICE, AND ELECTRONIC DEVICE

(71) Applicant: IDEMITSU KOSAN CO., LTD., Tokyo (JP)

(72) Inventors: Tasuku Haketa, Sodegaura (JP); Hirokatsu Ito, Sodegaura (JP); Yu Kudo, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/176,762

(22) Filed: Oct. 31, 2018

(65) Prior Publication Data

US 2019/0088879 A1    Mar. 21, 2019

Related U.S. Application Data

(63) Continuation of application No. PCT/JP2018/029217, filed on Aug. 3, 2018.

(30) Foreign Application Priority Data

Aug. 3, 2017 (JP) .................. 2017-151141

(51) Int. Cl.
*H01L 51/50* (2006.01)
*H01L 51/00* (2006.01)
(Continued)

(52) U.S. Cl.
CPC .......... *H01L 51/006* (2013.01); *C07D 311/82* (2013.01); *C07D 335/12* (2013.01);
(Continued)

(58) Field of Classification Search
None
See application file for complete search history.

(56) References Cited

U.S. PATENT DOCUMENTS

2015/0295181 A1    10/2015    Mujica-Fernaud et al.
2015/0333277 A1    11/2015    Kim et al.

FOREIGN PATENT DOCUMENTS

CN    106977491    *    7/2017    ............ H01L 51/50
CN    106977491 A         7/2017
(Continued)

OTHER PUBLICATIONS

Chemistry for Engineering Students 2nd edition, section 6.59 (Year: 2009).*

(Continued)

*Primary Examiner* — Gregory D Clark
(74) *Attorney, Agent, or Firm* — Oblon, McClelland, Maier & Neustadt, L.L.P.

(57) ABSTRACT

A compound represented by formula (1) provides an organic electroluminescence device having a low driving voltage and an excellent emission efficiency:

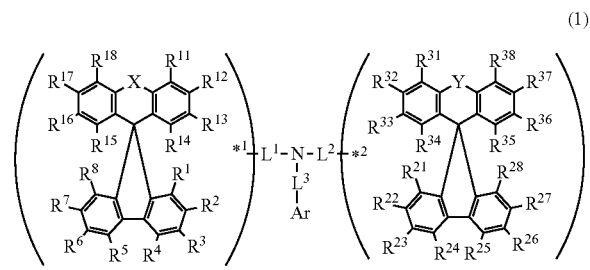

(1)

wherein $R^1$ to $R^8$, $R^{11}$ to $R^{18}$, $R^{21}$ to $R^{28}$, $R^{31}$ to $R^{38}$, X, Y, $L^1$, $L^2$, $L^3$, and Ar are as defined in the description.

27 Claims, 1 Drawing Sheet

(51) Int. Cl.
*C07D 311/82* (2006.01)
*C07D 335/12* (2006.01)

(52) U.S. Cl.
CPC ...... *H01L 51/0073* (2013.01); *H01L 51/0074* (2013.01); *H01L 51/5012* (2013.01); *H01L 51/5056* (2013.01)

(56) References Cited

FOREIGN PATENT DOCUMENTS

| JP | 2016-505518 A | | 2/2016 | |
|---|---|---|---|---|
| KR | 10-2013-0140303 | | 12/2013 | |
| KR | 10-2015-0083917 | | 7/2015 | |
| KR | 10-2016-0127428 A | | 11/2016 | |
| KR | 10-2017-0138799 | * | 12/2017 | ........... C07D 307/94 |
| WO | 2014/072017 A1 | | 5/2014 | |
| WO | 2017/061832 A1 | | 4/2017 | |

OTHER PUBLICATIONS

International Search Report dated Nov. 6, 2018 issued in corresponding application PCT/JP2018/029217.
Chu et al.-"Synthesis and Optoelectronic Properties of Blue-Emitting Star-Burst Oligomers Based on Triphenylamine and Spiro(fluorene-9,9'-xanthene)" Acta Phys.-Chim. Sin. 2012, 28(8), pp. 2000-2007.
Notice of Refusal dated Apr. 19, 2019 issued in corresponding Korean patent application No. 10-2018-7031457.

* cited by examiner

COMPOUND, MATERIAL FOR ORGANIC ELECTROLUMINESCENCE DEVICES, ORGANIC ELECTROLUMINESCENCE DEVICE, AND ELECTRONIC DEVICE

CROSS-REFERENCE TO RELATED APPLICATIONS

The present application is a continuation application of International Application No. PCT/JP2018/029217, filed Aug. 3, 2018, which claims priority to Japanese Patent Application No. 2017-151141, filed Aug. 3, 2017. The contents of these applications are incorporated herein by reference in their entirety.

TECHNICAL FIELD

The present invention relates to compounds, materials for organic electroluminescence devices comprising the compounds, organic electroluminescence devices comprising the compounds, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with a high efficiency to develop a compound that transports electrons or holes into the light emitting region efficiently and facilitates the recombination of electrons and holes.

Patent Literature 1 discloses an amine compound wherein the central nitrogen atom has a group having a xanthene structure shown below, an aryl group, and a group selected from an aryl group and a heteroaryl group having a structure other than the xanthene structure. In the working examples, the amine compound is used in each hole transporting layer of an organic EL device having a four-layered hole transporting layer.

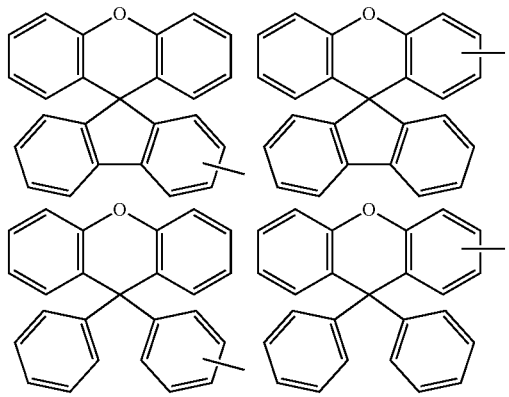

Patent Literature 2 discloses an amine compound wherein the central nitrogen atom has a group having a benzene-fused xanthene structure shown below, an aryl group, and a group selected from an aryl group and a heteroaryl group having a structure other than the xanthene structure. In the working examples, the amine compound is used in the hole transporting layer of an organic EL device.

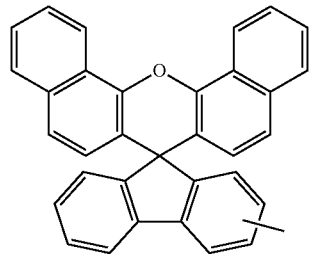

Patent Literature 3 discloses a diamine compound shown below and its analogue. In the working examples, the compound is used in a light emitting layer of an organic EL device as a host or a dopant.

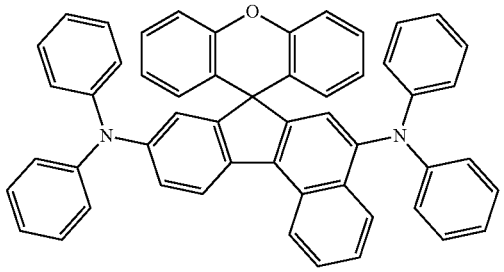 [SMILES: c1ccc(N(c2ccccc2)c2ccc3c(c2)C2(c4ccccc4Oc4ccccc42)c2cc(N(c4ccccc4)c4ccccc4)c4ccccc4c2-3)cc1]

Patent Literature 4 discloses an amine compound having one of a spiro(xanthenefluorenyl) group and a spiro(thioxanthenefluorenyl) group, an aryl group, and a 3-carbazolyl group, for example, a compound shown below. However, the performance of an organic EL device comprising the compound is not measured in the working examples. Therefore, the performance and utility of the compound as a material for organic EL device is not known.

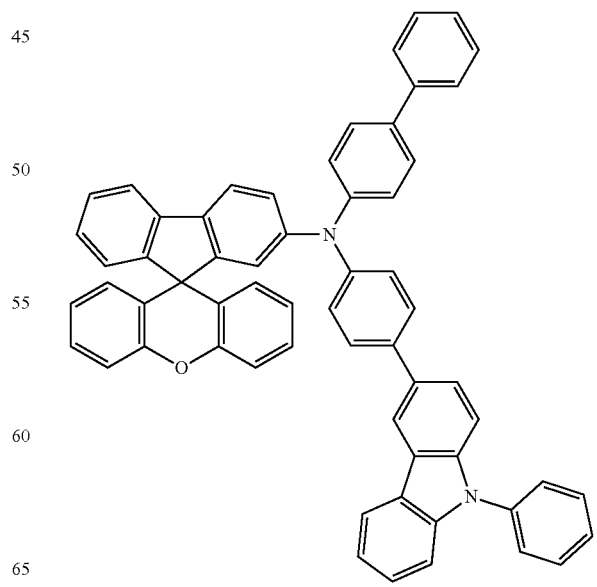

CITATION LIST

Patent Literature

Patent Literature 1: WO 2014/072017
Patent Literature 2: WO 2017/061832
Patent Literature 3: US 2015/0333277
Patent Literature 4: KR 10-2013-0140303A

SUMMARY OF INVENTION

Technical Problem

Various compounds useful for the production of organic EL devices have been reported. However, compounds that further improve the performance of organic EL devices have been still demanded.

The present invention has been made to solve the above problem and an object of the invention is to provide organic EL devices operable at a low driving voltage and exhibiting an excellent emission efficiency, and provide novel compounds providing such organic EL devices.

Solution to Problem

As a result of extensive research, the inventors have found that a monoamine compound represented by formula (1) in which at least two selected from a spiro(xanthenefluorene) skeleton and a spiro(thioxanthenefluorene) skeleton are bonded to the central nitrogen atom directly or via a linker provides an organic EL device that is operated at a low driving voltage and exhibits an excellent emission efficiency.

In an aspect, the invention provides a compound represented by formula (1) (hereinafter also referred to as "compound (1)"):

mono-, di-, or tri-substituted silyl group having a substituent selected from a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a halogen atom, a cyano group, or a nitro group;

adjacent two selected from $R^1$ to $R^4$, adjacent two selected from $R^5$ to $R^8$, adjacent two selected from $R^{11}$ to $R^{14}$, adjacent two selected from $R^{15}$ to $R^{18}$, adjacent two selected from $R^{21}$ to $R^{24}$, adjacent two selected from $R^{25}$ to $R^{28}$, adjacent two selected from $R^{31}$ to $R^{34}$, and adjacent two selected from $R^{35}$ to $R^{38}$ may be bonded to each other to form a ring structure;

provided that one selected from $R^1$ to $R^8$ and $R^{11}$ to $R^{18}$ is a single bond bonded to *1, or a ring atom of the ring structure formed by adjacent two selected from $R^1$ to $R^4$, adjacent two selected from $R^5$ to $R^8$, adjacent two selected from RH to $R^{14}$, or adjacent two selected from $R^{15}$ to $R^{18}$ is bonded to *1;

provided that one selected from $R^{21}$ to $R^{28}$ and $R^{31}$ to $R^{38}$ is a single bond bonded to *2, or a ring atom of the ring structure formed by adjacent two selected from $R^{21}$ to $R^{24}$, adjacent two selected from $R^{25}$ to $R^{28}$, adjacent two selected from $R^{31}$ to $R^{34}$, or adjacent two selected from $R^{35}$ to $R^{38}$ is bonded to *2;

X is an oxygen atom or a sulfur atom;
Y is an oxygen atom or a sulfur atom;
each of $L^1$, $L^2$, and $L^3$ is independently a single bond, a substituted or unsubstituted arylene group having 6 to 30 ring carbon atoms, or a substituted or unsubstituted heteroarylene group having 5 to 30 ring atoms;

Ar is a substituted or unsubstituted aryl group having 6 to 30 ring carbon atoms, a substituted or unsubstituted nitro-

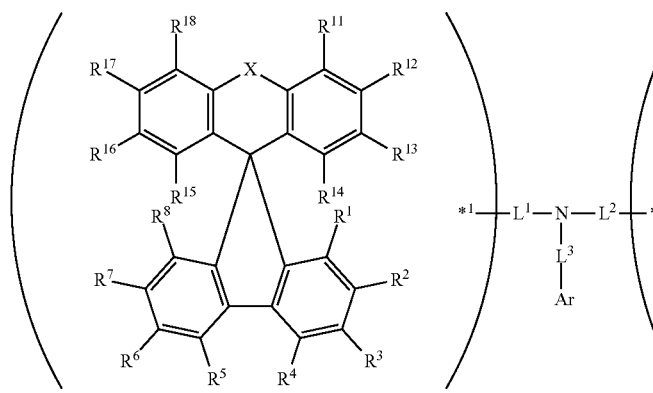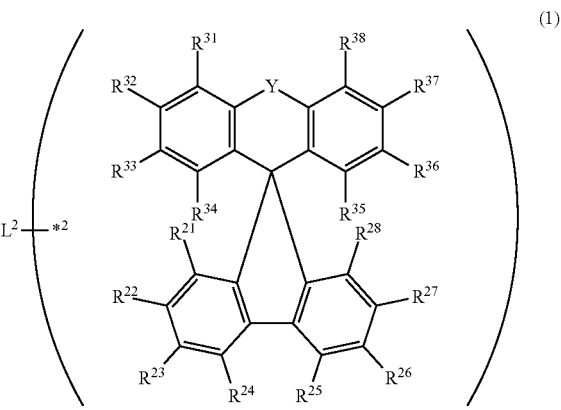

(1)

wherein:

each of $R^1$ to $R^8$, $R^{11}$ to $R^{18}$, $R^{21}$ to $R^{28}$, and $R^{31}$ to $R^{38}$ is independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted heteroaryl group having 5 to 30 ring atoms, a substituted or unsubstituted aralkyl group having 7 to 36 ring carbon atoms, a substituted or unsubstituted alkoxy group having 1 to 30 carbon atoms, a substituted or unsubstituted aryloxy group having 6 to 30 ring carbon atoms, a gen-comprising heteroaryl group having 5 to 30 ring atoms, a substituted or unsubstituted oxygen-comprising heteroaryl group having 5 to 30 ring atoms, or a substituted or unsubstituted sulfur-comprising heteroaryl group having 5 to 30 ring atoms; and when an optional substituent is present, the optional substituent referred to by "substituted or unsubstituted" is selected from the group consisting of an alkyl group having 1 to 30 carbon atoms, a cycloalkyl group having 3 to 30 ring carbon atoms, an aryl group having 6 to 30 ring carbon atoms, a heteroaryl group having 5 to 30 ring atoms, a substituted or unsubstituted aralkyl group having 7 to 36 ring carbon atoms, an alkoxy group having 1 to 30 carbon atoms, an aryloxy group having 6 to 30 ring carbon atoms, a mono-, di-, or tri-substituted silyl group having a substituent selected from an alkyl group having 1 to 30 carbon atoms and an aryl group having 6 to 30 ring carbon atoms, a haloalkyl group having 1 to 30 carbon atoms, a haloalkoxy group having 1 to 30 carbon atoms, a halogen atom, a cyano group, and a nitro group.

In another aspect, the invention provides a material for organic electroluminescence devices comprising the compound (1).

In still another aspect, the invention provides an organic electroluminescence device comprising a cathode, an anode, and an organic layer disposed between the cathode and the anode, wherein the organic layer comprises a light emitting layer and at least one layer of the organic layer comprises the compound (1).

In still another aspect, the invention provides an electronic device comprising the organic electroluminescence device.

Advantageous Effects of Invention

The compound (1) provides an organic EL device that is operated at a low driving voltage and an improved emission efficiency.

DESCRIPTION OF EMBODIMENTS

Figure 1:
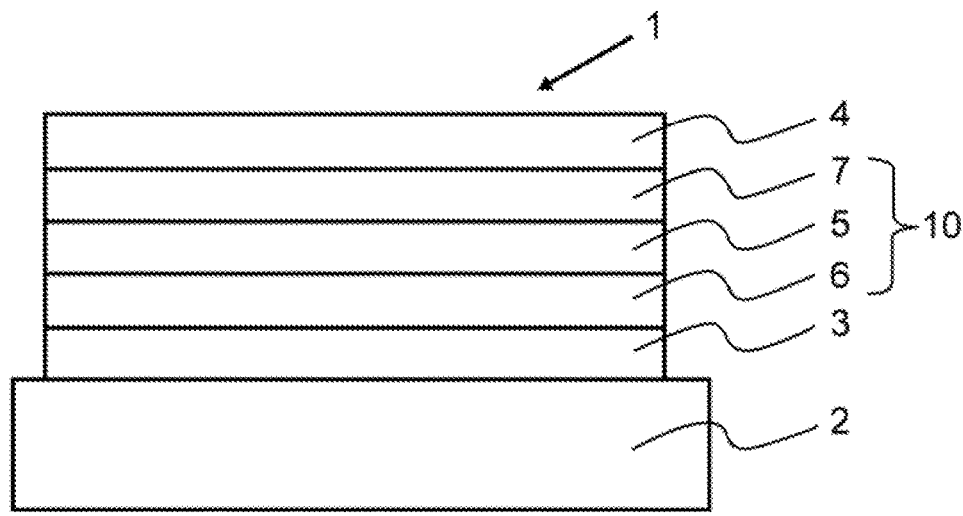
FIG. 1 is a schematic view showing the structure of an organic EL device in an embodiment of the invention.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms that form the ring itself of a compound in which a series of atoms is bonded to form a ring, for example, a monocyclic compound, a fused ring compound, a cross-linked compound, a carbocyclic compound, and a heterocyclic compound. If the ring has a substituent, the carbon atom in the substituent is not included in the ring carbon atom. Unless otherwise noted, the same applies to the number of "ring carbon atoms" mentioned below. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirobifluorene ring), the carbon atom in the fluorene substituent is not counted as the ring carbon atom of the fluorene ring.

The number of "ring atom" referred to herein means the number of the atoms that form the ring itself of a compound in which a series of atoms is bonded to form a ring, for example, a monocyclic compound, a fused ring compound, a cross-linked compound, a carbocyclic compound, and a heterocyclic compound. The atom not forming the ring, for example, hydrogen atom bonding to the atom that forms the ring and the atom in the substituent bonding to the atom that forms the ring are not counted as the ring atom. Unless otherwise noted, the same applies to the number of "ring atoms" mentioned below. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent on the ring carbon atom of a pyridine ring or a quinazoline ring are not counted as the ring atom. In case of a fluorene ring to which a fluorene substituent is bonded (inclusive of a spirobifluorene ring), the atom in the fluorene substituent is not counted as the ring atom of the fluorene ring.

The compound in an aspect of the invention (compound (1)) is represented by formula (1):

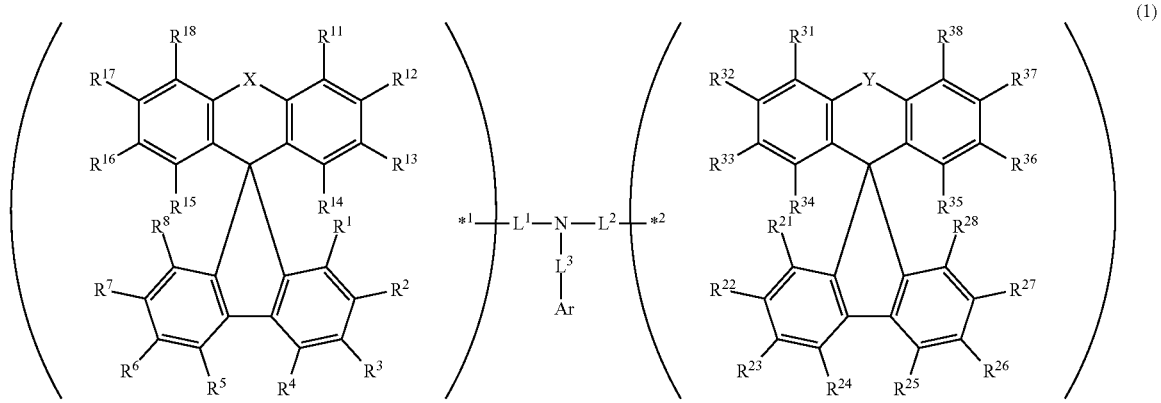

Each symbol in formula (1) and formulae mentioned below will be described below in detail.

Each of $R^1$ to $R^8$, $R^{11}$ to $R^{18}$, $R^{21}$ to $R^{28}$, and $R^{31}$ to $R^{38}$ is independently a hydrogen atom; a substituted or unsubstituted alkyl group having 1 to 30, preferably 1 to 18, more preferably 1 to 8 carbon atoms; a substituted or unsubstituted cycloalkyl group having 3 to 30, preferably 3 to 10, more preferably 3 to 8, still more preferably 5 or 6 ring carbon atoms; a substituted or unsubstituted aryl group having 6 to 30, preferably 6 to 25, more preferably 6 to 18 ring carbon atoms; a substituted or unsubstituted heteroaryl group having 5 to 30, preferably 5 to 24, more preferably 5 to 13 ring atoms; a substituted or unsubstituted aralkyl group having 7 to 36, preferably 7 to 26, more preferably 7 to 20 ring carbon atoms; a substituted or unsubstituted alkoxy group having 1 to 30, preferably 1 to 18, more preferably 1 to 8 carbon atoms; a substituted or unsubstituted aryloxy group having 6 to 30, preferably 6 to 25, more preferably 6 to 18 ring carbon atoms; a mono-, di-, or tri-substituted silyl group having a substituent selected from a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms; a substituted or unsubstituted haloalkyl group having 1 to 30, preferably 1 to 18, more preferably 1 to 8 carbon atoms; a substituted or unsubstituted haloalkoxy group having 1 to 30, preferably 1 to 18, more preferably 1 to 8 carbon atoms; a halogen atom; a cyano group; or a nitro group.

The alkyl group of the substituted or unsubstituted alkyl group having 1 to 30 carbon atoms is, for example, a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), or a dodecyl group (inclusive of isomeric groups). Preferred is a methyl group, an ethyl group, a n-propyl group, an isopropyl group, a n-butyl group, an isobutyl group, a s-butyl group, a t-butyl group, or a pentyl group (inclusive of isomeric groups); more preferred is a methyl group, an ethyl group, a n-propyl group, an isopropyl group, a n-butyl group, an isobutyl group, a s-butyl group, or a t-butyl group; and still more preferred is a methyl group or a t-butyl group.

The cycloalkyl group of the substituted or unsubstituted cycloalkyl group having 3 to 30 ring carbon atoms is, for example, a cyclopropyl group, a cyclobutyl group, a cyclopentyl group, a cyclohexyl group, or a cycloheptyl group, and preferably a cyclopentyl group or a cyclohexyl group.

The aryl group of the substituted or unsubstituted aryl group having 6 to 30 ring carbon atoms is, for example, a phenyl group, a biphenylyl group, a terphenylyl group, a naphthyl group, an acenaphthylenyl group, a biphenylenyl group, a fluorenyl group, a s-indacenyl group, an as-indacenyl group, an anthryl group, a benzanthryl group, an aceanthryl group, a phenanthryl group, a benzophenanthryl group, a phenalenyl group, a naphthacenyl group, a fluoranthenyl group, a pyrenyl group, a chrysenyl group, a benzochrysenyl group, a triphenylenyl group, a pentacenyl group, a picenyl group, or a pentaphenyl group. Preferred is a phenyl group, a biphenylyl group, a terphenylyl group, or a naphthyl group; more preferred is a phenyl group, a biphenylyl group, or a naphthyl group; and still more preferred is a phenyl group.

The substituted aryl group is preferably a 9,9-dimethylfluorenyl group, a 9,9-diphenylfluorenyl group, or a 9,9'-spirobifluorenyl group.

The heteroaryl group of the substituted or unsubstituted heteroaryl group having 5 to 30 ring atoms comprises 1 to 5, preferably 1 to 3, more preferably 1 to 2 ring hetero atoms, which is selected, for example, from a nitrogen atom, a sulfur atom, and an oxygen atom. The free valance of the heteroaryl group is present on a ring carbon atom or may be present on a ring nitrogen atom, if structurally possible.

The heteroaryl group is, for example, a pyrrolyl group, an imidazolyl group, a pyrazolyl group, a triazolyl group, a furyl group, a thienyl group, an oxazolyl group, an isoxazolyl group, an oxadiazolyl group, a thiazolyl group, an isothiazolyl group, a thiadiazolyl group, a pyridyl group, a pyridazinyl group, a pyrimidinyl group, a pyrazinyl group, a triazinyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, an indazolyl group, a phenanthrolinyl group, a phenanthridinyl group, an acridinyl group, a phenazinyl group, a carbazolyl group, a benzocarbazolyl group, a xanthenyl group, a benzofuranyl group, an isobenzofuranyl group, a dibenzofuranyl group, a naphthobenzofuranyl group, a benzothiophenyl group (a benzothienyl group, the same applies below), a dibenzothiophenyl group (a dibenzothienyl group, the same applies below), or a naphthobenzothiophenyl group (a naphthobenzothienyl group, the same applies below). Preferred is a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, a naphthobenzofuranyl group, a dibenzothiophenyl group, a naphthobenzothiophenyl group, a carbazolyl group, or a benzocarbazolyl group; and more preferred is a thienyl group, a benzothiophenyl group, a dibenzofuranyl group, a naphthobenzofuranyl group, a dibenzothiophenyl group, a naphthobenzothiophenyl group, a carbazolyl group, or a benzocarbazolyl group.

The substituted heteroaryl group is, for example, a 9-phenylcarbazolyl group, a 9-biphenylylcarbazolyl group, a 9-phenylphenylcarbazolyl group, a 9-naphthylcarbazolyl group, a diphenylcarbazole-9-yl group, a phenyldibenzofuranyl group, or a phenyldibenzothiophenyl group (a phenyldibenzothienyl group).

The aryl portion in the aralkyl group of the substituted or unsubstituted aralkyl group having 7 to 36 ring carbon atoms is selected from the aryl group having 6 to 30, preferably 6 to 25, more preferably 6 to 18 ring carbon atoms which is mentioned above, and the alkyl portion is selected from the alkyl group having 1 to 30, preferably 1 to 18, more preferably 1 to 8 carbon atoms which is mentioned above. The aralkyl group is preferably a benzyl group, a phenethyl group or a phenylpropyl group, with a benzyl group being more preferred.

The alkyl portion in the alkoxy group of the substituted or unsubstituted alkoxy group having 1 to 30 carbon atoms is selected from the alkyl group having 1 to 30, preferably 1 to 18, more preferably 1 to 8 carbon atoms which is mentioned above. The alkoxy group is preferably a t-butoxy group, a propoxy group, an ethoxy group, or a methoxy group, with an ethoxy group and a methoxy group being more preferred and a methoxy group being still more preferred.

The aryl portion in the aryloxy group of the substituted or unsubstituted aryloxy group having 6 to 30 ring carbon atoms is selected from the aryl group having 6 to 30, preferably 6 to 25, more preferably 6 to 18 ring carbon atoms which is mentioned above. The aryloxy group is preferably a terphenyloxy group, a biphenyloxy group, or a phenoxy group, with a biphenyloxy group and a phenoxy group being preferred and a phenoxy group being more preferred.

The substituent of the mono-, di- or tri-substituted silyl group is selected from the alkyl group having 1 to 30, preferably 1 to 18, more preferably 1 to 8 carbon atoms which is mentioned above and the aryl group having 6 to 30, preferably 6 to 25, more preferably 6 to 18 ring carbon atoms which is mentioned above. Preferred is a tri-substituted silyl group, for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group.

The haloalkyl group of the substituted or unsubstituted haloalkyl group having 1 to 30 carbon atoms is an alkyl group having 1 to 30, preferably 1 to 18, more preferably 1 to 8 carbon atoms, wherein at least one hydrogen atom, preferably 1 to 7 hydrogen atoms, or all hydrogen atoms is(are) replaced by a halogen atom. The halogen atom is selected from a fluorine atom, a chlorine atom, a bromine atom, and an iodine atom, and preferably a fluorine atom.

The haloalkyl group is preferably a fluoroalkyl group having 1 to 30, preferably 1 to 18, more preferably 1 to 8 carbon atoms, more preferably a heptafluoropropyl group (inclusive of isomeric groups), a pentafluoroethyl group, a 2,2,2-trifluoroethyl group, or a trifluoromethyl group, still more preferably a pentafluoroethyl group, a 2,2,2-trifluoroethyl group, or a trifluoromethyl group, and particularly preferably a trifluoromethyl group.

The haloalkyl portion in the haloalkoxy group of the substituted or unsubstituted haloalkoxy group is selected from the haloalkyl group having 1 to 30, preferably 1 to 18, more preferably 1 to 8 carbon atoms which is mentioned above. The haloalkoxy group is preferably a fluoroalkoxy group having 1 to 30, preferably 1 to 18, more preferably 1 to 8 carbon atoms, more preferably a heptafluoropropoxy group (inclusive of isomeric groups), a pentafluoroethoxy group, a 2,2,2-trifluoroethoxy group, or a trifluoromethoxy group, still more preferably a pentafluoroethoxy group, a 2,2,2-trifluoroethoxy group, or a trifluoromethoxy group, and particularly preferably a trifluoromethoxy group.

The halogen atom is a fluorine atom, a chlorine atom, a bromine atom, or an iodine atom with a fluorine atom being preferred.

In formula (1), one selected from $R^1$ to $R^8$ and $R^{11}$ to $R^{18}$ may be a single bond bonded to *1. Alternatively, adjacent two selected from $R^1$ to $R^4$, adjacent two selected from $R^5$ to $R^8$, adjacent two selected from $R^{11}$ to $R^{14}$, and adjacent two selected from $R^{15}$ to $R^{18}$ may be bonded to each other to form a ring structure, and the ring atom of the ring structure, for example, a carbon atom or a nitrogen atom, may be bonded to *1. Namely, *1 may be bonded to any of the carbon atom of the benzene ring in the fluorene structure, the carbon atom of the benzene ring in the xanthene or thioxanthene structure, and the ring atom of the ring structure.

In formula (1), one selected from $R^{21}$ to $R^{28}$ and $R^{31}$ to $R^{38}$ may be a single bond bonded to *2. Alternatively, adjacent two selected from $R^{21}$ to $R^{24}$, adjacent two selected from $R^{25}$ to $R^{28}$, adjacent two selected from $R^{31}$ to $R^{34}$, and adjacent two selected from $R^{35}$ to $R^{38}$ may be bonded to each other to form a ring structure, and the ring atom of the ring structure, for example, a carbon atom or a nitrogen atom, may be bonded to *2. Namely, *2 may be bonded to any of the carbon atom of the benzene ring in the fluorene structure, the carbon atom of the benzene ring in the xanthene or thioxanthene structure, and the ring atom of the ring structure.

Therefore, in a preferred embodiment of the invention, the spiro(xanthenefluorene) skeleton or the spiro(thioxanthenefluorene) skeleton:

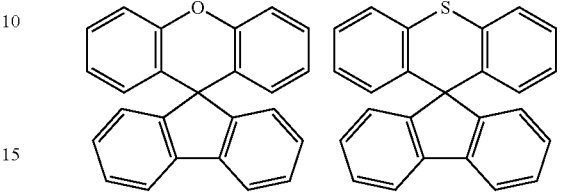

Spiro(xanthenefluorene) skeleton  Spiro(thioxanthenefluorene) skeleton that is bonded to *1 or *2 is selected from the following structures:

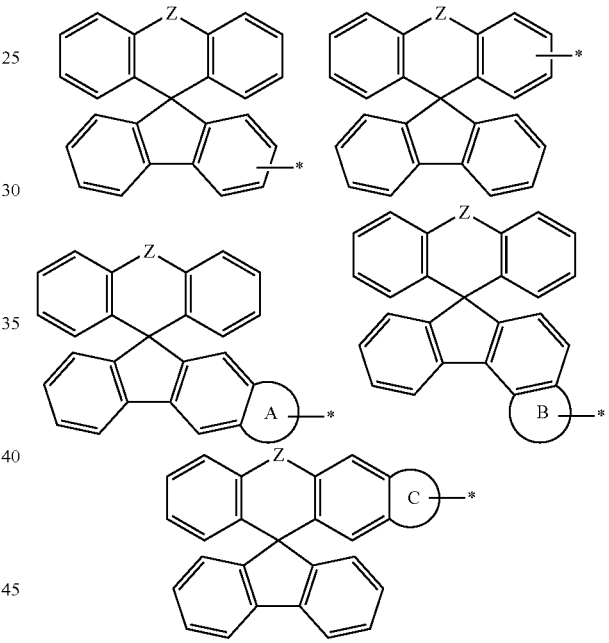

wherein:
Z is X or Y;
* means that the carbon atom of the benzene ring or the ring atom of the ring structure A, B, or C is bonded to *1 or *2; and
each R omitted for conciseness is as defined in formula (1).

In an embodiment of the invention, $R^1$ to $R^8$ and $R^{11}$ to $R^{18}$ not a single bond bonded to *1, and, not forming the ring structure may be all hydrogen atoms.

In an embodiment of the invention, $R^{21}$ to $R^{28}$ and $R^{31}$ to $R^{38}$ not a single bond bonded to *2, and, not forming the ring structure may be all hydrogen atoms.

In another embodiment of the invention, one selected from $R^1$ to $R^8$ and $R^{11}$ to $R^{18}$ is a single bond bonded to *1, and the rest thereof may be all hydrogen atoms.

In another embodiment of the invention, one selected from $R^{21}$ to $R^{28}$ and $R^{31}$ to $R^{38}$ is a single bond bonded to *2, and the rest thereof may be all hydrogen atoms.

As described above, adjacent two selected from $R^1$ to $R^4$, adjacent two selected from $R^5$ to $R^8$, adjacent two selected from $R^{11}$ to $R^{14}$, and adjacent two selected from $R^{15}$ to $R^{18}$ may be bonded to each other to form a ring structure. In an embodiment of the invention, none of the adjacent two mentioned above may form a ring structure.

As described above, adjacent two selected from $R^{21}$ to $R^{24}$, adjacent two selected from $R^{25}$ to $R^{28}$, adjacent two selected from $R^{31}$ to $R^{34}$, and adjacent two selected from $R^{35}$ to $R^{38}$ may be bonded to each other to form a ring structure. In an embodiment of the invention, none of the adjacent two mentioned above may form a ring structure.

In a preferred embodiment of the invention, the spiro(xanthenefluorene) skeleton or spiro(thioxanthenefluorene) skeleton having the ring structure is selected from the following structures:

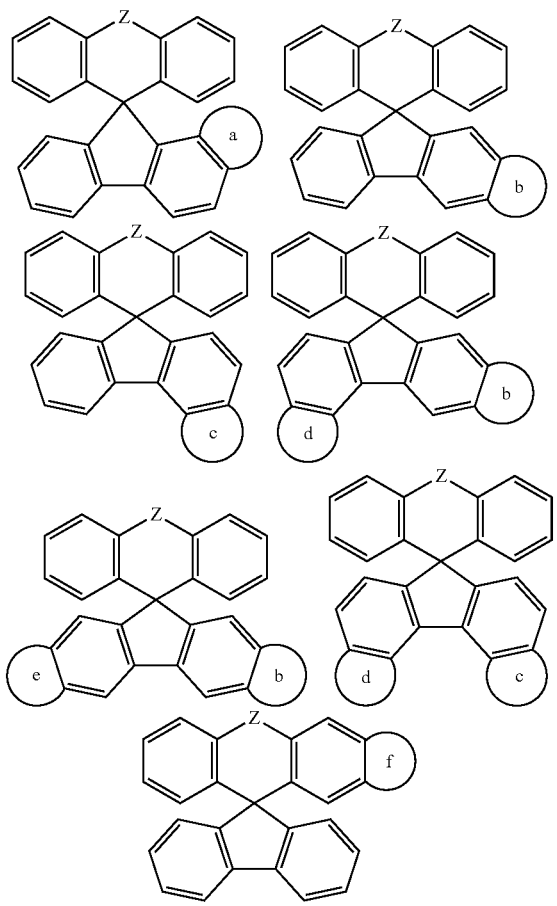

wherein:
Z is X or Y;
a carbon atom of the benzene ring or a ring atom of the ring structure a, b, c, d, e, or f is bonded to *1 or *2; and
each R omitted for conciseness is as defined in formula (1).

Examples of the ring structure include a substituted or unsubstituted aromatic hydrocarbon ring having 6 to 18 ring carbon atoms, a substituted or unsubstituted aliphatic hydrocarbon ring having 5 to 18 ring carbon atoms, a substituted or unsubstituted aromatic heterocyclic ring having 5 to 18 ring atoms, and a substituted or unsubstituted aliphatic heterocyclic ring having 5 to 18 ring atoms. The ring structure may be a fused ring structure.

Examples of the aromatic hydrocarbon ring having 6 to 18 ring carbon atoms include benzene, biphenylene, naphthalene, anthracene, benzanthracene, phenanthrene, benzophenanthrene, phenalene, pyrene, chrysene, and triphenylene.

Examples of the aliphatic hydrocarbon ring having 5 to 18 ring carbon atoms include a cyclopentene ring, a cyclopentadiene ring, a cyclohexene ring, a cyclohexadiene ring, and an aliphatic ring obtained by partially hydrogenating the aromatic hydrocarbon ring having 6 to 18 ring carbon atoms.

Examples of the aromatic heterocyclic ring having 5 to 18 ring atoms include pyrrole, furan, thiophene, pyridine, imidazole, pyrazole, indole, isoindole, benzofuran, isobenzofuran, benzothiophene, benzimidazole, indazole, dibenzofuran, naphthobenzofuran, dibenzothiophene, naphthobenzothiophene, carbazole, and benzocarbazole.

Examples of the aliphatic heterocyclic ring having 5 to 18 ring atoms includes an aliphatic ring obtained by partially hydrogenating the aromatic heterocyclic ring having 5 to 18 ring atoms.

The ring structure is preferably a benzene ring.

In an embodiment of the invention, one selected from $R^1$ to $R^8$ and $R^{11}$ to $R^{18}$ is preferably a single bond bonded to *1, more preferably one selected from $R^2$ to $R^7$, $R^{12}$, and $R^{17}$ is a single bond bonded to *1, still more preferably one selected from $R^2$ to $R^7$ is a single bond bonded to *1, and particularly preferably one selected from $R^2$, $R^4$, $R^5$, and $R^7$ is a single bond bonded to *1.

In an embodiment of the invention, one selected from $R^{21}$ to $R^{28}$ and $R^{31}$ to $R^{38}$ is preferably a single bond bonded to *2, more preferably one selected from $R^{22}$ to $R^{27}$, $R^{32}$, and $R^{37}$ is a single bond bonded to *2, still more preferably one selected from $R^{22}$ to $R^{27}$ is a single bond bonded to *2, and particularly preferably one selected from $R^{22}$, $R^{24}$, $R^{25}$, and $R^{27}$ is a single bond bonded to *2

Therefore, the compound (1) in a particularly preferred embodiment of the invention includes the compound represented by any of formulae (2) to (7):

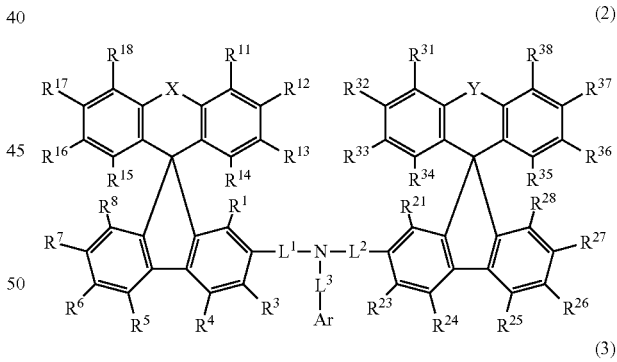

(2)

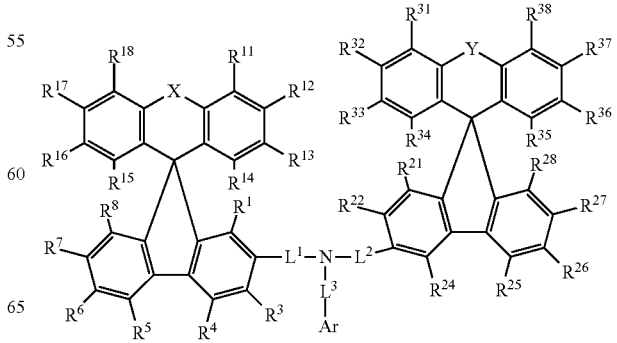

(3)

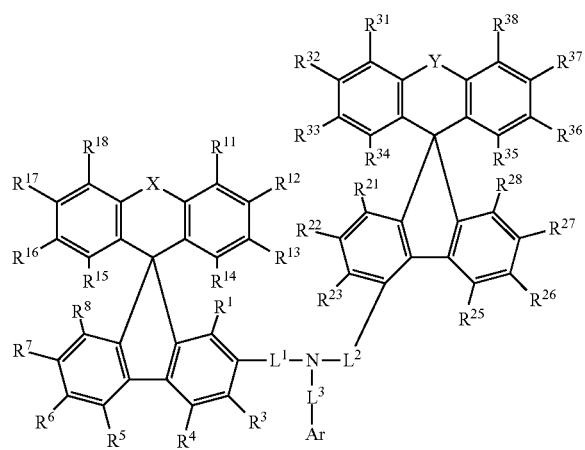

(4)

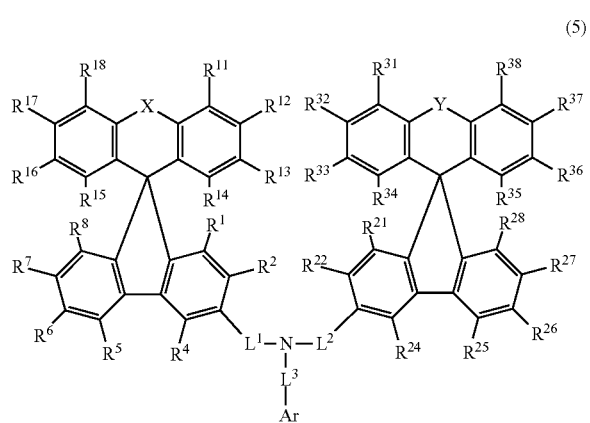

(5)

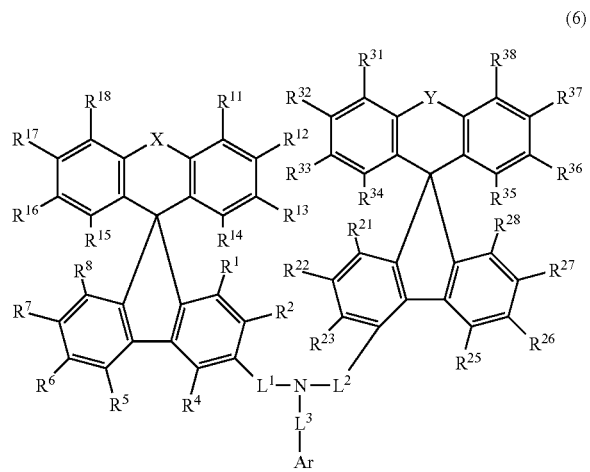

(6)

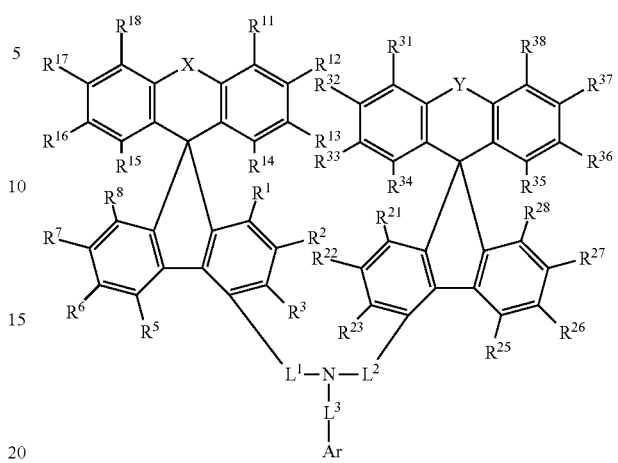

(7)

wherein $R^1$ to $R^8$, $R^{11}$ to $R^{18}$, $R^{21}$ to $R^{28}$, $R^{31}$ to $R^{38}$, X, Y, $L^1$, $L^2$, and $L^3$ are as defined above.

In another embodiment of the invention, the ring atom, for example, a carbon atom or a nitrogen atom, of any of the aromatic hydrocarbon ring having 6 to 18 ring carbon atoms, the aliphatic hydrocarbon ring having 5 to 18 ring carbon atoms, the aromatic heterocyclic ring having 5 to 18 ring atoms, and the aliphatic heterocyclic ring having 5 to 18 ring atoms may be bonded to *1 or *2.

Each of $L^1$, $L^2$, and $L^3$ is independently a single bond, a substituted or unsubstituted arylene group having 6 to 30, preferably 6 to 25, more preferably 6 to 18 ring carbon atoms, or a substituted or unsubstituted heteroarylene group having 5 to 30, preferably 5 to 24, more preferably 5 to 13 ring atoms.

The arylene group of the substituted or unsubstituted arylene group having 6 to 30 ring carbon atom for $L^1$ and $L^2$ is, for example, a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluoranthenylene group, a fluorenylene group, or a 9,9'-spirobefluorenylene group. Preferred is a phenylene group, a biphenylylene group, a terphenylylene group, or a naphthylene group; more preferred is a group selected from the following formulae:

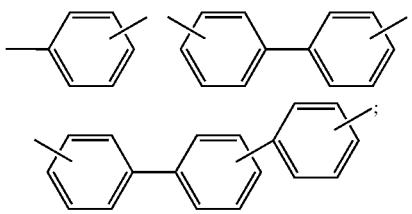

still more preferred is a group selected from the following formulae:

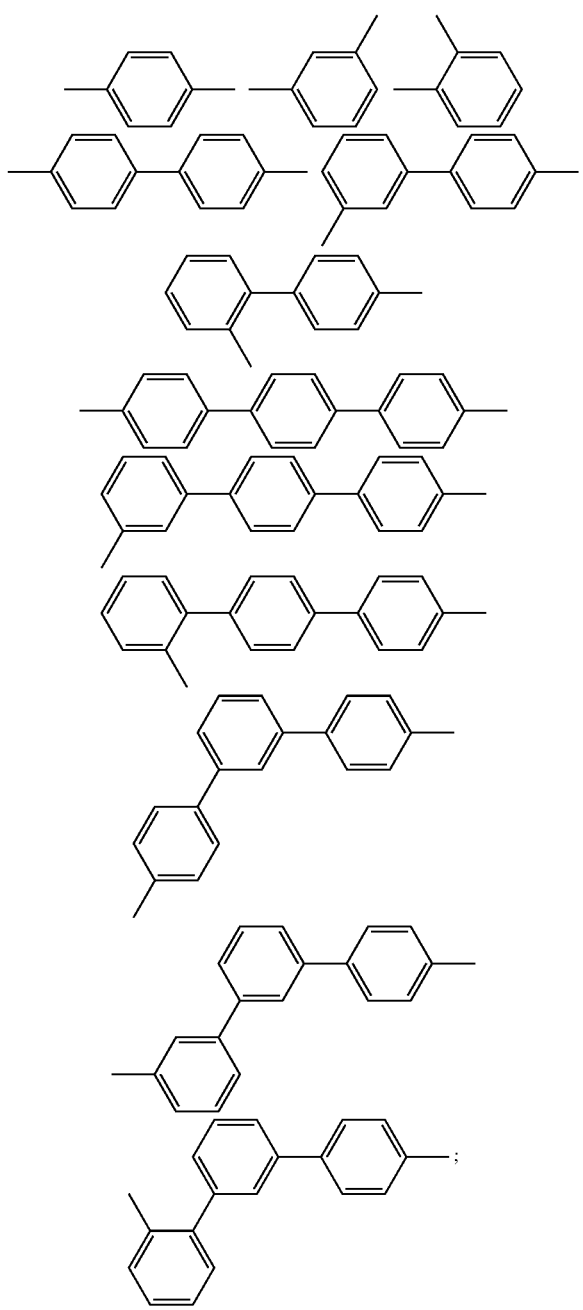

still more preferred is an o-phenylene group, a m-phenylene group, a p-phenylene group, a 4,4'-biphenylylene group, a 4,3'-biphenylylene group, or a 4,2'-biphenylylene group; still more preferred is an o-phenylene group, a m-phenylene group, or a p-phenylene group; and particularly preferred is a p-phenylene group.

The substituted arylene group is preferably a 9,9-dimethylfluorenediyl group, a 9,9-diphenylfluorenediyl group, or a 9,9'-spirobifluorenediyl group.

The heteroarylene group of the substituted or unsubstituted heteroarylene group having 5 to 30 ring atoms for $L^1$ and $L^2$ includes 1 to 5, preferably 1 to 3, and more preferably 1 to 2 ring hetero atom. The ring hetero atom is, for example, selected from a nitrogen atom, a sulfur atom, and an oxygen atom. The free valence is present on a ring carbon atom or may be present on a nitrogen atom, if structurally possible.

Examples of the heteroarylene group include a divalent residue of an aromatic heterocyclic ring selected from pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, benzocarbazole, xanthene, benzofuran, isobenzofuran, dibenzofuran, naphthobenzofuran, benzothiophene, dibenzothiophene, naphthobenzothiophene, benzoxazole, benzisoxazole, phenoxazine, benzothiazole, benzisothiazole, and phenothiazine. Preferred is a divalent residue of an aromatic heterocyclic ring selected from pyridine, pyrimidine, triazine, indole, quinoline, quinazoline, quinoxaline, benzimidazole, indazole, phenanthroline, phenanthridine, acridine, carbazole, benzocarbazole, benzofuran, dibenzofuran, naphthobenzofuran, benzothiophene, dibenzothiophene, naphthobenzothiophene, and benzoxazole; and more preferred is a divalent residue of an aromatic heterocyclic ring selected from pyridine, pyrimidine, triazine, carbazole, benzocarbazole, benzofuran, dibenzofuran, naphthobenzofuran, benzothiophene, and dibenzothiophene.

One of two free valences of the arylene group or the heteroarylene group for $L^1$ and $L^2$ is bonded to the central nitrogen atom and the other is bonded to the spiro(xanthenefluorene) skeleton or the spiro(thioxanthenefluorene) skeleton.

Each of $L^1$ and $L^2$ is preferably a single bond or a substituted or unsubstituted arylene group having 6 to 30 ring carbon atom. In an embodiment of the invention, $L^1$ and $L^2$ are preferably both single bonds. In another embodiment of the invention, one of $L^1$ and $L^2$ is preferably a single bond and the other is preferably a substituted or unsubstituted arylene group having 6 to 30 ring carbon atoms. In another embodiment of the invention, each of $L^1$ and $L^2$ is preferably a substituted or unsubstituted arylene group having 6 to 30 ring carbon atoms. The details of the arylene group are as mentioned above.

The arylene group of the substituted or unsubstituted arylene group having 6 to 30 ring carbon atoms for $L^3$ is, for example, a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluoranthenylene group, a fluorenylene group, or a 9,9'-spirobefluorenylene group. Preferred is a phenylene group, a biphenylylene group, a terphenylylene group, a naphthylene group, a phenanthrylene group, or a fluorenylene group; more preferred is a group selected from the following formulae:

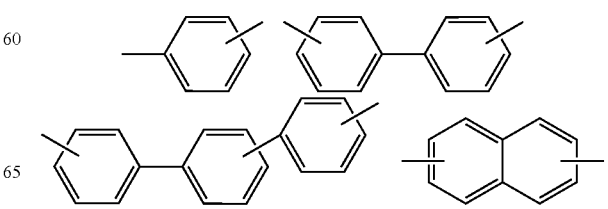

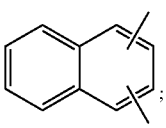

still more preferred is a group selected from the following formulae:

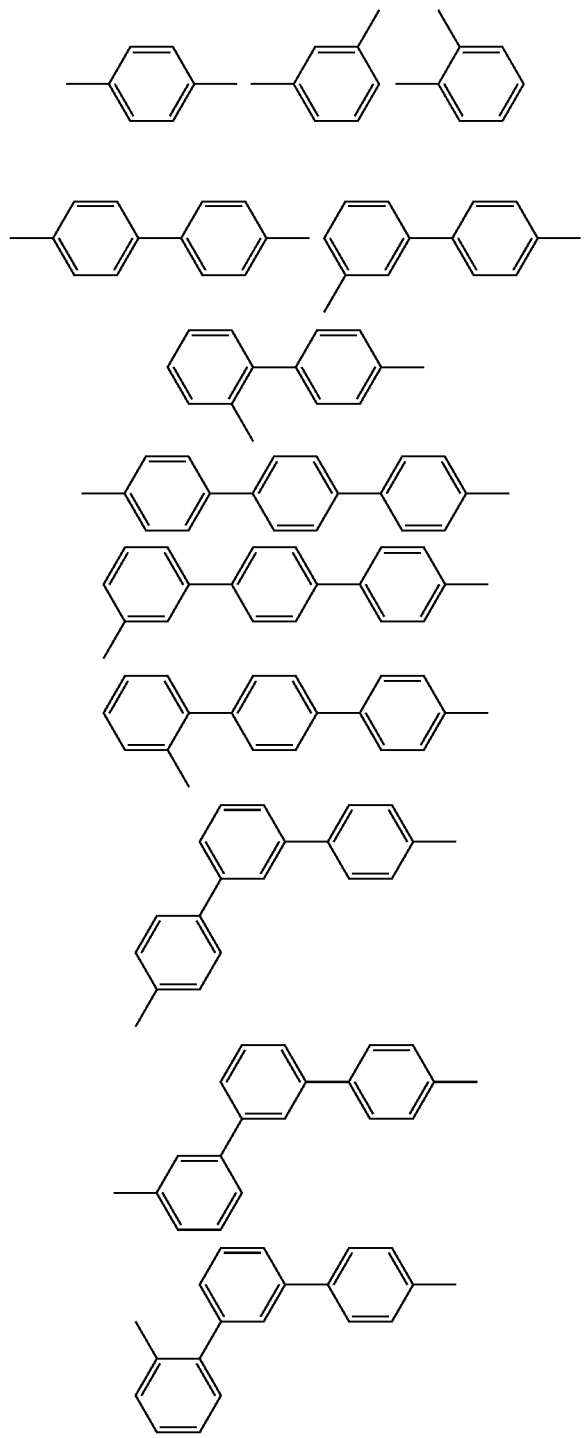

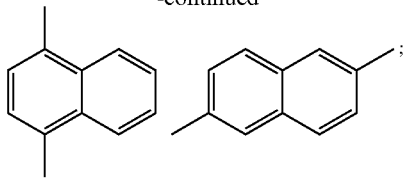

still more preferred is an o-phenylene group, a m-phenylene group, a p-phenylene group, a 4,4'-biphenylylene group, a 4,3'-biphenylylene group, a 4,2'-biphenylylene group, a 1,4-naphthylene group, or a 2,6-naphthylene group; still more preferred is an o-phenylene group, a m-phenylene group, a p-phenylene group, a 1,4-naphthylene group, or a 2,6-naphthylene group; and particularly preferred is a p-phenylene group.

The substituted arylene group is preferably a 9,9-dimethylfluorenediyl group, a 9,9-diphenylfluorenediyl group, or a 9,9'-spirobifluorenediyl group.

The heteroarylene group of the substituted or unsubstituted heteroarylene group having 5 to 30 ring atoms for $L^3$ includes 1 to 5, preferably 1 to 3, more preferably 1 to 2 ring hetero atoms. The ring hetero atom is selected, for example, from a nitrogen atom, a sulfur atom, and an oxygen atom. The free valence is present on a ring carbon atom or may be present on a nitrogen atom, if structurally possible.

Examples of the heteroarylene group include a divalent residue of an aromatic heterocyclic ring selected from pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, benzocarbazole, xanthene, benzofuran, isobenzofuran, dibenzofuran, naphthobenzofuran, benzothiophene, dibenzothiophene, naphthobenzothiophene, benzoxazole, benzisoxazole, phenoxazine, benzothiazole, benzisothiazole, and phenothiazine. Preferred is a divalent residue of an aromatic heterocyclic ring selected from pyridine, pyrimidine, triazine, indole, quinoline, quinazoline, quinoxaline, benzimidazole, indazole, phenanthroline, phenanthridine, acridine, carbazole, benzocarbazole, benzofuran, dibenzofuran, naphthobenzofuran, benzothiophene, dibenzothiophene, naphthobenzothiophene, and benzoxazole; and more preferred is a divalent residue of an aromatic heterocyclic ring selected from pyridine, pyrimidine, triazine, carbazole, benzocarbazole, benzofuran, dibenzofuran, naphthobenzofuran, benzothiophene, and dibenzothiophene.

One of two free valence of the arylene group or the heteroarylene group for $L^3$ is bonded to the central nitrogen atom and the other is bonded to the spiro(xanthenefluorene) skeleton or the spiro(thioxanthenefluorene) skeleton.

$L^3$ is preferably a single bond or a substituted or unsubstituted arylene group having 6 to 30 ring carbon atoms. In an embodiment of the invention, $L^3$ is preferably a single bond. In another embodiment of the invention, $L^3$ is preferably a substituted or unsubstituted arylene group having 6 to 30 ring carbon atoms, for example, an o-phenylene group, a m-phenylene group, a p-phenylene group, a 1,4-naphthylene group, or a 2,6-naphthylene group.

Ar is a substituted or unsubstituted aryl group having 6 to 30, preferably 6 to 25, more preferably 6 to 18 ring carbon atoms; a substituted or unsubstituted a nitrogen-comprising heteroaryl group having 5 to 30, preferably 5 to 24, more preferably 5 to 13 ring atoms; a substituted or unsubstituted oxygen-comprising heteroaryl group having 5 to 30, preferably 5 to 24, more preferably 5 to 13 ring atoms; a substituted or unsubstituted sulfur-comprising heteroaryl group having 5 to 30, preferably 5 to 24, more preferably 5 to 13 ring atoms.

In an embodiment of the invention, Ar is preferably a substituted or unsubstituted aryl group having 6 to 30 ring carbon atoms, a substituted or unsubstituted oxygen-comprising heteroaryl group having 5 to 30 ring atoms, or a substituted or unsubstituted sulfur-comprising heteroaryl group having 5 to 30 ring atoms.

In an embodiment of the invention, Ar is preferably a substituted or unsubstituted aryl group having 6 to 30 ring carbon atoms.

In another embodiment of the invention, Ar is preferably a substituted or unsubstituted nitrogen-comprising heteroaryl group having 5 to 30 ring atoms.

In another embodiment of the invention, Ar is preferably a substituted or unsubstituted oxygen-comprising heteroaryl group having 5 to 30 ring atoms.

In still another embodiment of the invention, Ar is preferably a substituted or unsubstituted sulfur-comprising heteroaryl group having 5 to 30 ring atoms.

The aryl group of the substituted or unsubstituted aryl group having 6 to 30 ring carbon atoms for Ar is, for example, a phenyl group, a biphenylyl group, a terphenylyl group, a naphthyl group, an acenaphthylenyl group, a biphenylenyl group, a fluorenyl group, a s-indacenyl group, an as-indacenyl group, an anthryl group, a benzanthryl group, an aceanthryl group, a phenanthryl group, a benzophenanthryl group, a phenalenyl group, a naphthacenyl group, a fluoranthenyl group, a pyrenyl group, a chrysenyl group, a benzochrysenyl group, a triphenylenyl group, a pentacenyl group, a picenyl group, or a pentaphenyl group. Preferred is a phenyl group, a biphenylyl group, a terphenylyl group, a naphthyl group, a fluorenyl group, a s-indacenyl group, an as-indacenyl group, an anthryl group, a benzanthryl group, a phenanthryl group, a benzophenanthryl group, a fluoranthenyl group, a pyrenyl group, a chrysenyl group, a benzochrysenyl group, or a triphenylenyl group. More preferred is a phenyl group, a biphenylyl group, a terphenylyl group, a naphthyl group, a fluorenyl group, a phenanthryl group, or a triphenylenyl group. Still more preferred is a phenyl group, a p-biphenylyl group, a m-biphenylyl group, an o-biphenylyl group, a p-terphenyl-4-yl group, a p-terphenyl-3-yl group, a p-terphenyl-2-yl group, a m-terphenyl-3'-yl group, a m-terphenyl-4-yl group, a 1-naphthyl group, a 2-naphthyl group, a 2-phenanthryl group, a 9-phenanthryl group, a 2-triphenylenyl group, a fluorene-2-yl group, or a fluorene-4-yl group.

The substituted aryl group is preferably a 9,9'-spirobifluorenyl group, a 9,9-diphenyfluorenyl group, or a 9,9-dimethylfluorenyl group, and more preferably a 9,9'-spirobifluorene-2-yl group, a 9,9'-spirobifluorene-4-yl group, a 9,9-diphenylfluorene-2-yl group, a 9,9-diphenylfluorene-4-yl group, a 9,9-dimethylfluorene-2-yl group, or a 9,9-dimethylfluorene-4-yl group.

The nitrogen-comprising heteroaryl group of the substituted or unsubstituted nitrogen-comprising heteroaryl group having 5 to 30 ring atoms for Ar is, for example, a pyrrolyl group, an imidazolyl group, a pyrazolyl group, a triazolyl group, an oxazolyl group, an isoxazolyl group, an oxadiazolyl group, a thiazolyl group, an isothiazolyl group, a thiadiazolyl group, a pyridyl group, a pyridazinyl group, a pyrimidinyl group, a pyrazinyl group, a triazinyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, an indazolyl group, a phenanthrolinyl group, a phenanthridinyl group, an acridinyl group, a phenazinyl group, a carbazolyl group, a benzocarbazolyl group, or a xanthenyl group.

The oxygen-comprising heteroaryl group of the substituted or unsubstituted oxygen-comprising heteroaryl group having 5 to 30 ring atoms for Ar is, for example, a furyl group, an oxazolyl group, an isoxazolyl group, an oxadiazolyl group, a xanthenyl group, a benzofuranyl group, an isobenzofuranyl group, a dibenzofuranyl group, a naphthobenzofuranyl group, a benzoxazolyl group, a benzisoxazolyl group, a phenoxazinyl group, or a monovalent residue of spiro[9H-xanthene-9,9'-[9H]fluorene]. Preferred is a furyl group, a benzofuranyl group, a dibenzofuranyl group, a naphthobenzofuranyl group, or a monovalent residue of spiro[9H-xanthene-9,9'-[9H]fluorene]. More preferred is a dibenzofuranyl group, a naphthobenzofuranyl group, or a monovalent residue of spiro[9H-xanthene-9,9'-[9H]fluorene]. Still more preferred is a dibenzofuranyl group or a monovalent residue of spiro[9H-xanthene-9,9'-[9H]fluorene]. Particularly preferred is a 1-dibenzofuranyl group, a 2-dibenzofuranyl group, a 3-dibenzofuranyl group, a 4-dibenzofuranyl group, a spiro[9H-xanthene-9,9'-[9H]fluorene]-2'-yl group, a spiro[9H-xanthene-9,9'-[9H]fluorene]-3'-yl group, or a spiro[9H-xanthene-9,9'-[9H]fluorene]-4'-yl group.

The sulfur-comprising heteroaryl group of the substituted or unsubstituted sulfur-comprising heteroaryl group having 5 to 30 ring atoms for Ar is, for example, a thienyl group, a thiazolyl group, an isothiazolyl group, a thiadiazolyl group, a benzothiophenyl group, a dibenzothiophenyl group, a naphthobenzothiophenyl group, a benzothiazolyl group, an benzisothiazolyl group, a phenothiazinyl group, or a monovalent residue of spiro[9H-thioxanthene-9,9'-[9H]fluorene]. Preferred is a thienyl group, a benzothiophenyl group, a dibenzothiophenyl group, a naphthobenzothiophenyl group, or a monovalent residue of spiro[9H-thioxanthene-9,9'-[9H]fluorene]. More preferred is a dibenzothiophenyl group, a naphthobenzothiophenyl group, or a monovalent residue of spiro[9H-thioxanthene-9,9'-[9H]fluorene]. Still more preferred is a dibenzothiophenyl group or a monovalent residue of spiro[9H-thioxanthene-9,9'-[9H]fluorene]. Particularly preferred is a 1-dibenzothiophenyl group, a 2-dibenzothiophenyl group, a 3-dibenzothiophenyl group, a 4-dibenzothiophenyl group, a spiro[9H-thioxanthene-9,9'-[9H]fluorene]-2'-yl group, a spiro[9H-thioxanthene-9,9'-[9H]fluorene]-3'-yl group, or a spiro[9H-thioxanthene-9,9'-[9H]fluorene]-4'-yl group.

In an embodiment of the invention, $L^3$ is selected from a single bond, a phenylene group, a biphenylene group, a terphenylene group, and a naphthylene group and preferably selected from a phenylene group and a naphthylene group, and Ar is selected from a phenyl group, a biphenylyl group, a terphenylyl group, a naphthyl group, a phenanthryl group, a triphenylenyl group, 9,9'-spirobifluorenyl group, 9,9-diphenylfluorenyl group, 9,9-dimethylfluorenyl group, a dibenzofuranyl group, a monovalent residue of spiro[9H-xanthene-9,9'-[9H]fluorene], a dibenzothiophenyl group, and a monovalent residue of spiro[9H-thioxanthene-9,9'-[9H]fluorene]. The details of each group are as described above.

When an optional substituent is present, the optional substituent referred to by "substituted or unsubstituted" herein is, unless otherwise noted, selected from the group consisting of a substituted or unsubstituted alkyl group having 1 to 30, preferably 1 to 18, more preferably 1 to 8 carbon atoms; a substituted or unsubstituted cycloalkyl group having 3 to 30, preferably 3 to 10, more preferably 3 to 8, still more preferably 5 or 6 ring carbon atoms; a substituted or unsubstituted aryl group having 6 to 30, preferably 6 to 25, more preferably 6 to 18 ring carbon atoms; a substituted or unsubstituted heteroaryl group having 5 to 30, preferably 5 to 24, more preferably 5 to 13 ring atoms, preferably, a substituted or unsubstituted oxygen-comprising or sulfur-comprising heteroaryl group having 5 to 30, preferably 5 to 24, more preferably 5 to 13 ring atoms; a substituted or unsubstituted aralkyl group having 7 to 36, preferably 7 to 26, more preferably 7 to 20 ring carbon atoms; a substituted or unsubstituted alkoxy group having 1 to 30, preferably 1 to 18, more preferably 1 to 8 carbon atoms; a substituted or unsubstituted aryloxy group having 6 to 30, preferably 6 to 25, more preferably 6 to 18 ring carbon atoms; a mono-, di-, or tri-substituted silyl group having a substituent selected from a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms; a substituted or unsubstituted haloalkyl group having 1 to 30, preferably 1 to 18, more preferably 1 to 8 carbon atoms; a substituted or unsubstituted haloalkoxy group having 1 to 30, preferably 1 to 18, more preferably 1 to 8 carbon atoms; a halogen atom; a cyano group; or a nitro group.

The details of the optional substituents are the same as those of the corresponding groups mentioned above with respect to $R^1$ to $R^8$, $R^{11}$ to $R^{18}$, $R^{21}$ to $R^{28}$, and $R^{31}$ to $R^{38}$. Unless otherwise noted, adjacent optional groups may be bonded to each other to form a ring.

The production method of the compound (1) is not particularly limited. One of ordinary skill in the art can easily produce the compound (1) by the method described in the examples mentioned below or by a method modifying the method described in the following examples with reference to known synthesis methods.

Examples of the compound (1) of the invention are shown below, although not limited thereto.

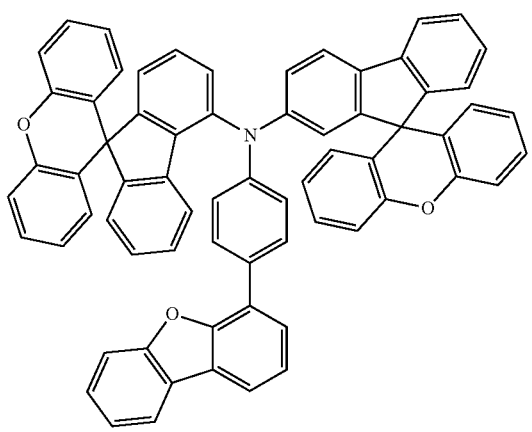

-continued

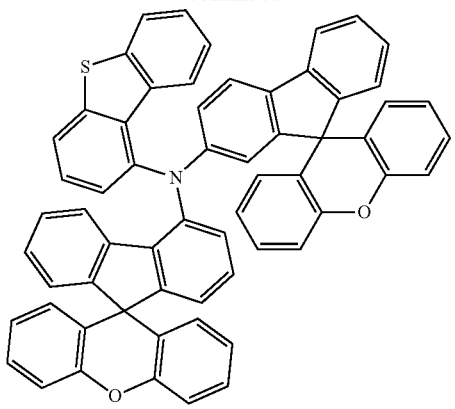

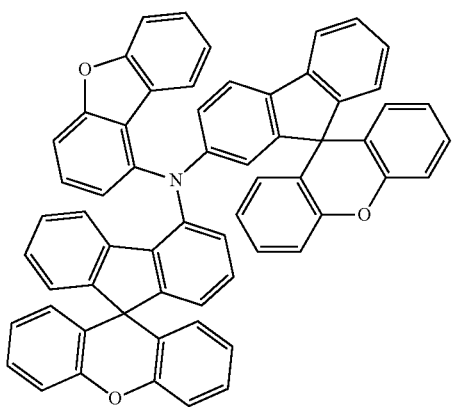

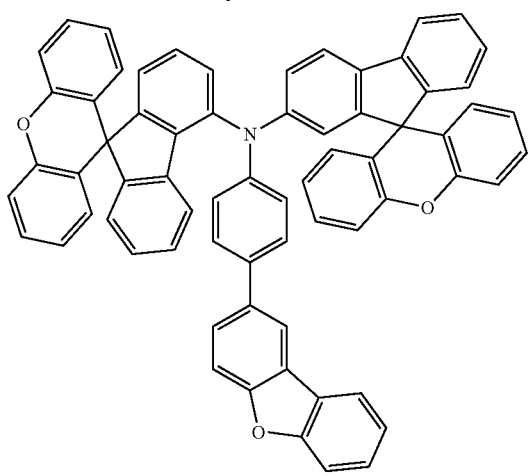

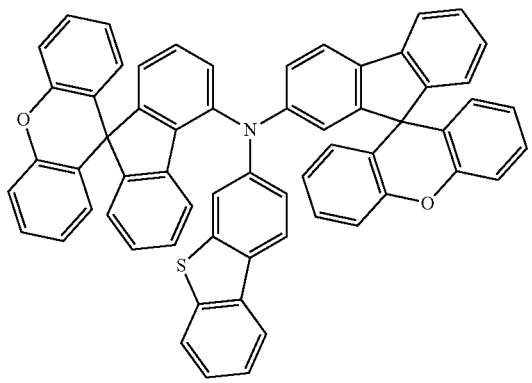

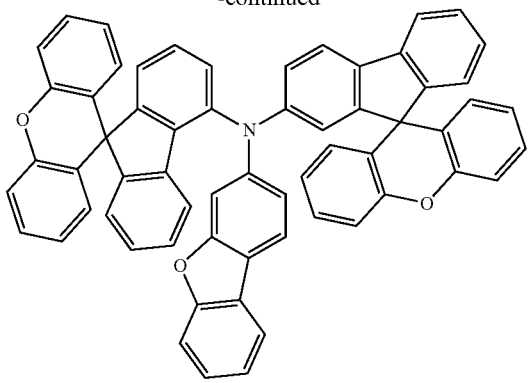
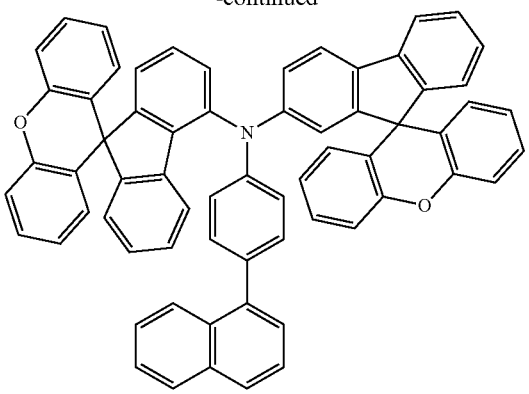
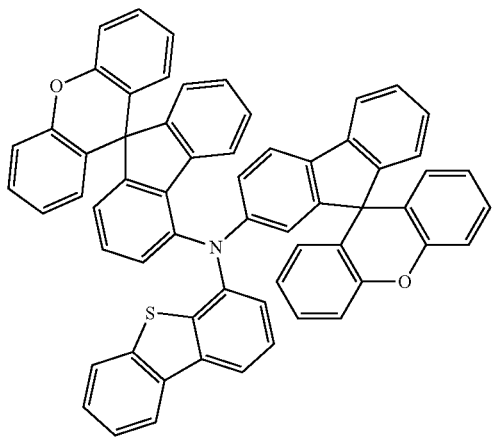
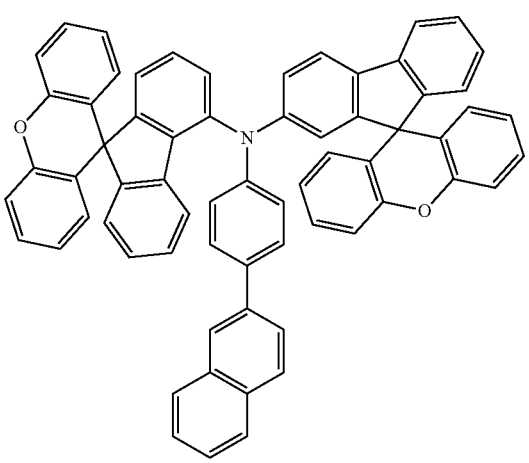
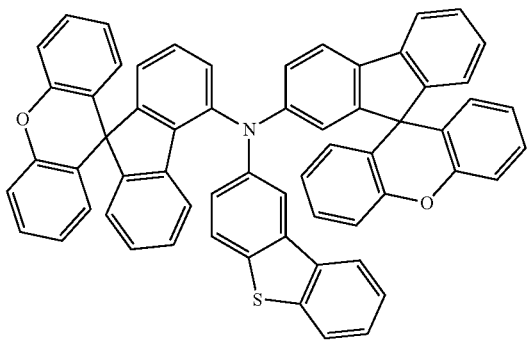
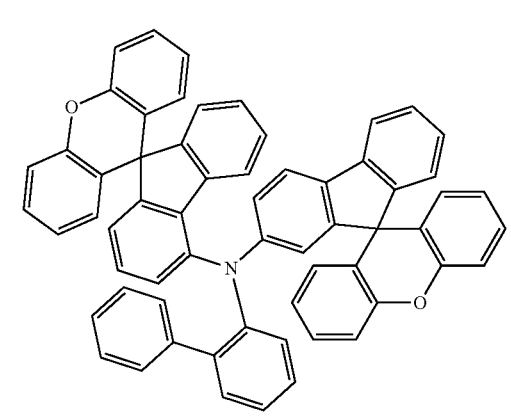
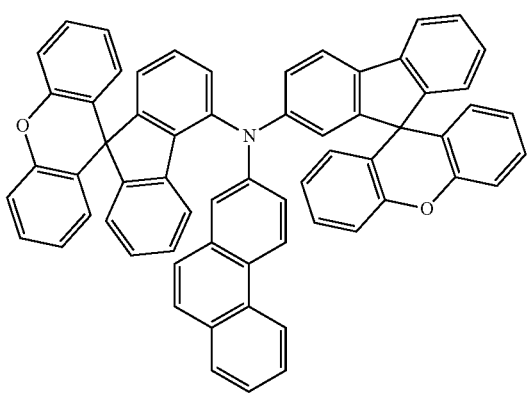
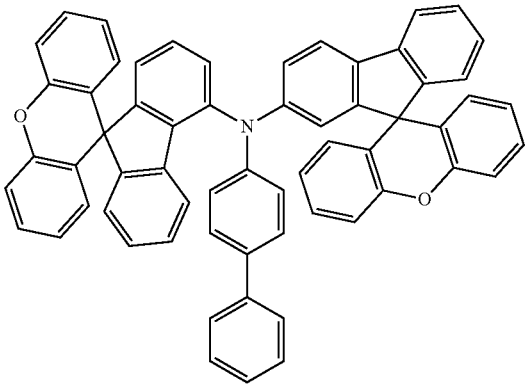

25
-continued
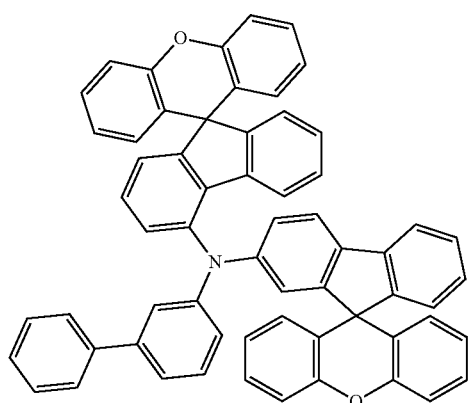
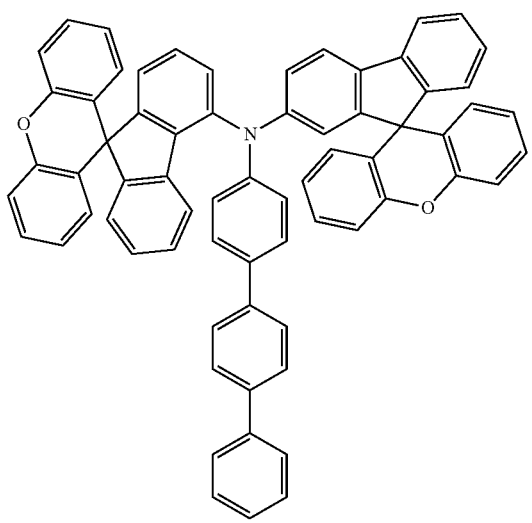
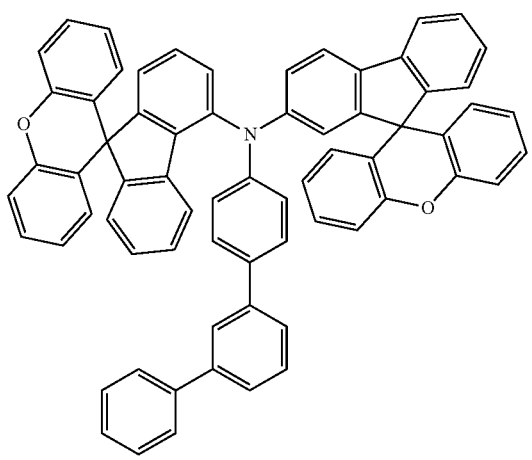
26
-continued
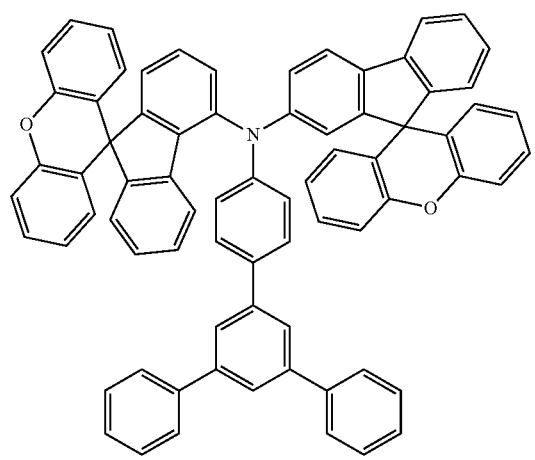
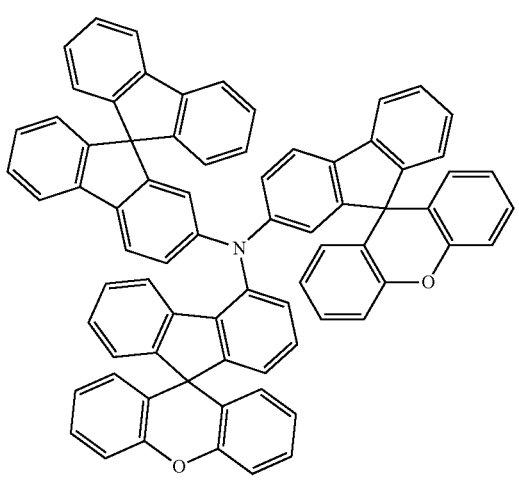
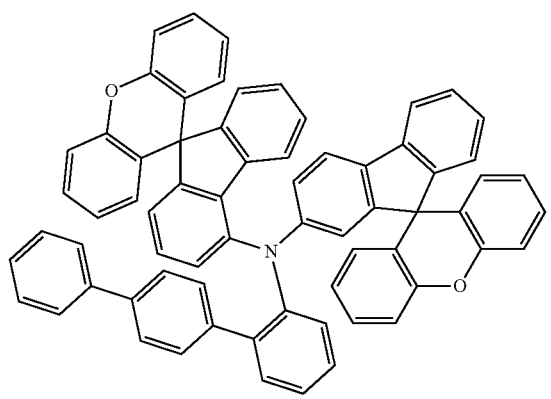

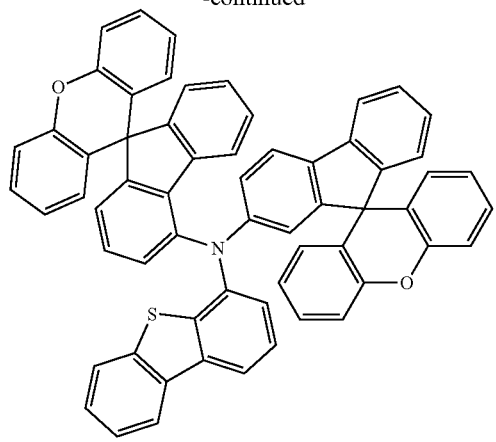
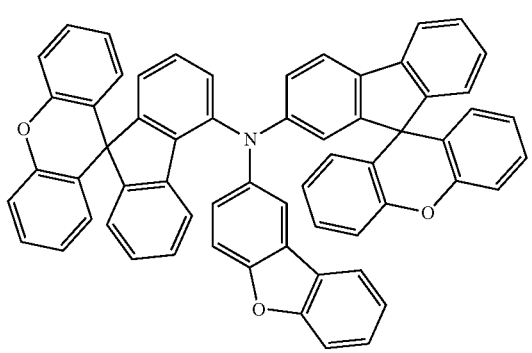
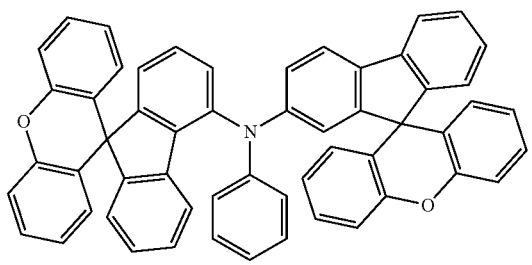
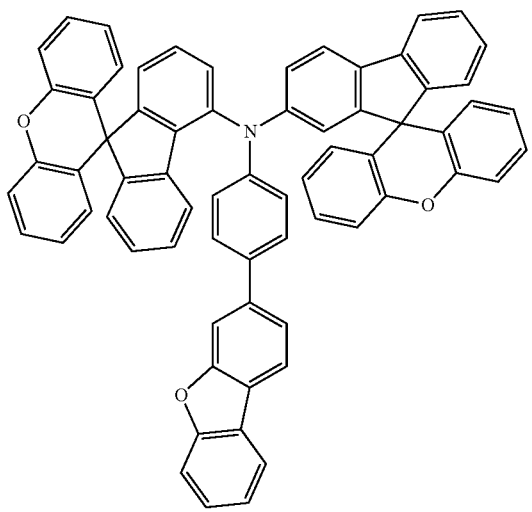
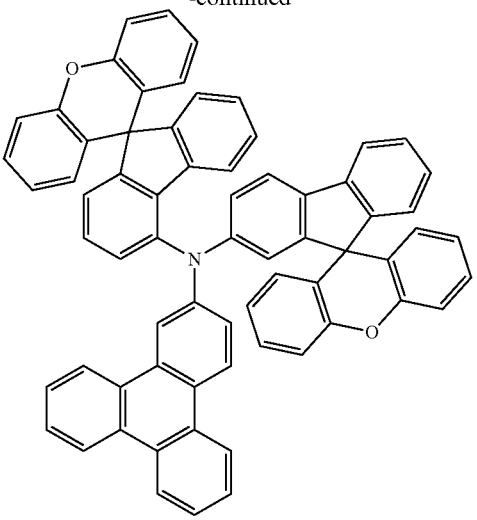
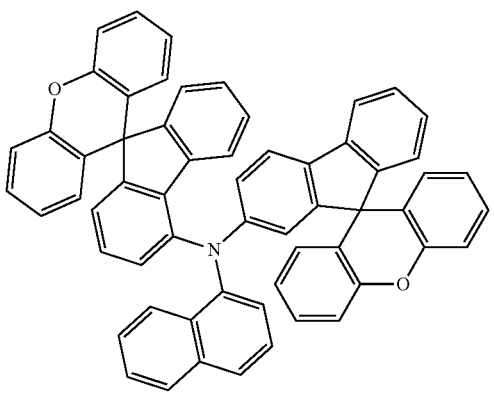
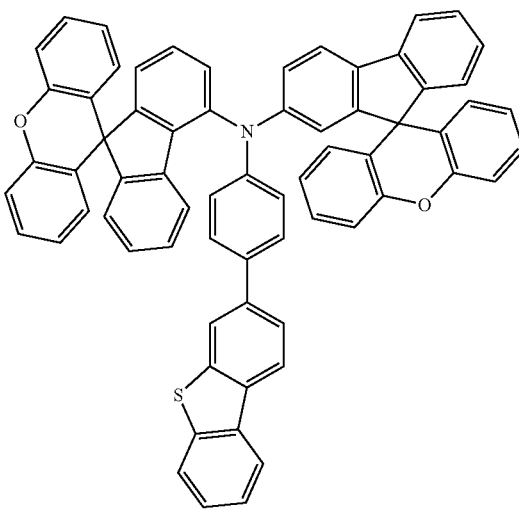

29
-continued
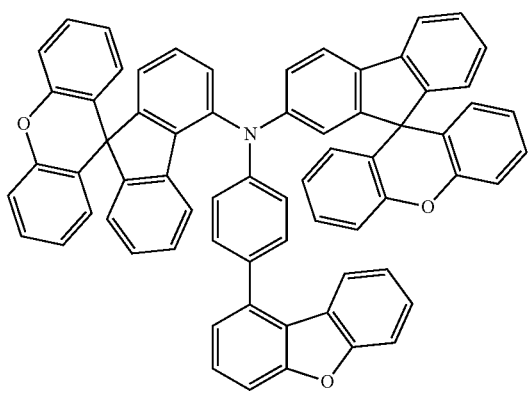
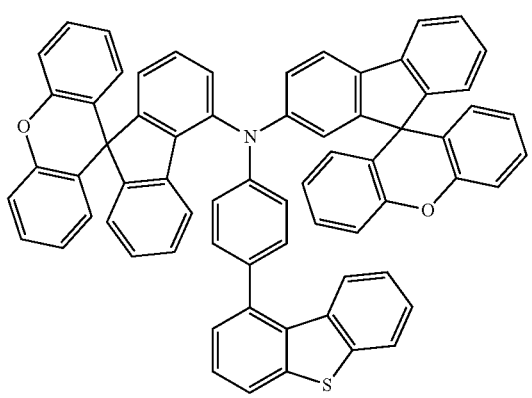
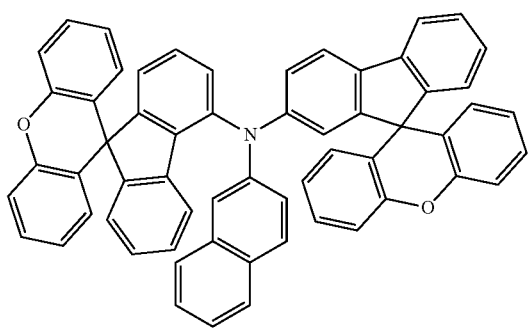
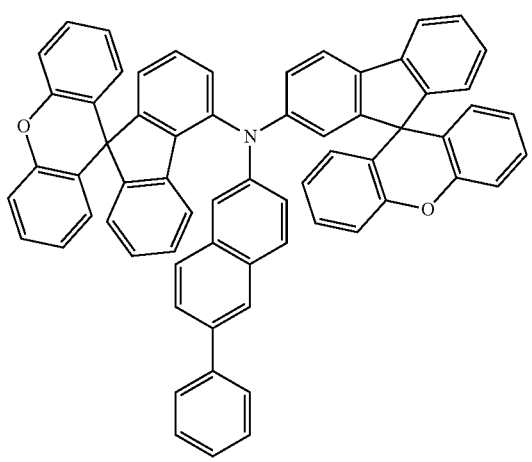
30
-continued
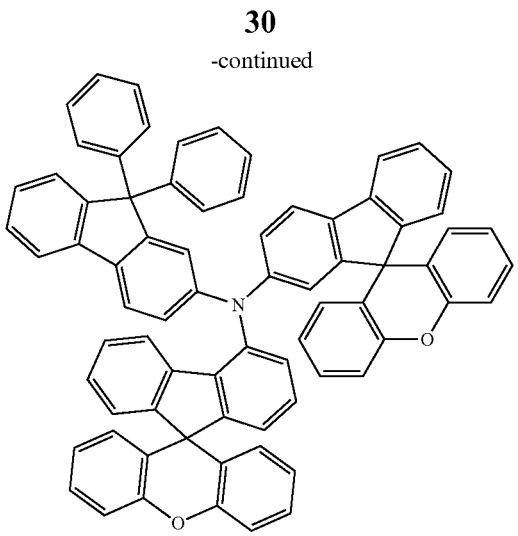
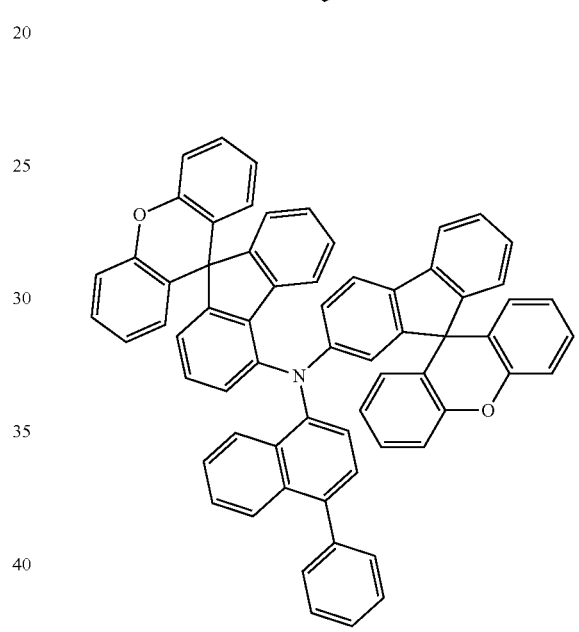
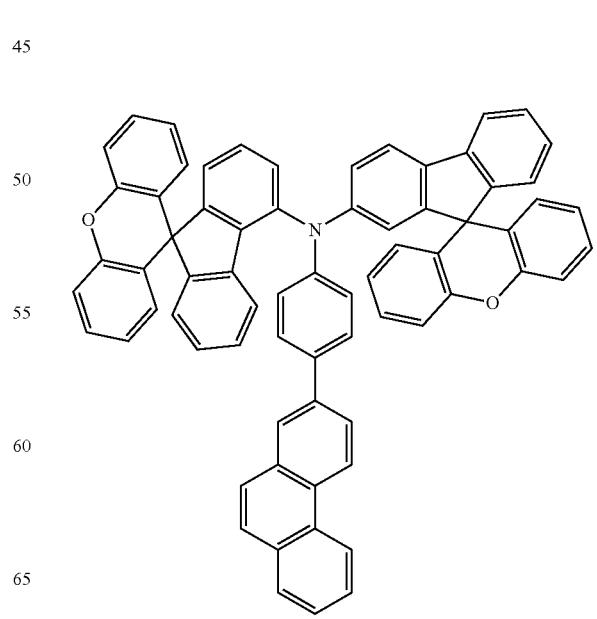

31
-continued
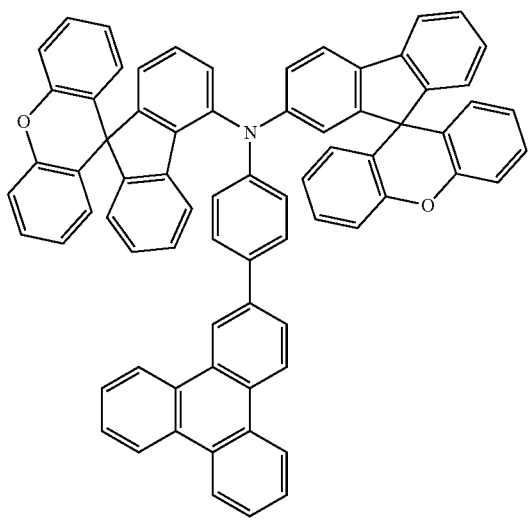
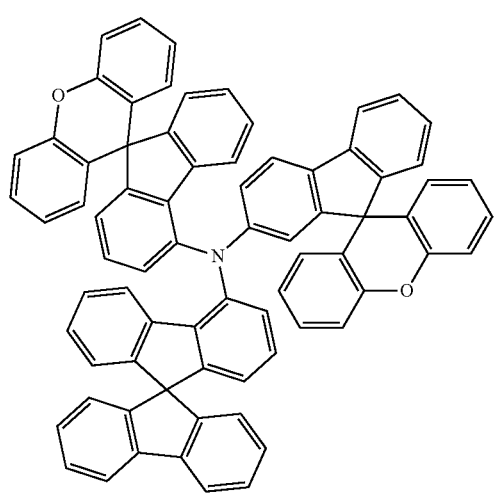
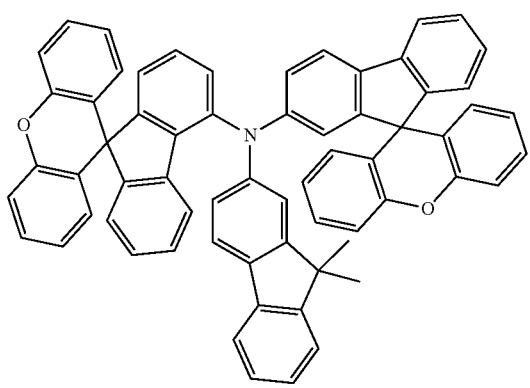
32
-continued
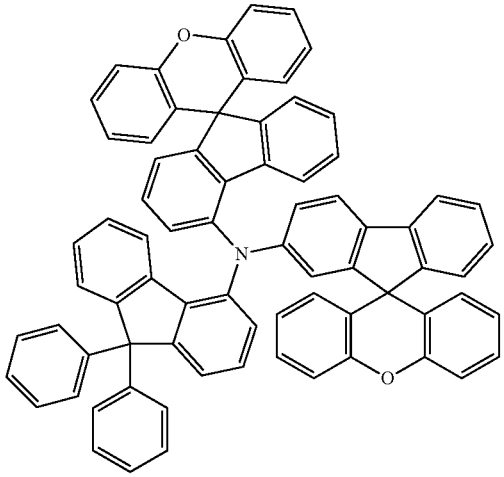
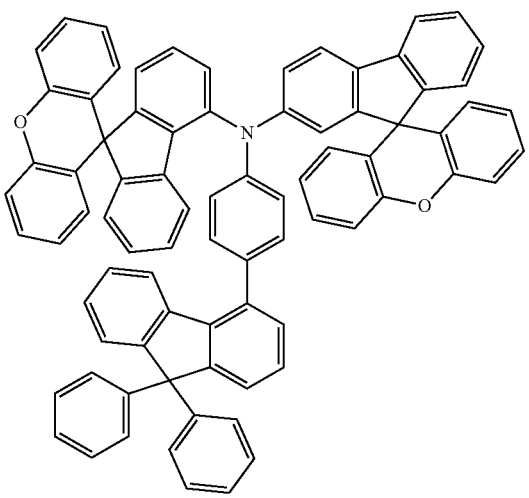
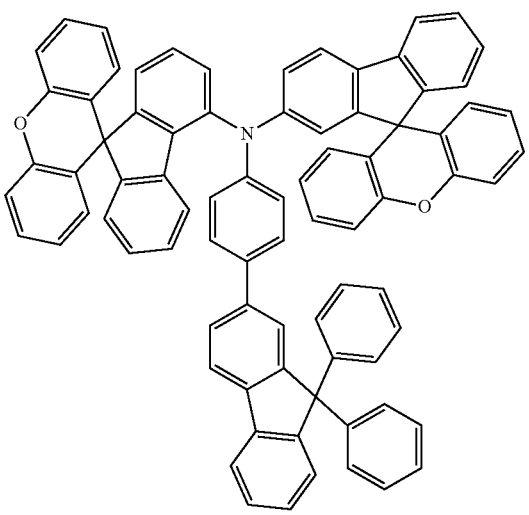

33
-continued
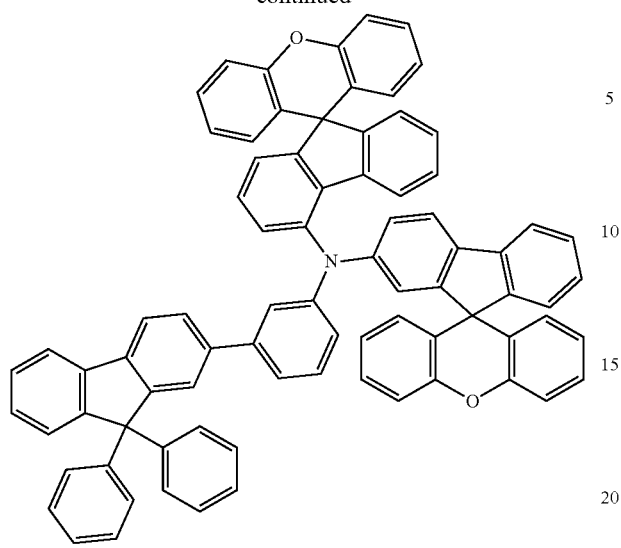
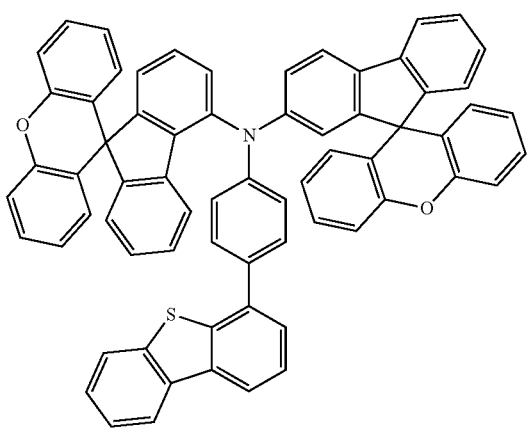
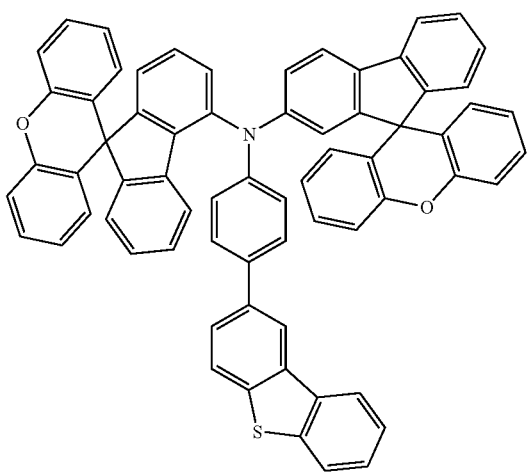
34
-continued
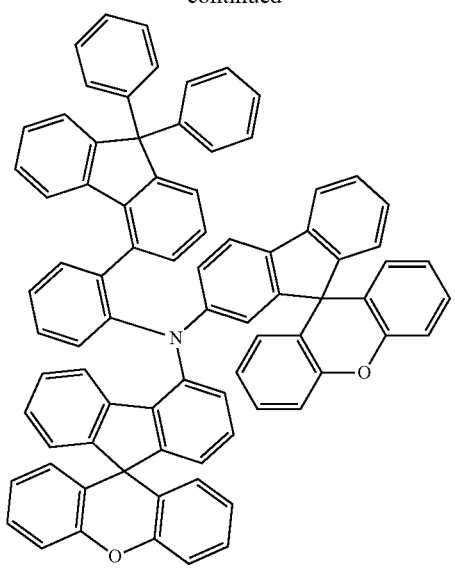
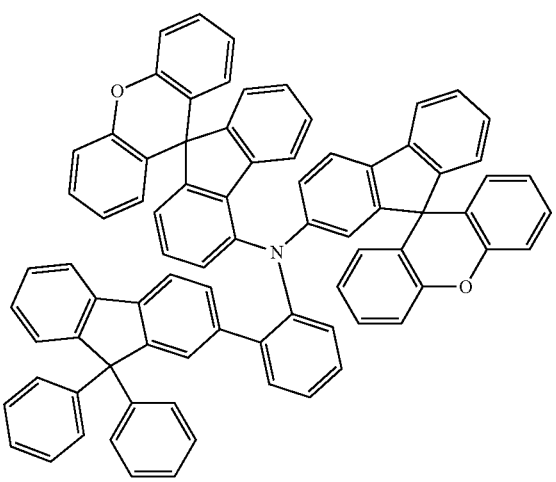
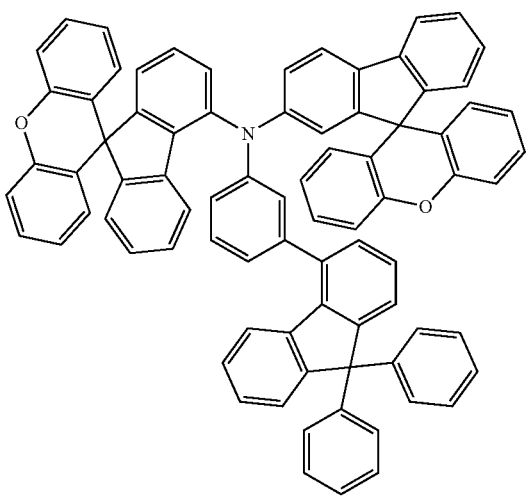

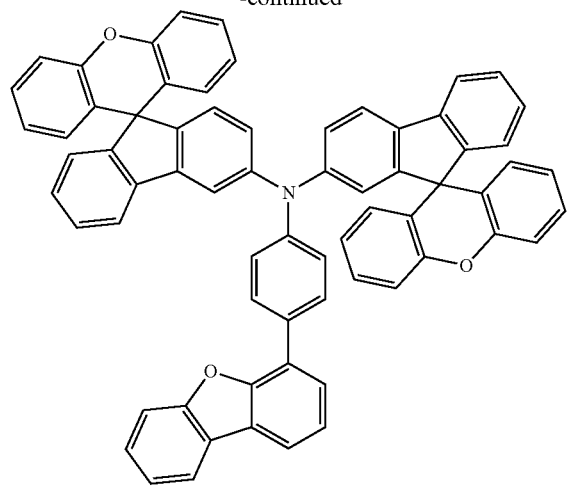
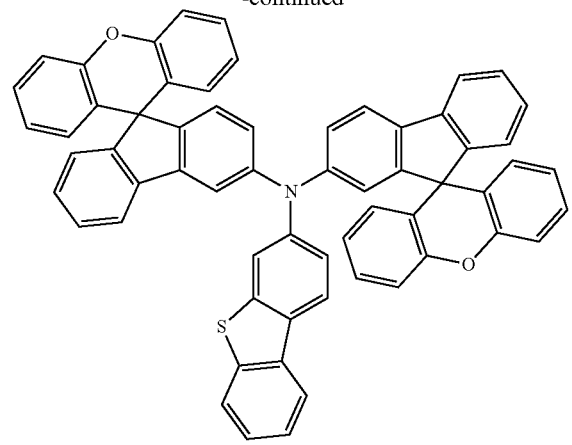
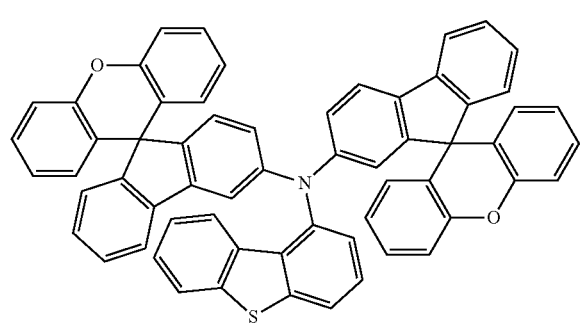
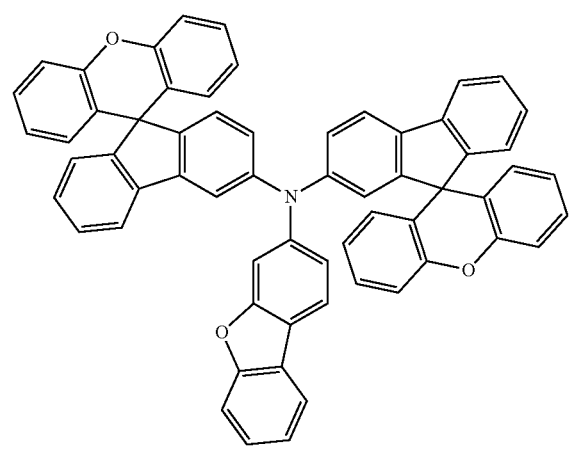
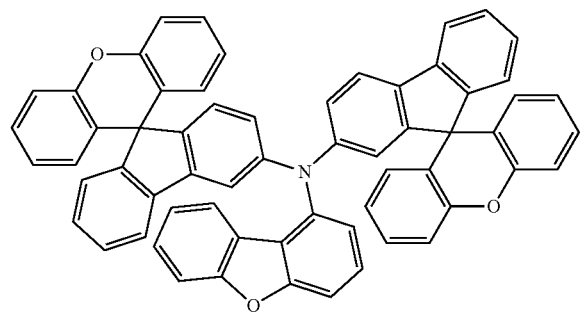
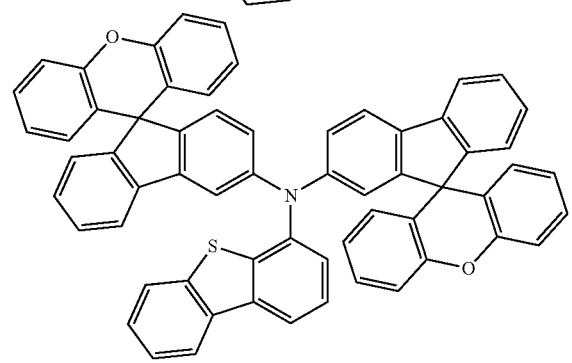
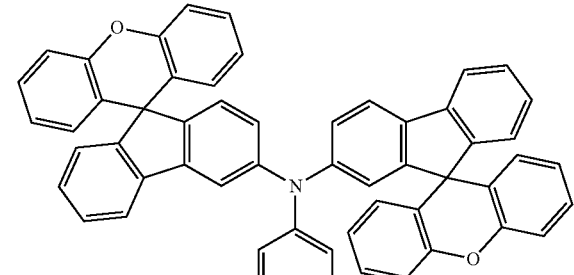
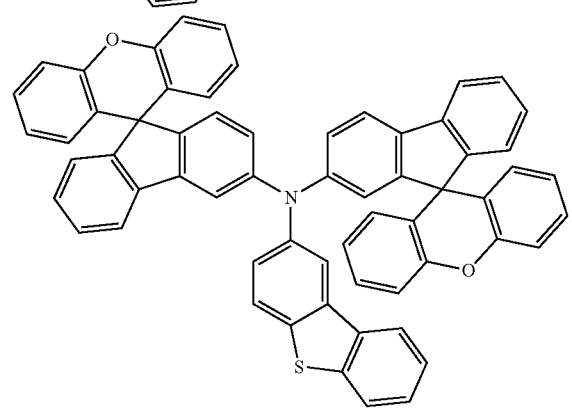

37
-continued
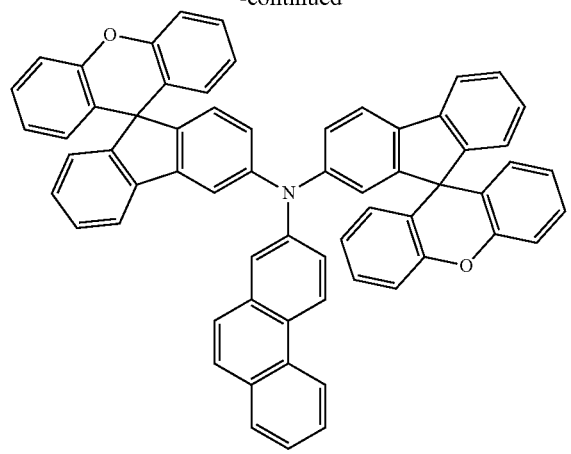
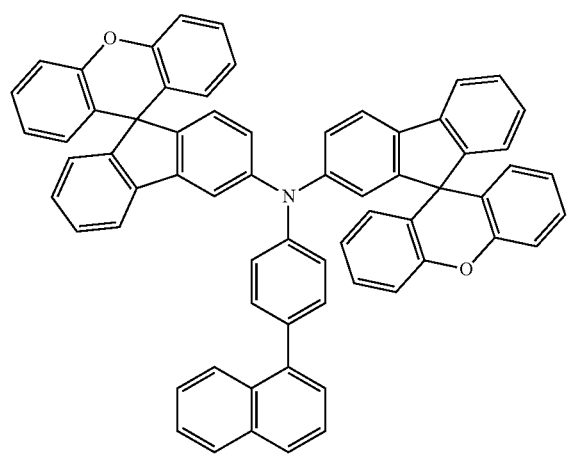
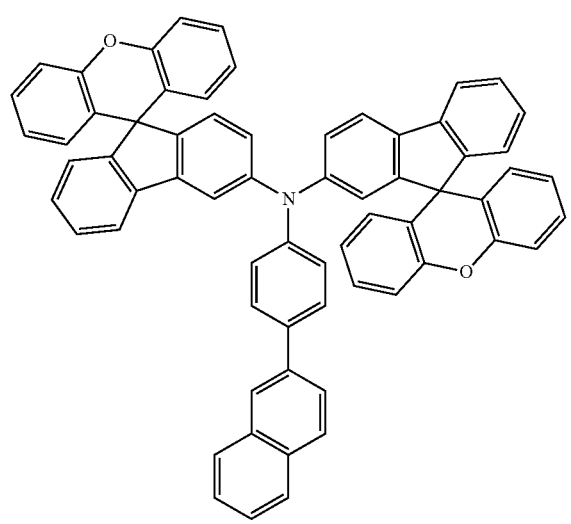
38
-continued
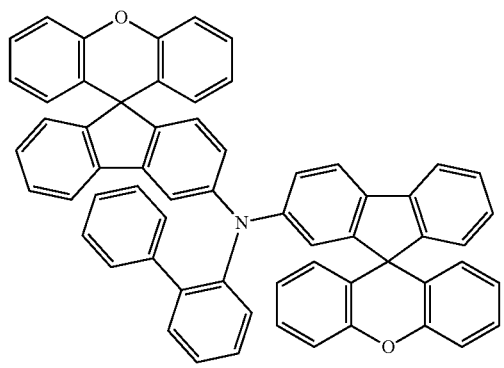
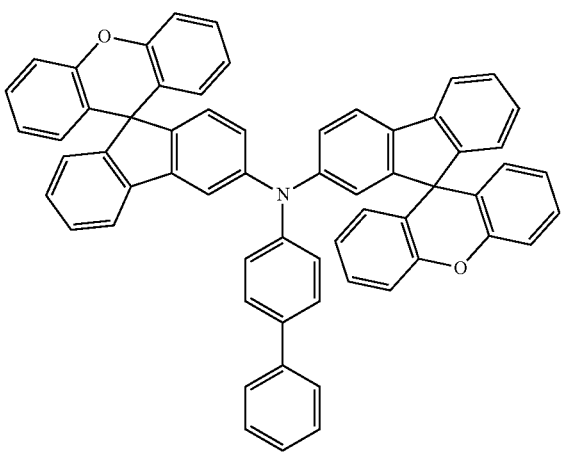
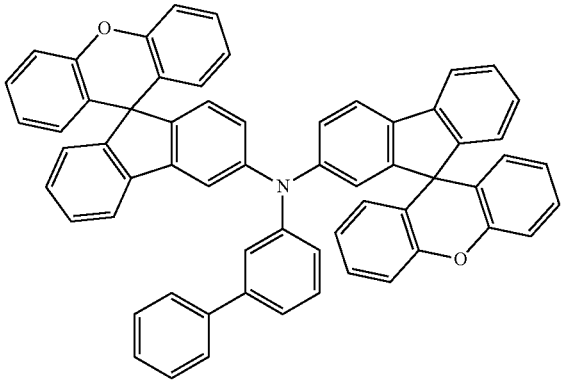

-continued
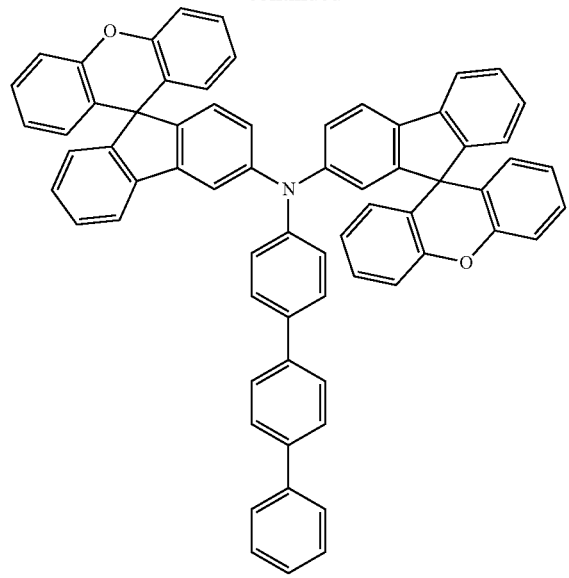
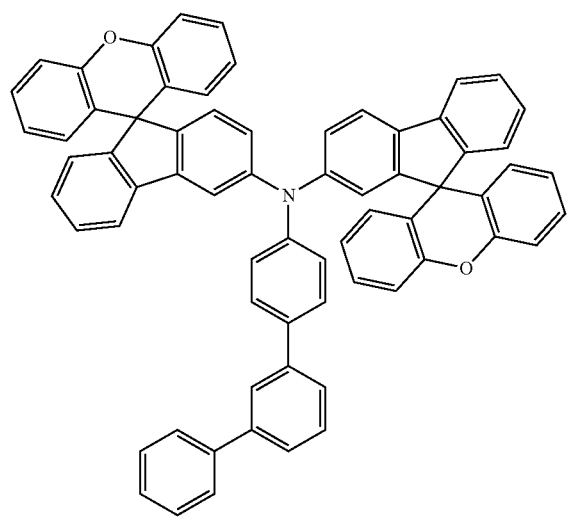
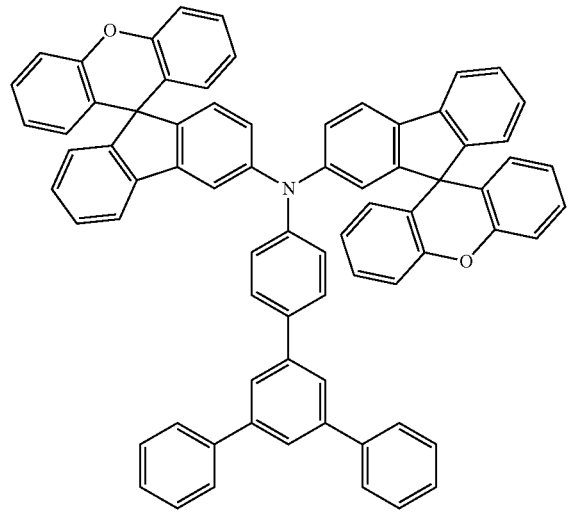
-continued
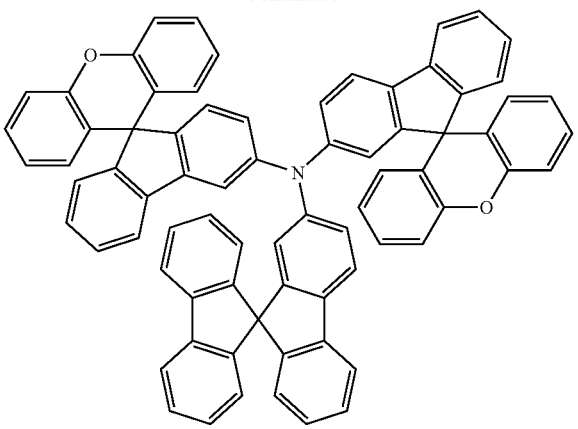
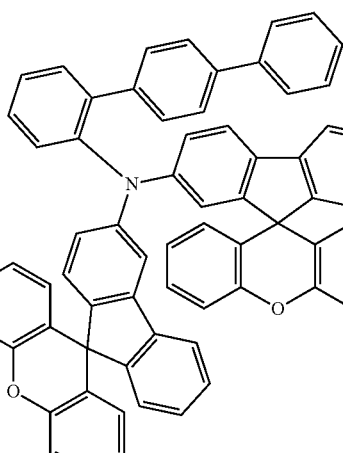
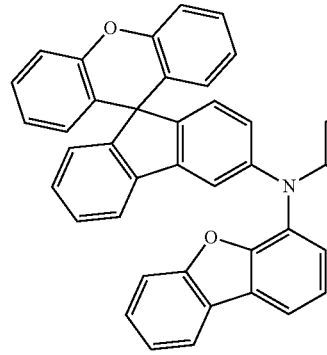
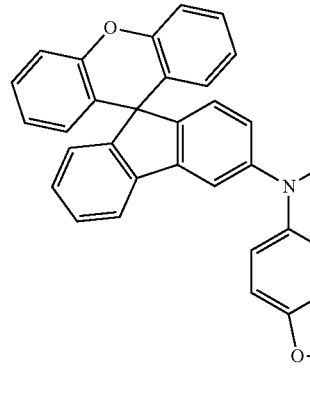

41
-continued
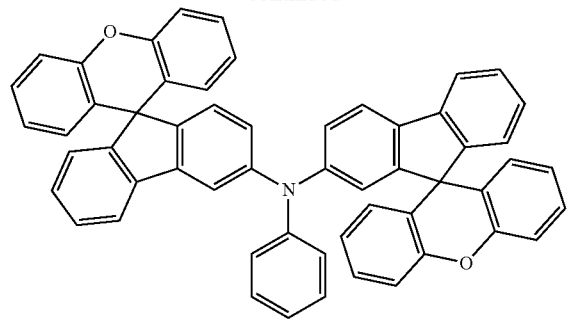
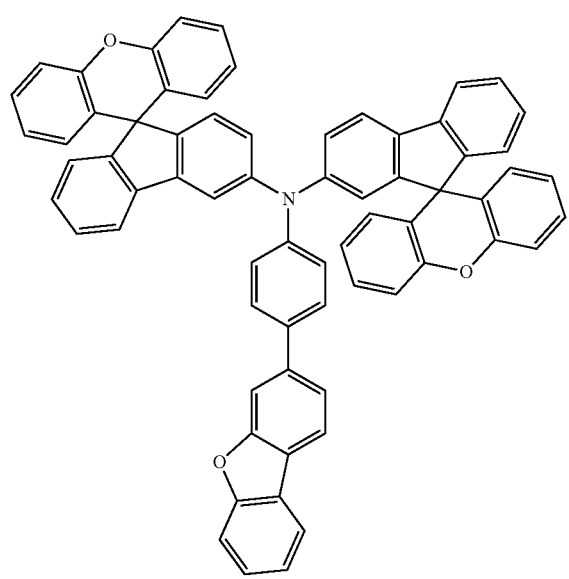
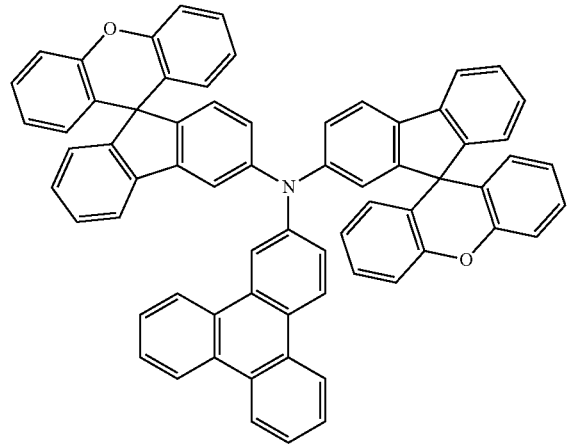
42
-continued
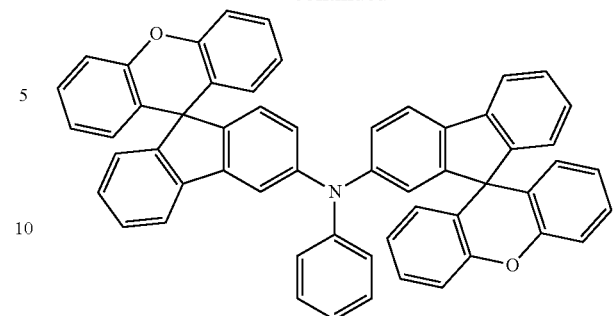
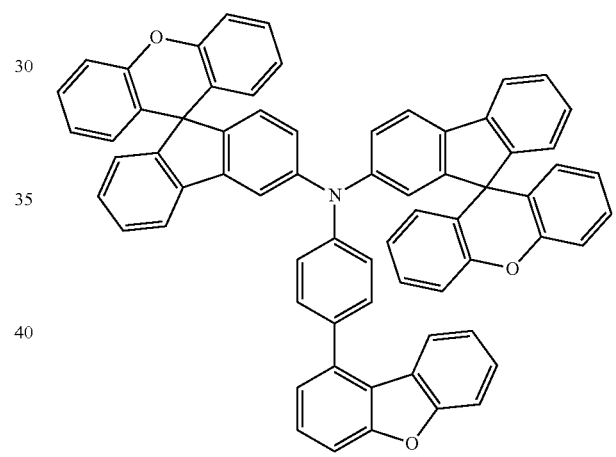
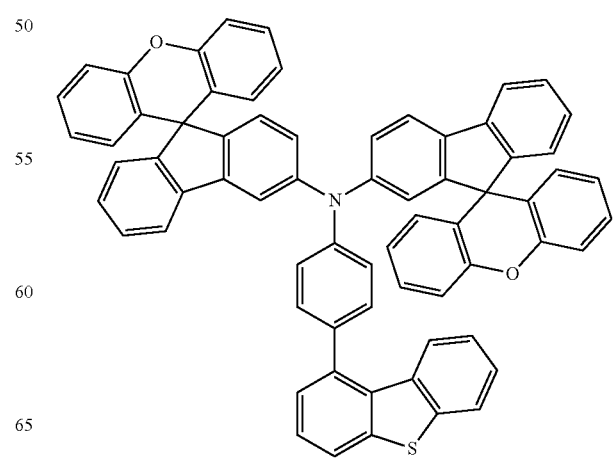

43
-continued
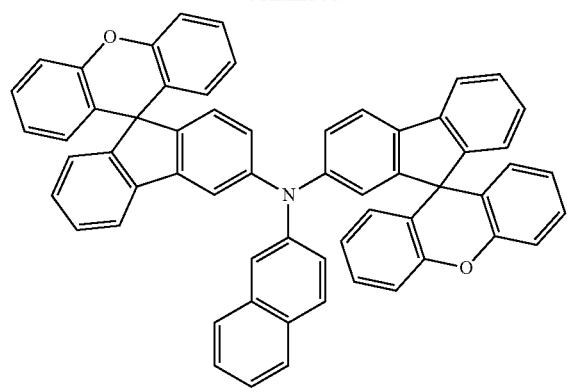
44
-continued
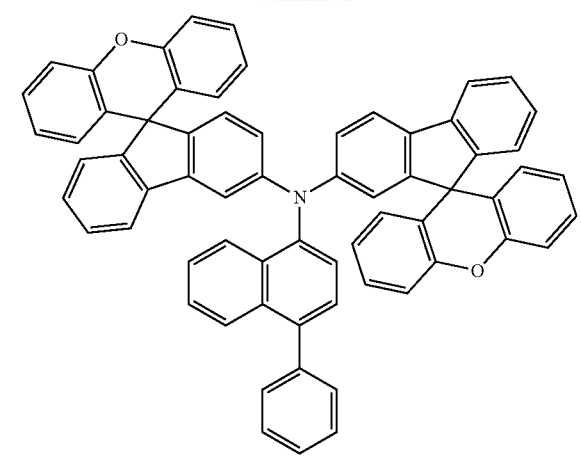
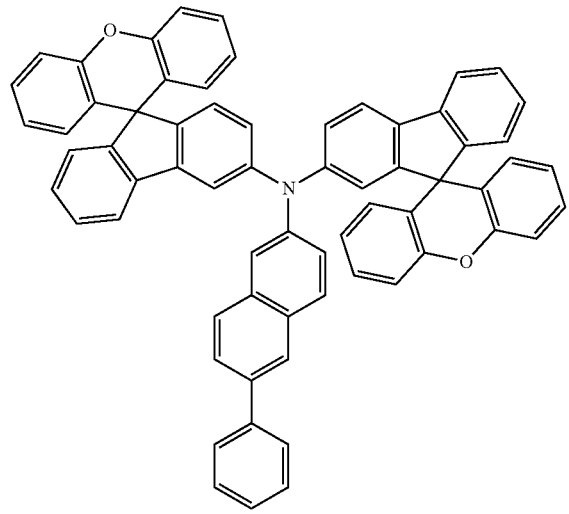
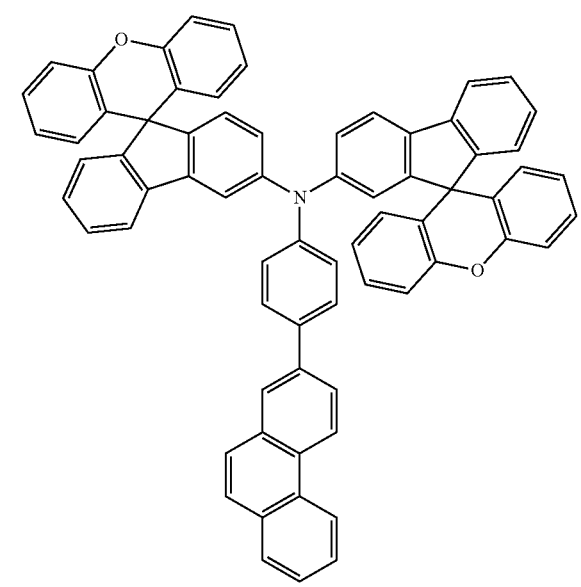
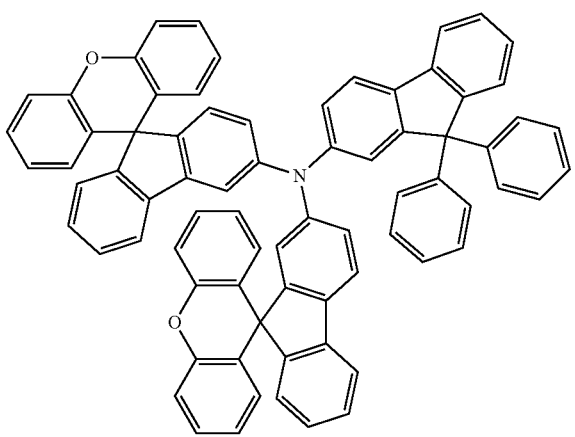

45
-continued
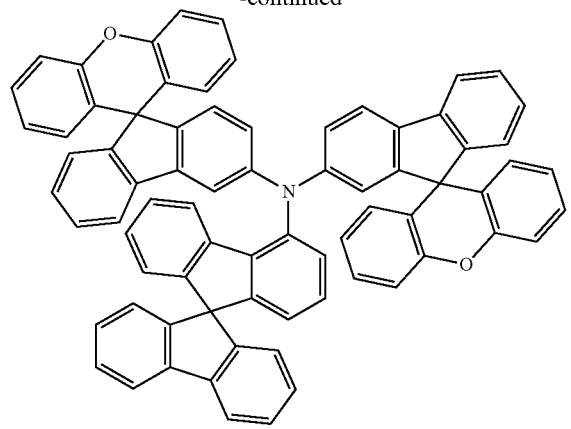
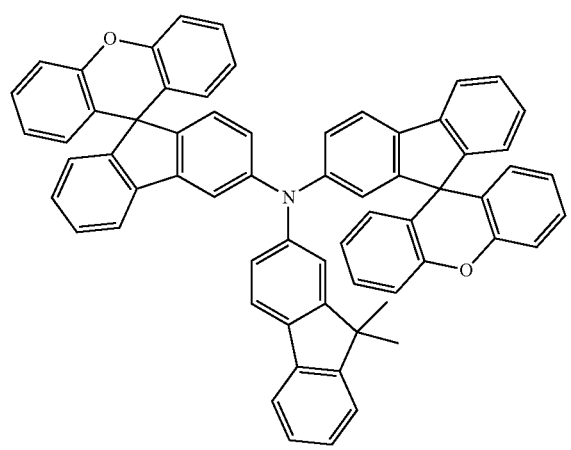
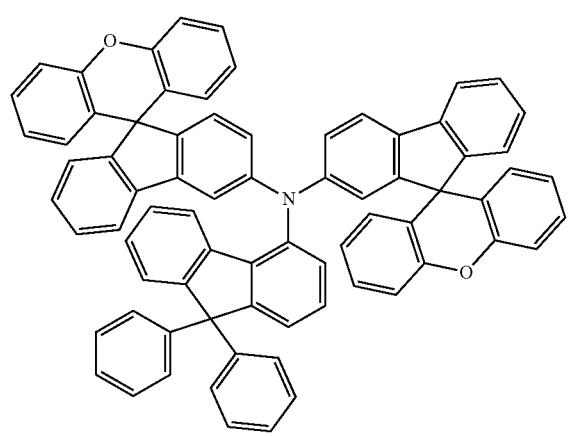
46
-continued
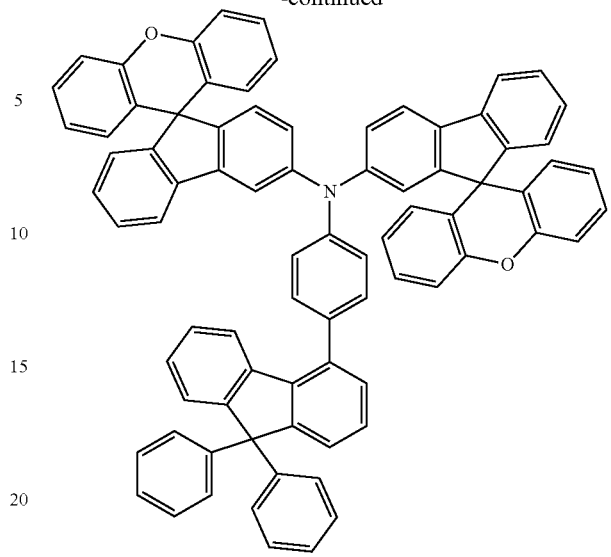
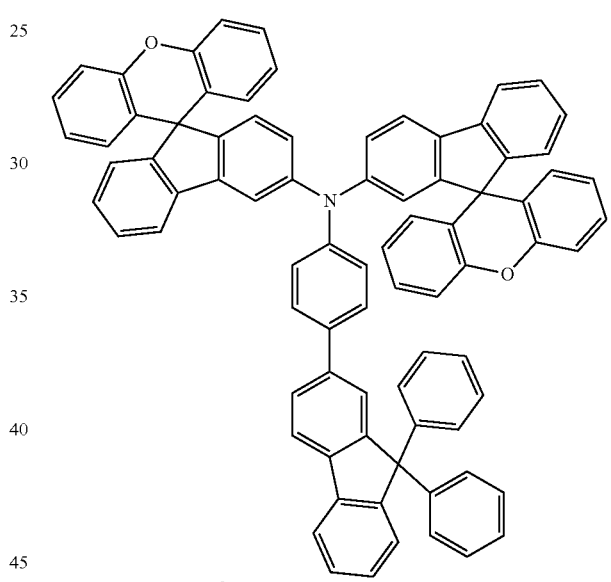
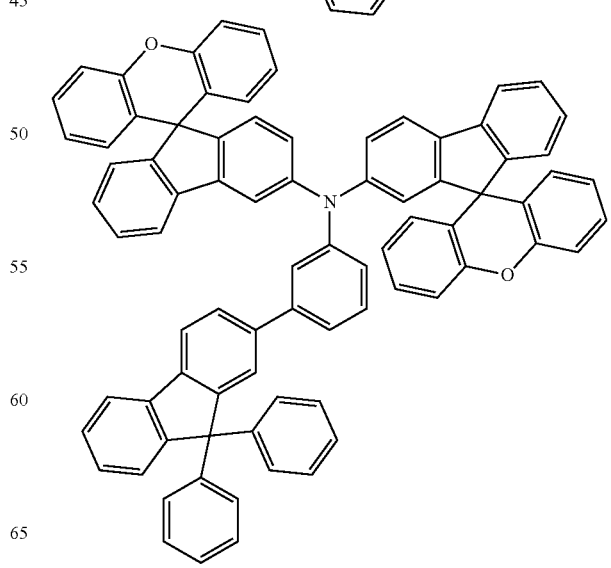

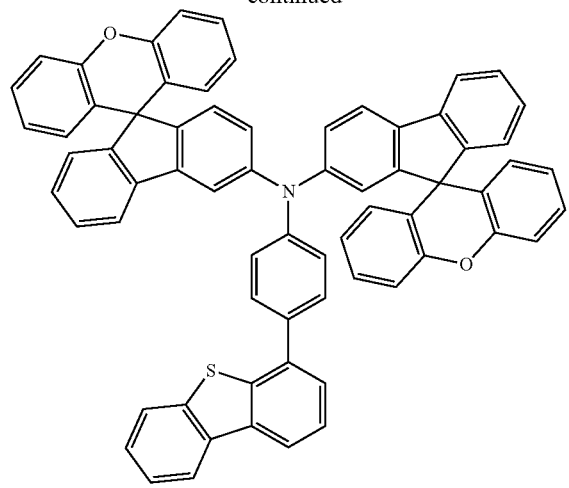
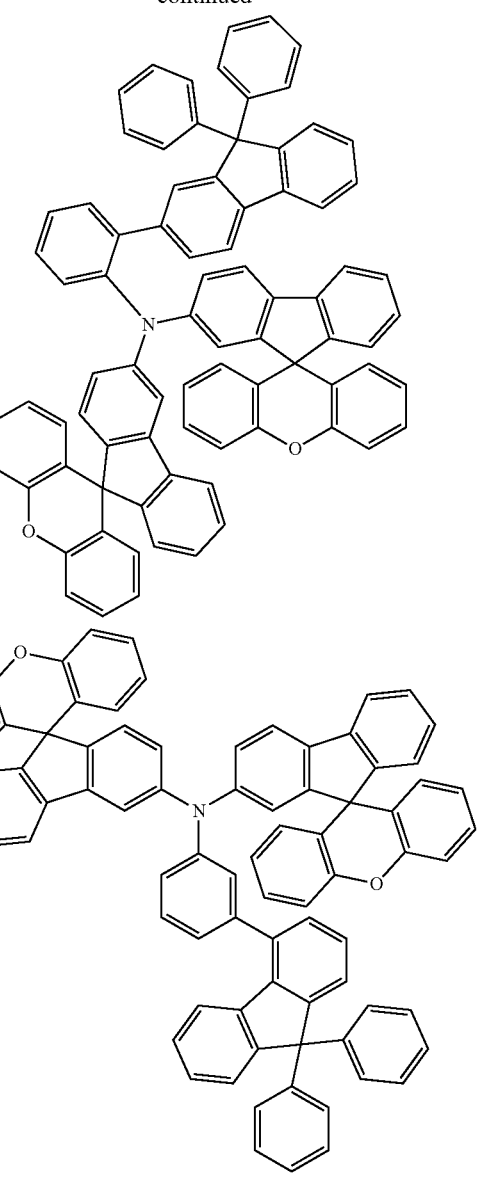
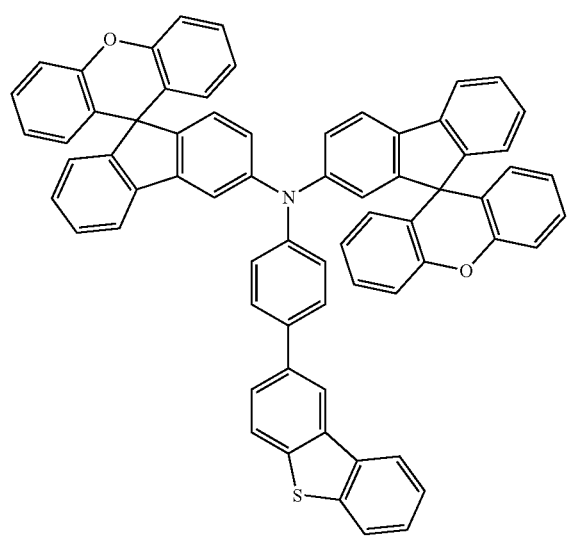
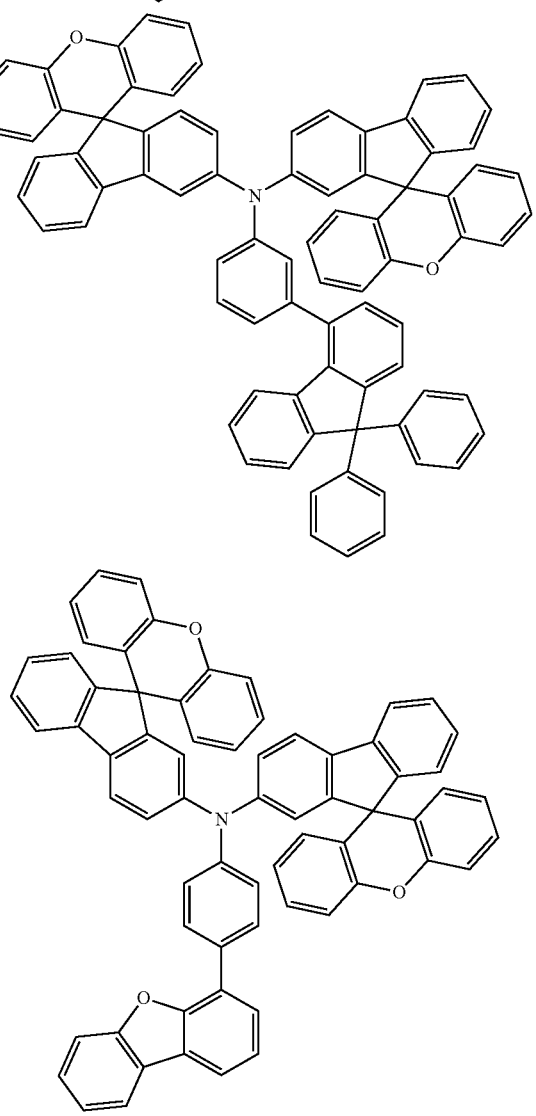
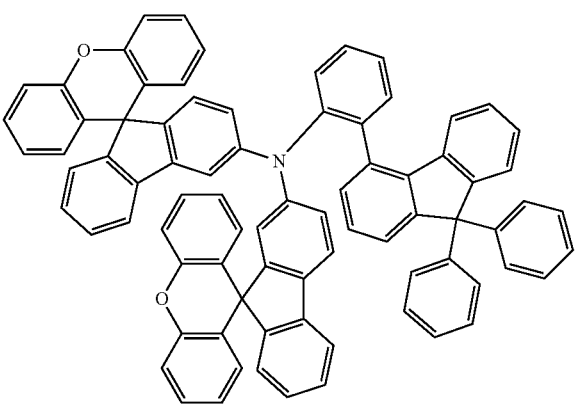

49
-continued
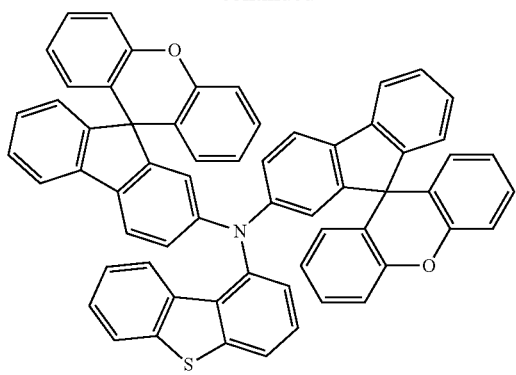
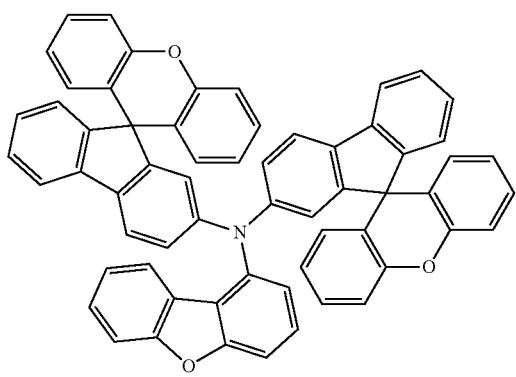
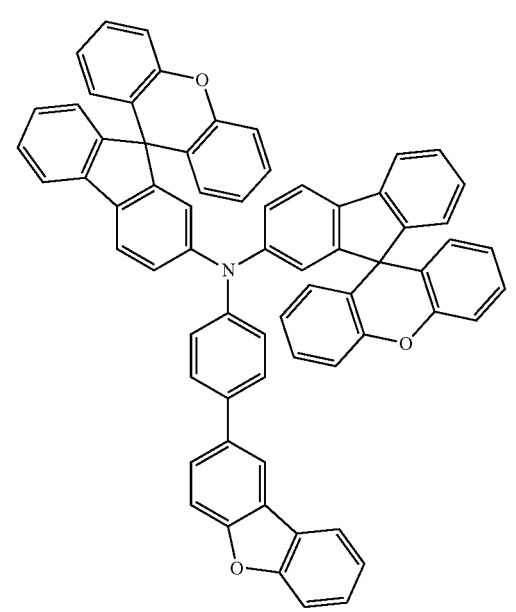
50
-continued
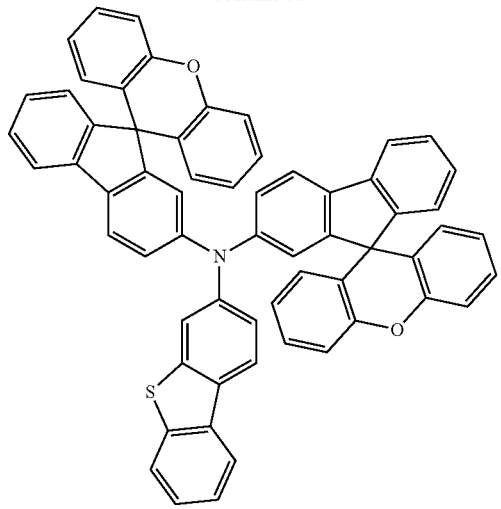
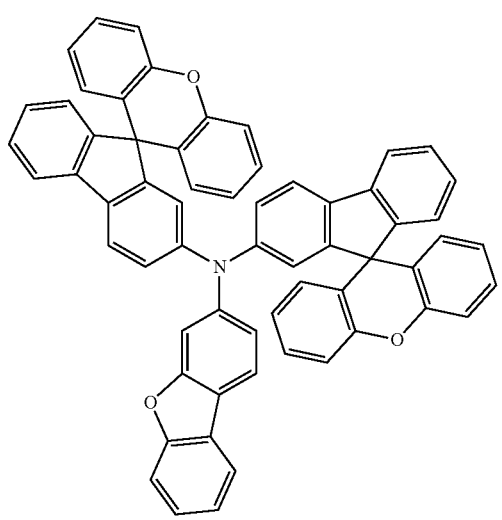
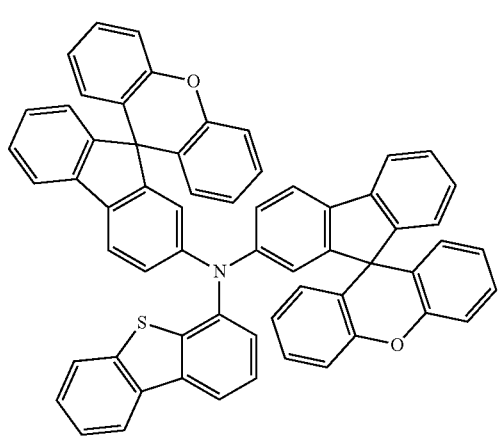

51
-continued
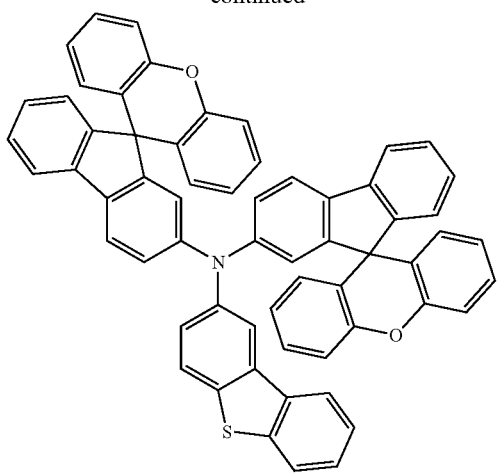
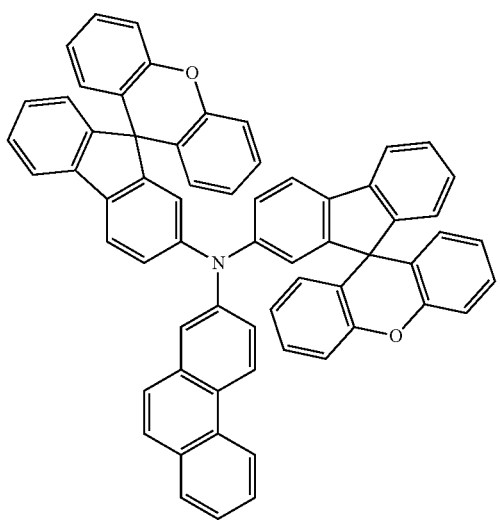
52
-continued
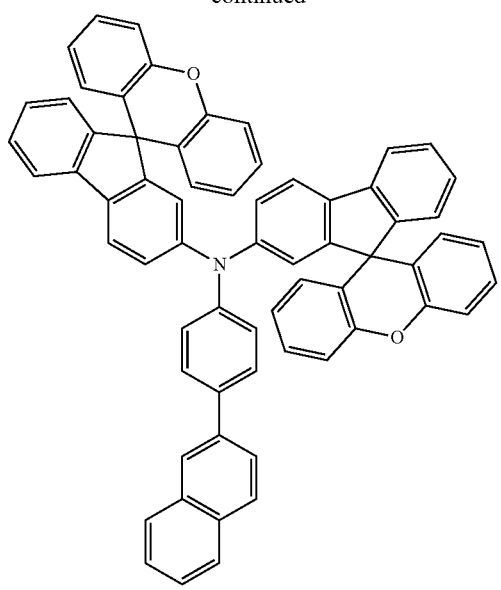
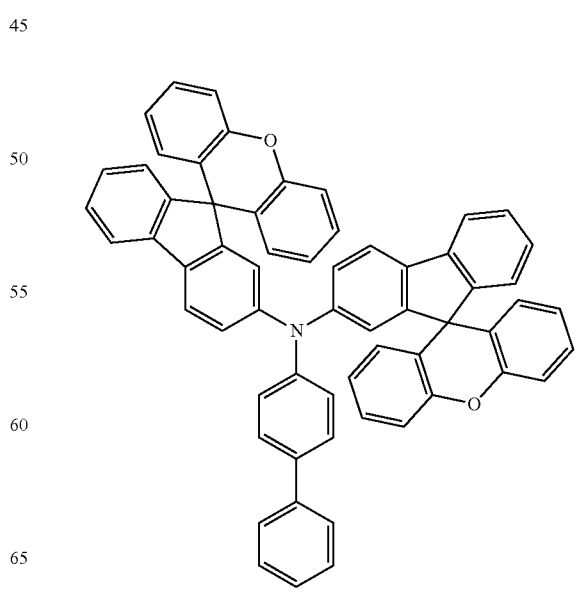

53
-continued
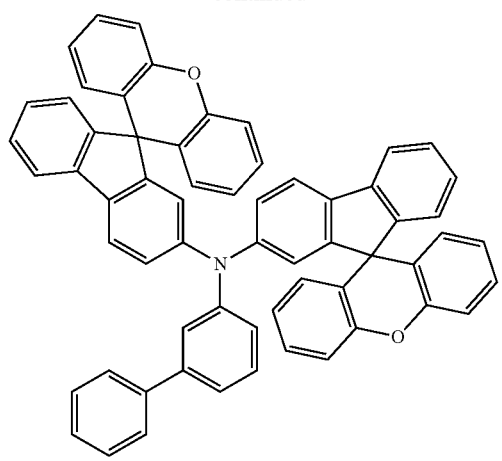
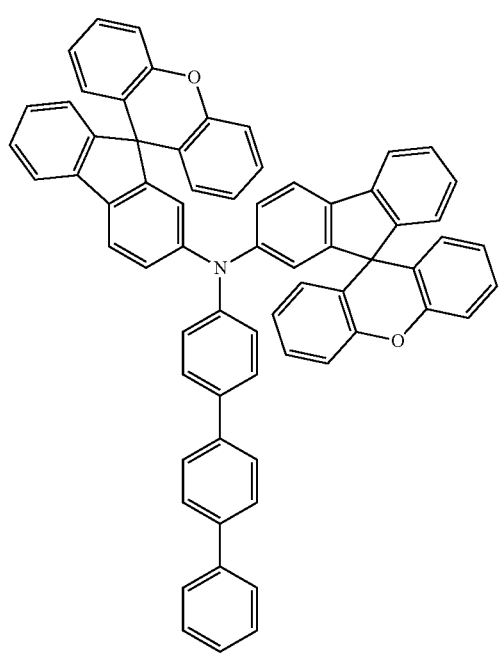
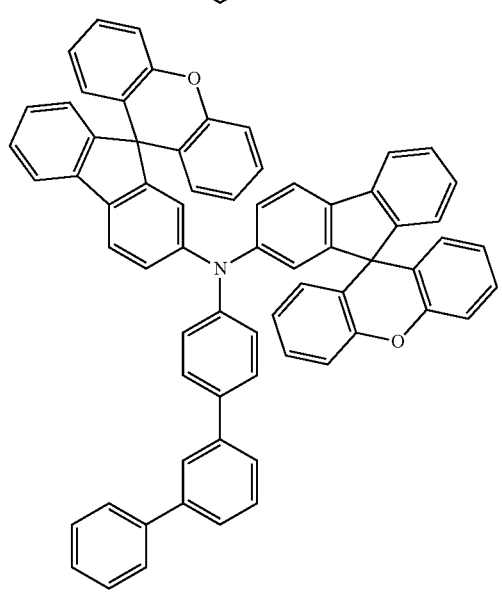
54
-continued
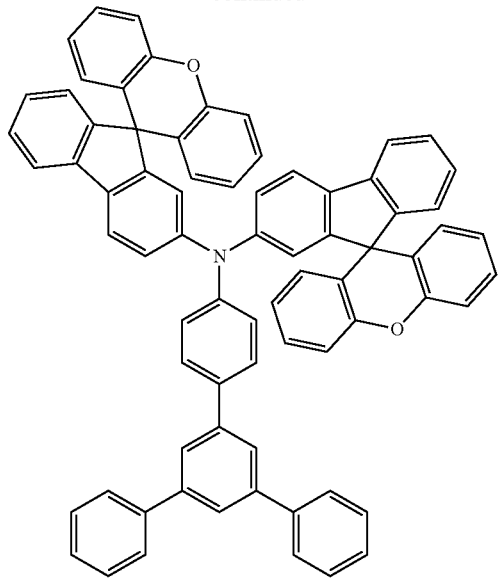
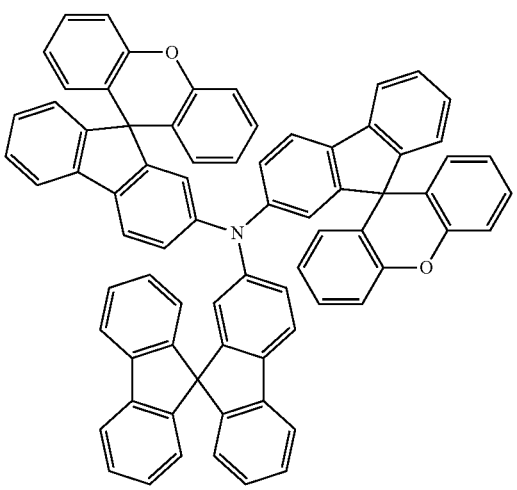
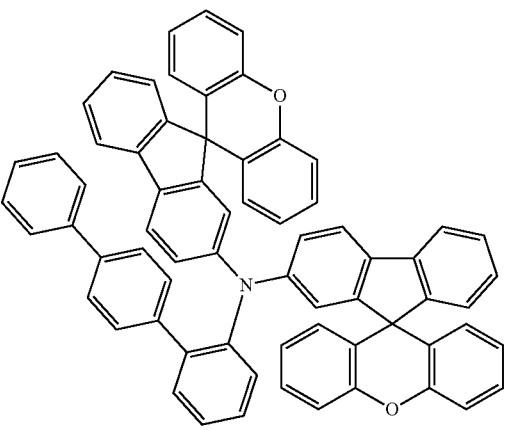

55
-continued
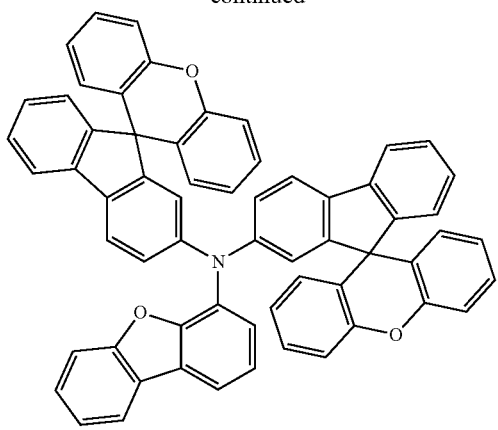
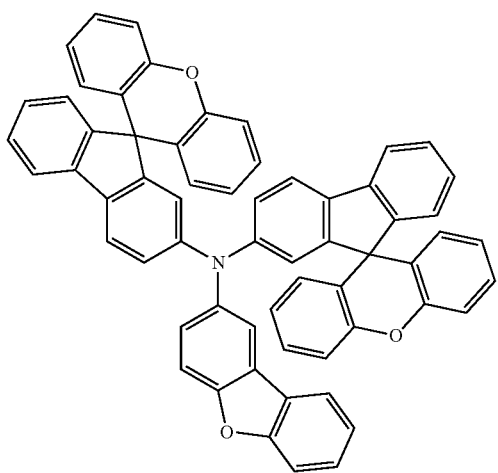
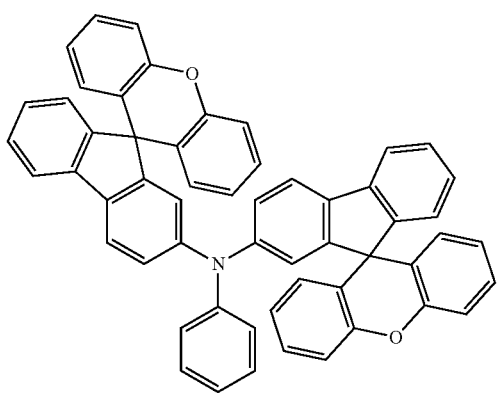
56
-continued
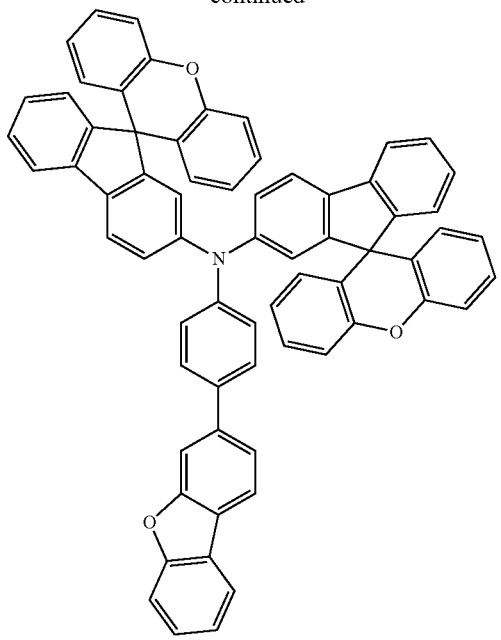
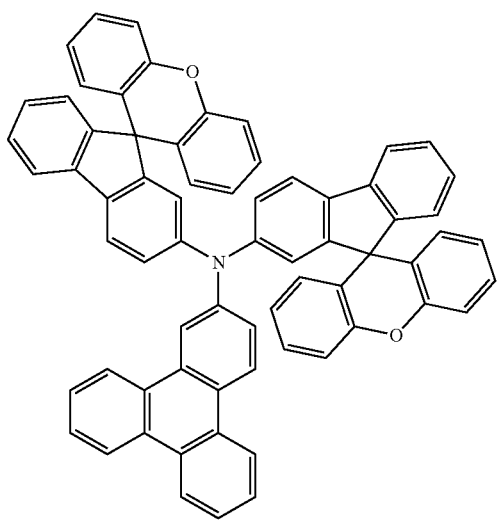
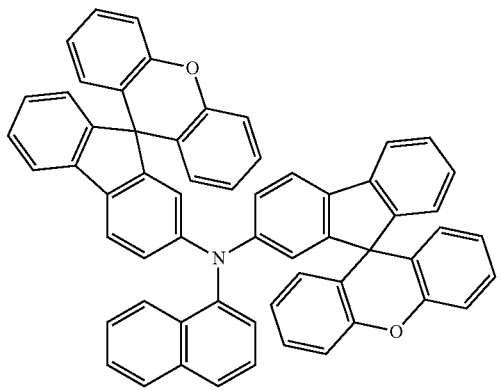

57
-continued
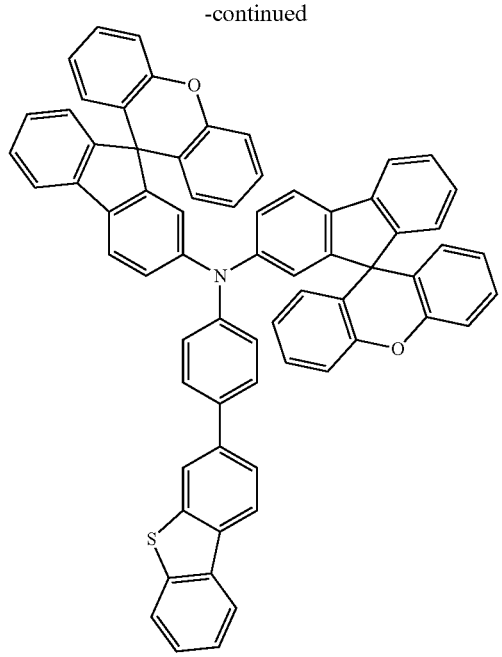
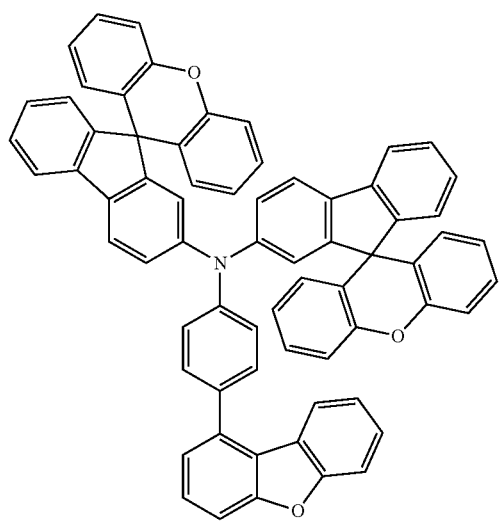
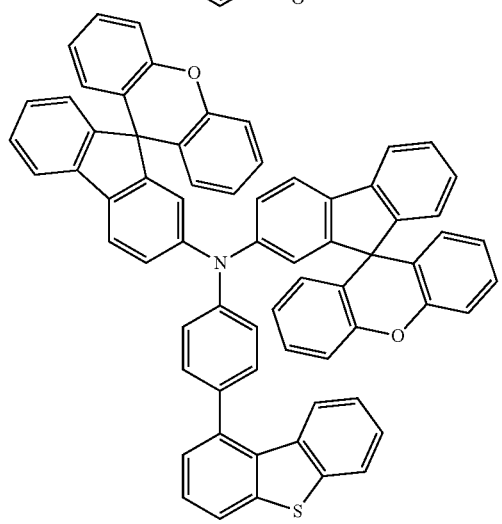
58
-continued
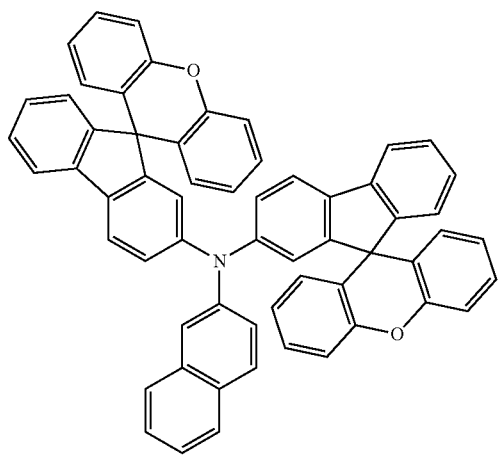
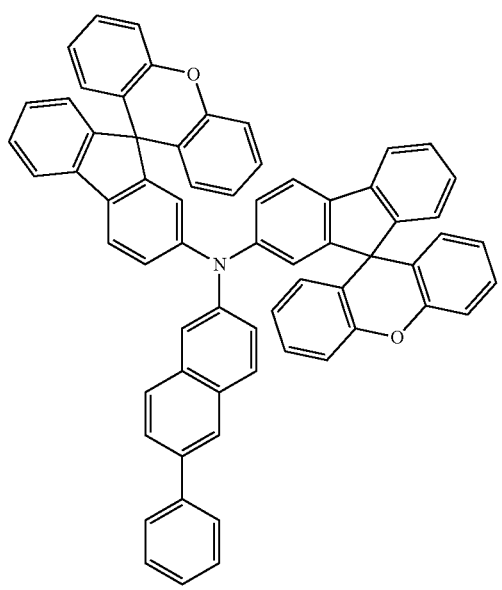
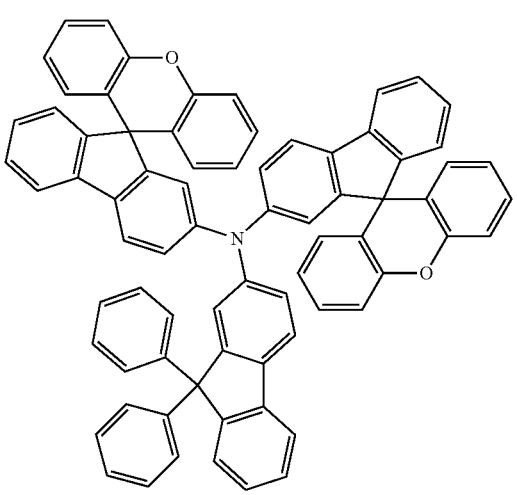

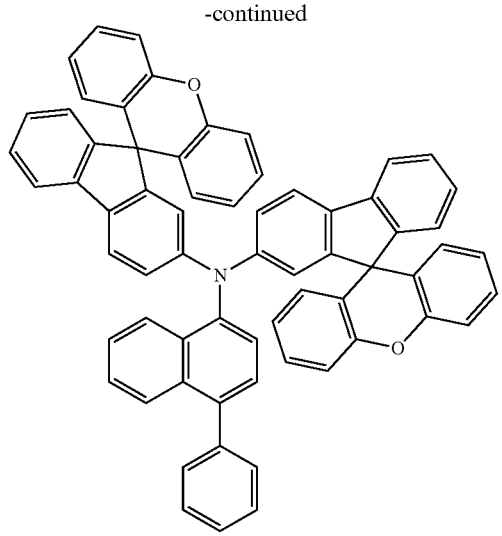
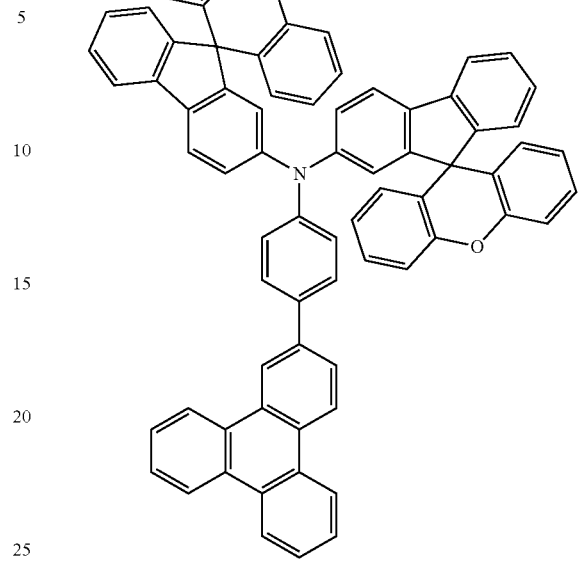
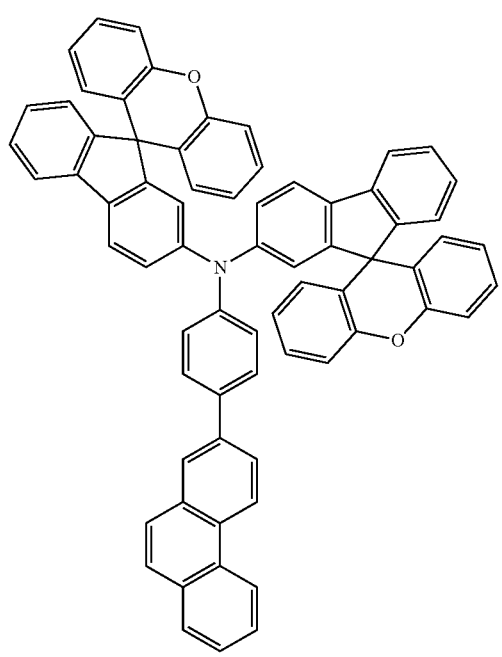
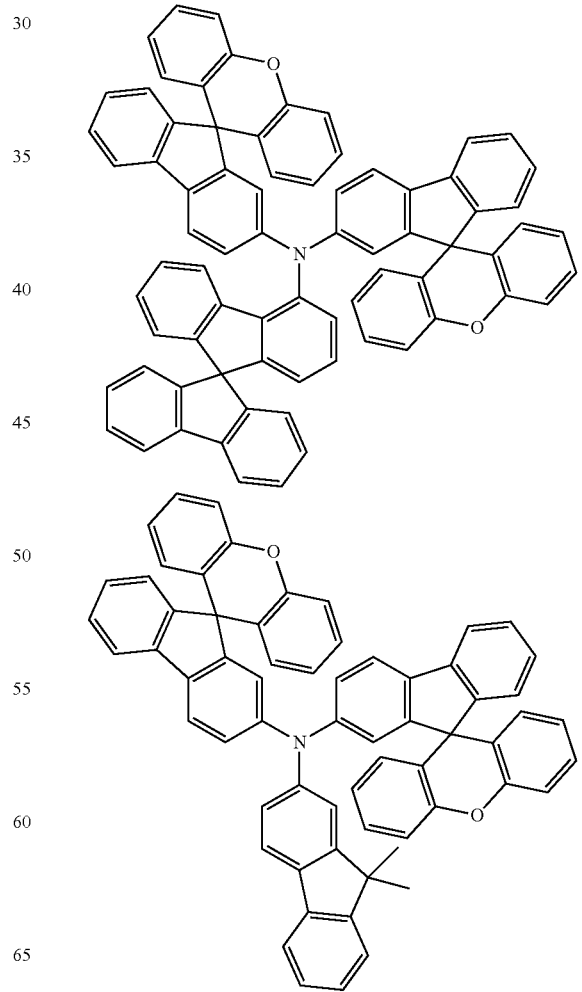

61
-continued
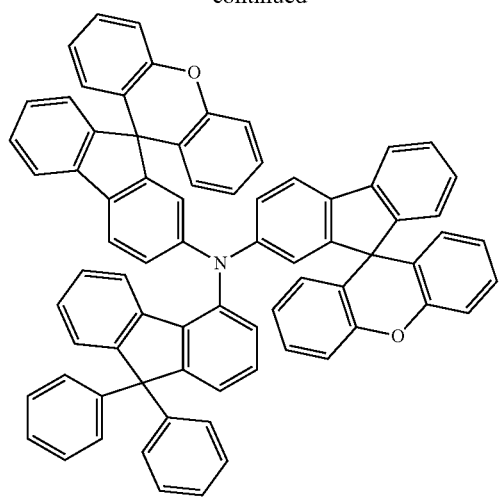
62
-continued
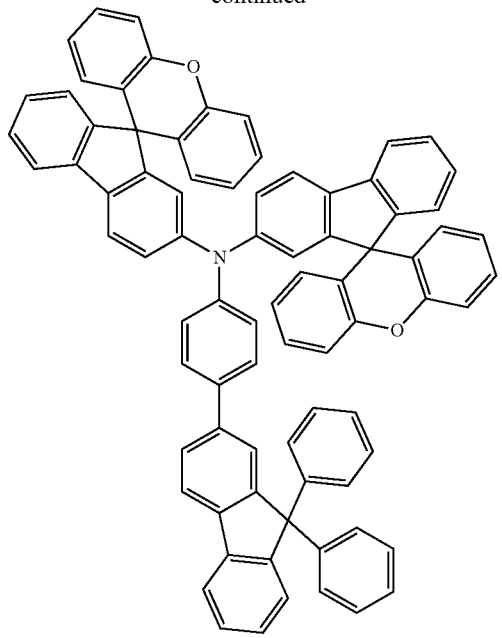
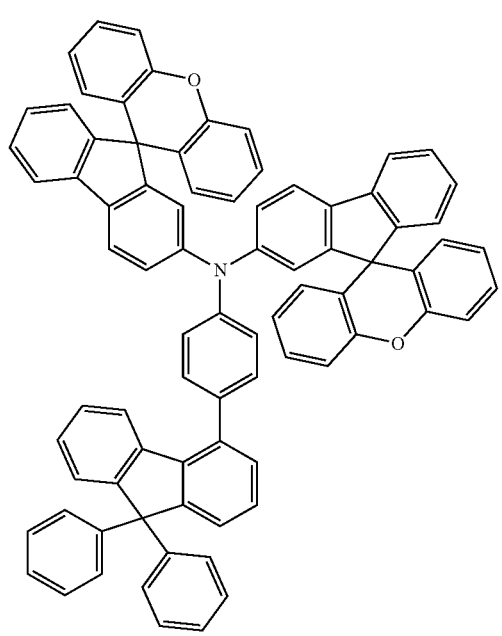
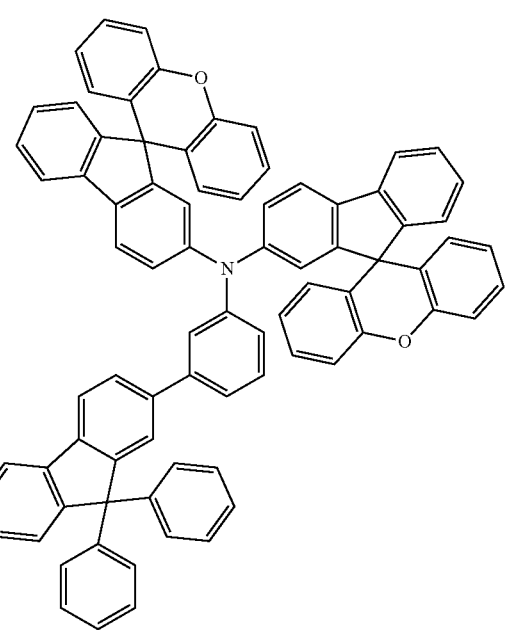

63
-continued
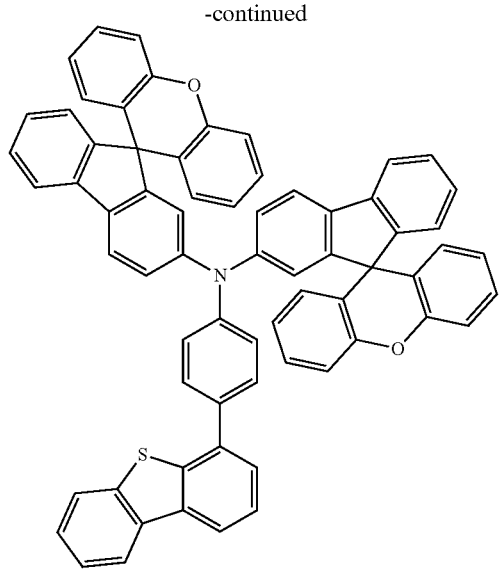
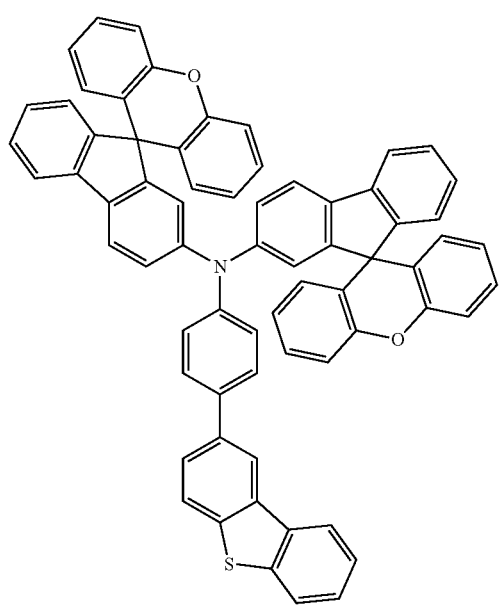
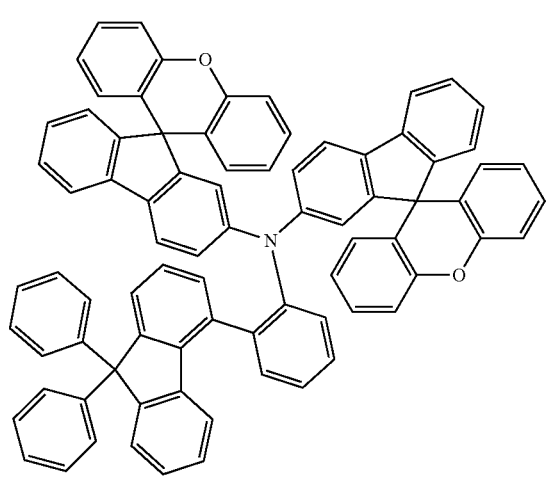
64
-continued
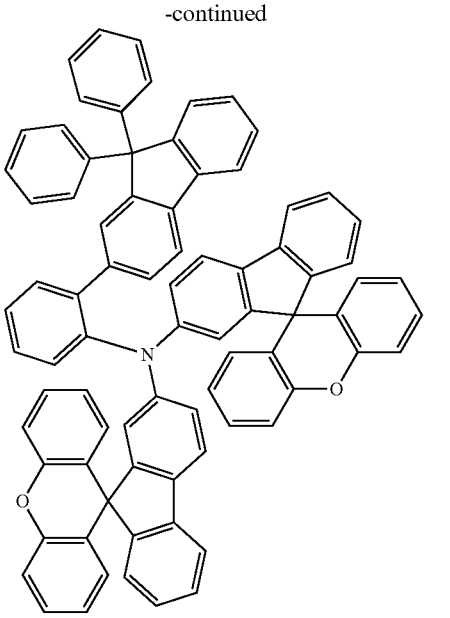
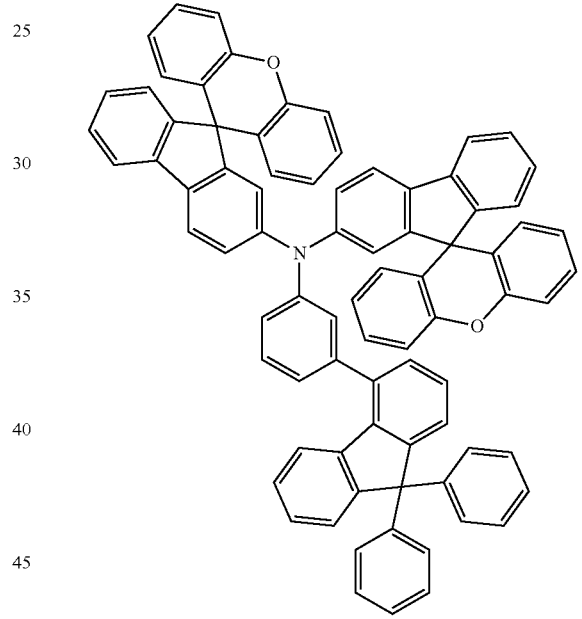
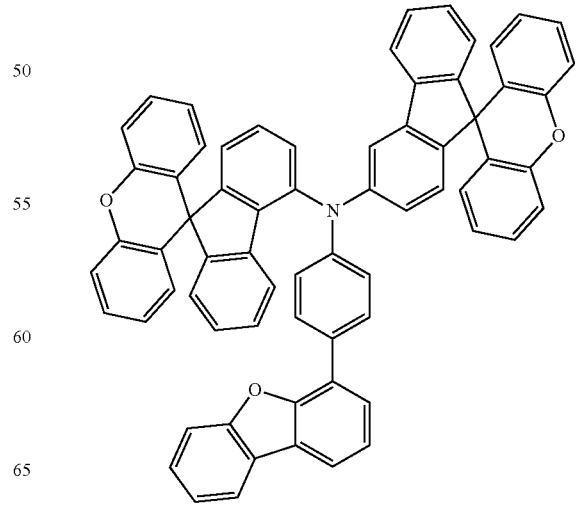

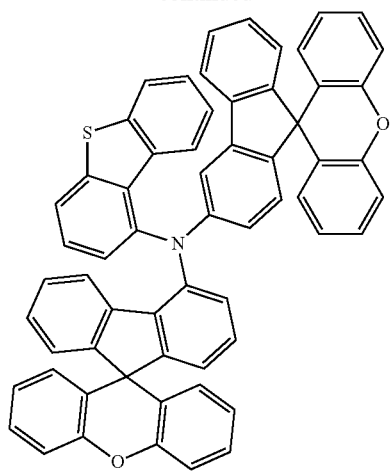
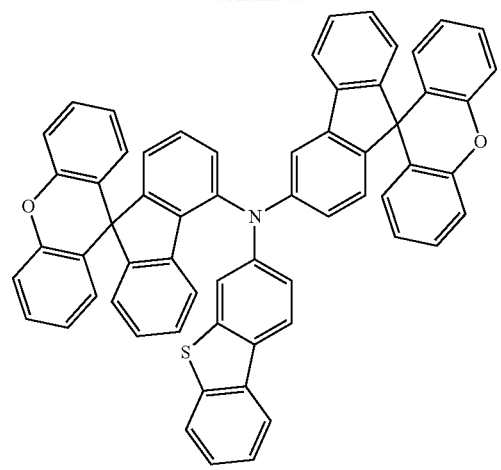
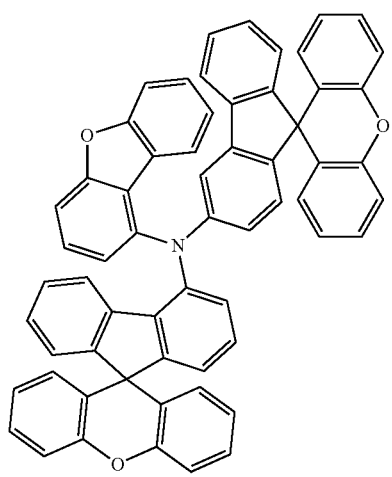
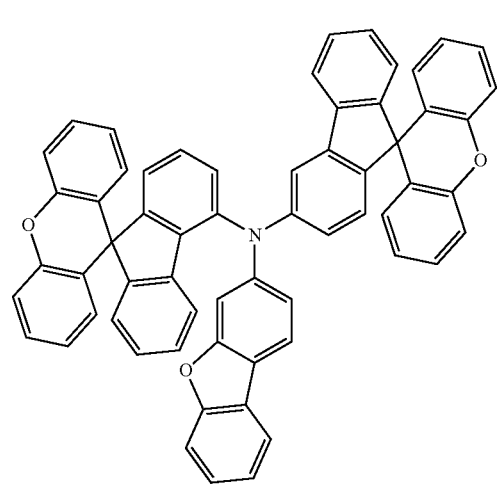
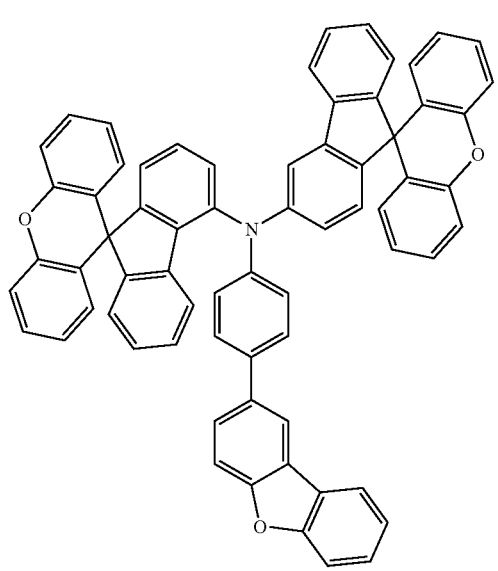
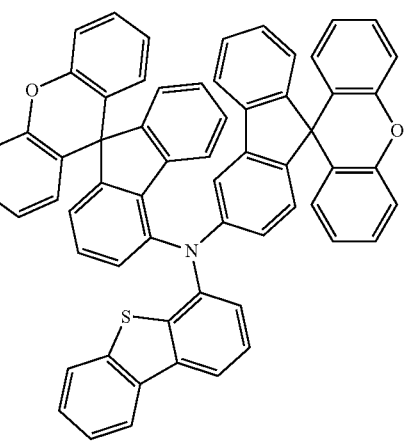

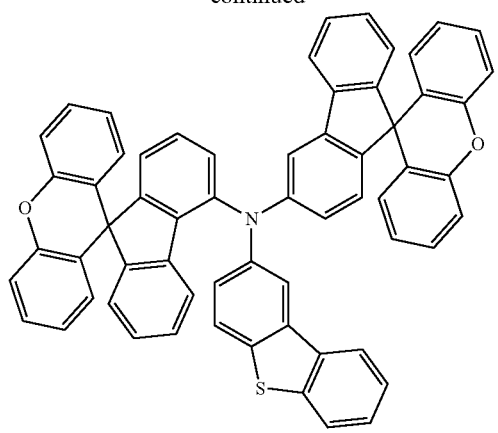
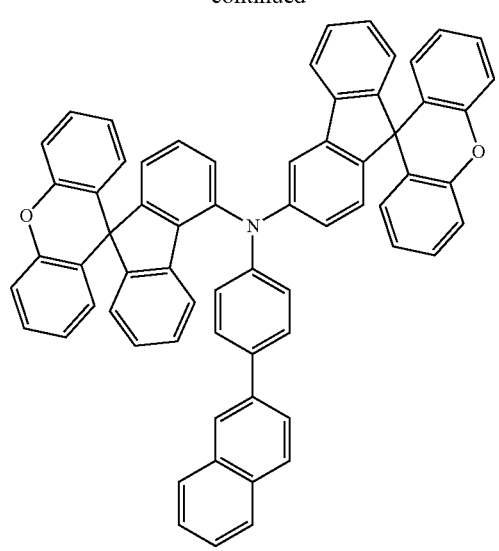
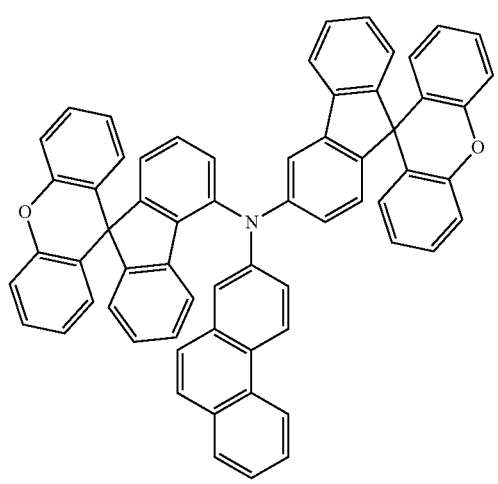
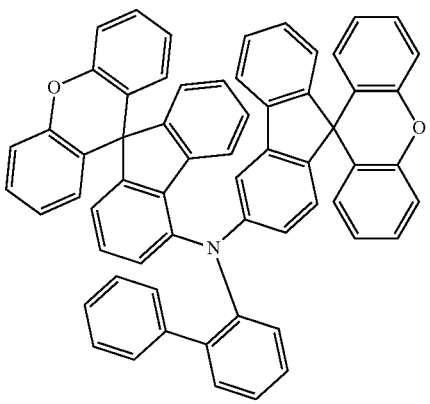
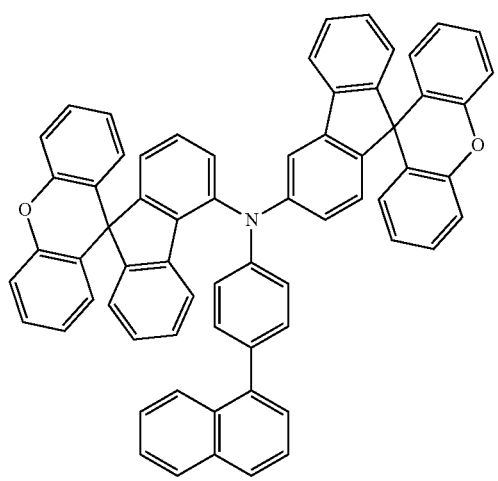
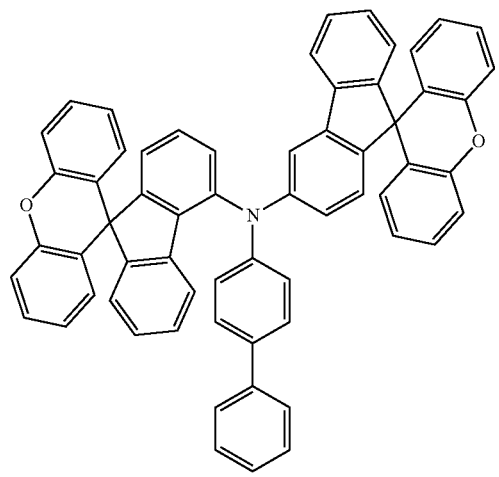

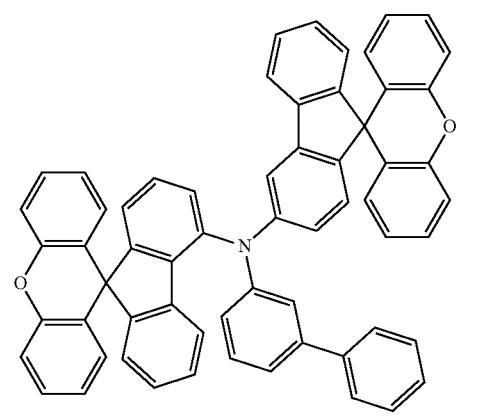
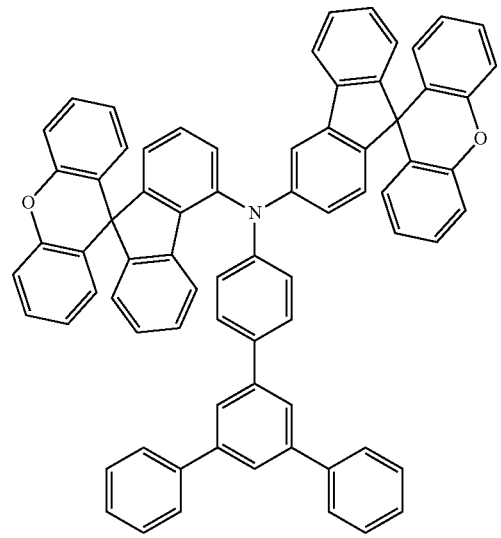
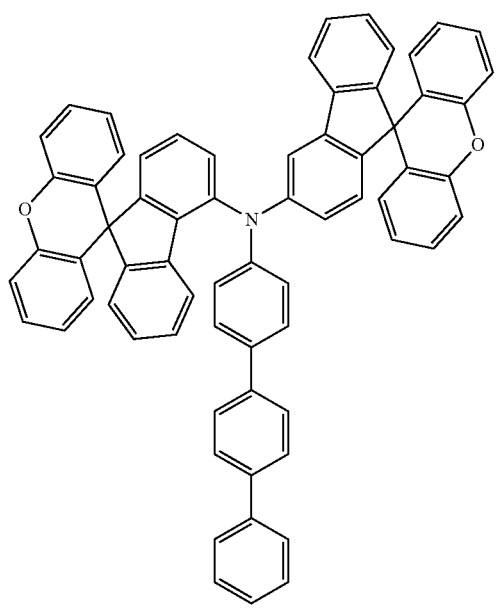
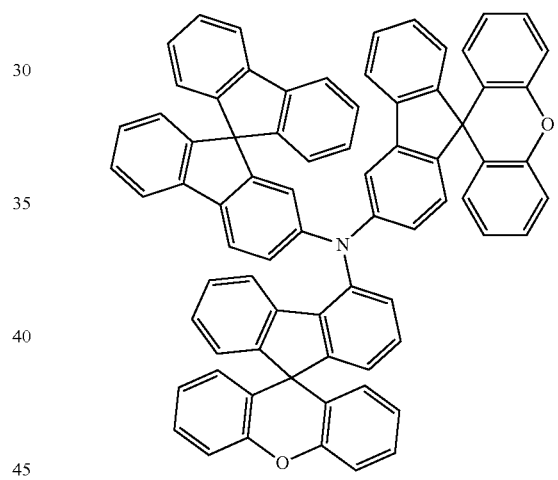
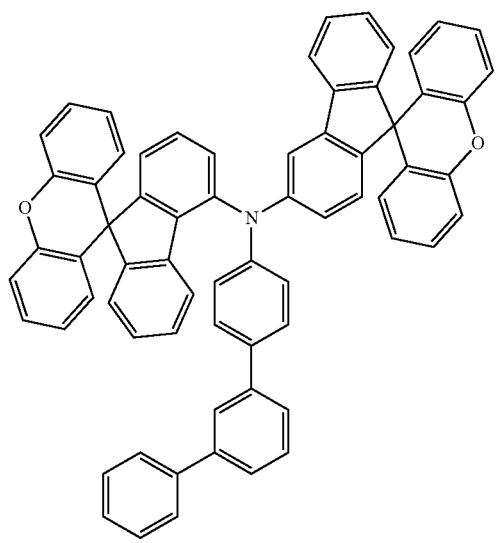
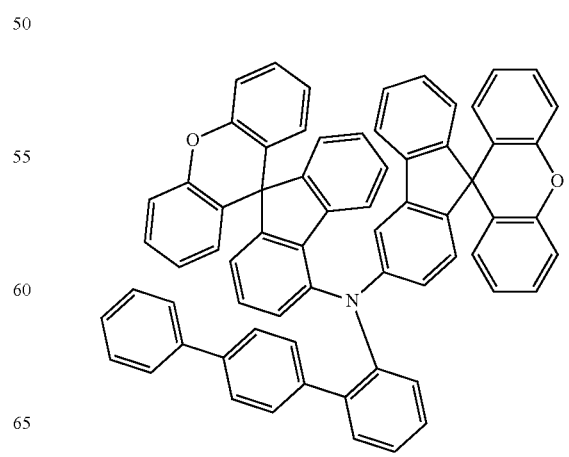

71
-continued
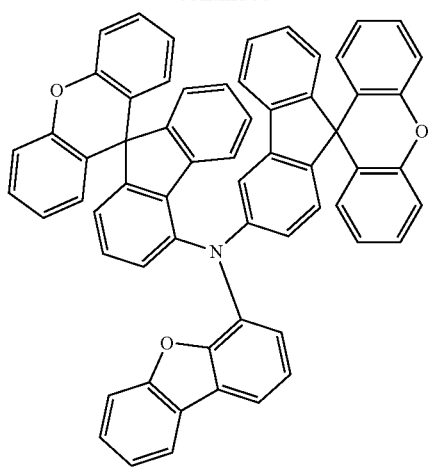
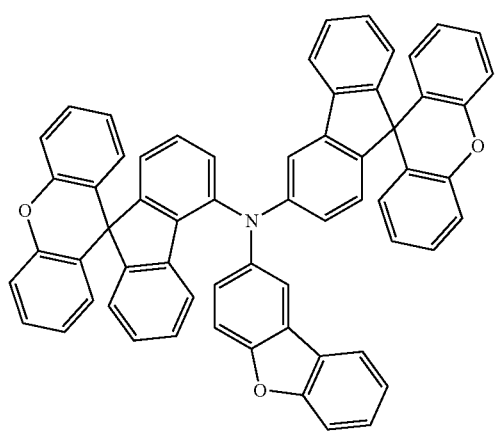
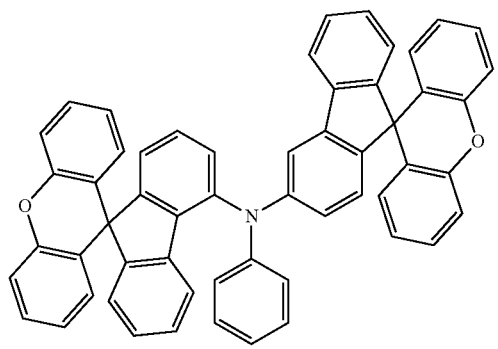
72
-continued
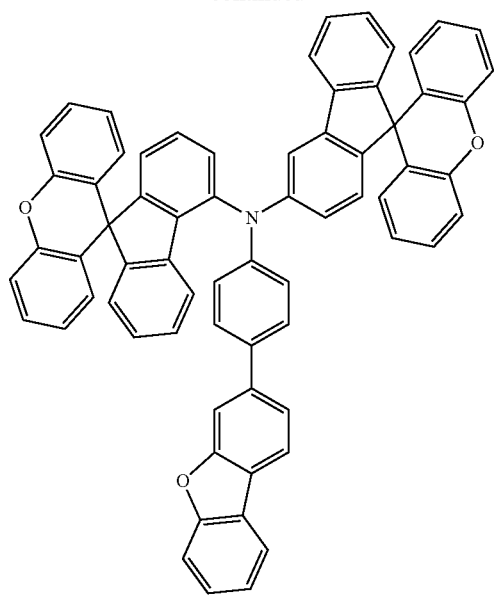
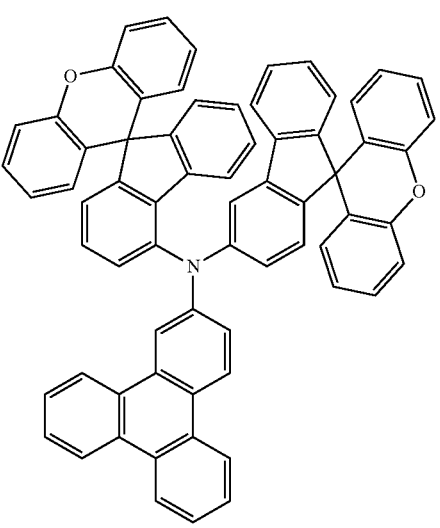
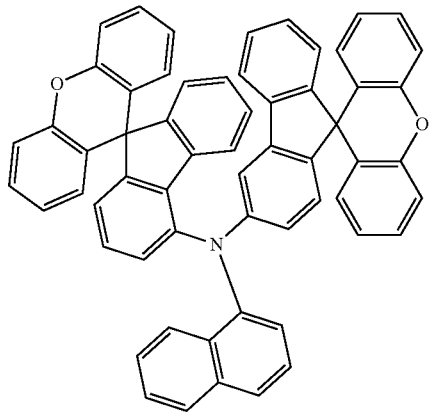

73
-continued
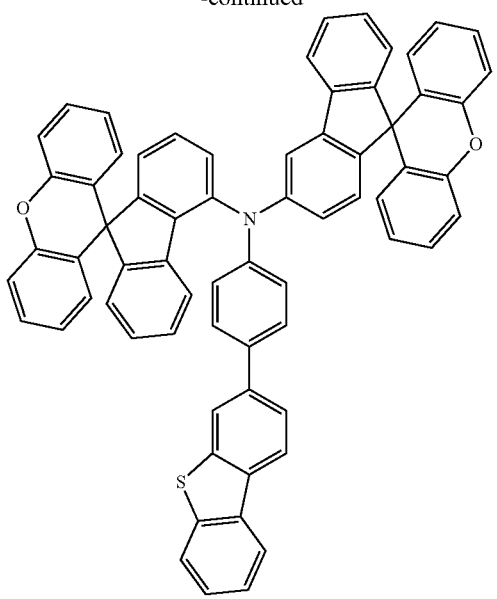
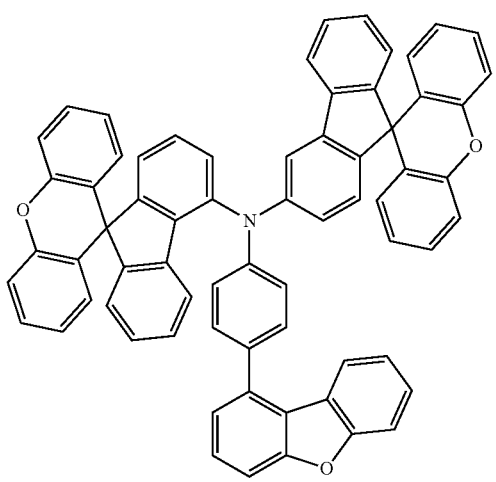
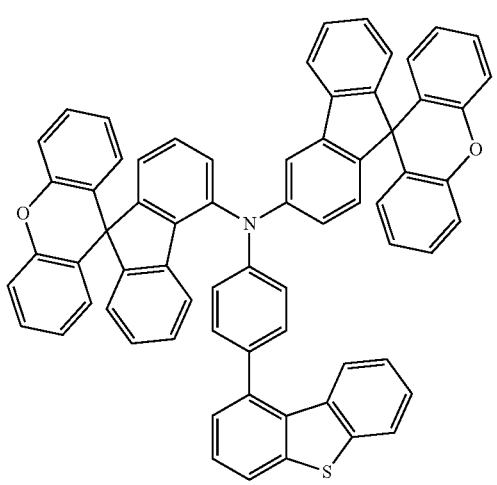
74
-continued
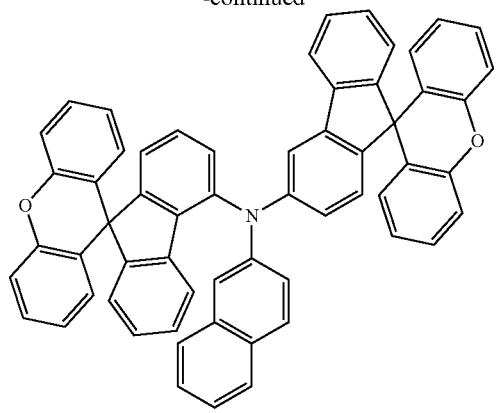
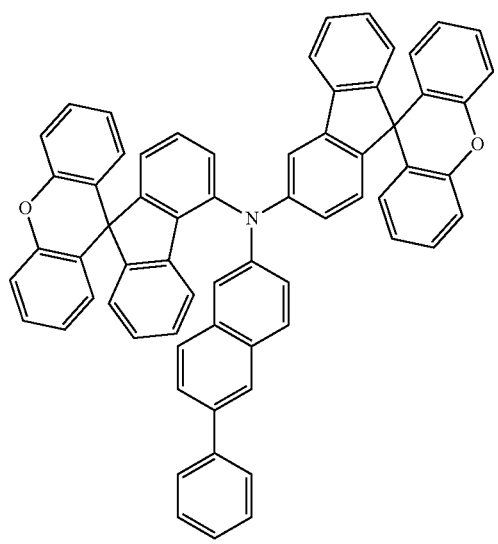
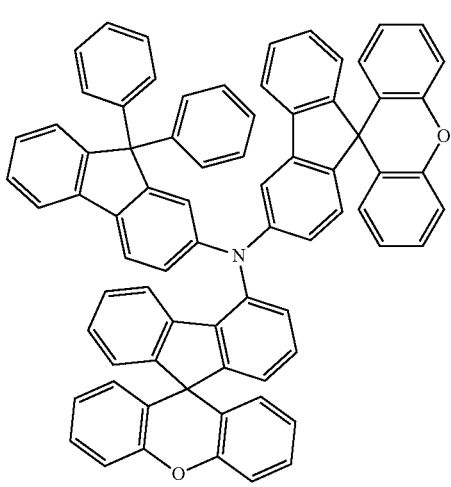

75
-continued
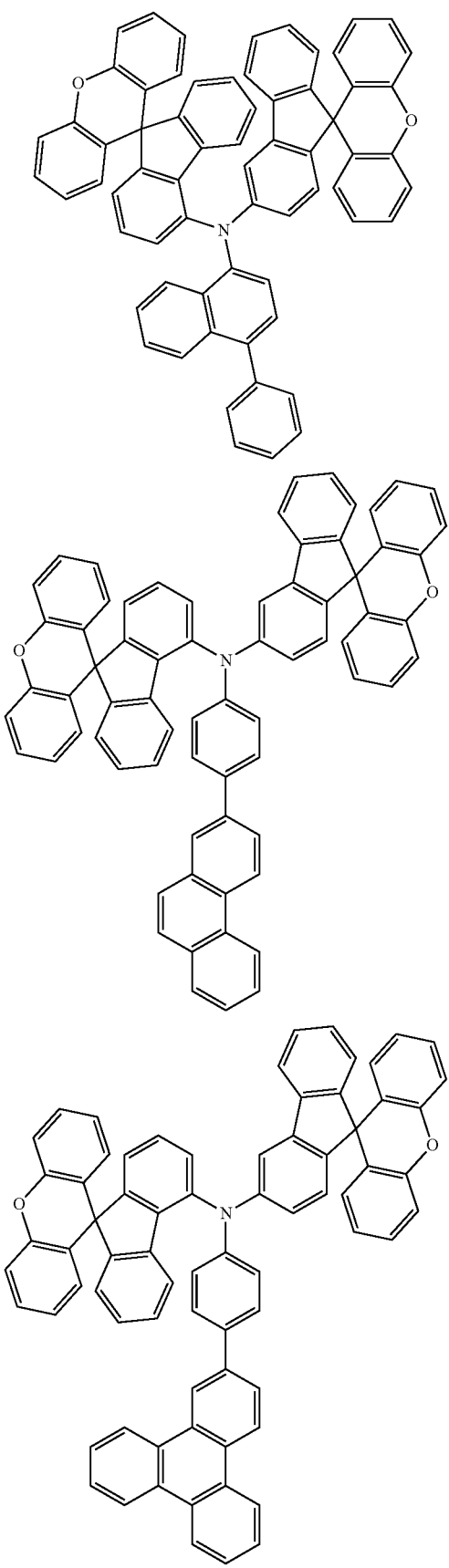
76
-continued
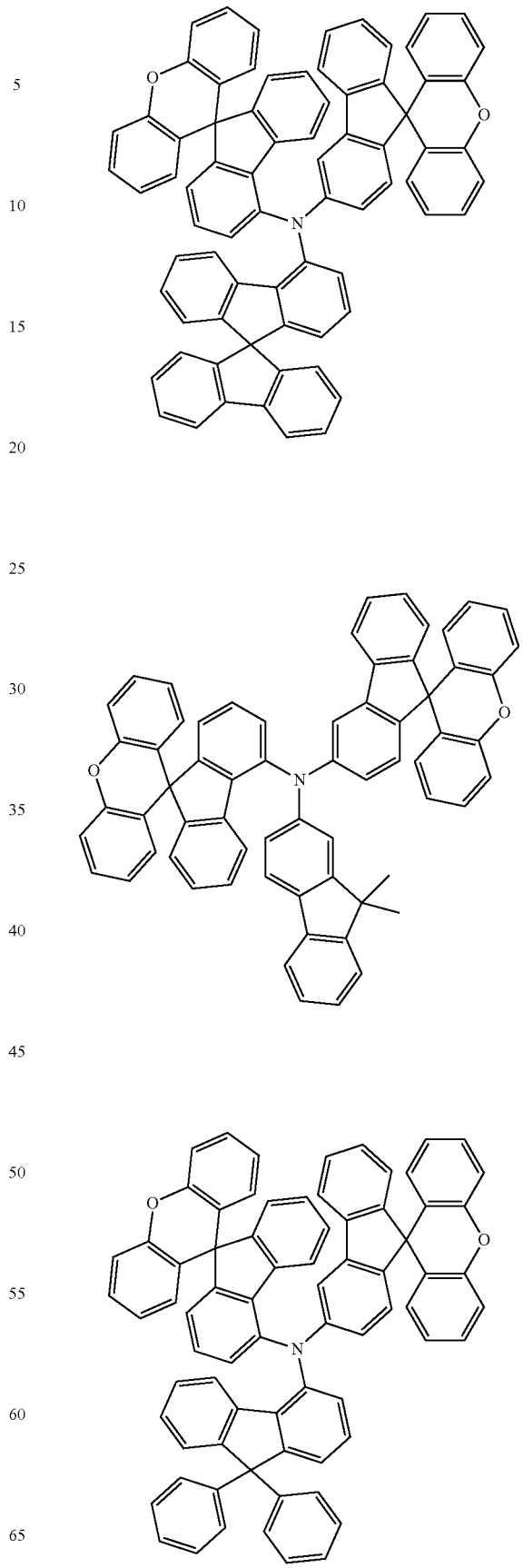

77
-continued
78
-continued
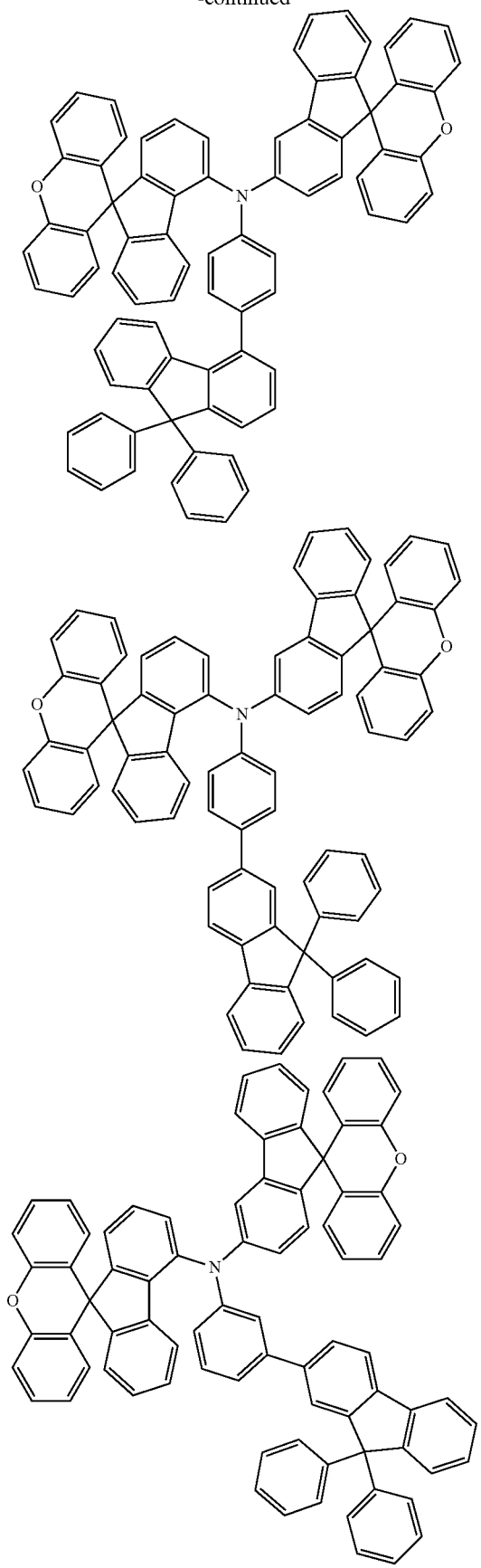
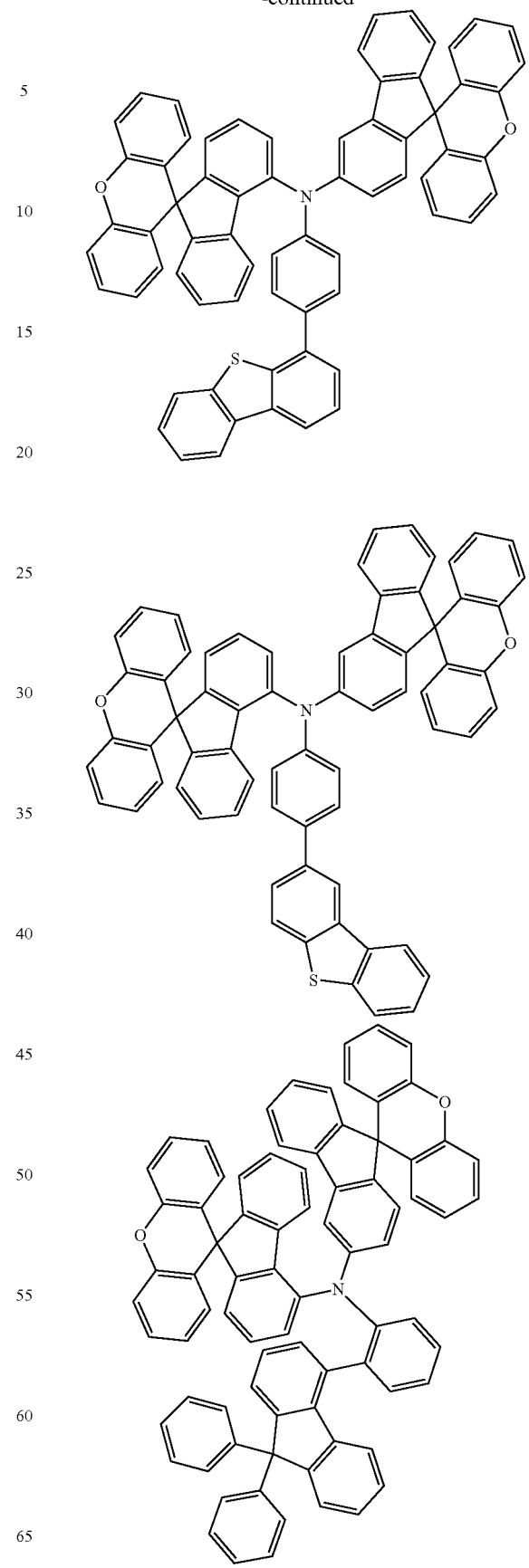

79
-continued
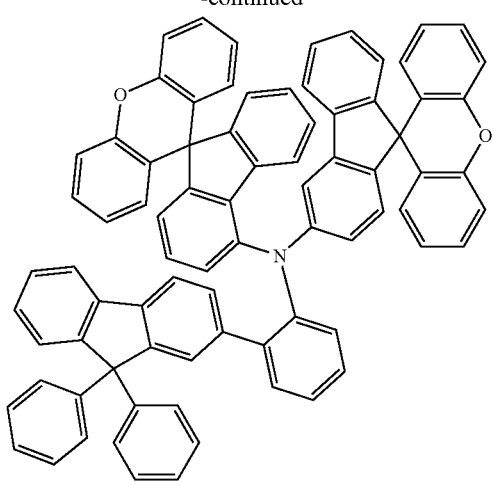
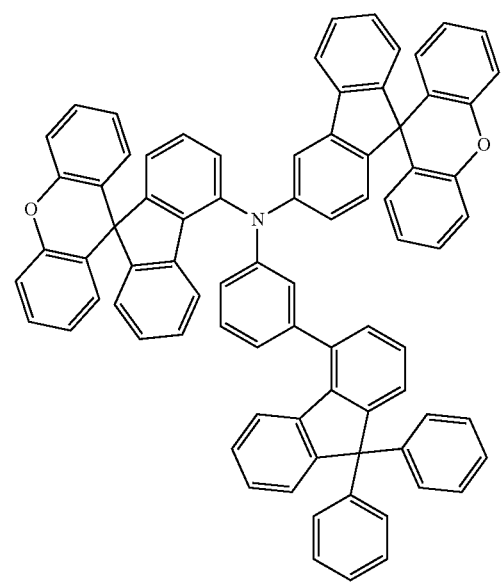
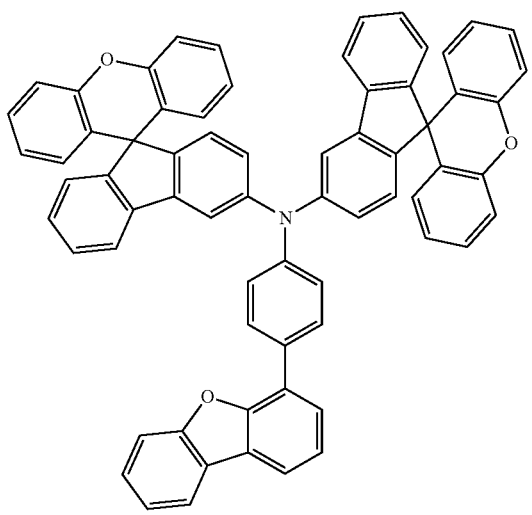
80
-continued
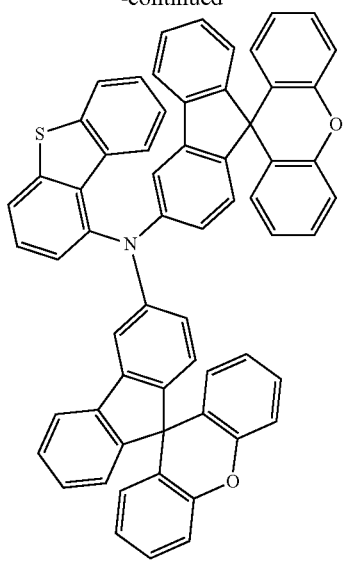
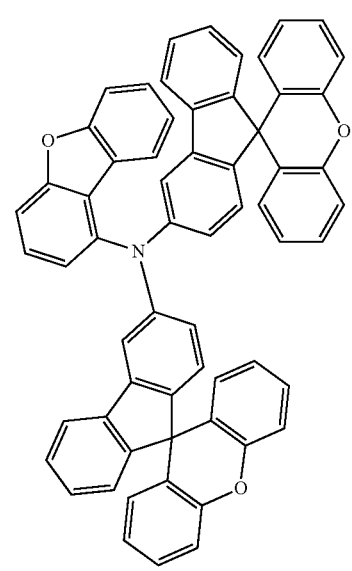
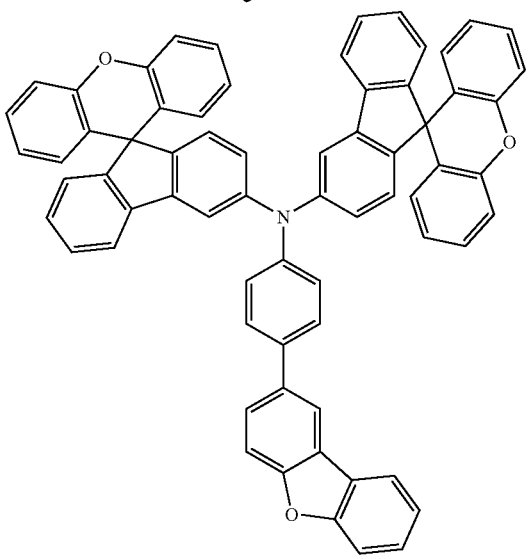

81
-continued
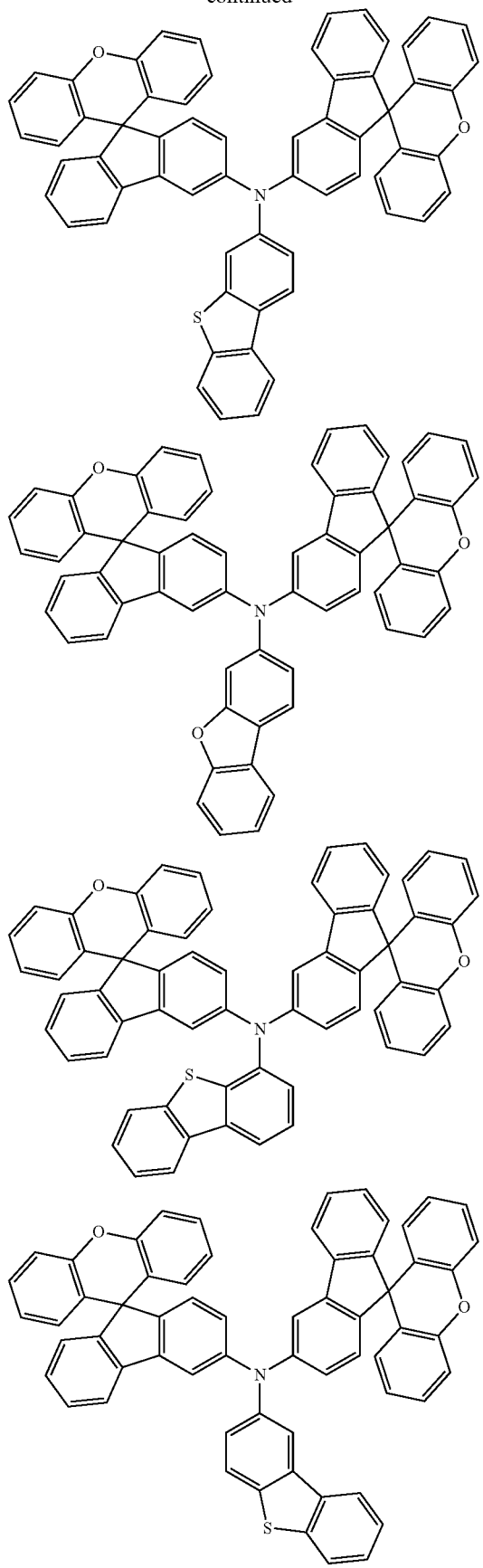
82
-continued
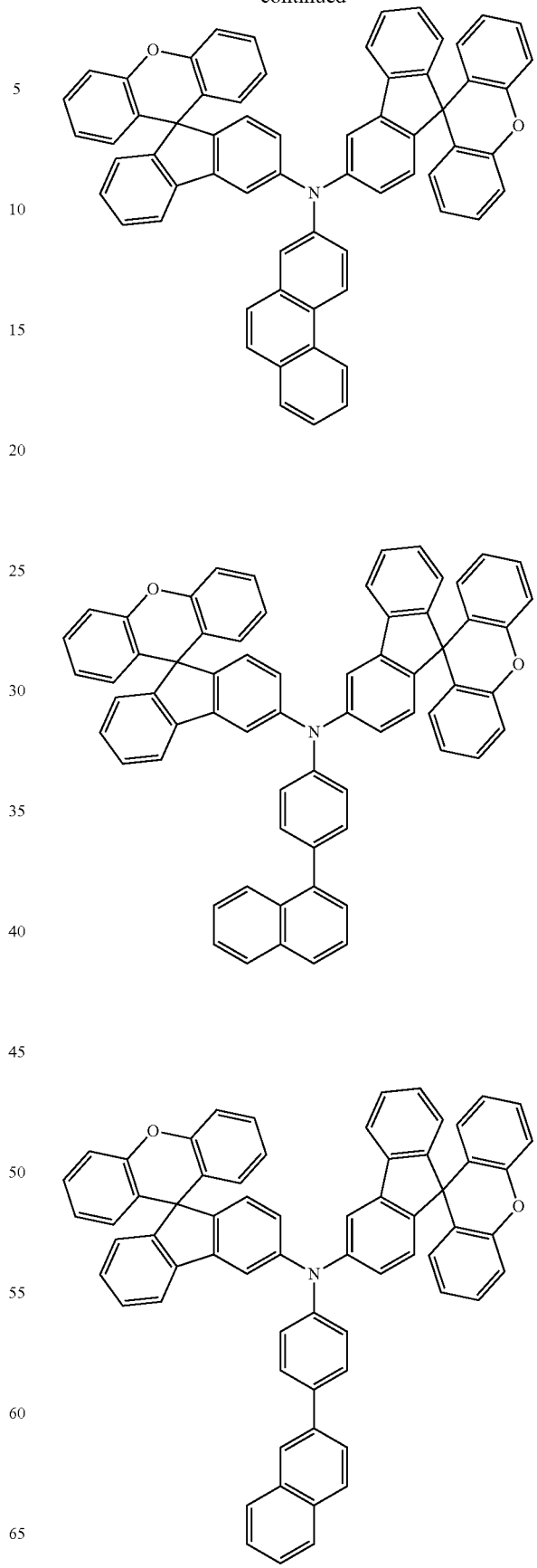

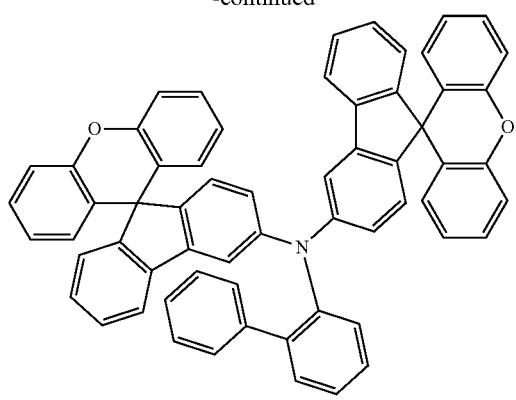
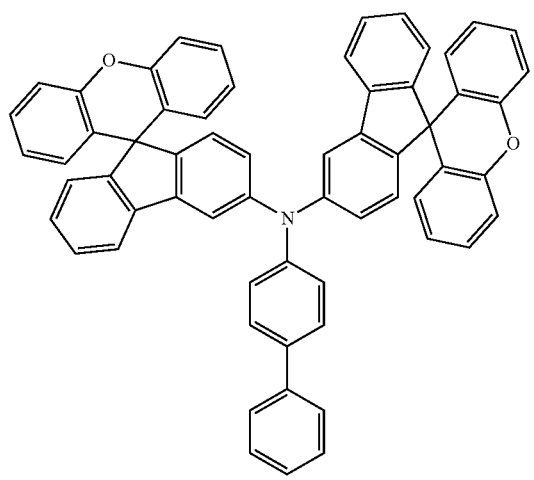
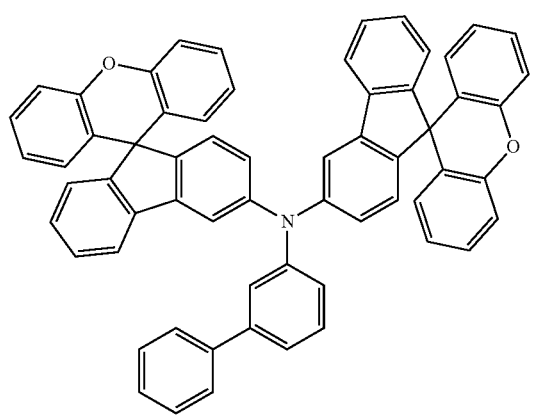
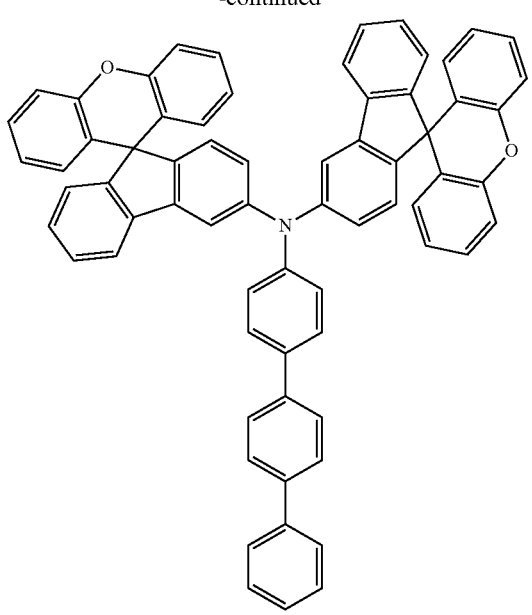
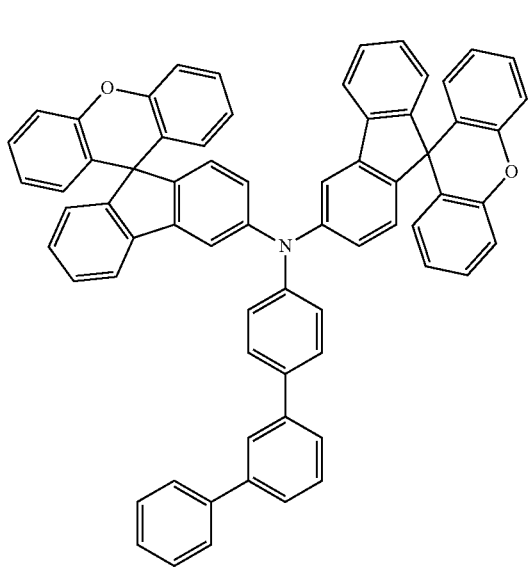
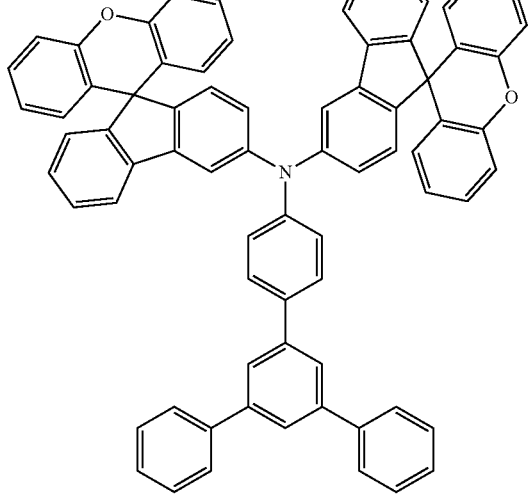

85
-continued
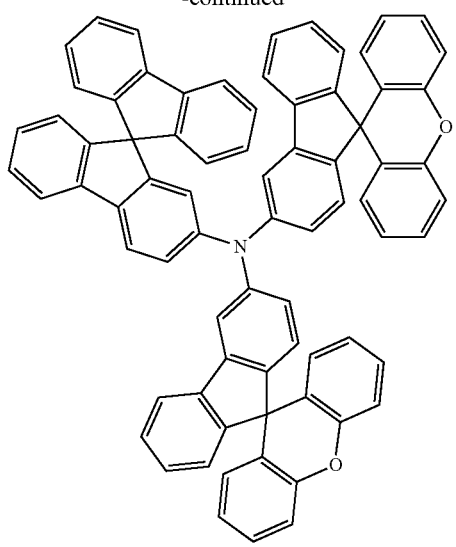
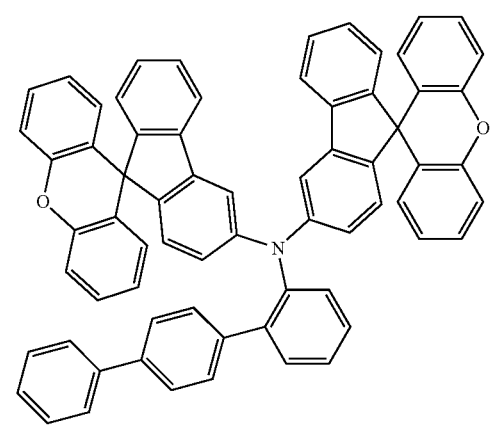
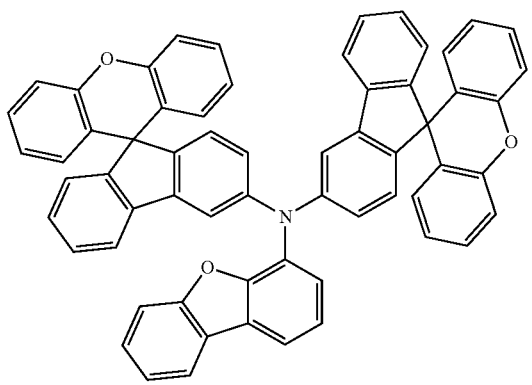
86
-continued
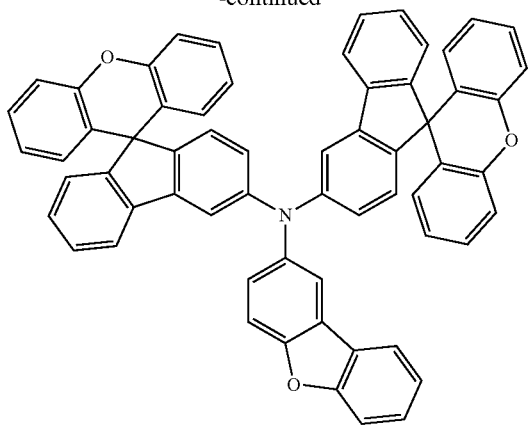

87
-continued
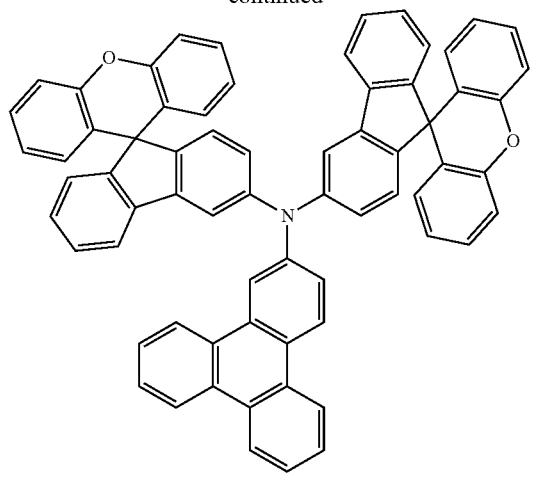
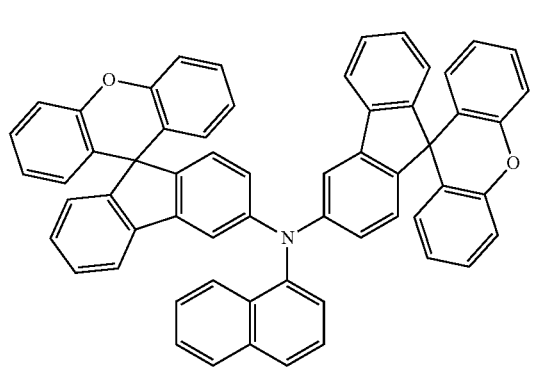
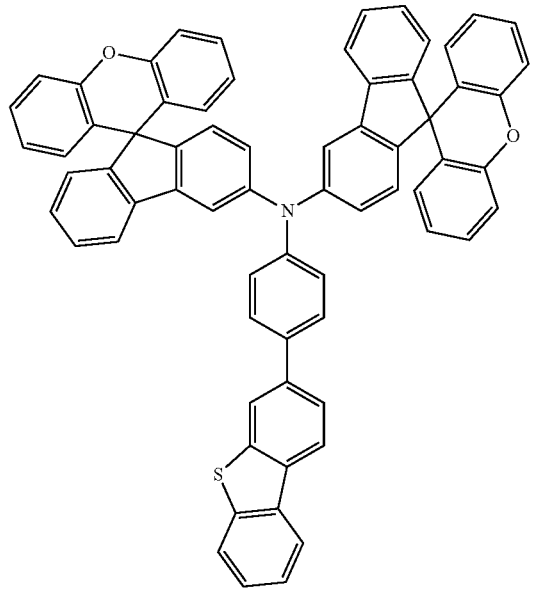
88
-continued
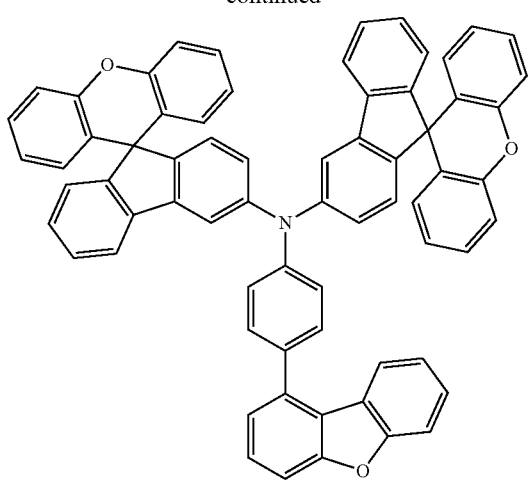
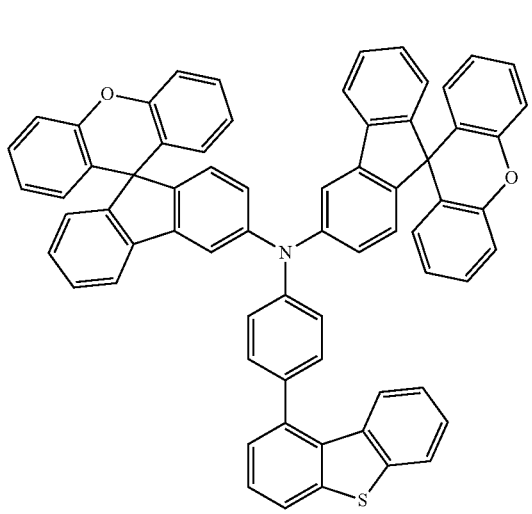
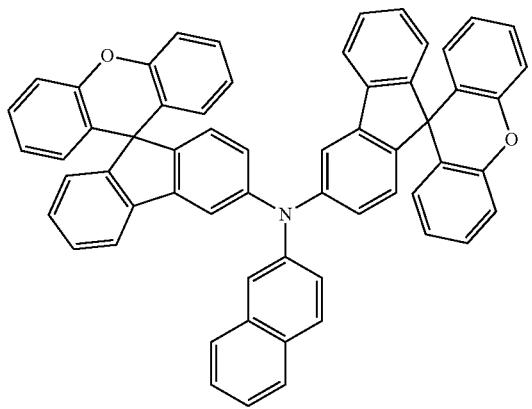

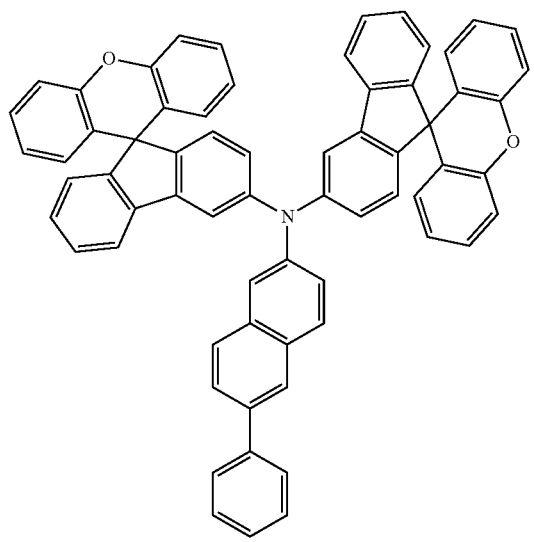
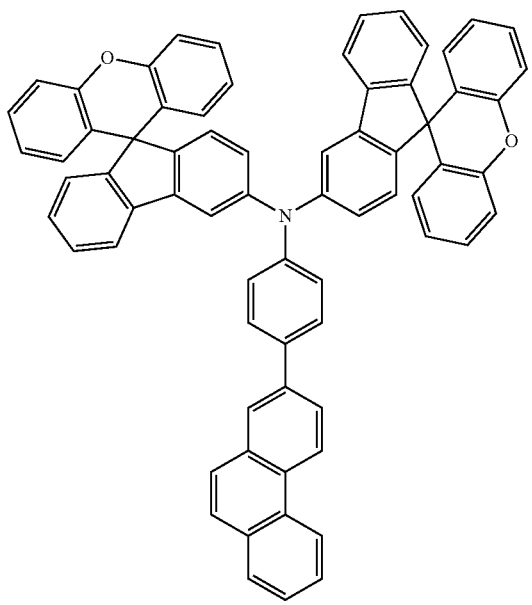
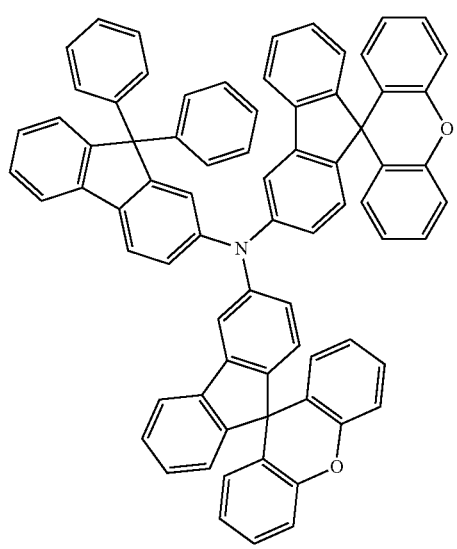
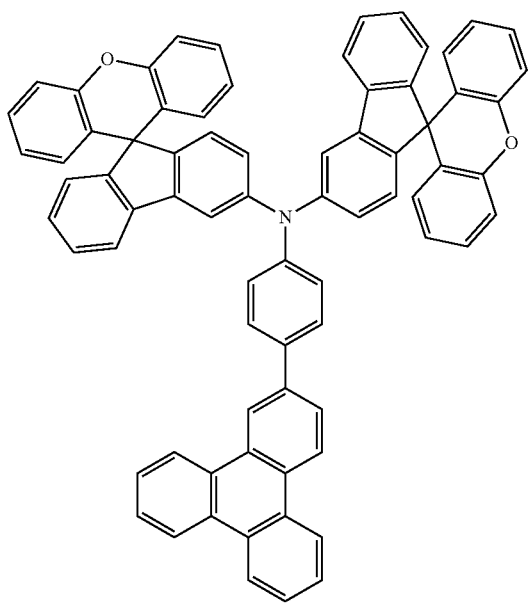
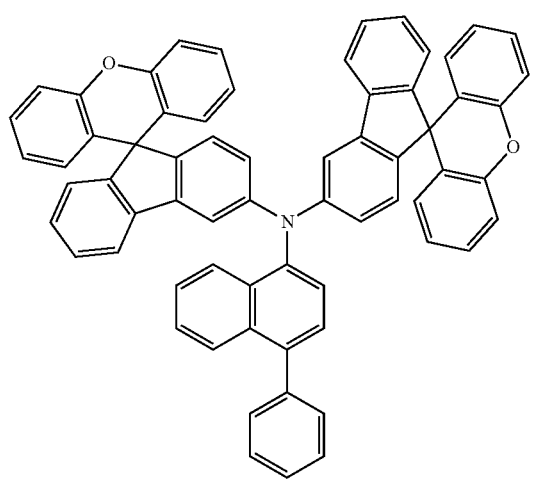
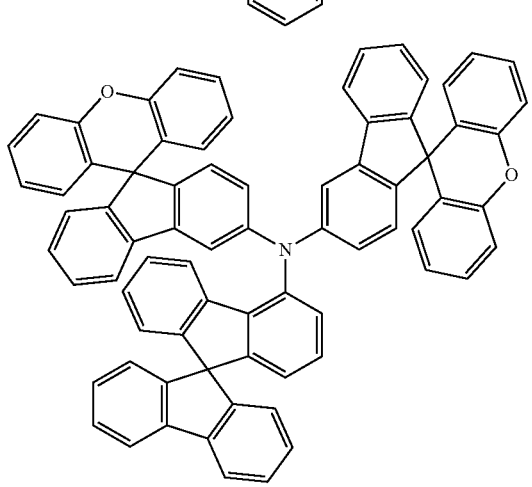

91
-continued
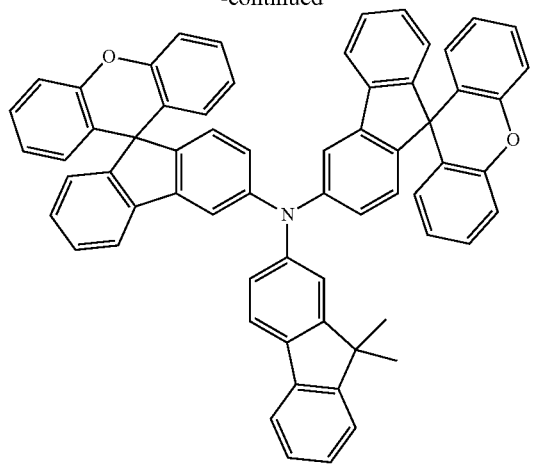
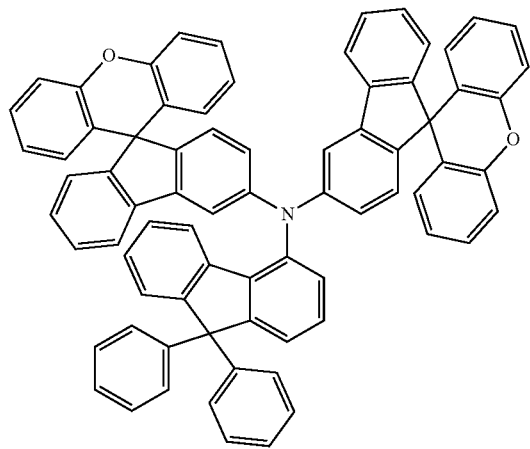
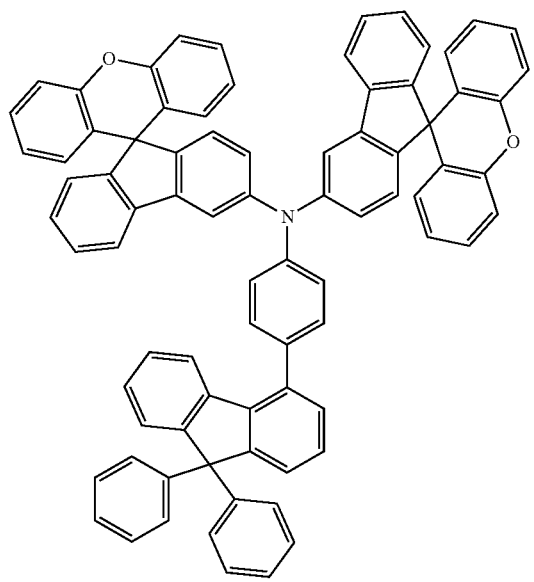
92
-continued
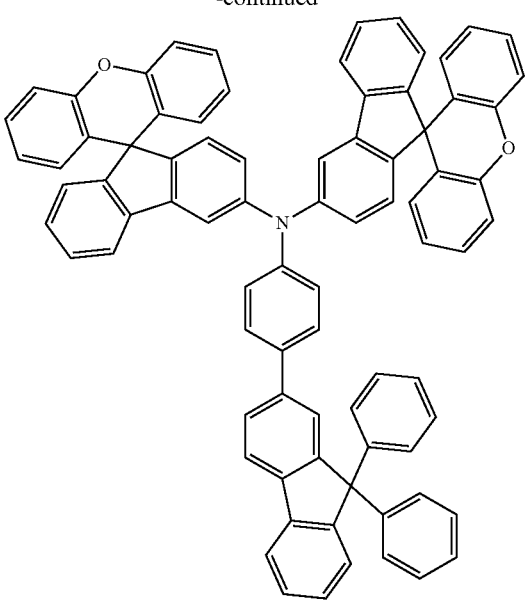
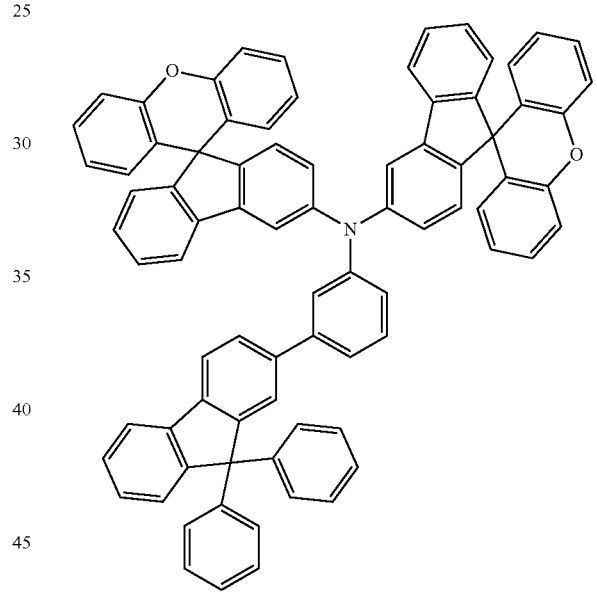
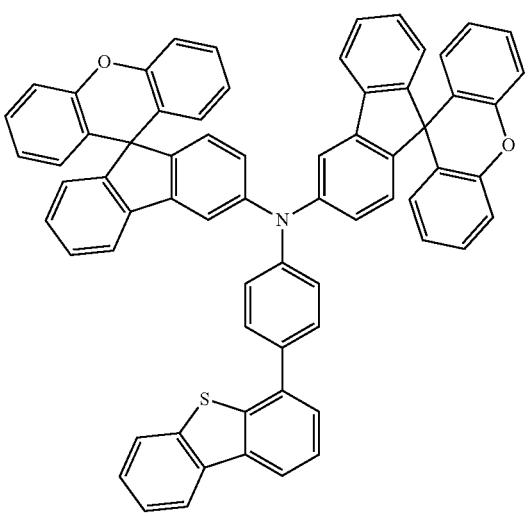

93
-continued
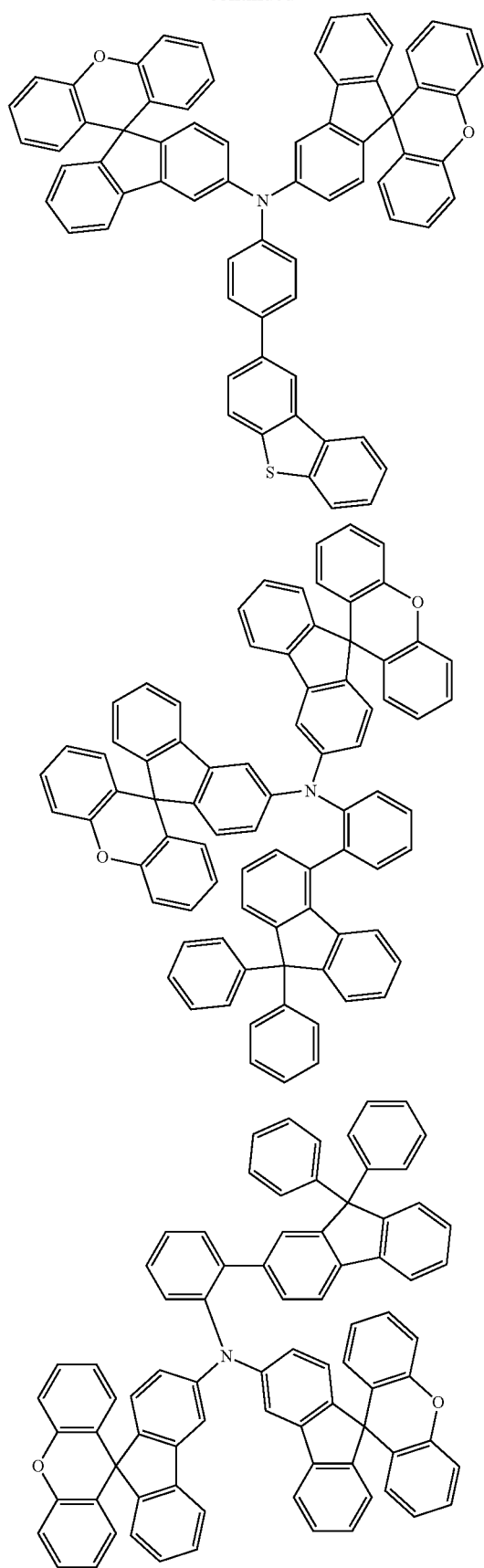
94
-continued
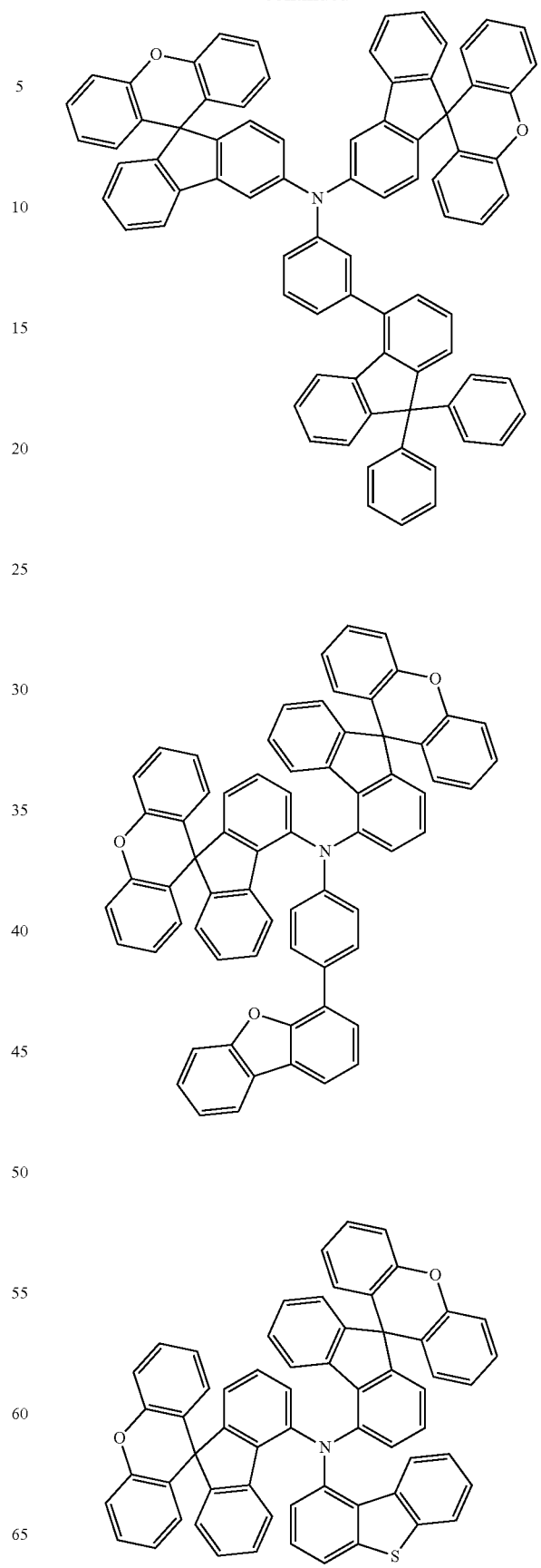

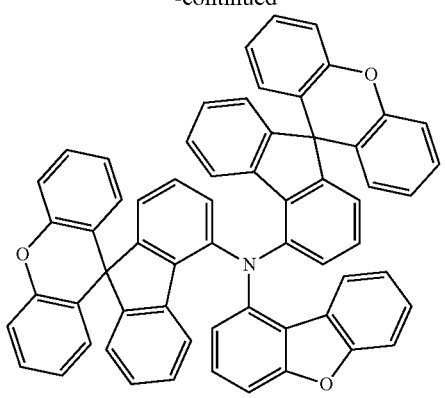
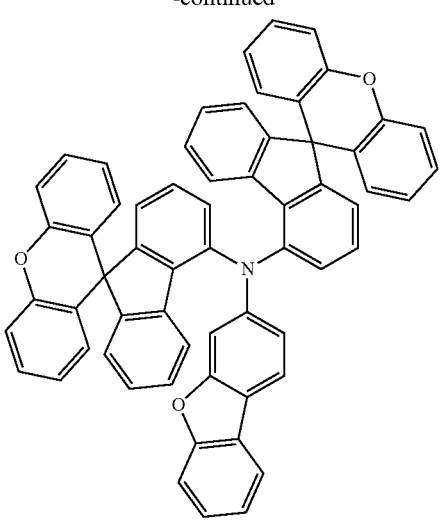
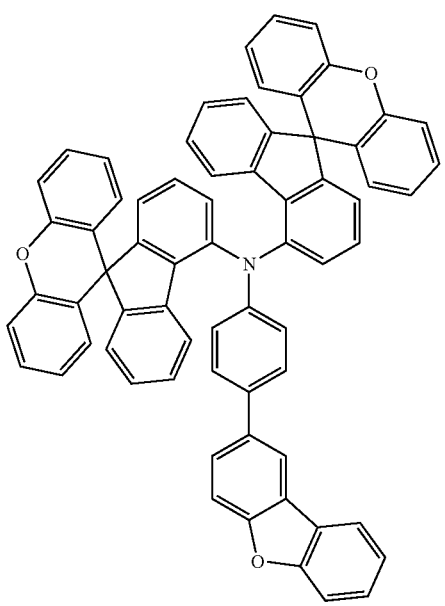
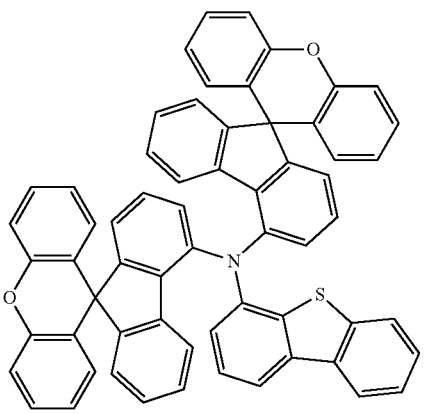
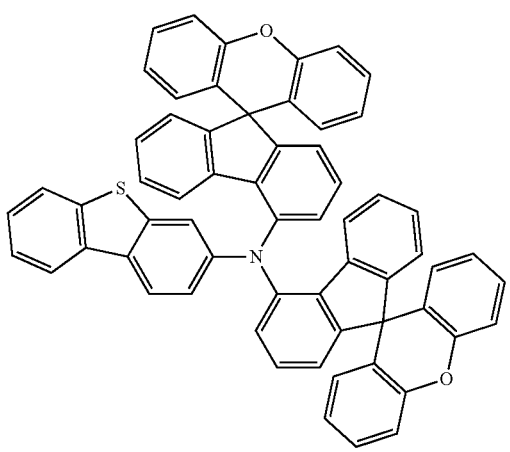
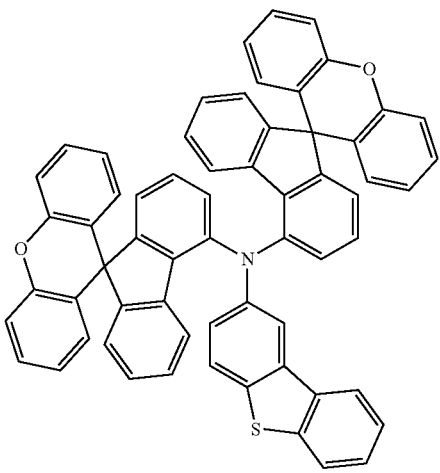

97
-continued
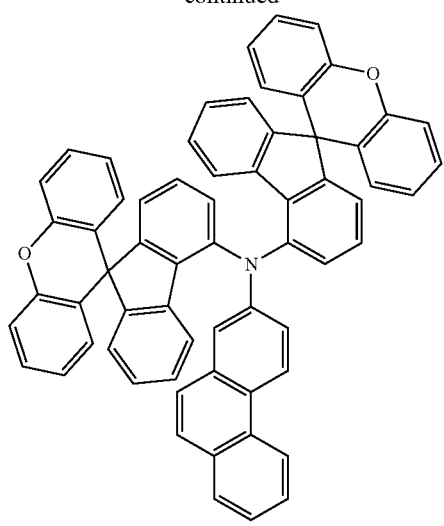
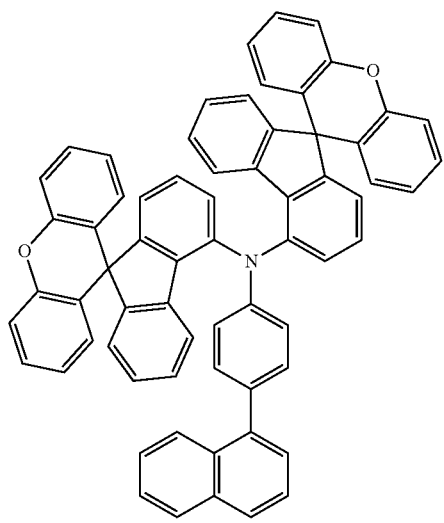
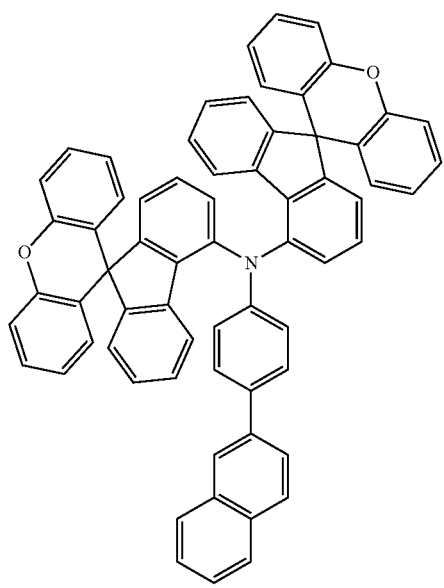
98
-continued
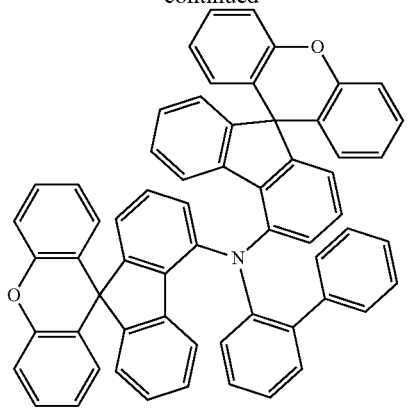
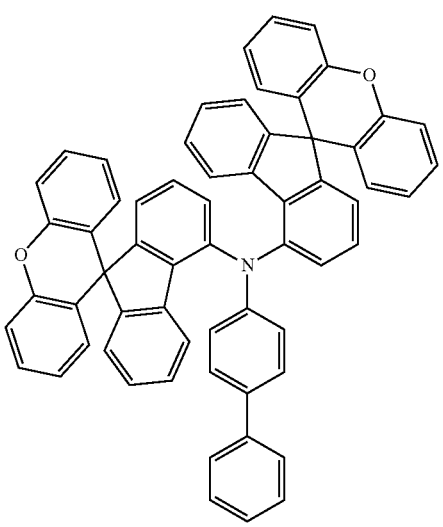
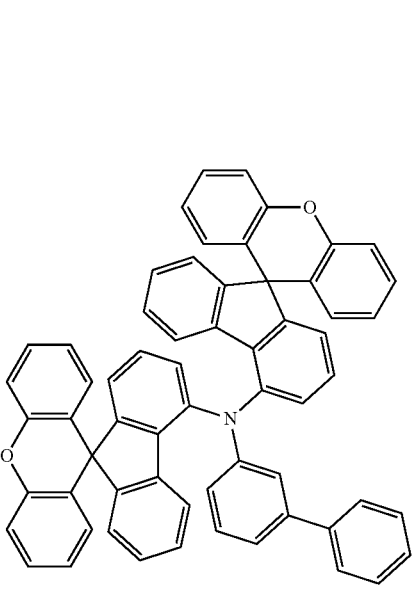

99
-continued
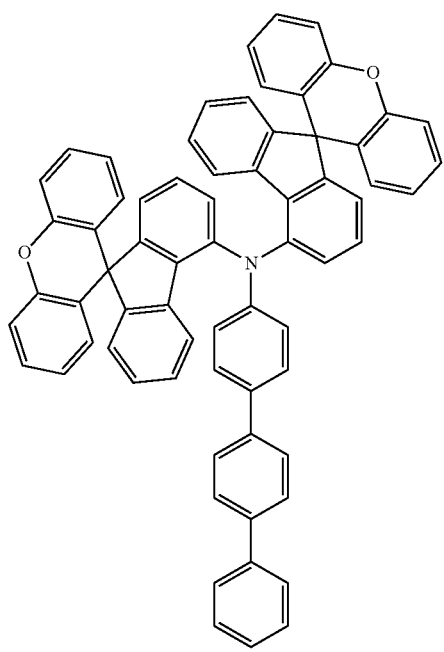
100
-continued
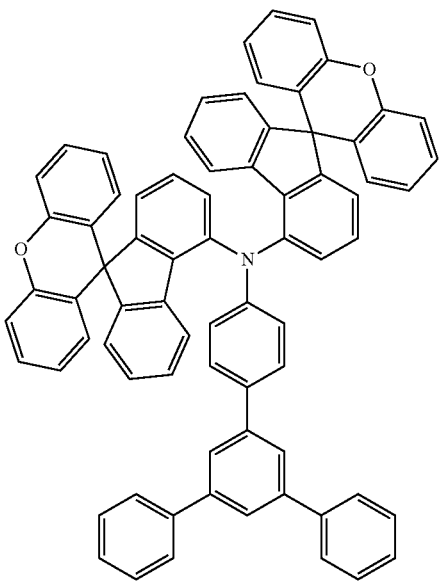
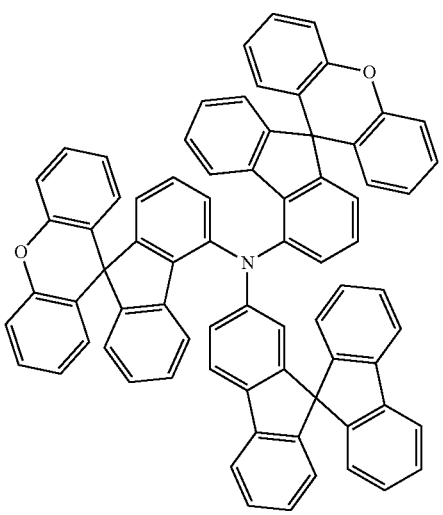
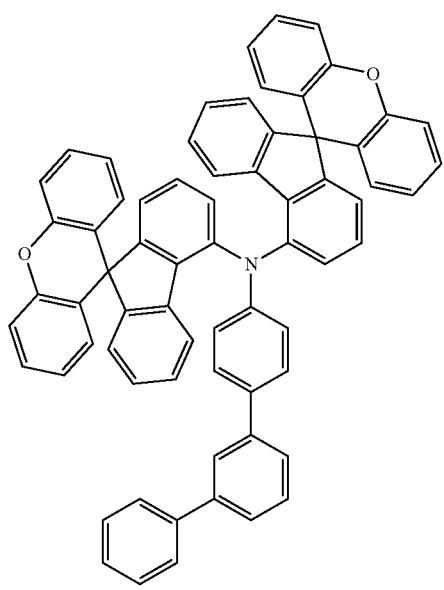
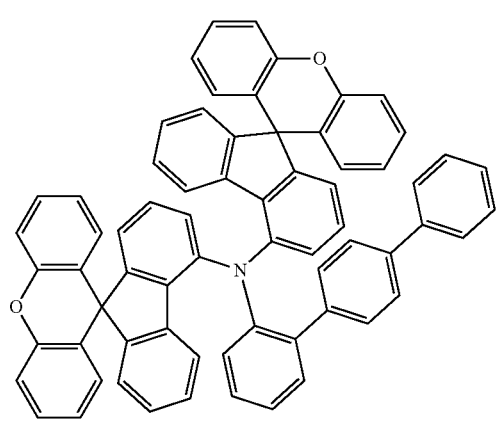

101
-continued
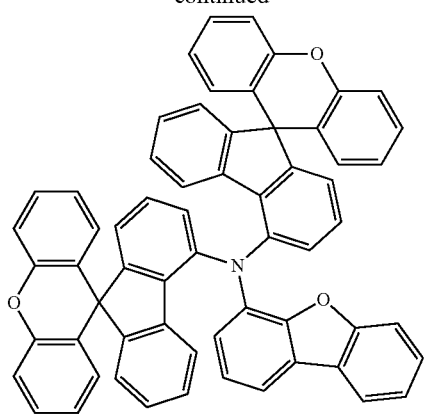
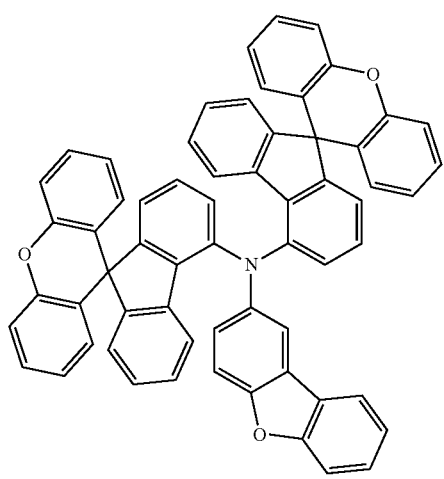
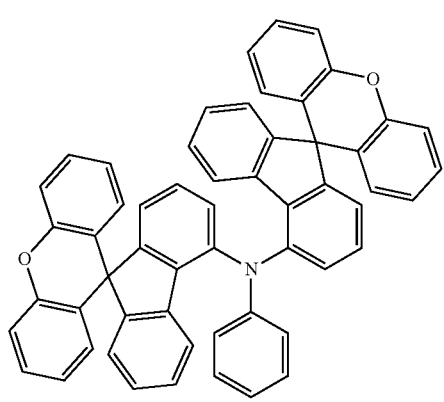
102
-continued
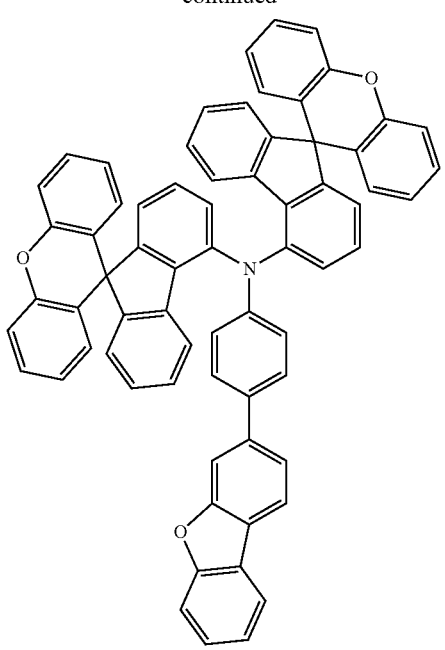
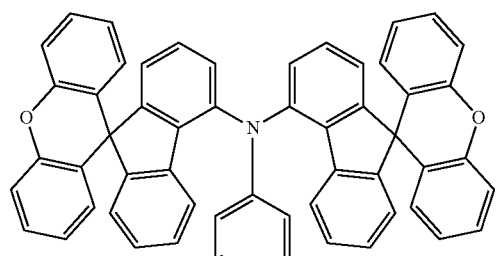
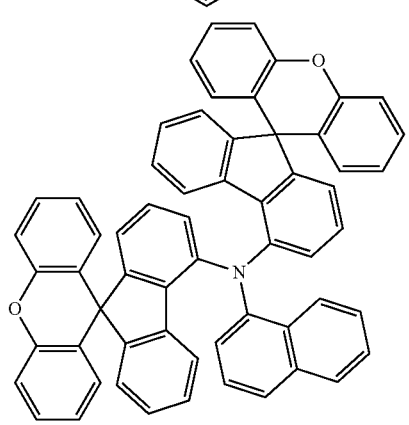

103
-continued
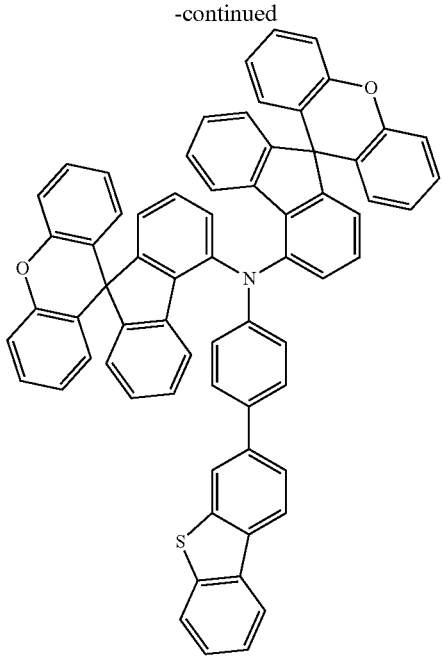
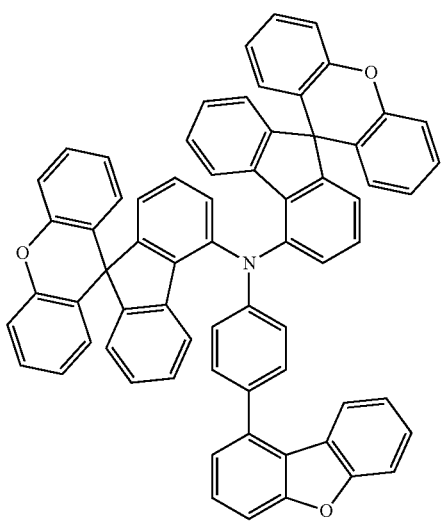
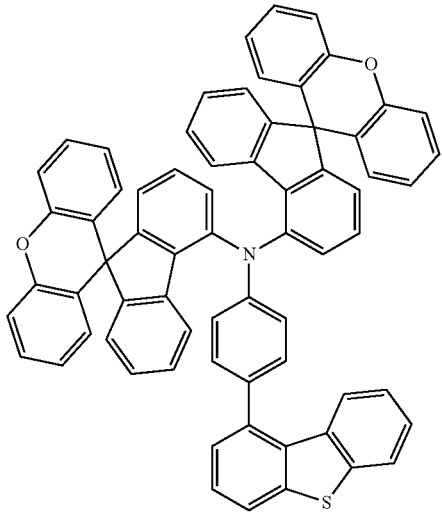
104
-continued
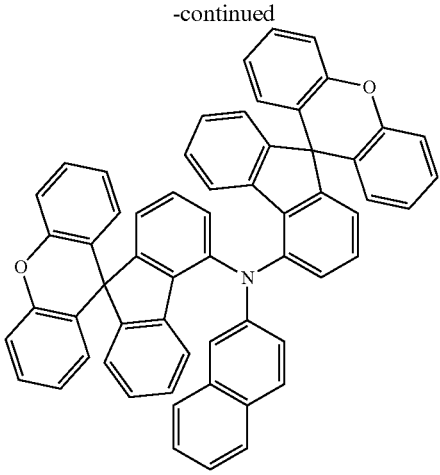
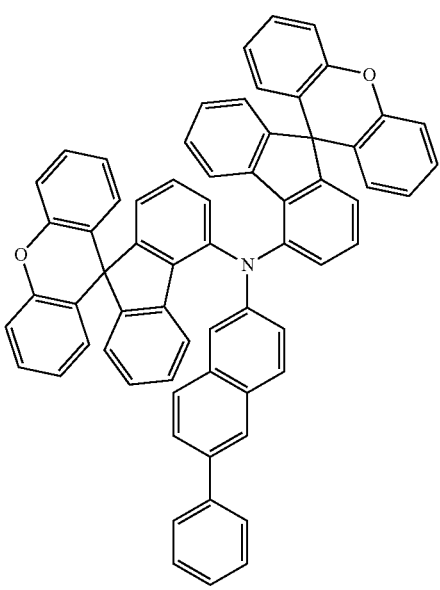
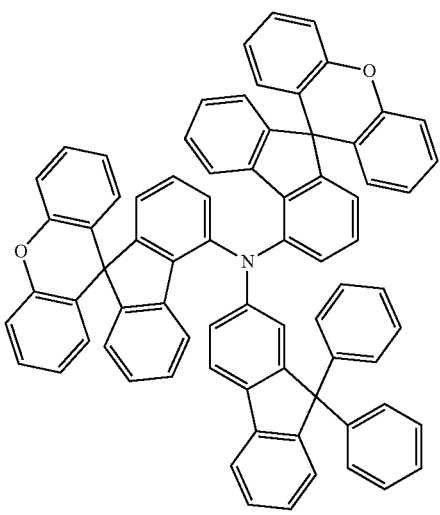

105
-continued
106
-continued
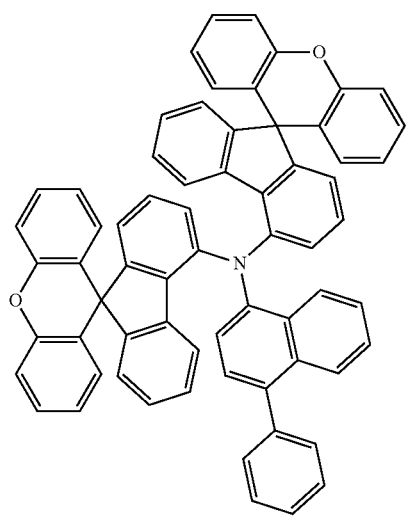
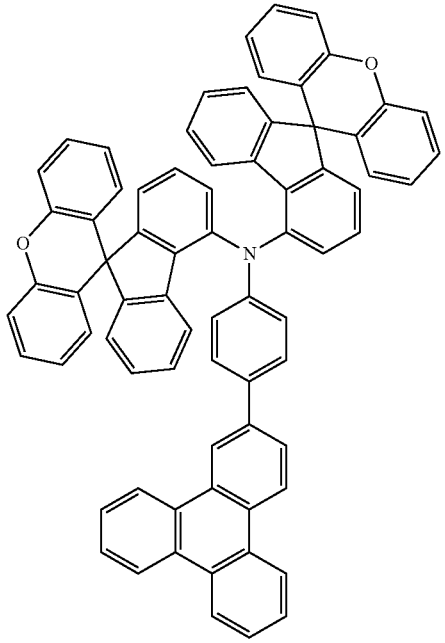
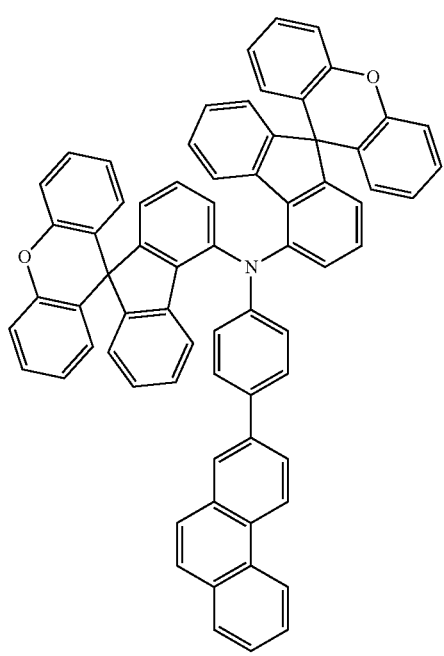
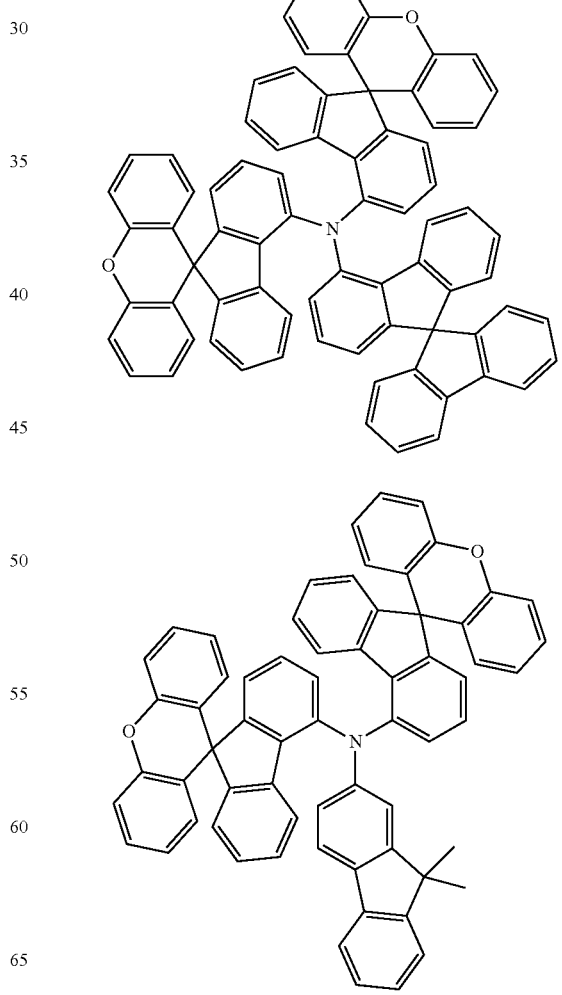

107
-continued
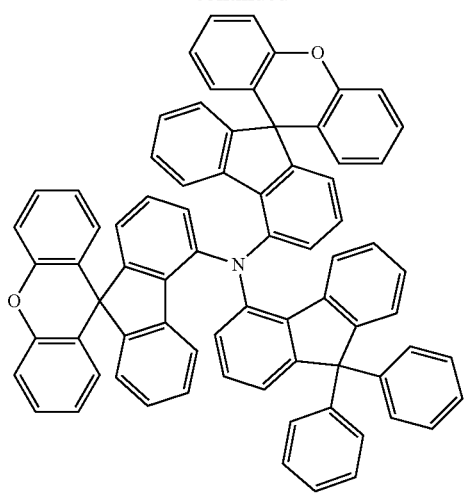
108
-continued
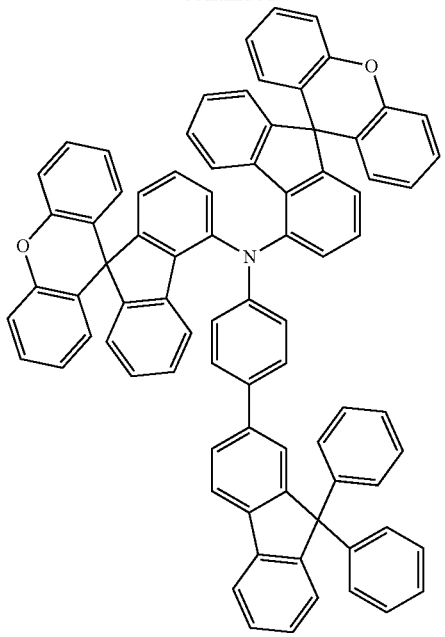
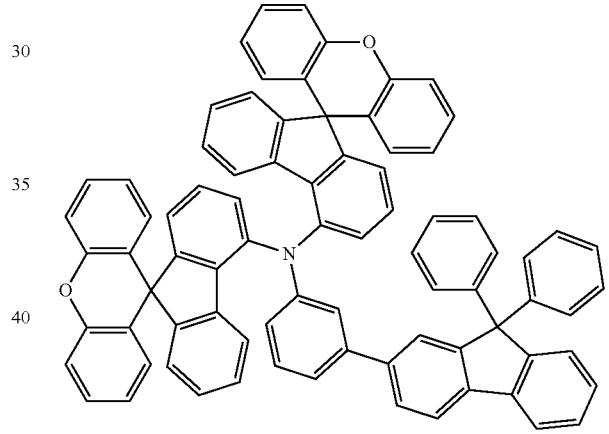
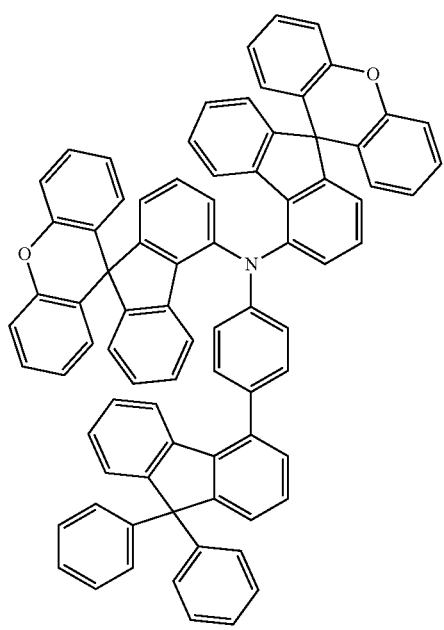
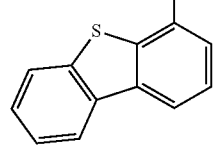

109
-continued
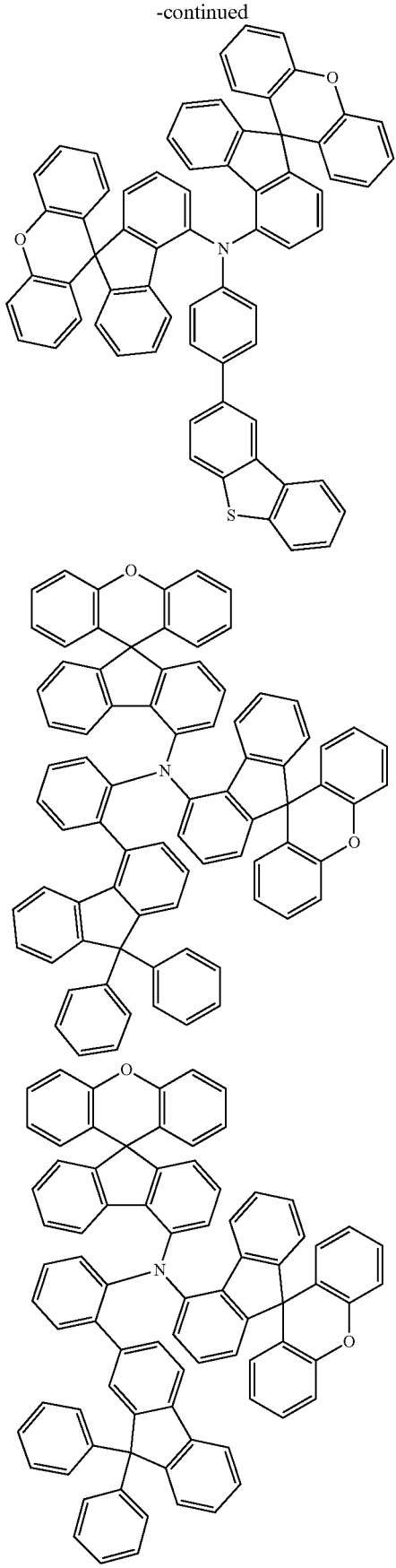
110
-continued
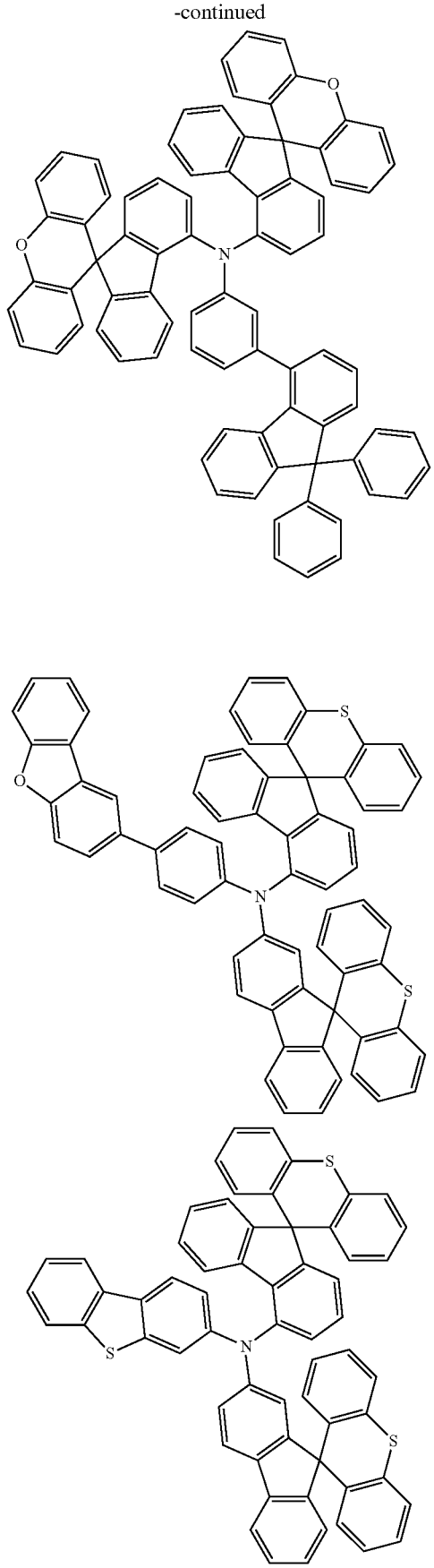

111
-continued
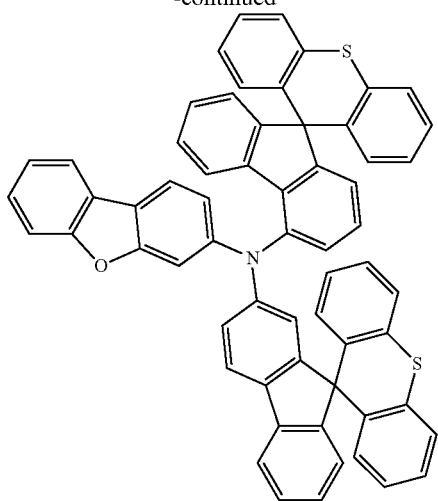
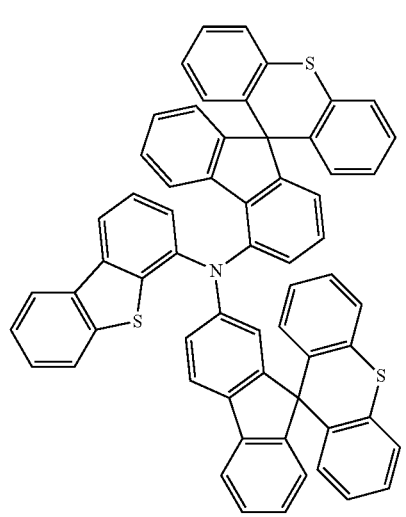
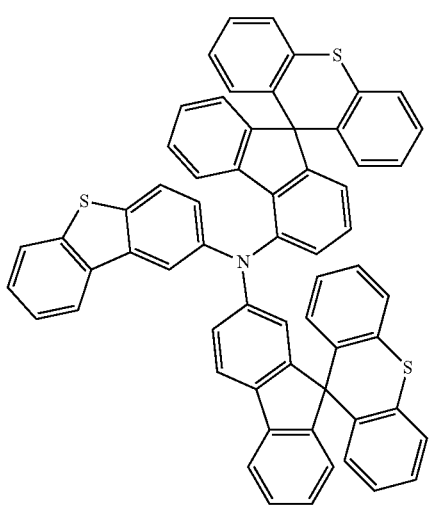
112
-continued
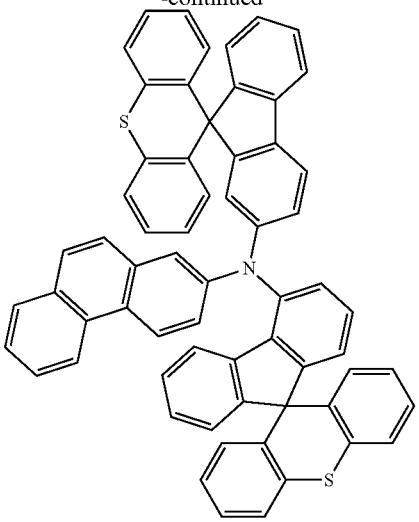
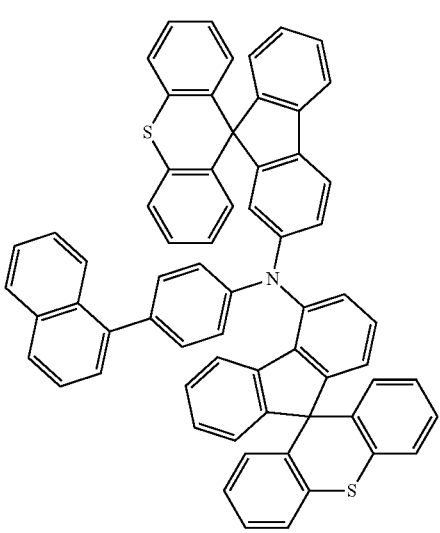
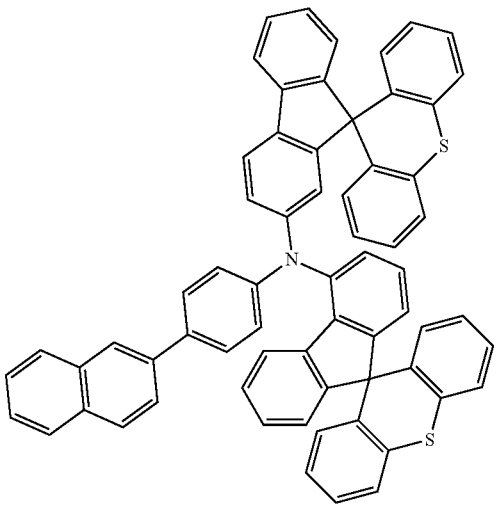

-continued
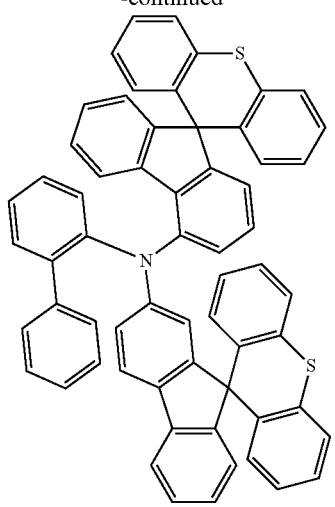
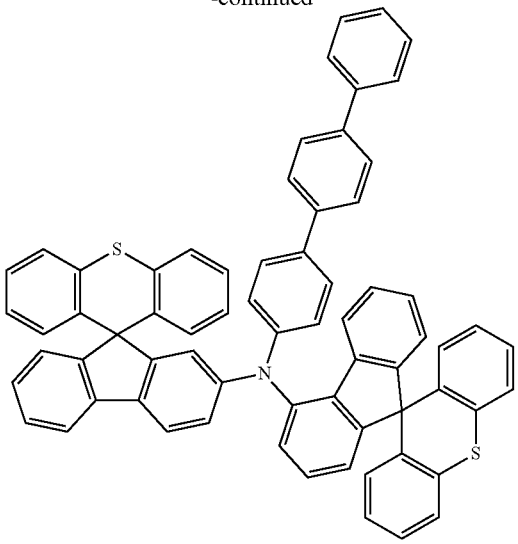
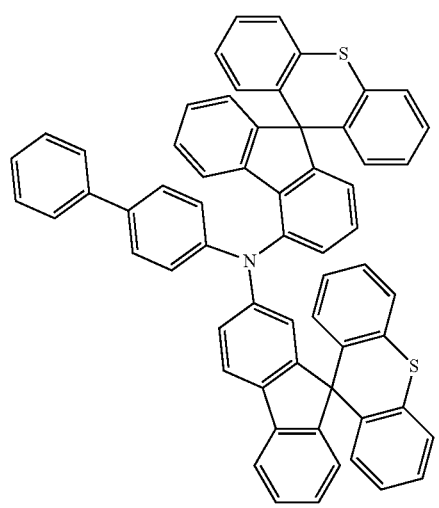
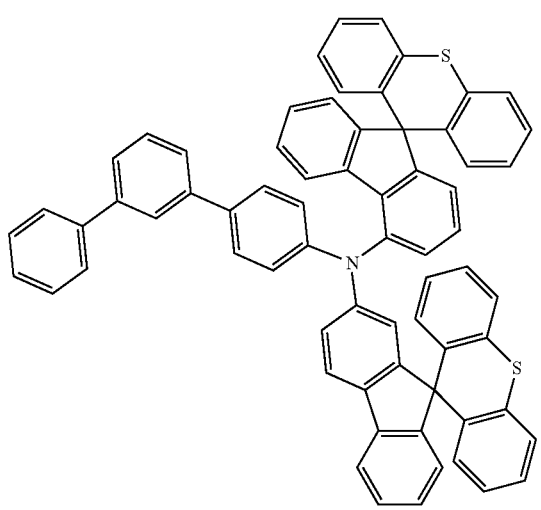
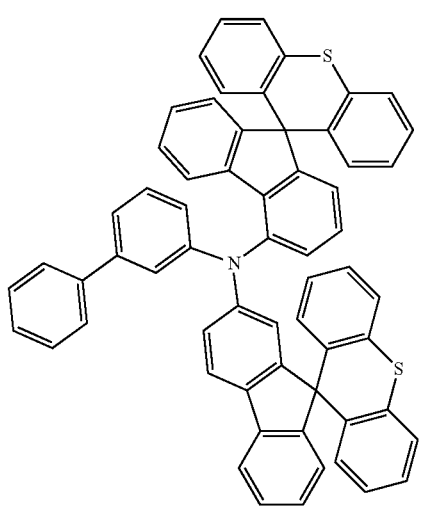
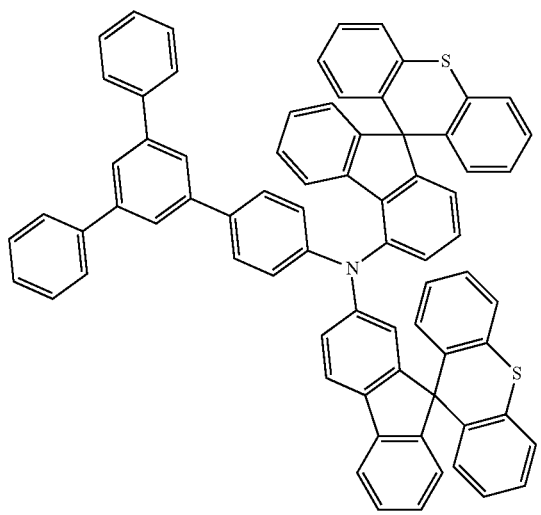

115
-continued
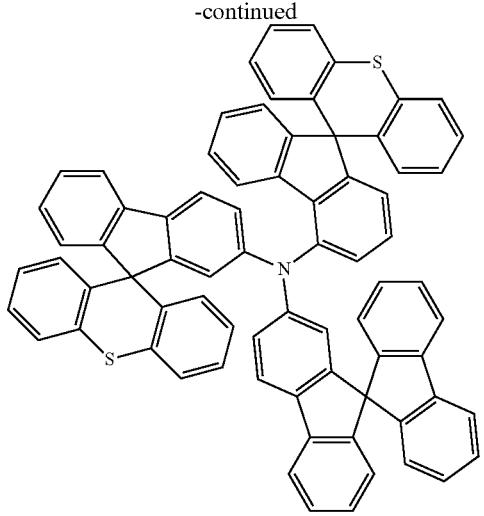
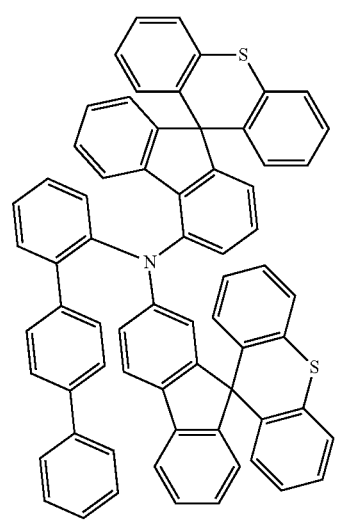
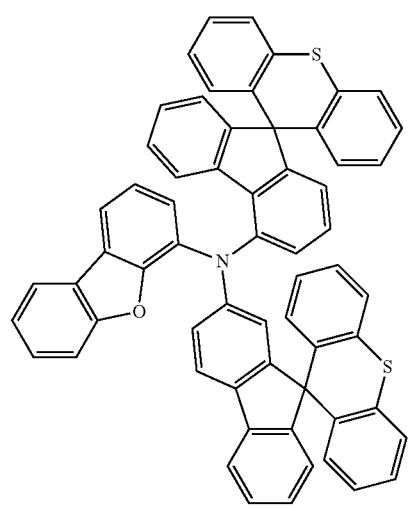
116
-continued
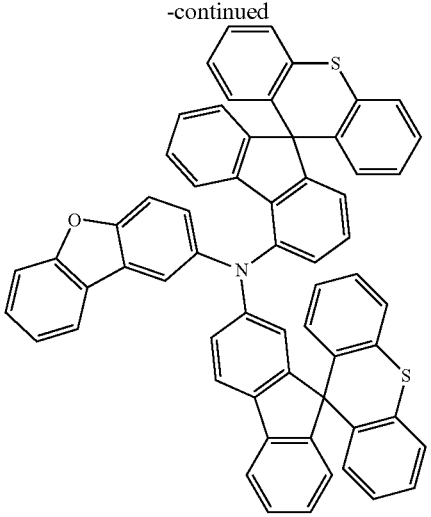
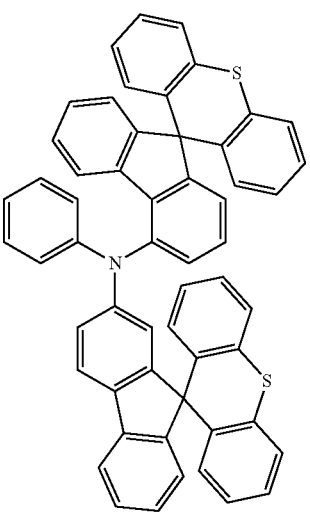
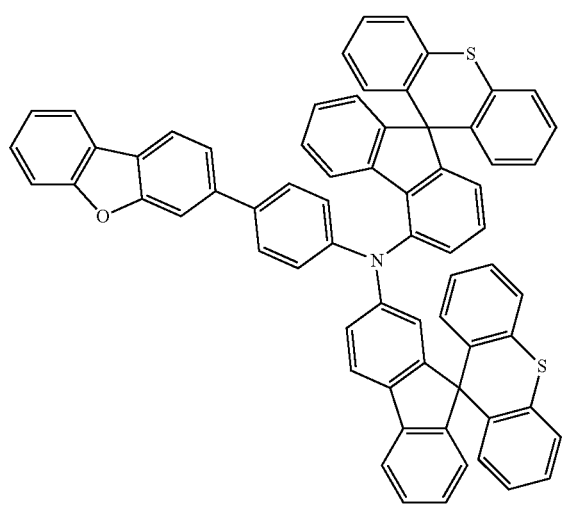

-continued
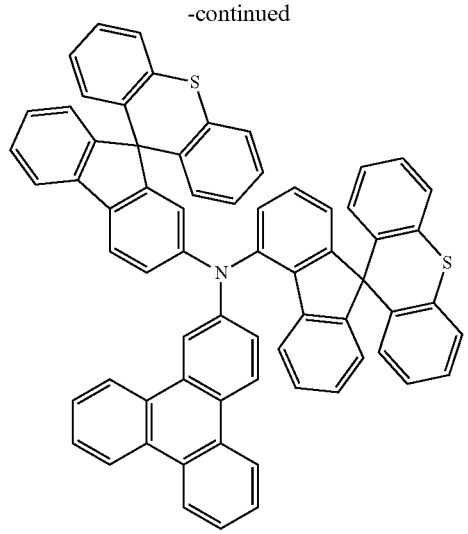
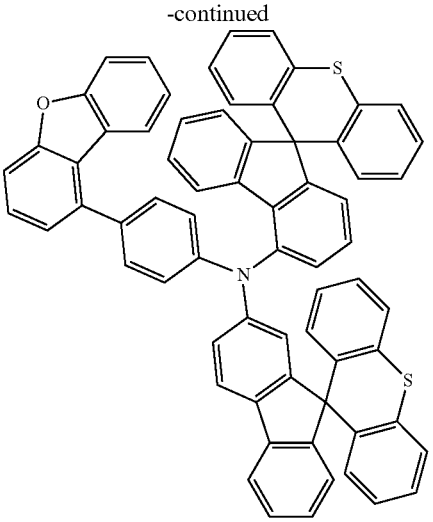
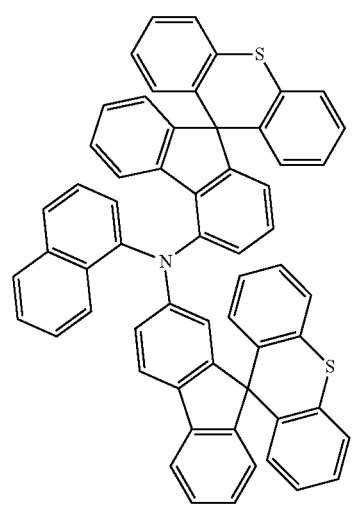
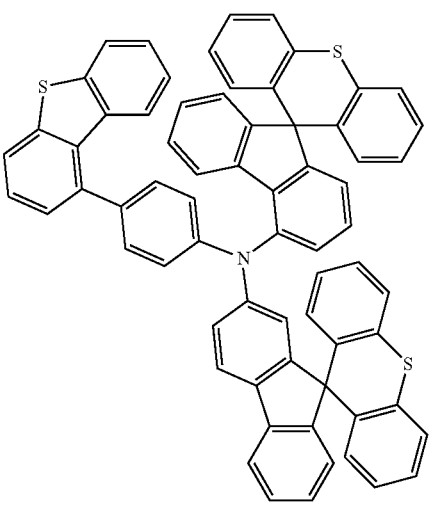
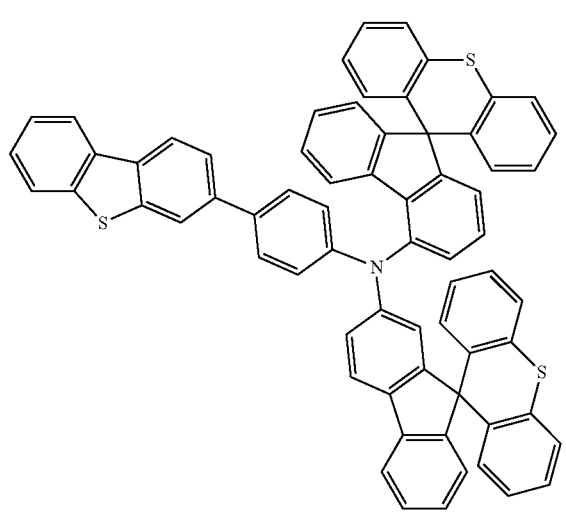
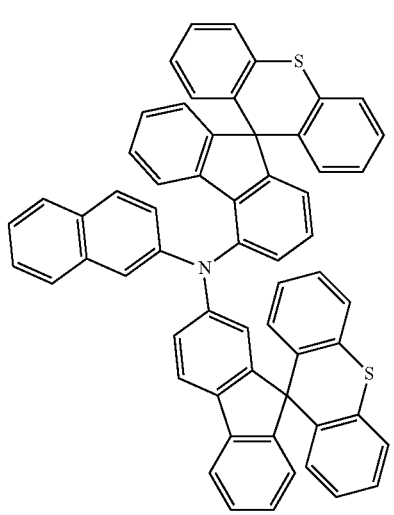

119
-continued
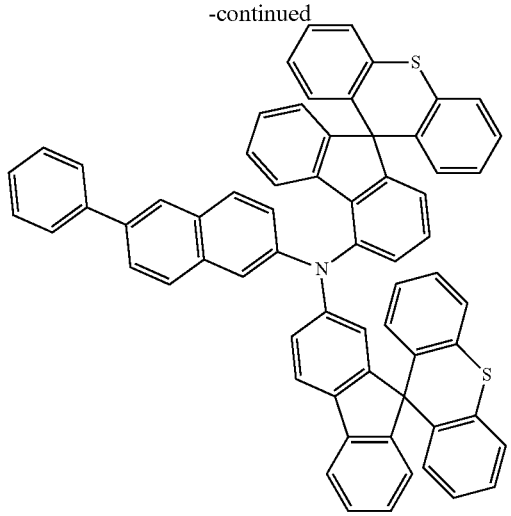
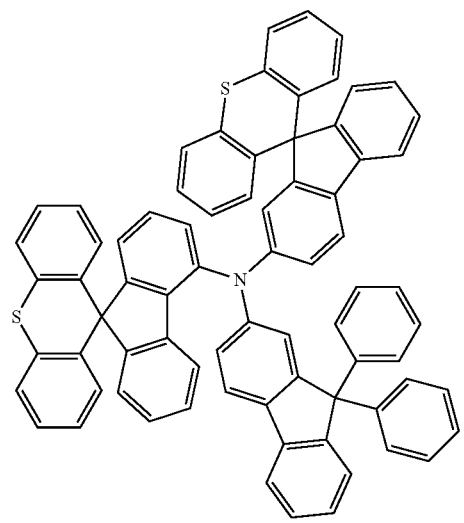
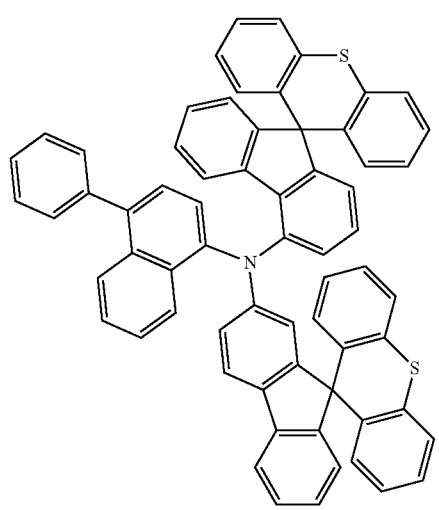
120
-continued
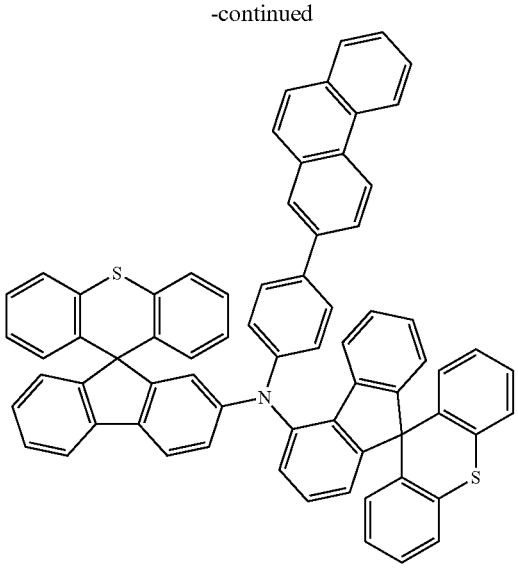
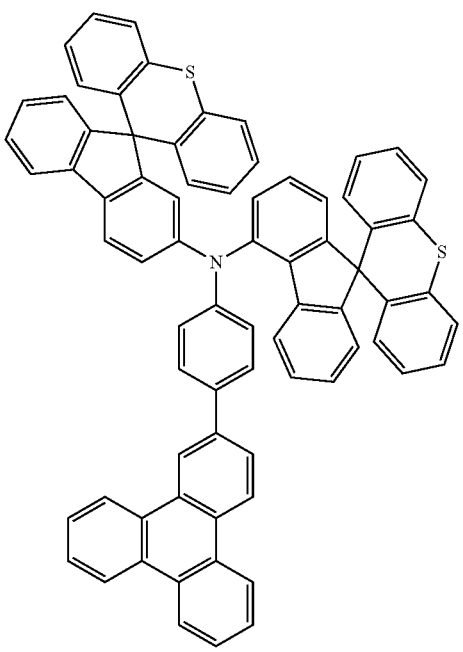
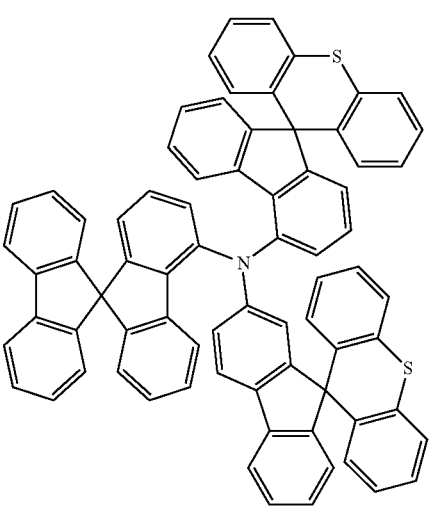

121
-continued
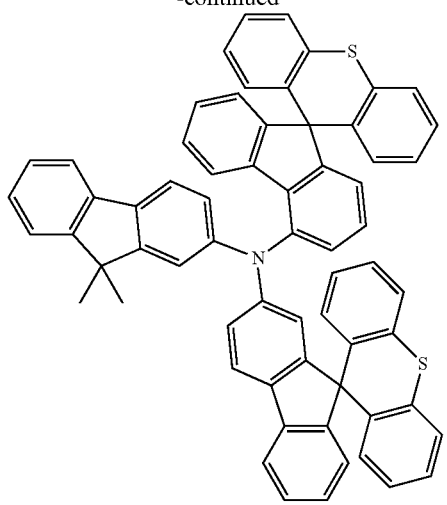
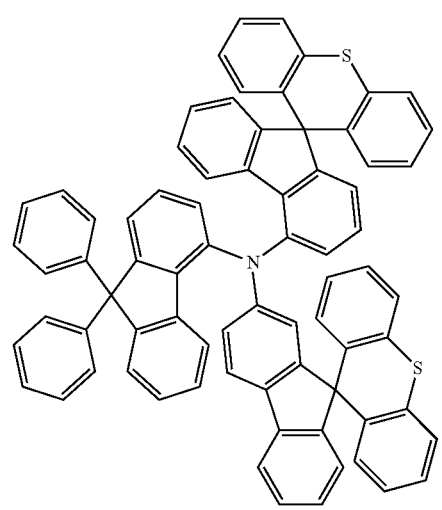
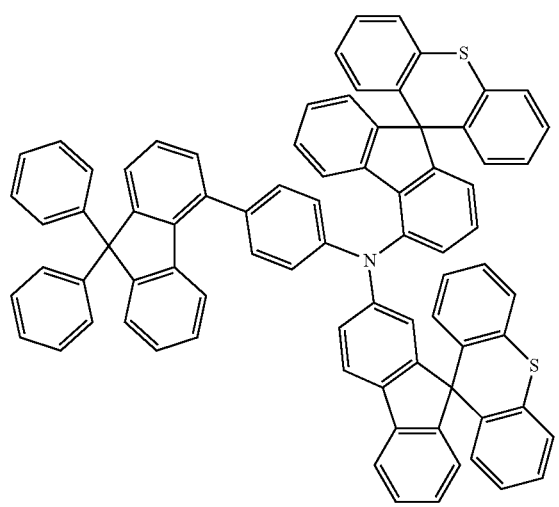
122
-continued
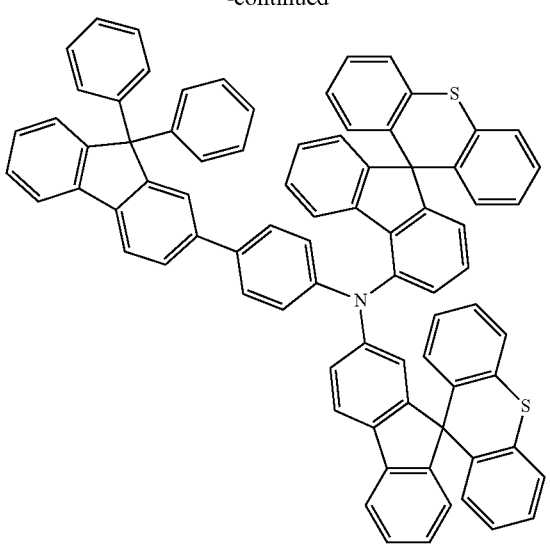
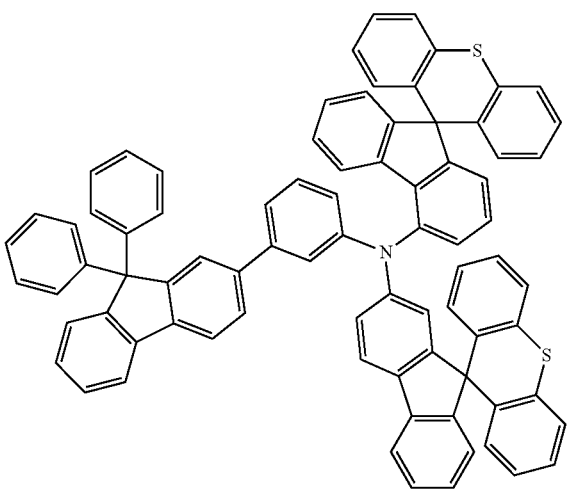
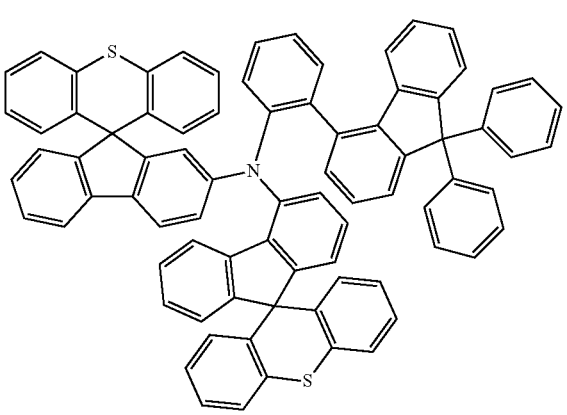

123
-continued
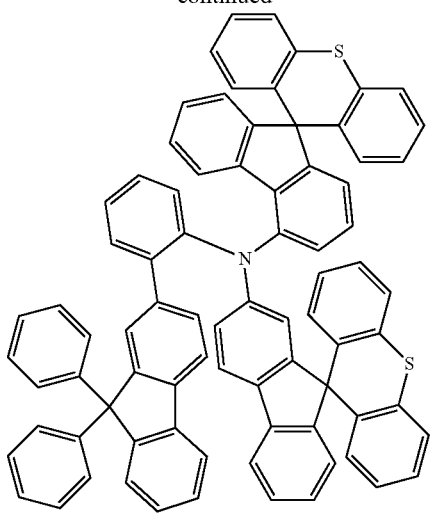
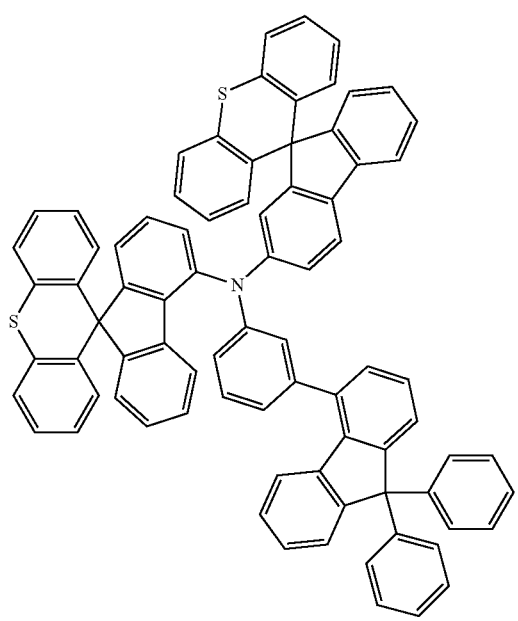
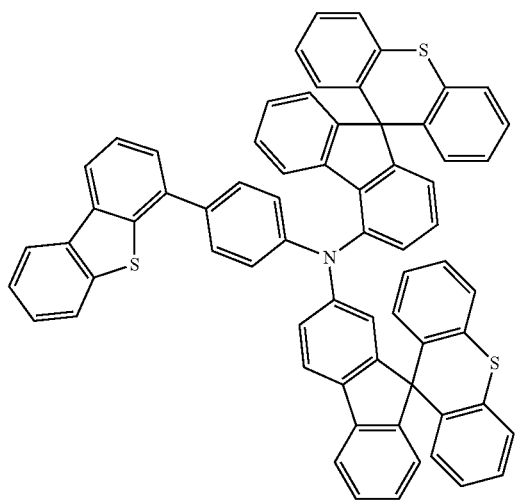
124
-continued
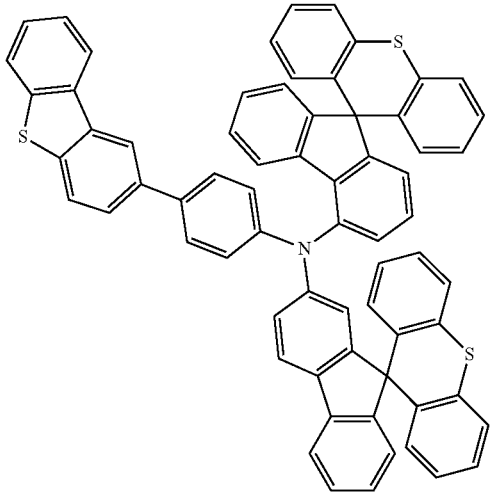
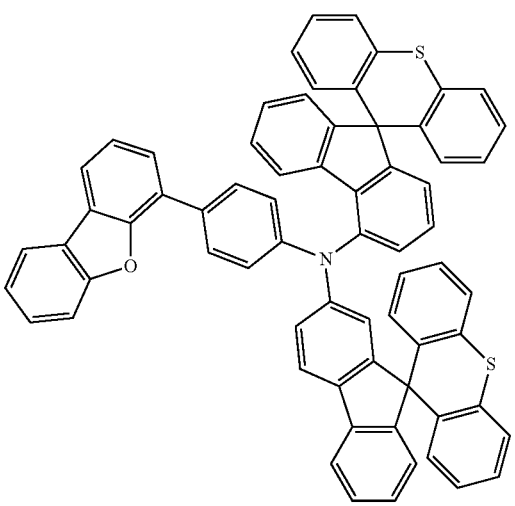
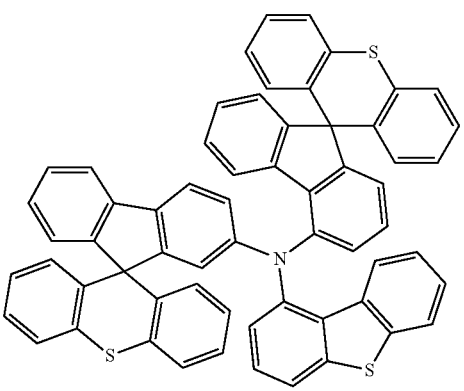

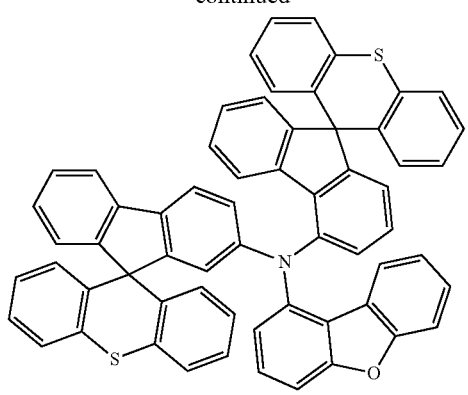
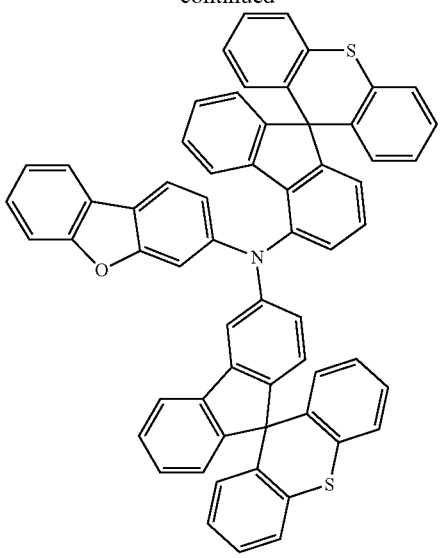
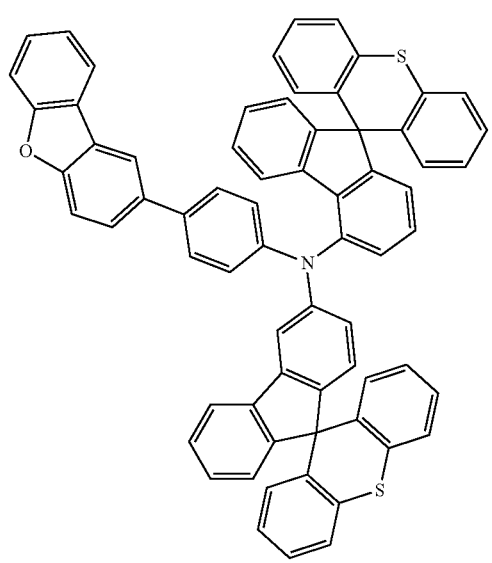
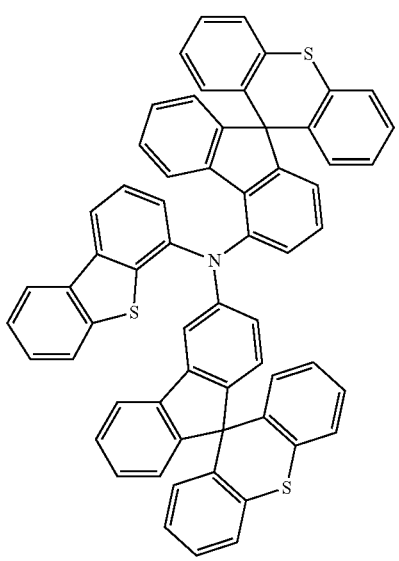
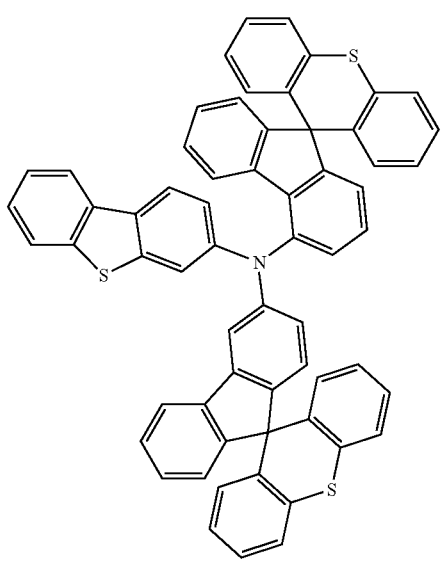
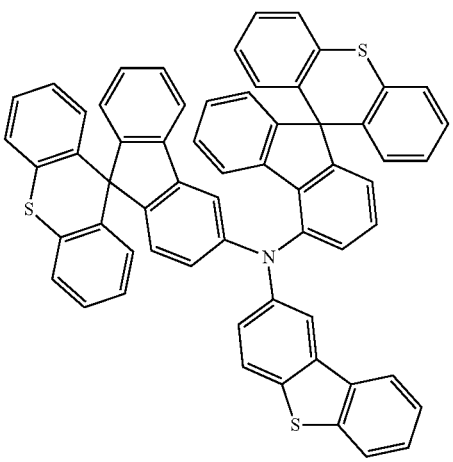

127
-continued
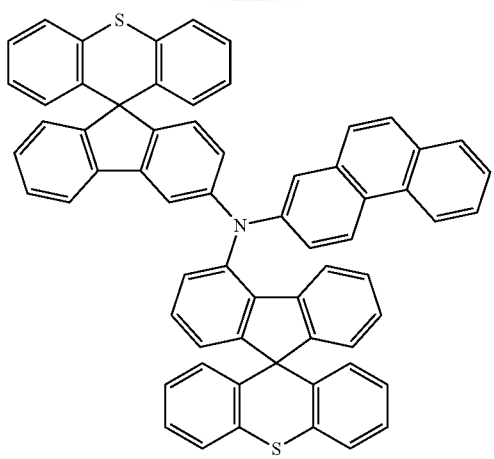
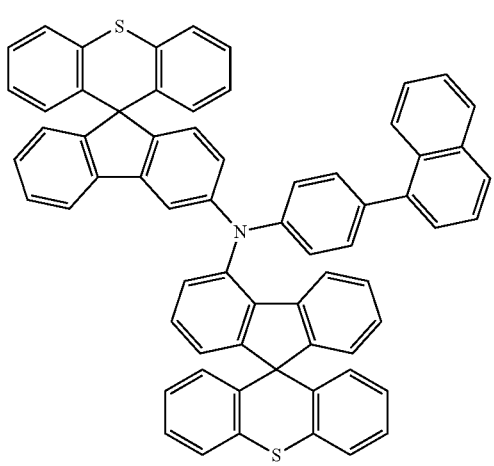
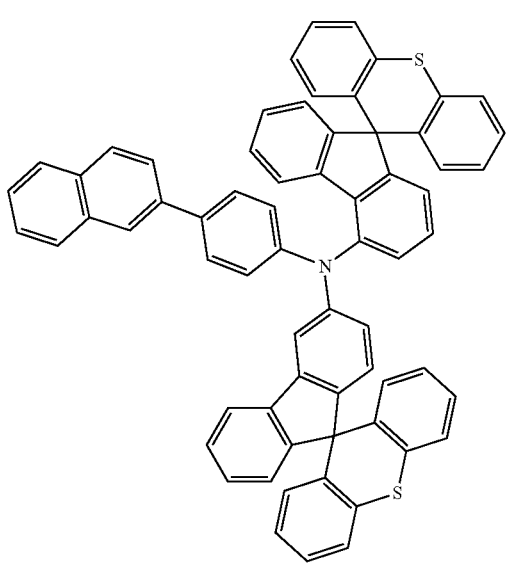
128
-continued
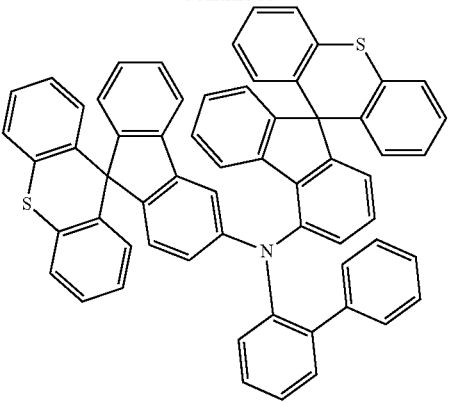
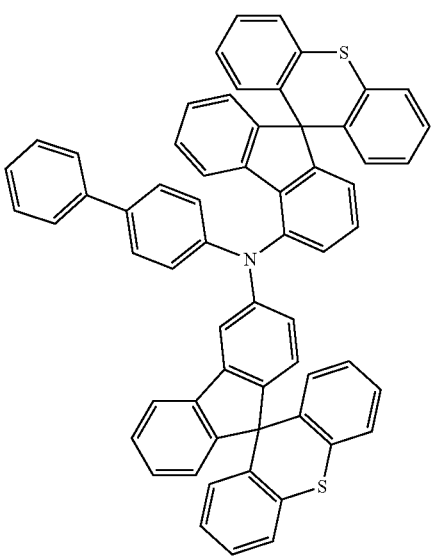
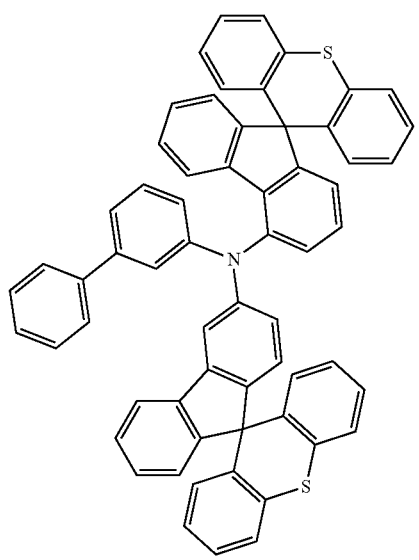

129
-continued
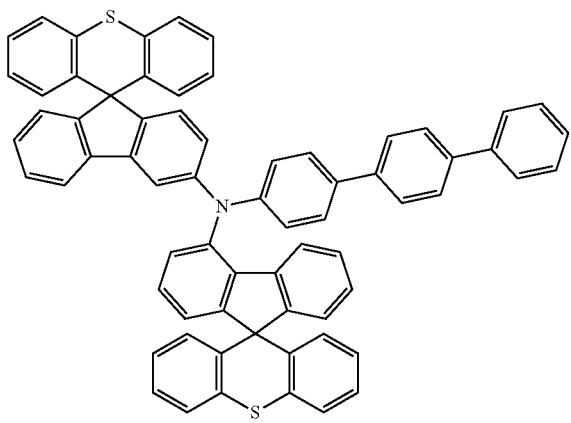
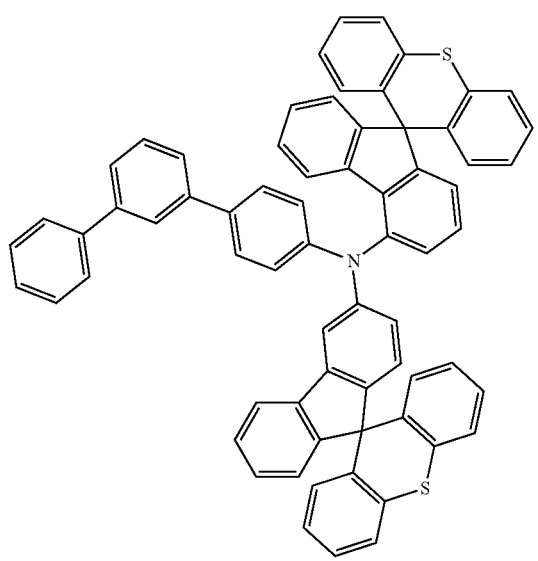
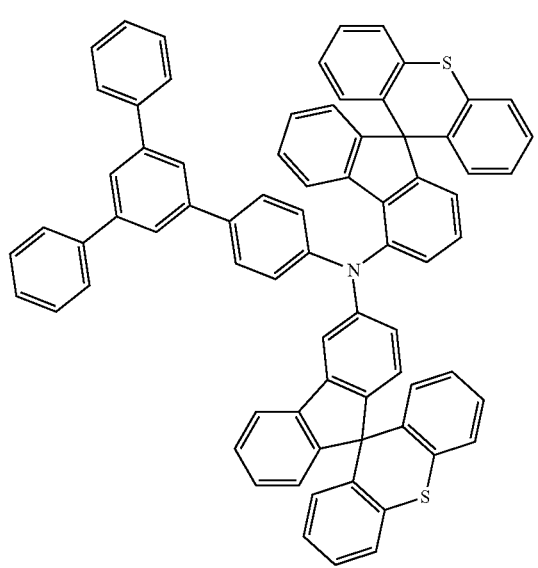
130
-continued
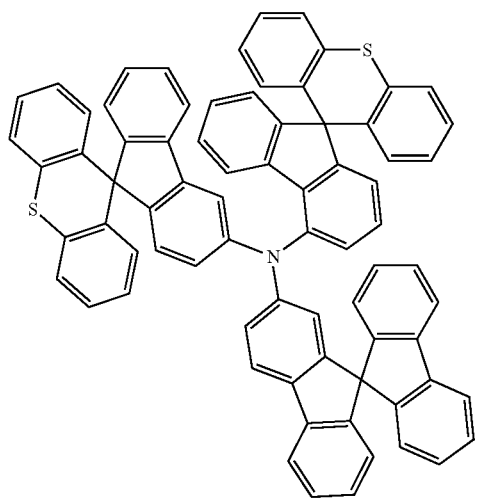
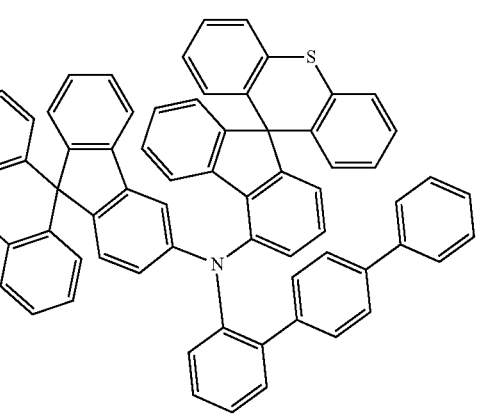
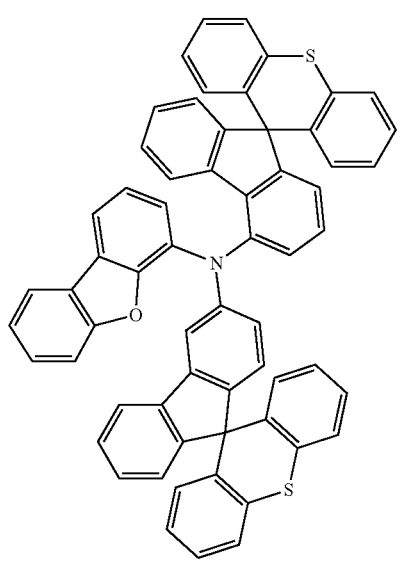

131
-continued
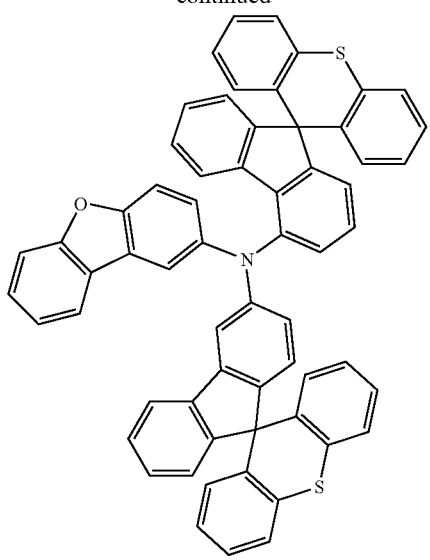
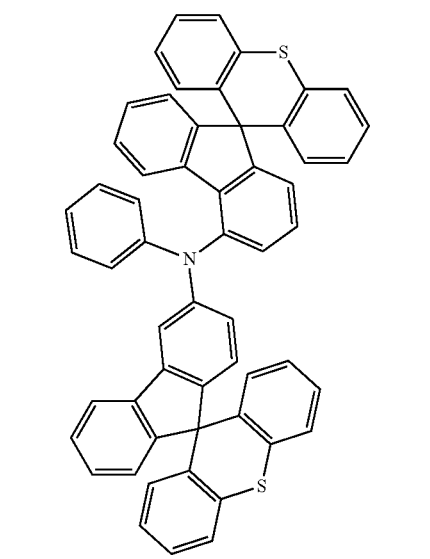
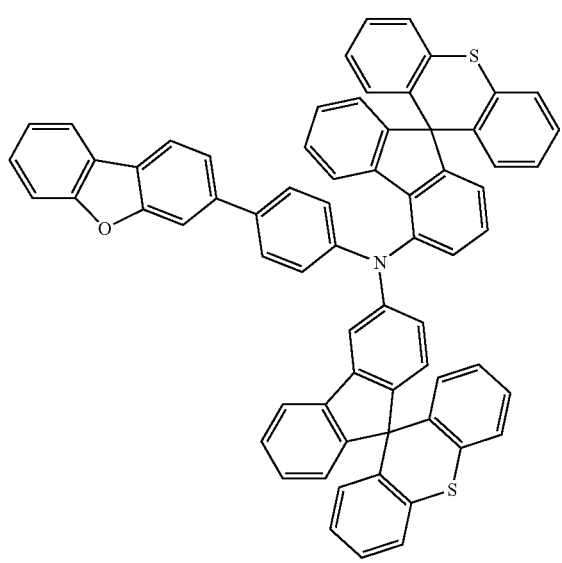
132
-continued
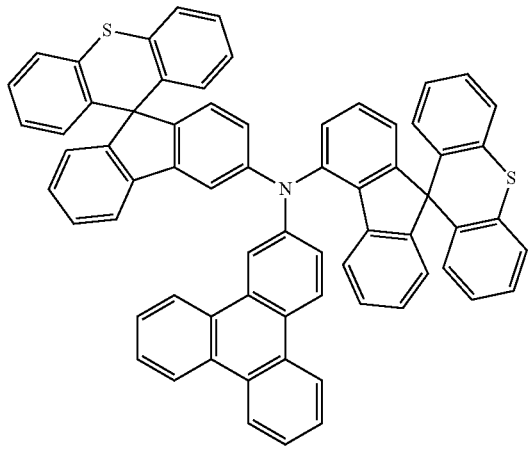
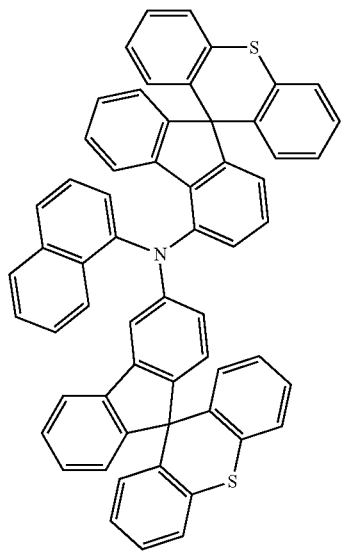
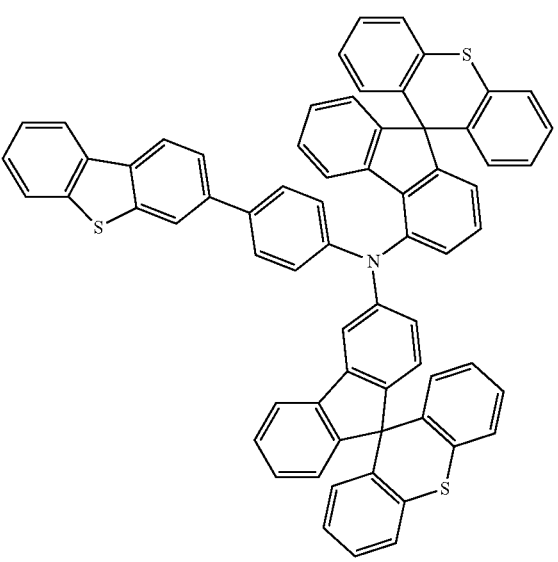

133
-continued
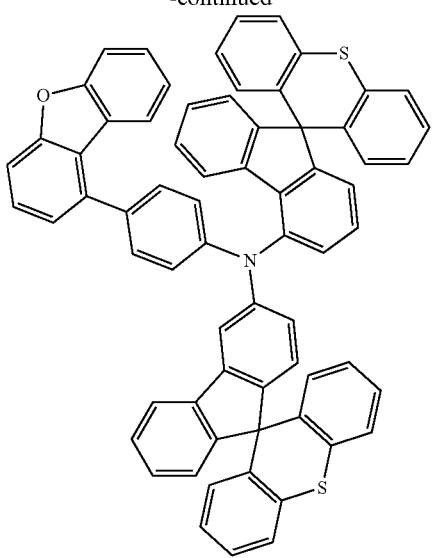
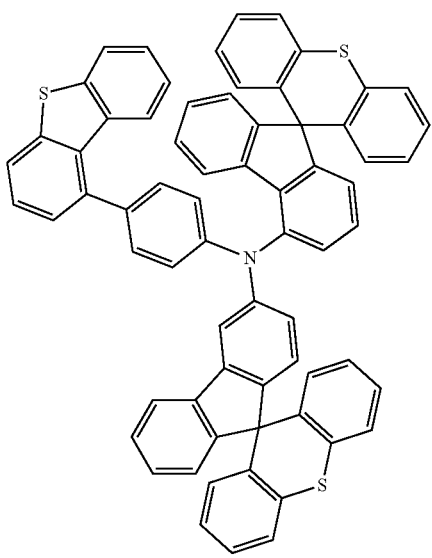
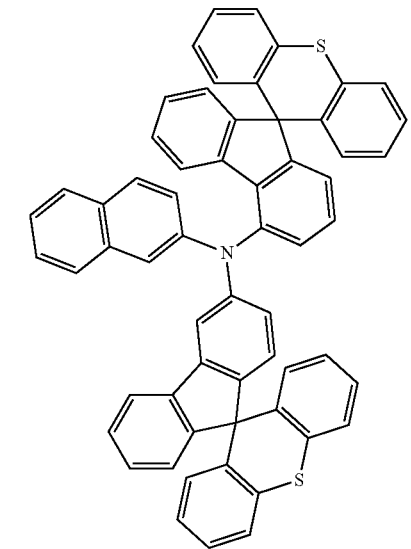
134
-continued
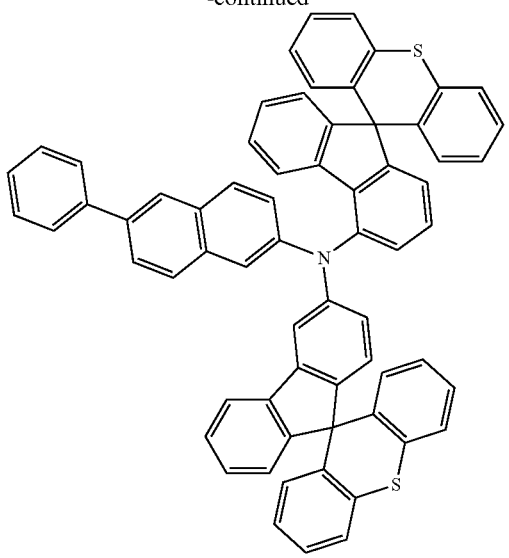

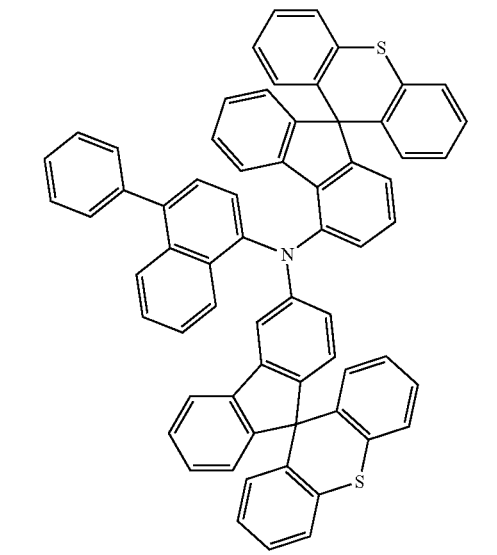

-continued
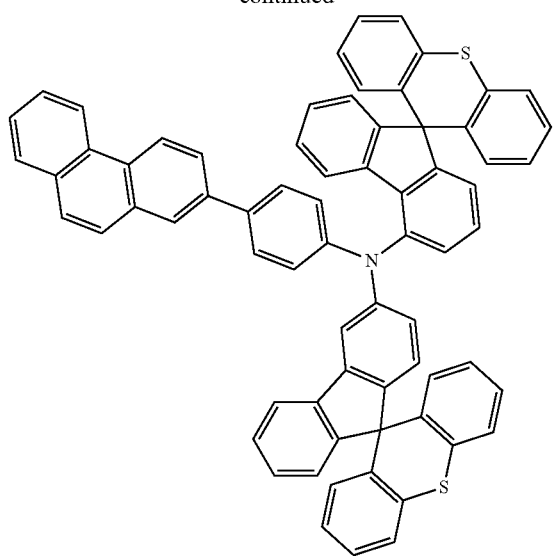
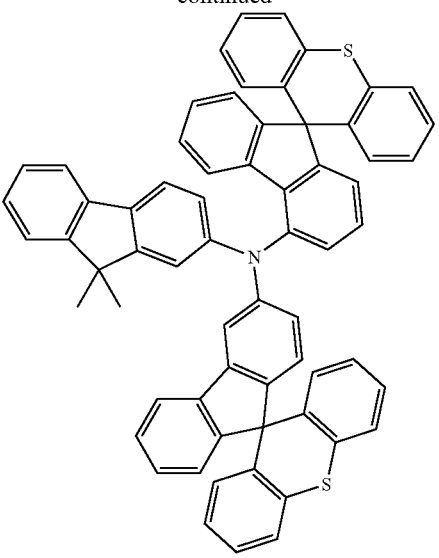
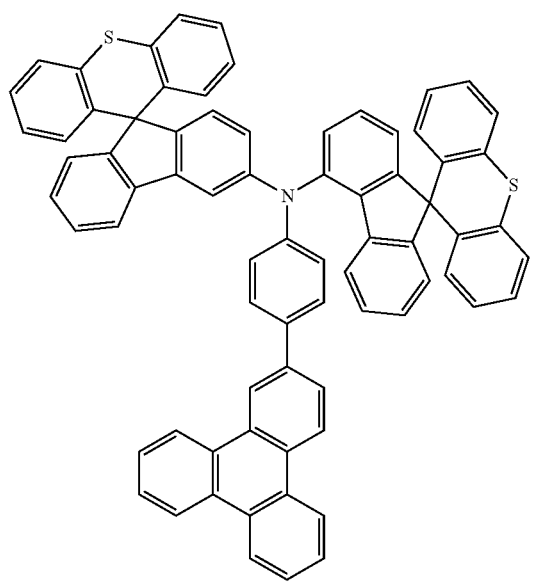
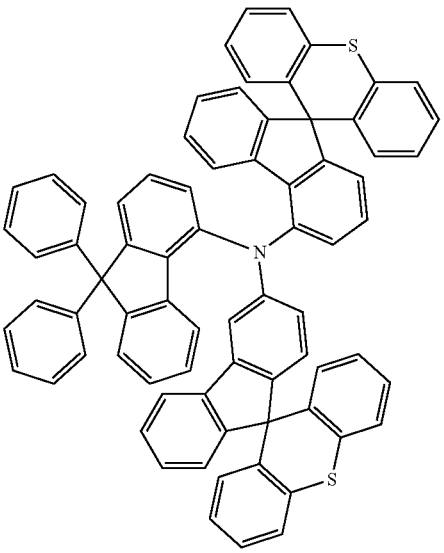
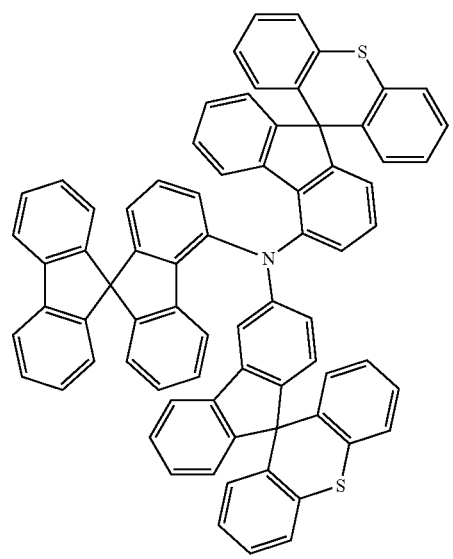
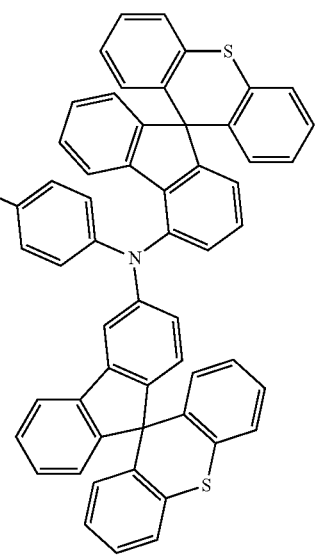

137
-continued
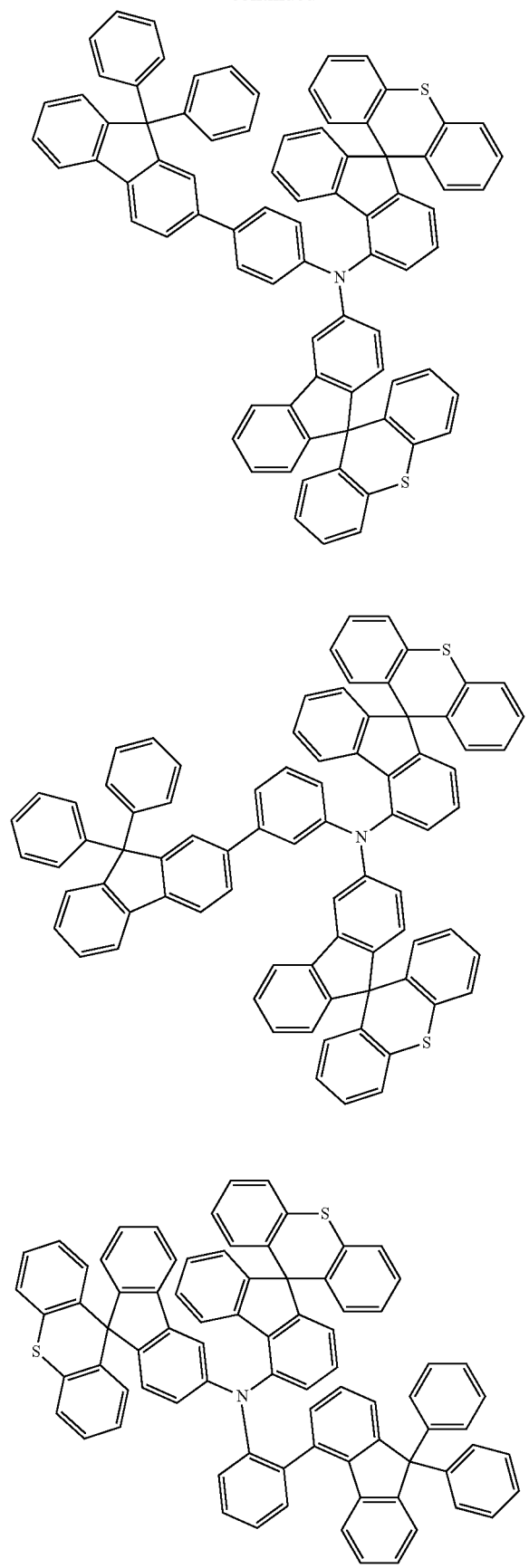
138
-continued
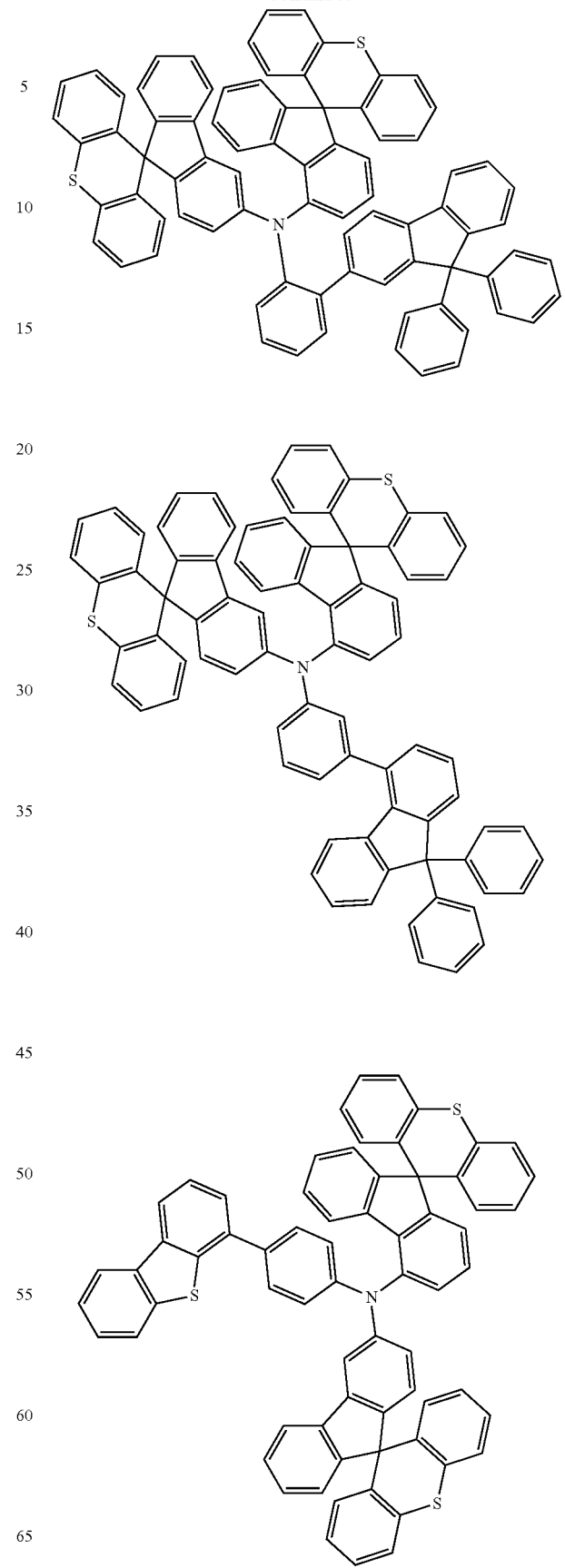

139
-continued
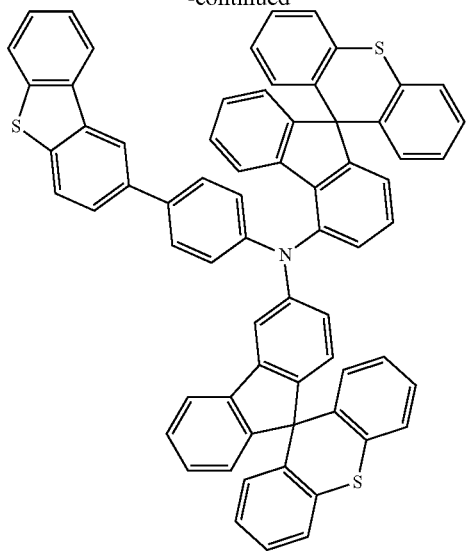
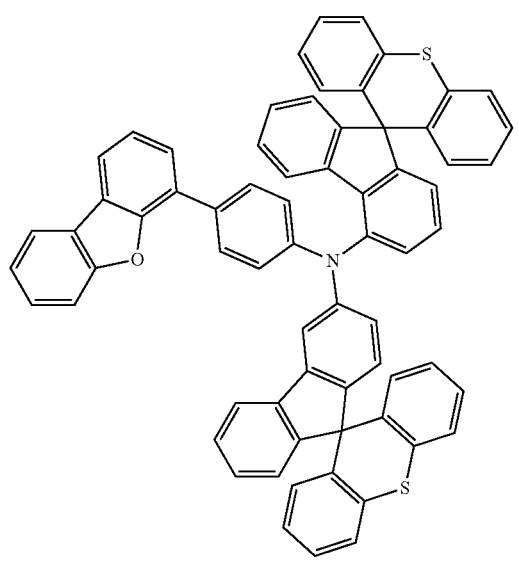
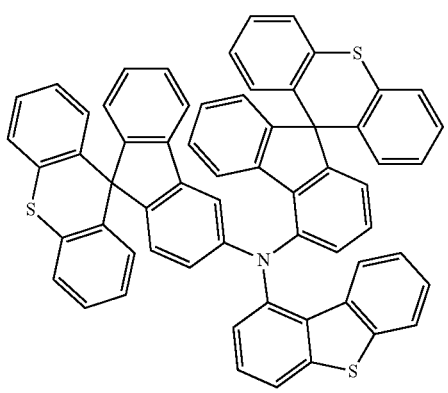
140
-continued
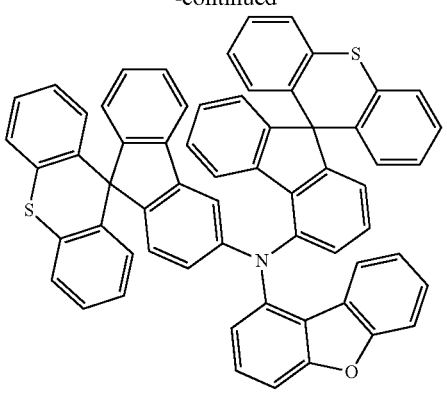
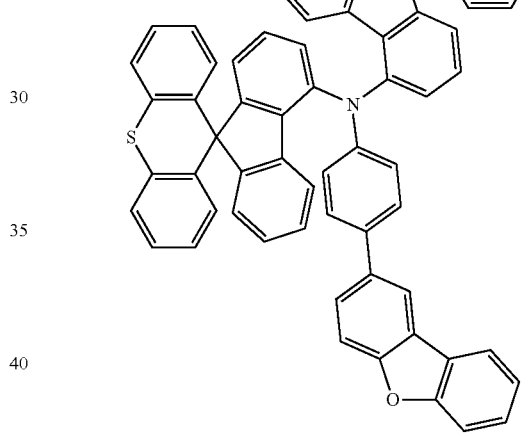
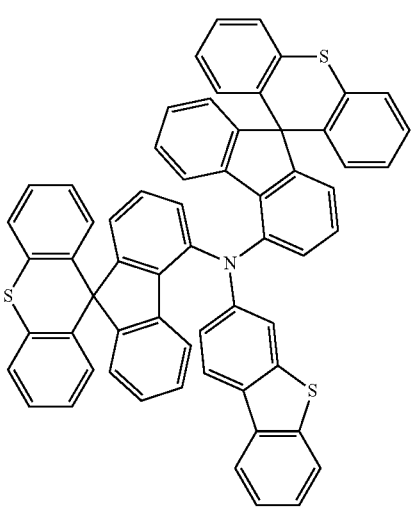

141
-continued
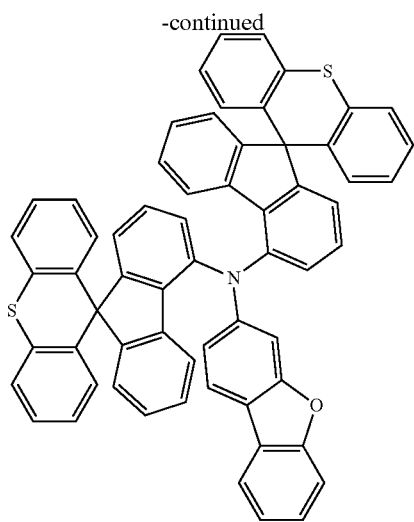
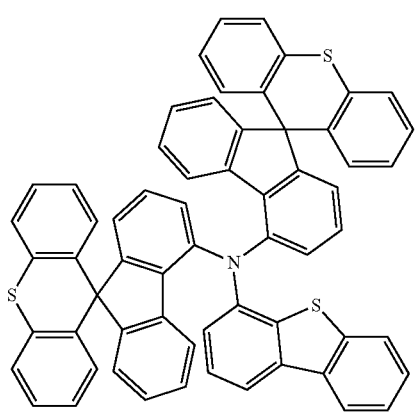
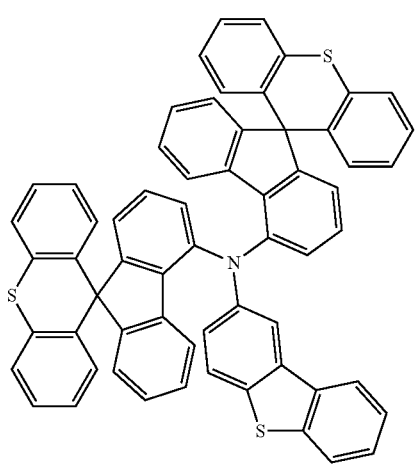
142
-continued
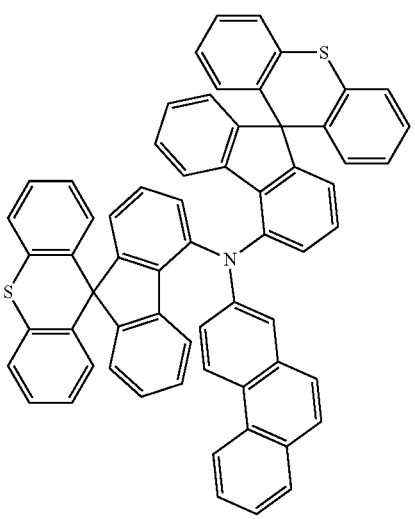
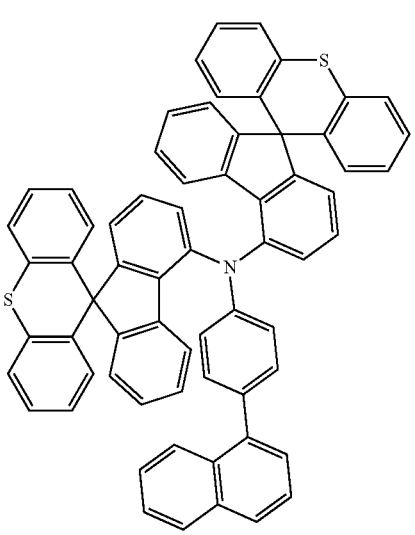
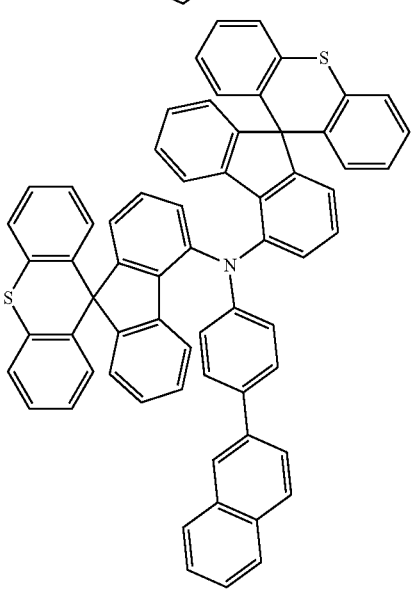

143
-continued
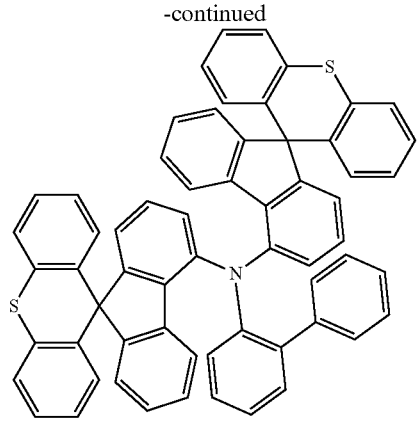
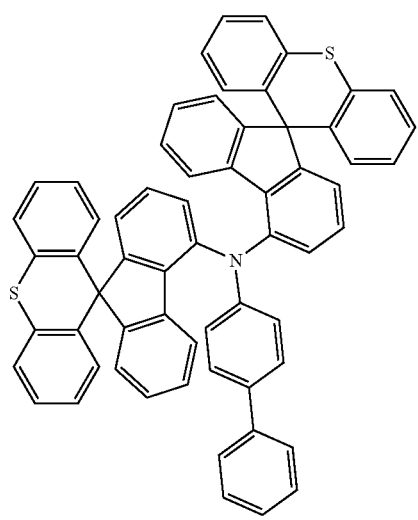
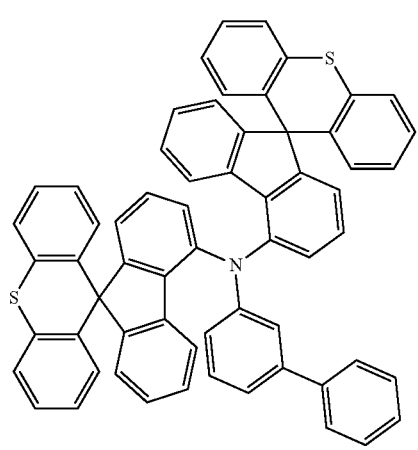
144
-continued
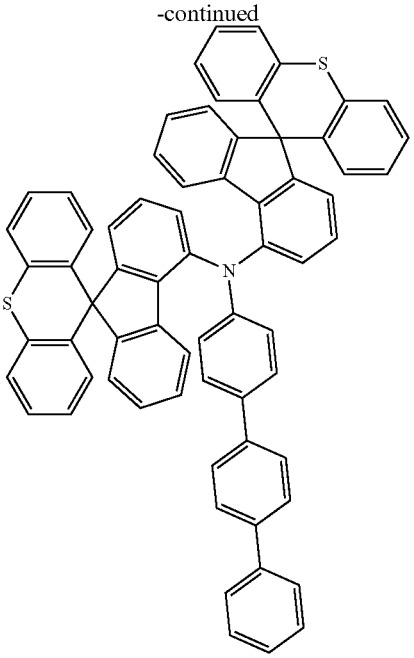
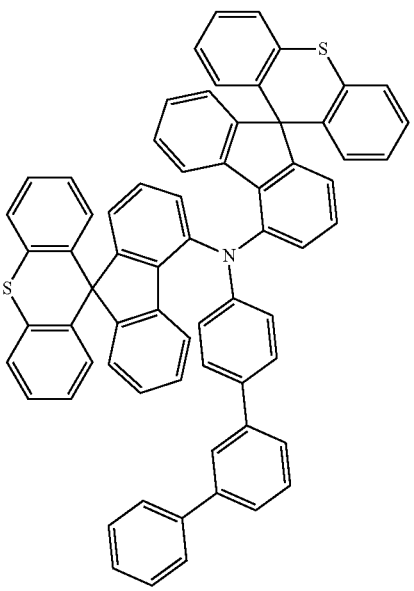

-continued
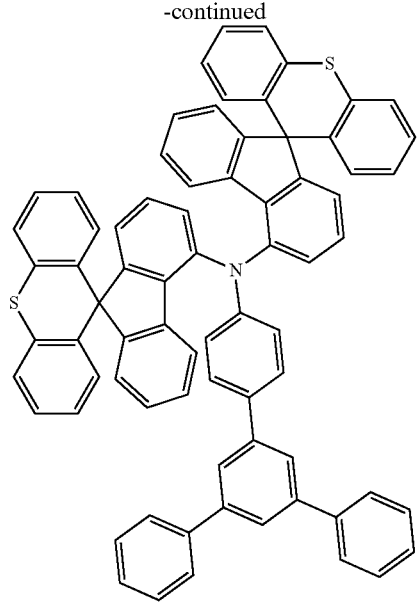
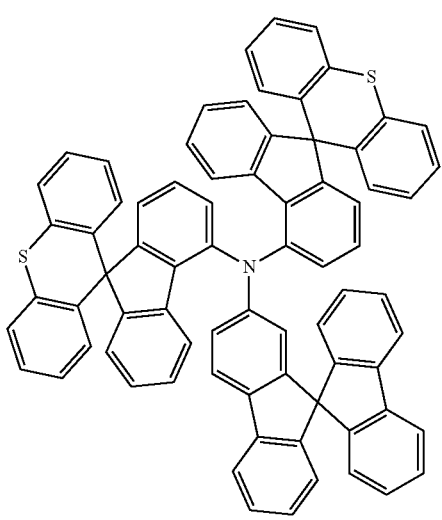
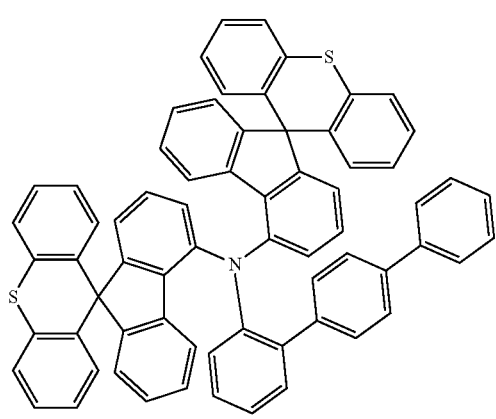
-continued
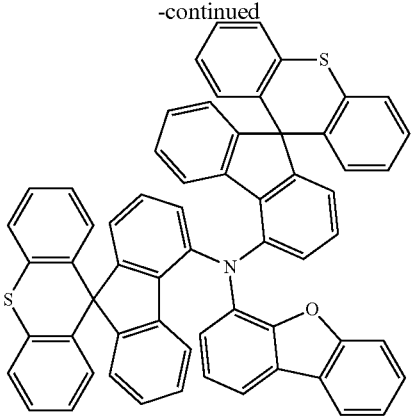
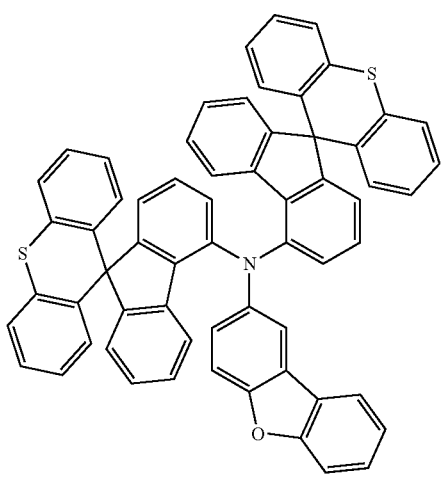
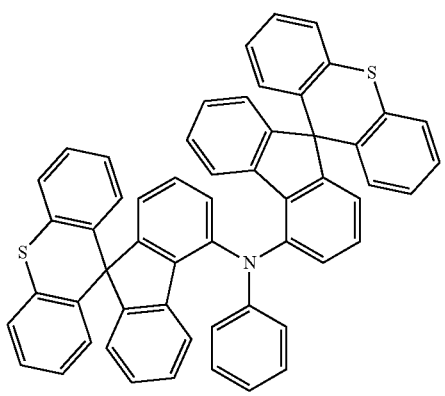

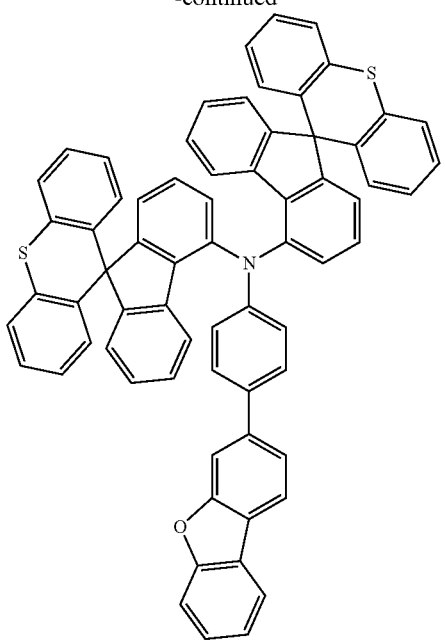
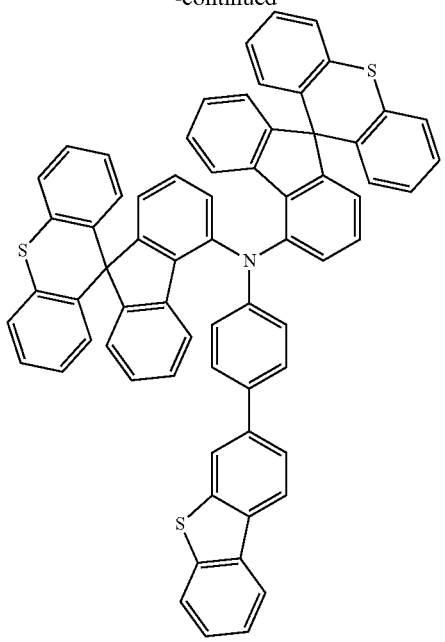
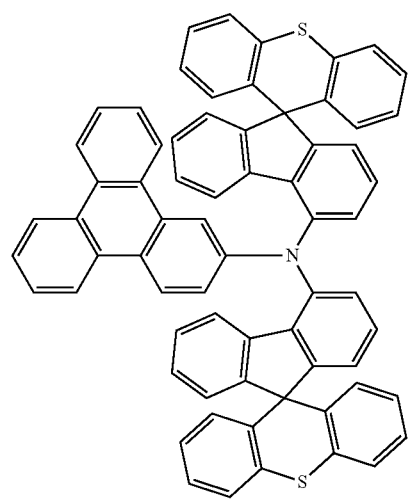
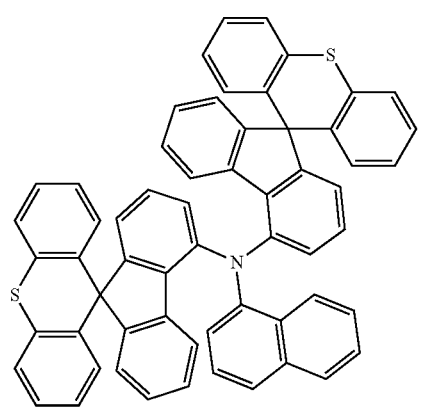
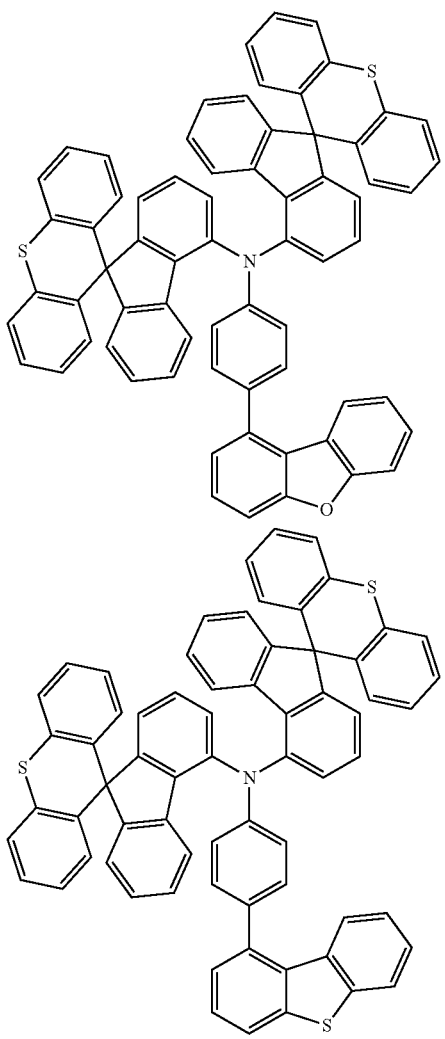

149
-continued
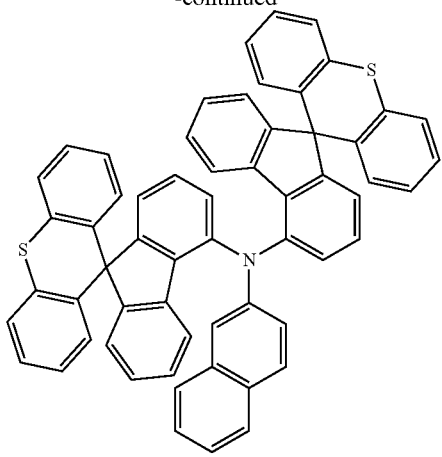
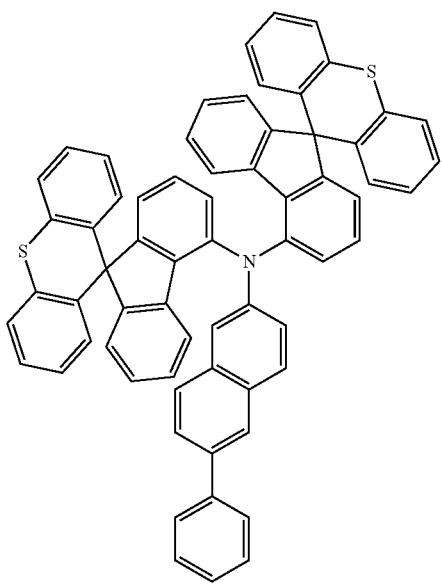
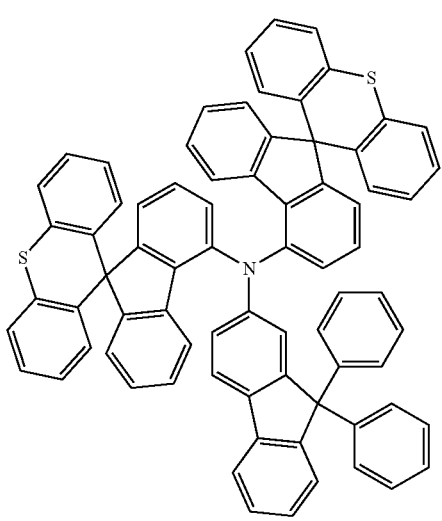
150
-continued
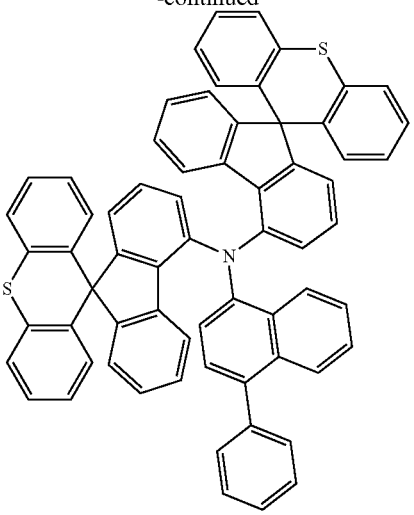
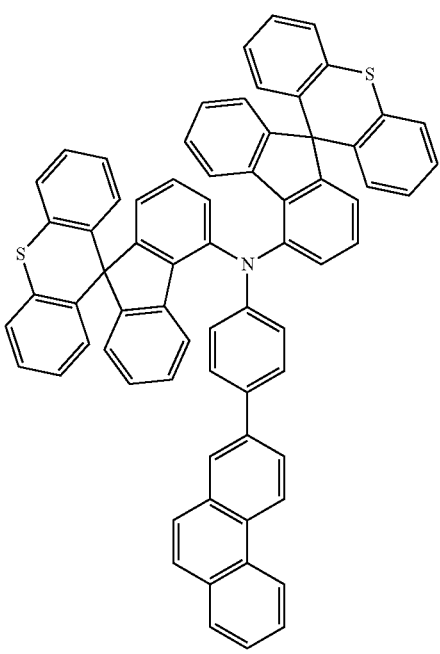

151
-continued
152
-continued
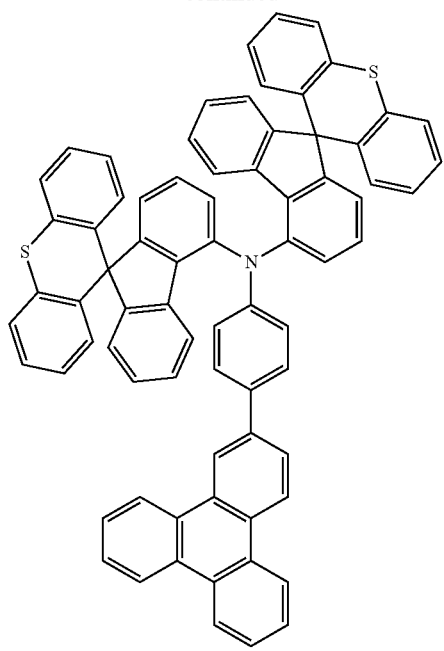
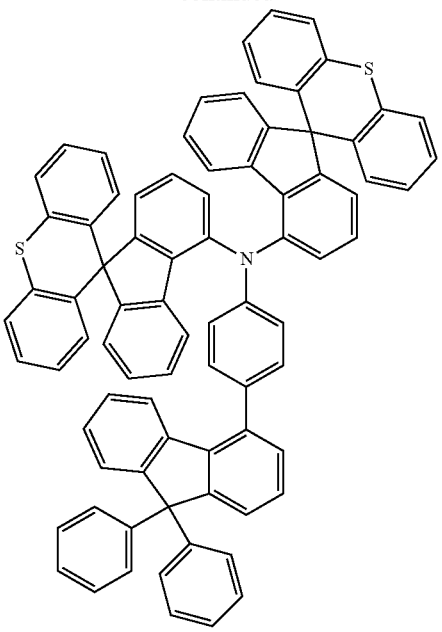
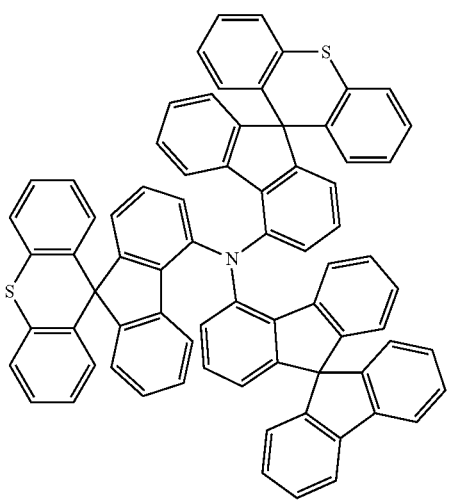
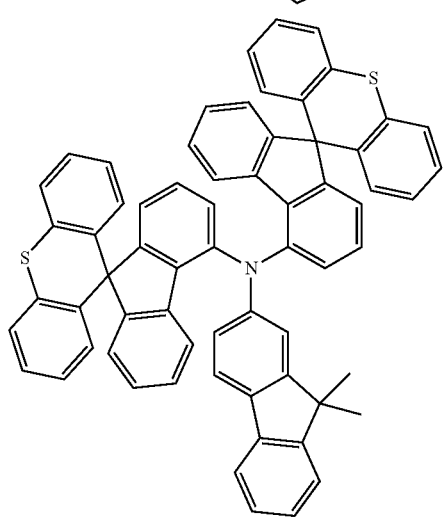
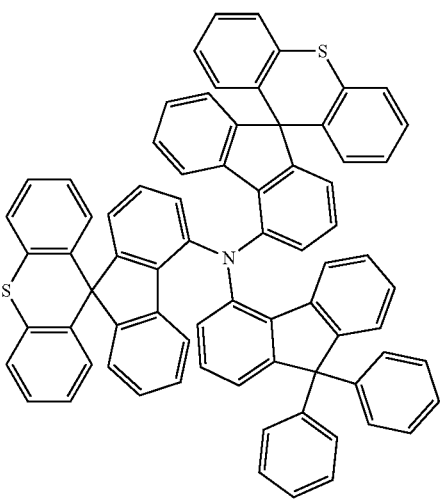

153
-continued
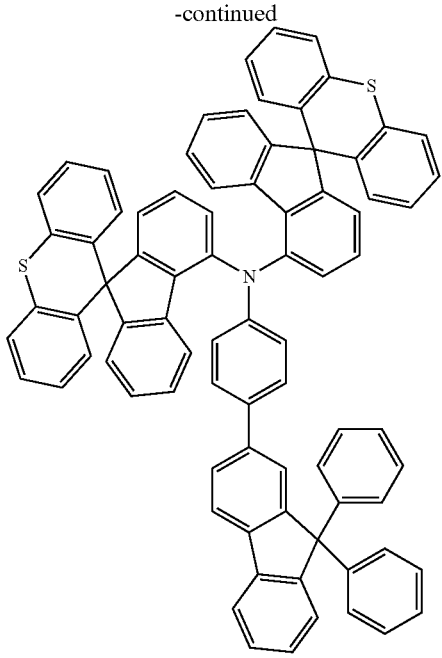
154
-continued
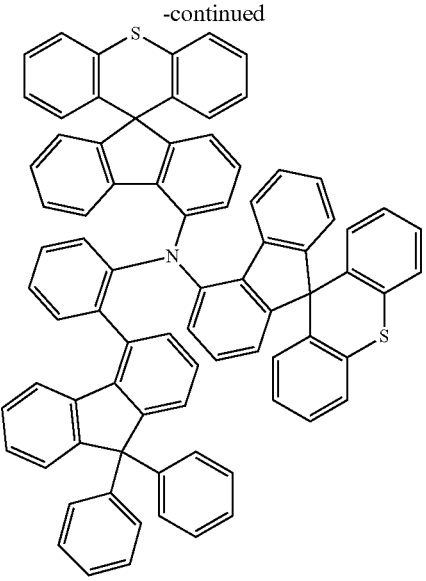
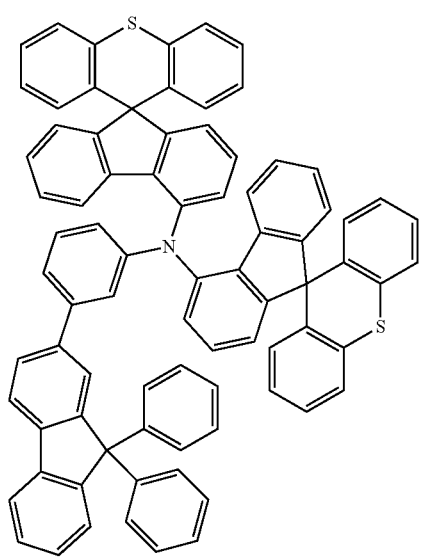
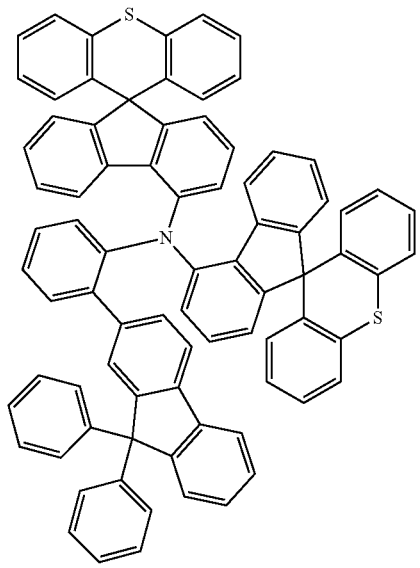

155
-continued
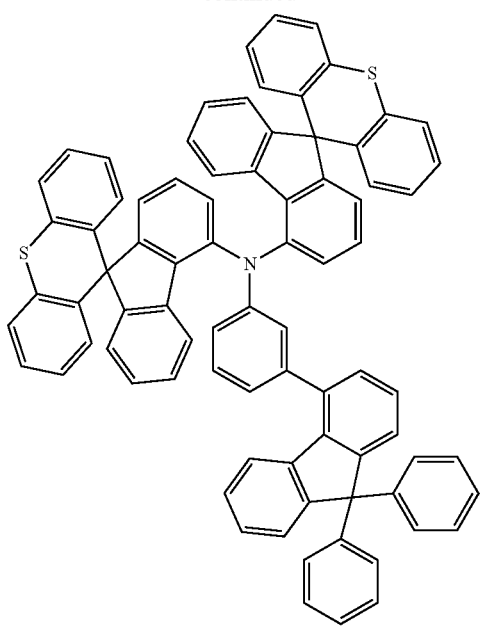
156
-continued
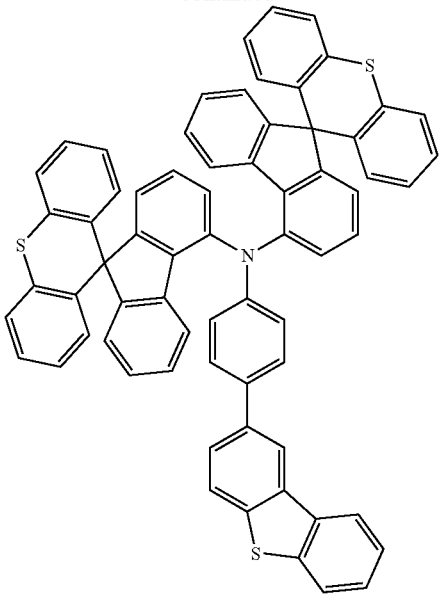
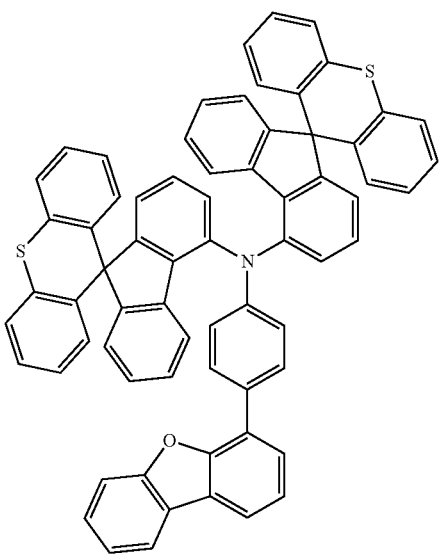
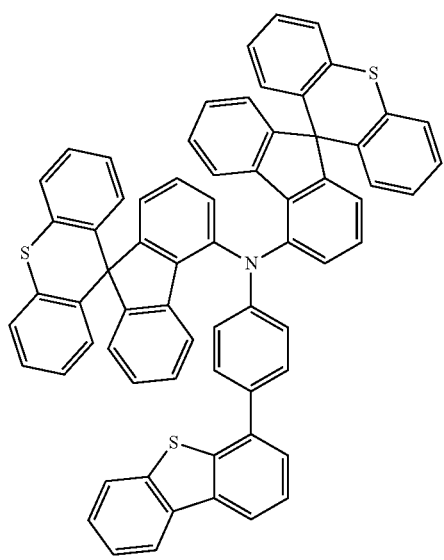
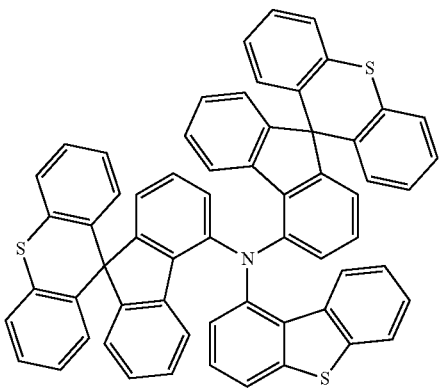

157
-continued
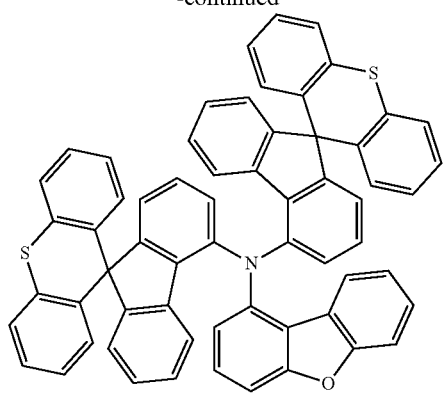
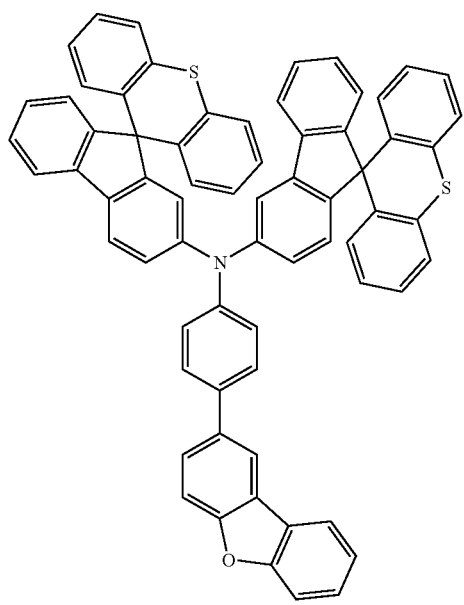
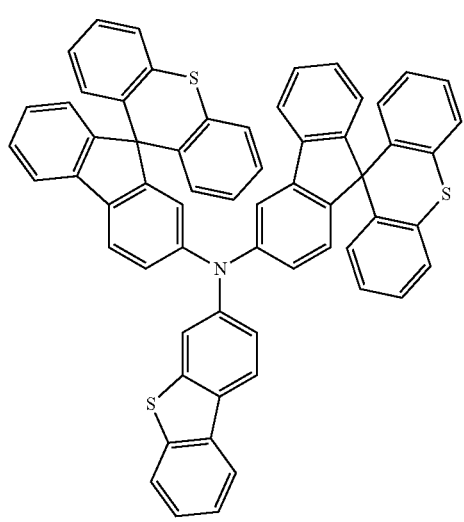
158
-continued
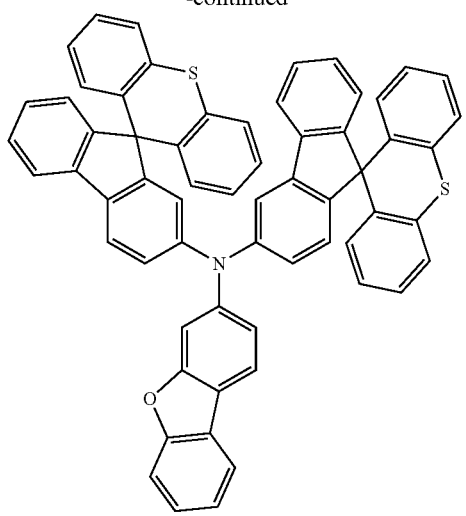
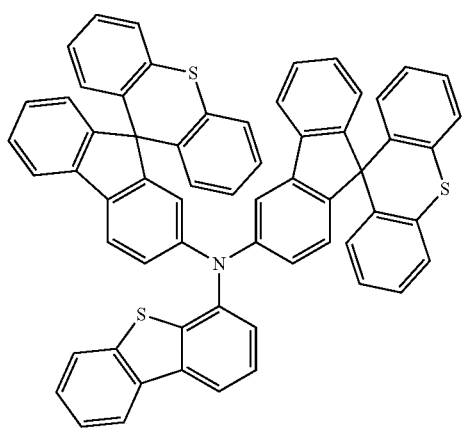
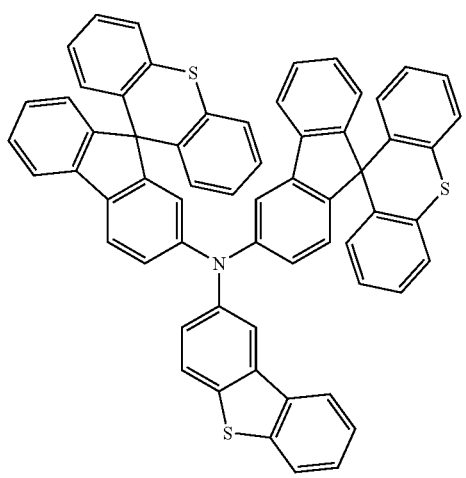

159
-continued
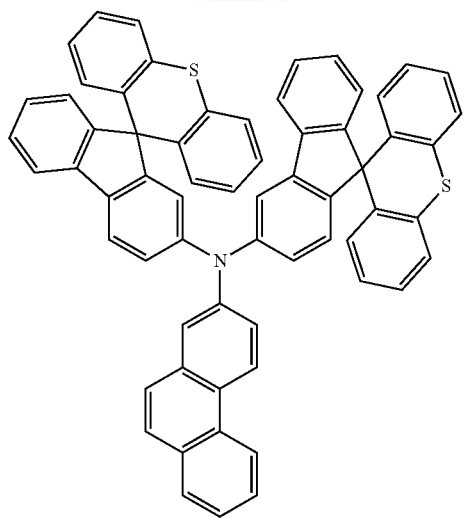
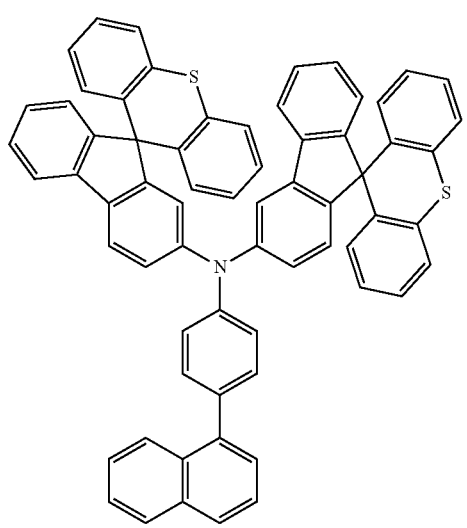
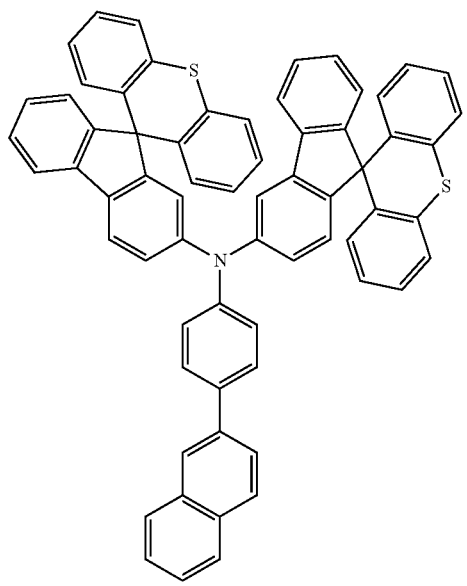
160
-continued
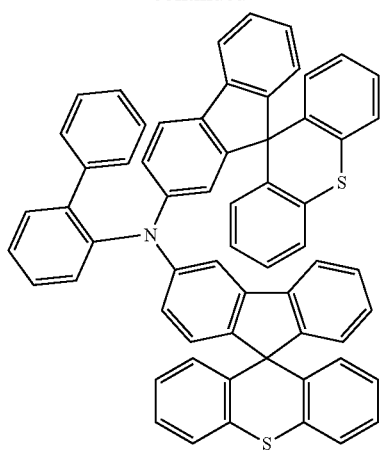
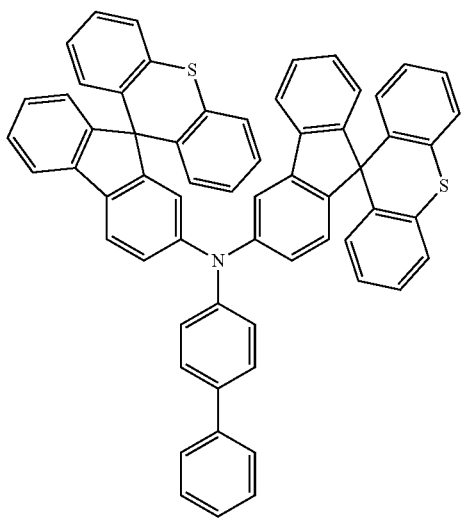
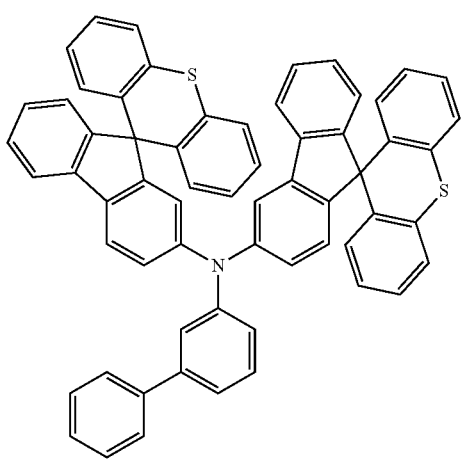

161
-continued
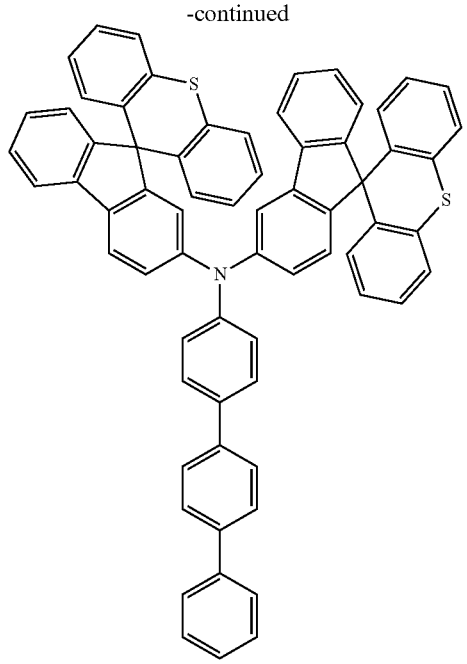
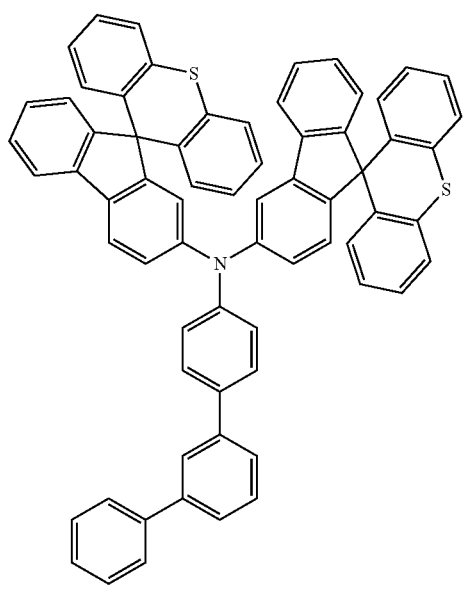
162
-continued
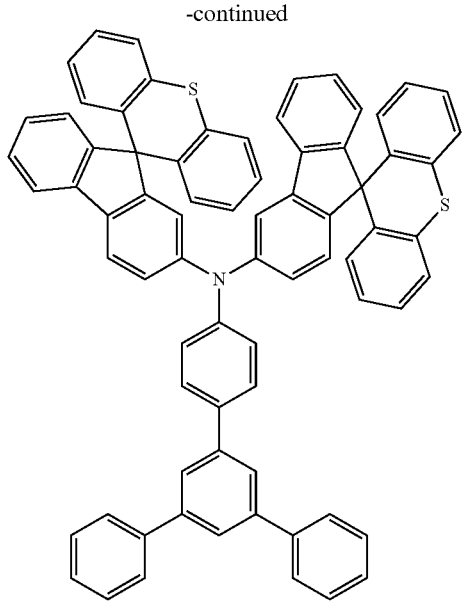
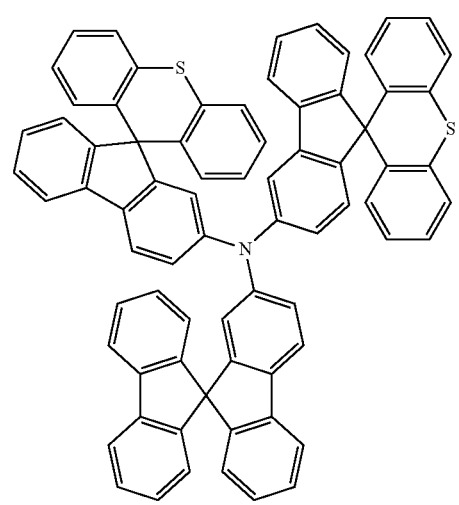
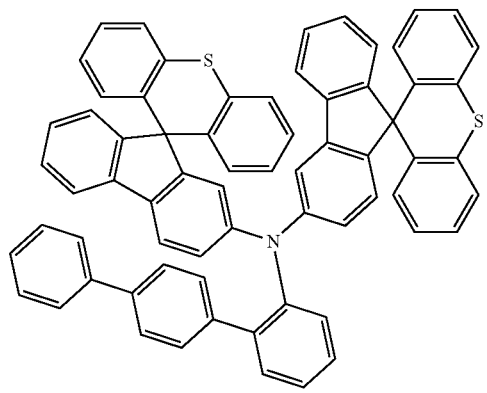

163
-continued
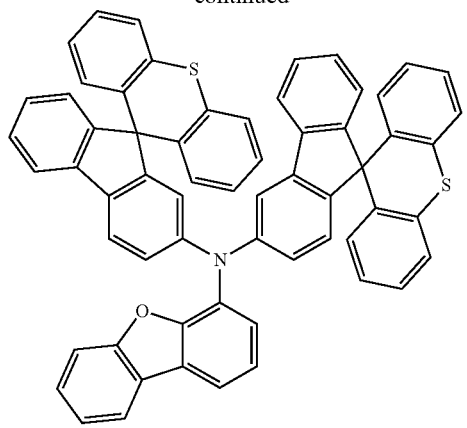
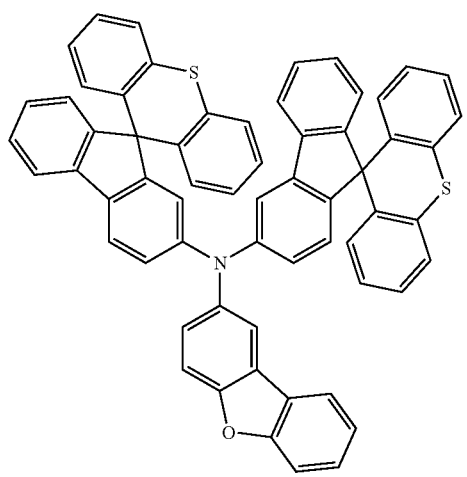
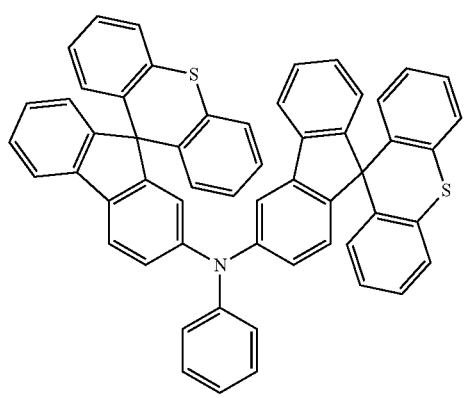
164
-continued
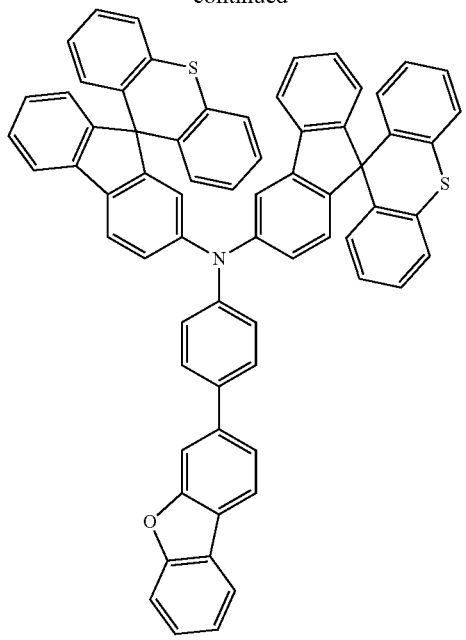
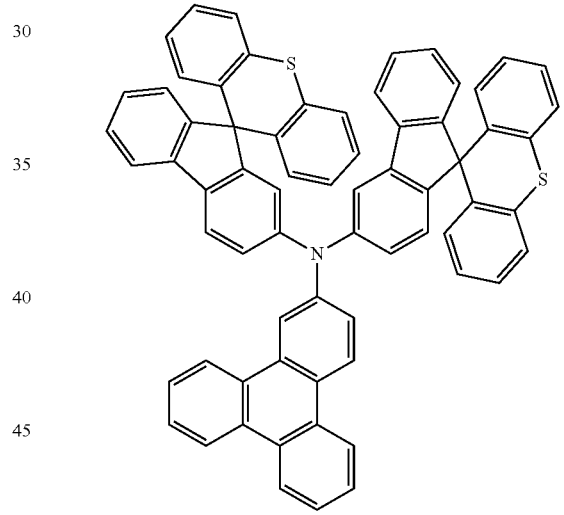
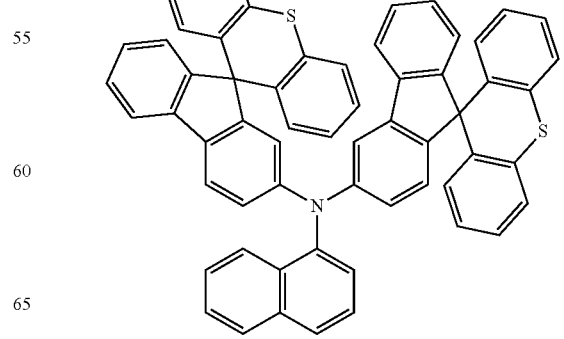

165
-continued
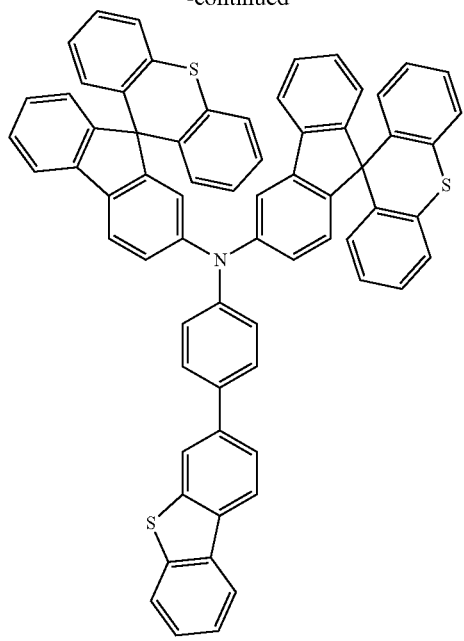
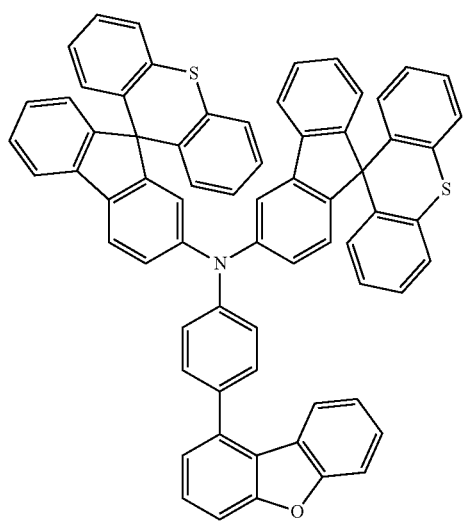
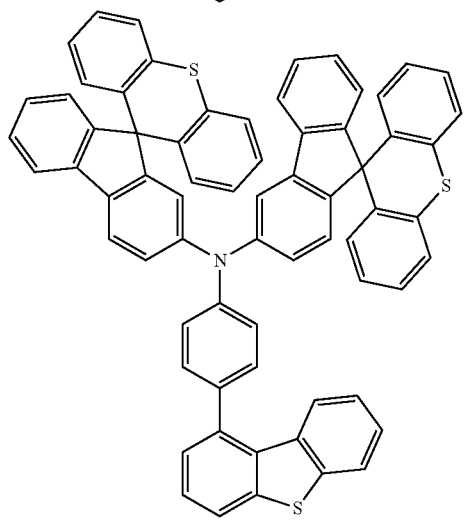
166
-continued
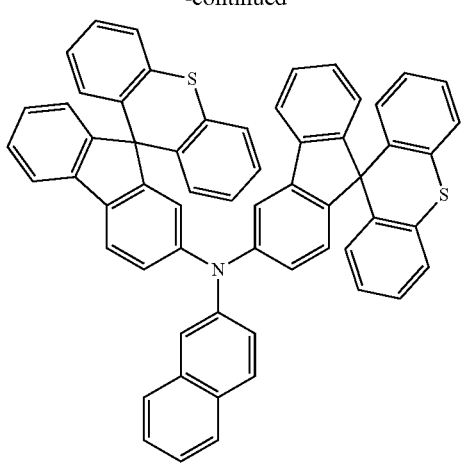
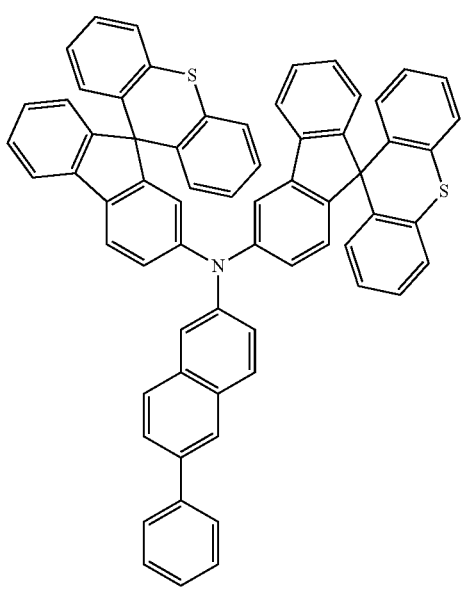
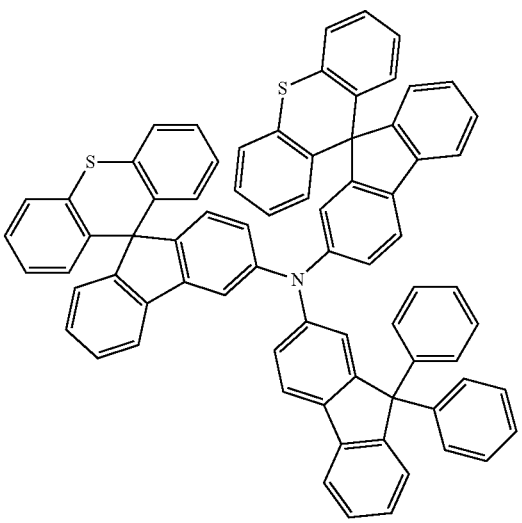

167
-continued
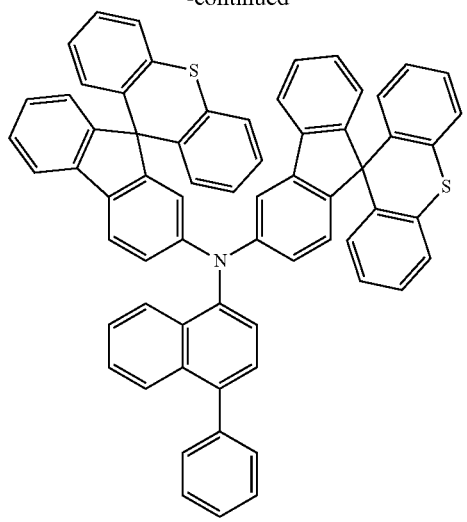
168
-continued
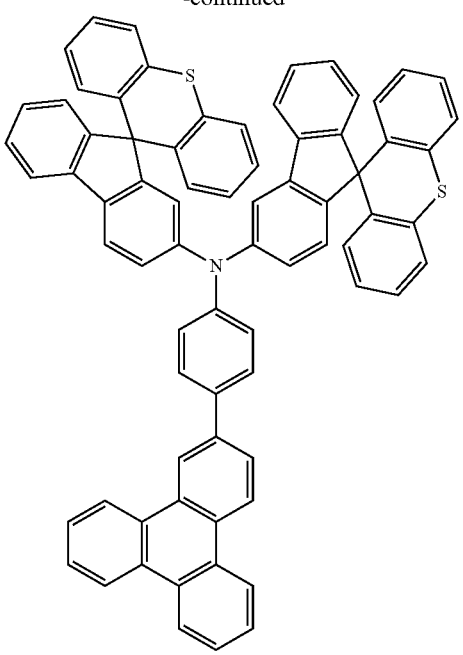
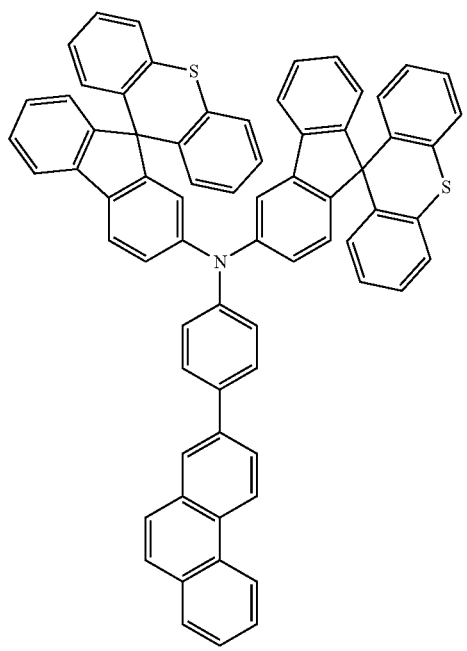
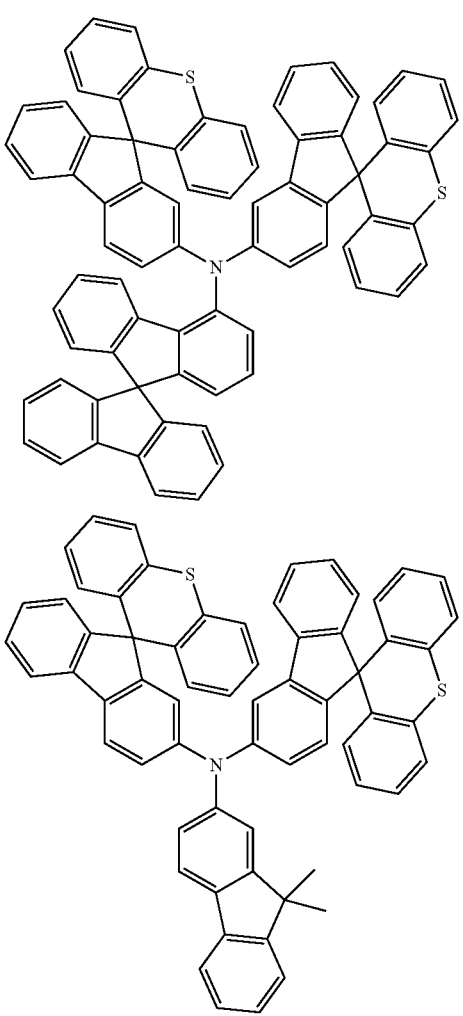

169
-continued
170
-continued
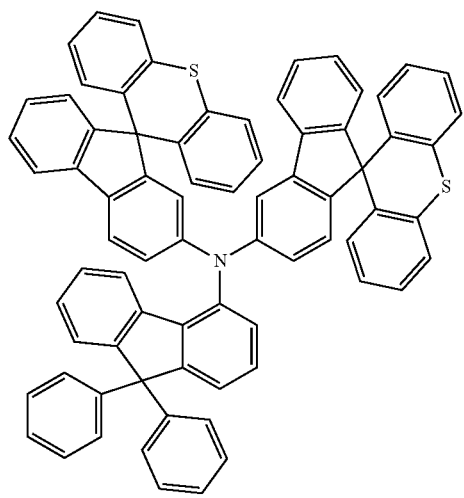
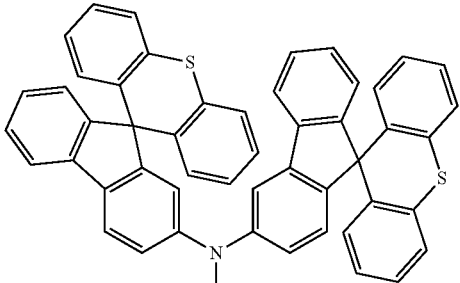
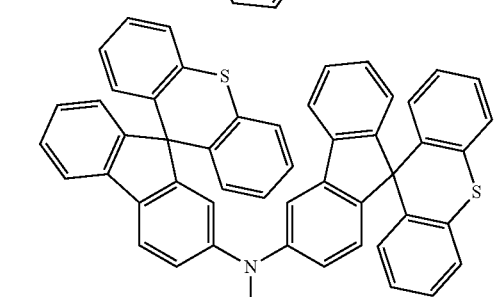
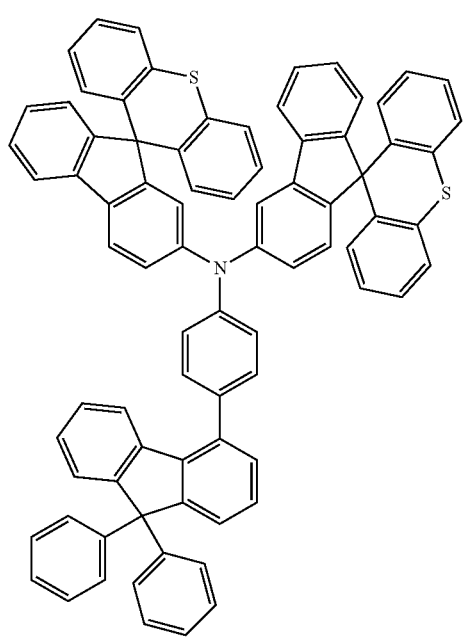
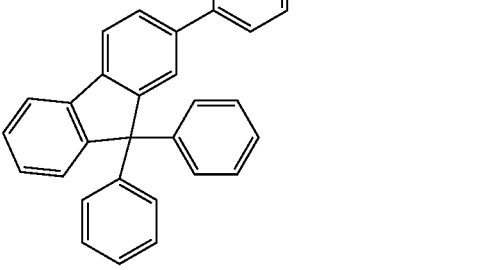
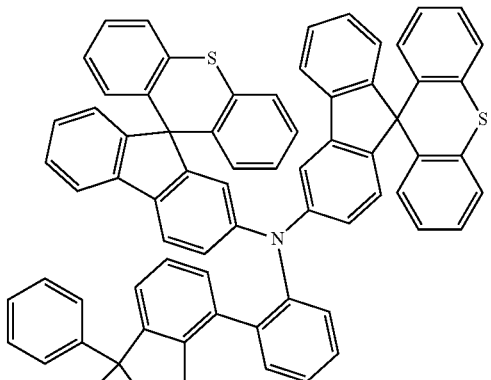

171
-continued
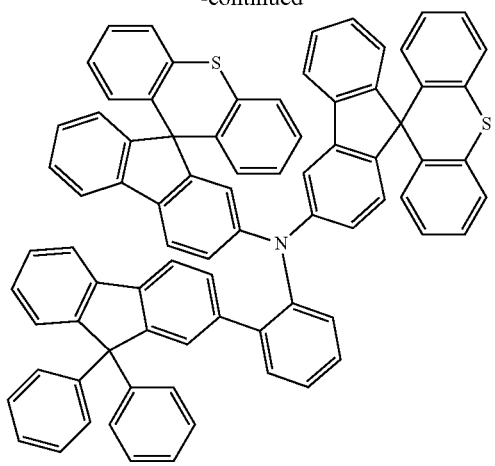
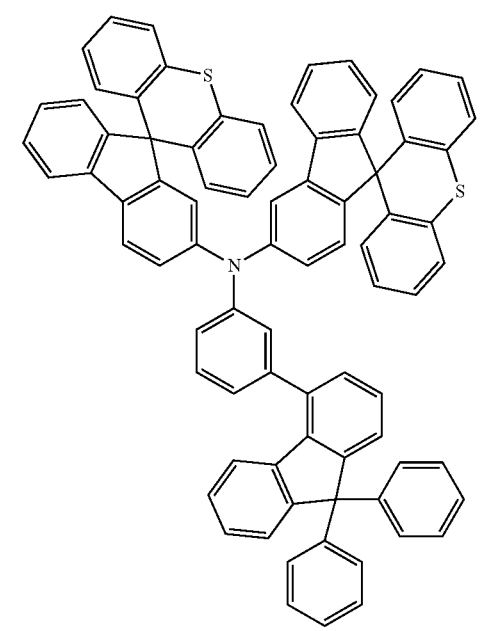
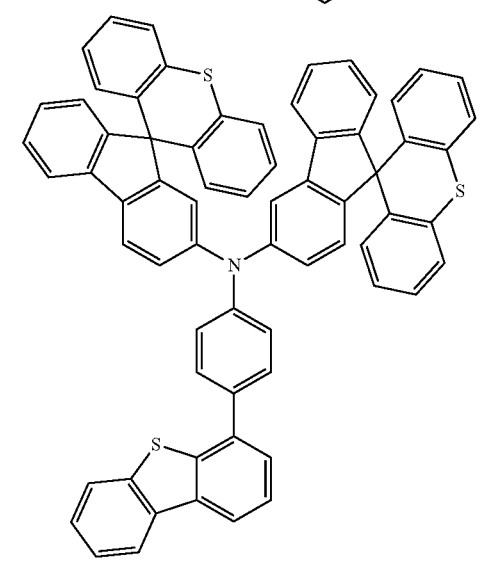
172
-continued
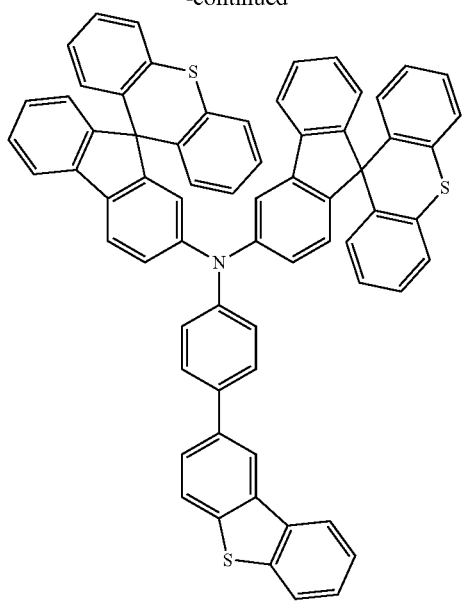
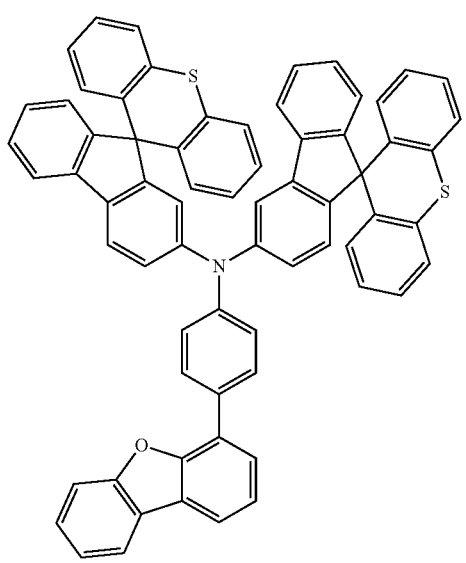
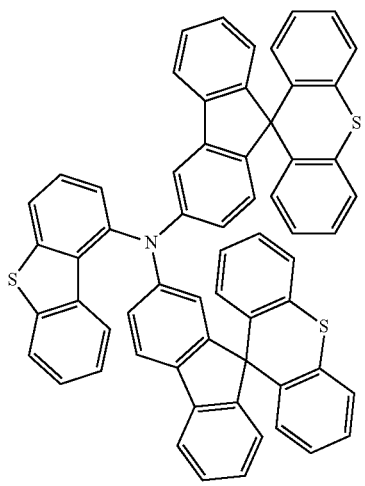

173
-continued
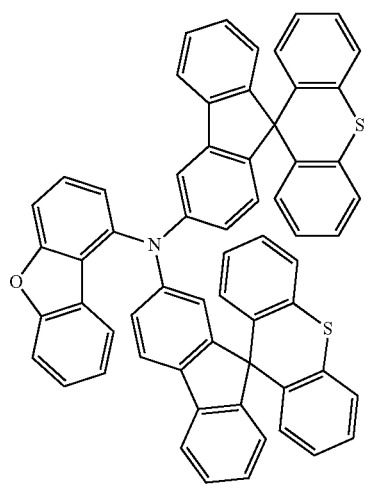
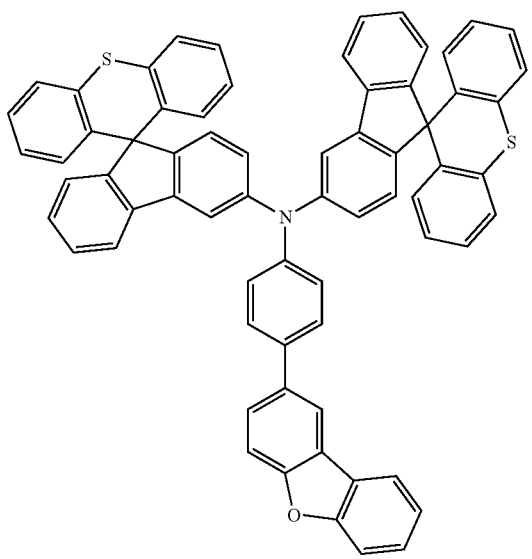
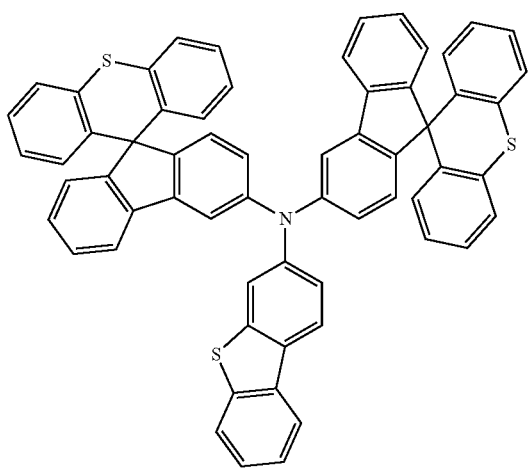
174
-continued
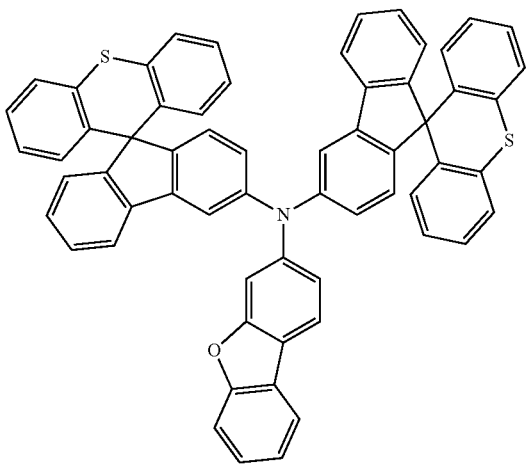
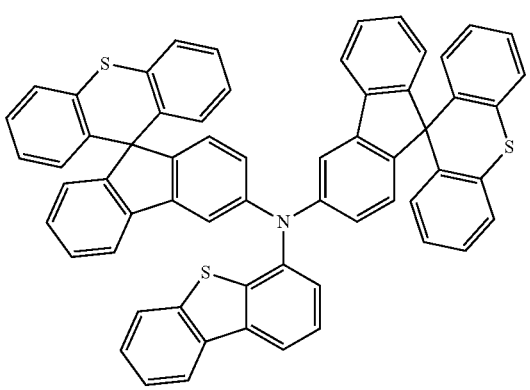
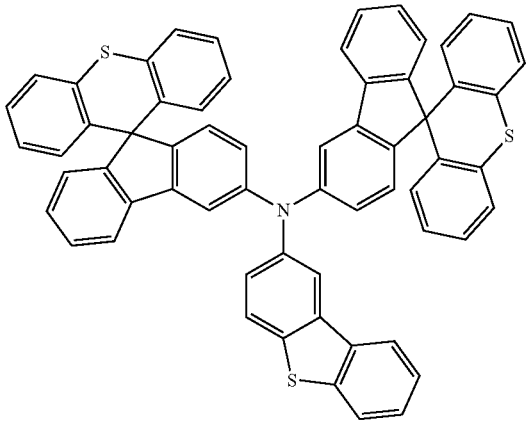

175
-continued
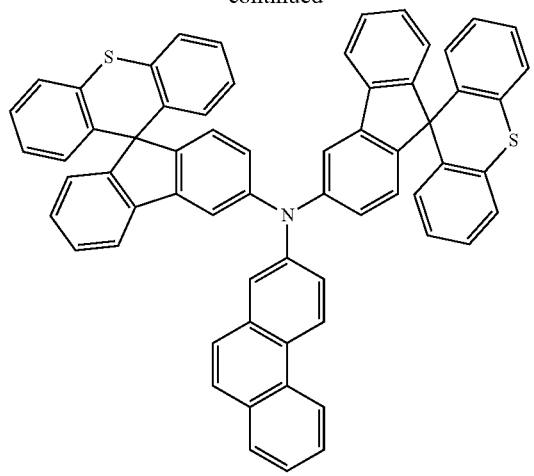
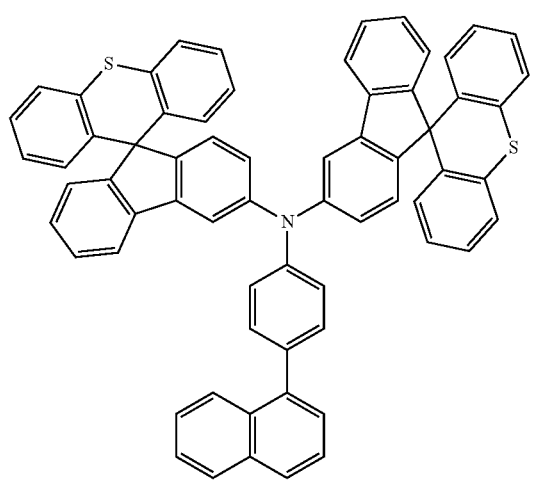
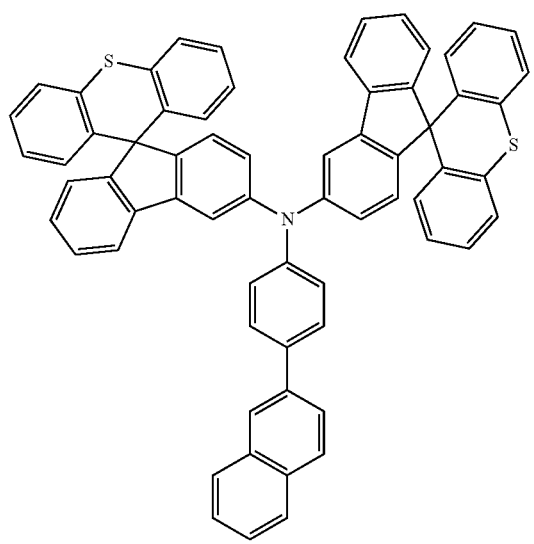
176
-continued
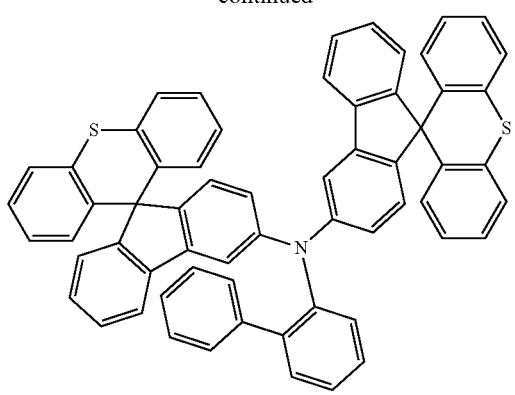
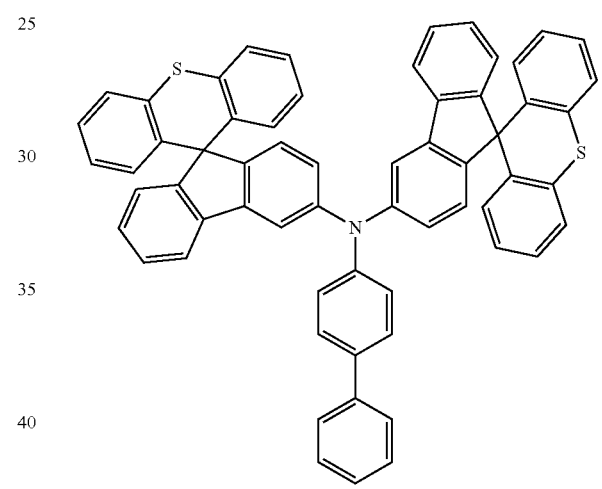
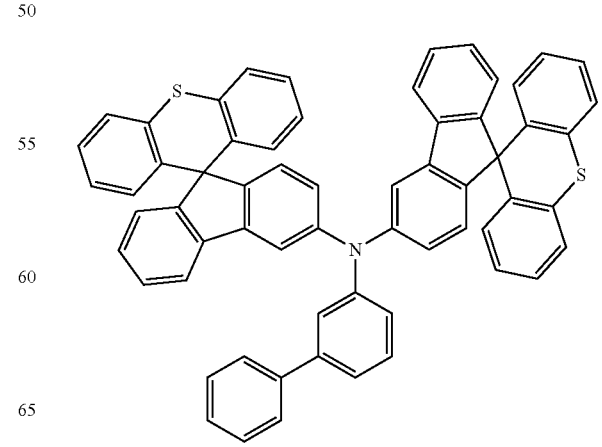

177
-continued
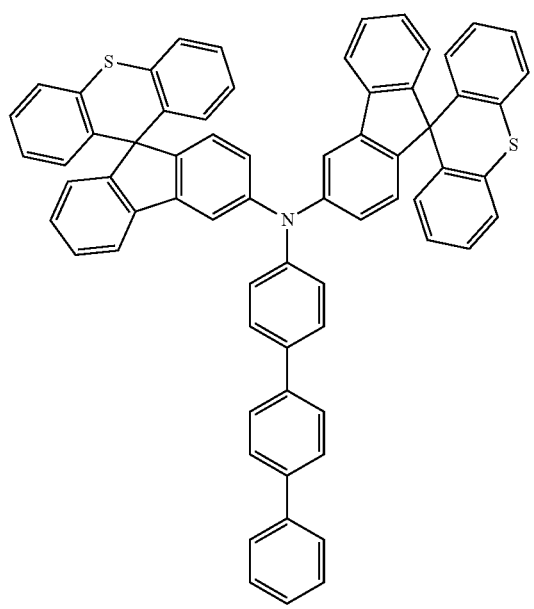
178
-continued
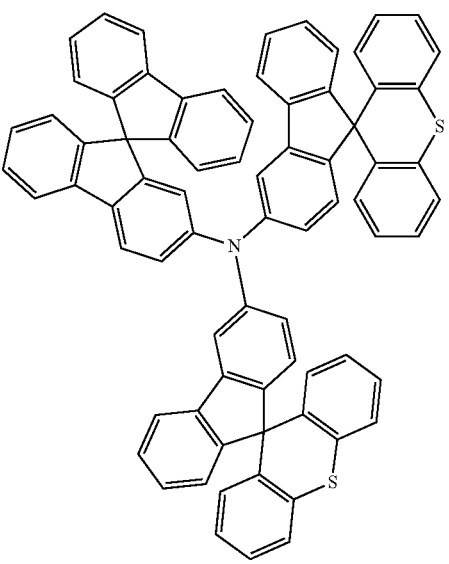
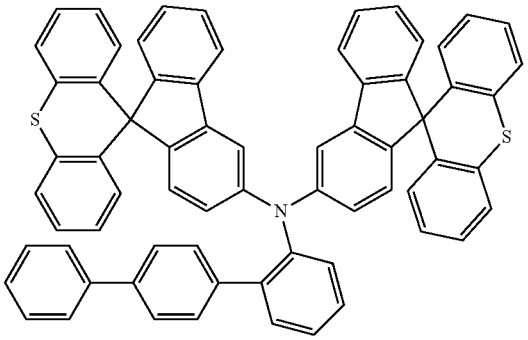
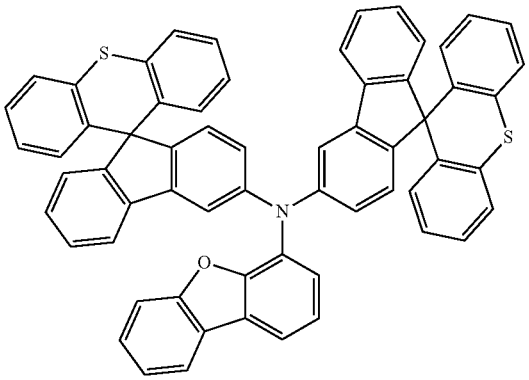
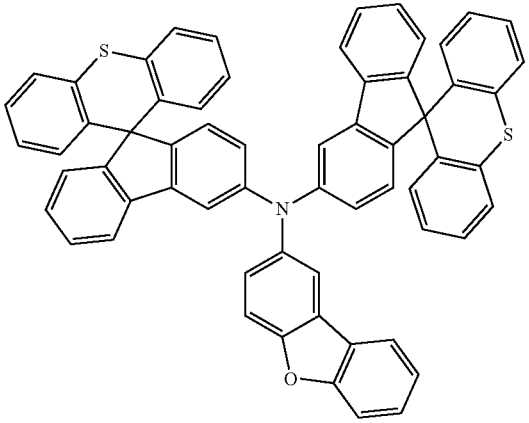

179
-continued
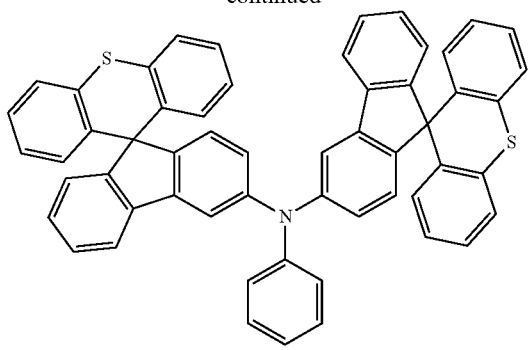
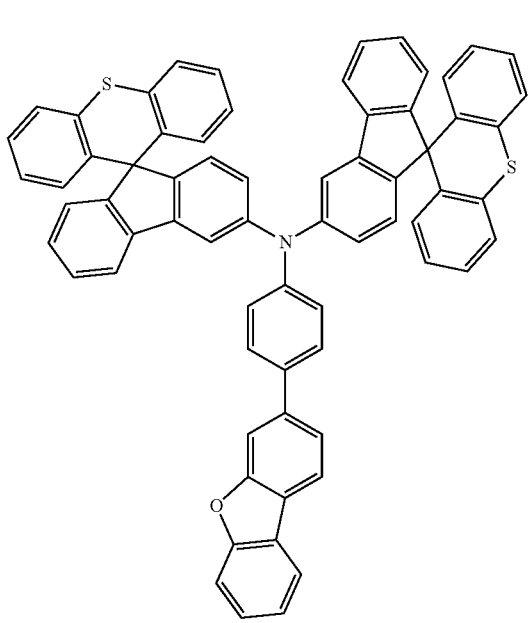
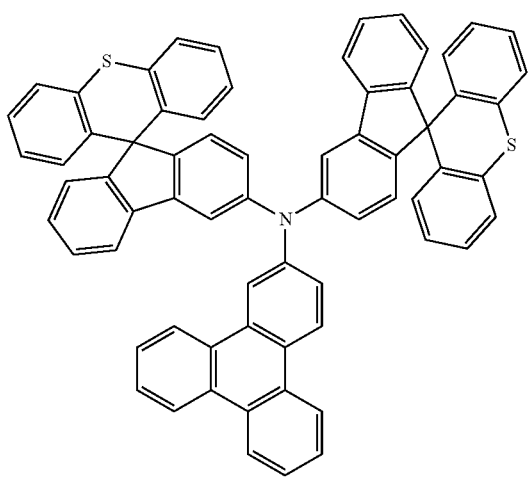
180
-continued
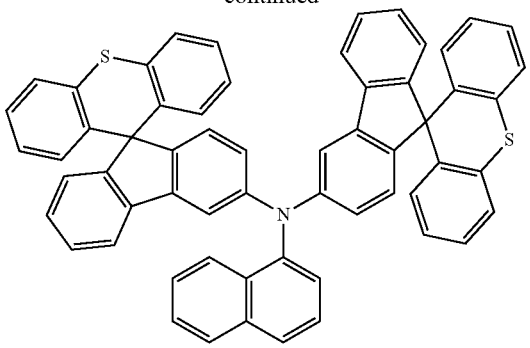
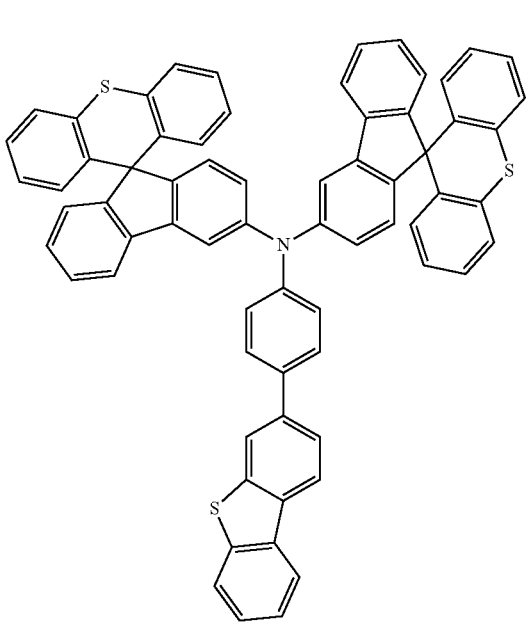
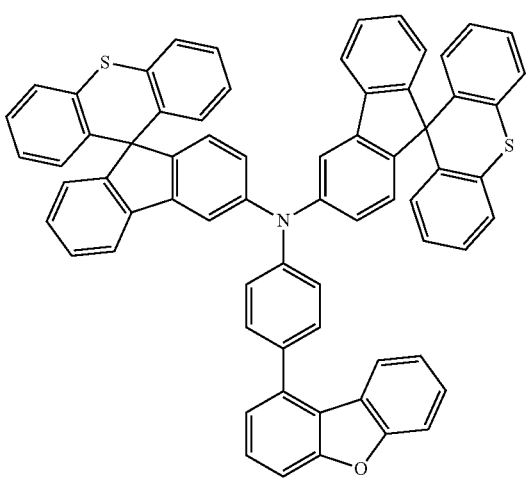

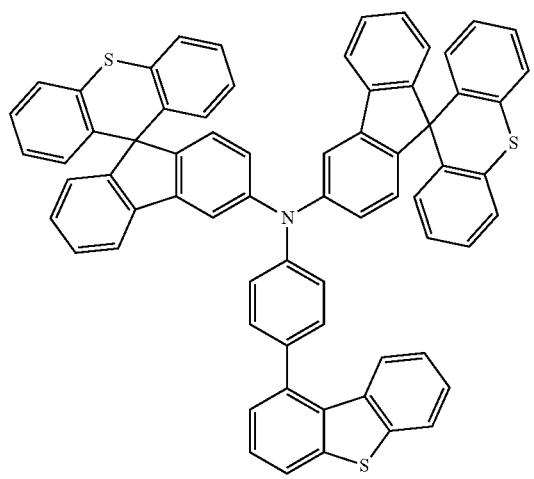
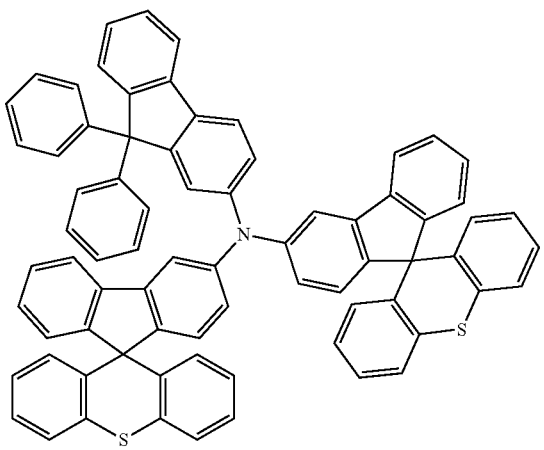
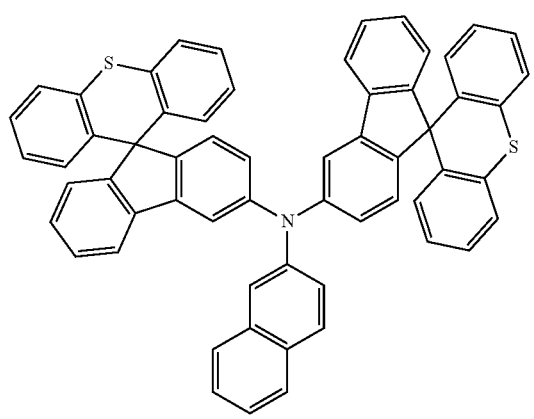
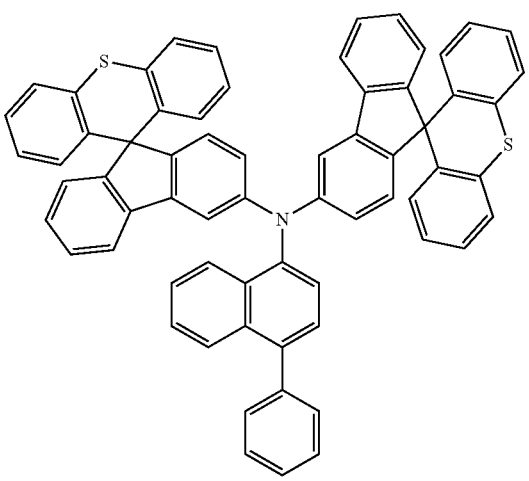
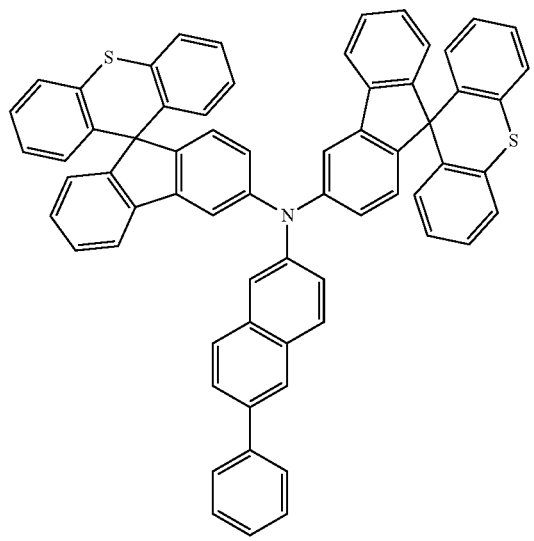
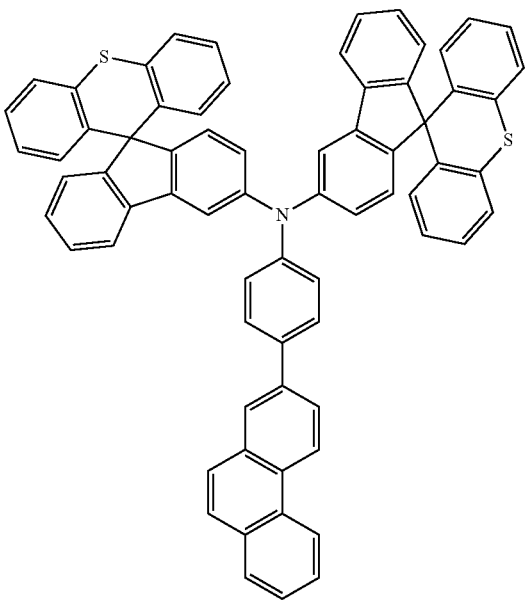

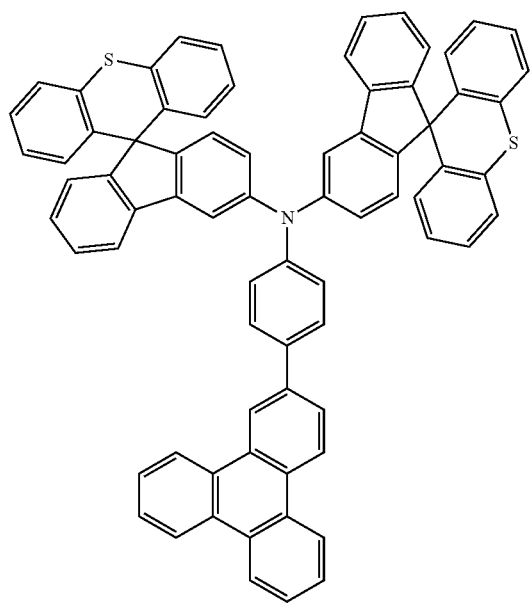
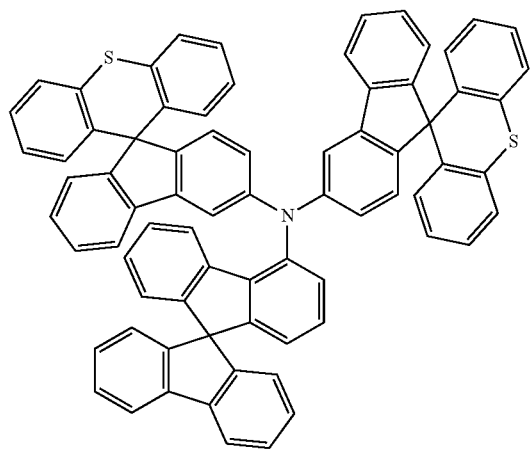
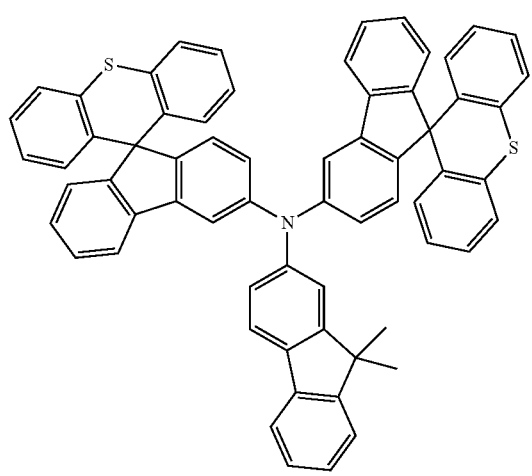
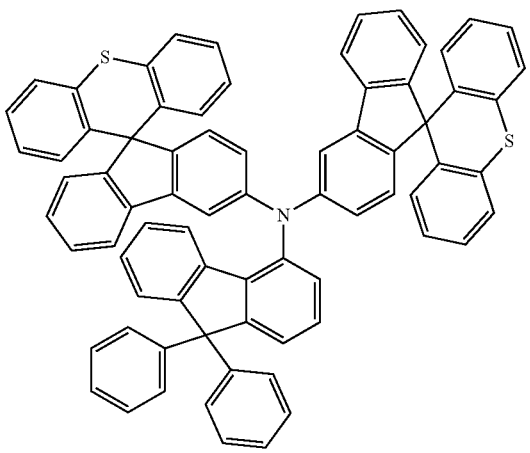
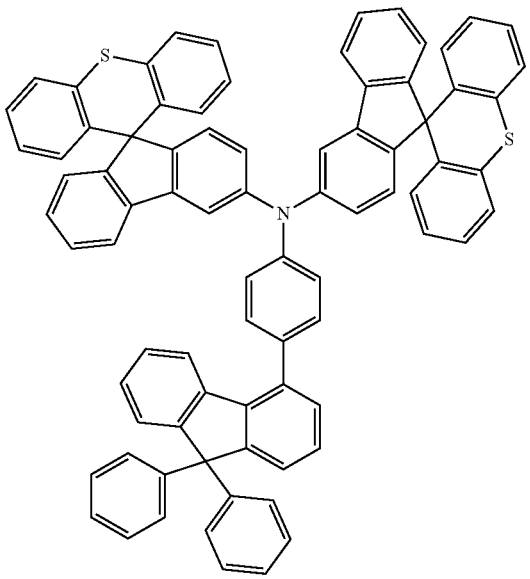
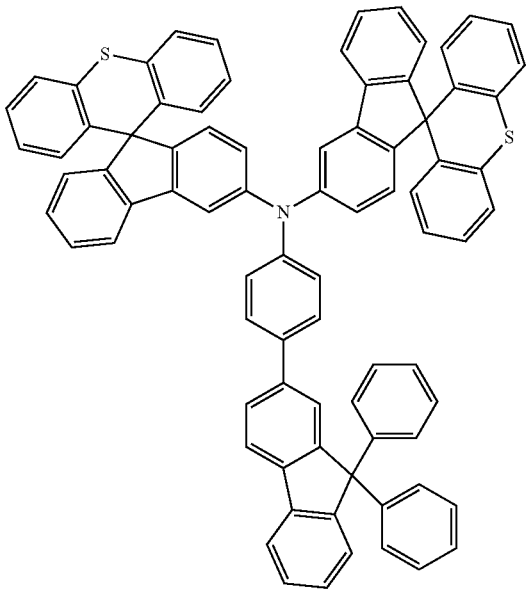

185
-continued
186
-continued
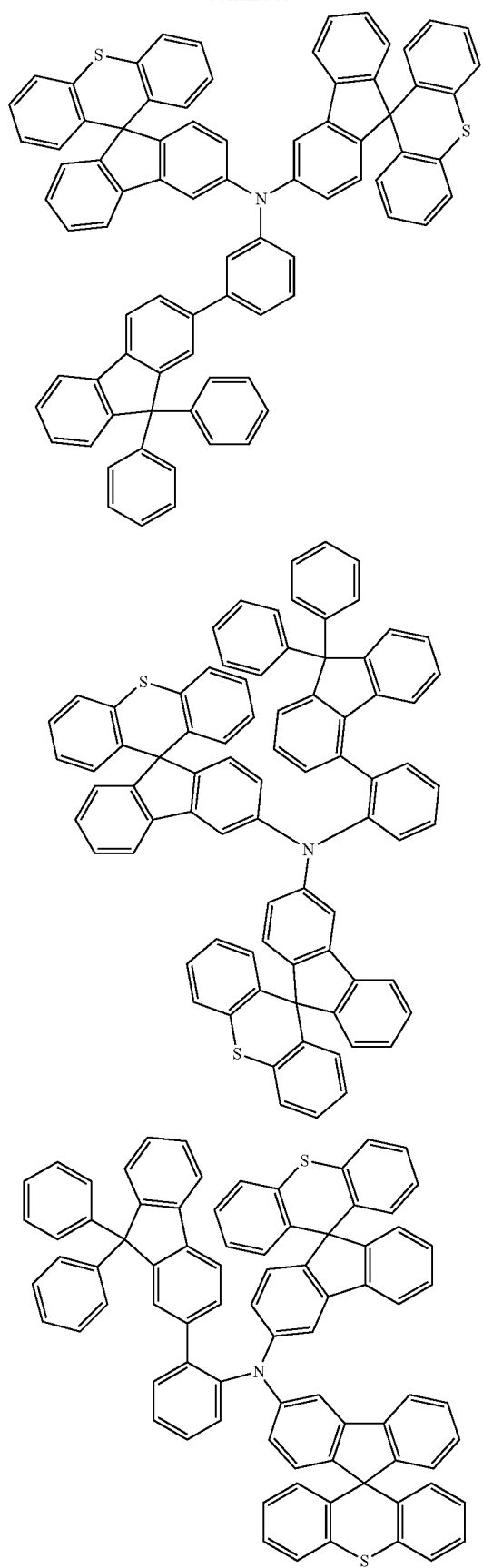
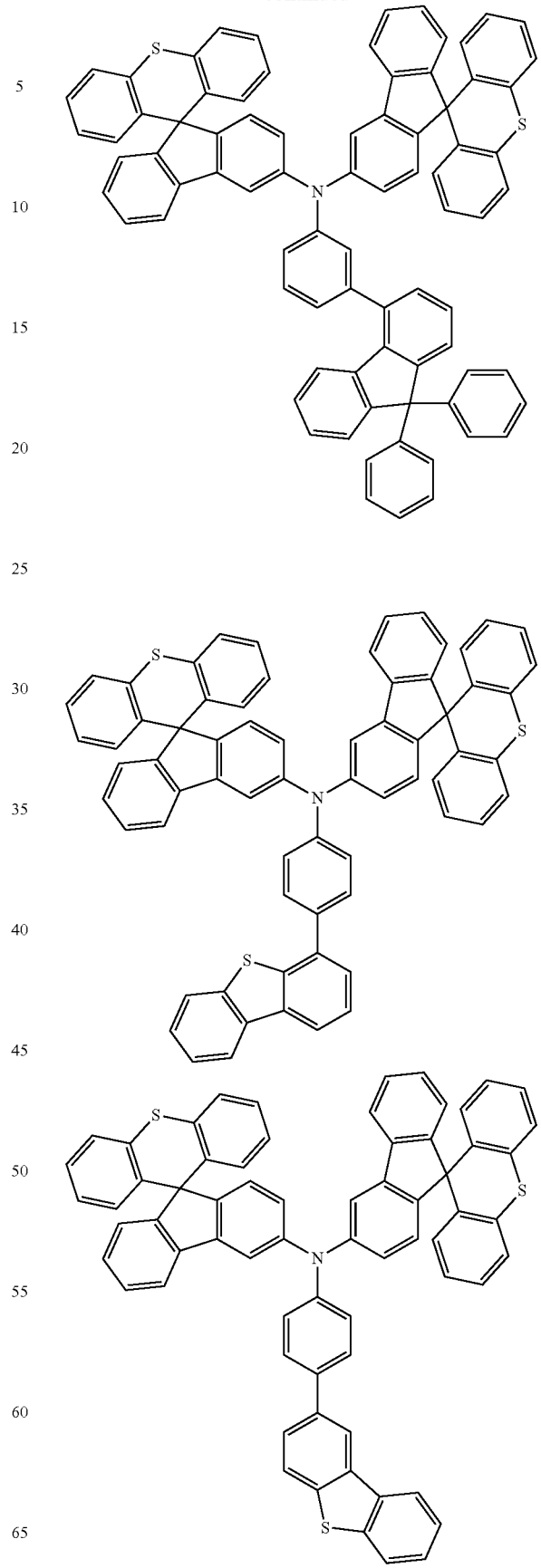

187
-continued
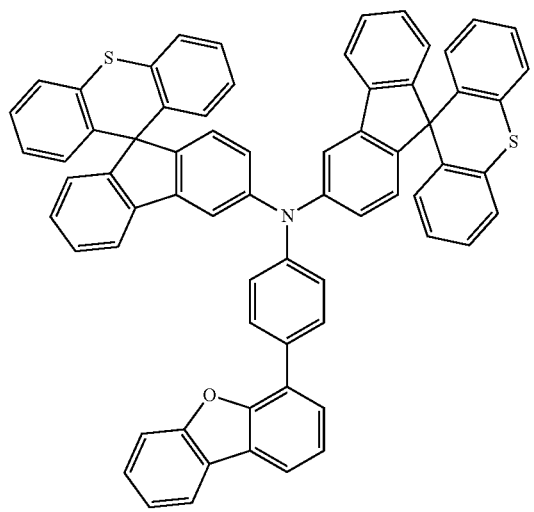
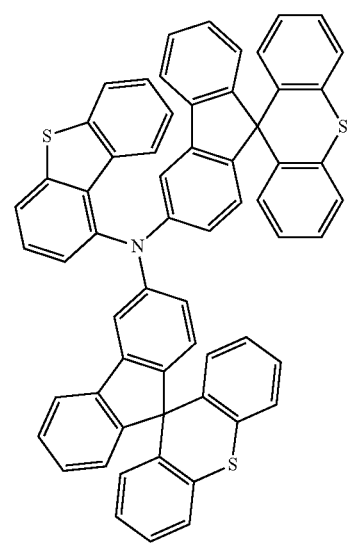
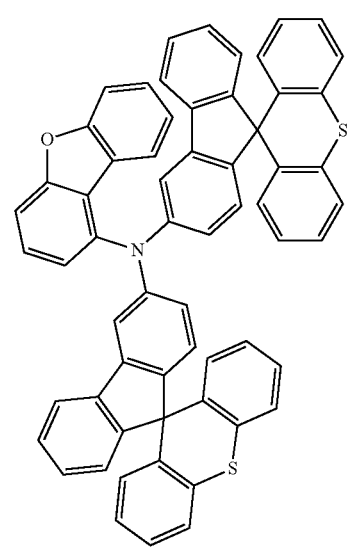
188
-continued
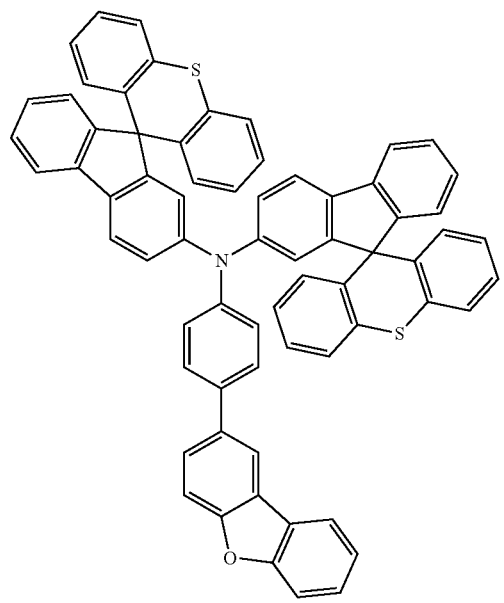
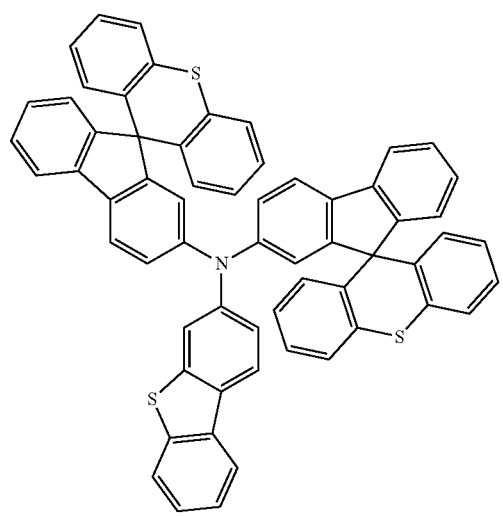
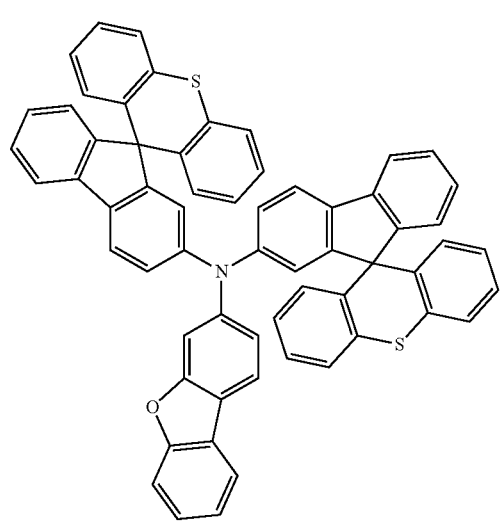

189
-continued
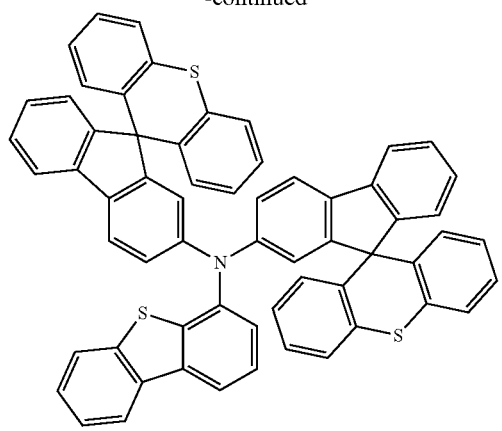
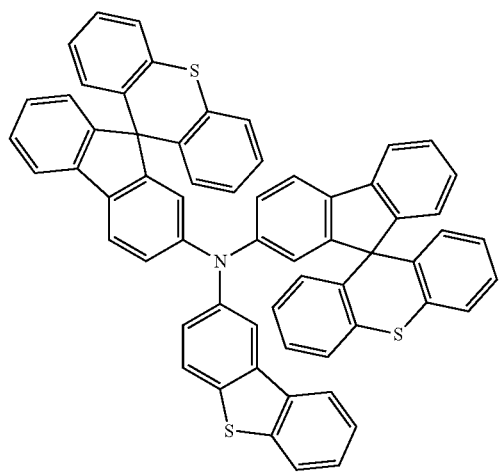
190
-continued
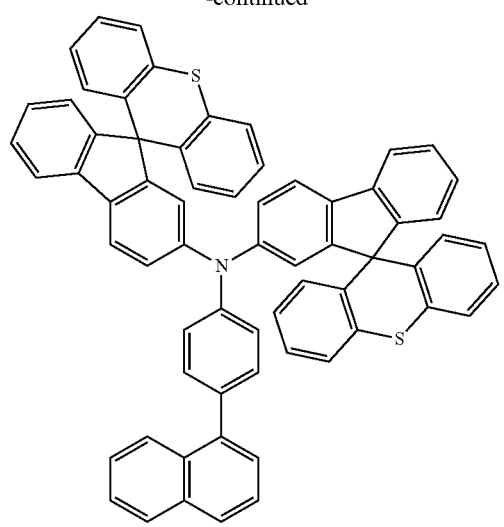
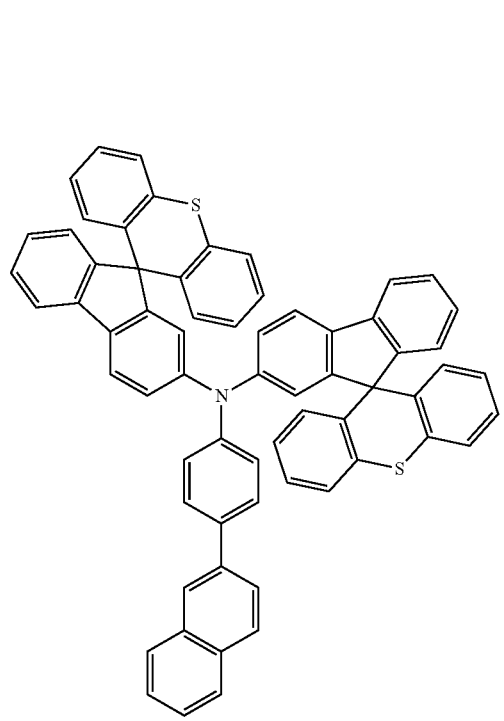
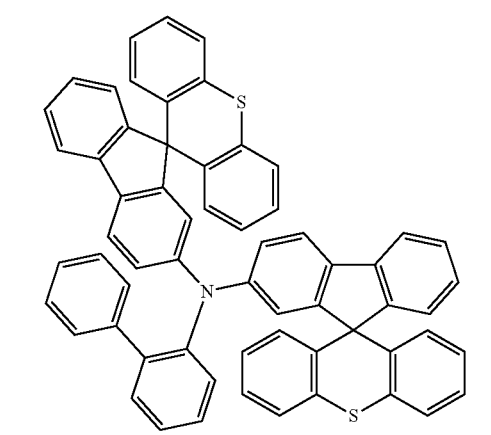

191
-continued
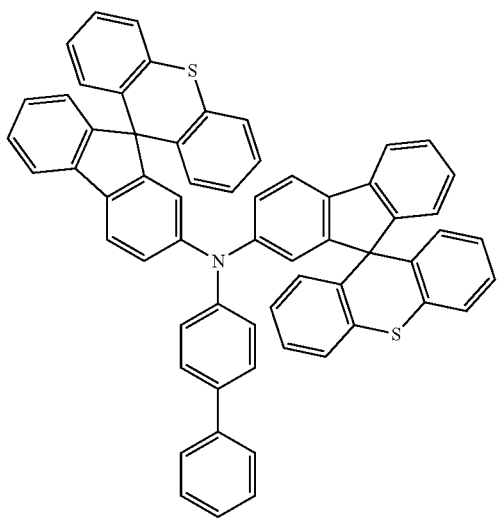
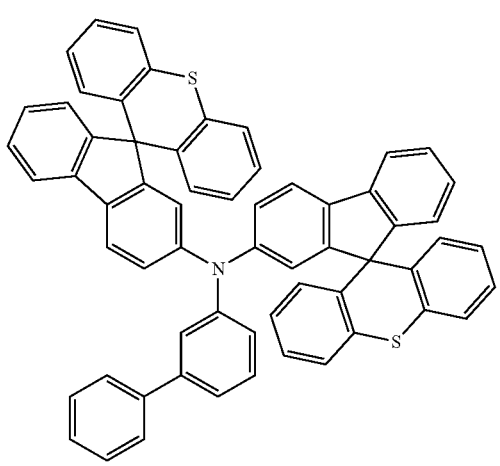
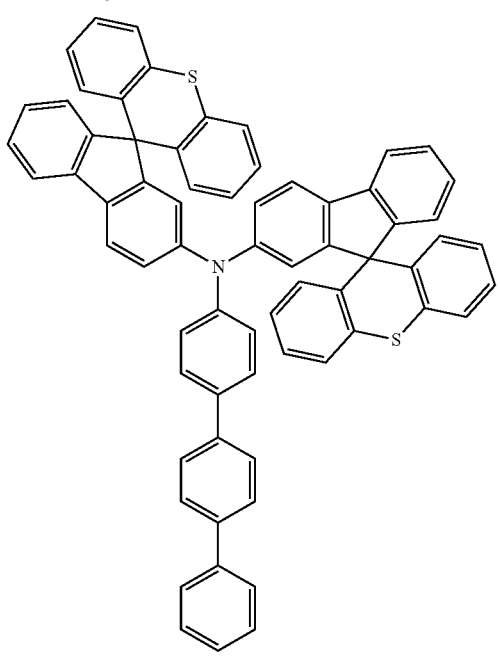
192
-continued
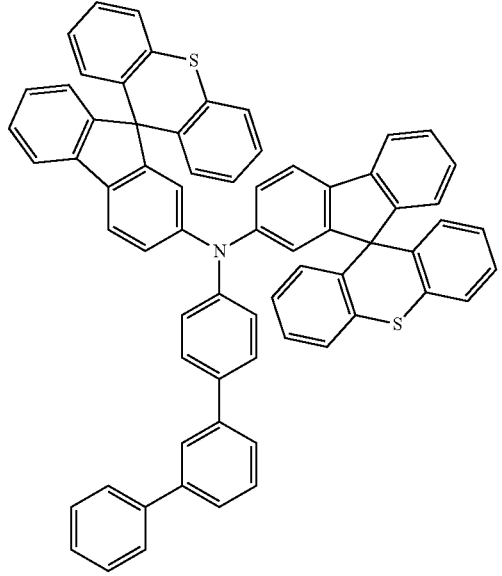
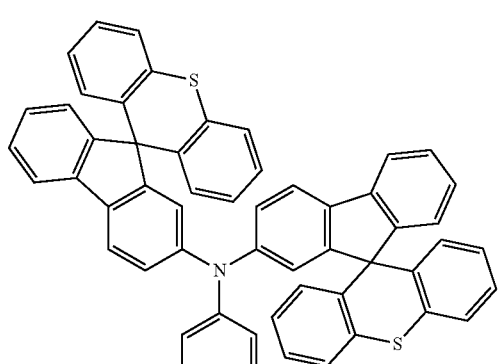
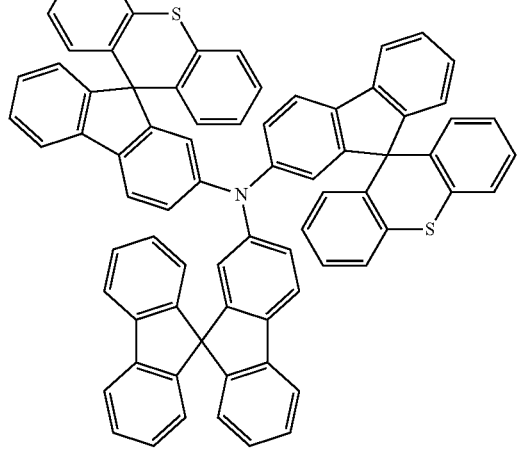

-continued
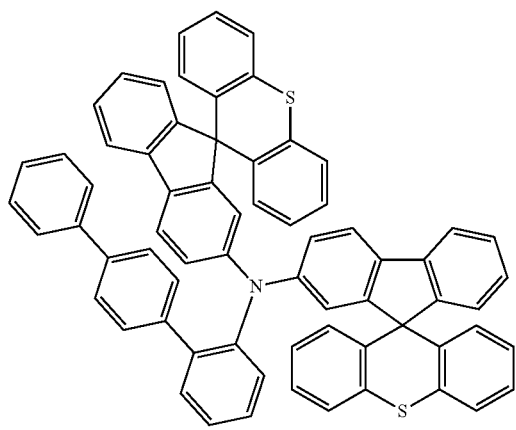
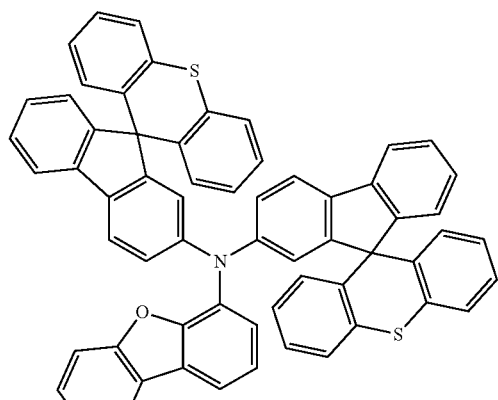
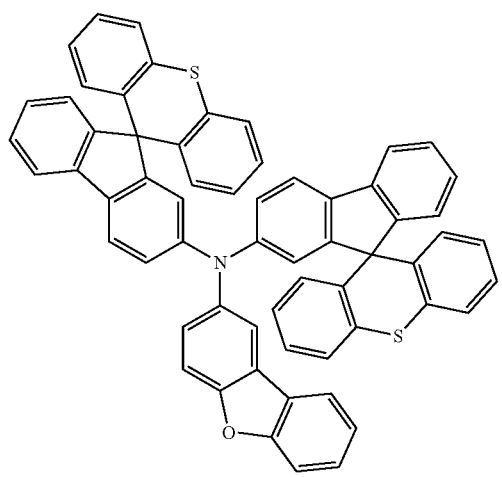
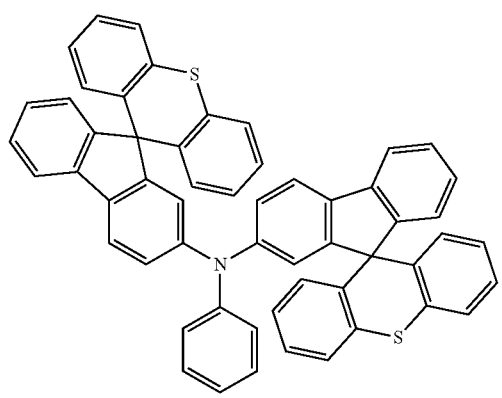
-continued
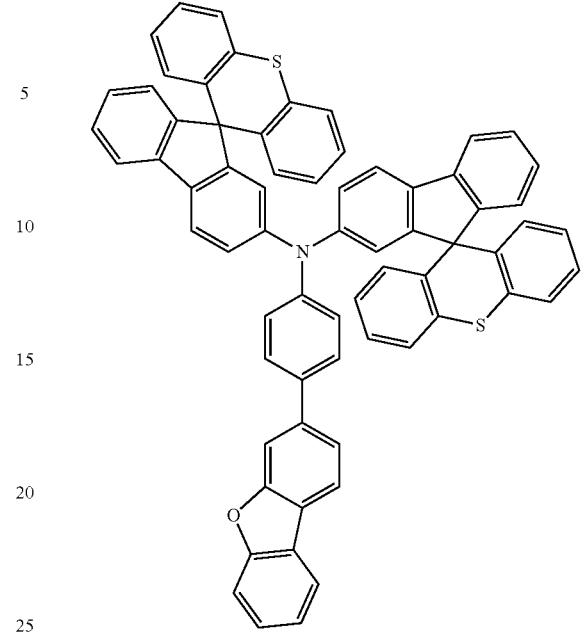
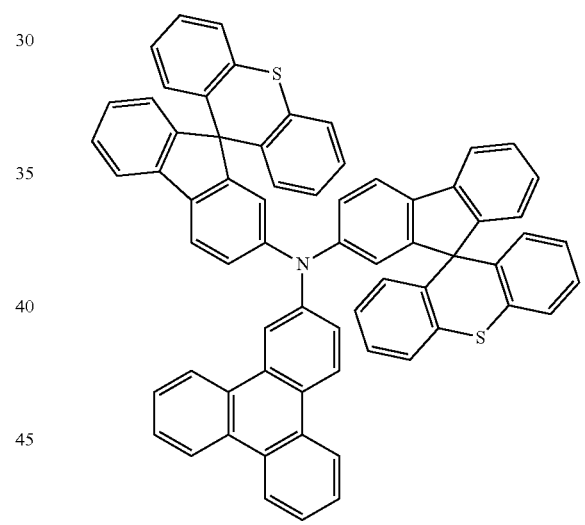
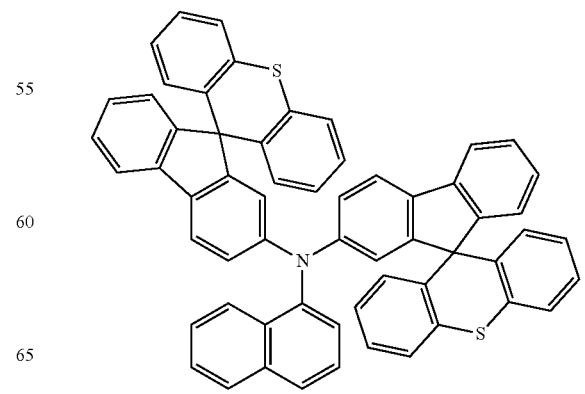

195
-continued
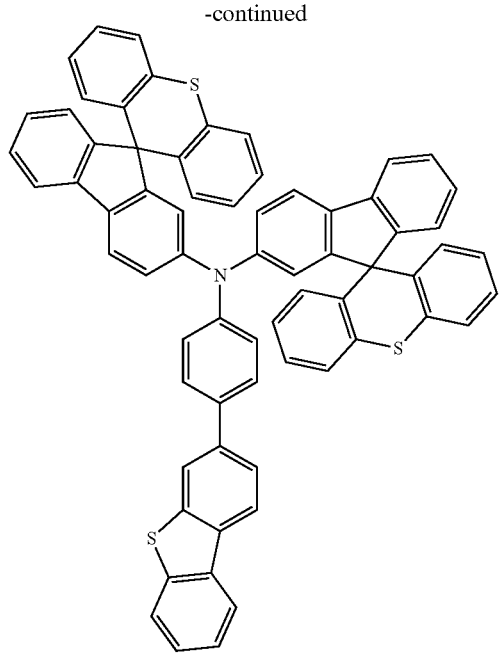
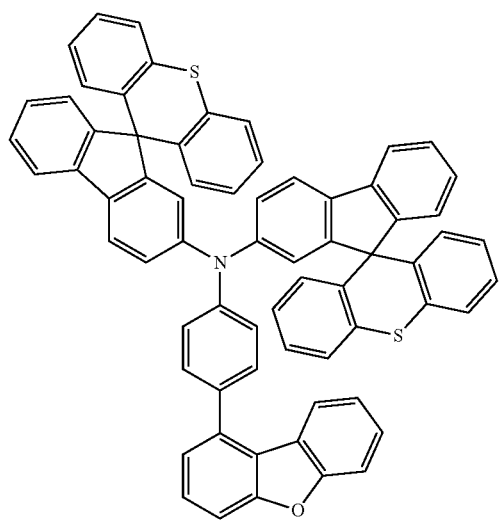
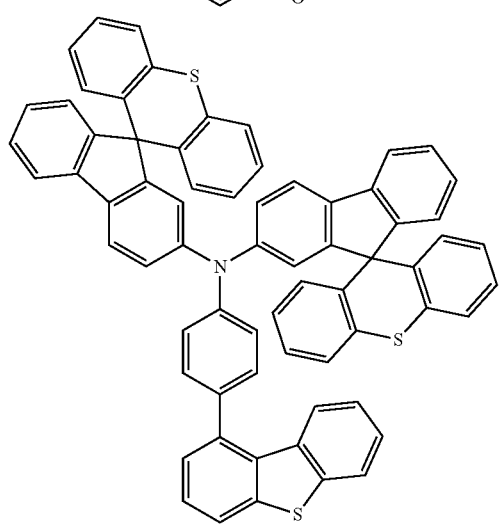
196
-continued
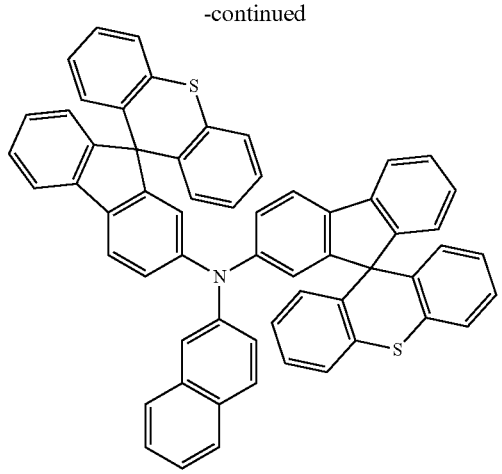
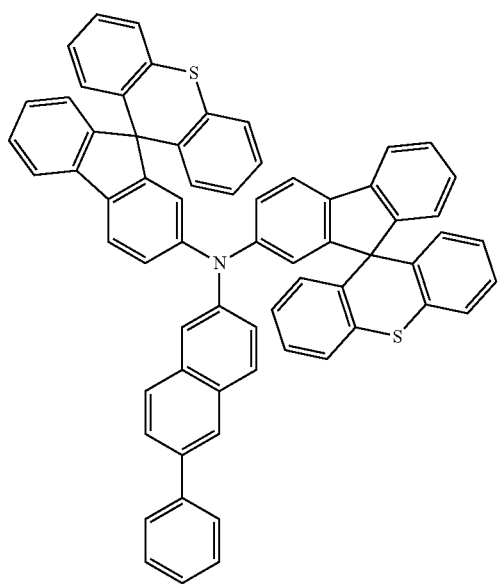
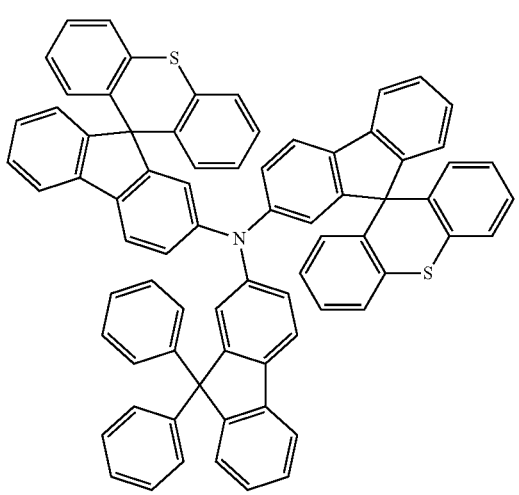

197
-continued
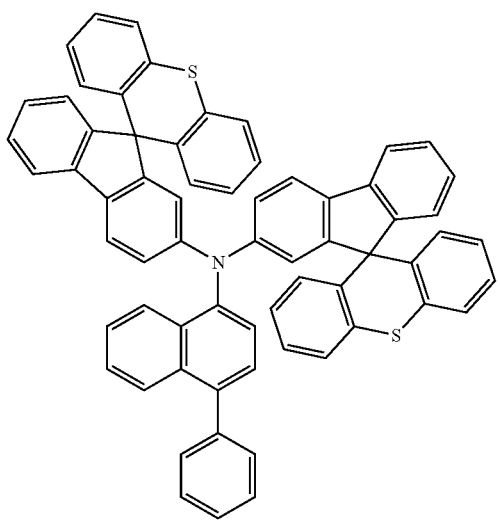
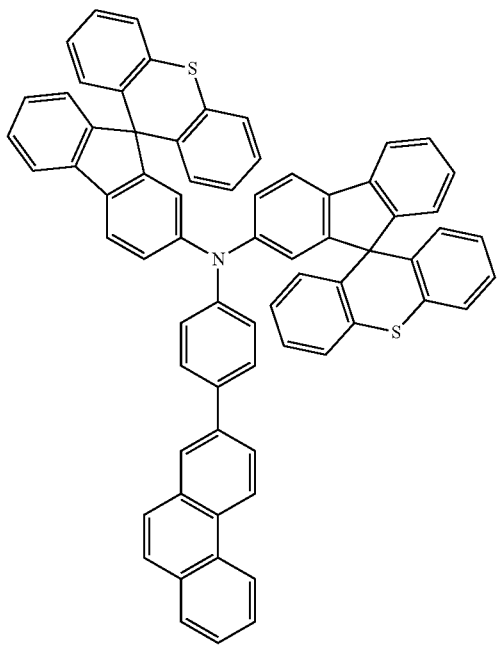
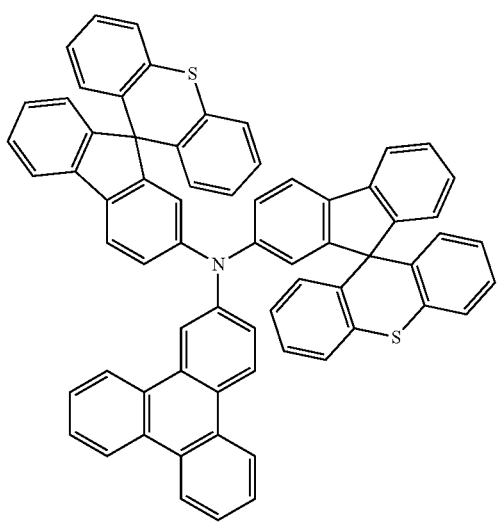
198
-continued
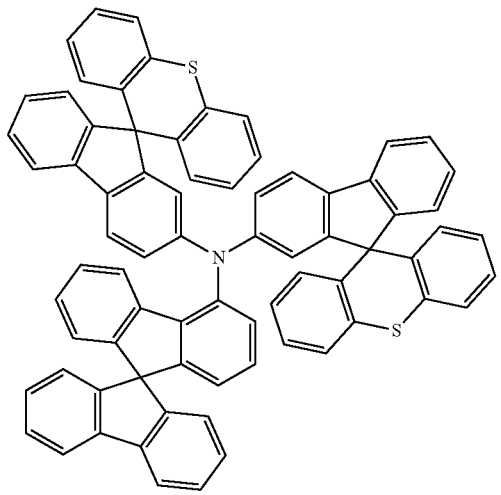
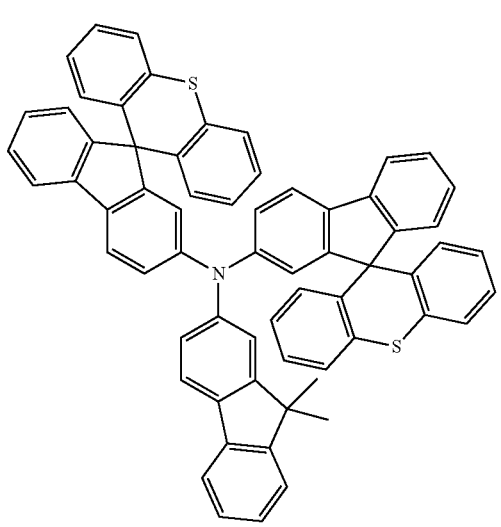
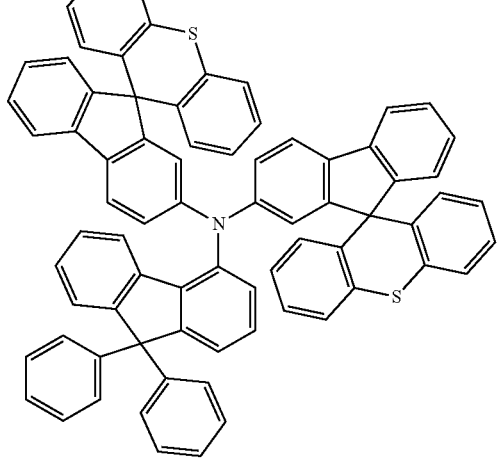

199
-continued
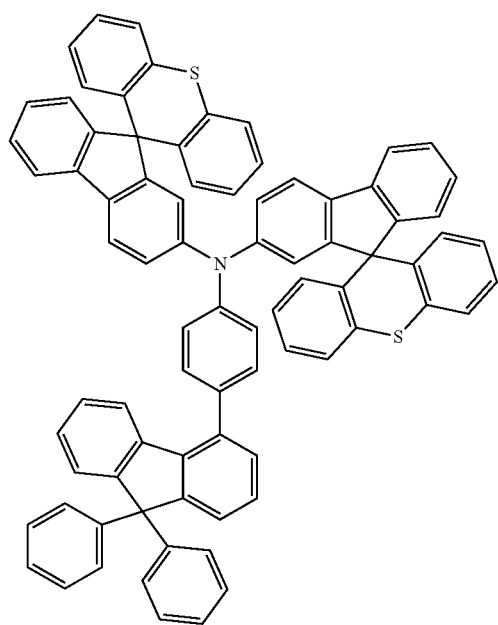
200
-continued
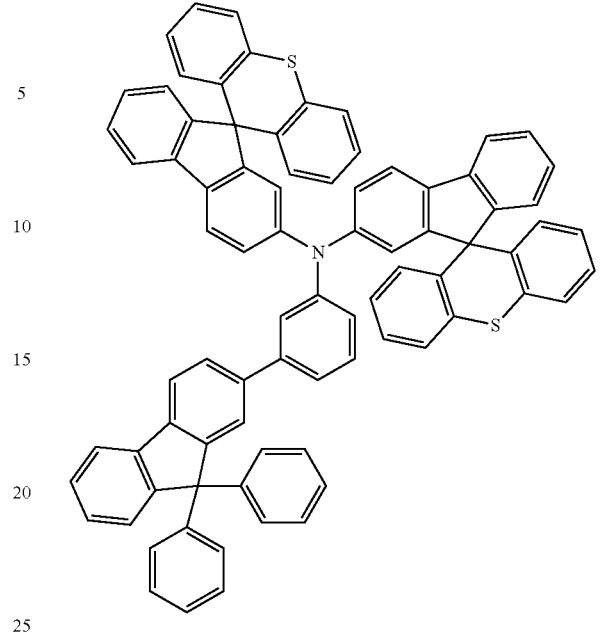
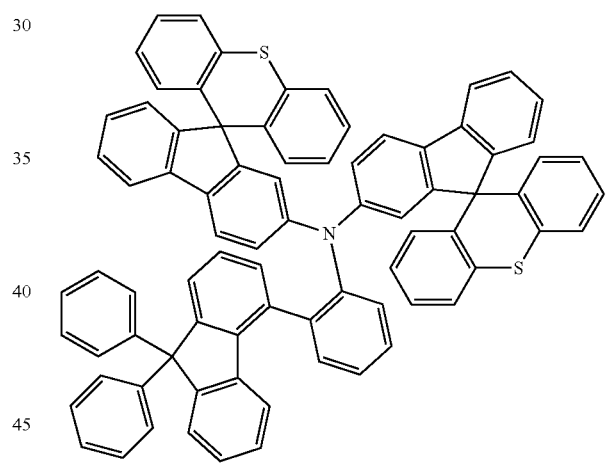
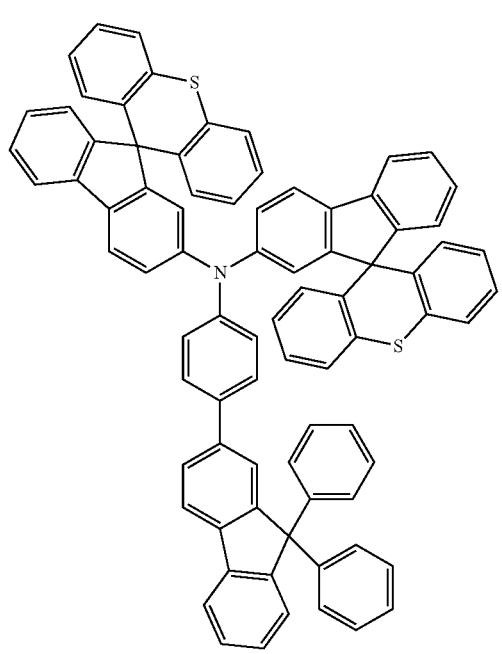
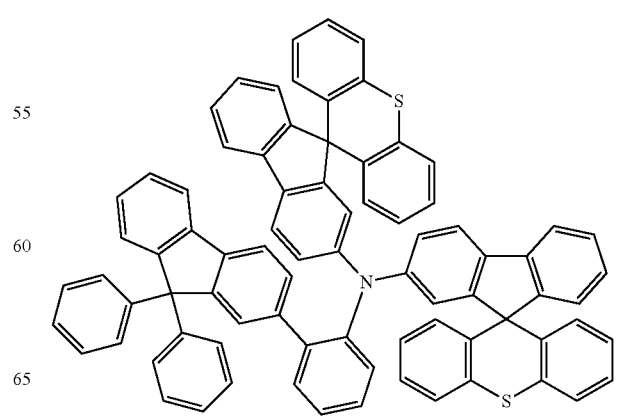

201
-continued
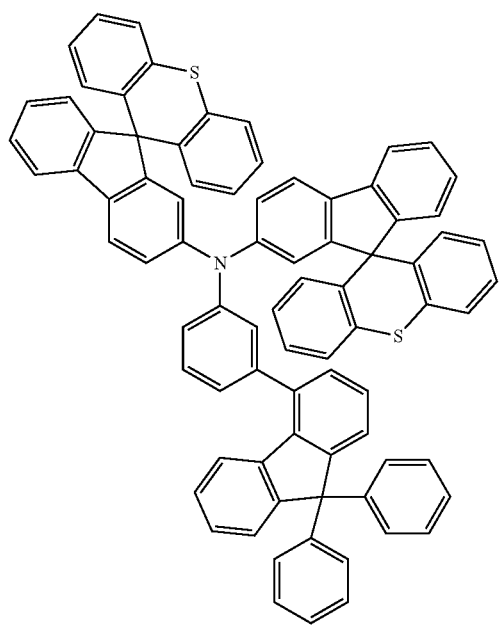
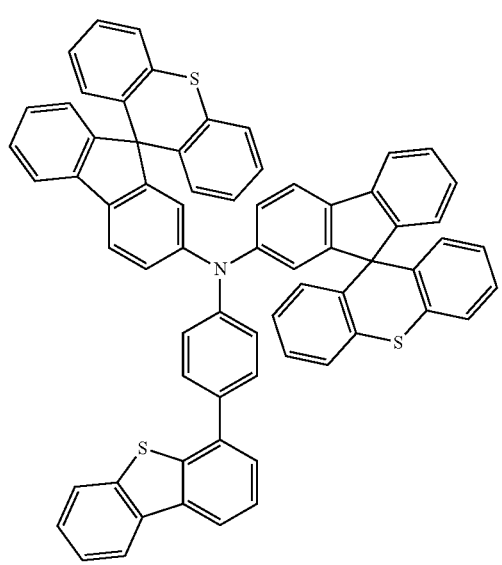
202
-continued
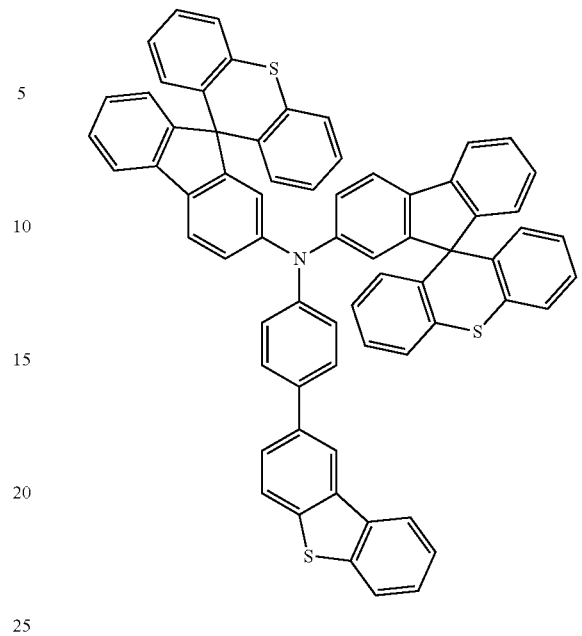
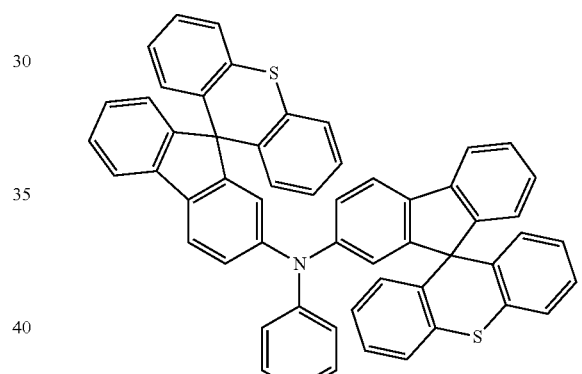
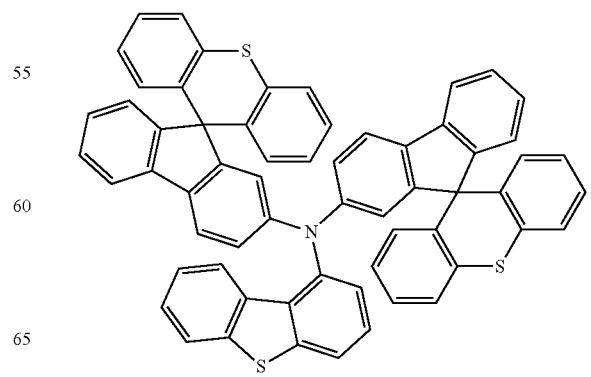

203
-continued
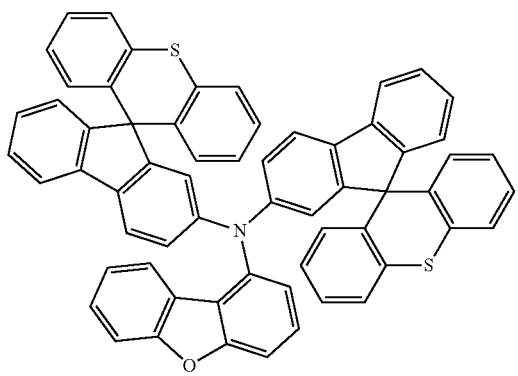
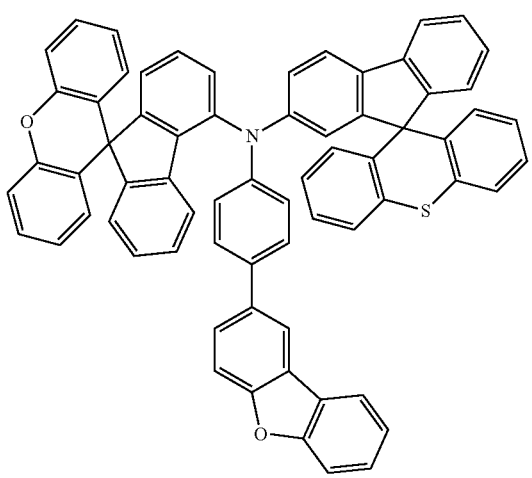
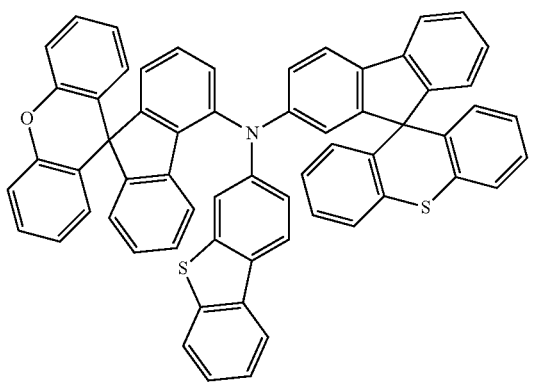
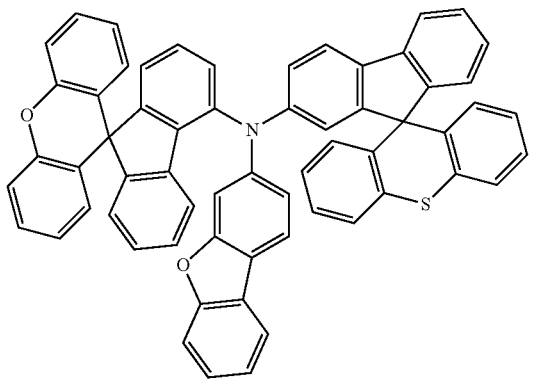
204
-continued
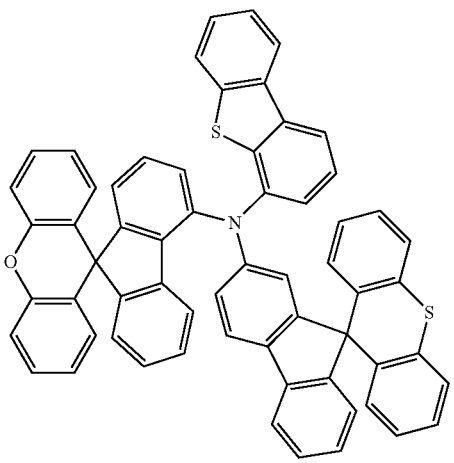
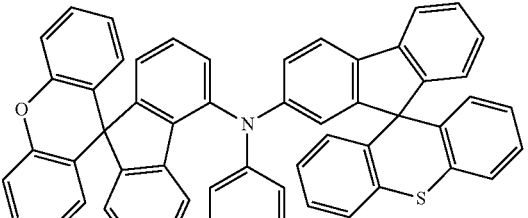
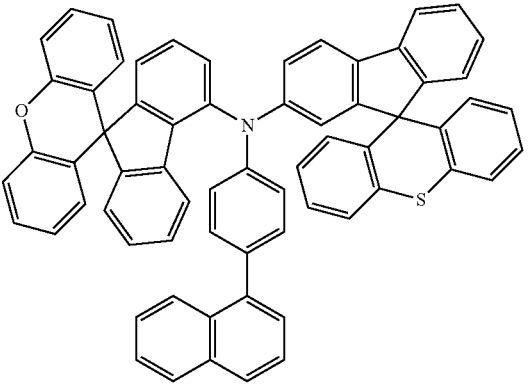

205
-continued
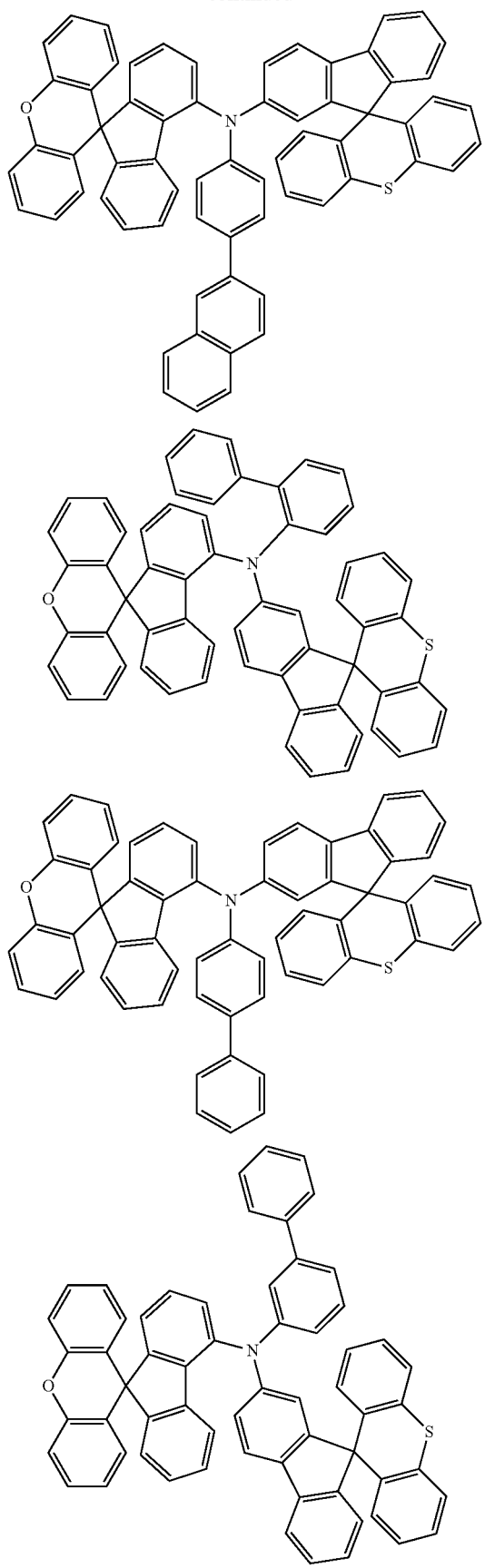
206
-continued
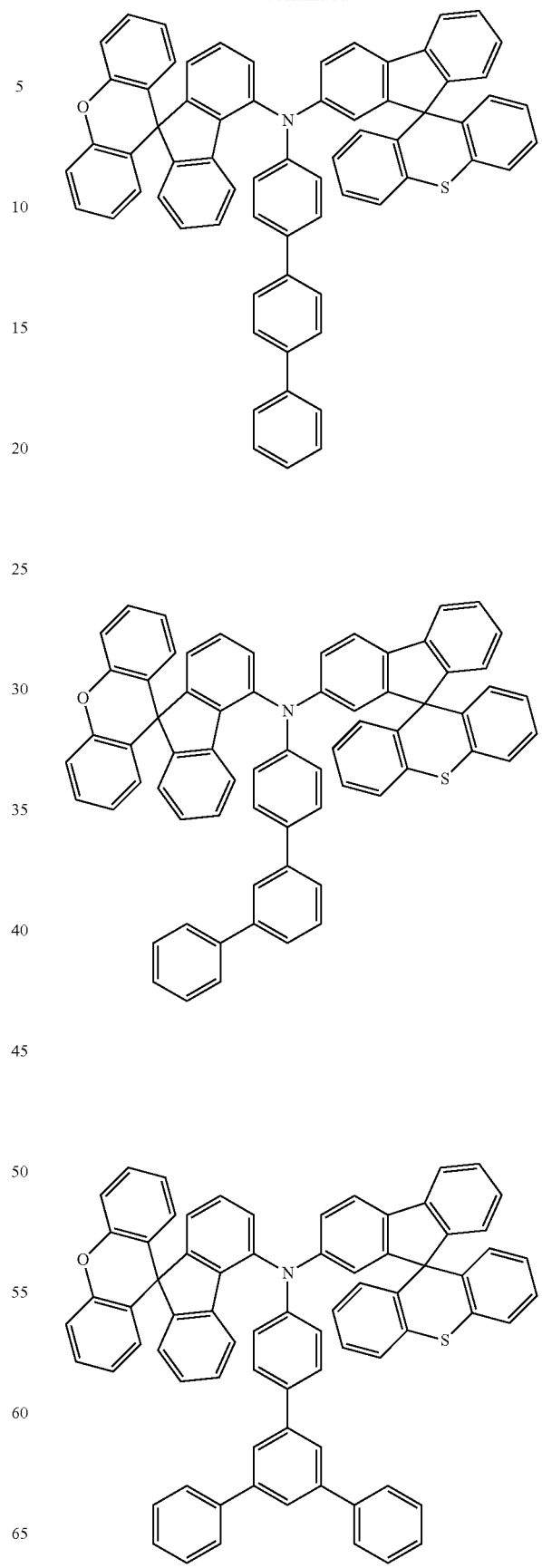

207
-continued
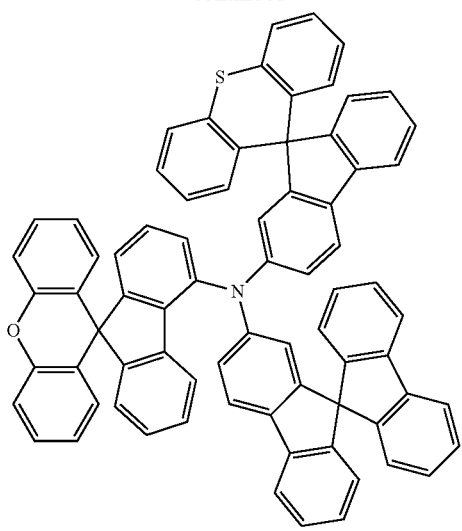
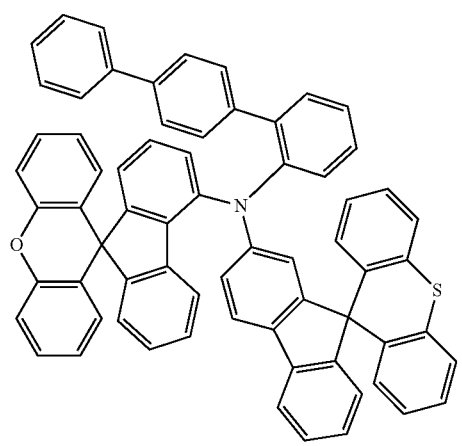
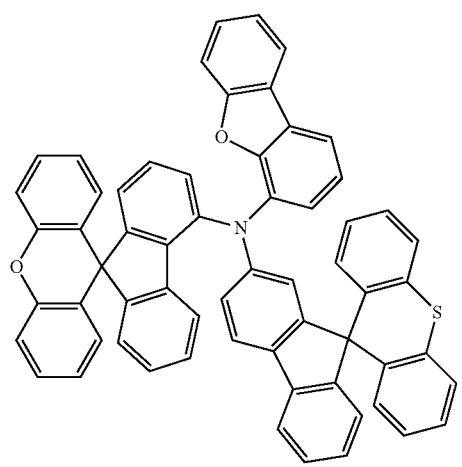
208
-continued
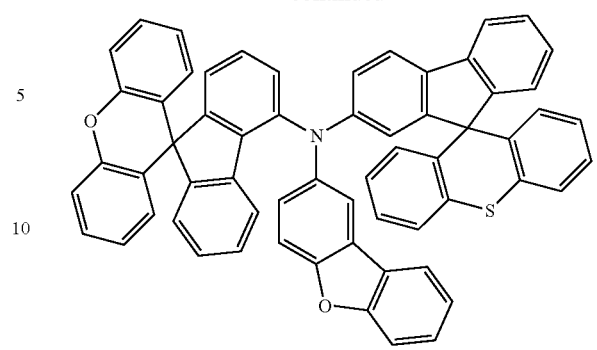
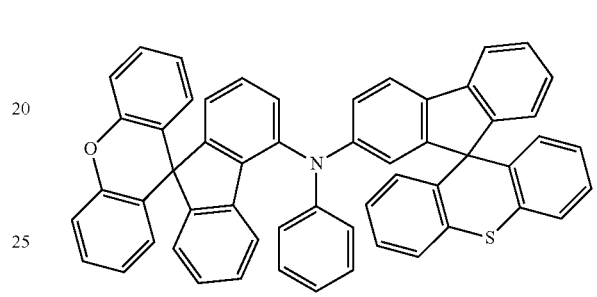
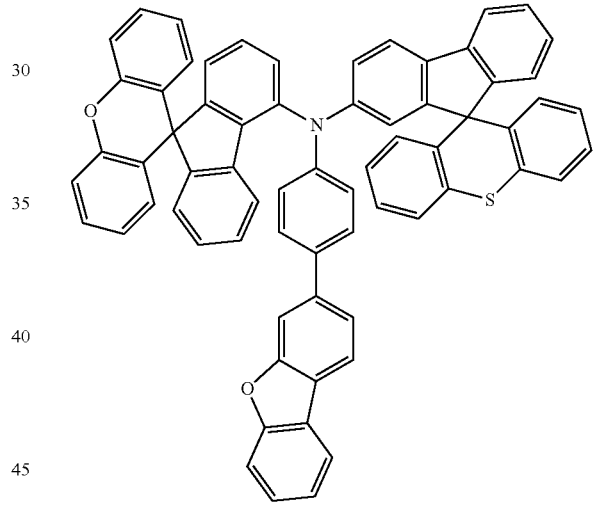
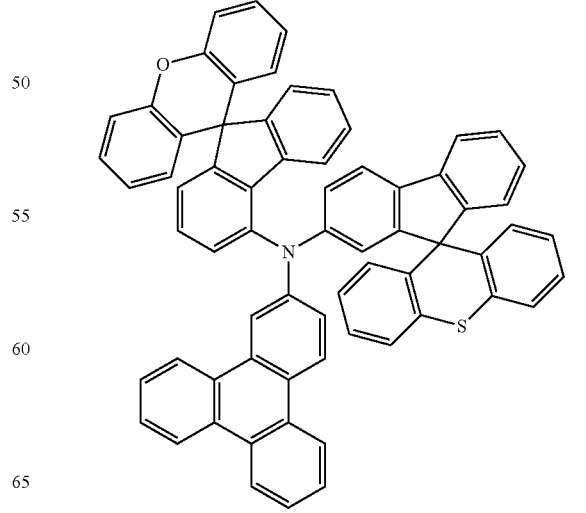

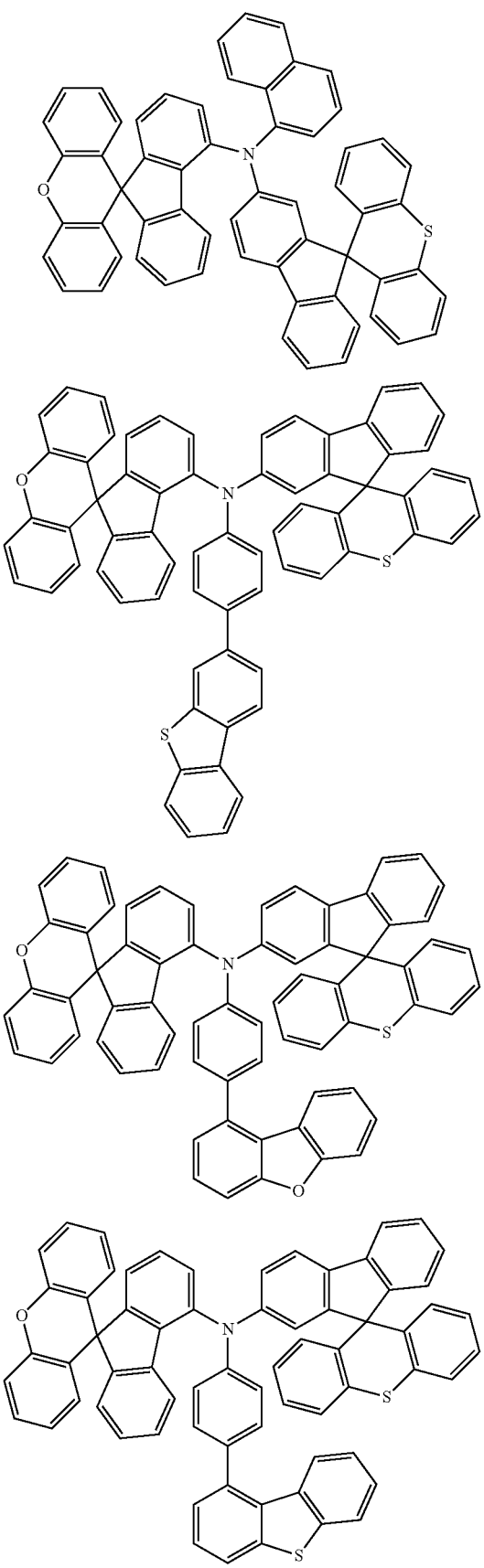
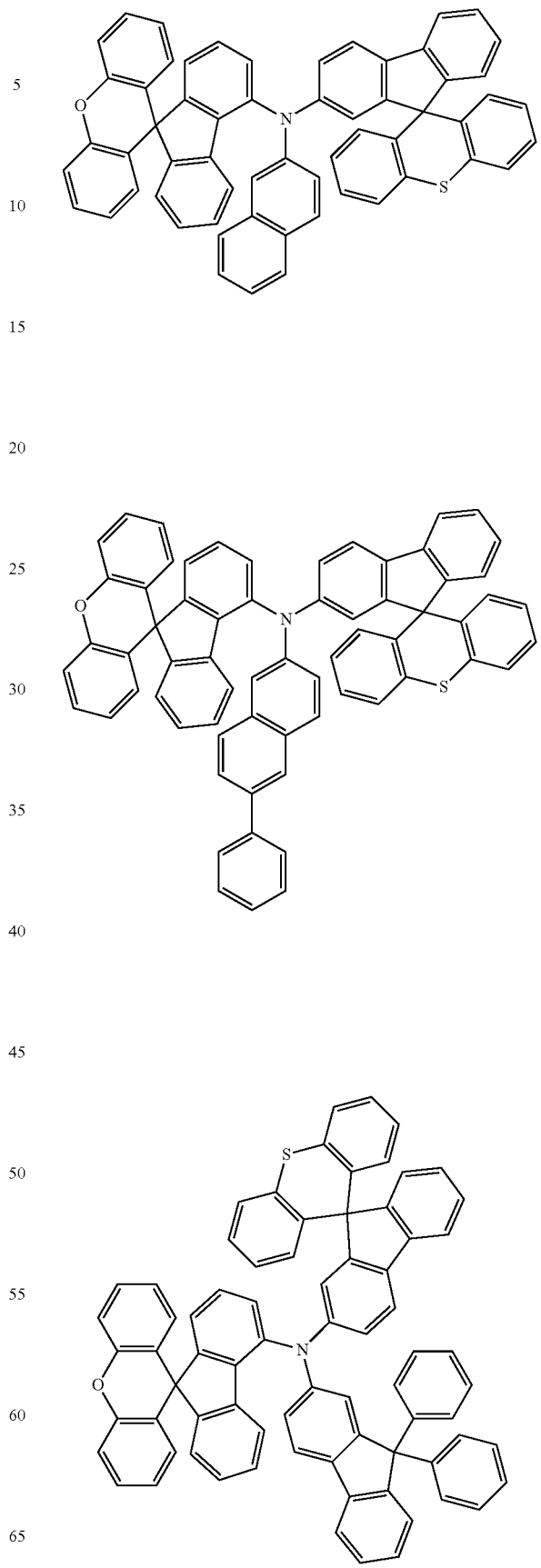

211
-continued
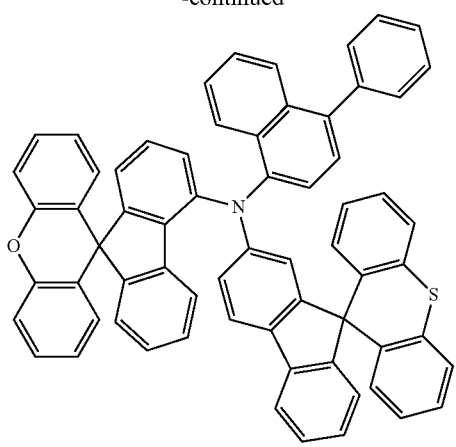
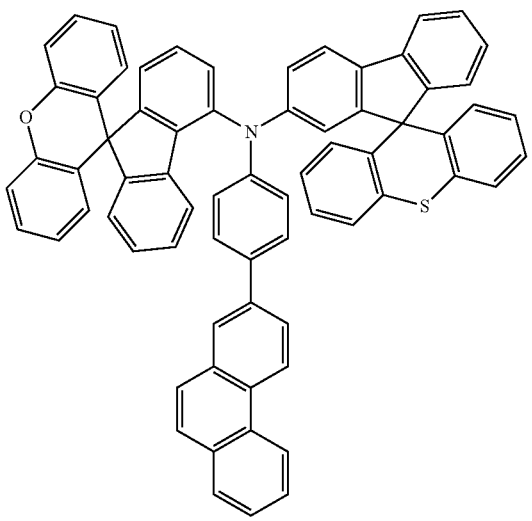
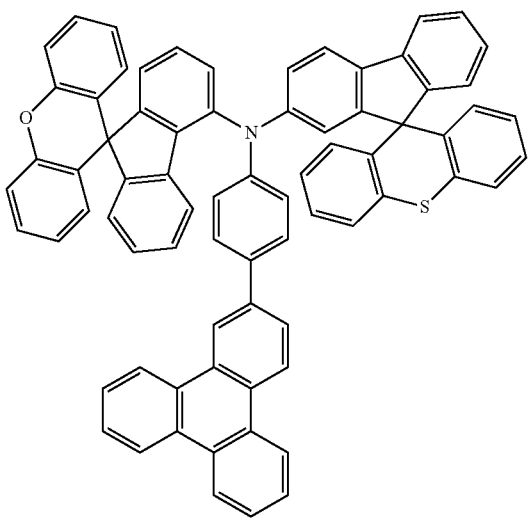
212
-continued
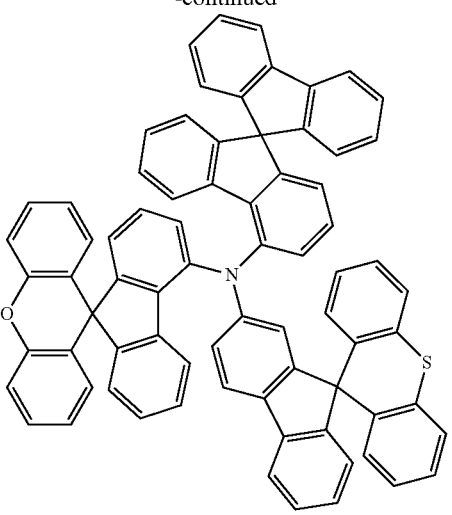
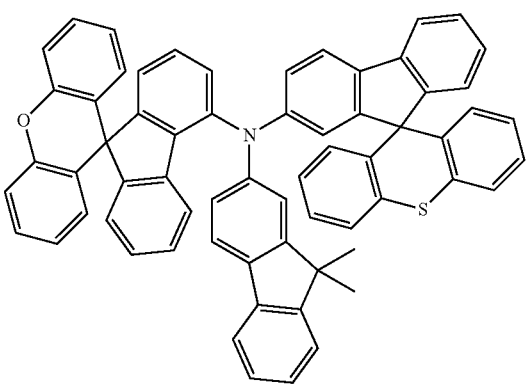
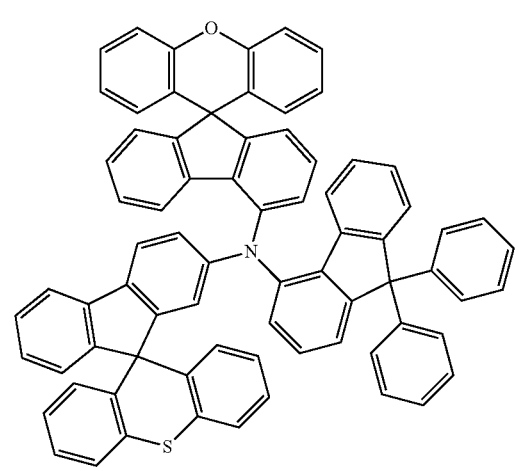

213
-continued
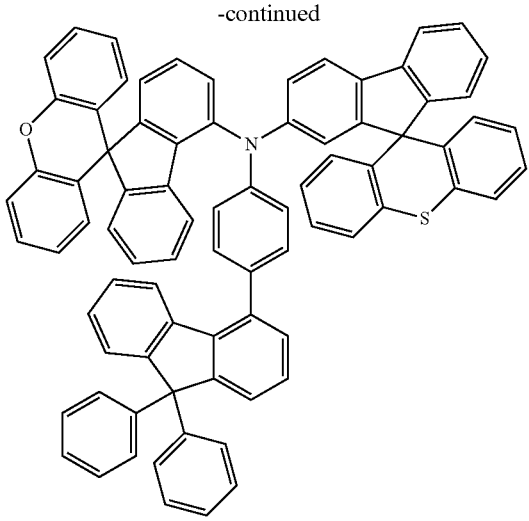
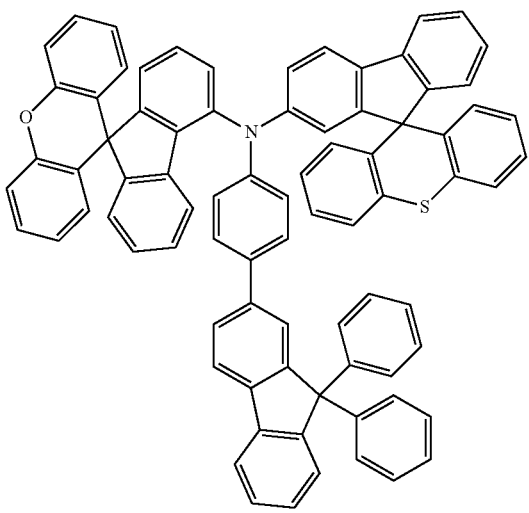
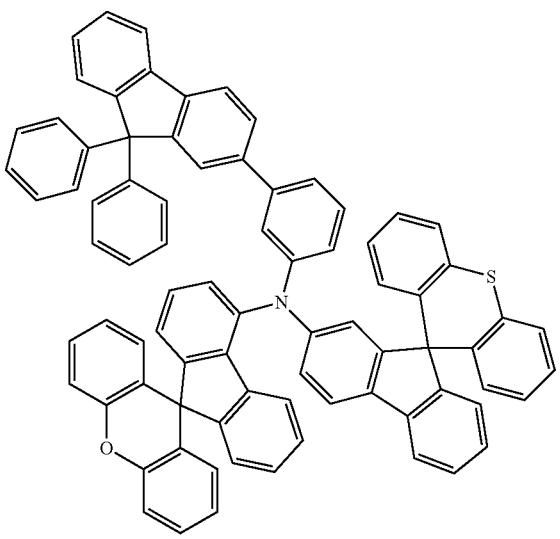
214
-continued
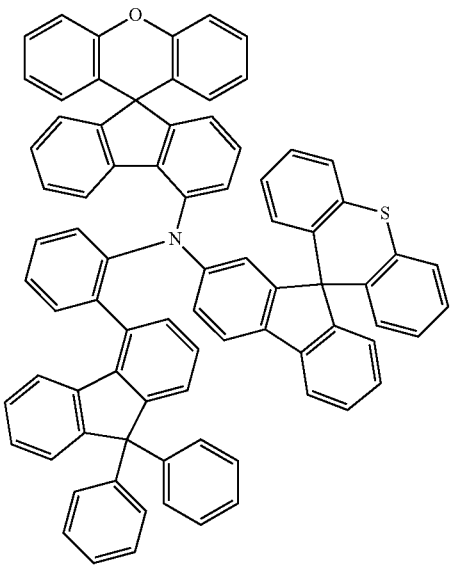
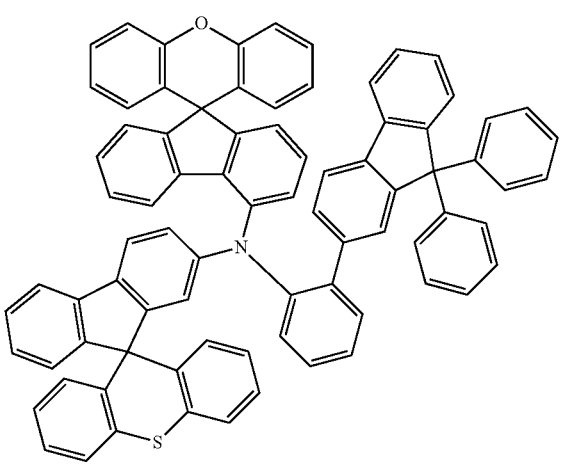
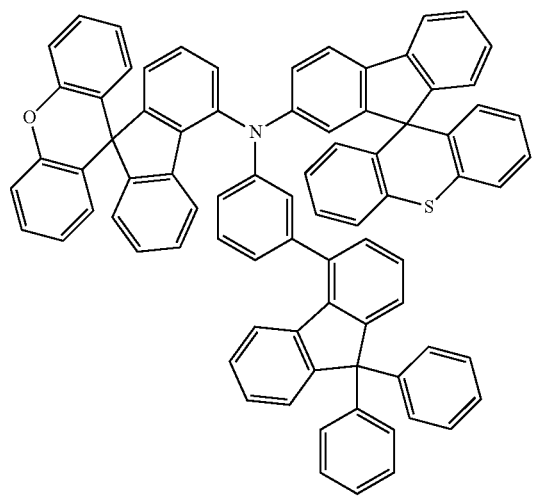

215
-continued
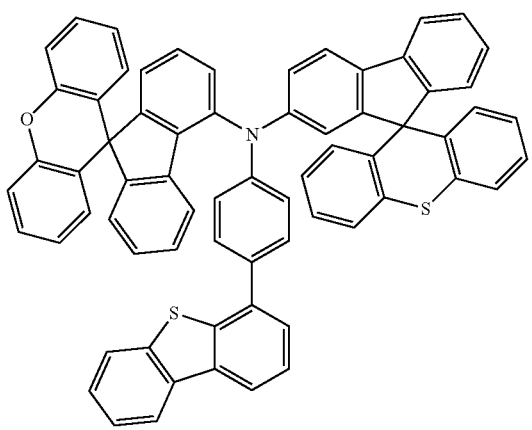
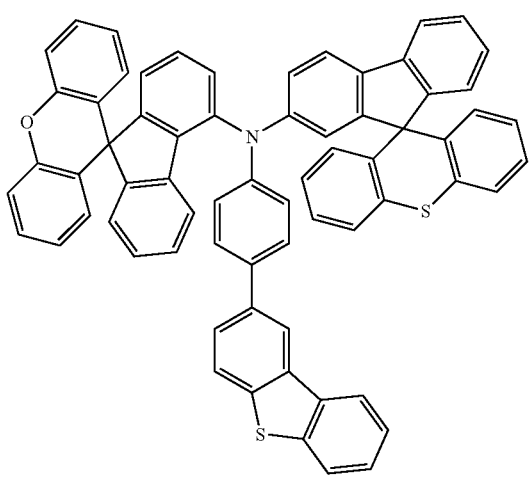
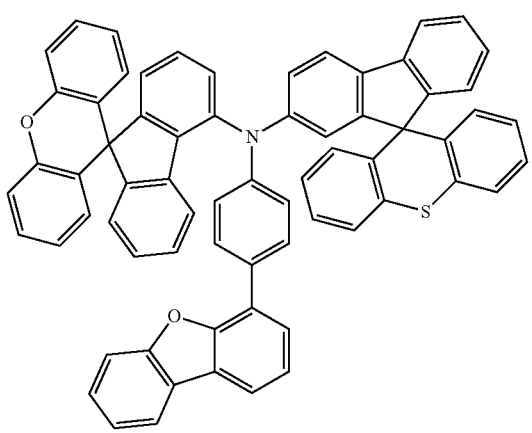
216
-continued
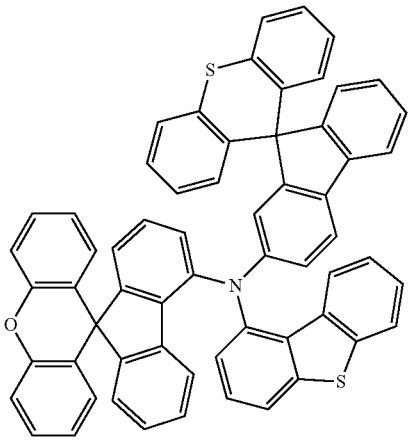
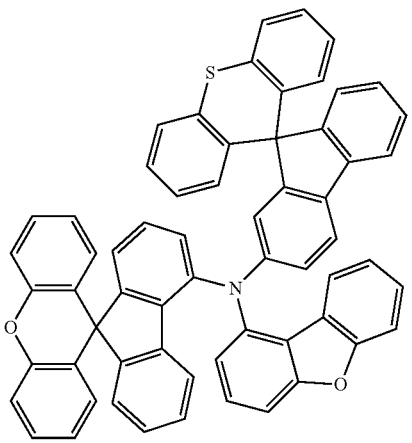
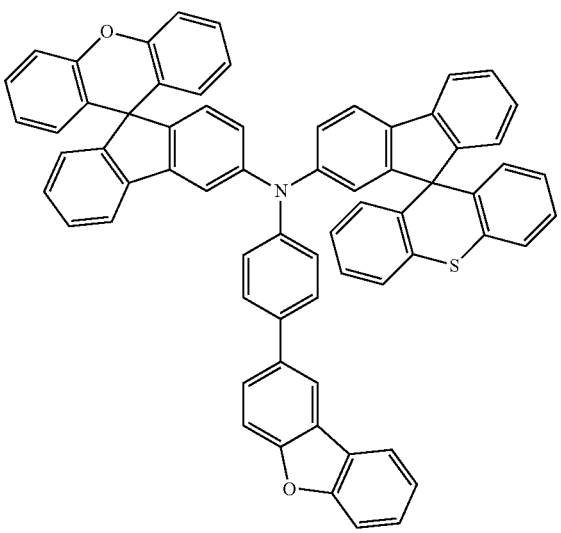

217
-continued
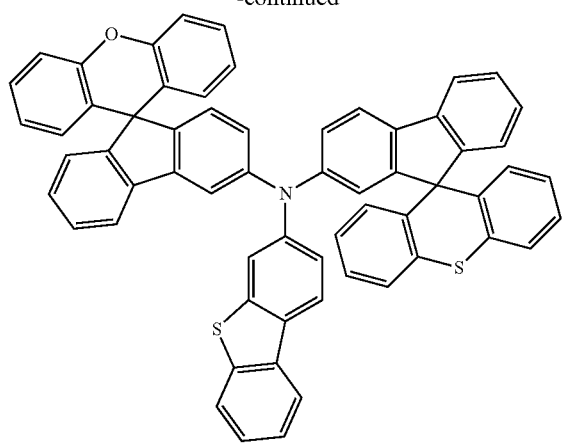
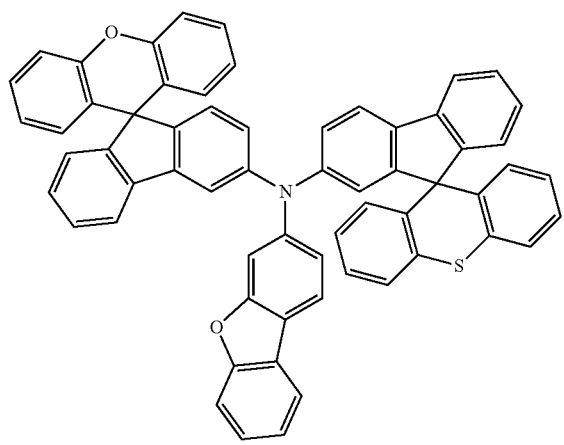
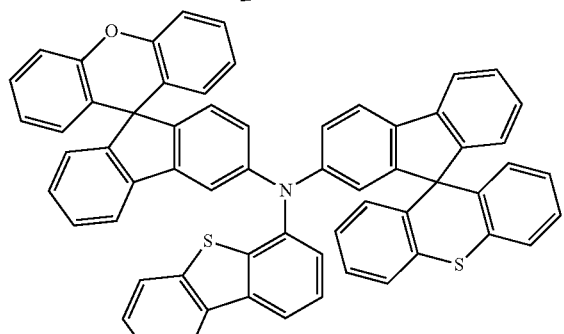
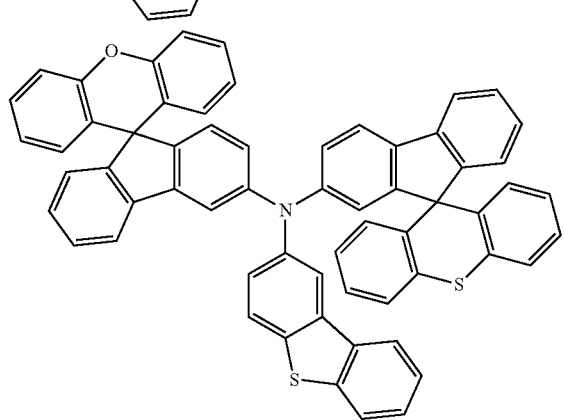
218
-continued
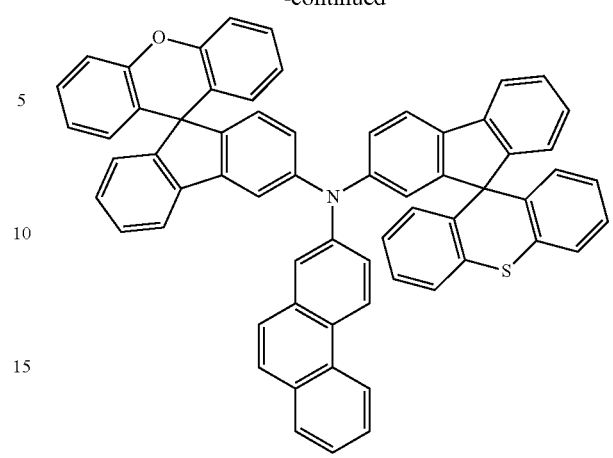
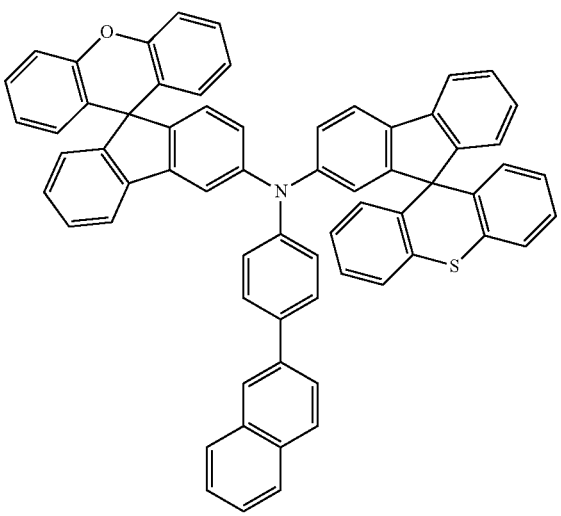

219
-continued
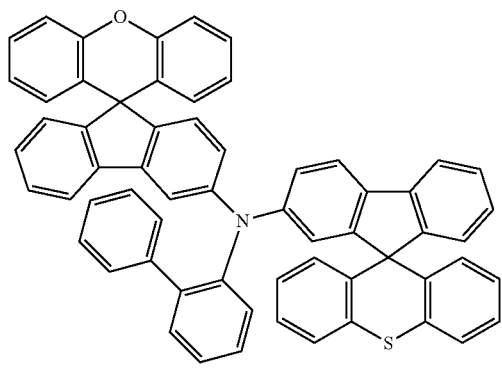
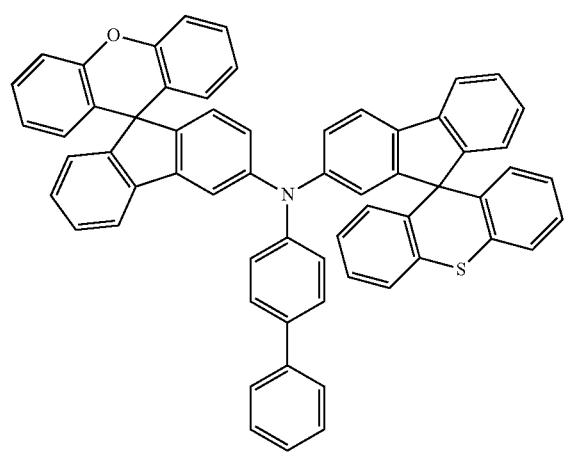
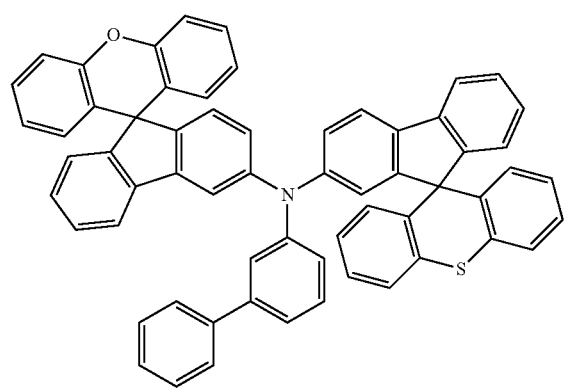
220
-continued
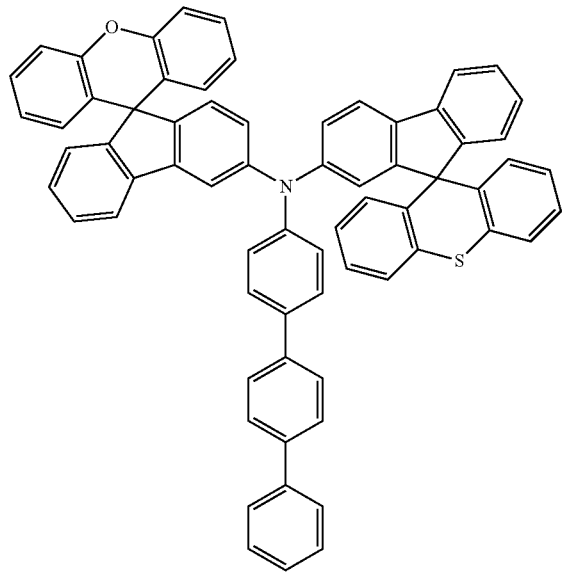
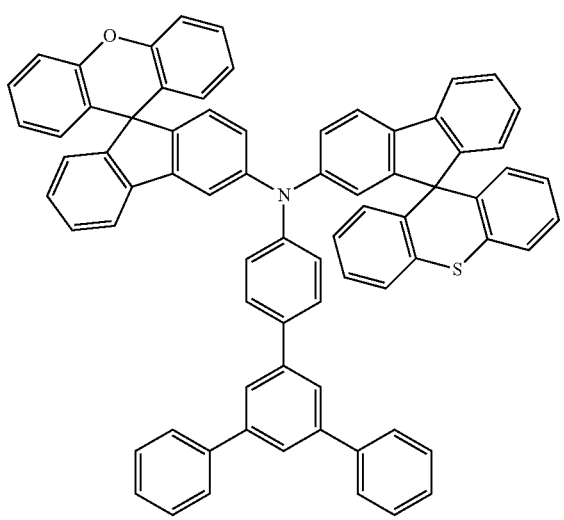

221
-continued
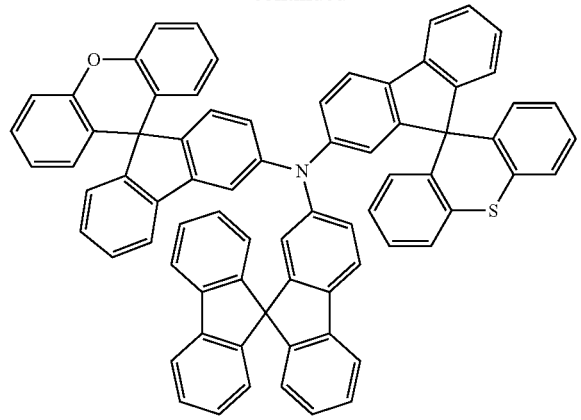
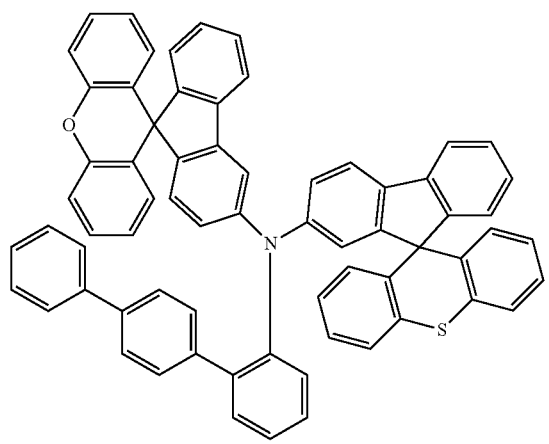
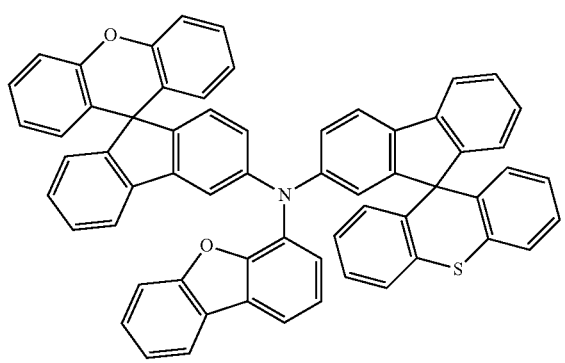
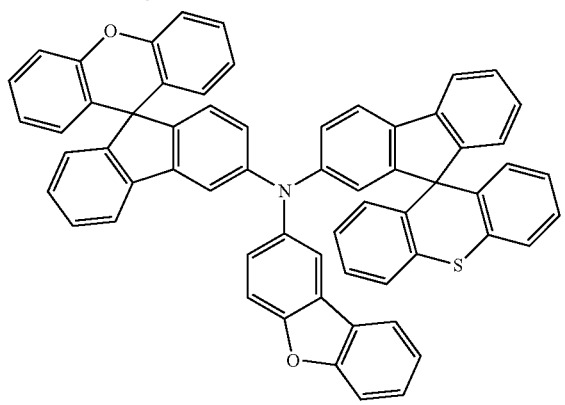
222
-continued
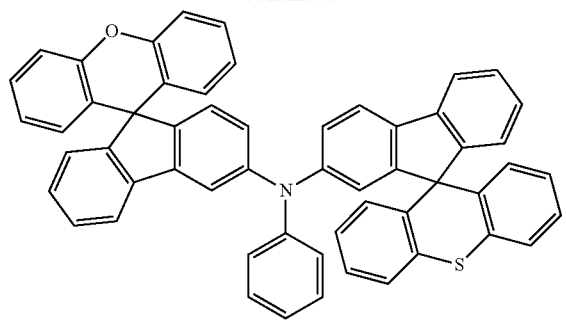
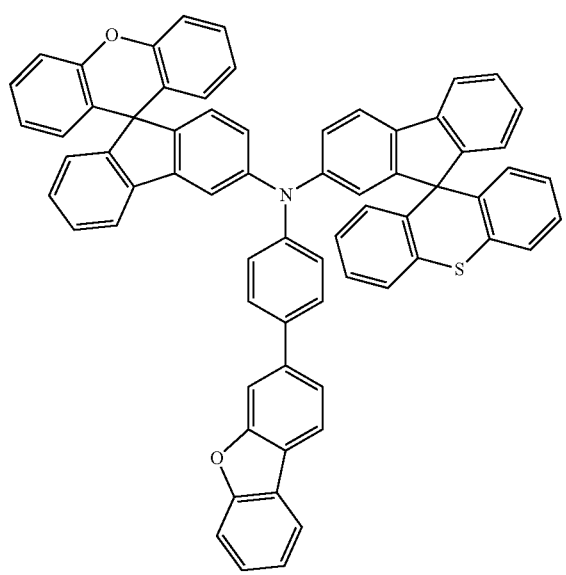
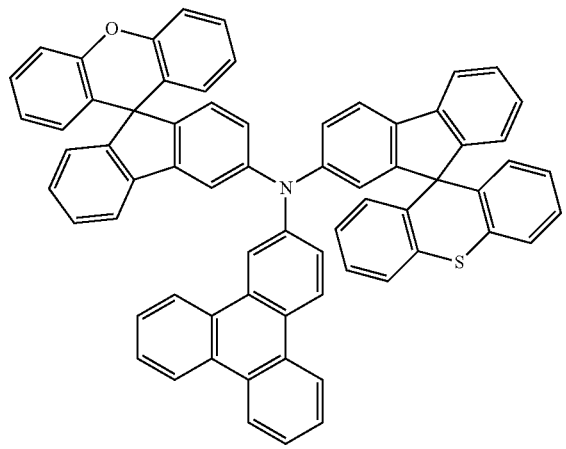

223
-continued
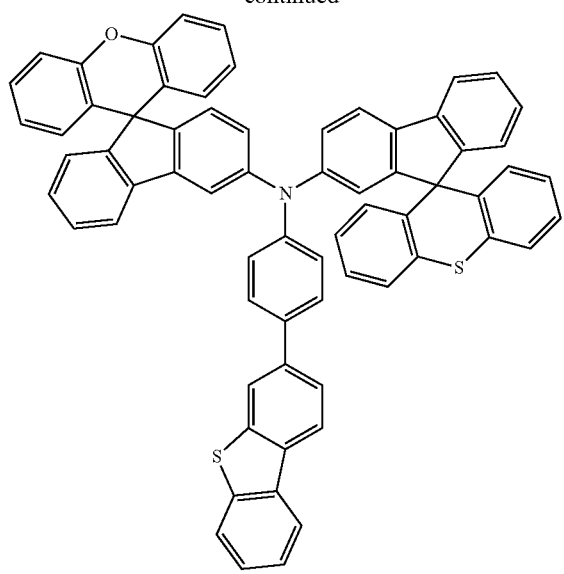
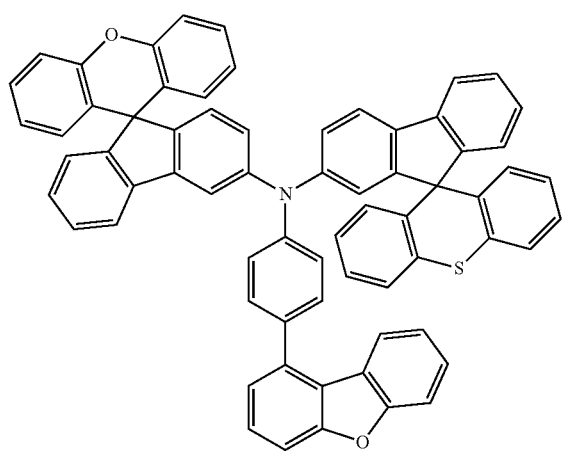
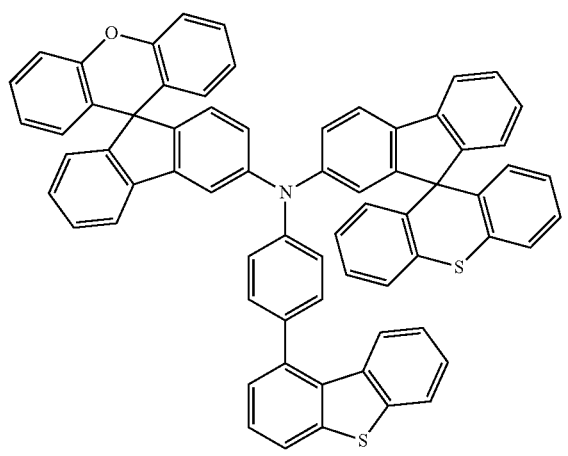
224
-continued
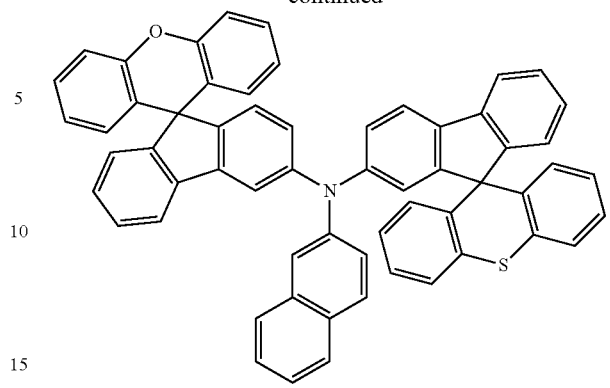
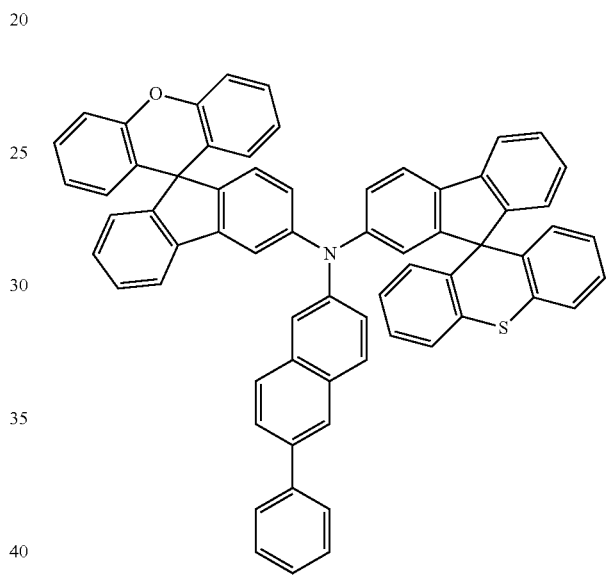
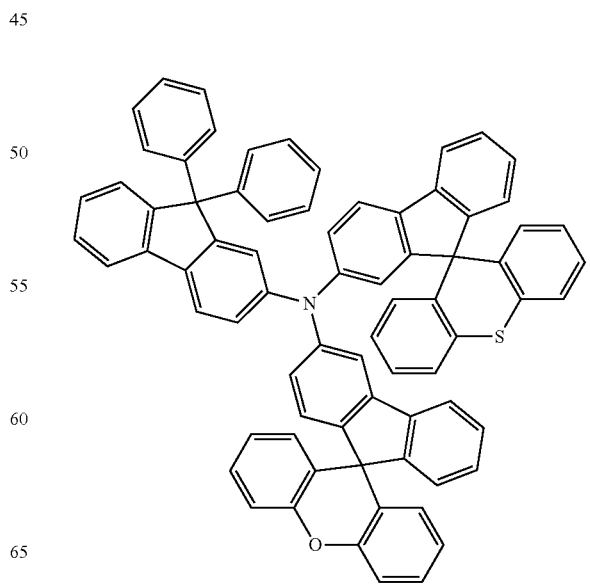

225
-continued
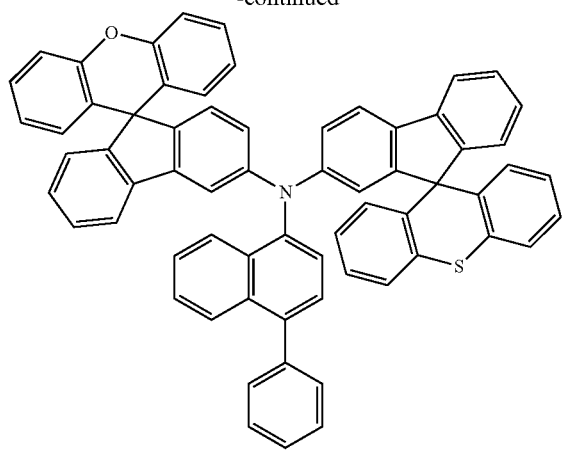
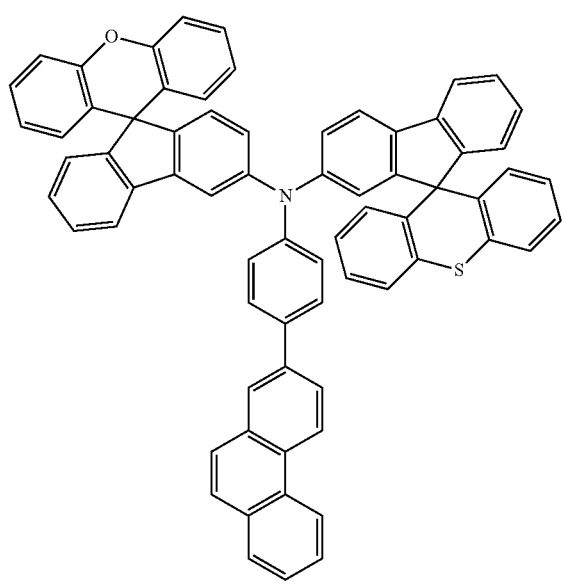
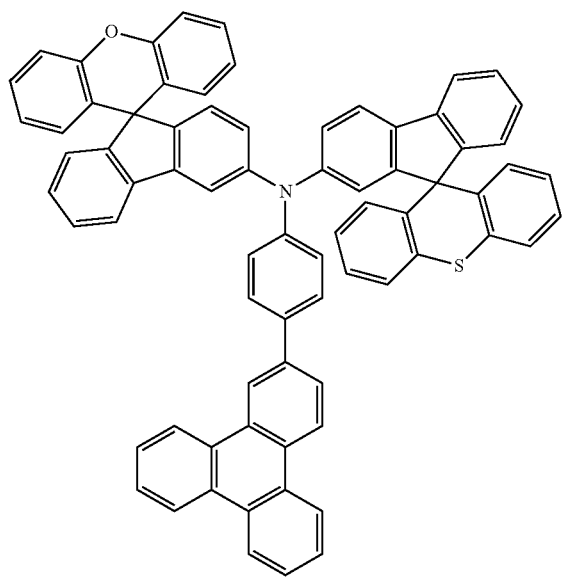
226
-continued
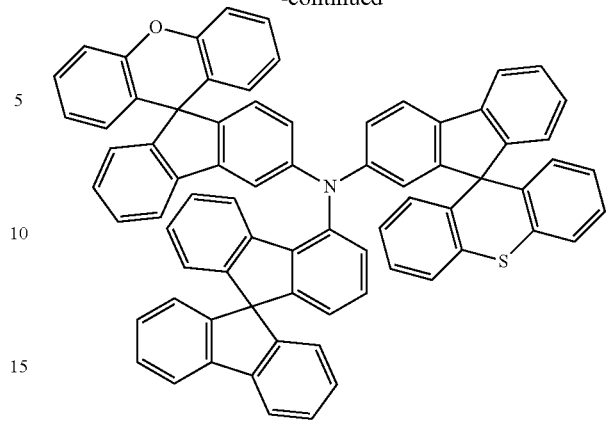
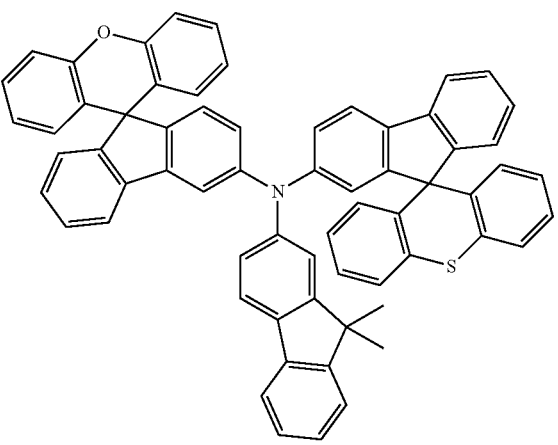

227
-continued
228
-continued
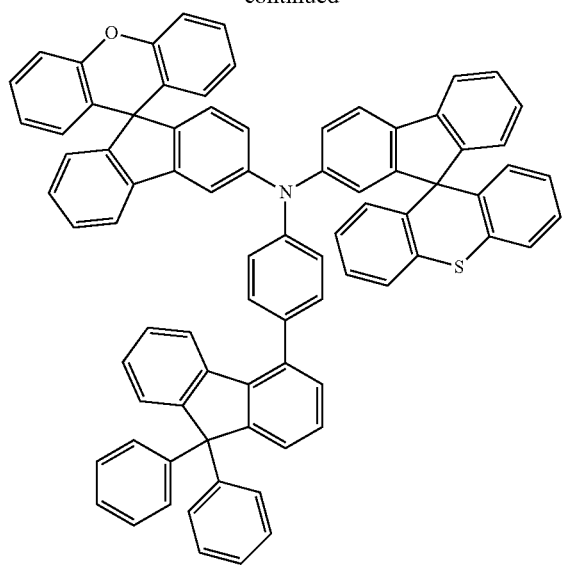
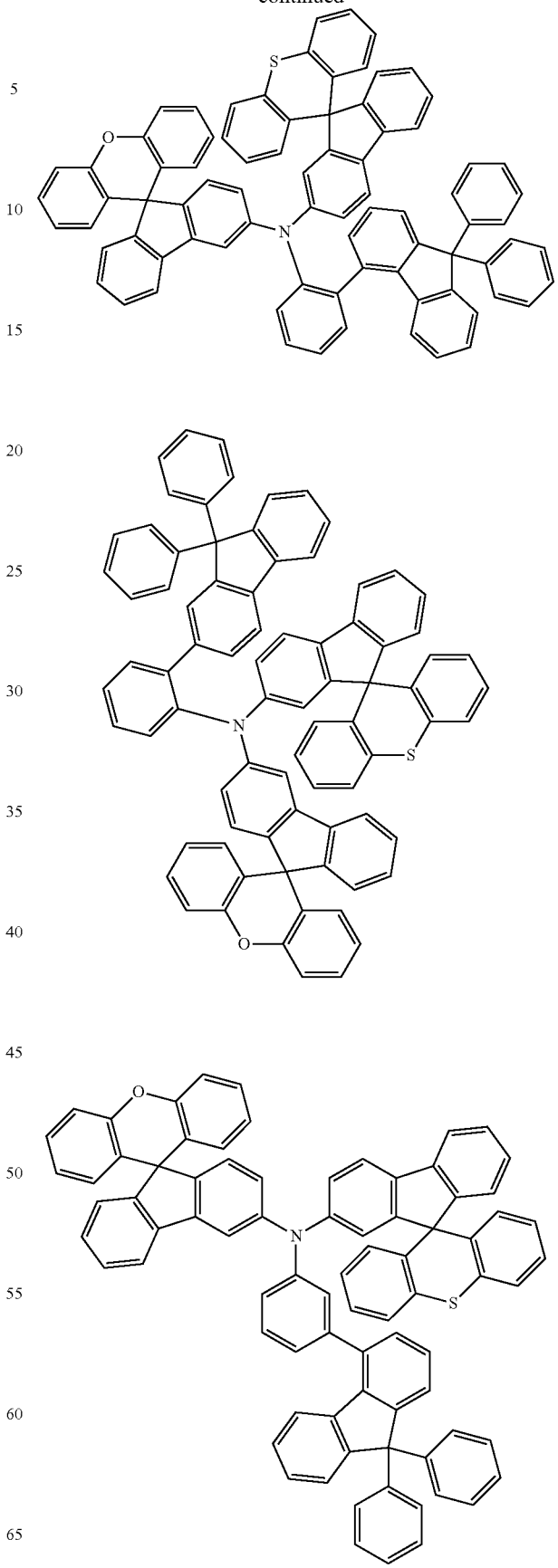

229
-continued
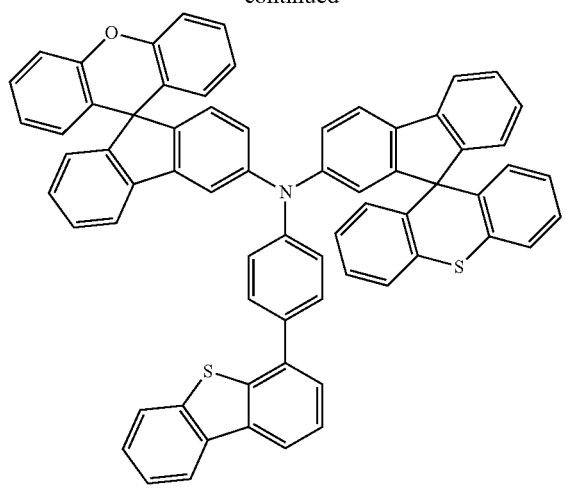
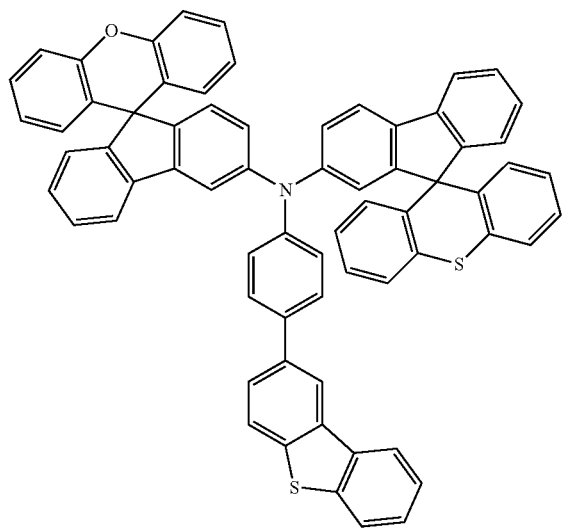
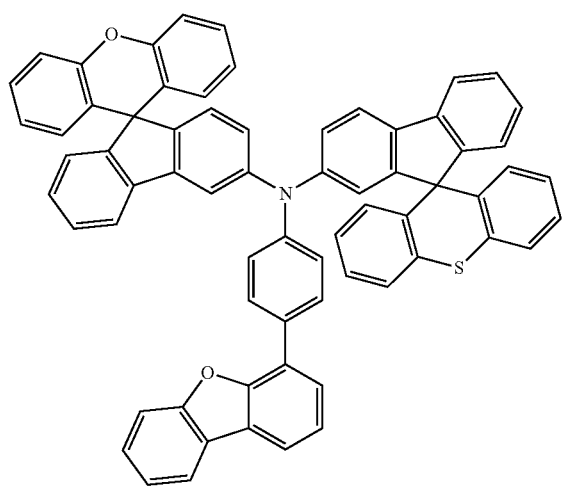
230
-continued
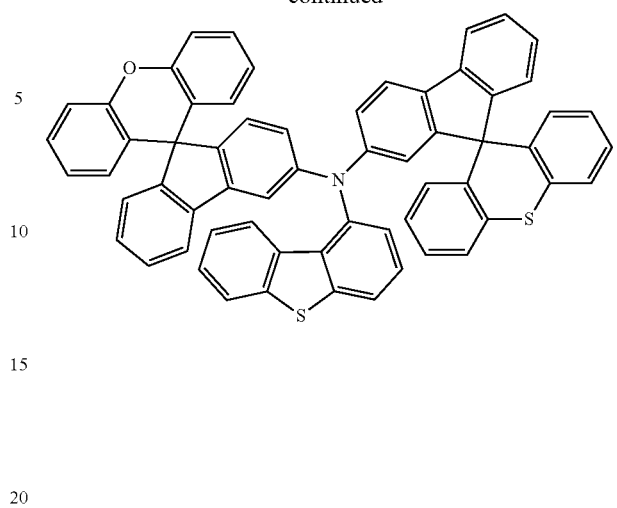
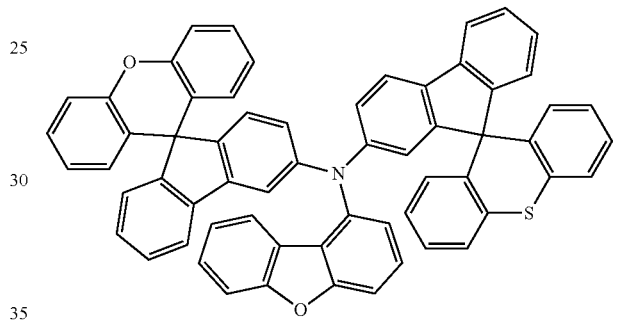
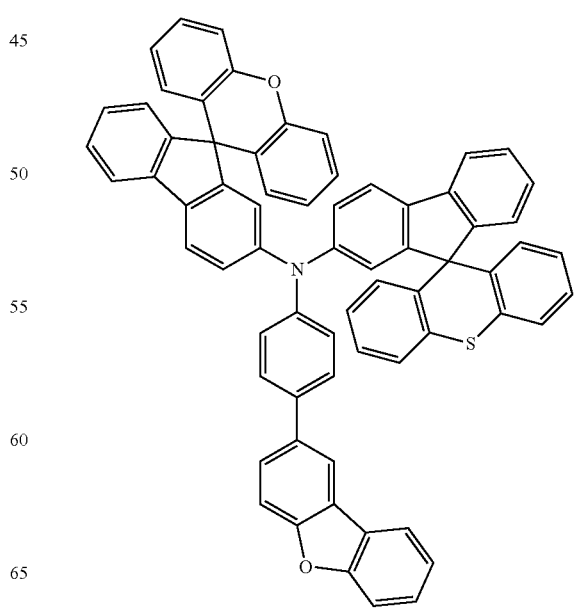

231
-continued
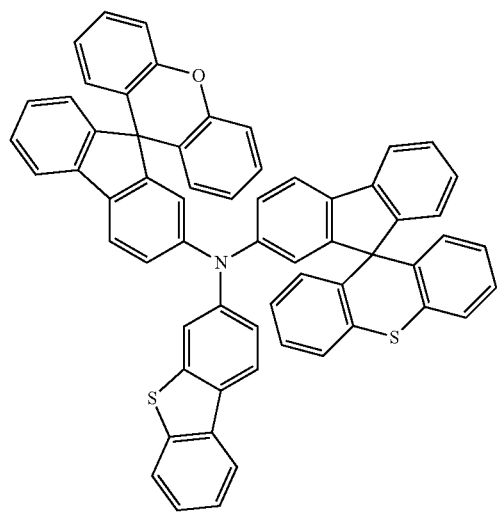
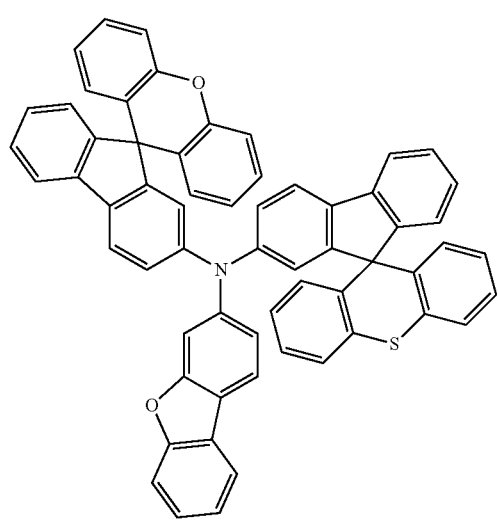
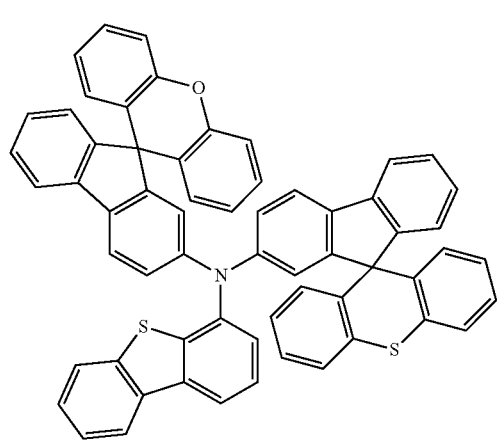
232
-continued
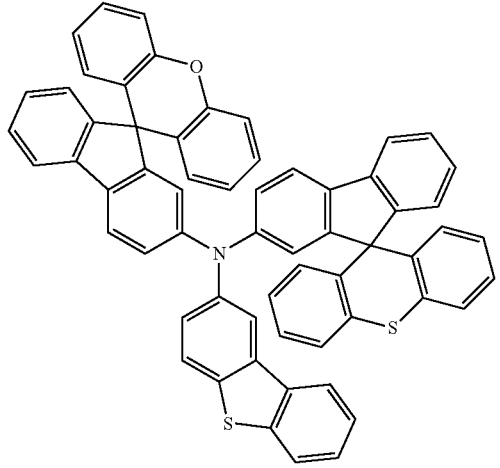
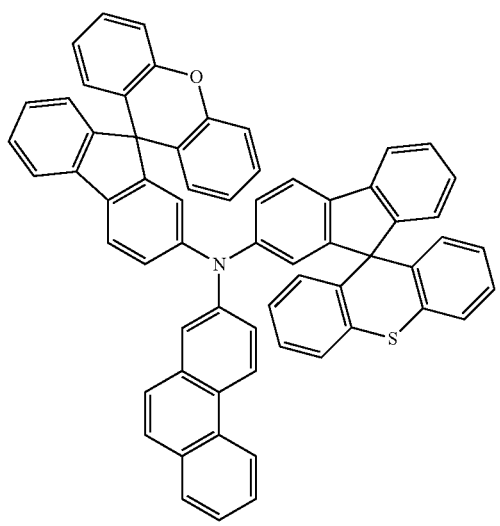
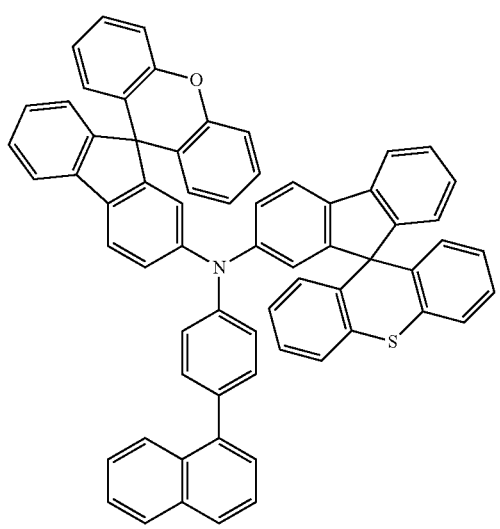

233
-continued
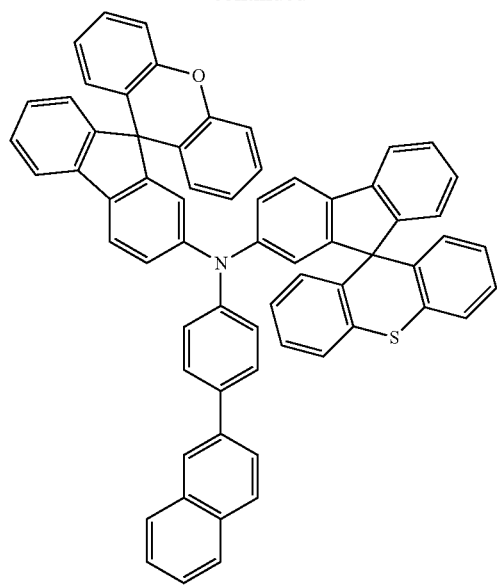
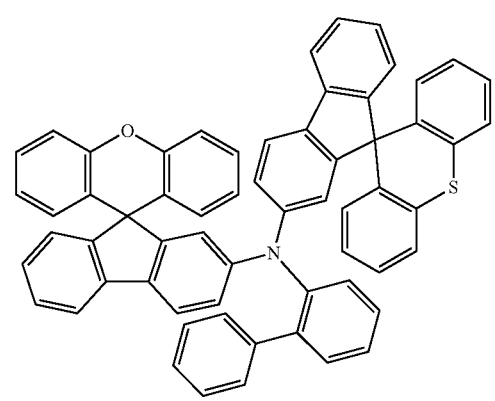
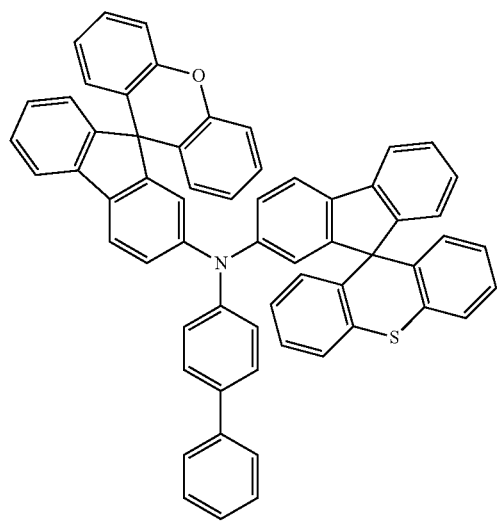
234
-continued
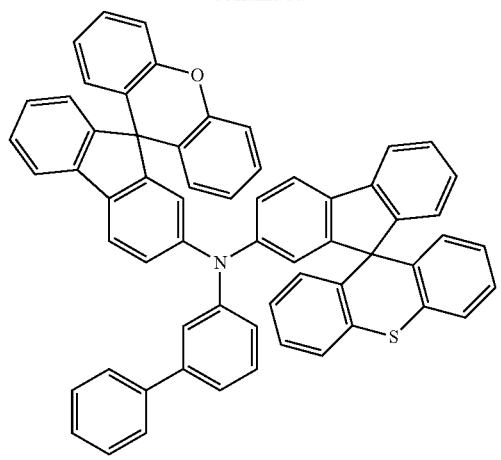
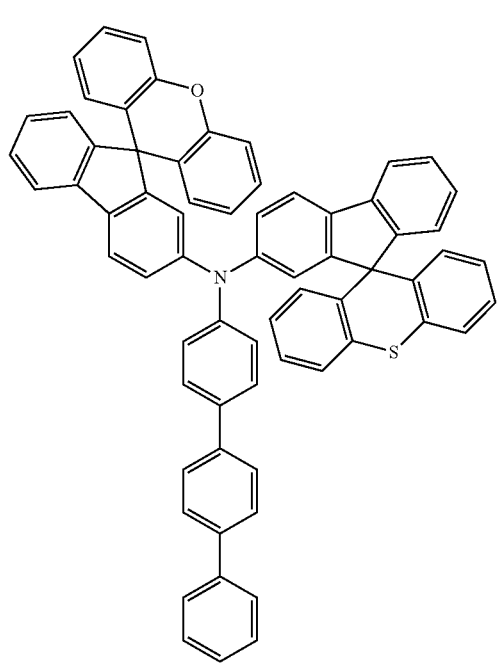
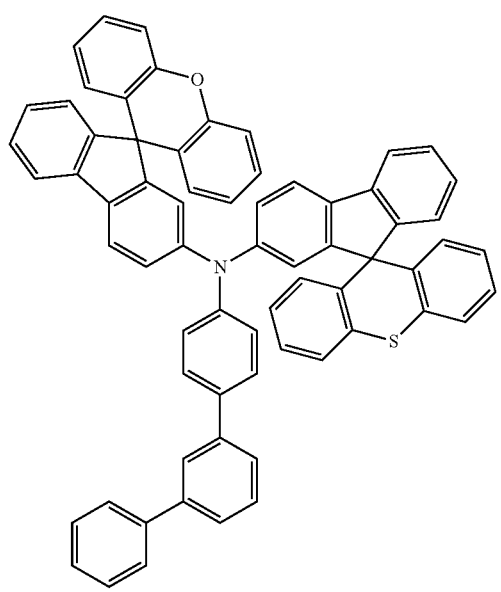

235
-continued
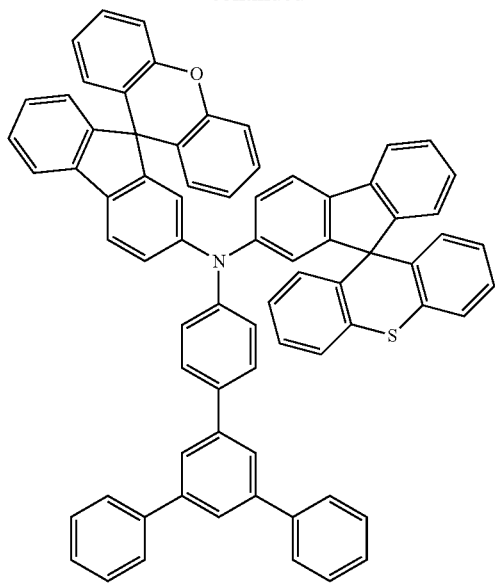
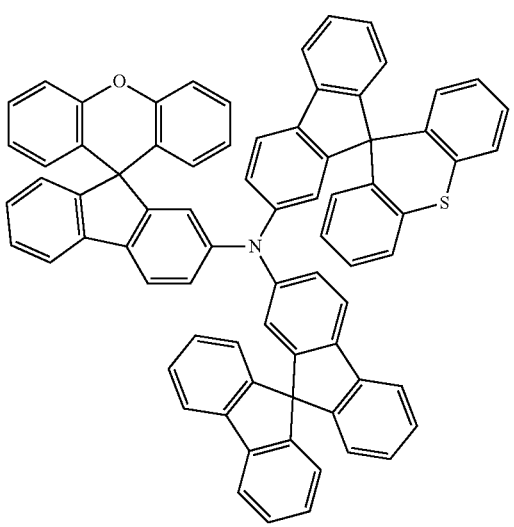
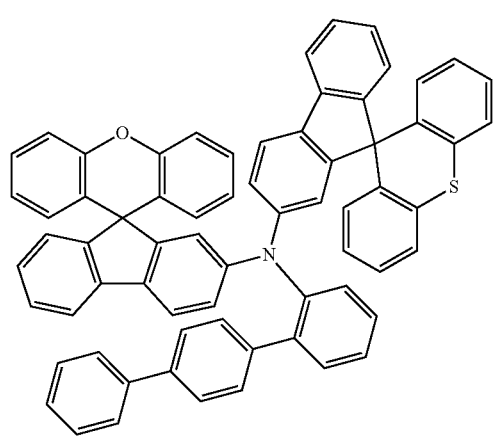
236
-continued
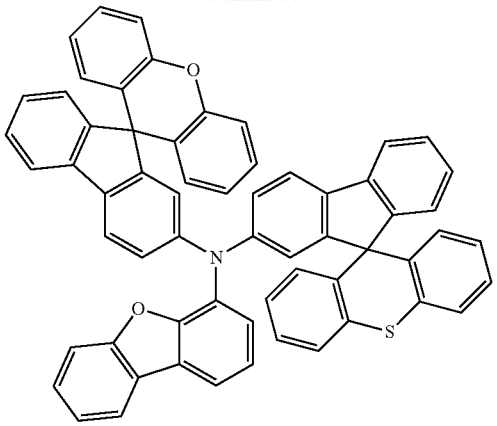
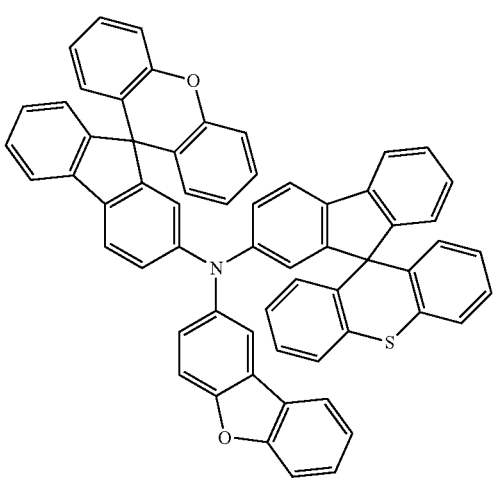
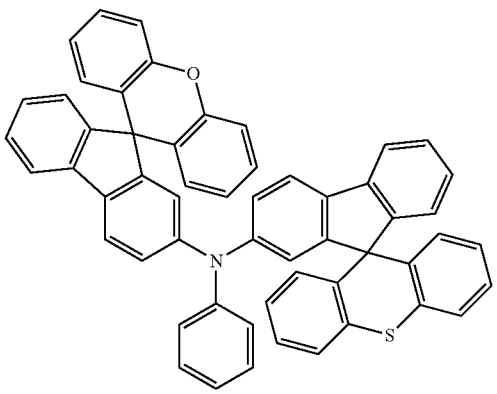

237
-continued
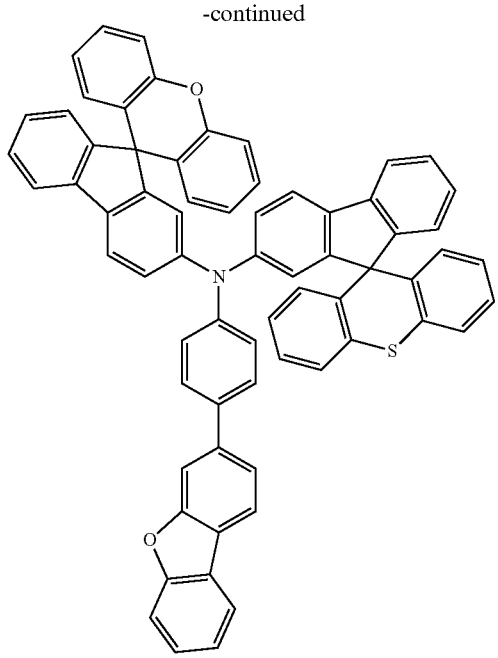
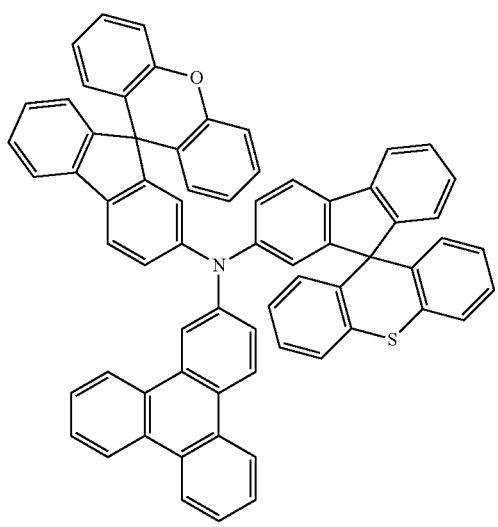
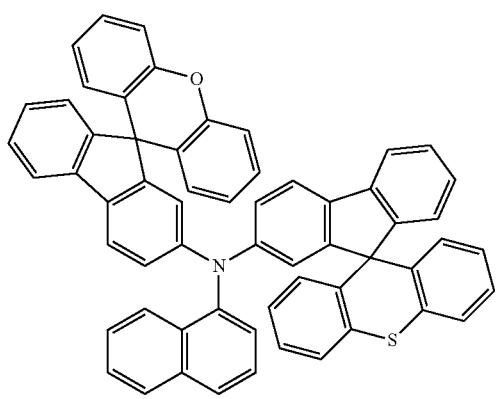
238
-continued
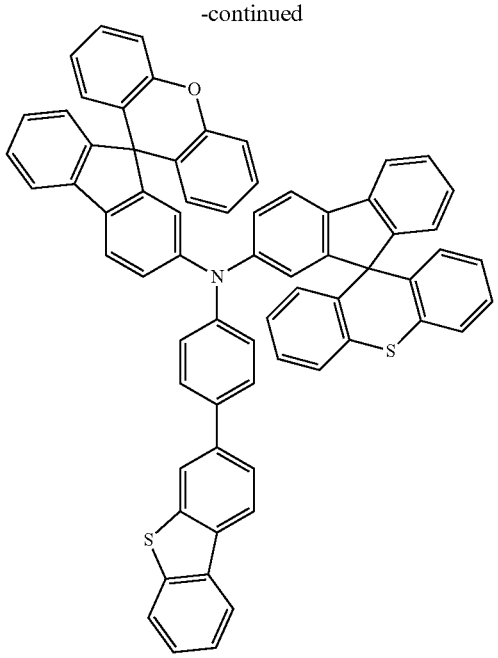
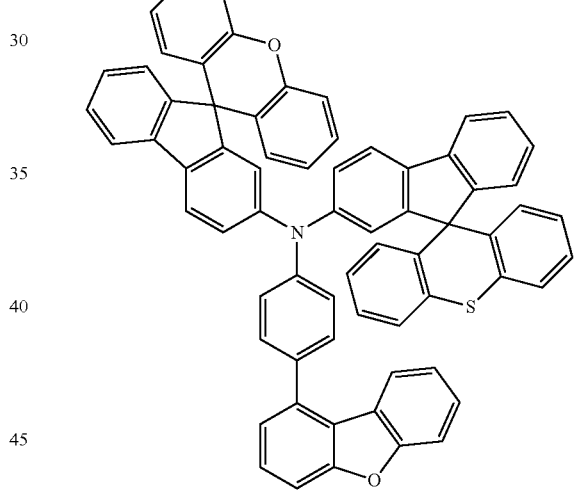
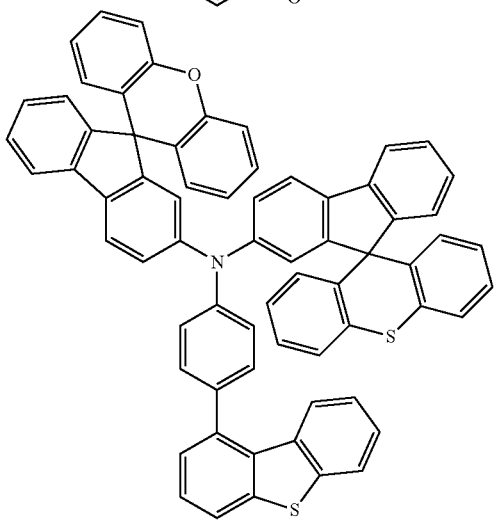

239
-continued
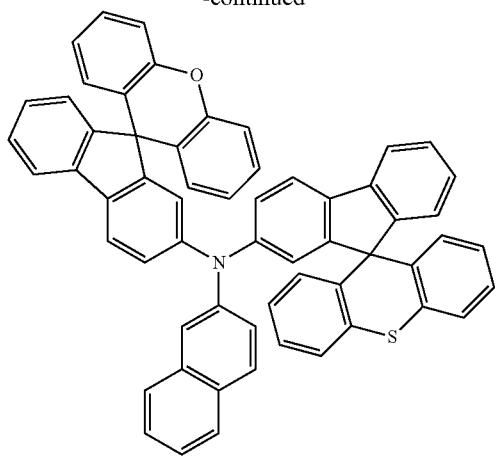
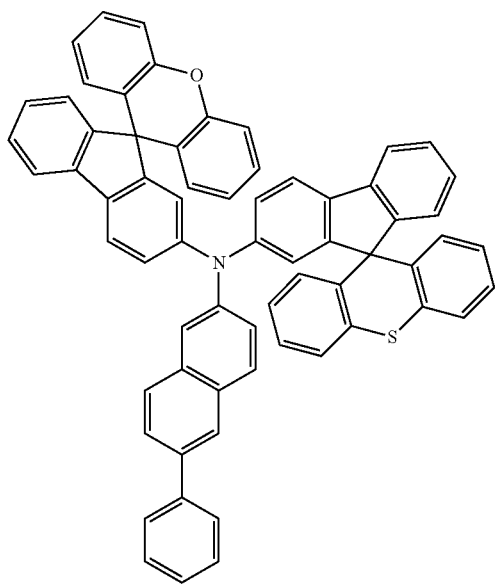
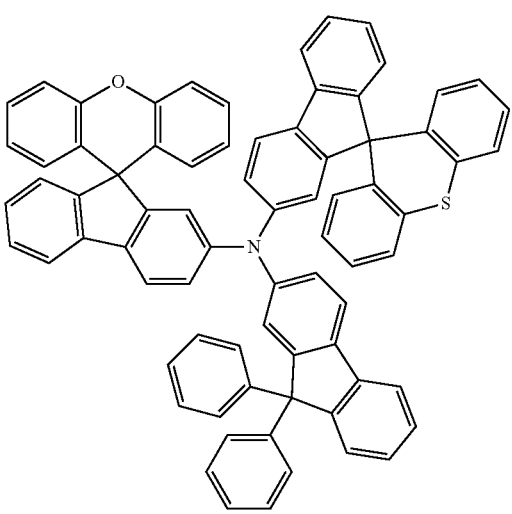
240
-continued
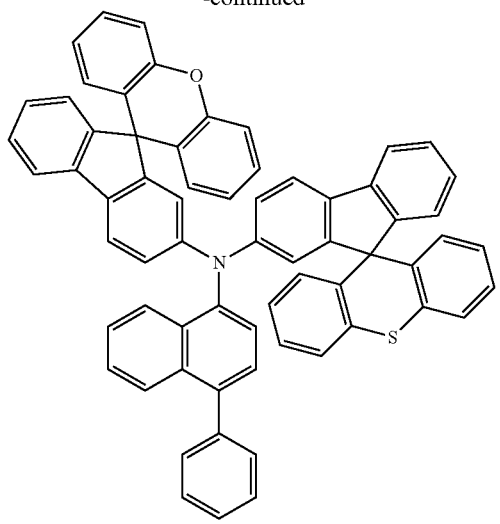
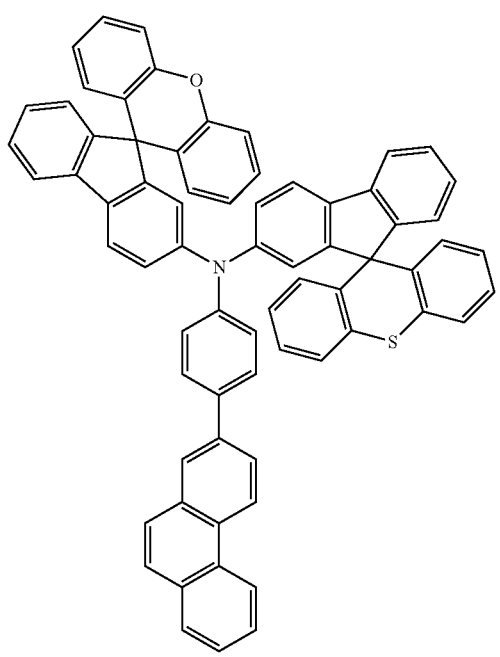

241
-continued
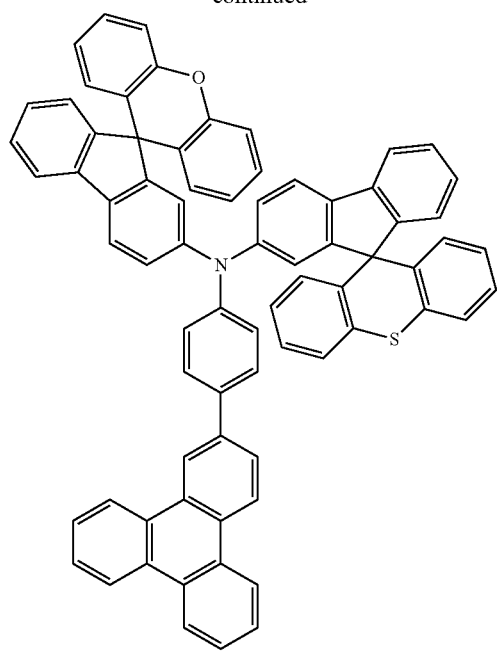
242
-continued
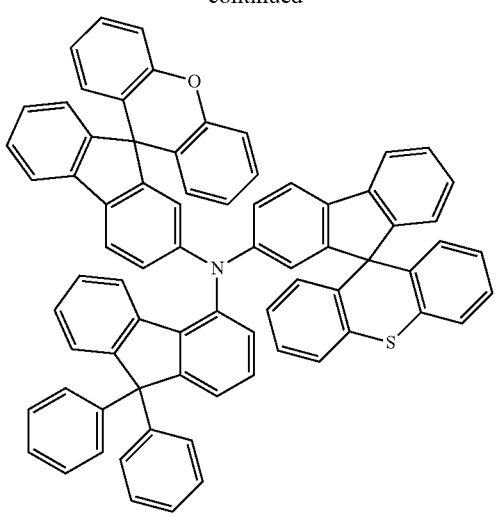
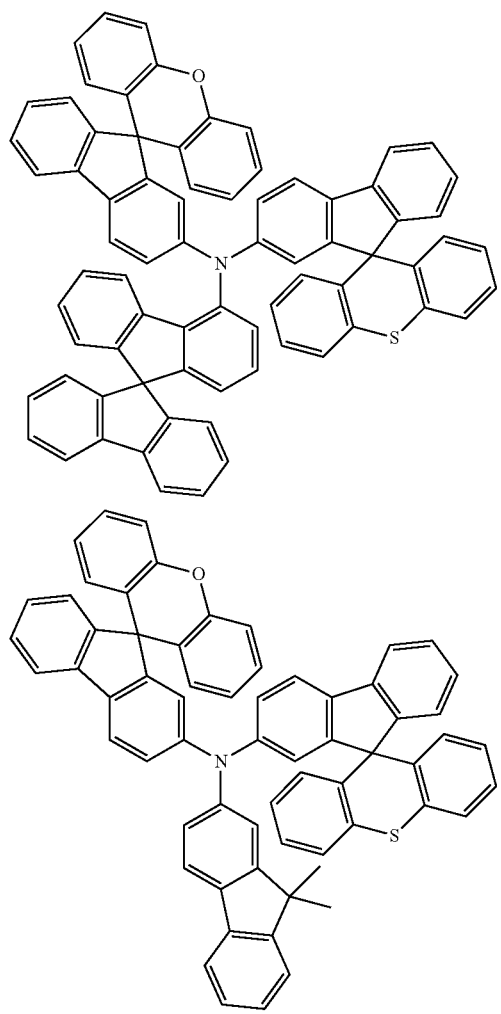
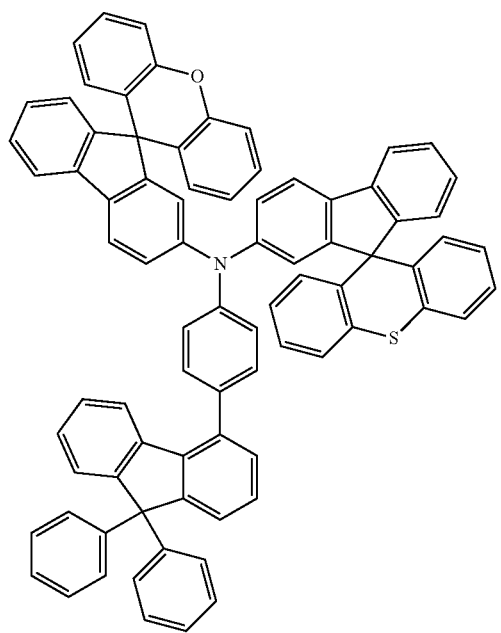

243
-continued
244
-continued
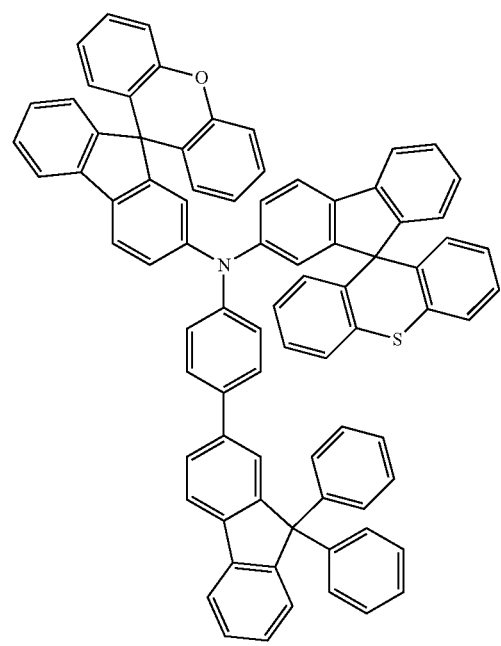
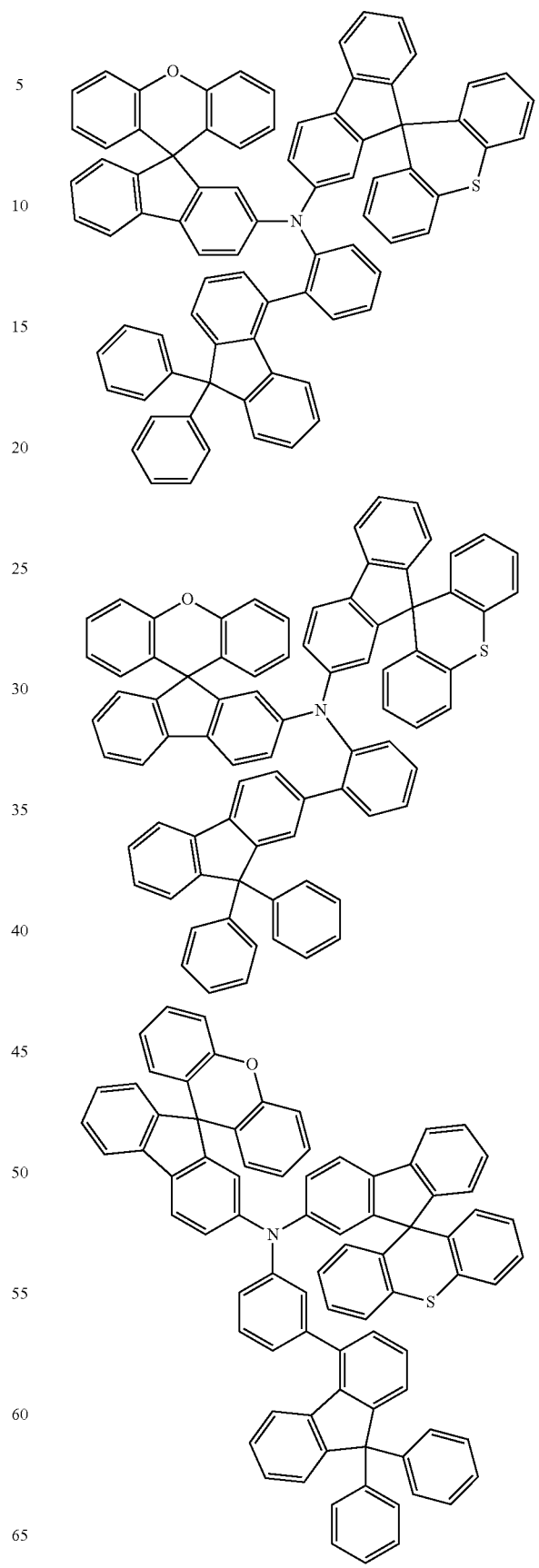

245
-continued
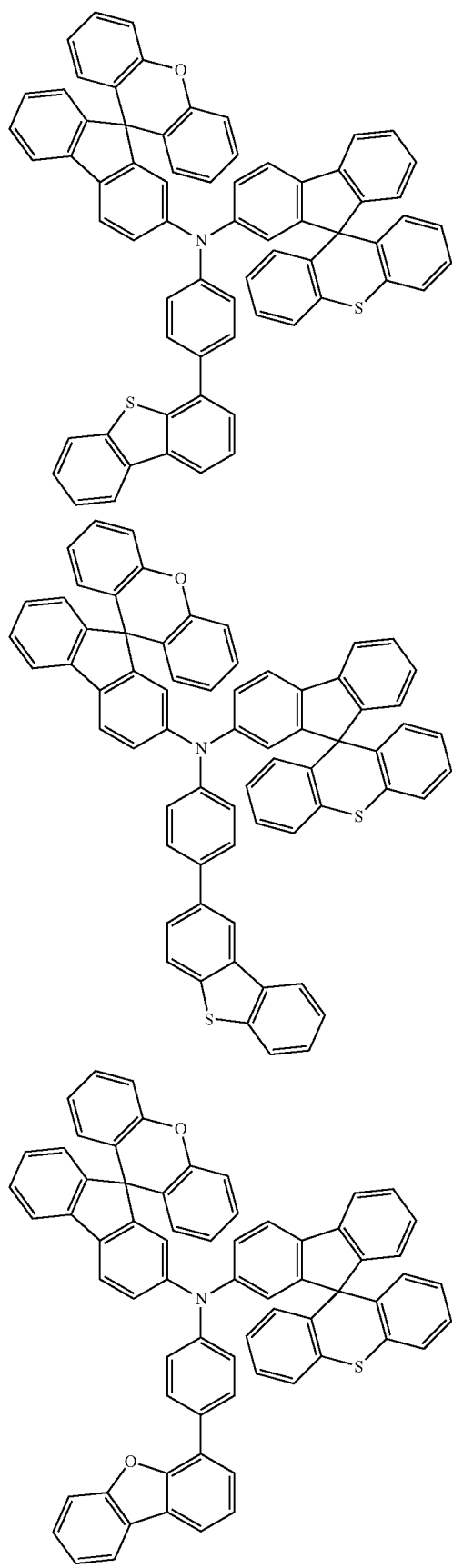
246
-continued
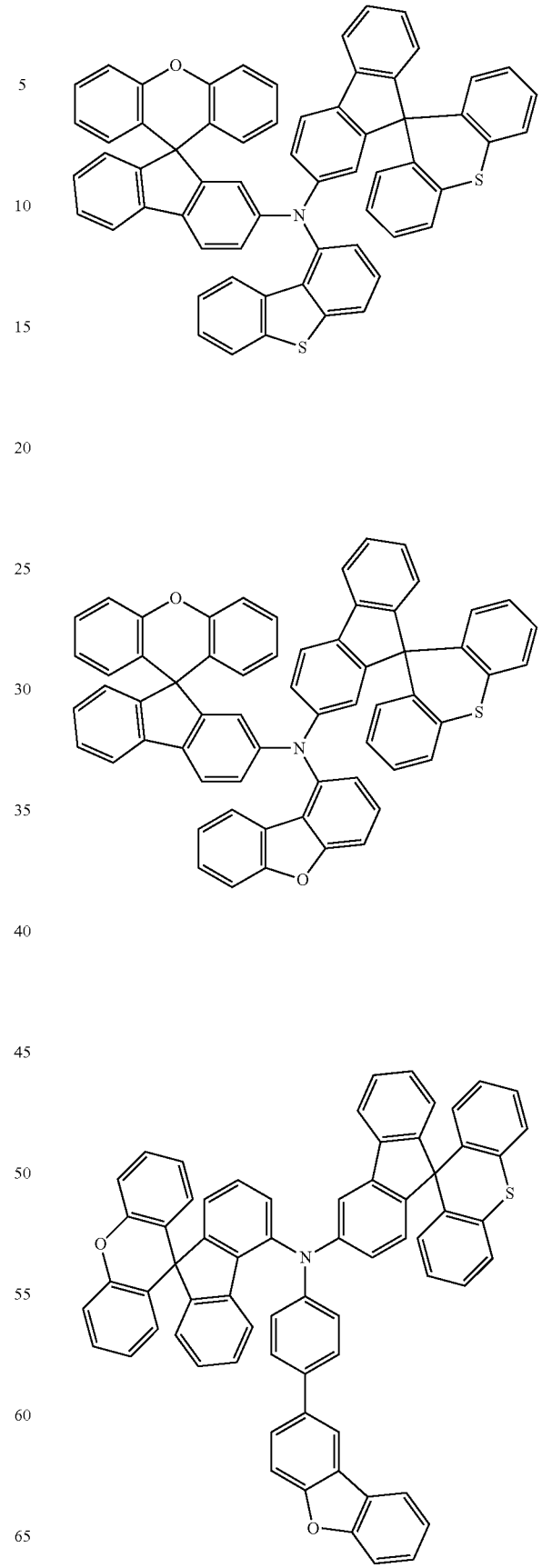

247
-continued
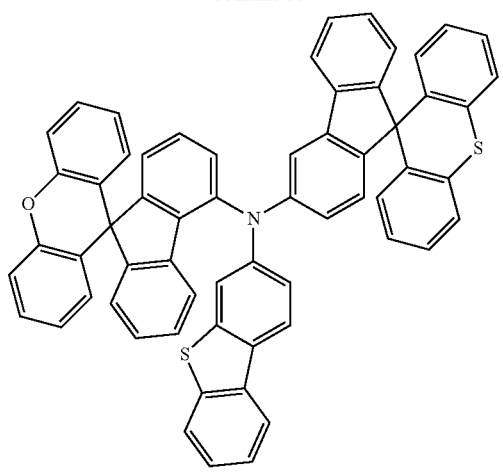
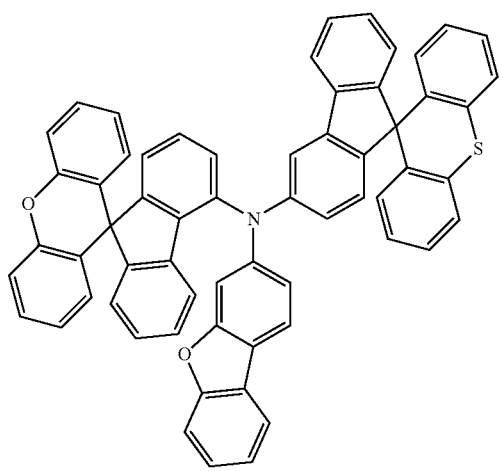
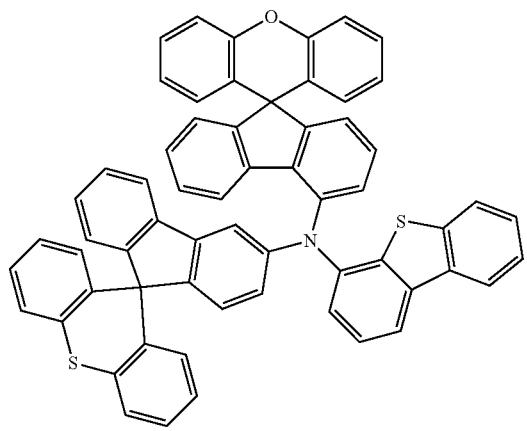
248
-continued
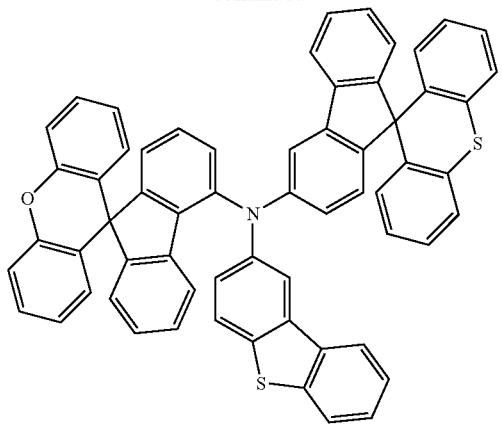
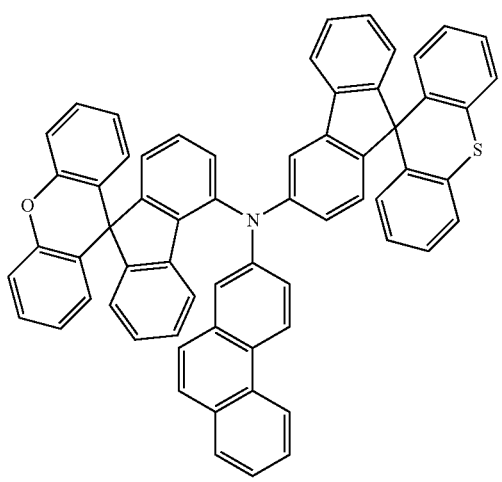
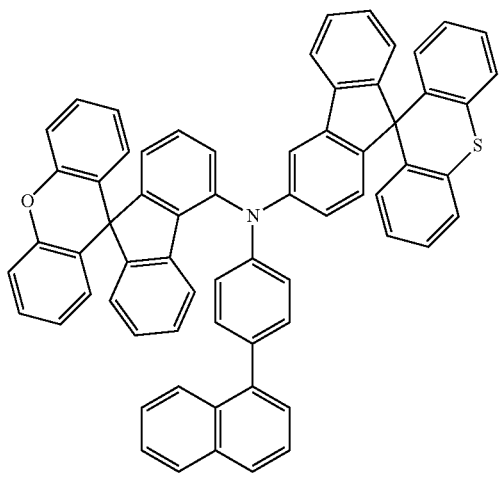

-continued
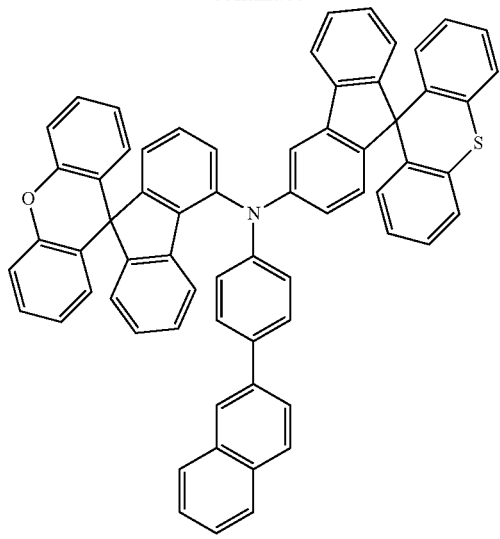
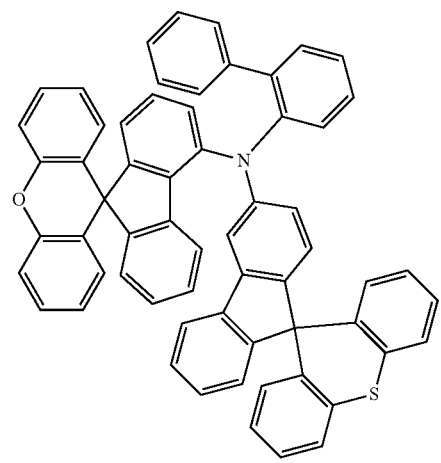
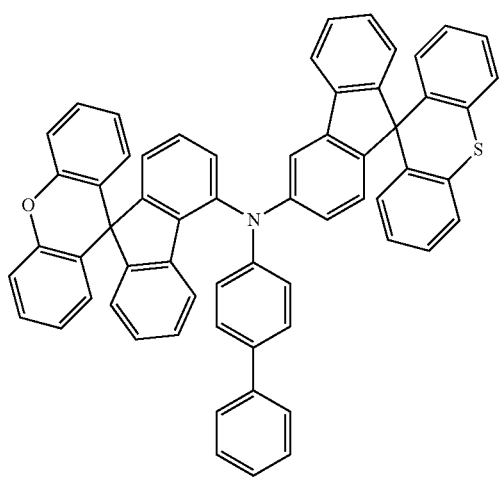
-continued
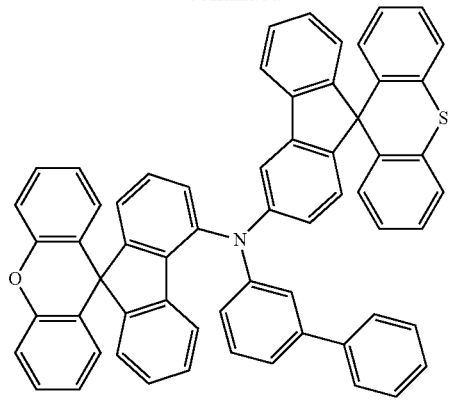
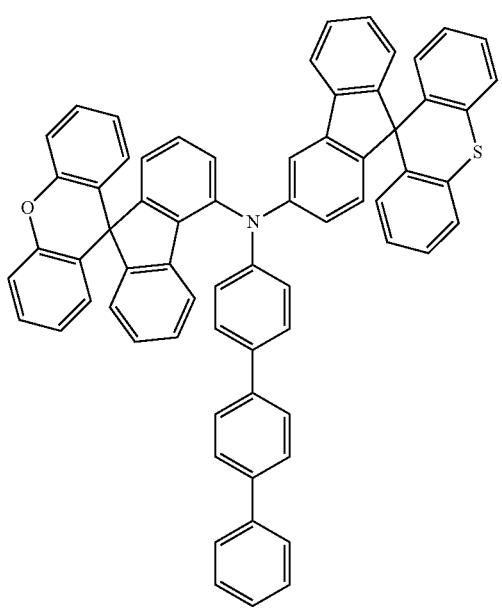
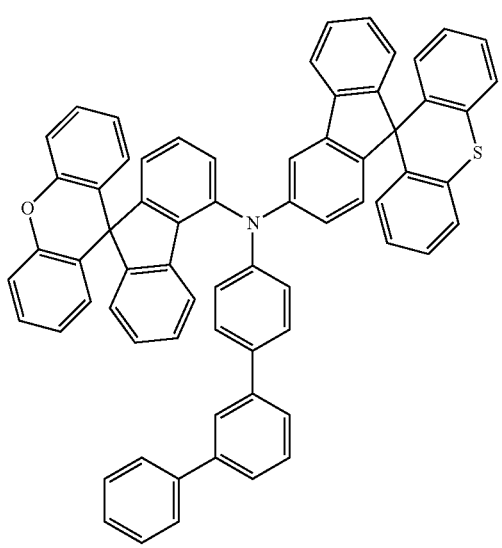

251
-continued
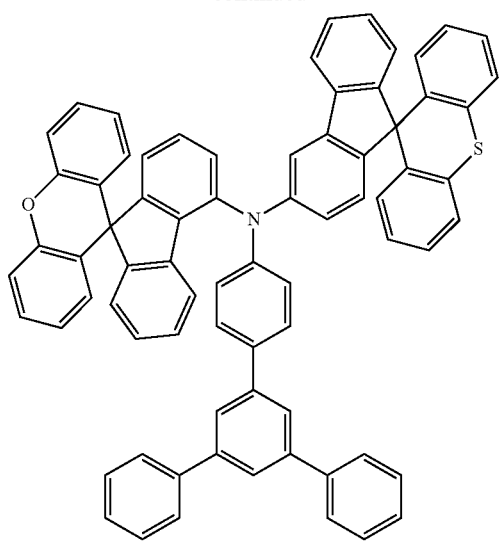
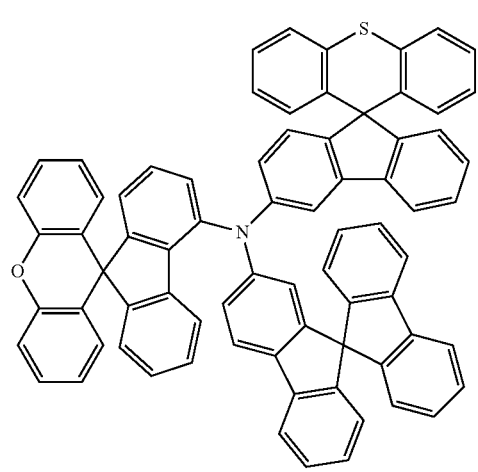
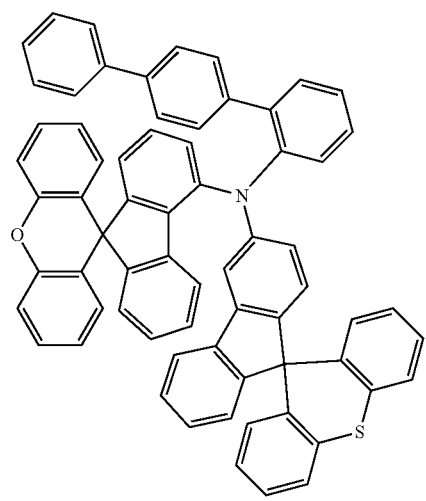
252
-continued
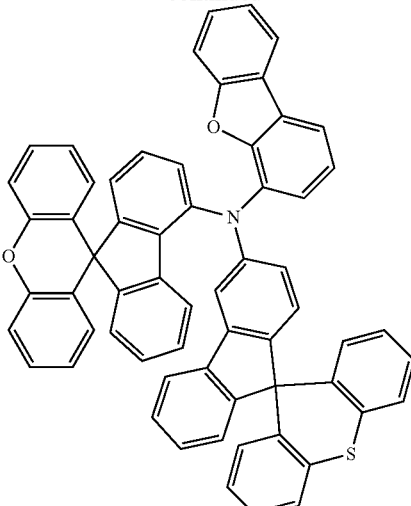
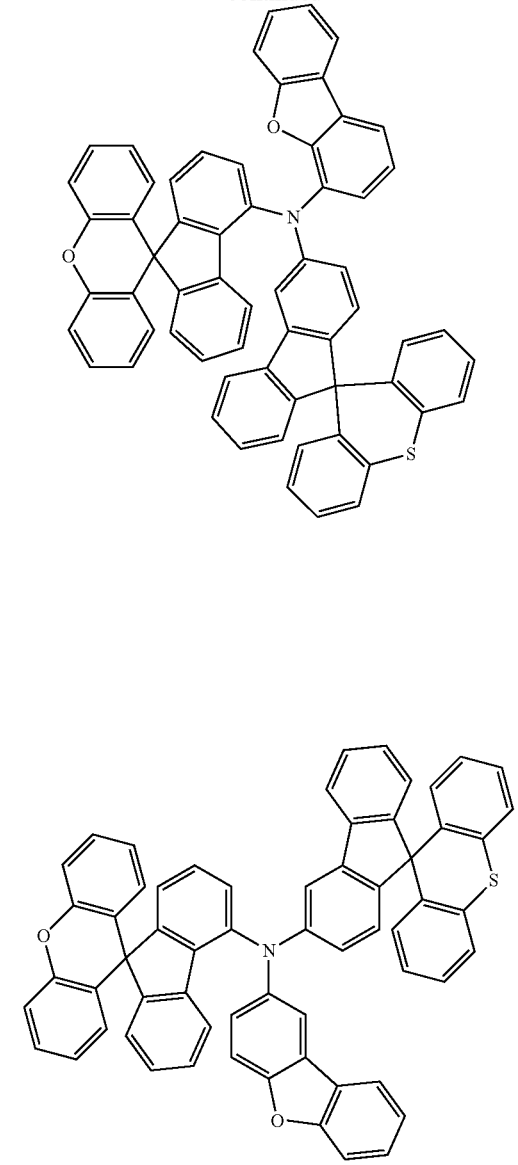
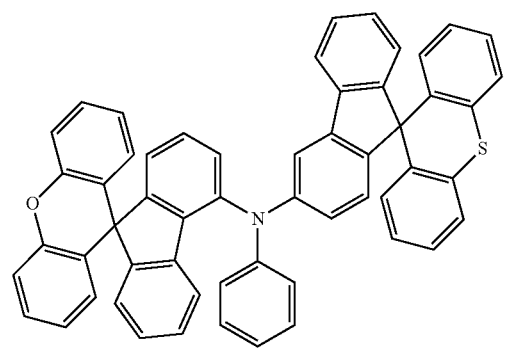

253
-continued
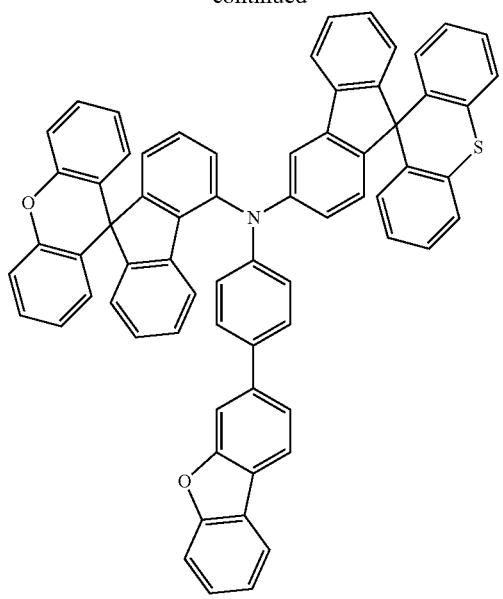
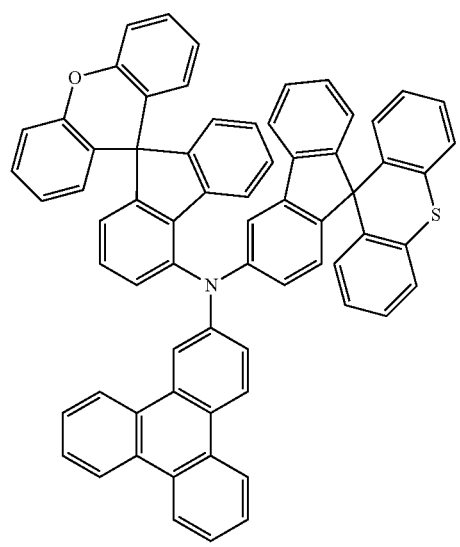
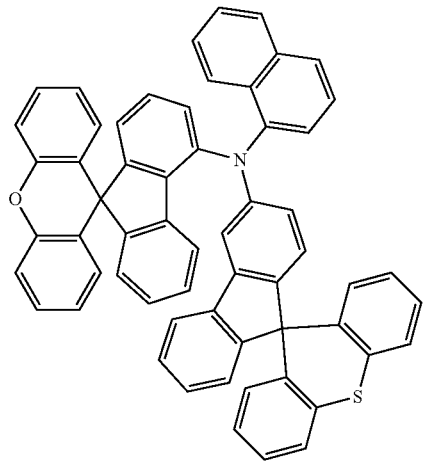
254
-continued
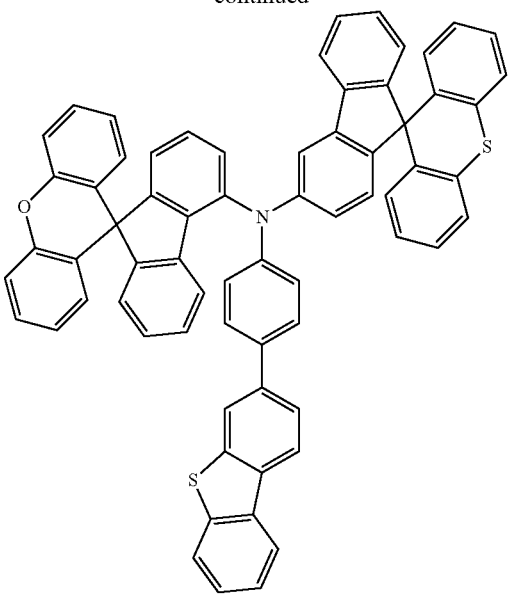
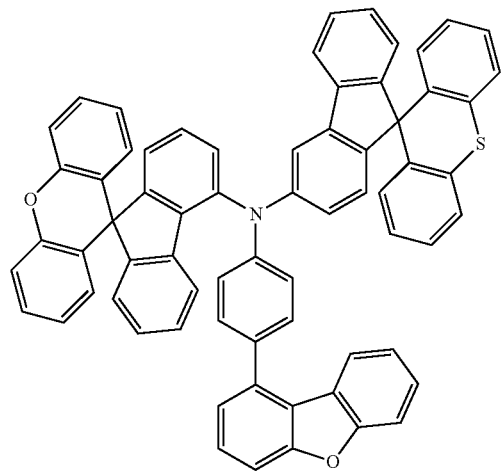
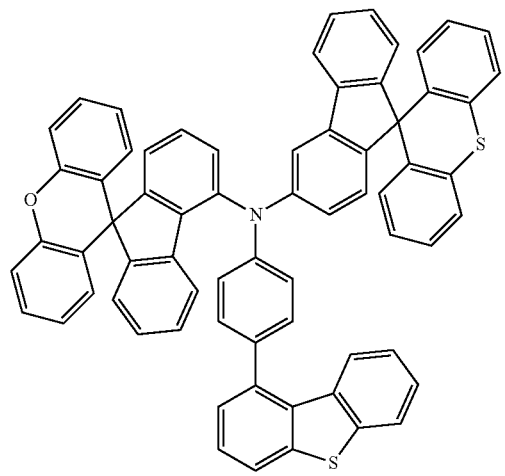

255
-continued
256
-continued
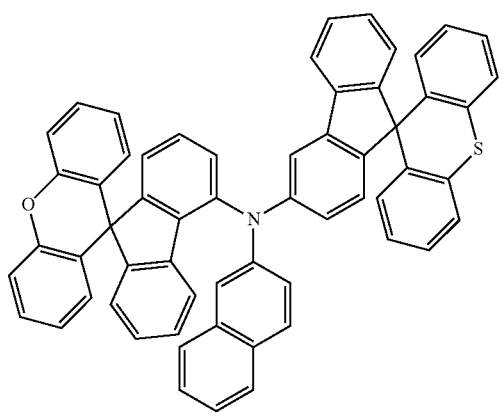
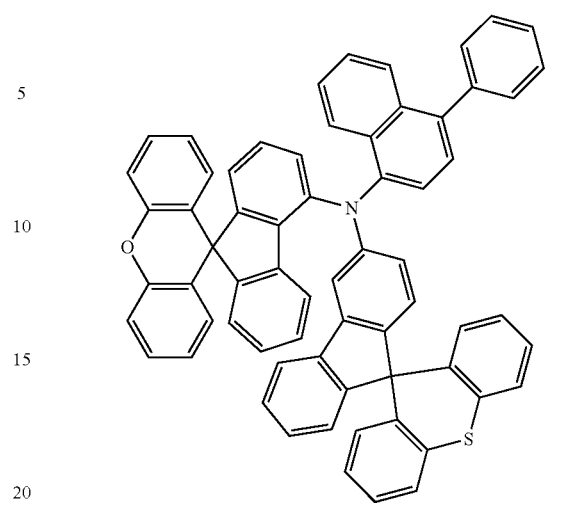
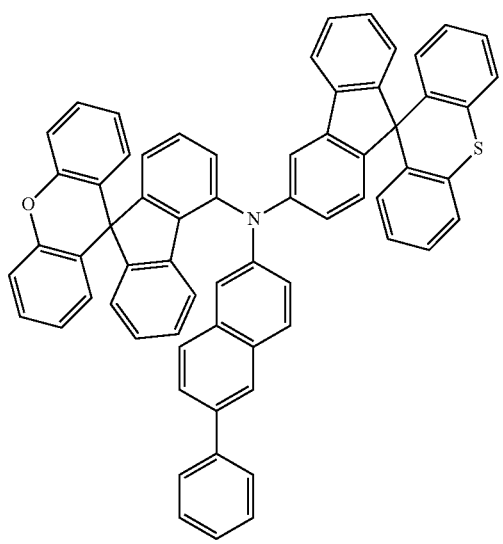
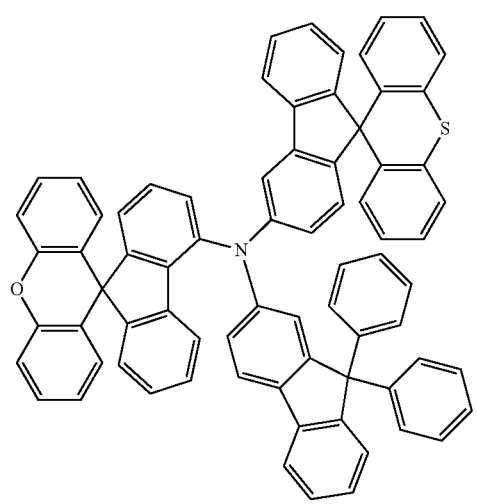

257
-continued
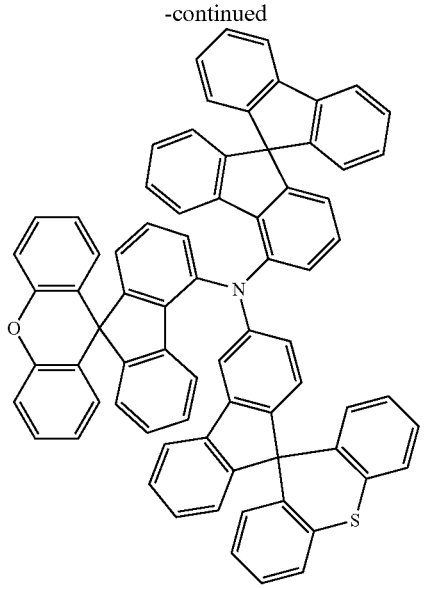
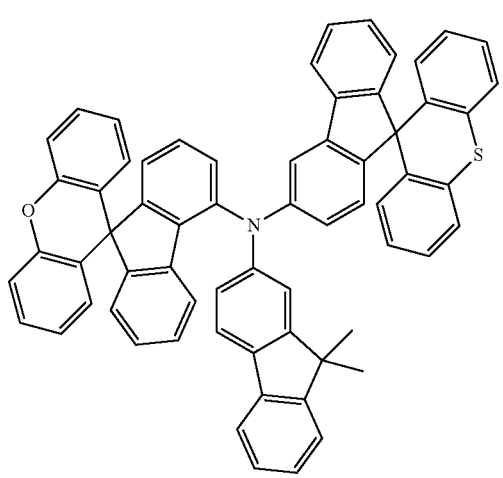
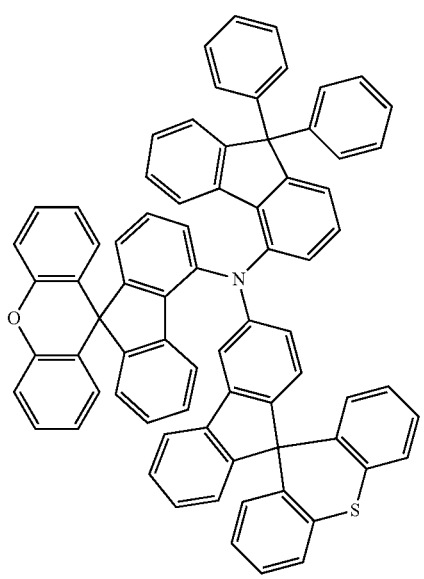
258
-continued
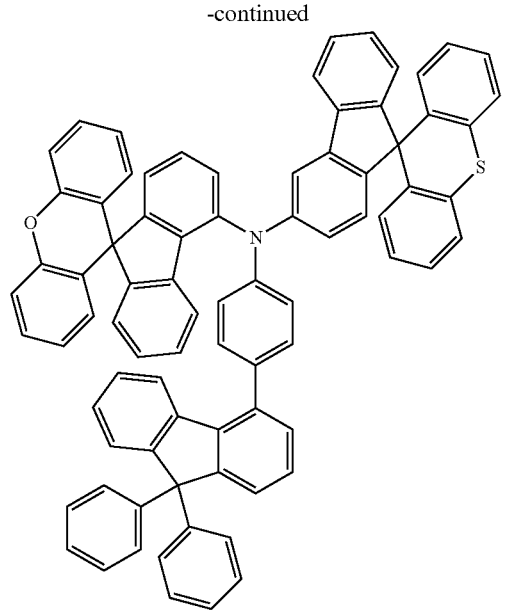
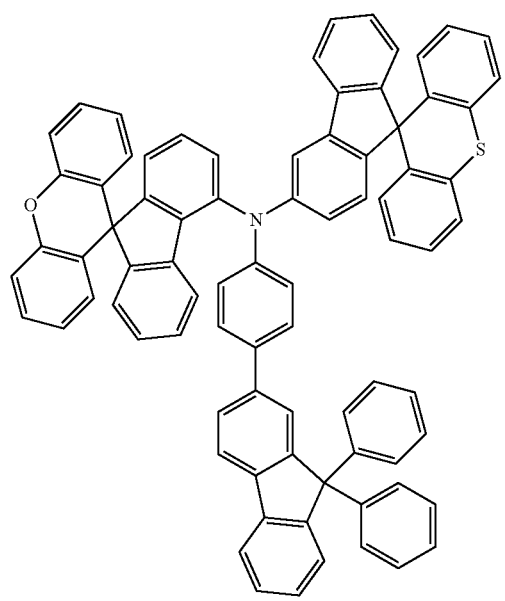

259
-continued
260
-continued
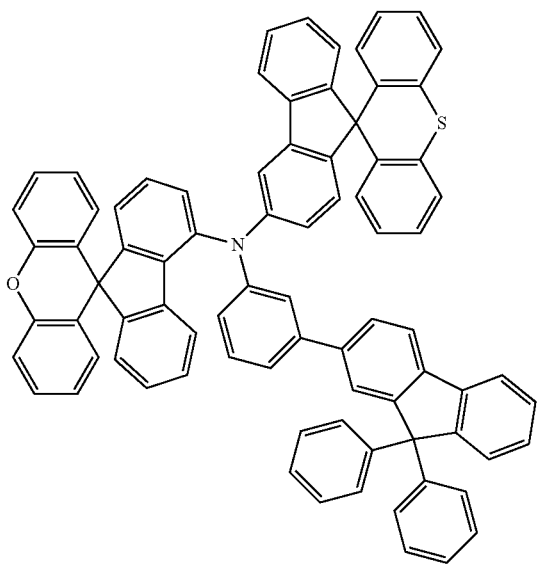
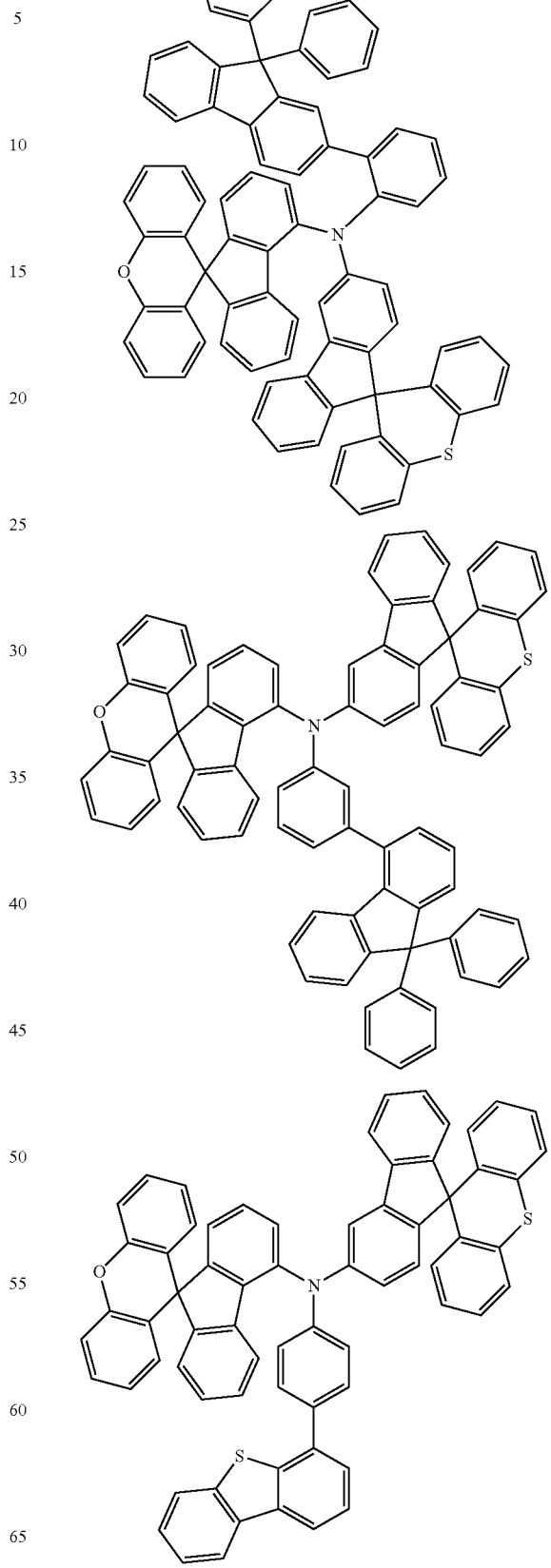

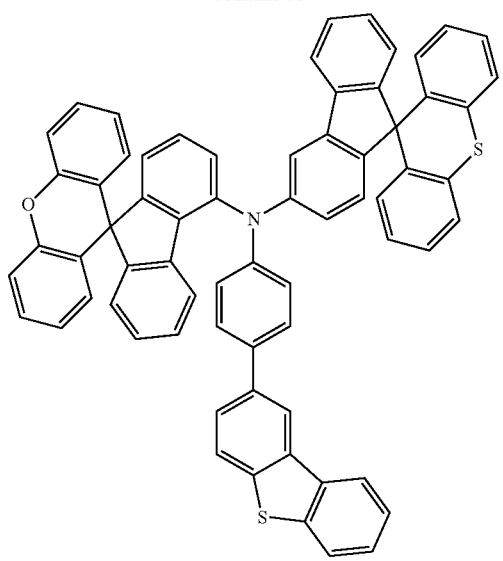
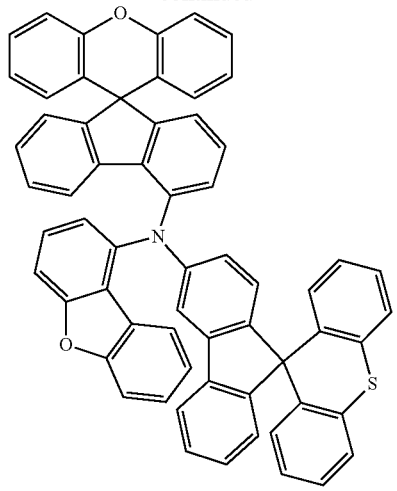
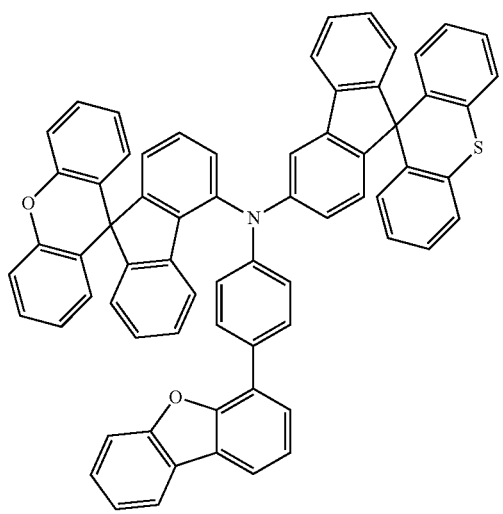
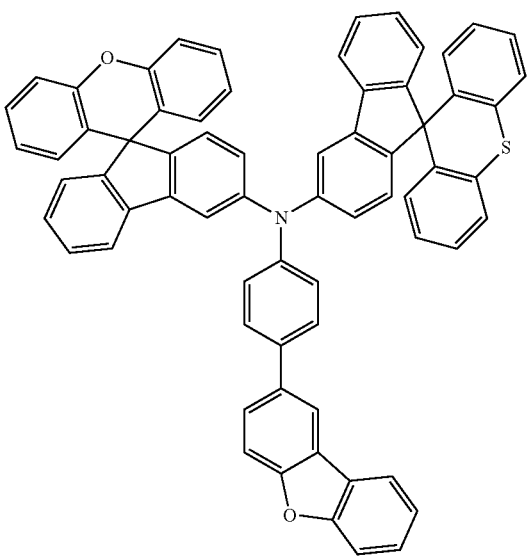
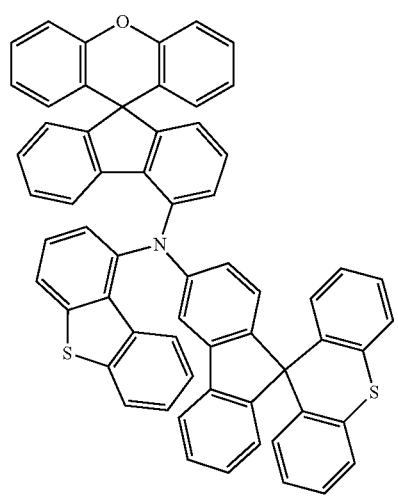
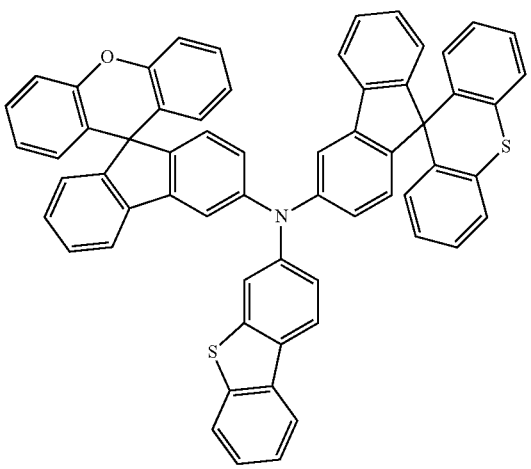

263
-continued
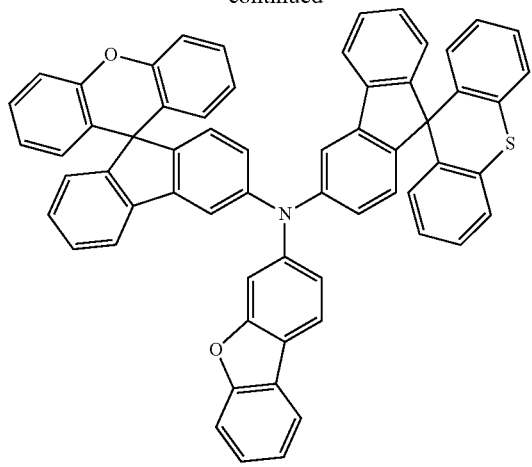
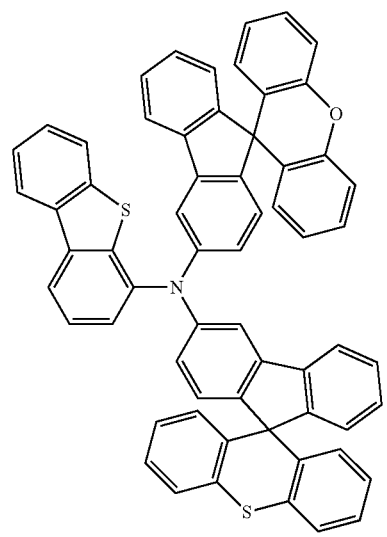
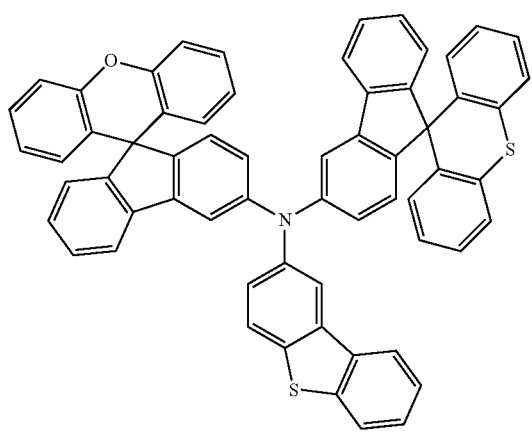
264
-continued
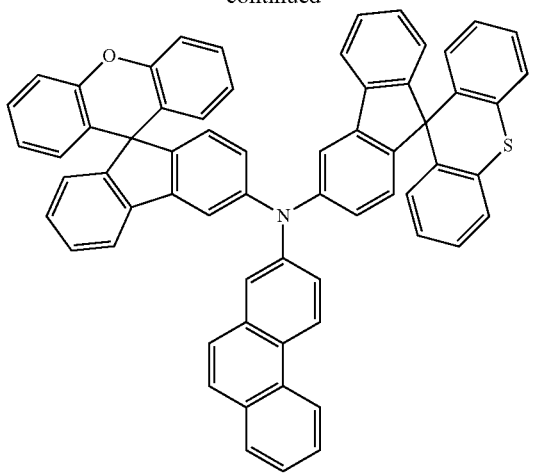
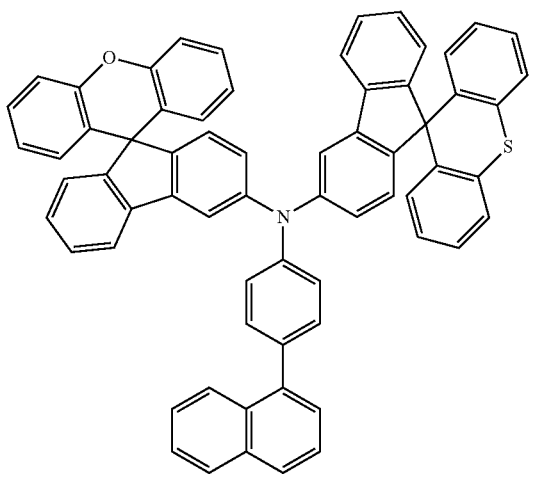
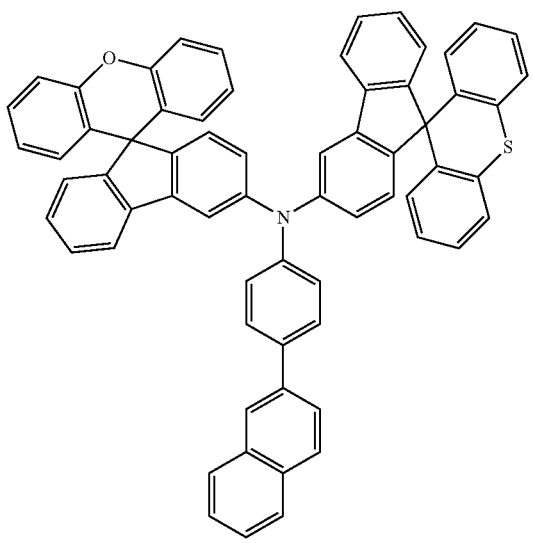

265
-continued
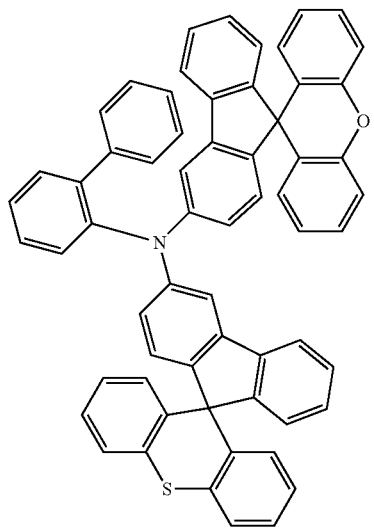
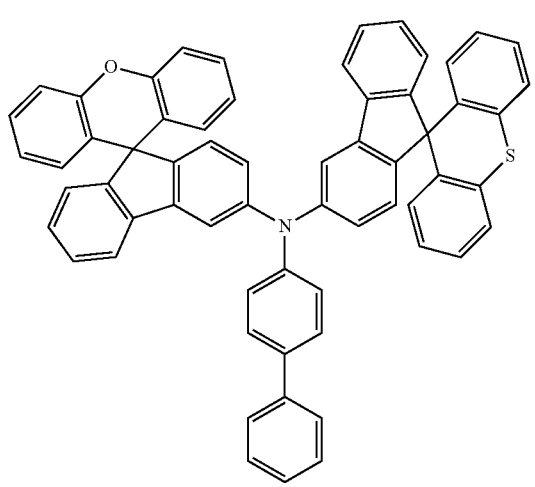
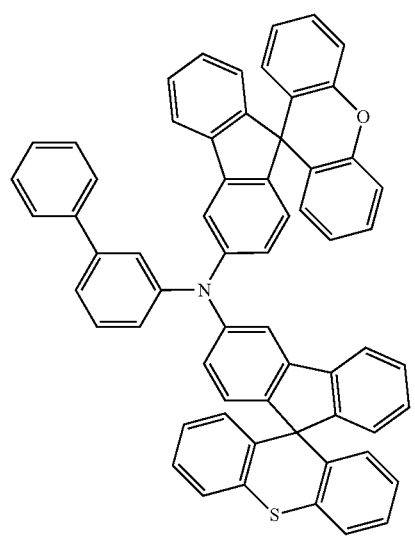
266
-continued
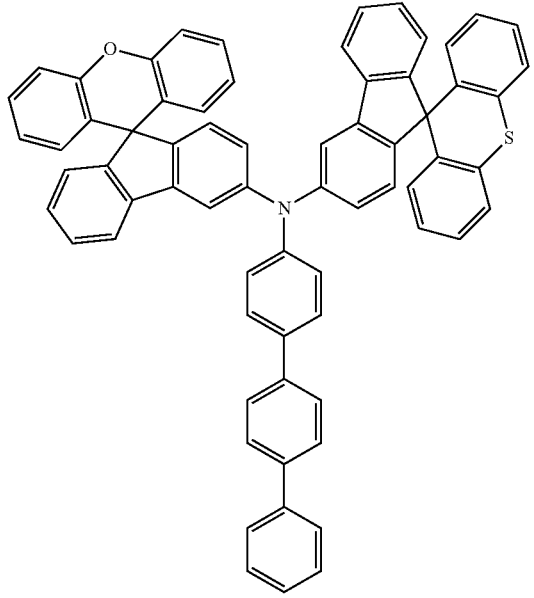
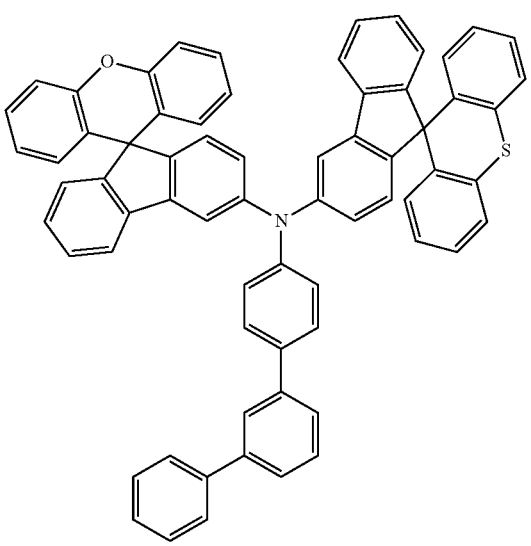
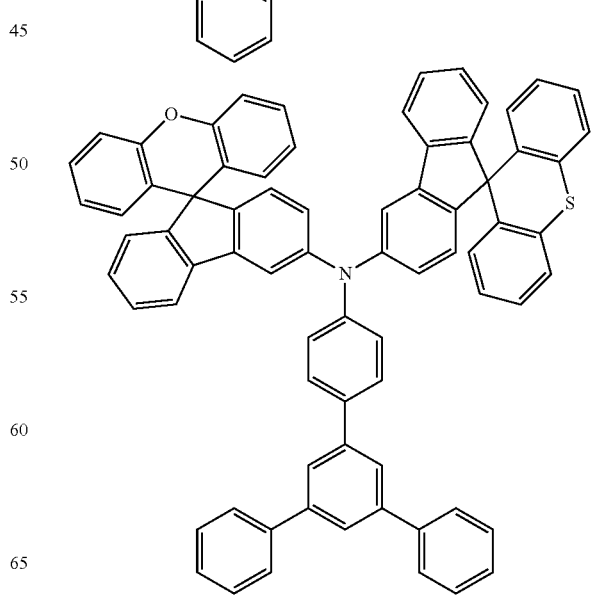

267
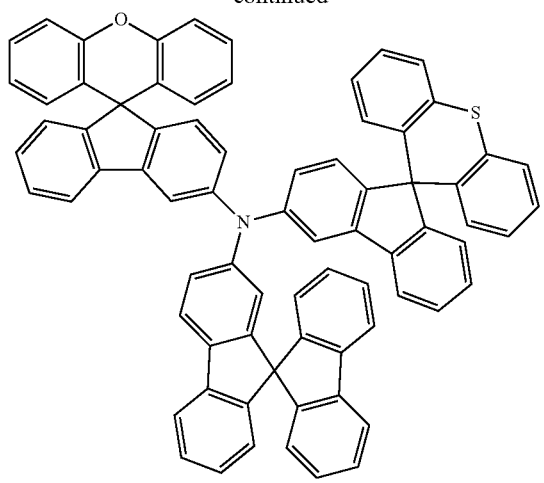
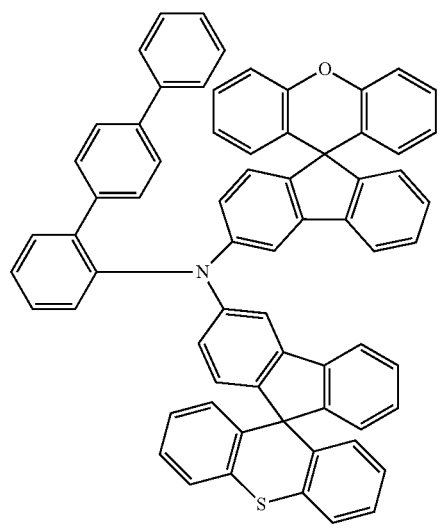
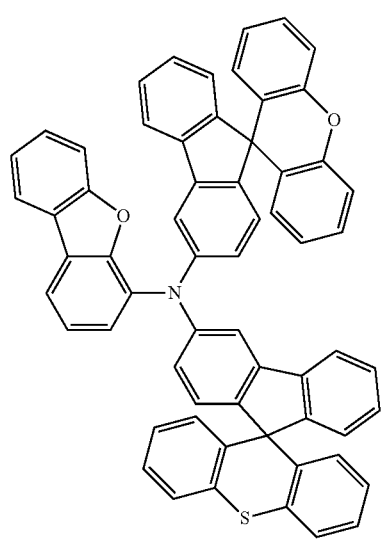
268
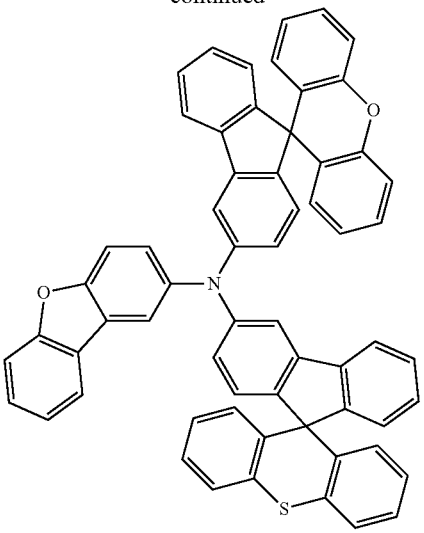
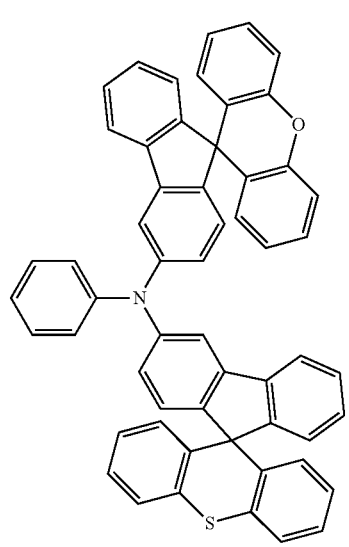
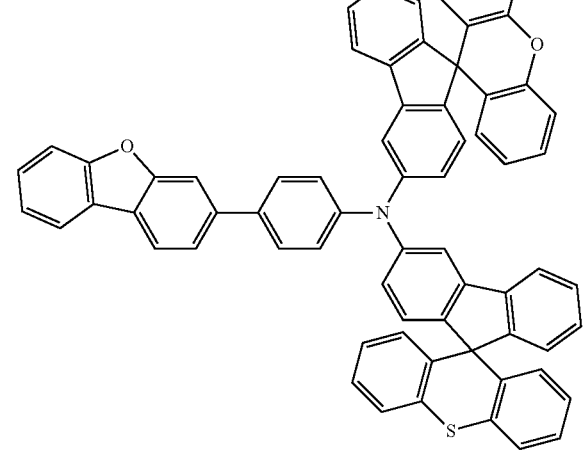

269
-continued
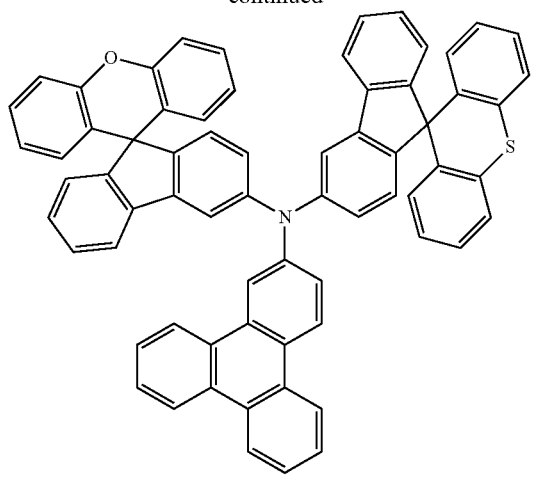
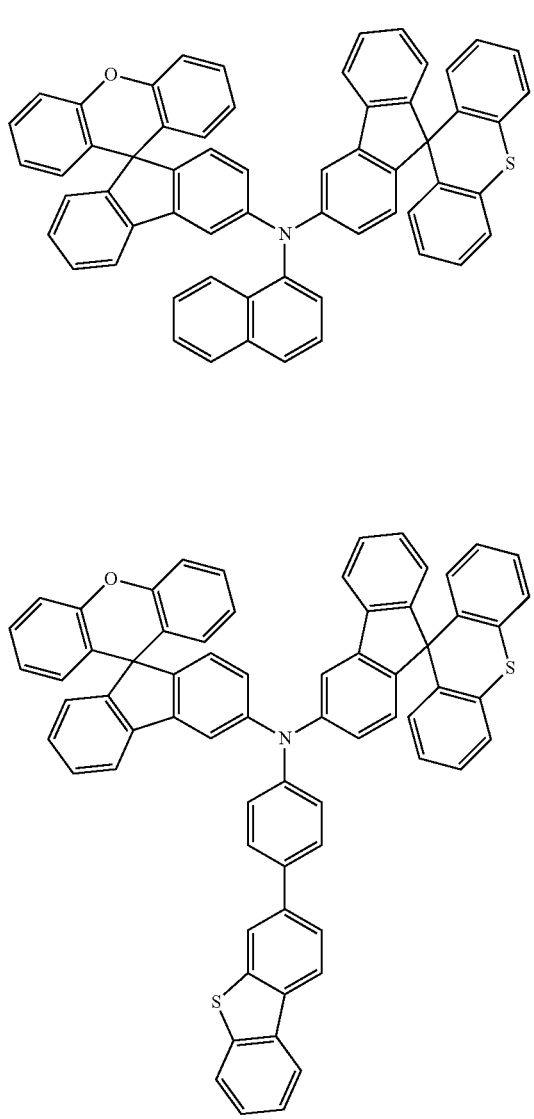
270
-continued
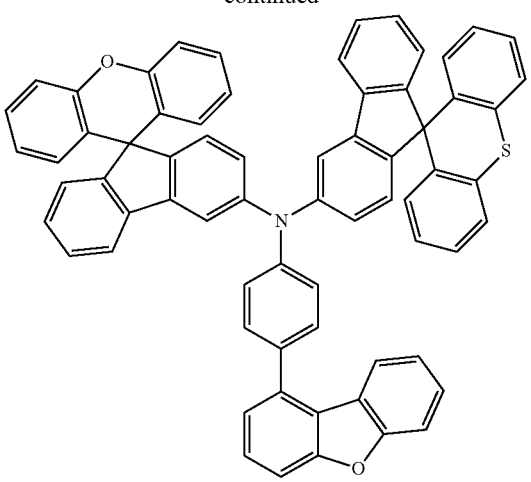
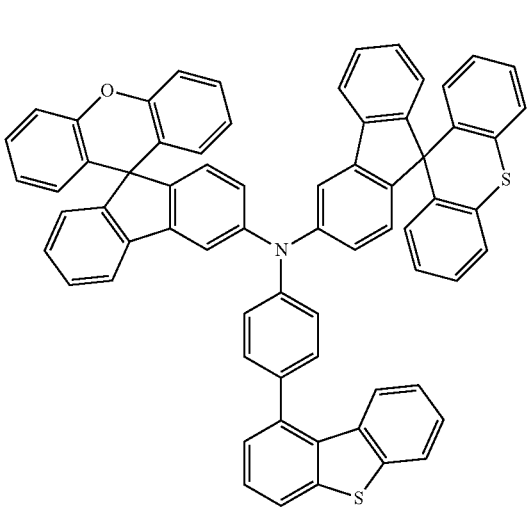
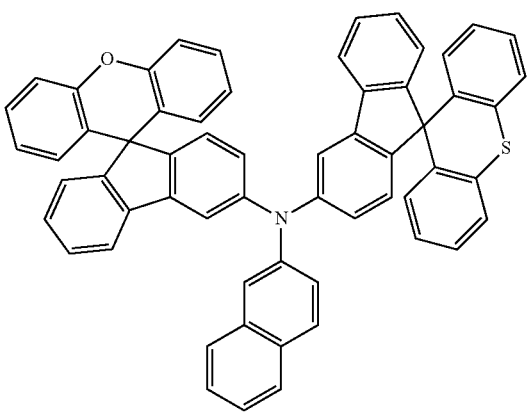

271
-continued
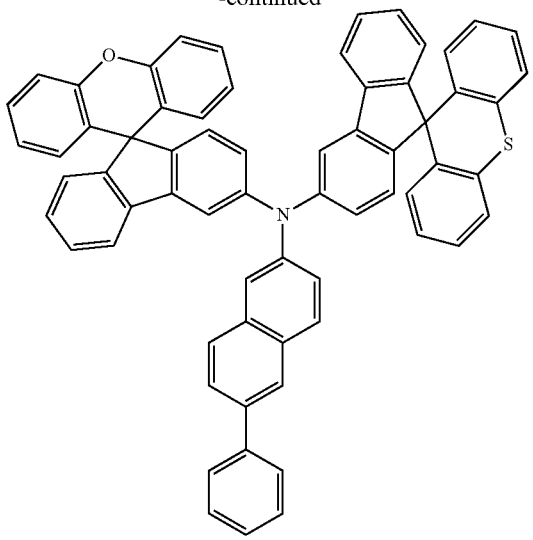
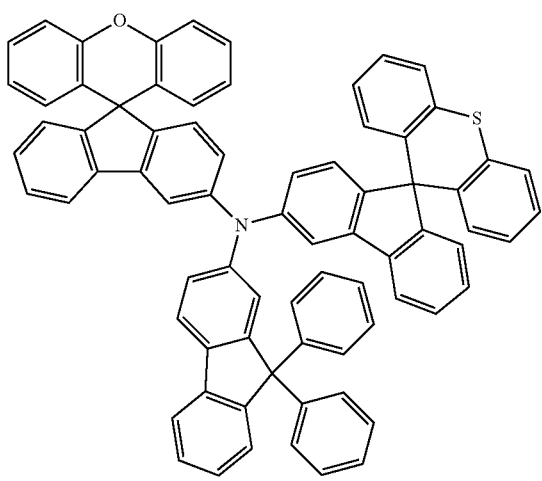
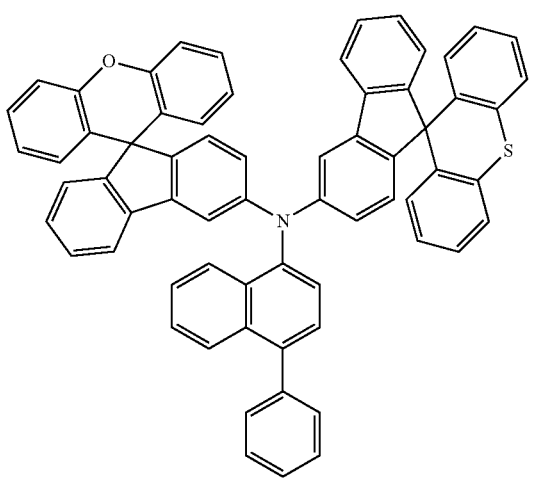
272
-continued
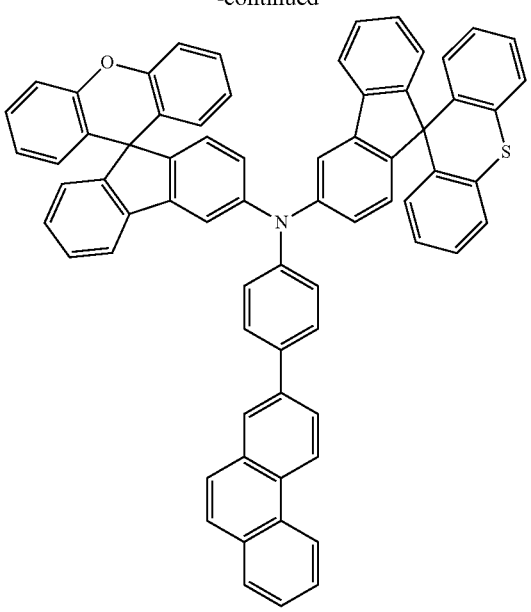
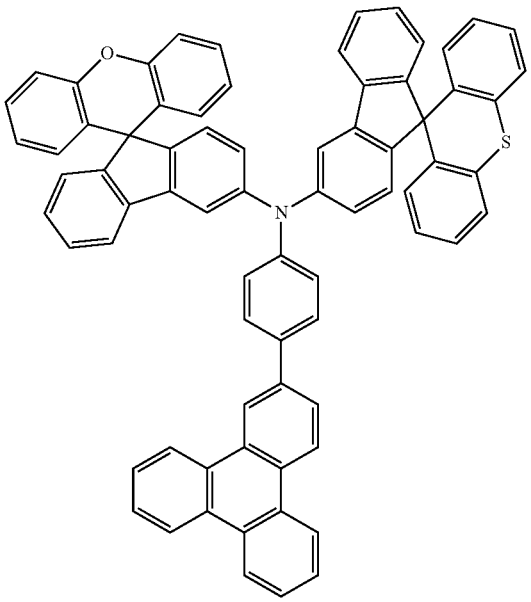
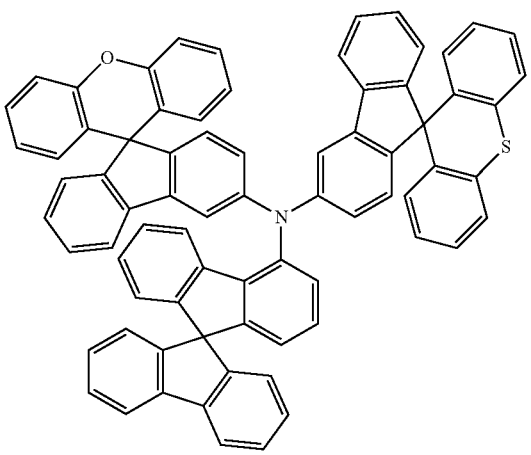

273
-continued
274
-continued
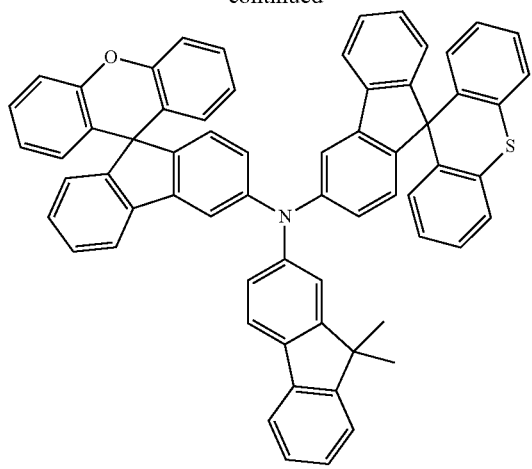
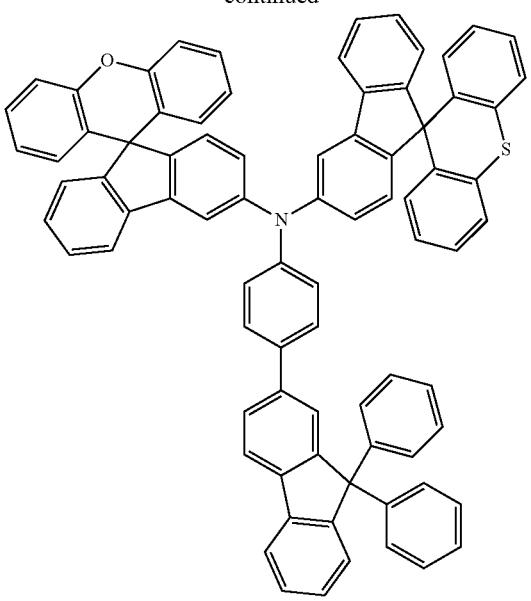
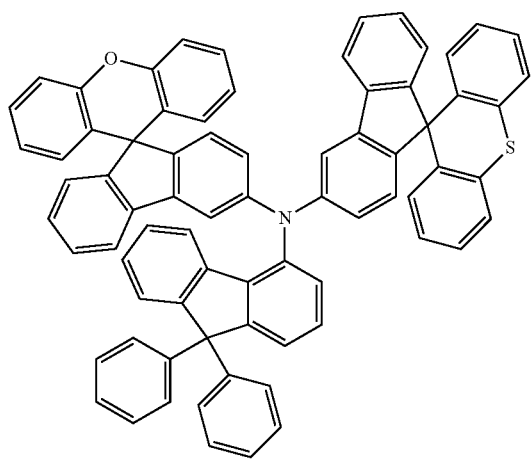
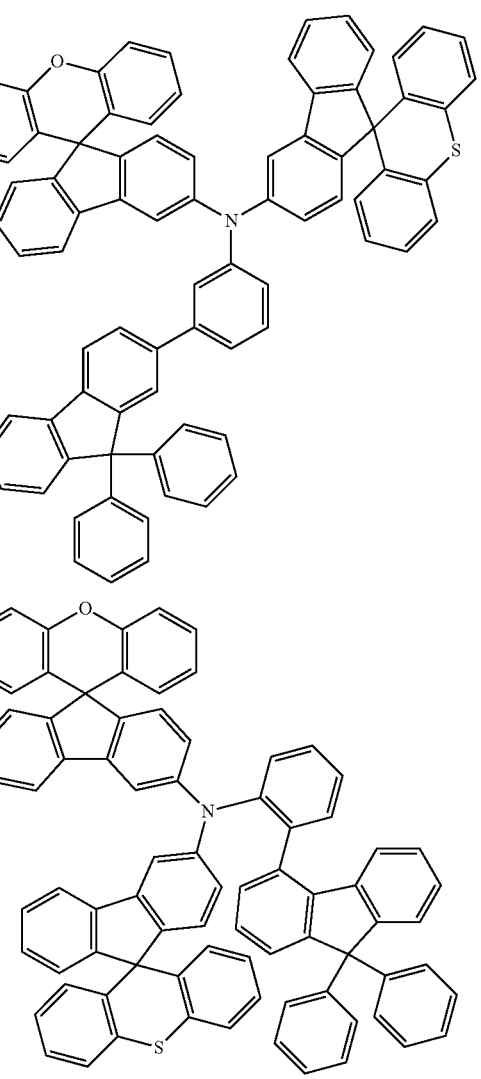

275
-continued
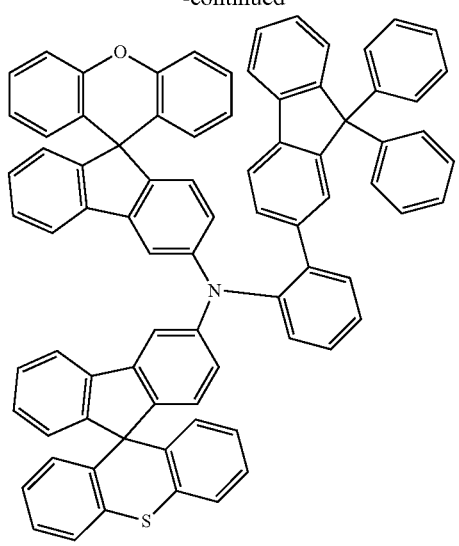
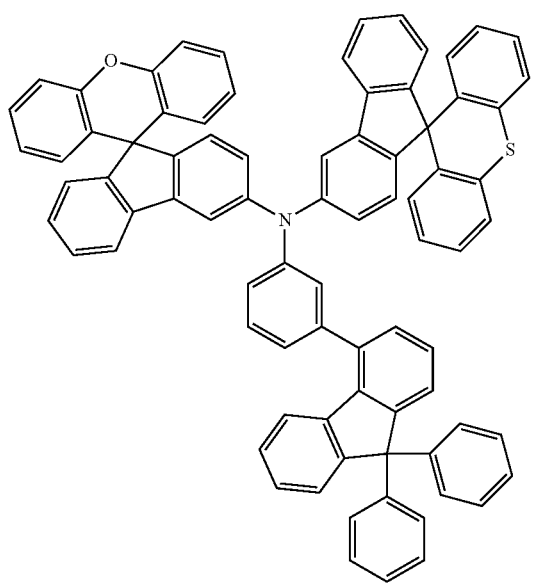
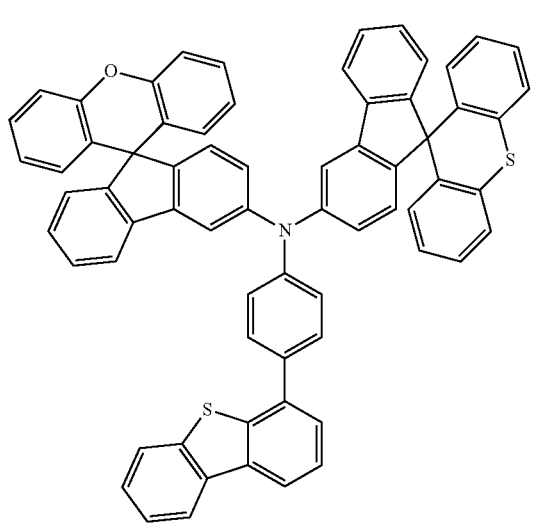
276
-continued
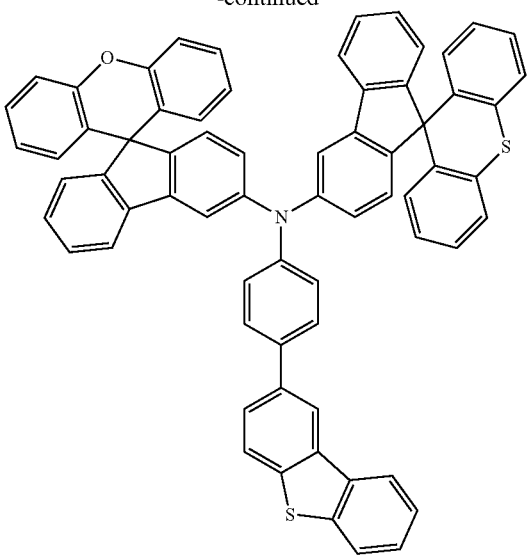
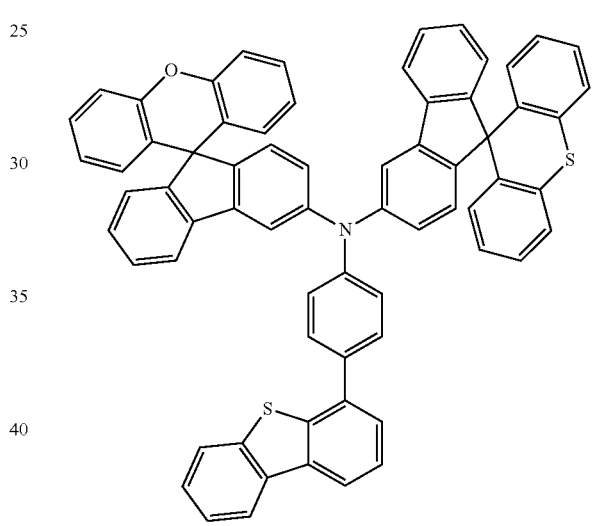
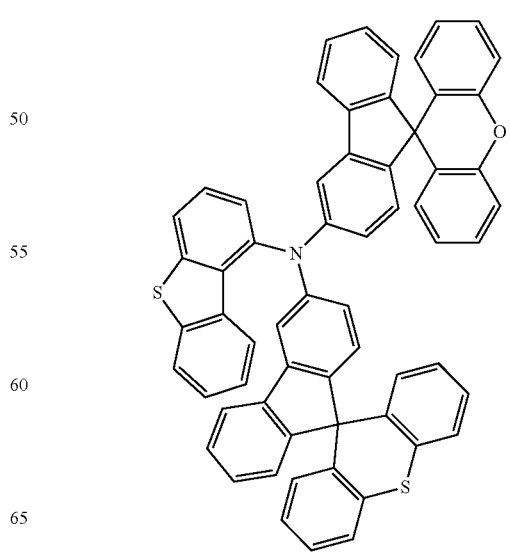

277
-continued
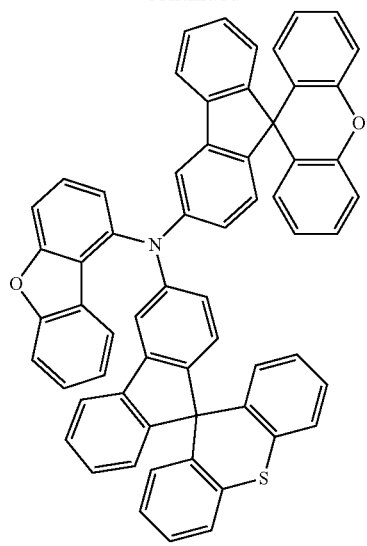
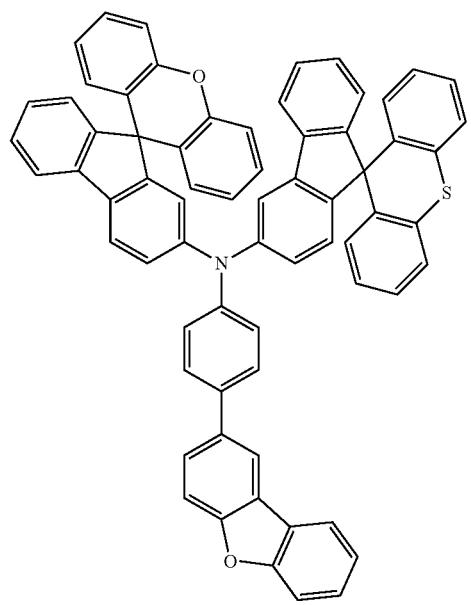
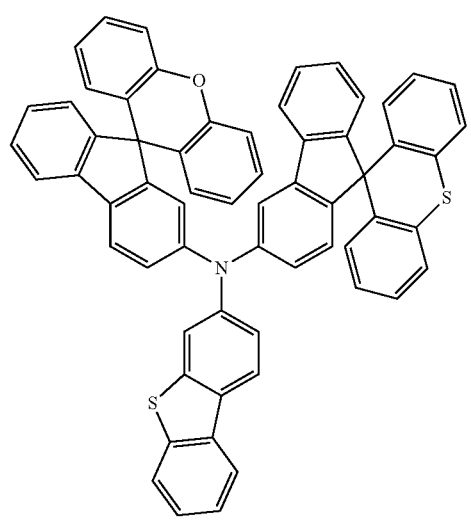
278
-continued
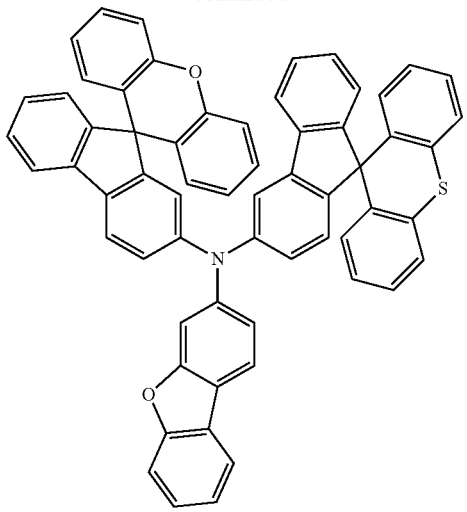
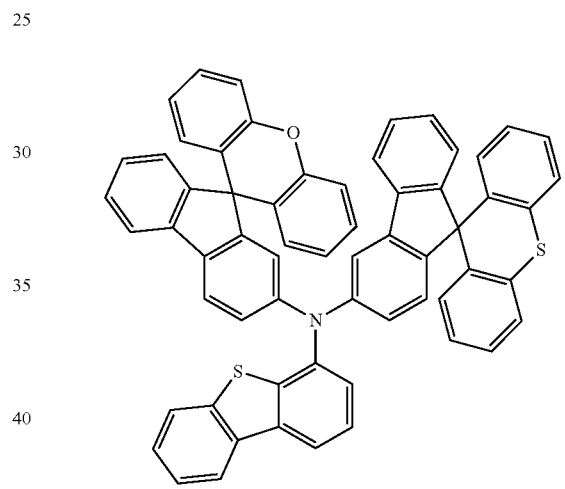
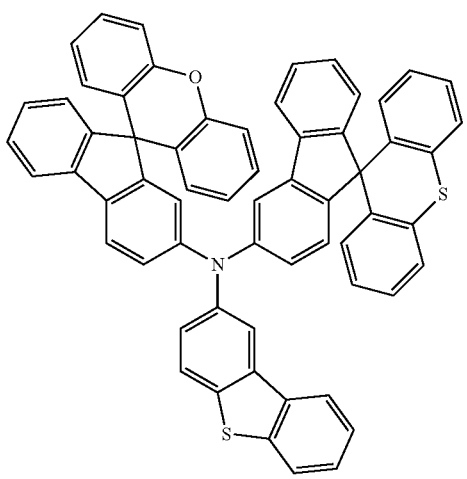

279
-continued
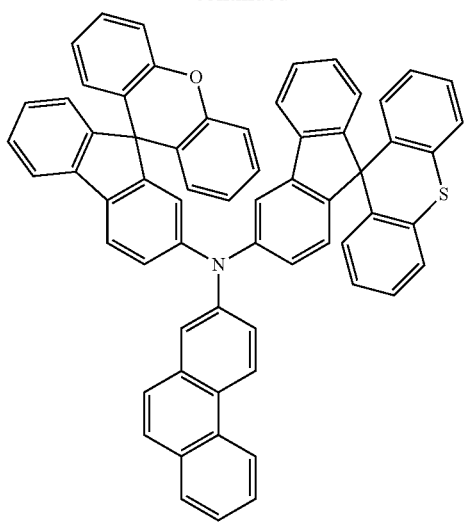
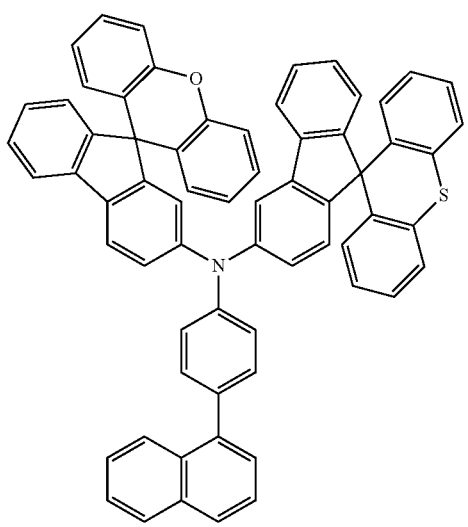
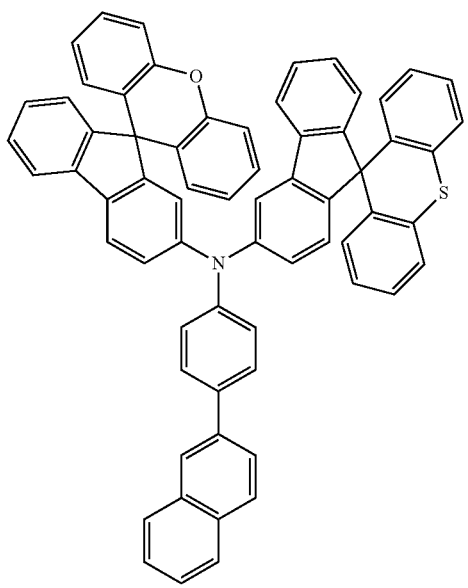
280
-continued
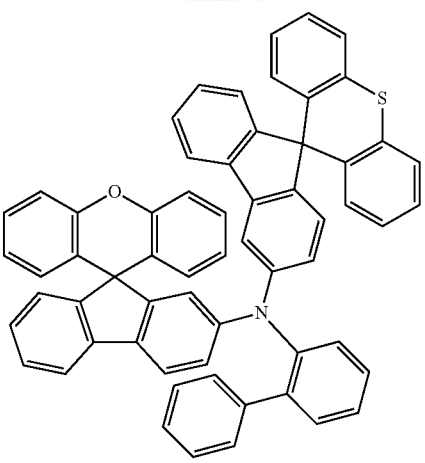
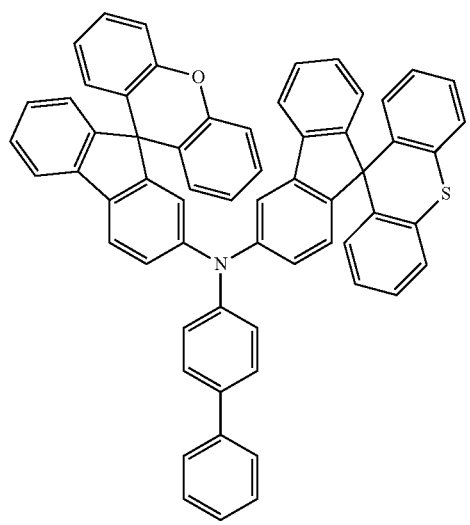
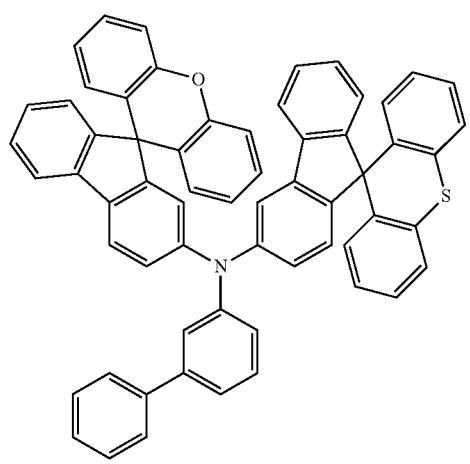

281
-continued
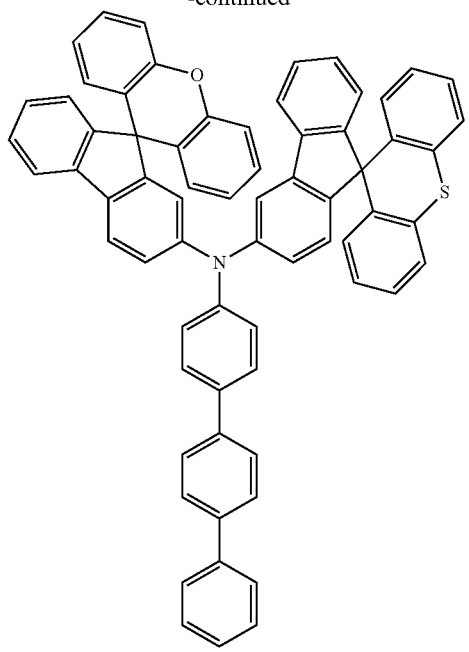
282
-continued
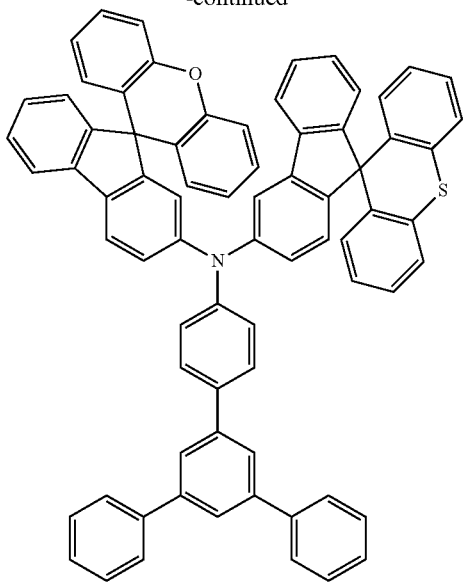
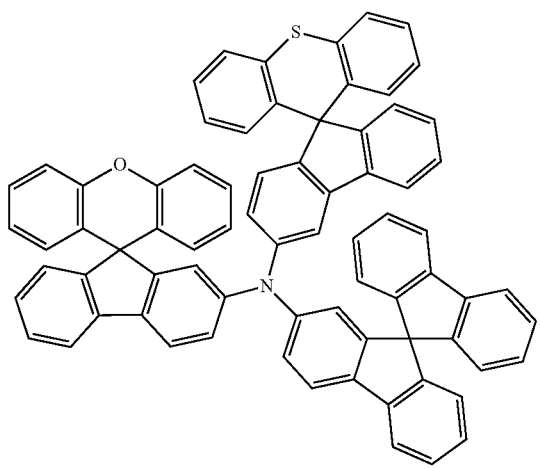
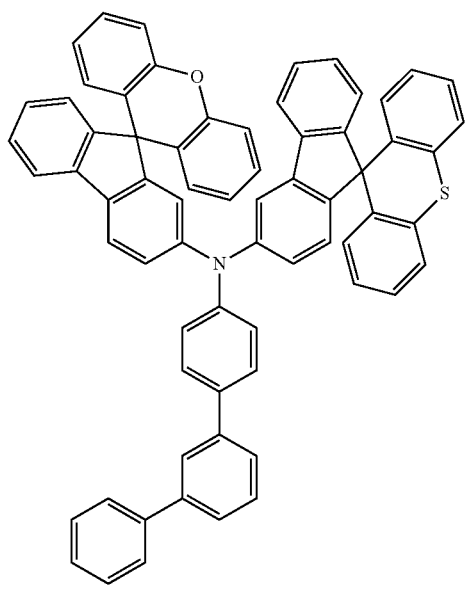
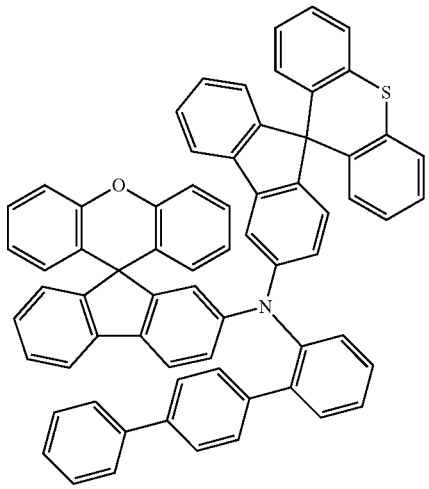

283
-continued
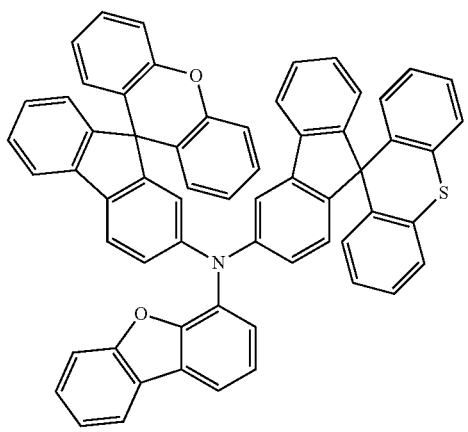
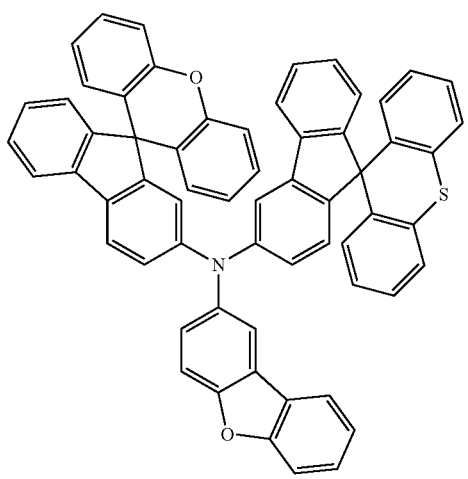
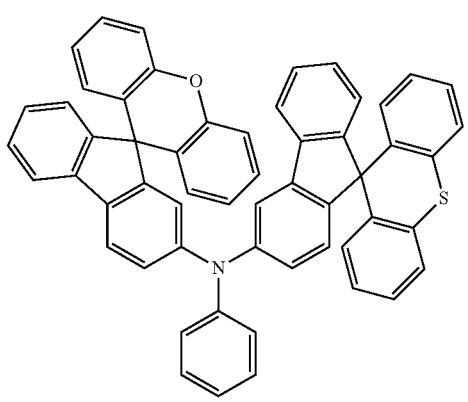
284
-continued
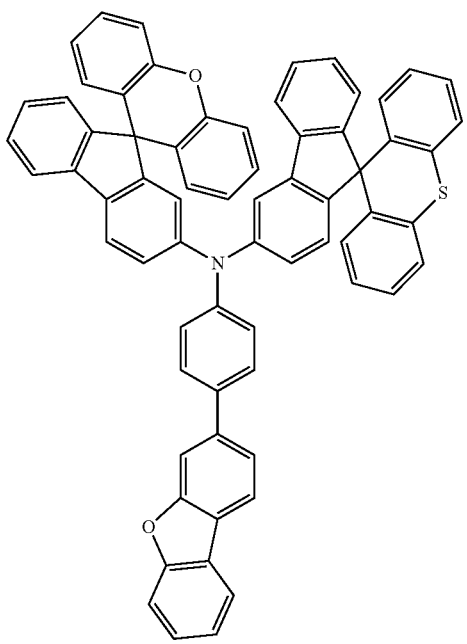
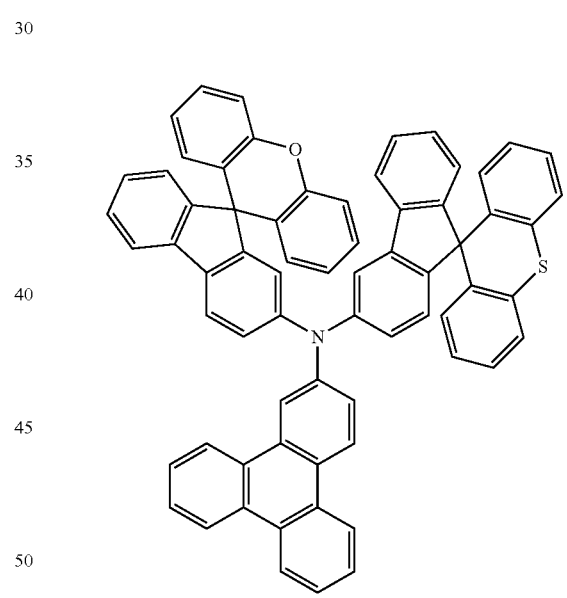
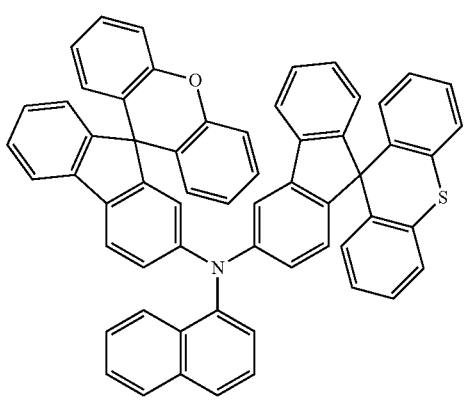

285
-continued
286
-continued
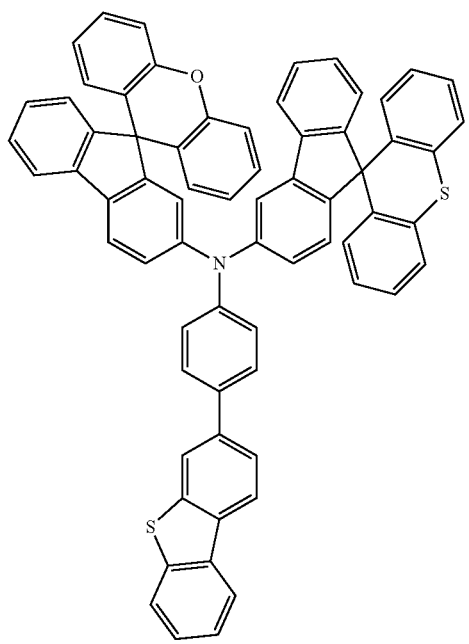
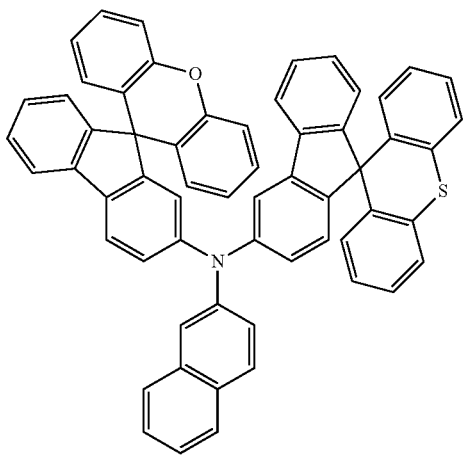
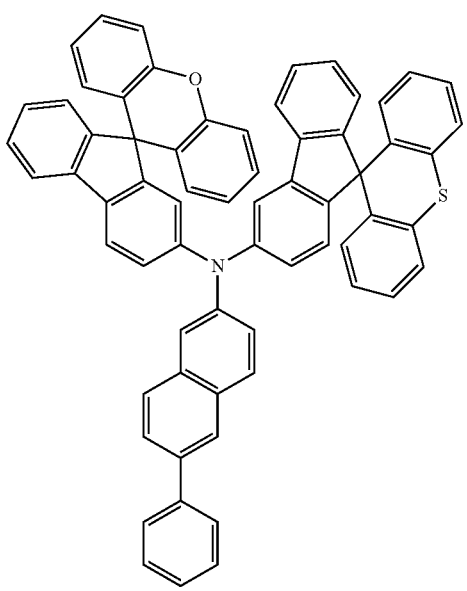
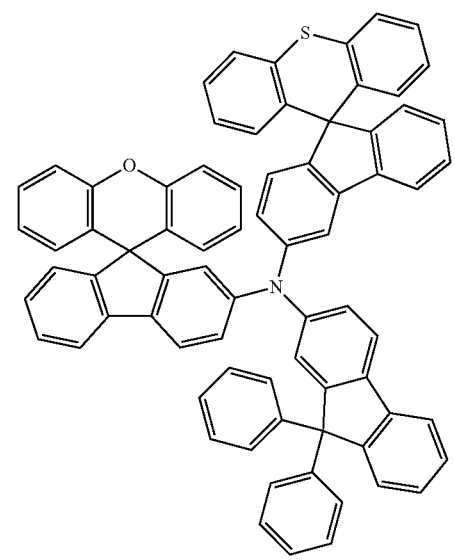

287
-continued
288
-continued
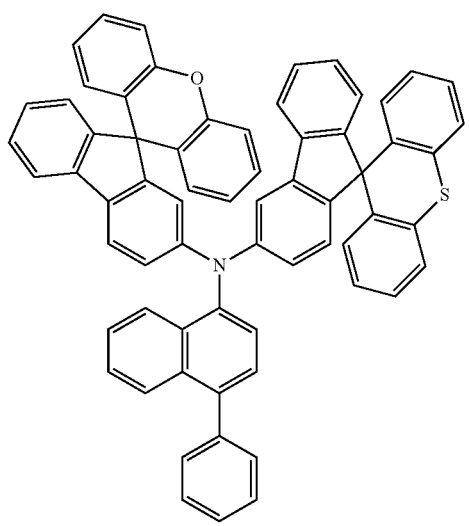
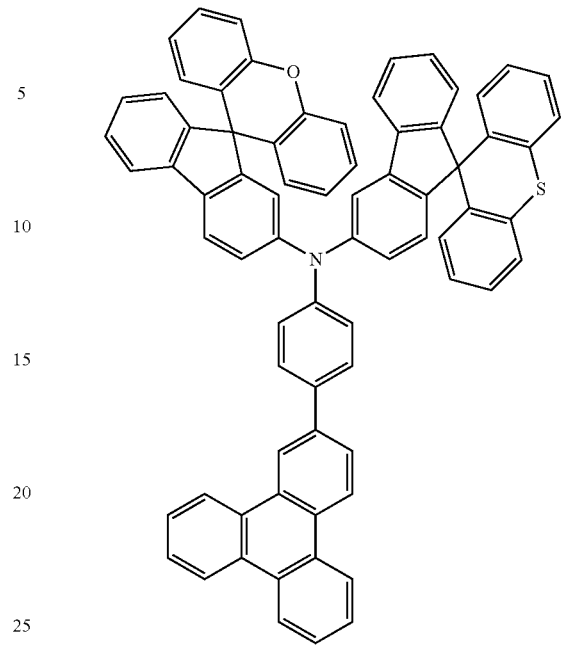
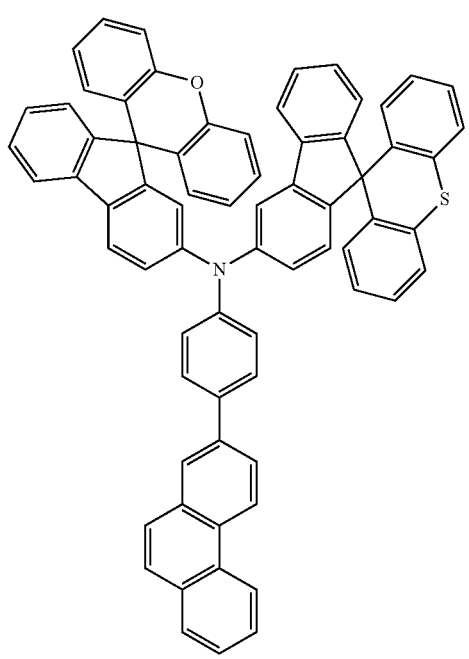
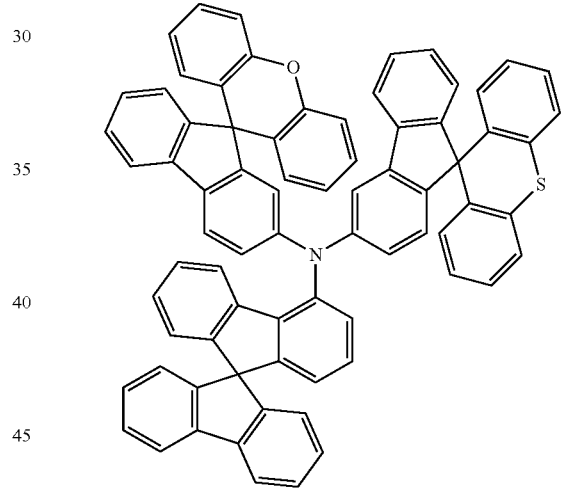
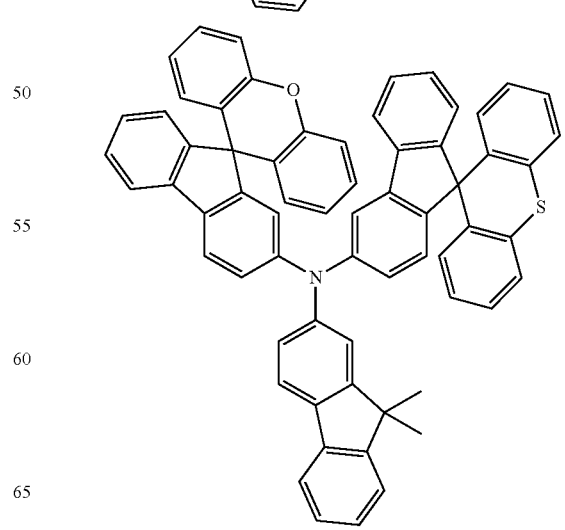

289
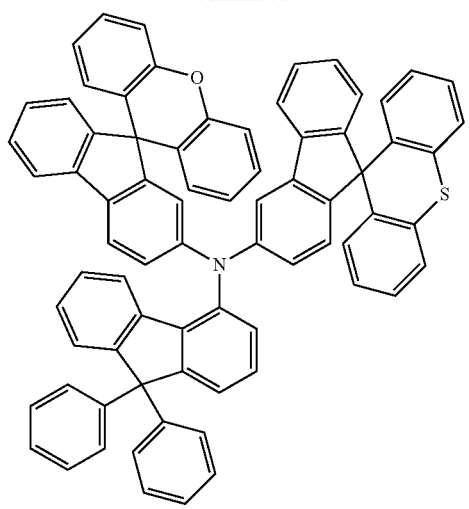
290
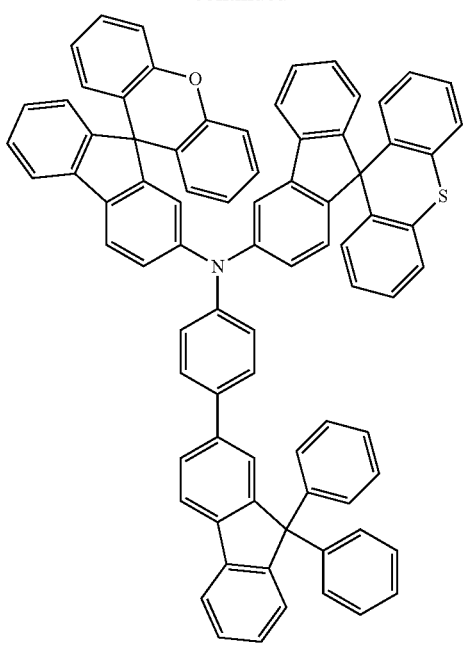
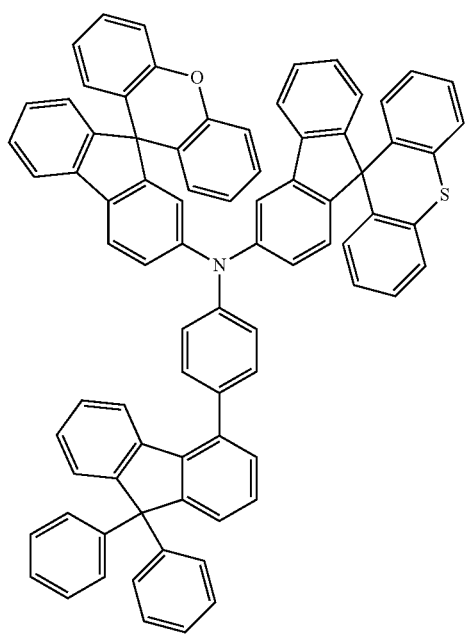
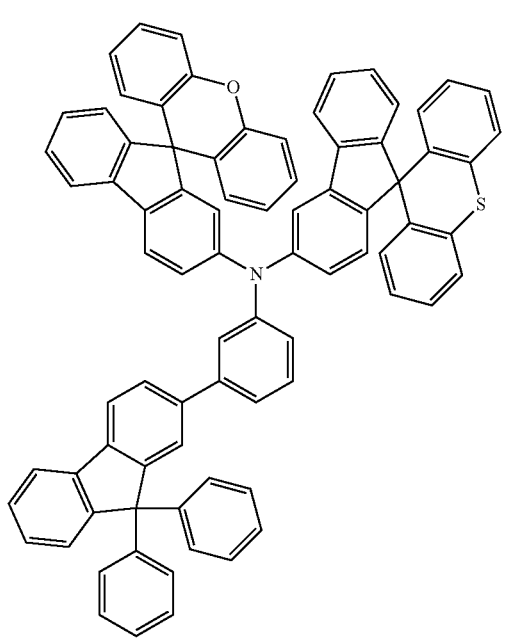

291
-continued
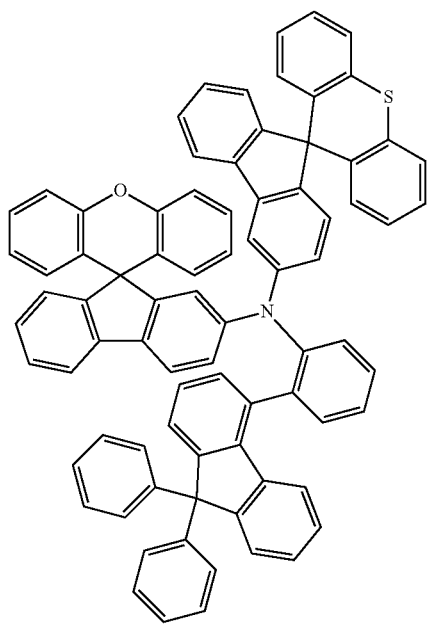
292
-continued
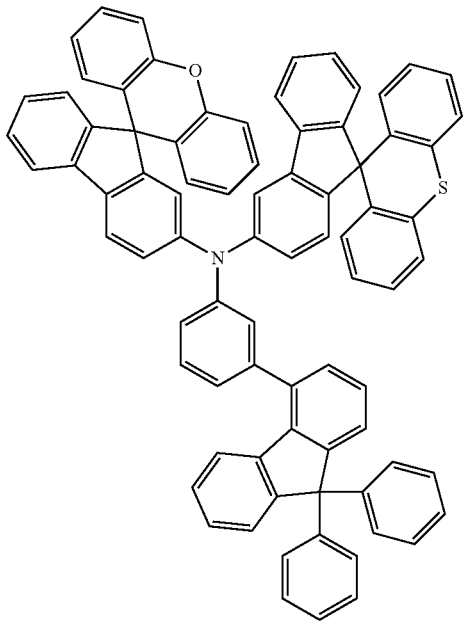
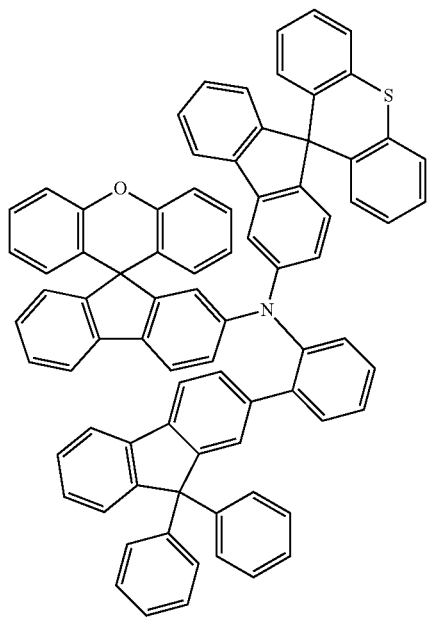
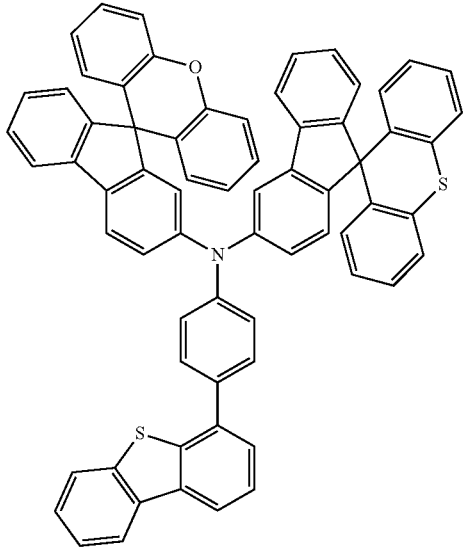

293
-continued
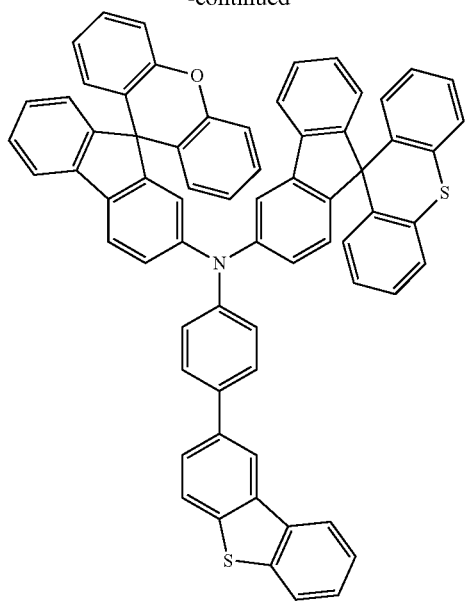
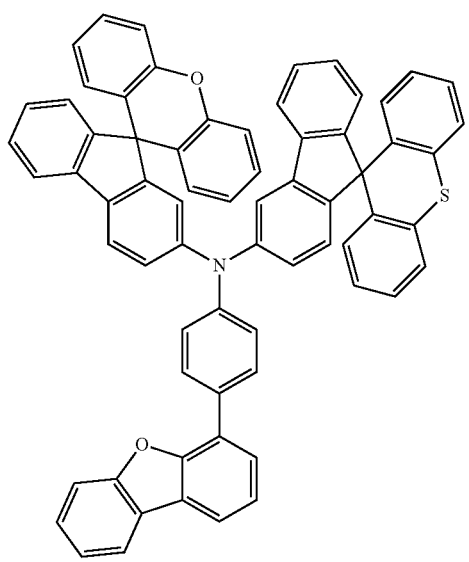
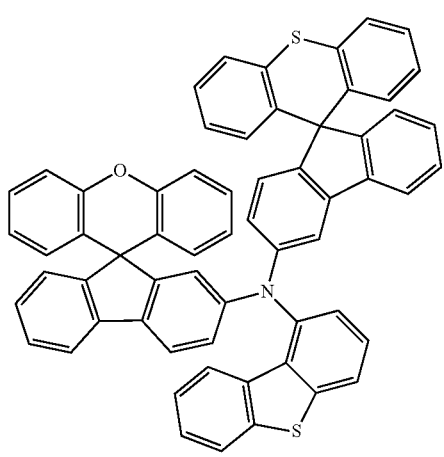
294
-continued
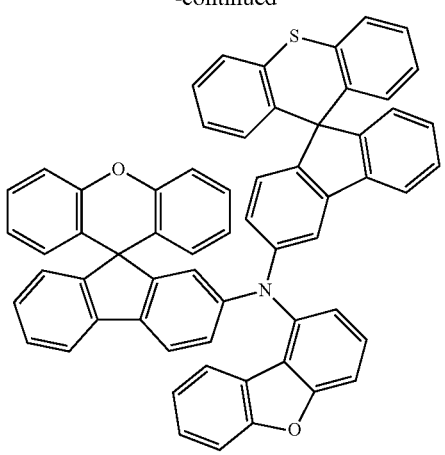
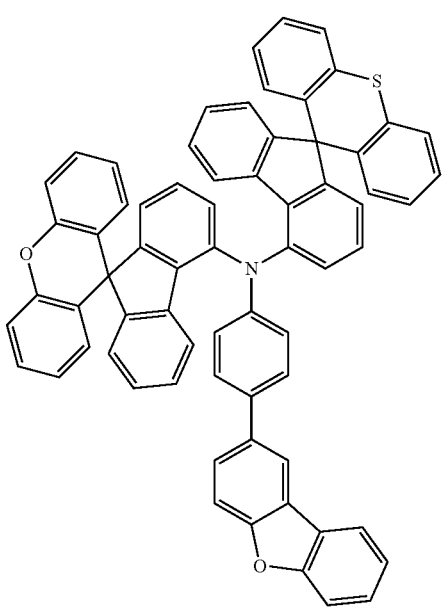
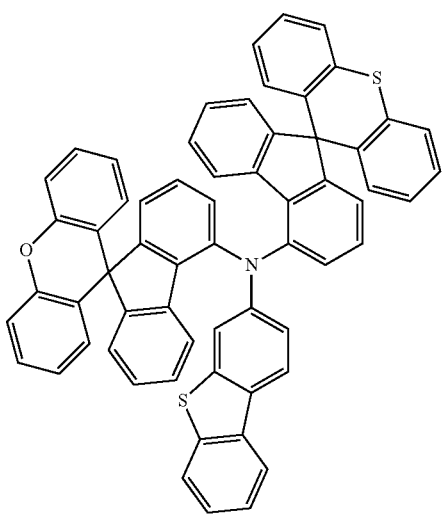

295
-continued
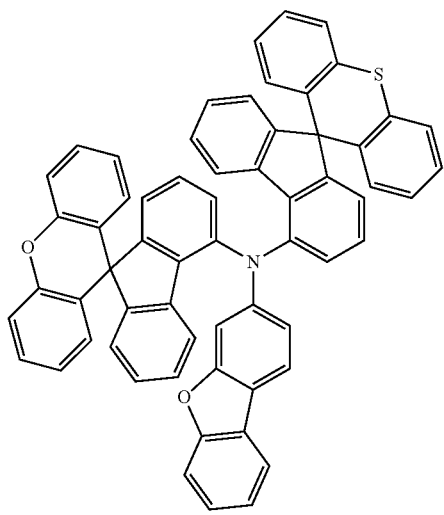
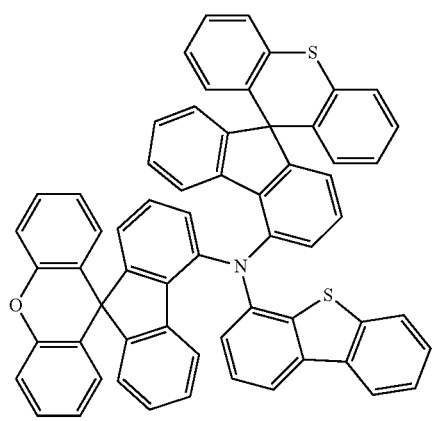
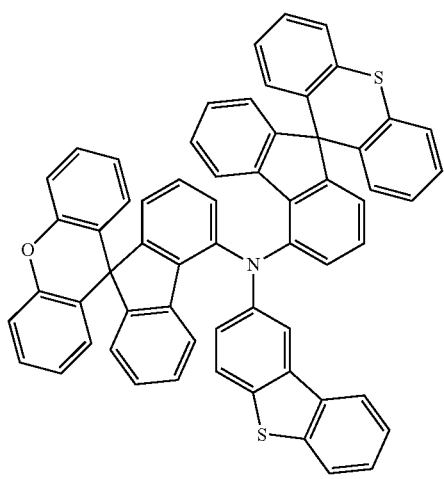
296
-continued
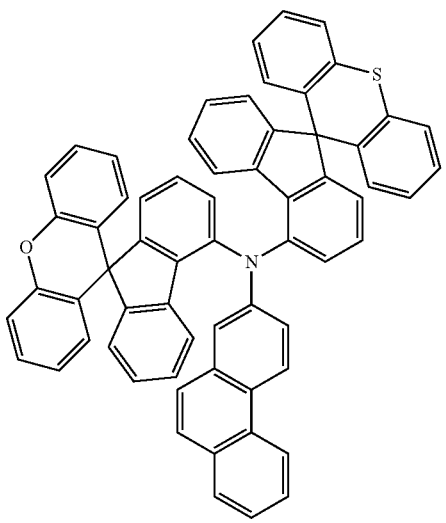
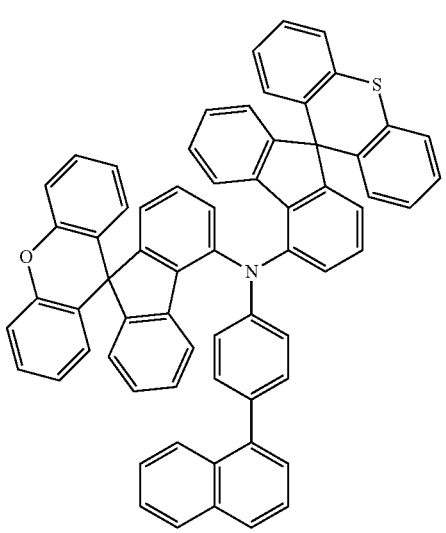

297
-continued
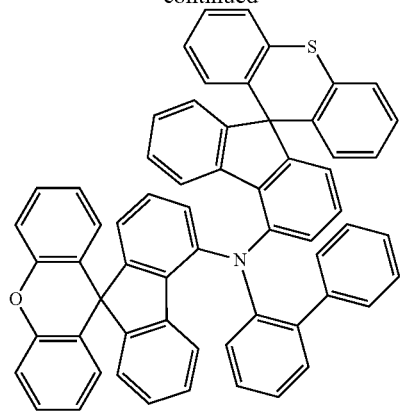
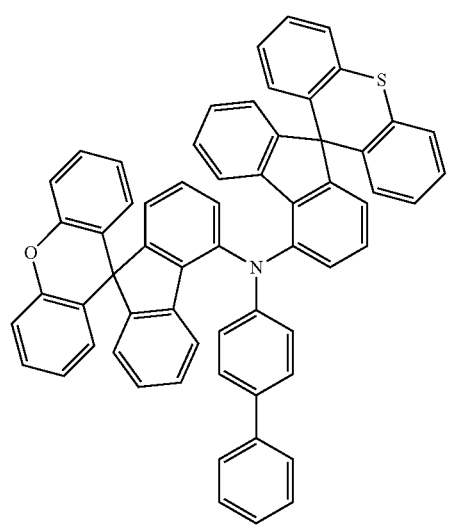
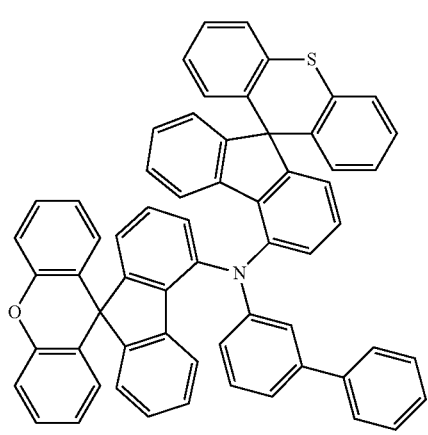
298
-continued
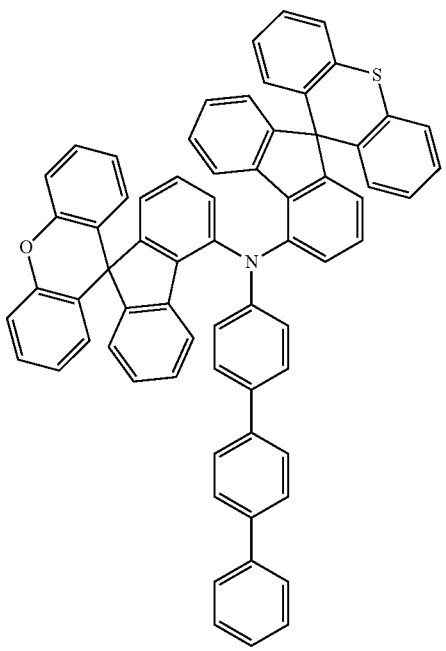
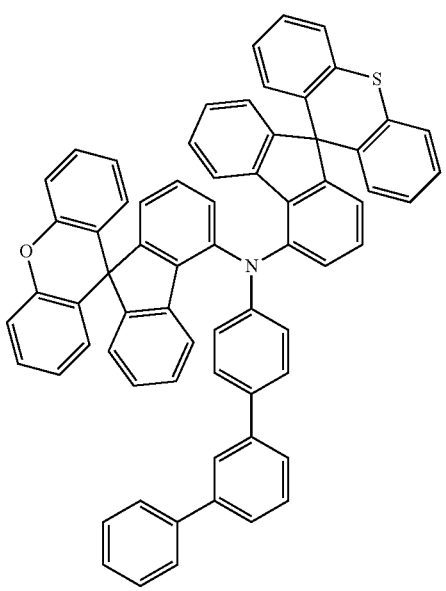

299
-continued
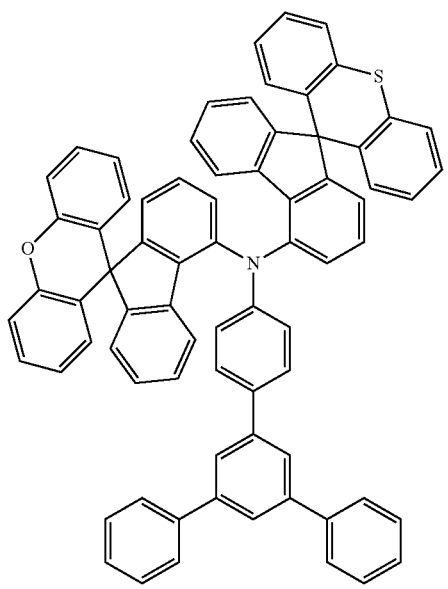
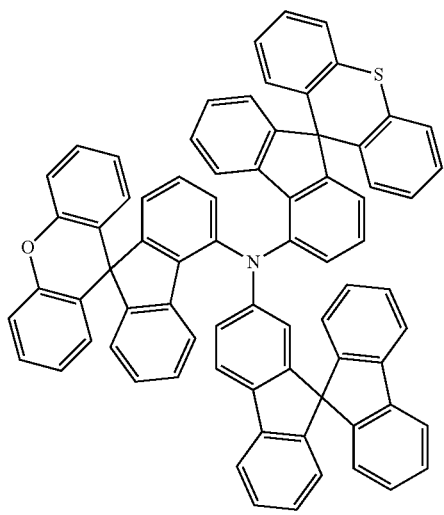
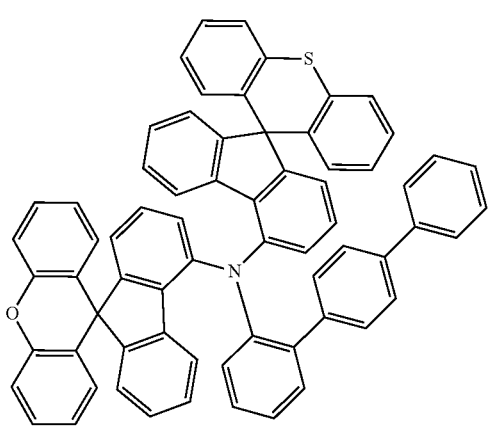
300
-continued
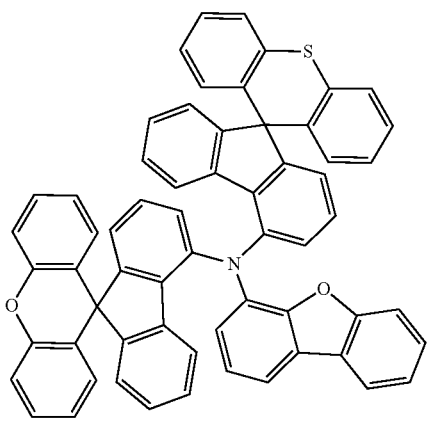
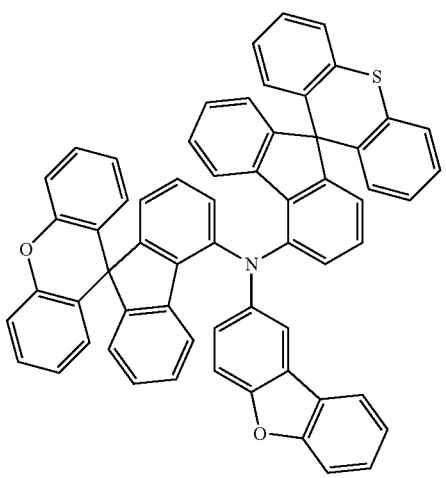
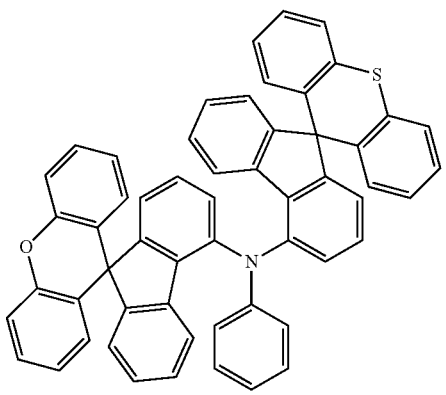

301
-continued
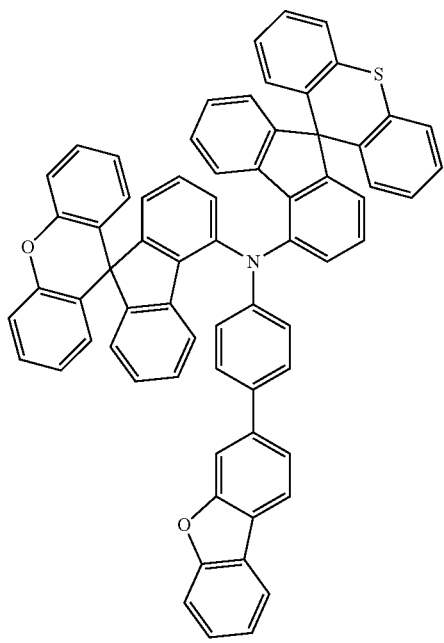
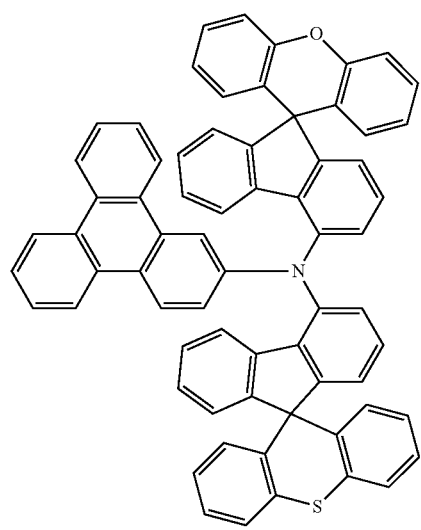
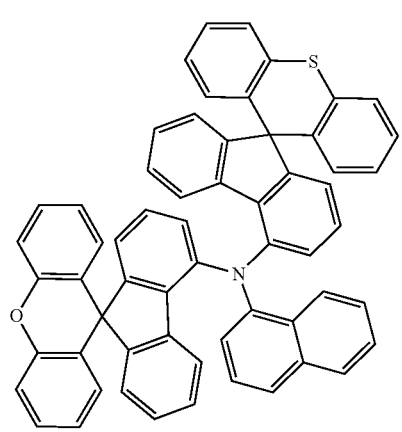
302
-continued
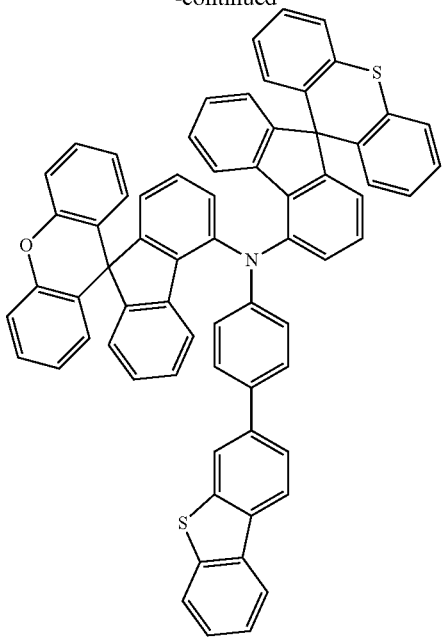
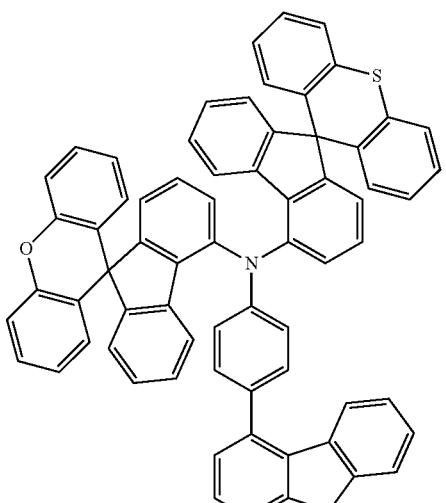
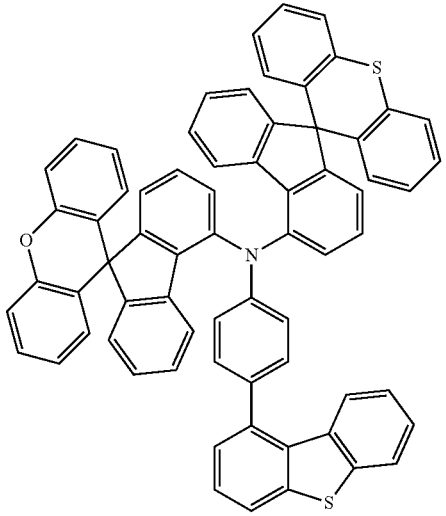

303
-continued
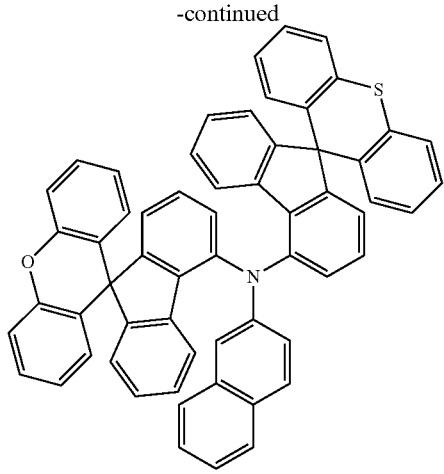
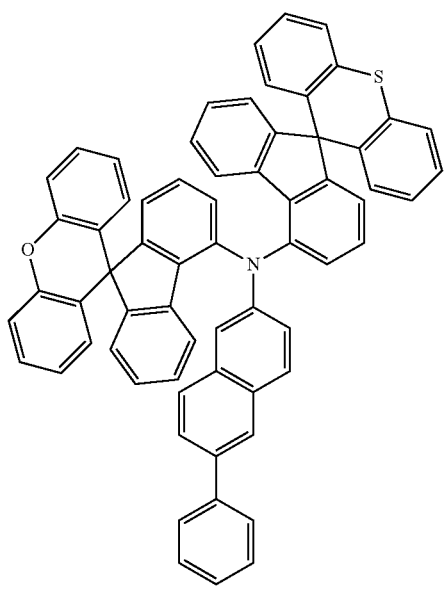
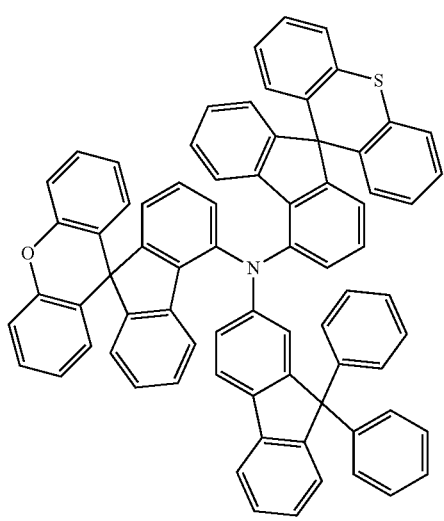
304
-continued
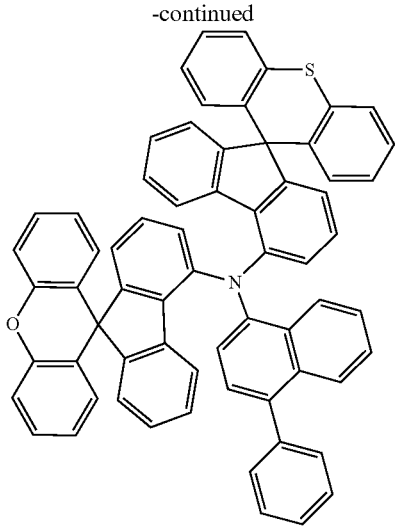
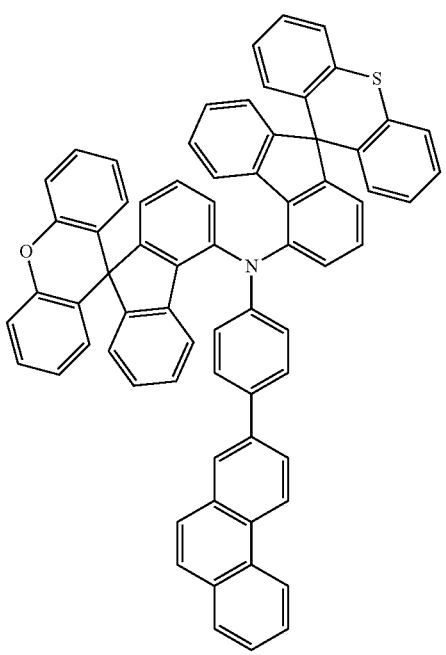

305
-continued
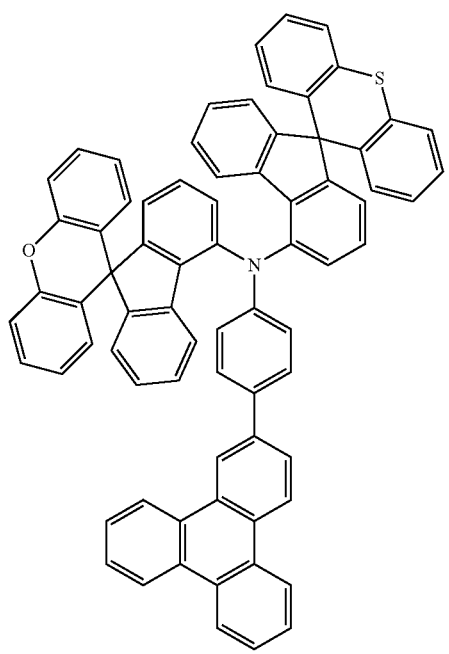
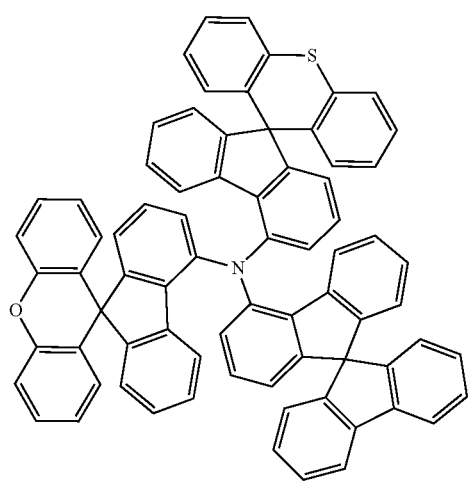
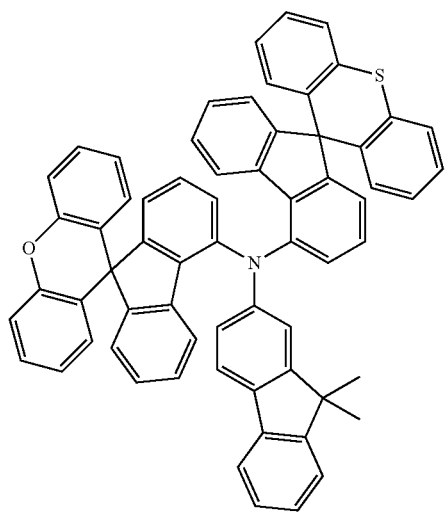
306
-continued
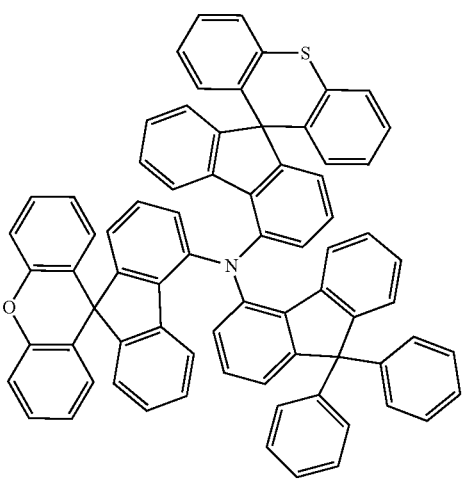
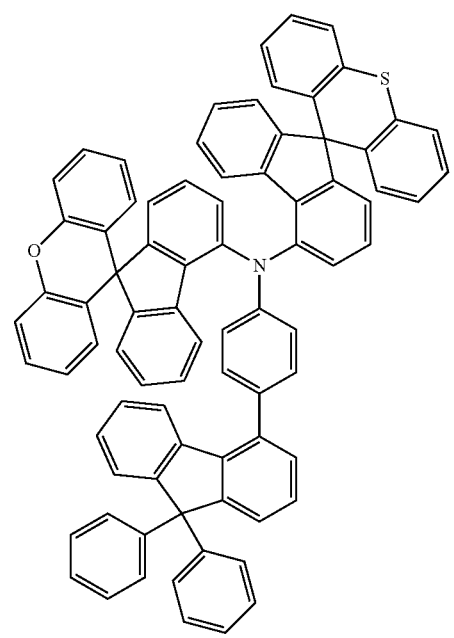

307
-continued
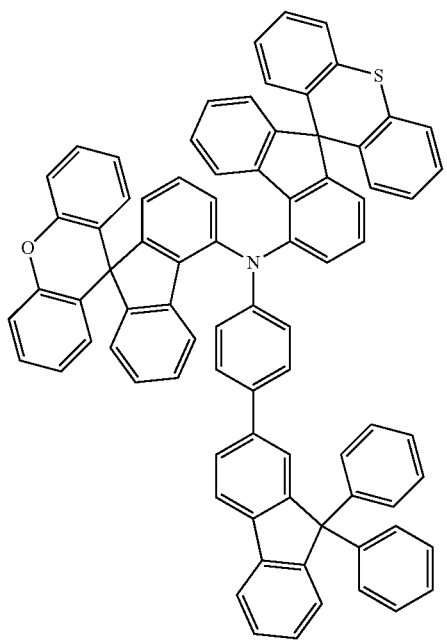
308
-continued
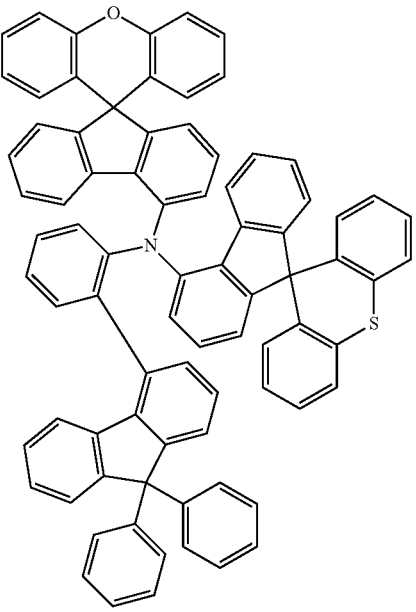
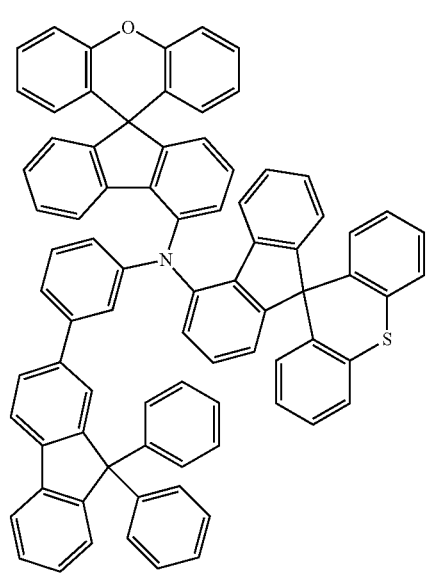
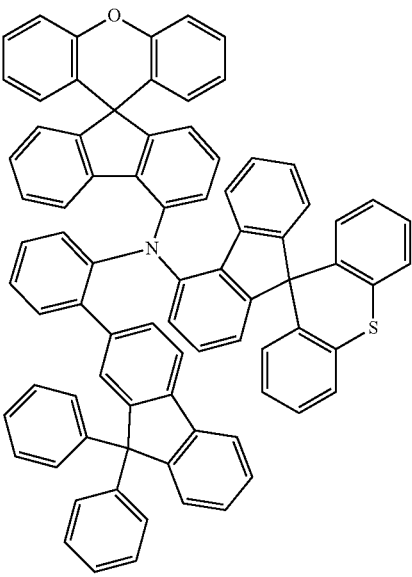

309
-continued
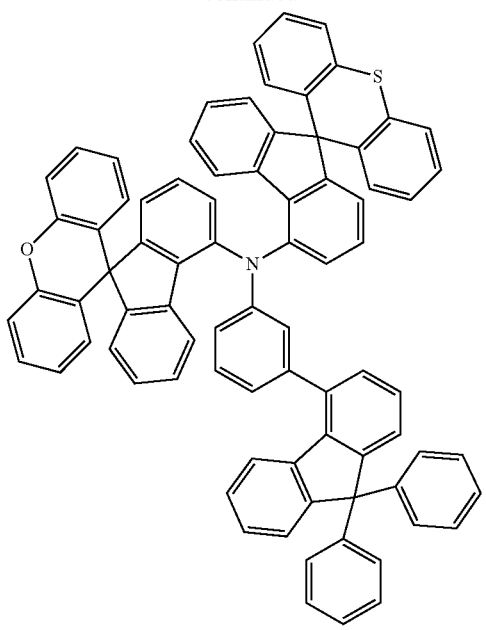
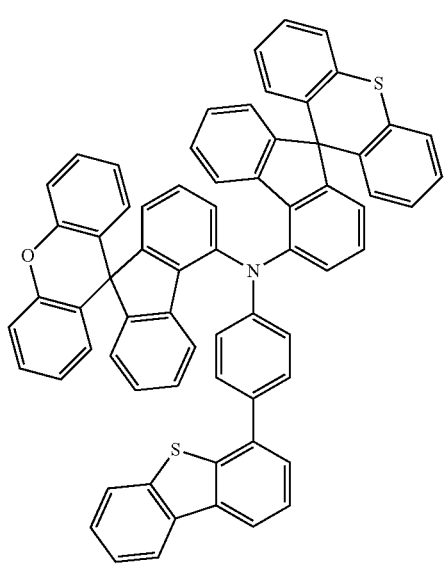
310
-continued
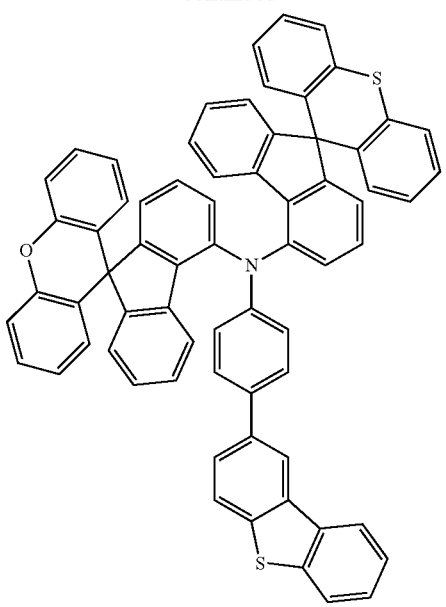
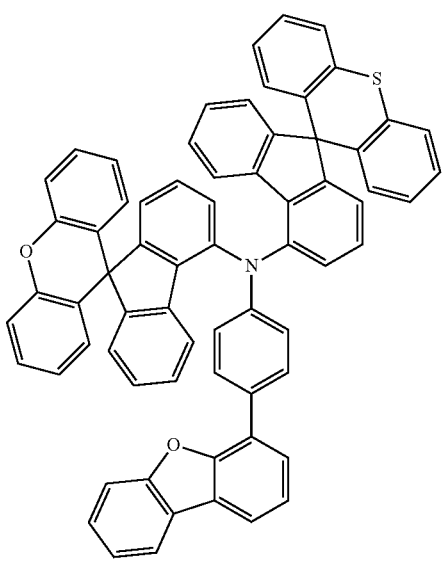
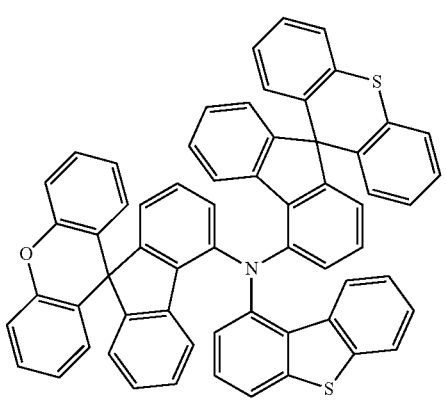

311
-continued
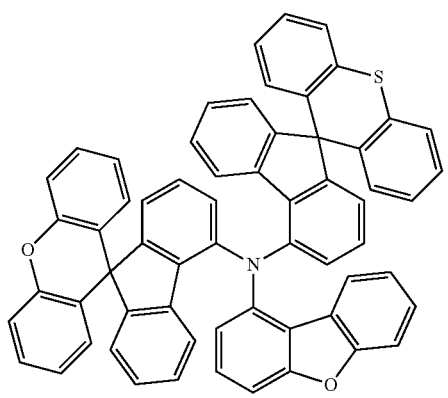
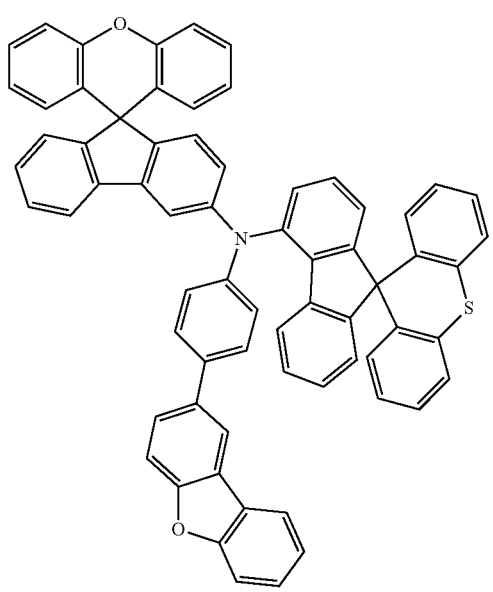
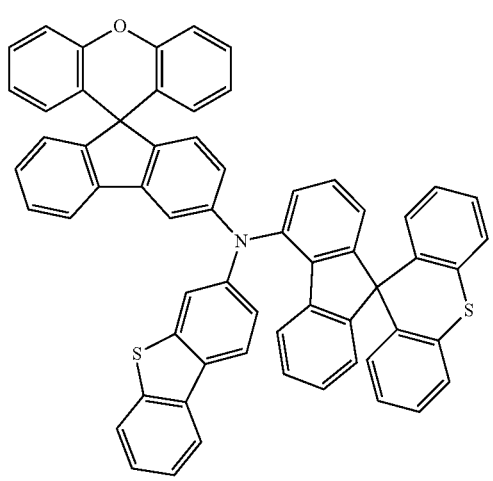
312
-continued
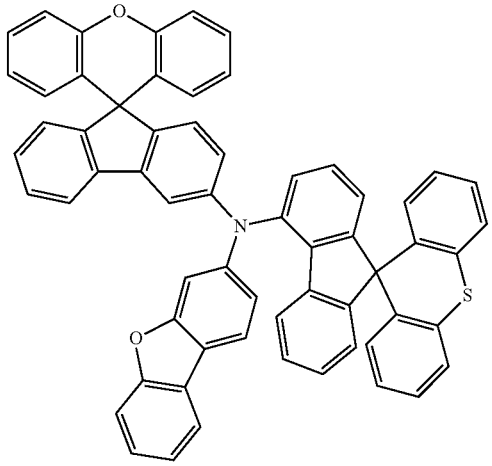
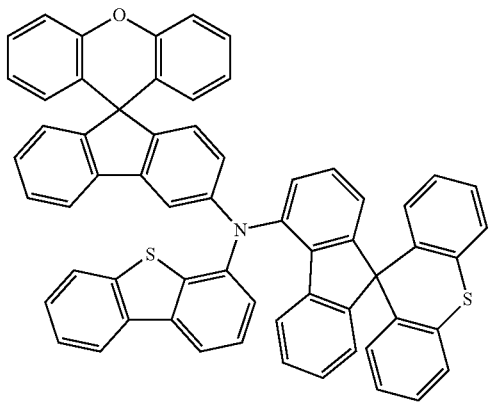
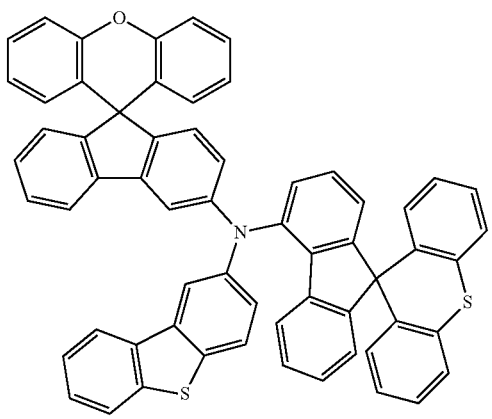

313
-continued
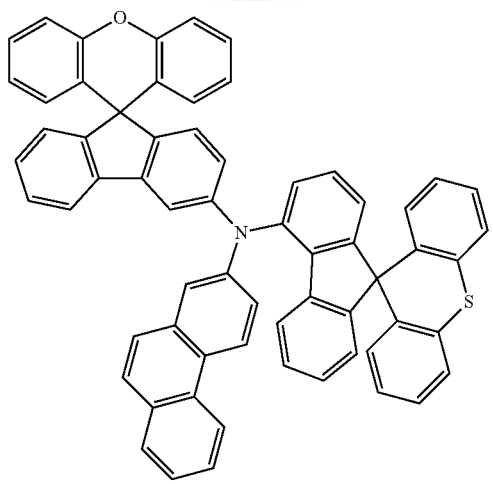
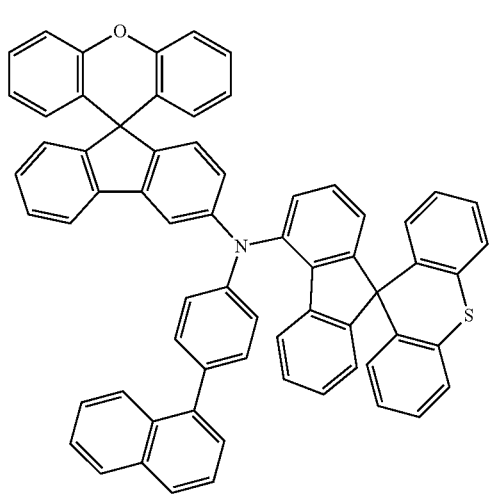
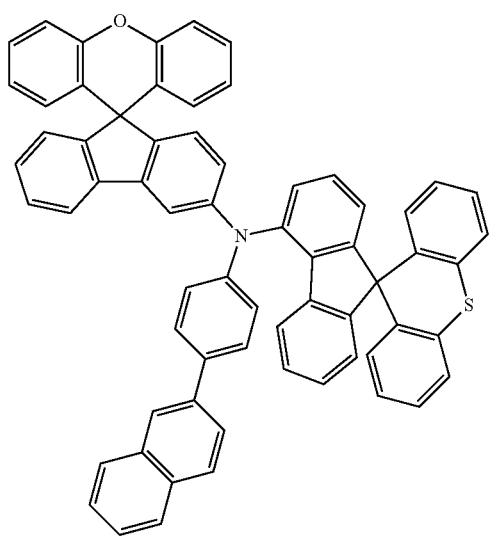
314
-continued
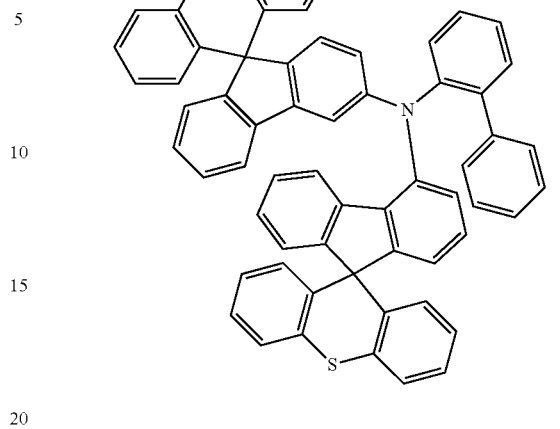
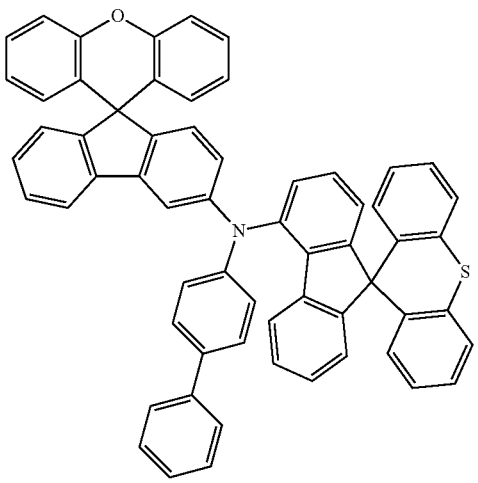
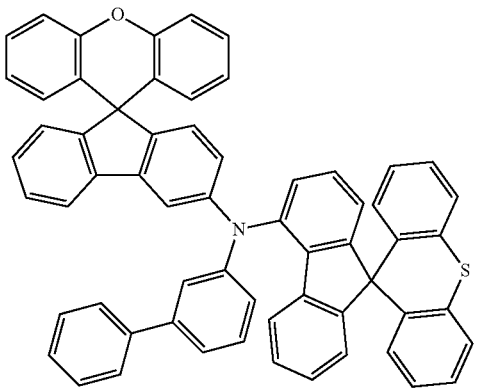

315
-continued
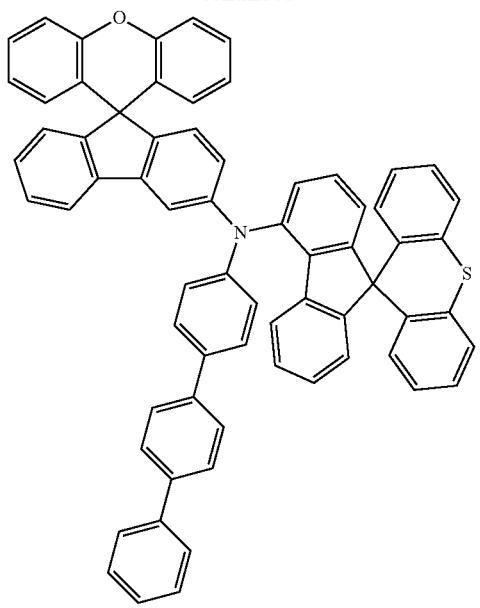
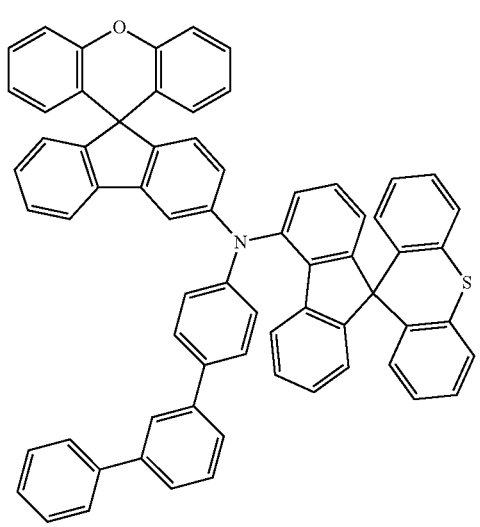
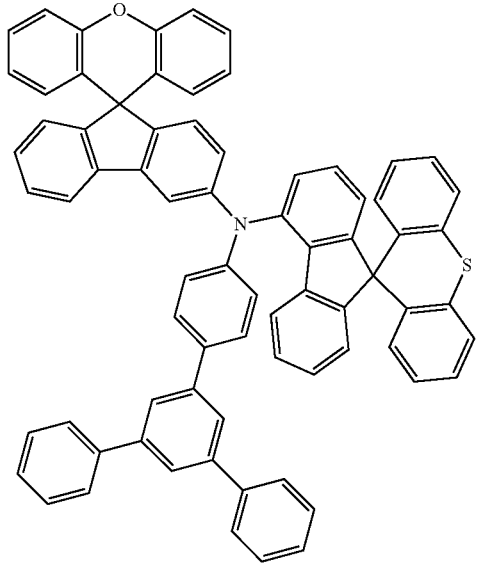
316
-continued
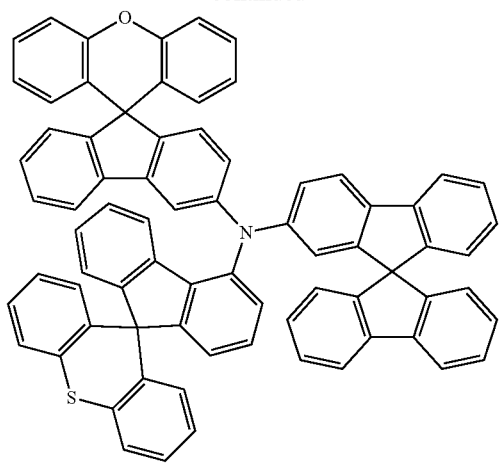
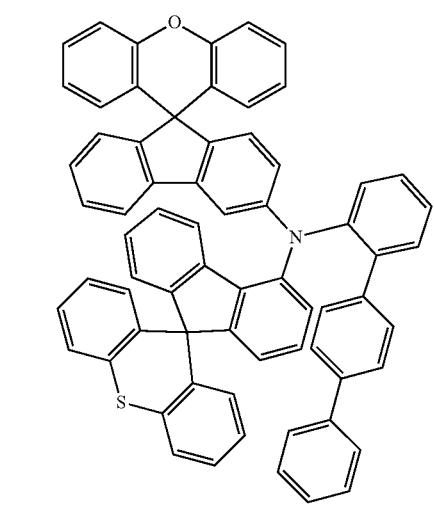
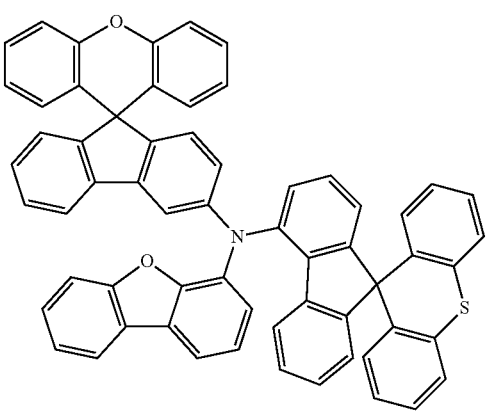

317
-continued
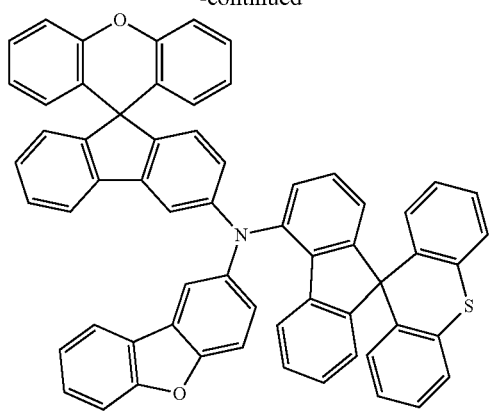
318
-continued
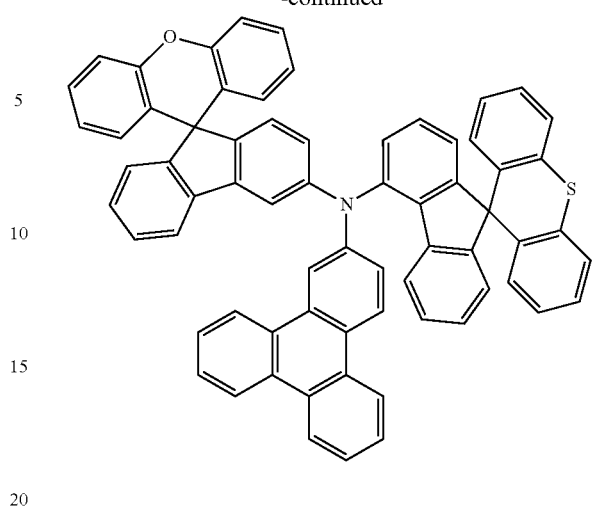
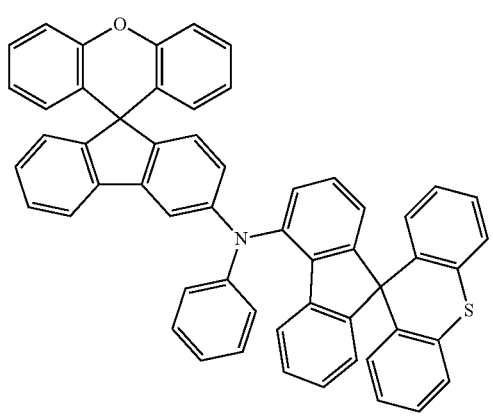
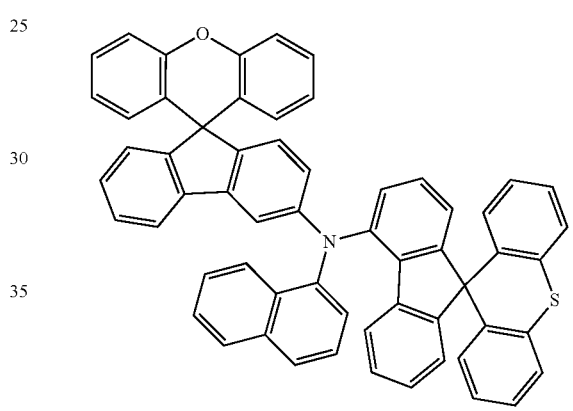
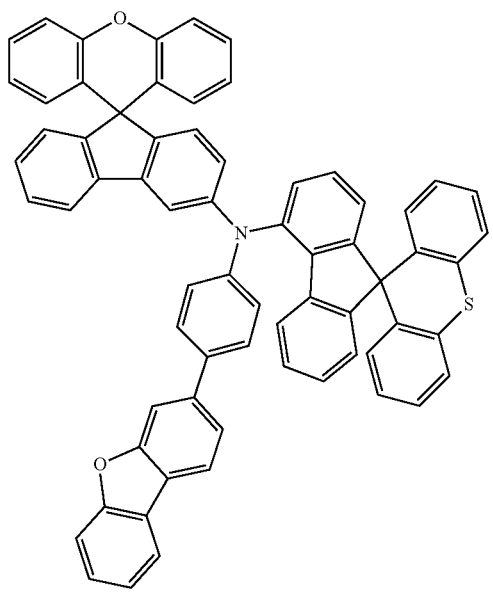
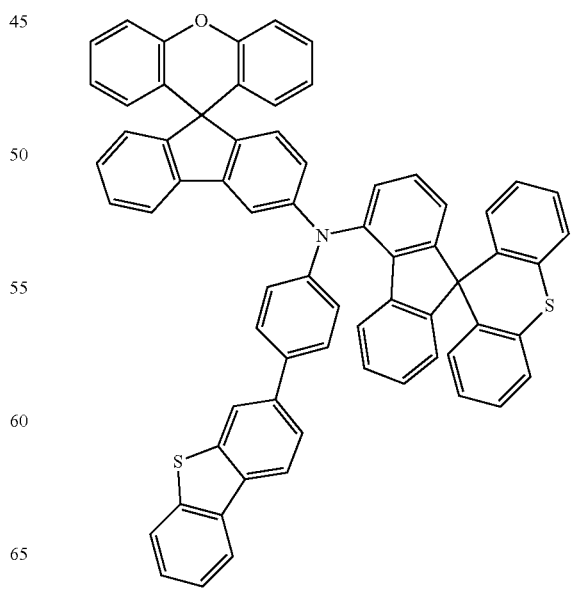

319
-continued
320
-continued
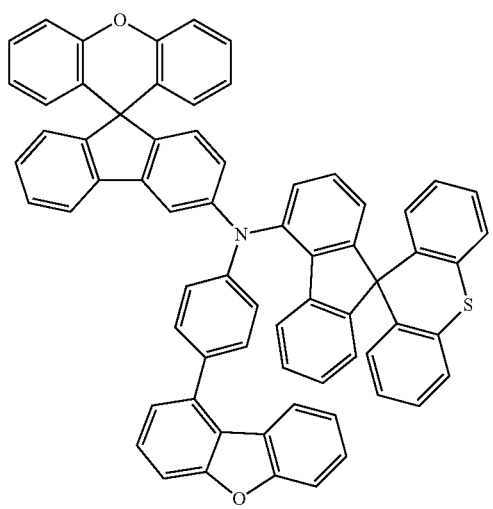
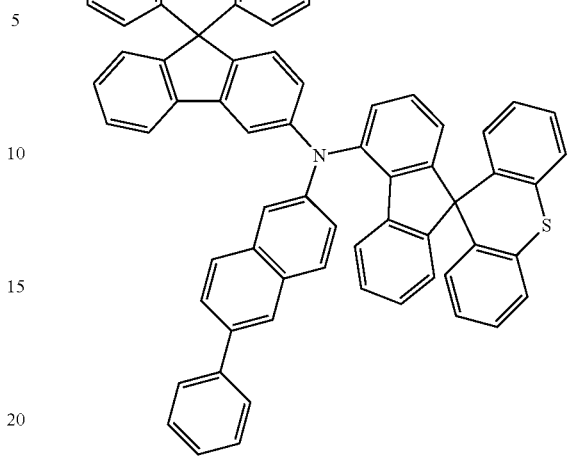
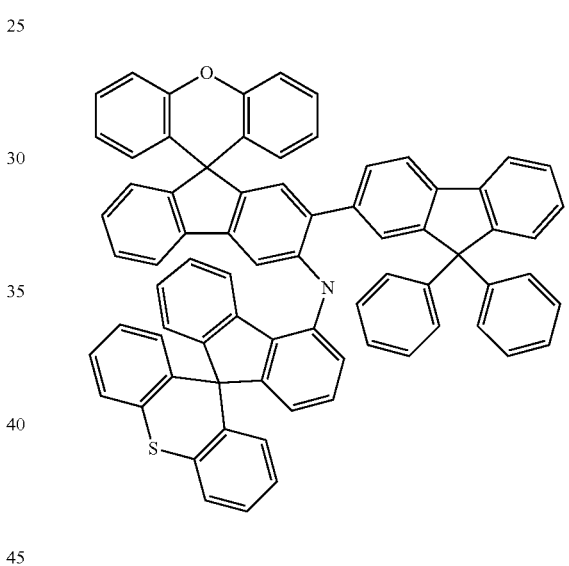
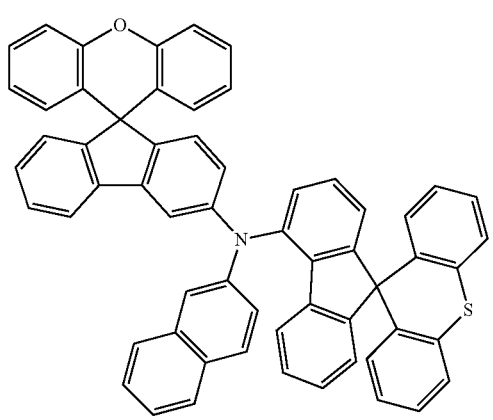
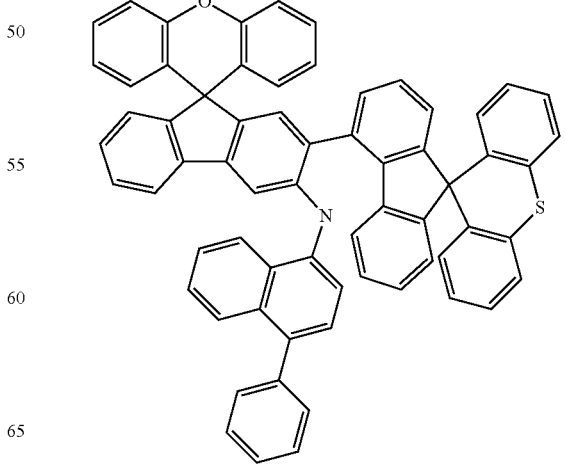

321
-continued
322
-continued
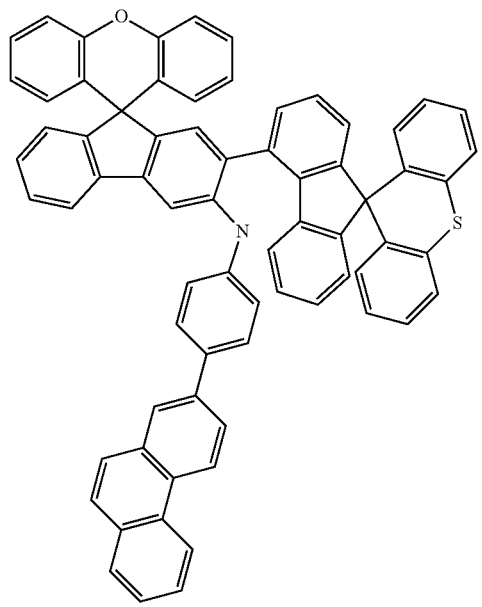
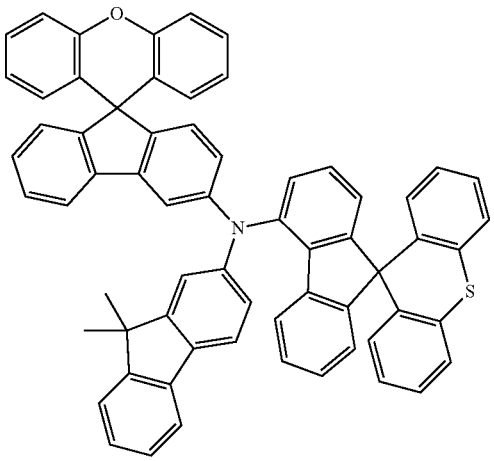
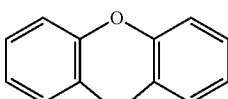
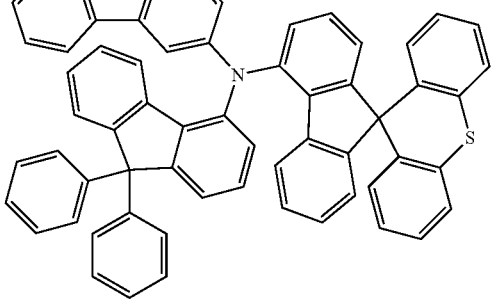
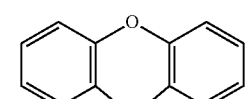
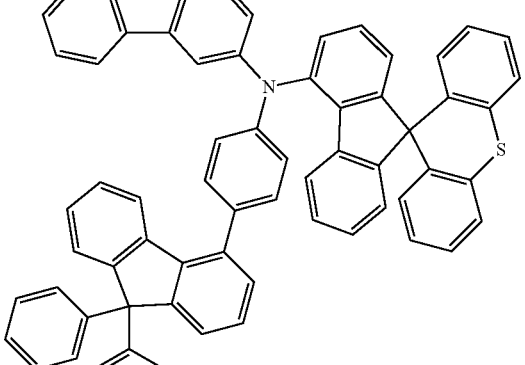

323
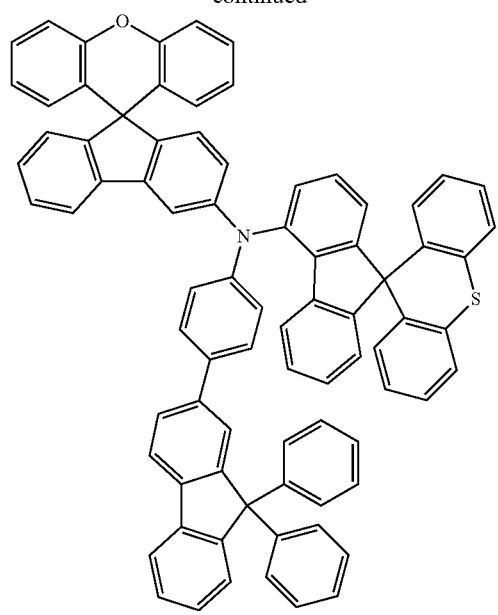
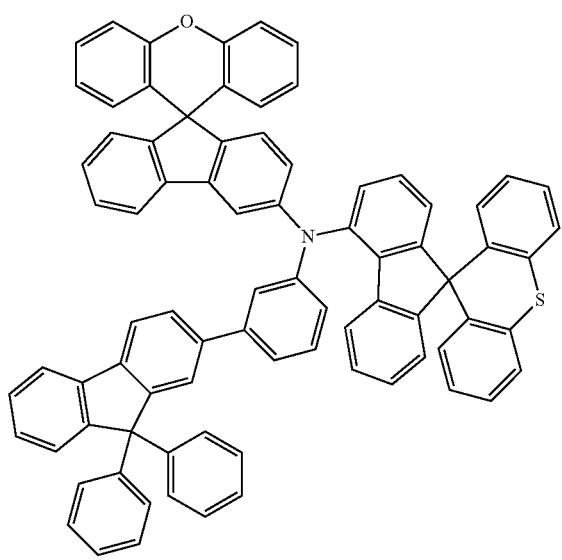
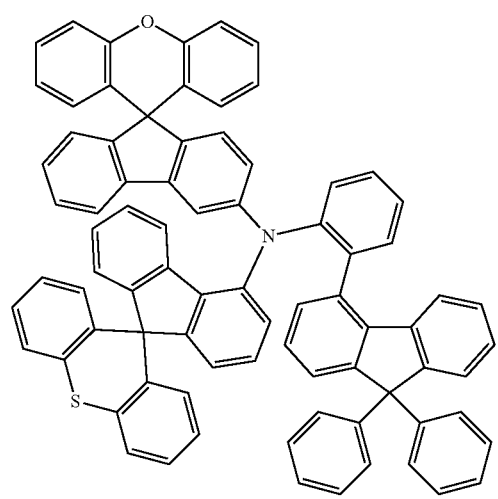
324
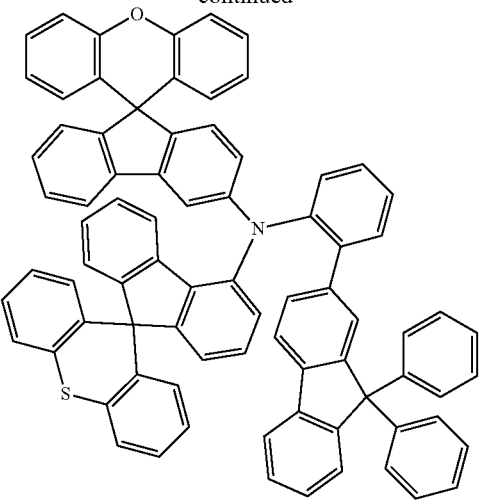
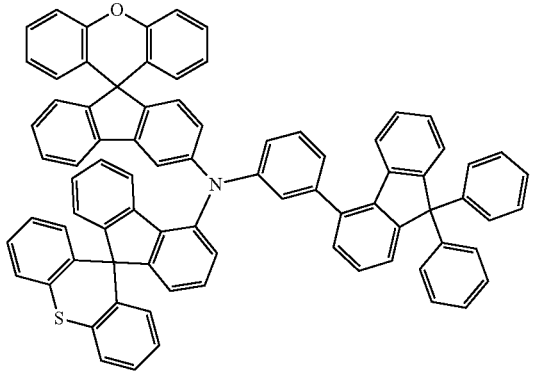
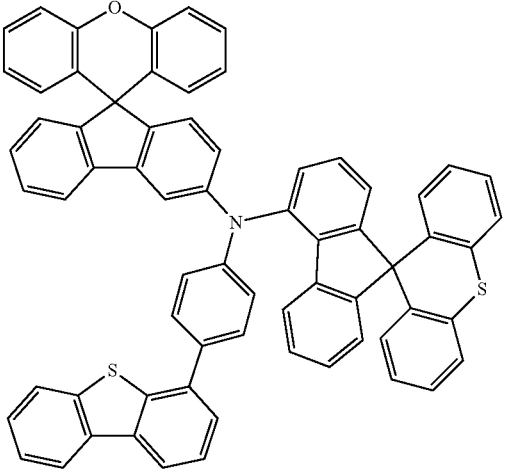

325
-continued
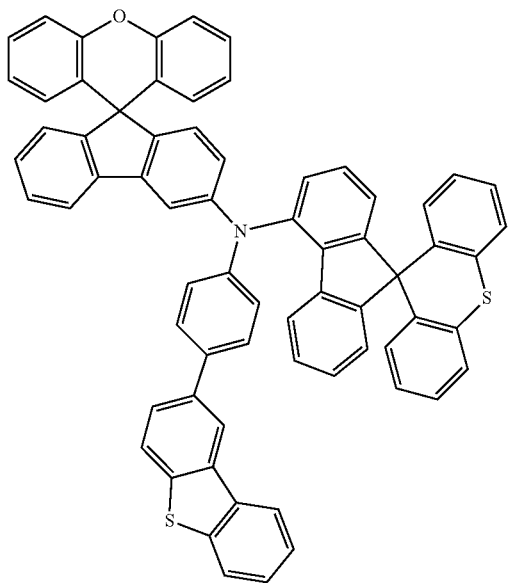
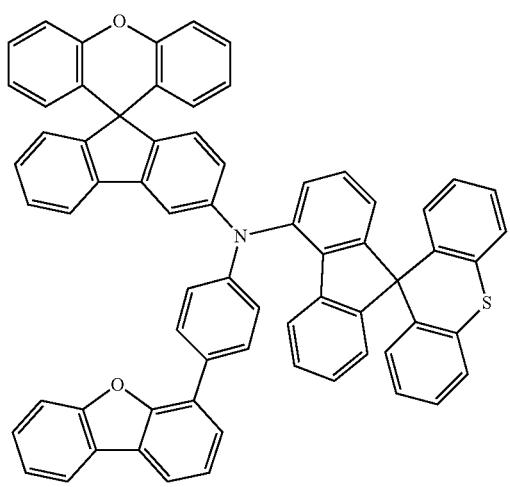
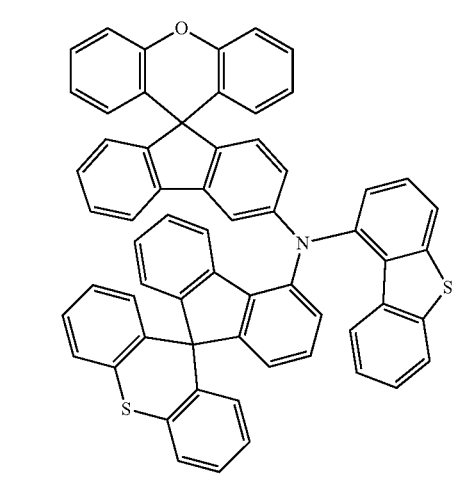
326
-continued
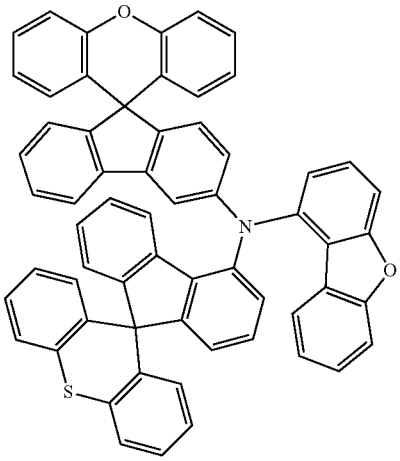
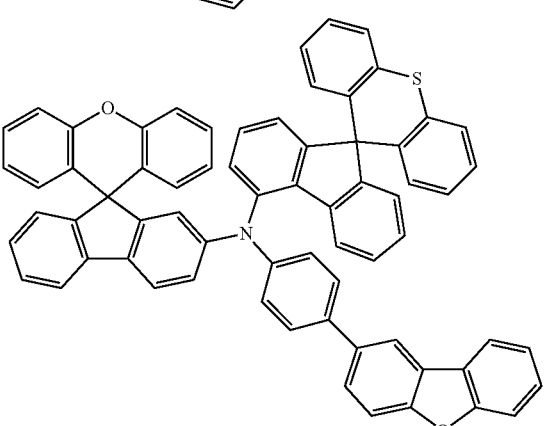
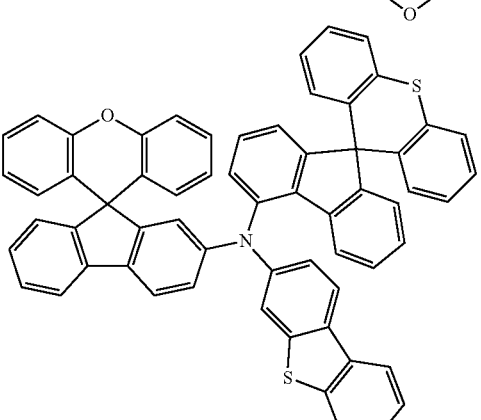
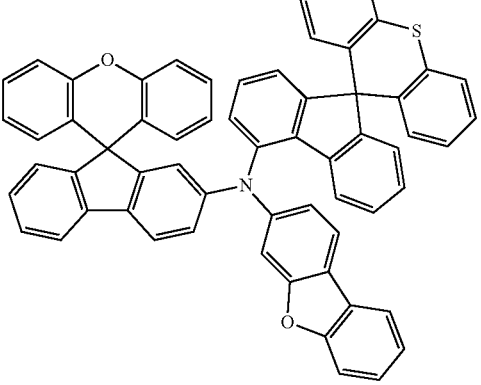

327
-continued
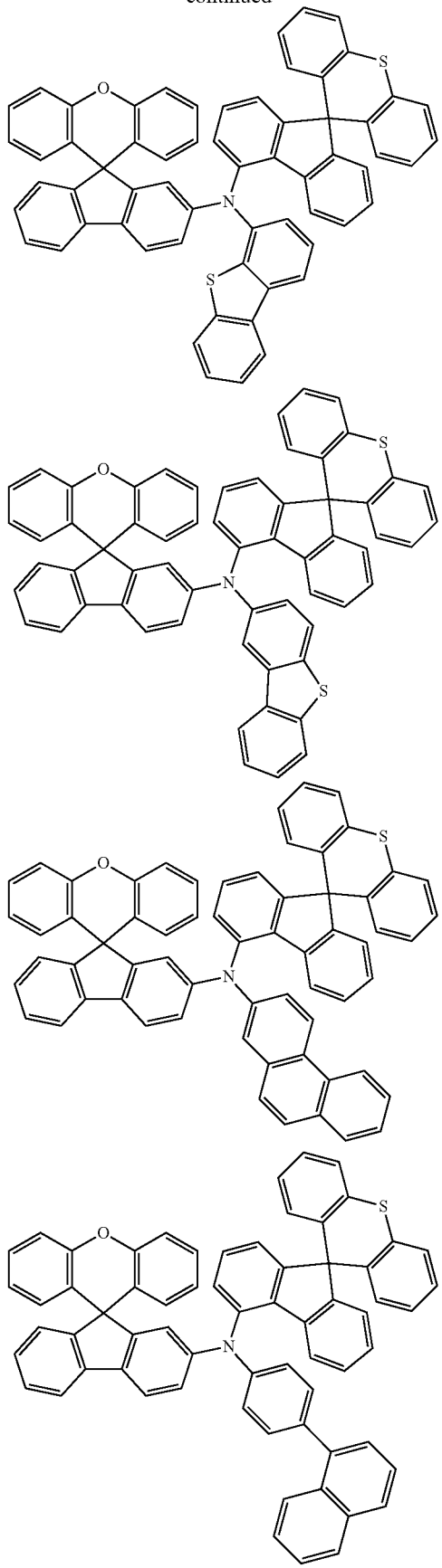
328
-continued
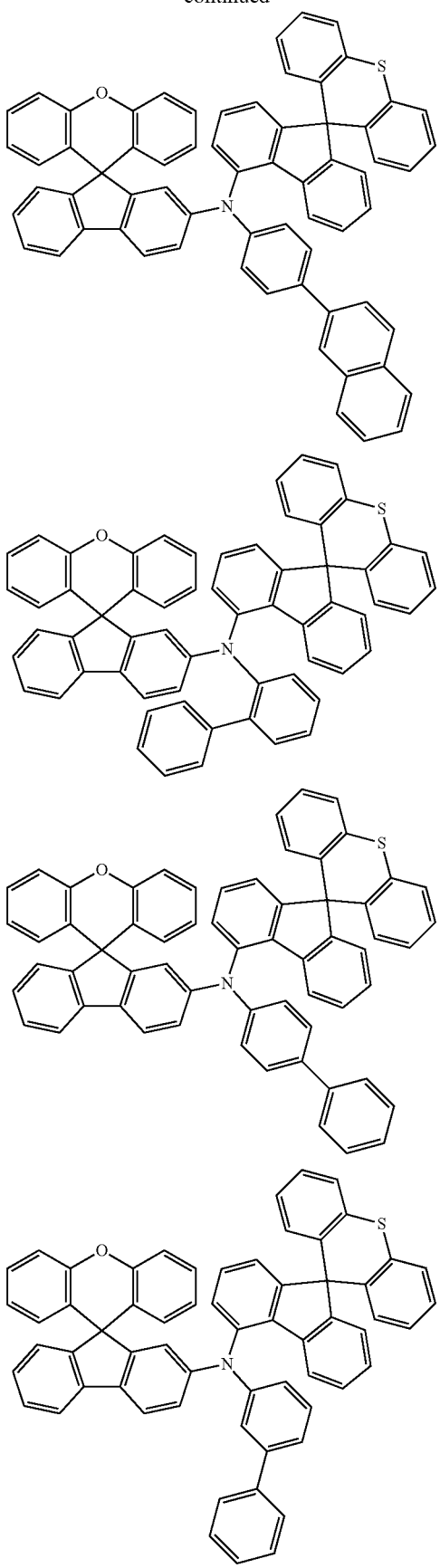

-continued
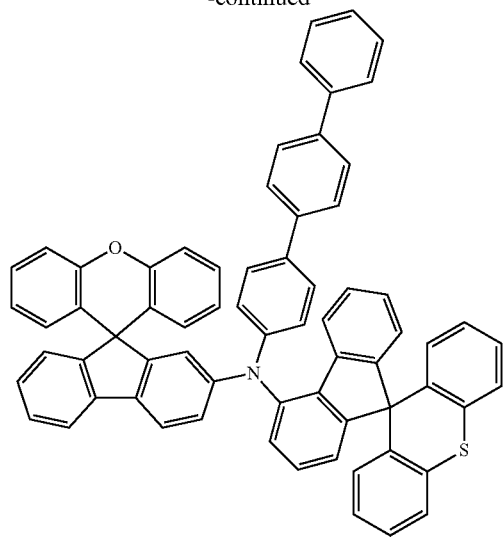
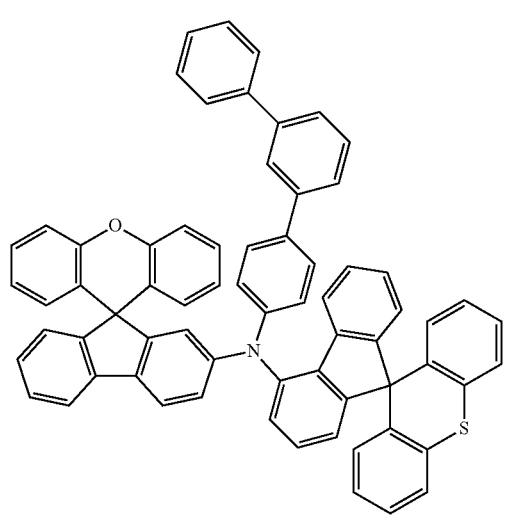
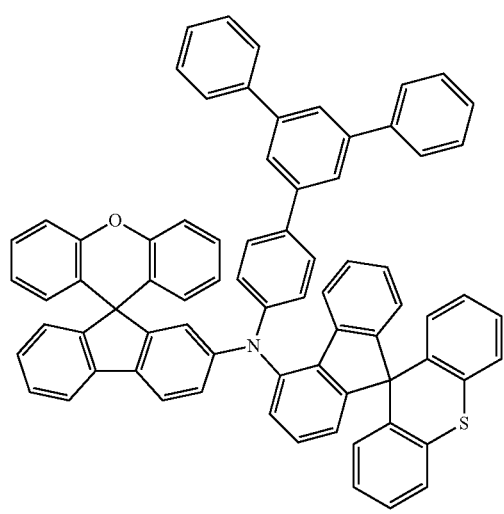
-continued
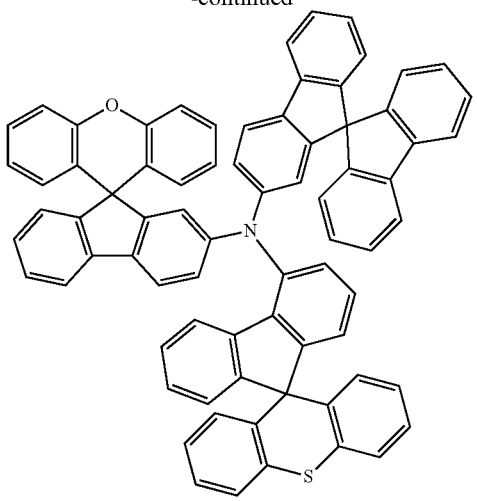
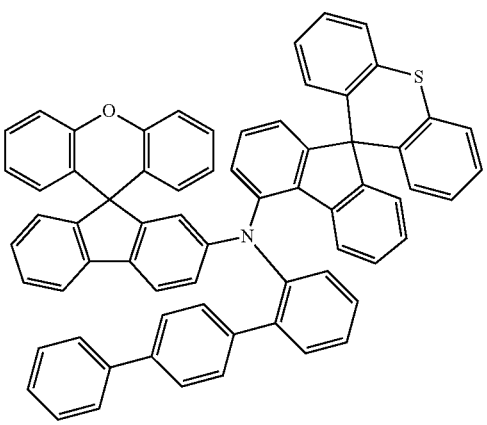
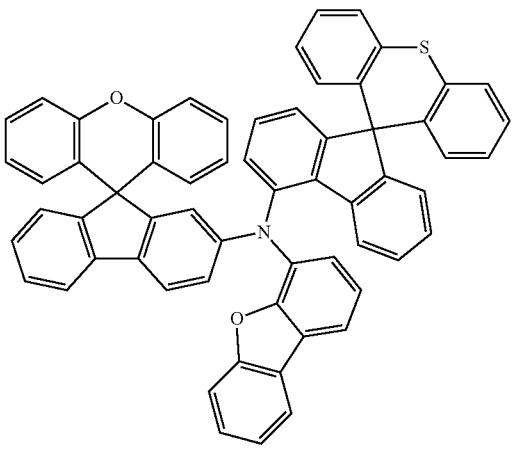

331
-continued
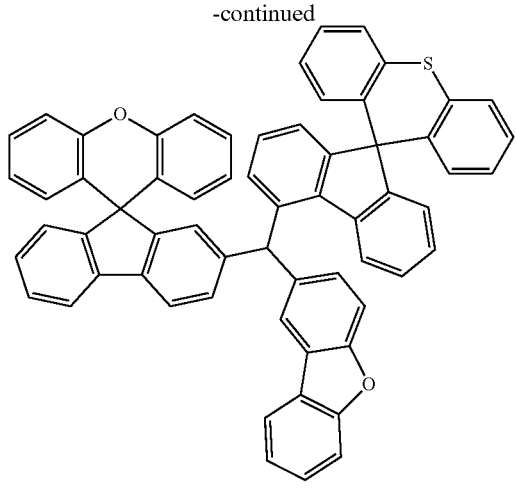
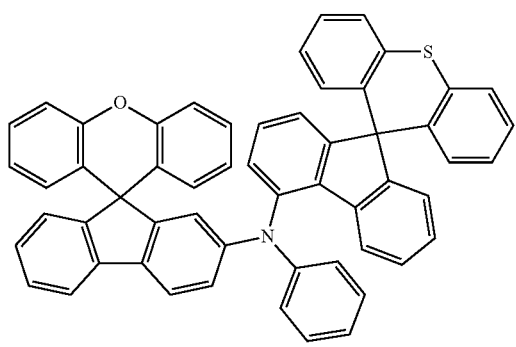
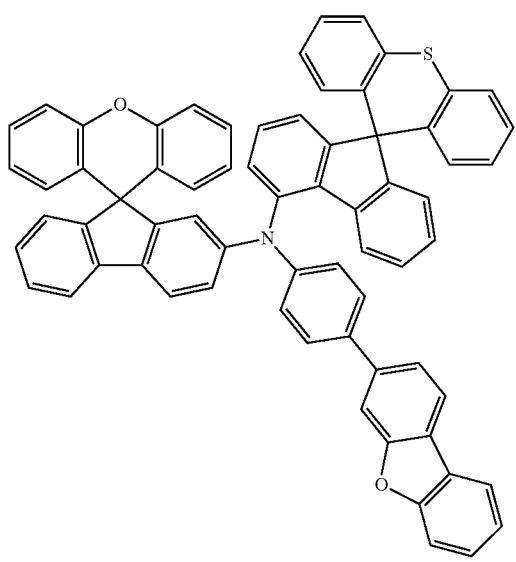
332
-continued
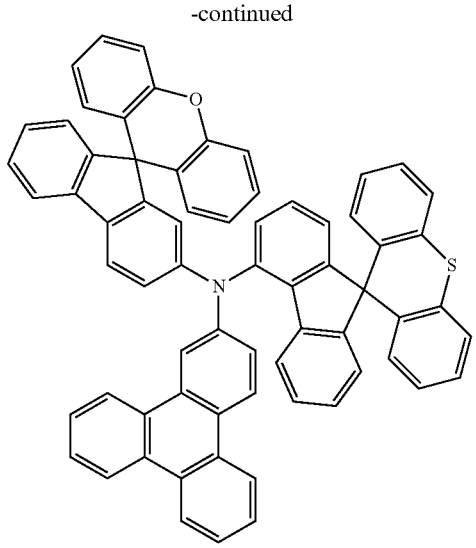
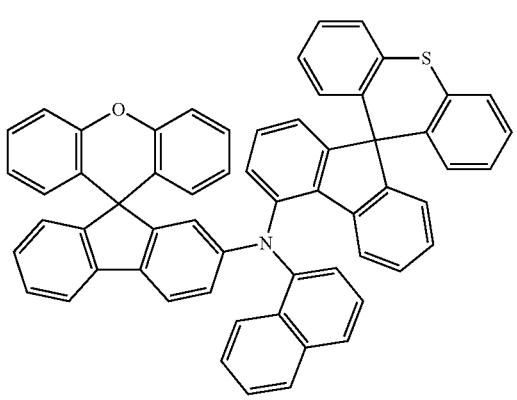
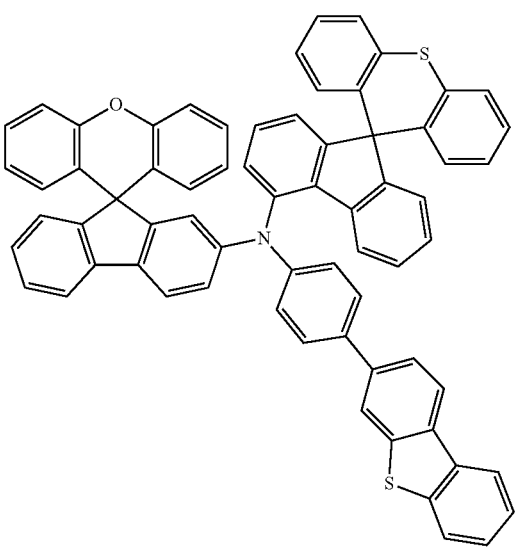

333
-continued
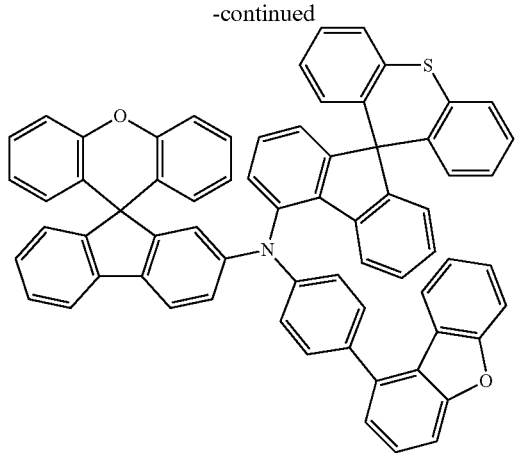
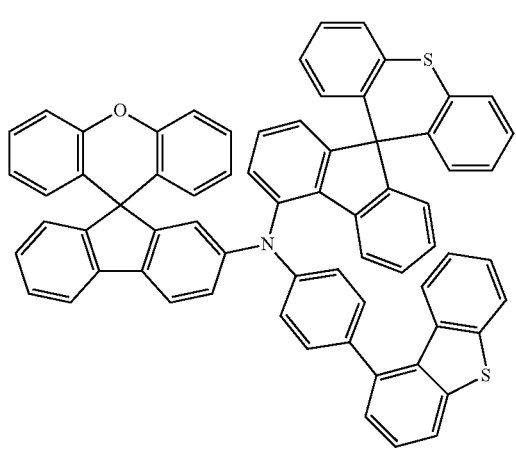
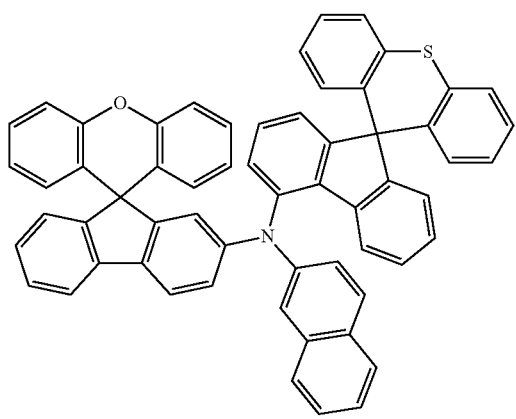
334
-continued
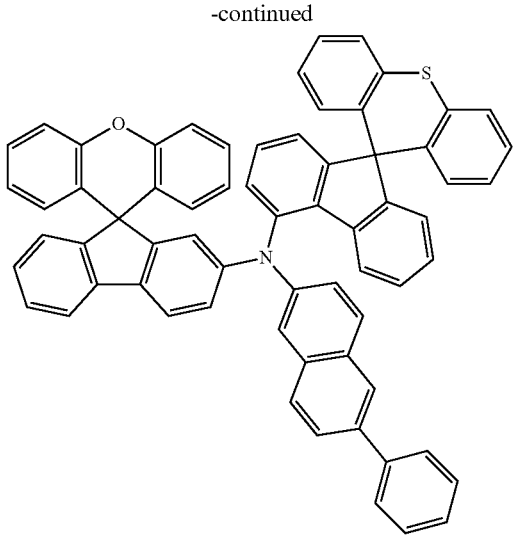
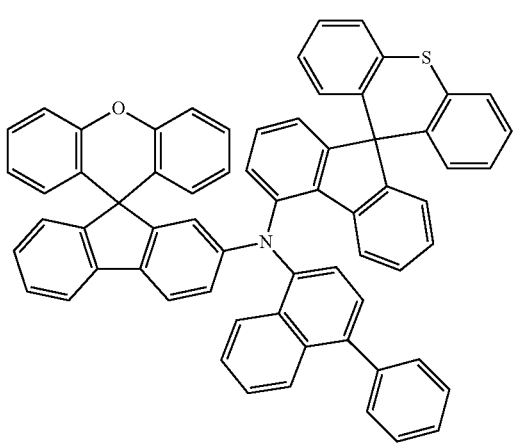

335
-continued
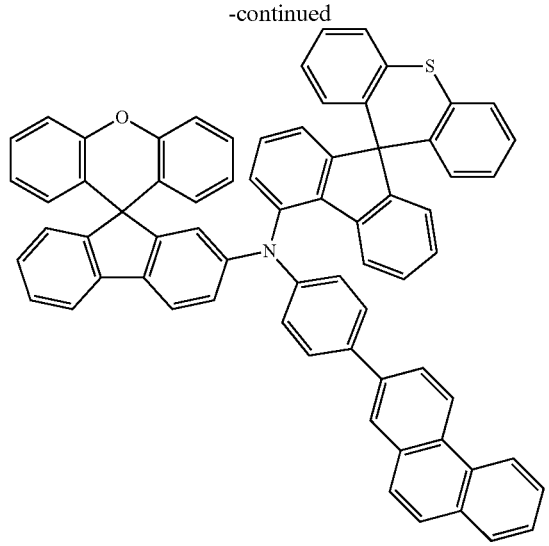
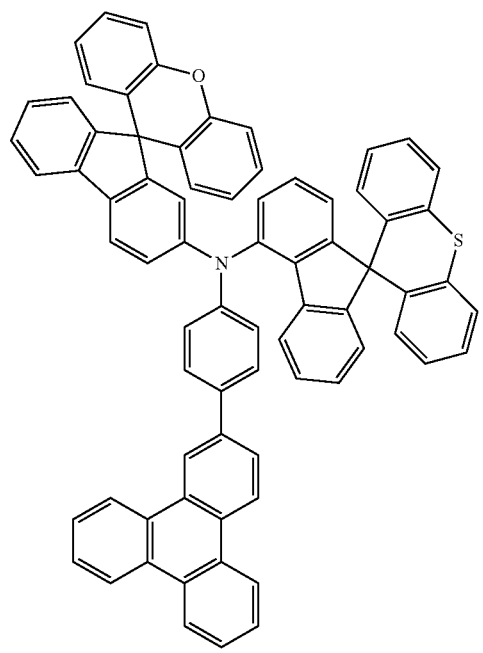
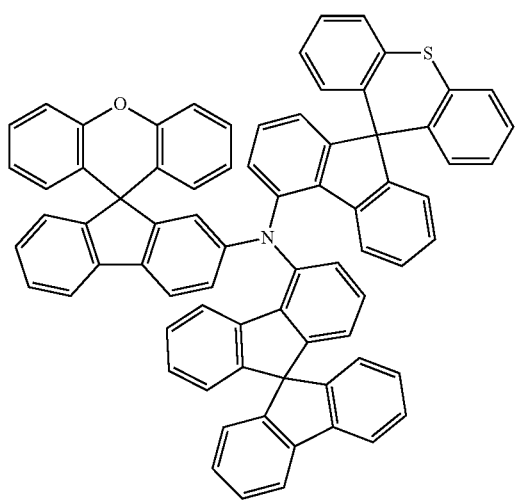
336
-continued
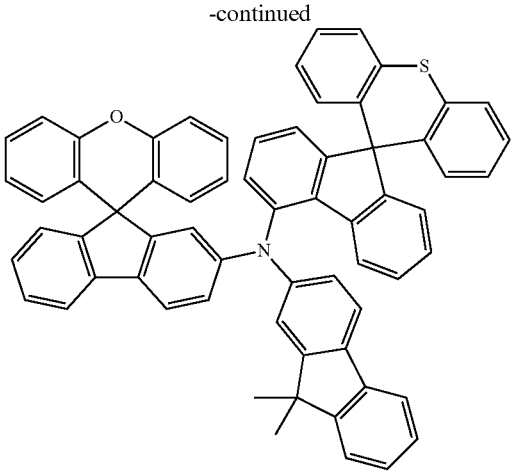
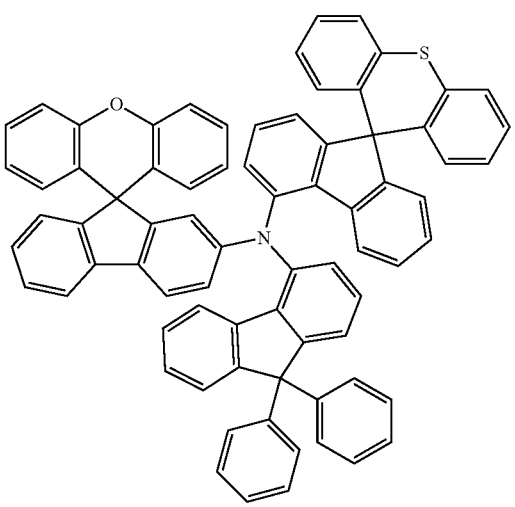
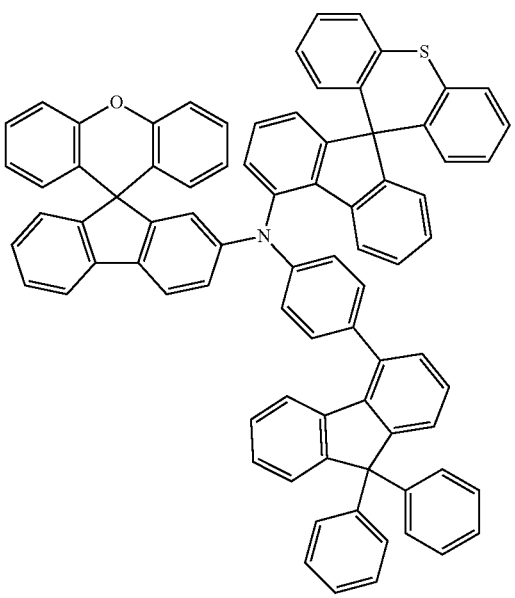

337
-continued
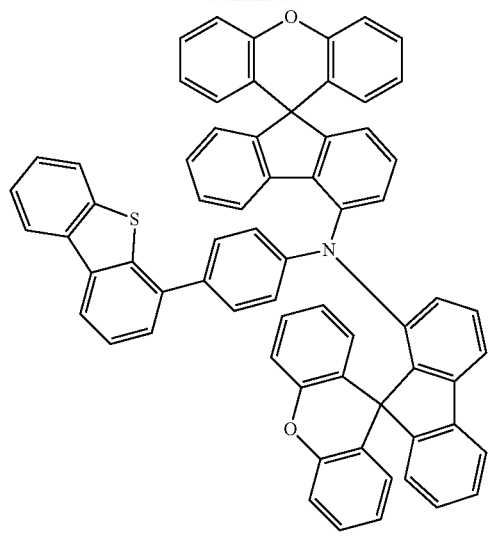
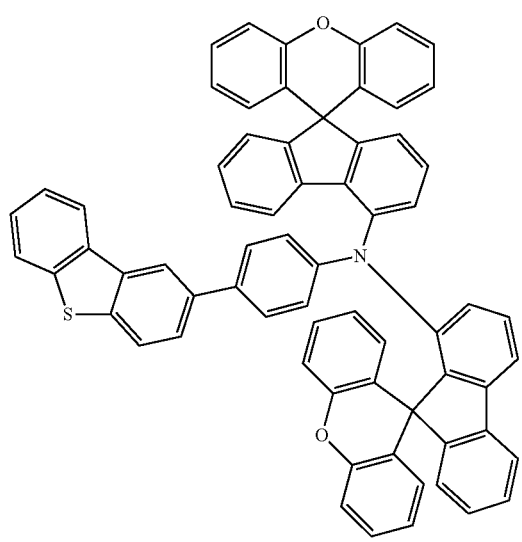
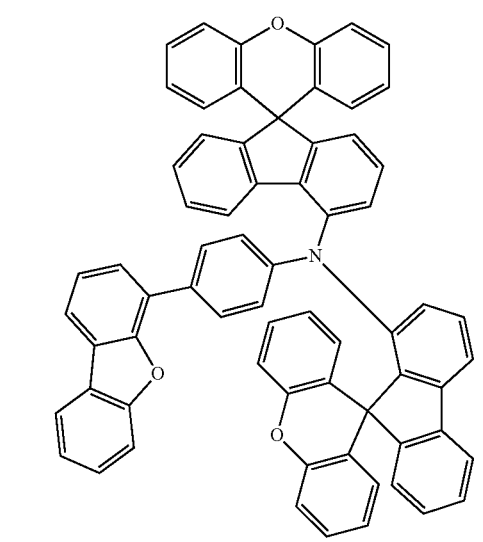
338
-continued
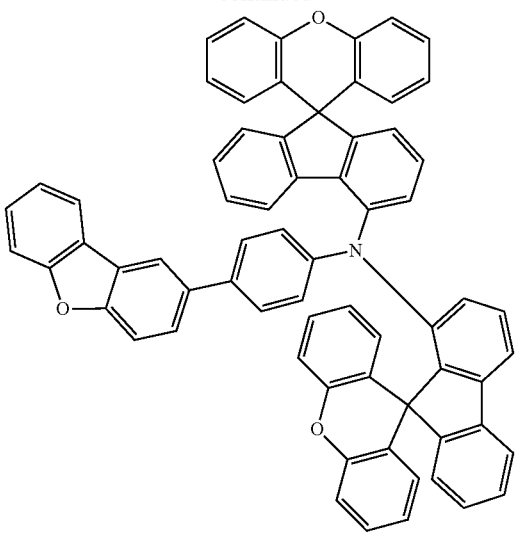
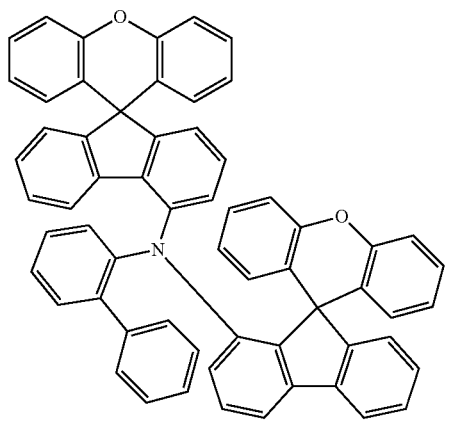
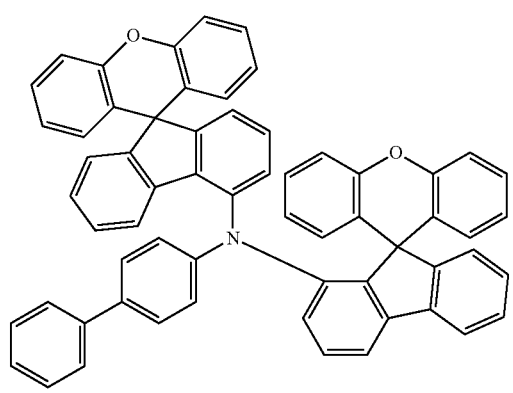

339
-continued
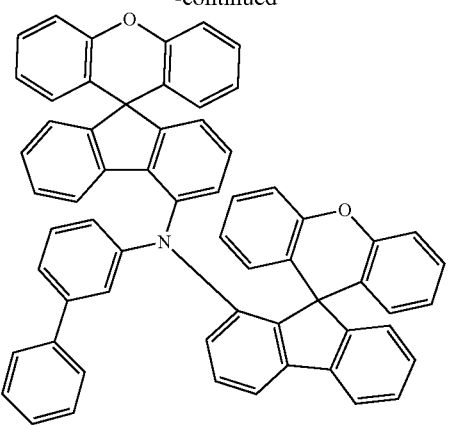
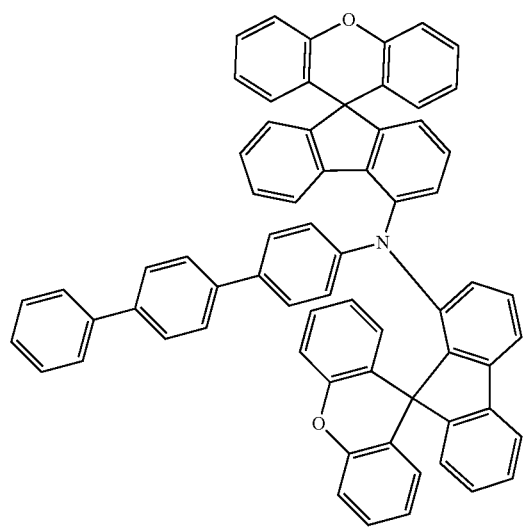
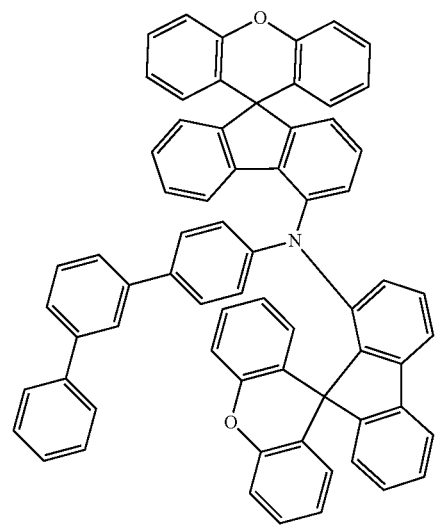
340
-continued
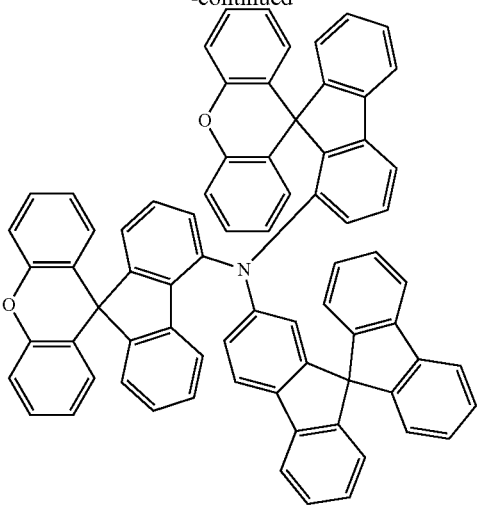
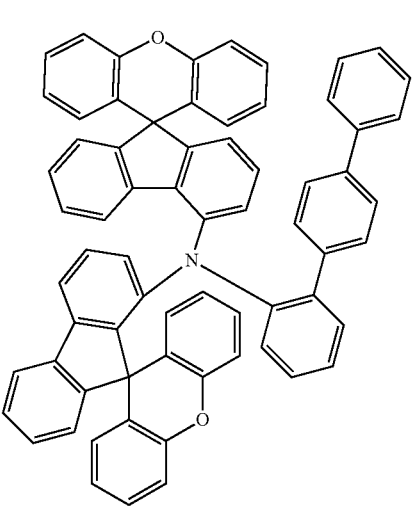
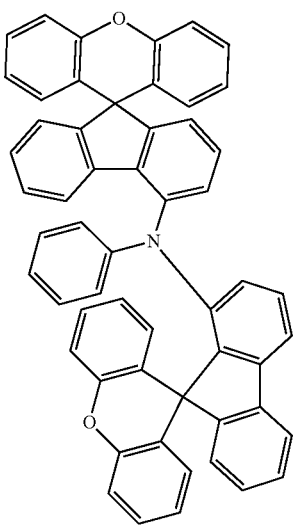

341
-continued
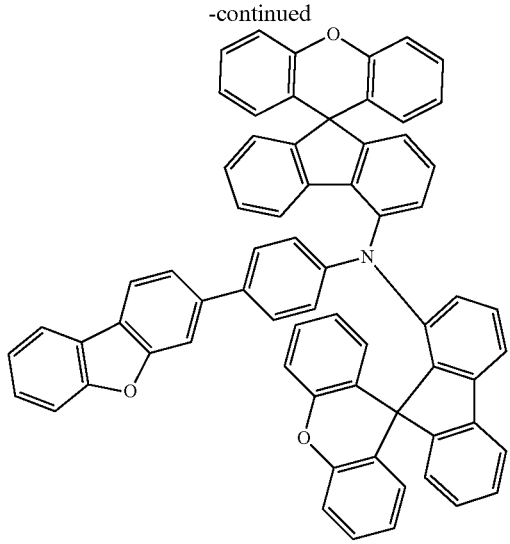
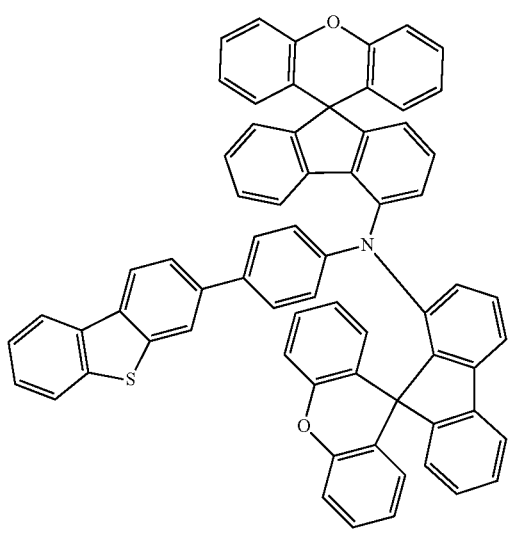
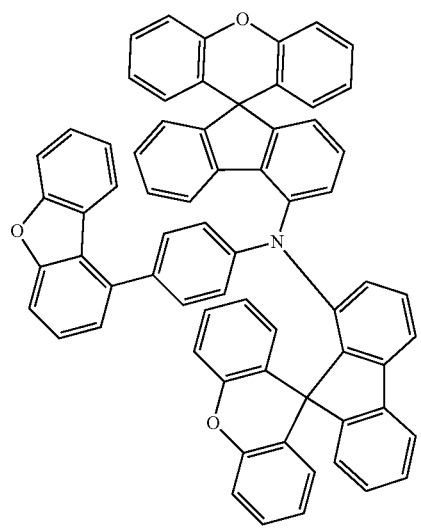
342
-continued
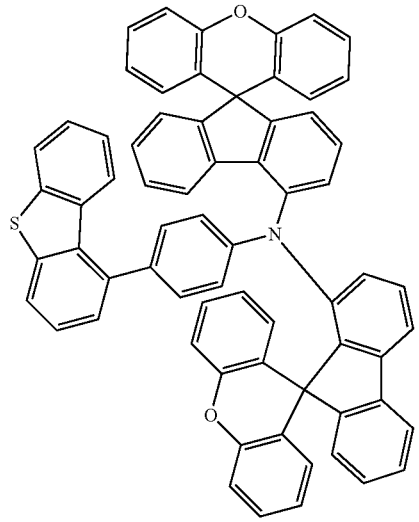
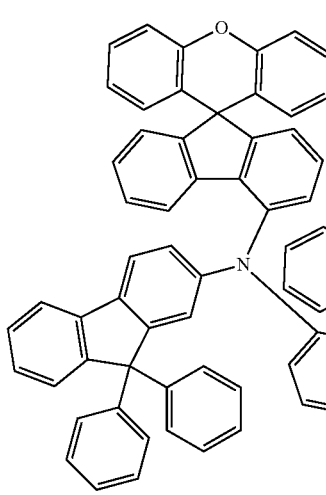
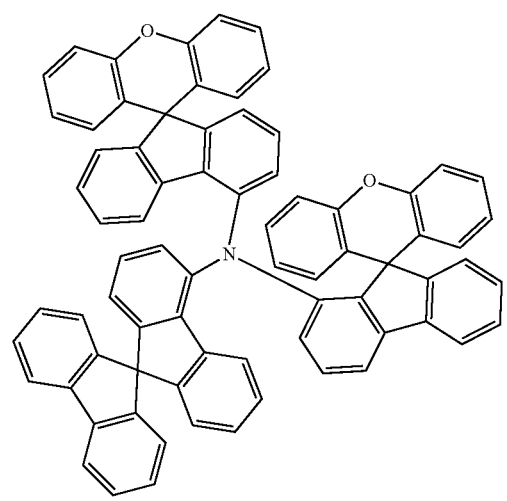

343
-continued
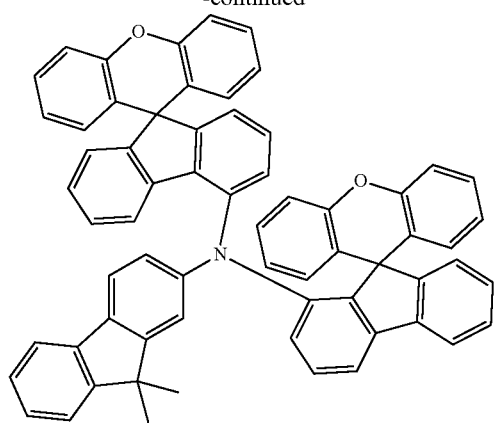
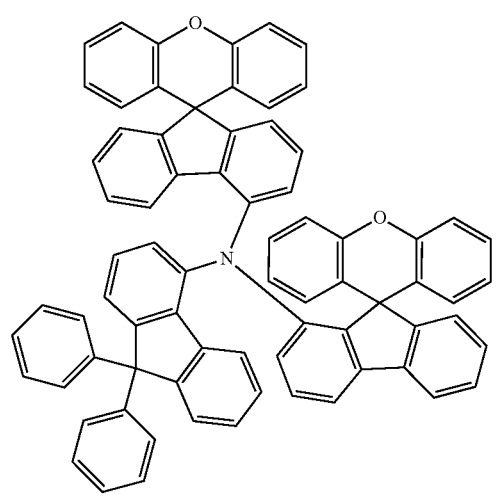
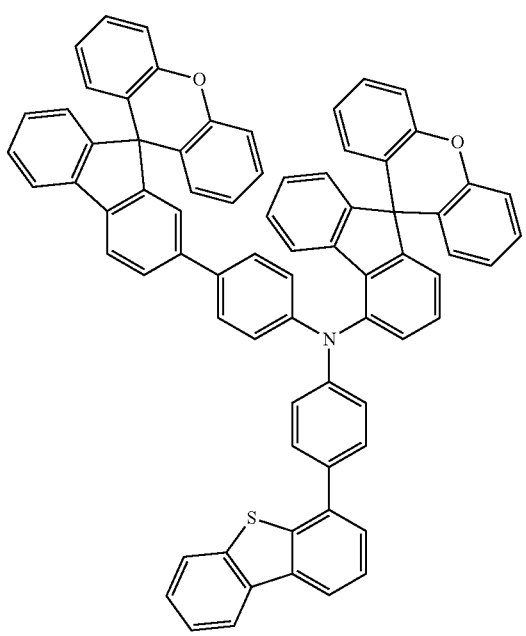
344
-continued
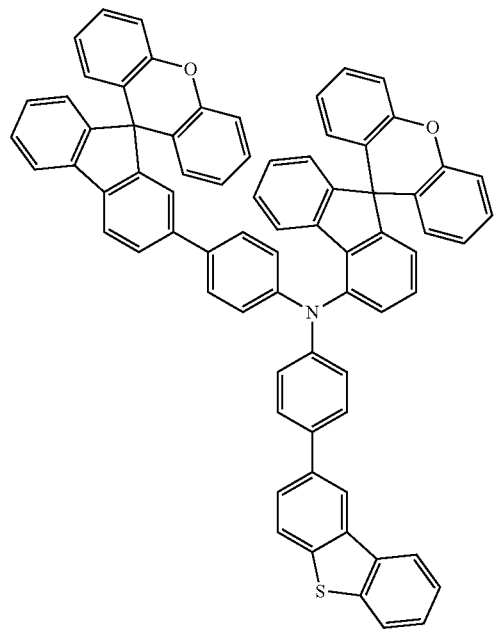
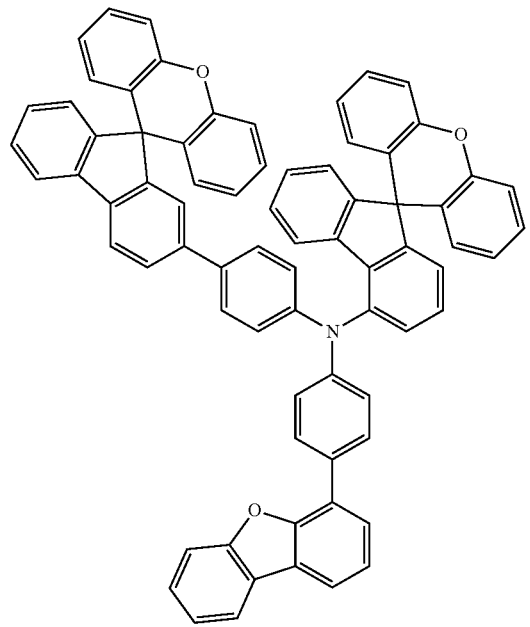

345
-continued
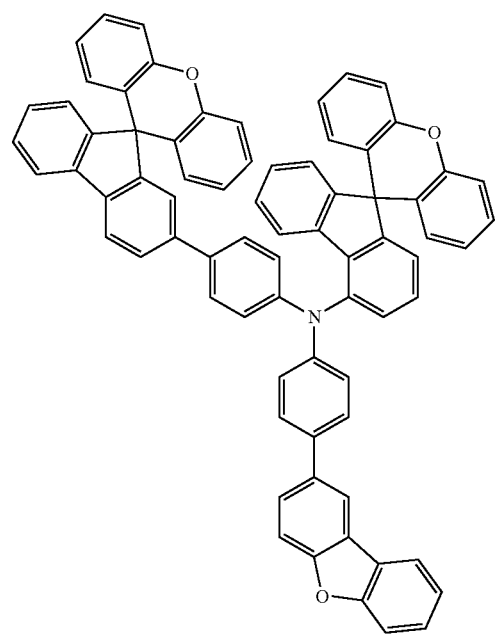
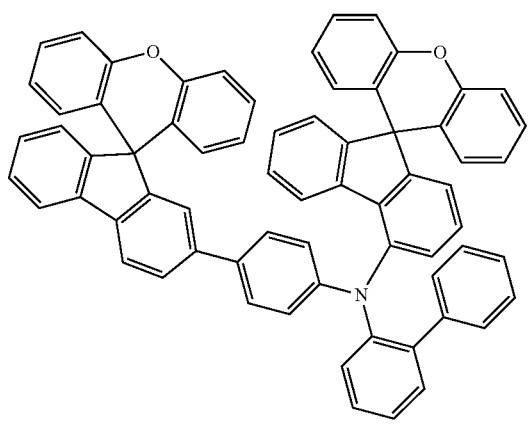
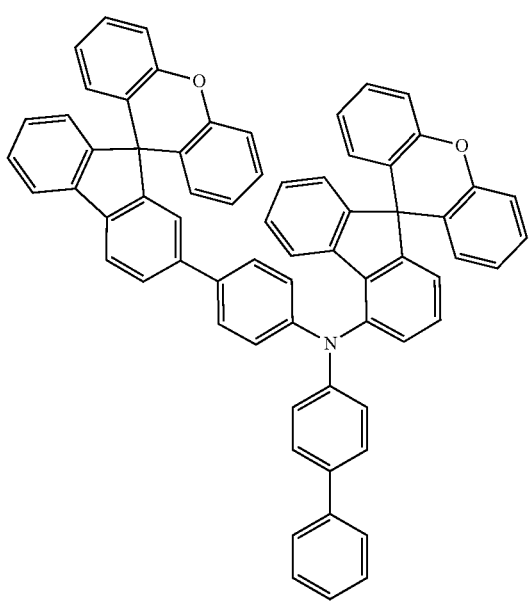
346
-continued
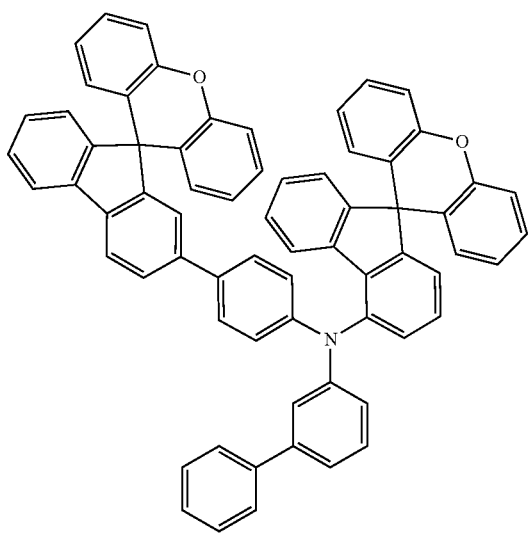
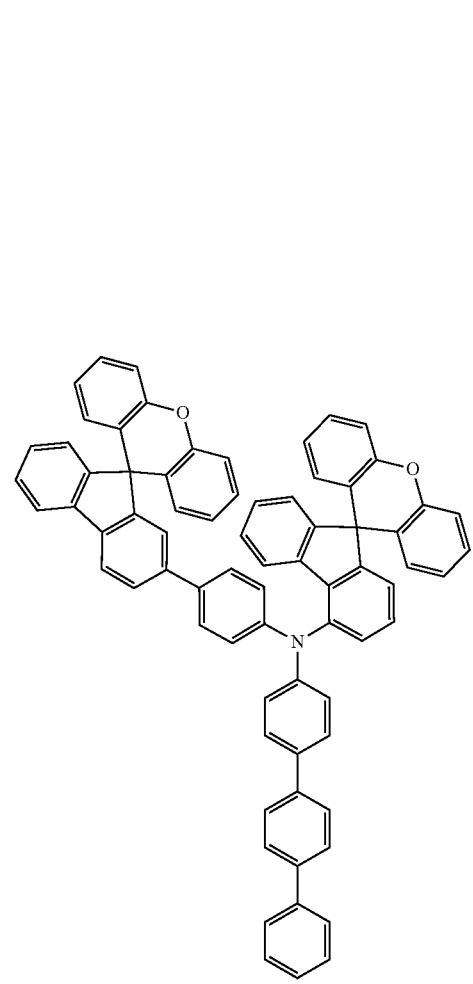

347
-continued
348
-continued
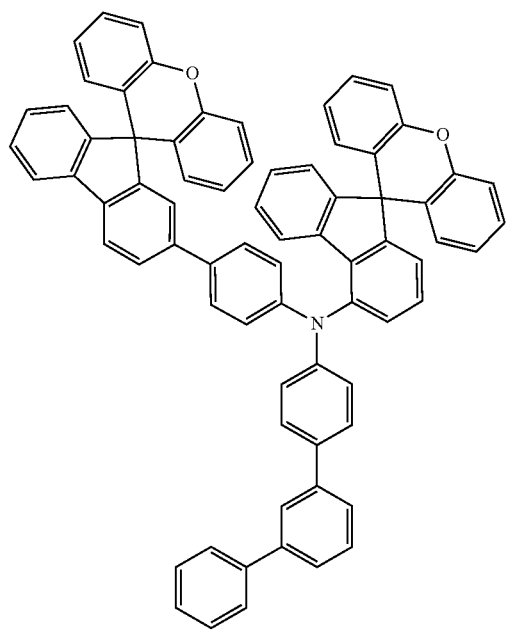
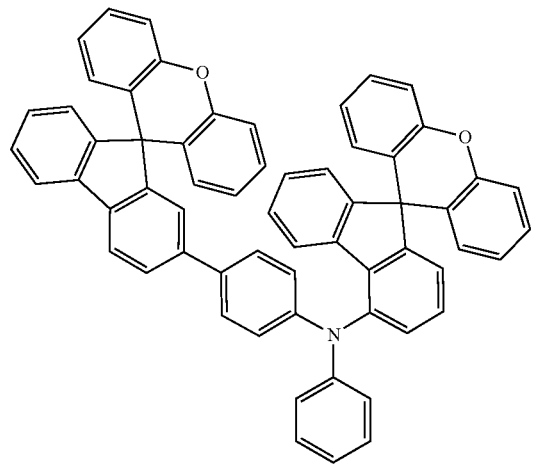
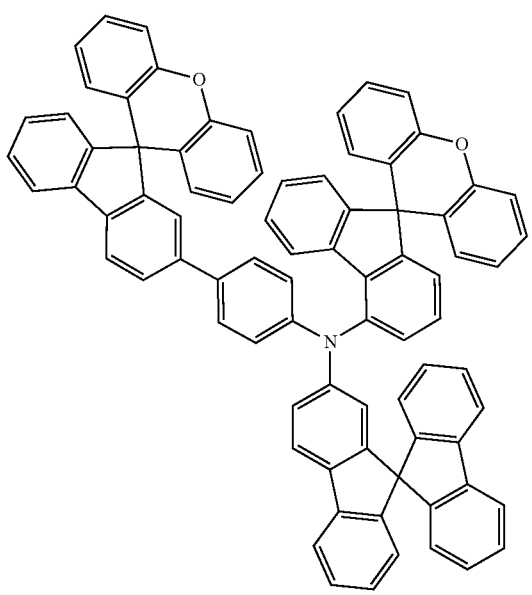
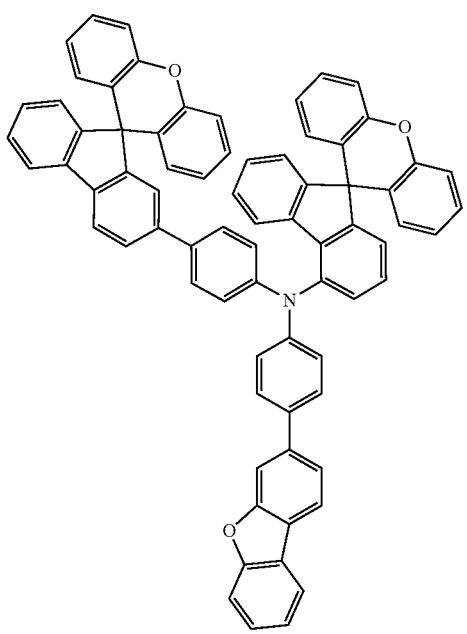
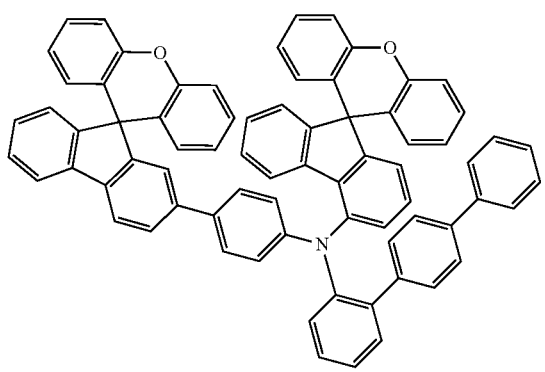
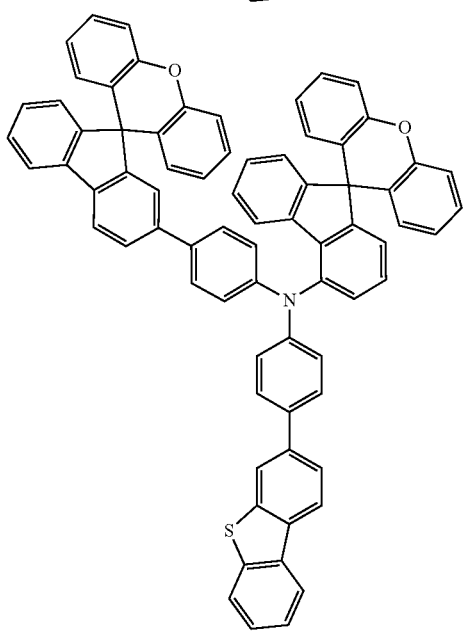

349
-continued
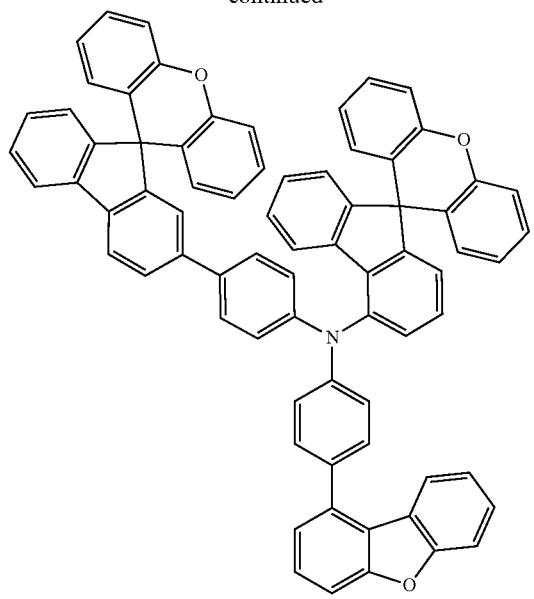
350
-continued
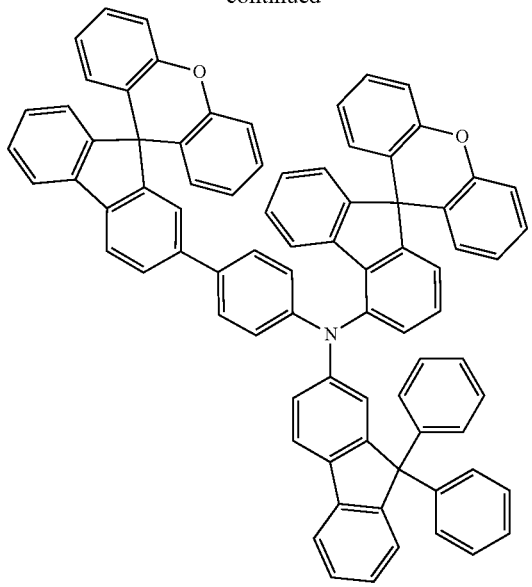
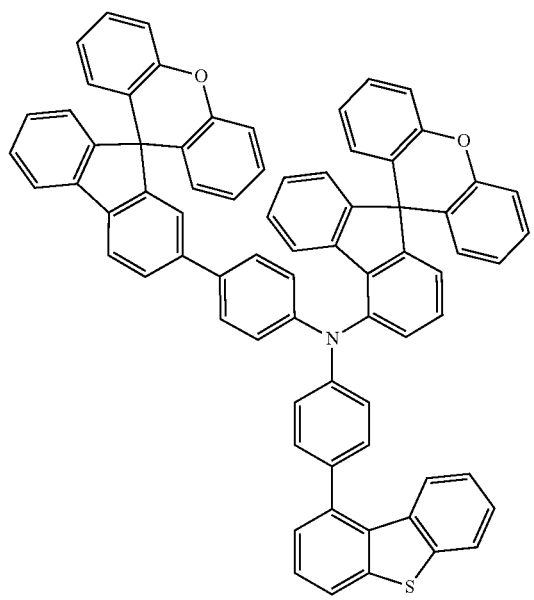
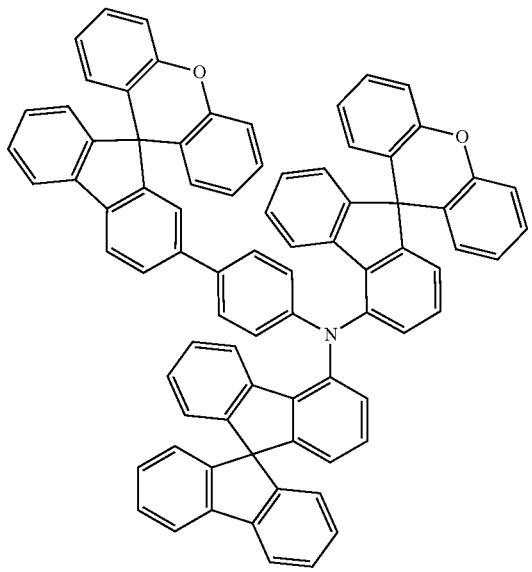

351
-continued
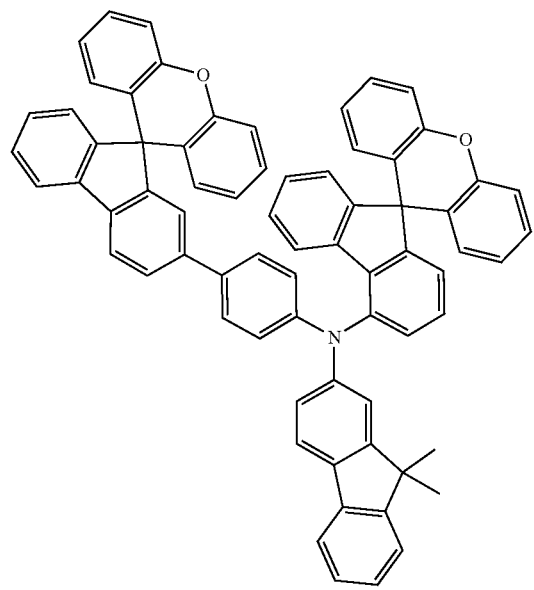
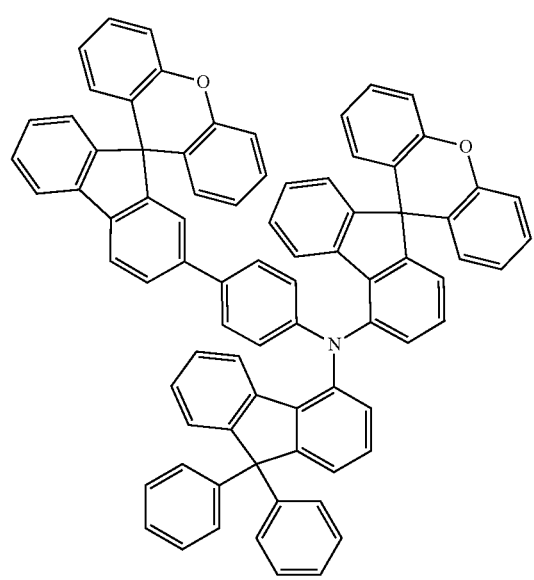
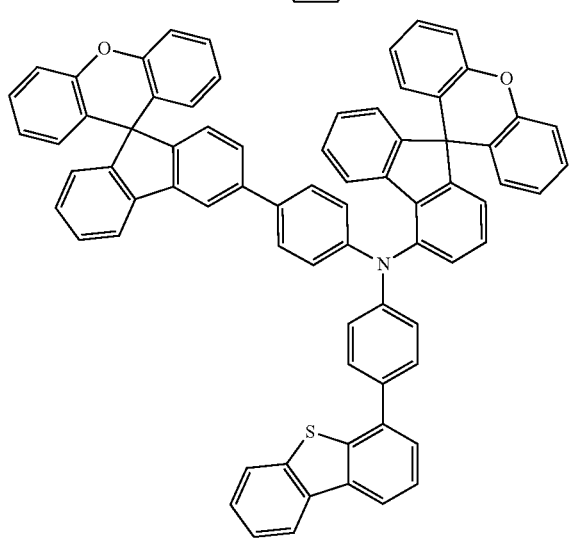
352
-continued
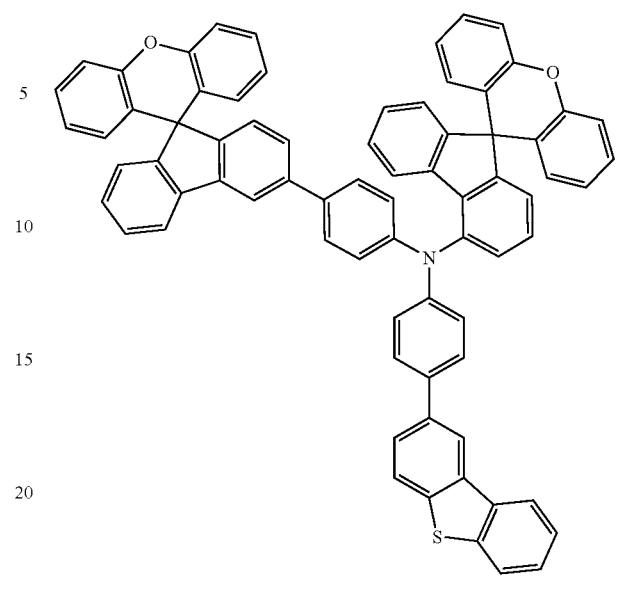
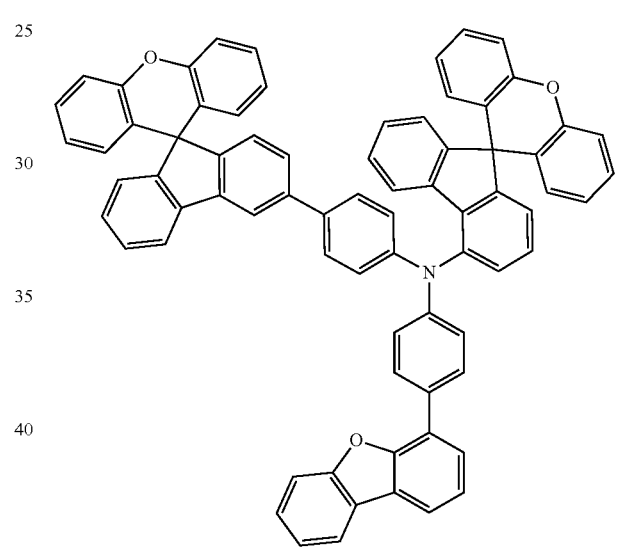
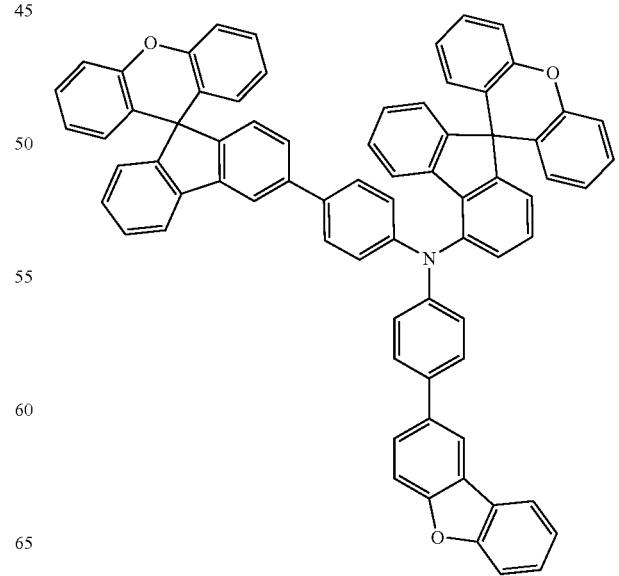

353
-continued
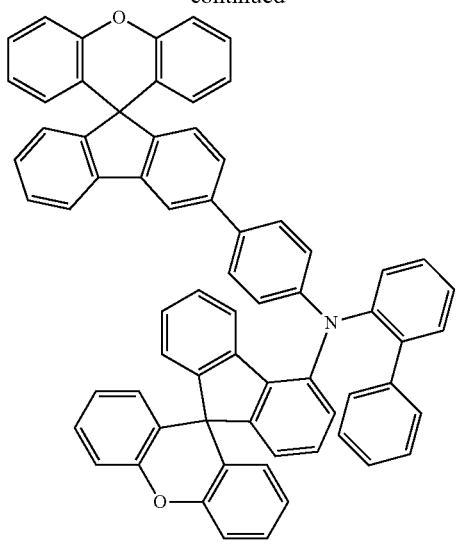
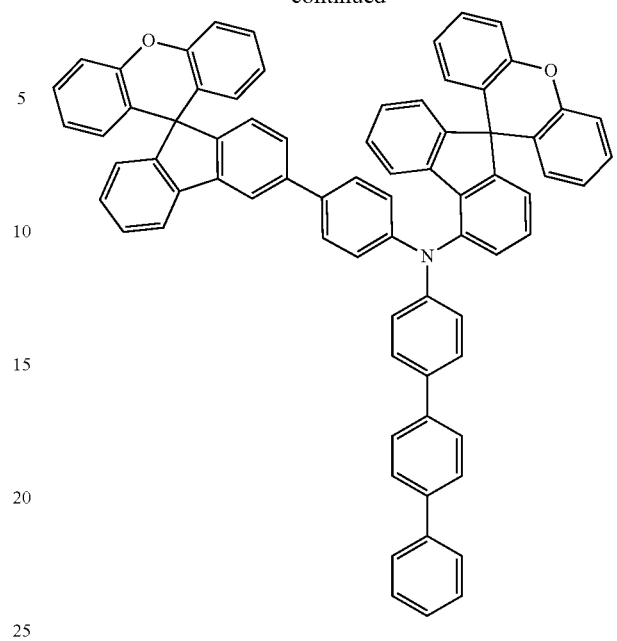
354
-continued
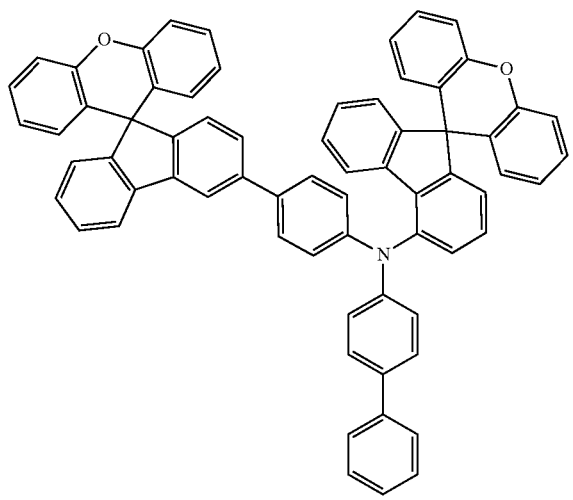
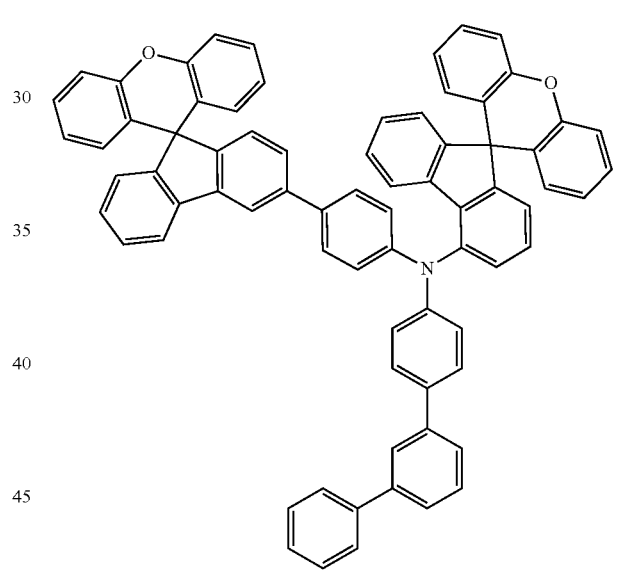
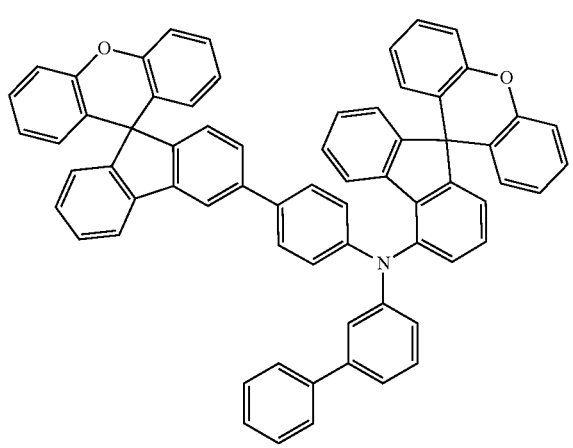
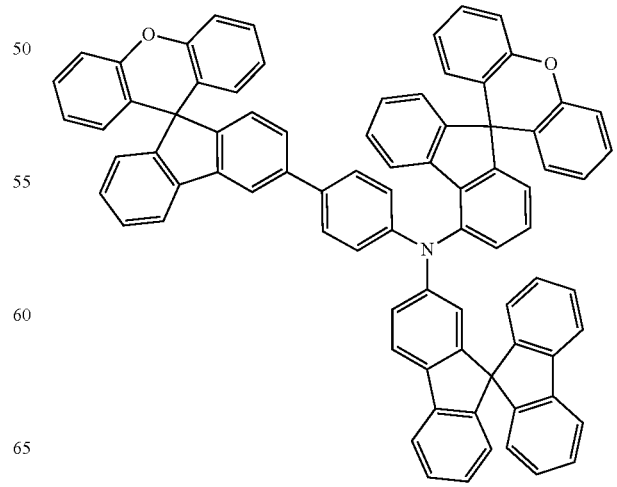

355
-continued
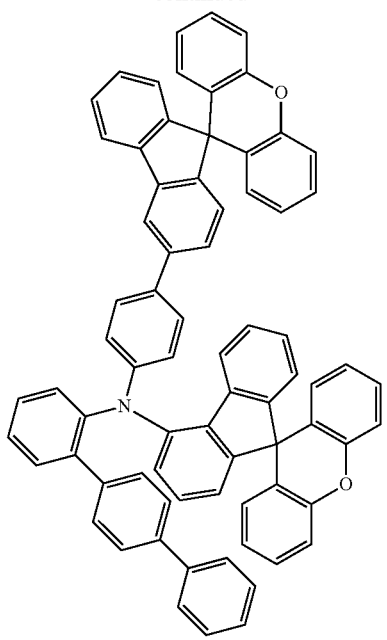
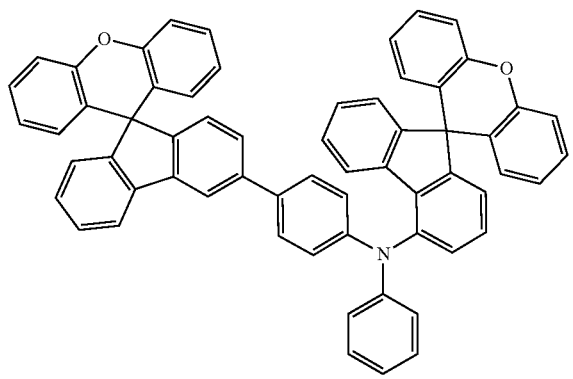
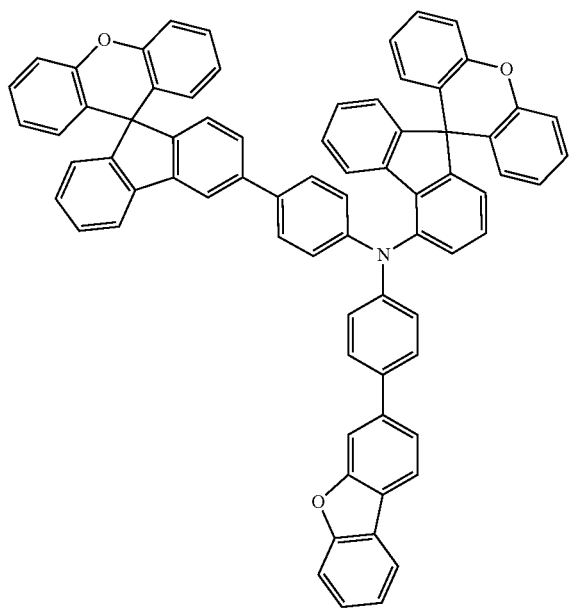
356
-continued
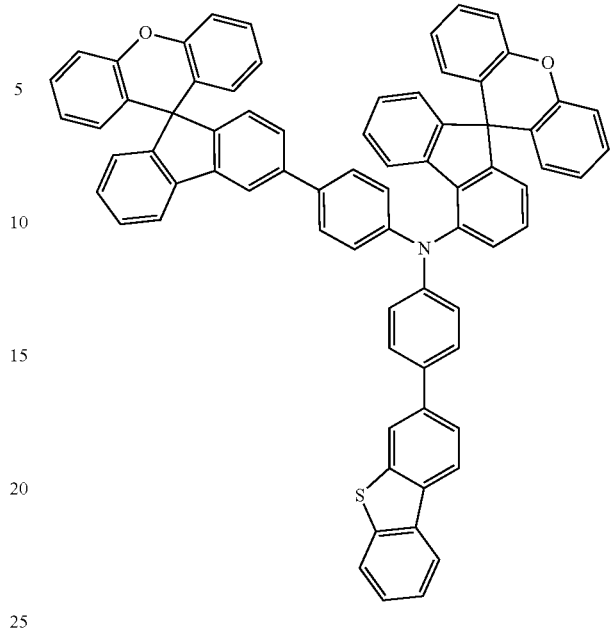
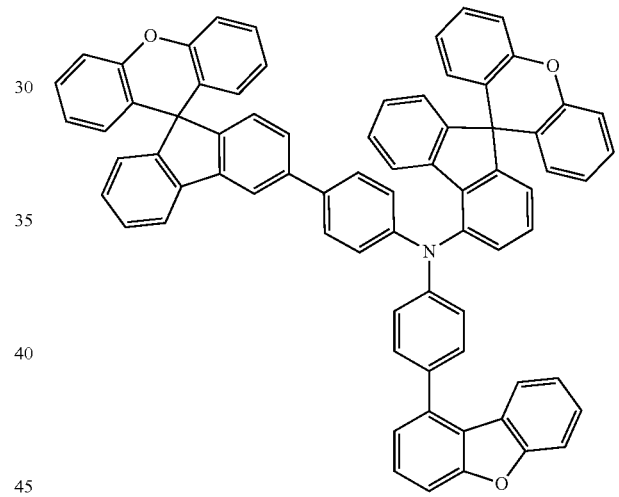
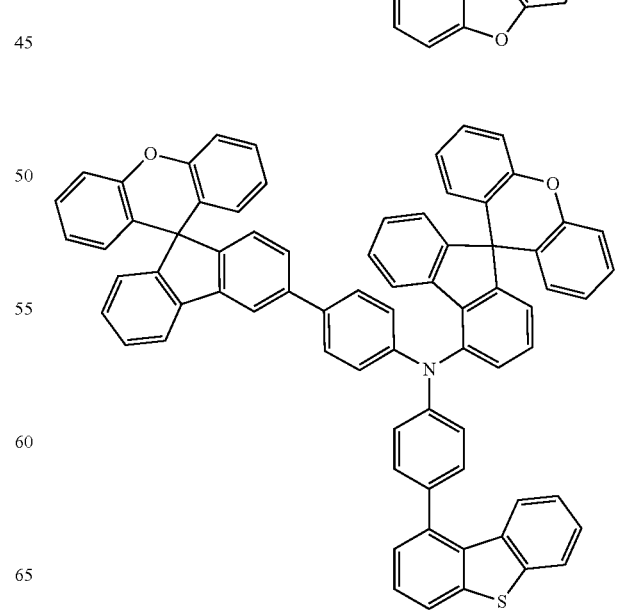

357
-continued
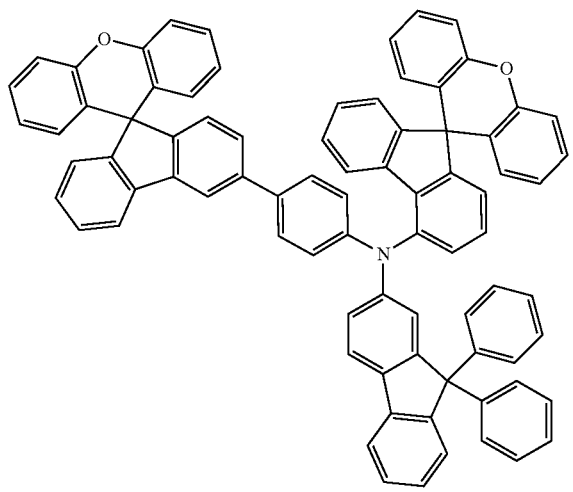
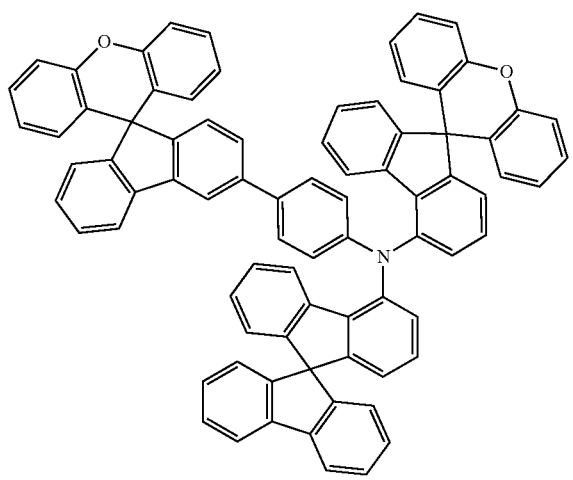
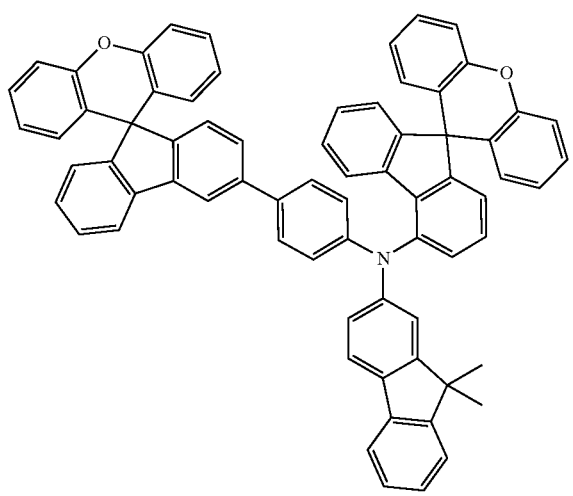
358
-continued
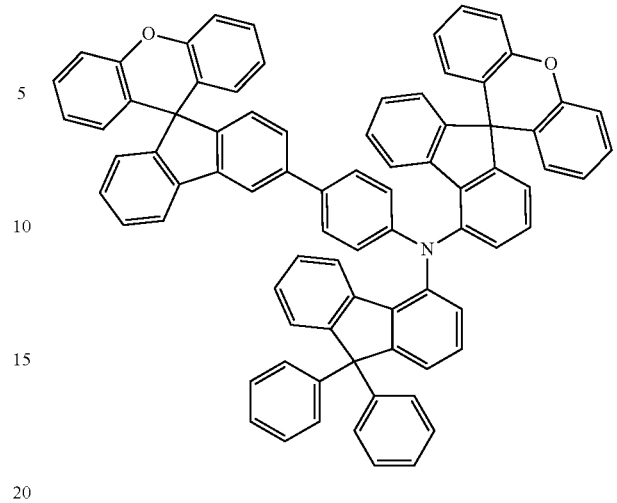
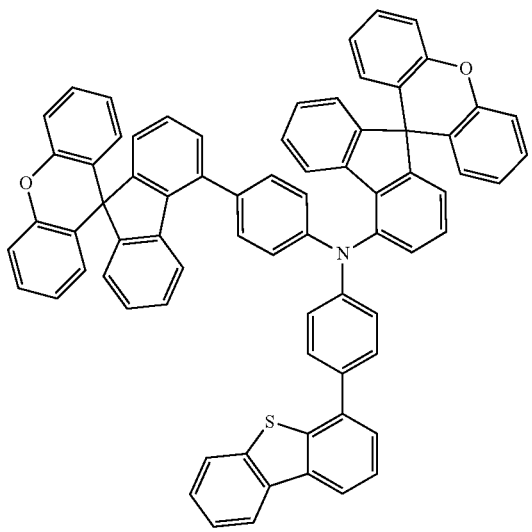
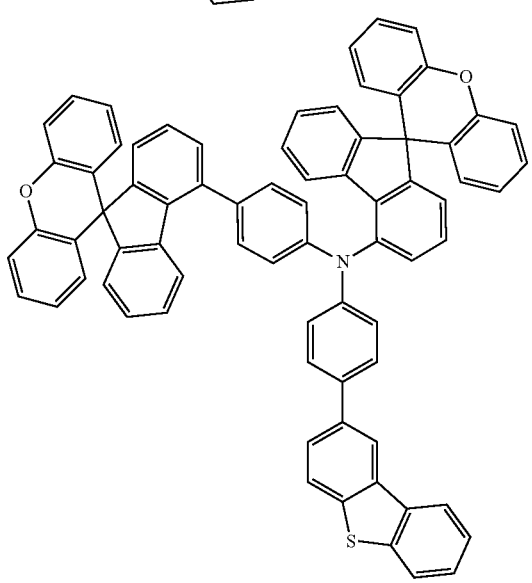

359
-continued
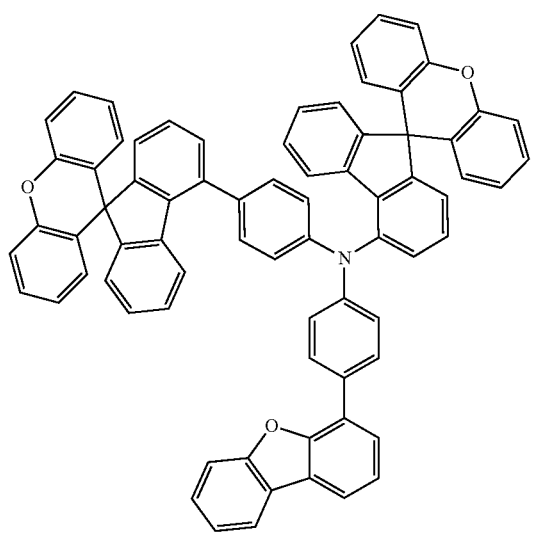
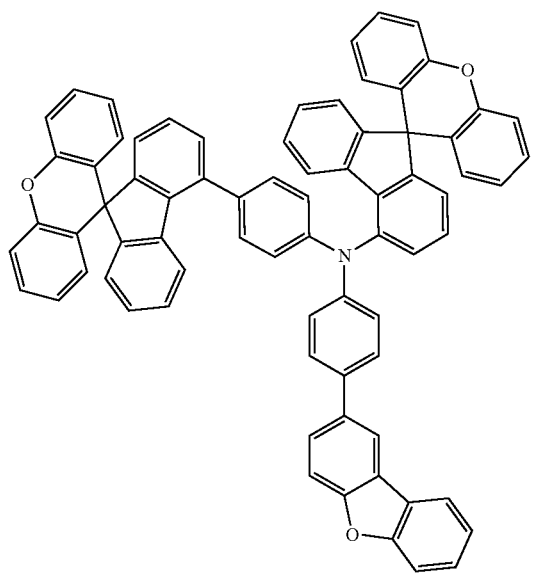
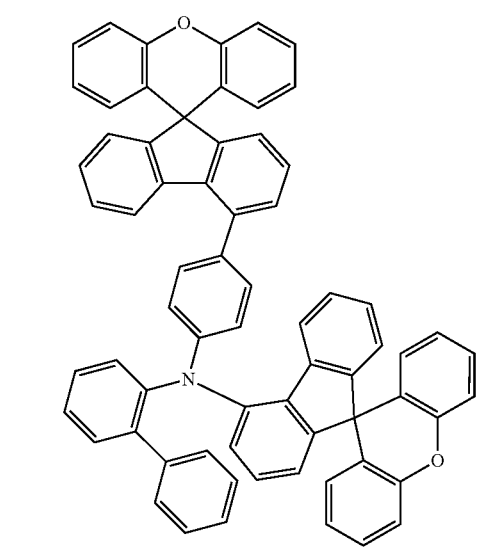
360
-continued
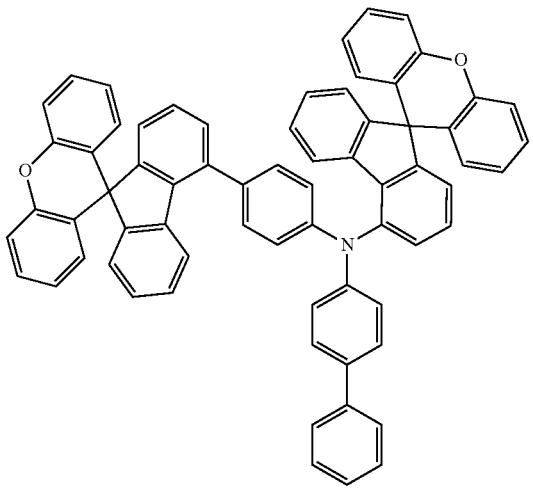
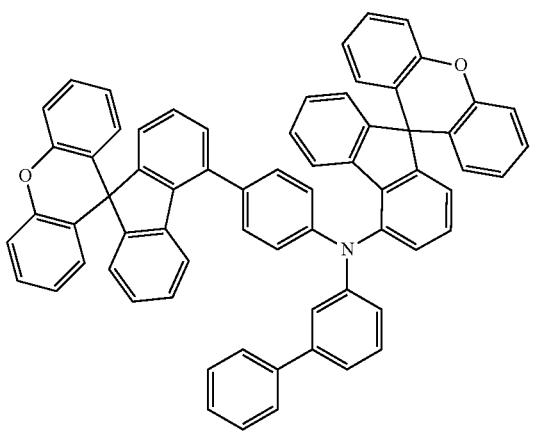
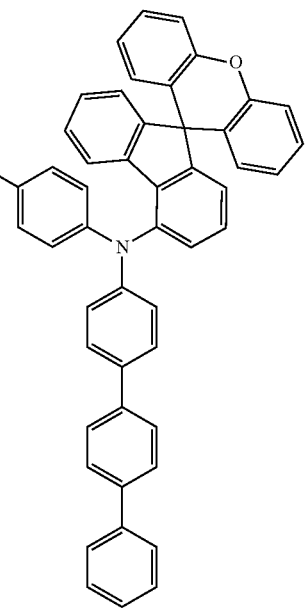

361
-continued
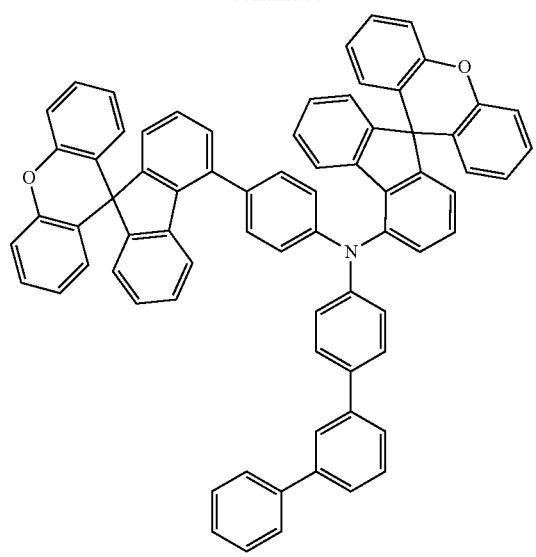
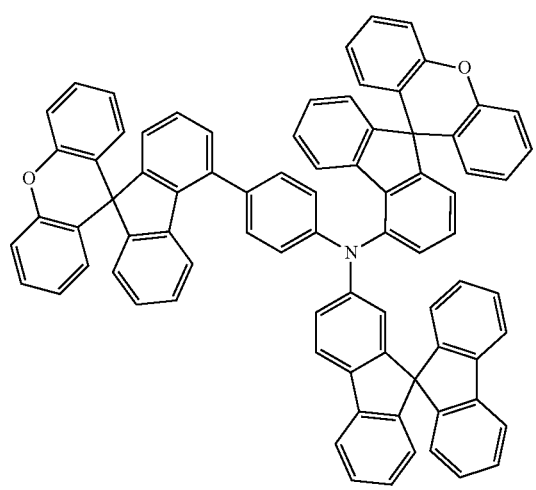
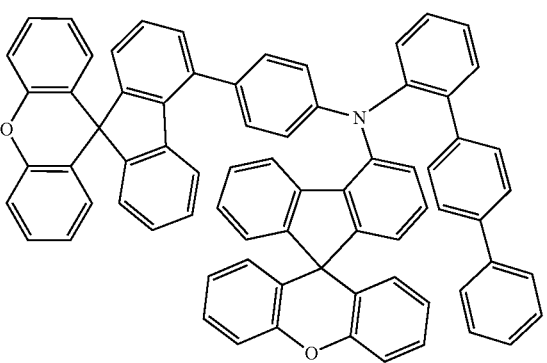
362
-continued
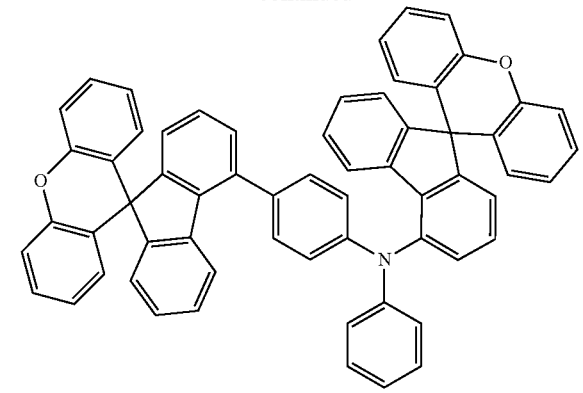
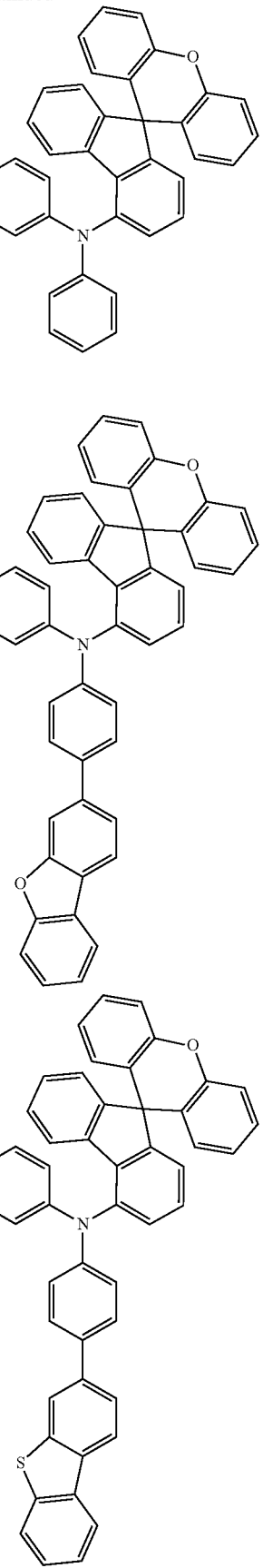

363
-continued
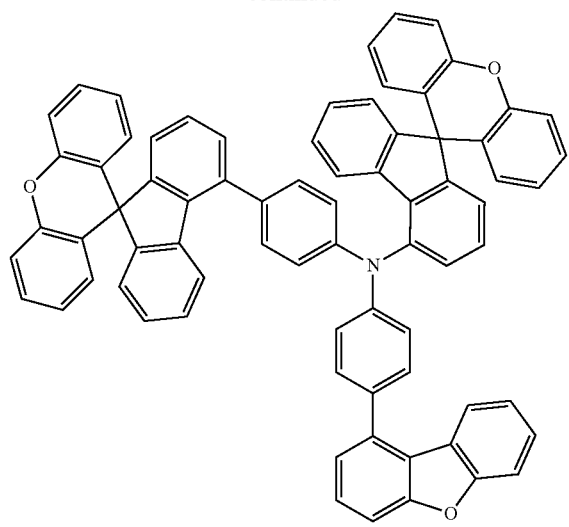
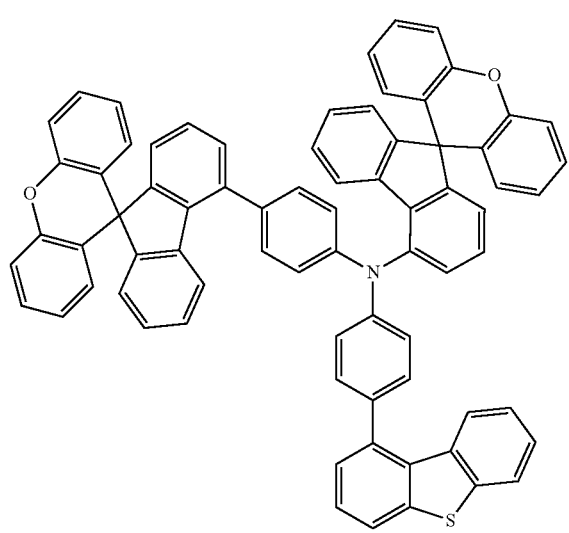
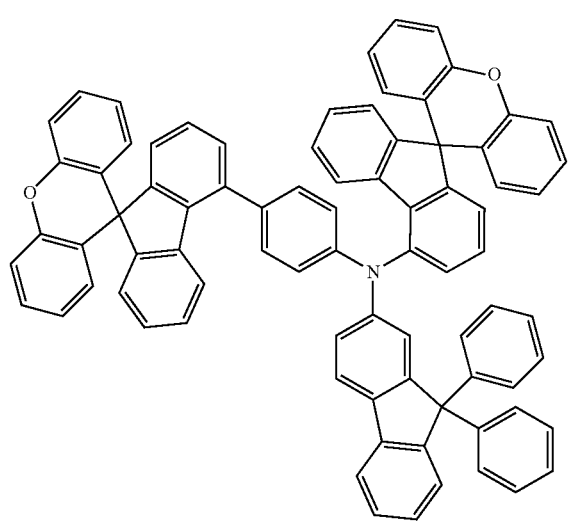
364
-continued
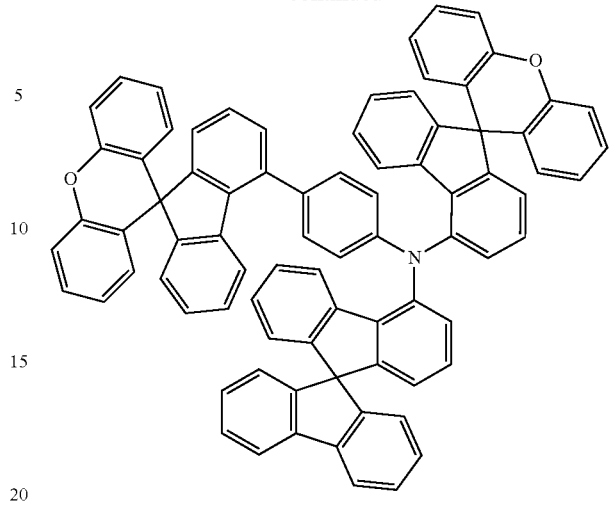
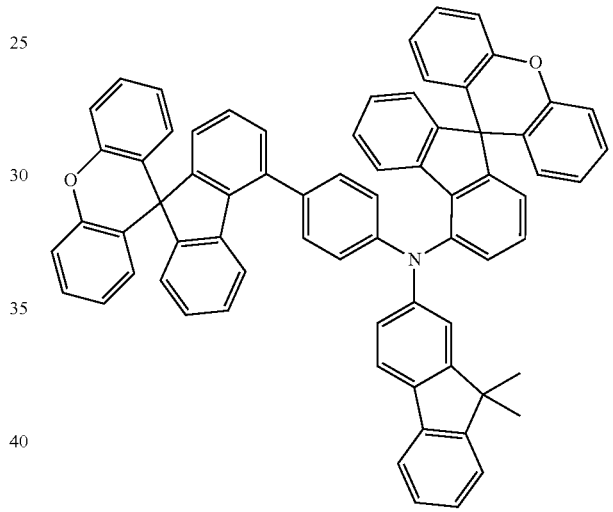
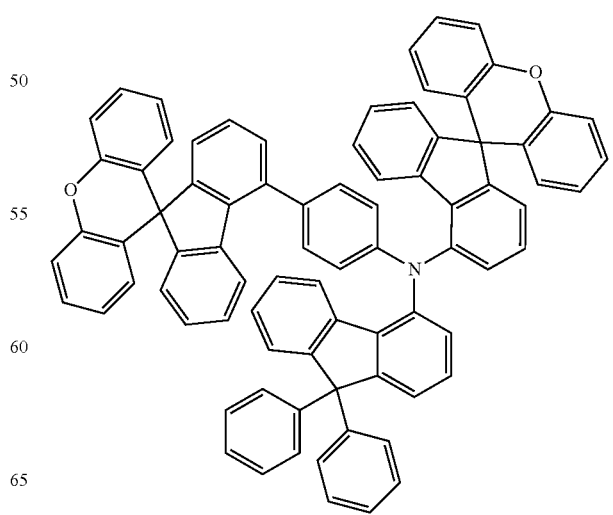

365
-continued

366
-continued

367
-continued
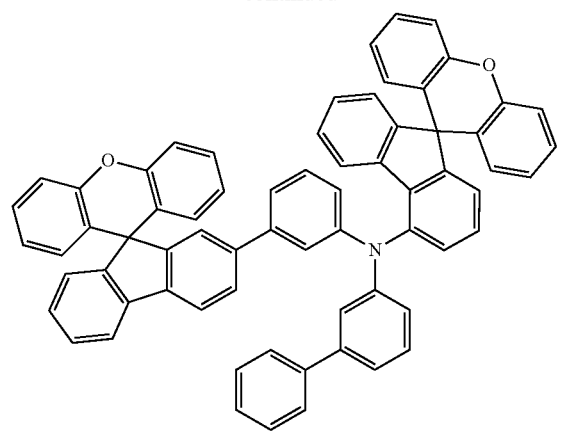
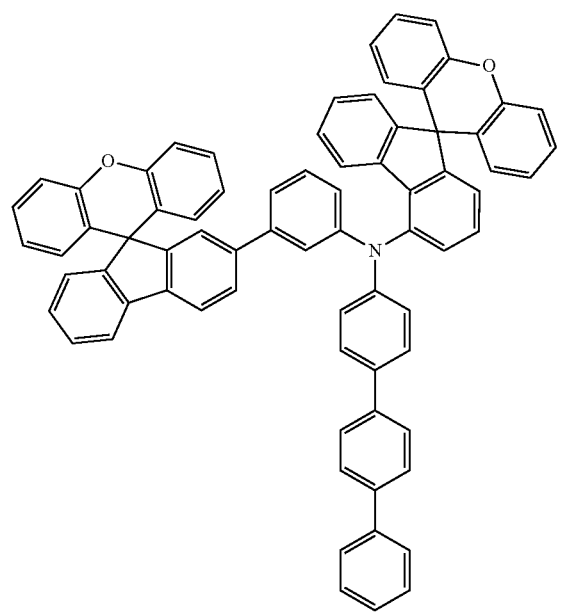
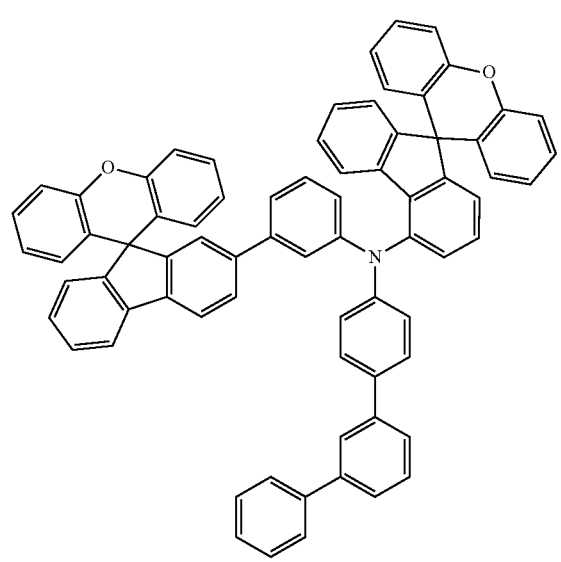
368
-continued
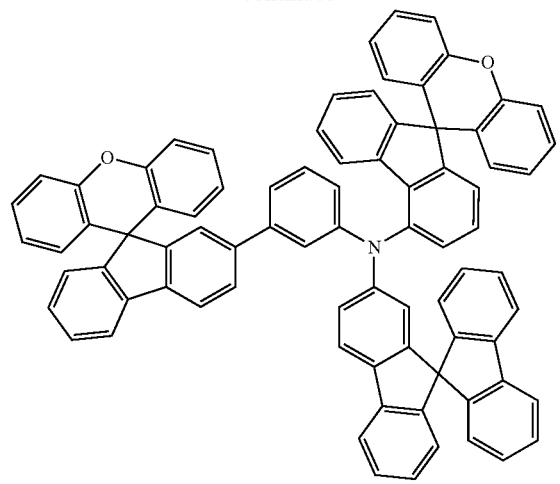
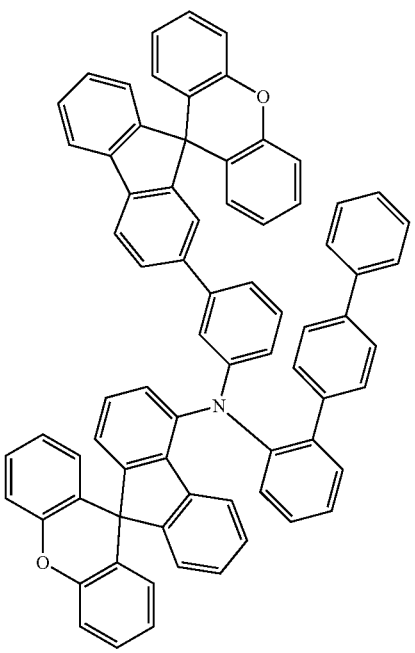
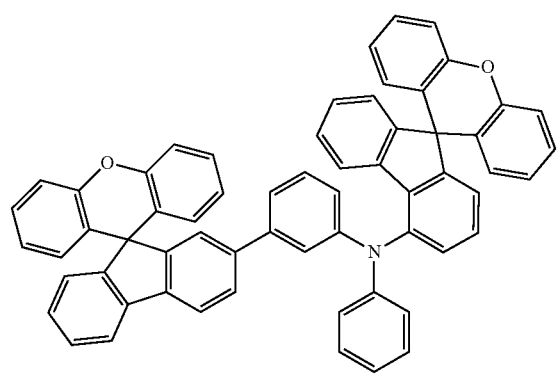

369 -continued
370 -continued
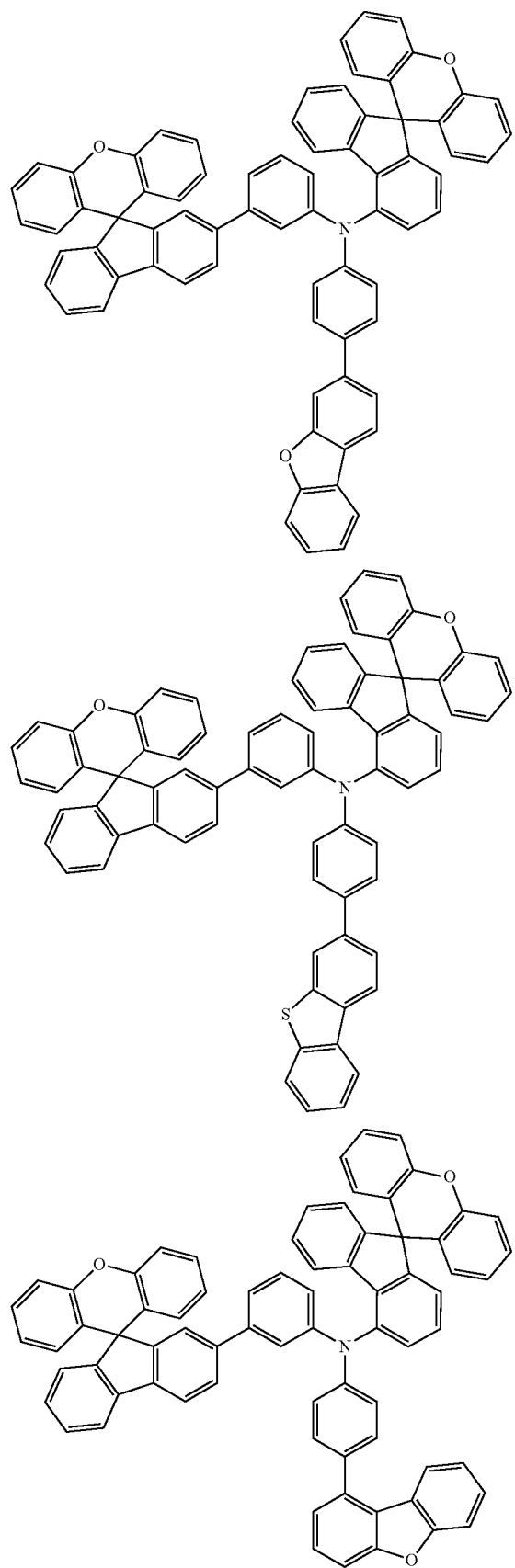
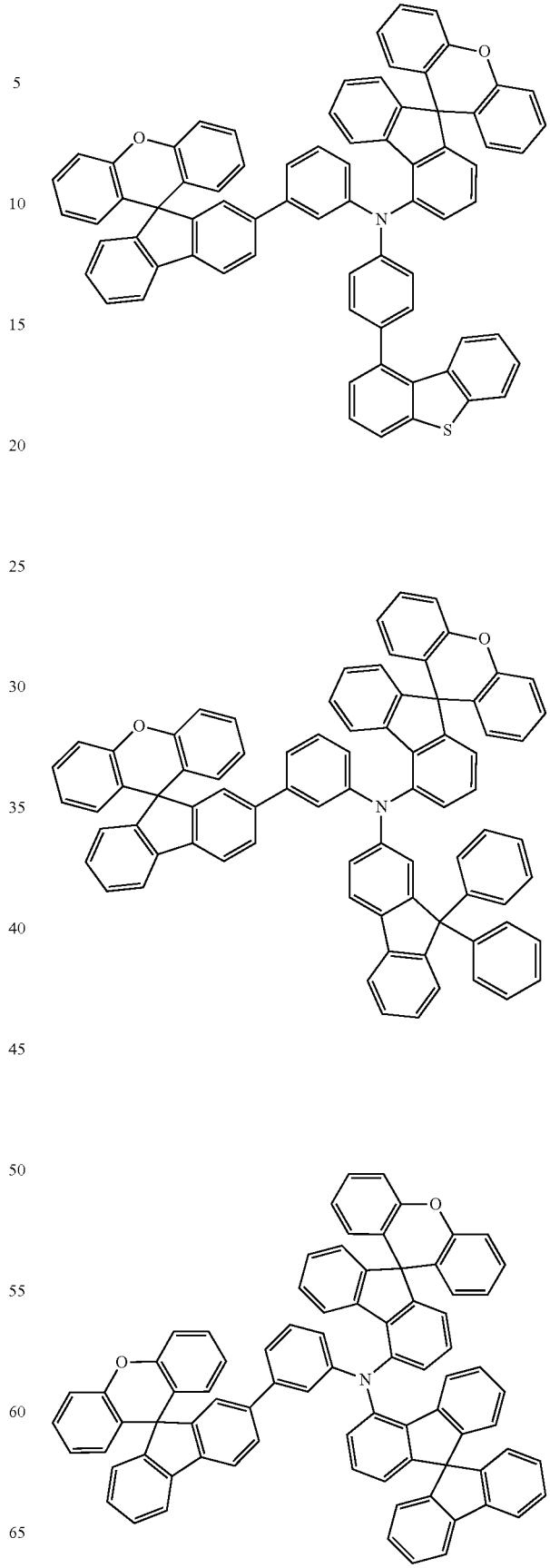

371
-continued
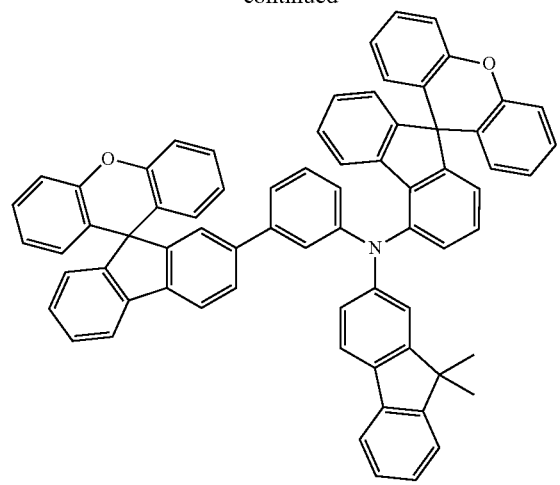
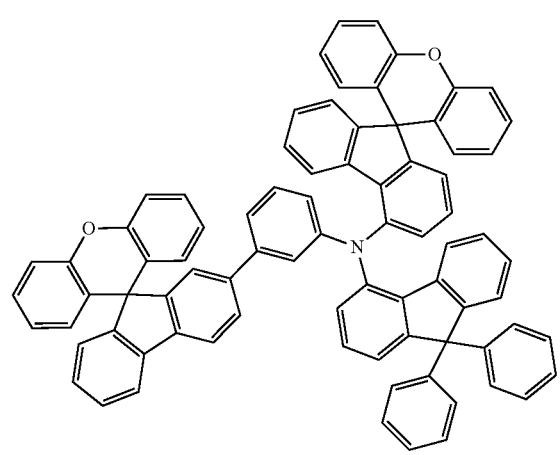
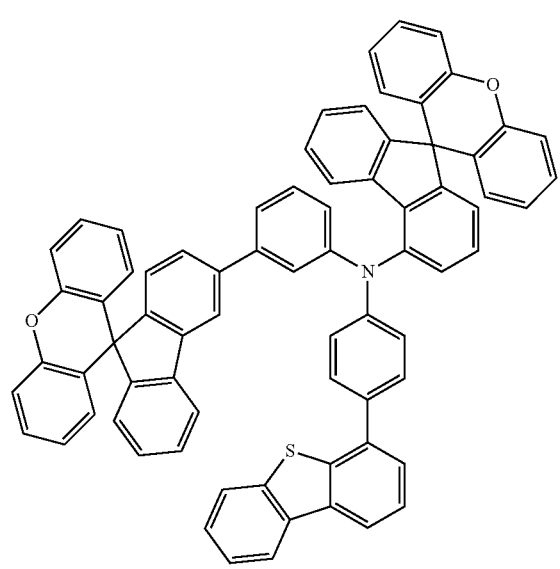
372
-continued
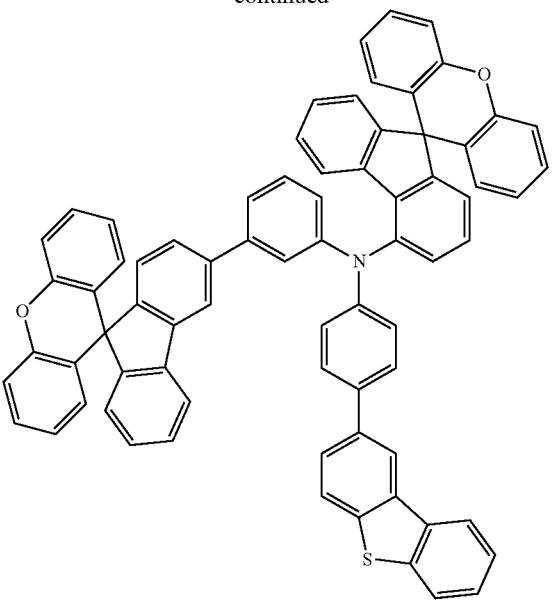
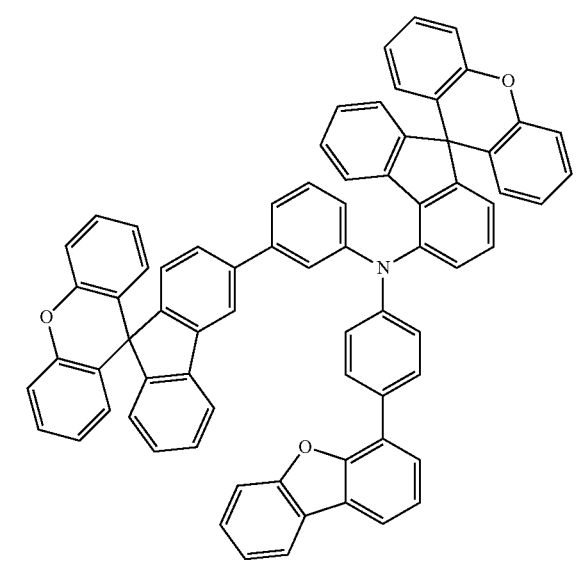

373
-continued
374
-continued
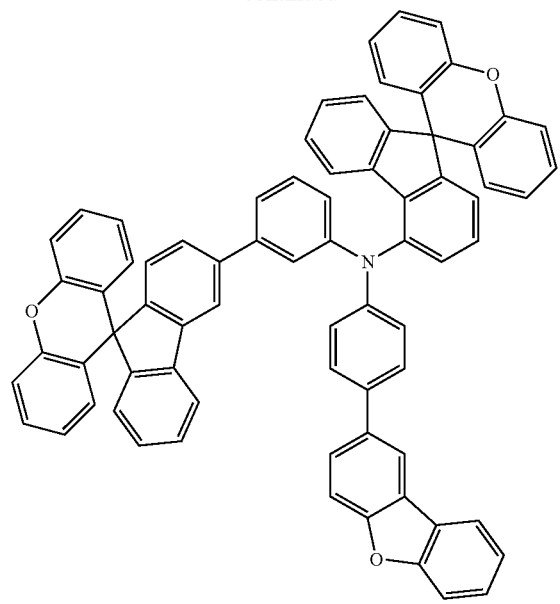
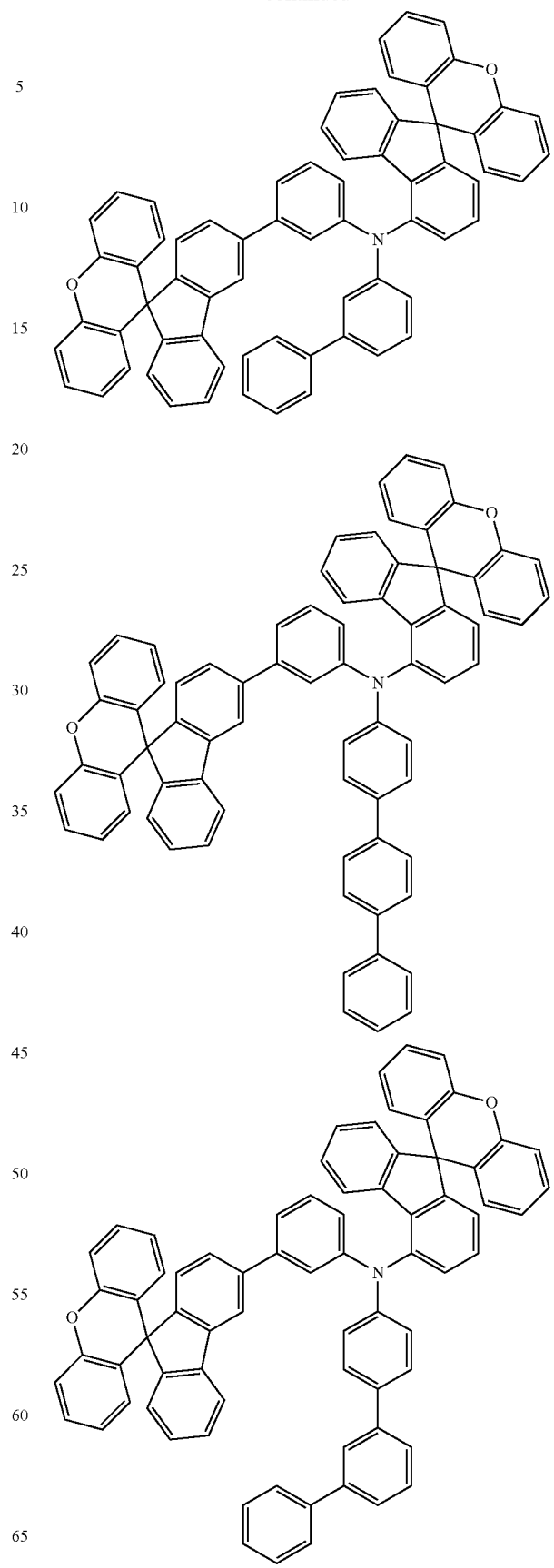

375
-continued
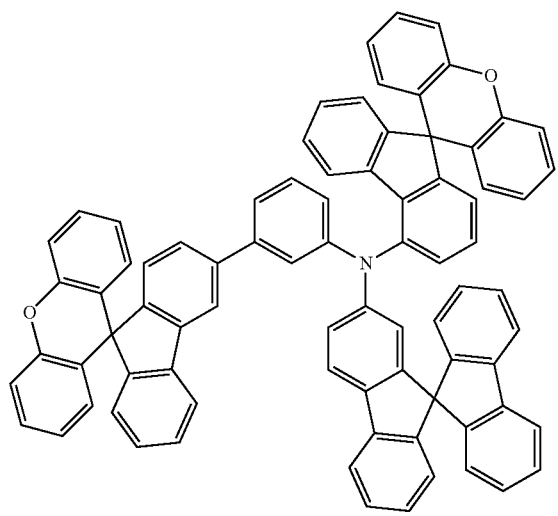
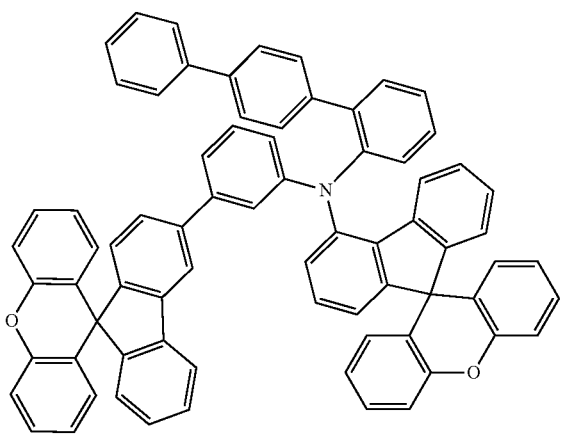
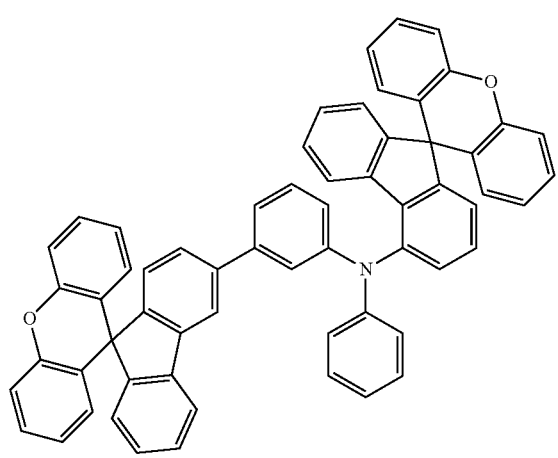
376
-continued
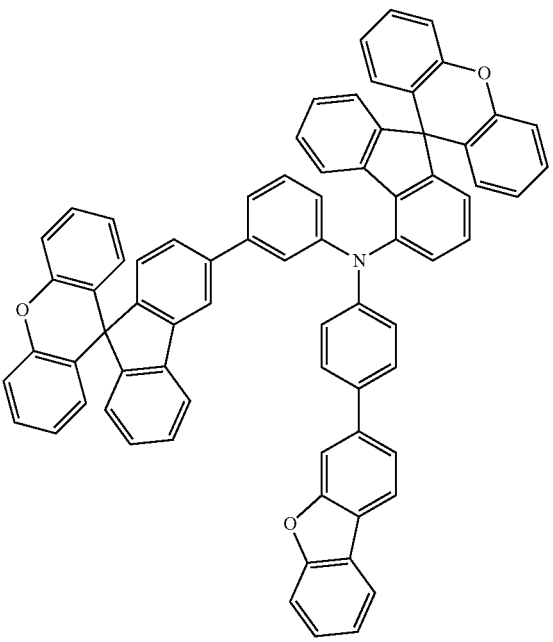
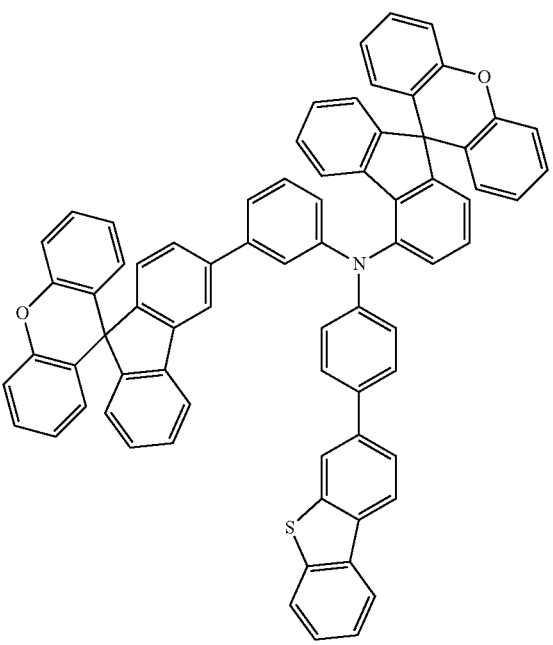

377
-continued
378
-continued
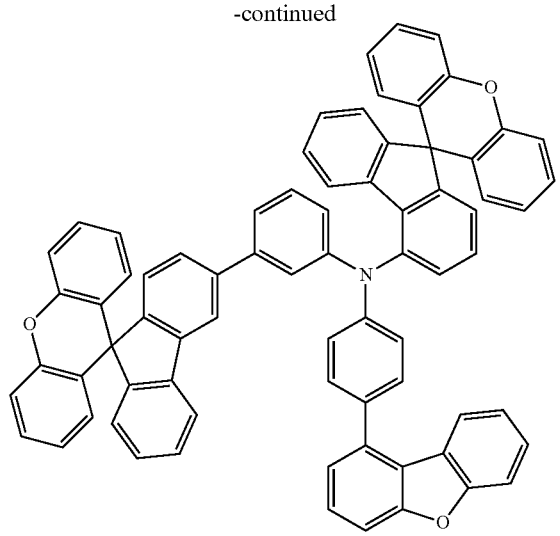
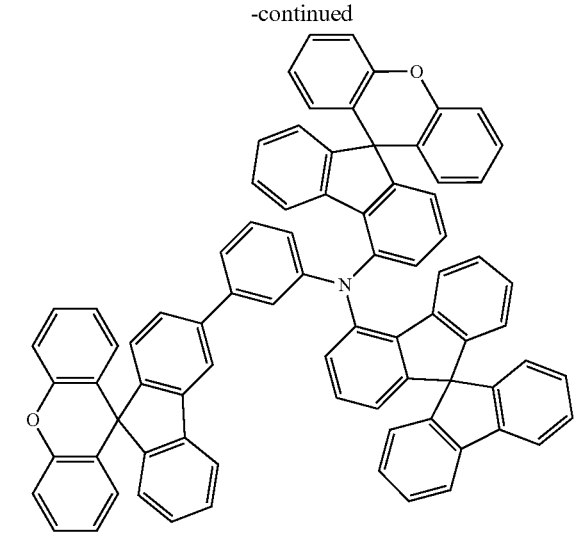
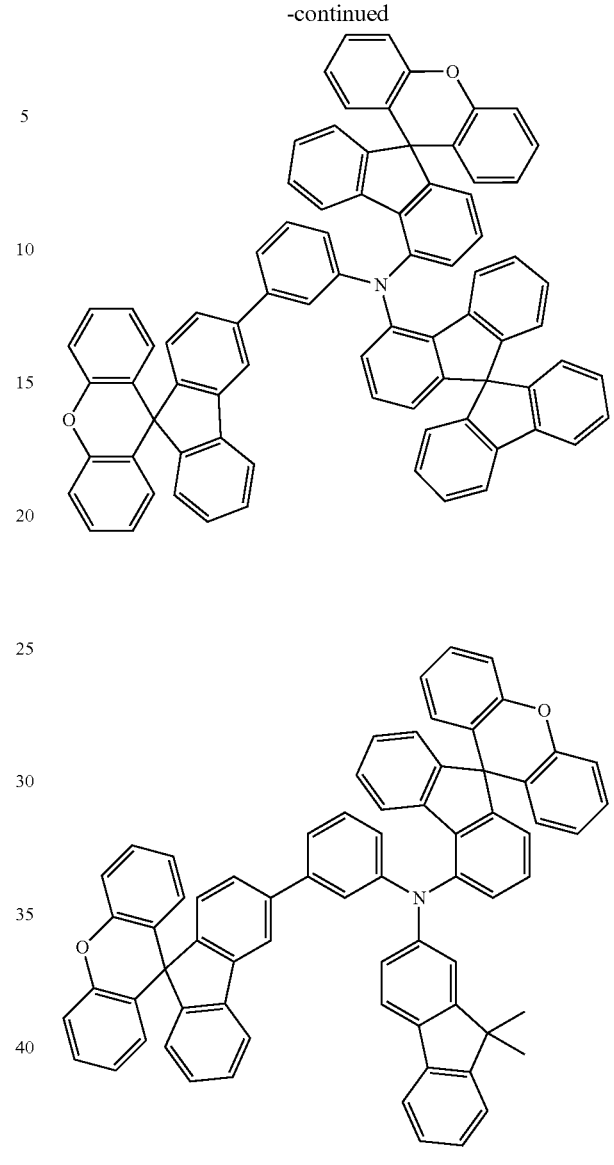
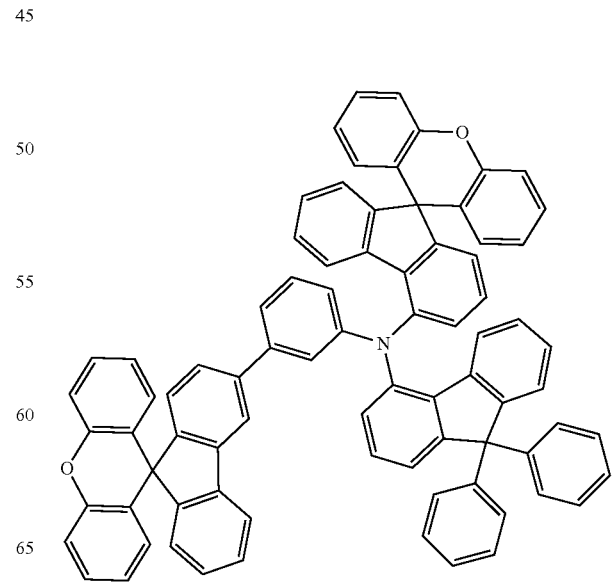

379
-continued
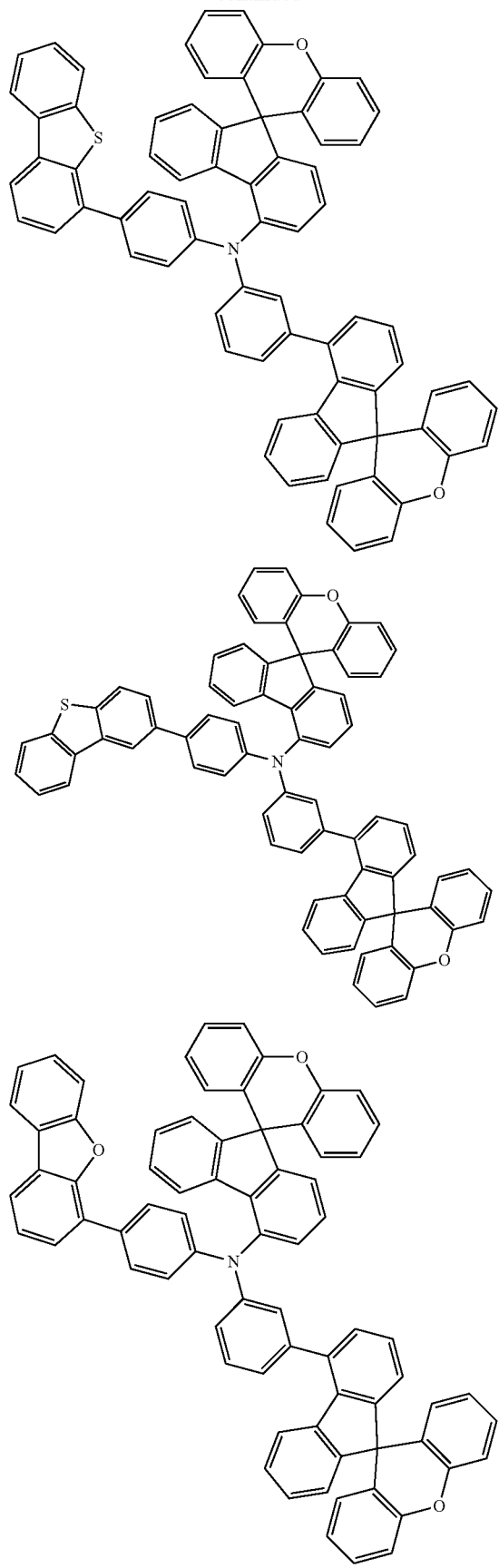
380
-continued
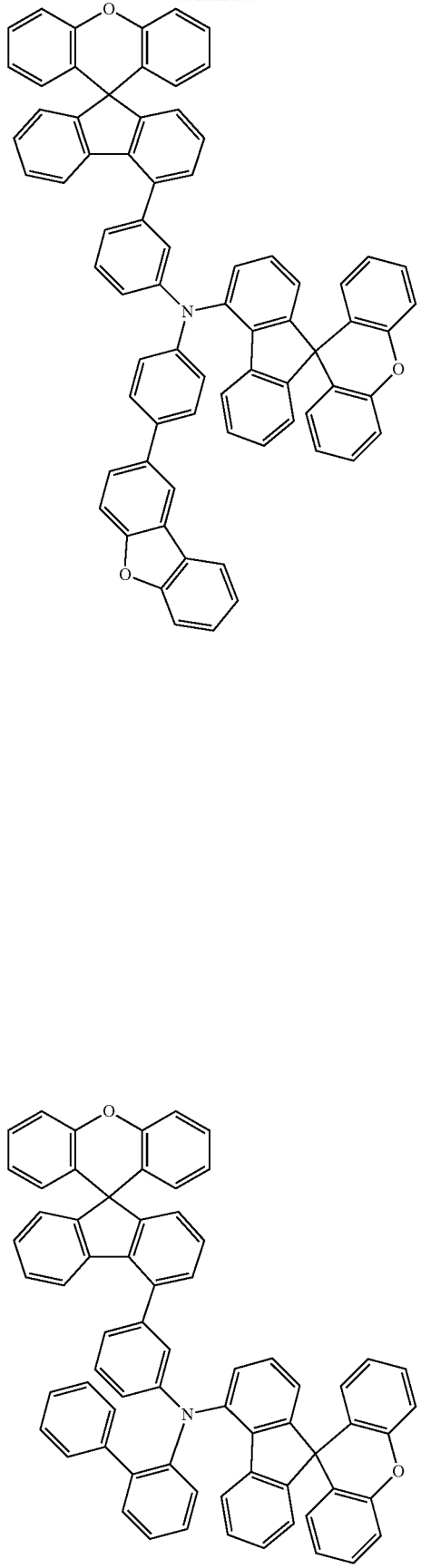

381
-continued
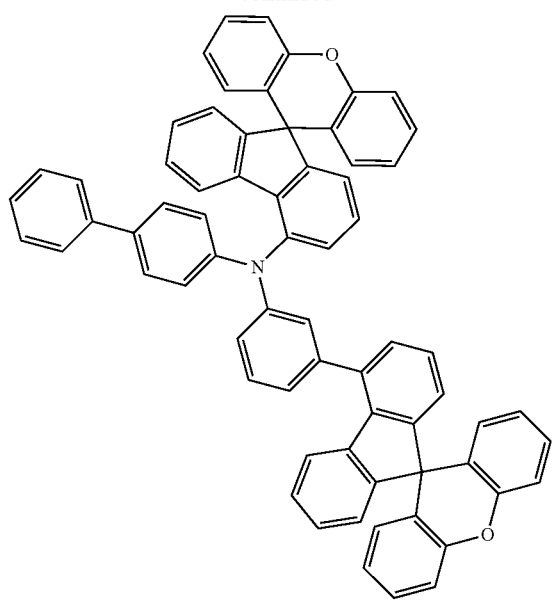
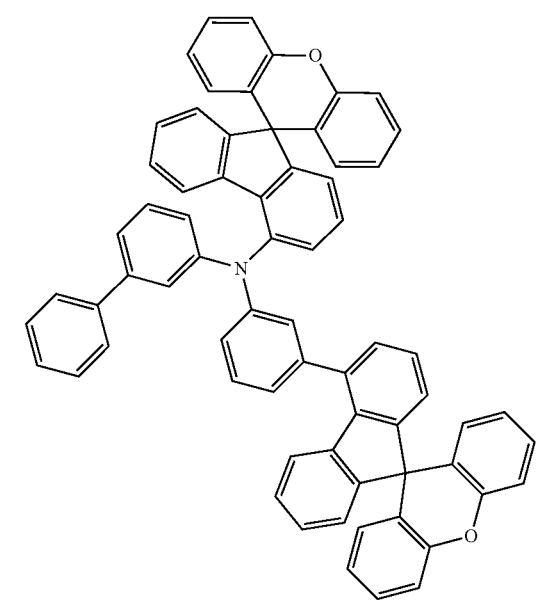
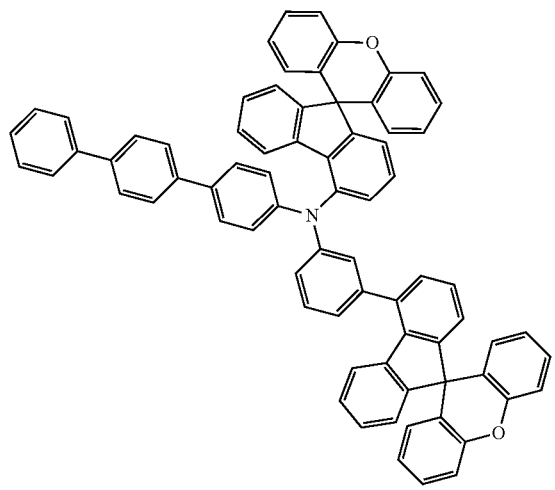
382
-continued
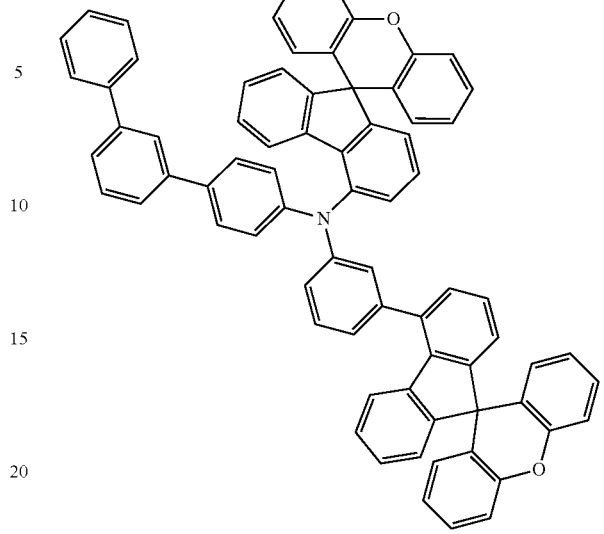
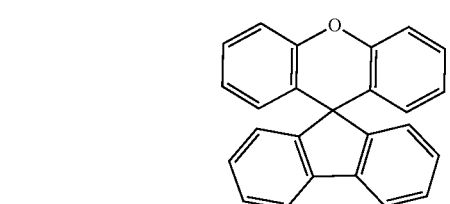
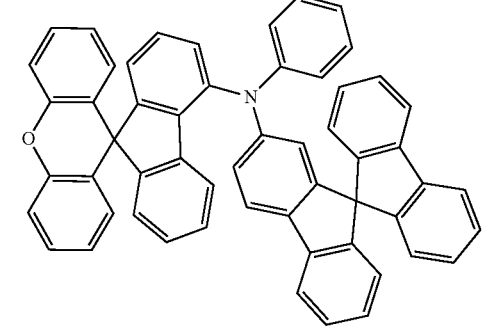
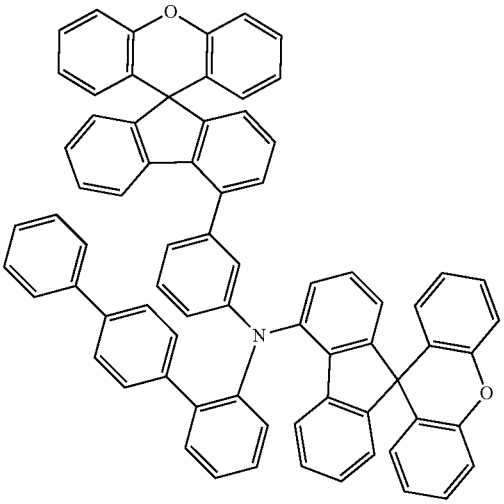

383
-continued
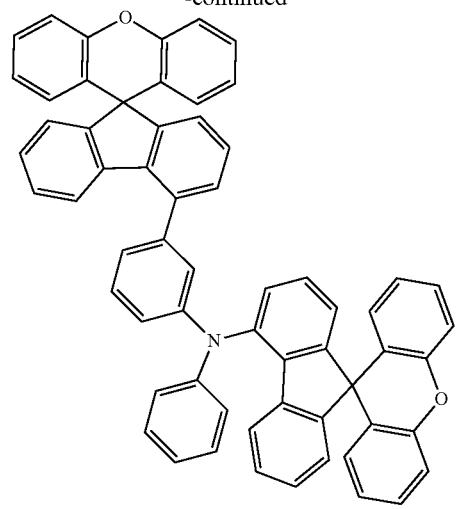
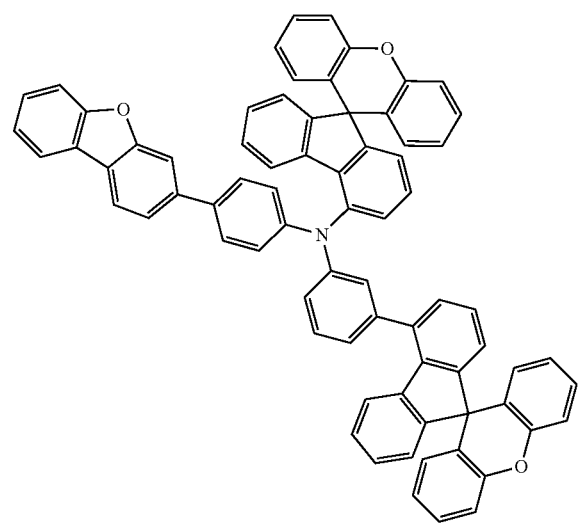
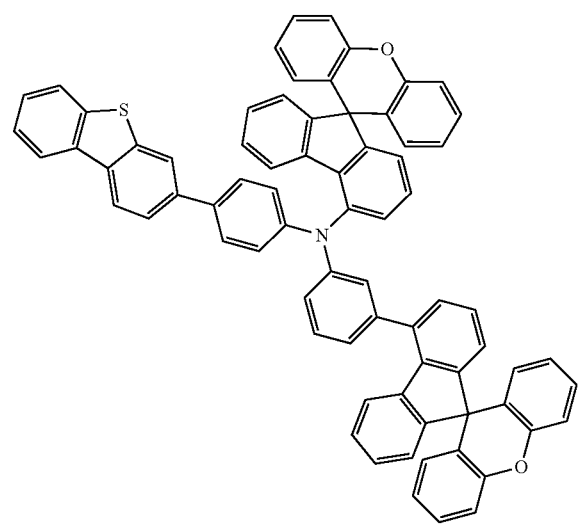
384
-continued
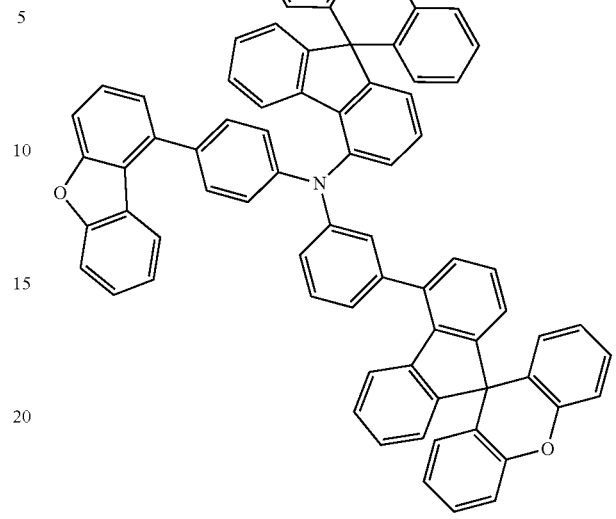
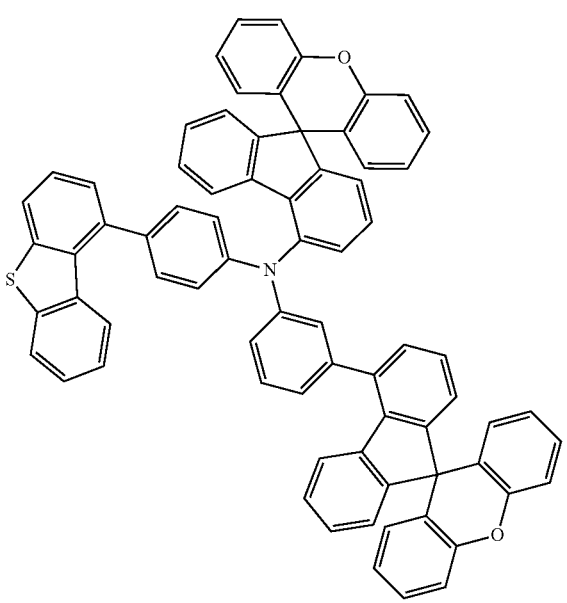

385
-continued
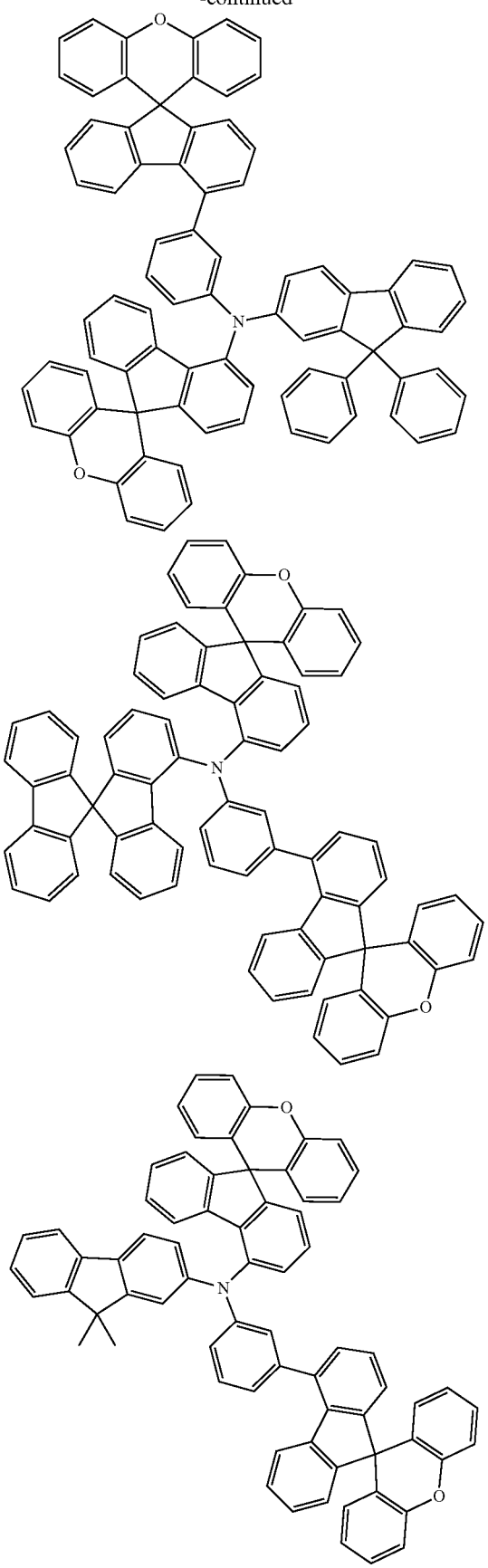
386
-continued
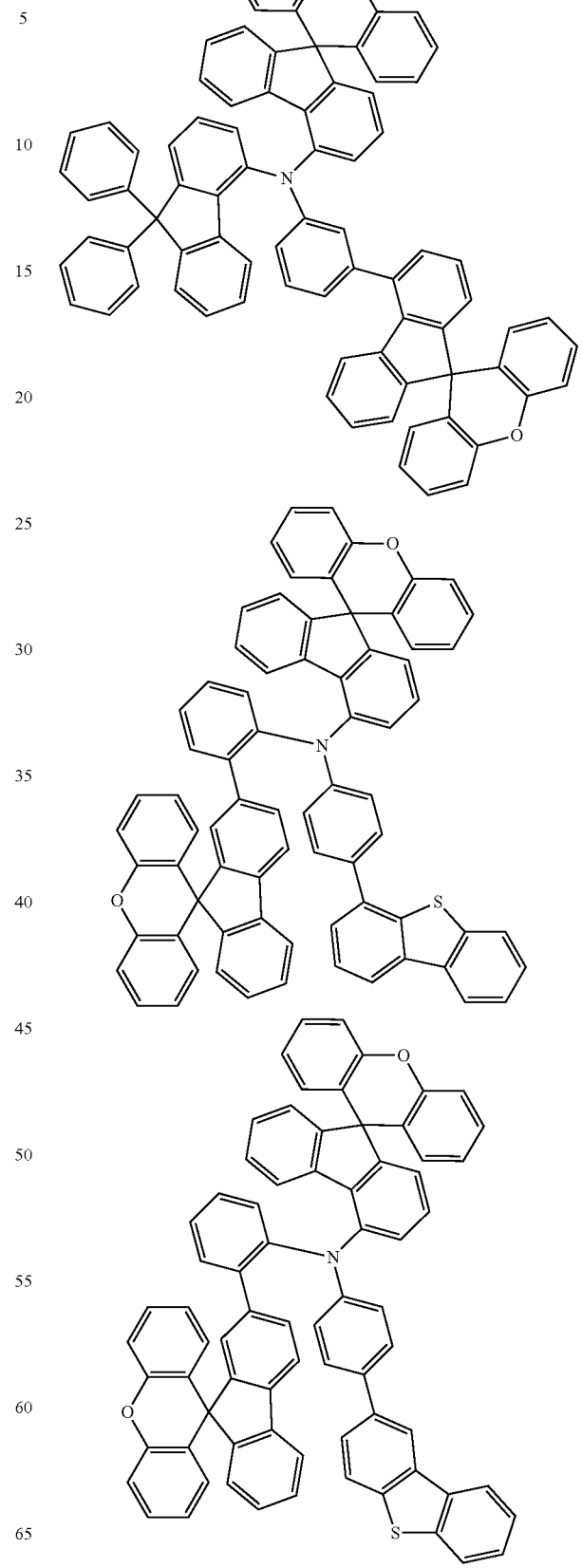

387
-continued
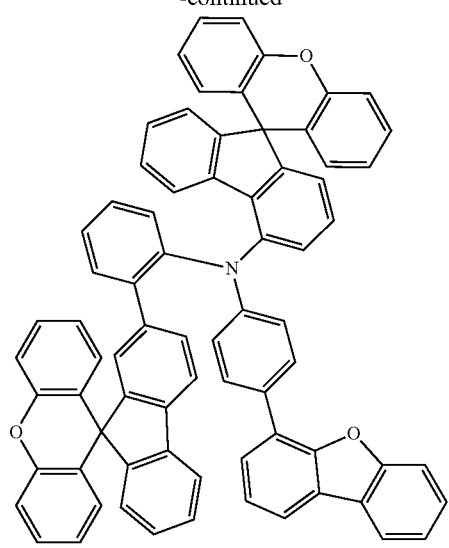
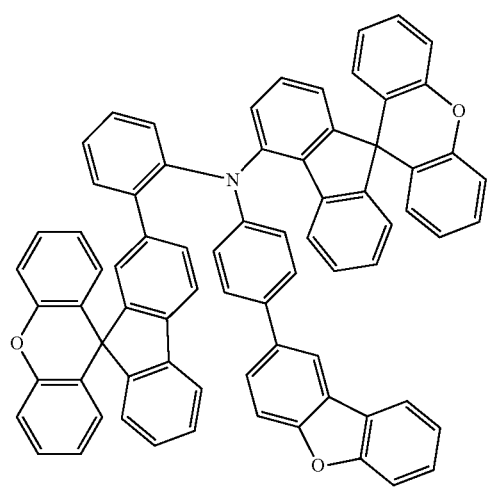
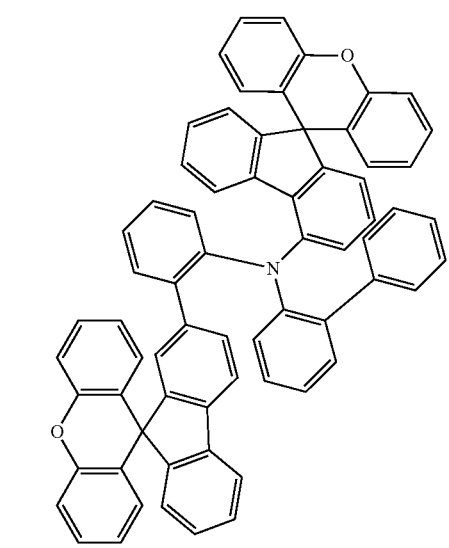
388
-continued
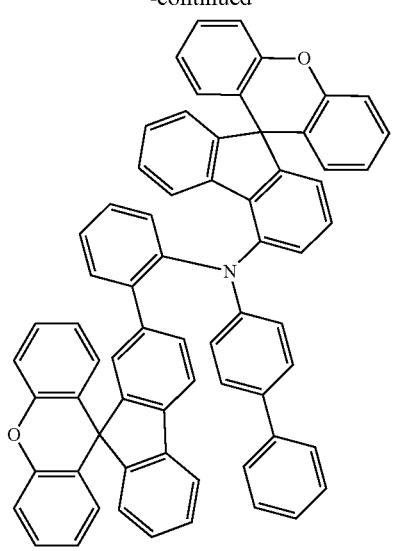
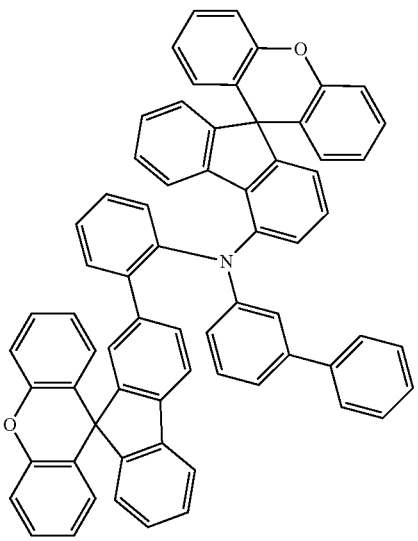
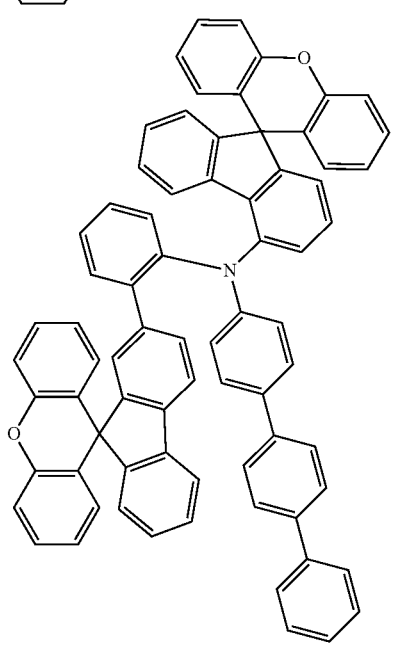

389
-continued
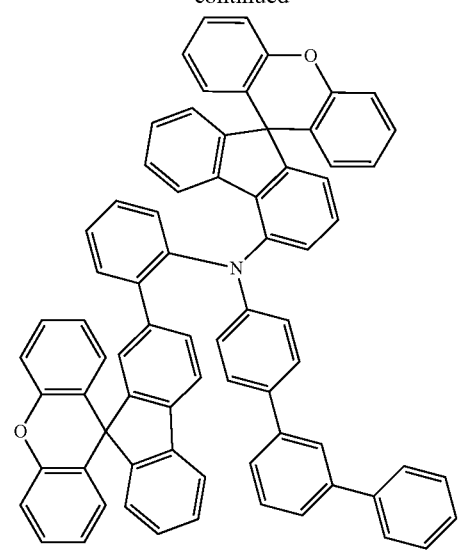
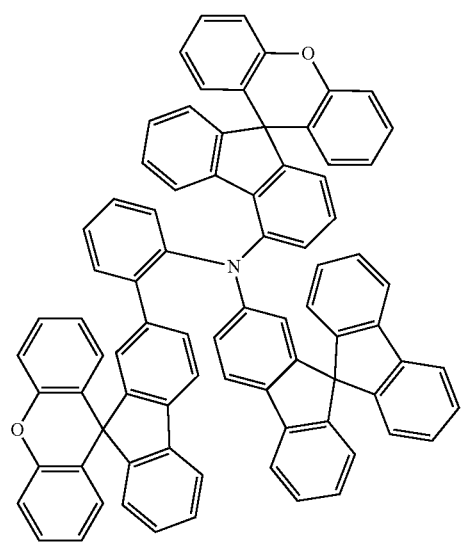
390
-continued
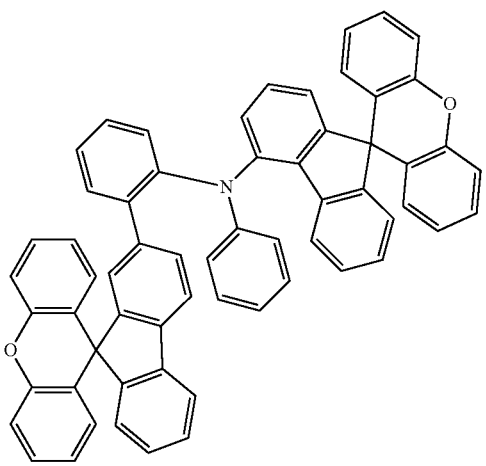
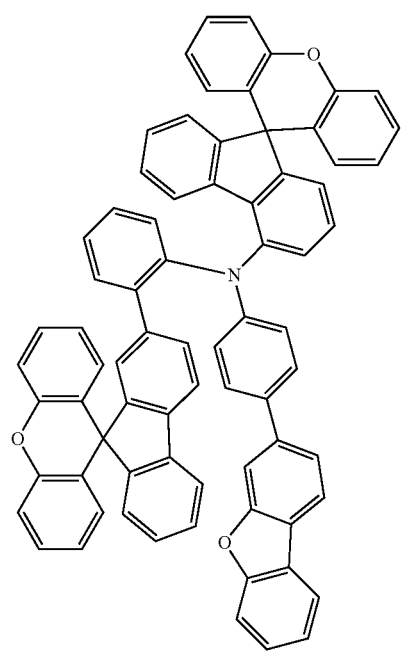

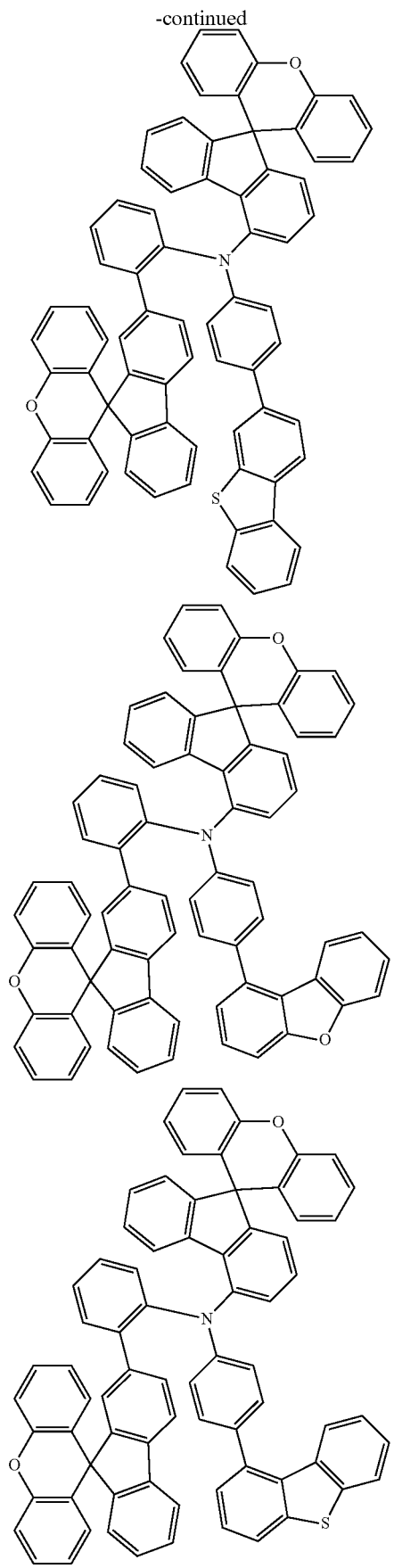

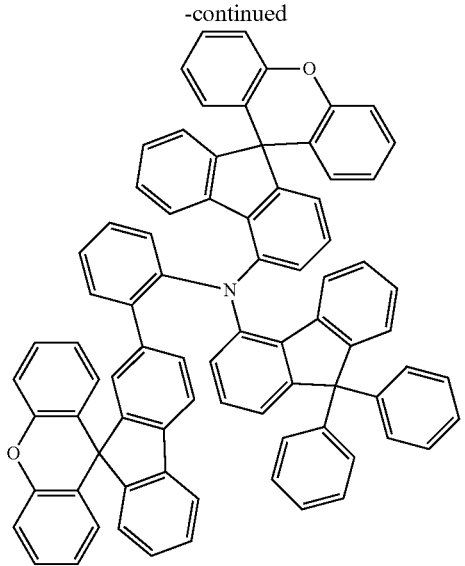
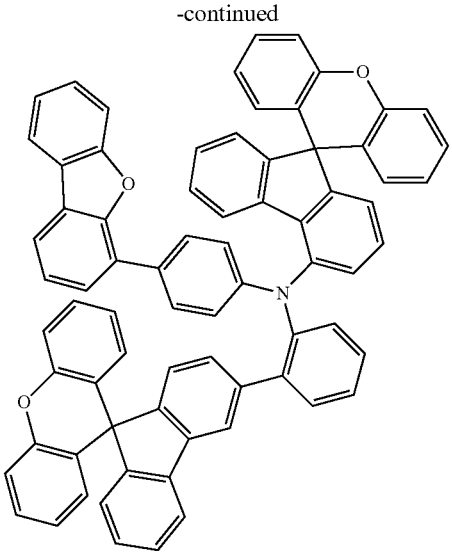
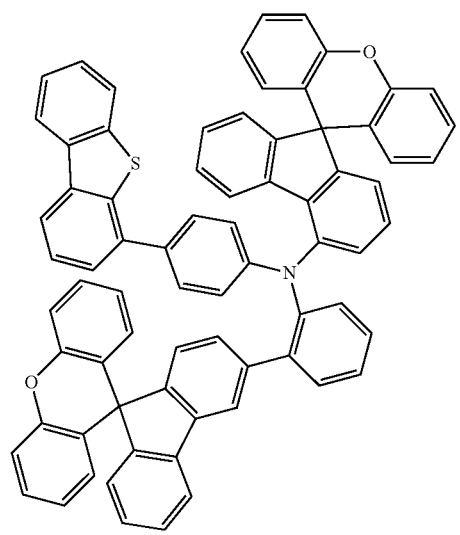
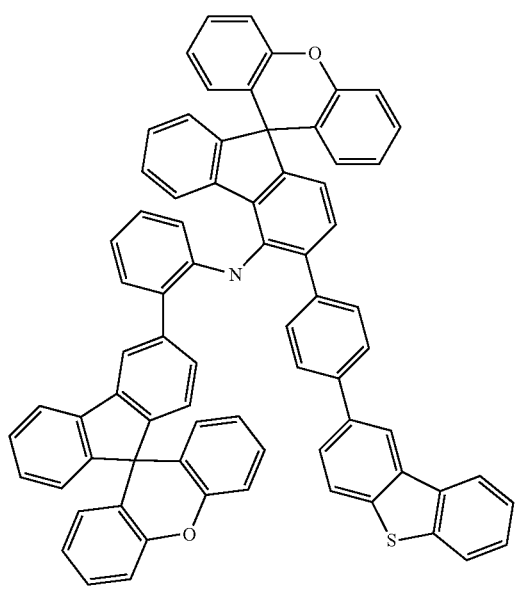
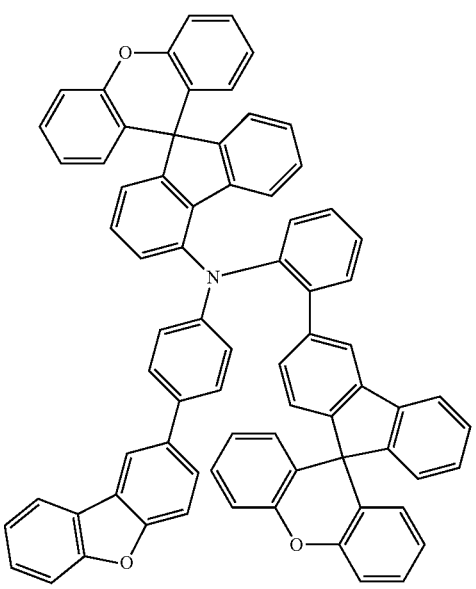

395
-continued
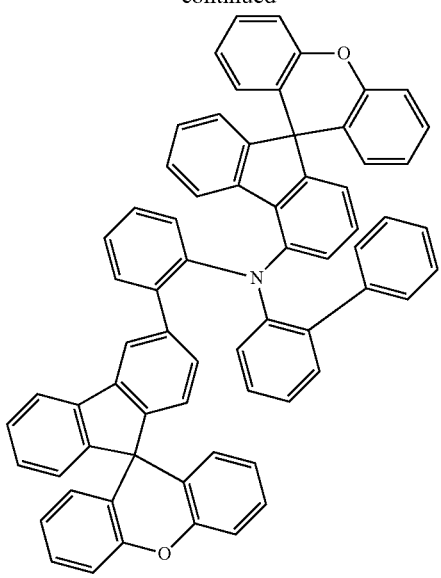
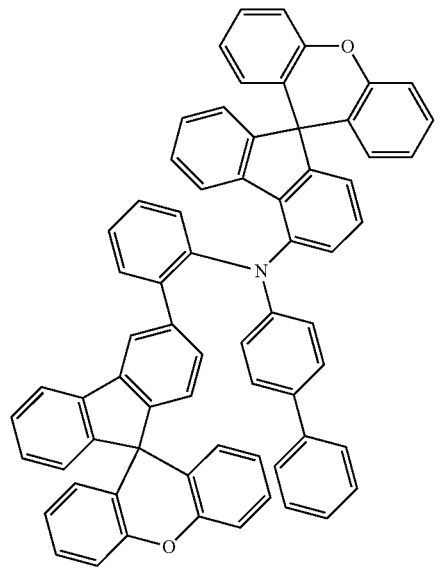
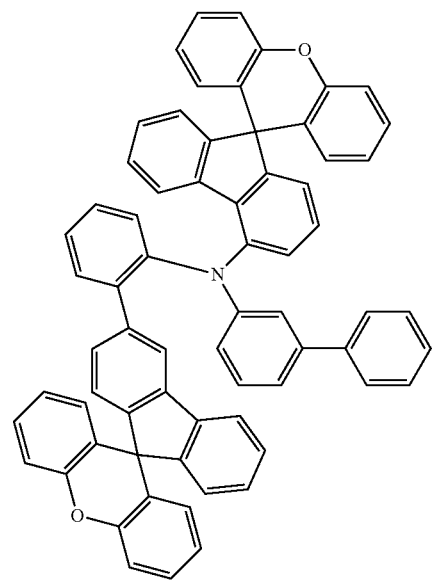
396
-continued
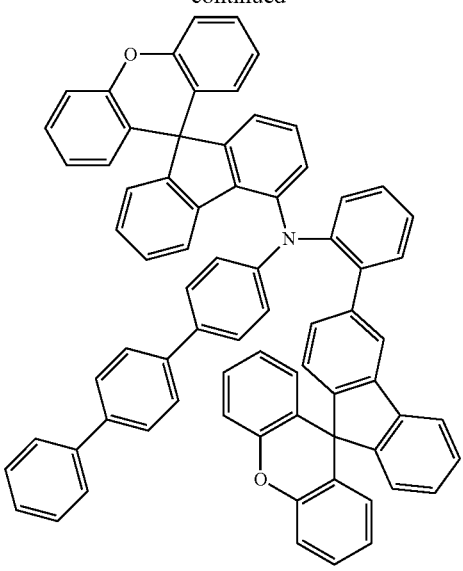
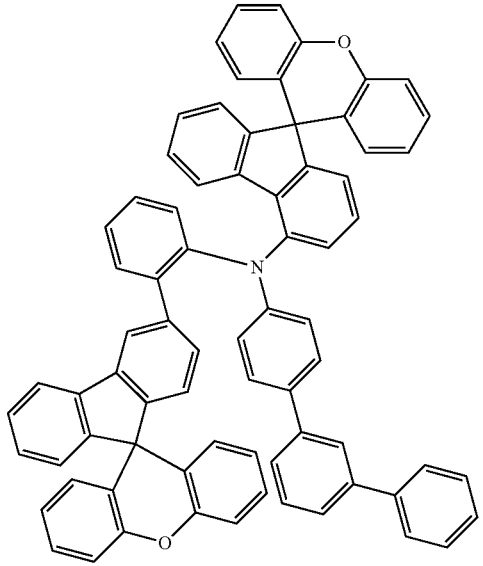
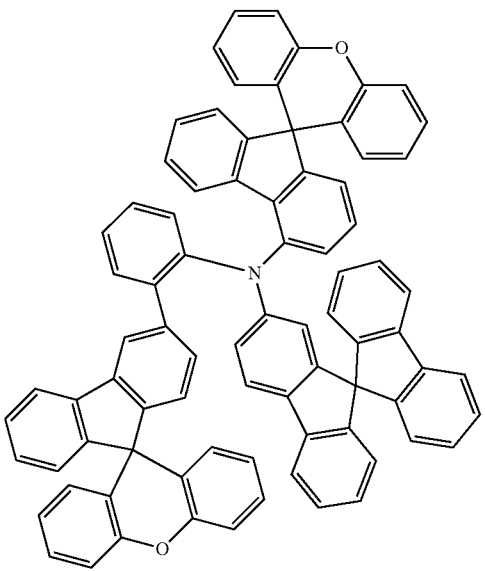

397
-continued
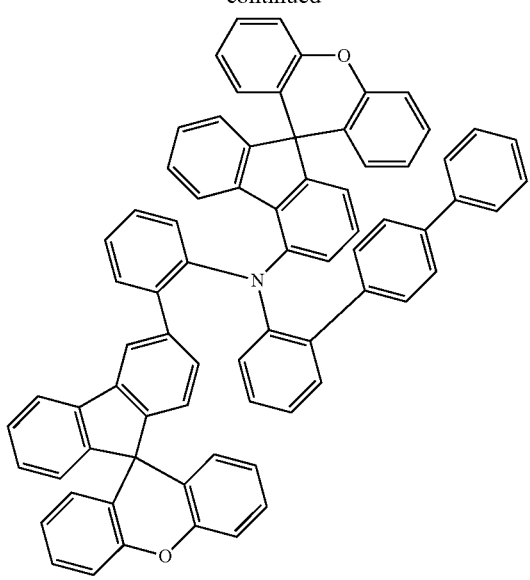
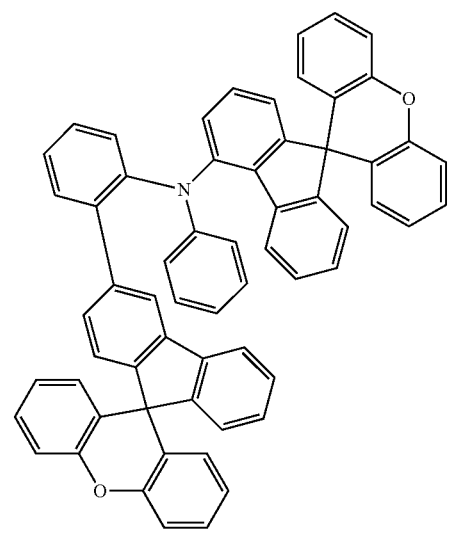
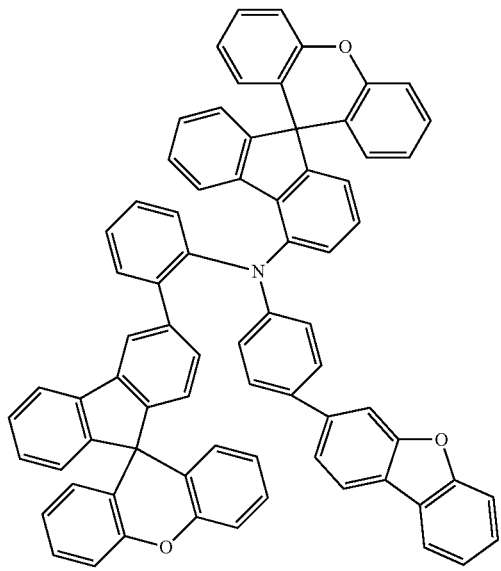
398
-continued
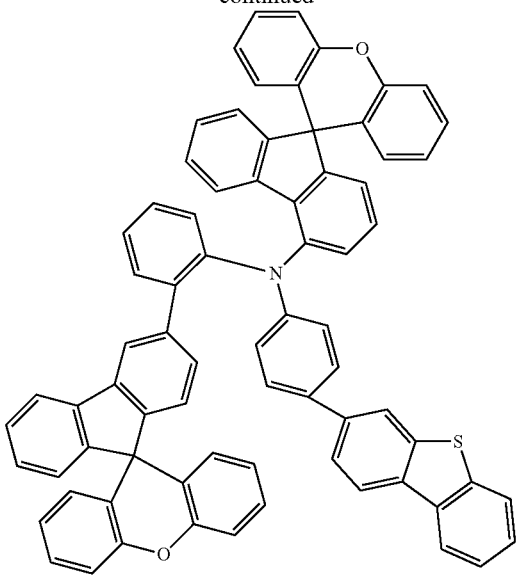
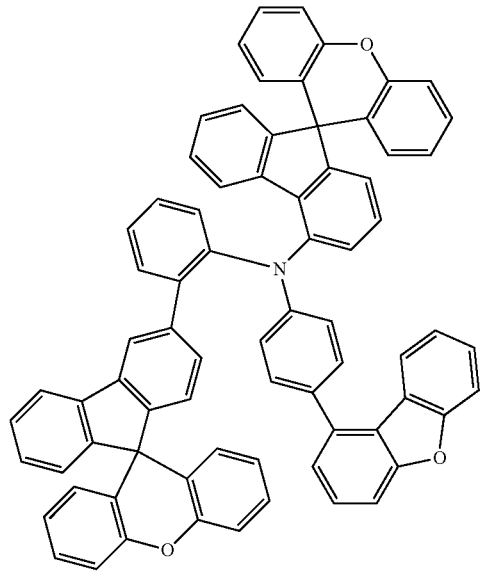
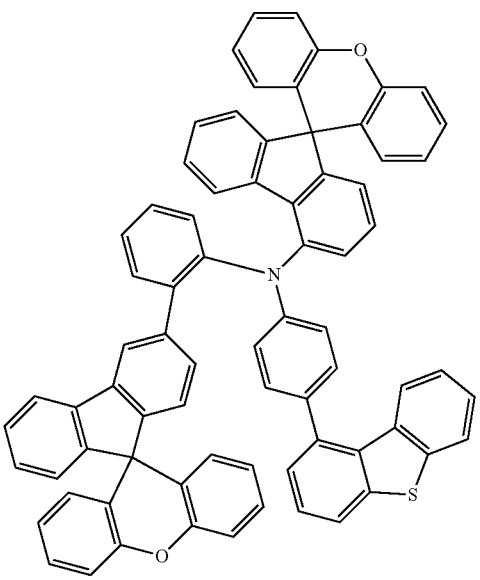

399
-continued
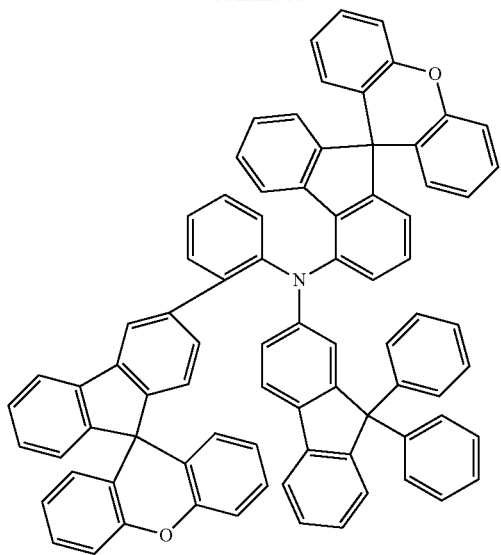
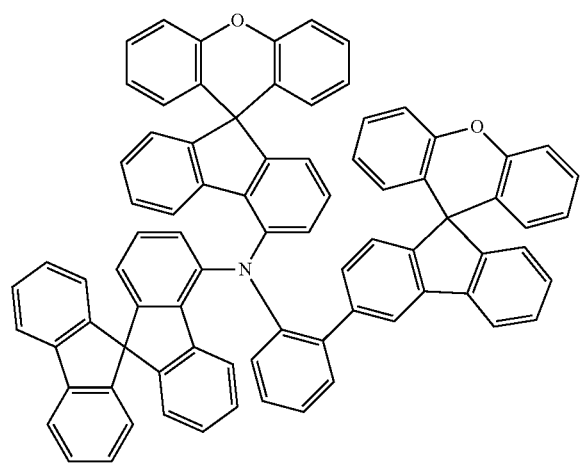
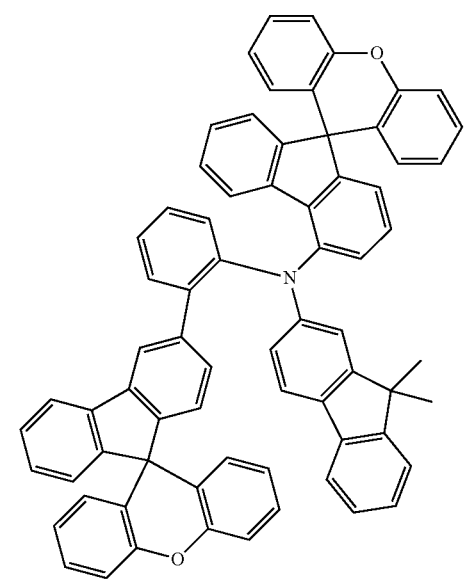
400
-continued
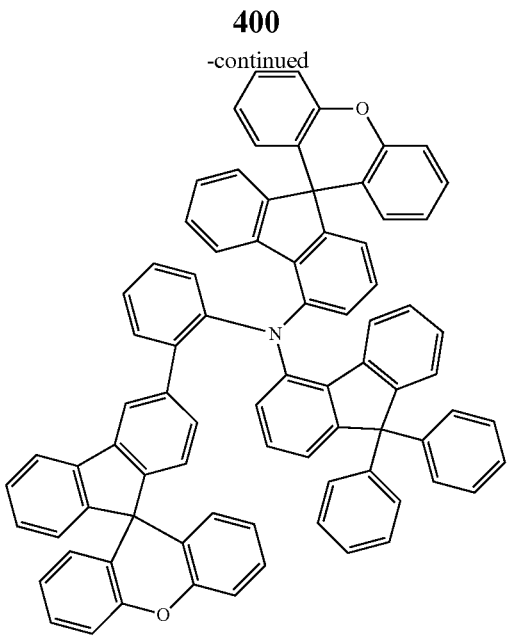
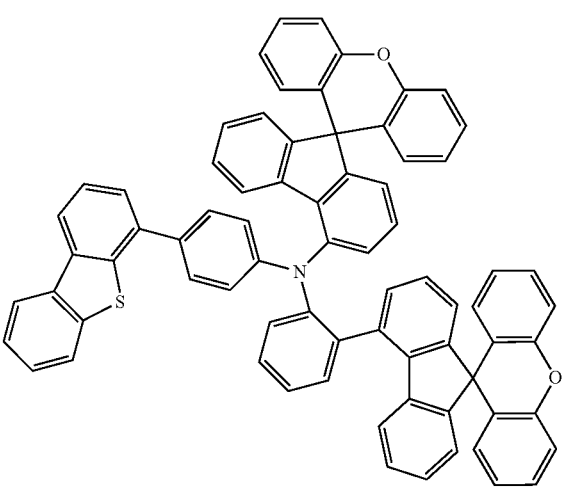
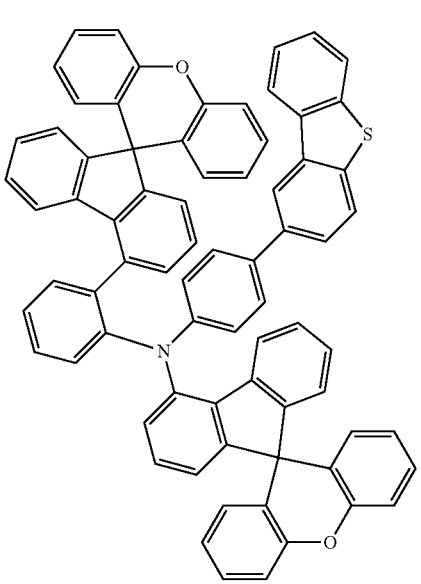

401
-continued
402
-continued
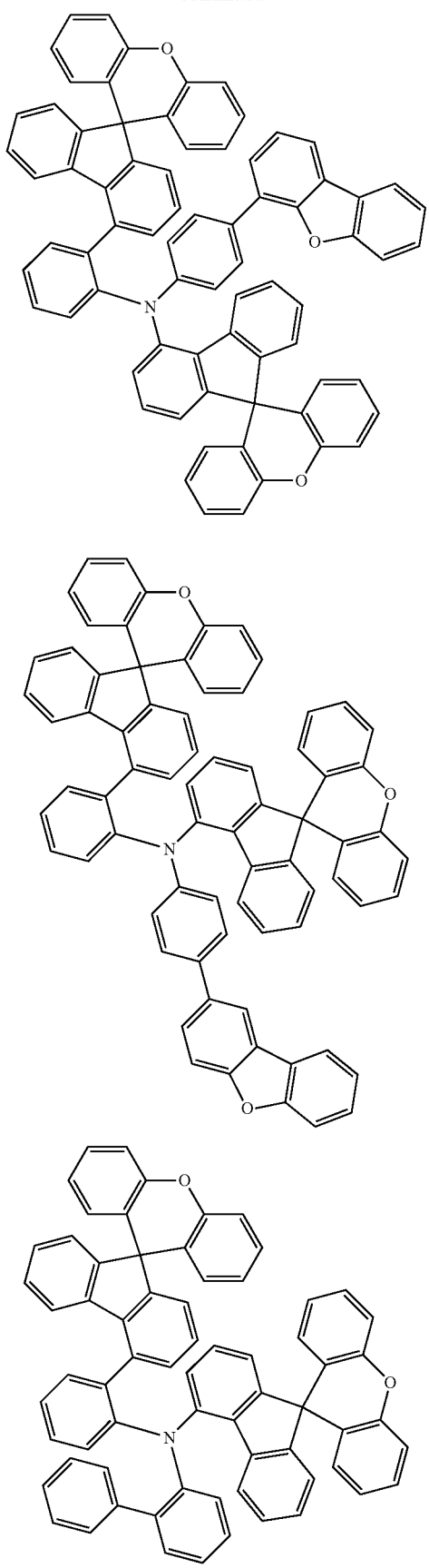
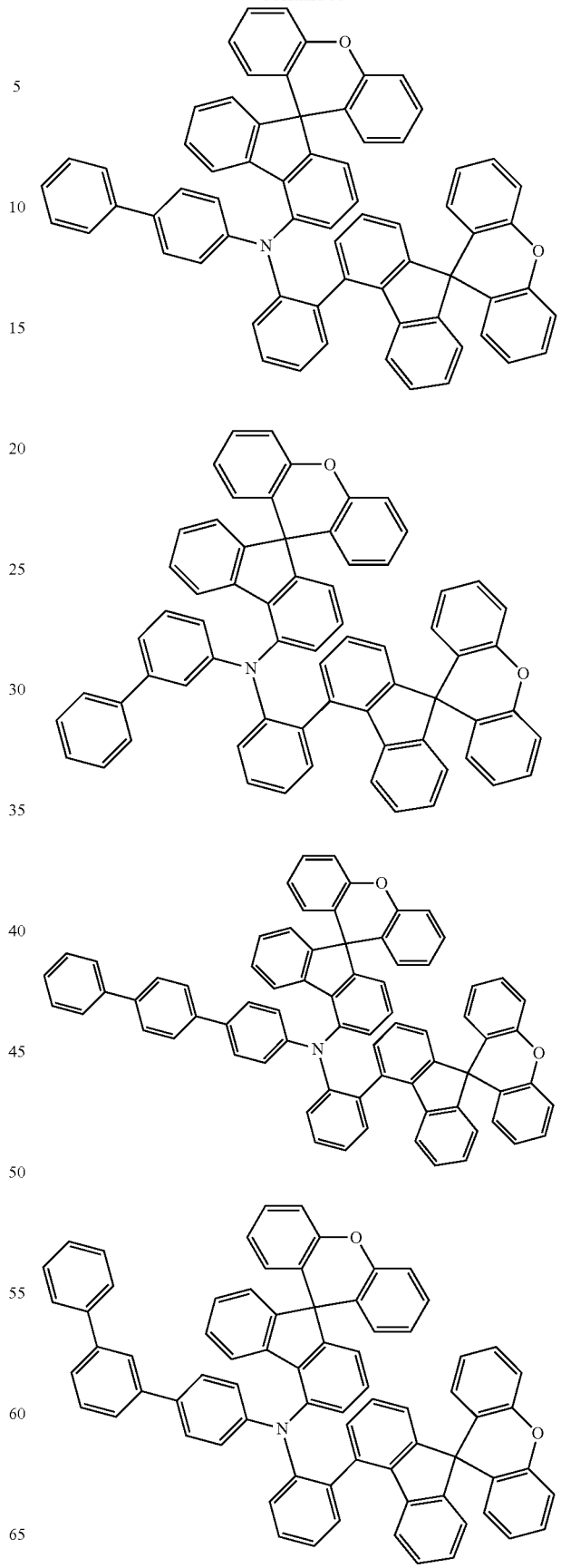

403
-continued
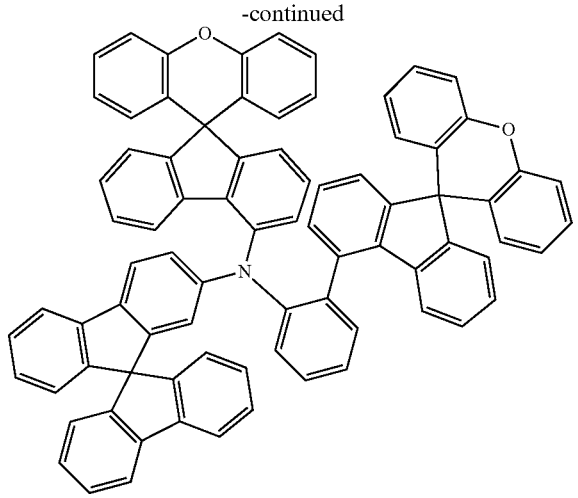
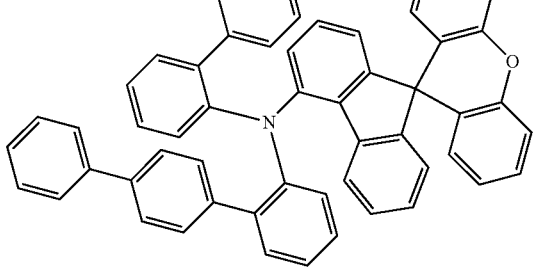
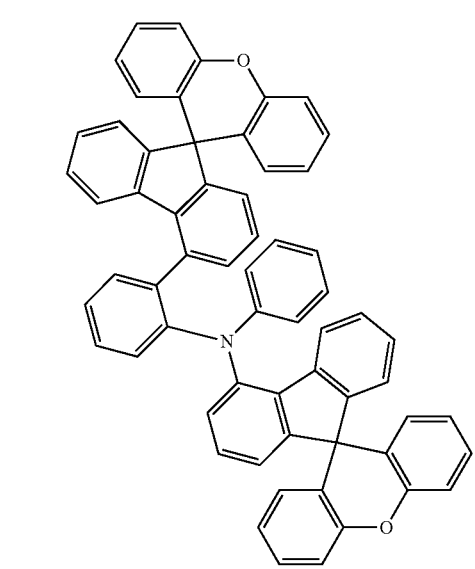
404
-continued
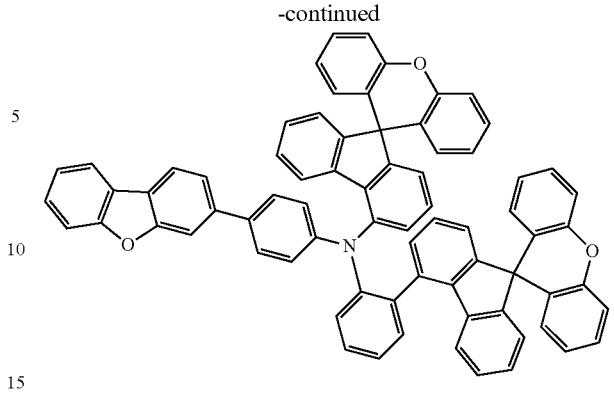
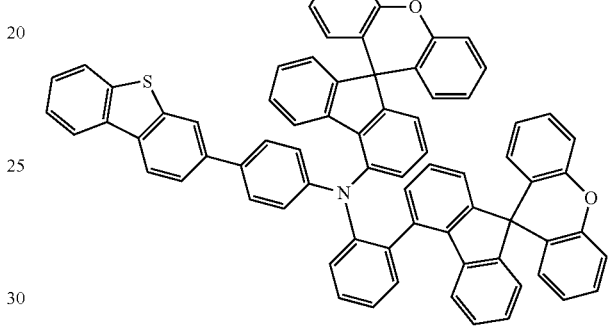
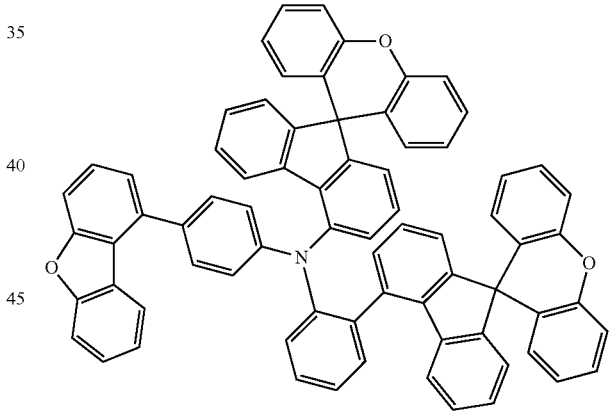
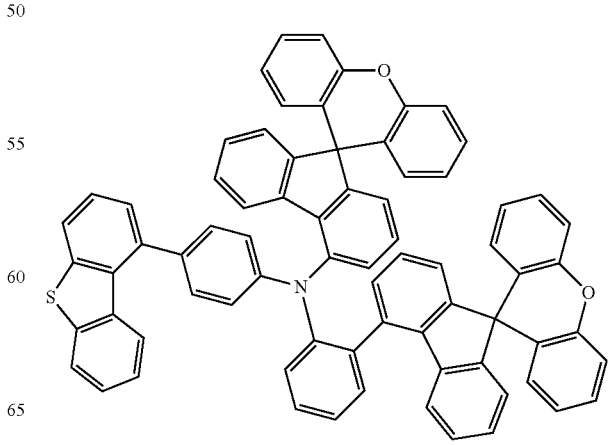

405
-continued
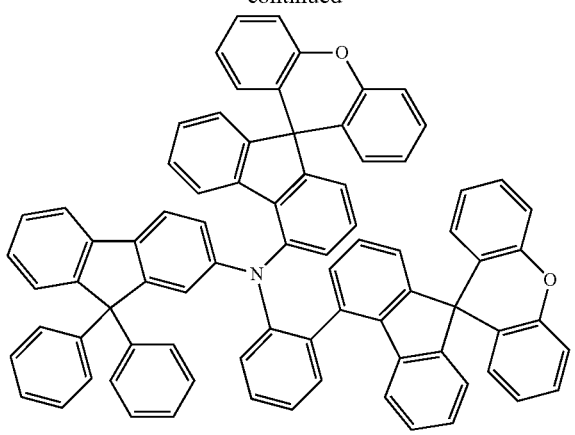
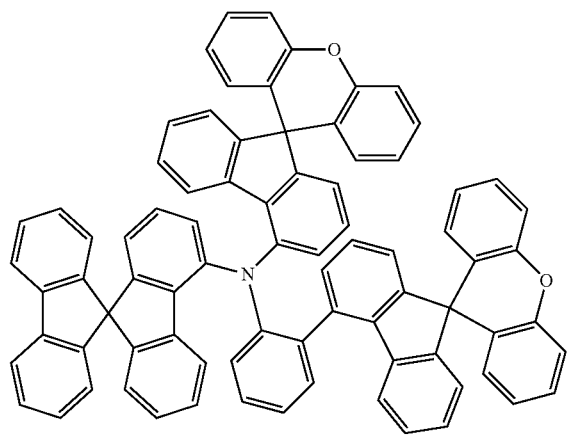
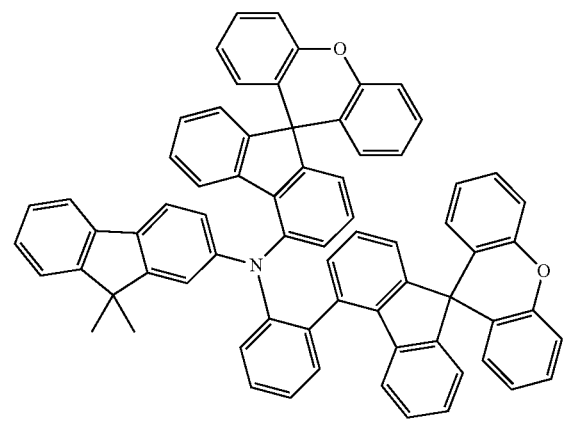
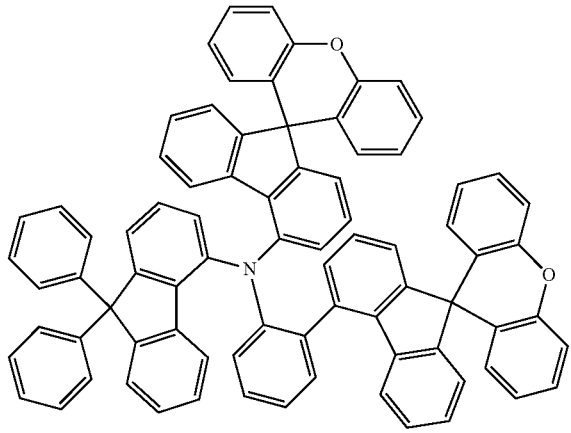
406
-continued
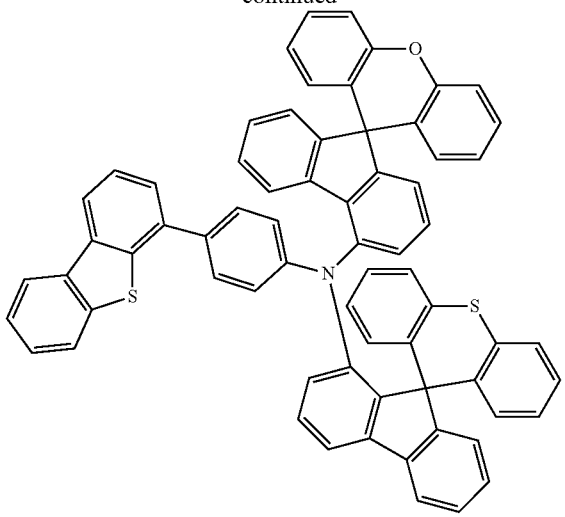
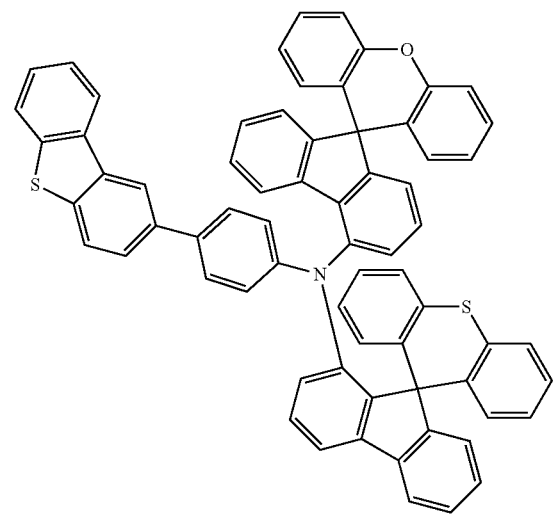
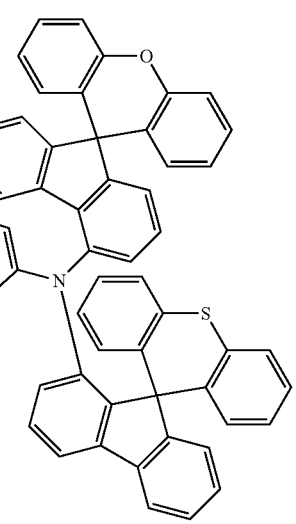

407
-continued
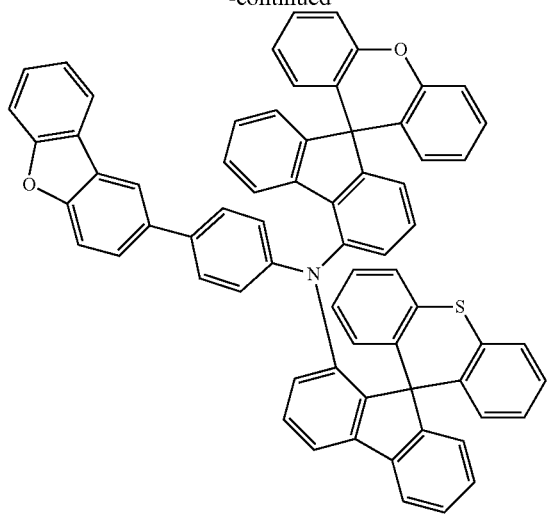
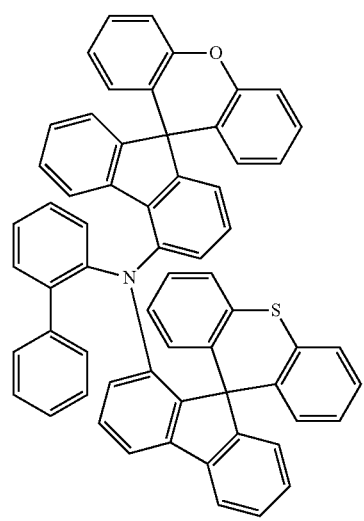
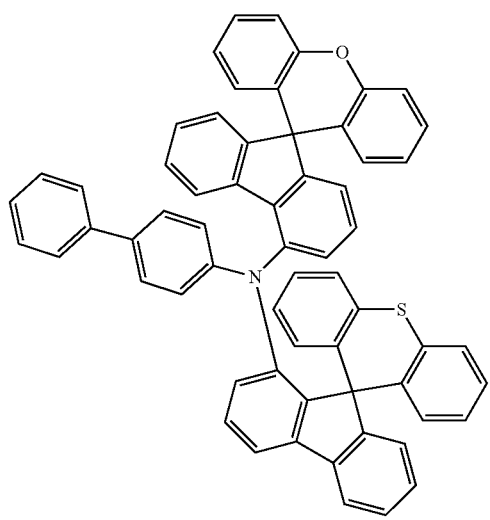
408
-continued
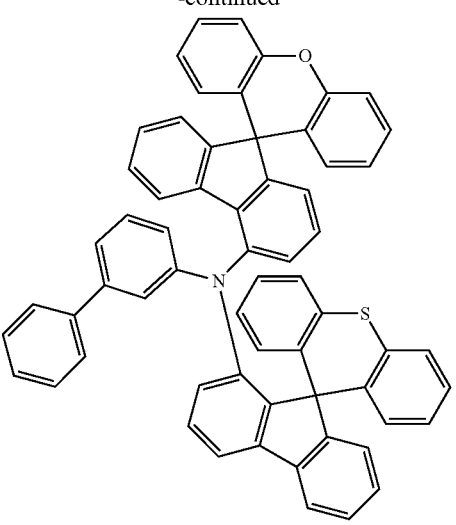
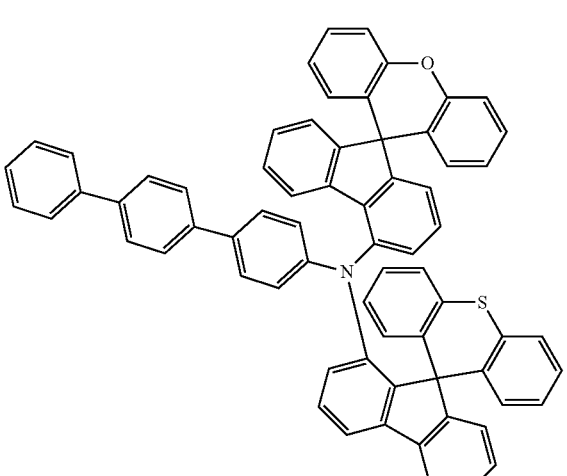
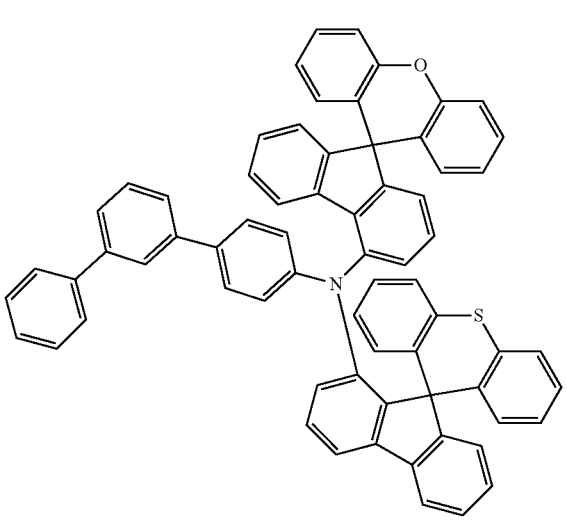

409
-continued
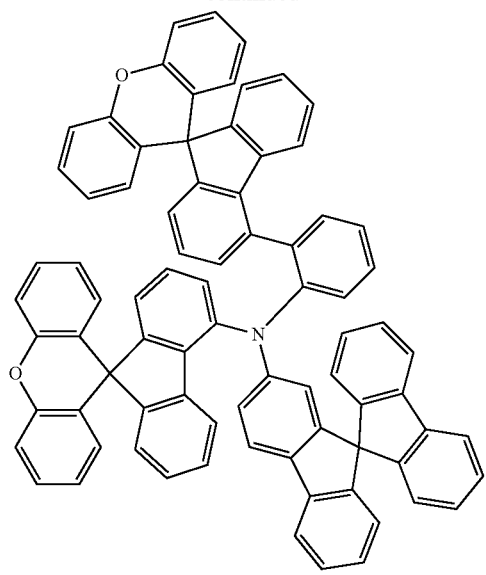
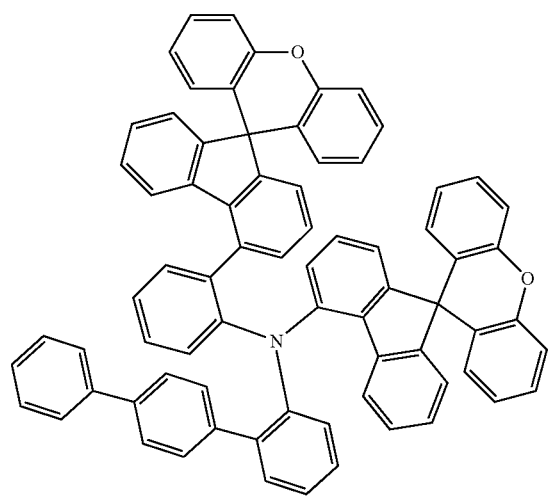
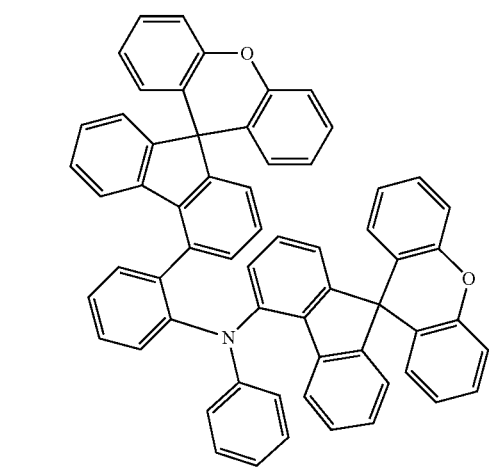
410
-continued
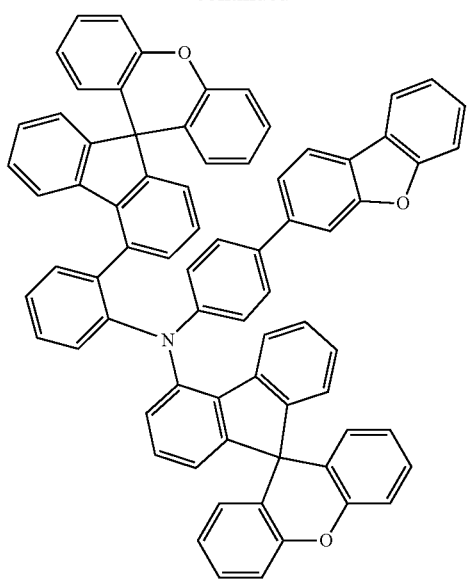
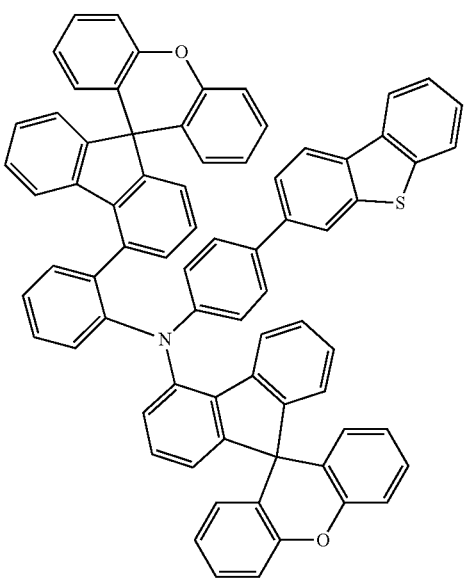
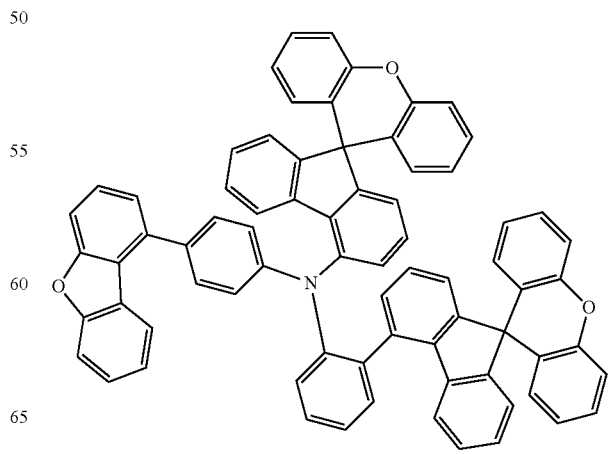

411
-continued
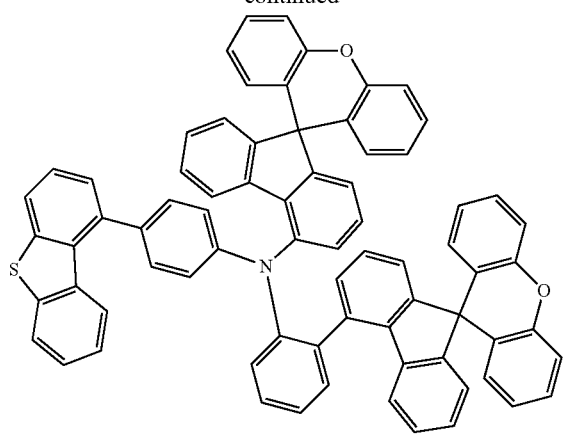
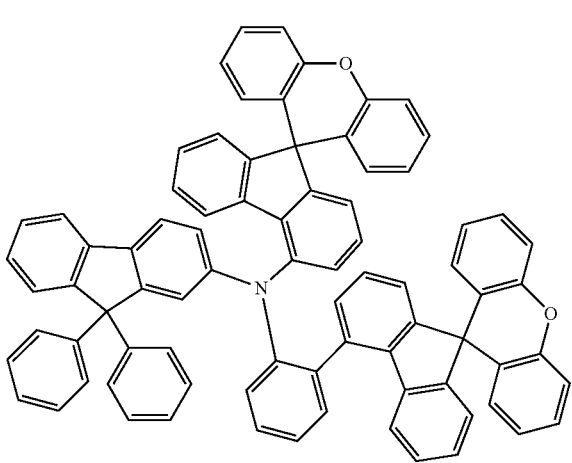
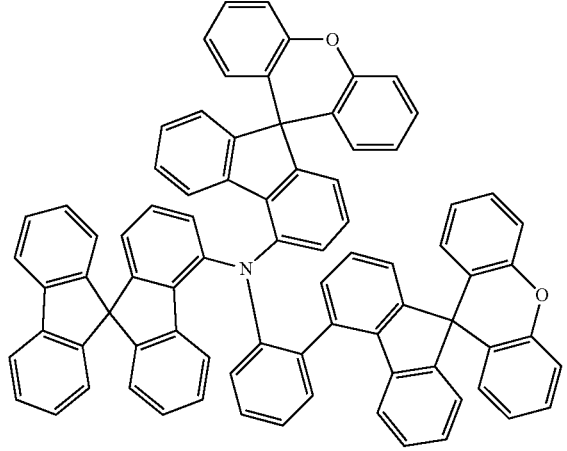
412
-continued
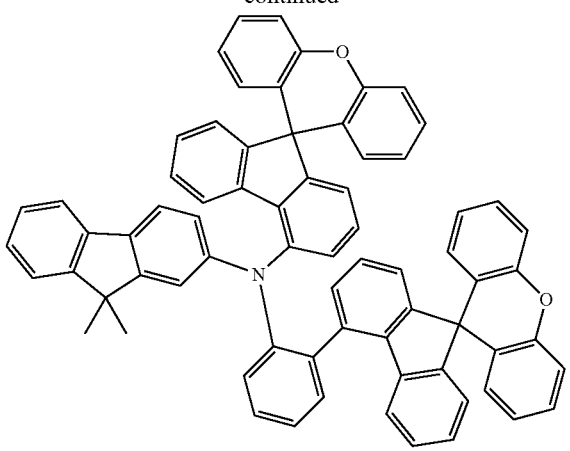
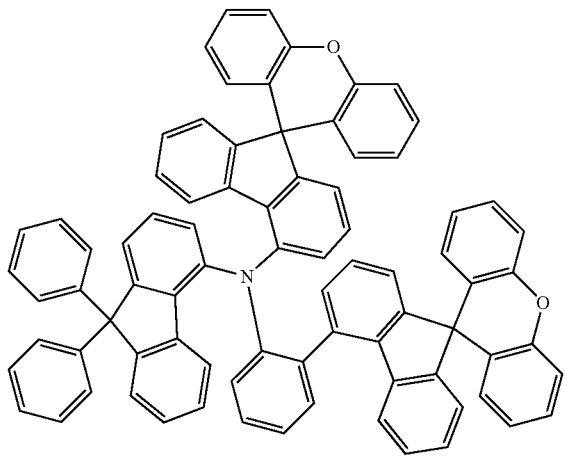
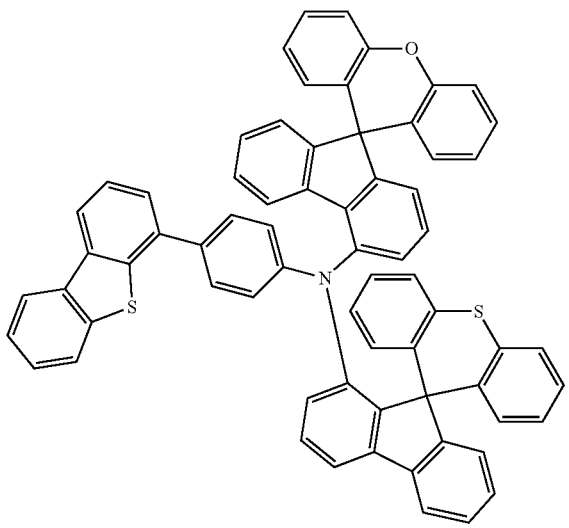

413
-continued
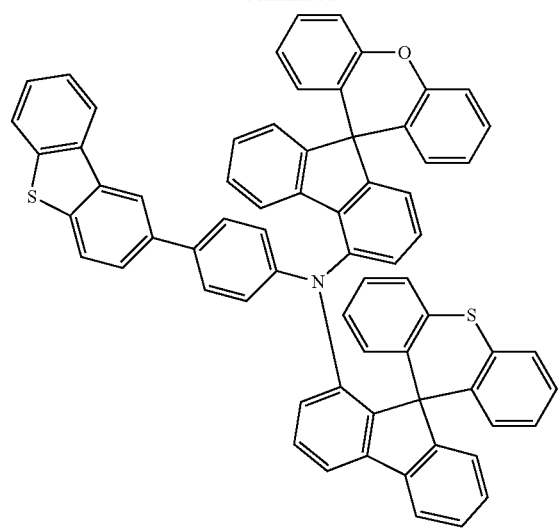
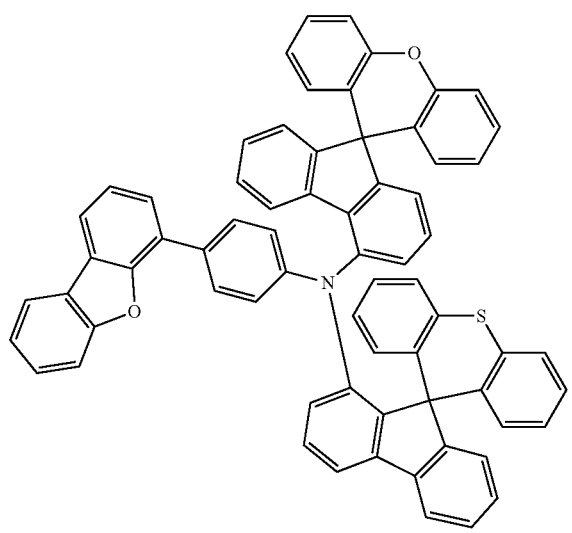
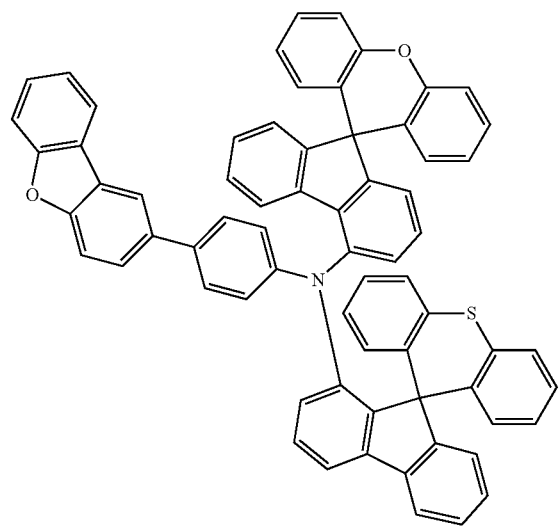
414
-continued
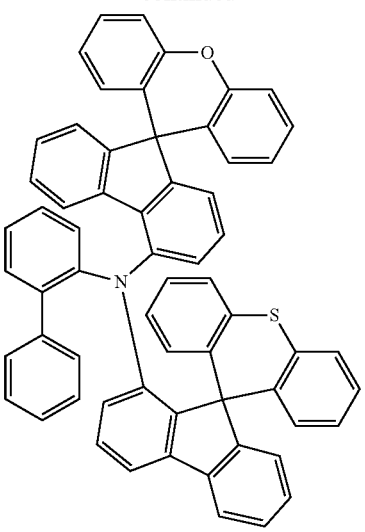
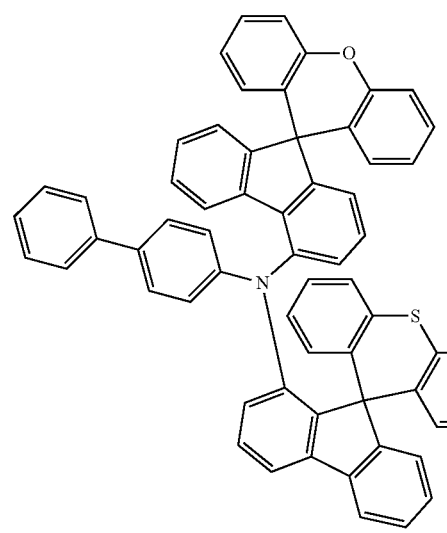
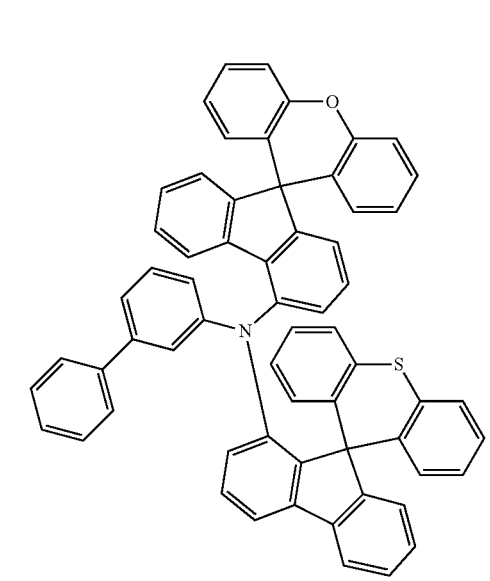

415
-continued
416
-continued
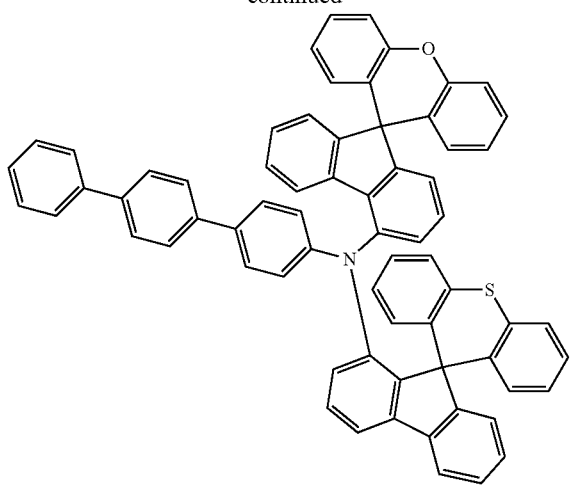
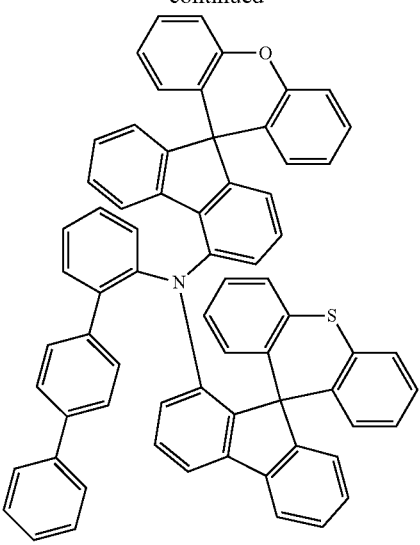
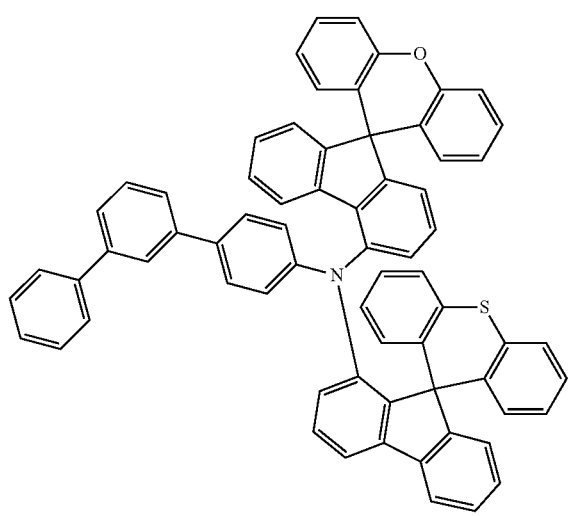
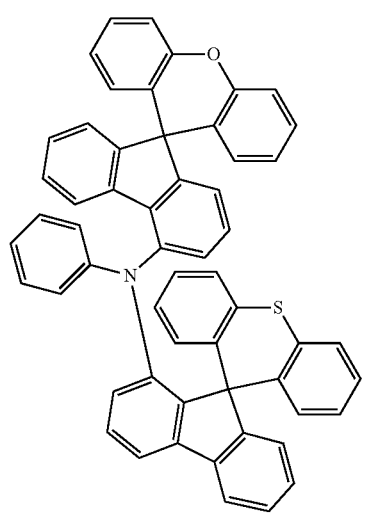
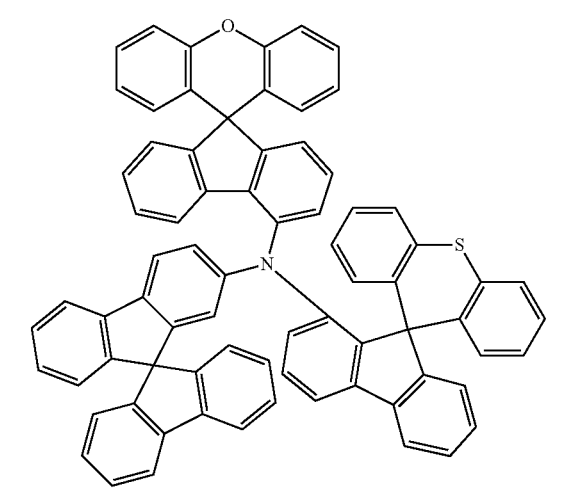
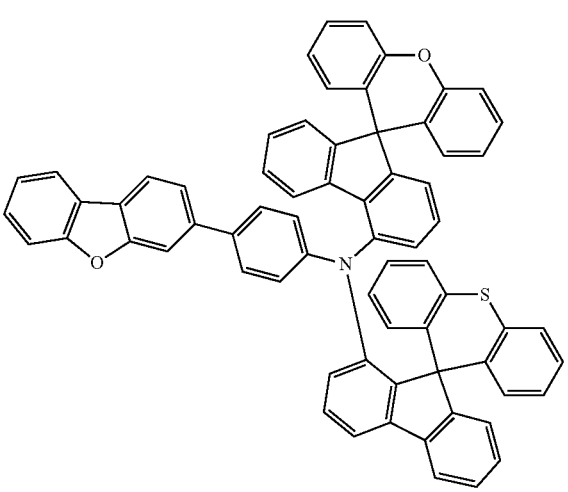

417
-continued
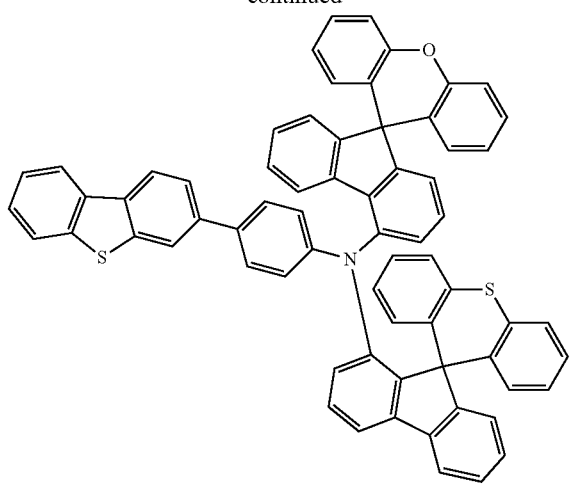
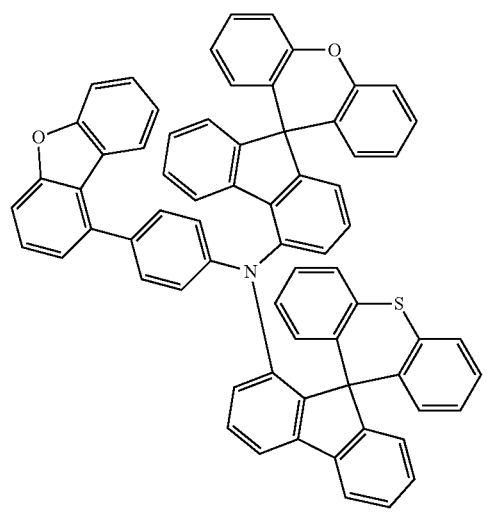
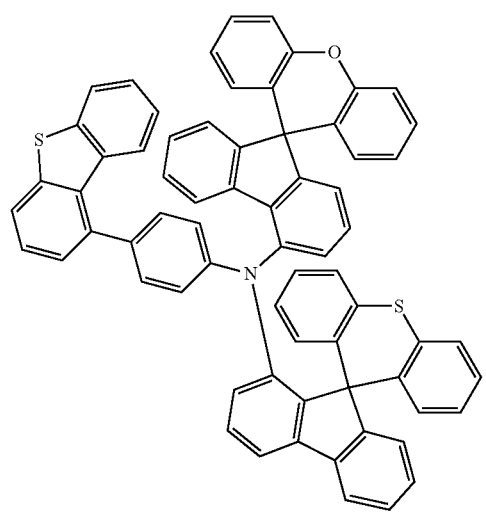
418
-continued
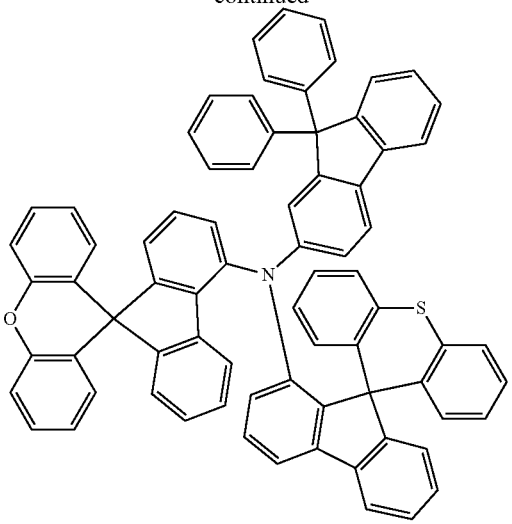
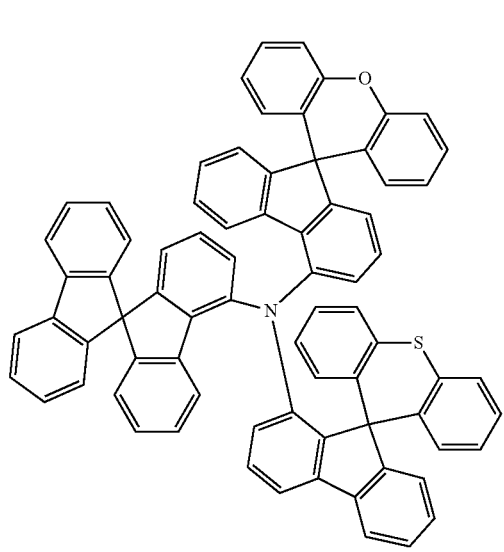
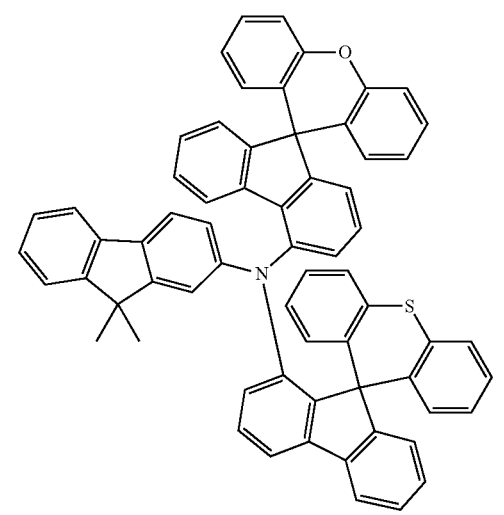

-continued
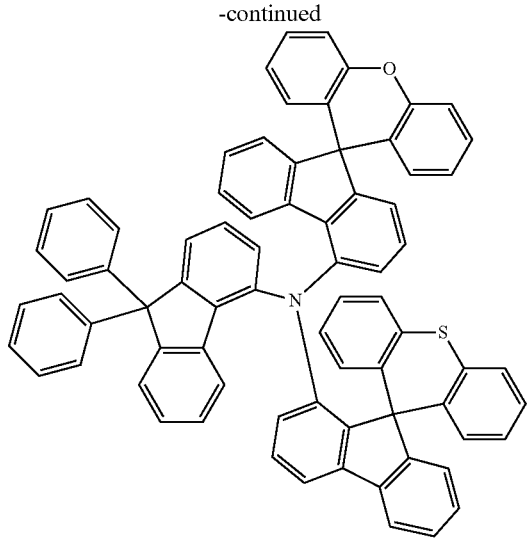
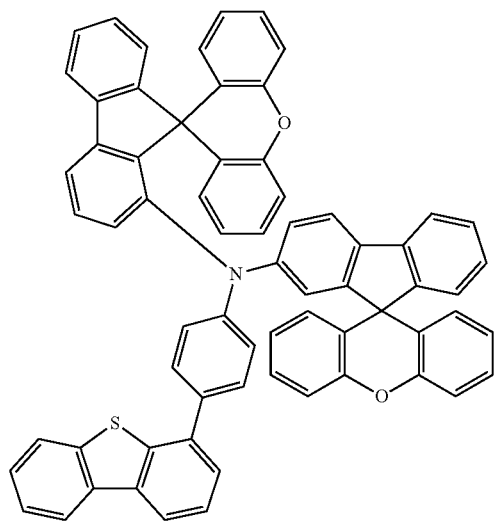
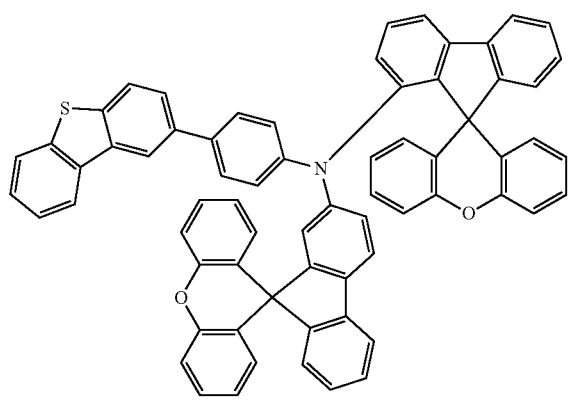
-continued
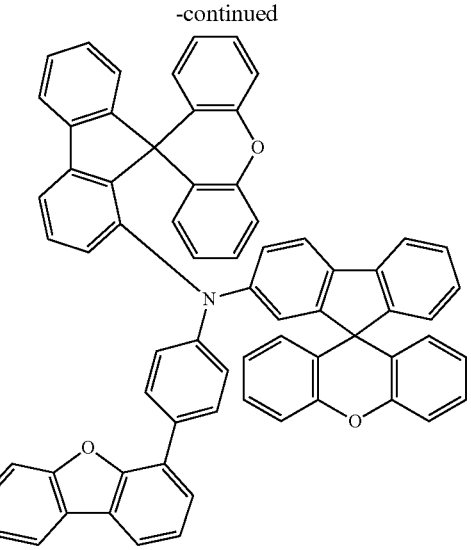
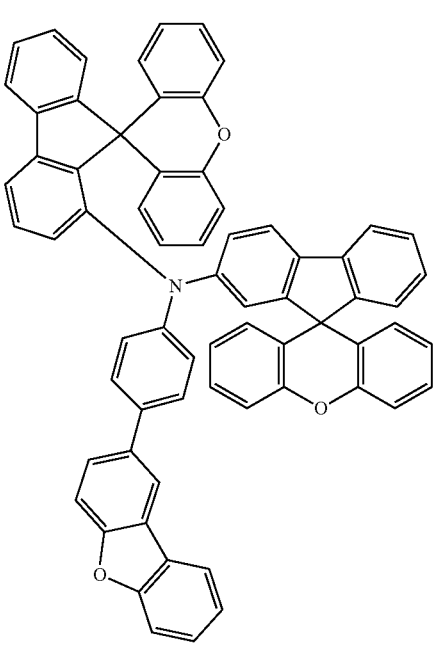
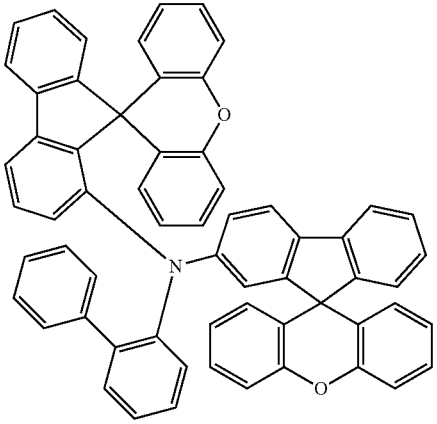

421
-continued
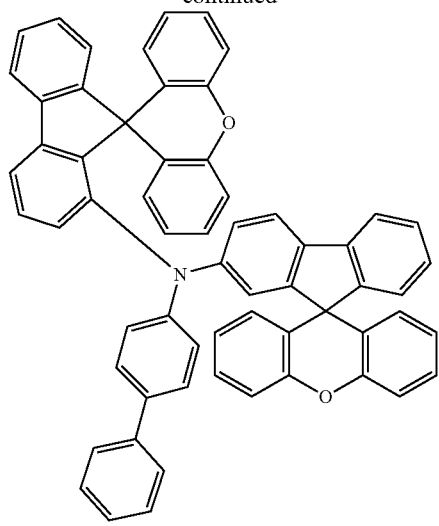
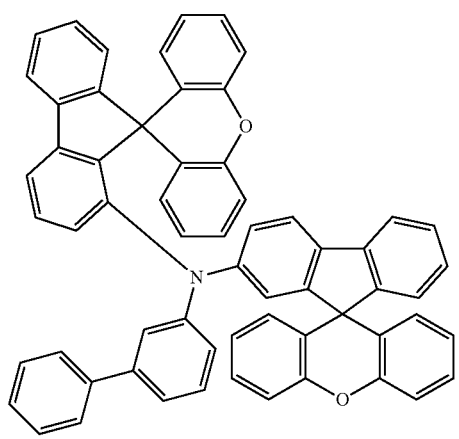
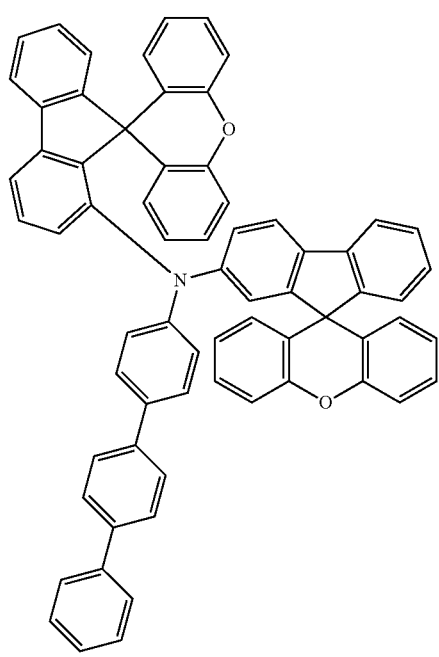
422
-continued
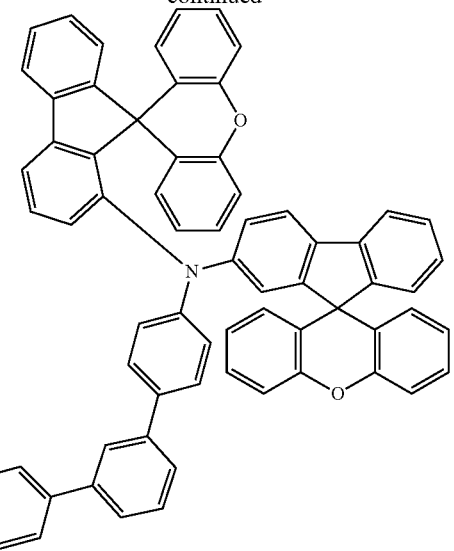
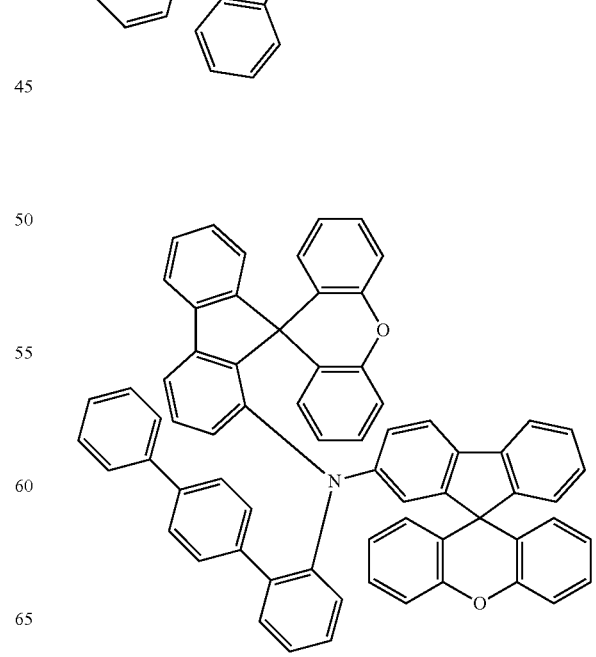

423
-continued
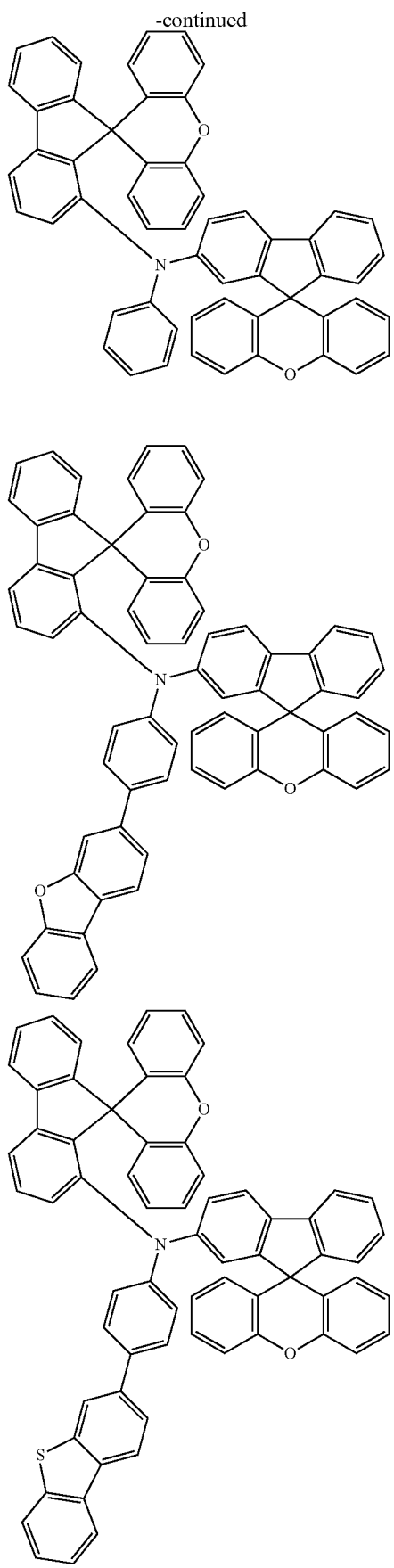
424
-continued
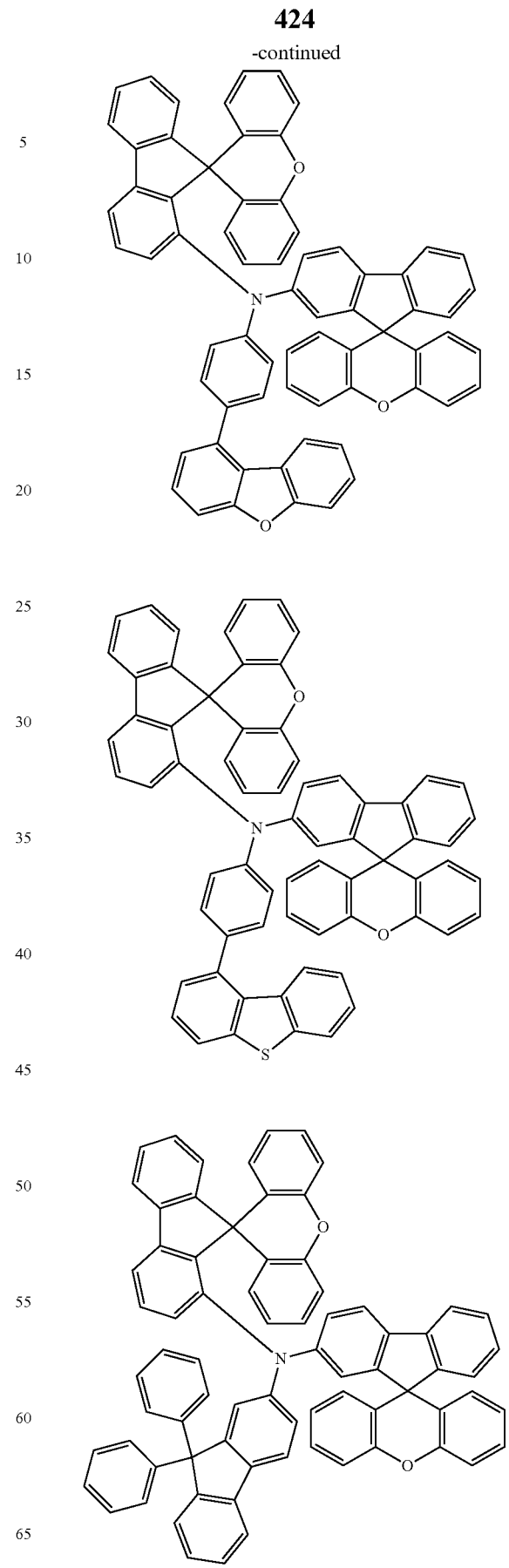

425
-continued
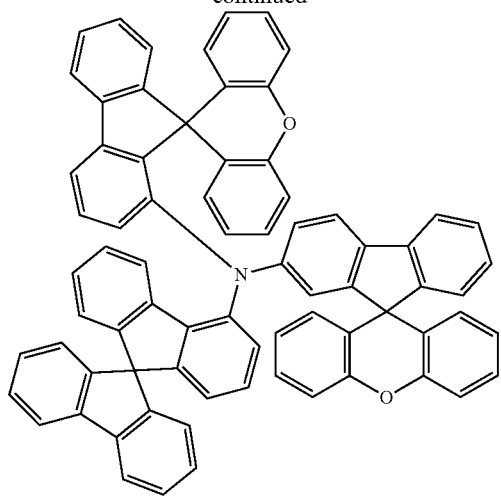
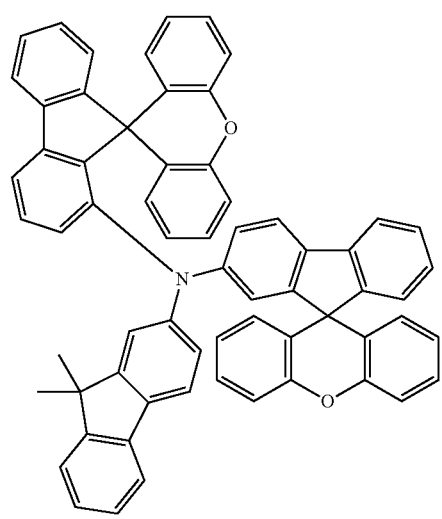
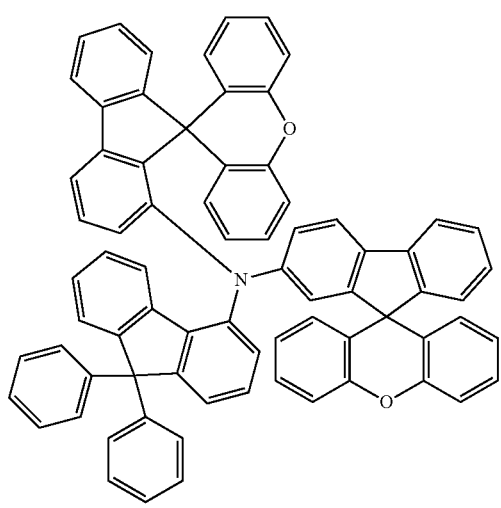
426
-continued
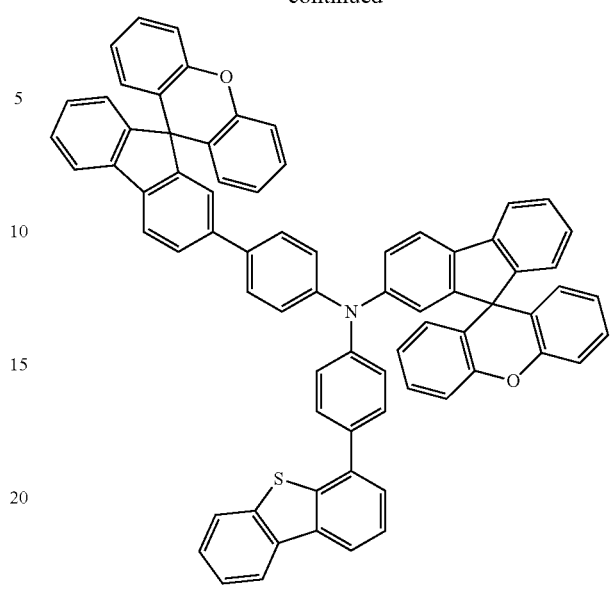

427
-continued
428
-continued
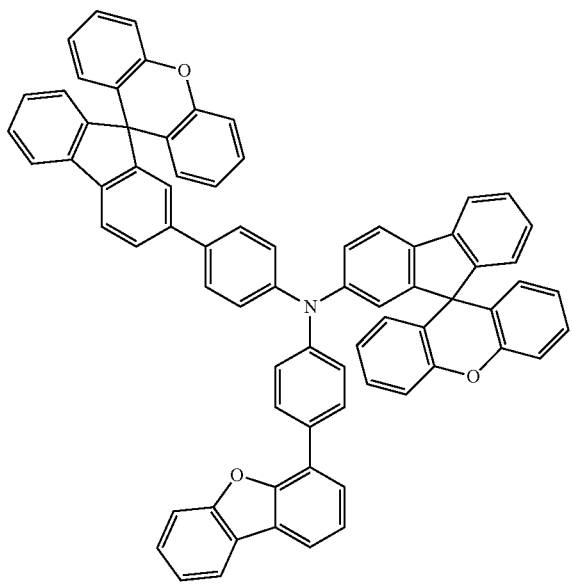
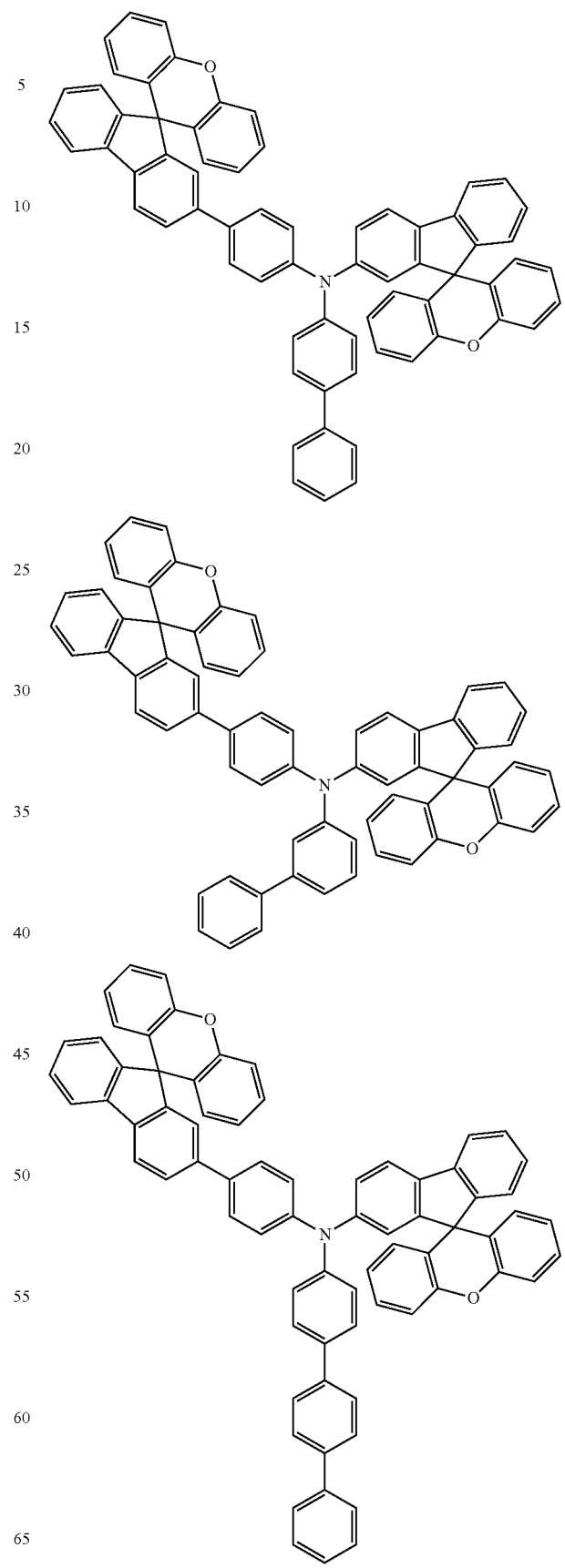

429
-continued
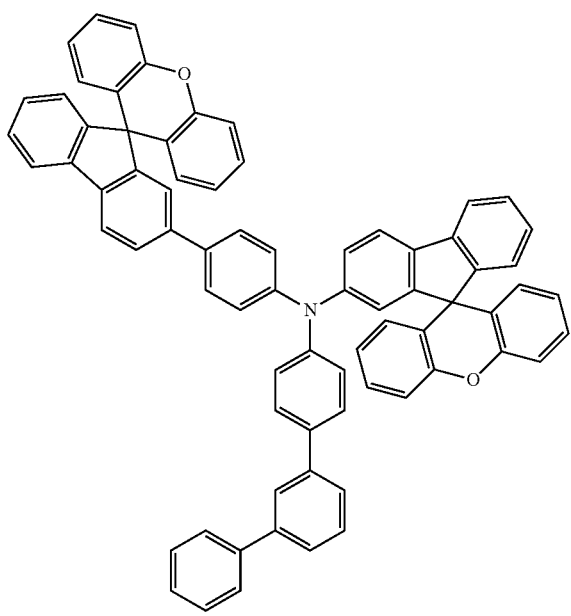
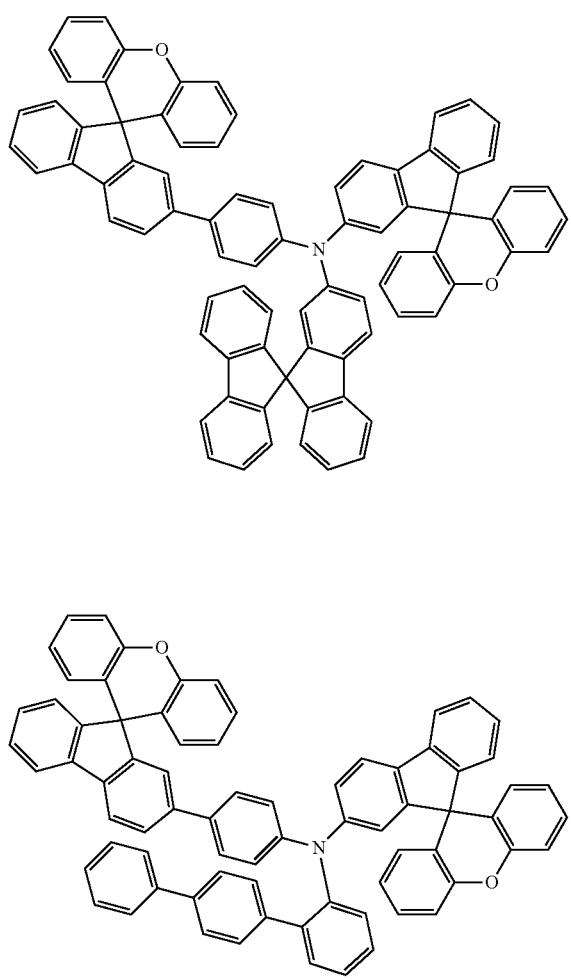
430
-continued
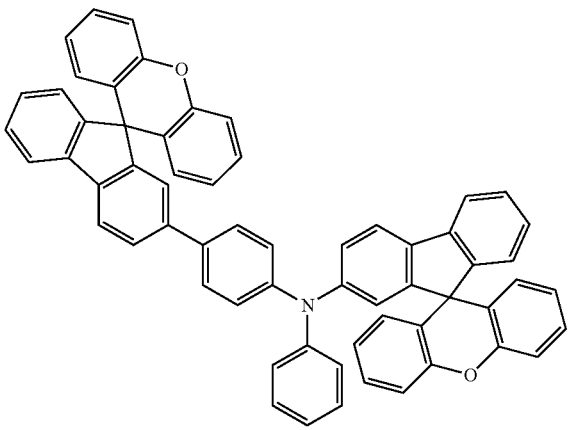
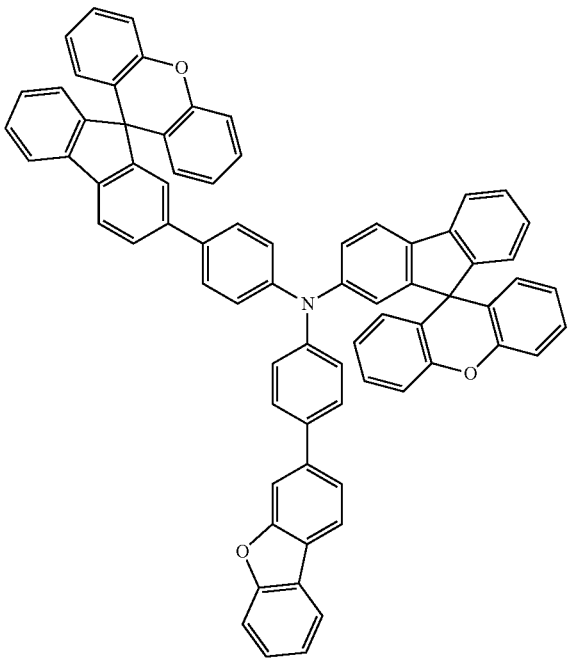

431
-continued
432
-continued
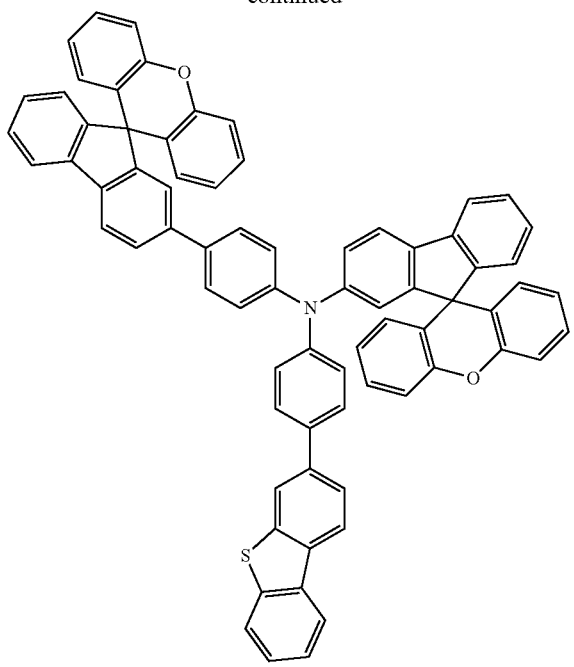
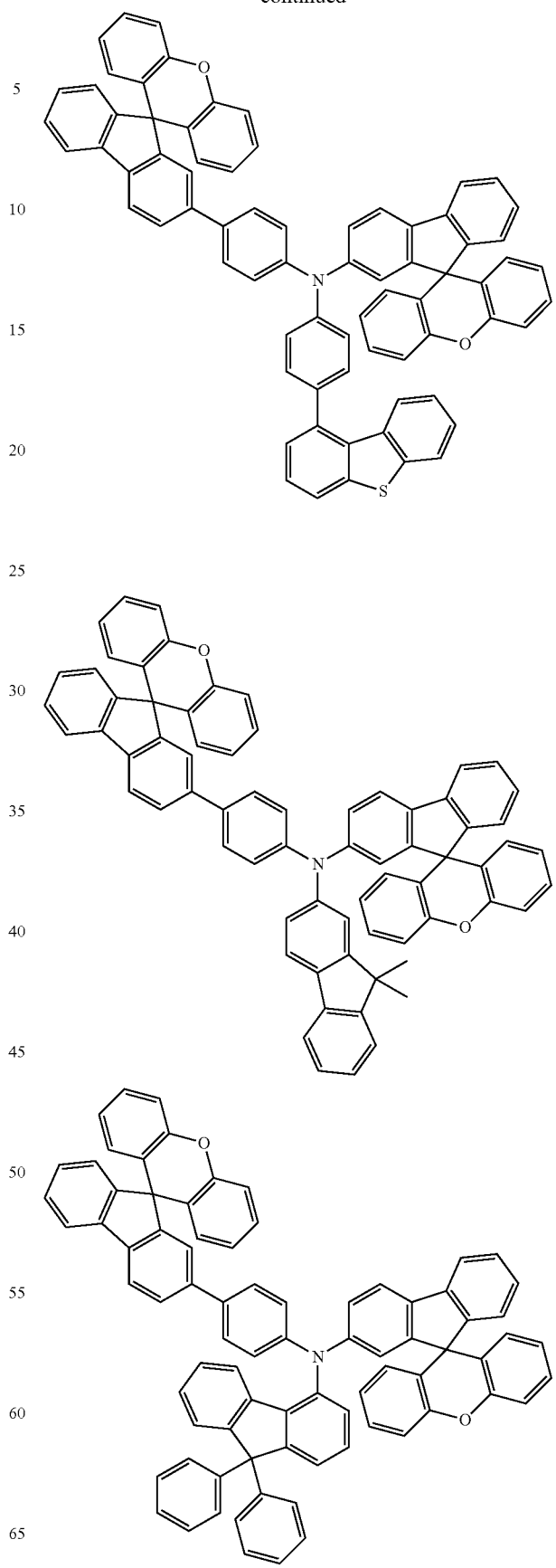

433
-continued
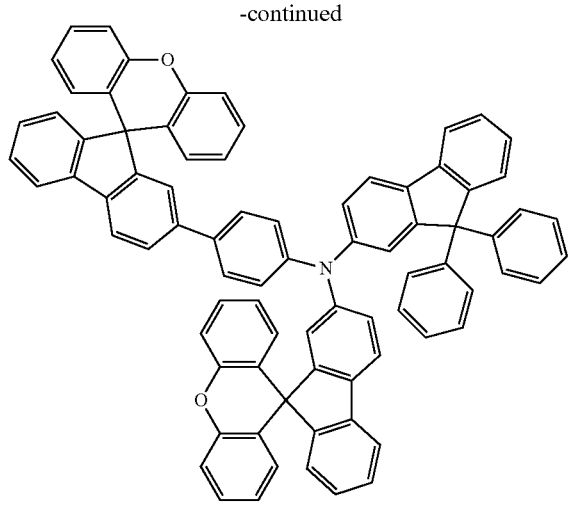
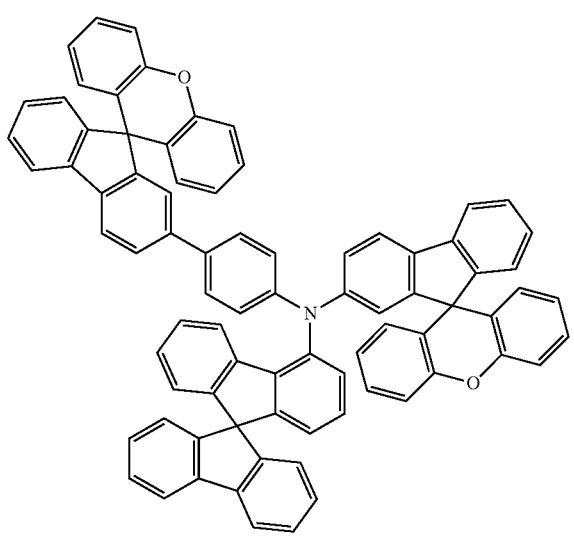
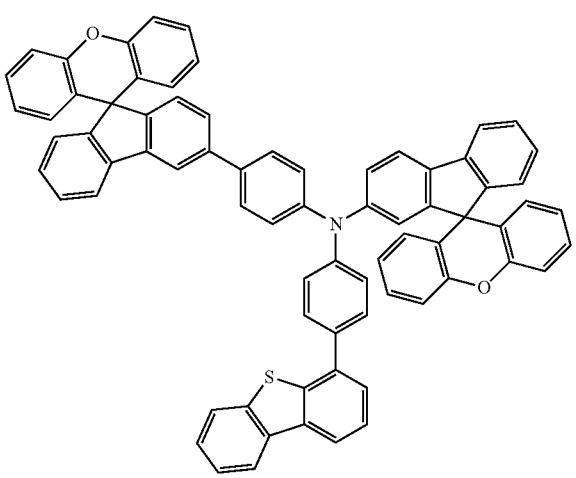
434
-continued
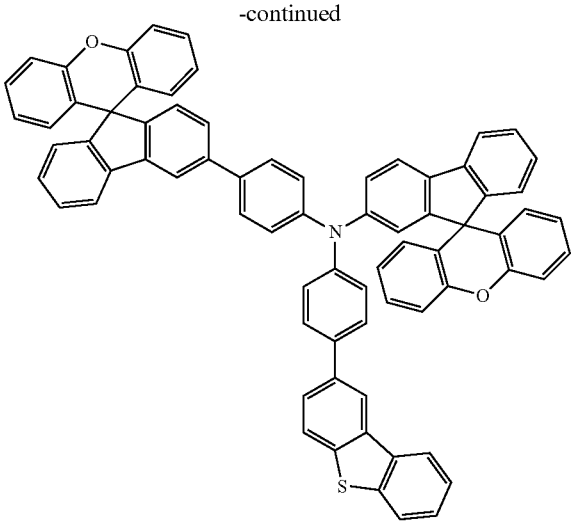
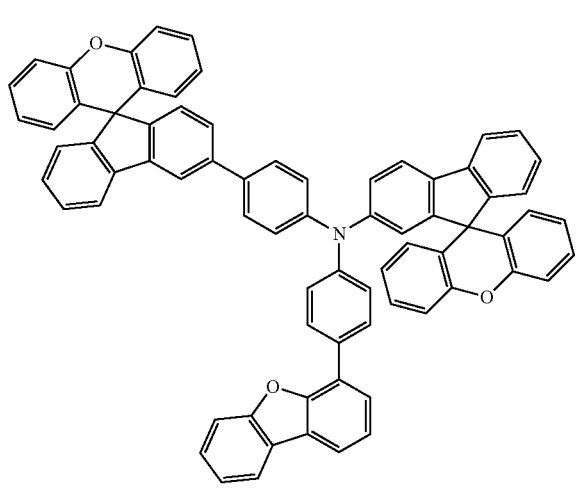
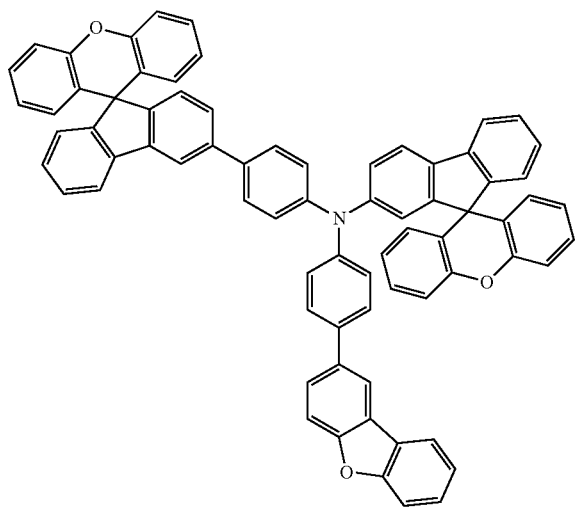

435
-continued
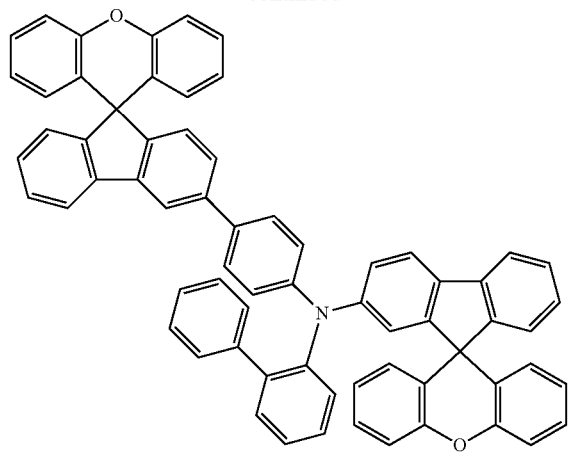
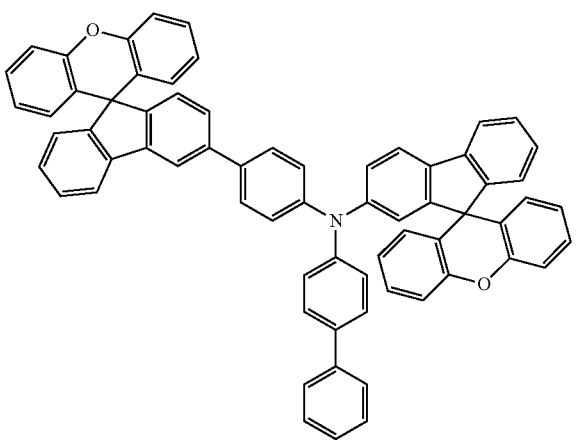
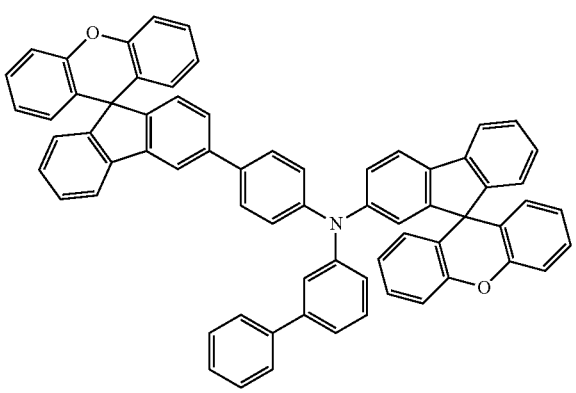
436
-continued
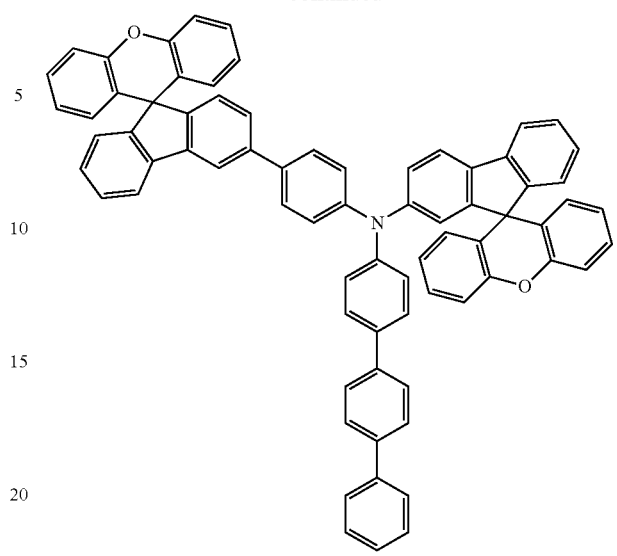
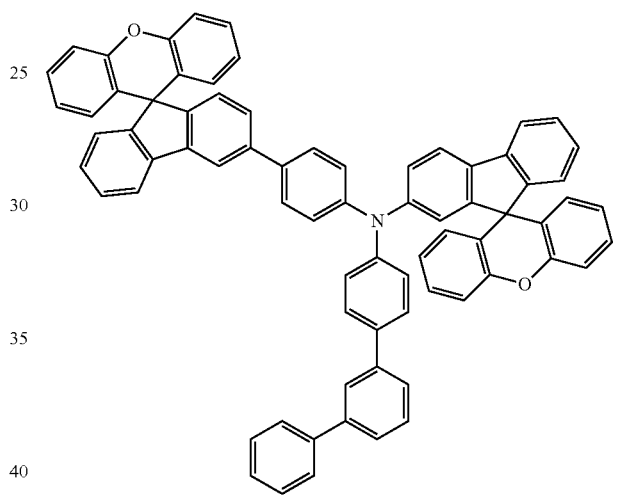
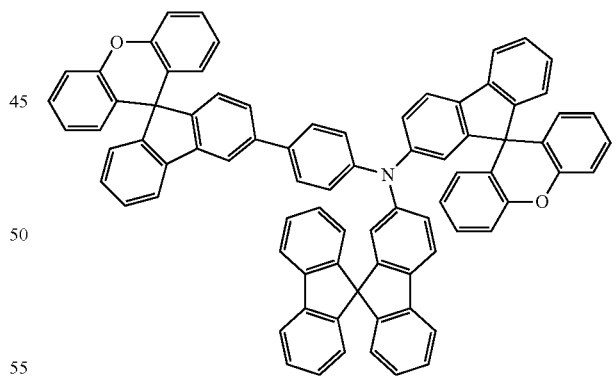
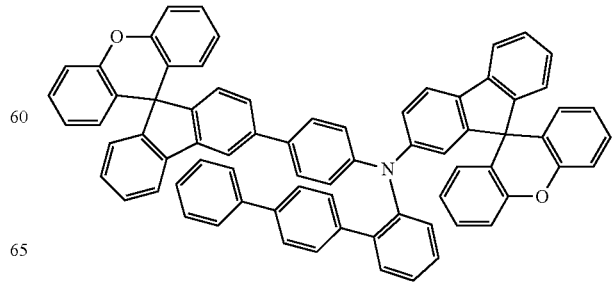

437
-continued
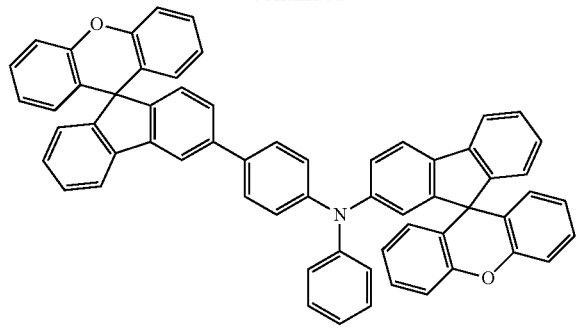
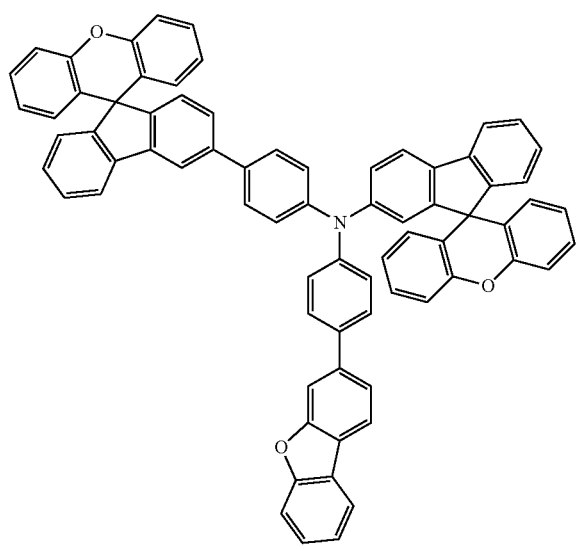
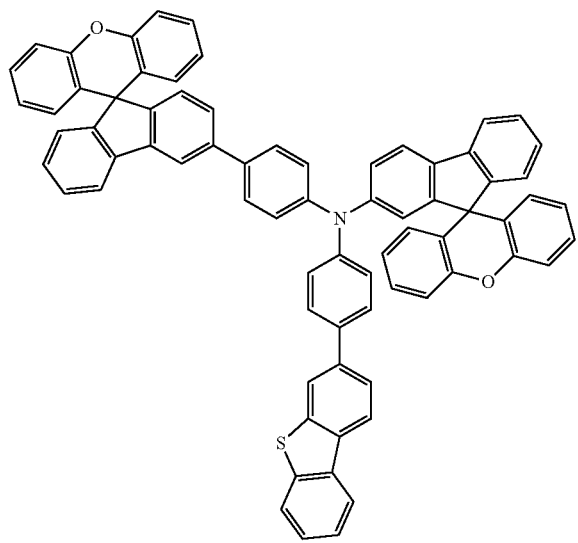
438
-continued
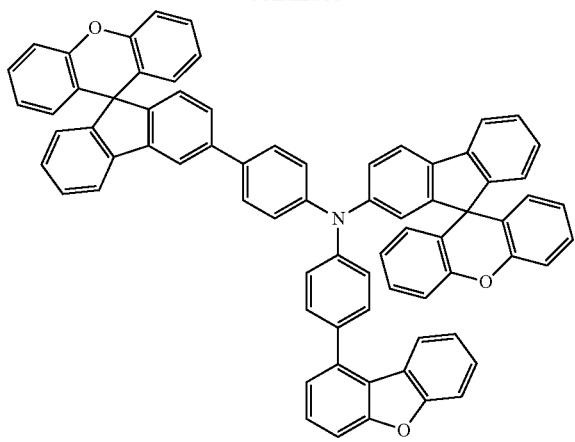
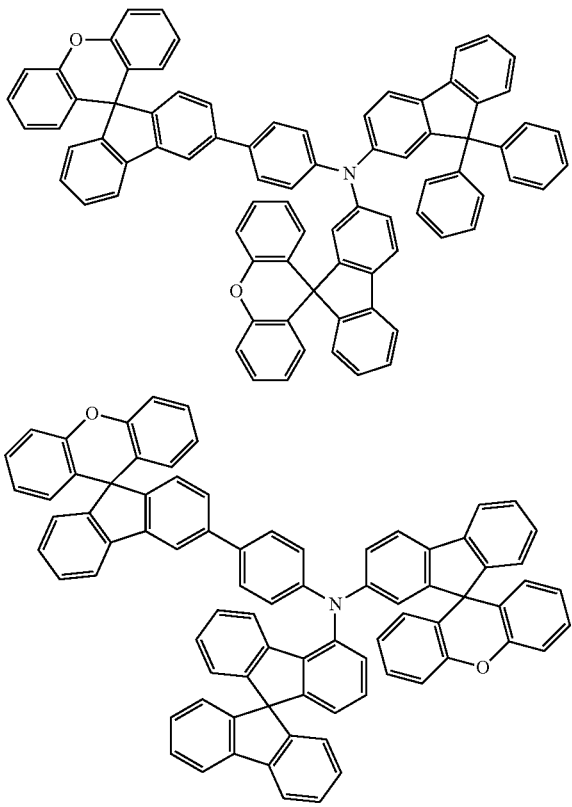

439
-continued
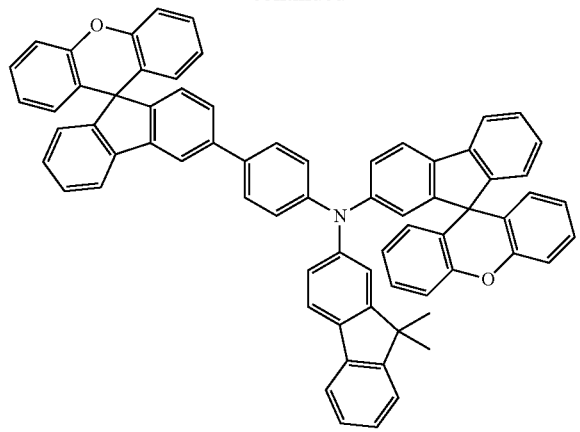
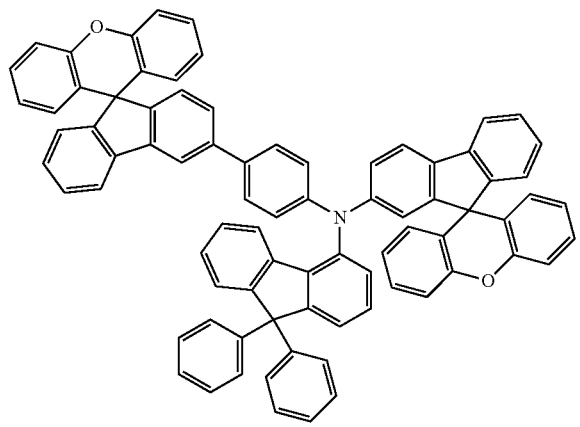
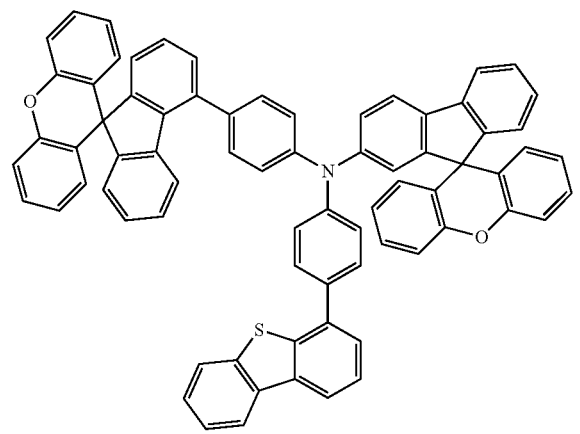
440
-continued
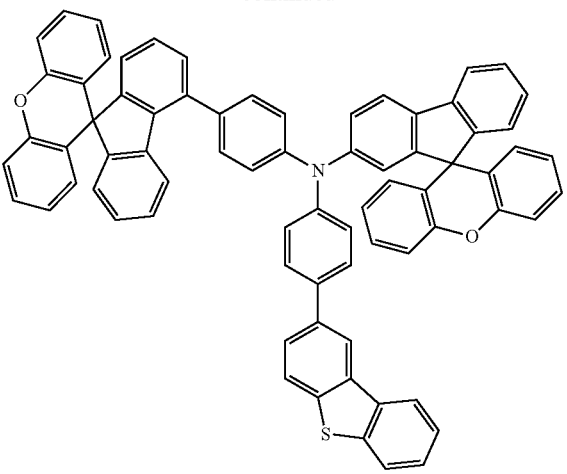
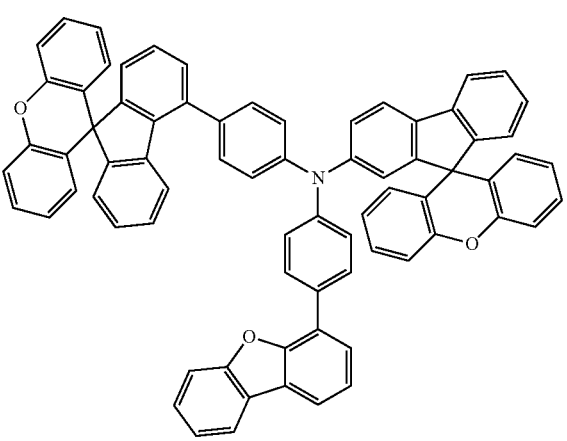
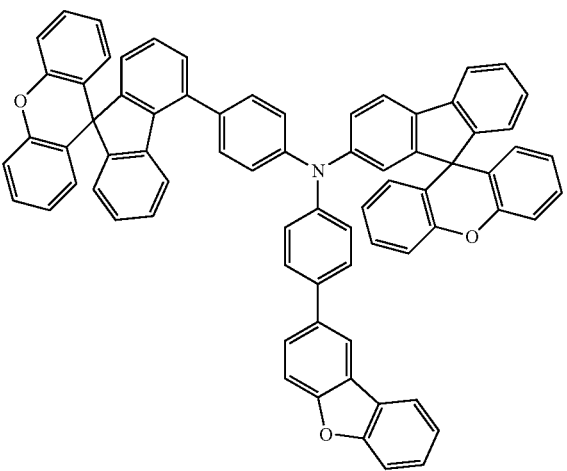

441
-continued
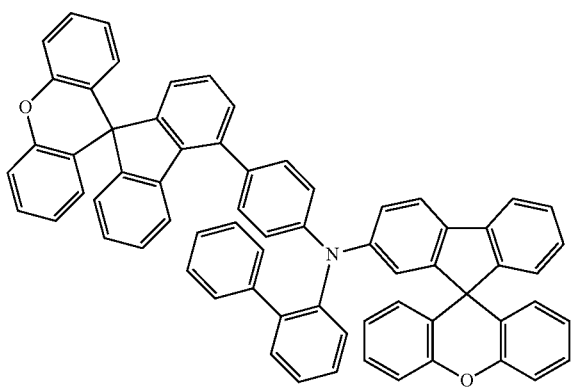
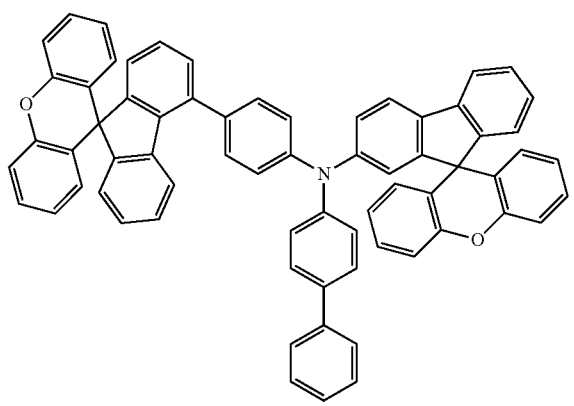
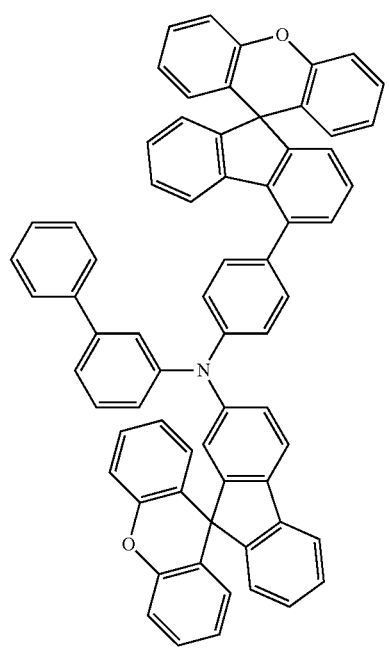
442
-continued
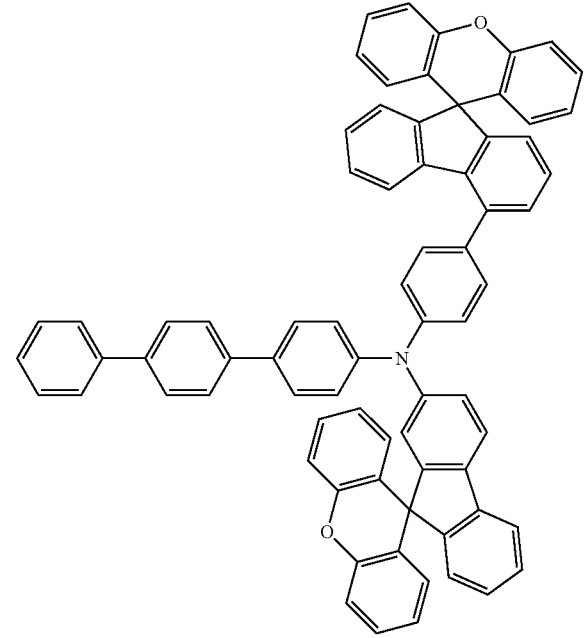
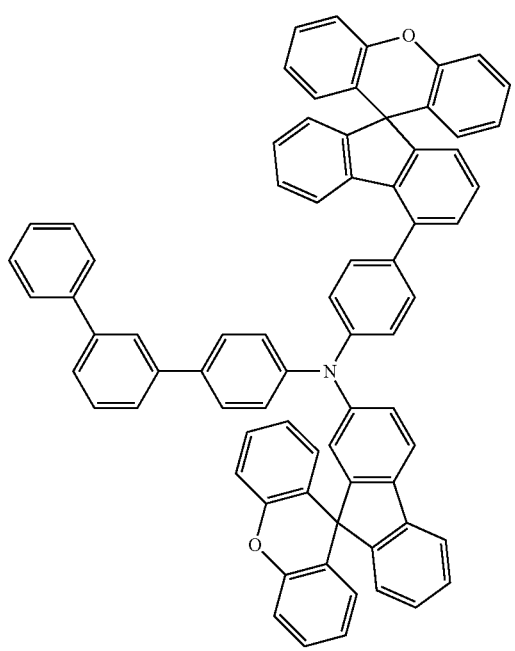

443
-continued
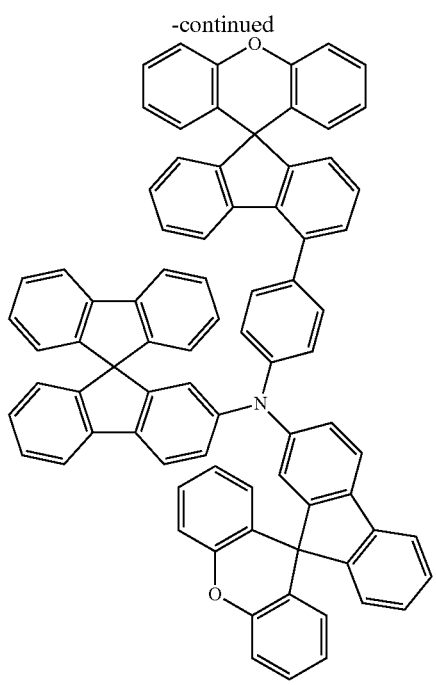
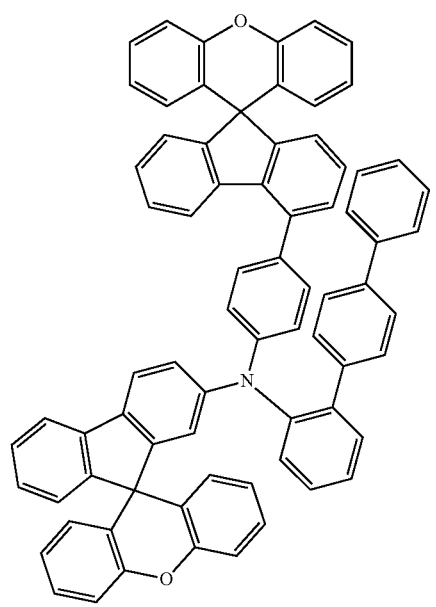
444
-continued
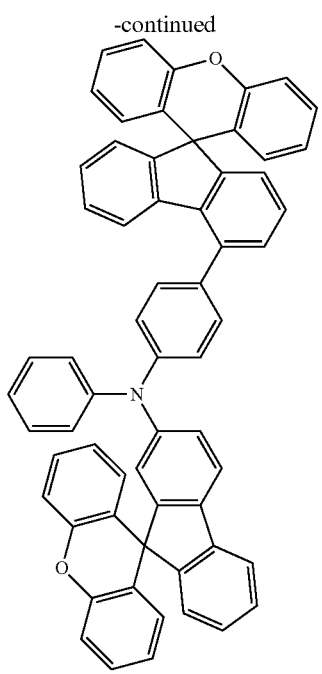
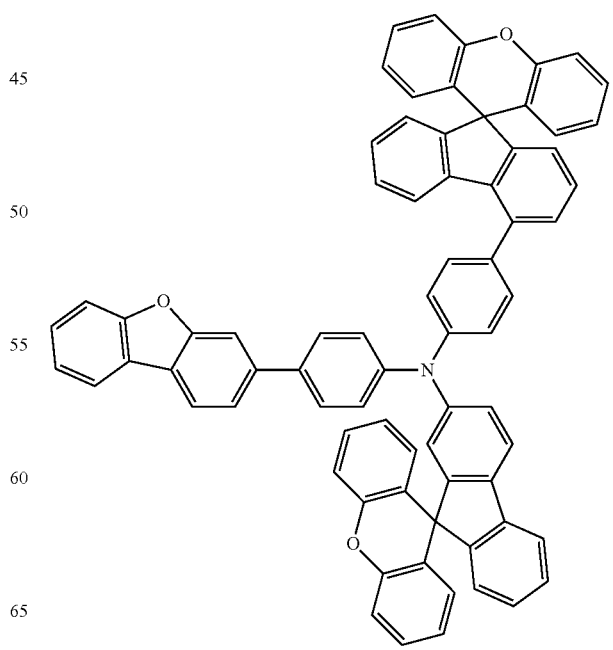

445
-continued
446
-continued
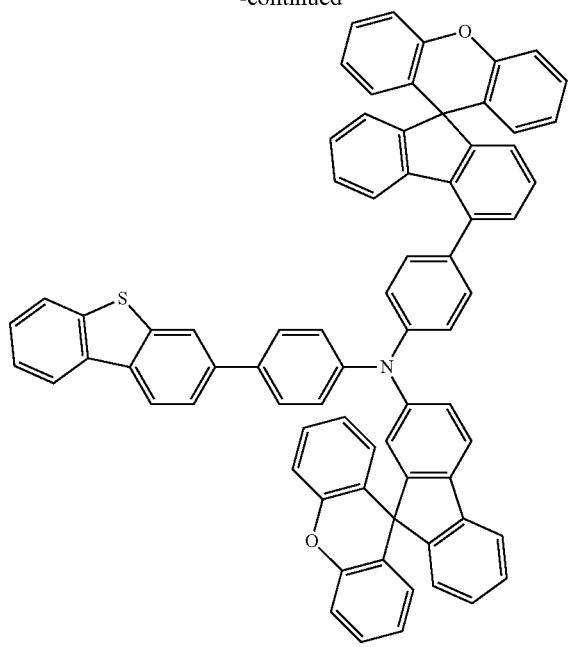
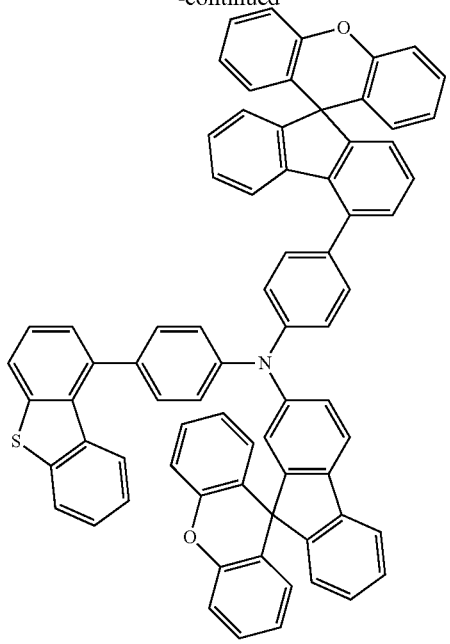
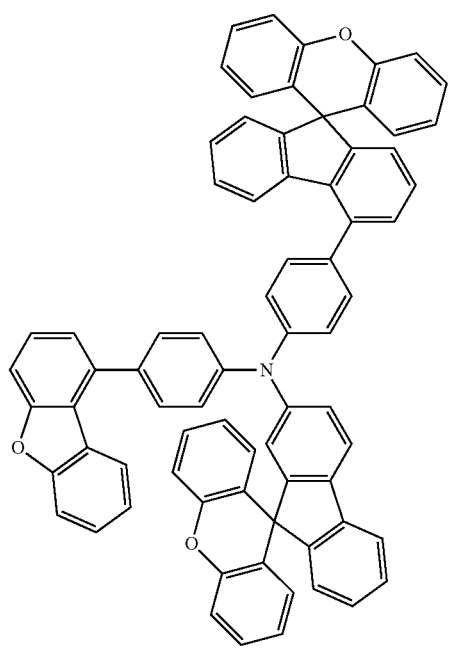
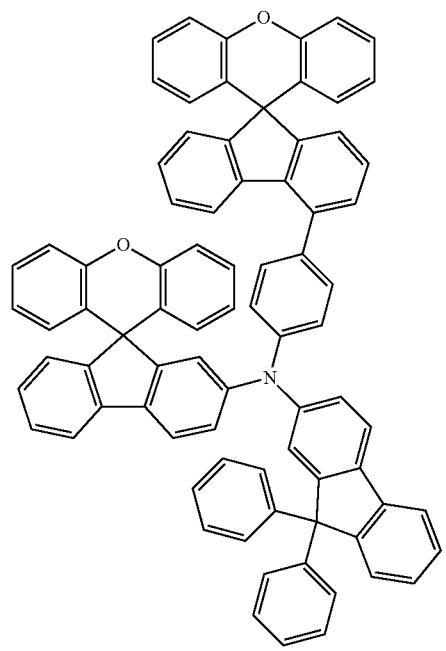

447
-continued
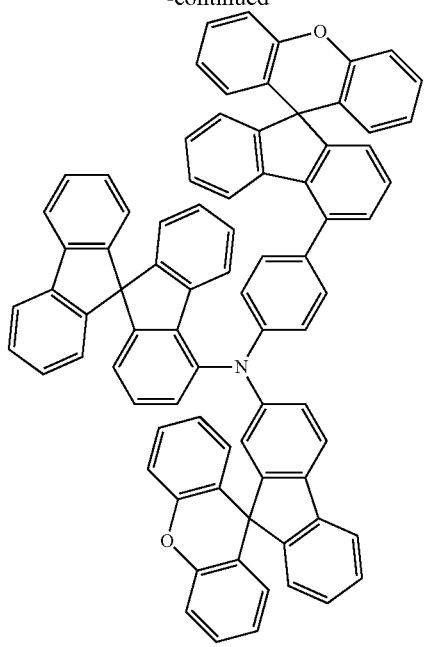
448
-continued
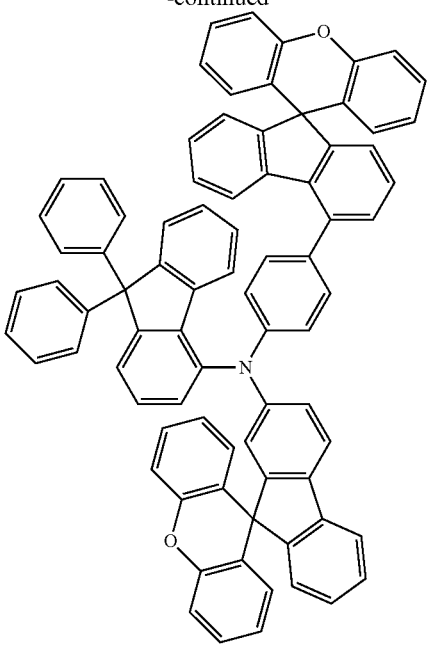
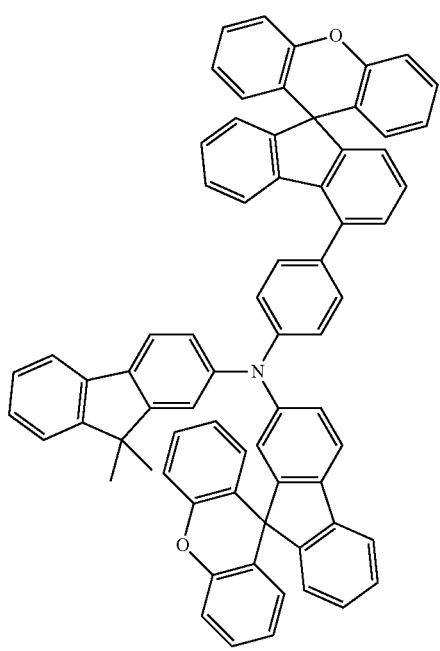
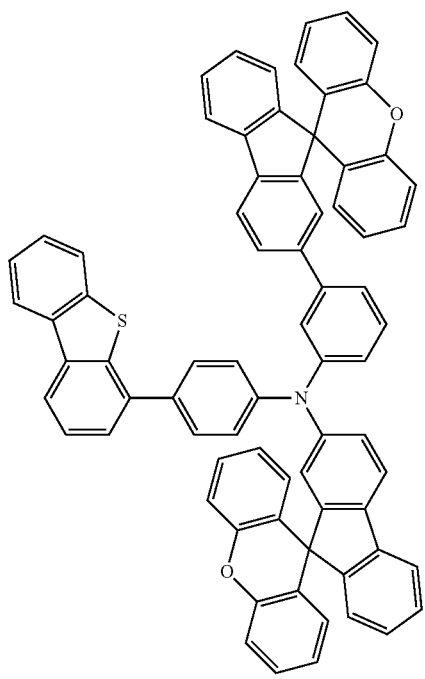

449
-continued
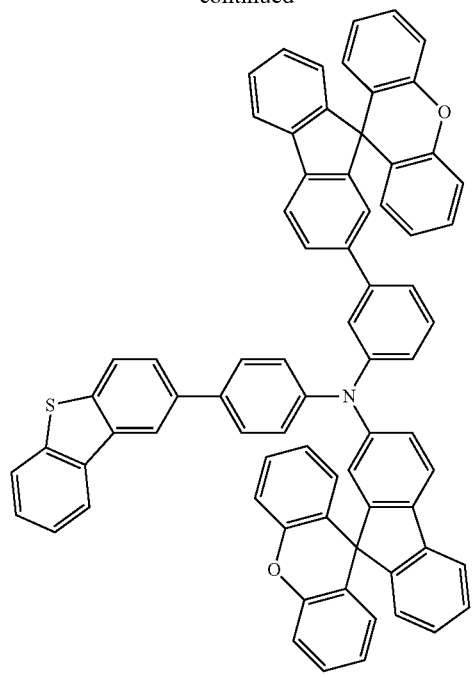
450
-continued
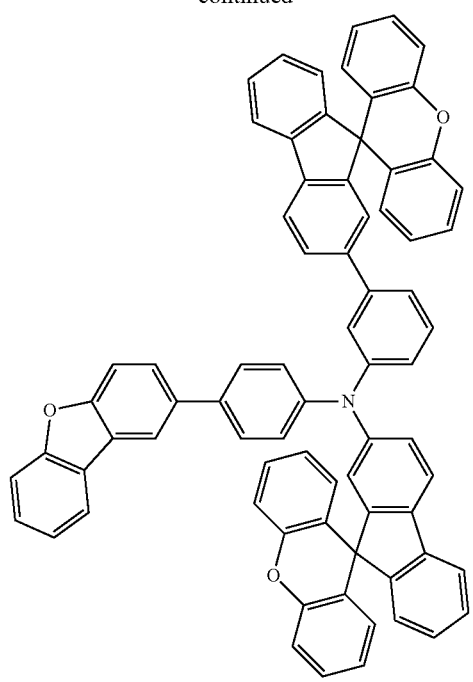
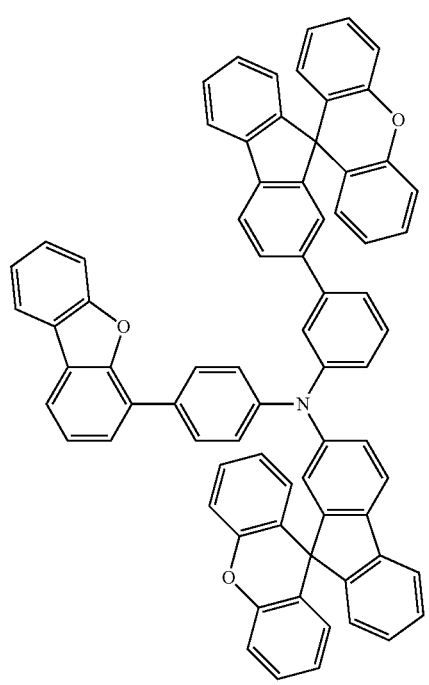
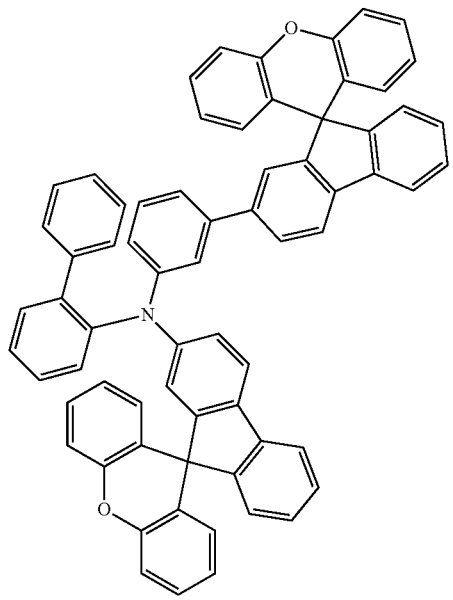

451
-continued
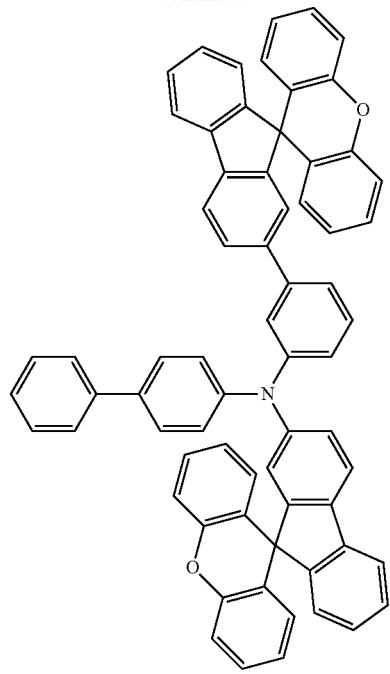
452
-continued
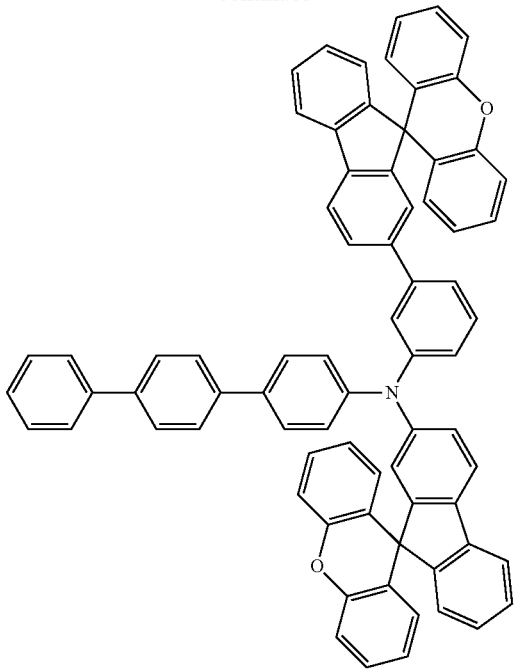
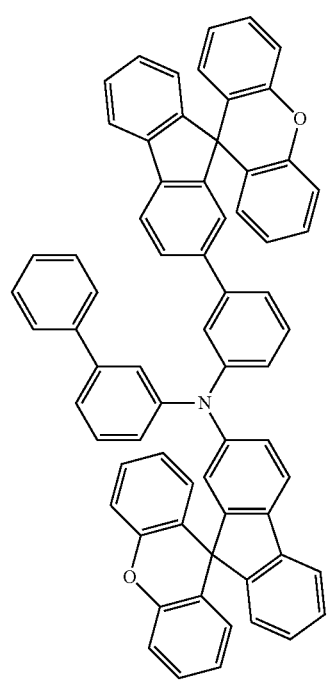
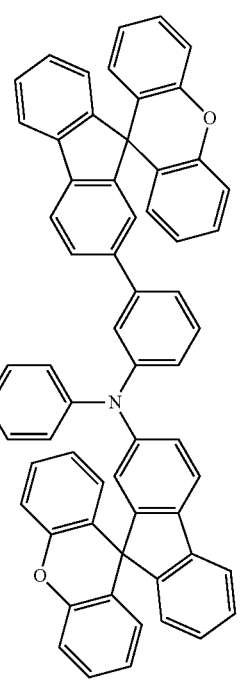

453
-continued
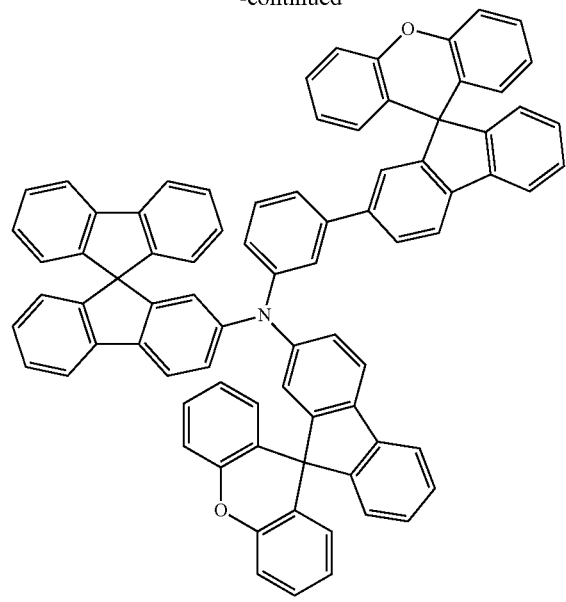
454
-continued
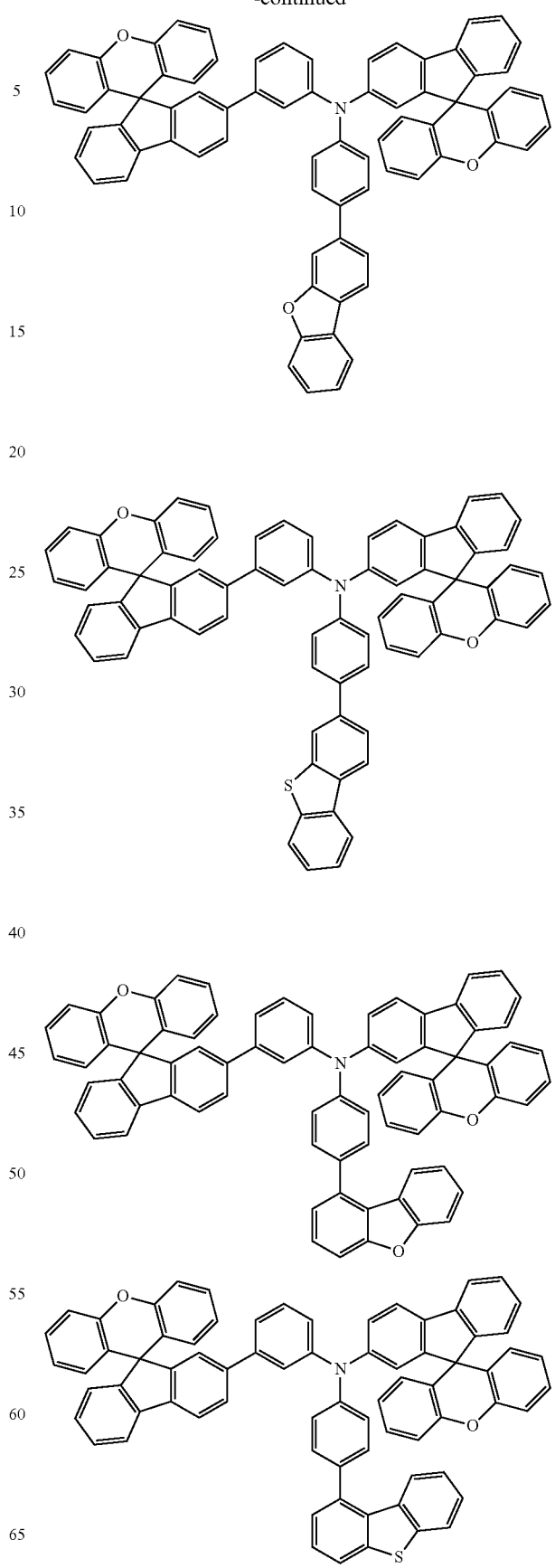

455
-continued
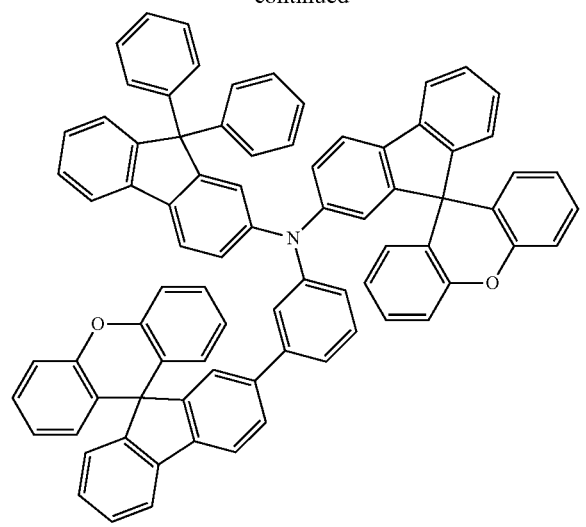
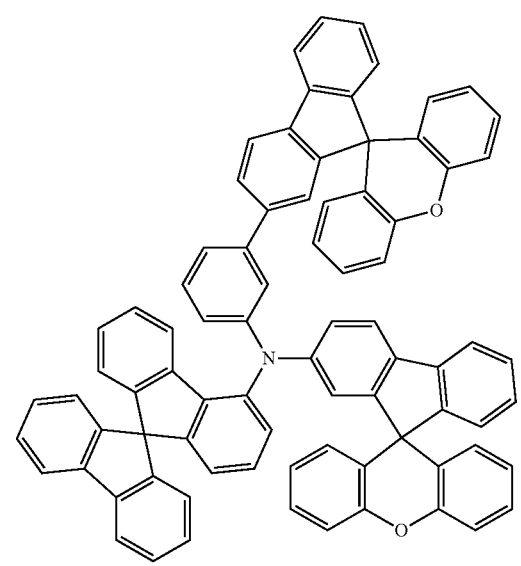
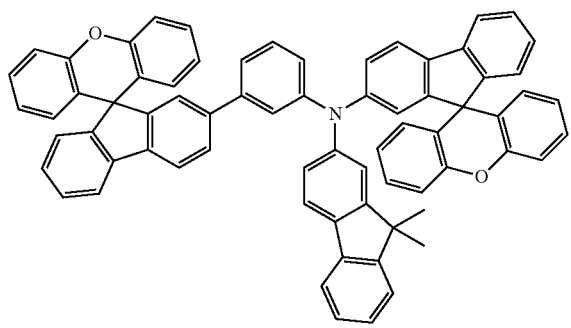
456
-continued
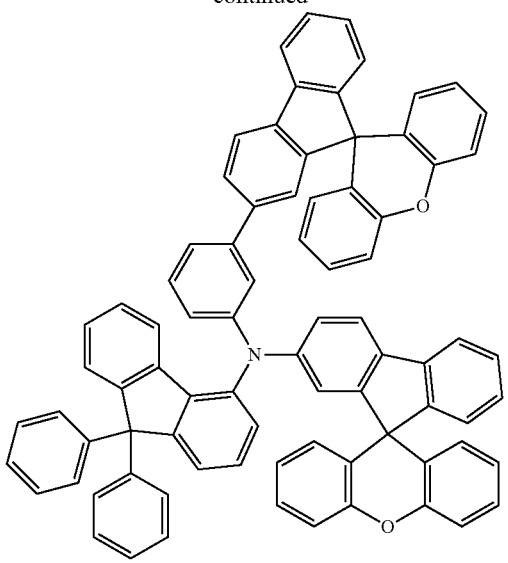
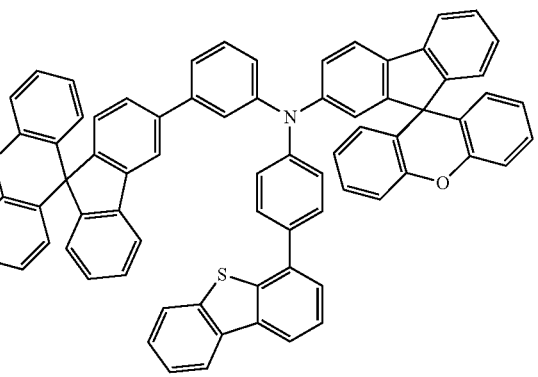
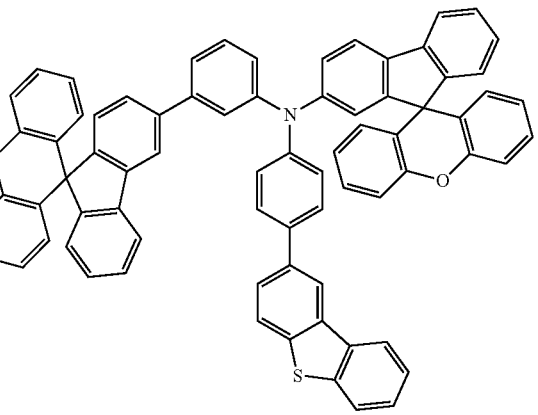
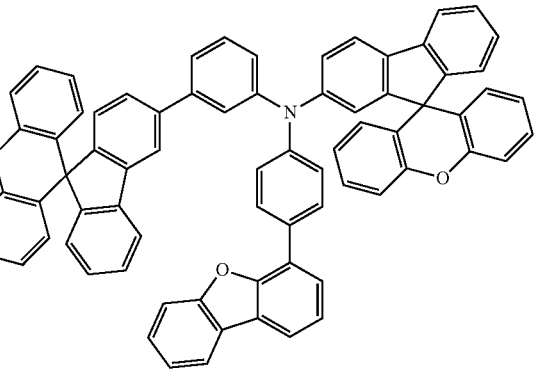

457
-continued
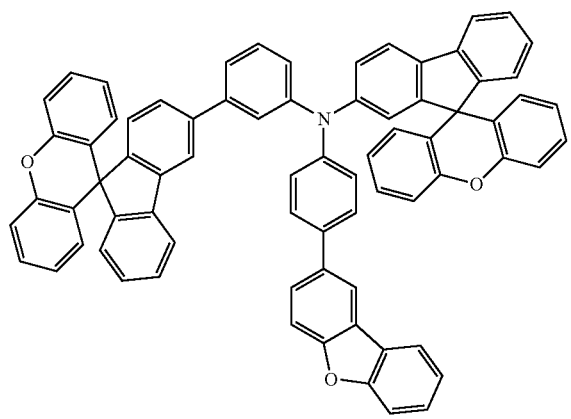
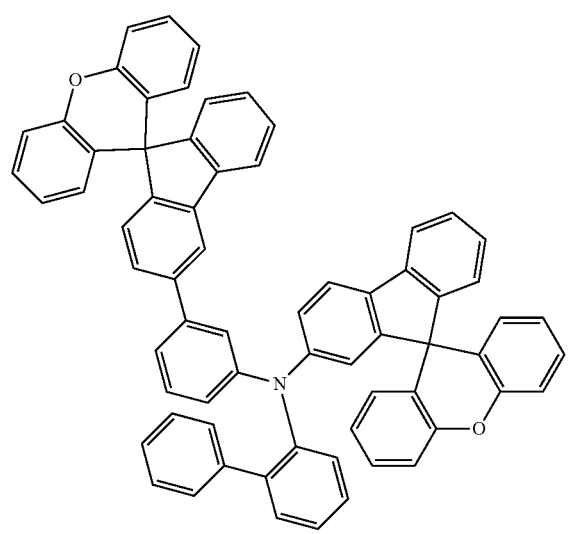
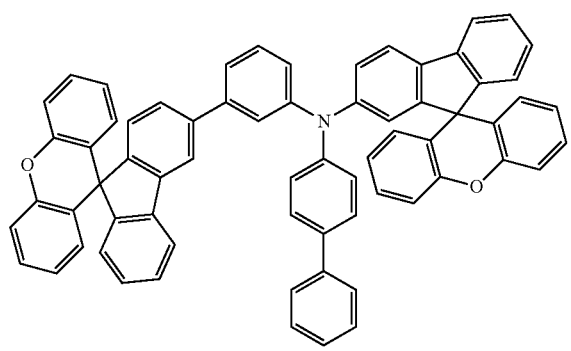
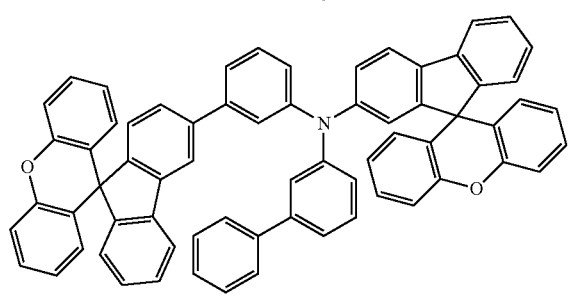
458
-continued
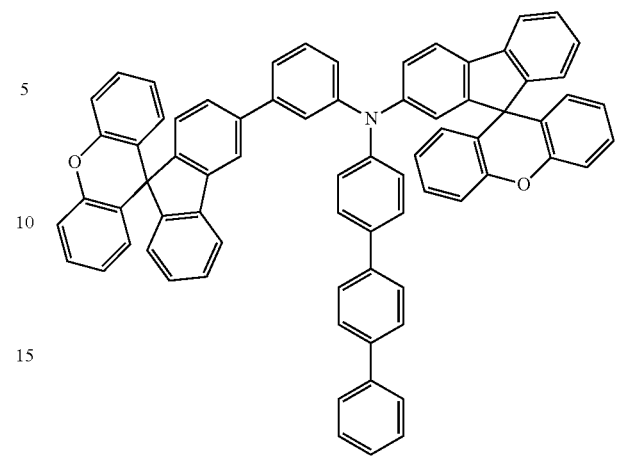
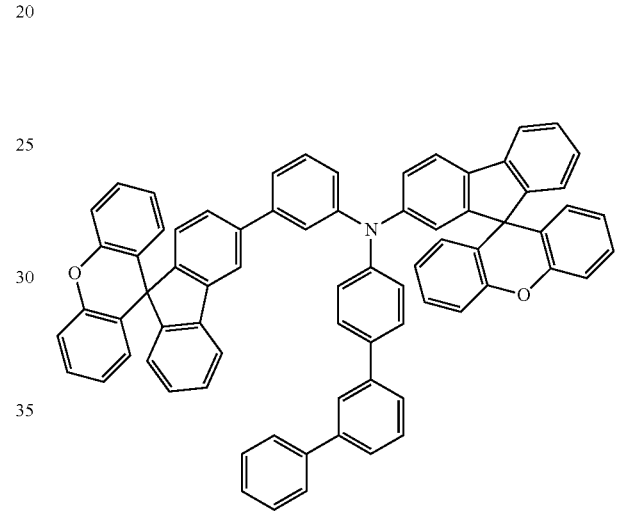
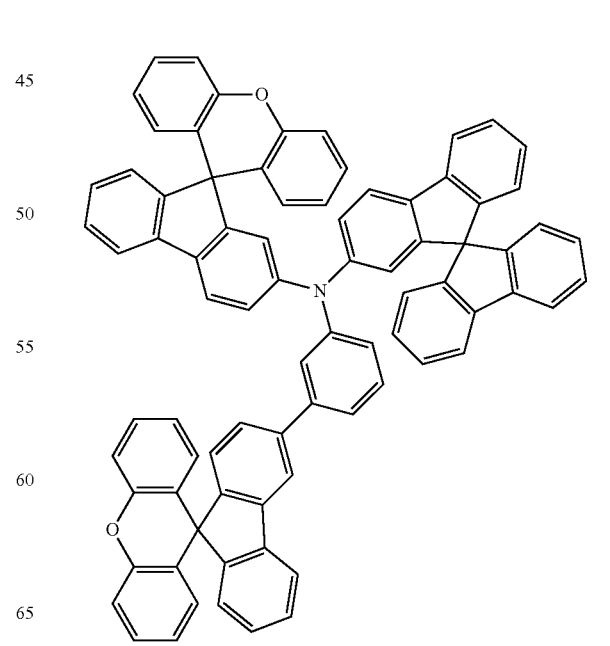

459
-continued
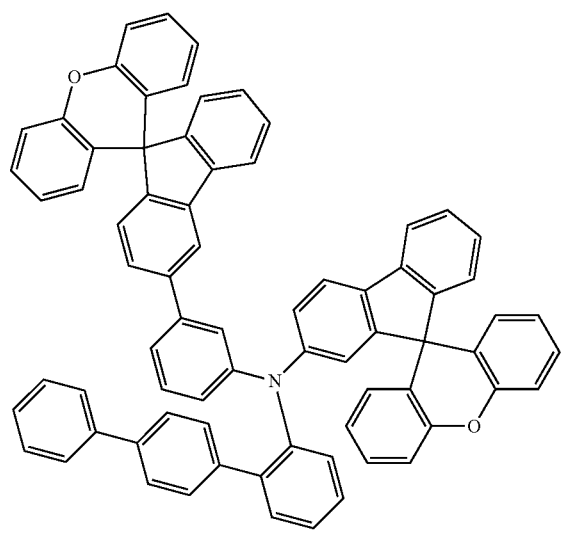
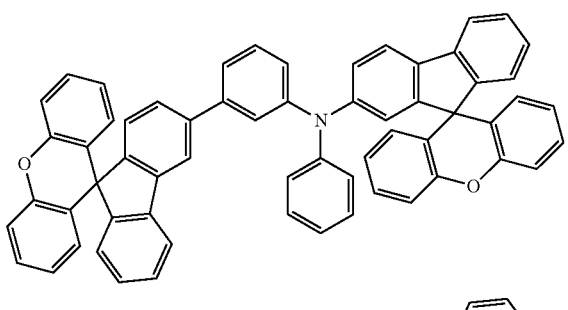
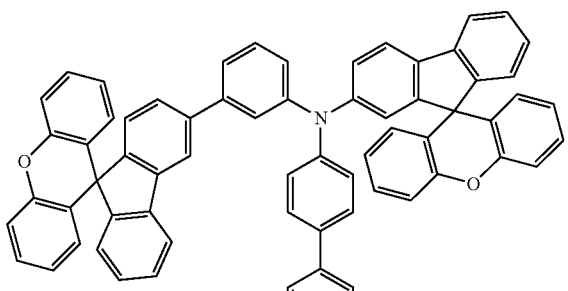
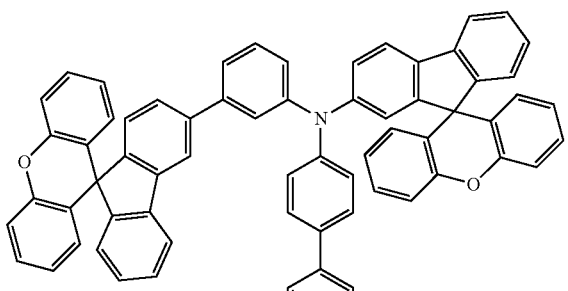
460
-continued
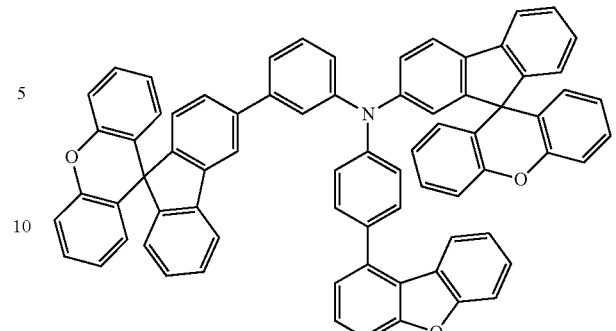
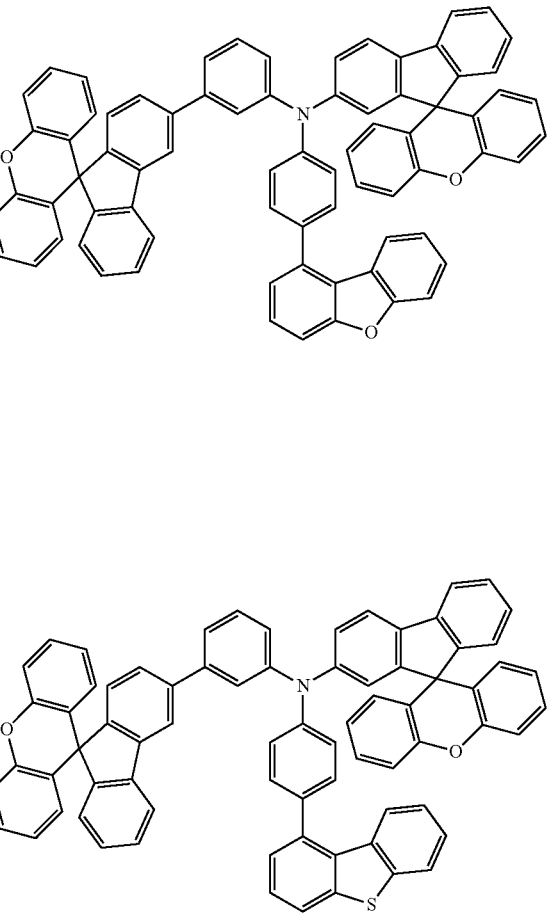

461
-continued
462
-continued
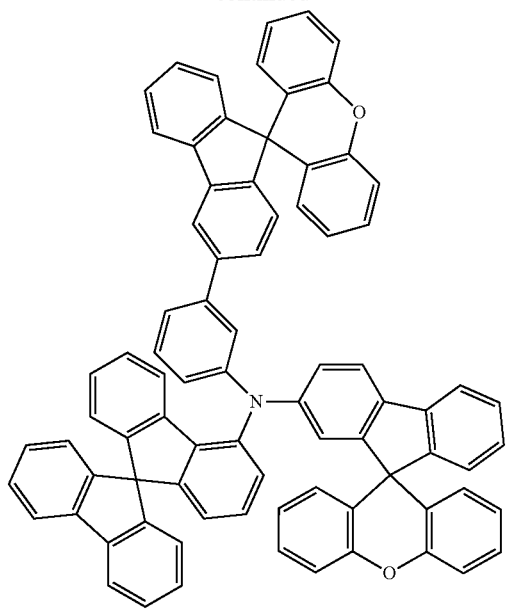
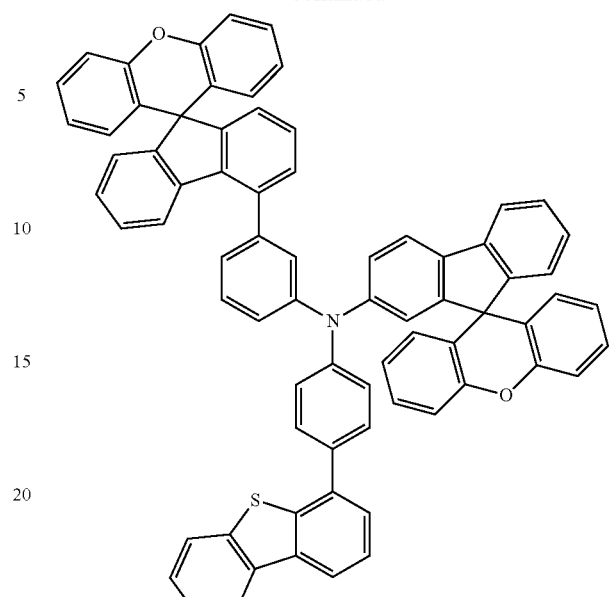
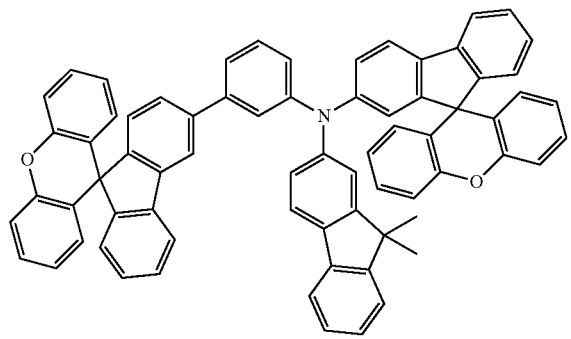
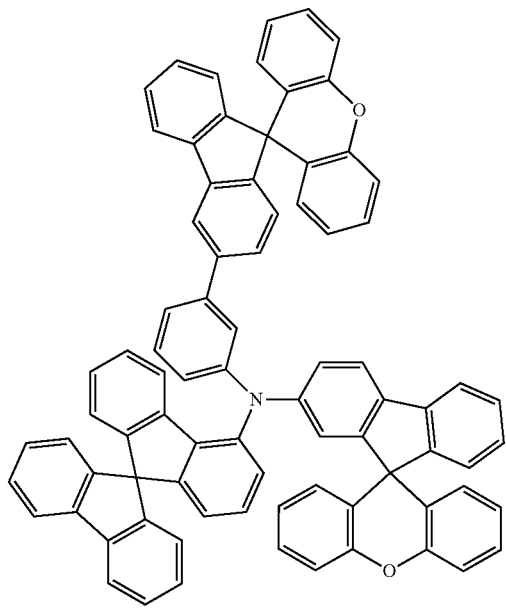
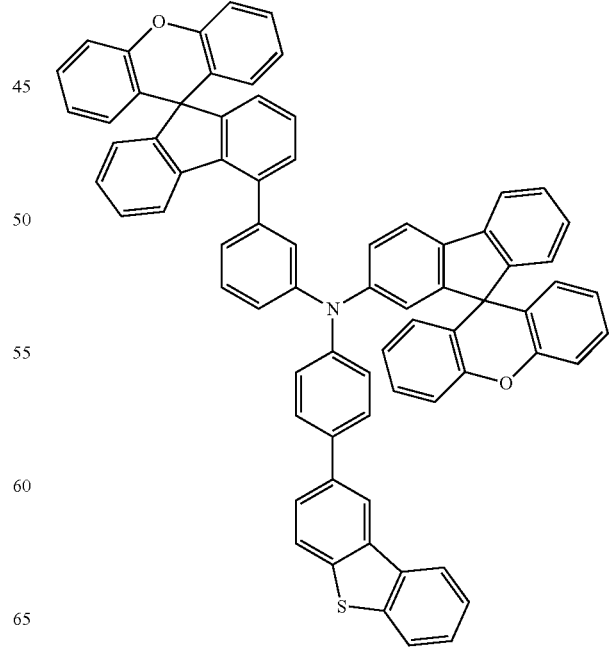

463
-continued
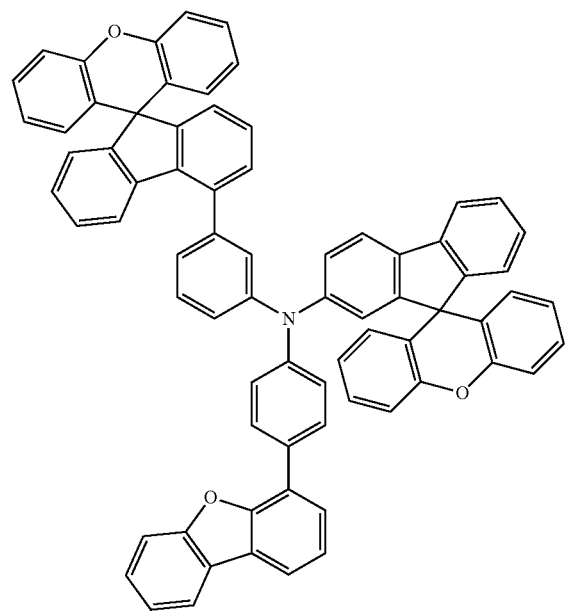
464
-continued
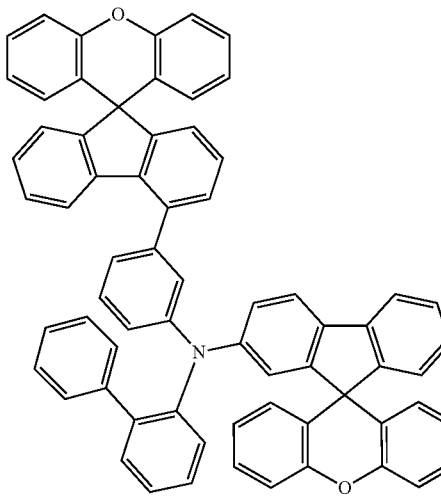
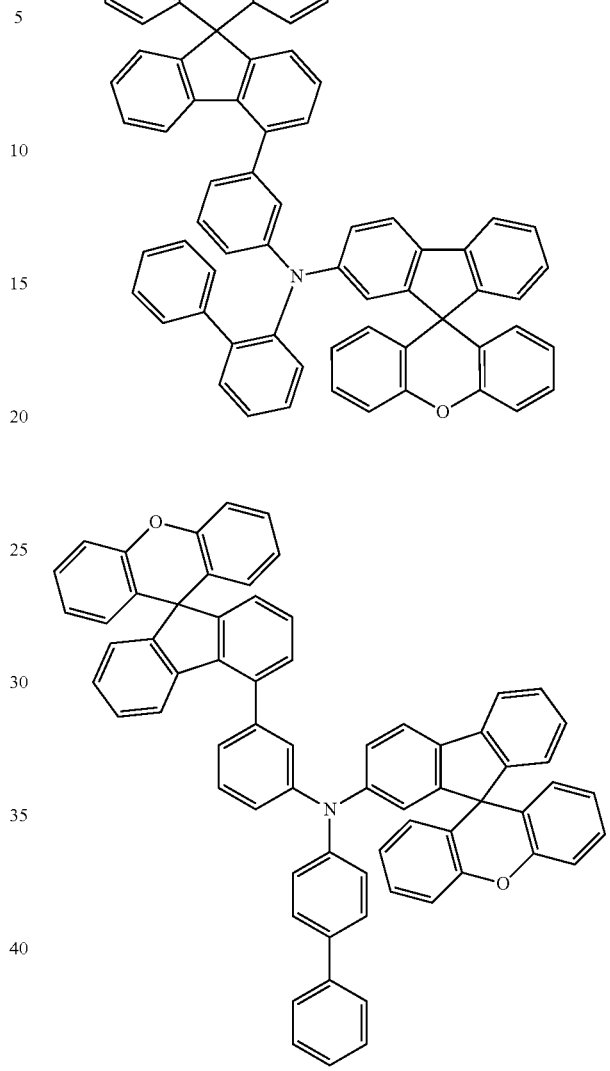
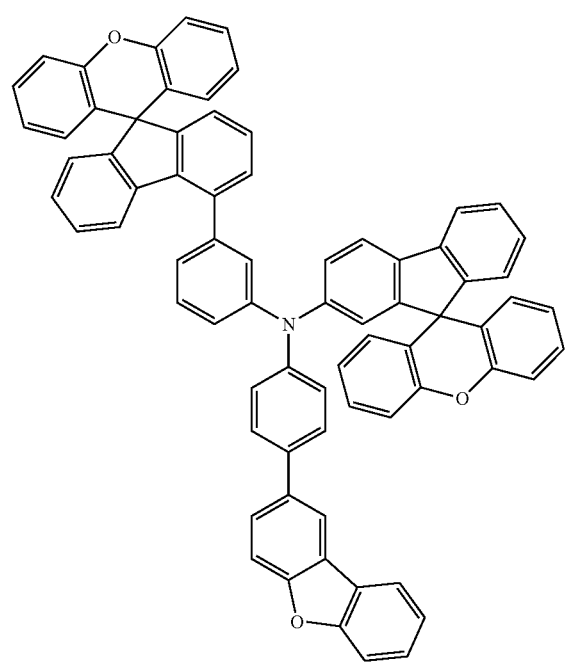
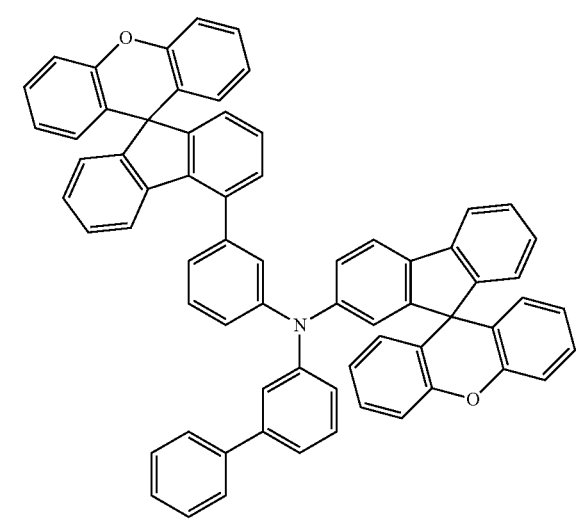

465
-continued
466
-continued
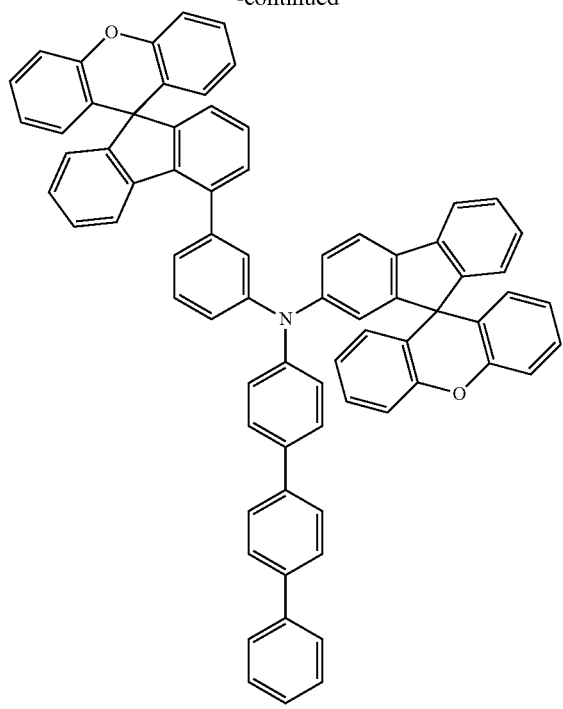
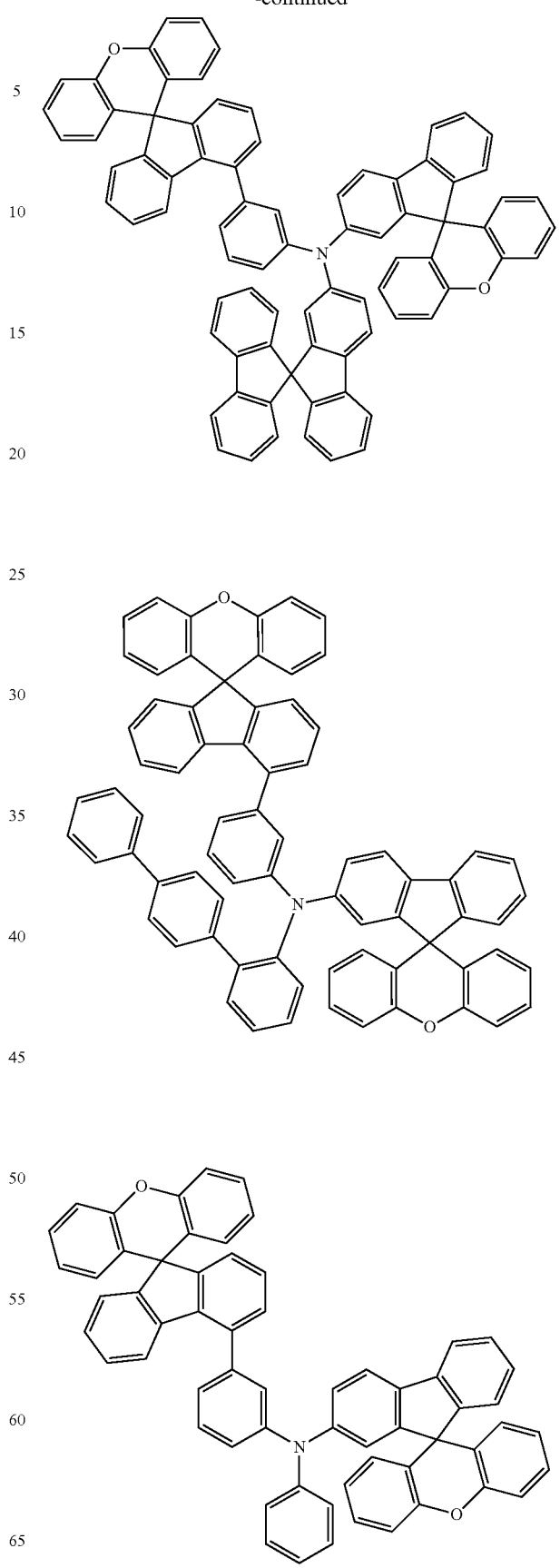

467
-continued
468
-continued
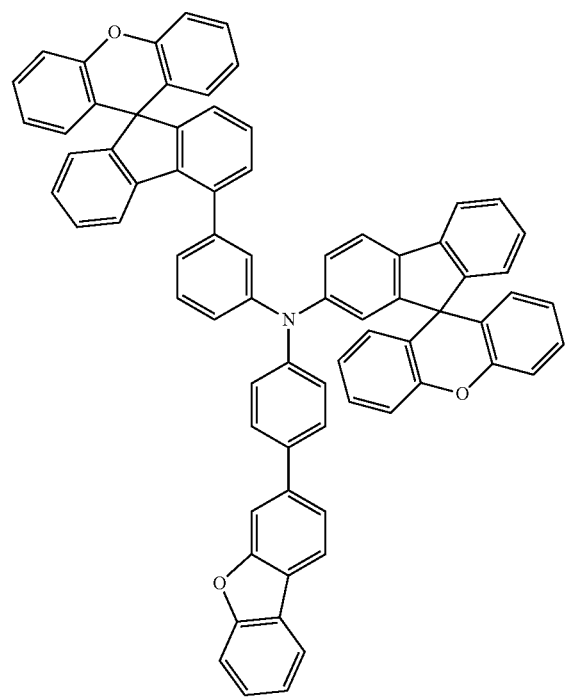
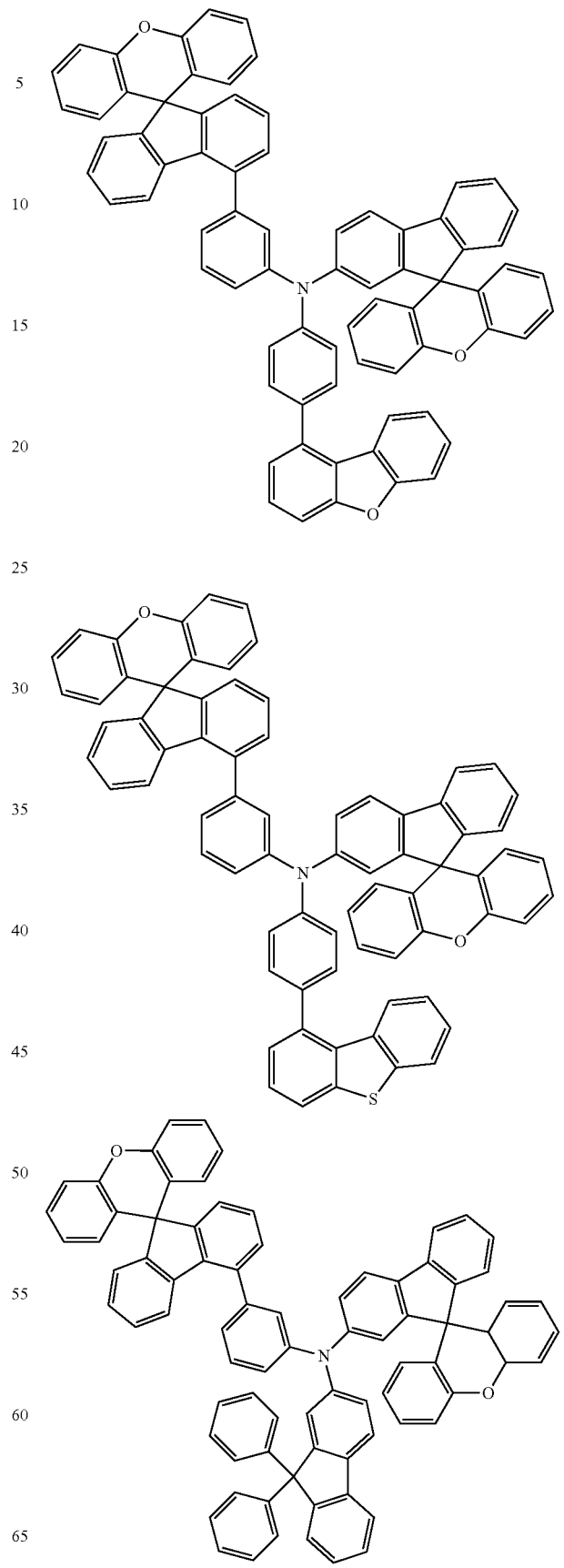

469
-continued
470
-continued
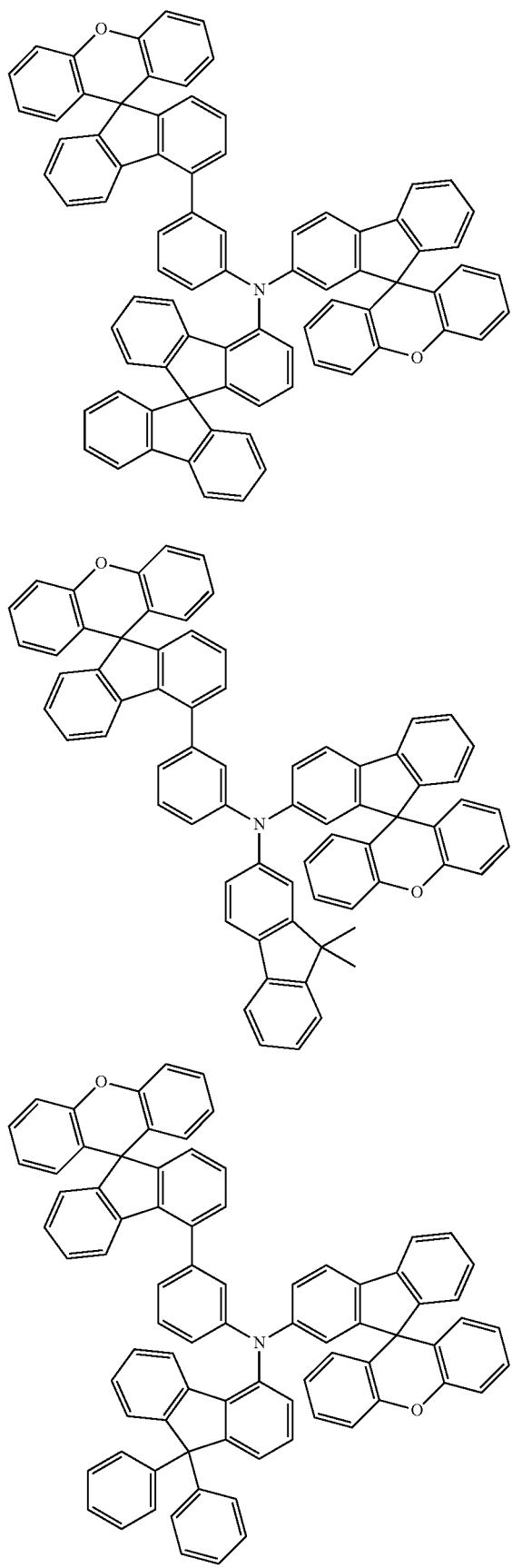 [SMILES: c1cc(-c2cccc3c2-c2ccccc2C32c3ccccc3Oc3ccccc32)cc(N(c2ccc3c(c2)C2(c4ccccc4Oc4ccccc42)c2ccccc2-3)c2cccc3c2-c2ccccc2C32c3ccccc3-c3ccccc32)c1 ; CC1(C)c2ccccc2-c2ccc(N(c3cccc(-c4cccc5c4-c4ccccc4C54c5ccccc5Oc5ccccc54)c3)c3ccc4c(c3)C3(c5ccccc5Oc5ccccc53)c3ccccc3-4)cc21 ; c1ccc(C2(c3ccccc3)c3ccccc3-c3c(N(c4cccc(-c5cccc6c5-c5ccccc5C65c6ccccc6Oc6ccccc65)c4)c4ccc5c(c4)C4(c6ccccc6Oc6ccccc64)c4ccccc4-5)cccc32)cc1]
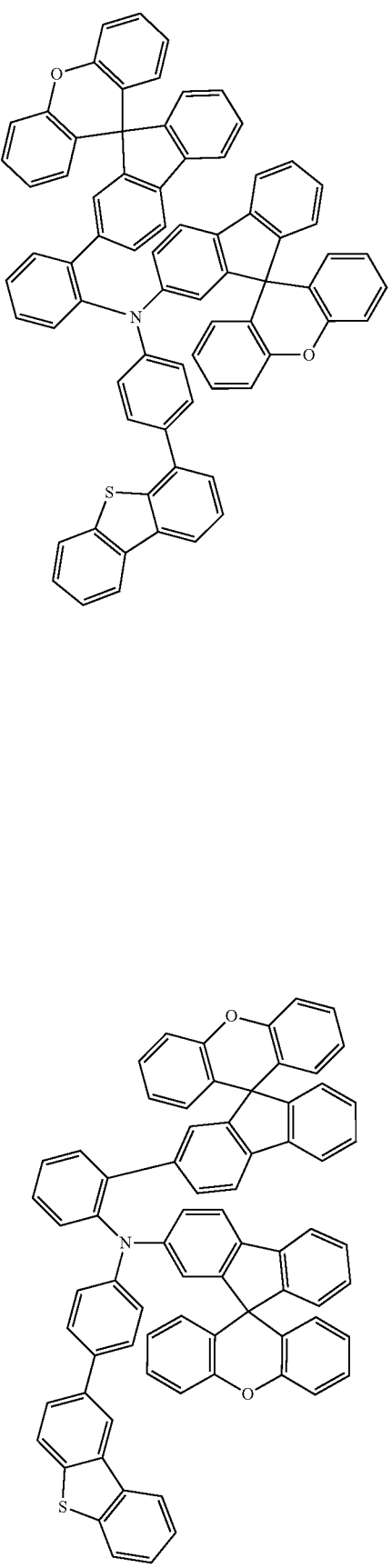

471
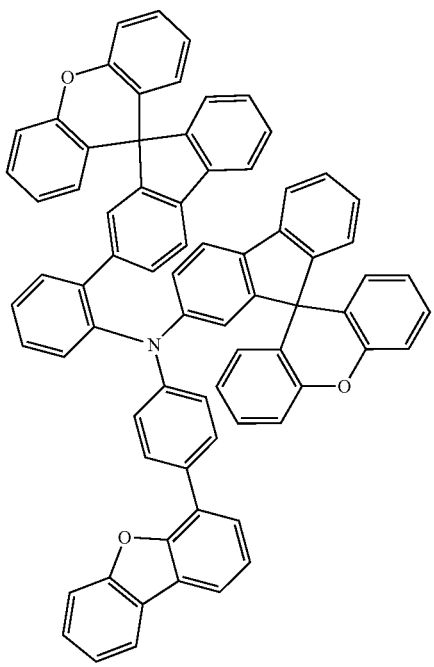
472
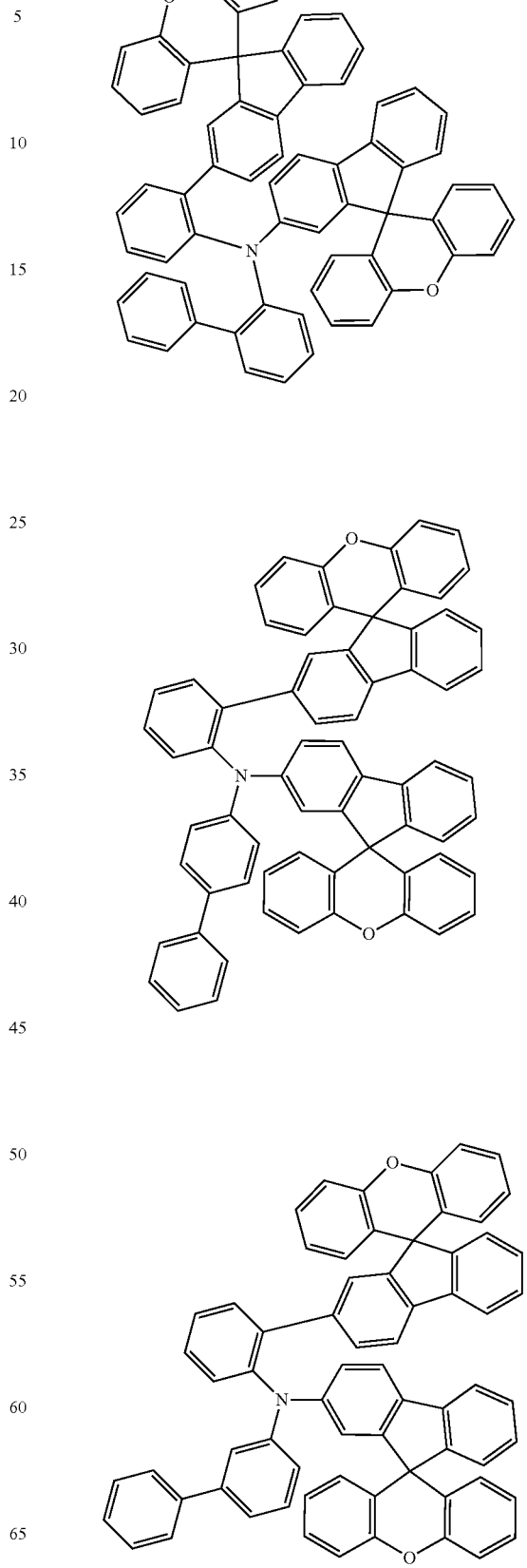

473
-continued
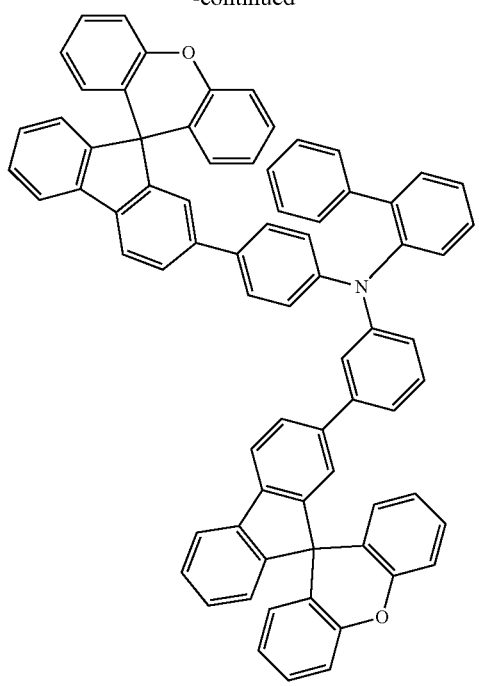
474
-continued
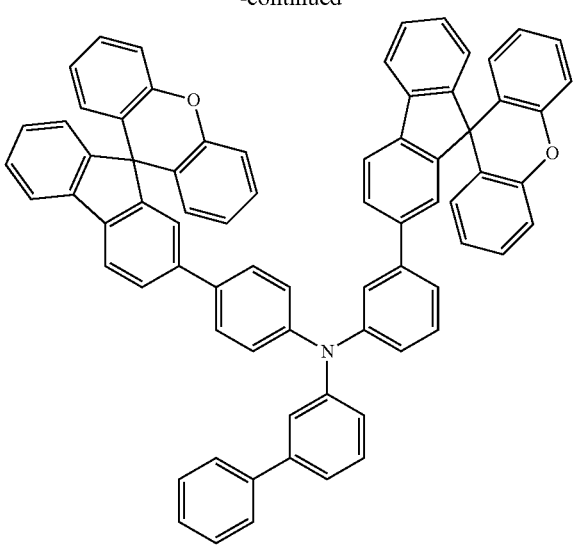
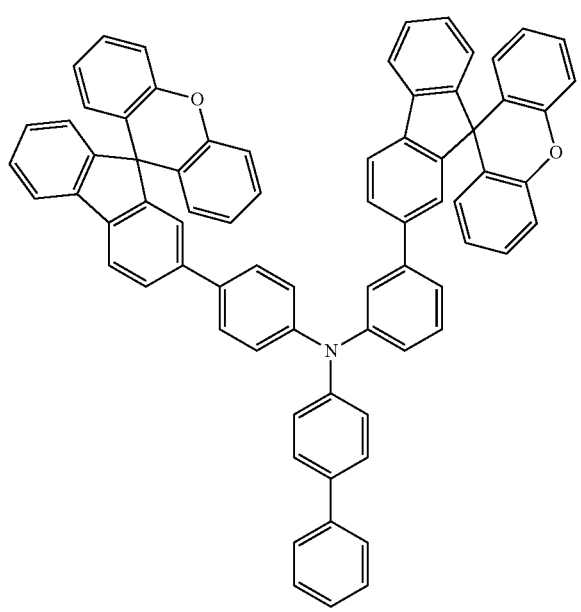
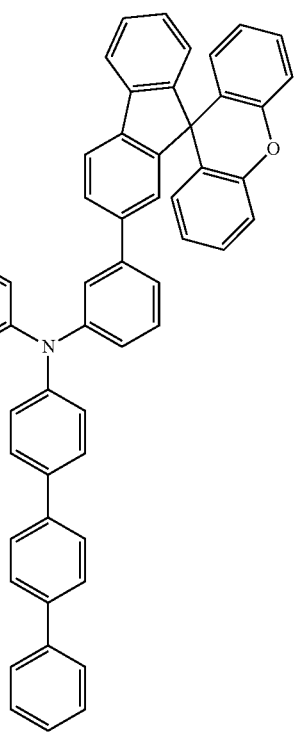

475
-continued
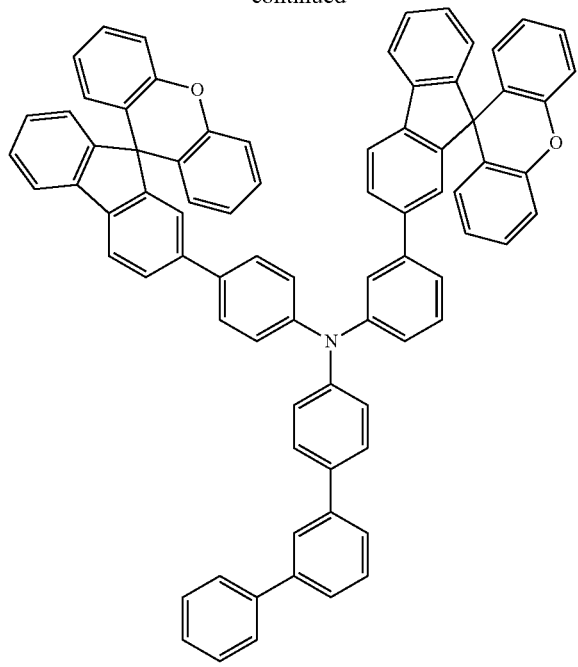
476
-continued
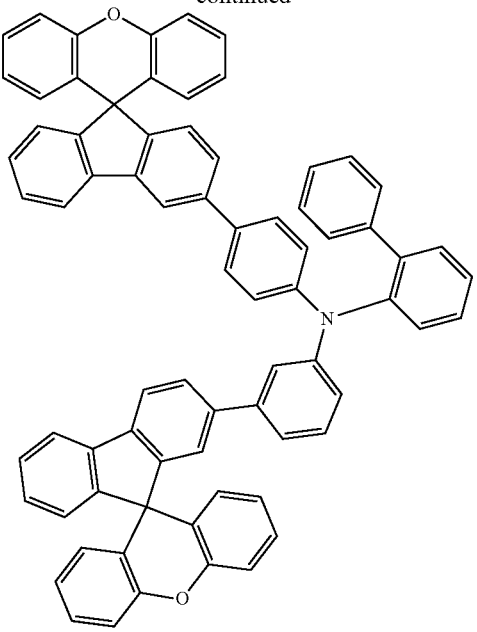
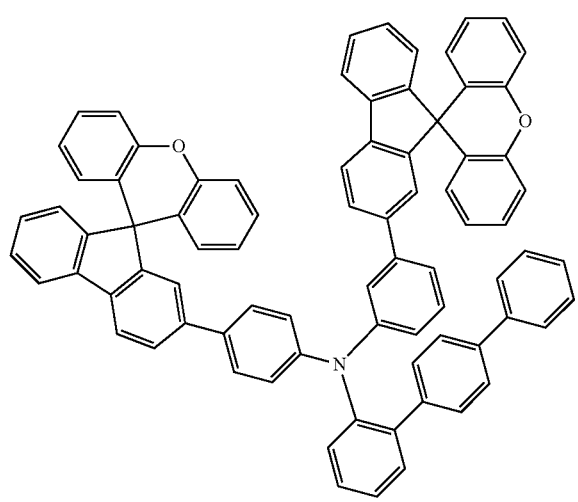
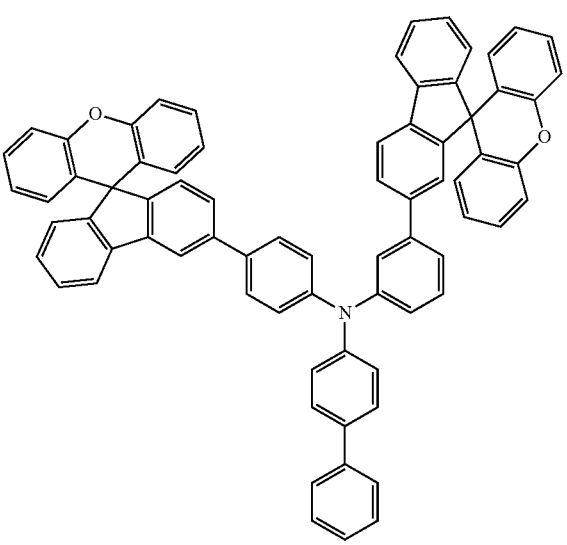

477
-continued
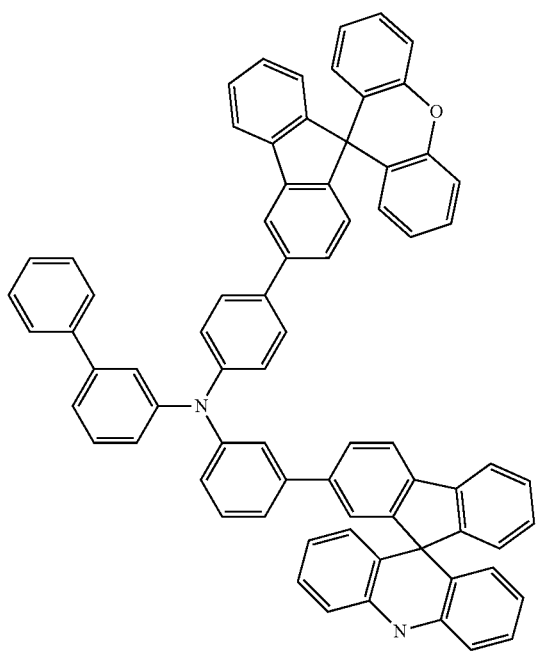
478
-continued
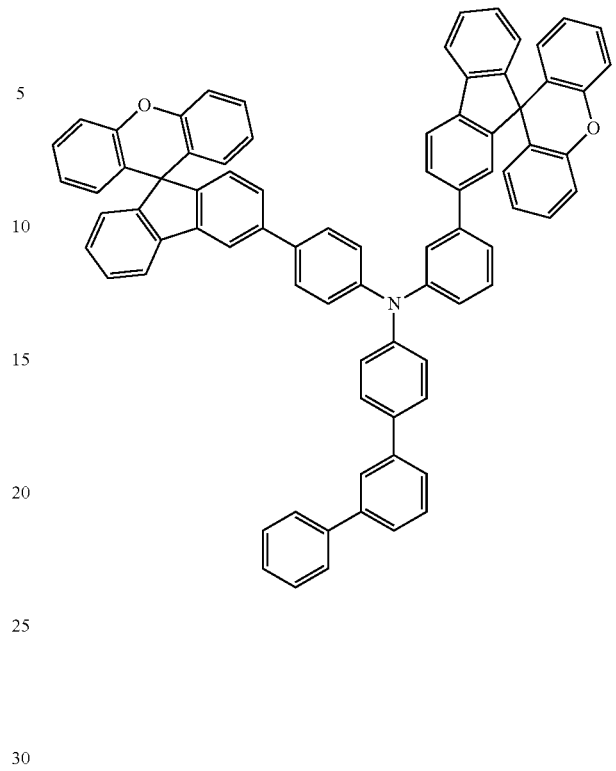
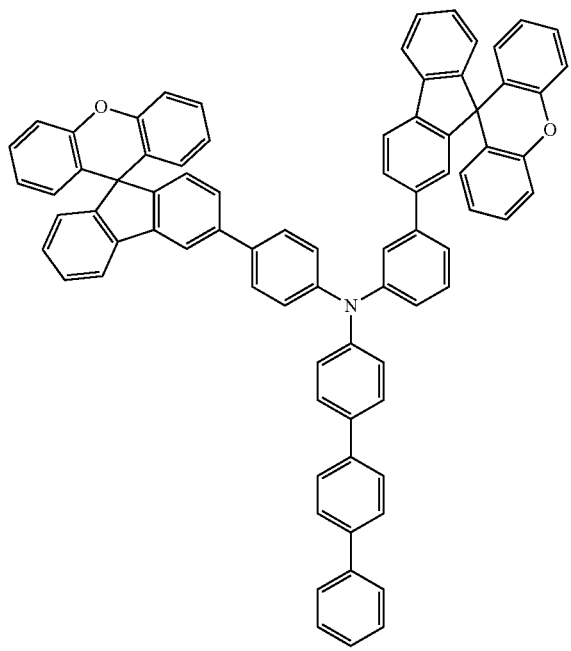
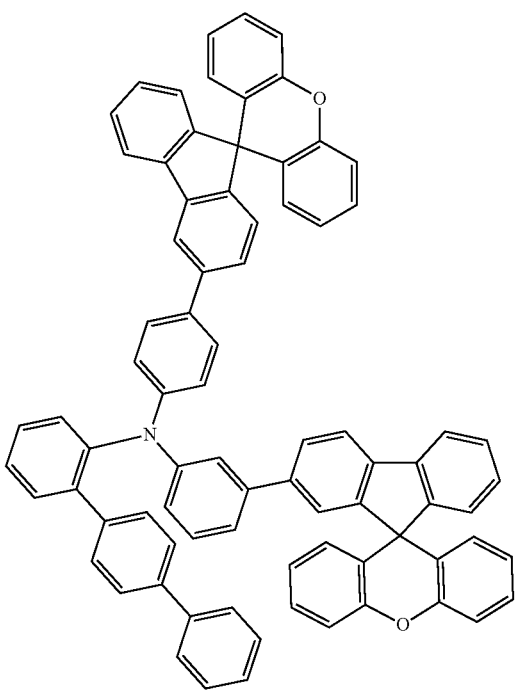

479
-continued
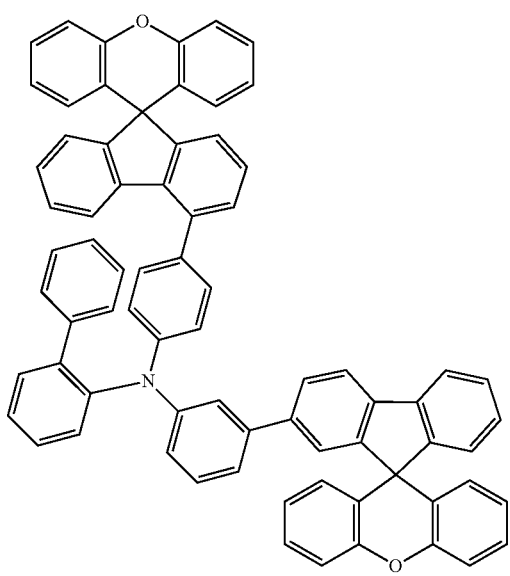
480
-continued
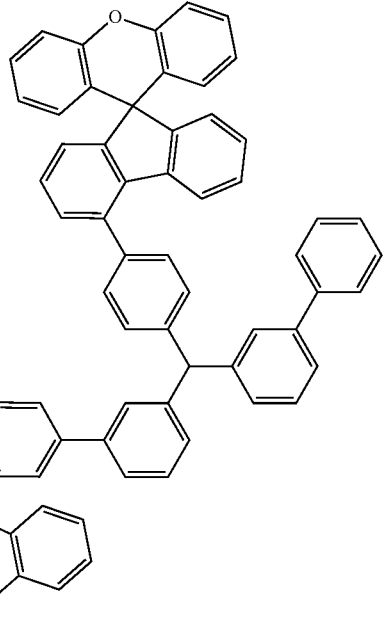
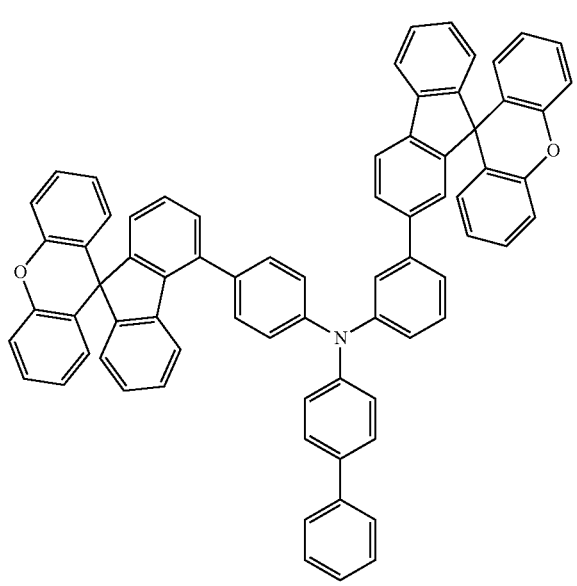
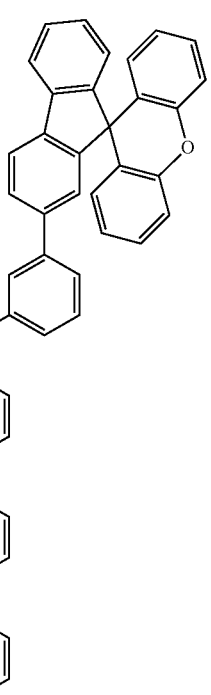

481
-continued
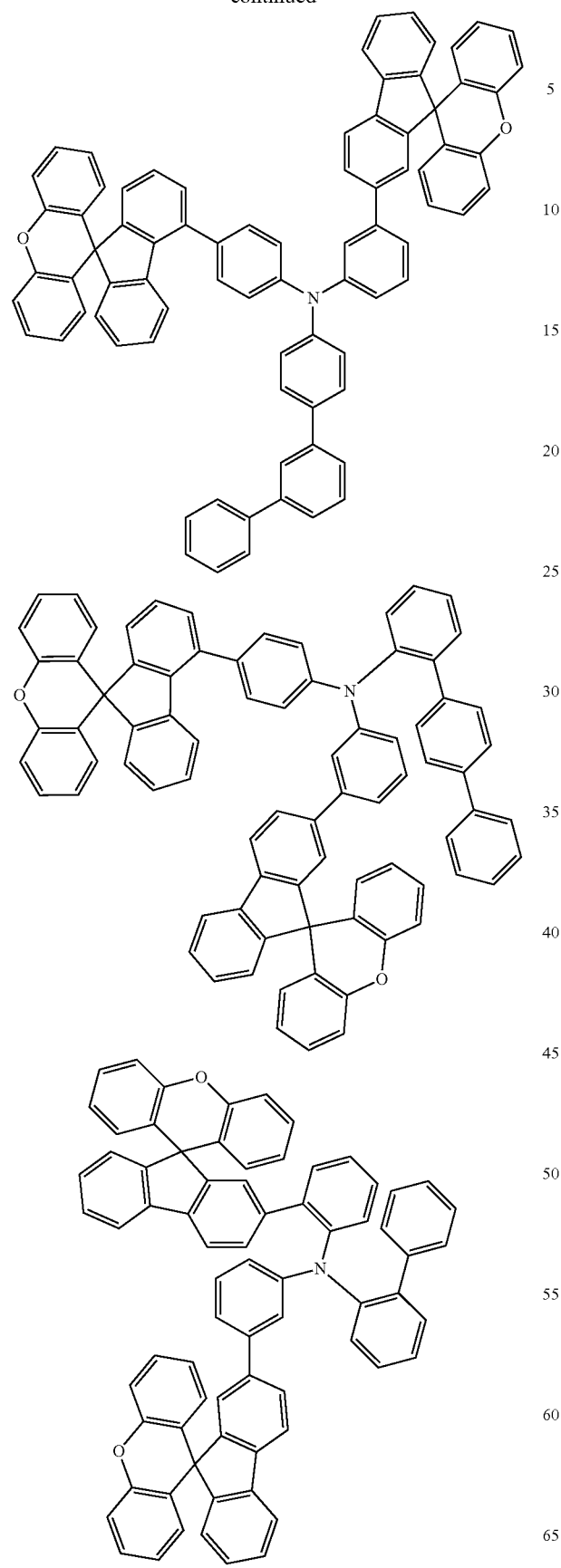
482
-continued
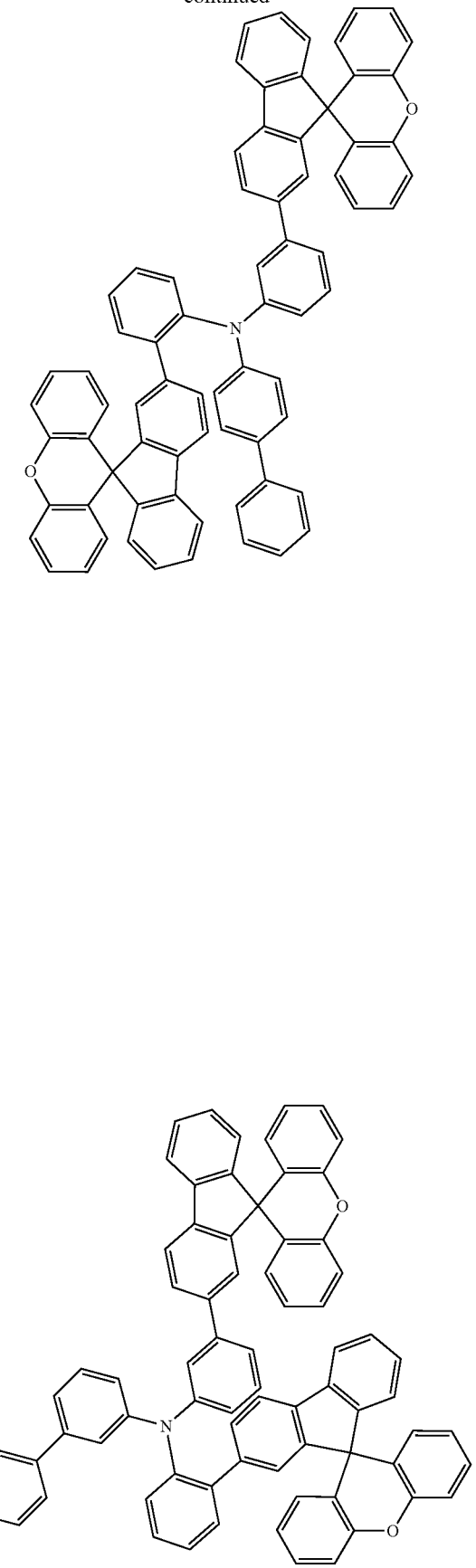

483
-continued
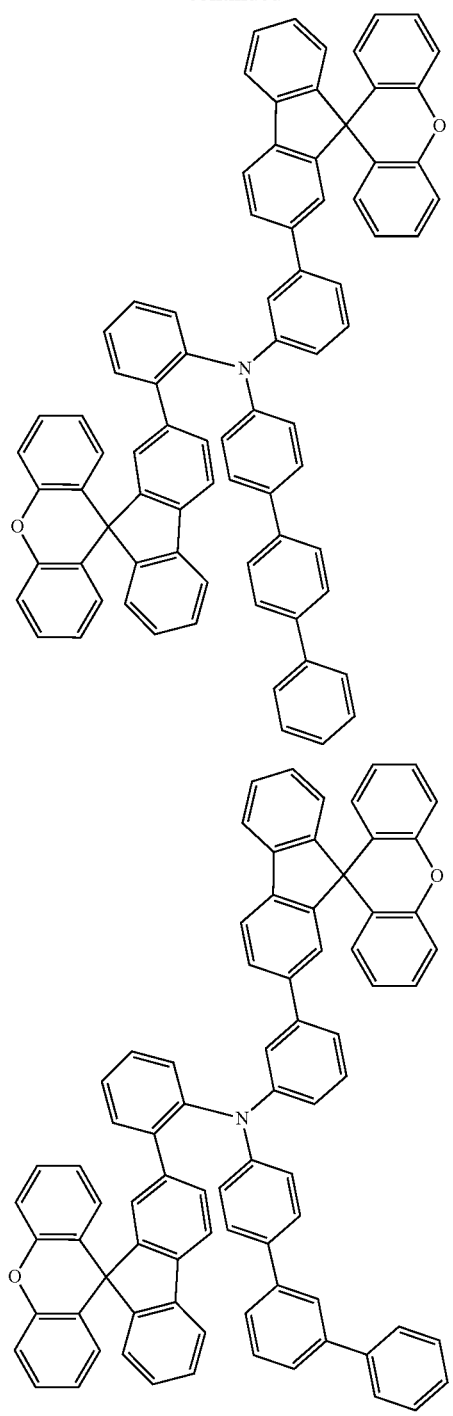
484
-continued
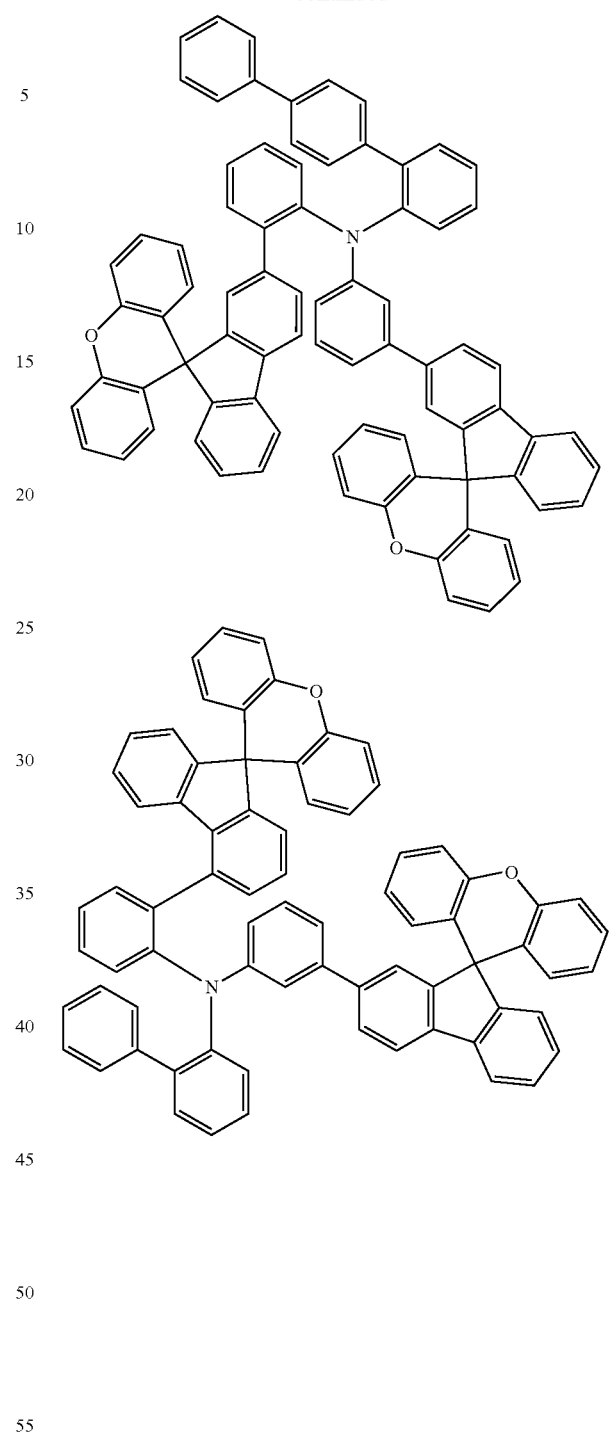

485
-continued
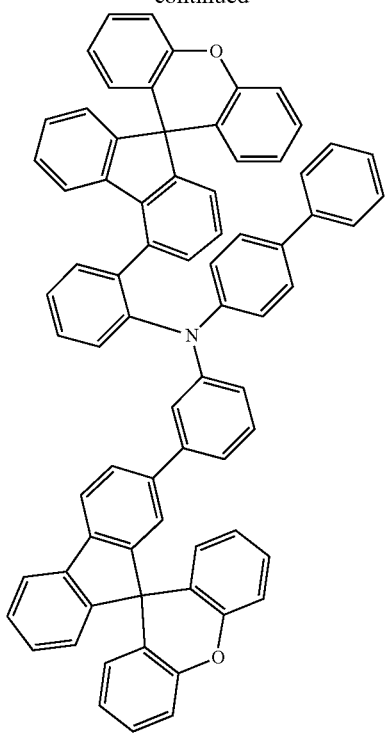
486
-continued
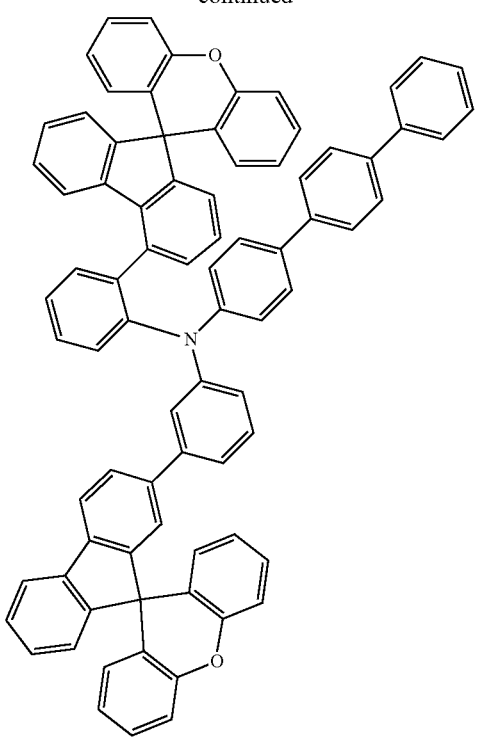
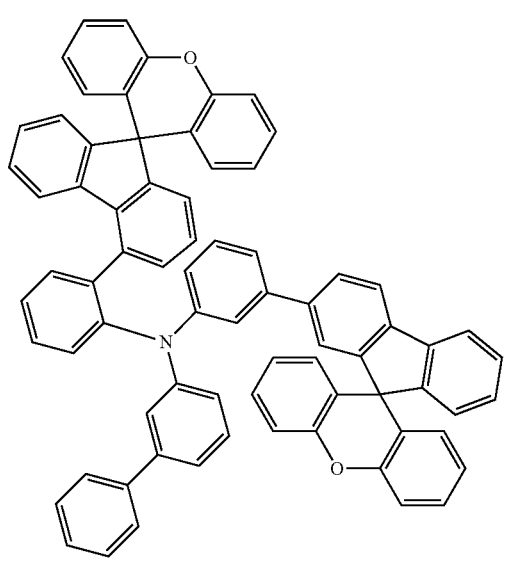

487
-continued
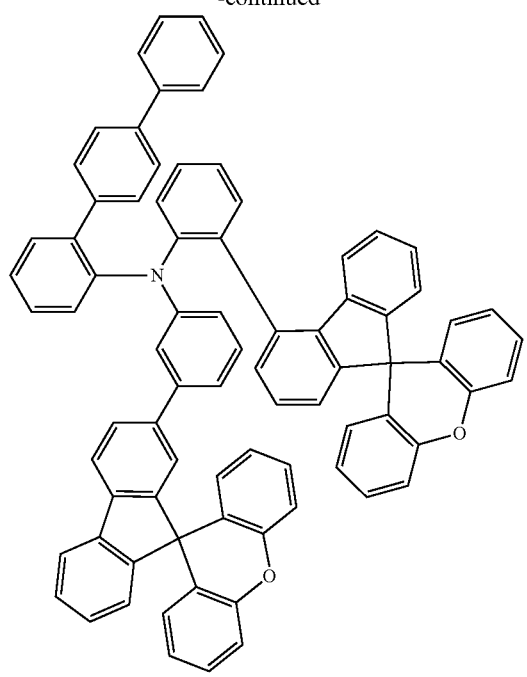
488
-continued
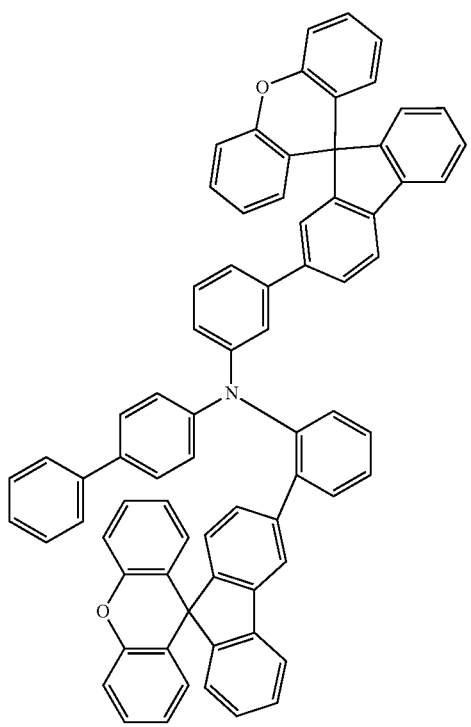
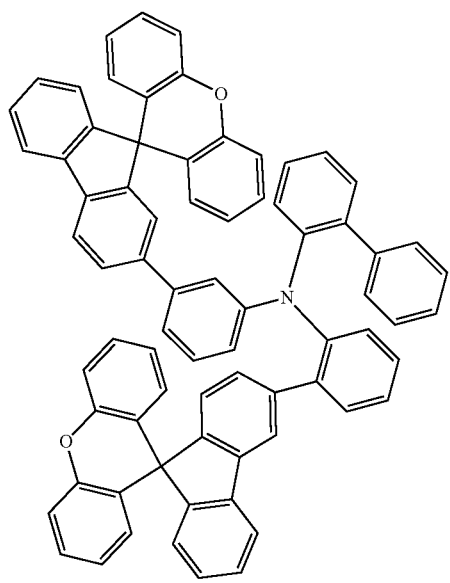
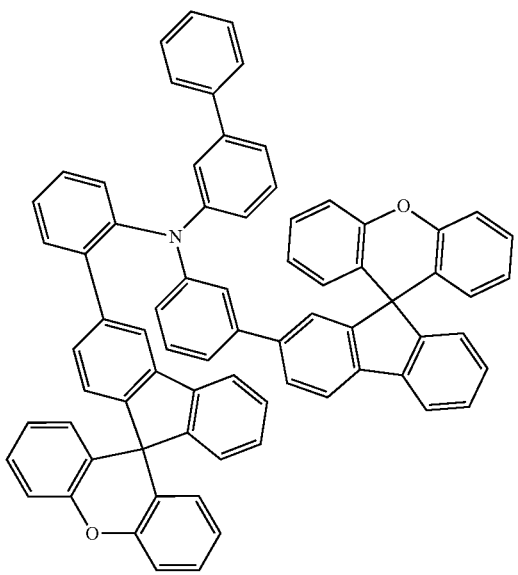

489
-continued
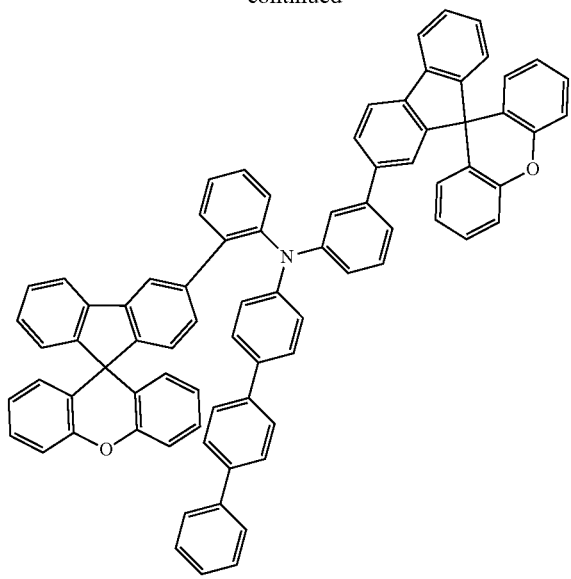
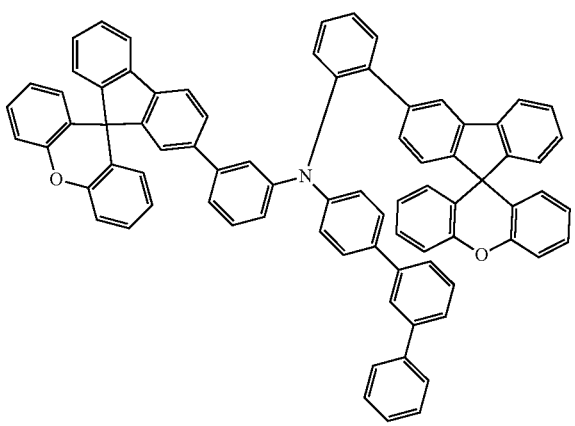
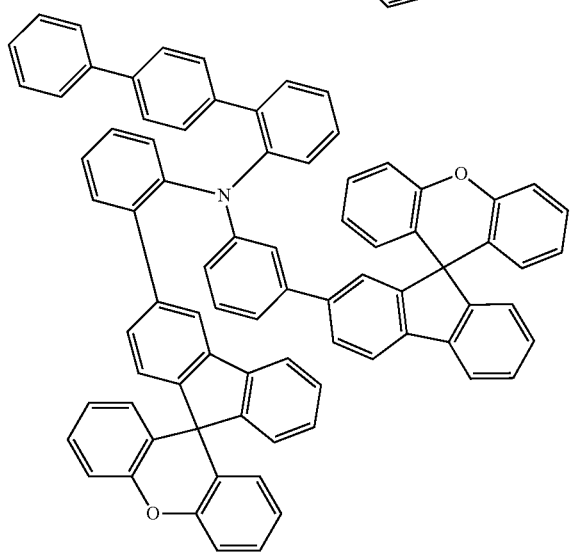
490
-continued
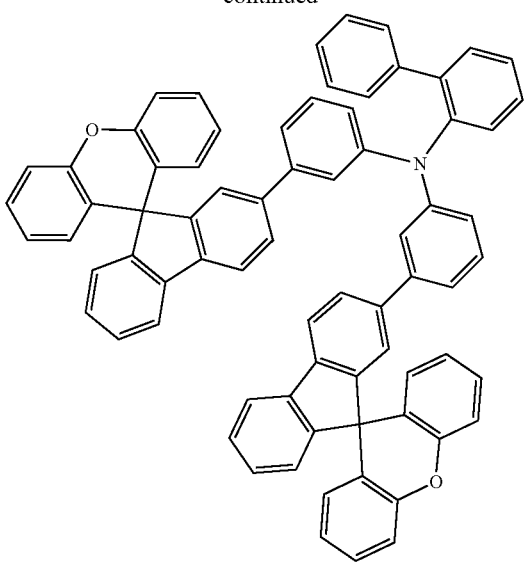
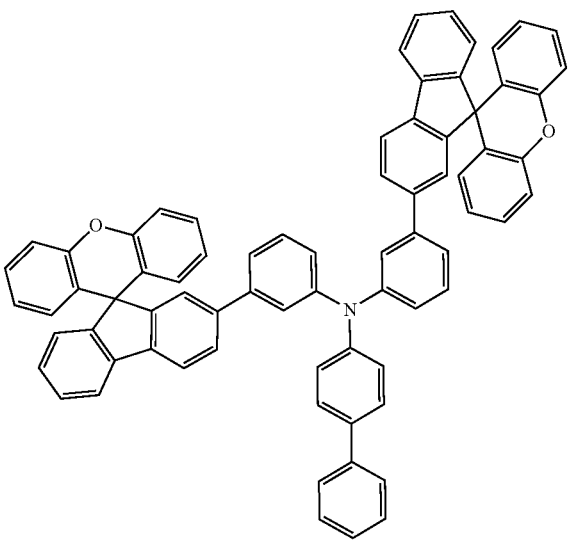

491 492
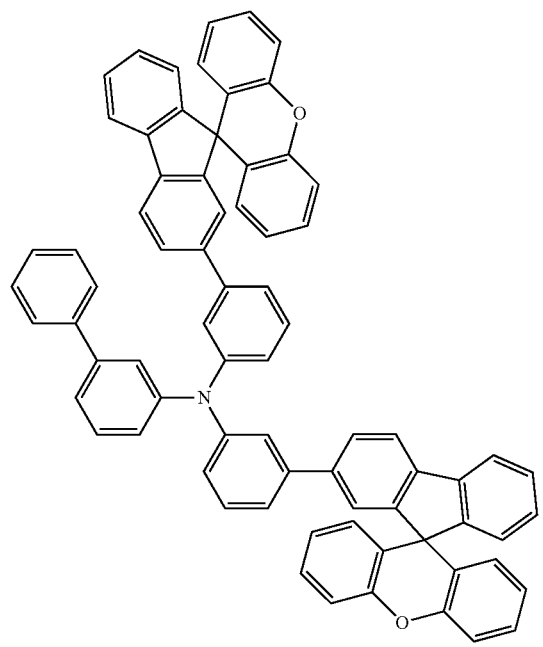
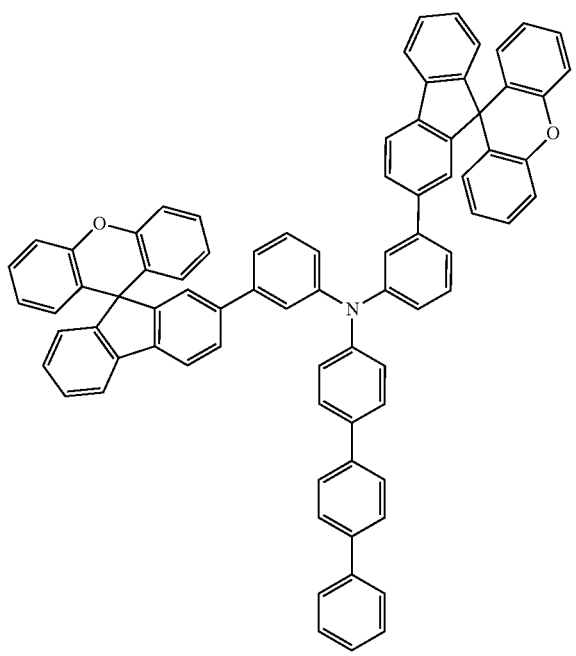
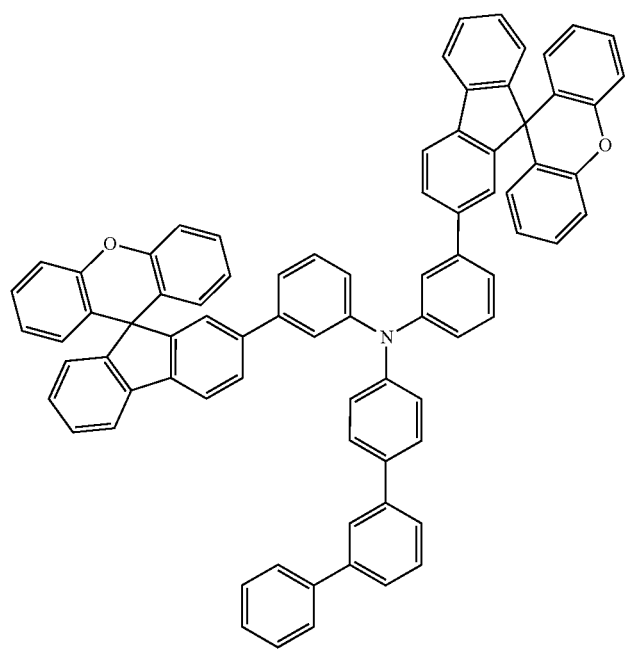
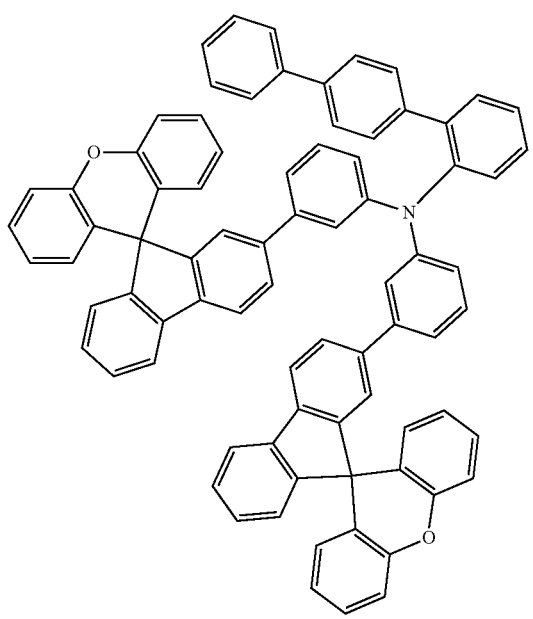

-continued
493
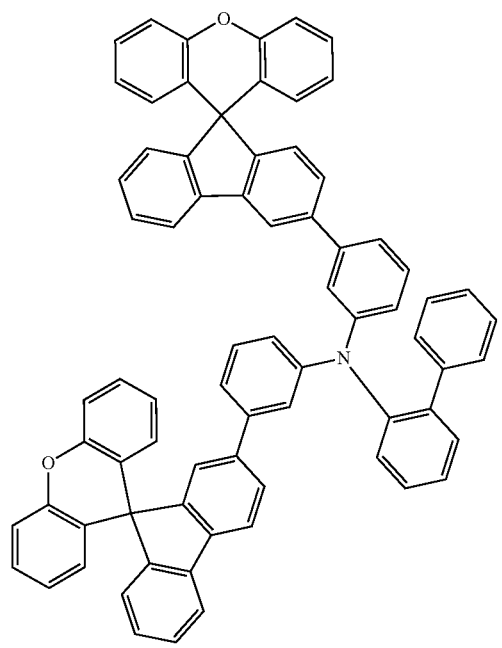
494
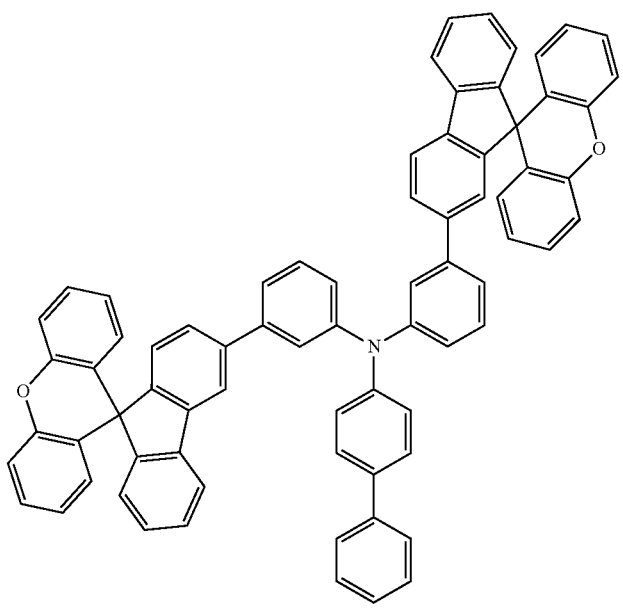
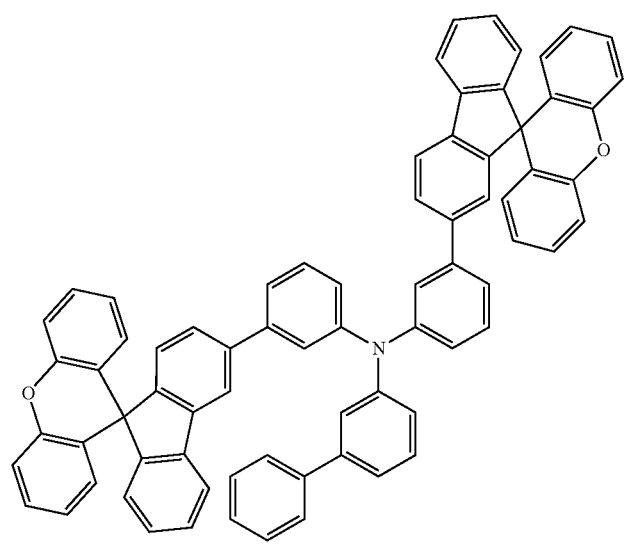

495  -continued  496
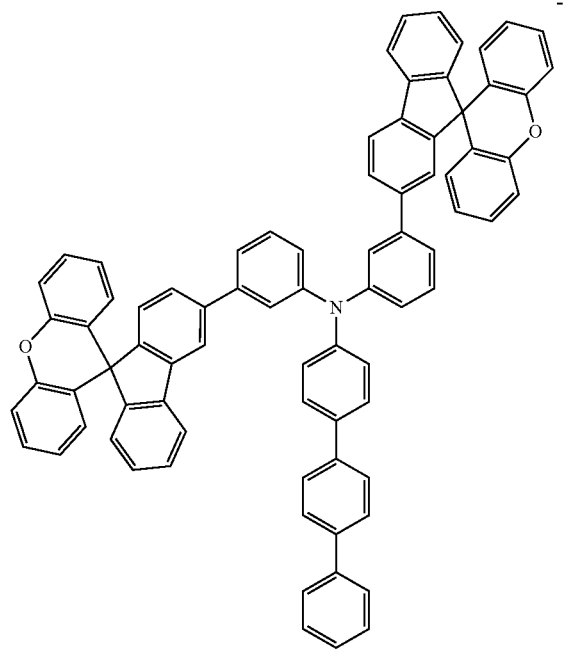
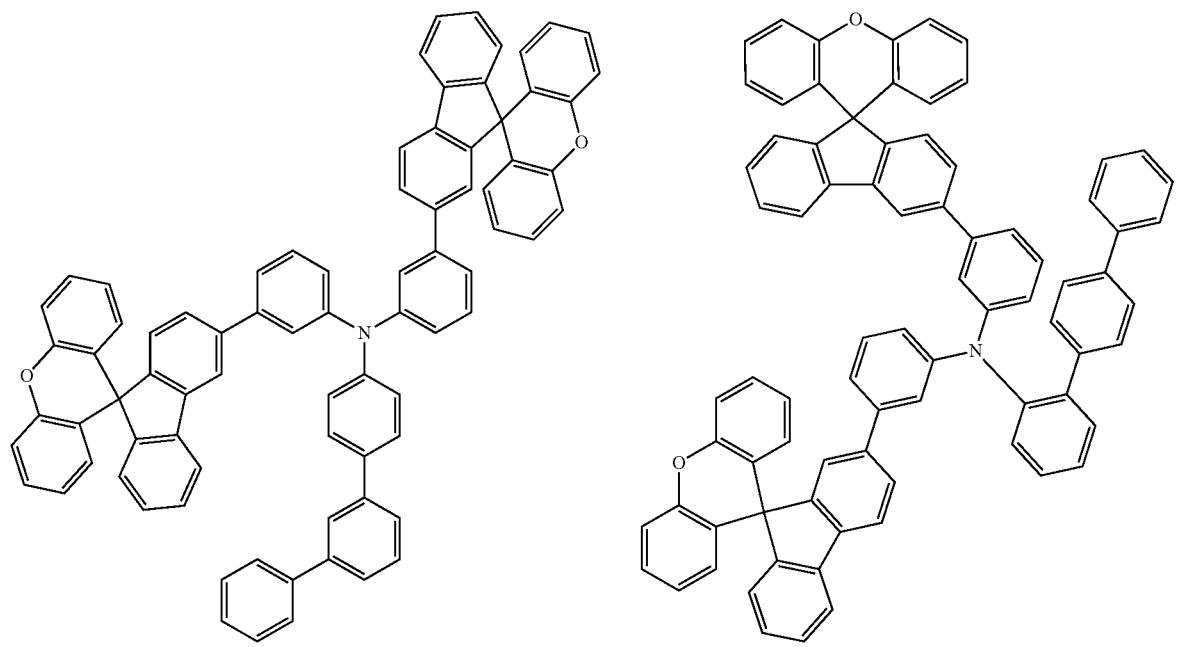

497 498
-continued
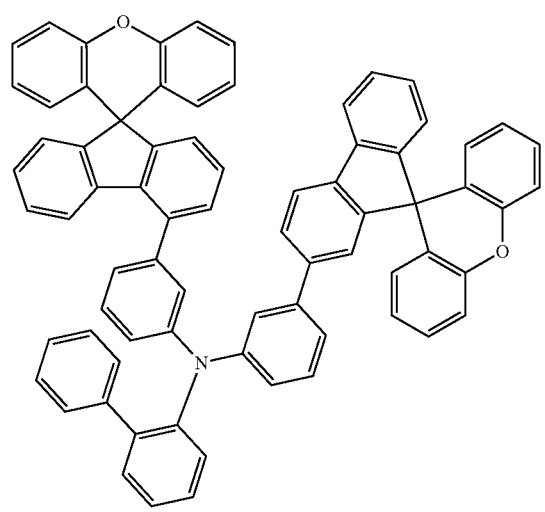
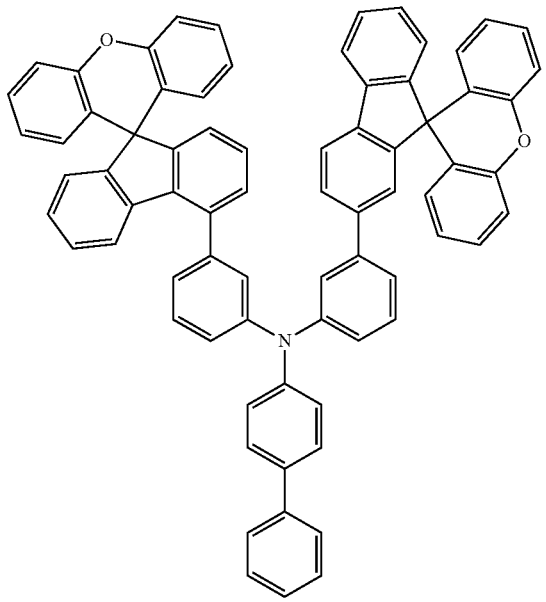
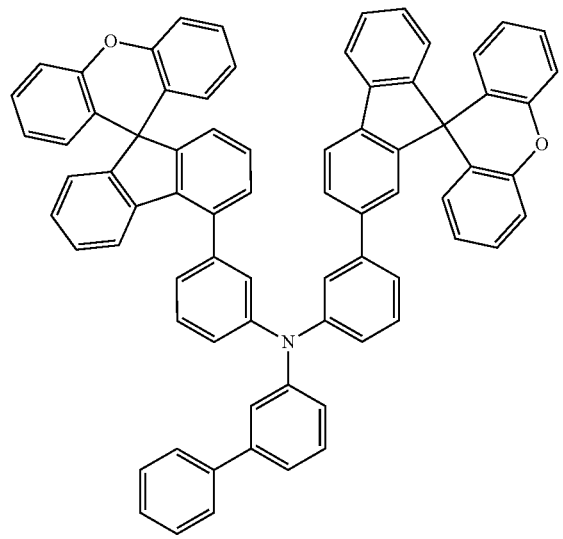
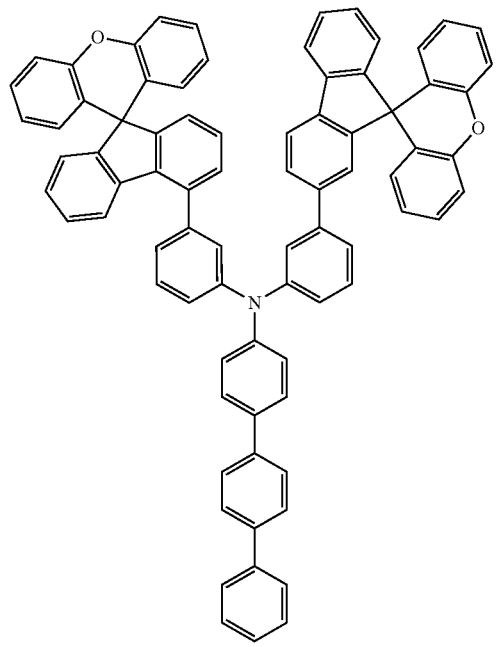

499
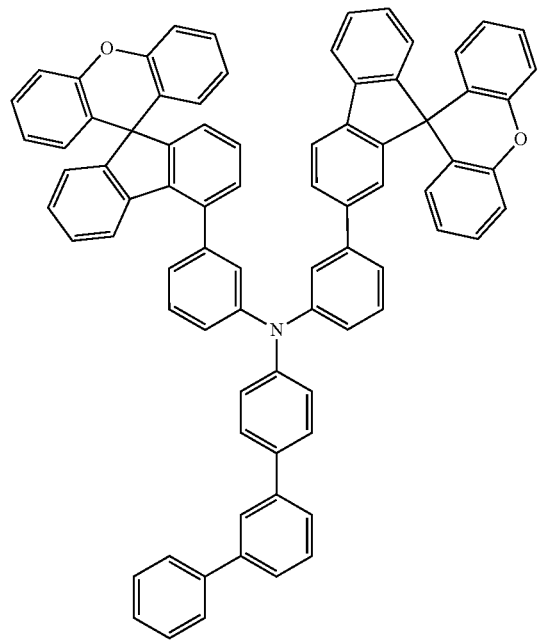
500
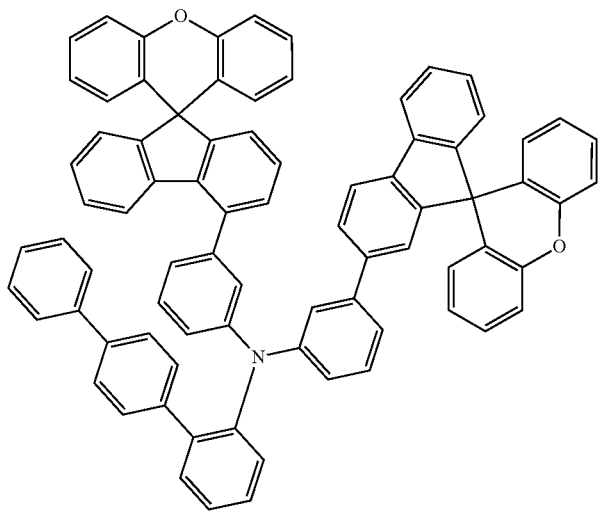
-continued
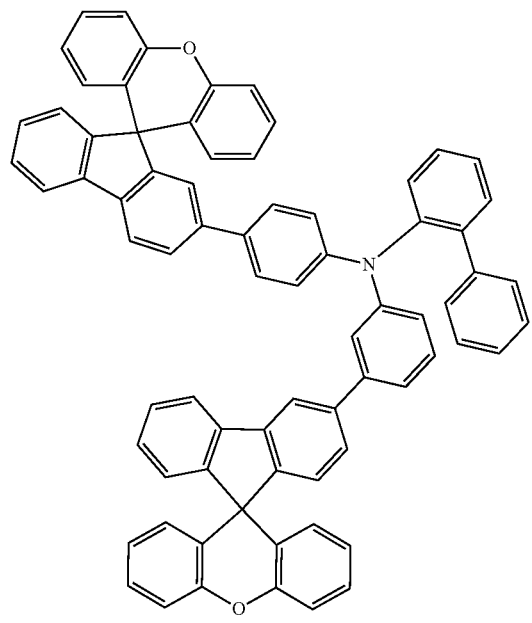
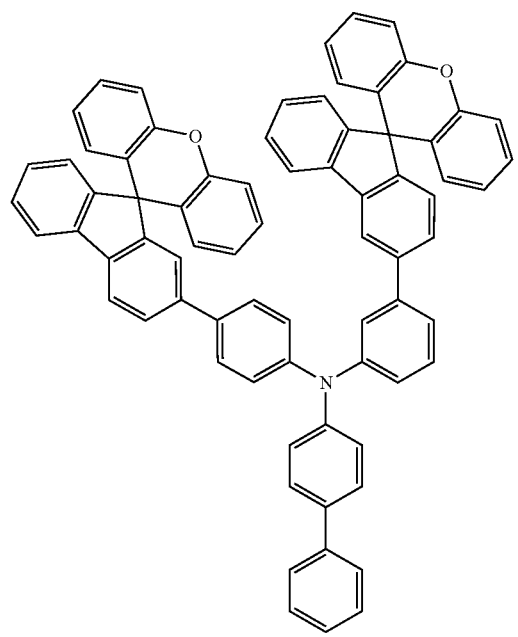

-continued
501
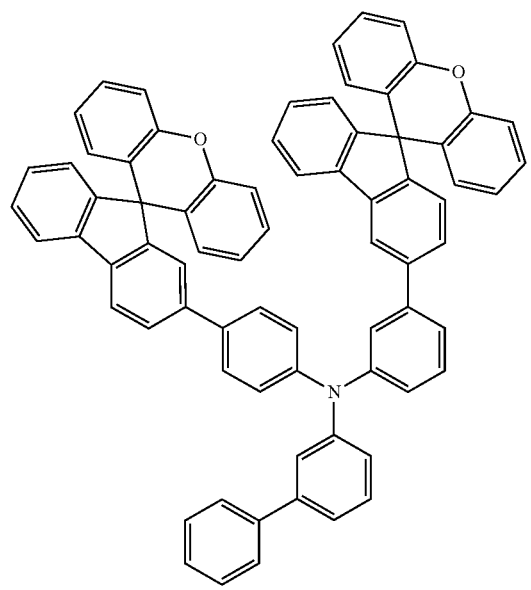
502
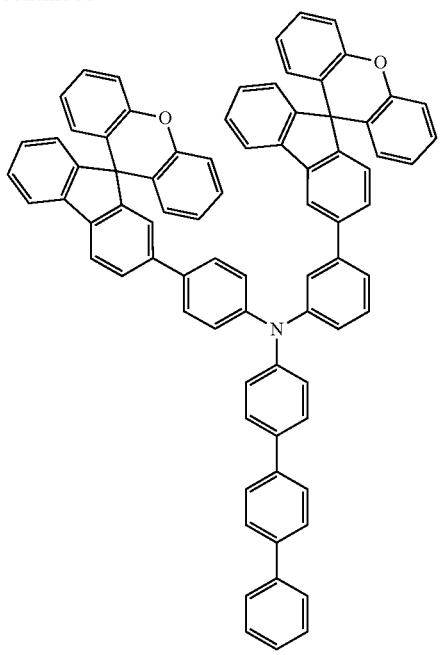
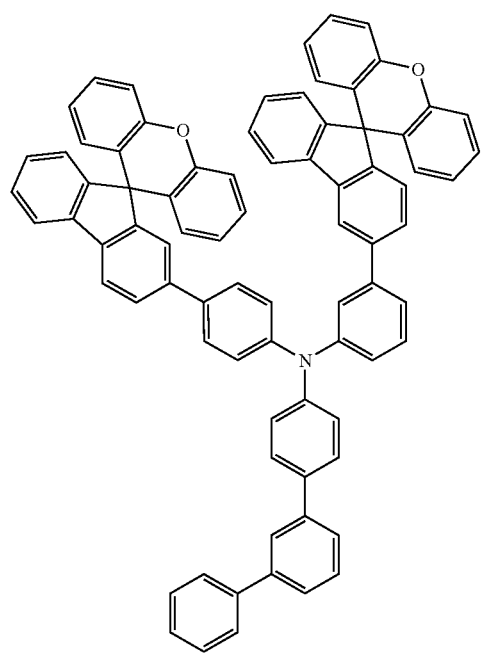
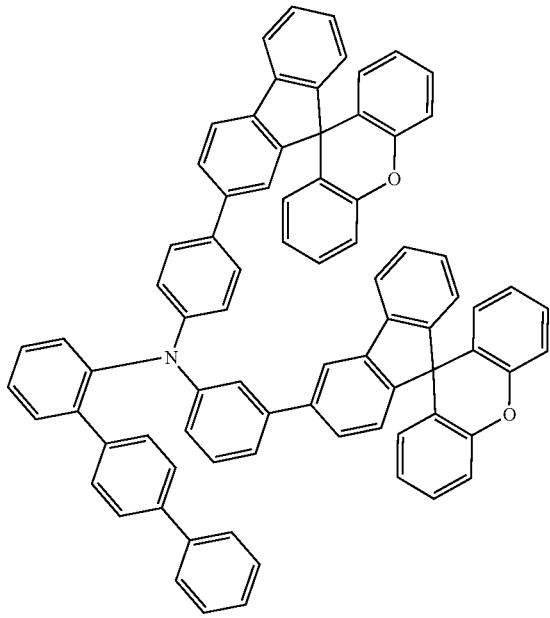

-continued
503
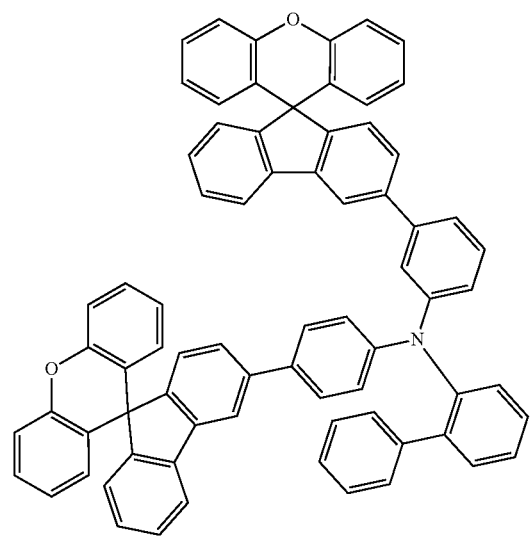
504
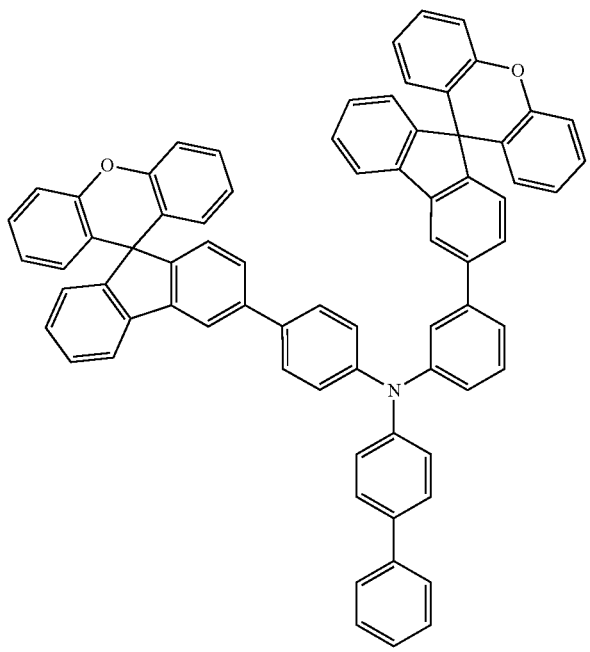
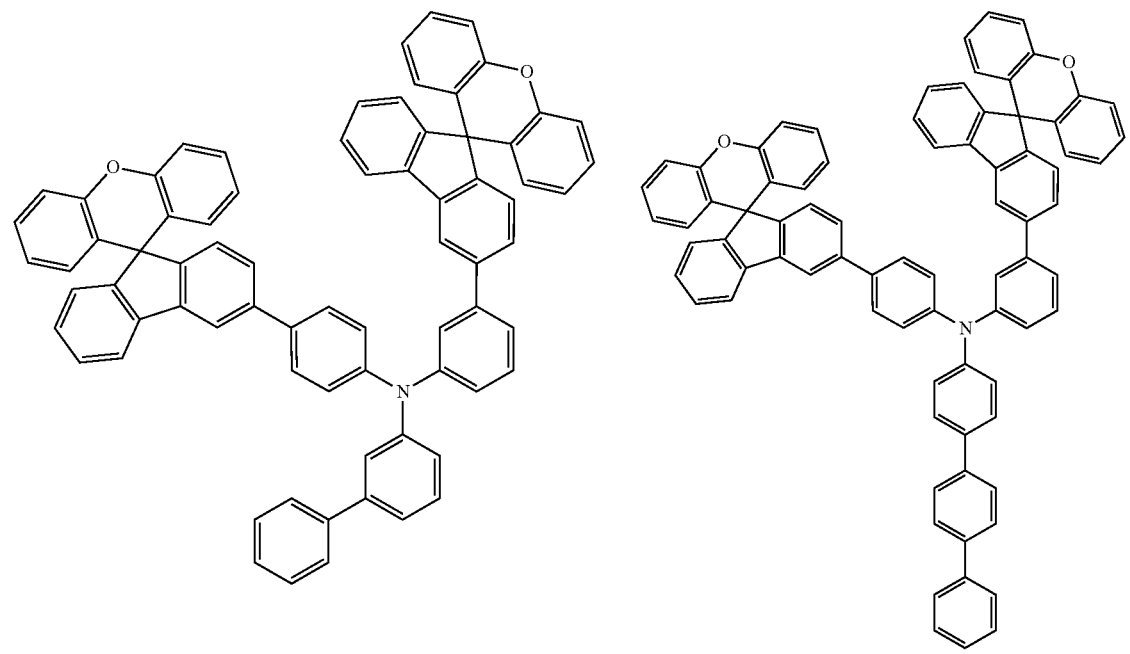

-continued
505
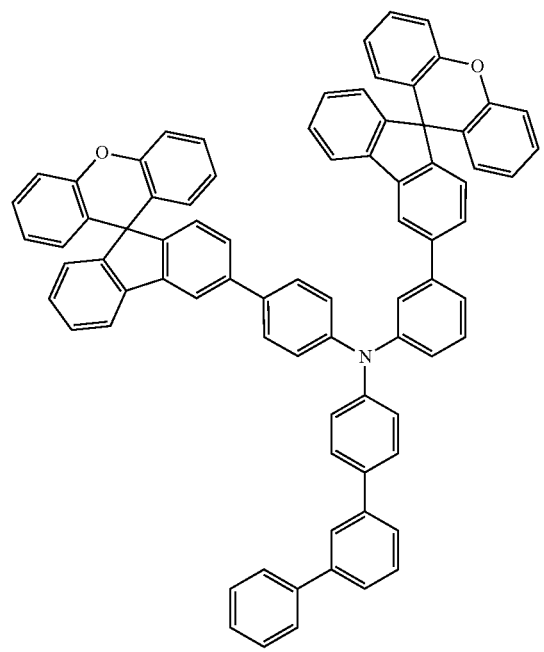
506
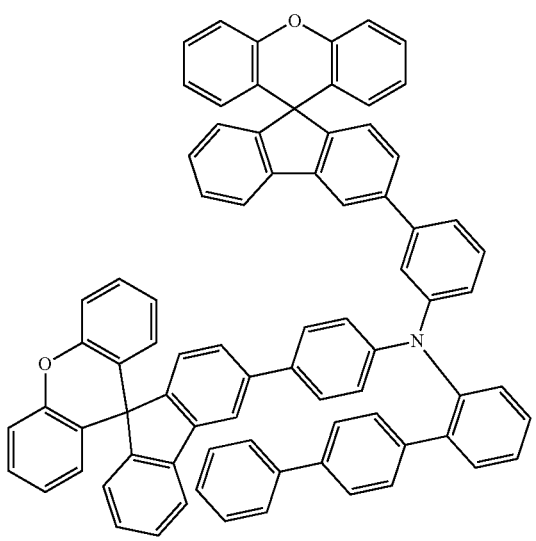
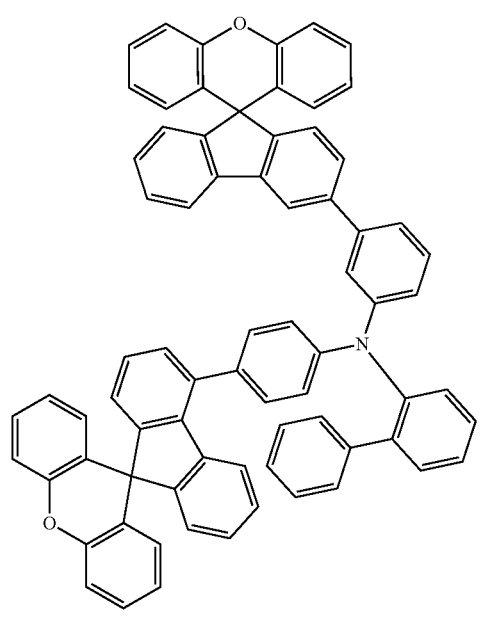
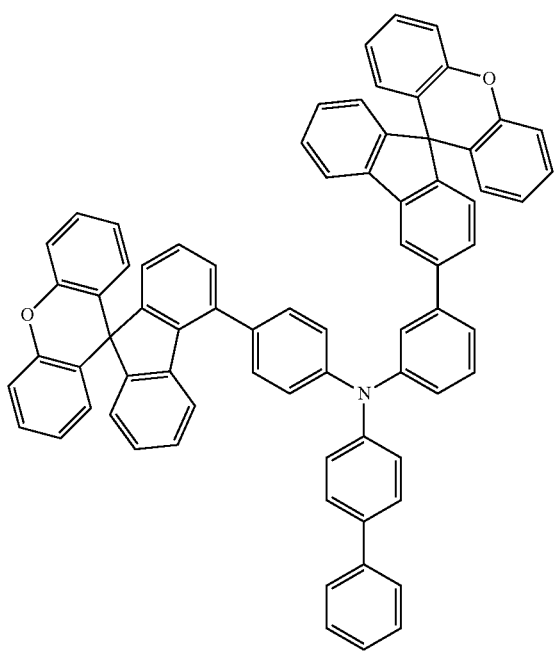

507
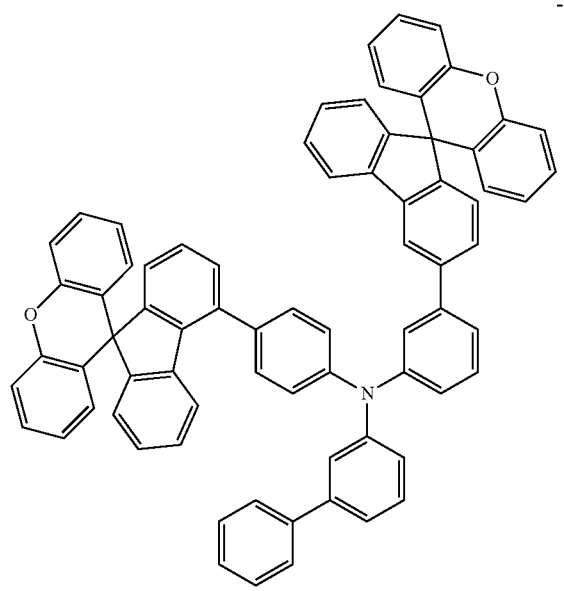
508
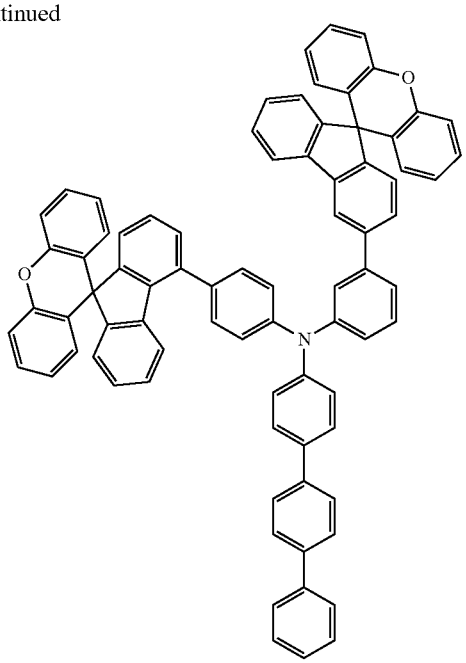
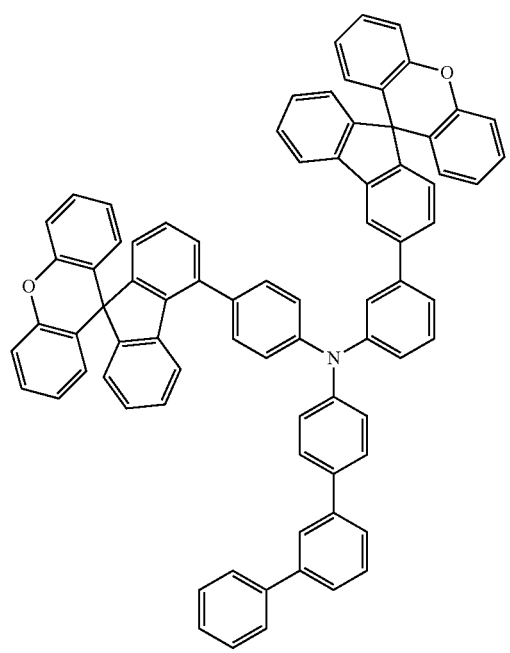
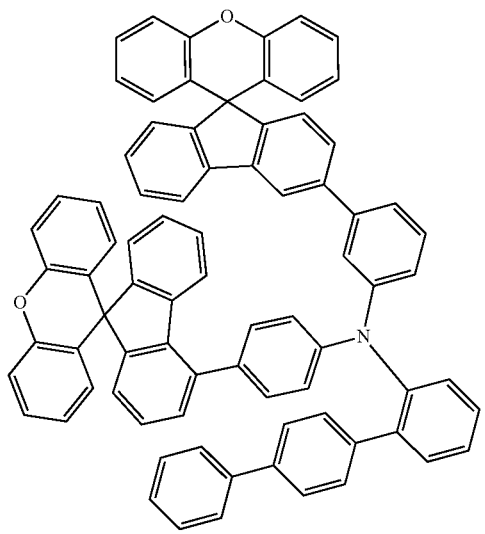

509
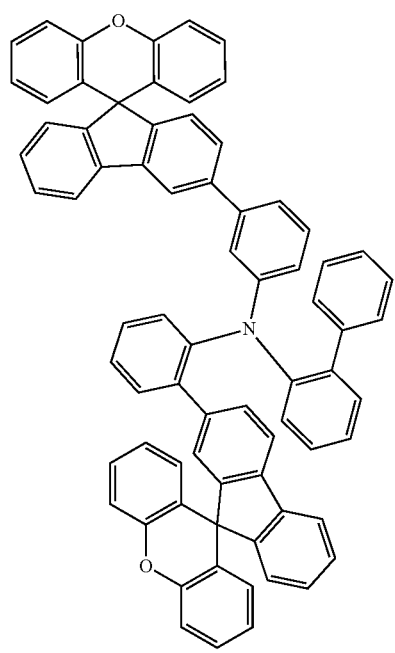
510
-continued
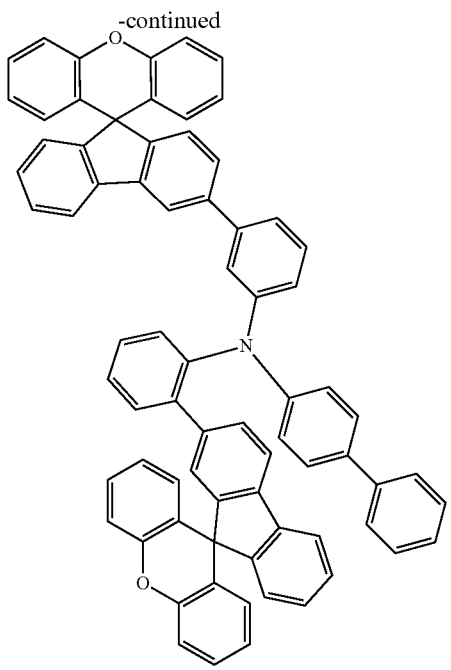
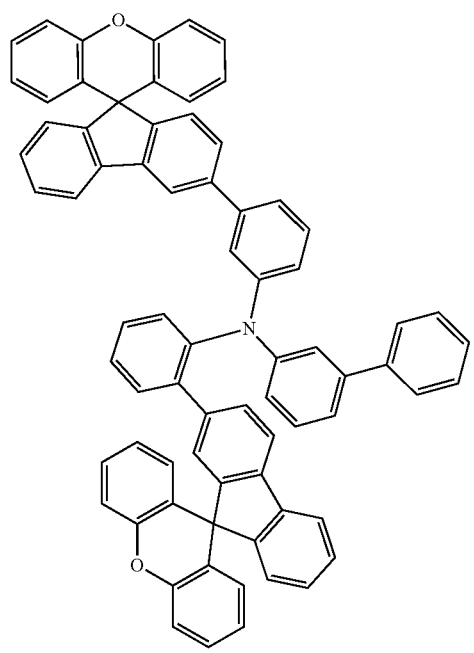
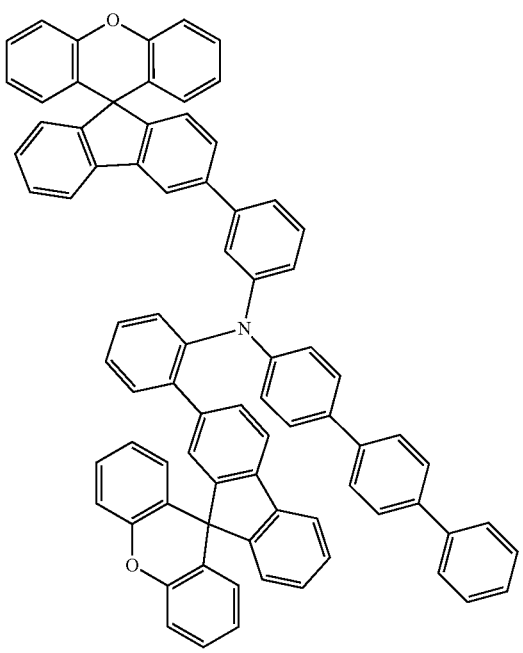

-continued
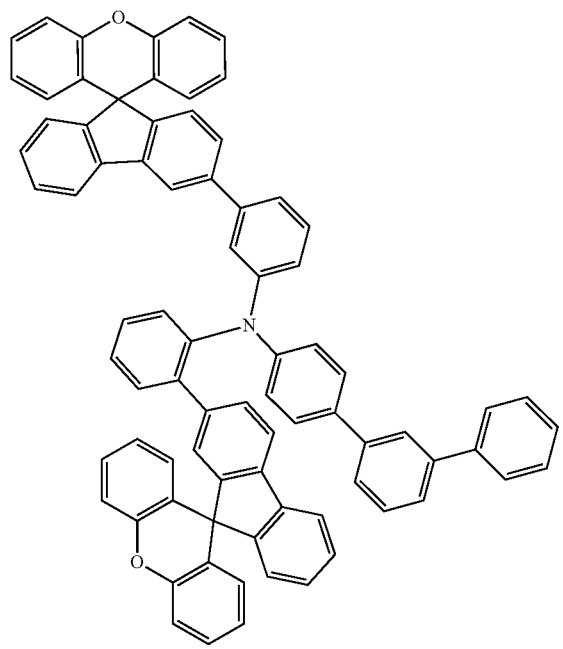
511
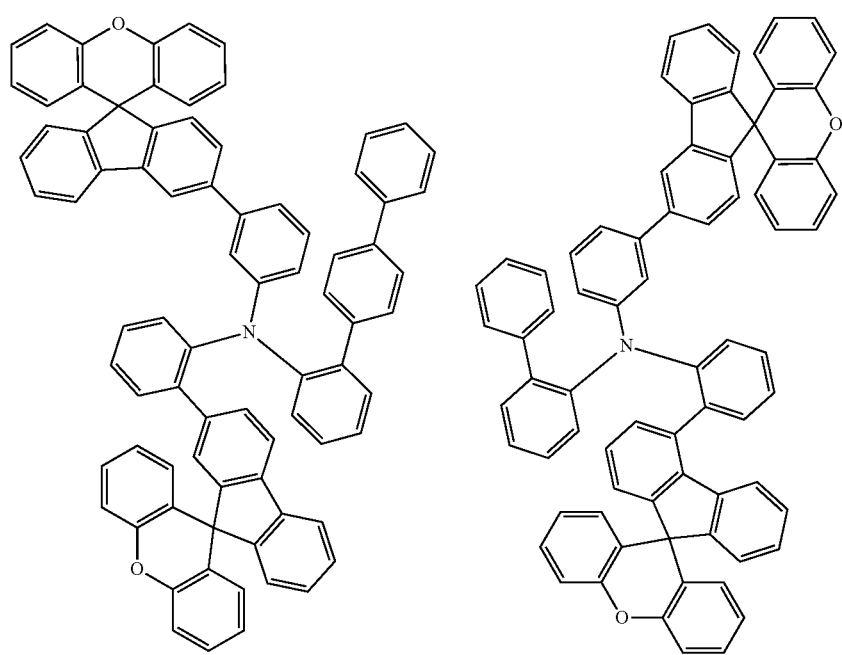 [SMILES: c1ccc(-c2ccc(-c3ccccc3N(c3cccc(-c4ccc5c(c4)-c4ccccc4C54c5ccccc5Oc5ccccc54)c3)c3ccccc3-c3ccc4c(c3)C3(c5ccccc5Oc5ccccc53)c3ccccc3-4)cc2)cc1 ; c1ccc(-c2ccccc2N(c2cccc(-c3ccc4c(c3)-c3ccccc3C43c4ccccc4Oc4ccccc43)c2)c2ccccc2-c2cccc3c2-c2ccccc2C32c3ccccc3Oc3ccccc32)cc1]
512

-continued
513
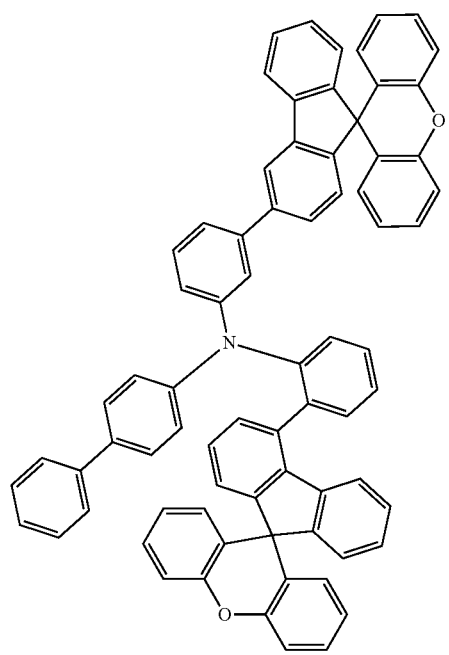
514
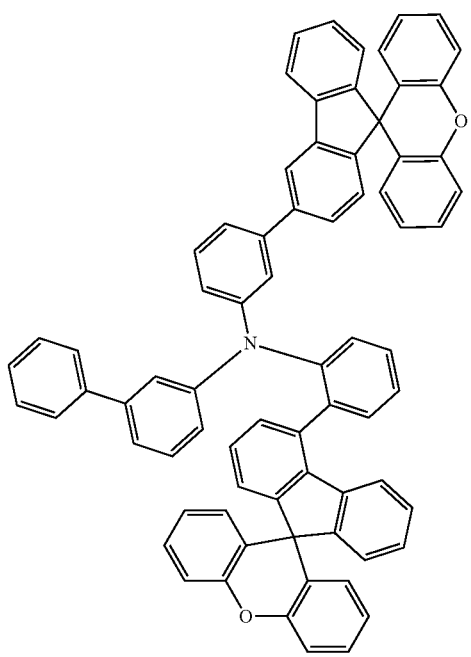
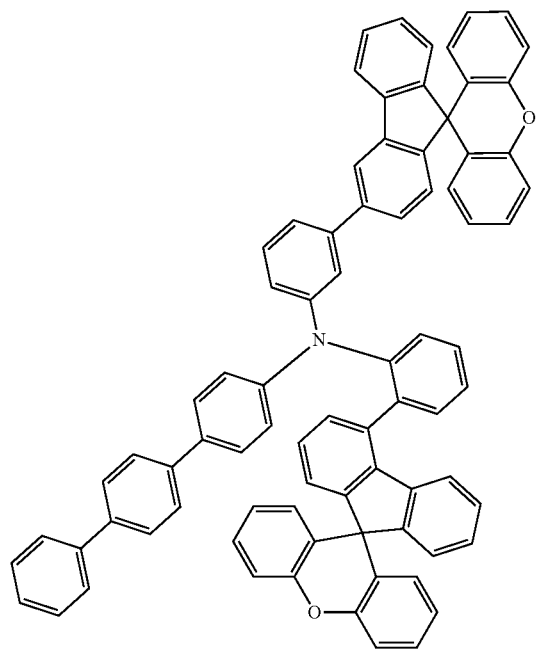
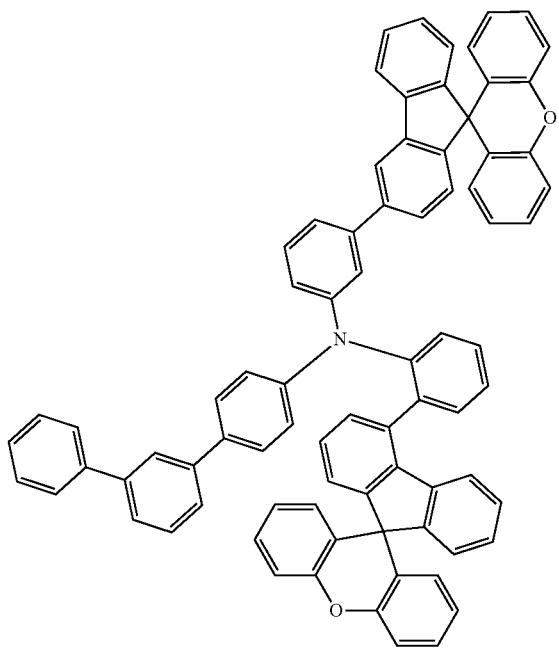

-continued
515
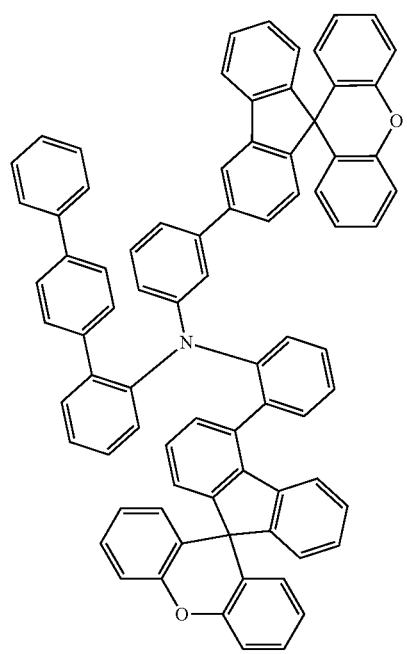
516
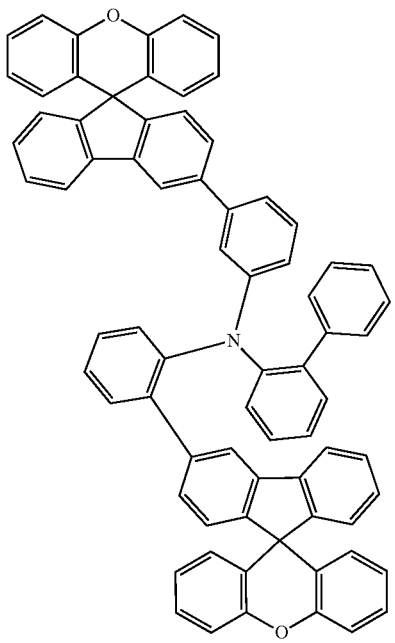
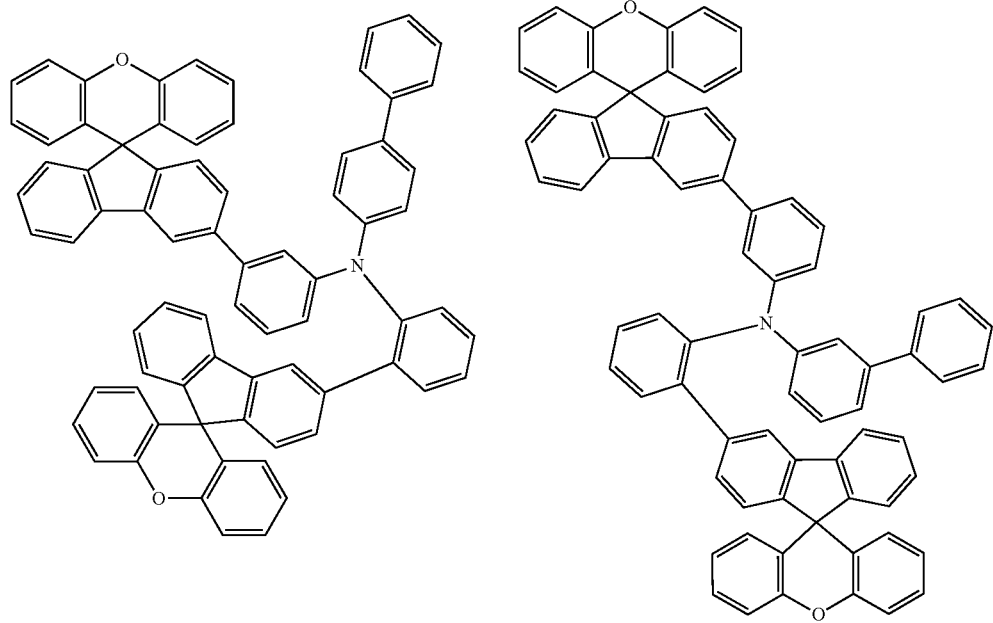

517
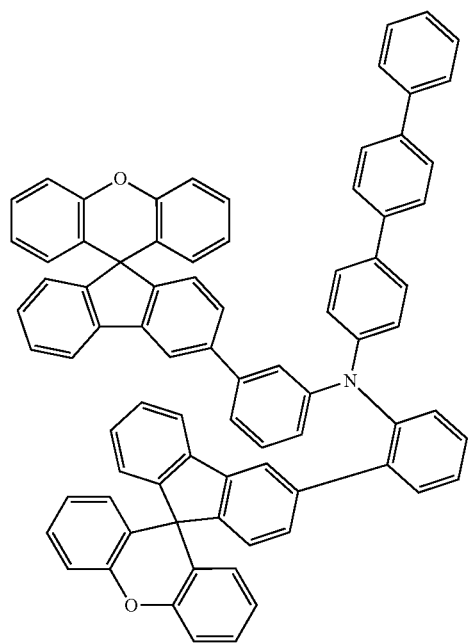
518
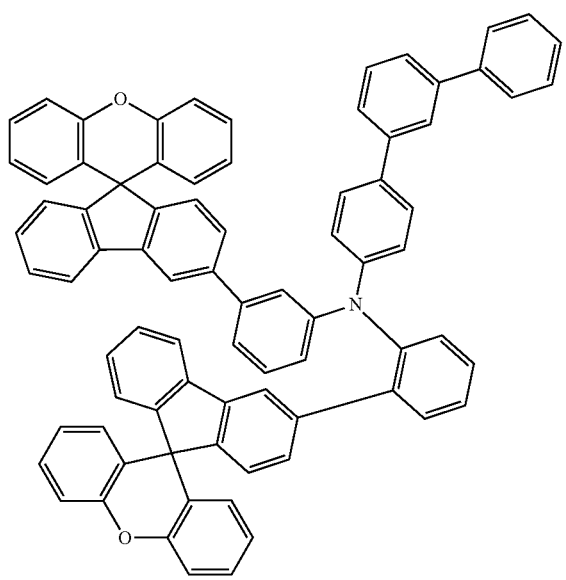
-continued
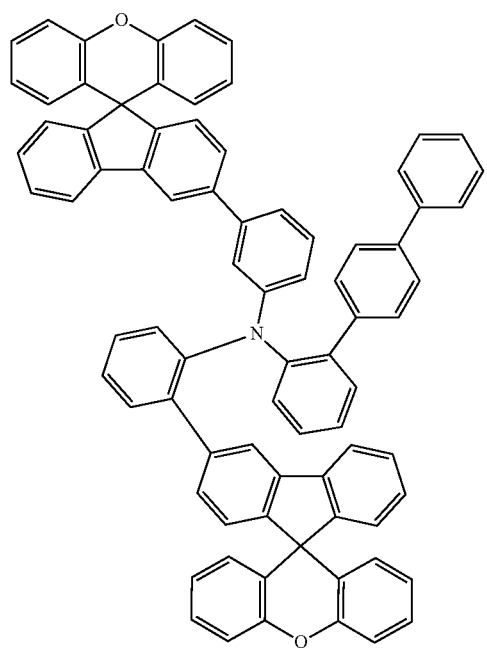
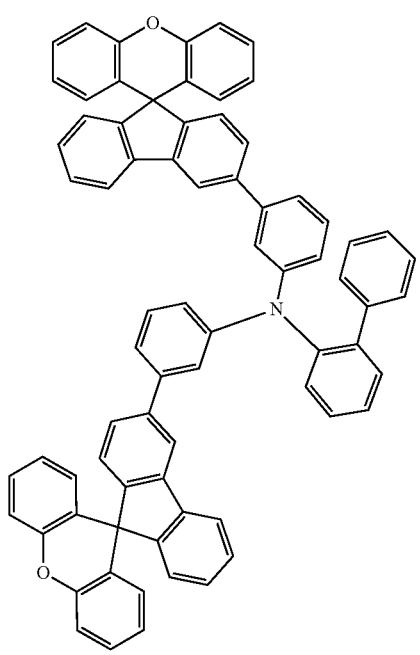

519
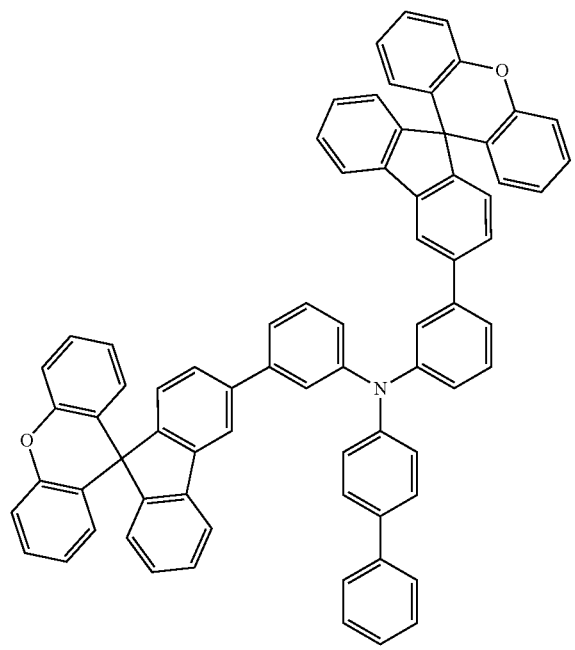
520
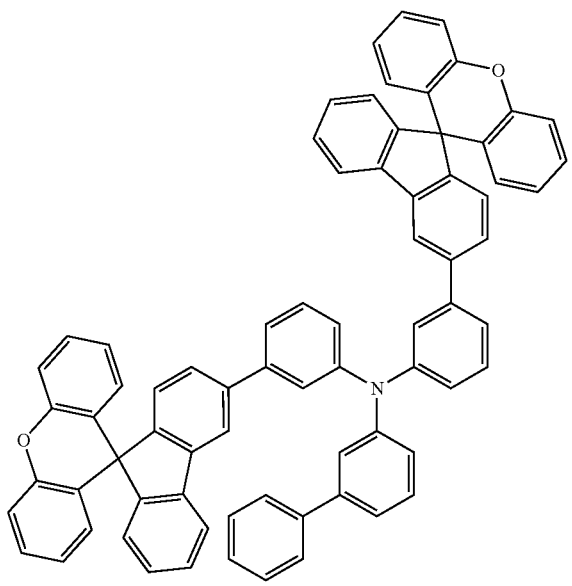
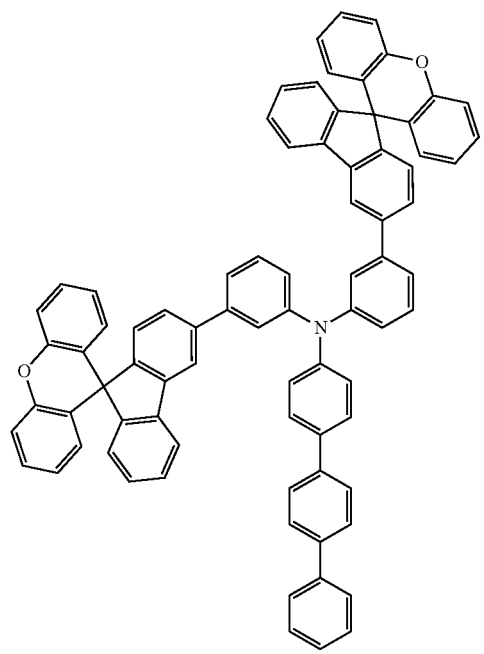
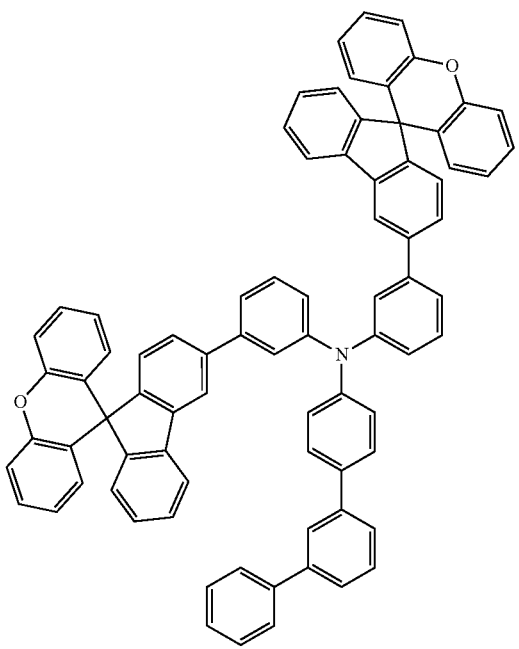

-continued
521
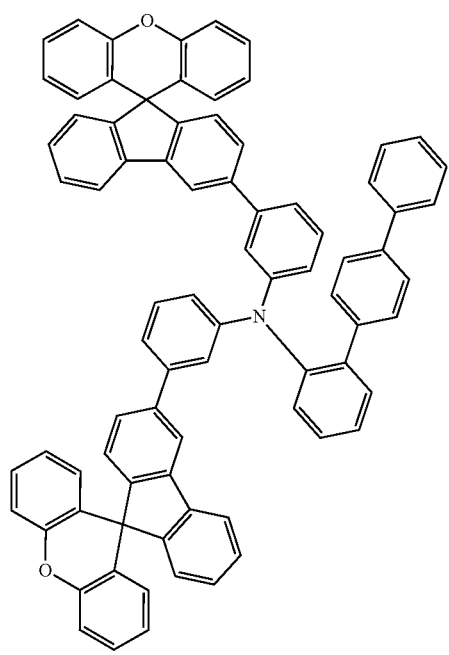
522
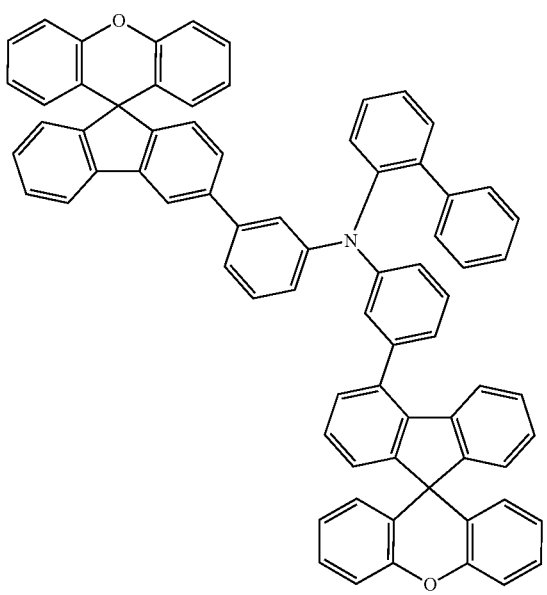
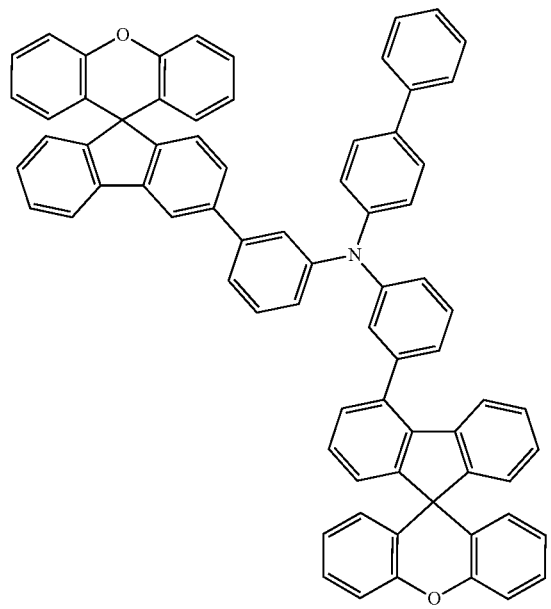
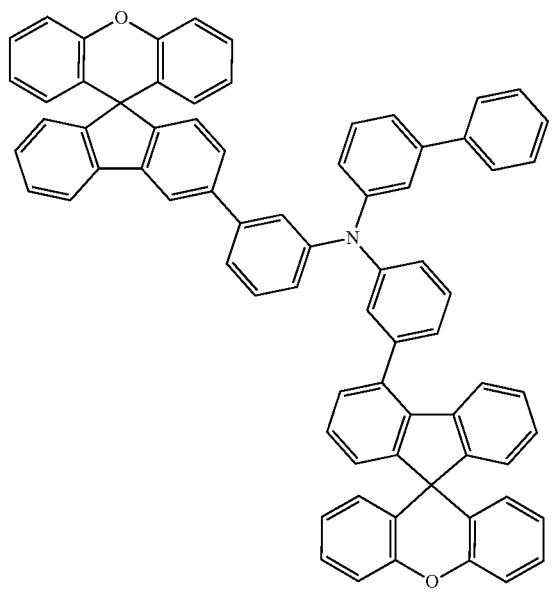

-continued
523
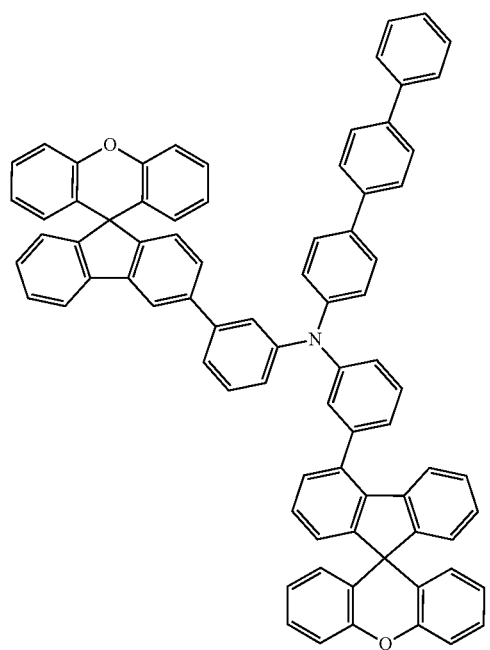
524
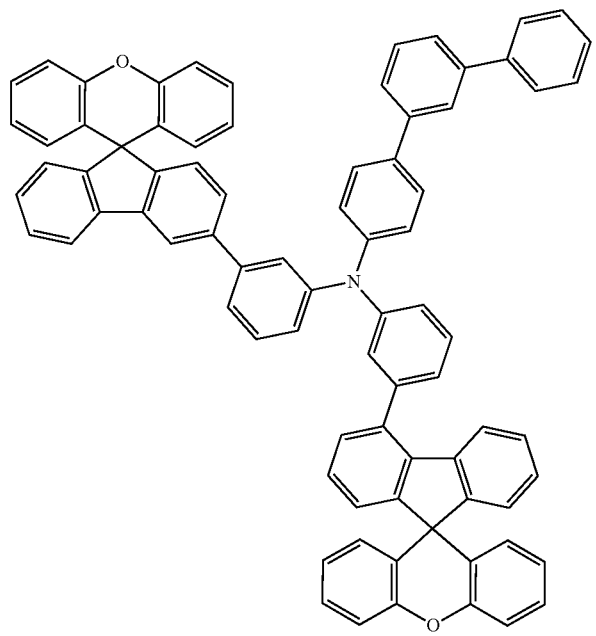
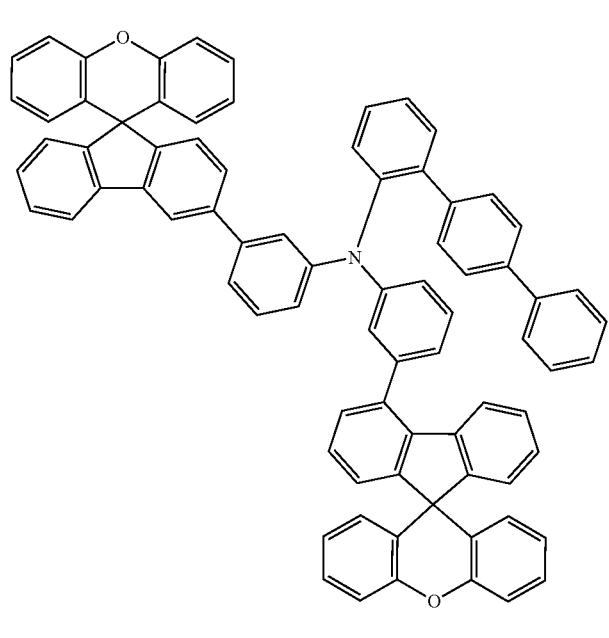
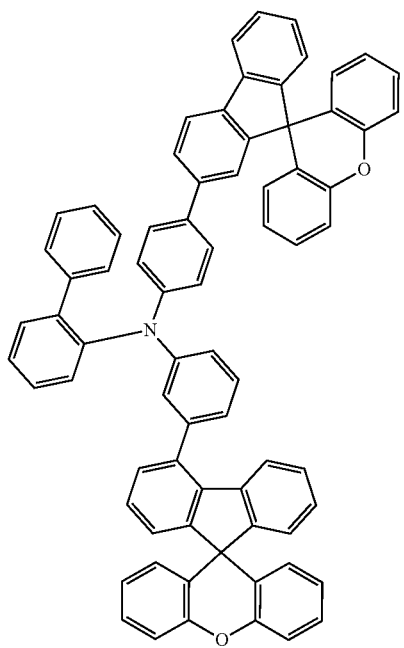

525 526
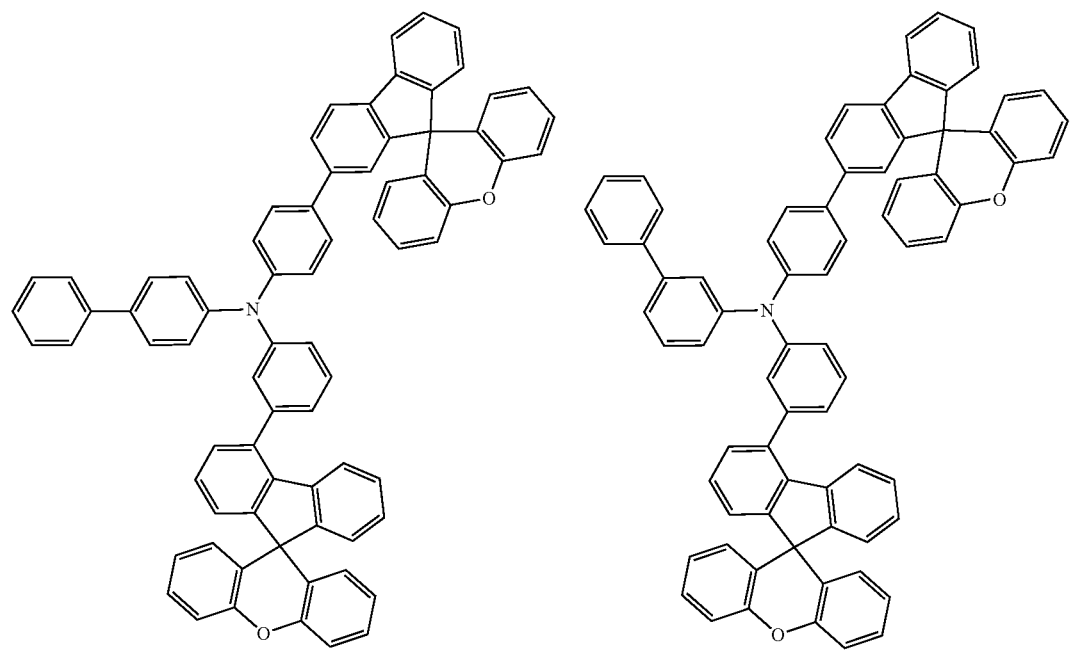
-continued
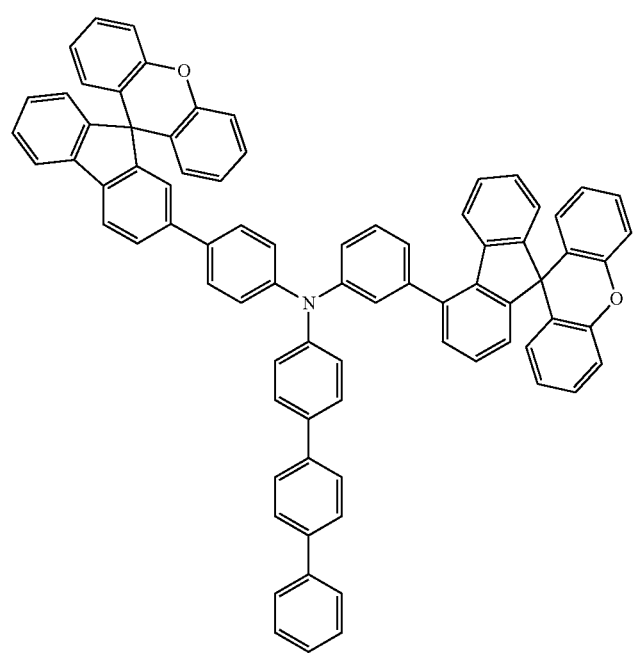

-continued
527
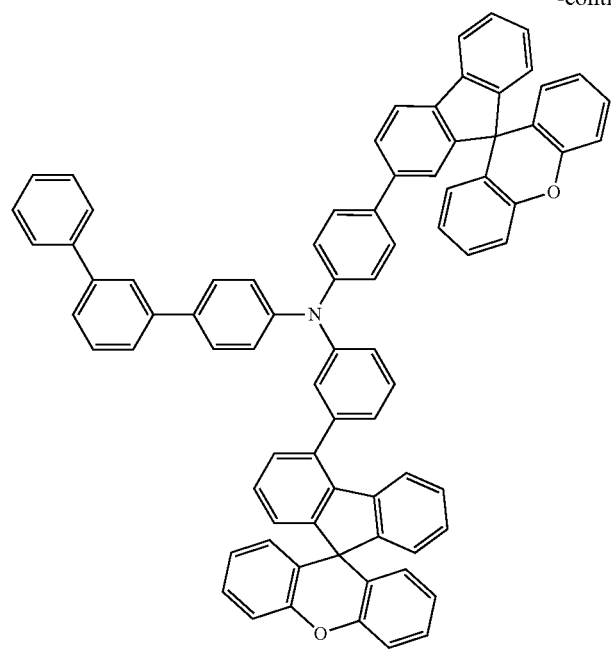
528
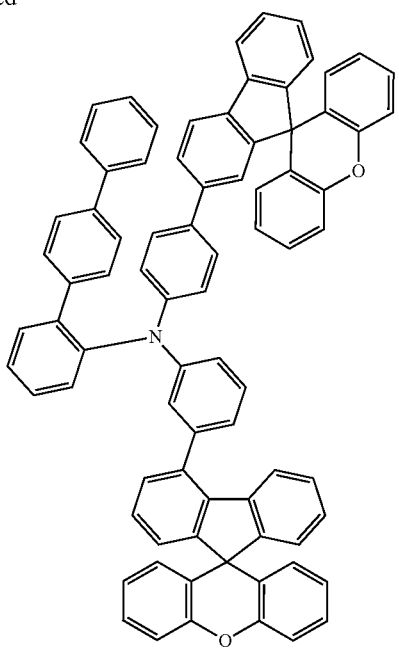
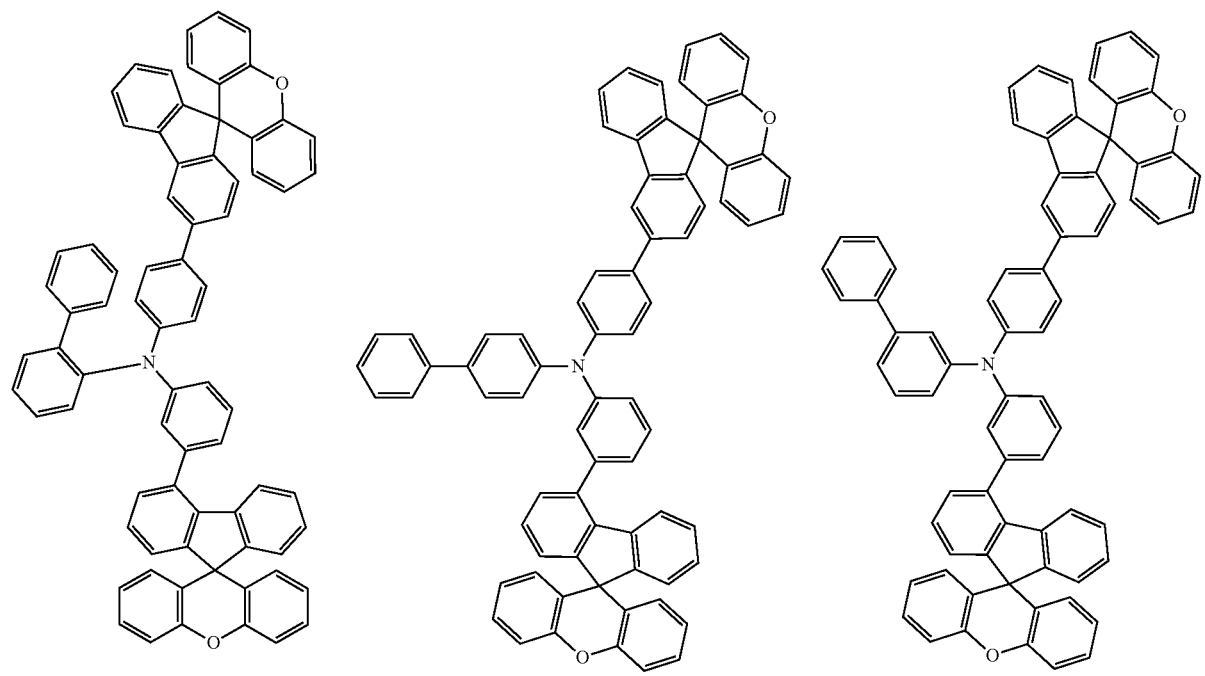

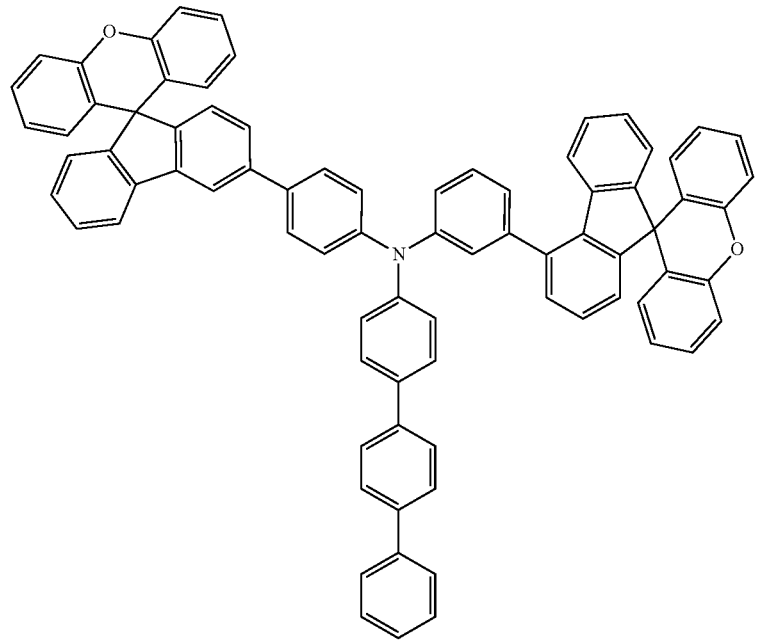
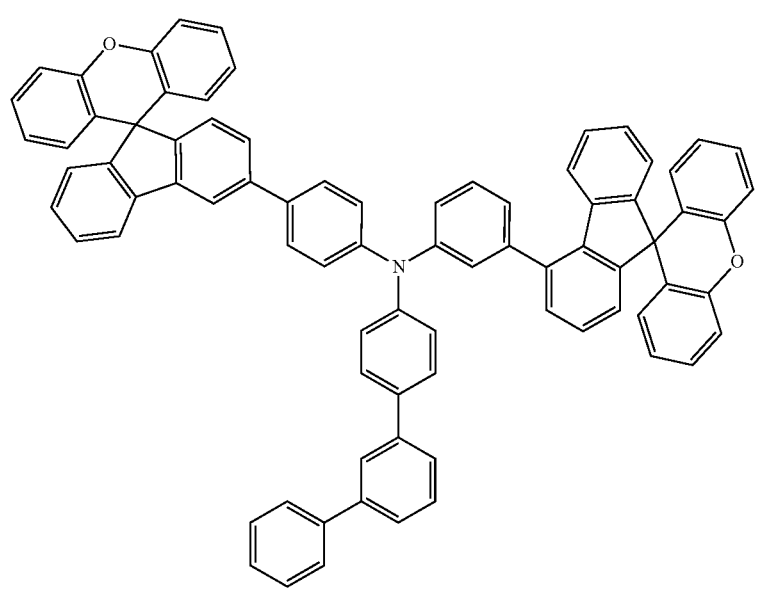
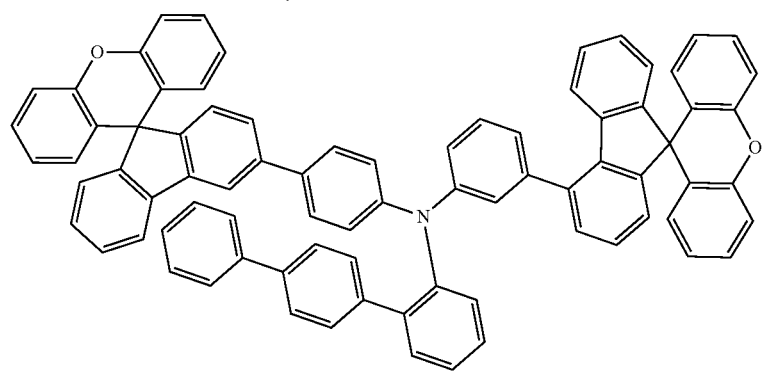

-continued
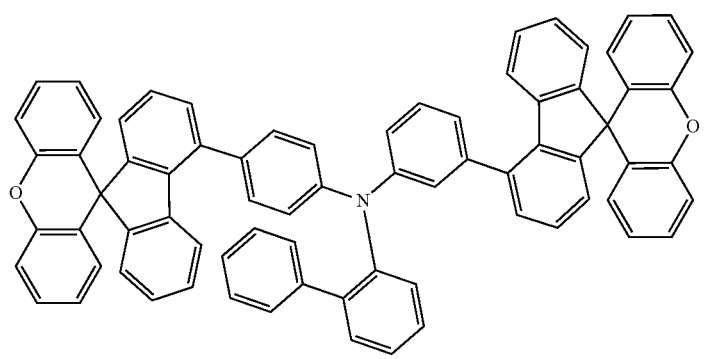
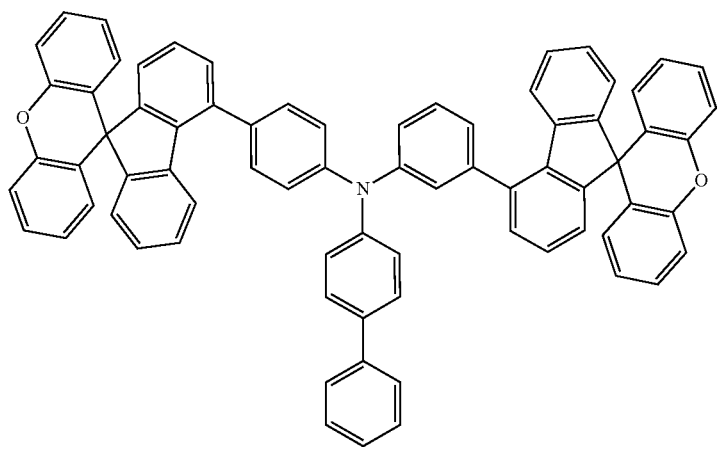
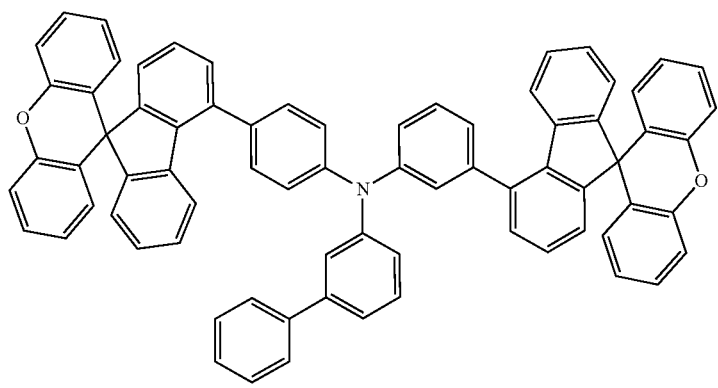

533
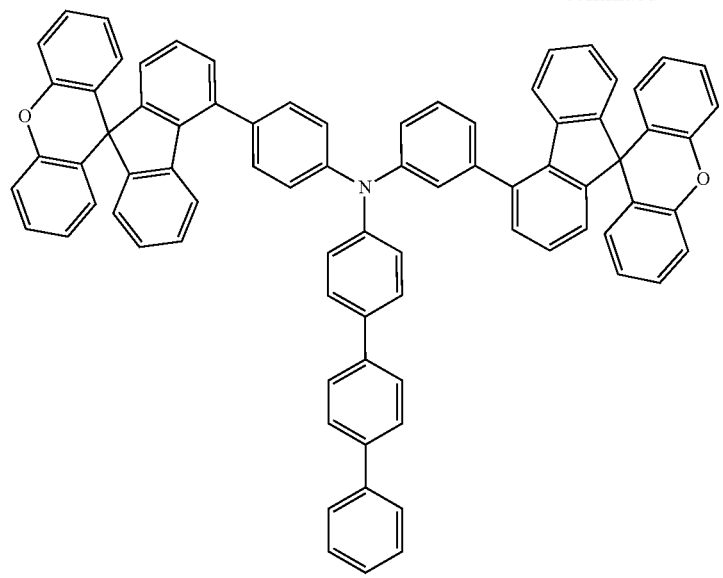
534
-continued
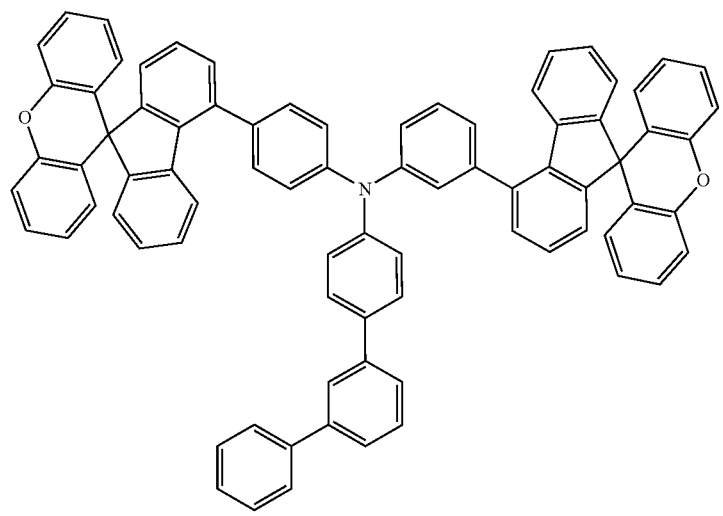
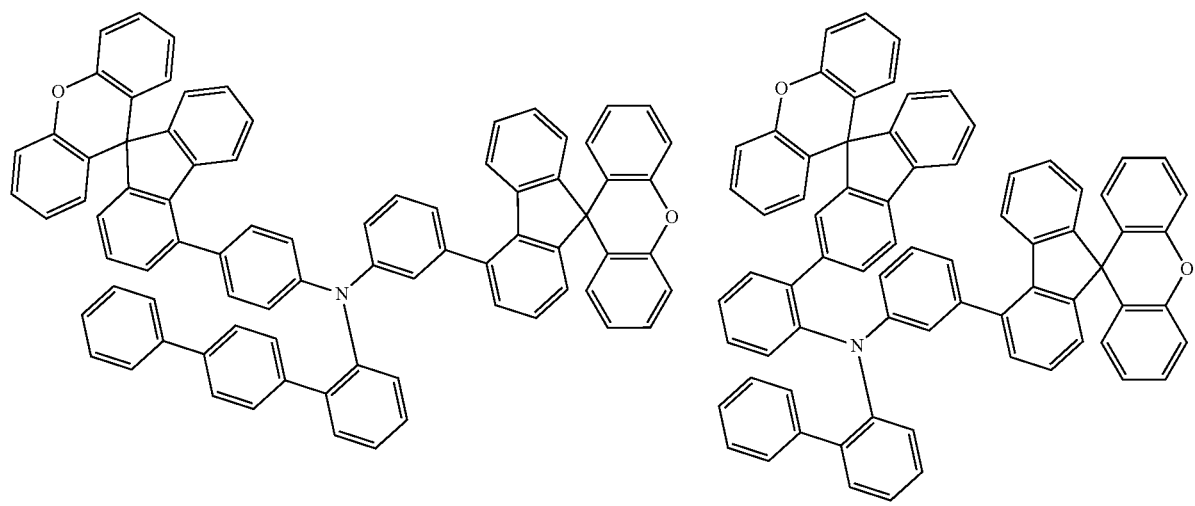

-continued
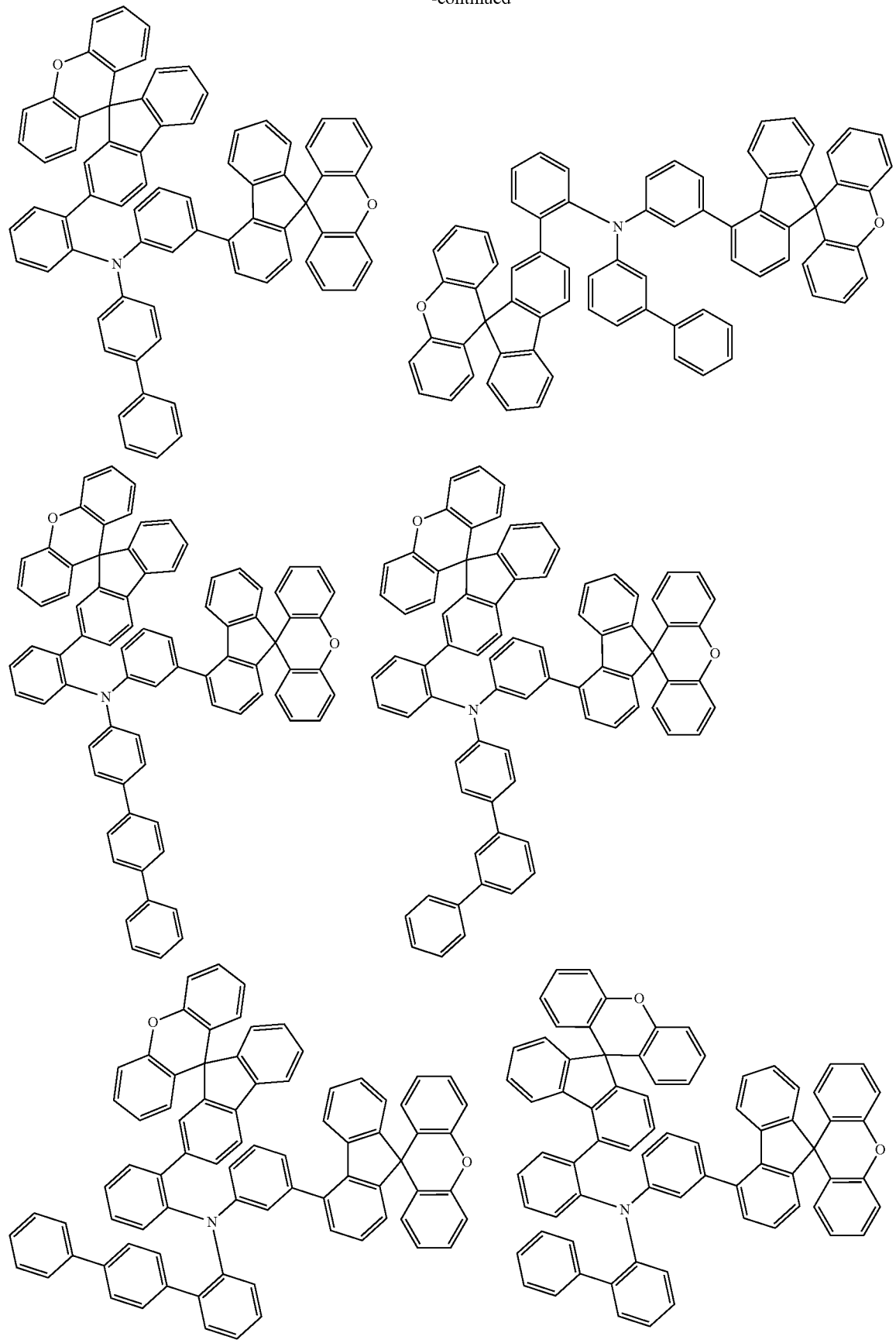

-continued
537
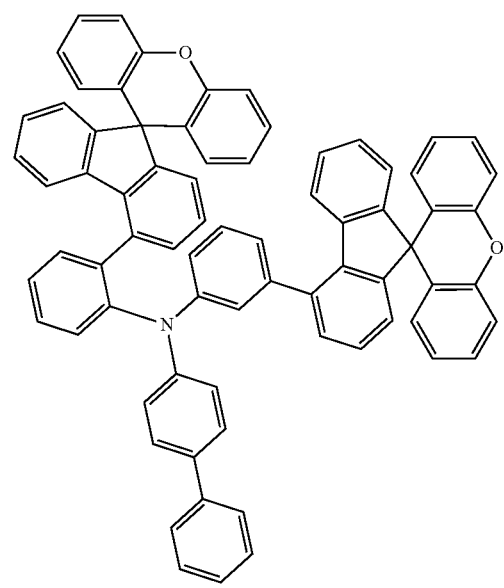
538
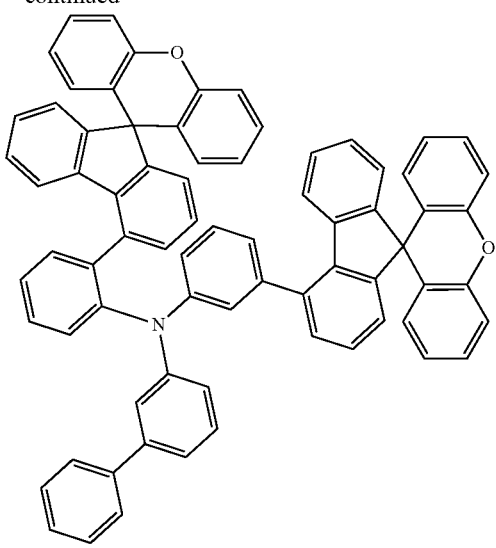
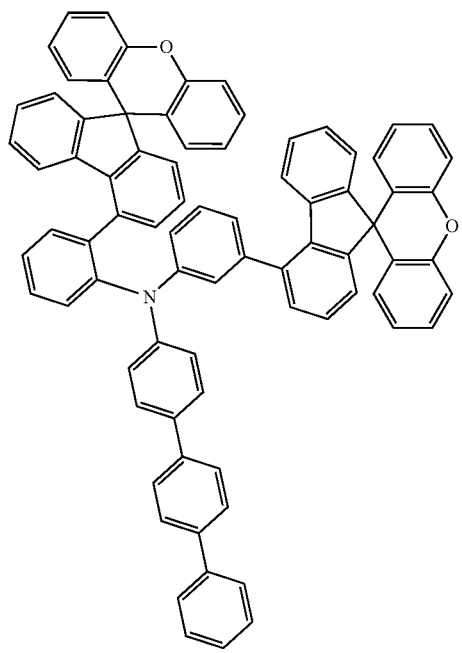
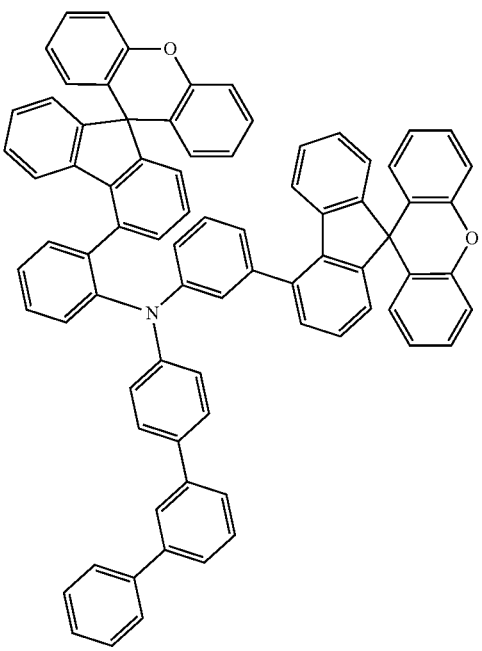
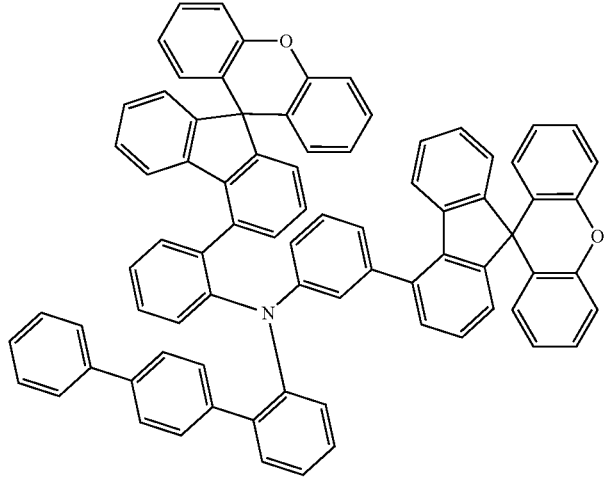

-continued
| 539 | 540 |
|---|---|
| 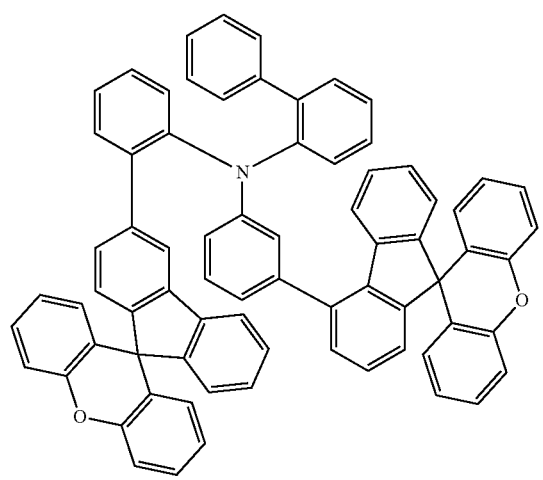 | 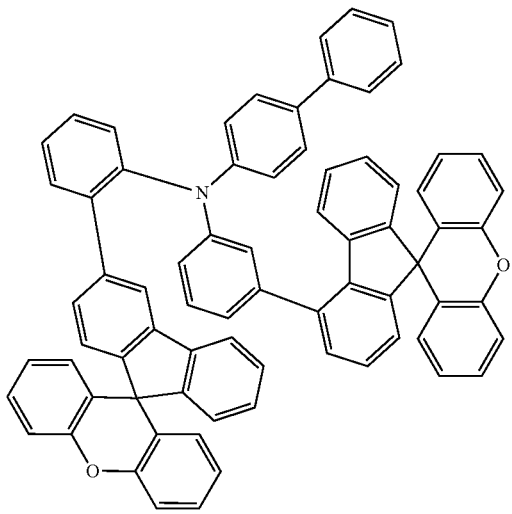 |
| 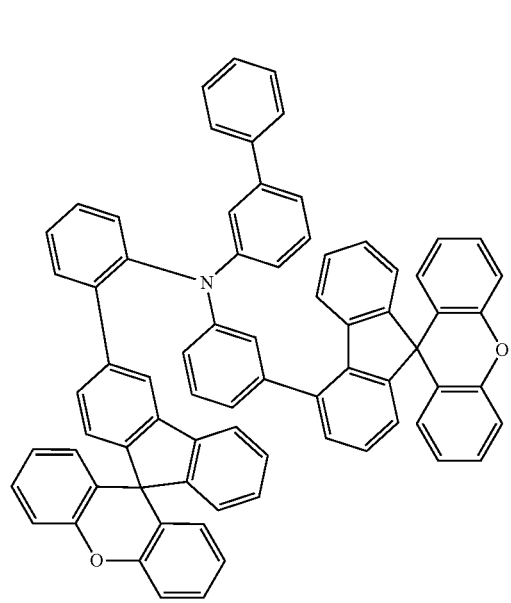 | 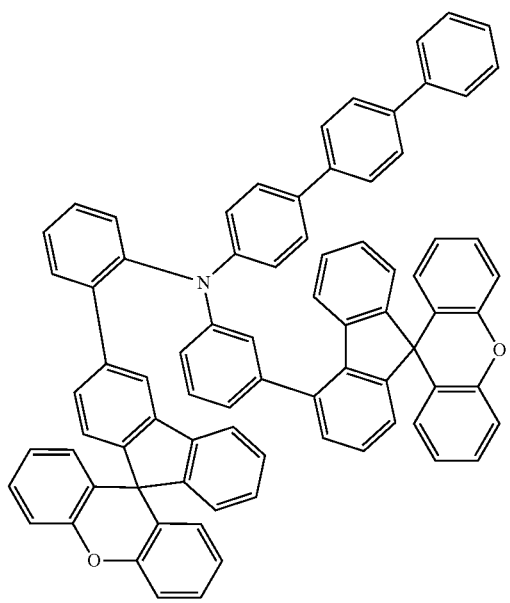 |
| 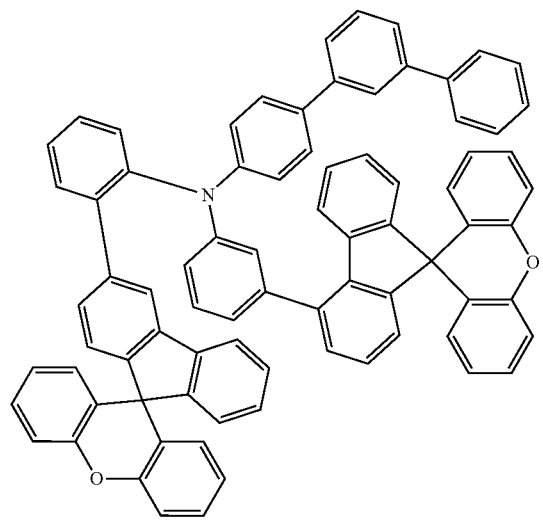 | 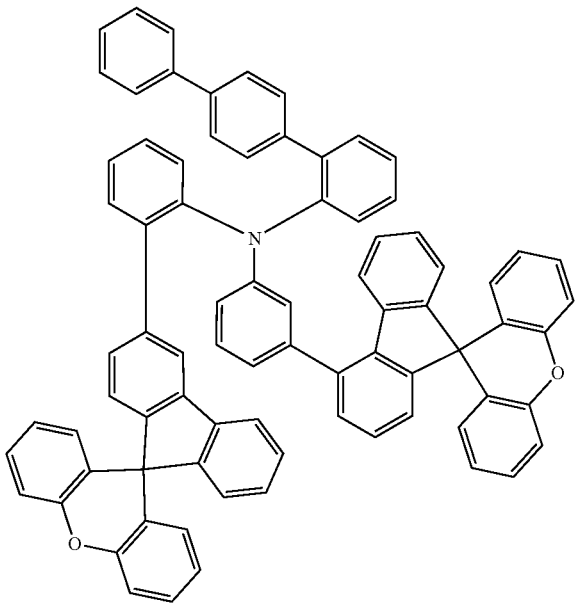 |

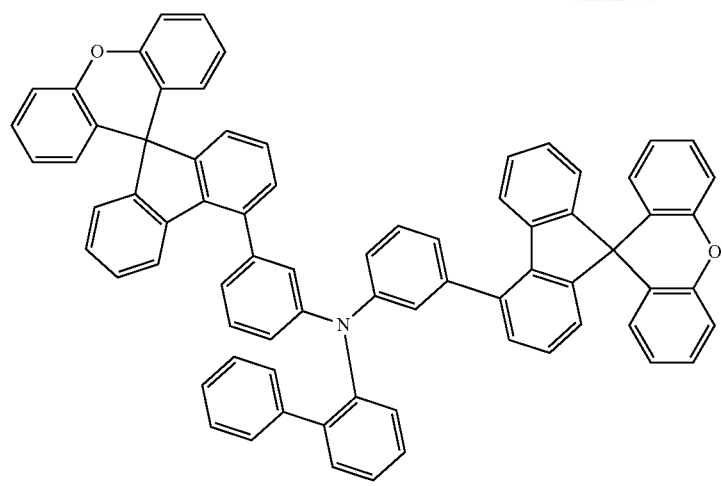
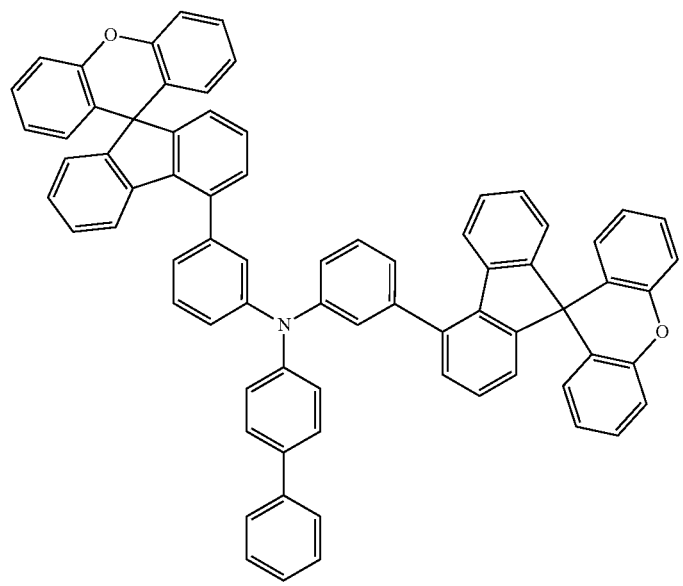
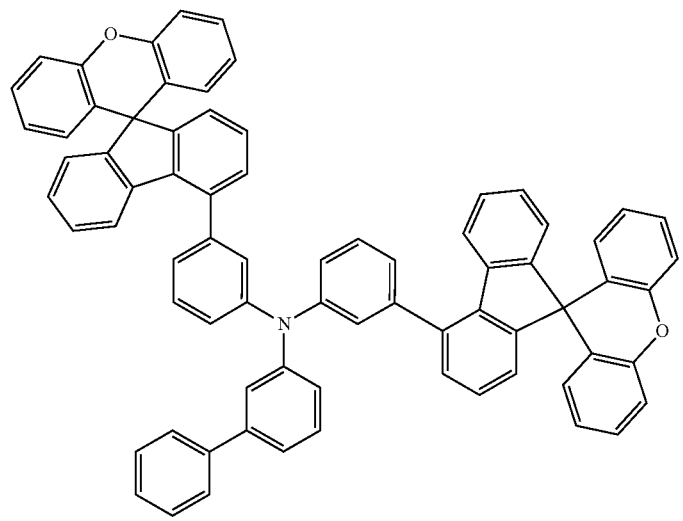

-continued
543
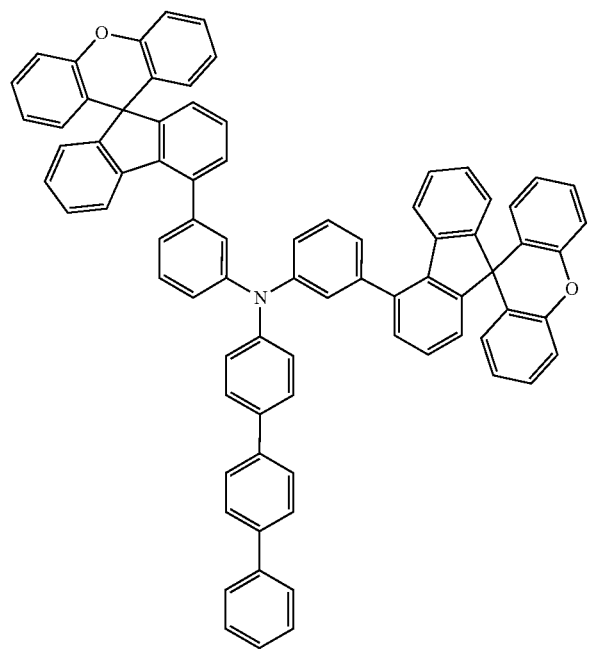
544
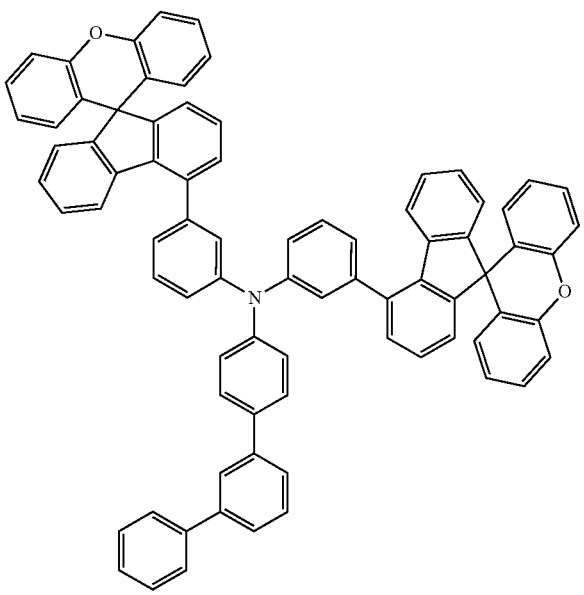
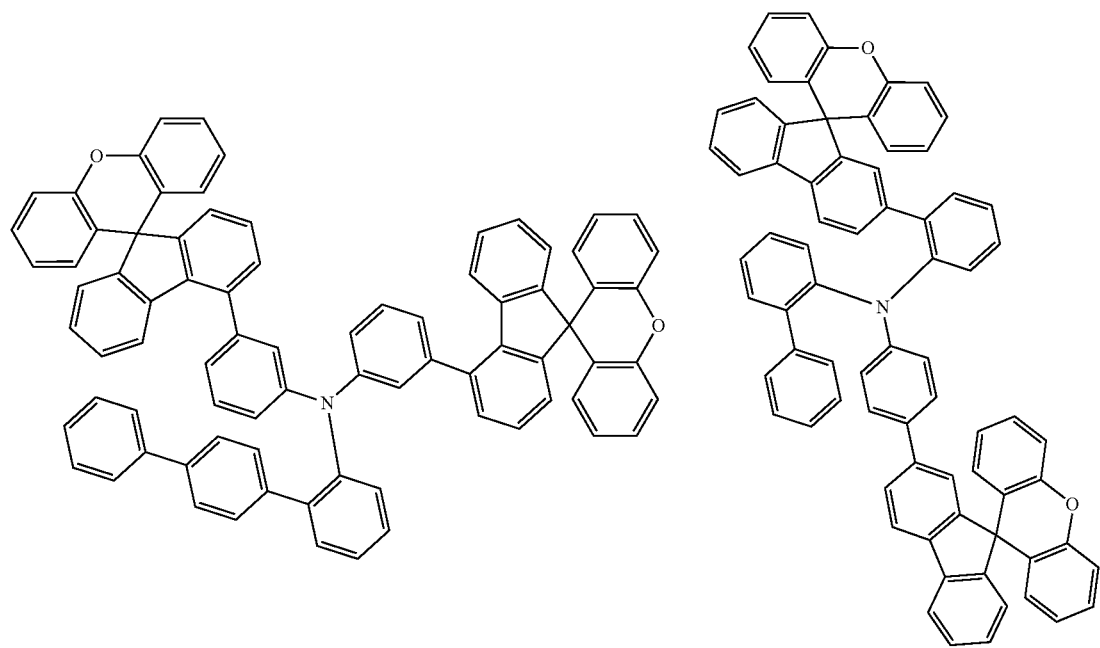

-continued
545
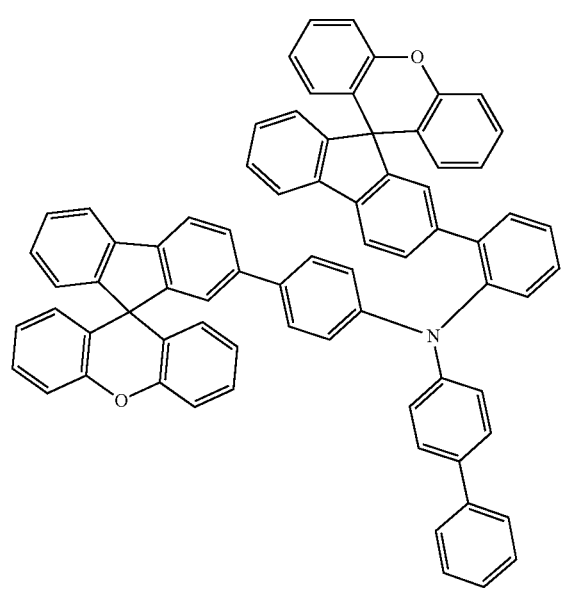
546
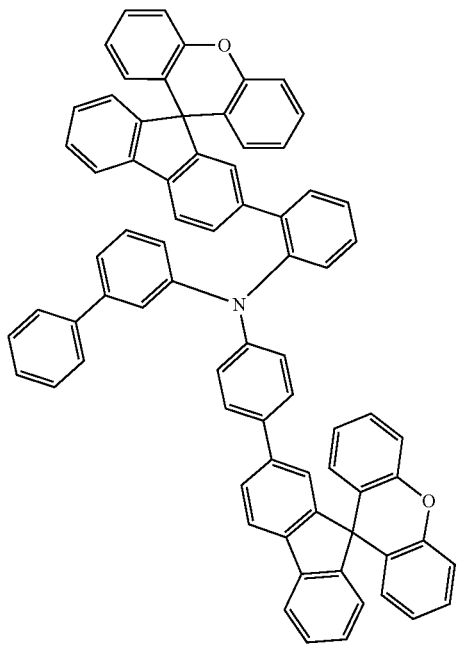
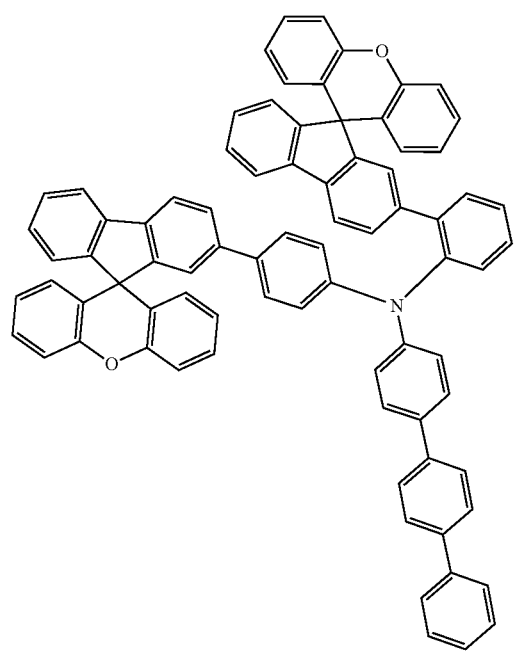
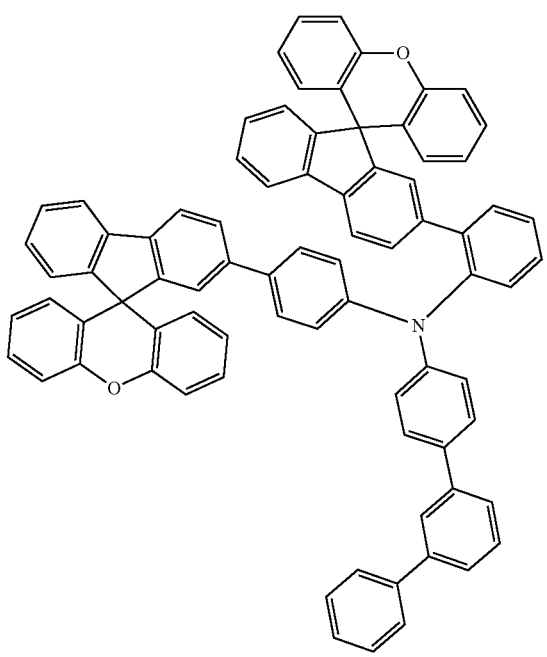

-continued
547
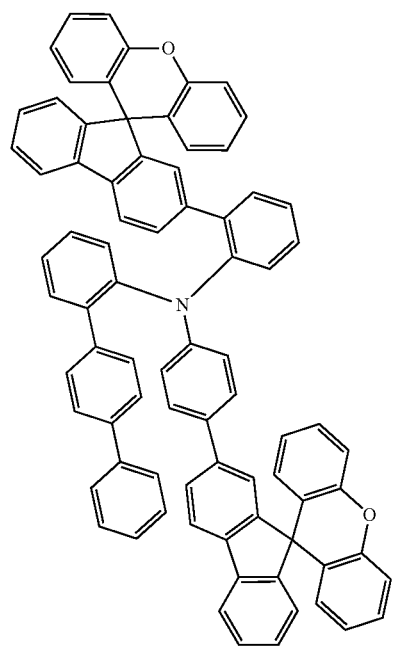
548
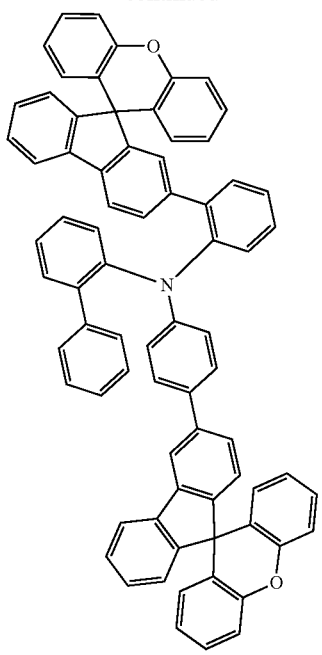
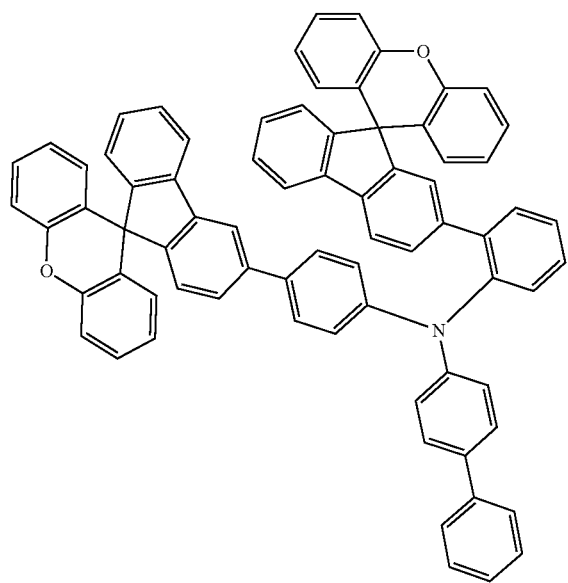
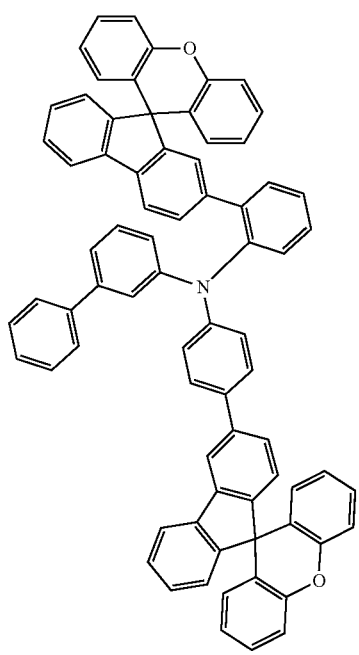

-continued
| 549 | 550 |
|---|---|
| 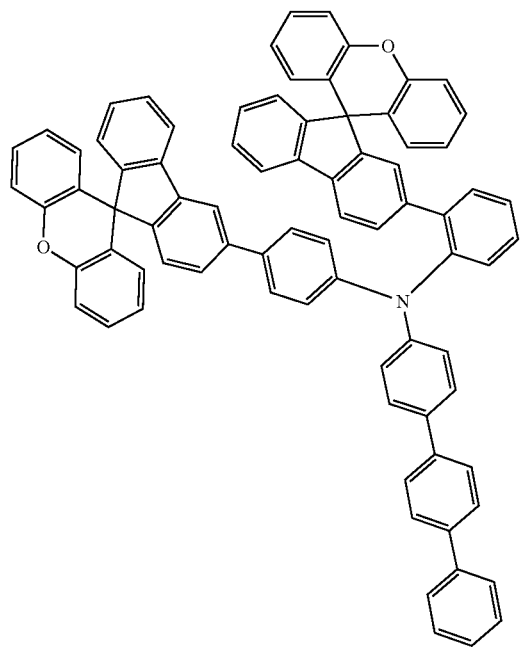 | 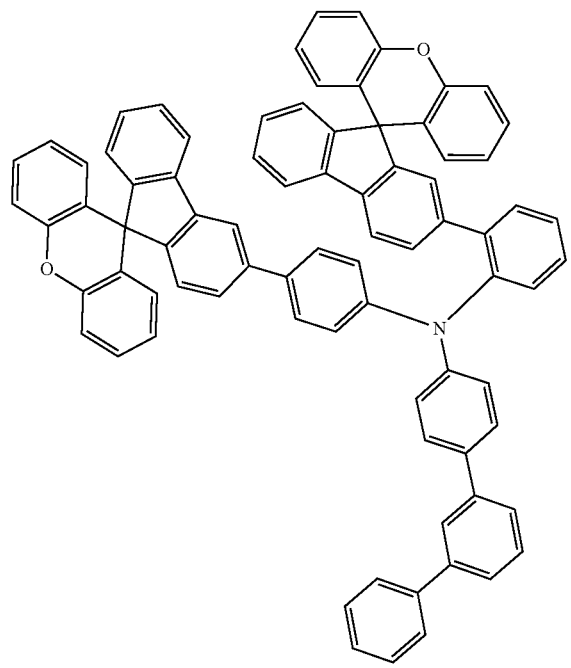 |
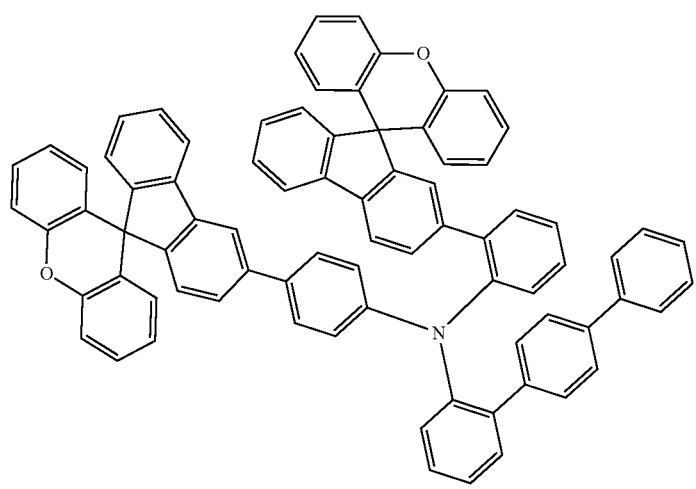

-continued
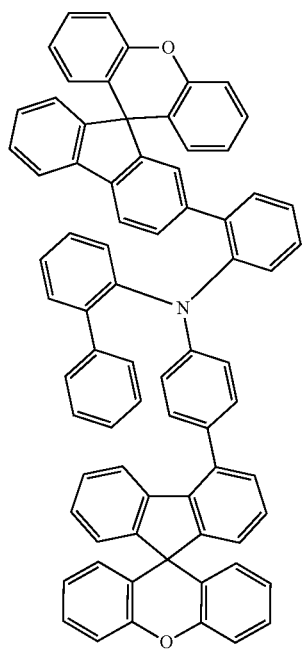
551
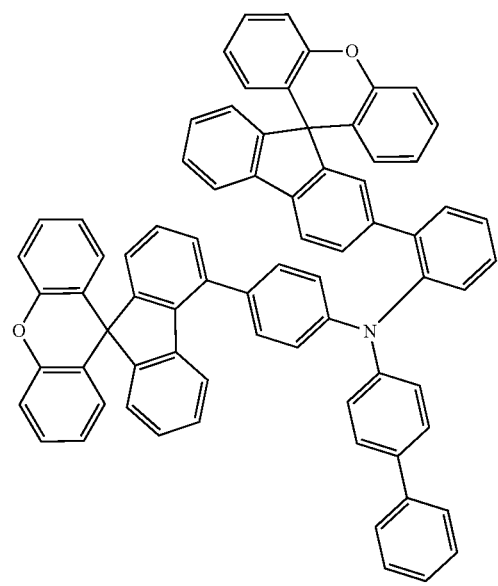
552
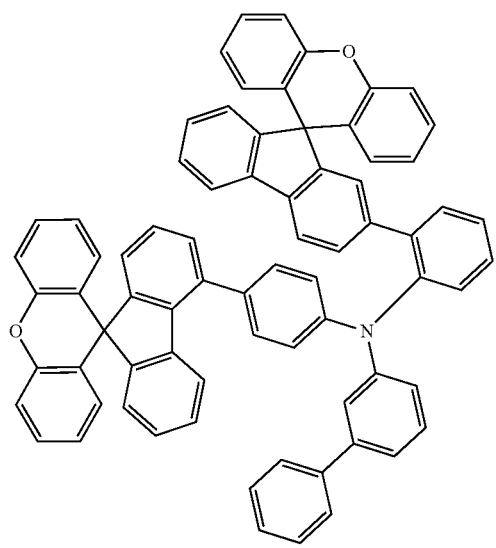
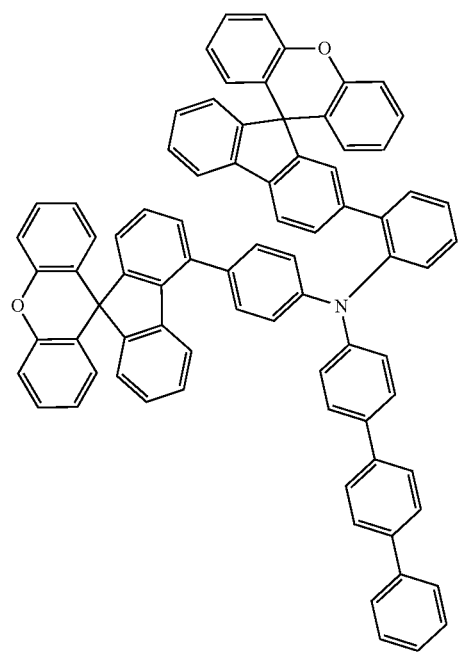

-continued
553
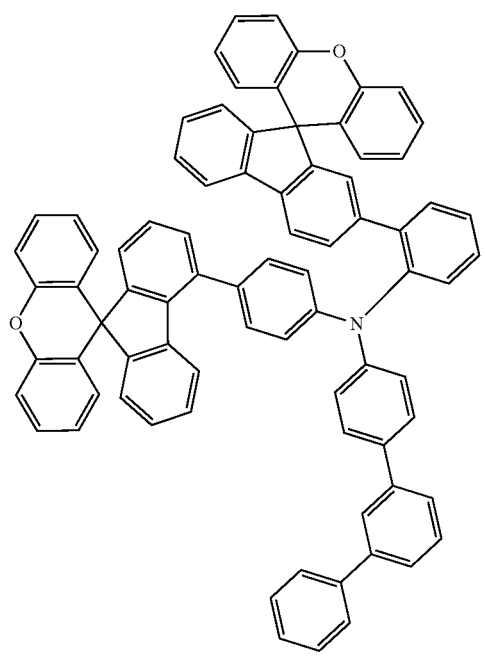
554
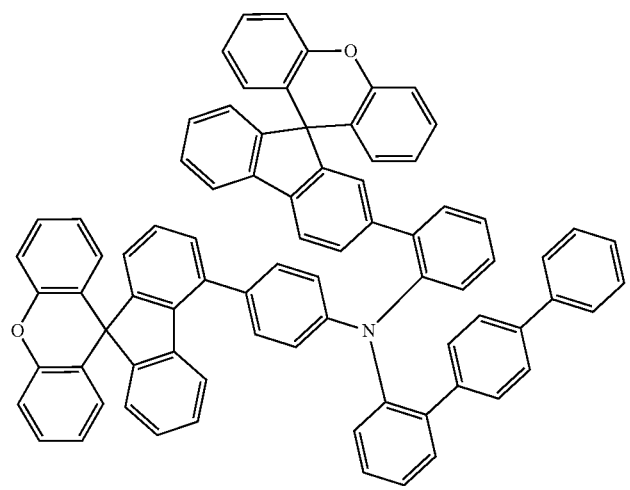
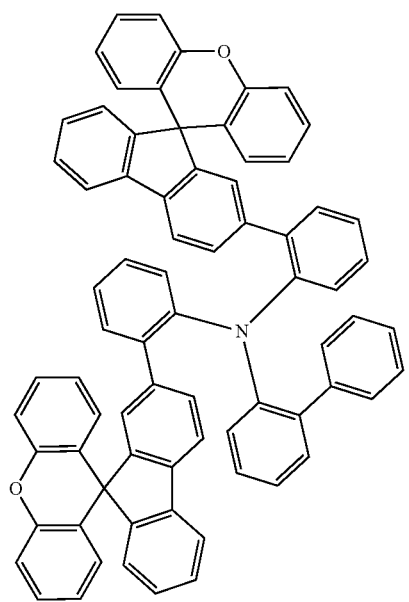
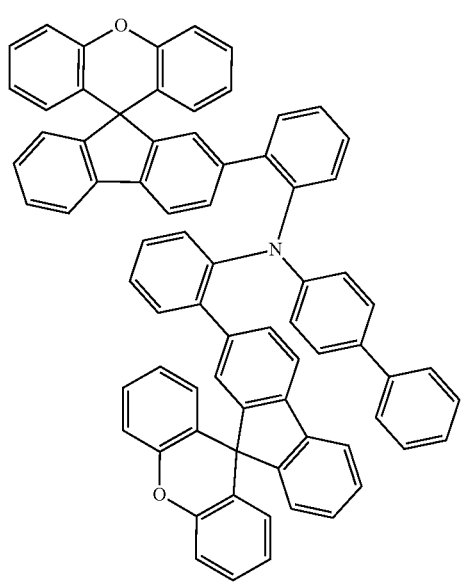

-continued
555
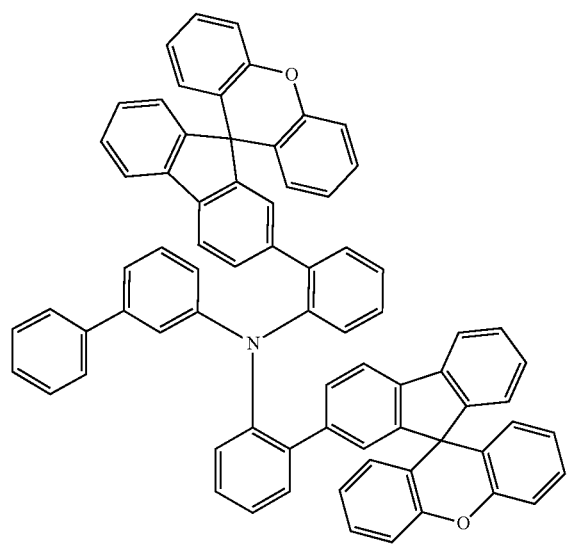
556
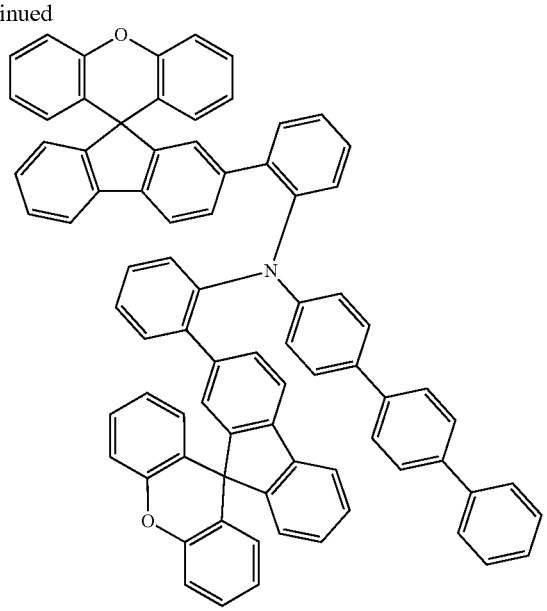
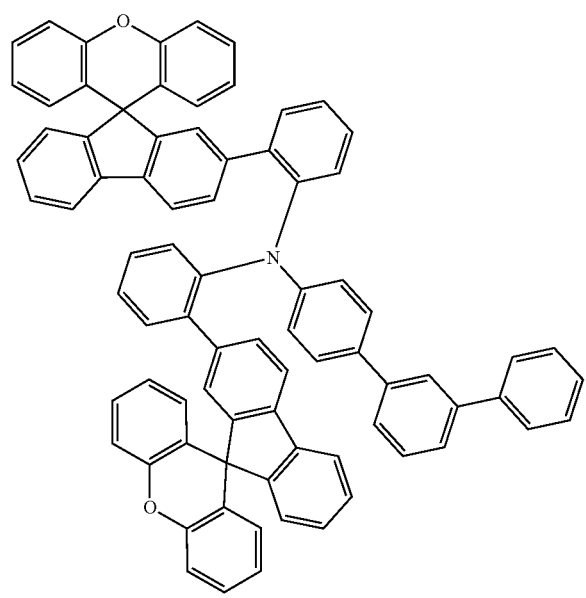
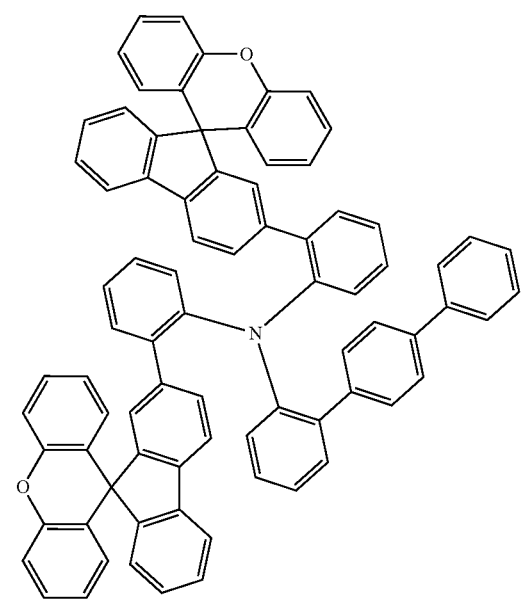

557
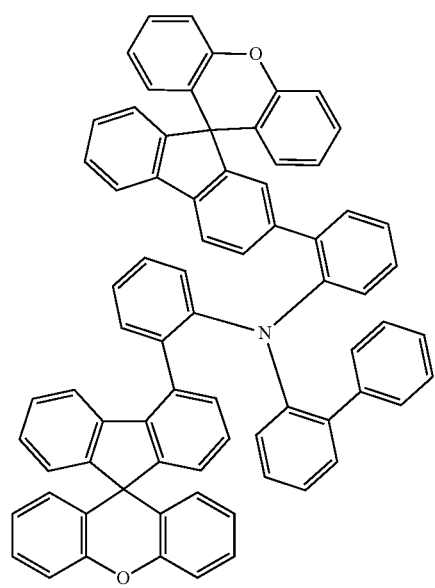
558
-continued
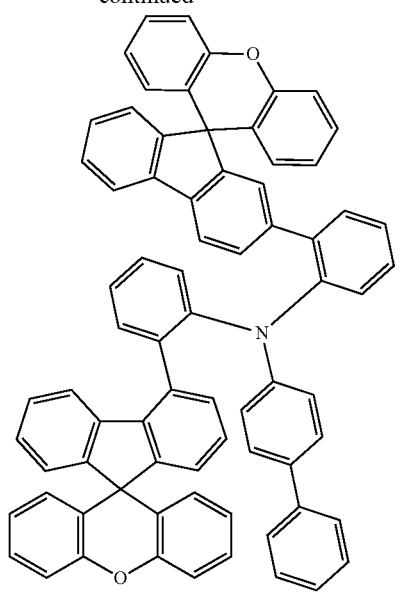
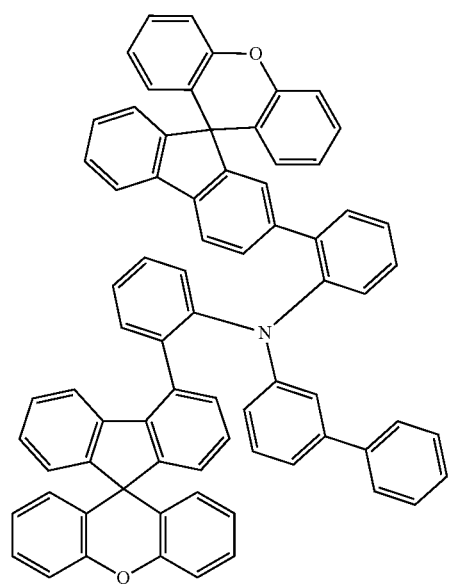
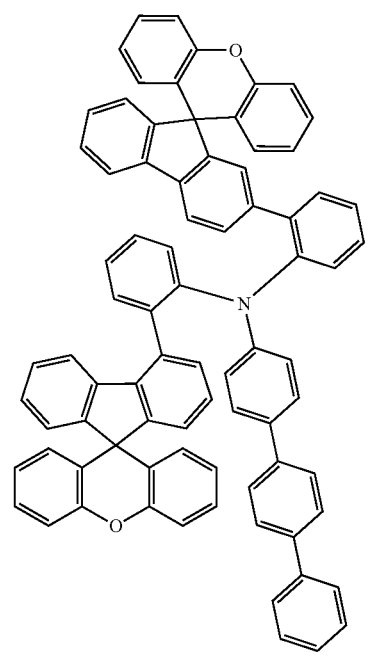

559
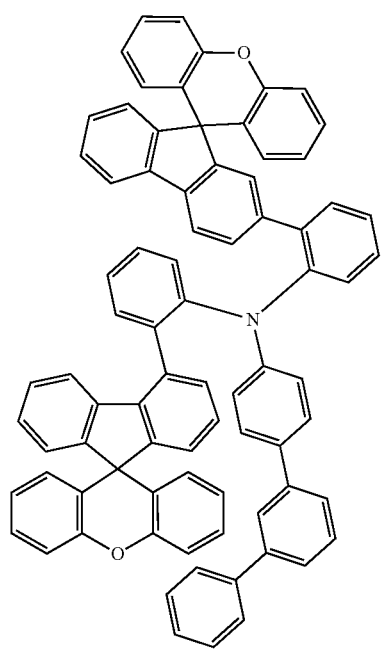
560
-continued
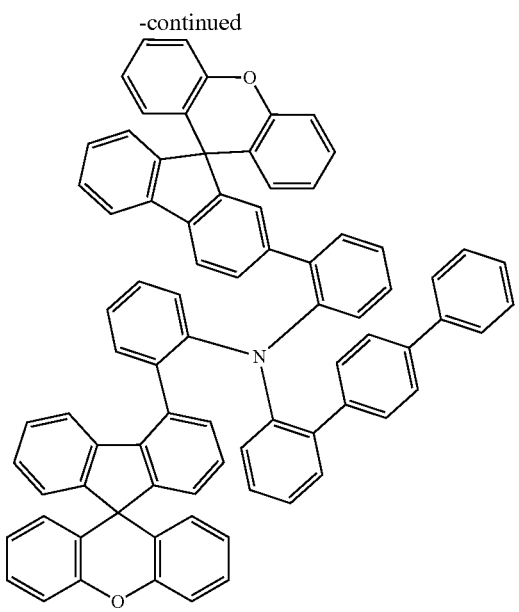
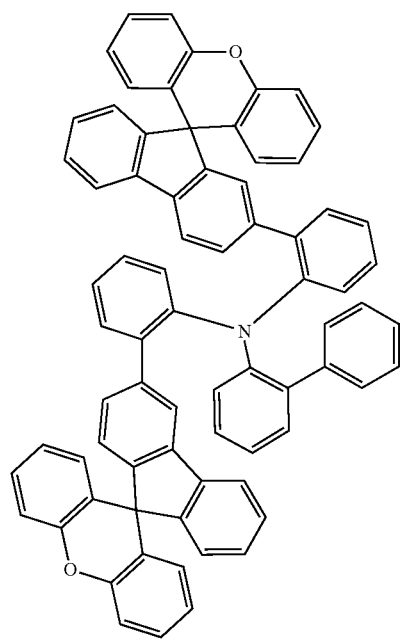
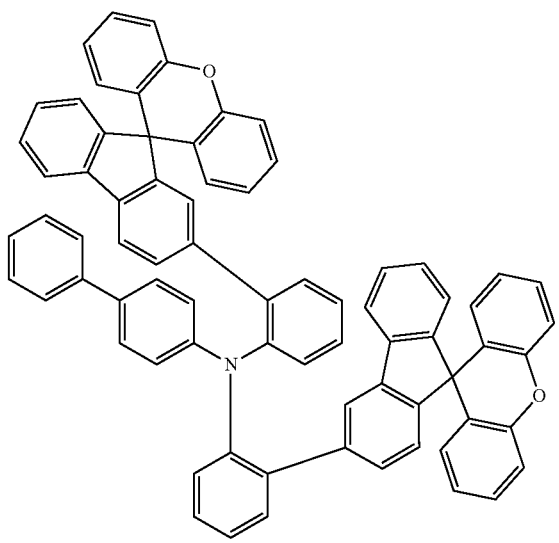

-continued
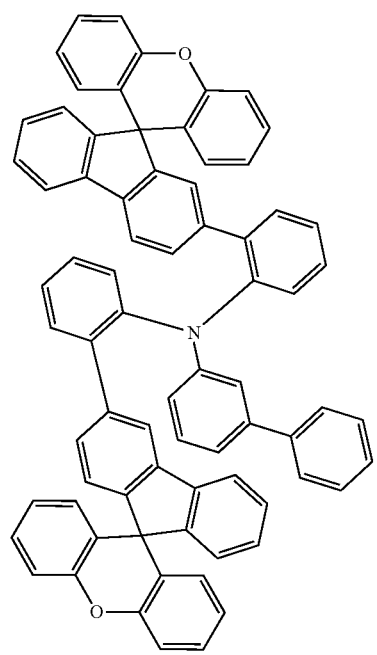
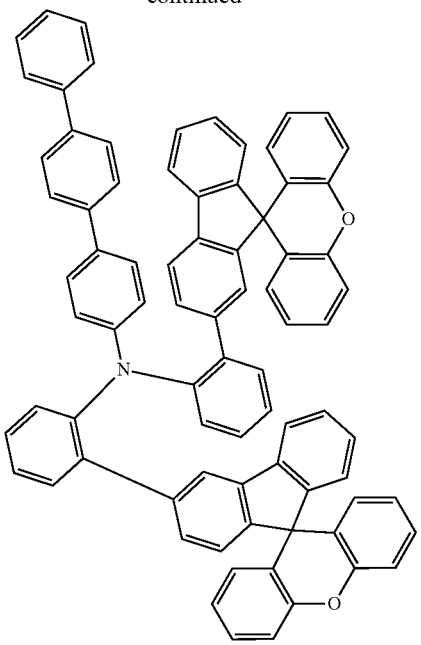
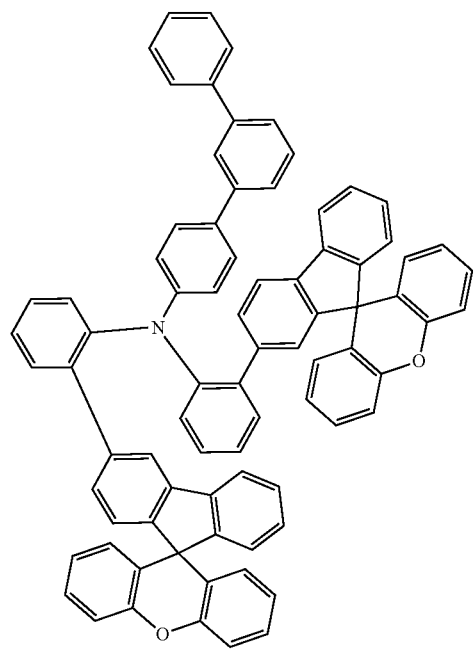
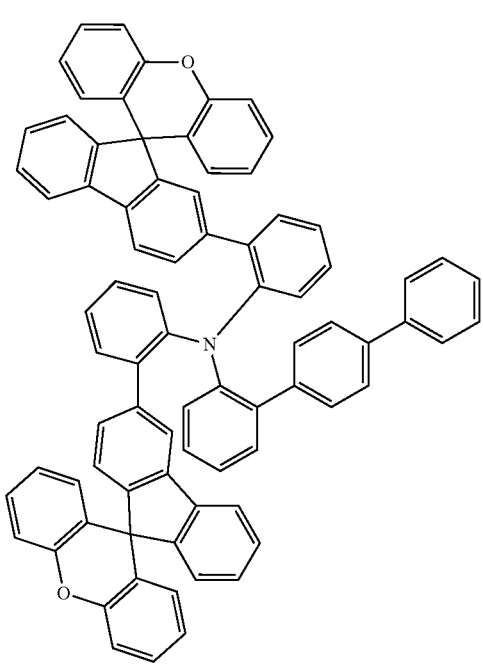

-continued
563
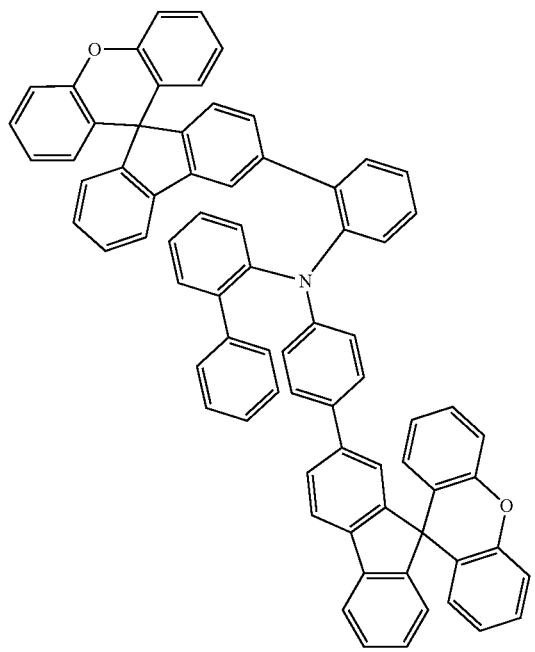
564
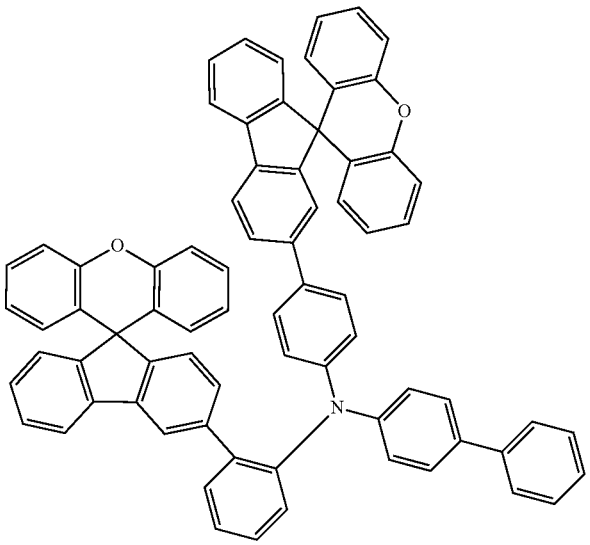
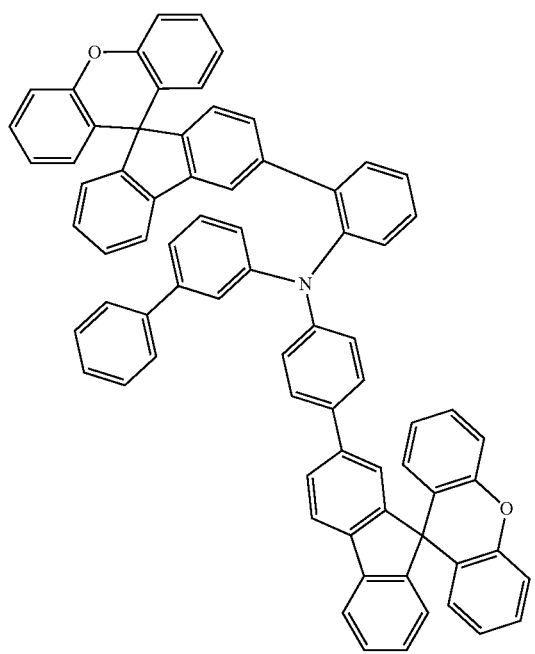
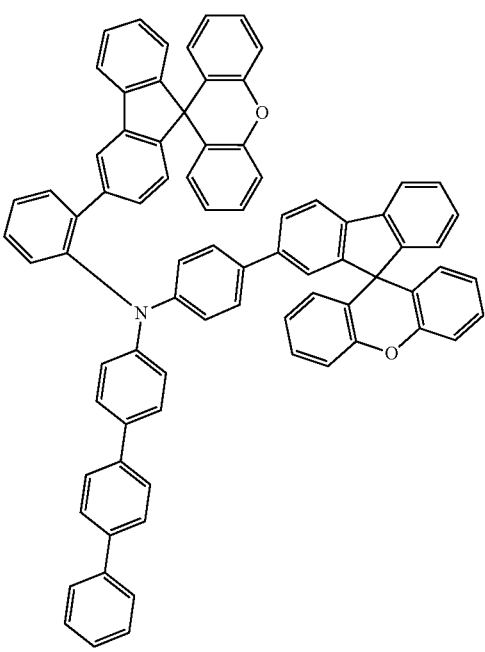

-continued
| 565 | 566 |
|---|---|
| 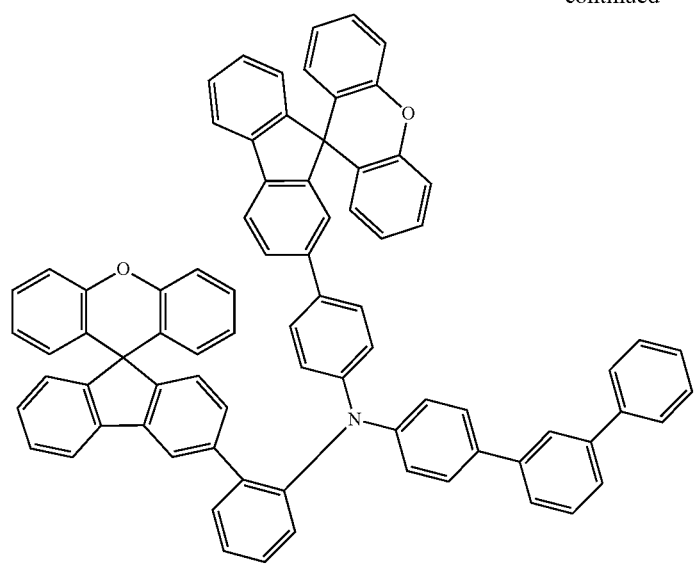 | |
| 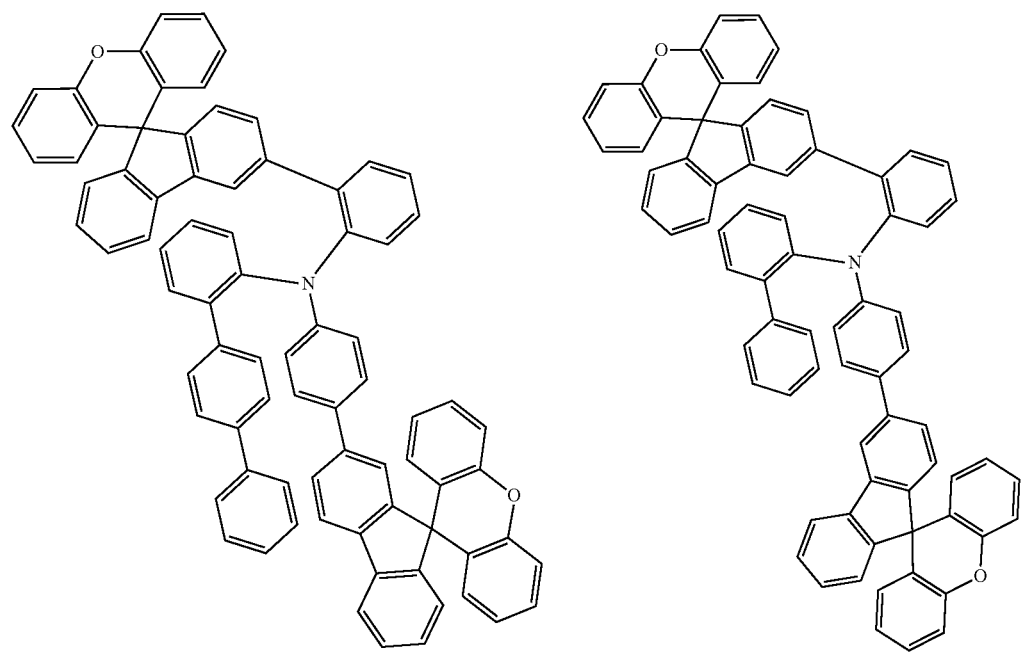 | |

567 568
-continued
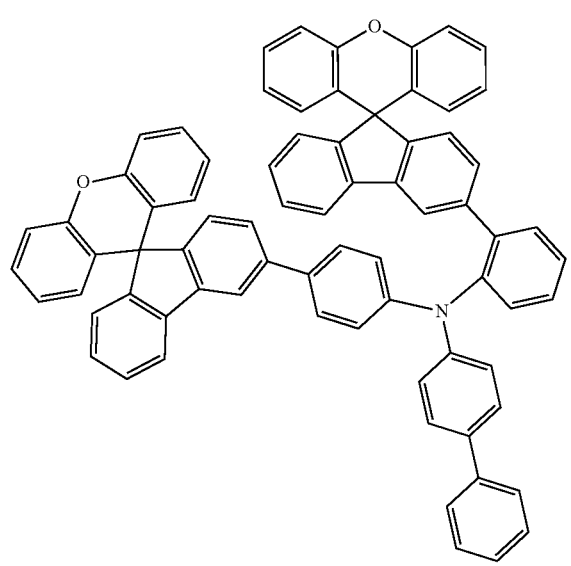 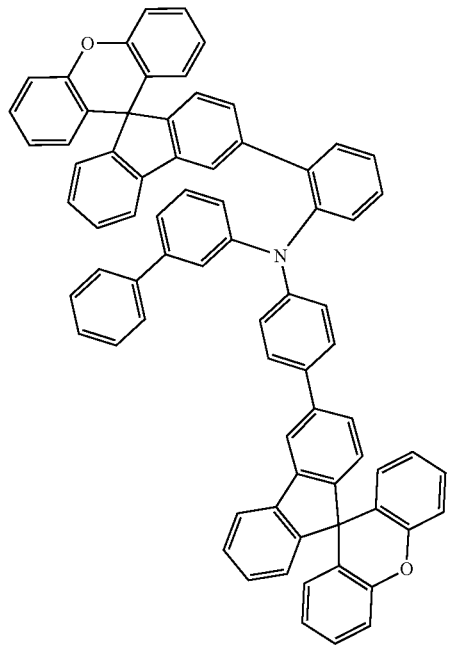
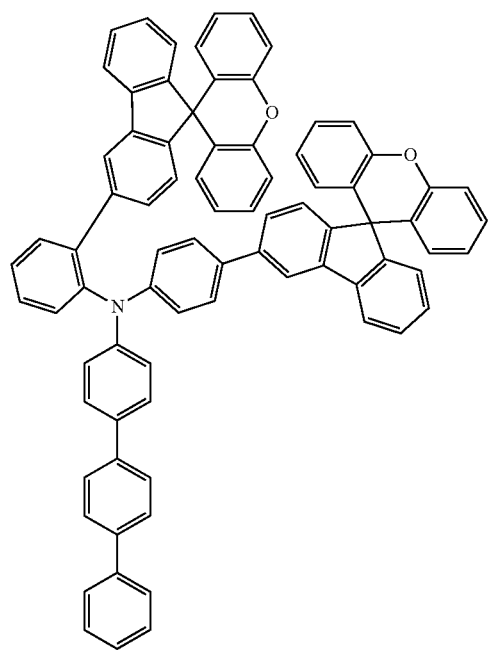 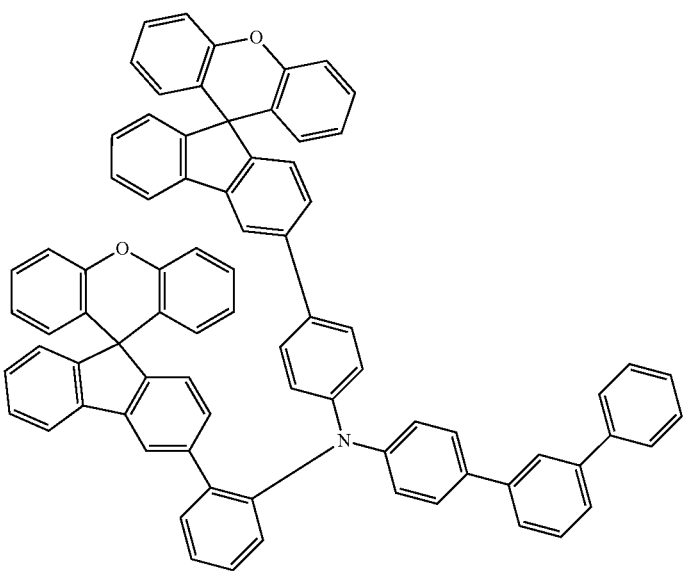

-continued
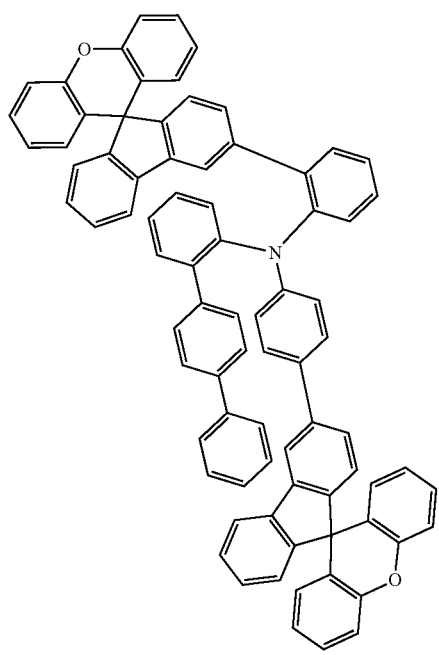
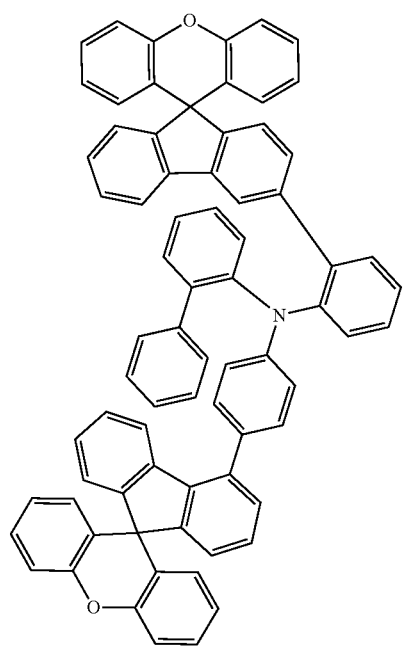
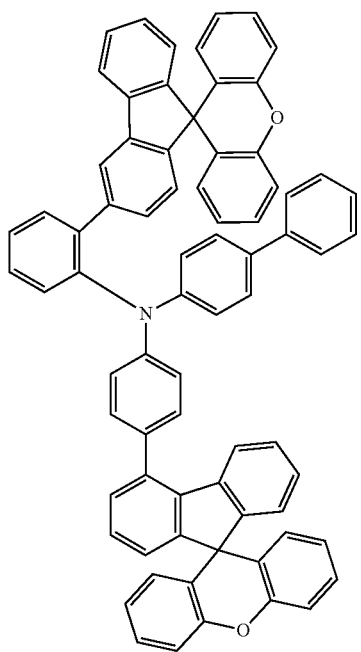
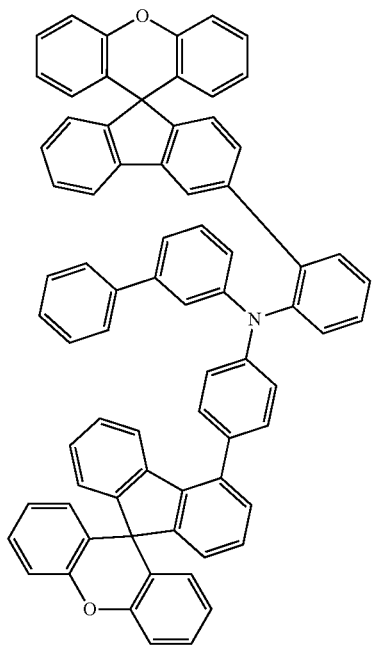

571
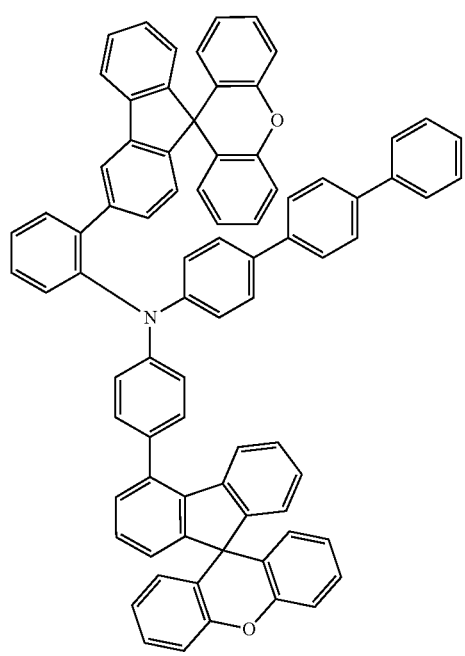
572
-continued
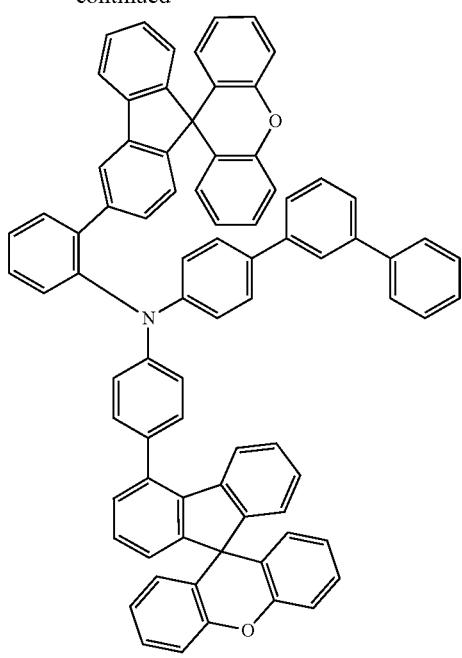
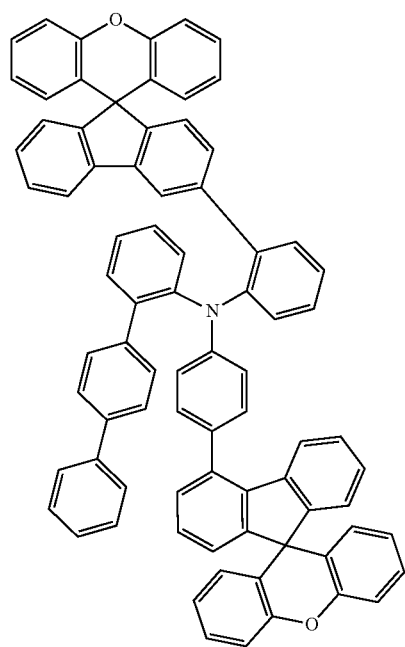
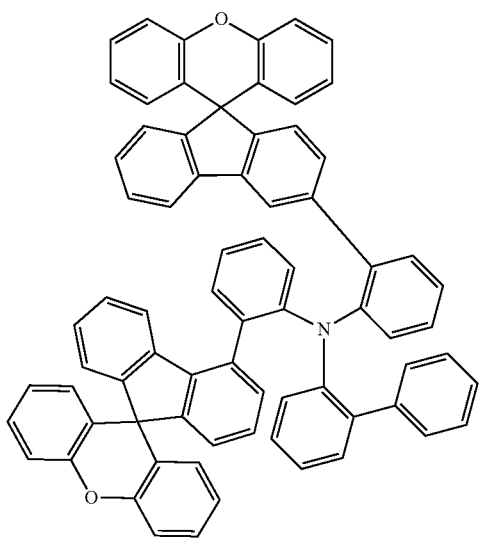

573
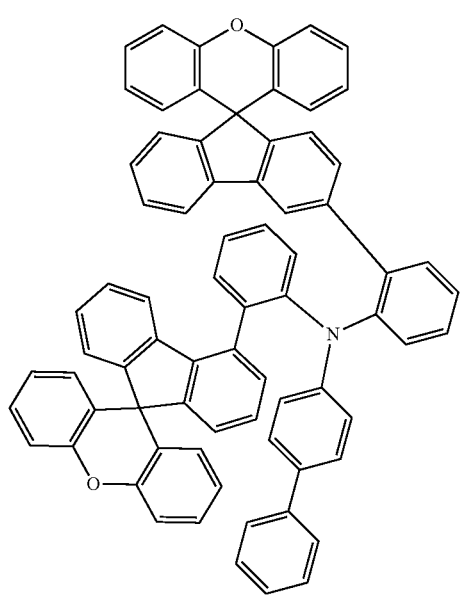
574
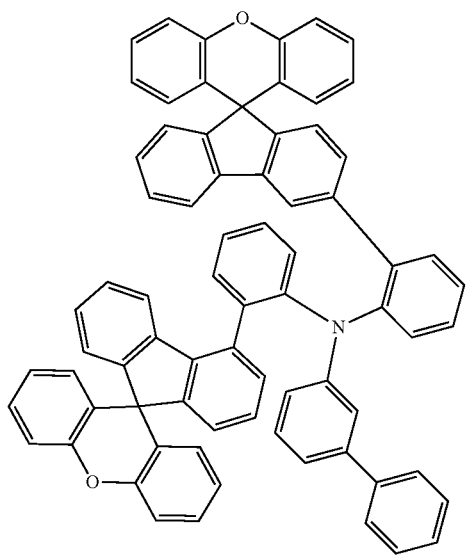
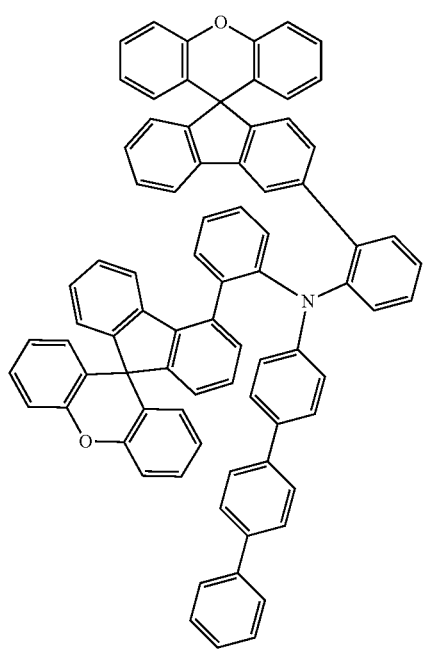
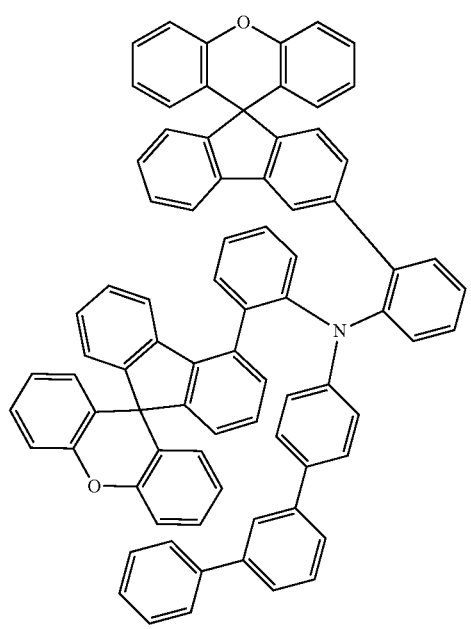

575
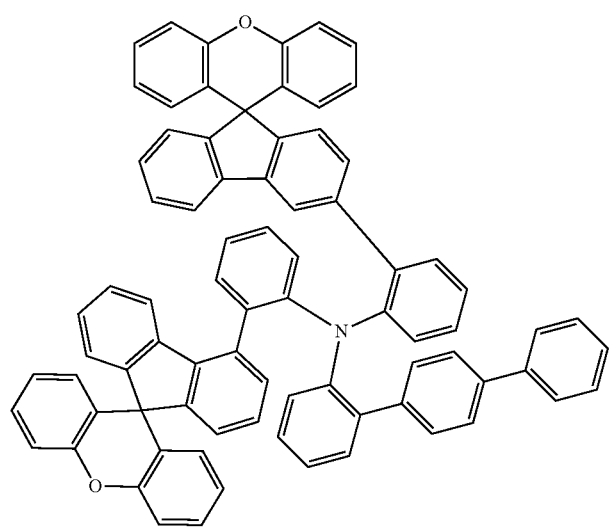
576
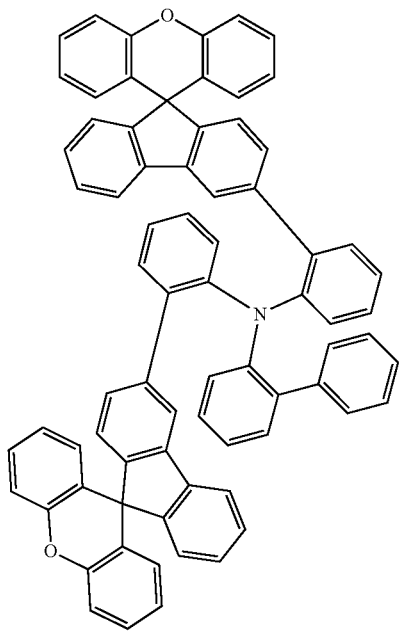
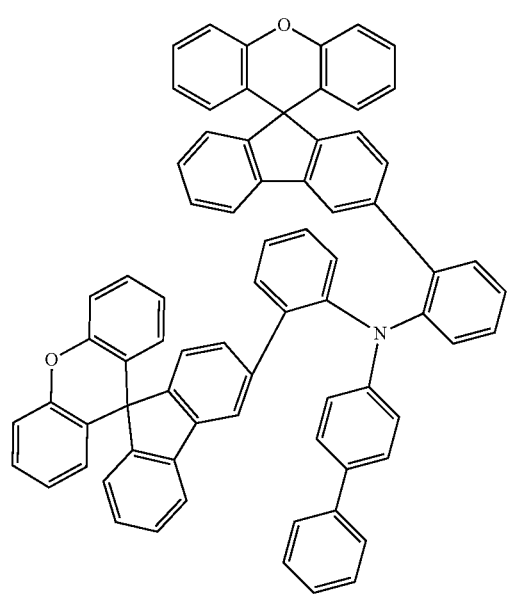
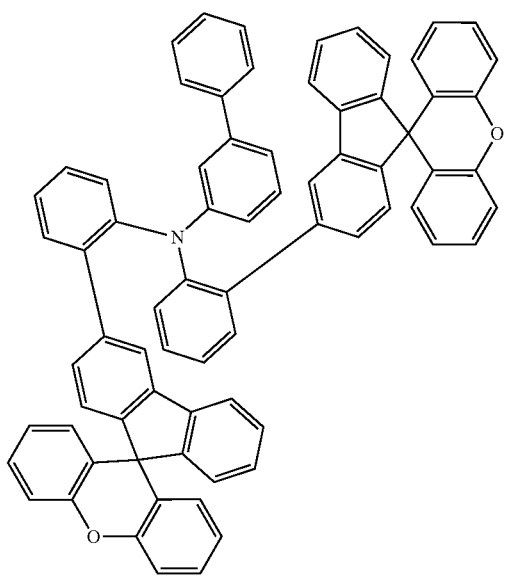

-continued
577
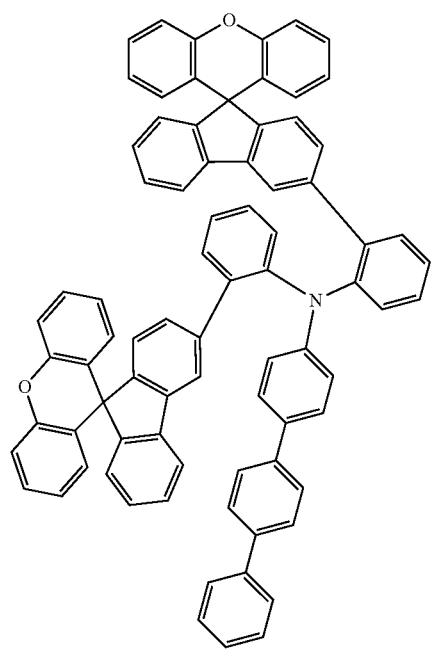
578
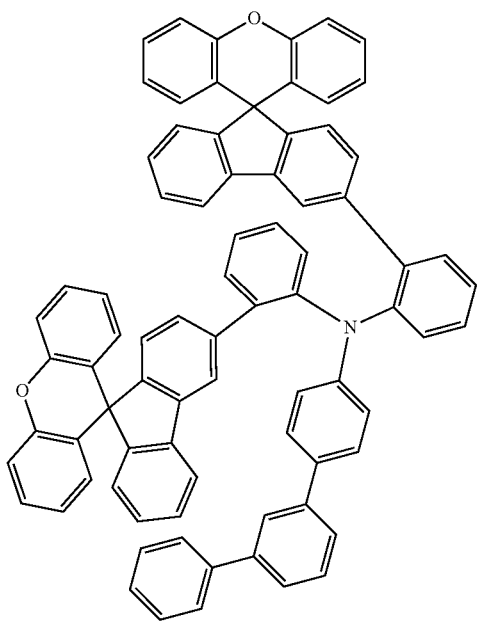
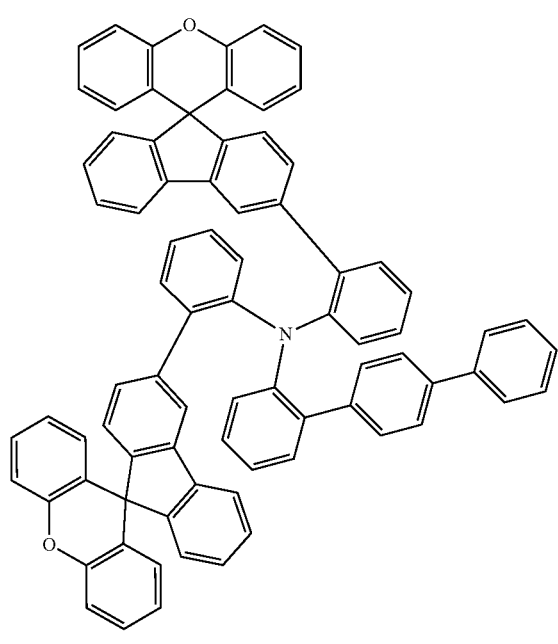
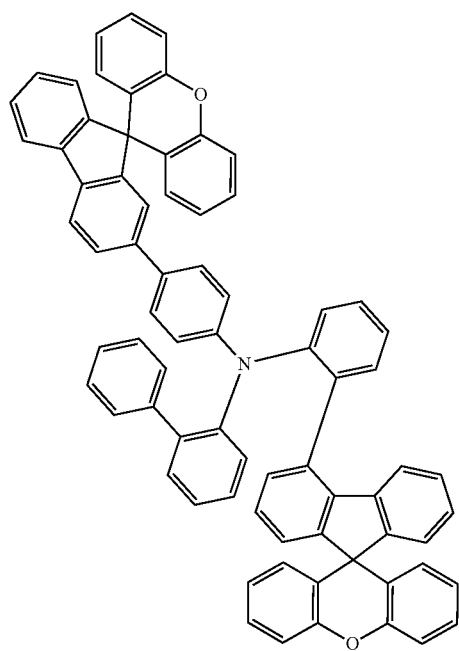

579
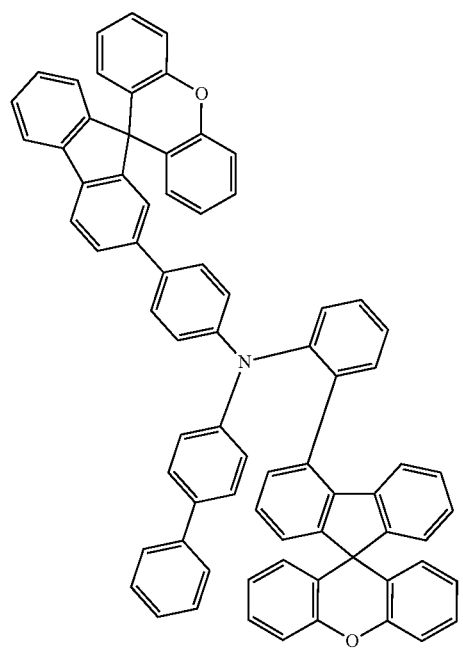
580
-continued
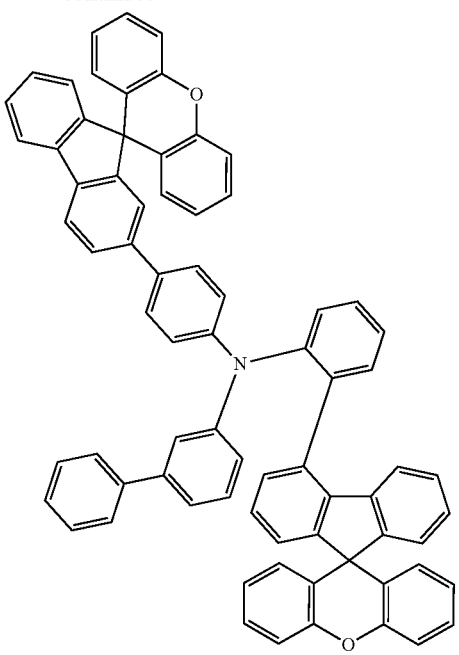
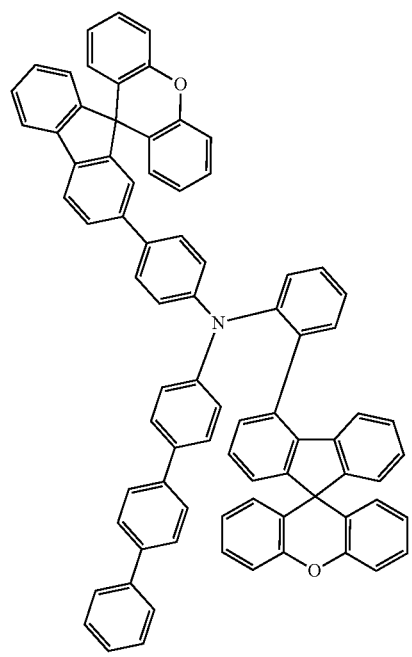
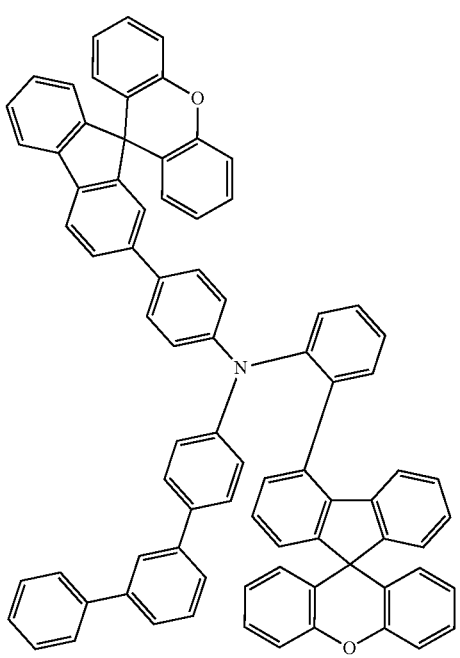

581
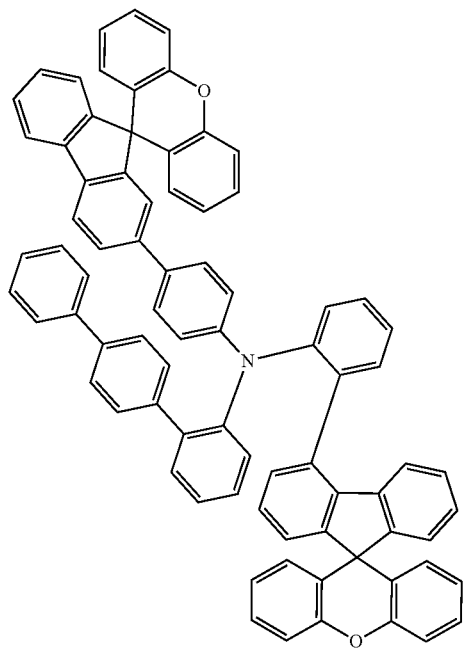
582
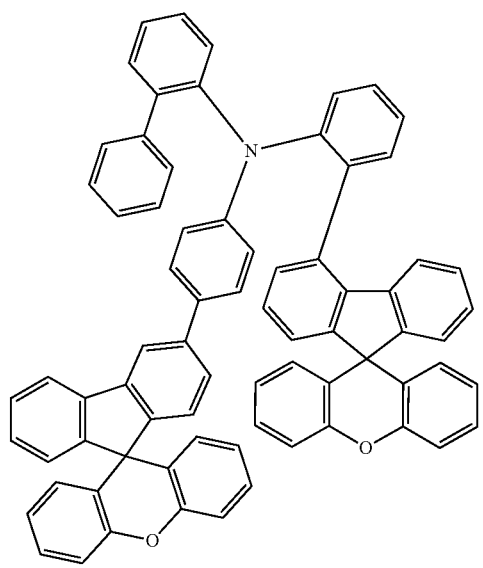
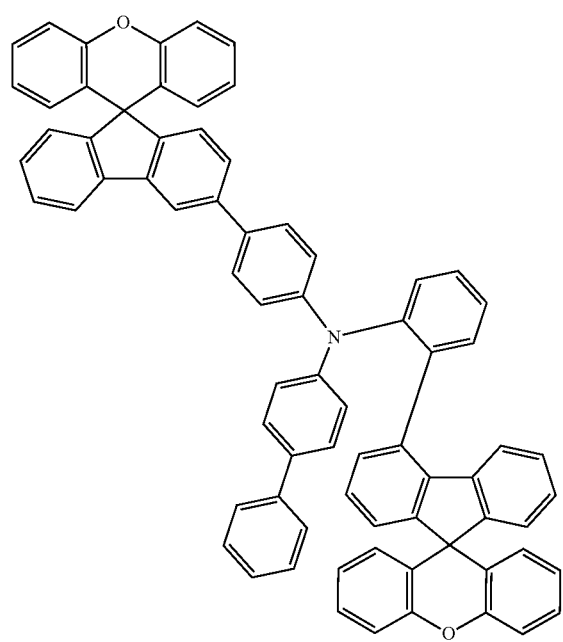
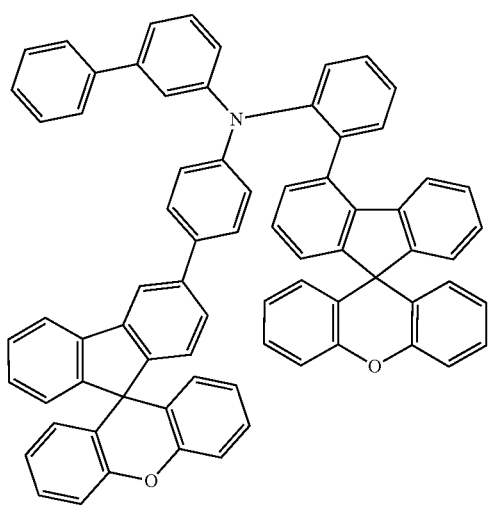

583
584
-continued
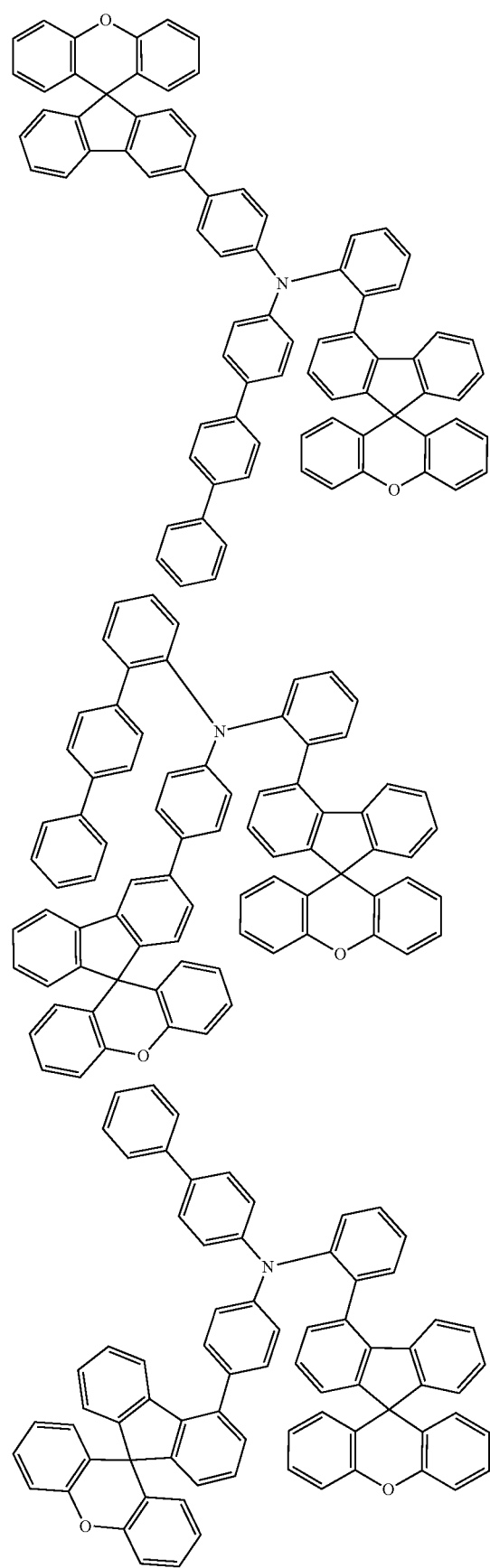
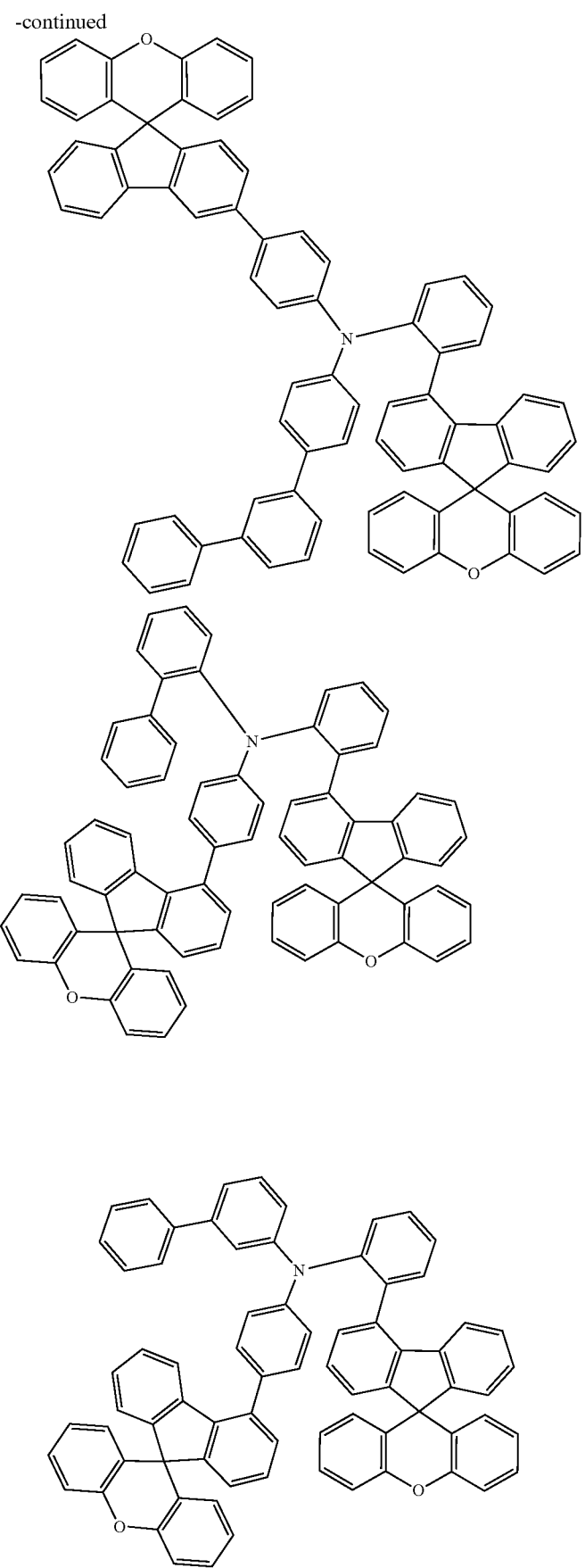

585
586
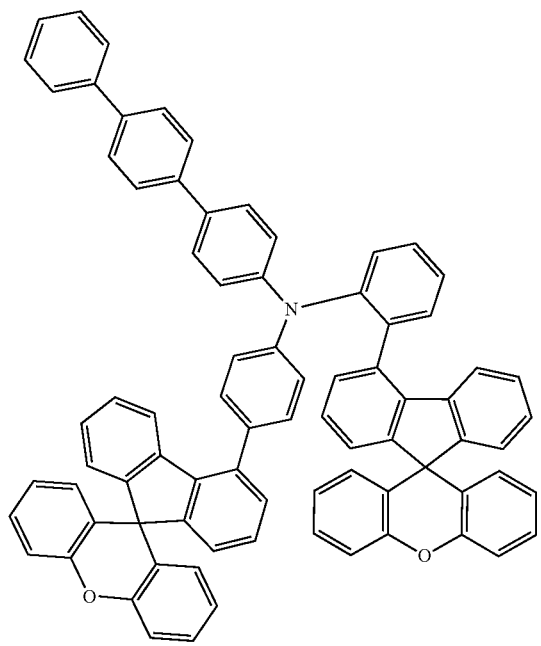
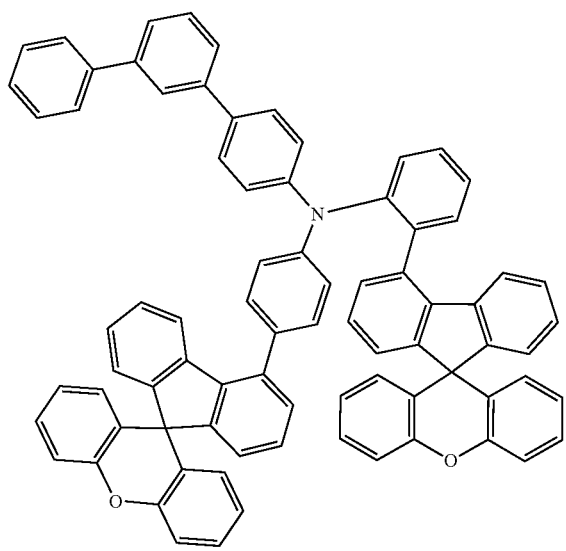
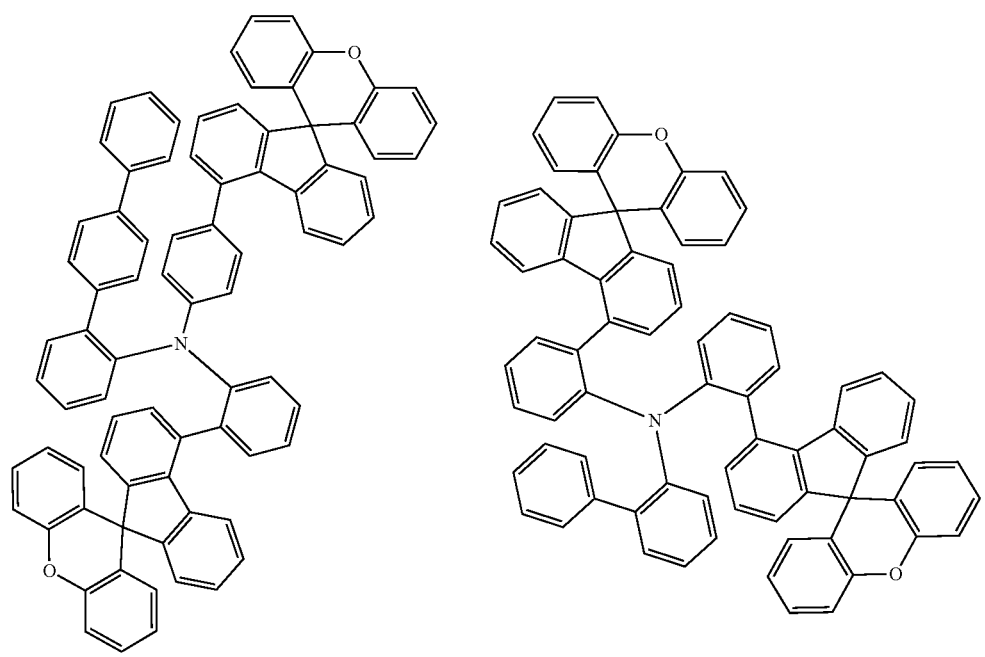

-continued
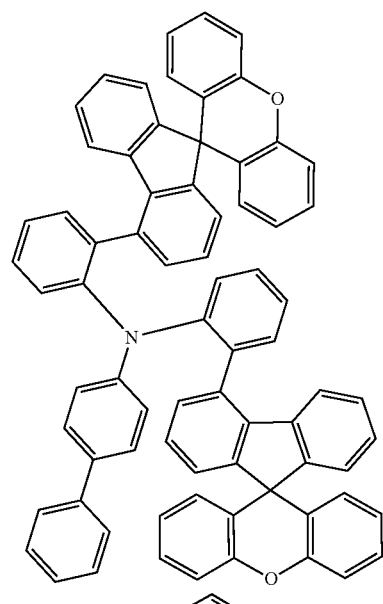
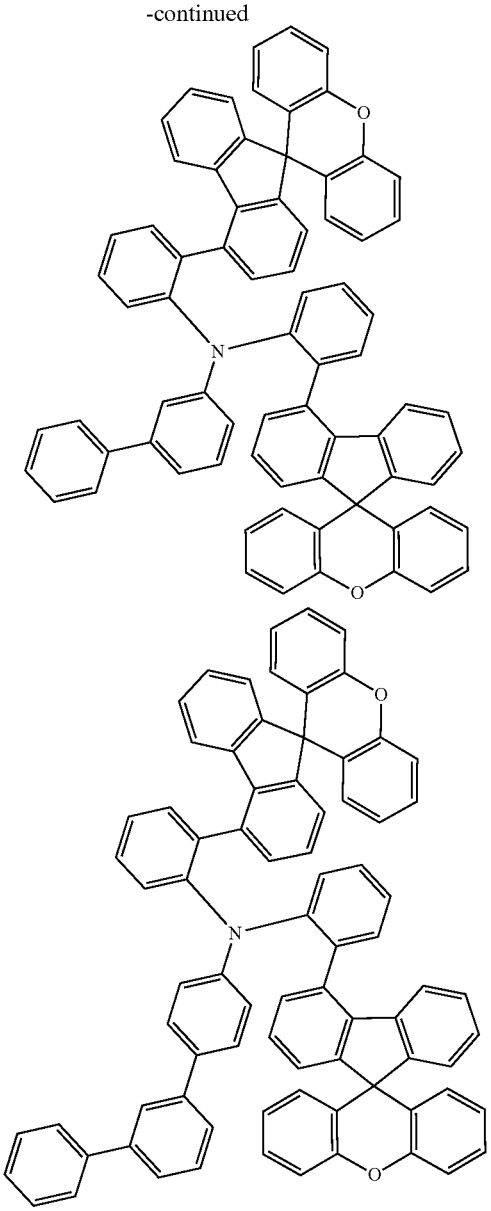
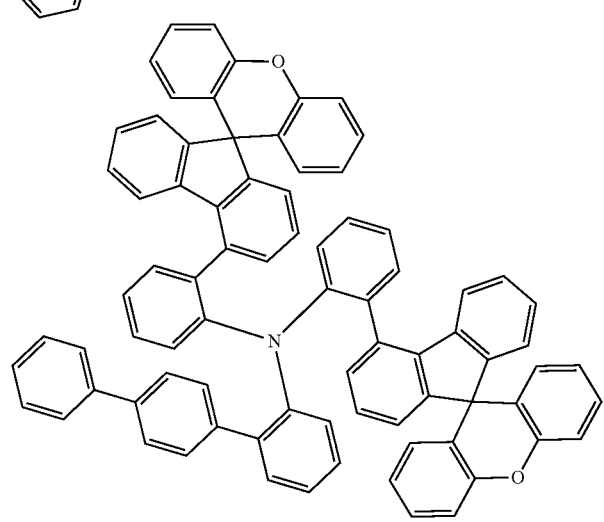

-continued
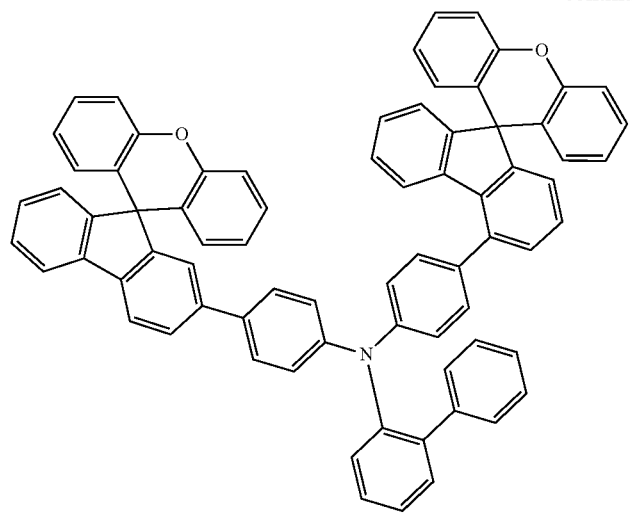
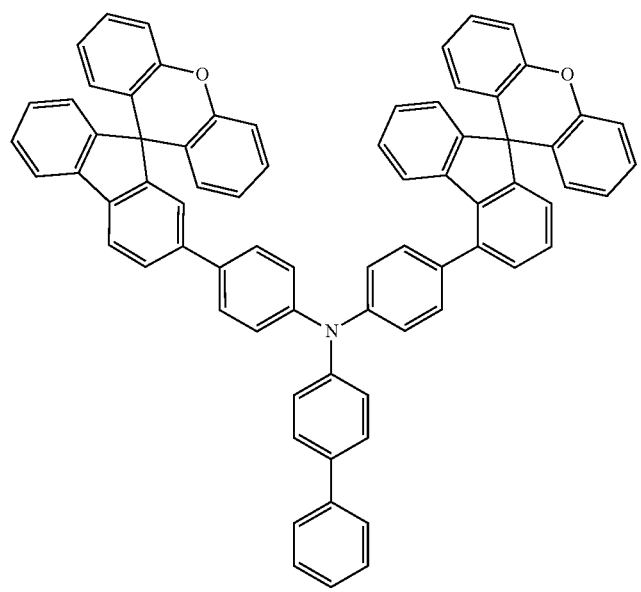
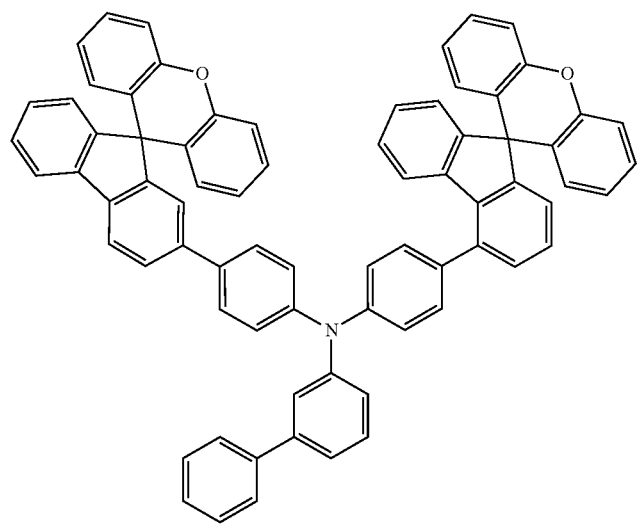

591 592
-continued
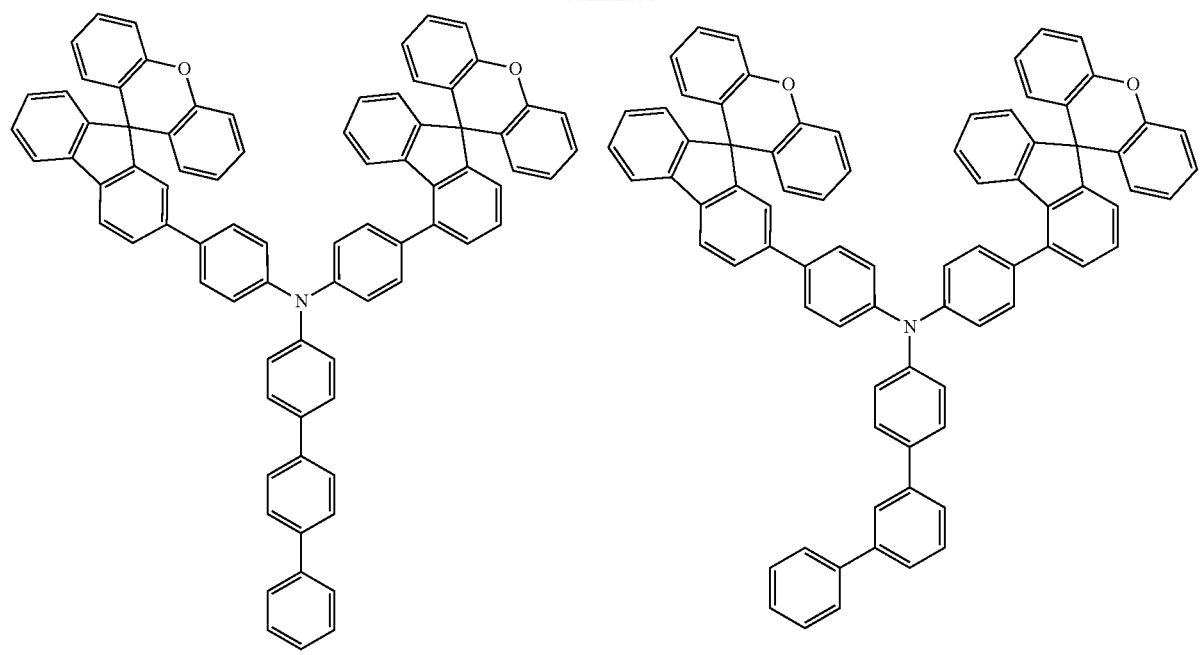
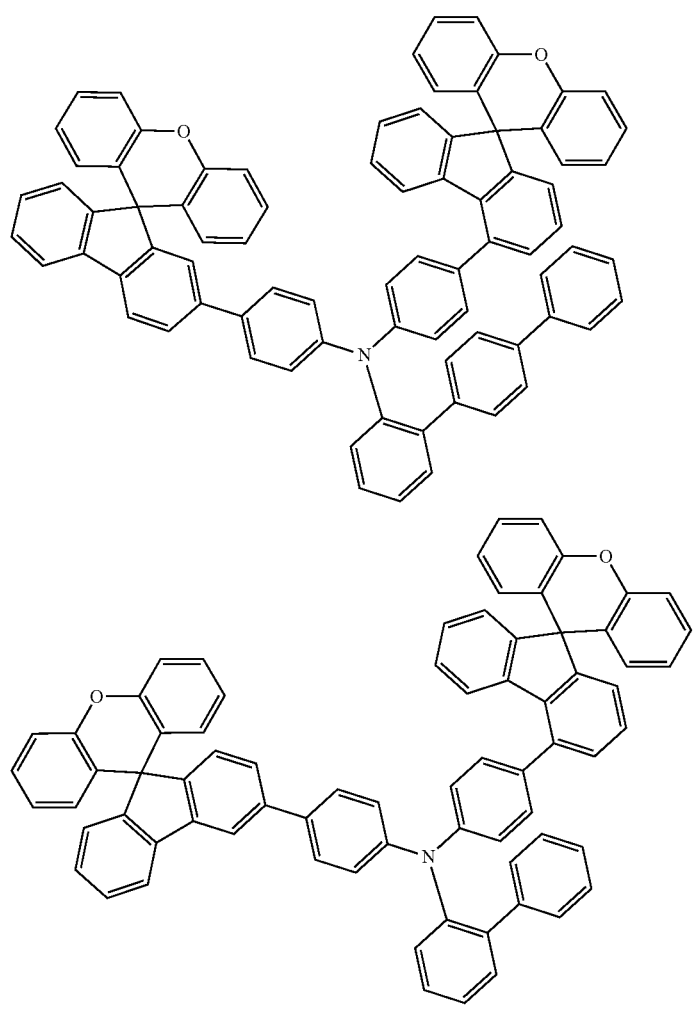

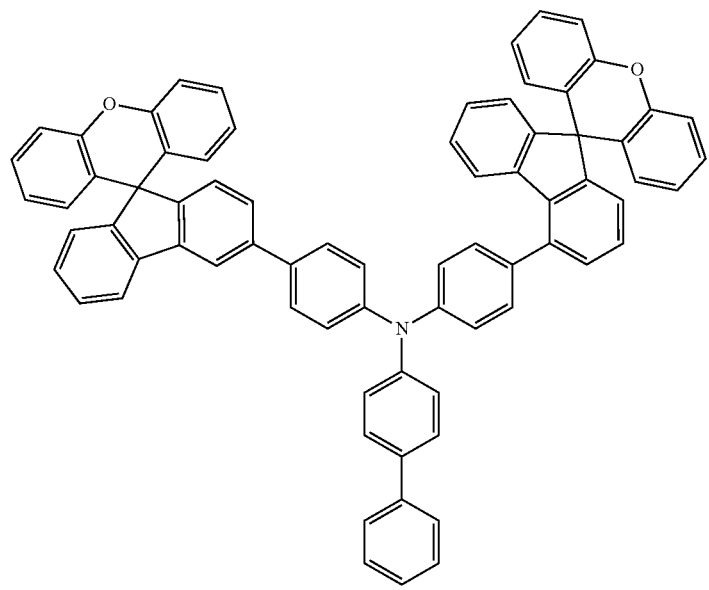
-continued
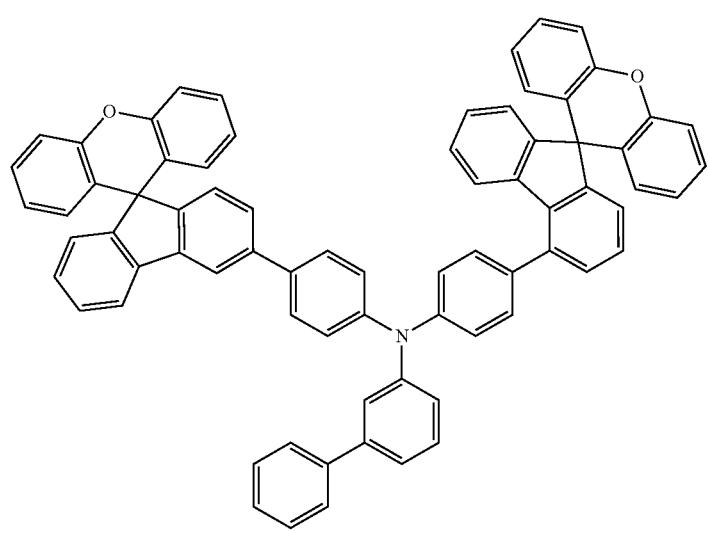

-continued
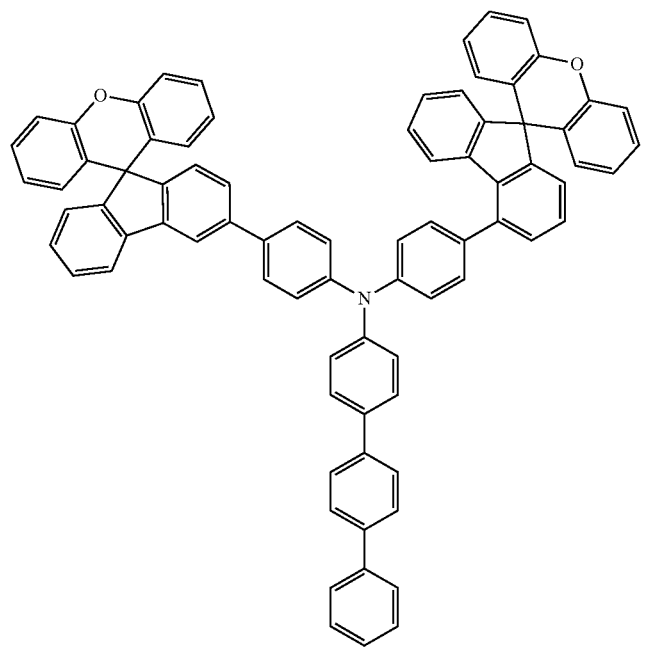
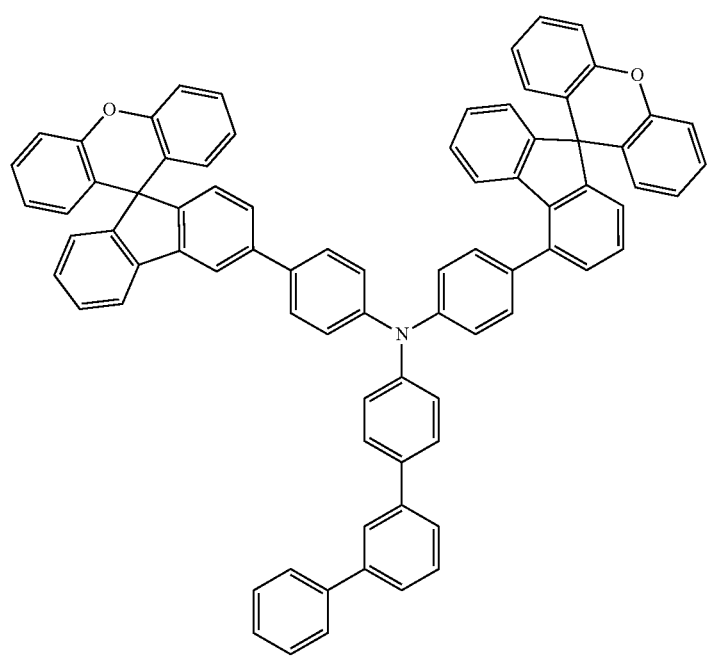

-continued
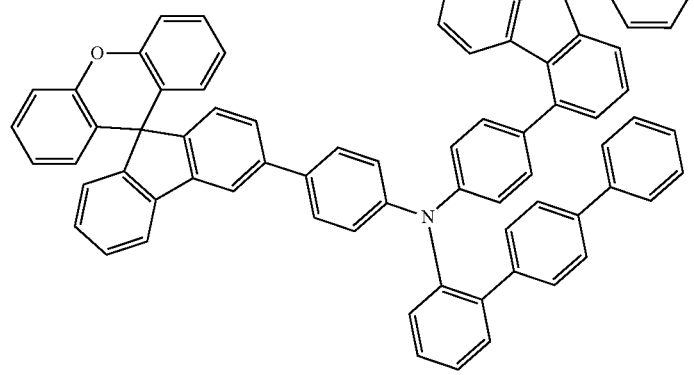
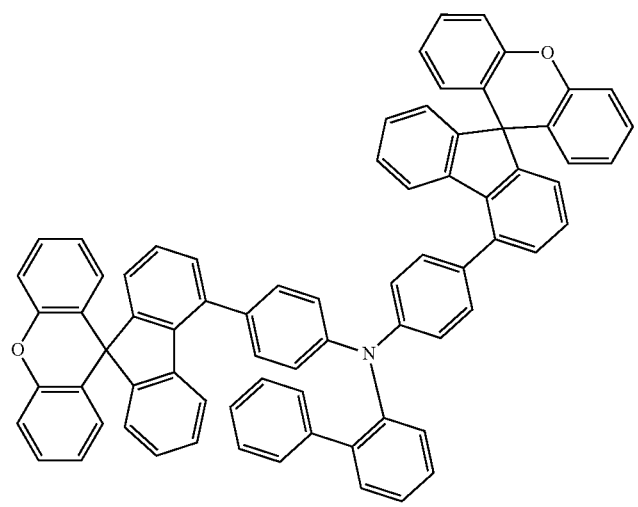
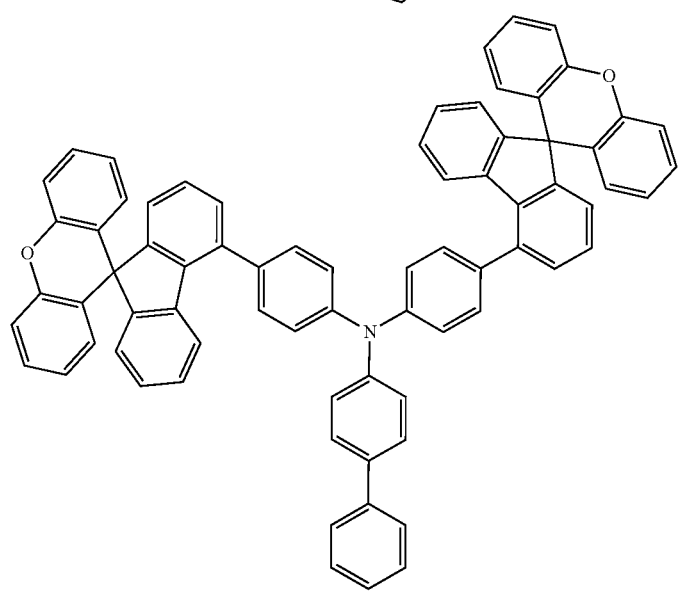

-continued
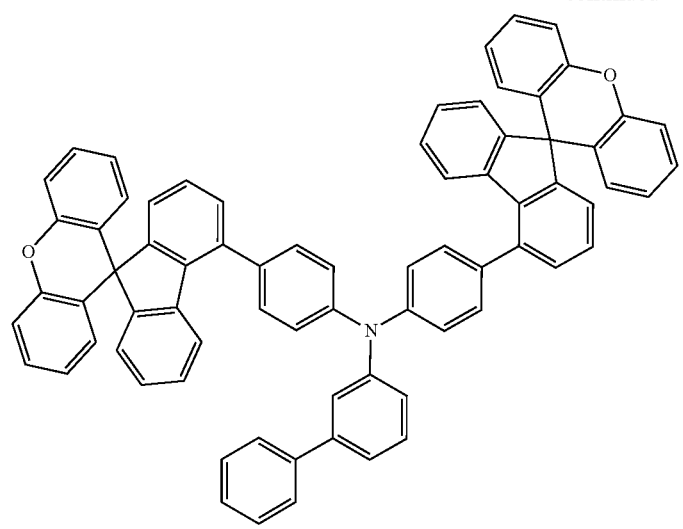
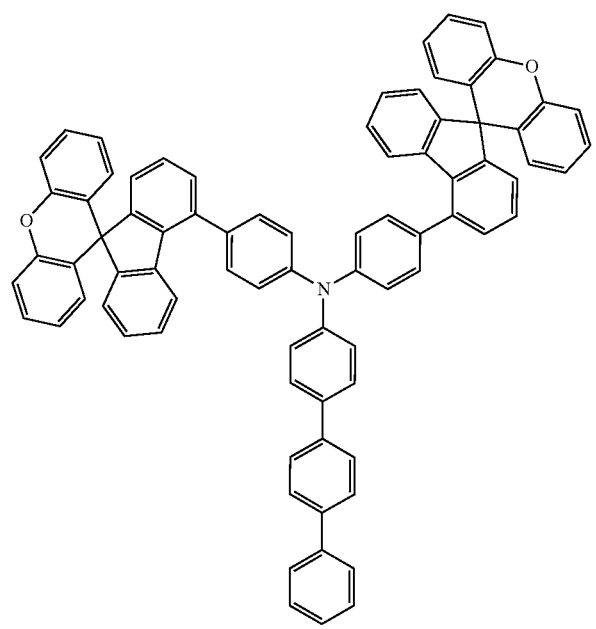

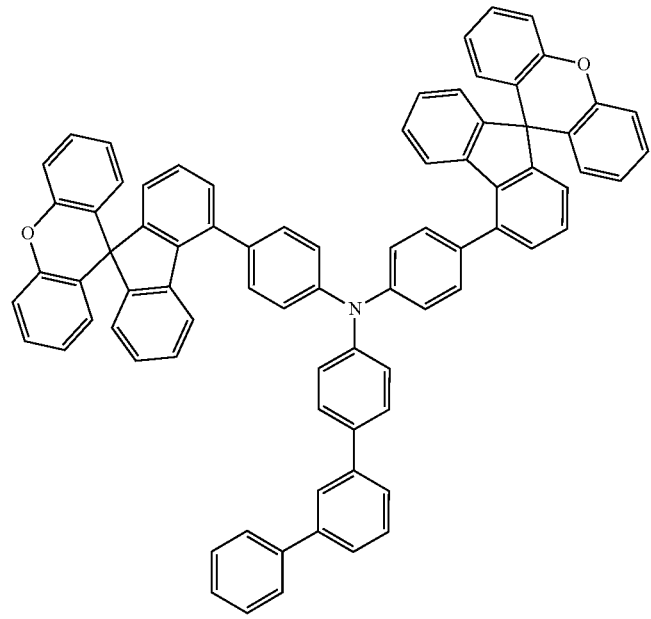
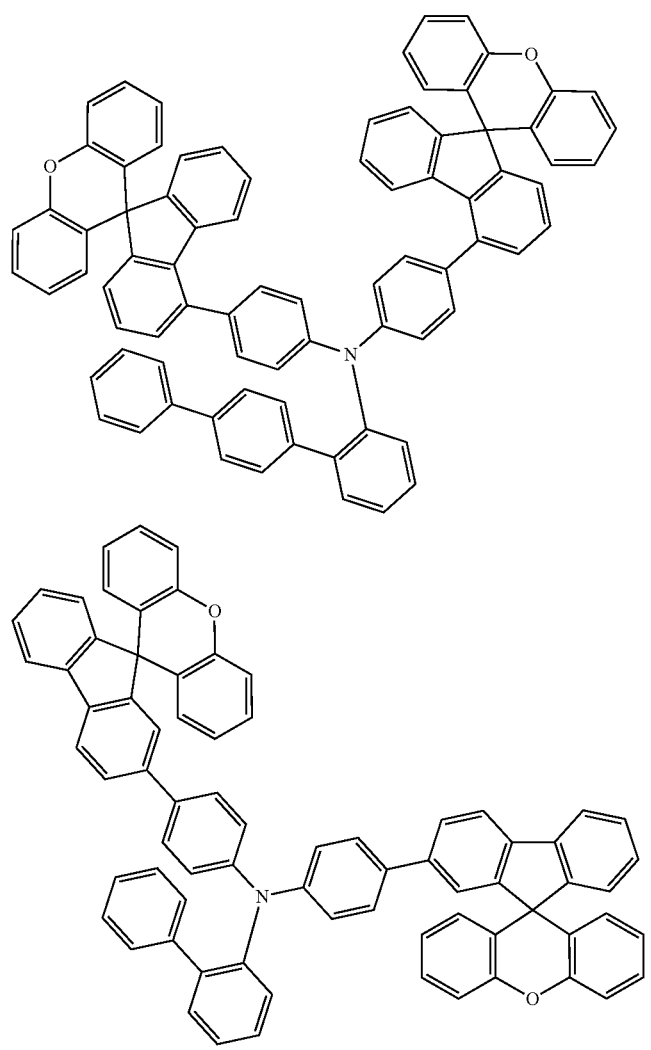

603
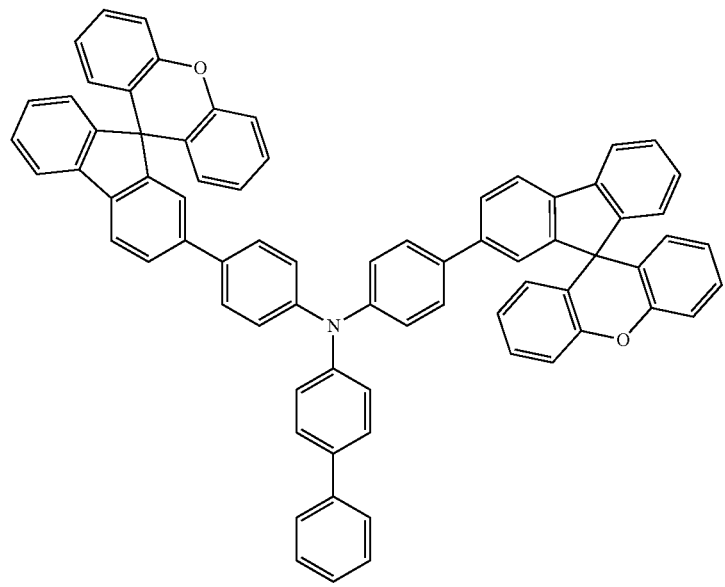
604
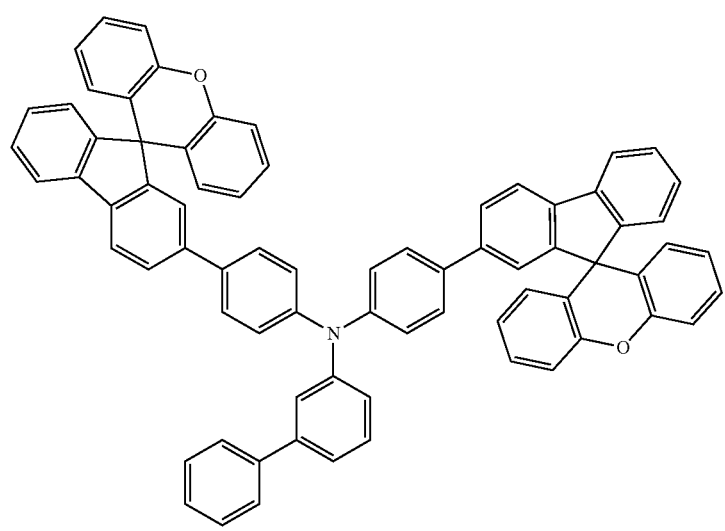

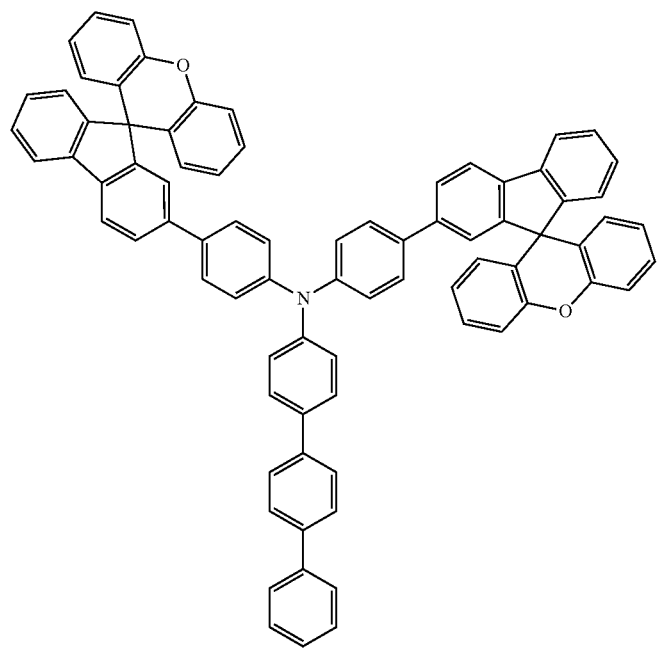
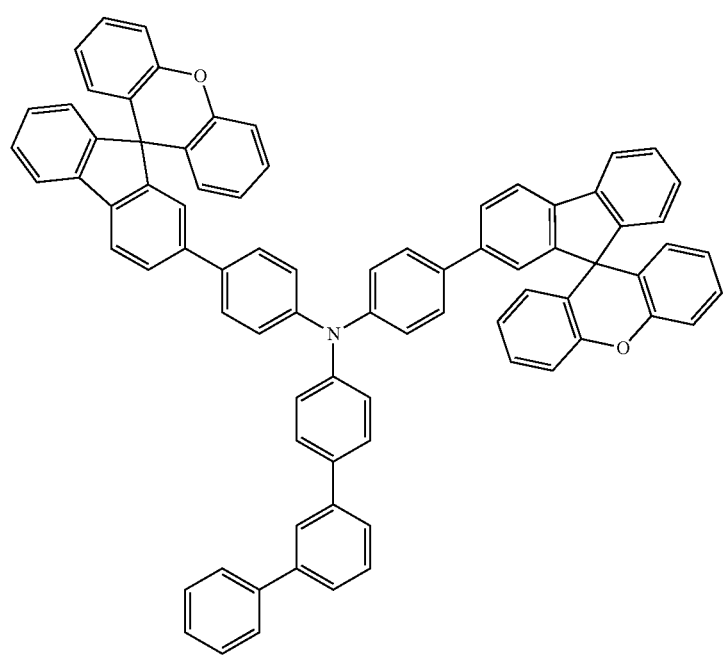

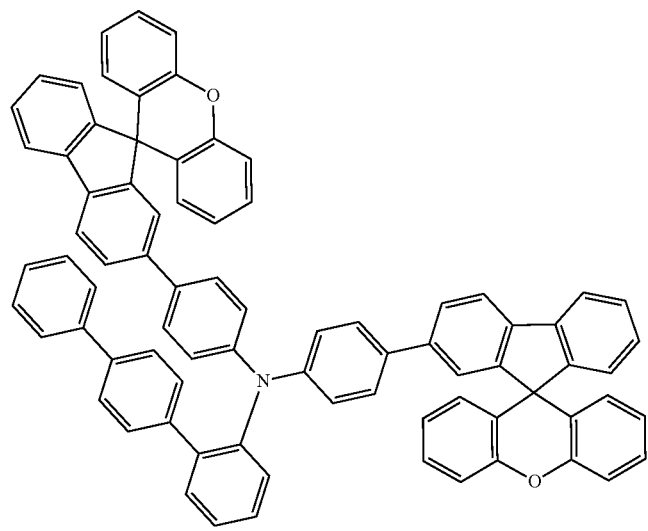
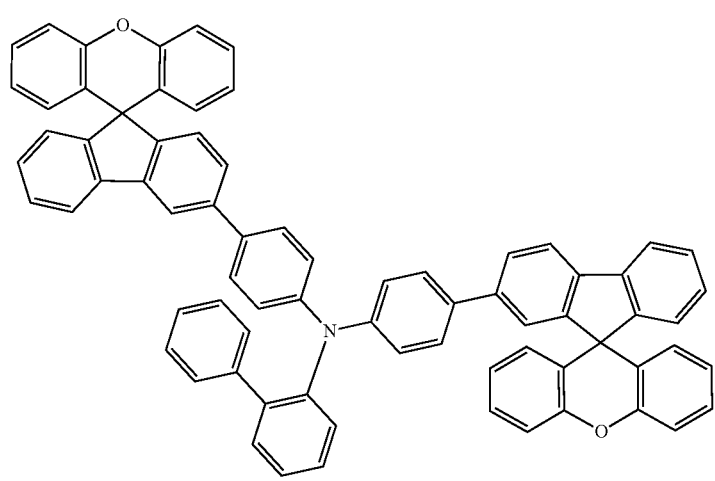
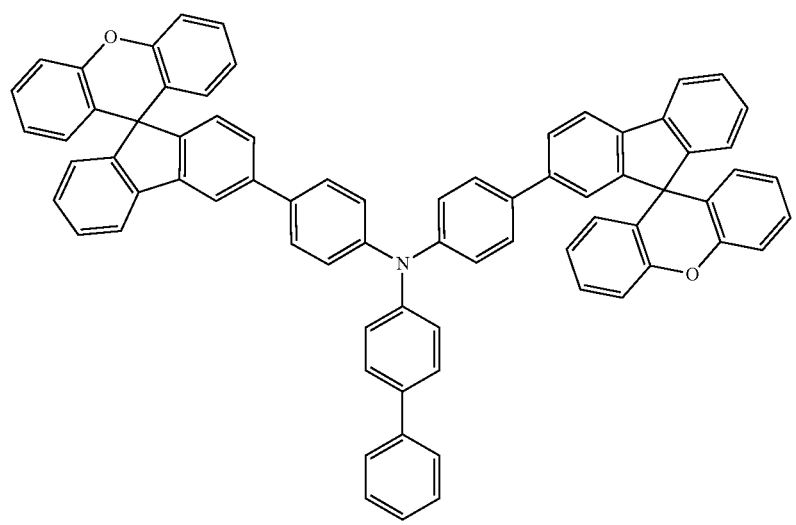

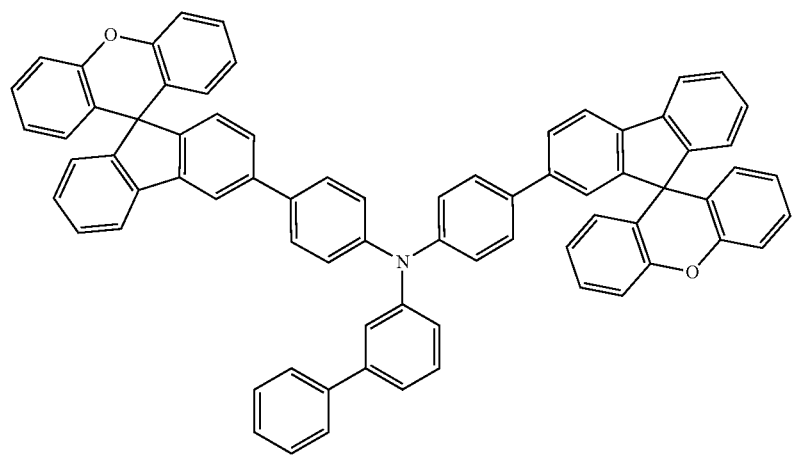
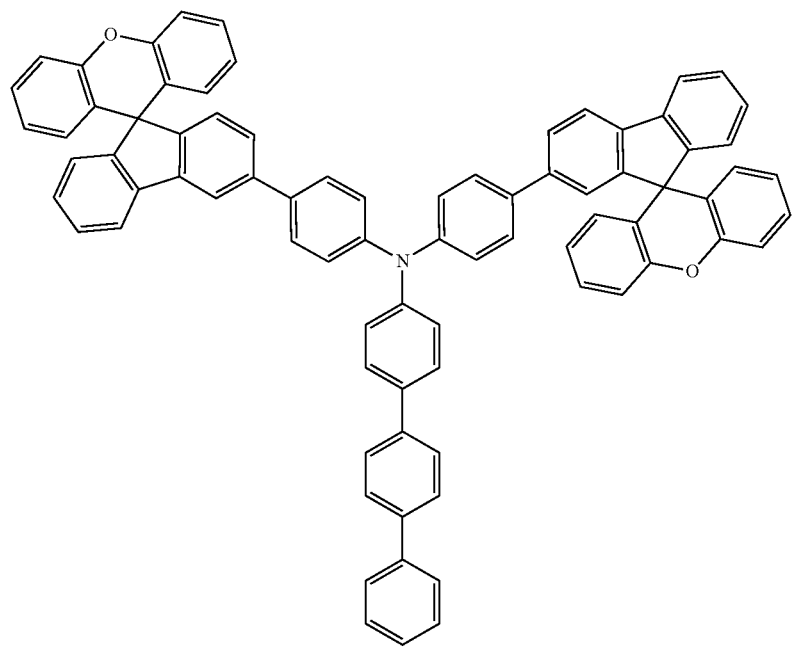
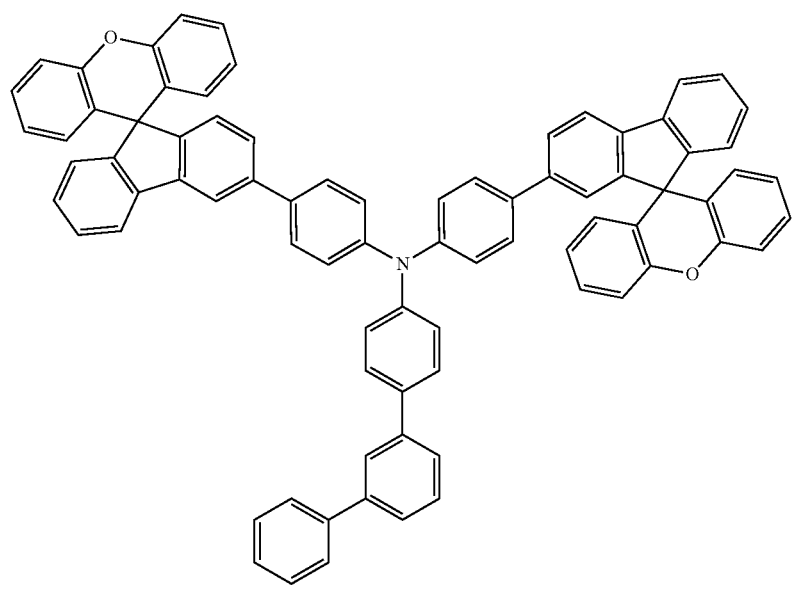

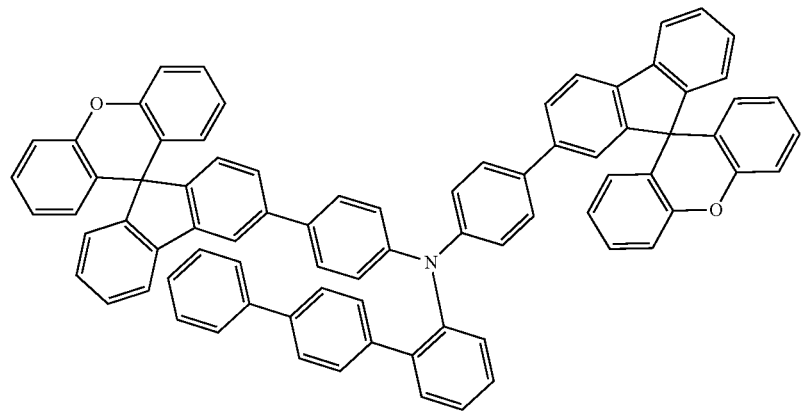
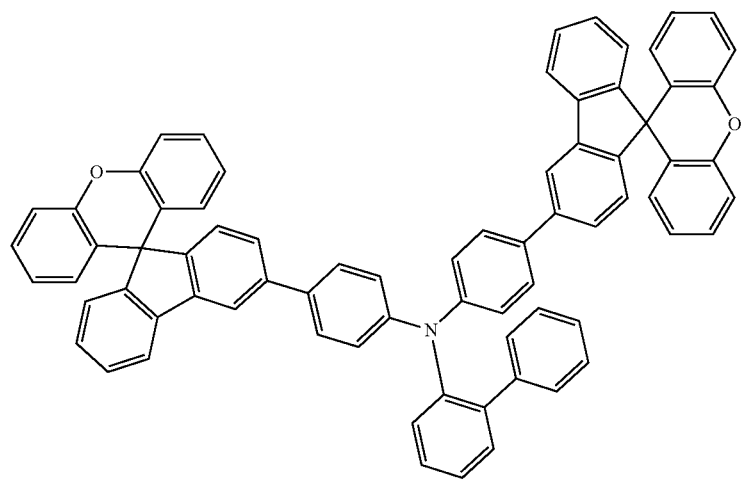
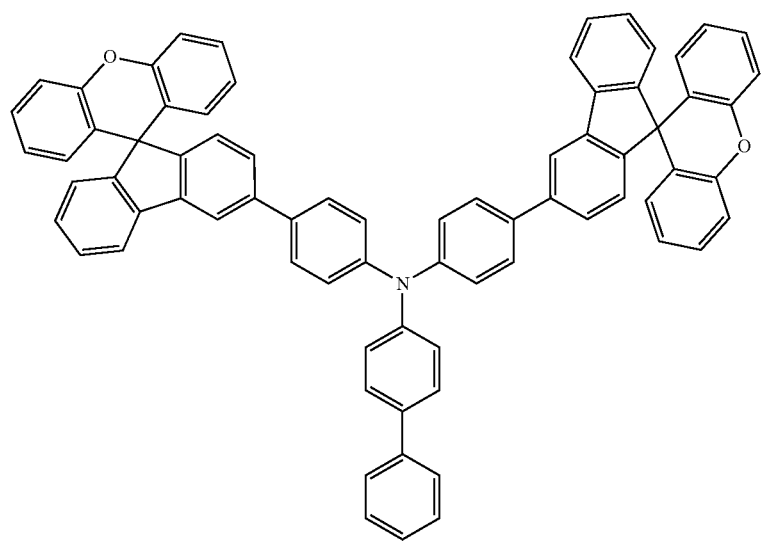

-continued
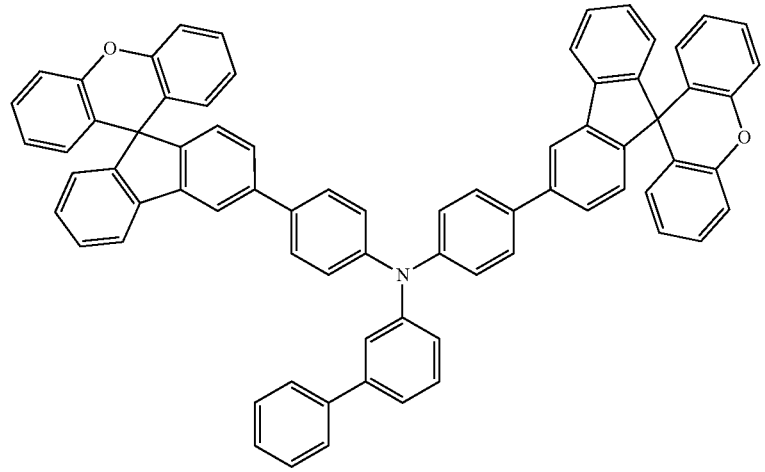
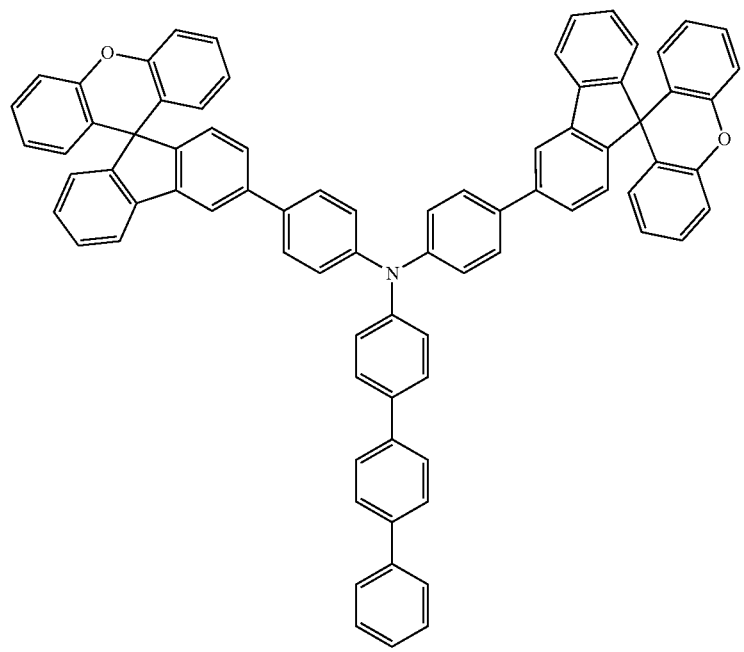
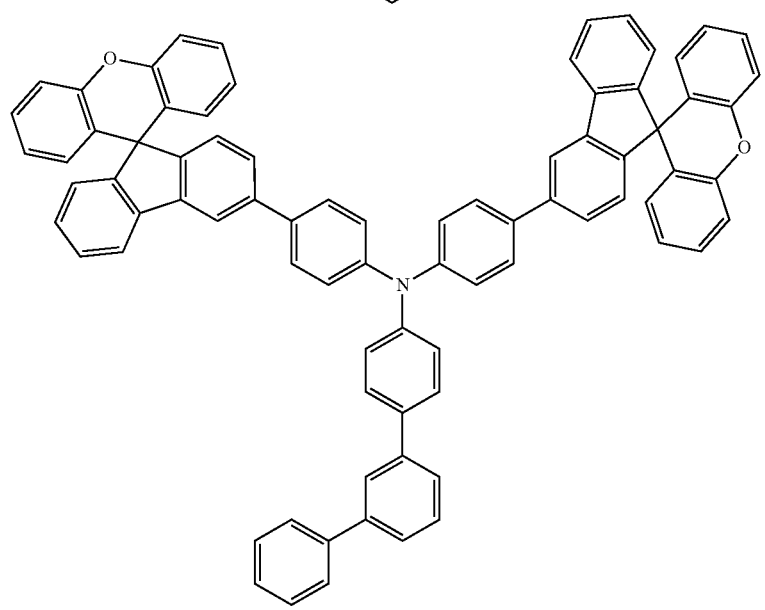

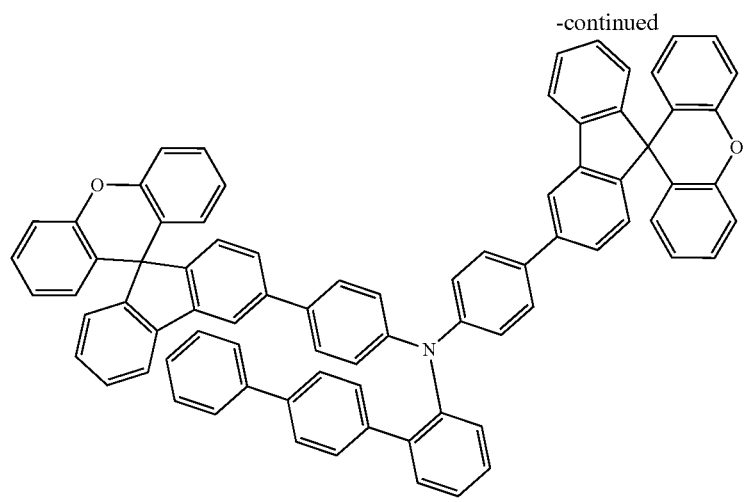
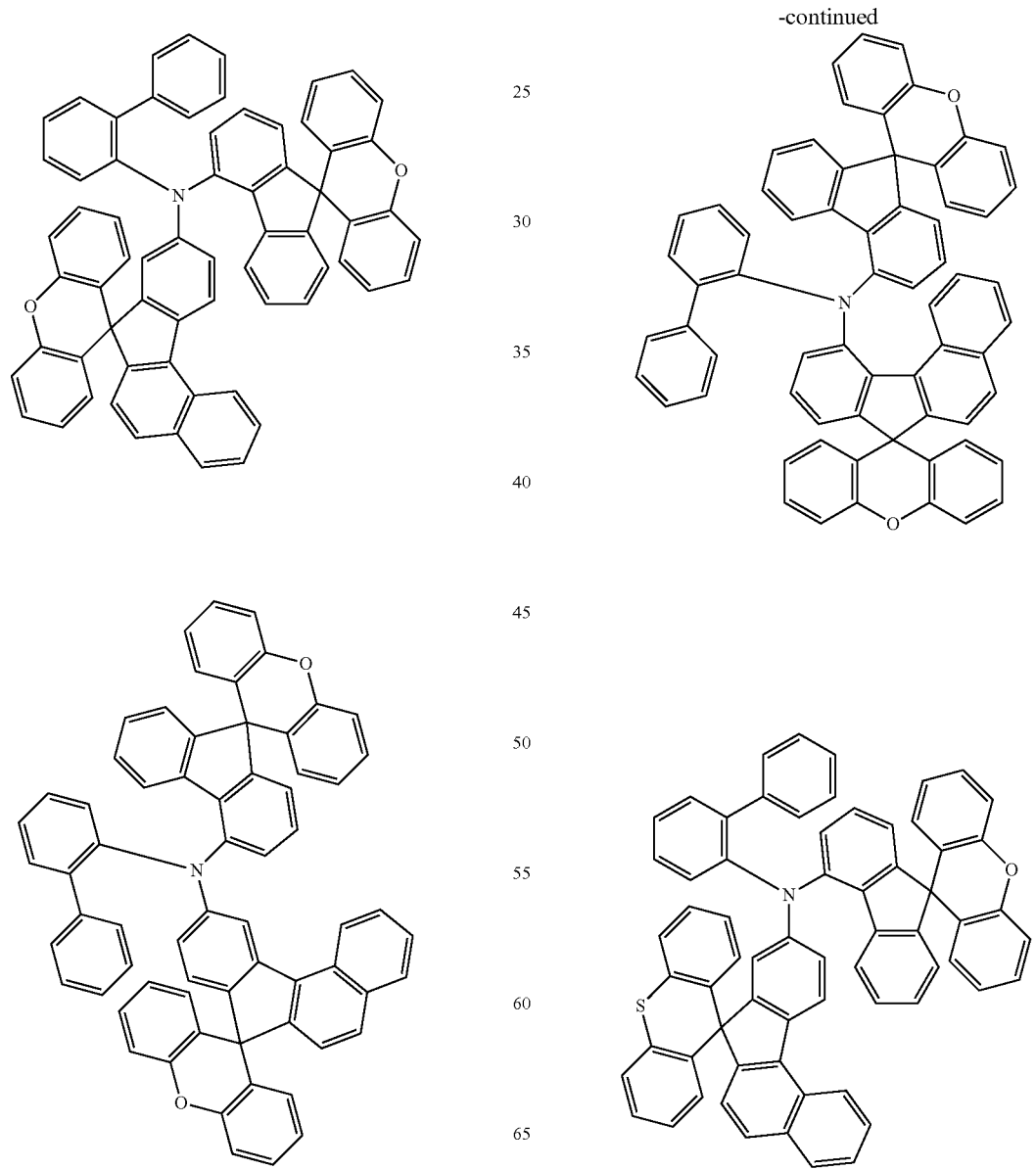

617
-continued
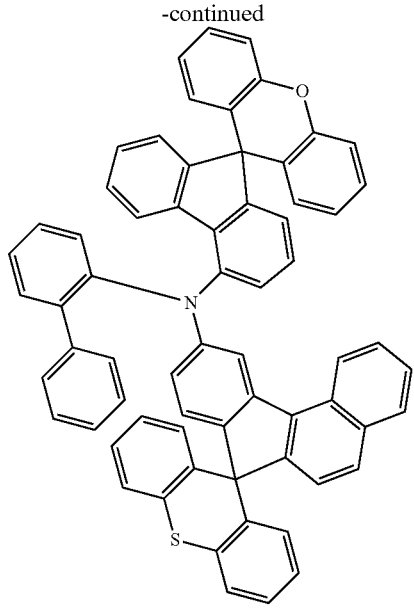
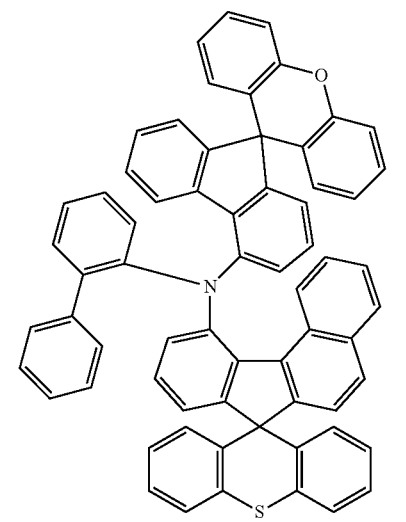
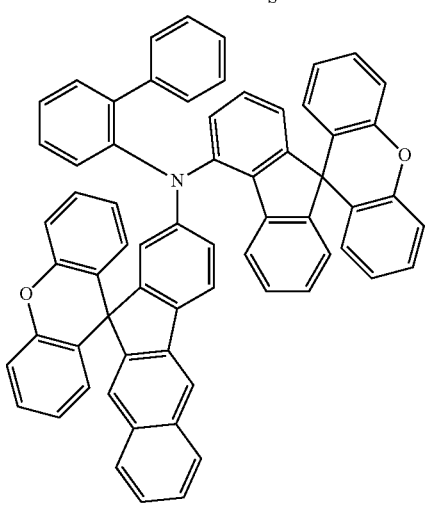
618
-continued
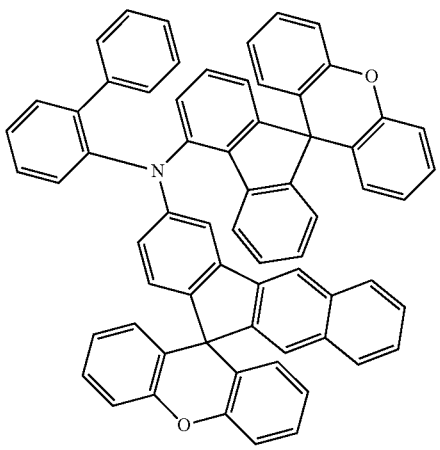
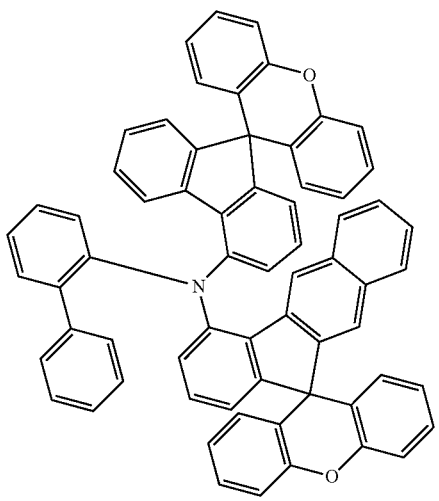
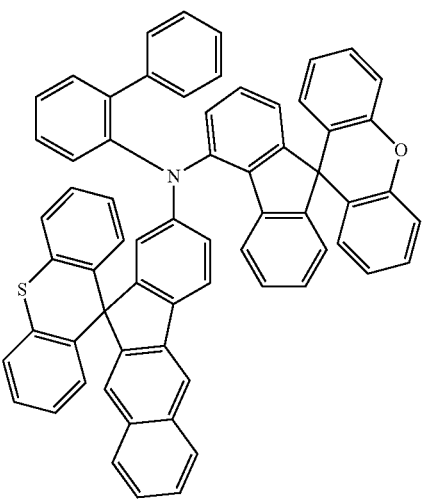

619
-continued
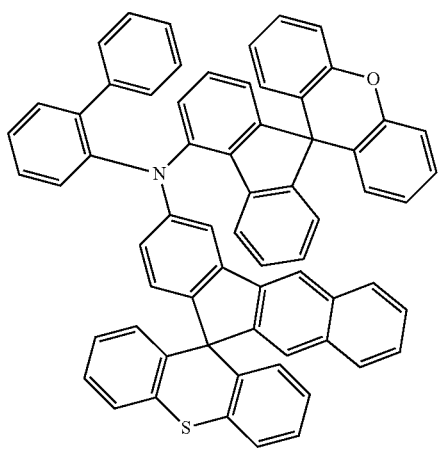
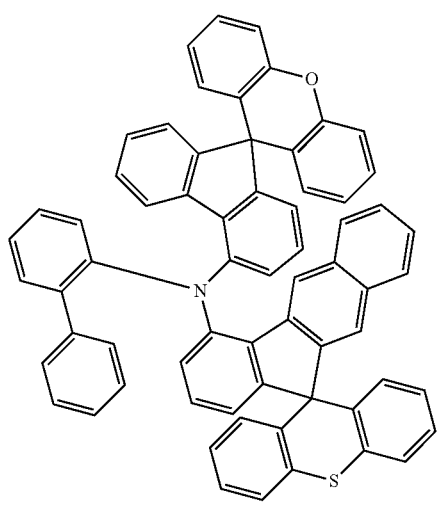
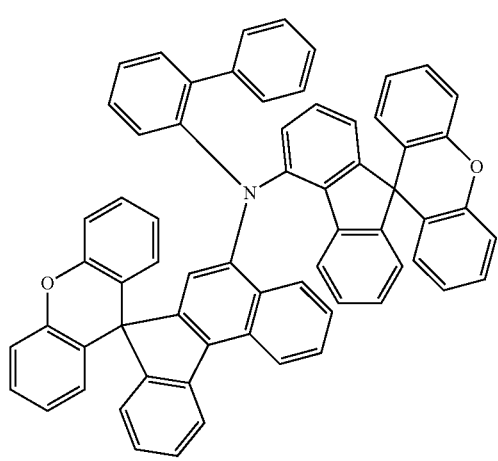
620
-continued
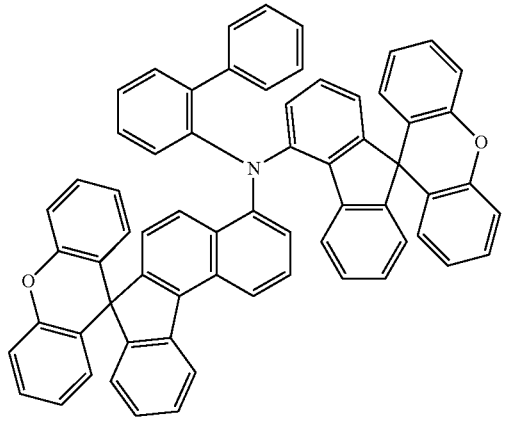
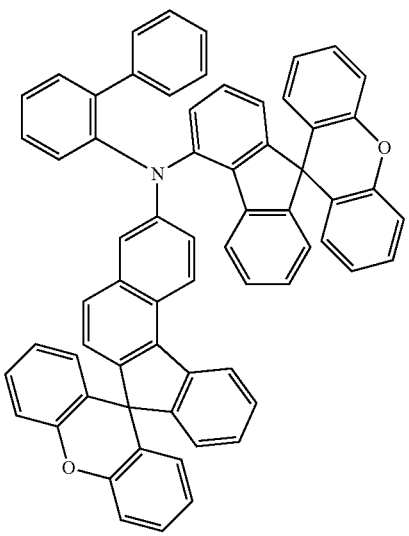
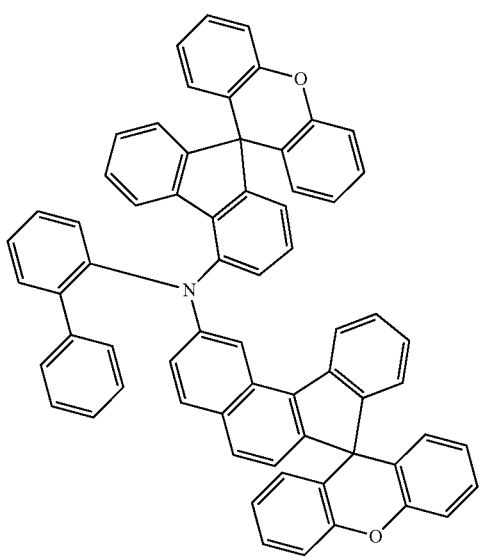

621
-continued
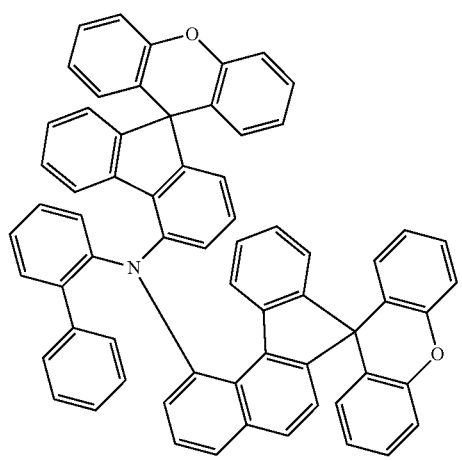
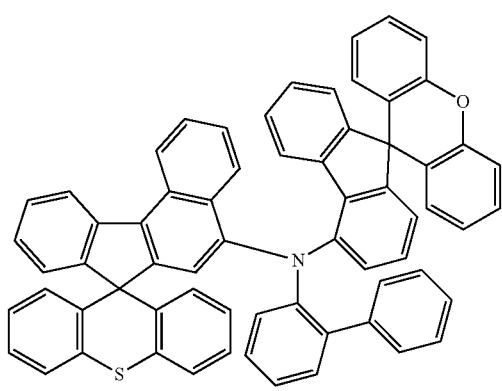
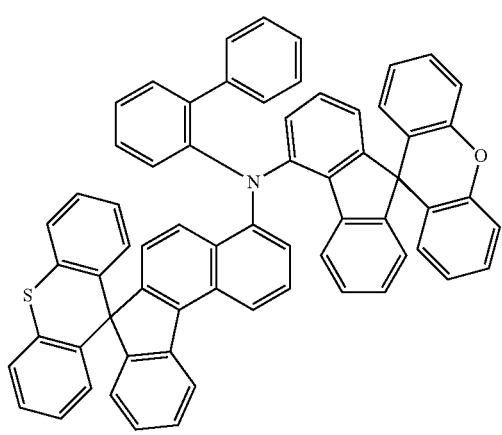
622
-continued
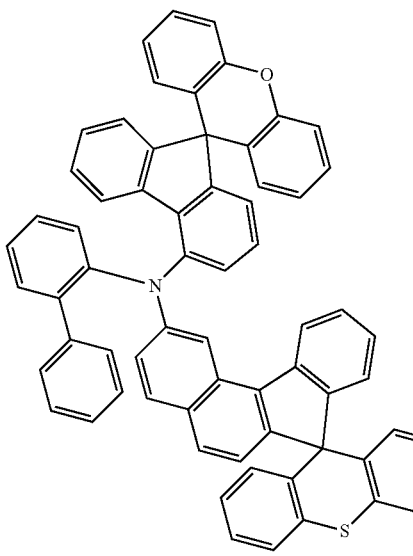
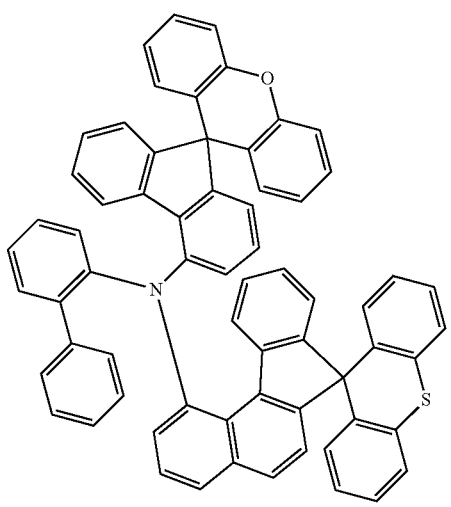

623
-continued
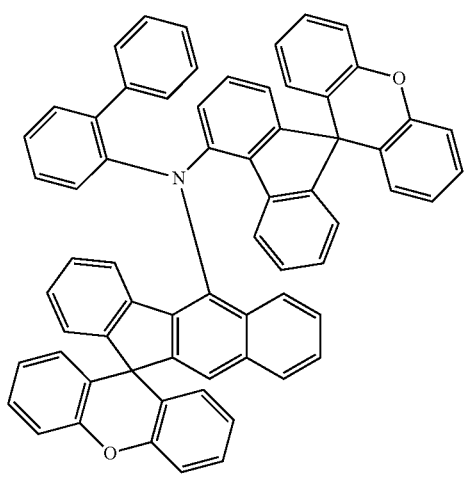
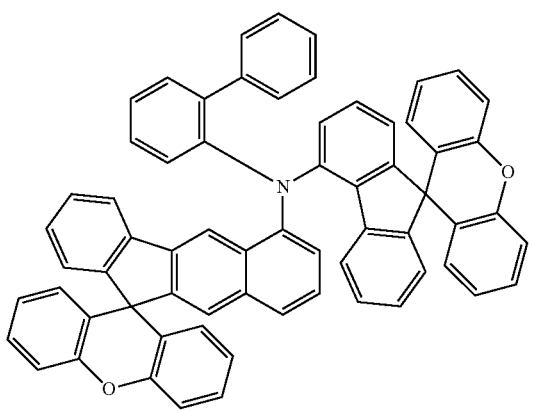
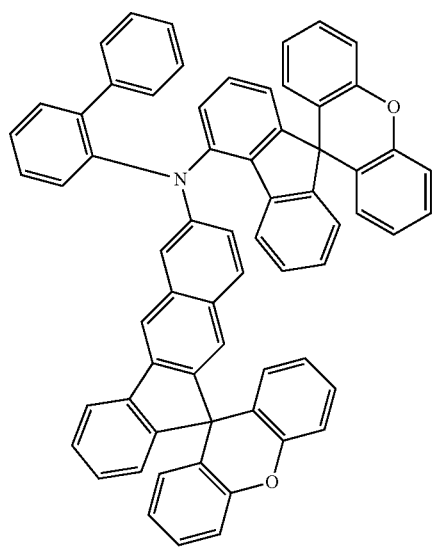
624
-continued
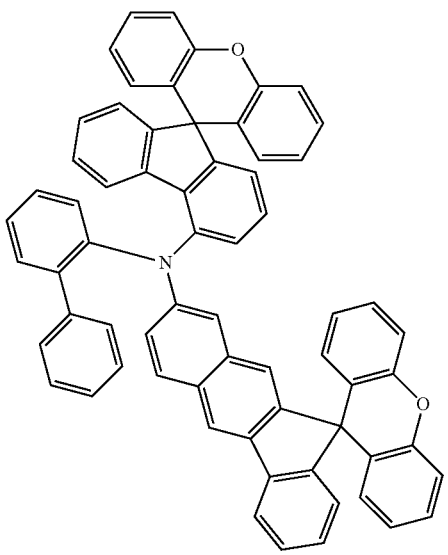
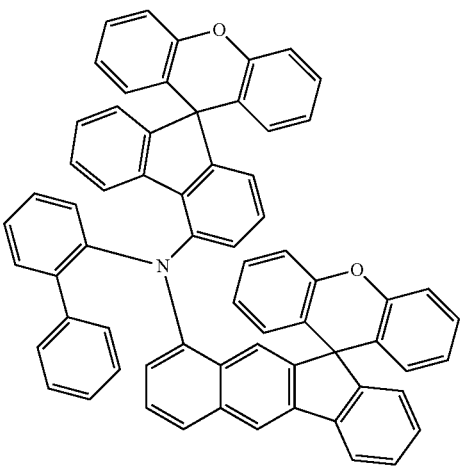
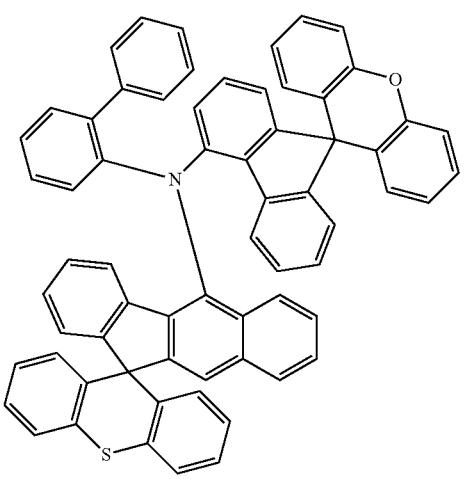

625
-continued
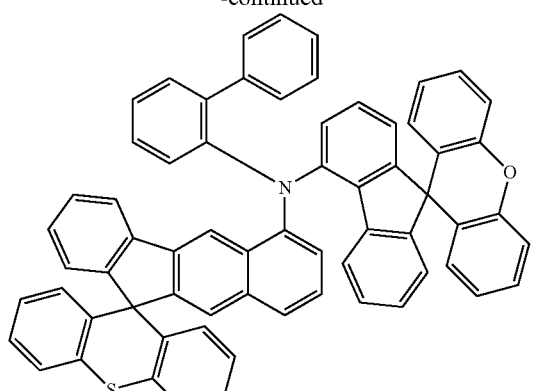
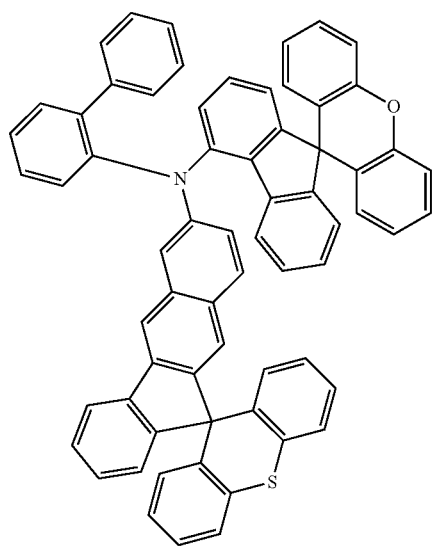
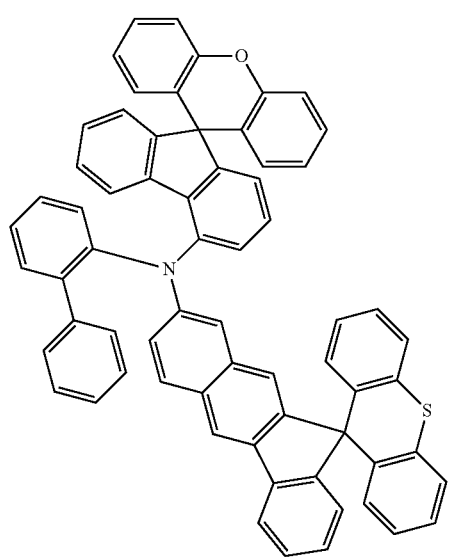
626
-continued
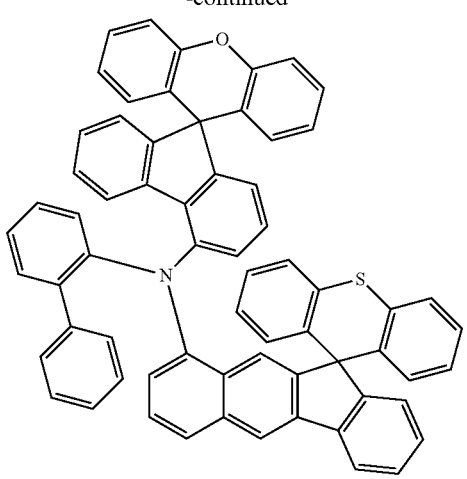
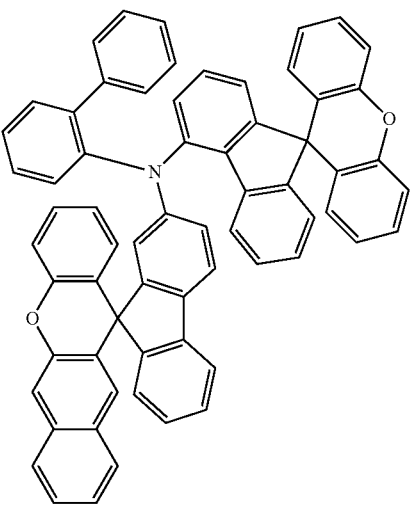
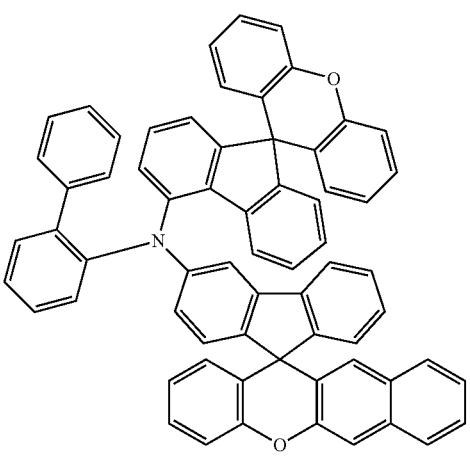

627
-continued
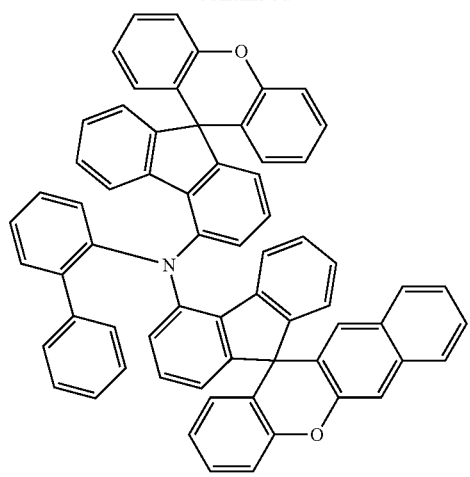
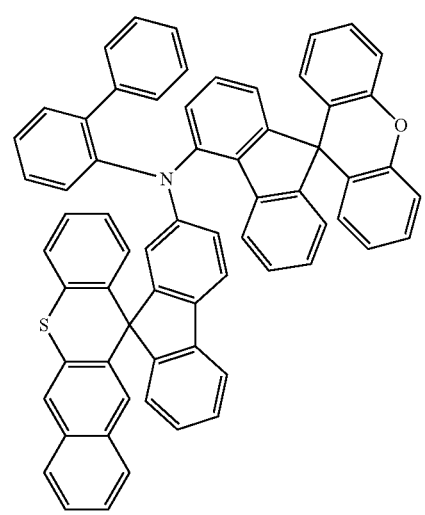
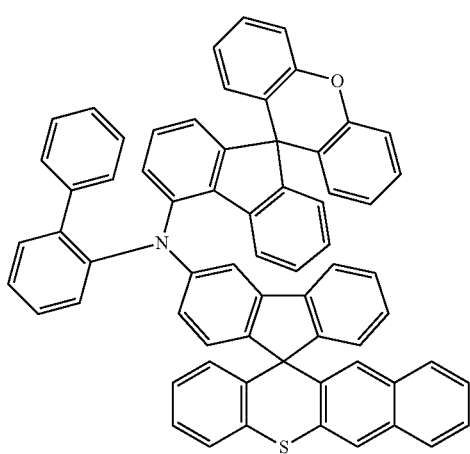
628
-continued
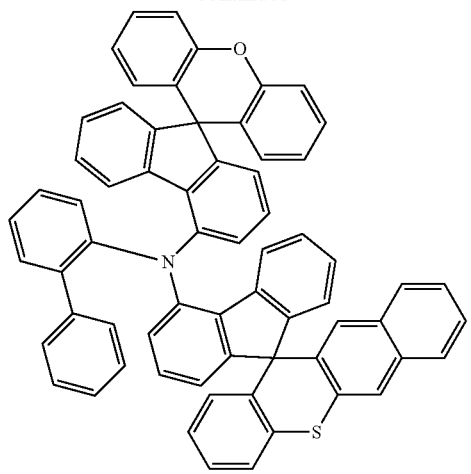
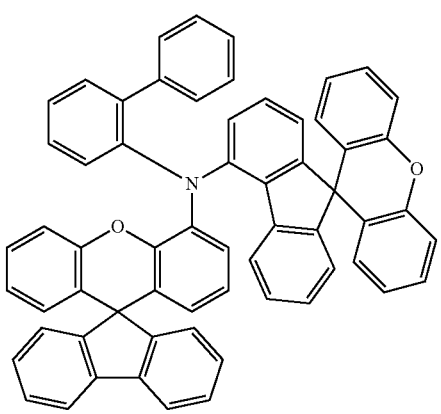
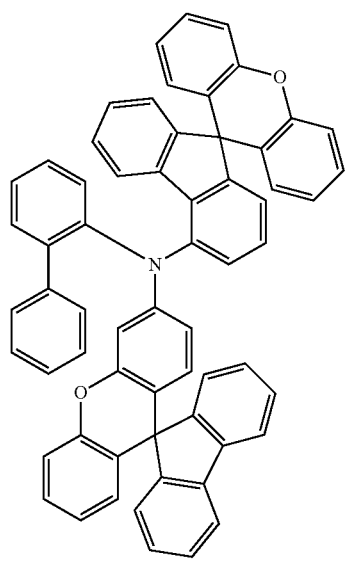

-continued
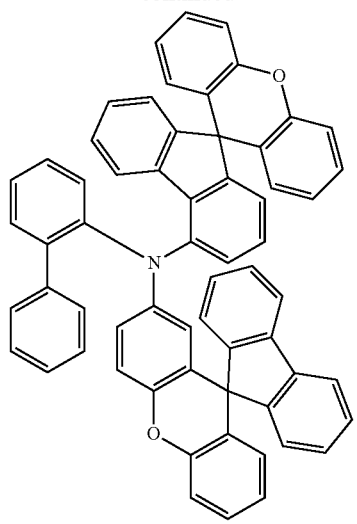
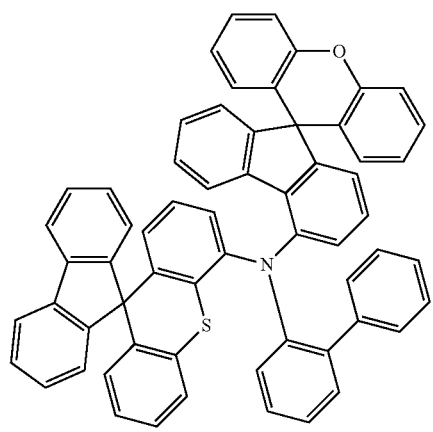
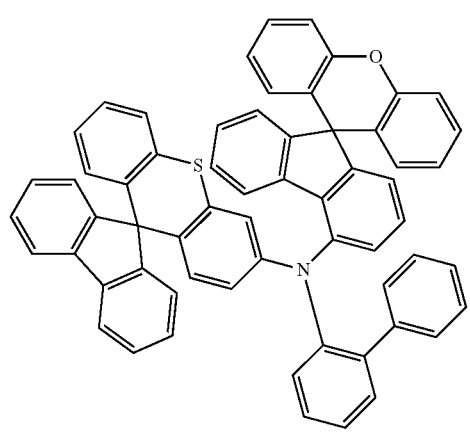
-continued
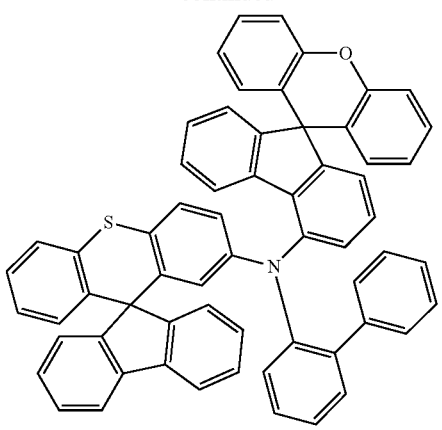
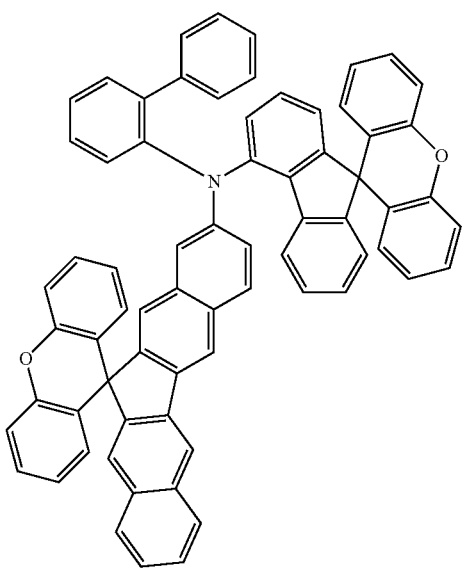
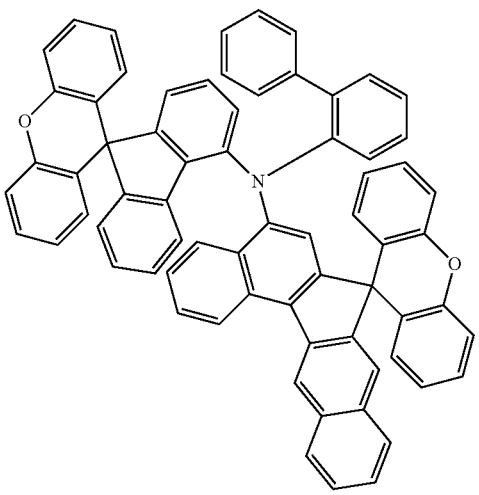

631
-continued
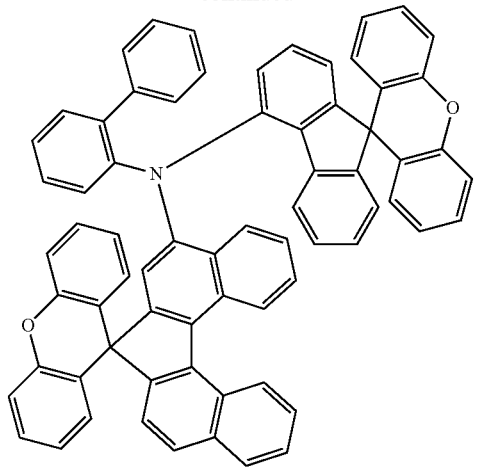
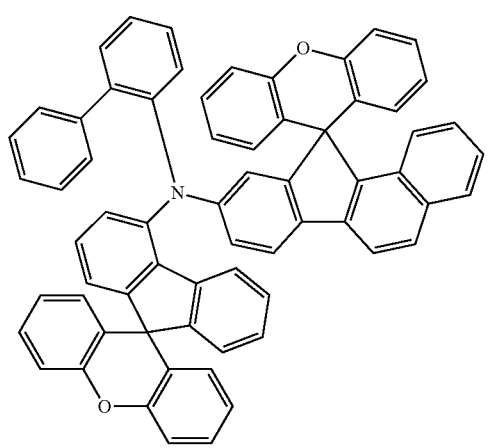
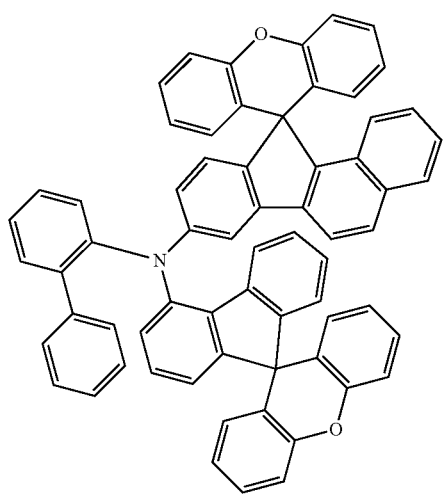
632
-continued
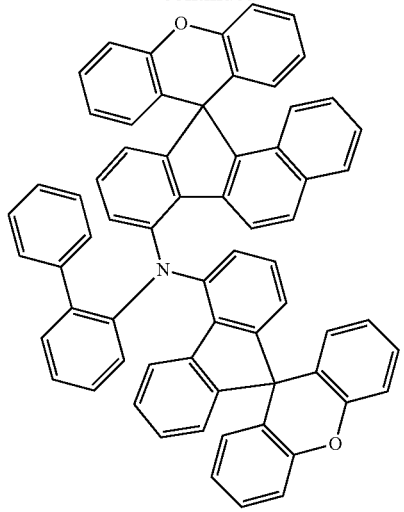
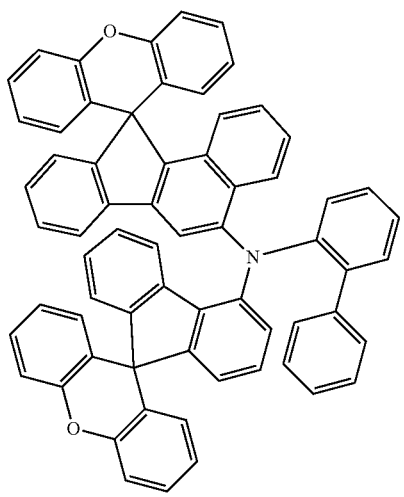
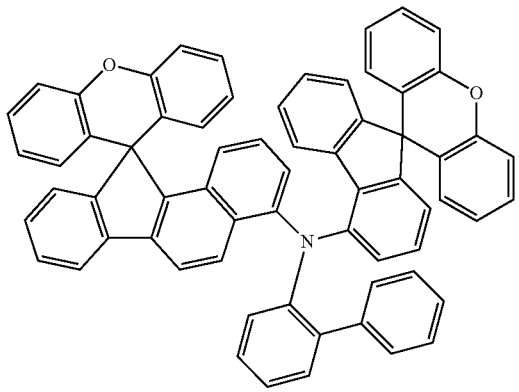

633
-continued
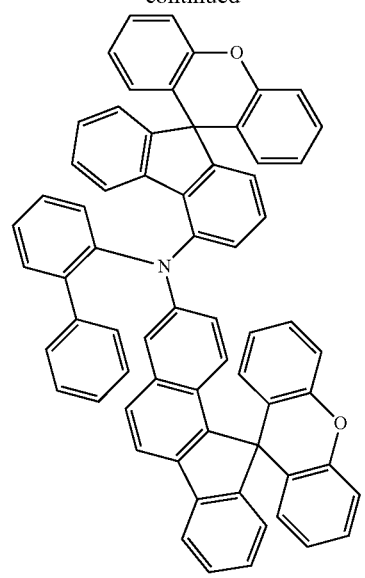
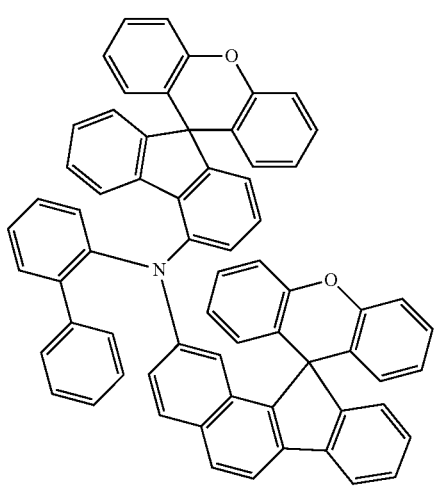
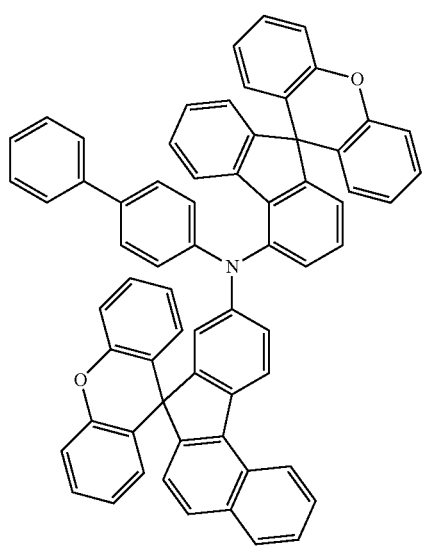
634
-continued
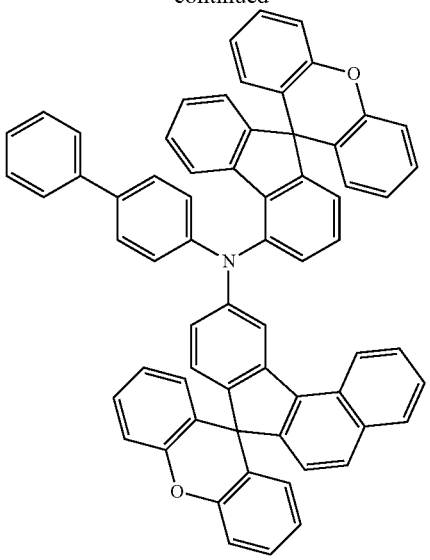
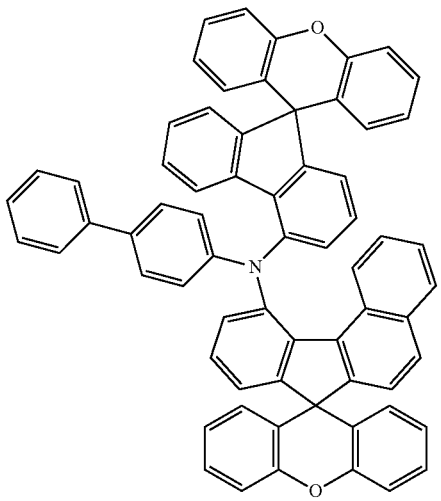
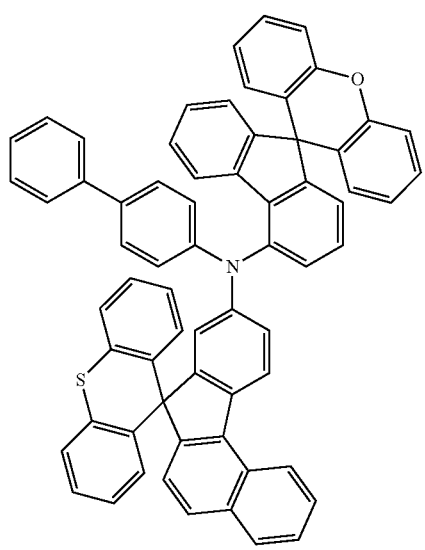

635
-continued
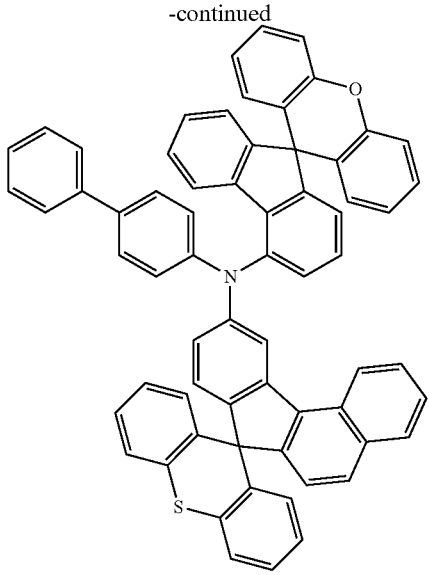
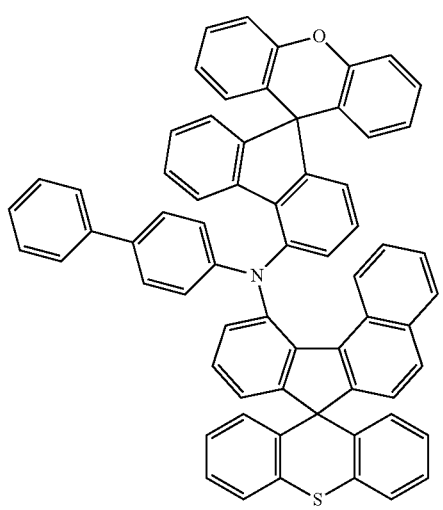
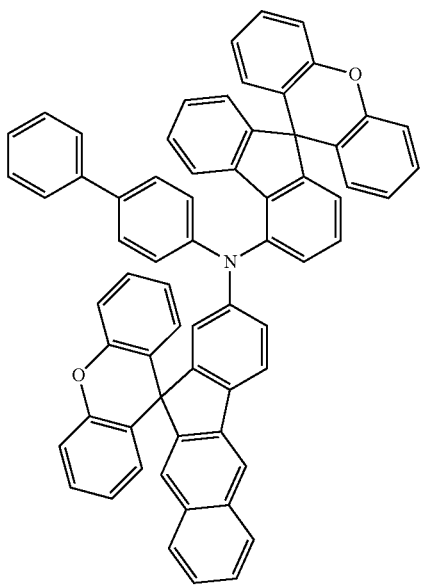
636
-continued
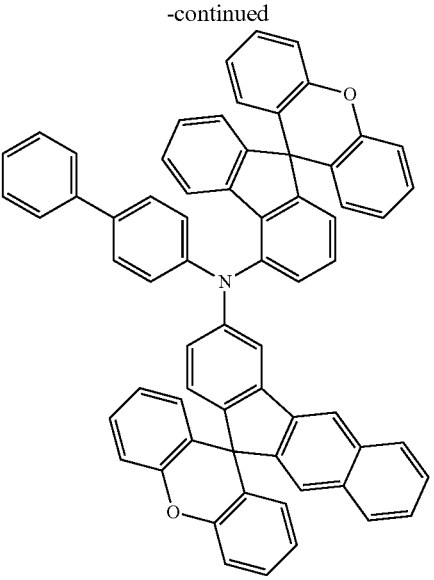
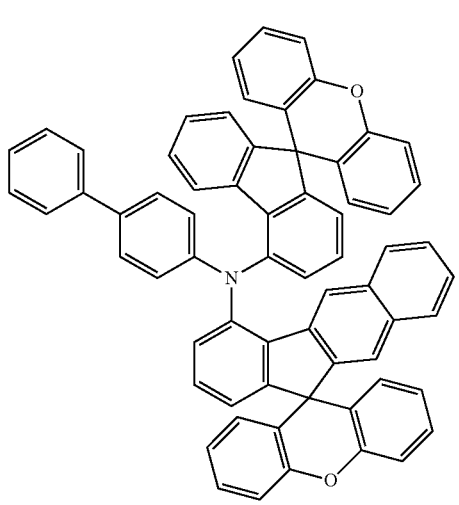
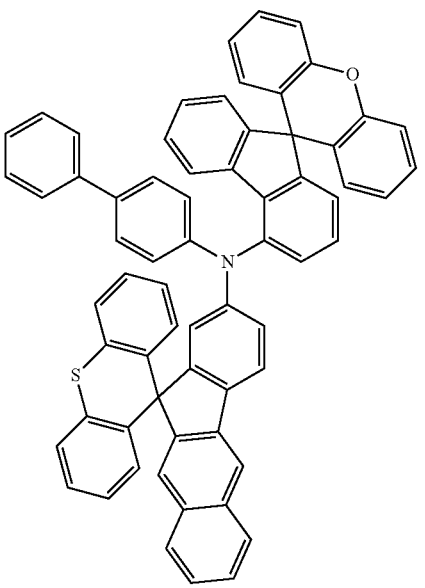

637
-continued
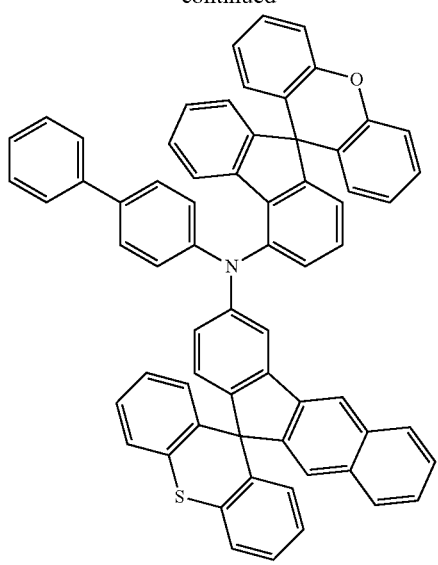
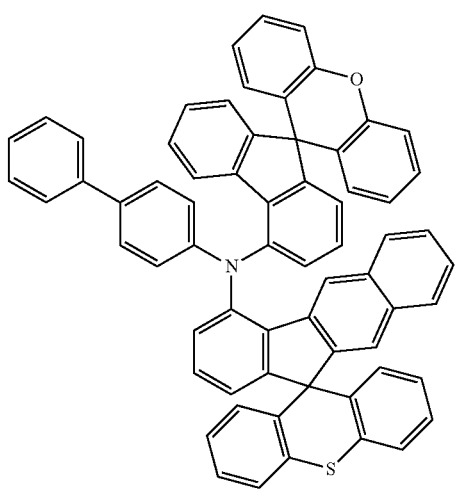
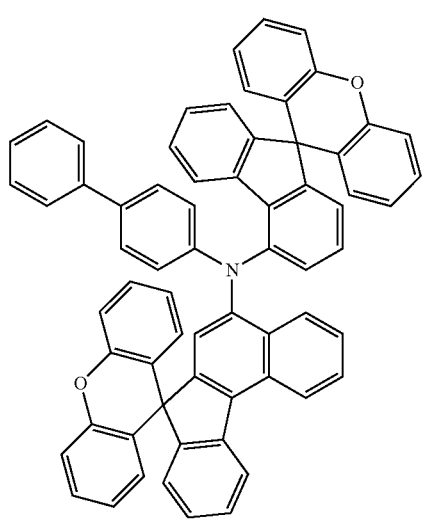
638
-continued
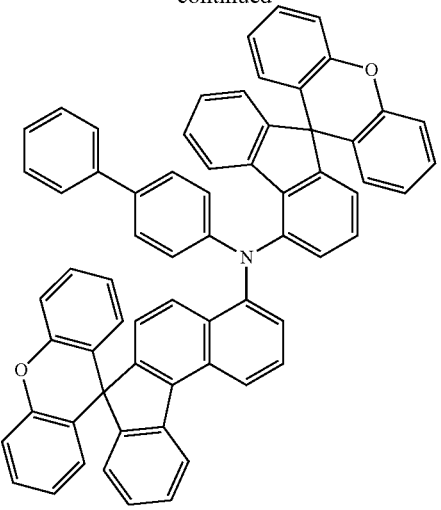
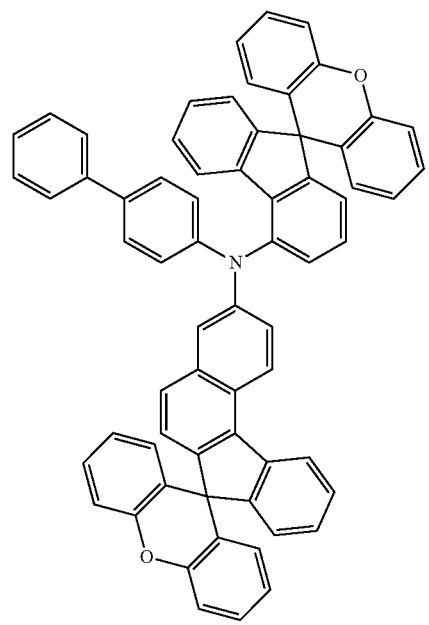
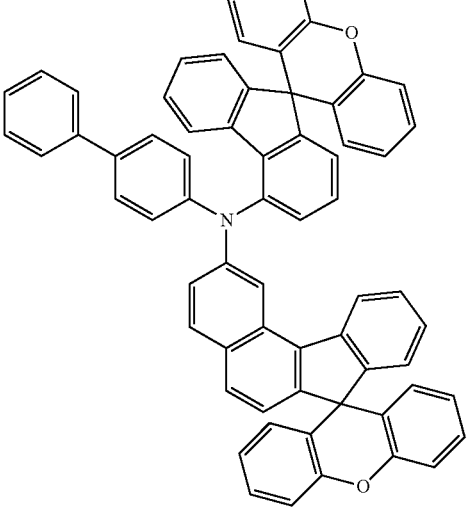

639
-continued
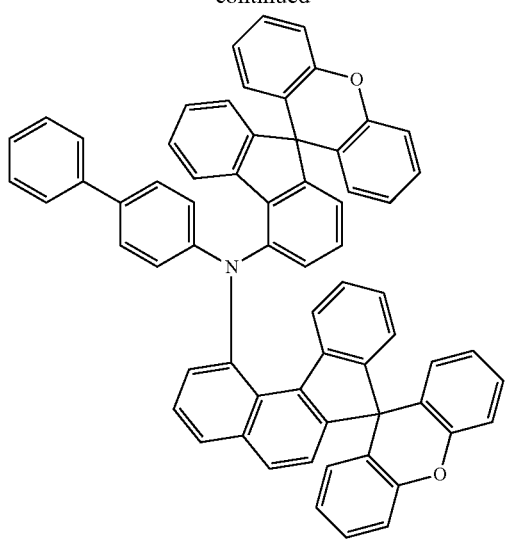
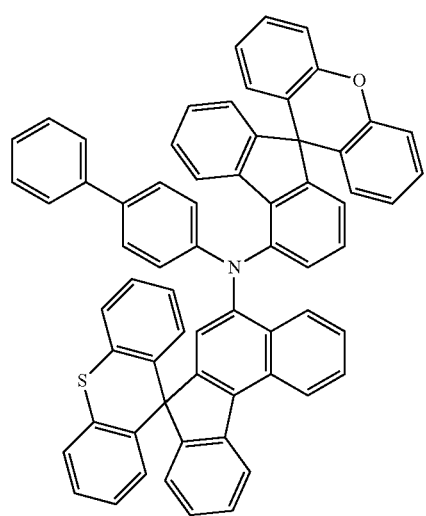
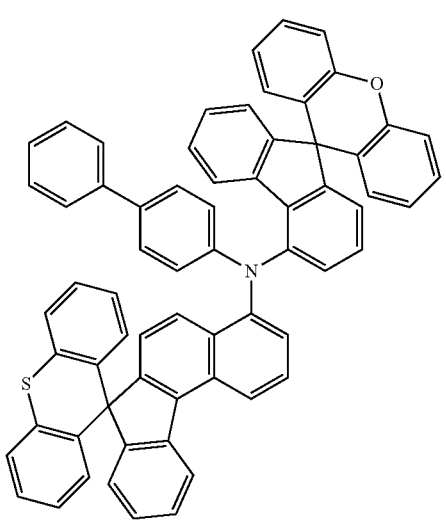
640
-continued
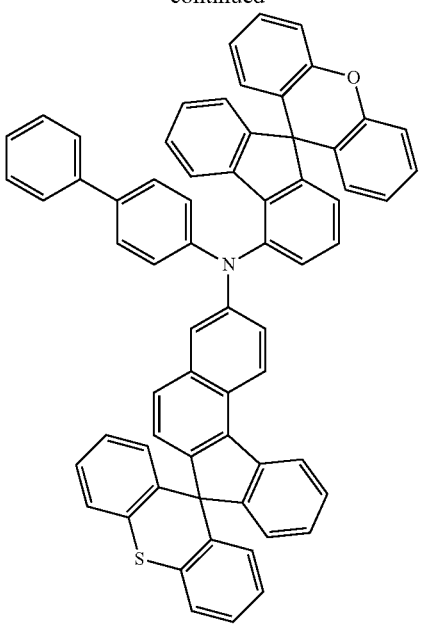
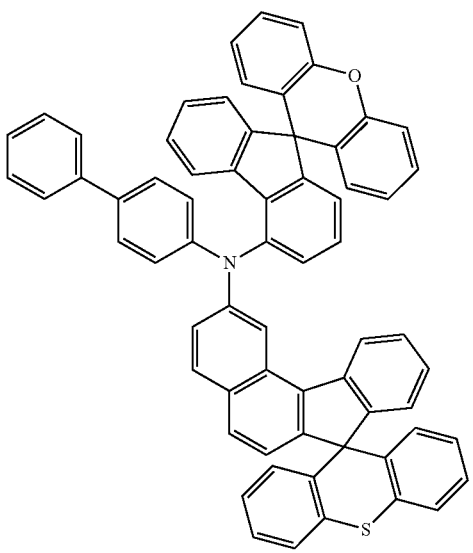
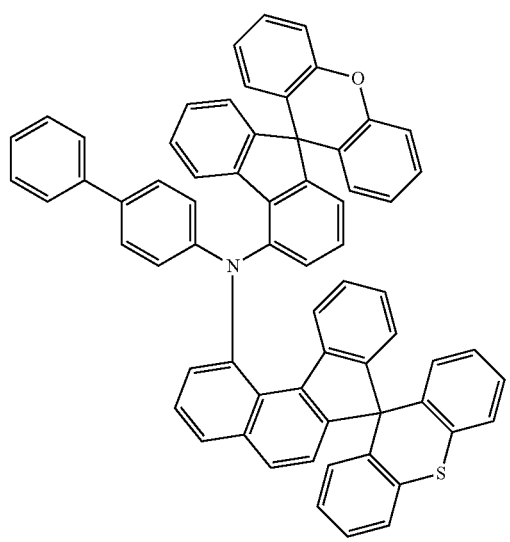

| 641 -continued | 642 -continued |
|---|---|
| 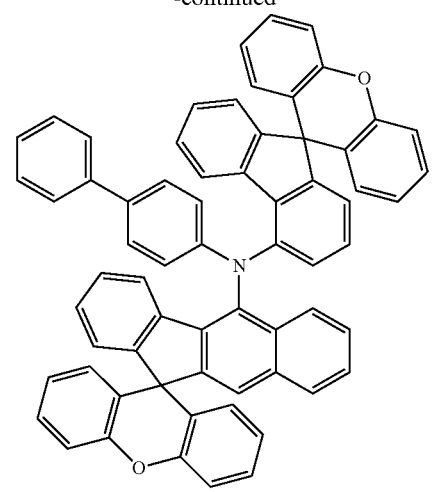 | 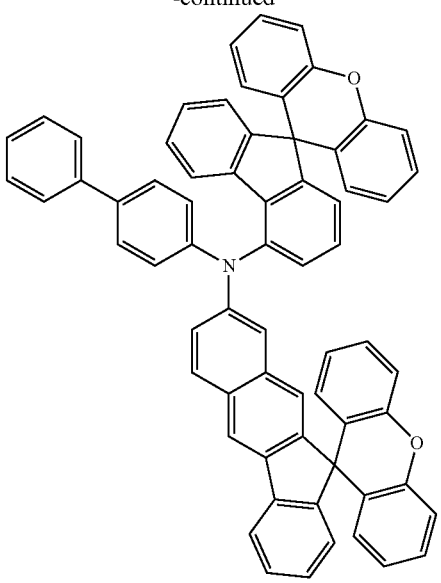 |
| 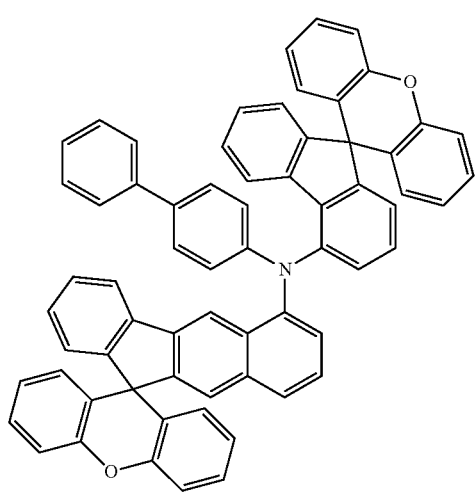 | 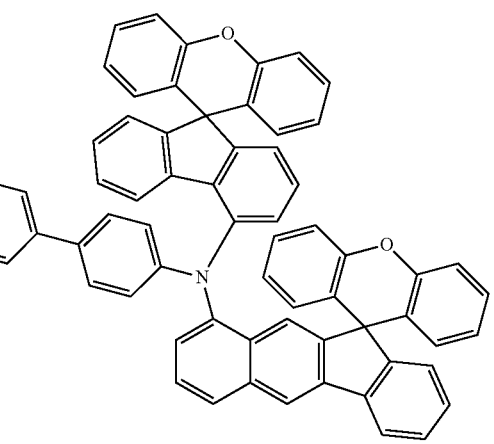 |
| 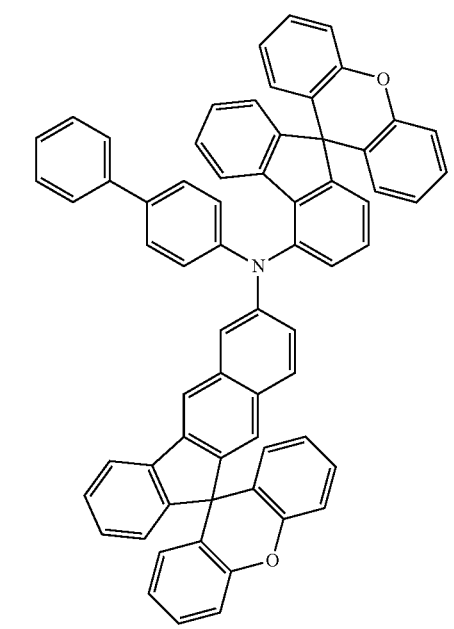 | 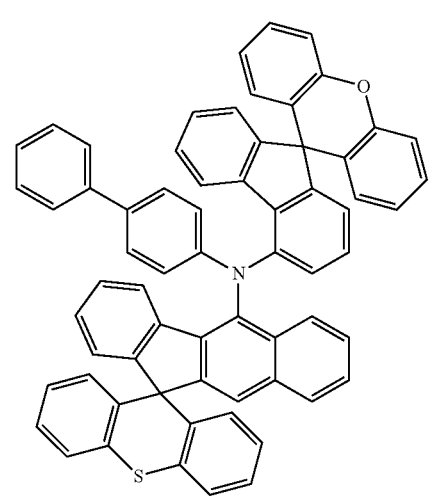 |

643
-continued
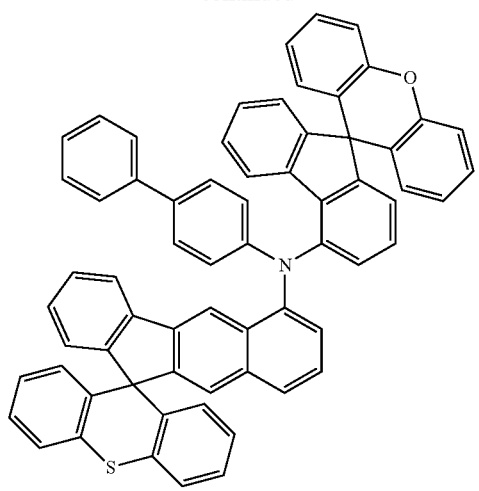
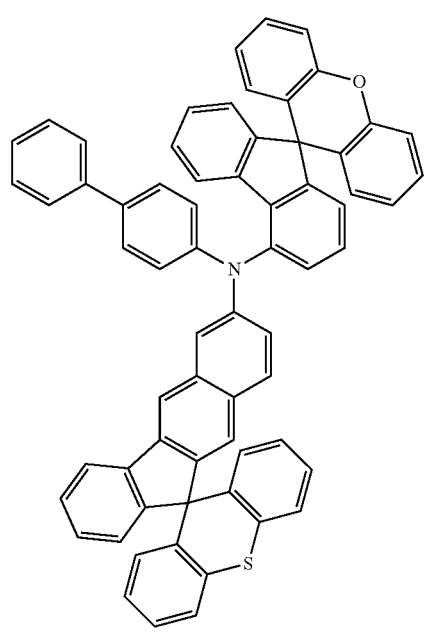
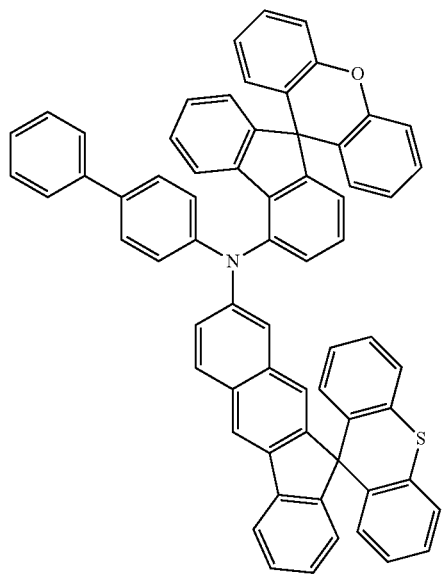
644
-continued
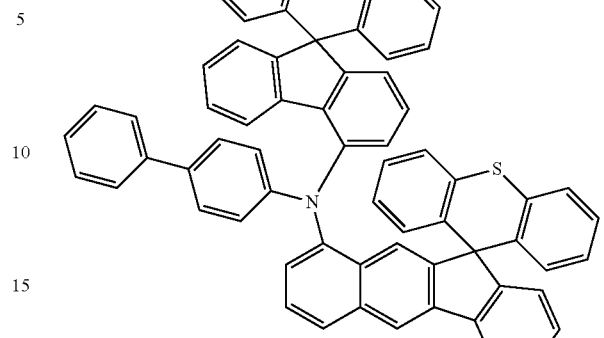
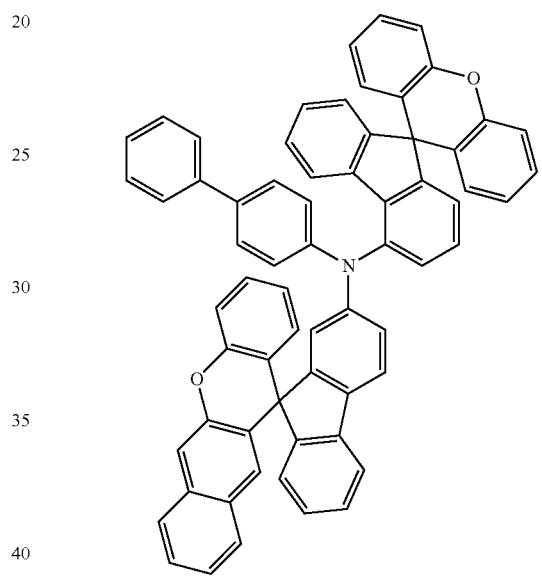
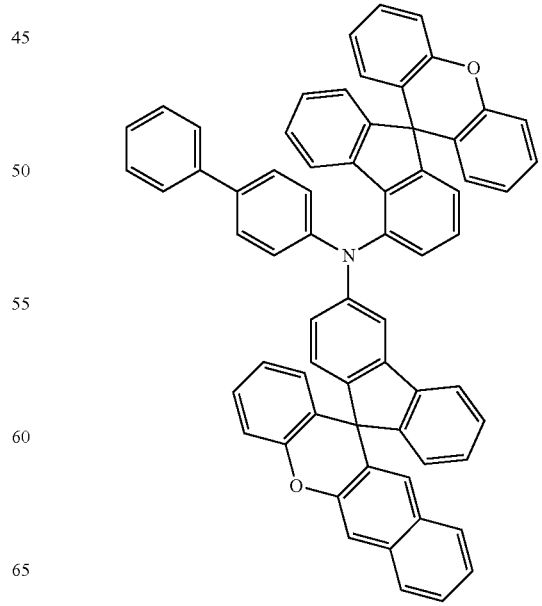

645
-continued
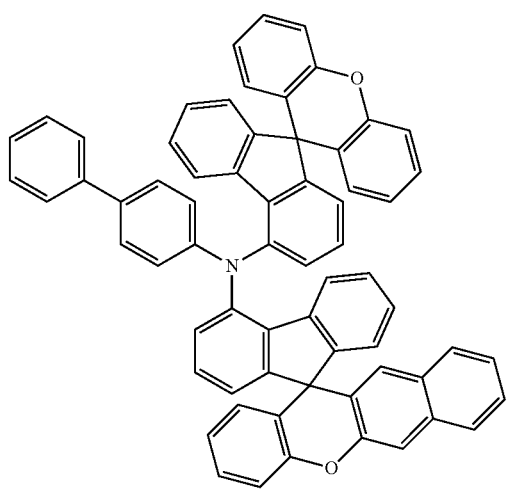
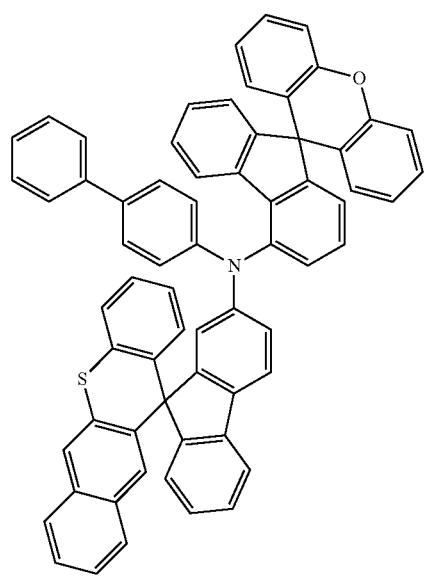
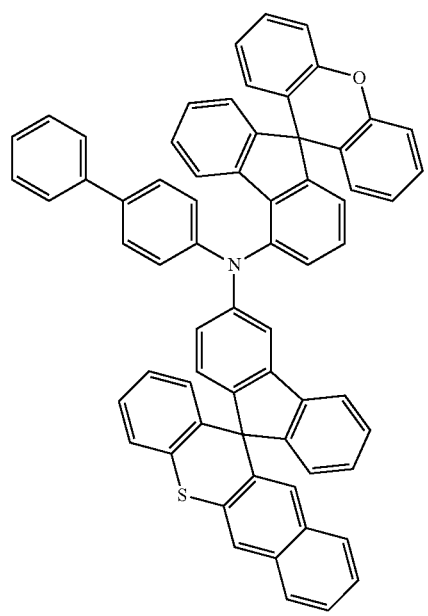
646
-continued
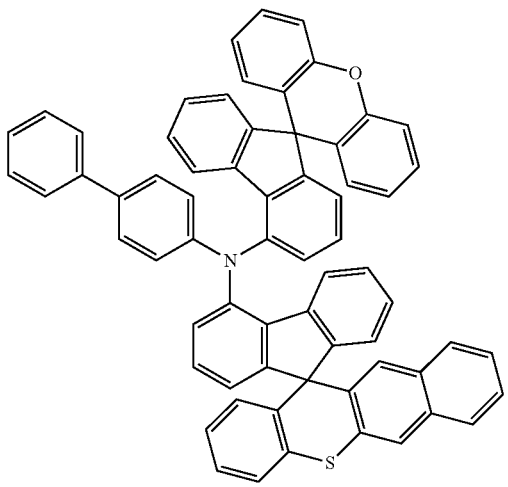 [SMILES: c1ccc(-c2ccc(N(c3cccc4c3-c3ccccc3C43c4ccccc4Oc4ccccc43)c3cccc4c3-c3ccccc3C43c4ccccc4Sc4cc5ccccc5cc43)cc2)cc1]
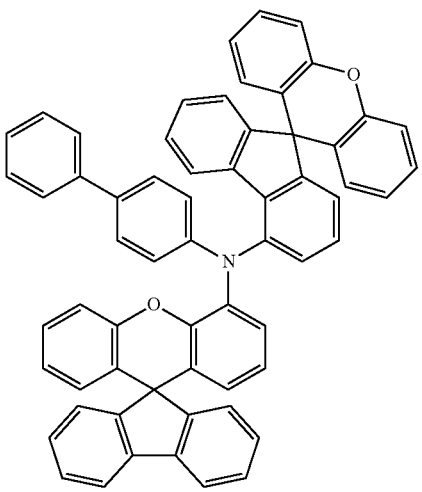
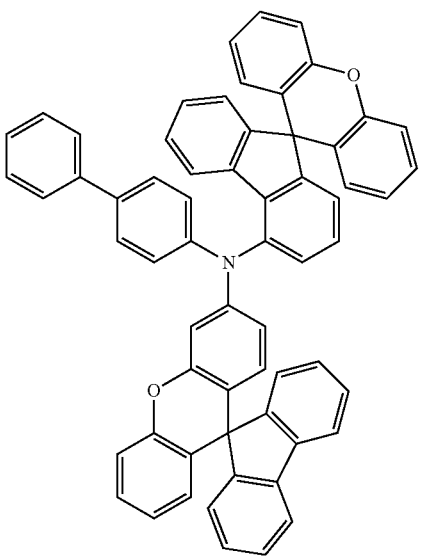

647
-continued
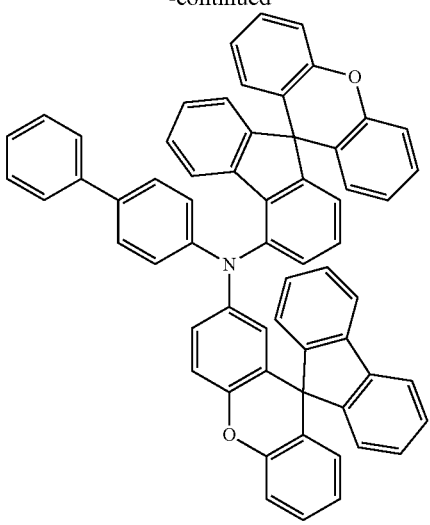
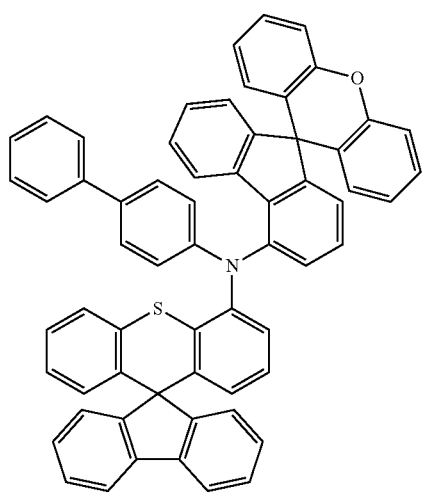
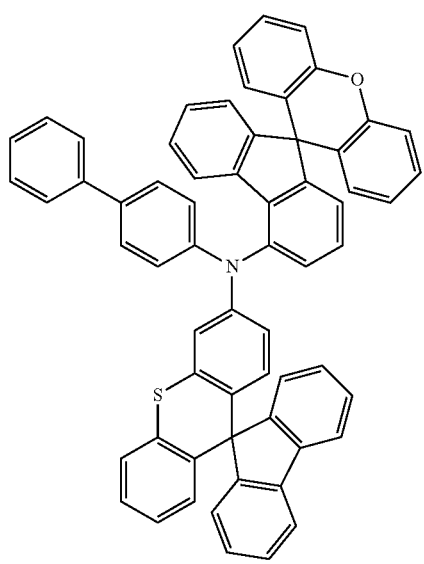
648
-continued
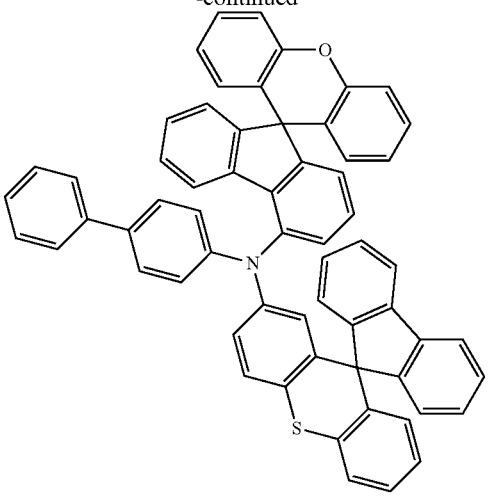
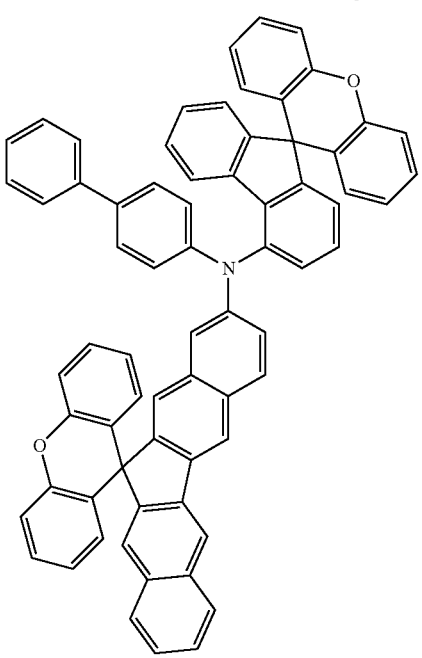
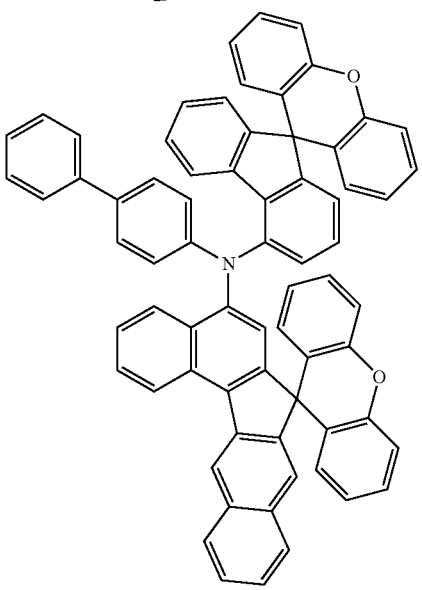

649
-continued
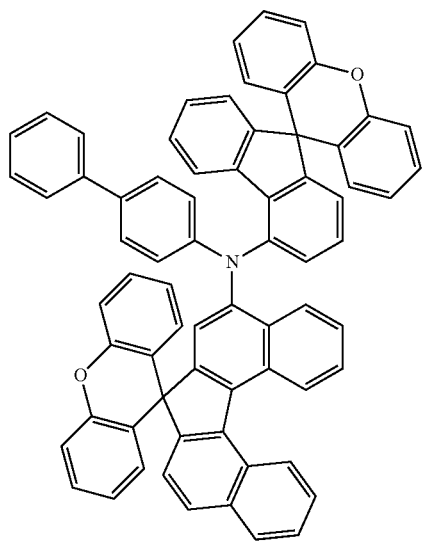
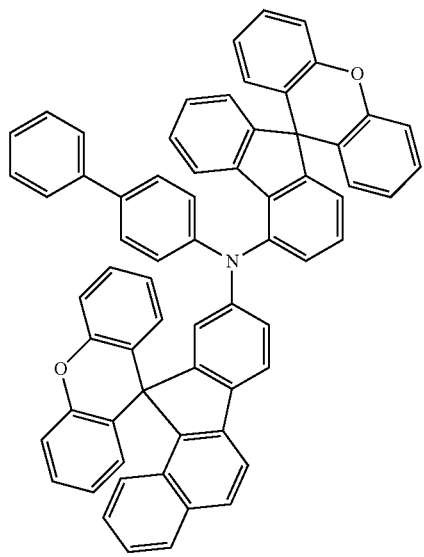
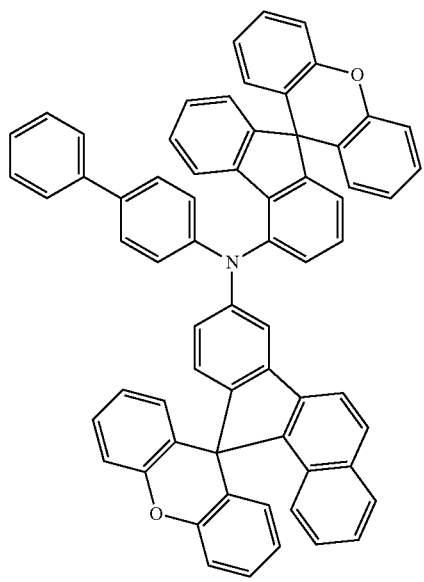
650
-continued
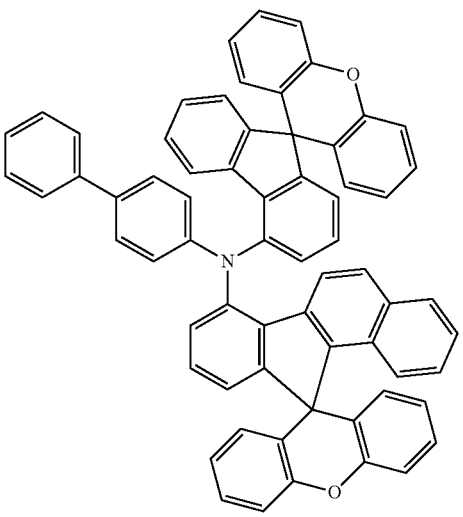
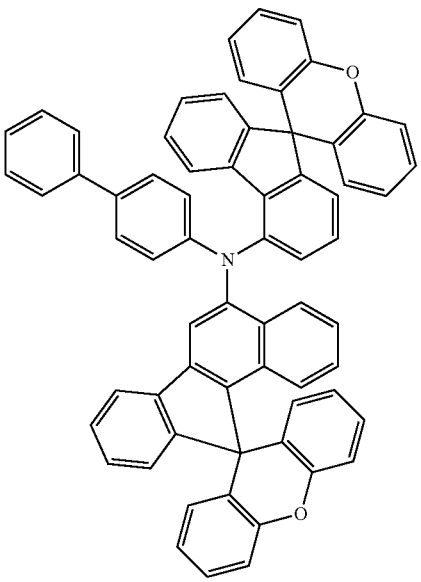
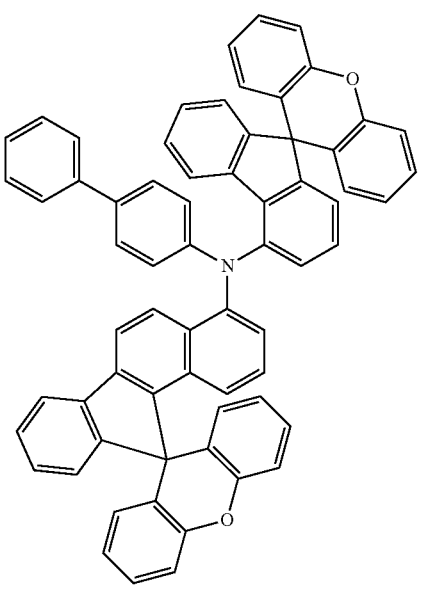

651
-continued
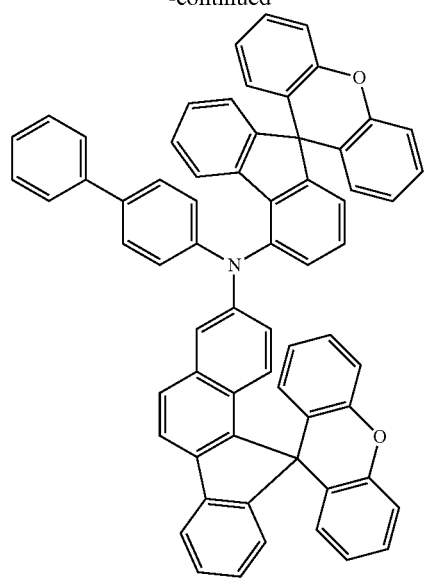
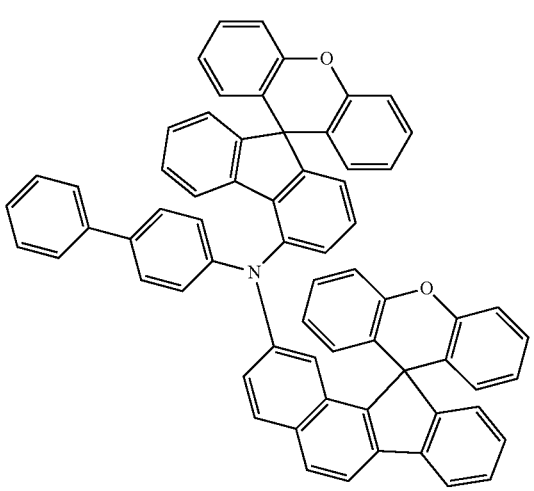
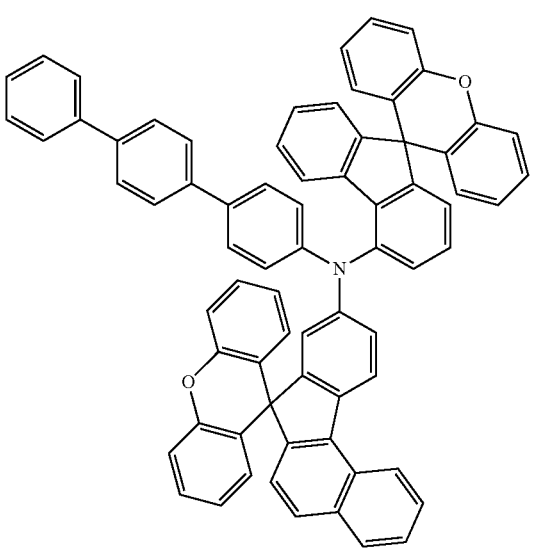
652
-continued
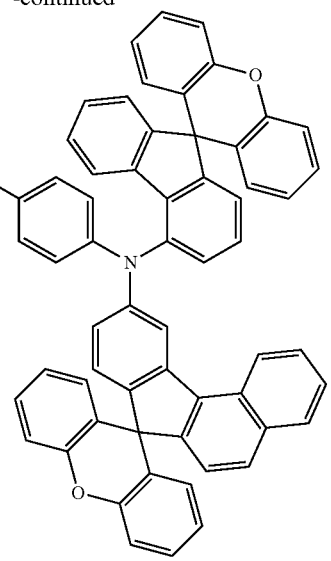
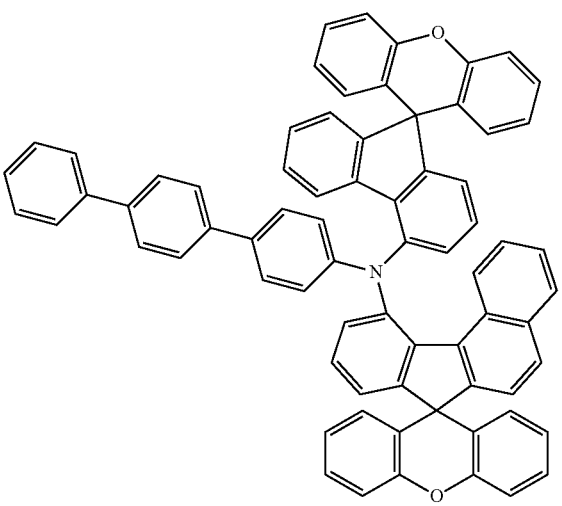
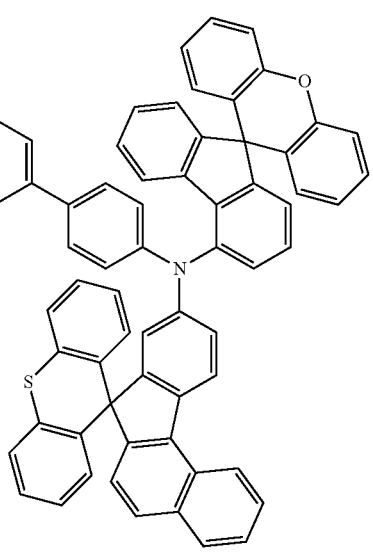

653
-continued
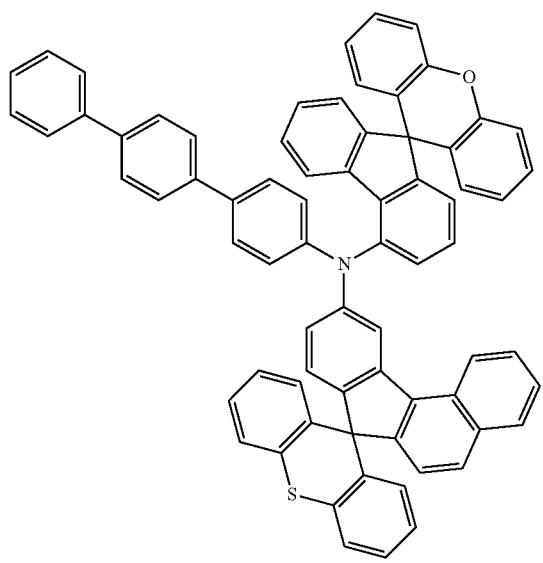
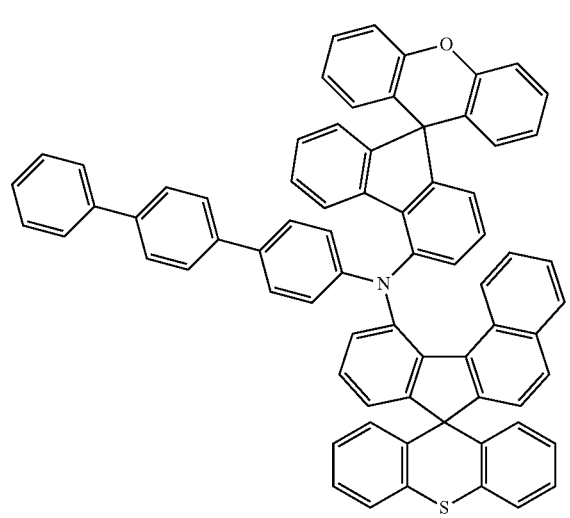
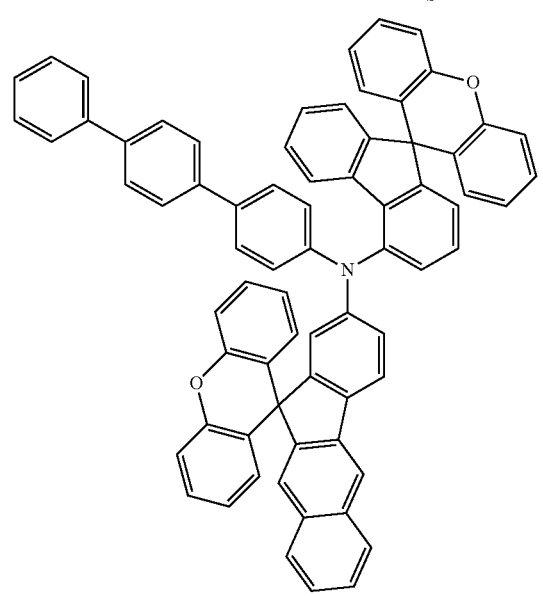
654
-continued
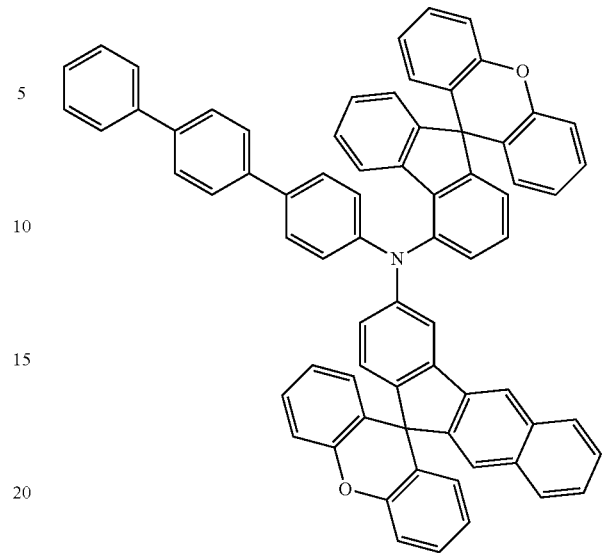
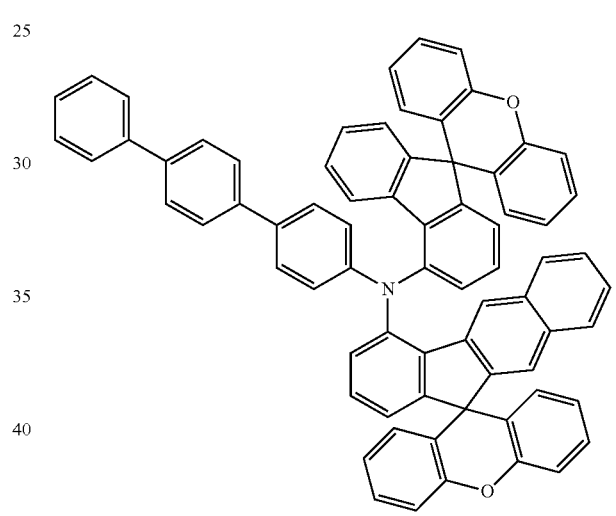
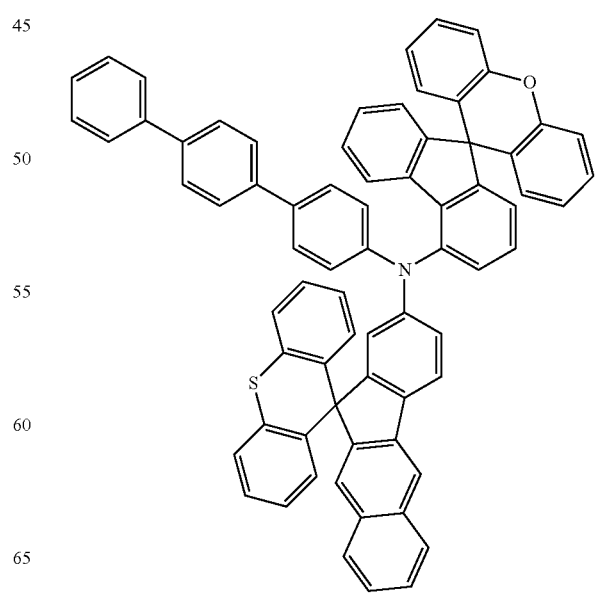

655
-continued
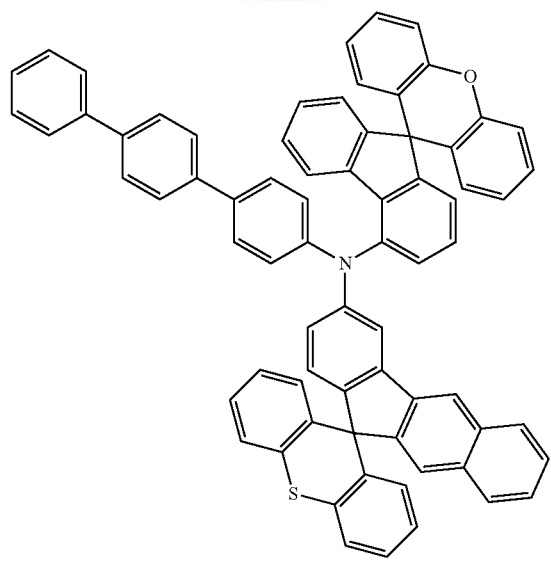
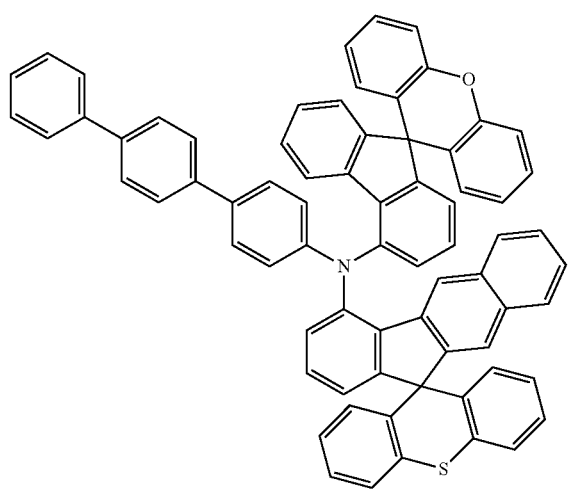
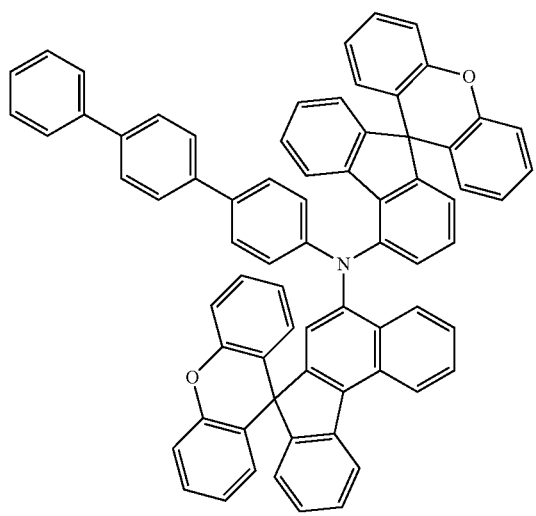
656
-continued
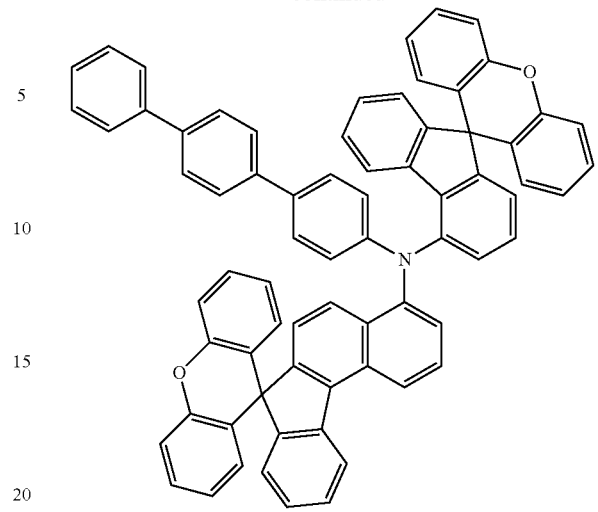
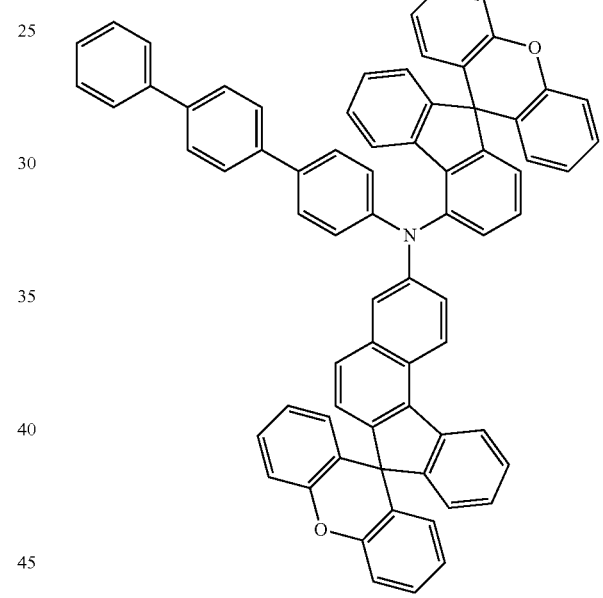
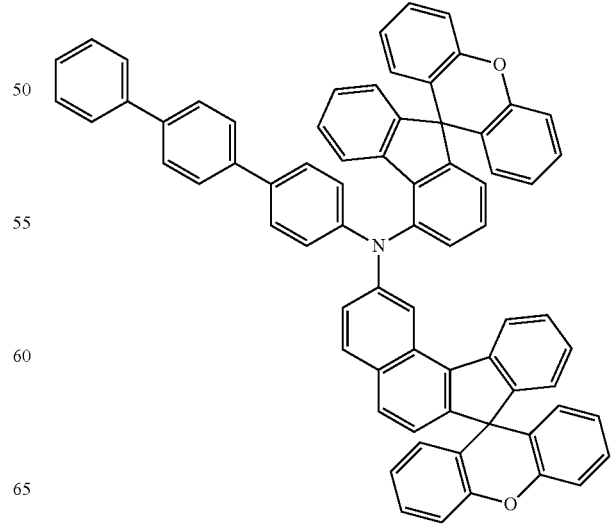

-continued
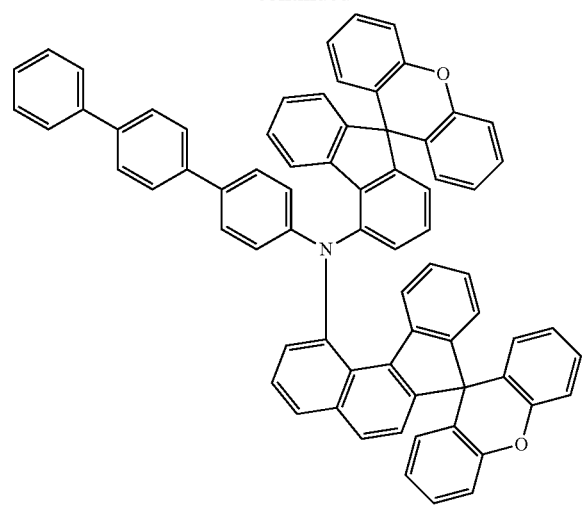
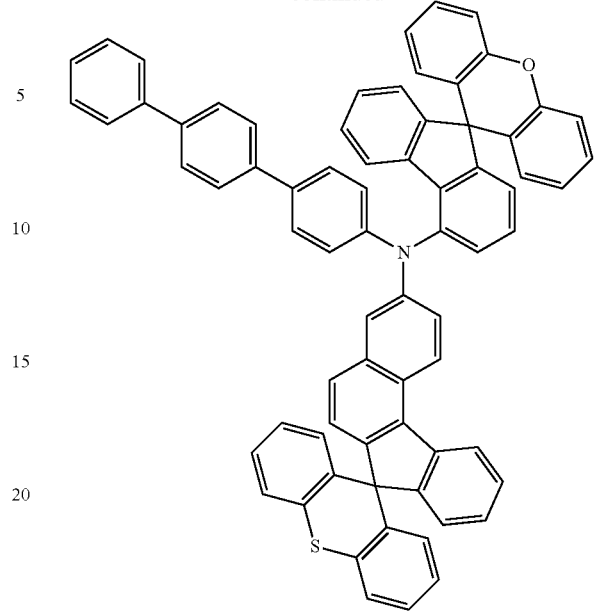
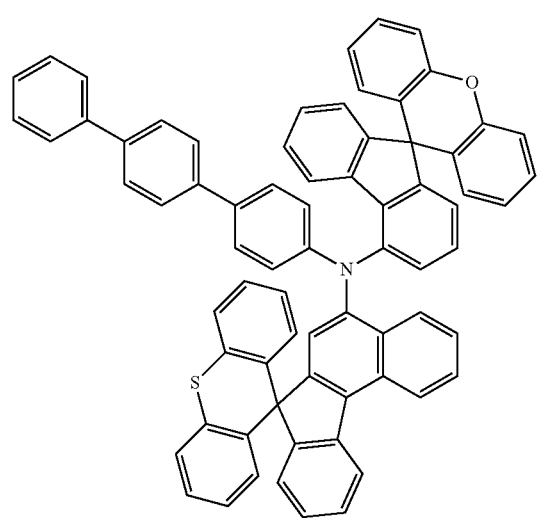
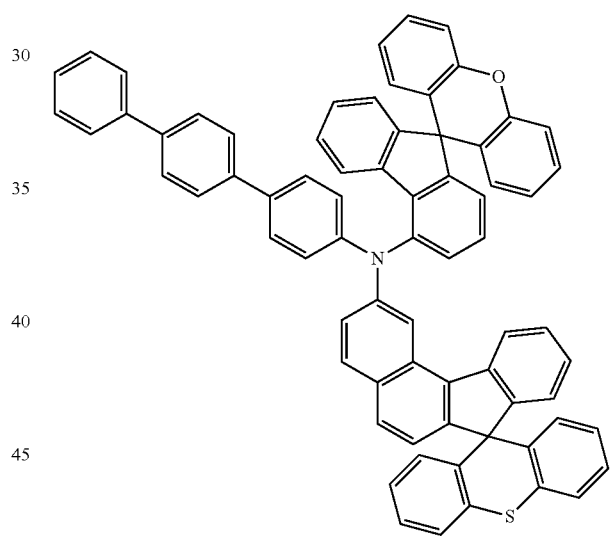
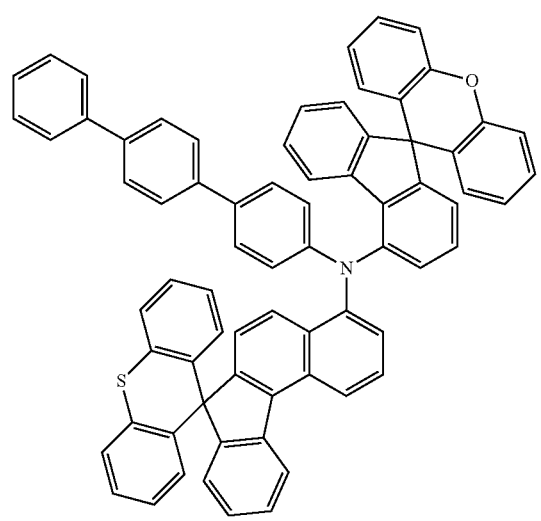
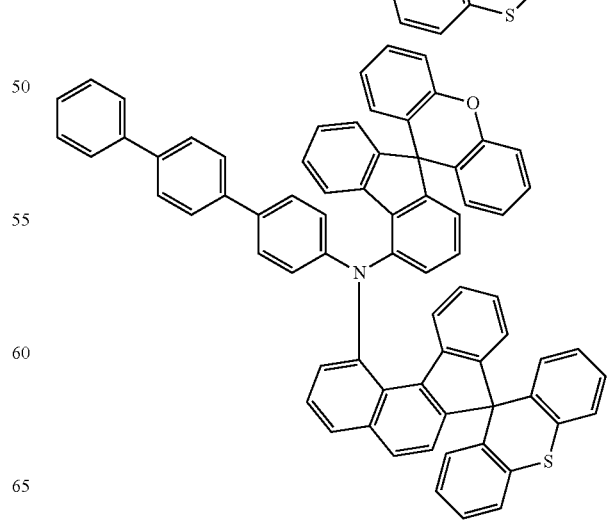

659
-continued
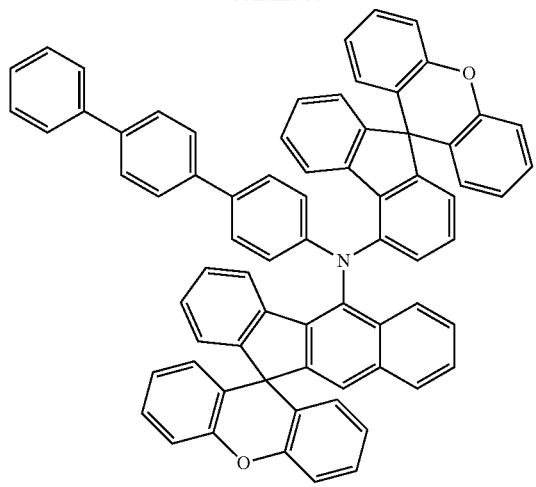
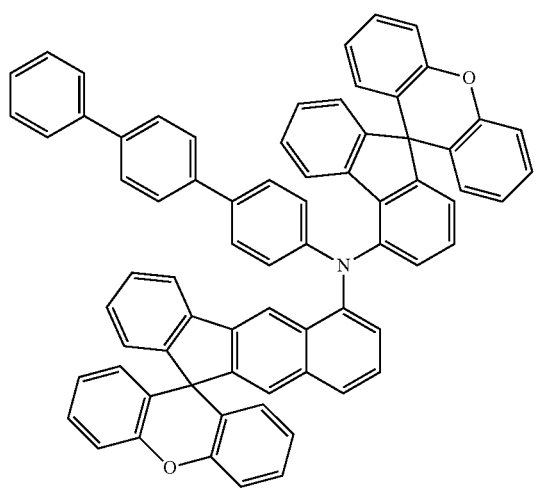
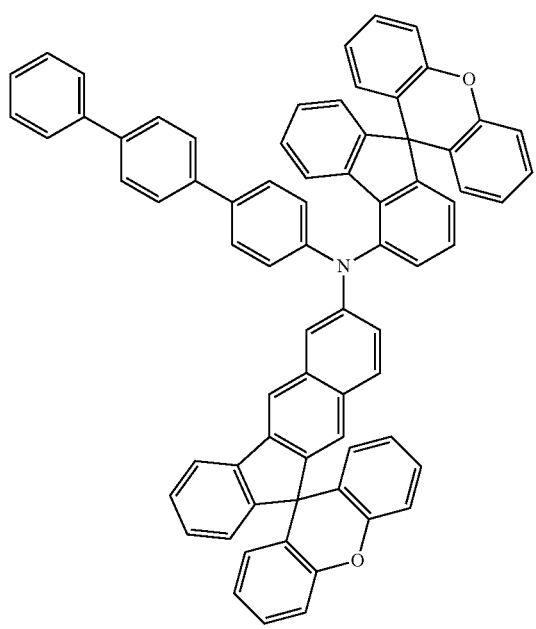
660
-continued
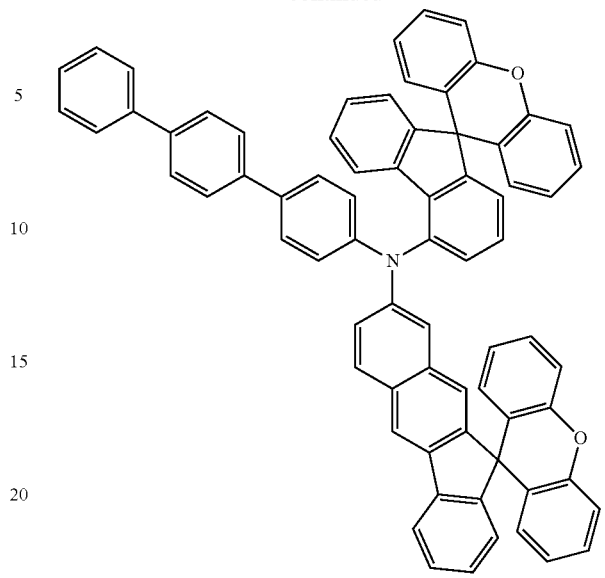
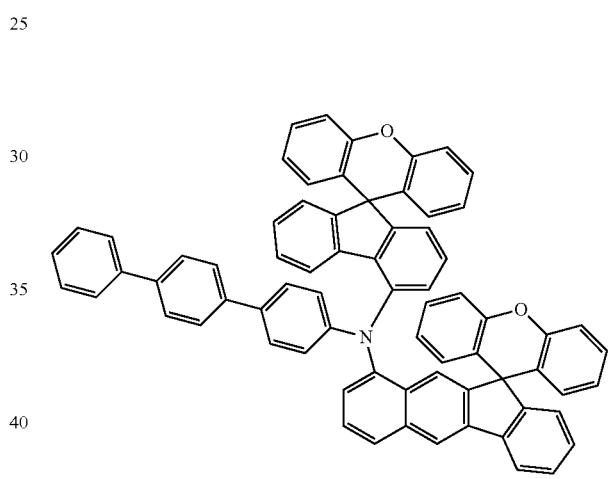
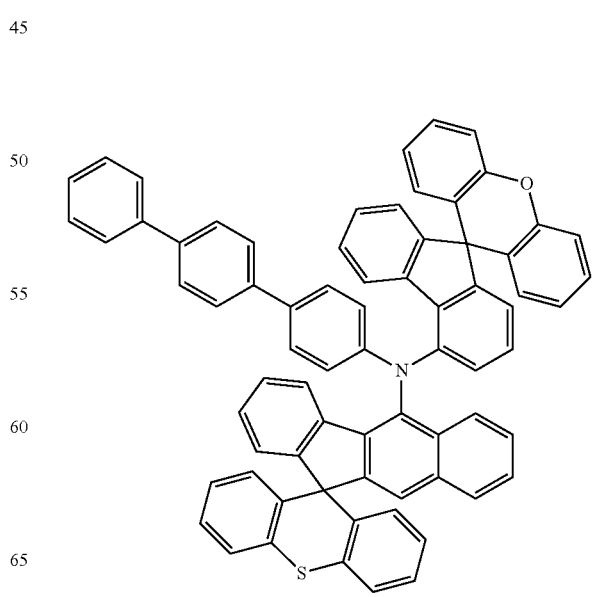

661
-continued
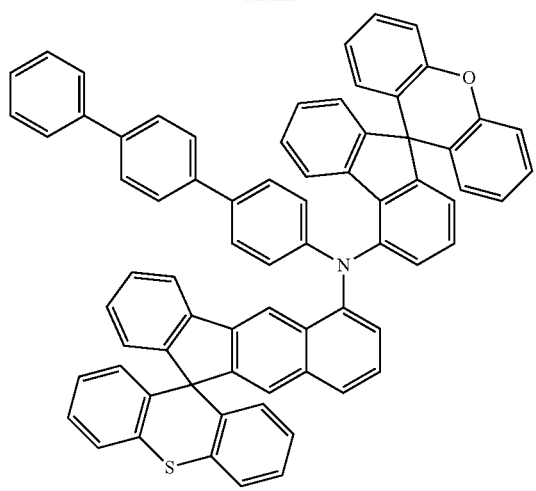
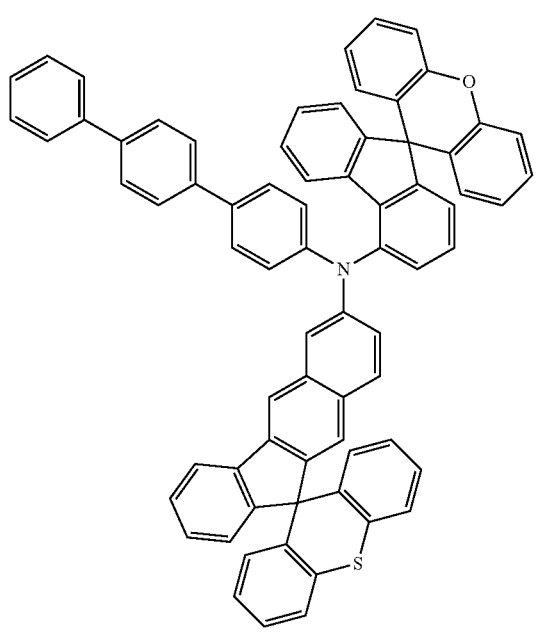
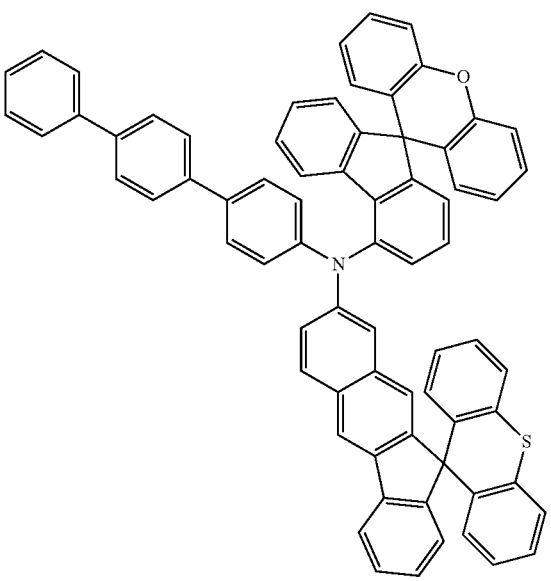
662
-continued
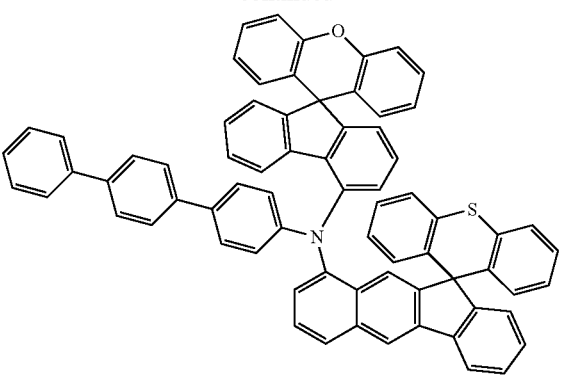
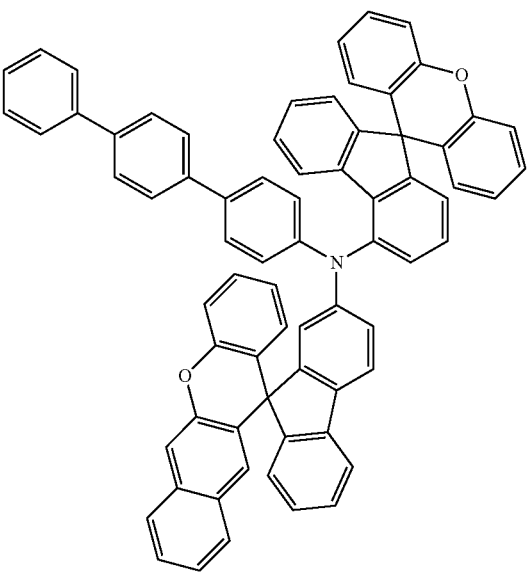
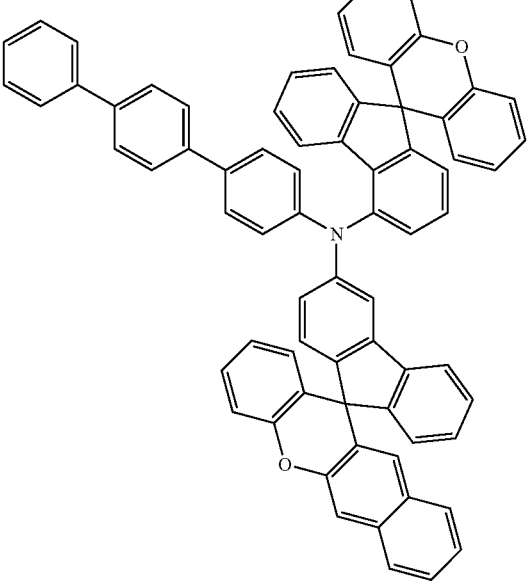

663
-continued
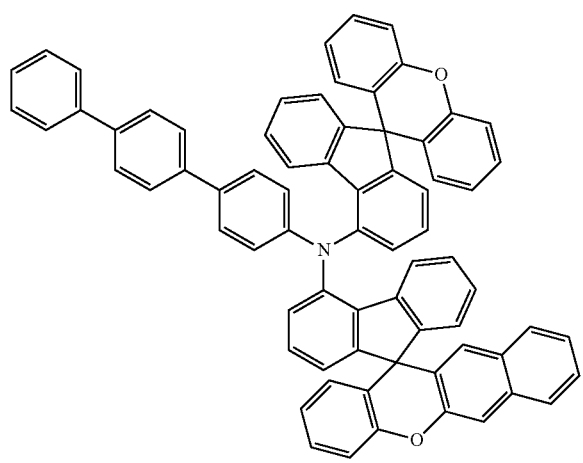 [SMILES: c1ccc(-c2ccc(-c3ccc(N(c4cccc5c4-c4ccccc4C54c5ccccc5Oc5ccccc54)c4cccc5c4-c4ccccc4C54c5ccccc5Sc5cc6ccccc6cc54)cc3)cc2)cc1]
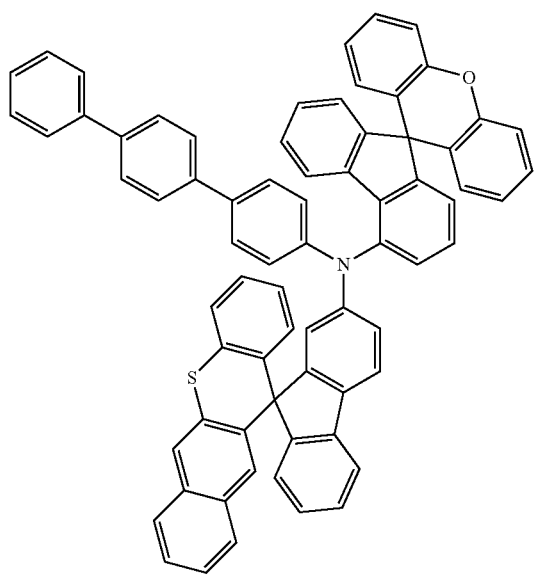
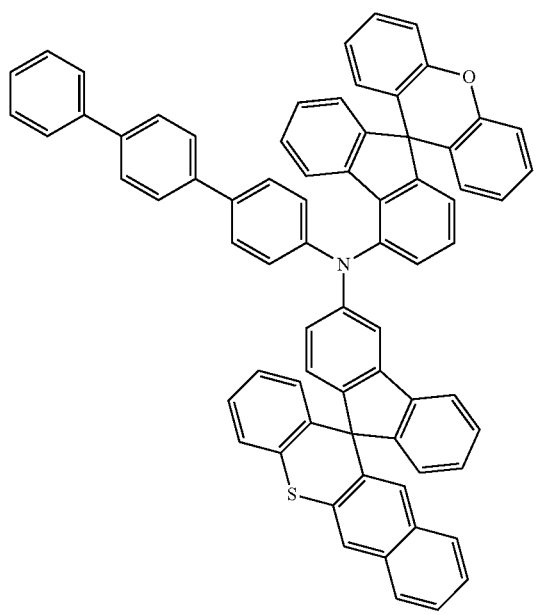
664
-continued
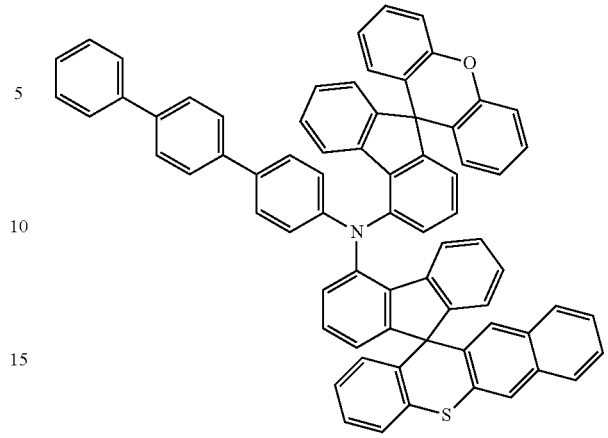
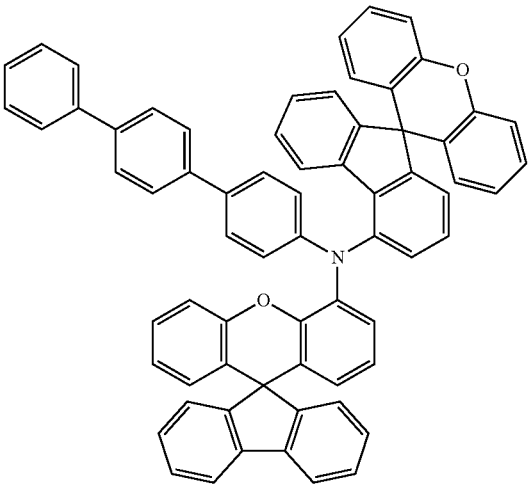
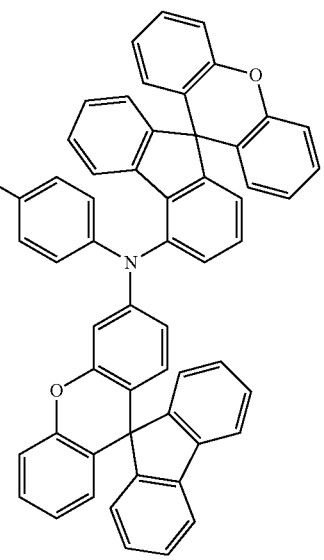

665
-continued
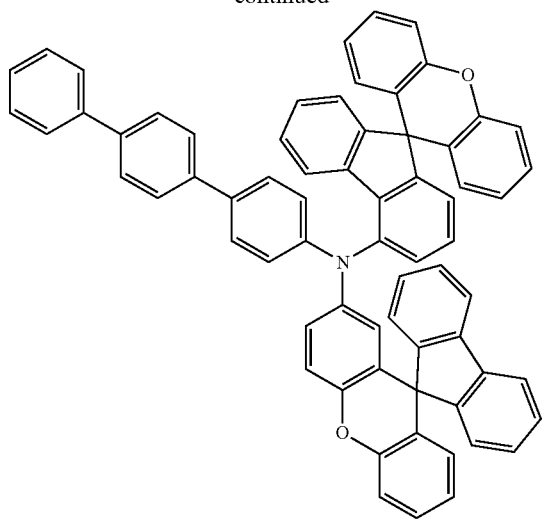
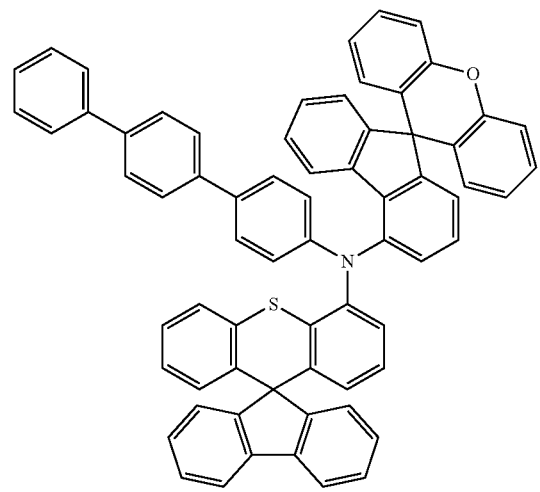
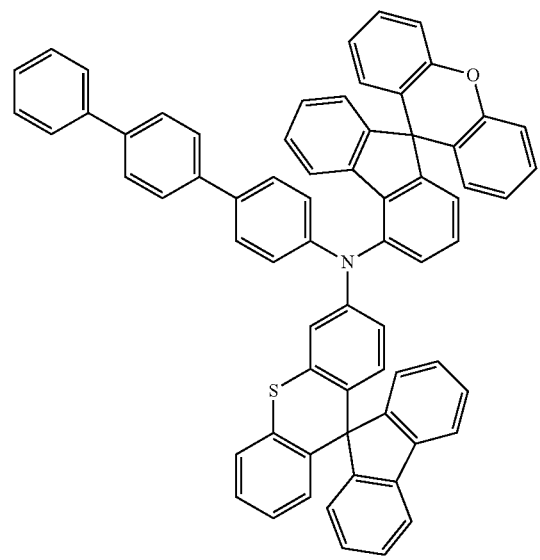
666
-continued
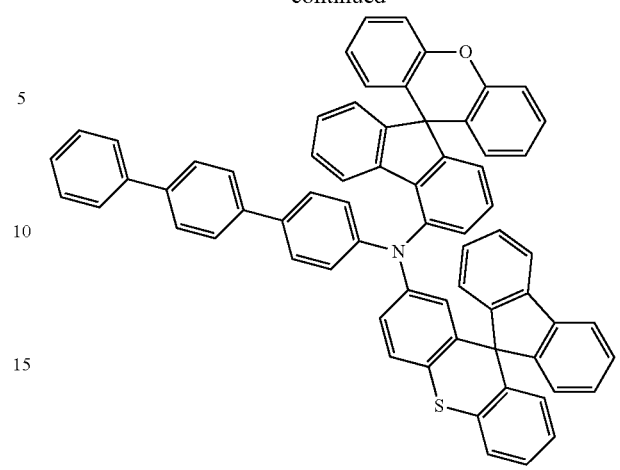
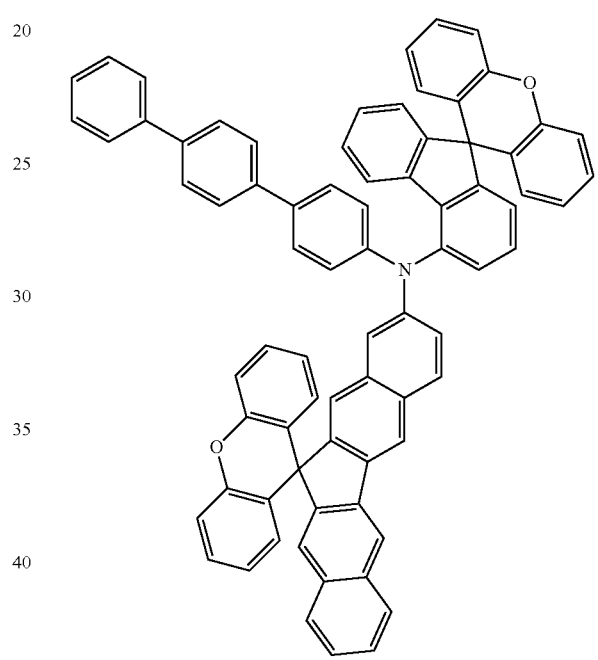
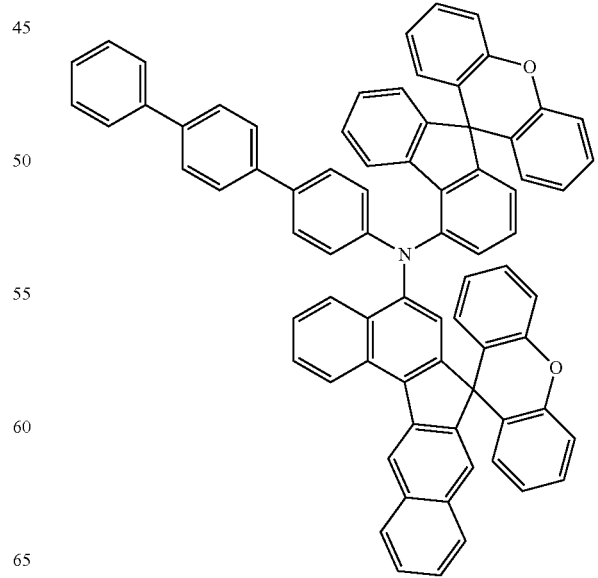

667
-continued
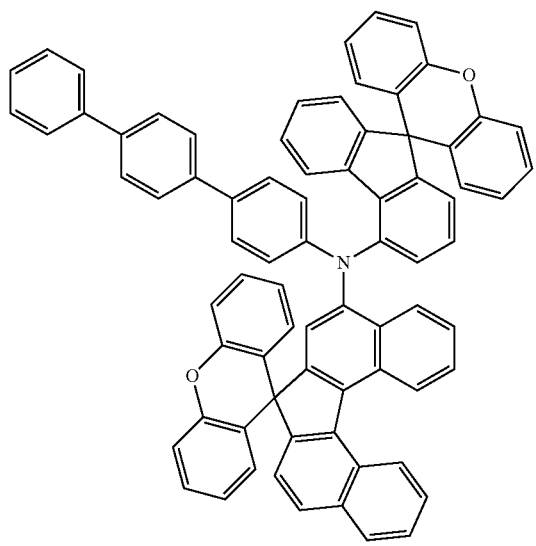
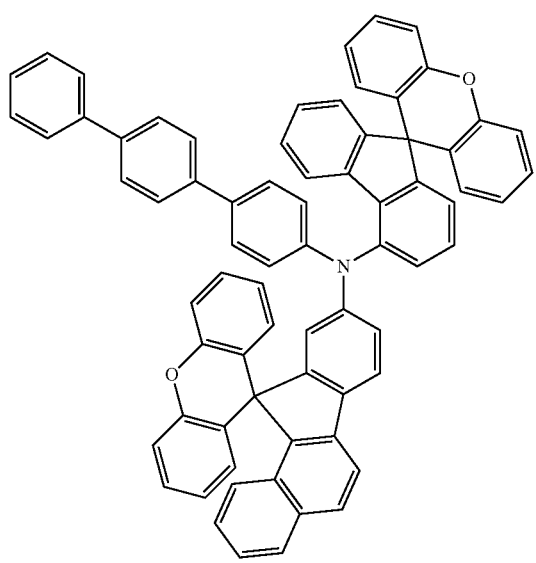
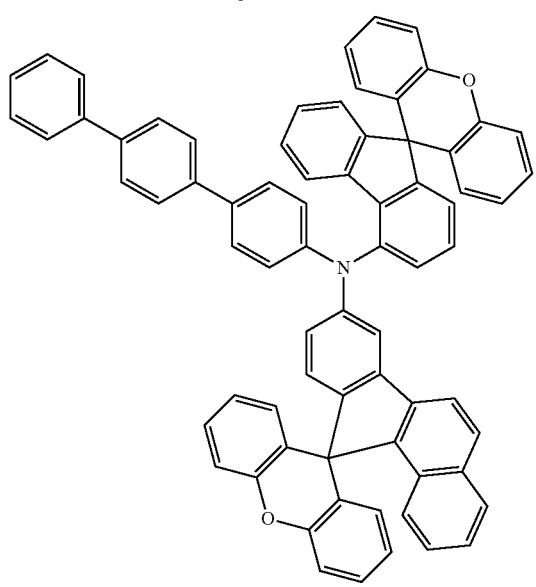
668
-continued
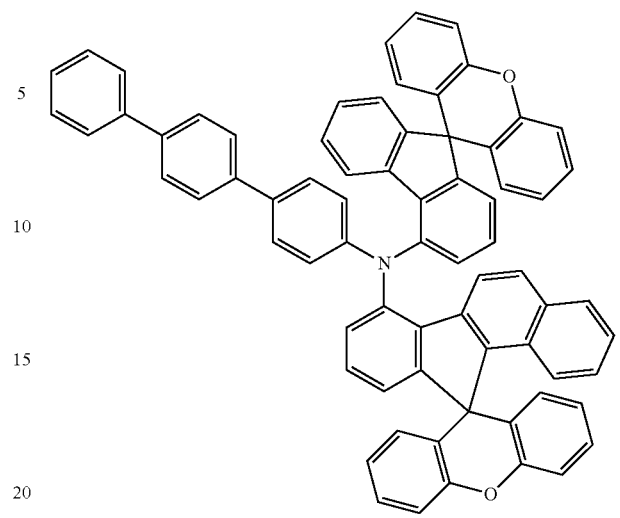
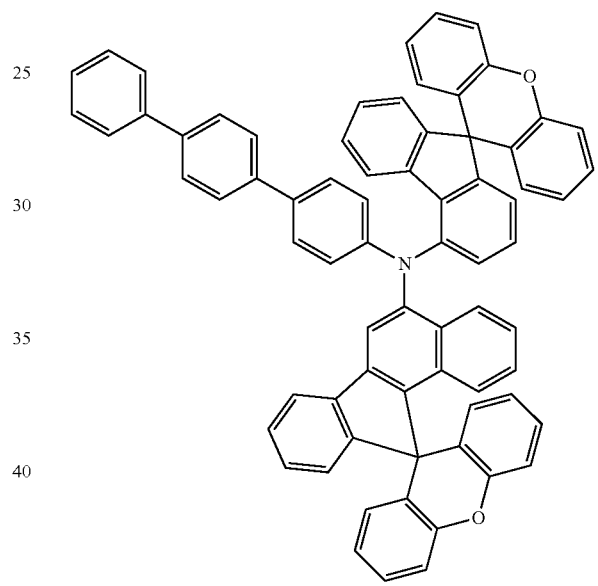
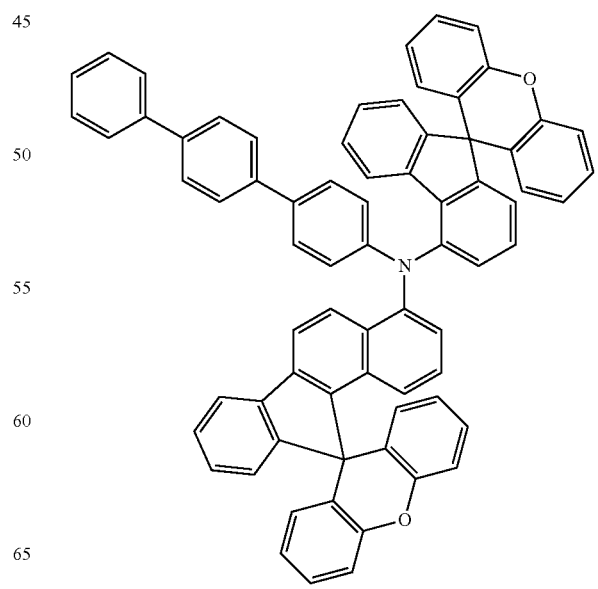

669
-continued
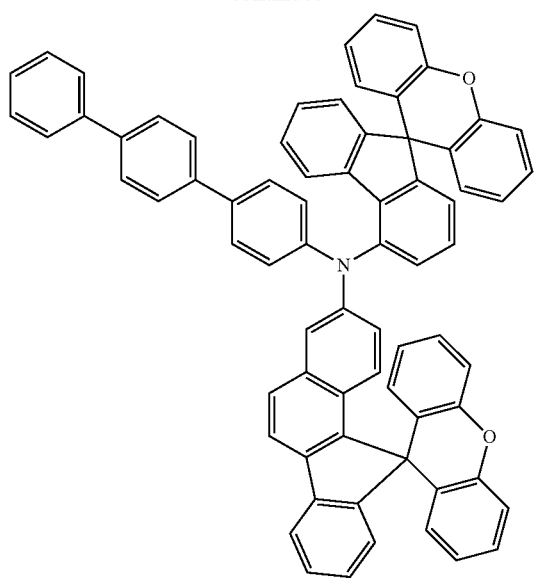
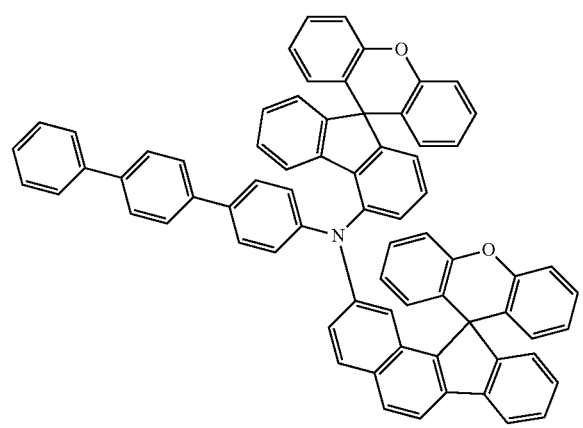
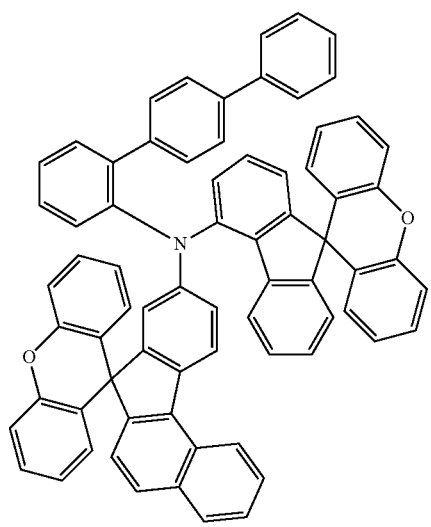
670
-continued
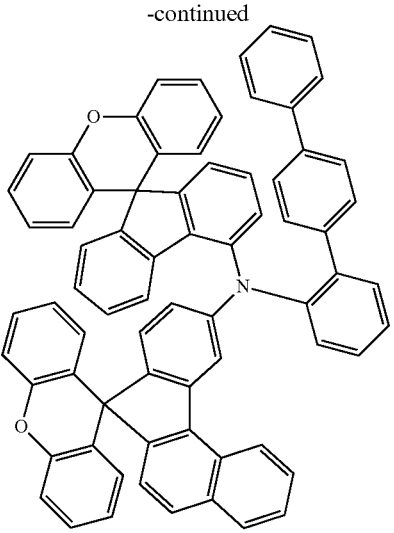
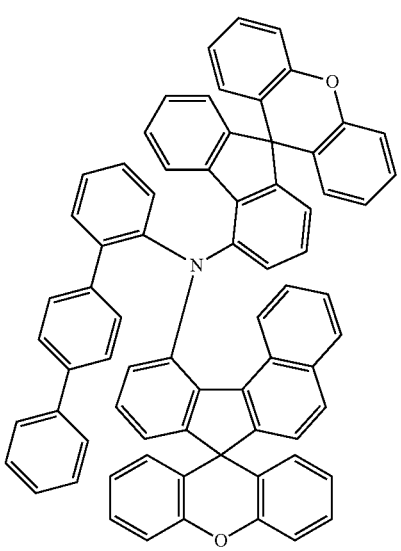
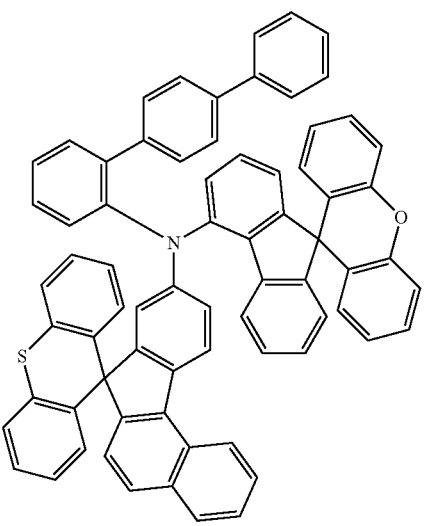

671
-continued
672
-continued
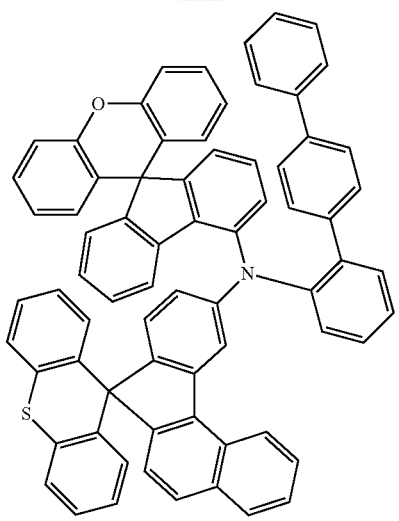
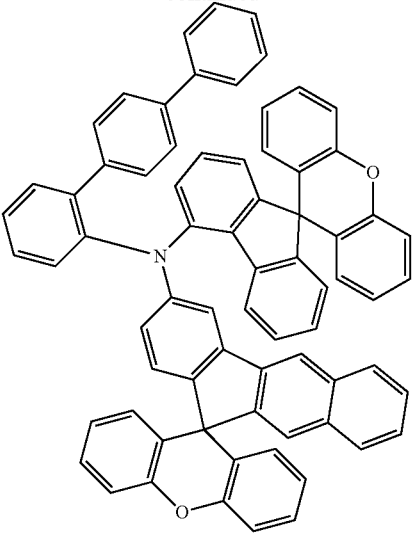
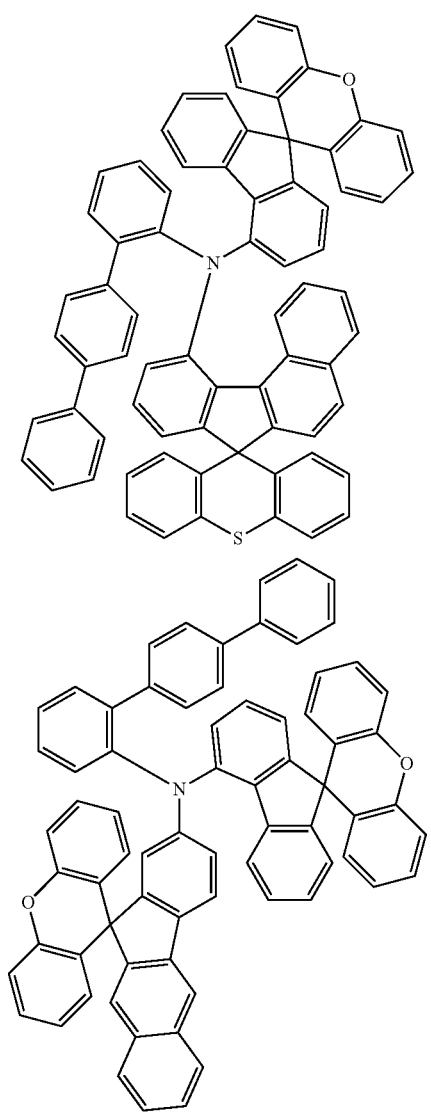
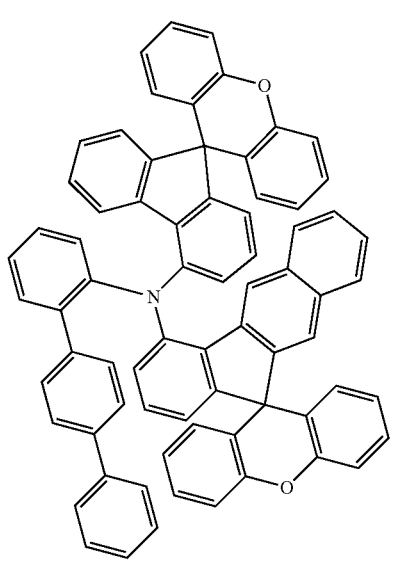
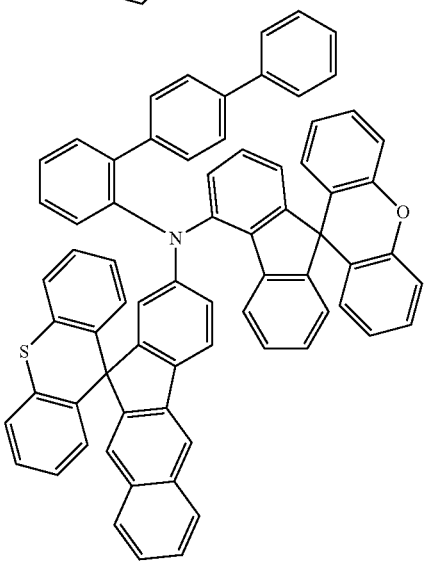

673
-continued
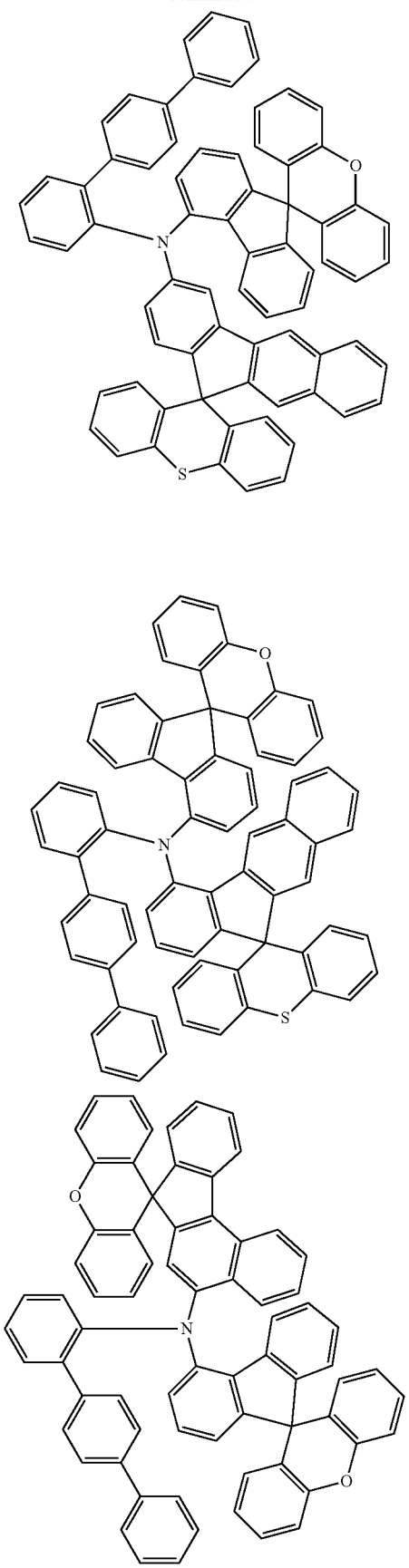
674
-continued
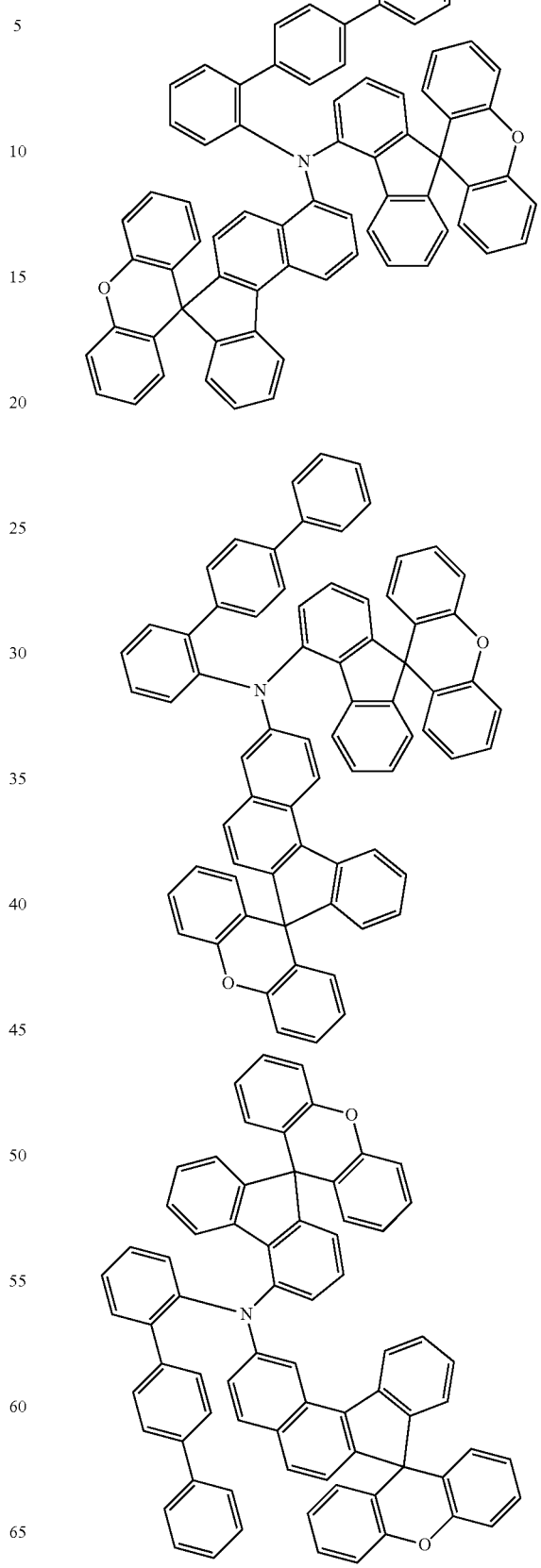

675
-continued
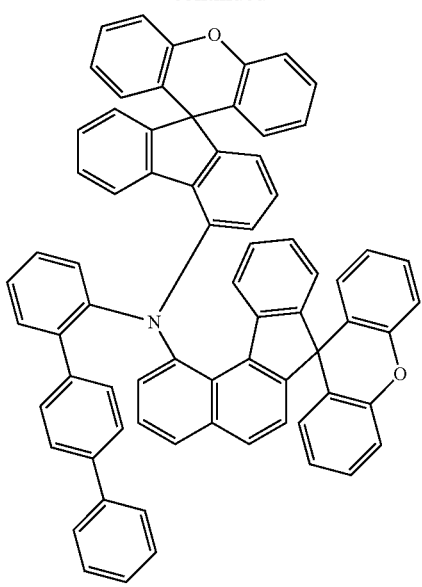
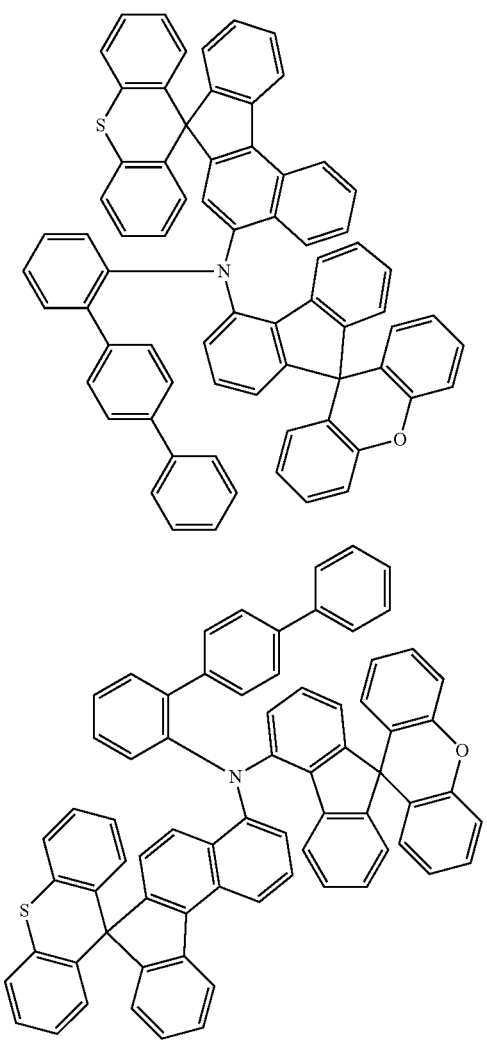
676
-continued
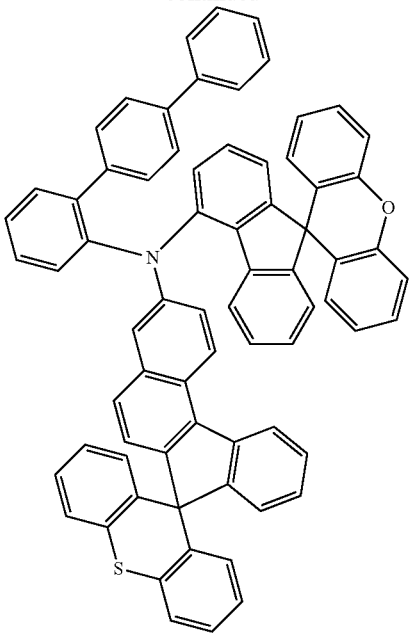
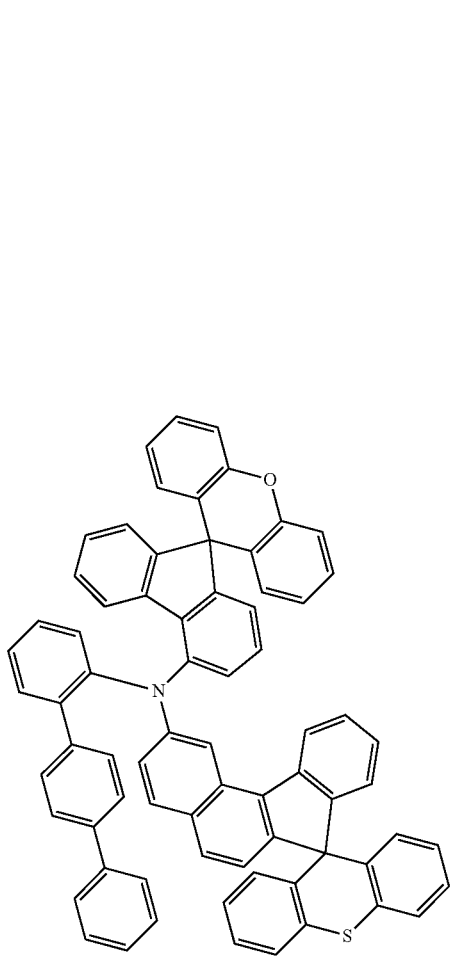

677
-continued
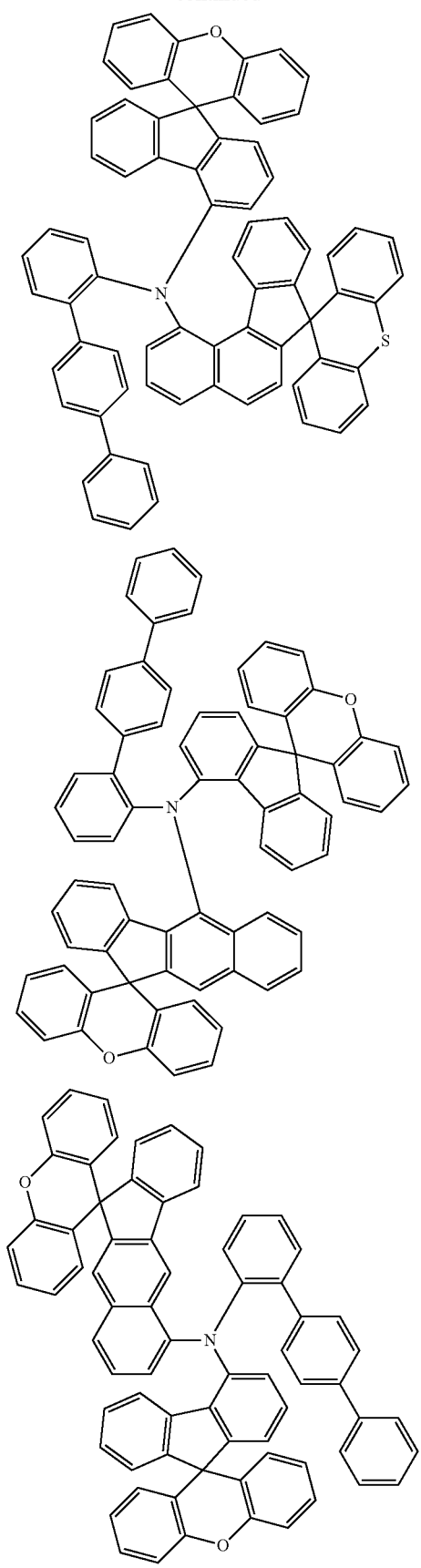
678
-continued
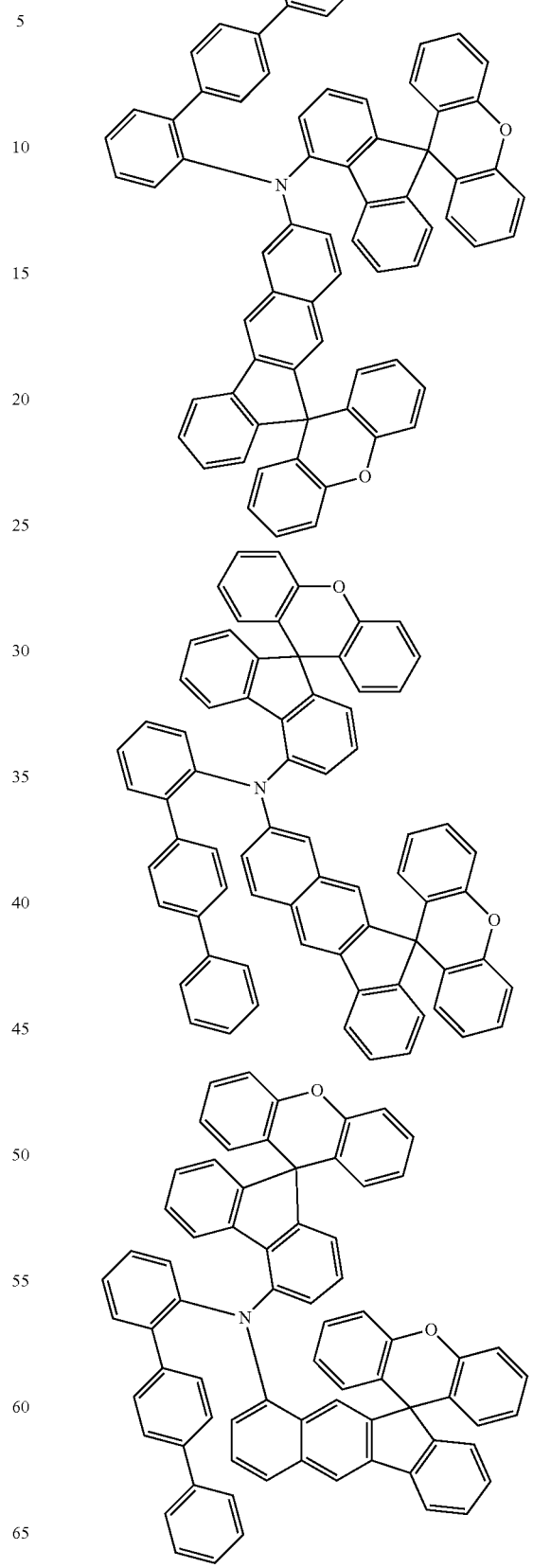

679
-continued
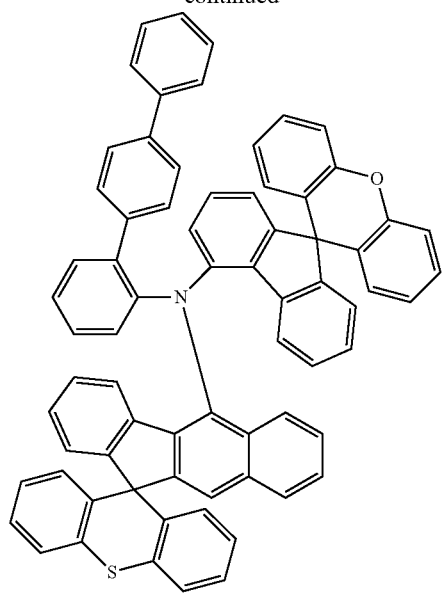
680
-continued
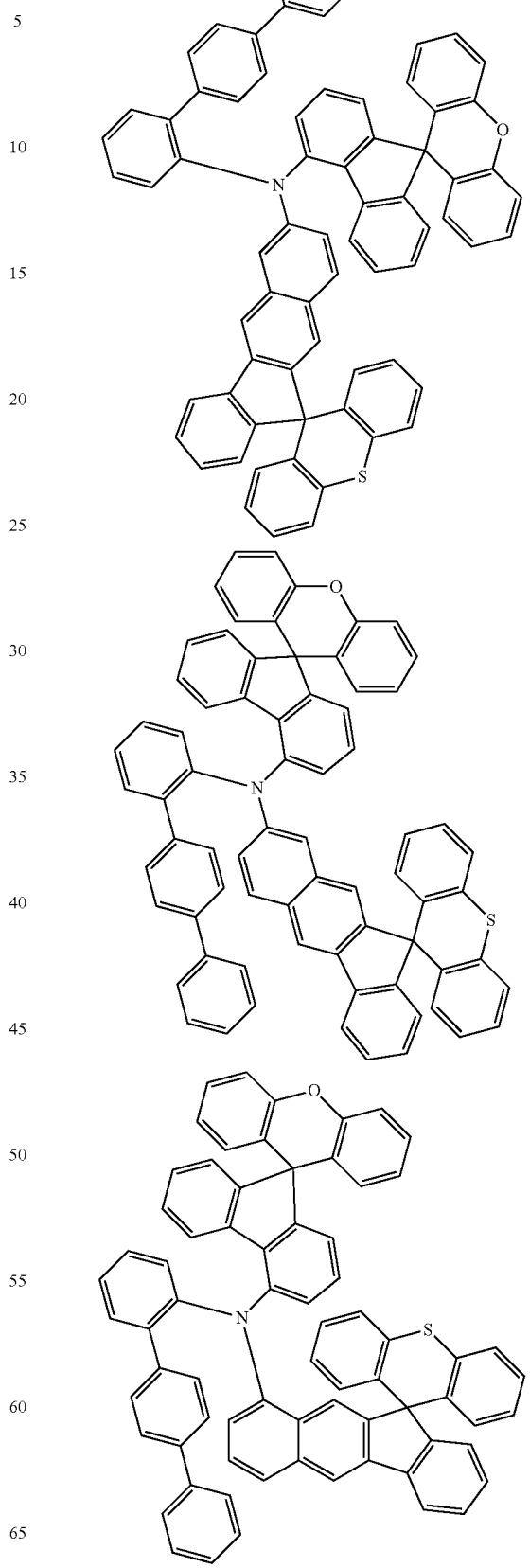
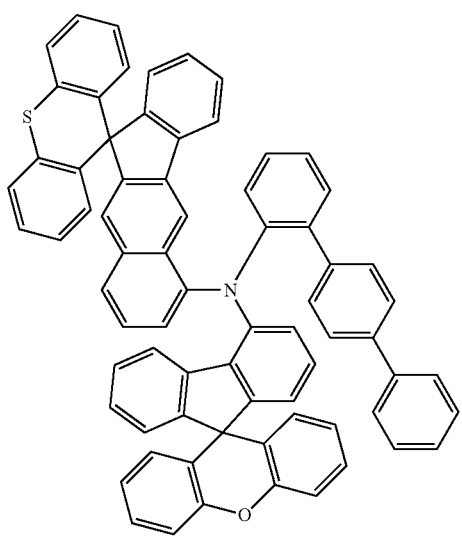

681
-continued
682
-continued
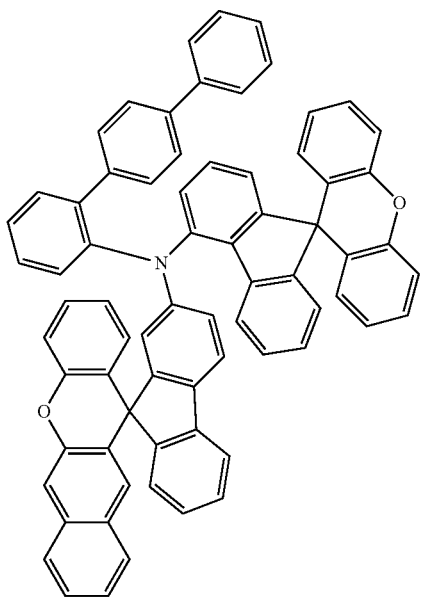
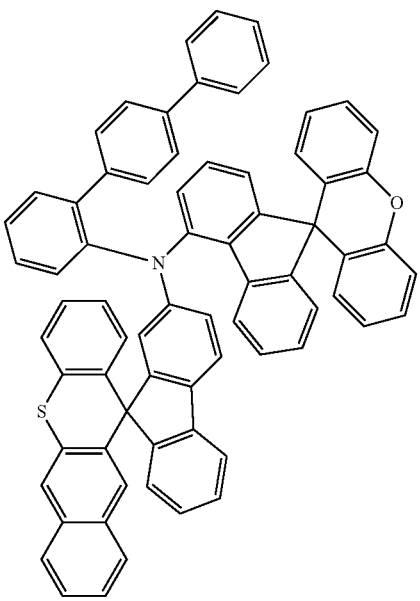
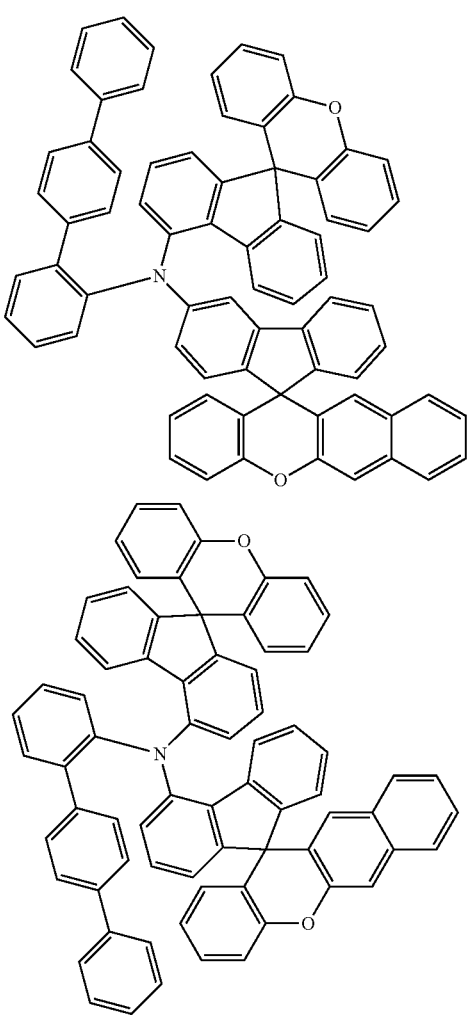
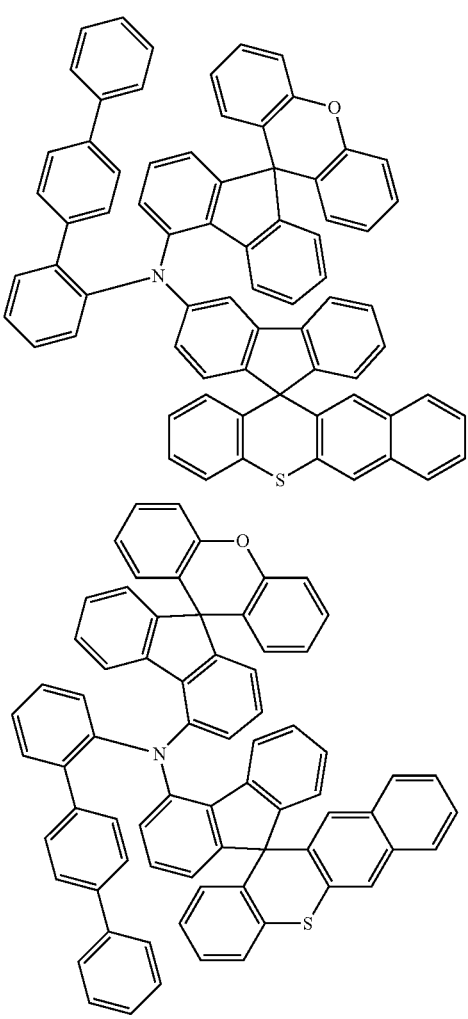

683
-continued
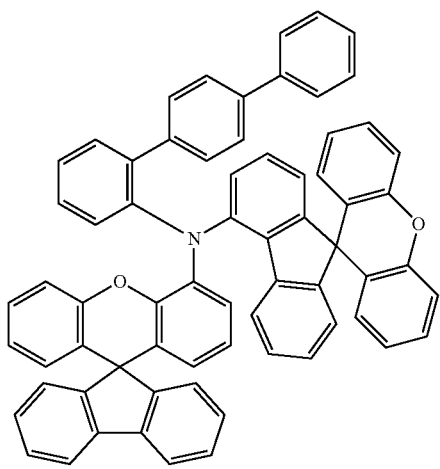
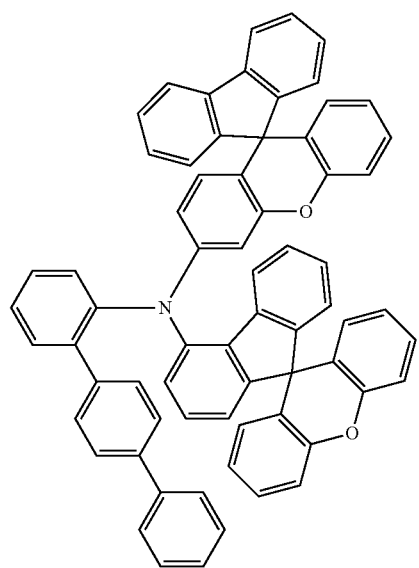
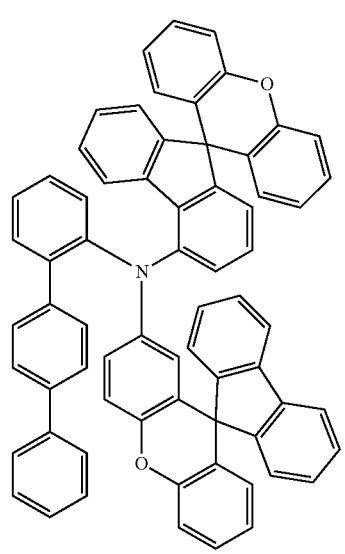
684
-continued
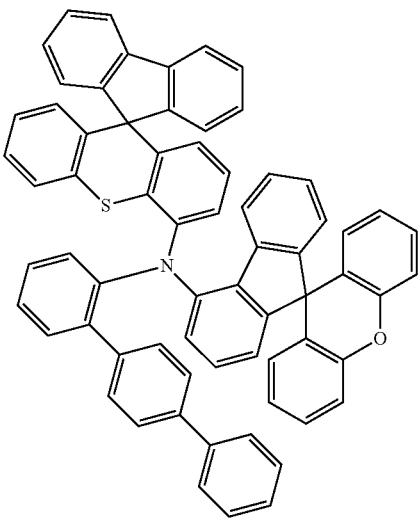
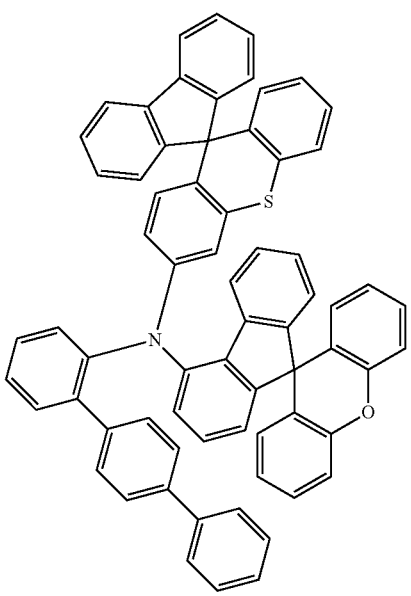
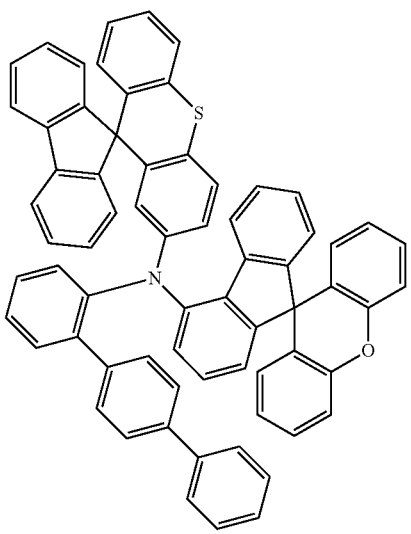

685
-continued
686
-continued
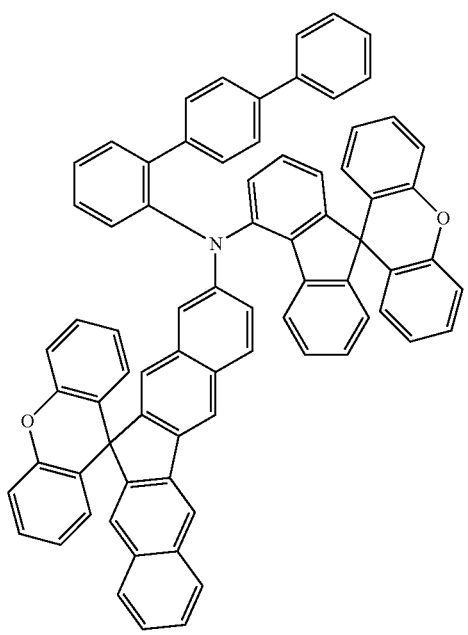
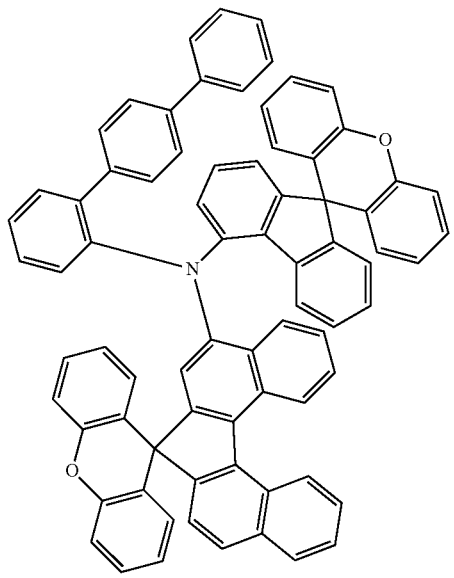
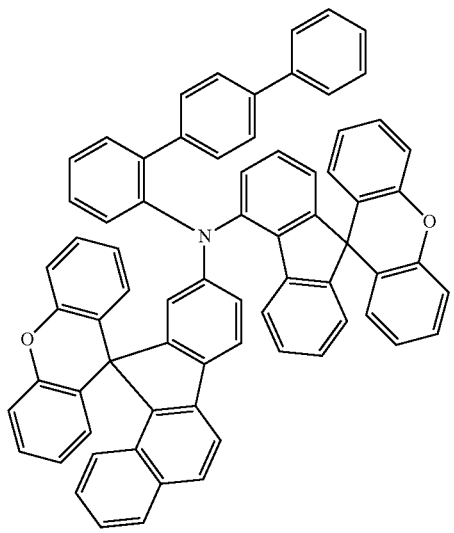
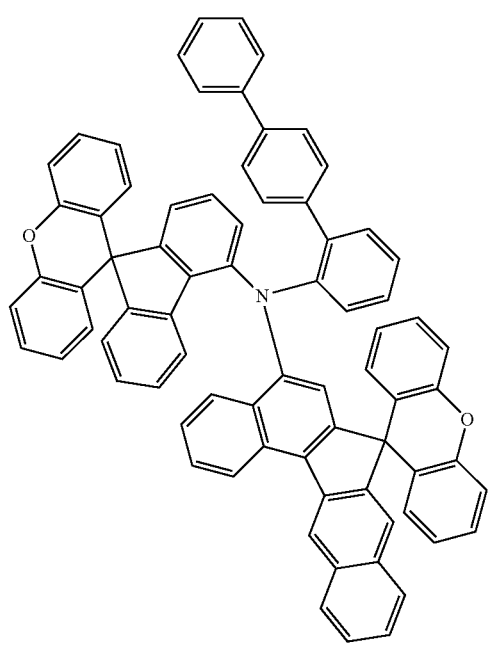
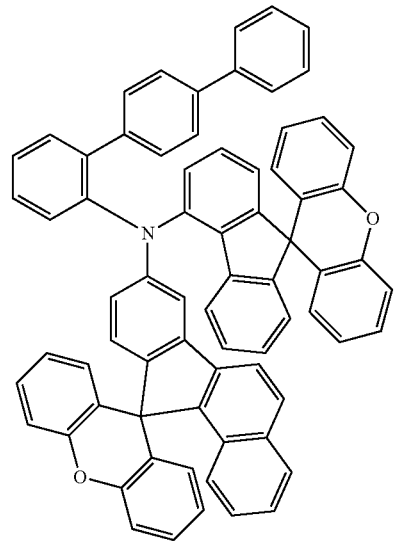

687
-continued
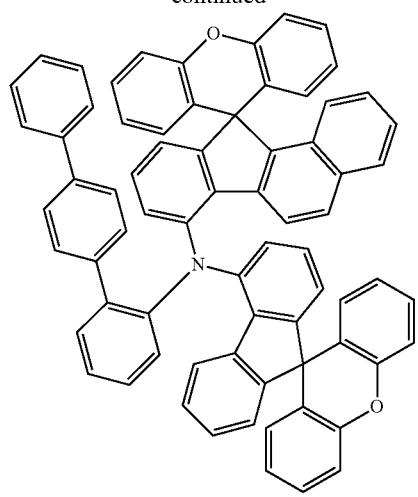
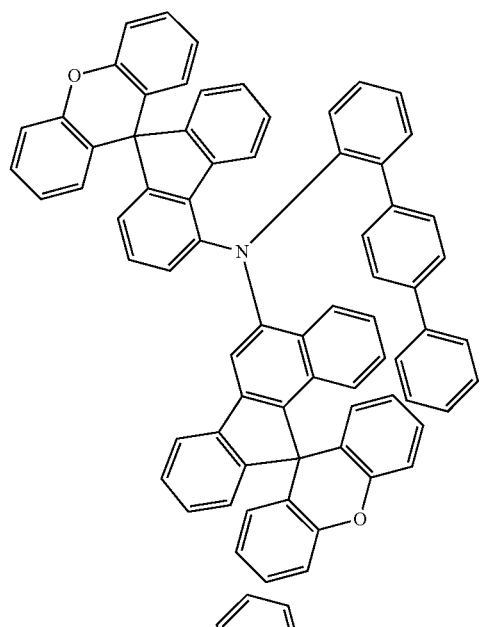
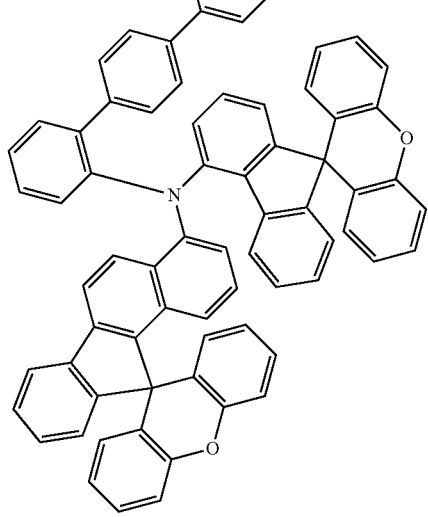
688
-continued
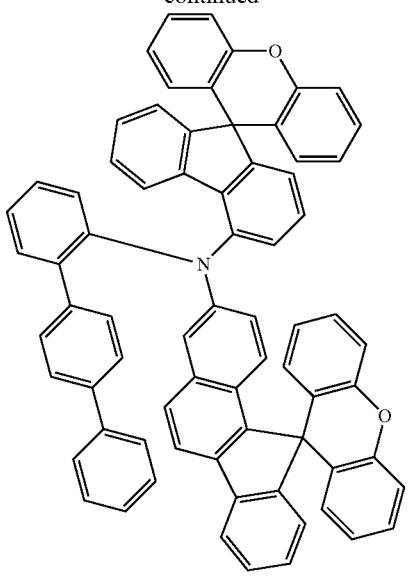
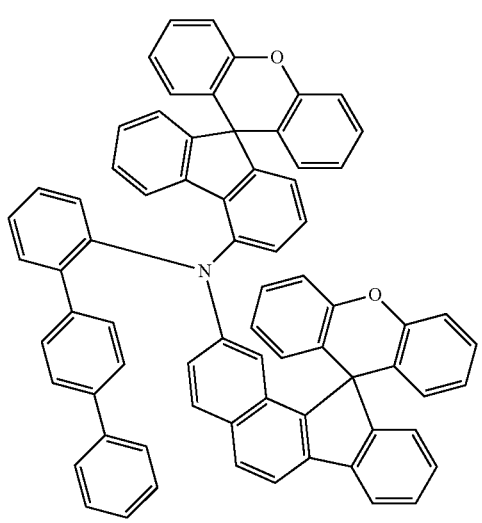
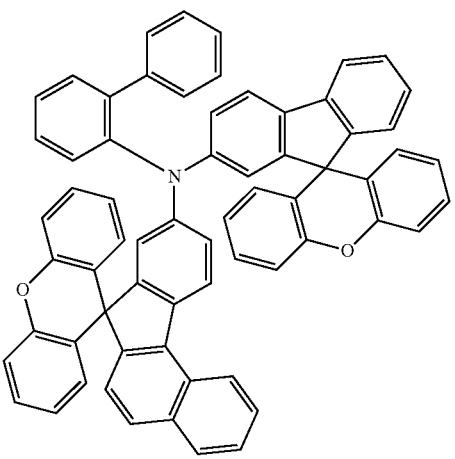

689
-continued
690
-continued
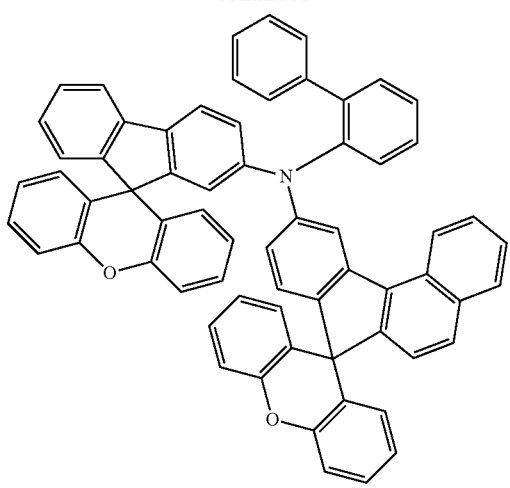
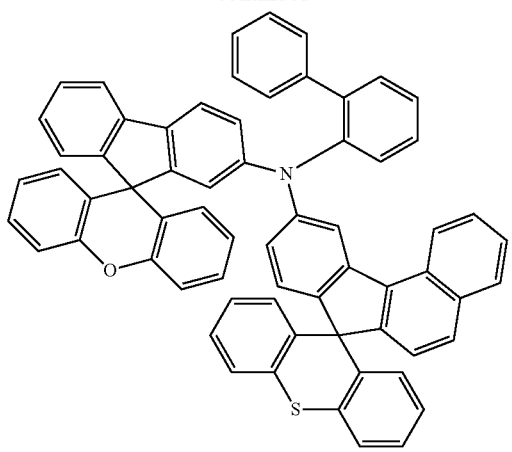
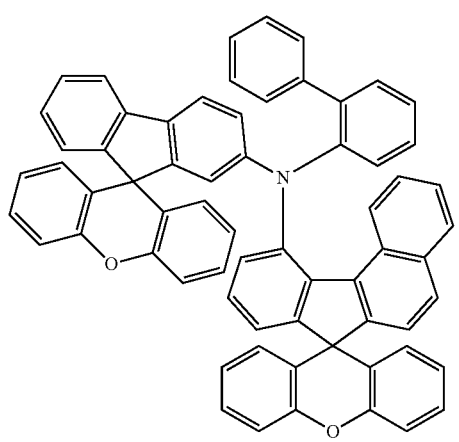
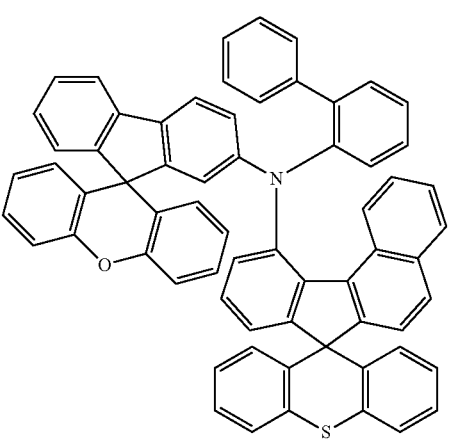
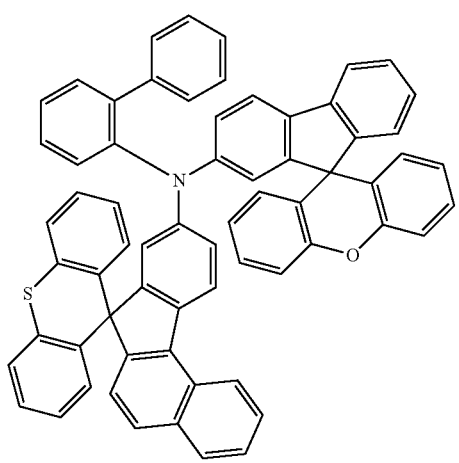
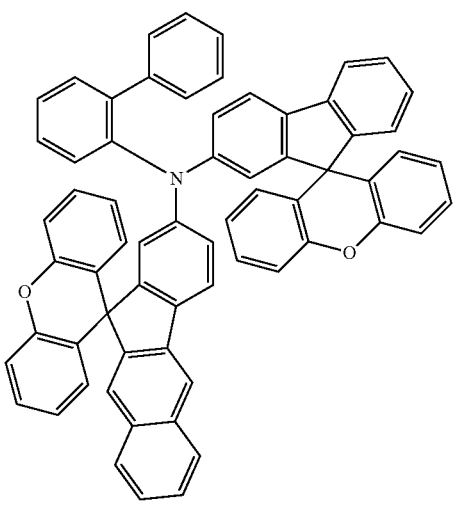

691
-continued
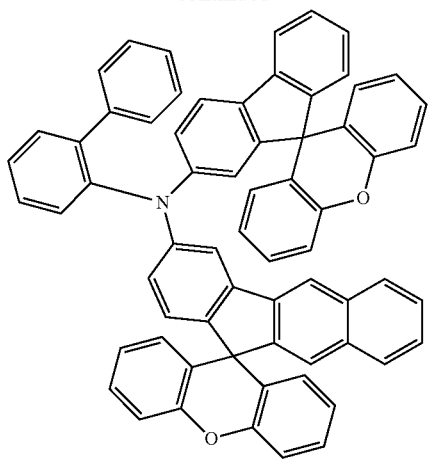
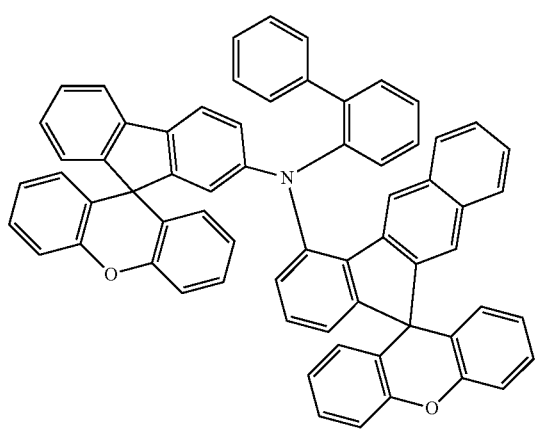
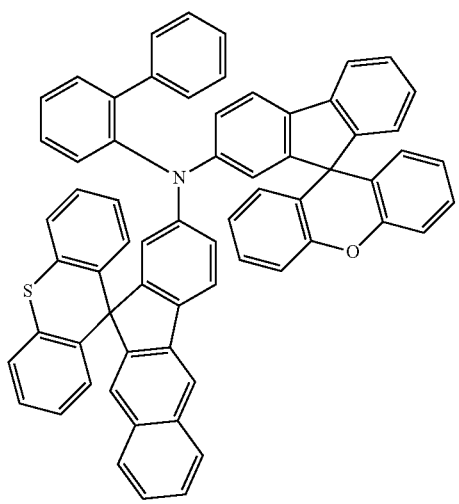
692
-continued
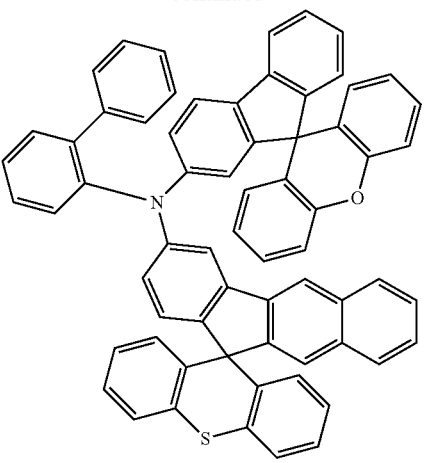
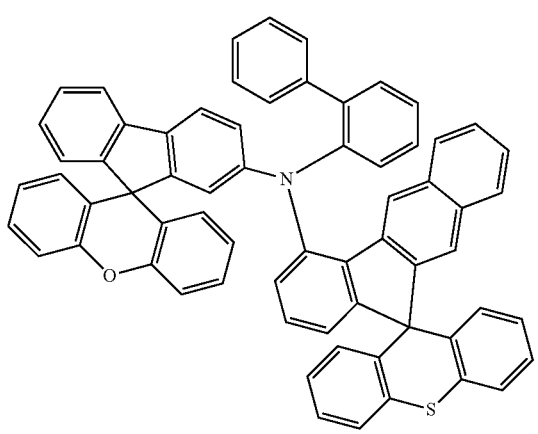
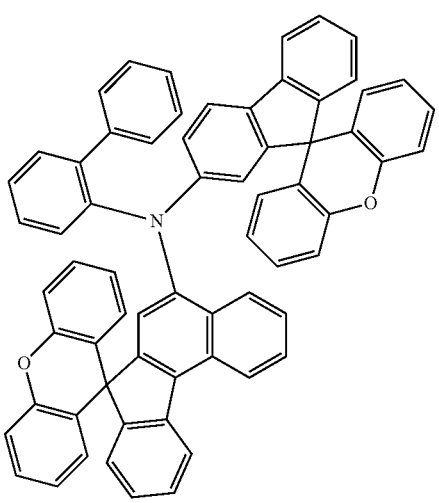

693
-continued
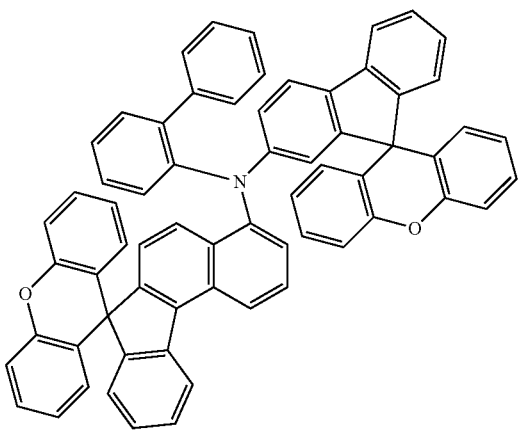
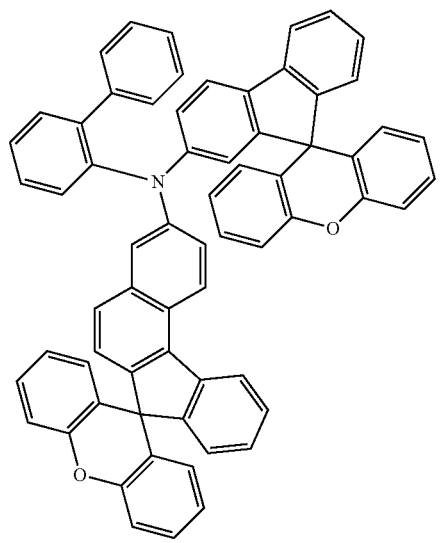
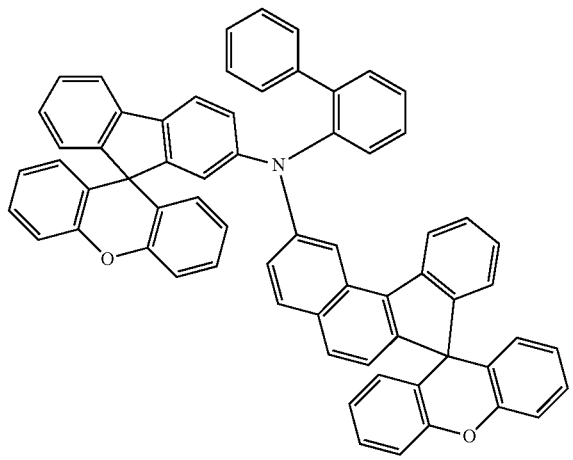
694
-continued
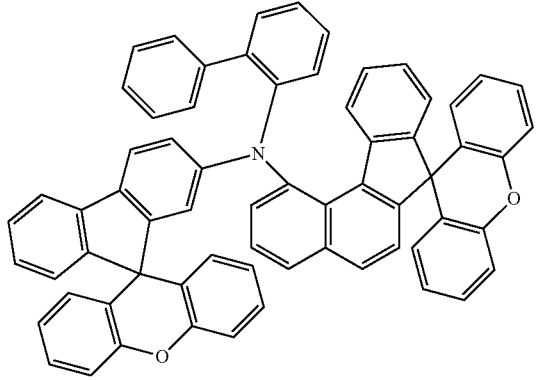
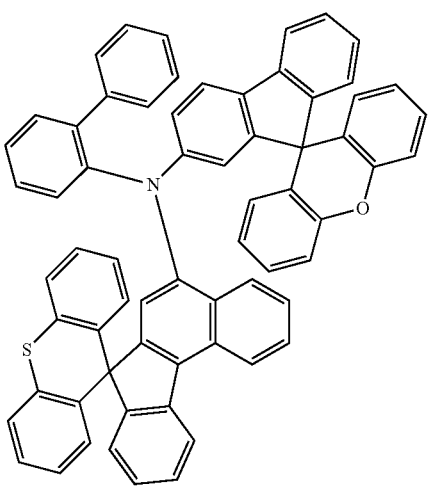
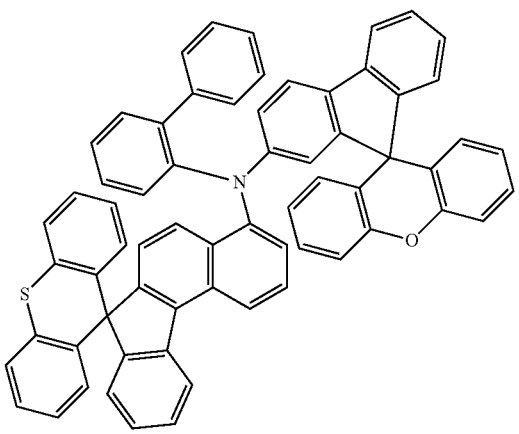

695
-continued
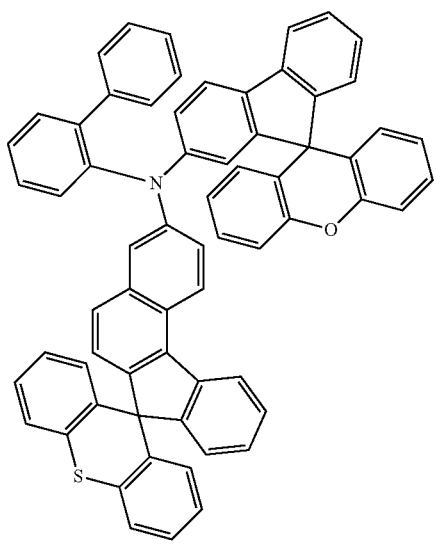
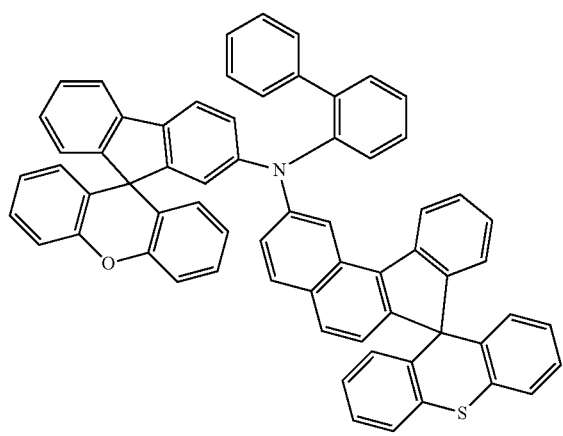
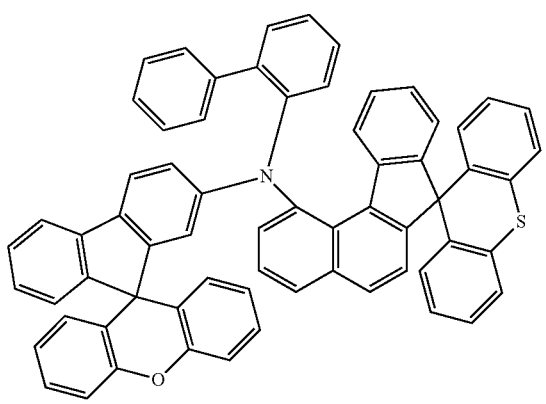
696
-continued
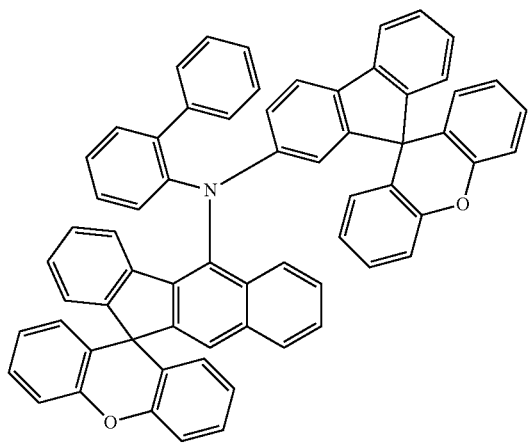
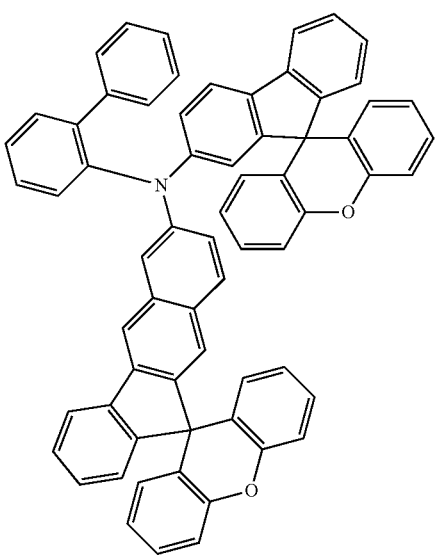

697
-continued
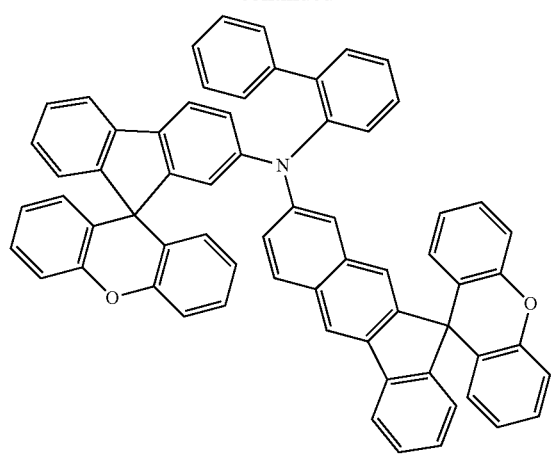
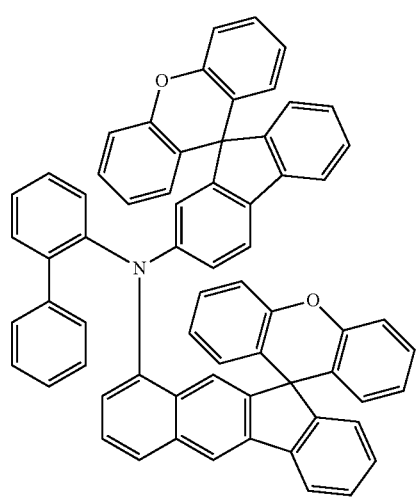
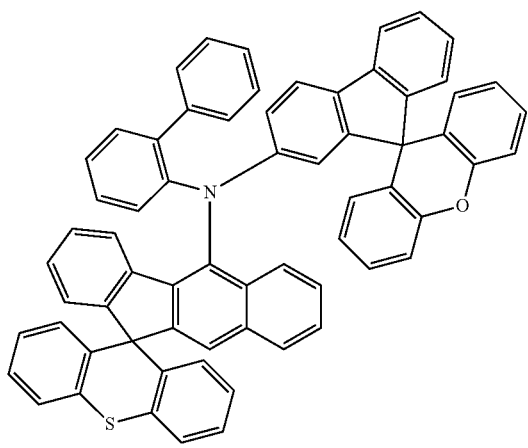
698
-continued
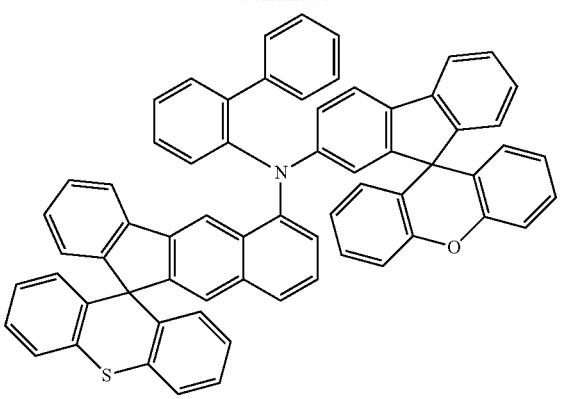
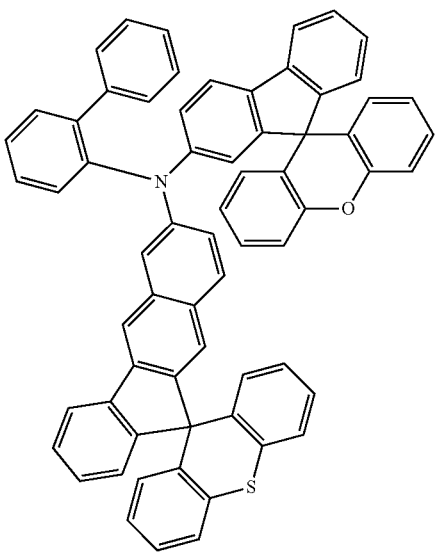
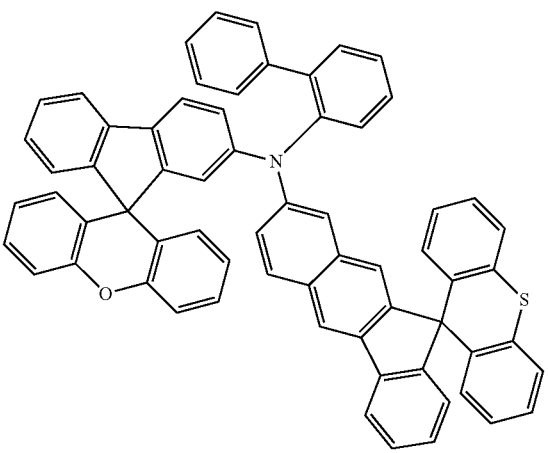

699
-continued
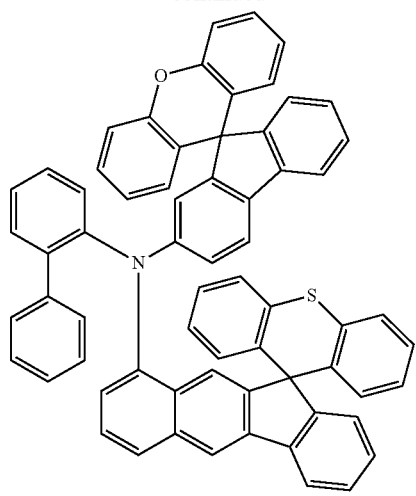
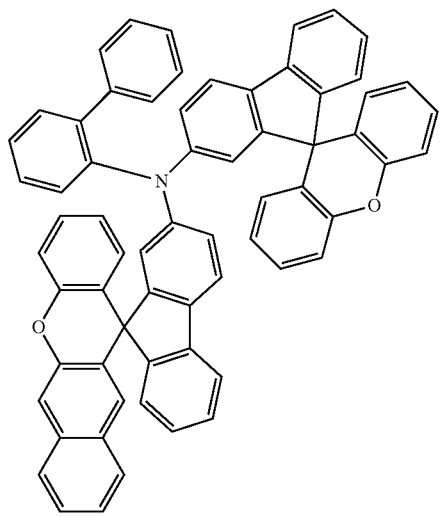
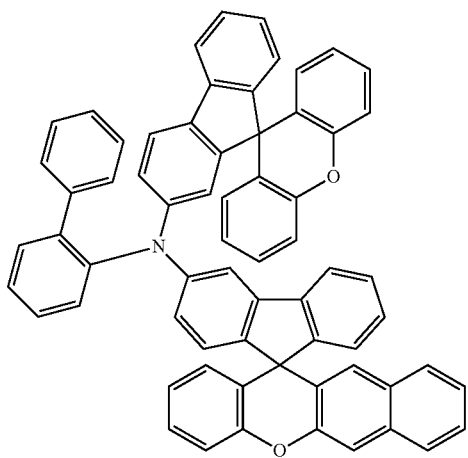
700
-continued
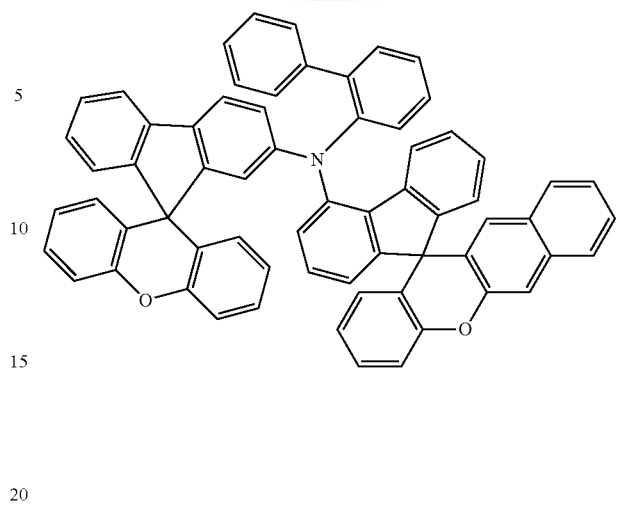

701
-continued
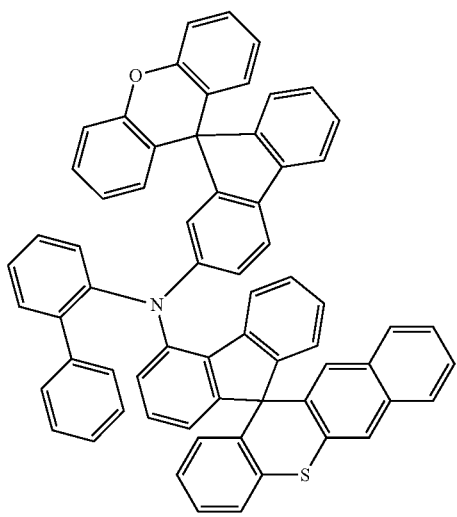
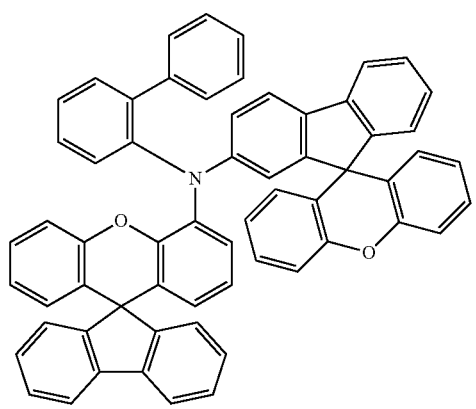
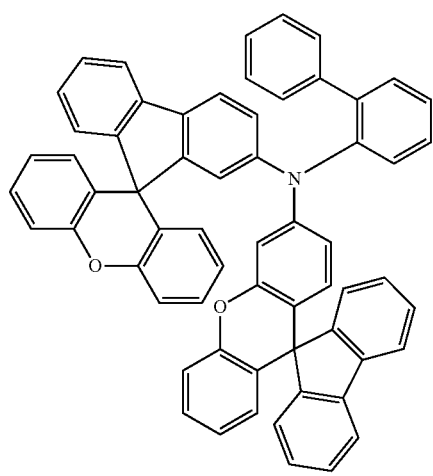
702
-continued
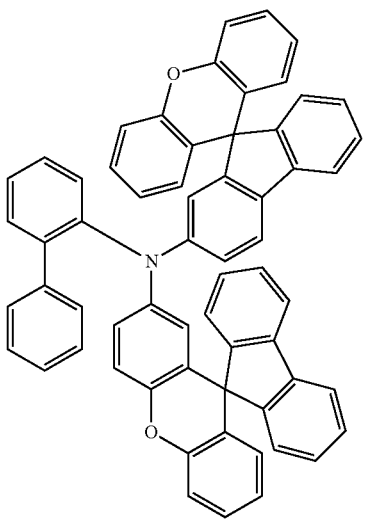
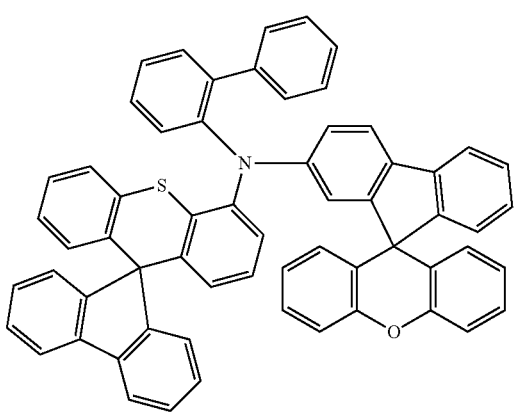
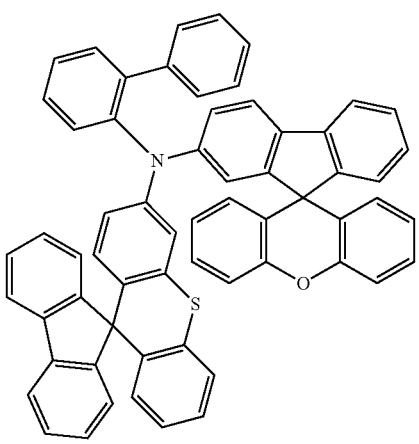

703
-continued
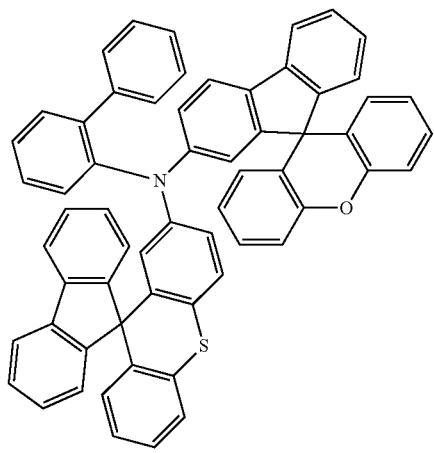
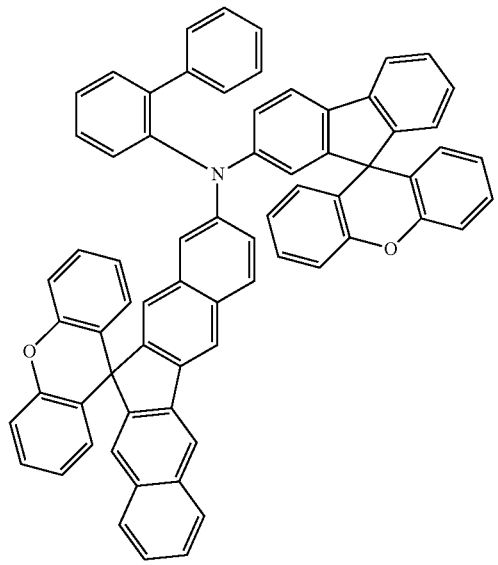
704
-continued
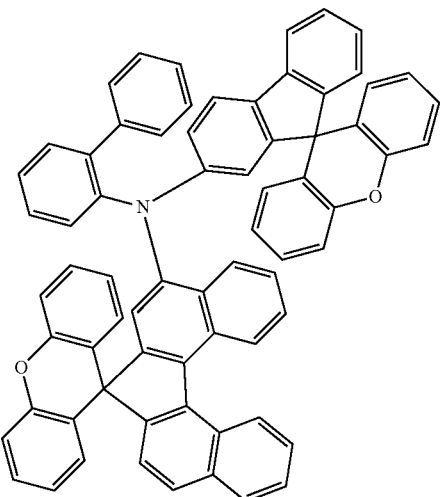
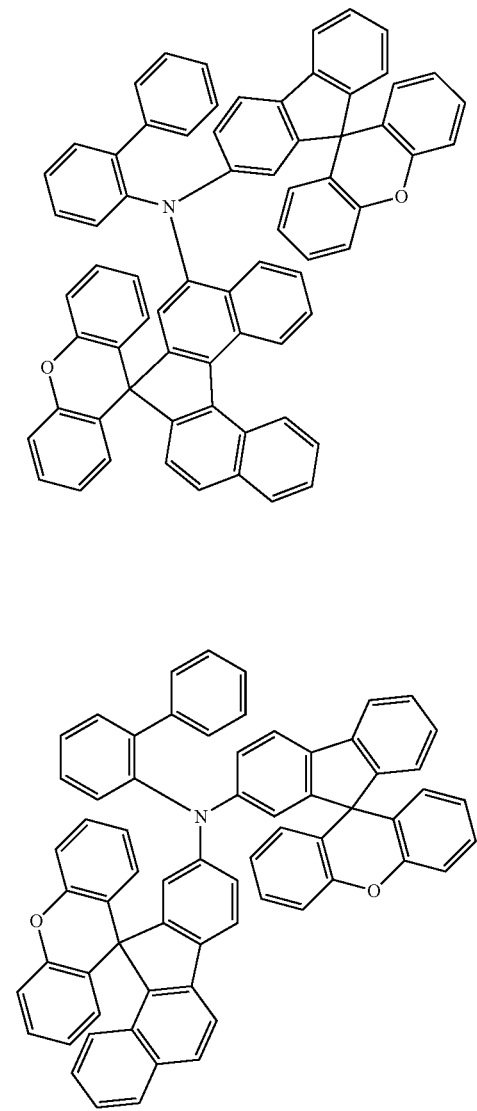
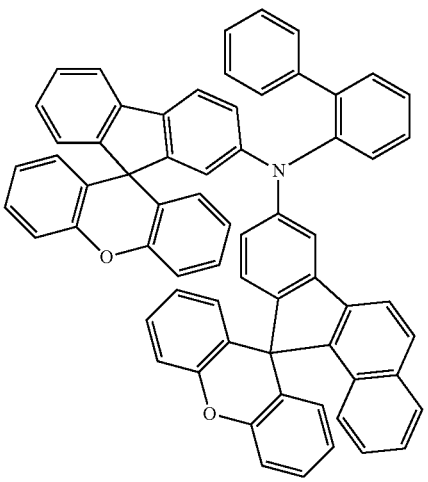

| 705 -continued | 706 -continued |
|---|---|
| 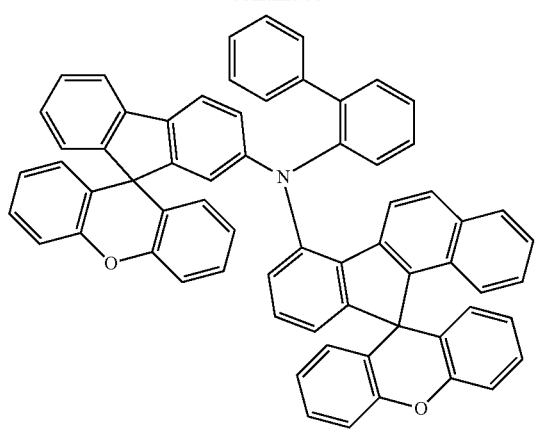 | 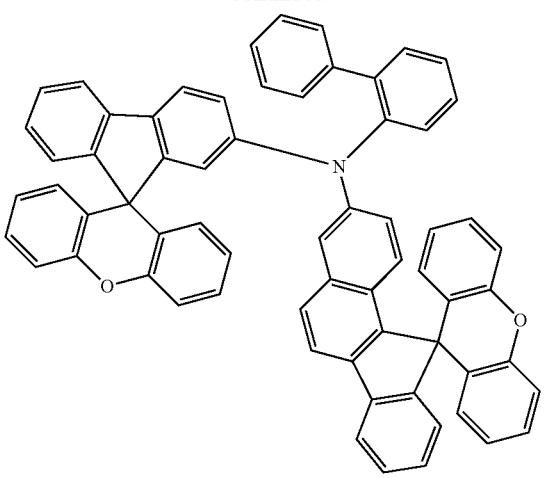 |
| 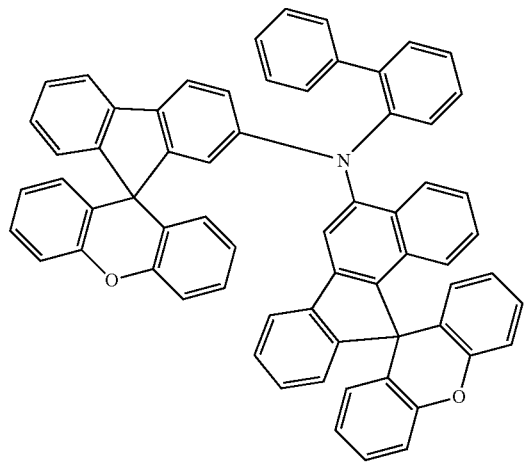 | 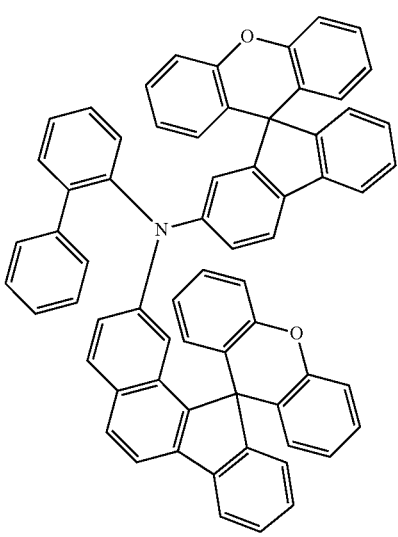 |
| 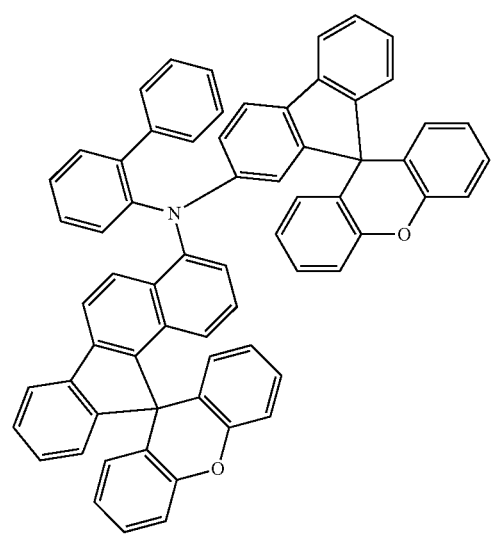 | 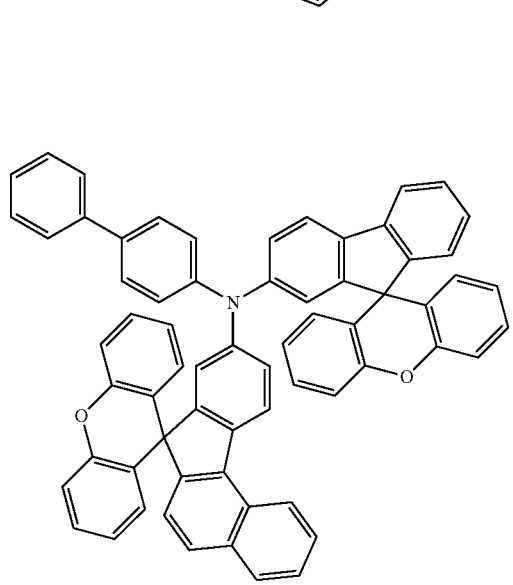 |

707
-continued
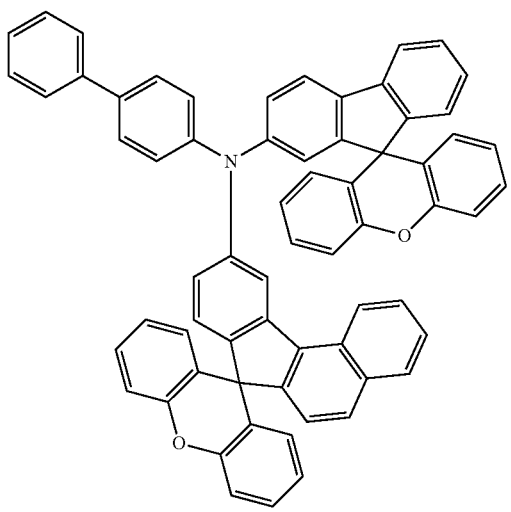
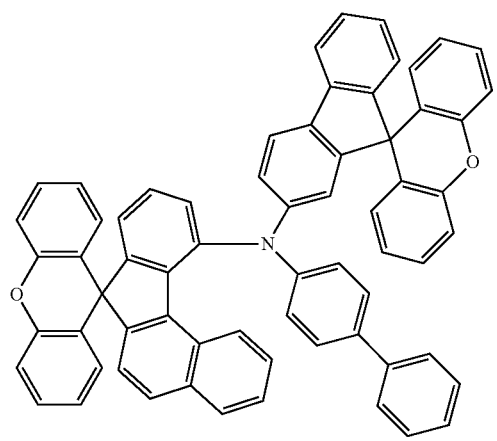
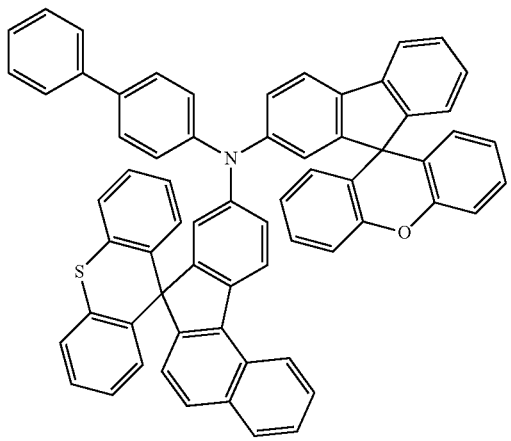
708
-continued
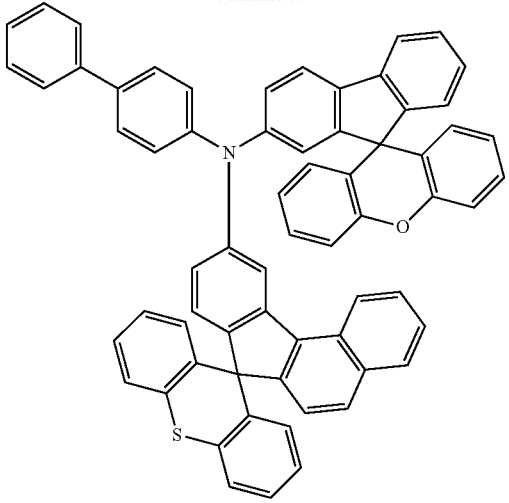
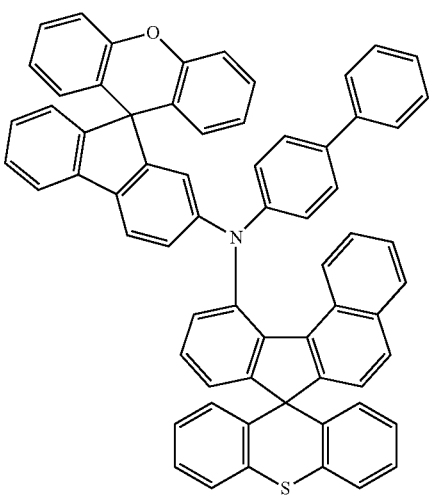
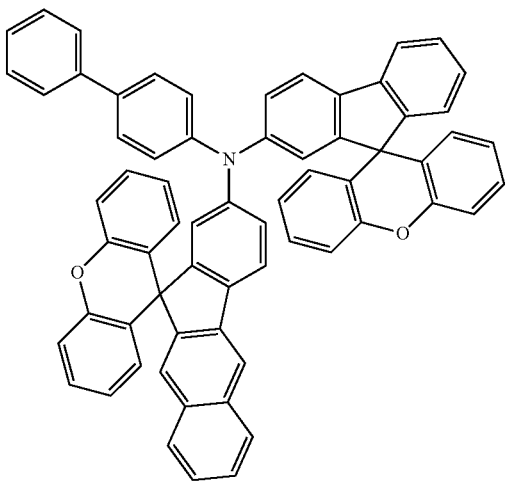

709
-continued
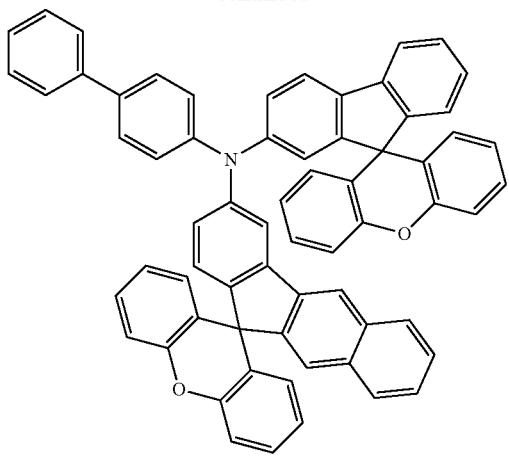
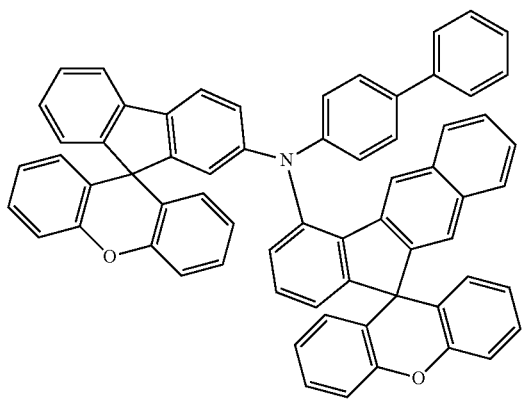
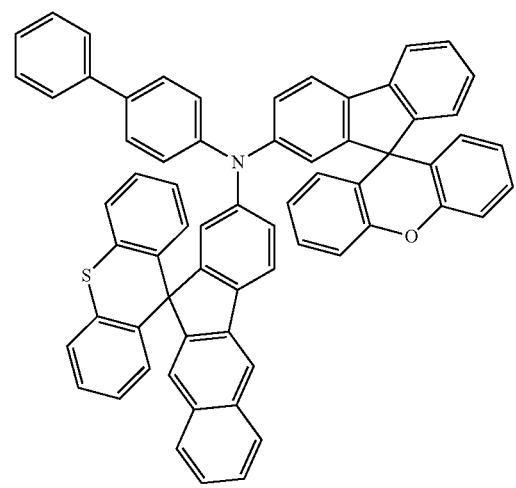
710
-continued
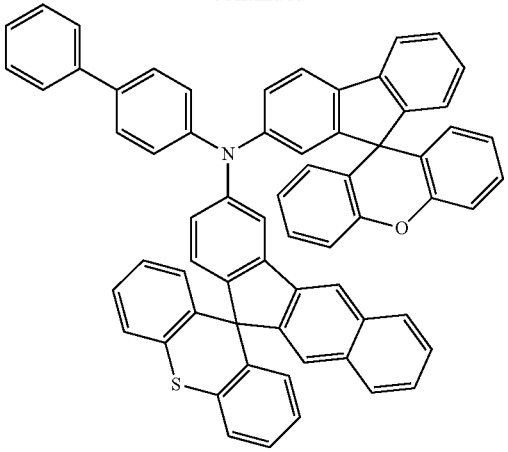
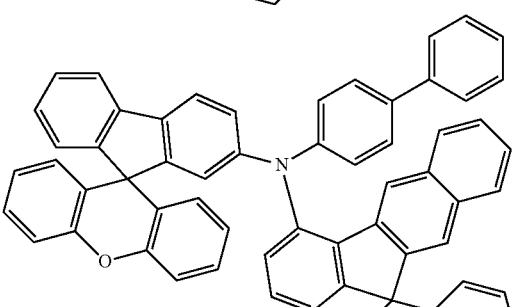
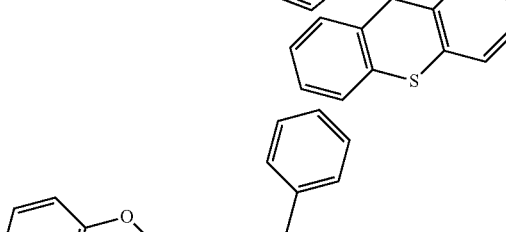
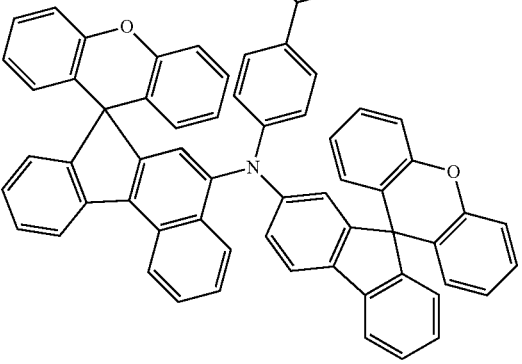
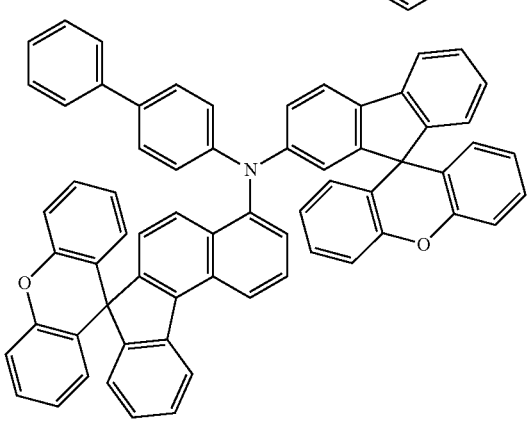

711
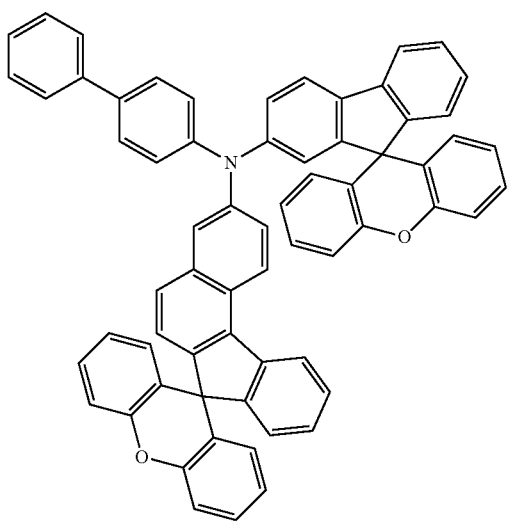
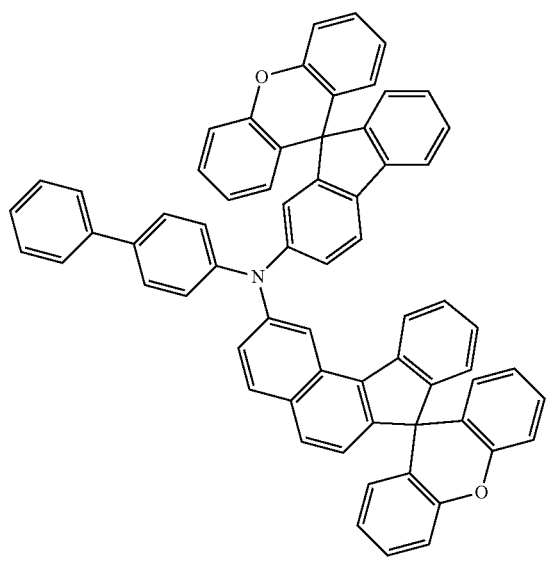
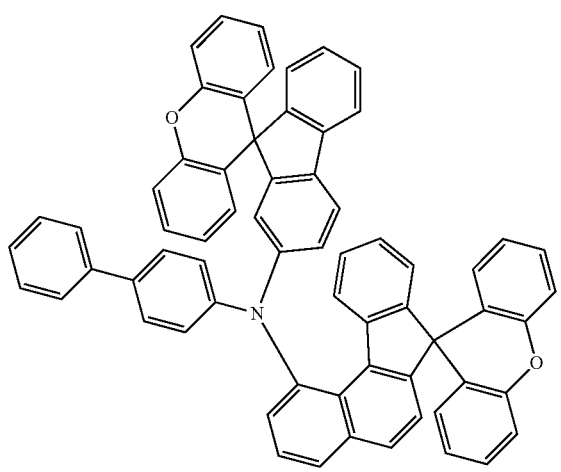
712
-continued
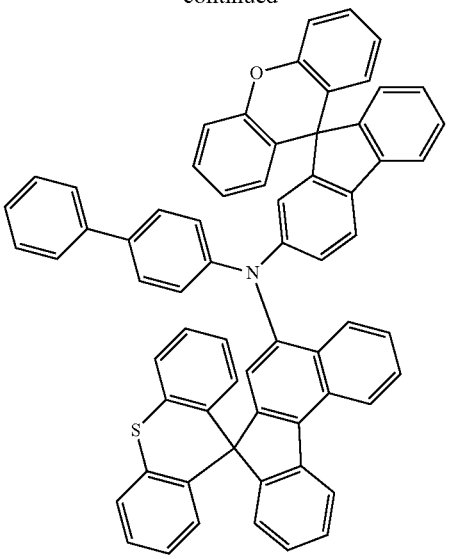
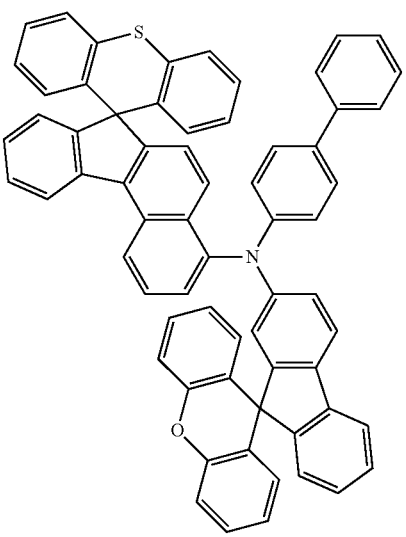
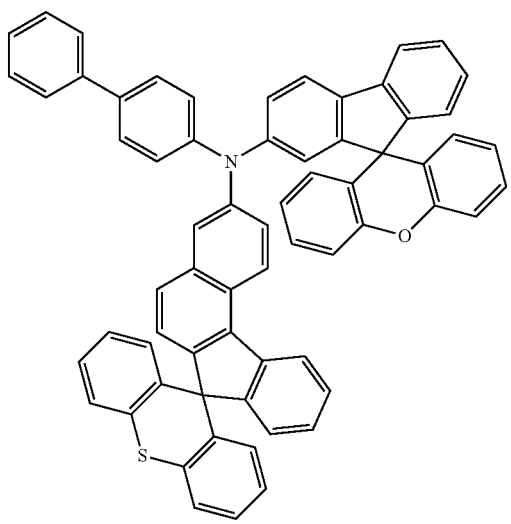

713
-continued
714
-continued
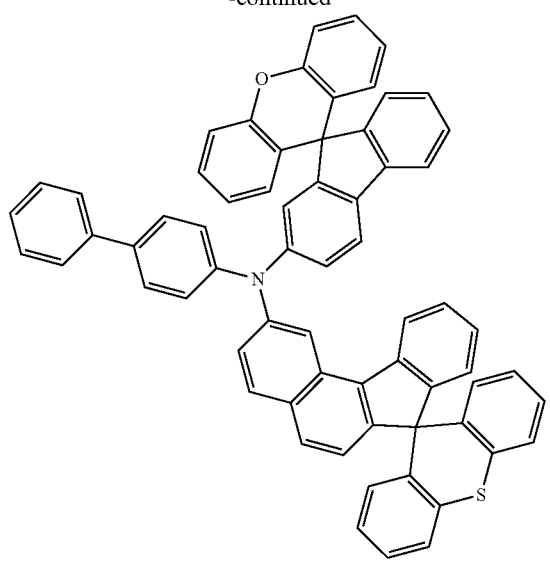
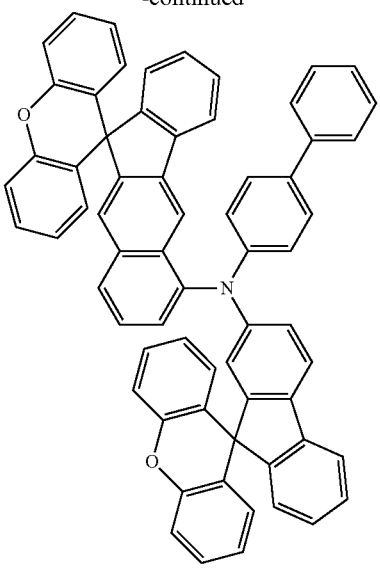
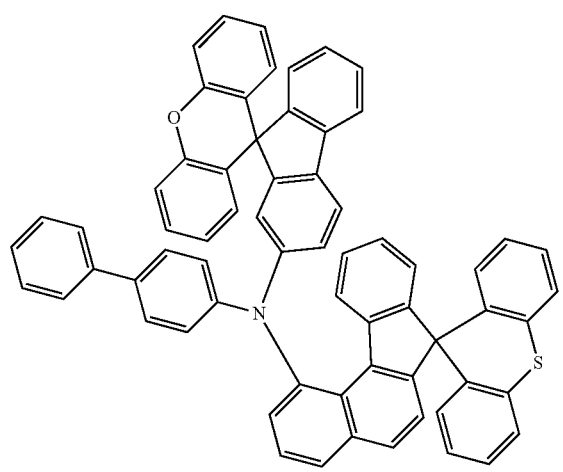
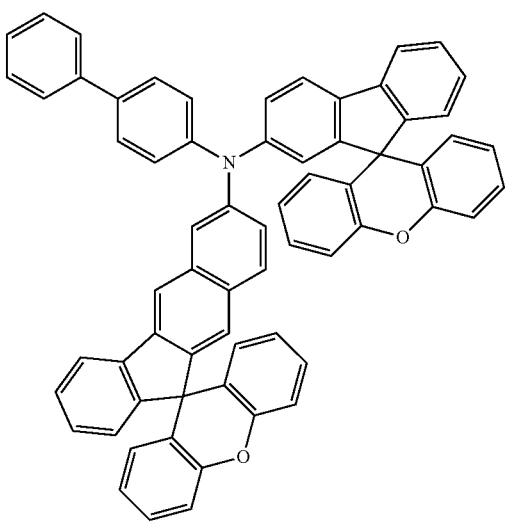
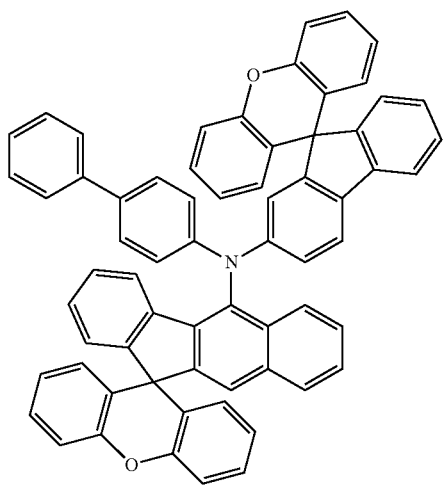
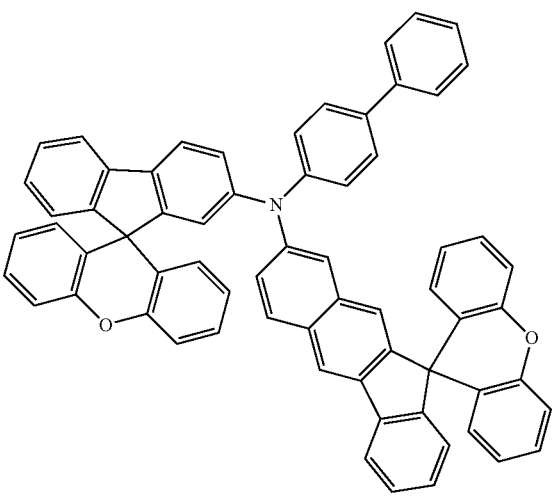

| 715 | 716 |
|---|---|
| 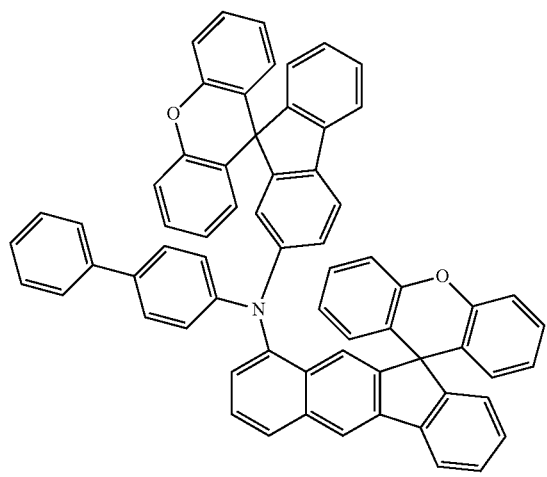 | 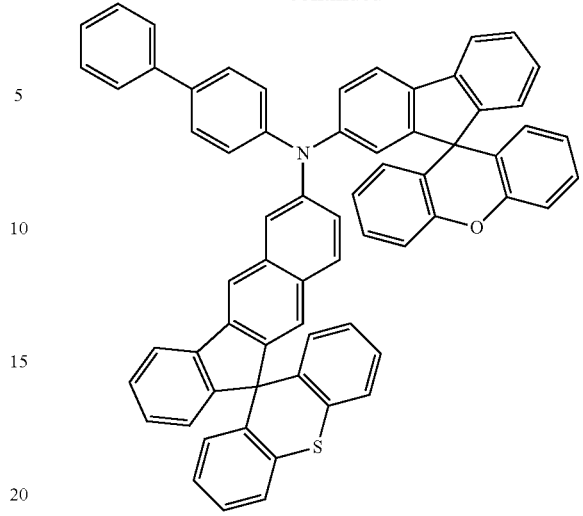 |
| 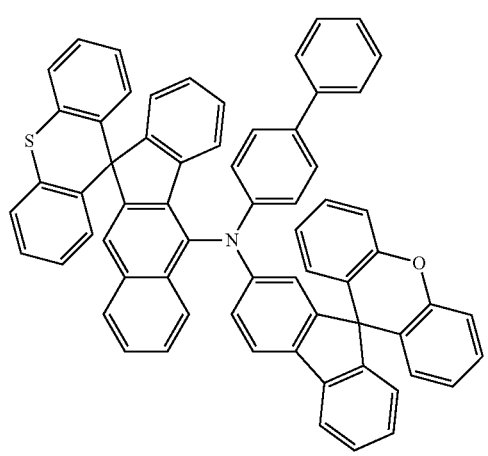 | 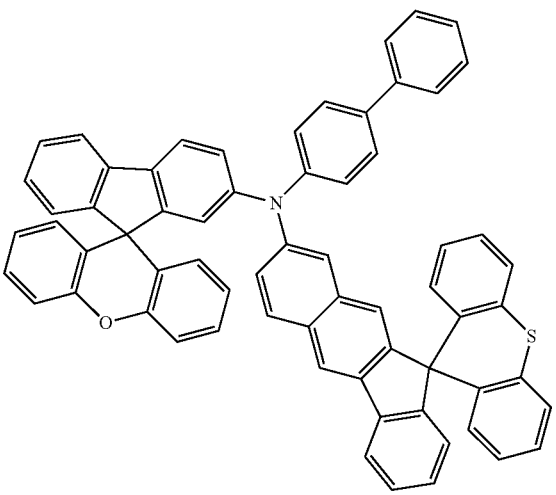 |
| 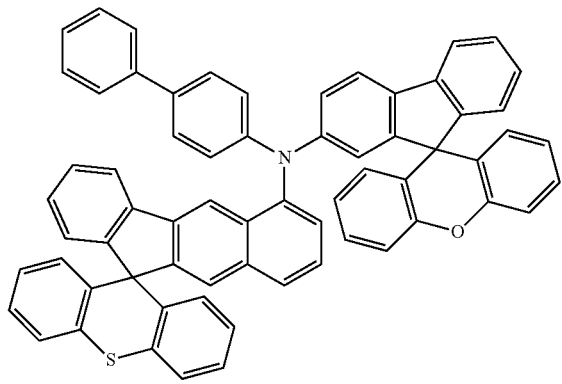 | 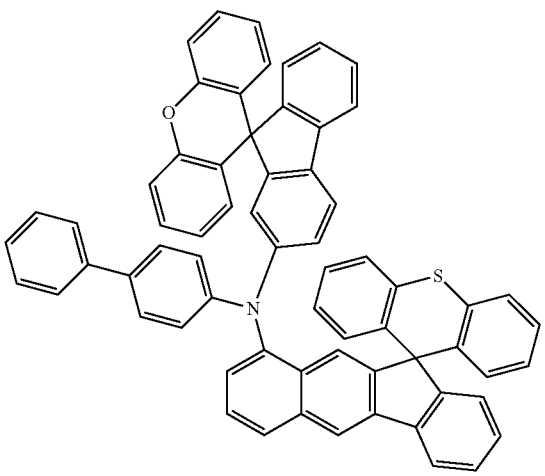 |

717
-continued
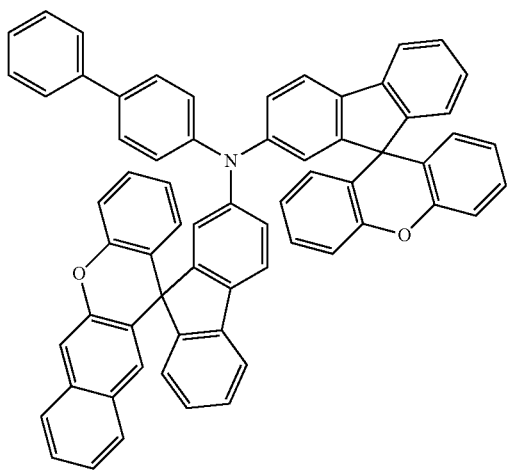
718
-continued
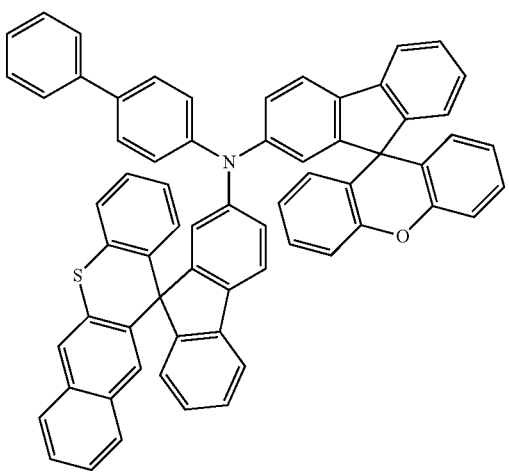
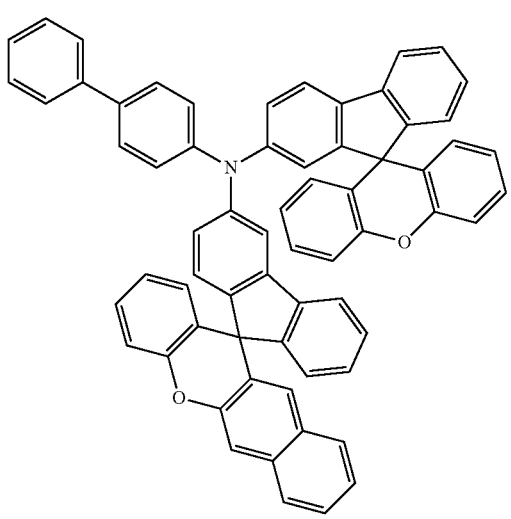
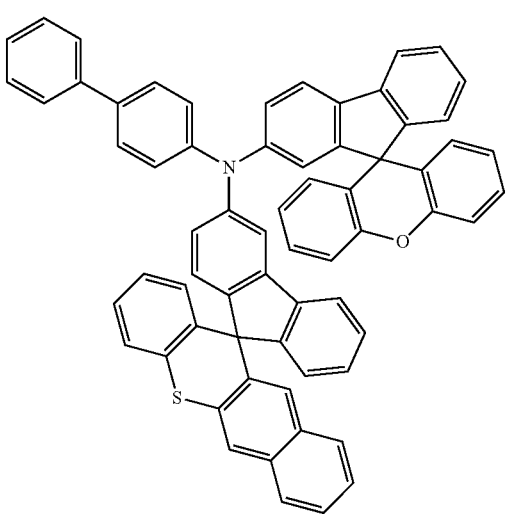
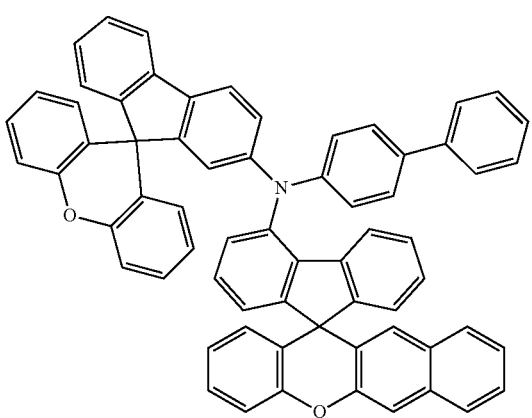
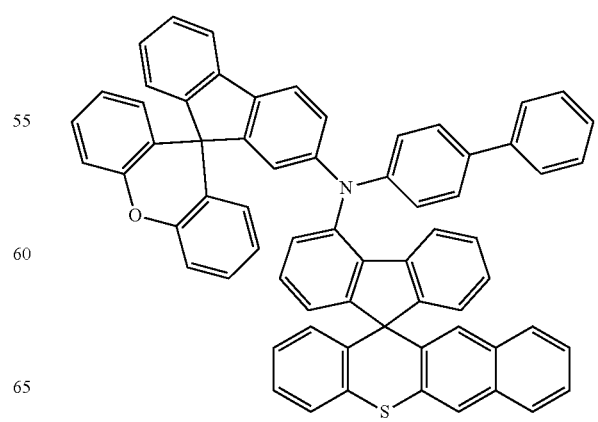

719
-continued
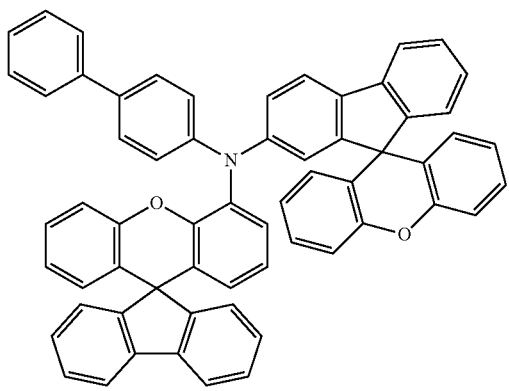
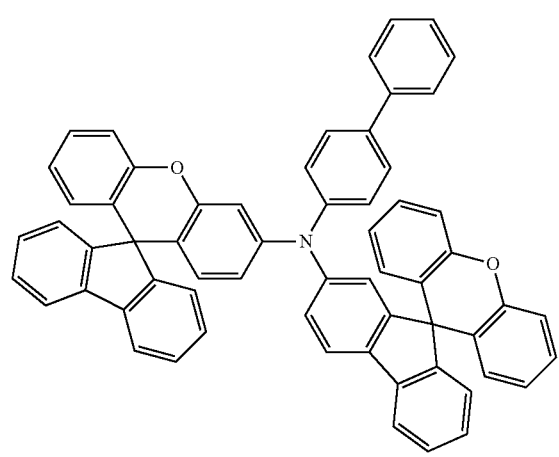
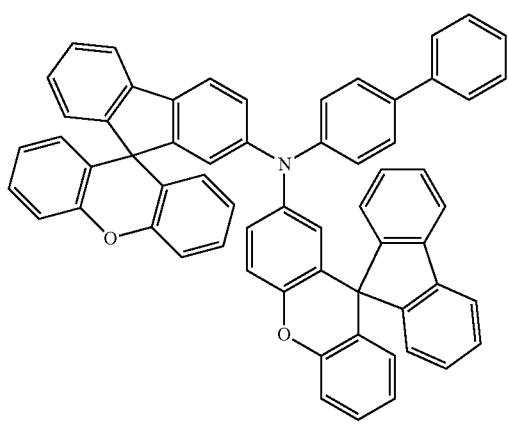
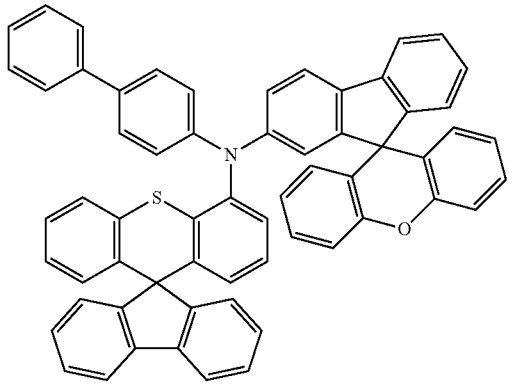
720
-continued
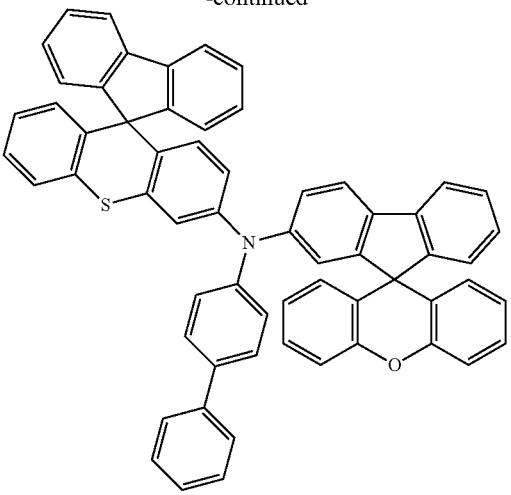
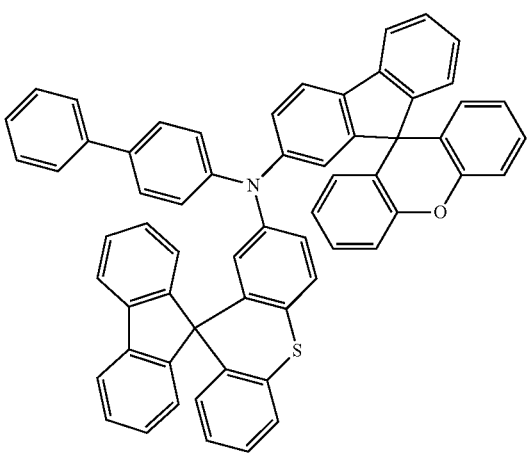
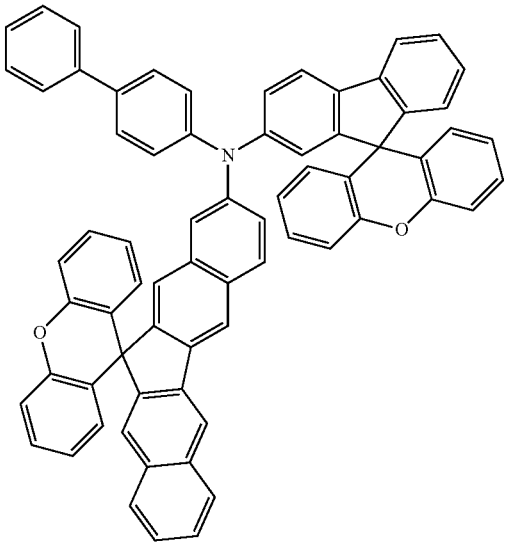

721
-continued
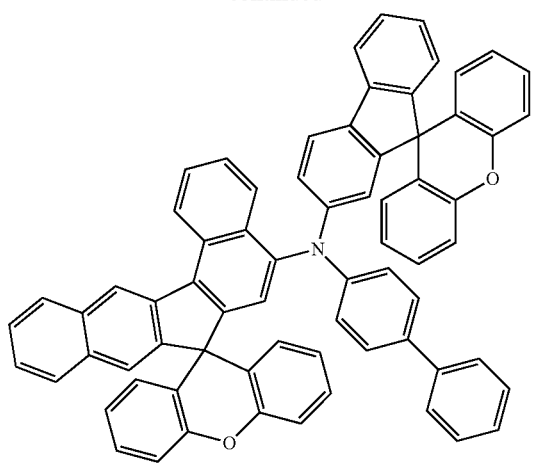
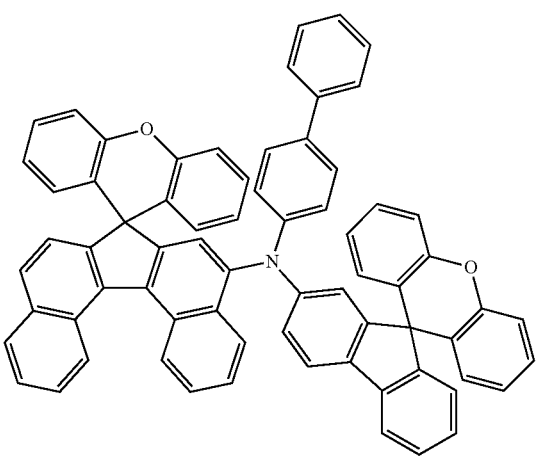
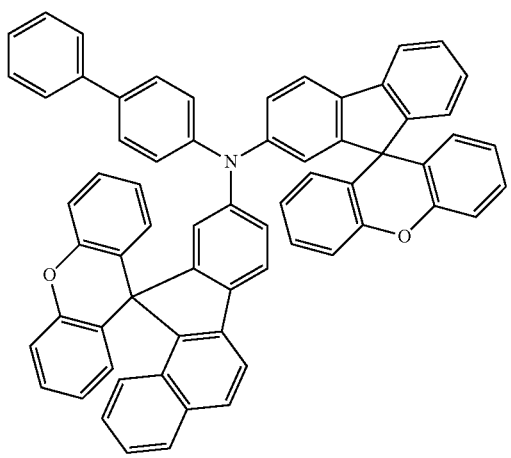
722
-continued
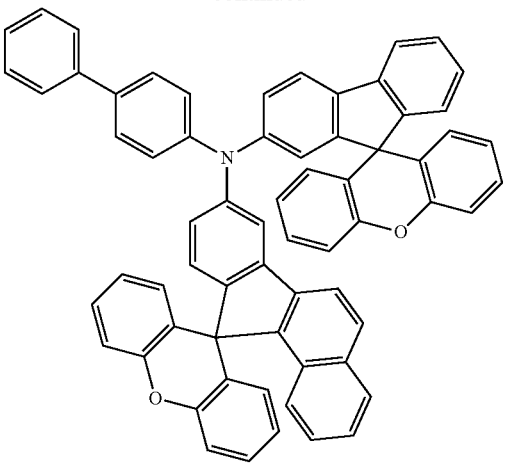
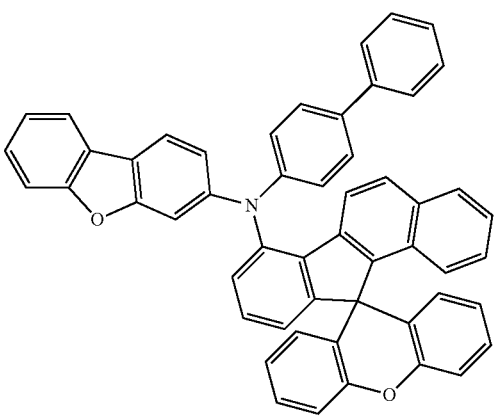
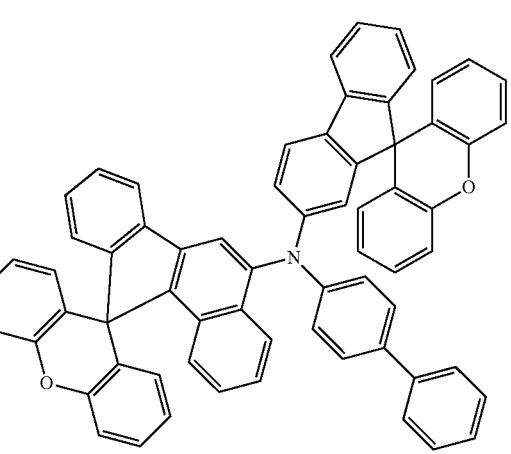

723
-continued
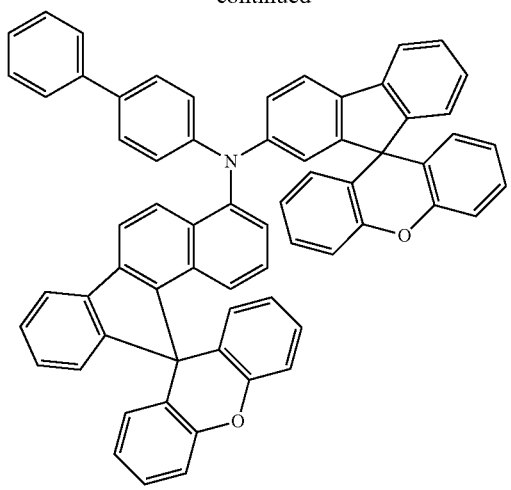
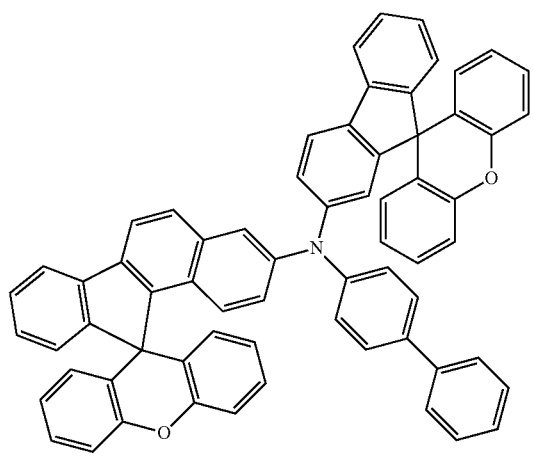
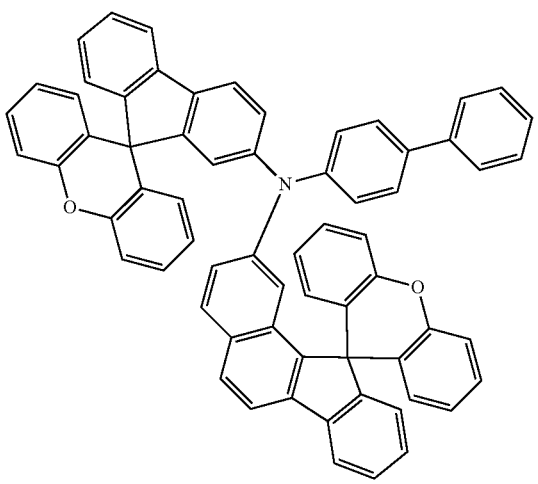
724
-continued
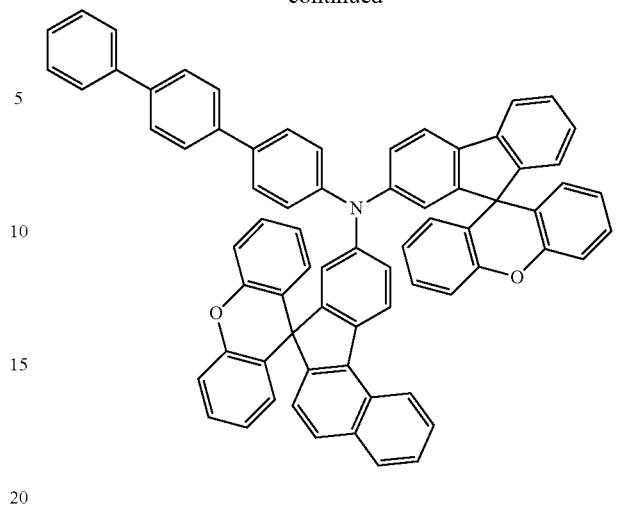
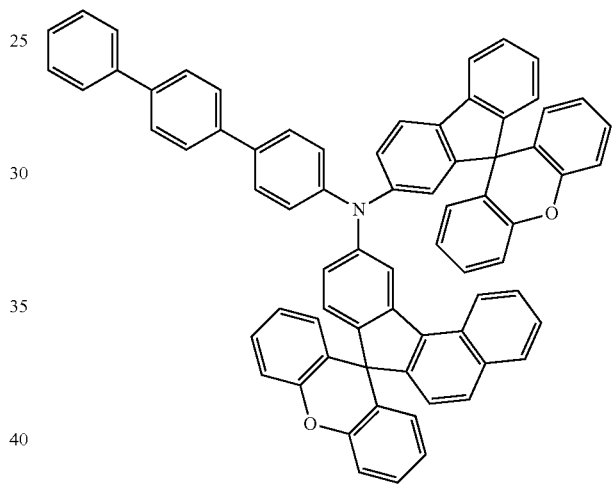
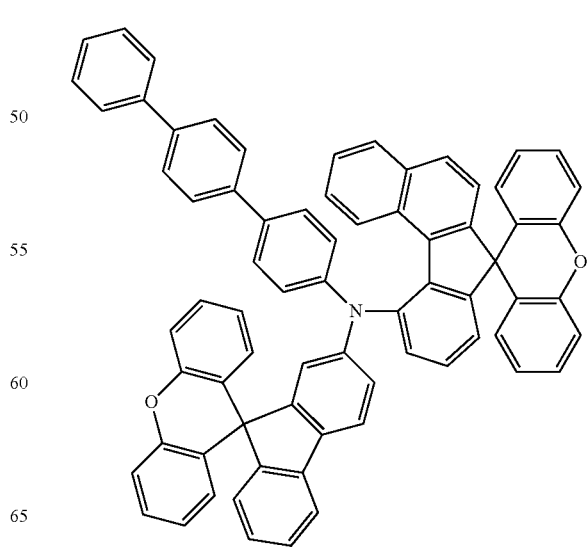

725
-continued
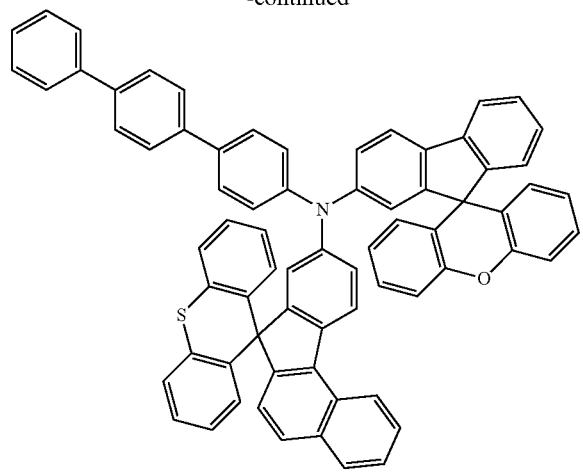
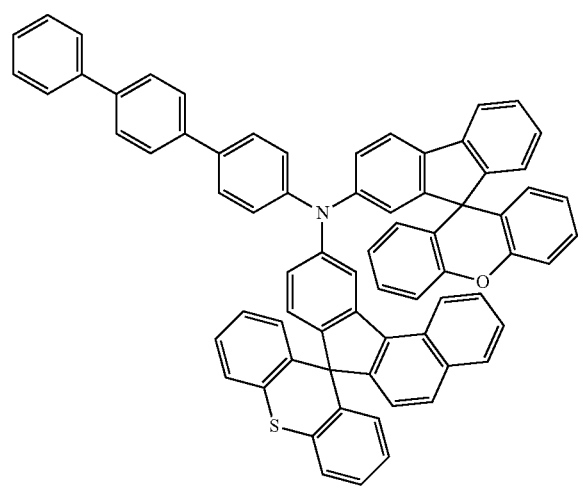
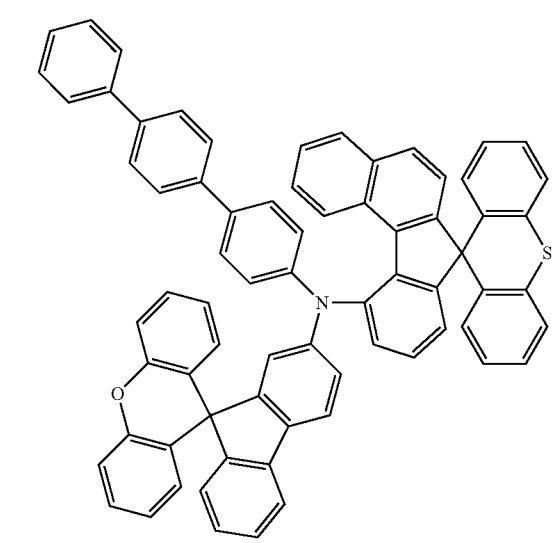
726
-continued
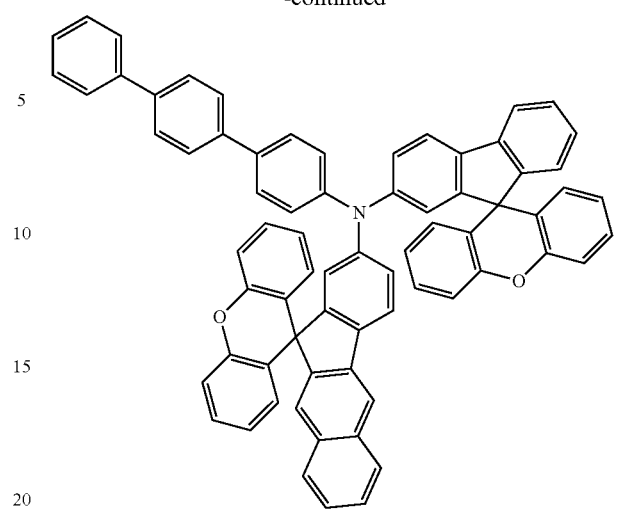
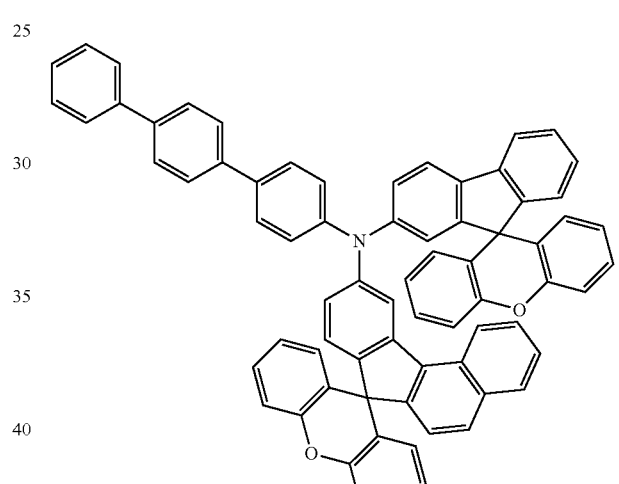
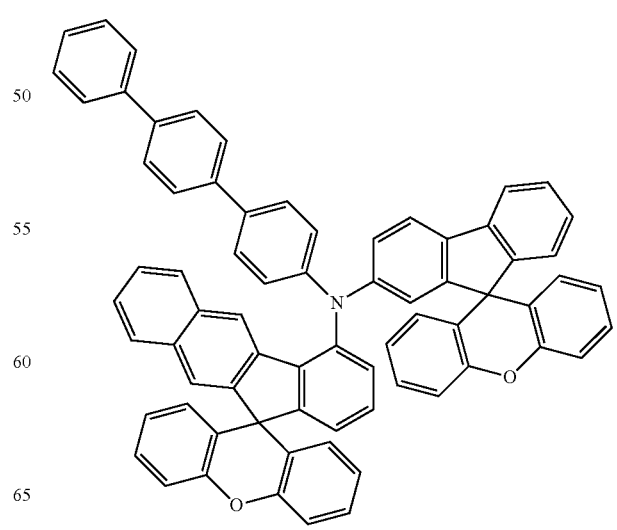

727
-continued
728
-continued
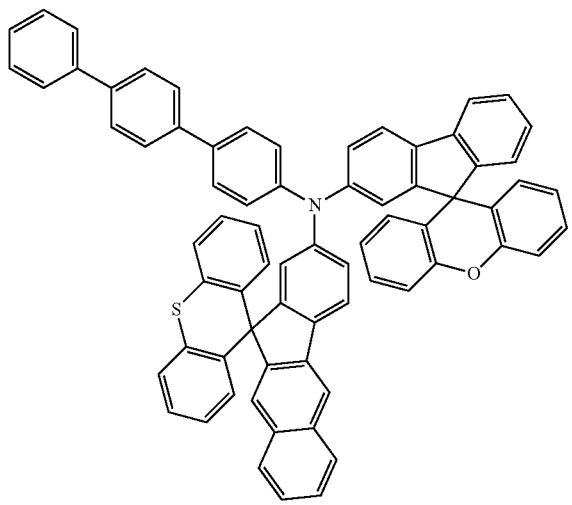
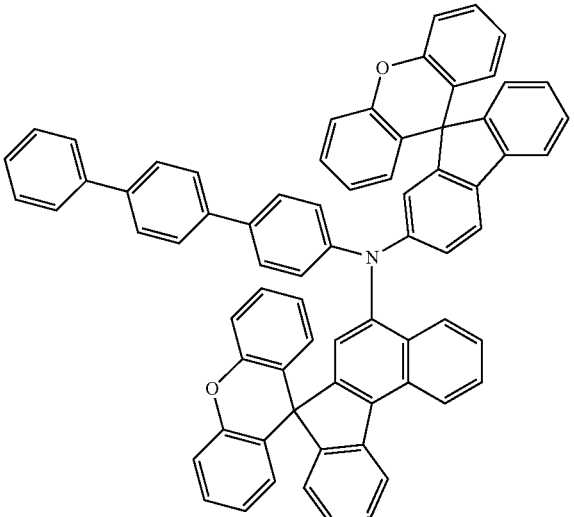
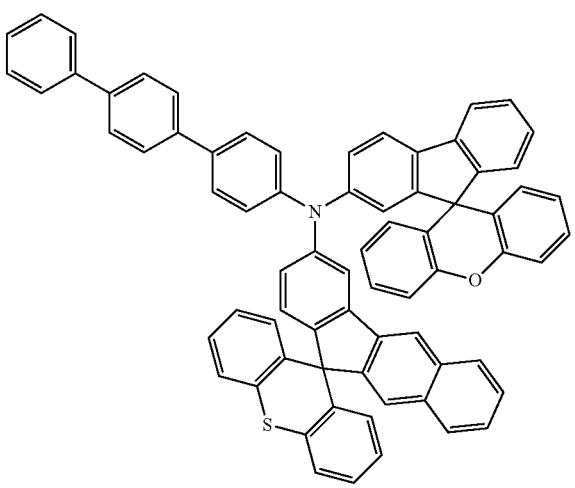
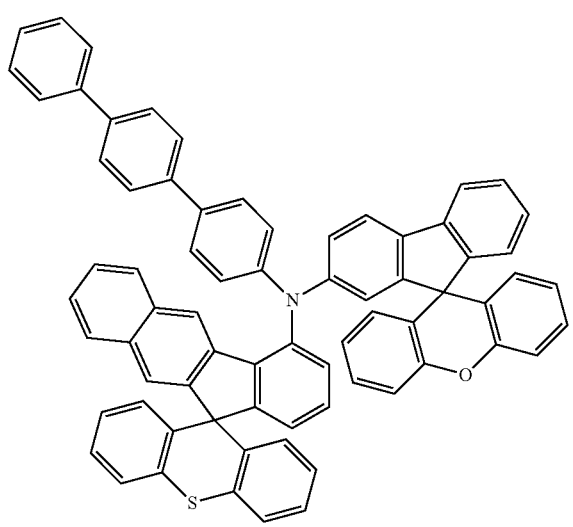
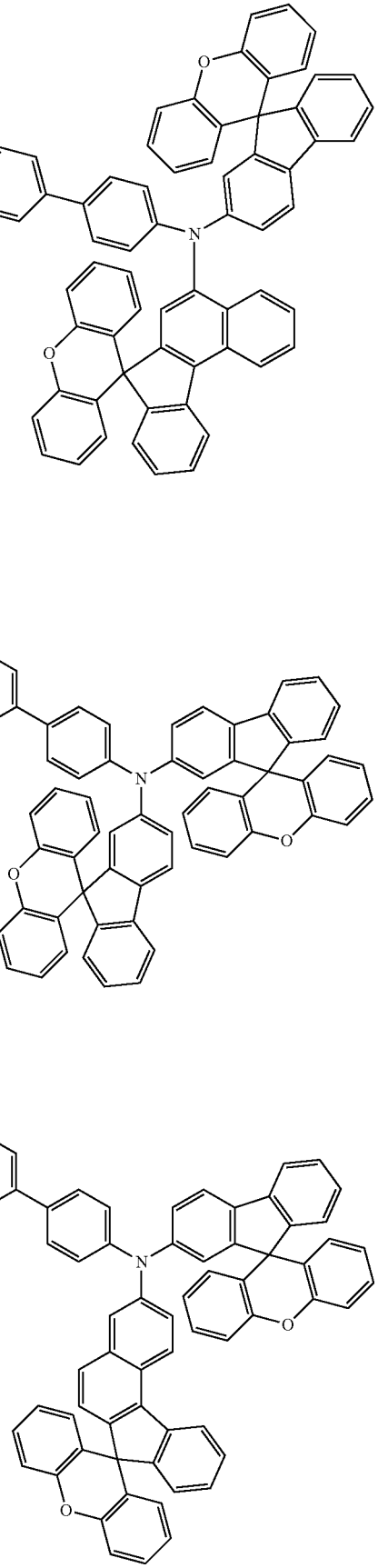

729
-continued
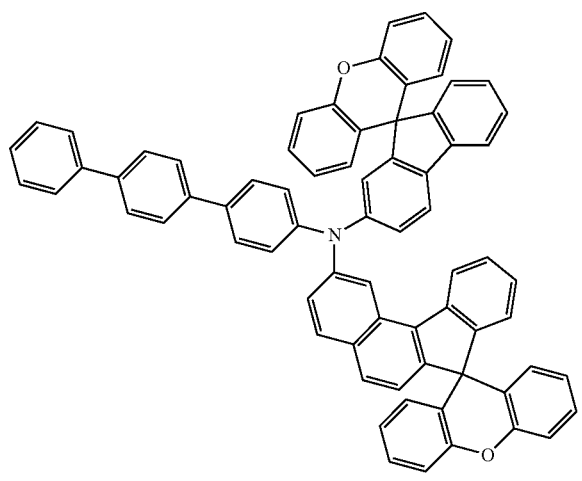
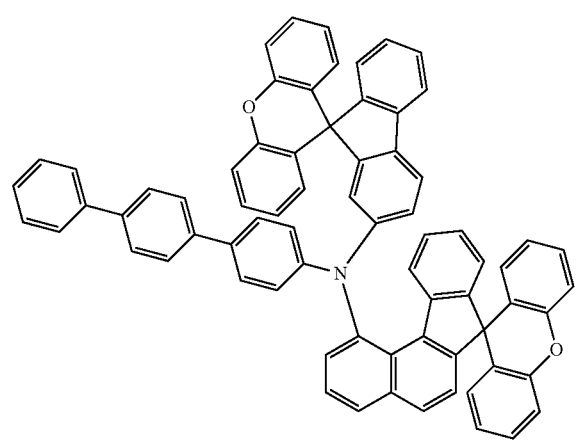
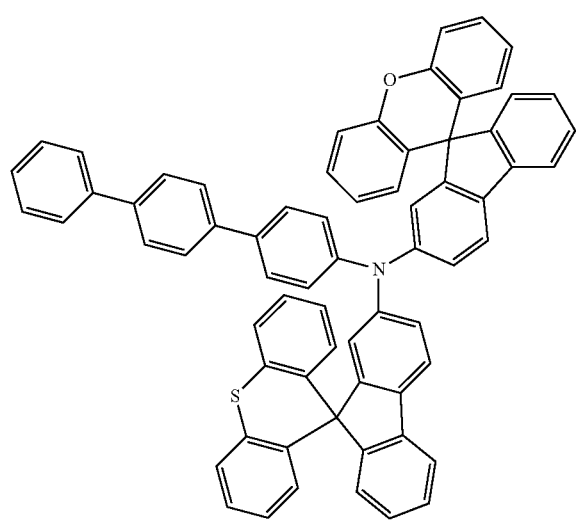
730
-continued
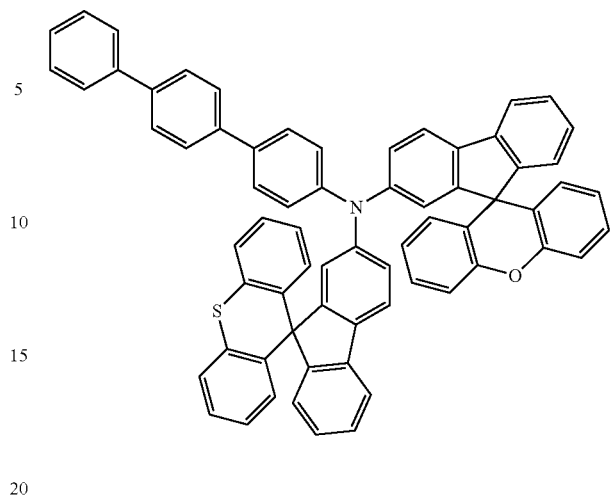
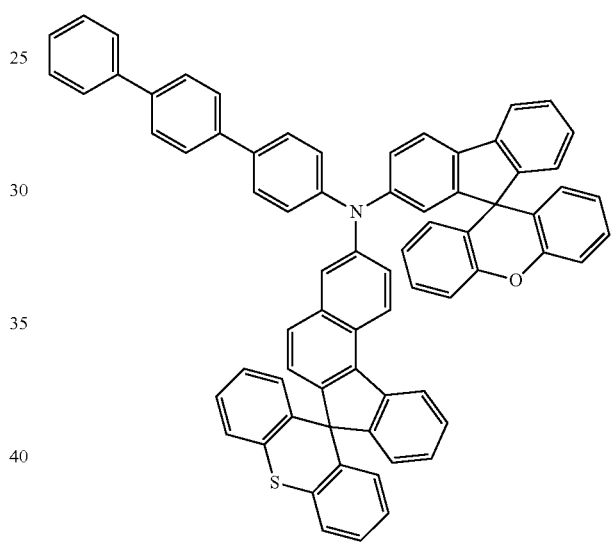
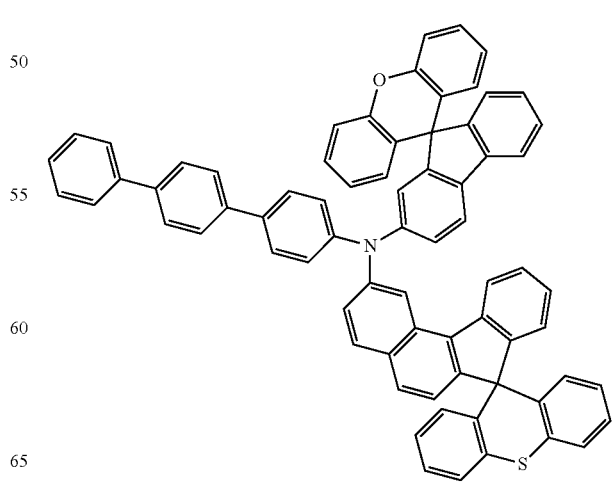

731
-continued
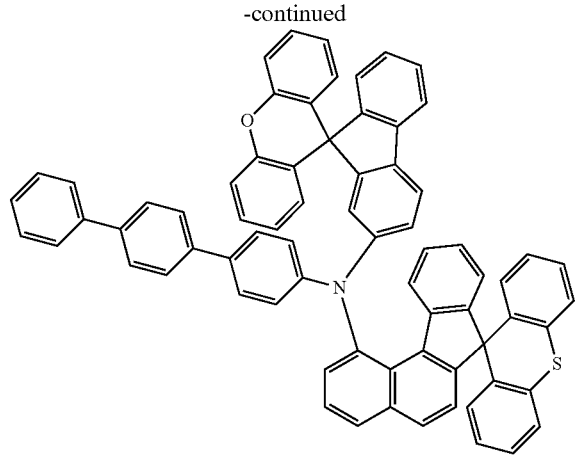
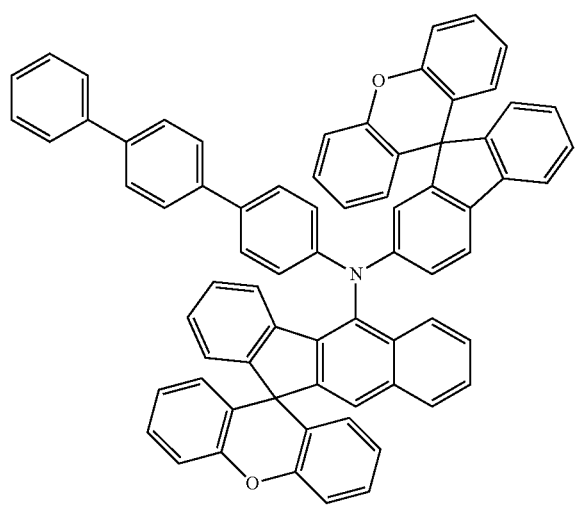
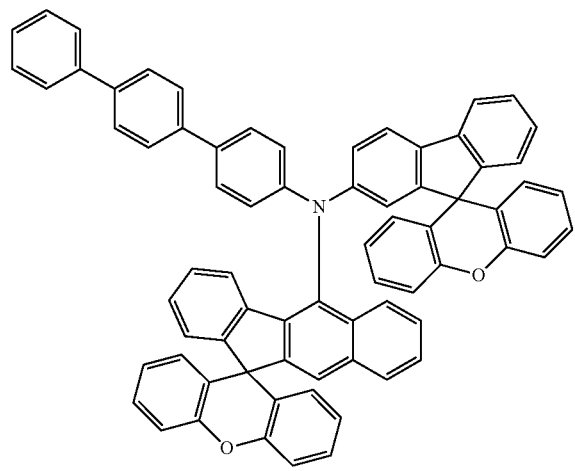
732
-continued
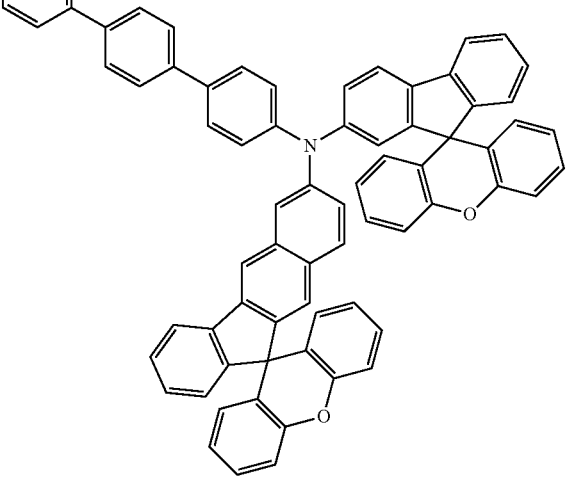
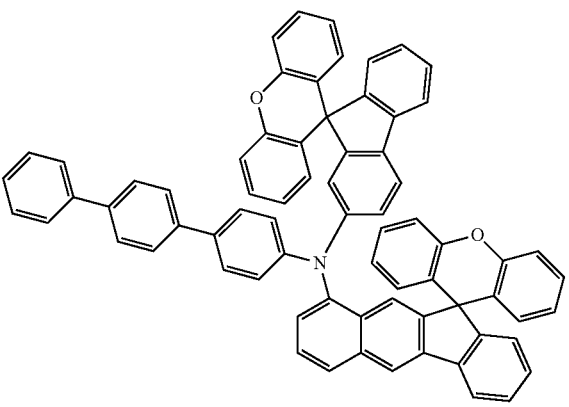

733
-continued
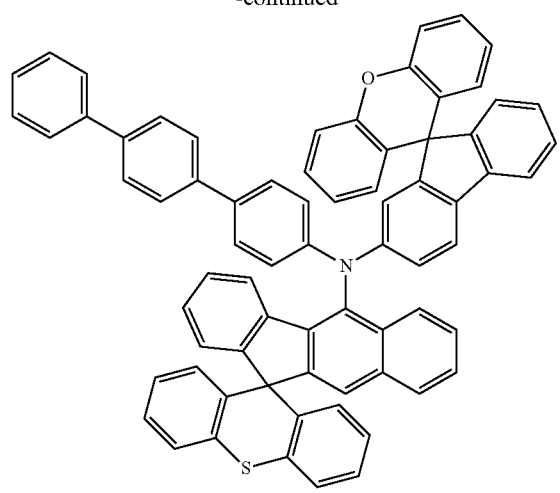
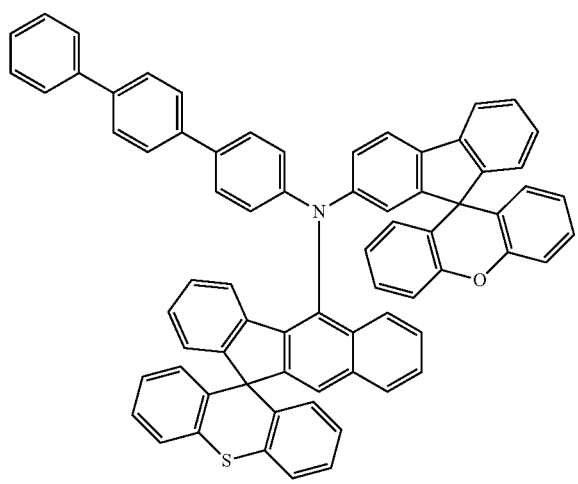
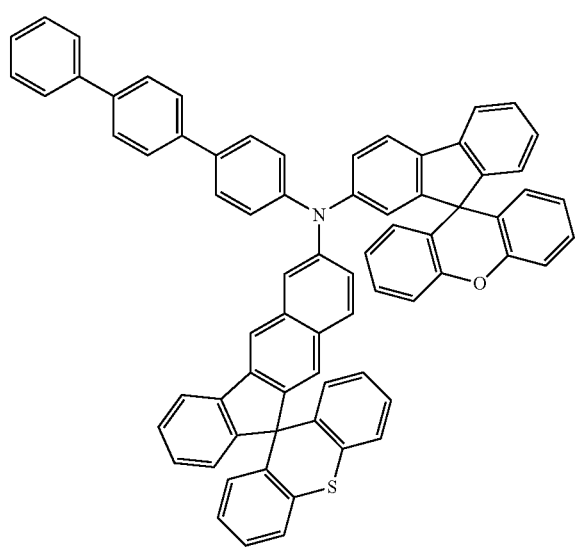
734
-continued
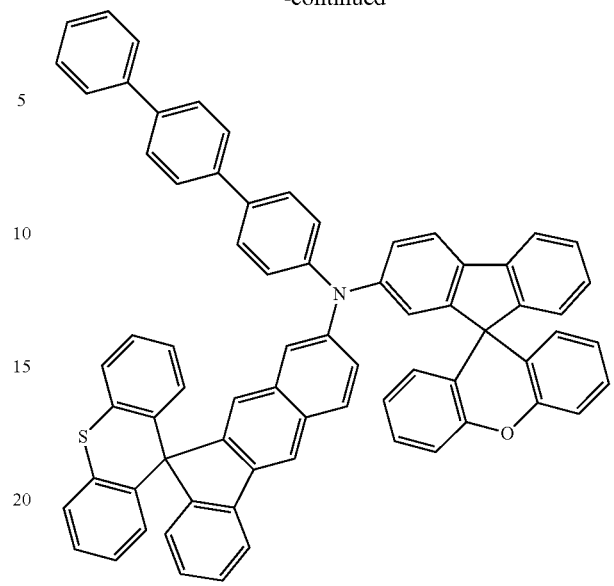
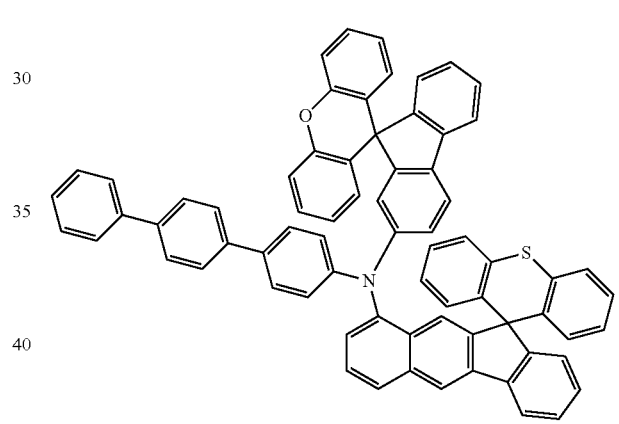
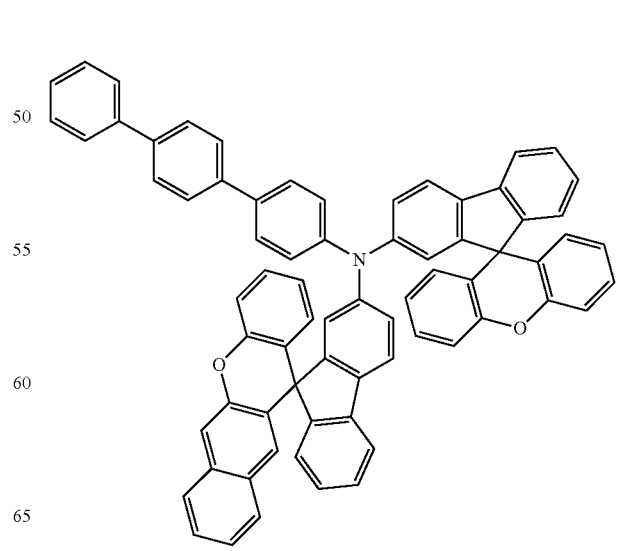

-continued
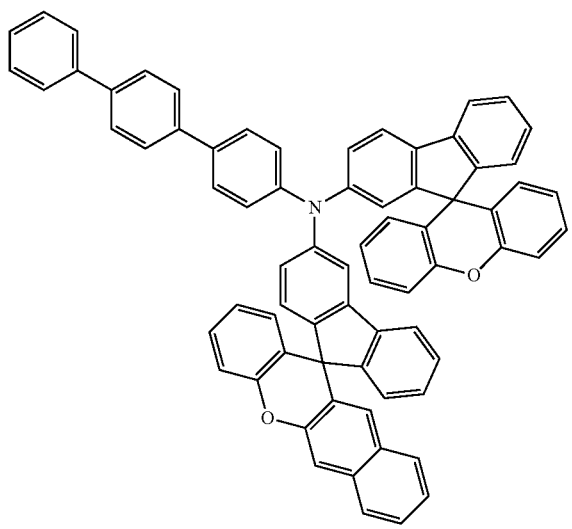
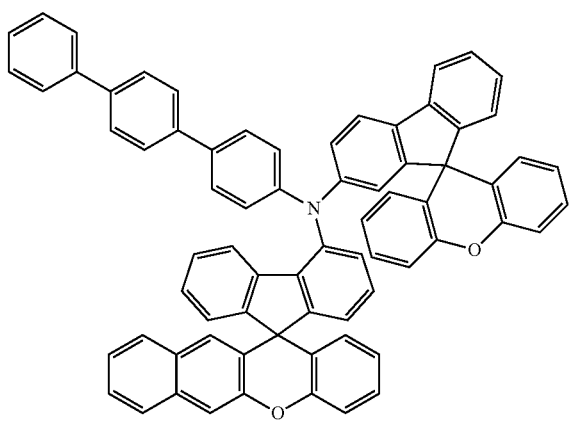
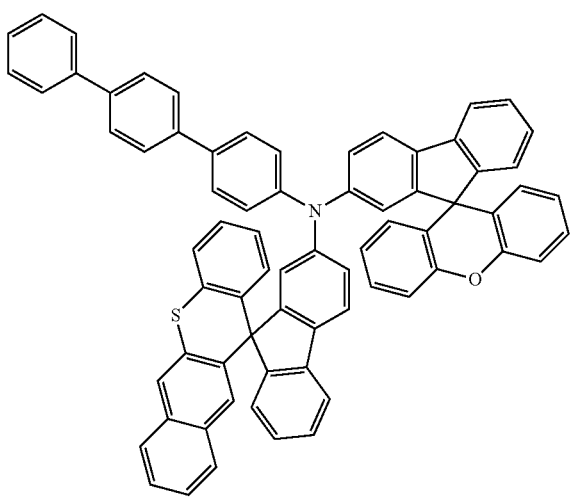
-continued
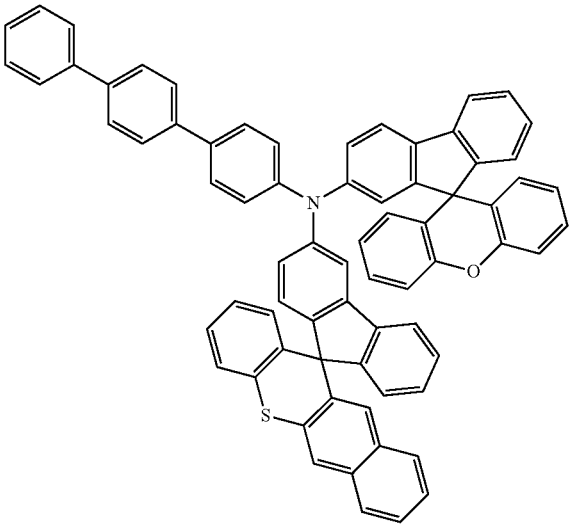
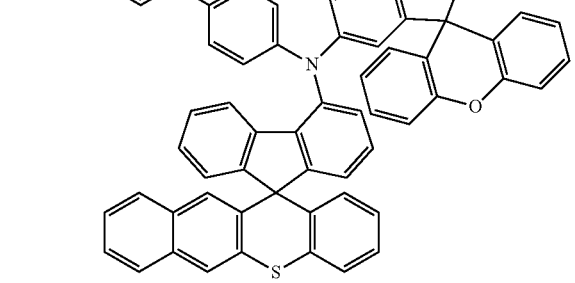
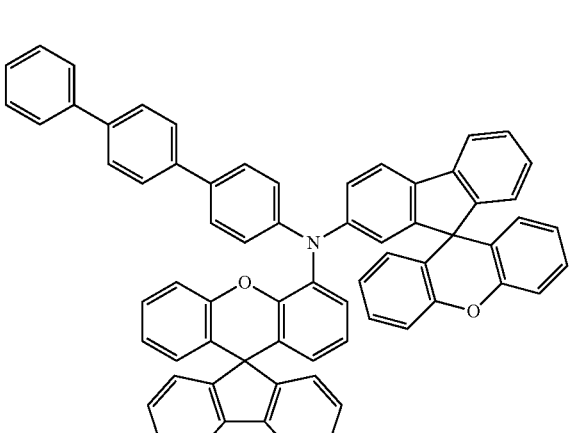

737
-continued
738
-continued
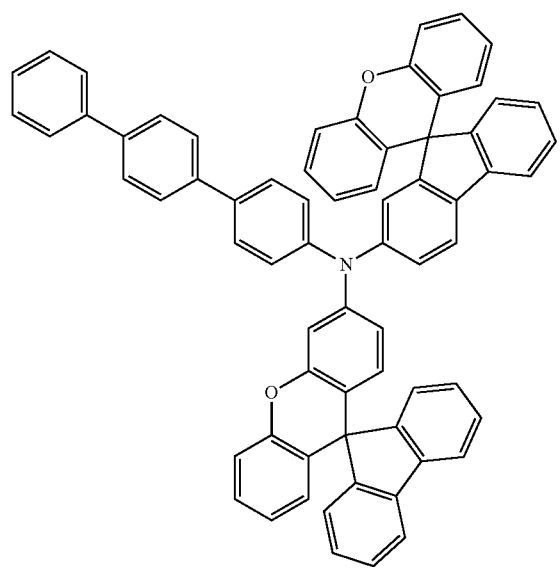
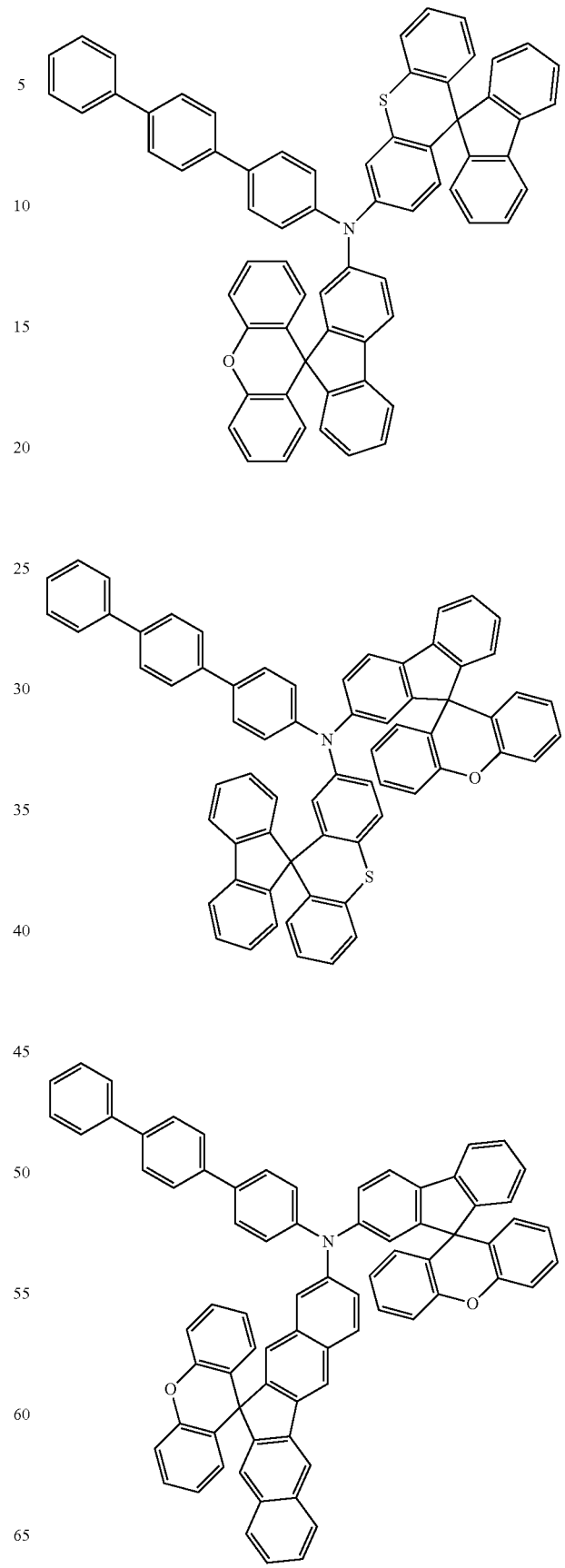

739
-continued
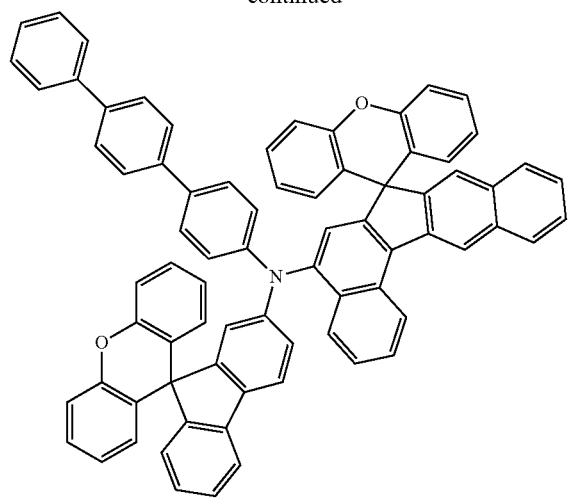
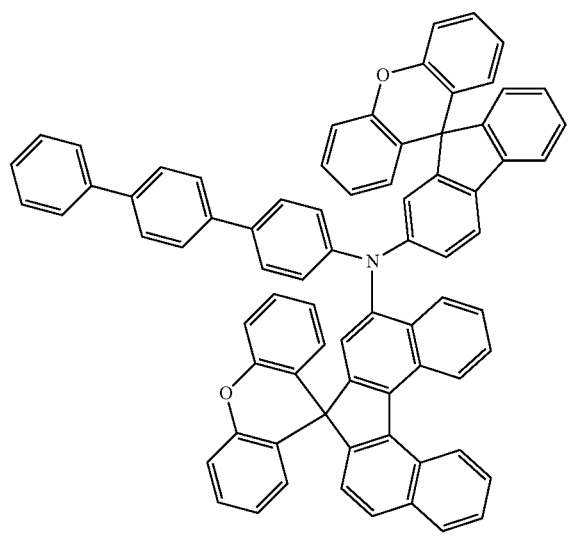
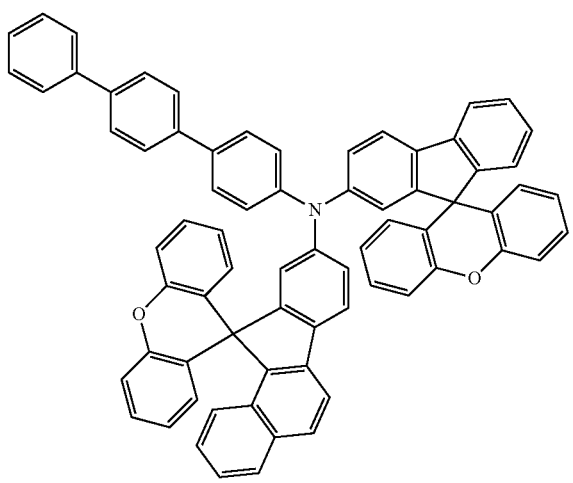
740
-continued
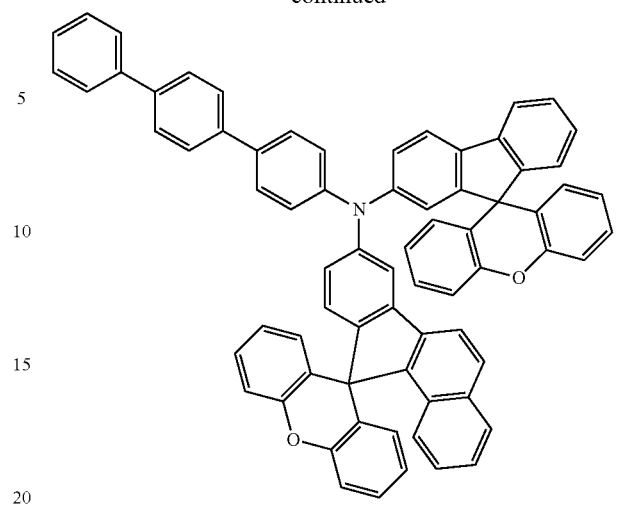
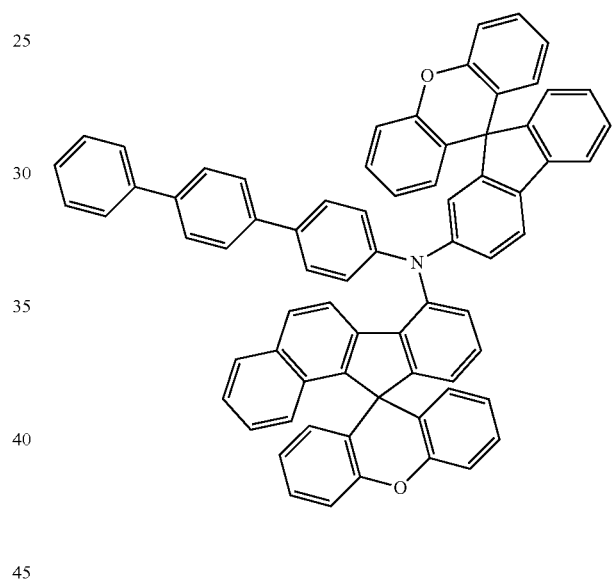
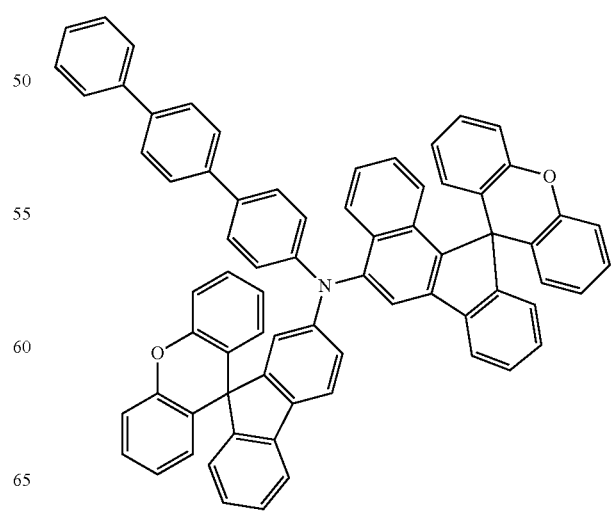

741
-continued
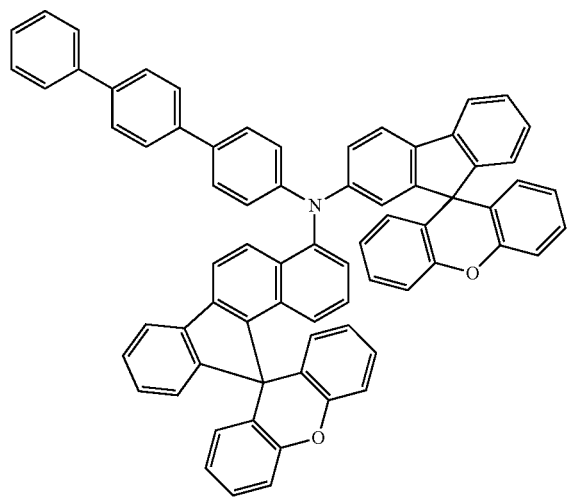
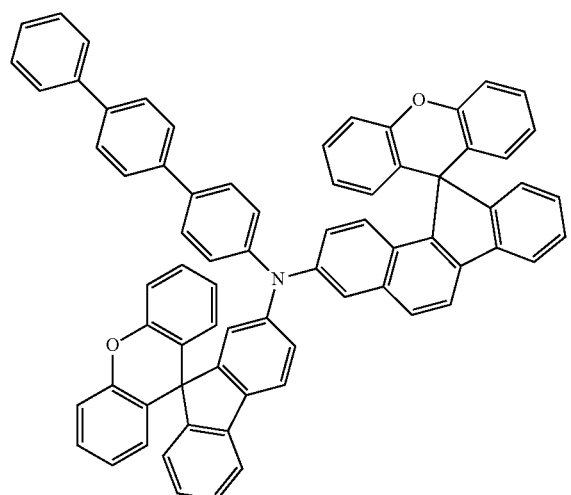
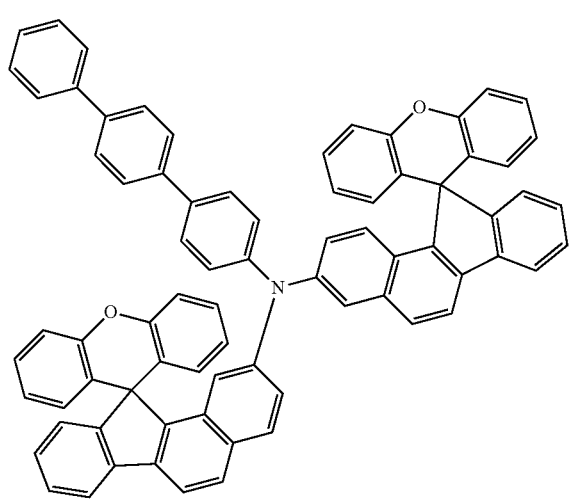
742
-continued
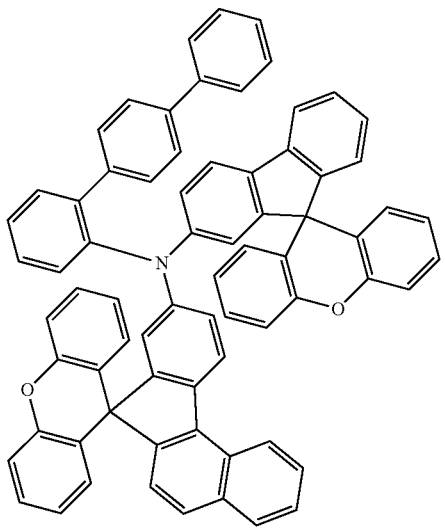
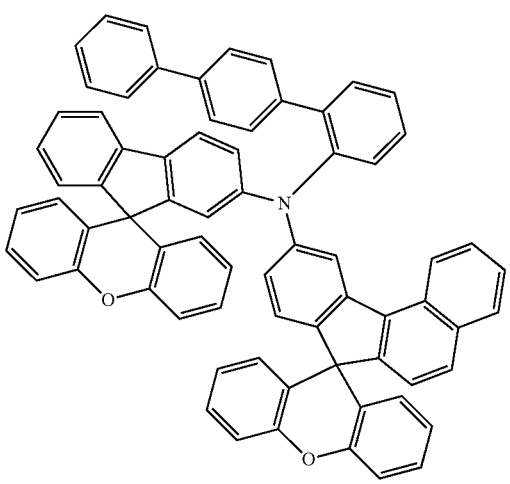
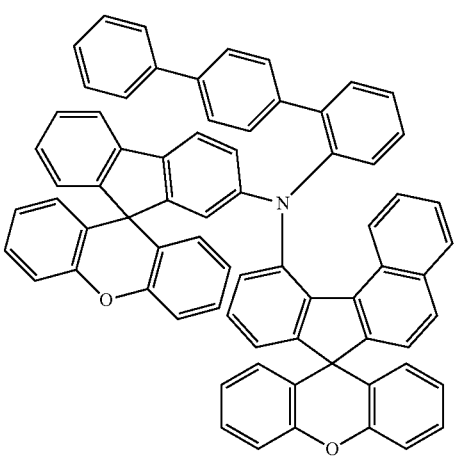

743
-continued
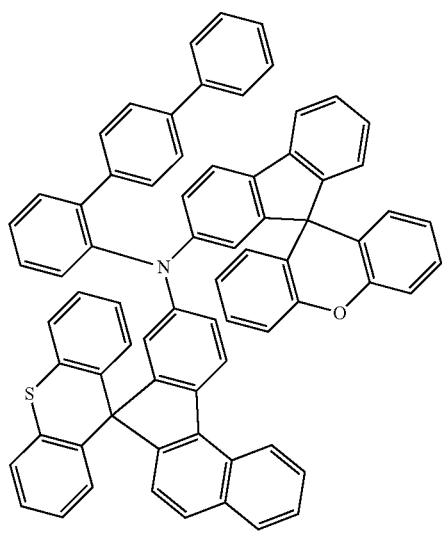
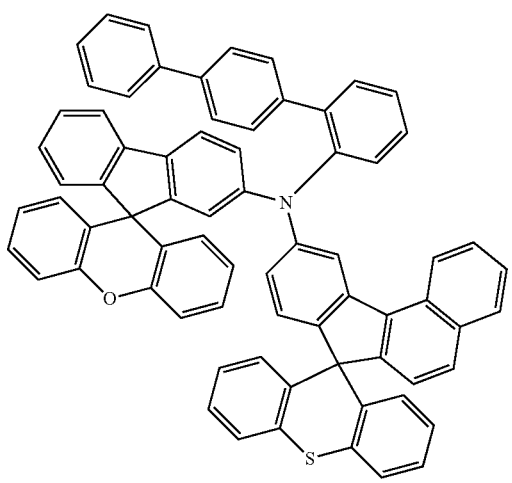
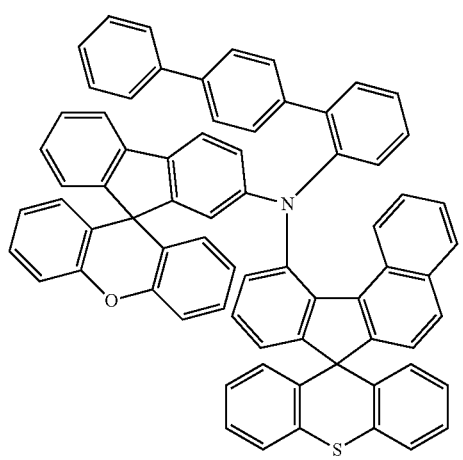
744
-continued
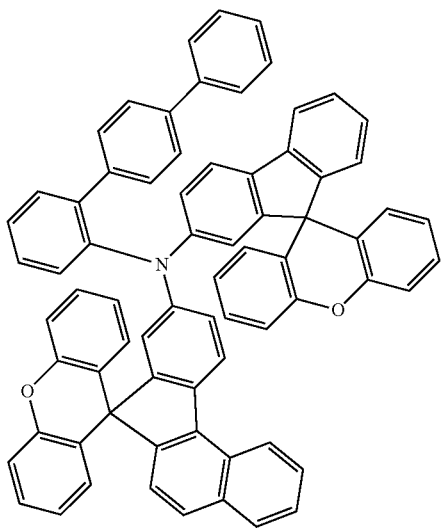
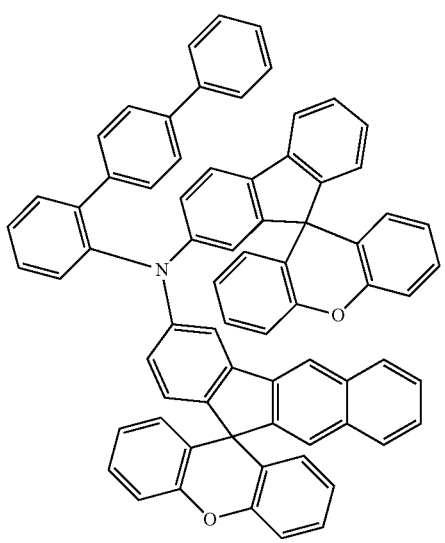
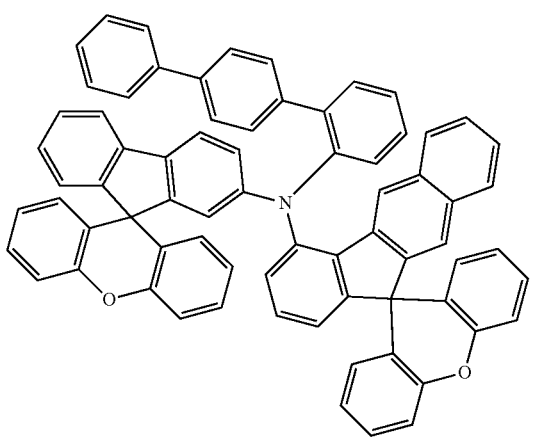

-continued
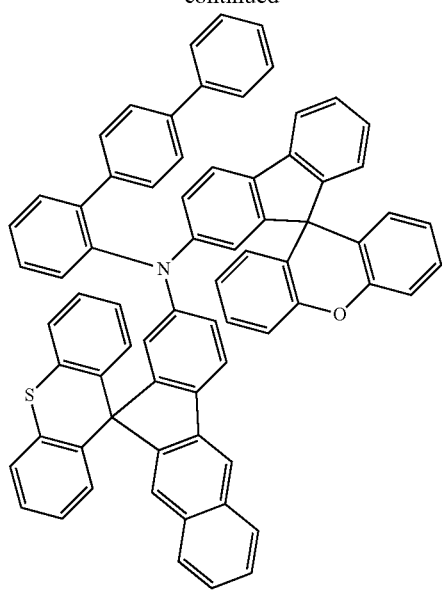
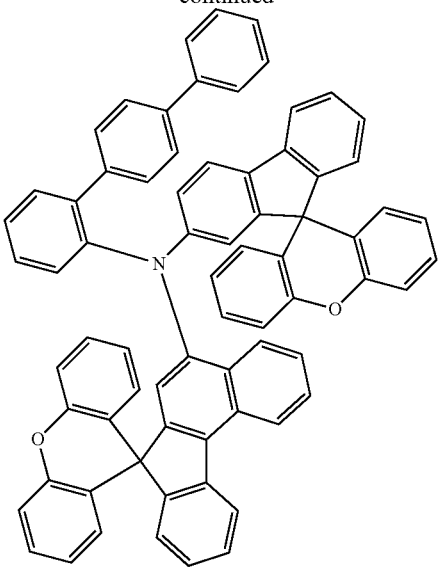
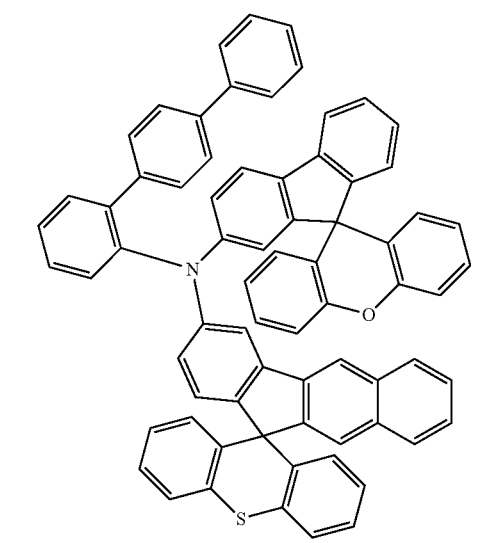
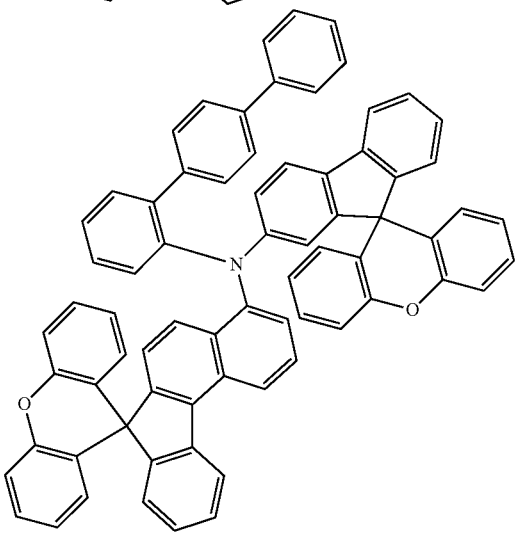
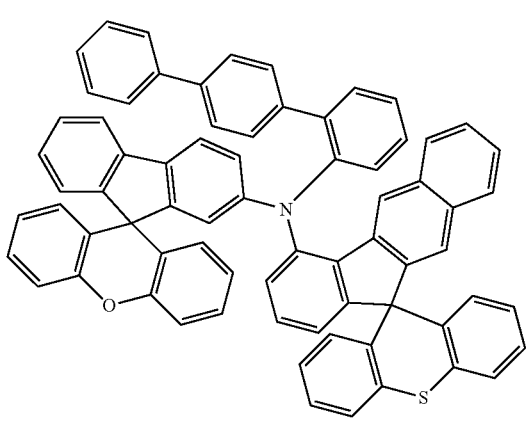

747
-continued
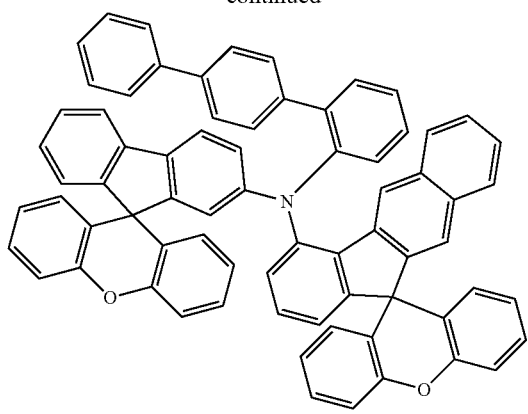
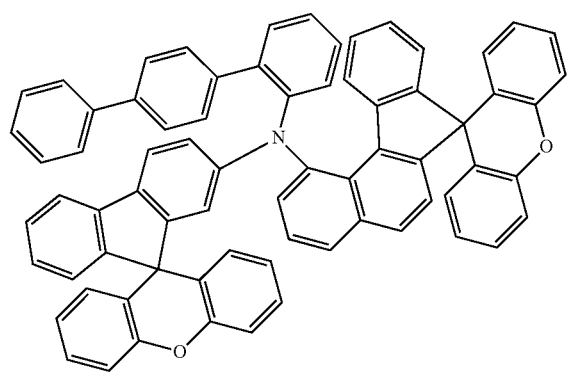
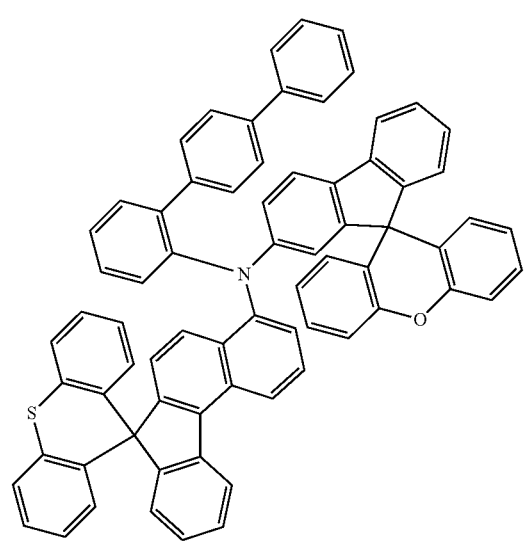
748
-continued
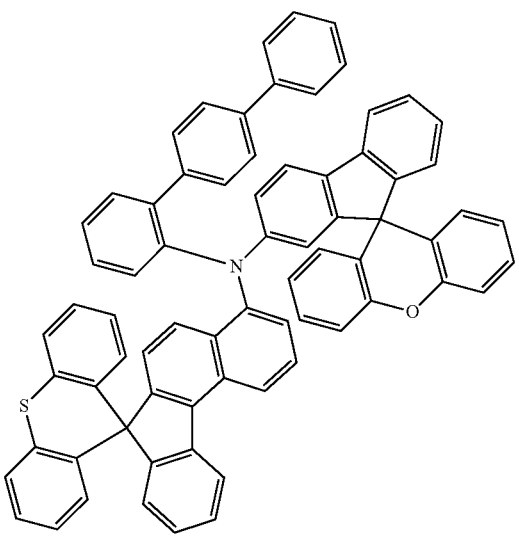
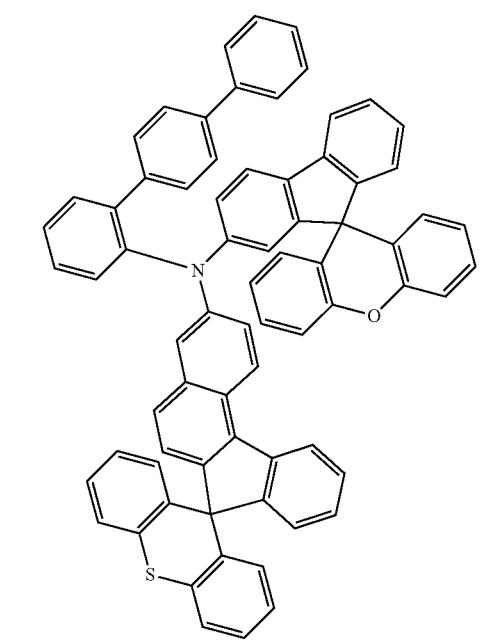
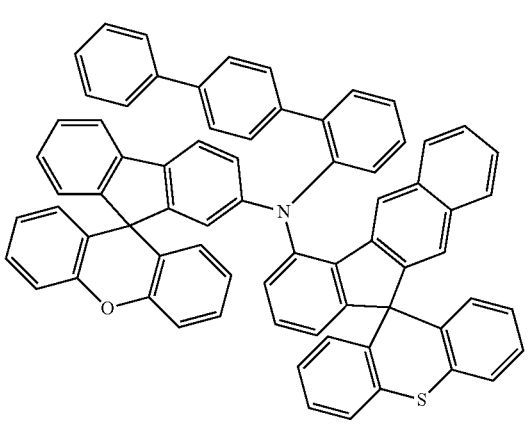

749
-continued
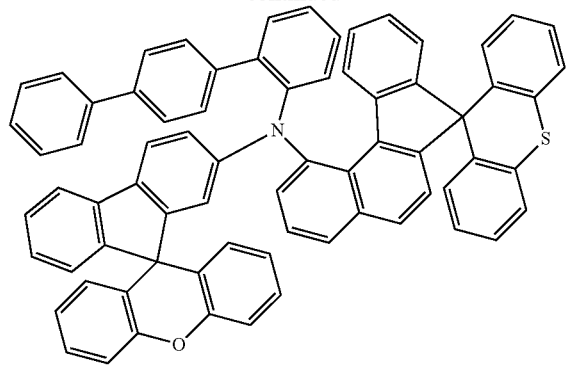
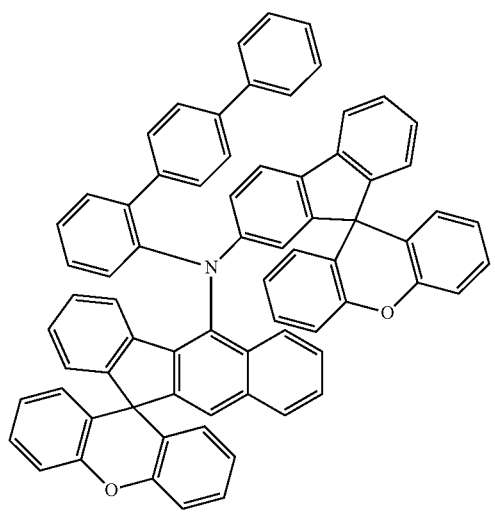
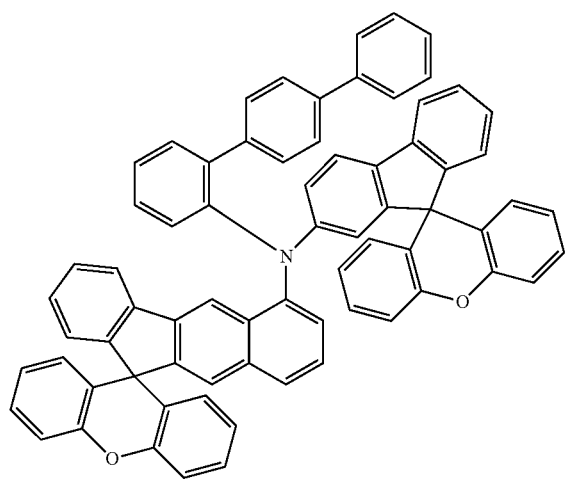
750
-continued
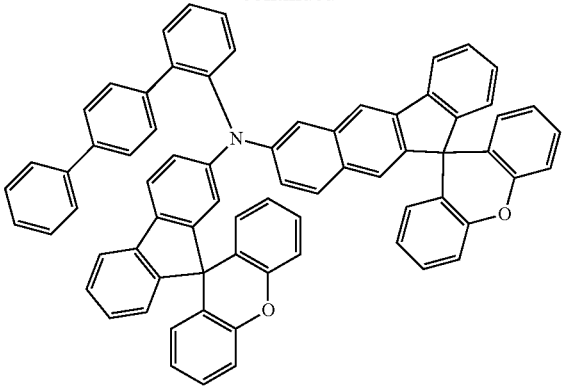
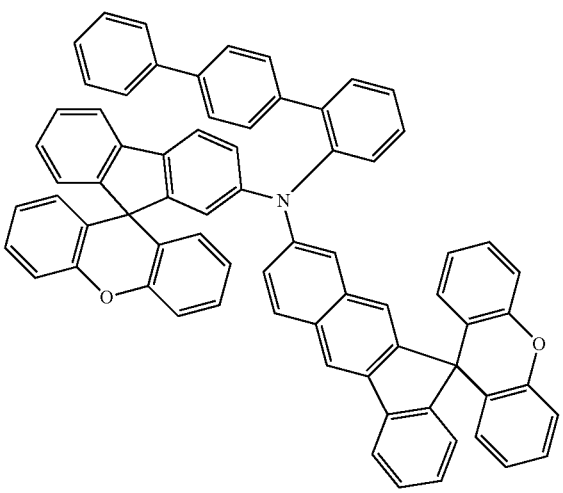
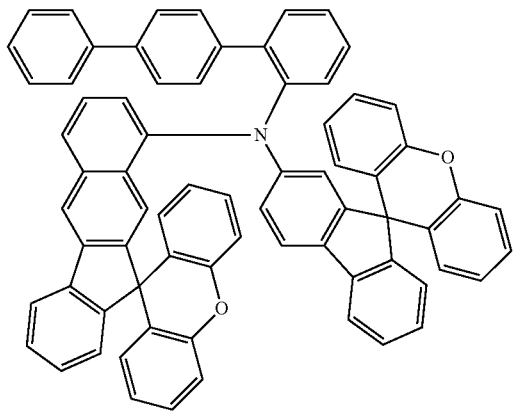

751
-continued
752
-continued
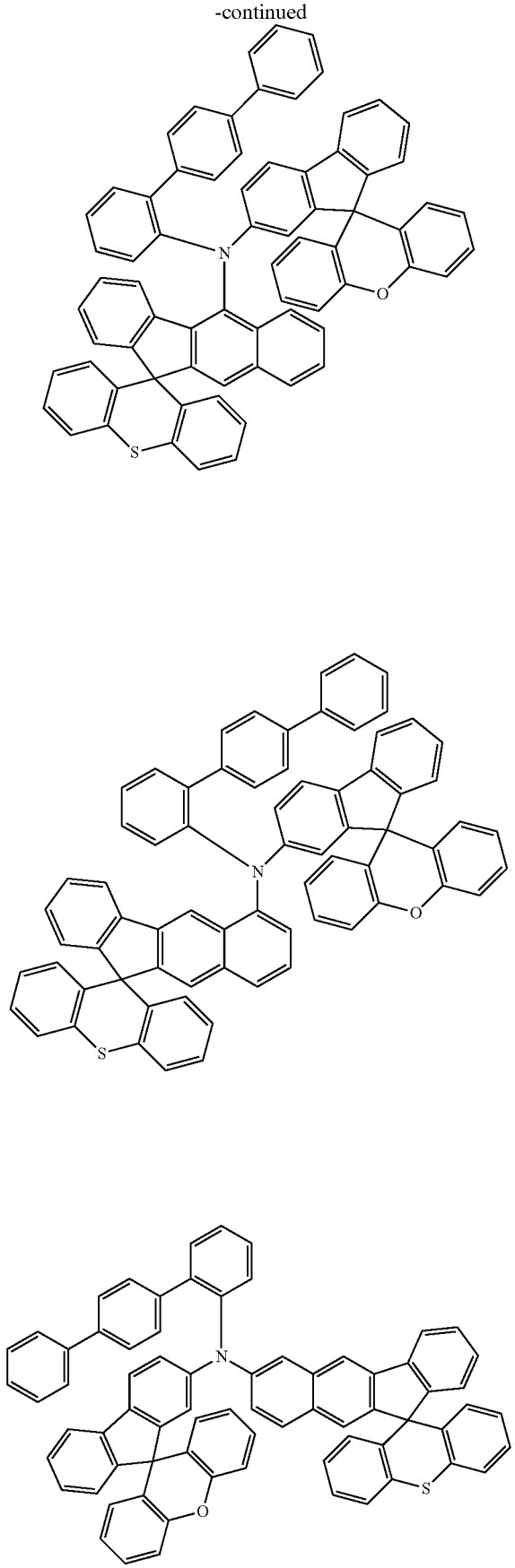
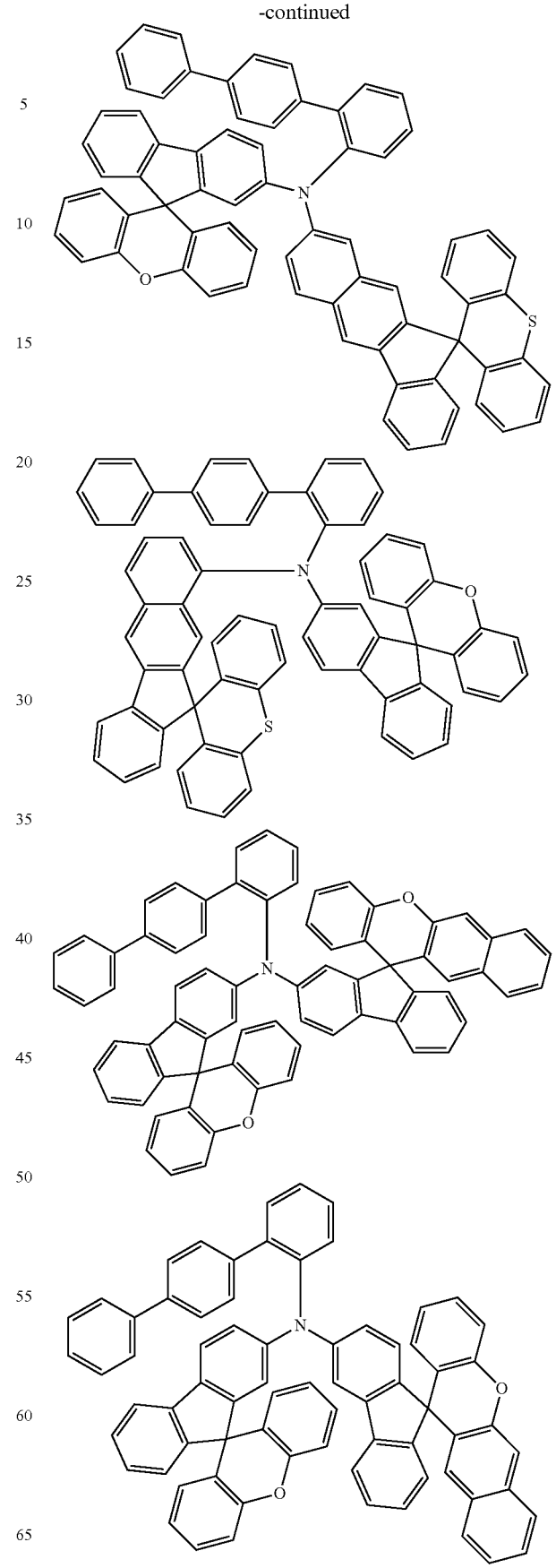

753
-continued
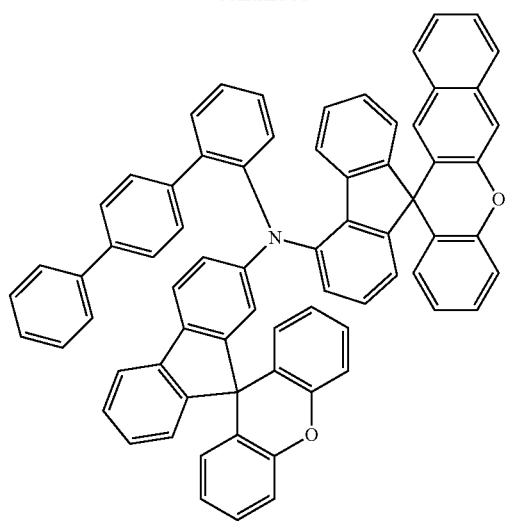
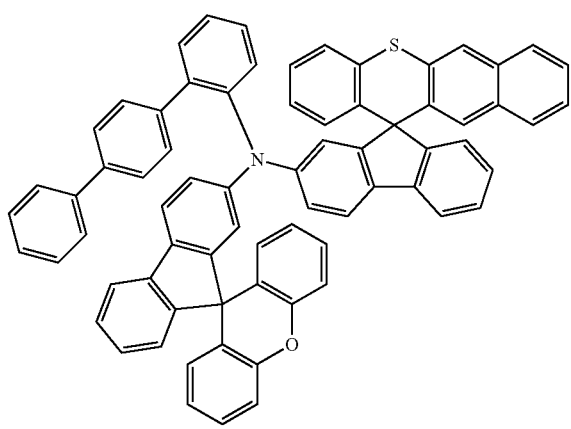
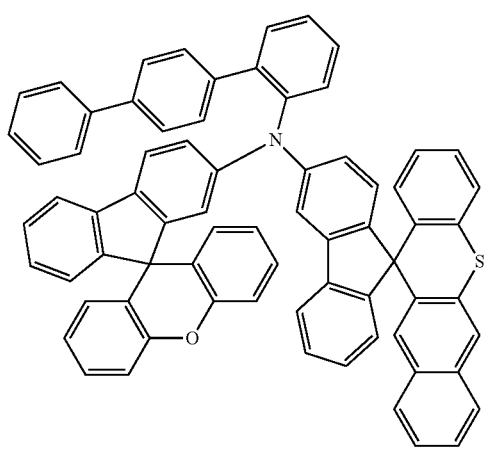
754
-continued
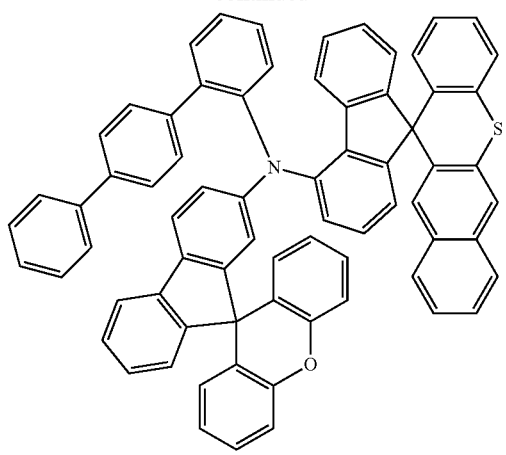
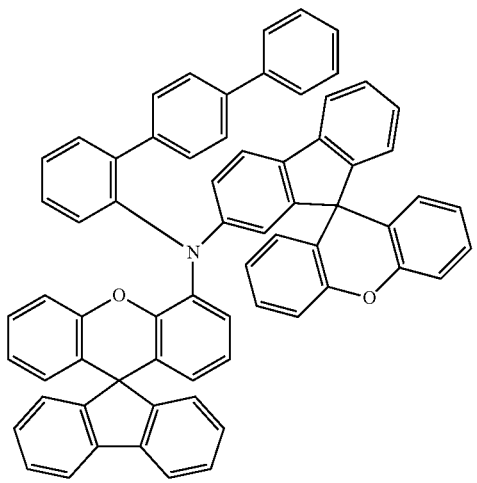
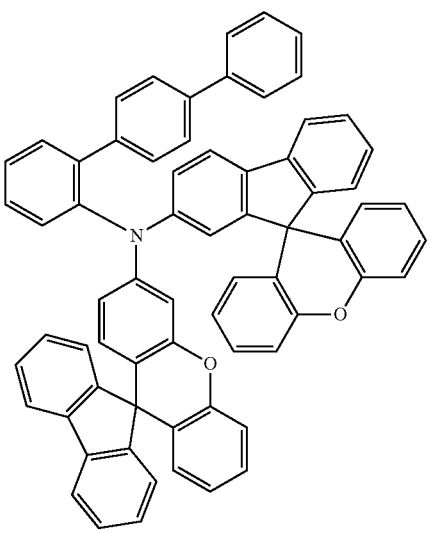

755
-continued
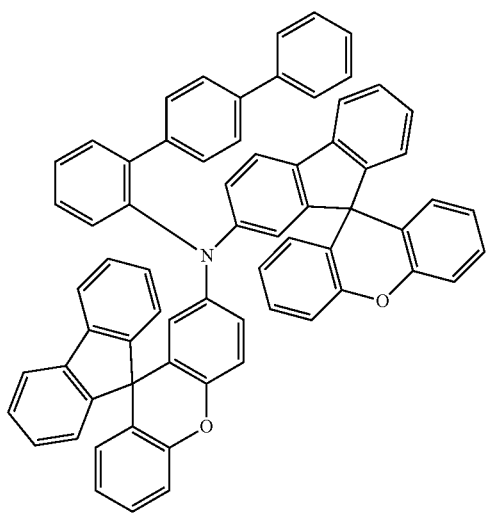
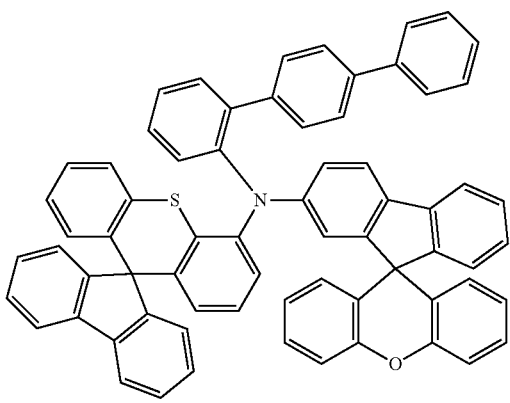
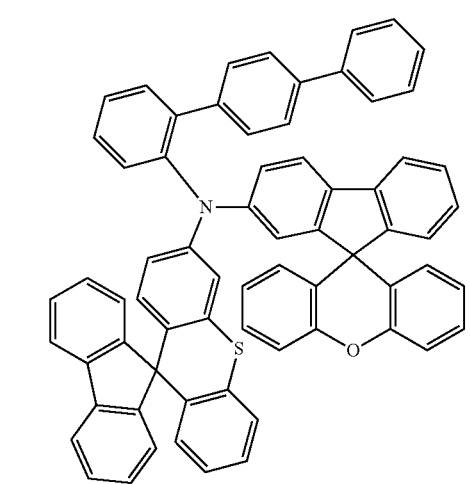
756
-continued
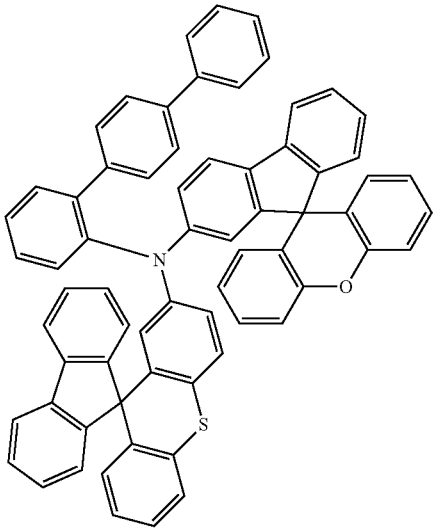
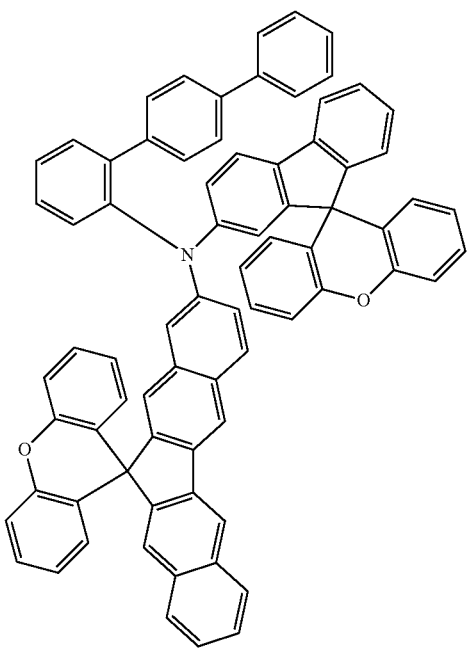
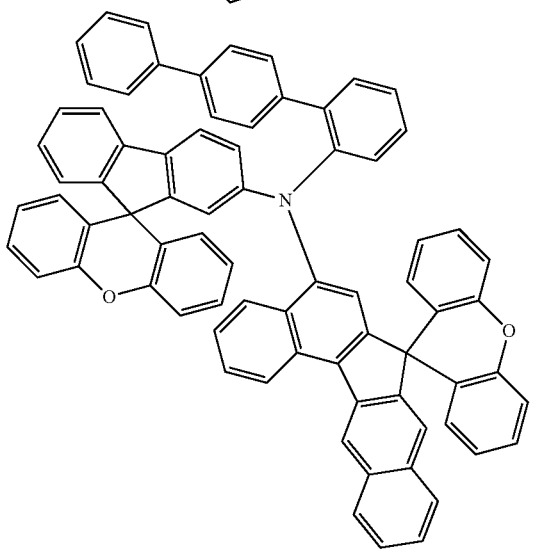

757
-continued
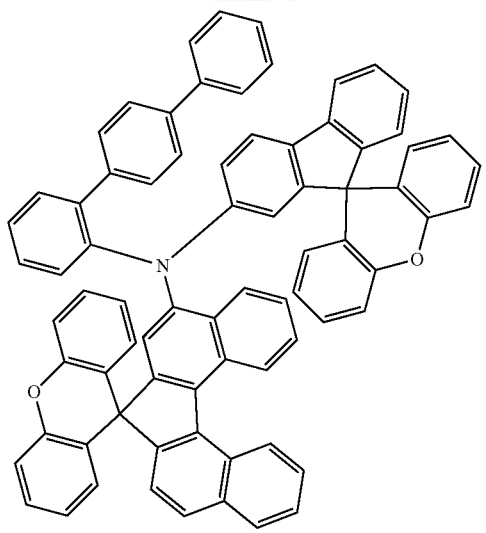
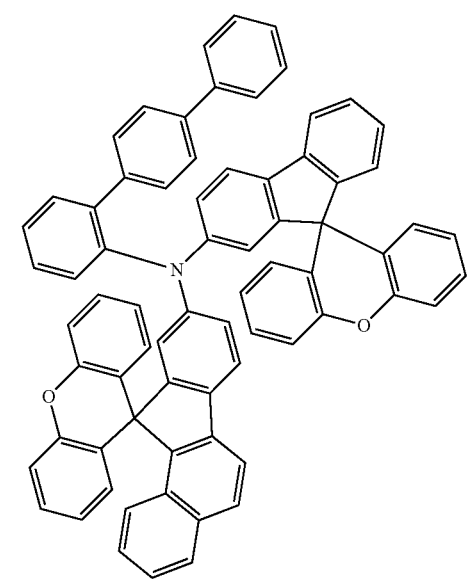
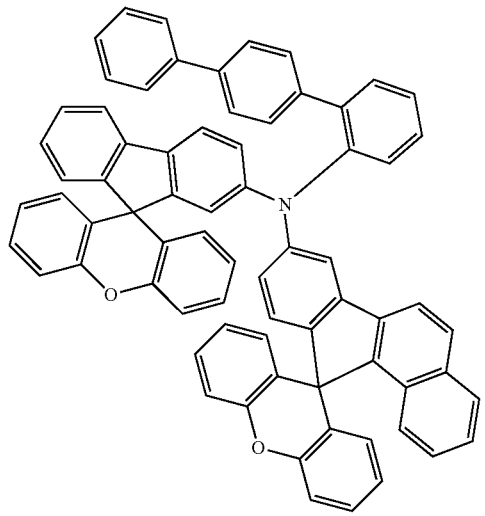
758
-continued
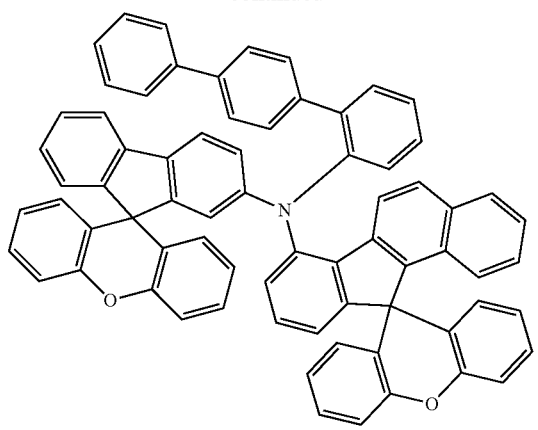
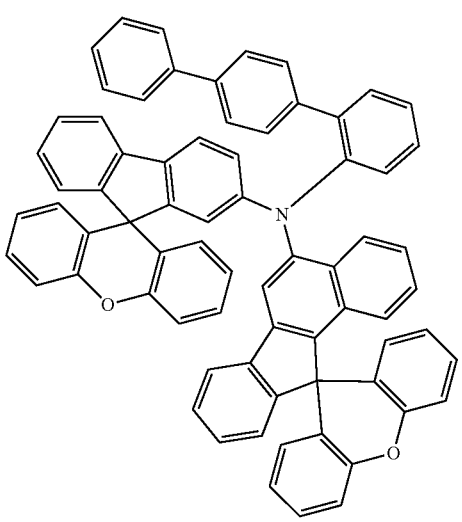
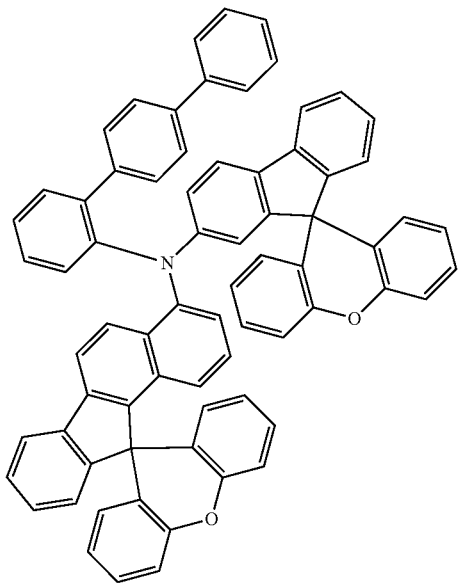

759
-continued
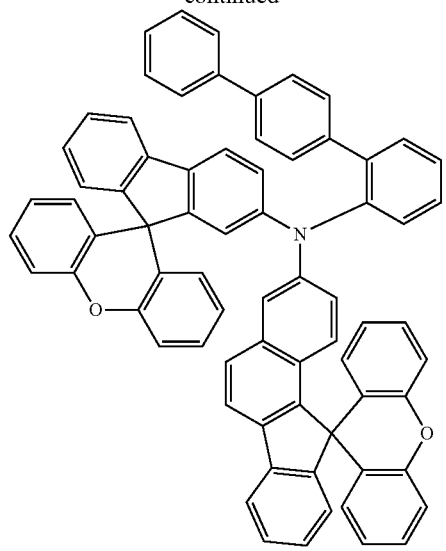
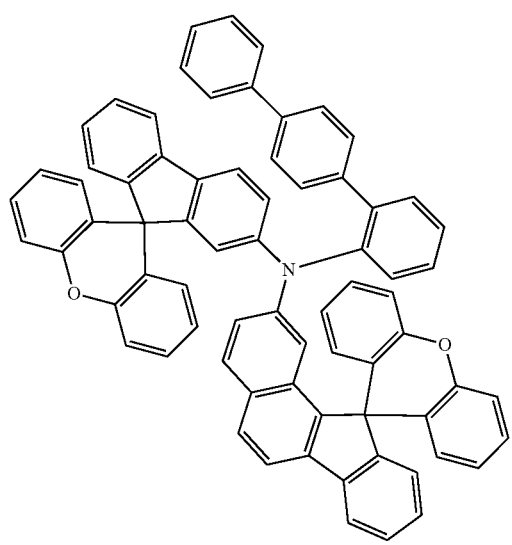
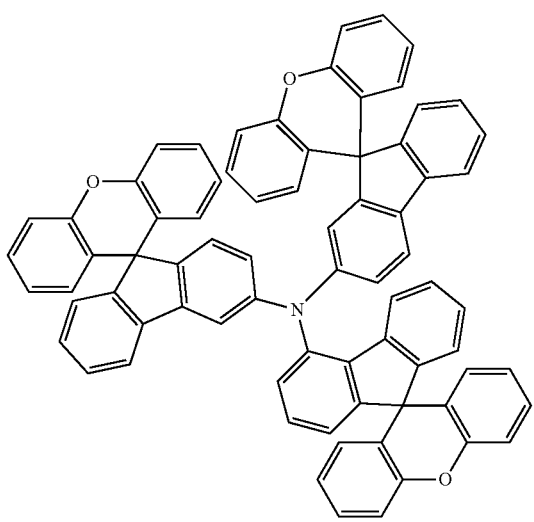
760
-continued
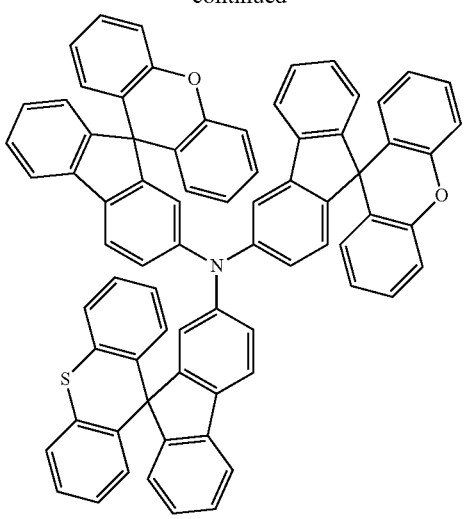
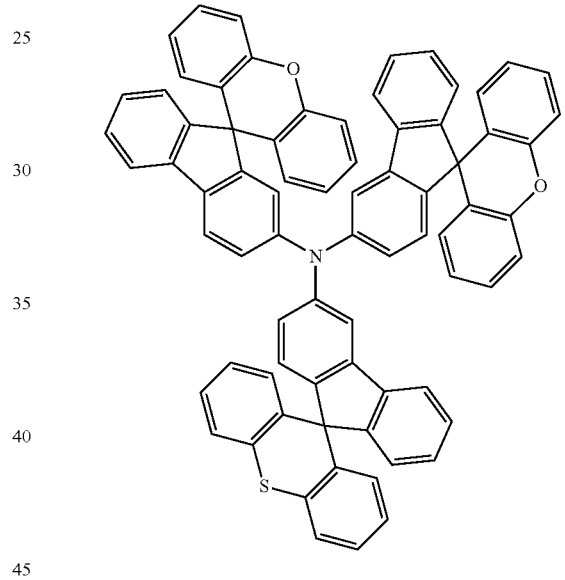
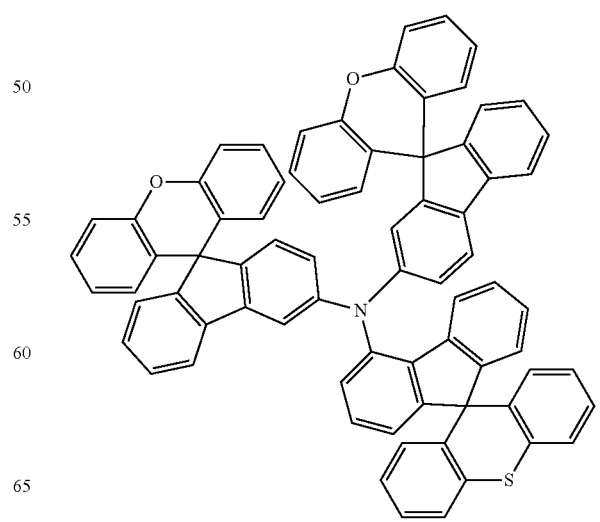

761
-continued
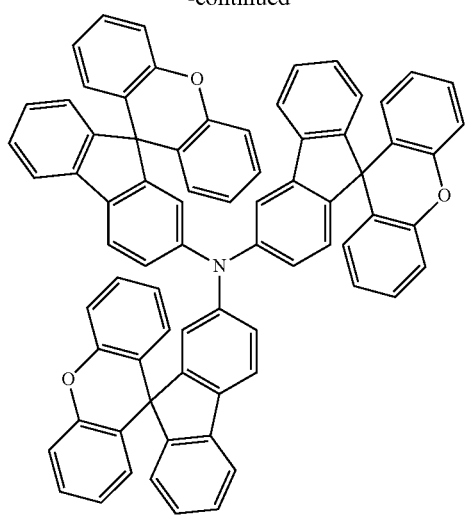
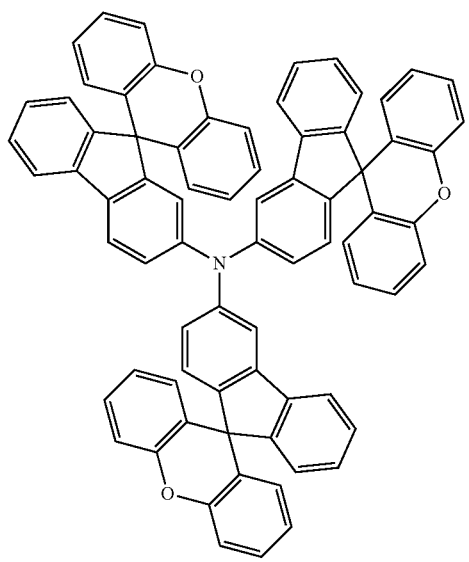
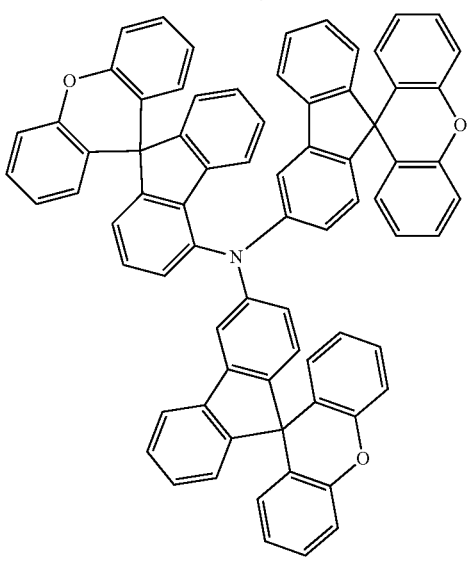
762
-continued
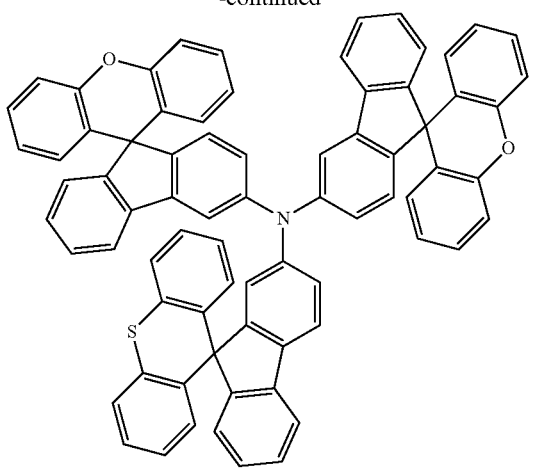
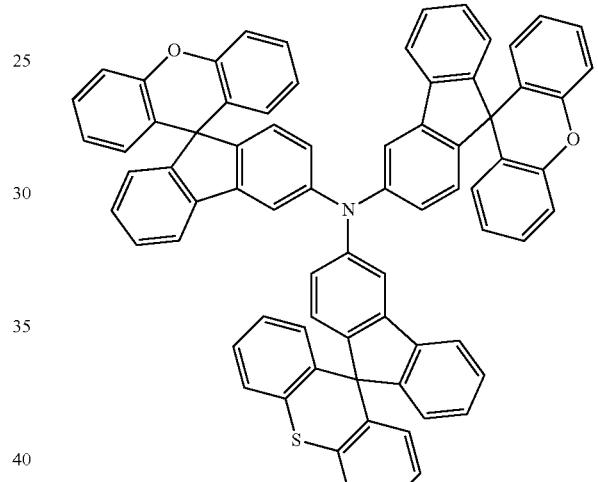
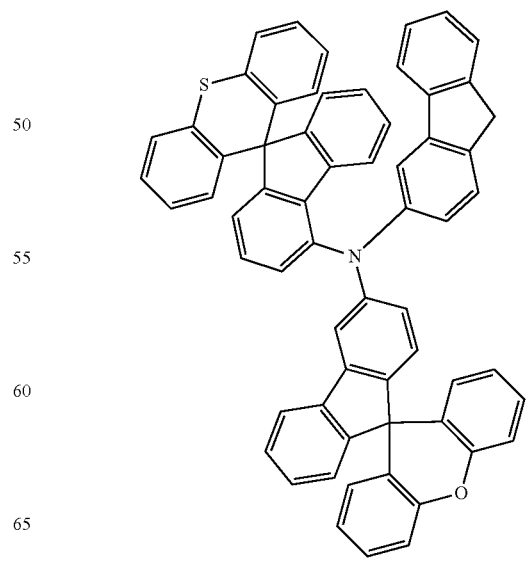

| 763 | 764 |
|---|---|
| 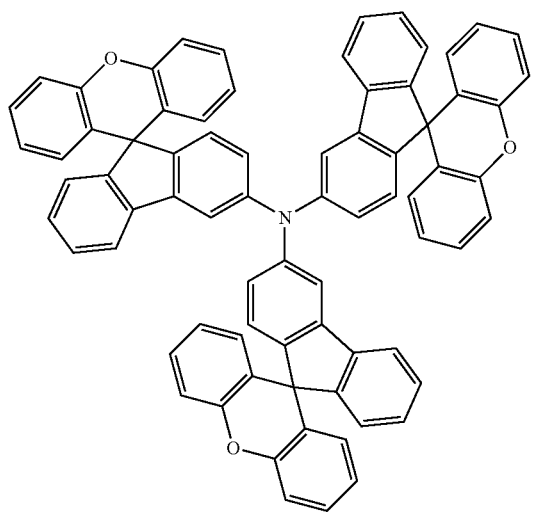 | 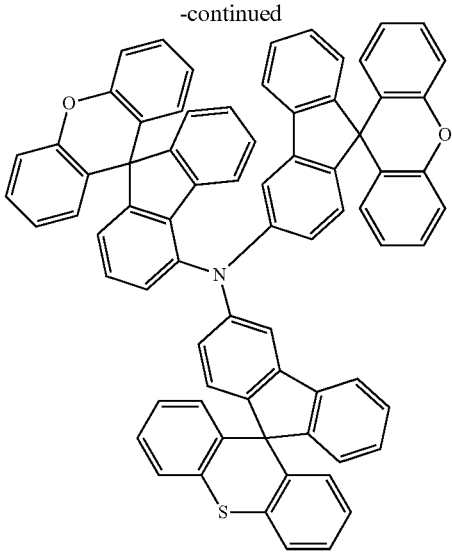 |

765
-continued
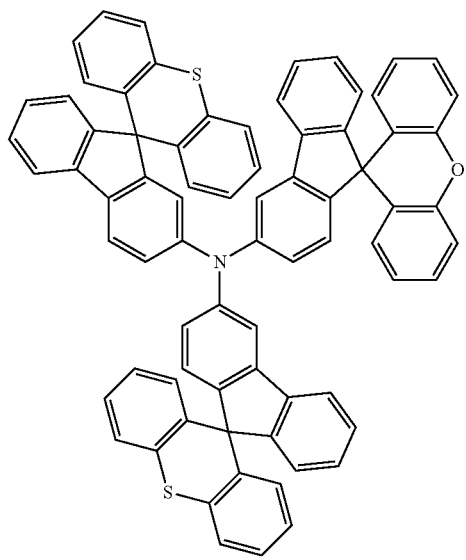
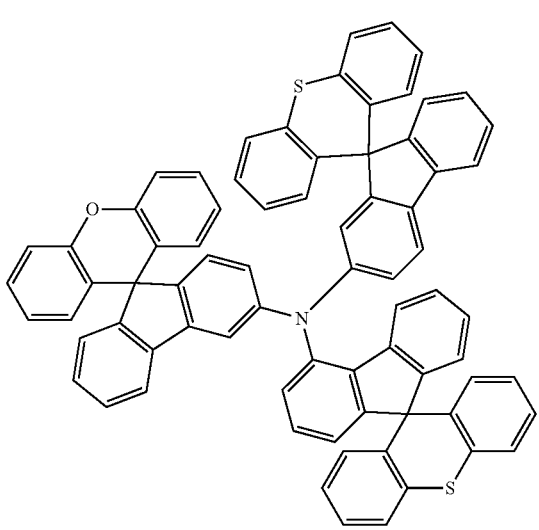
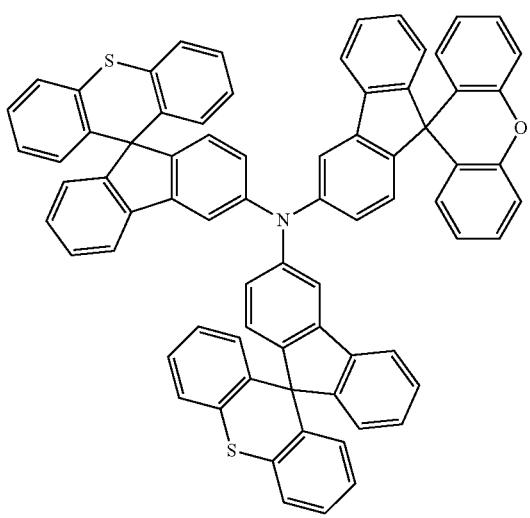
766
-continued
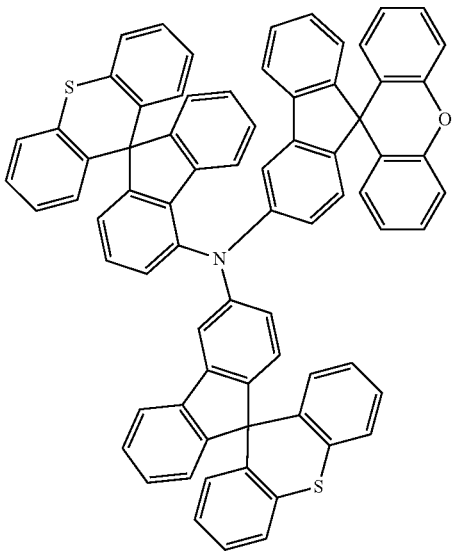
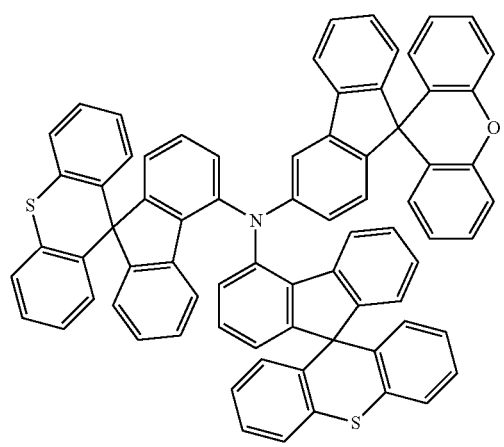
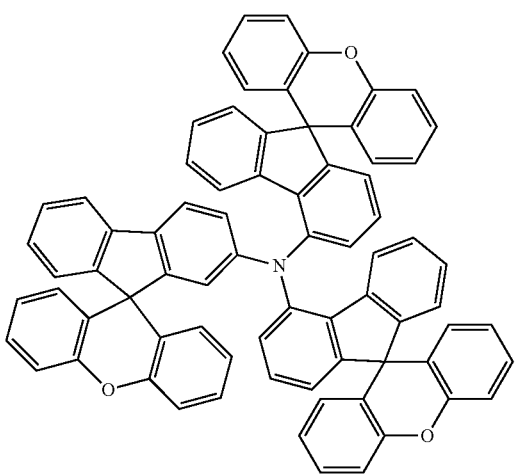

767
-continued
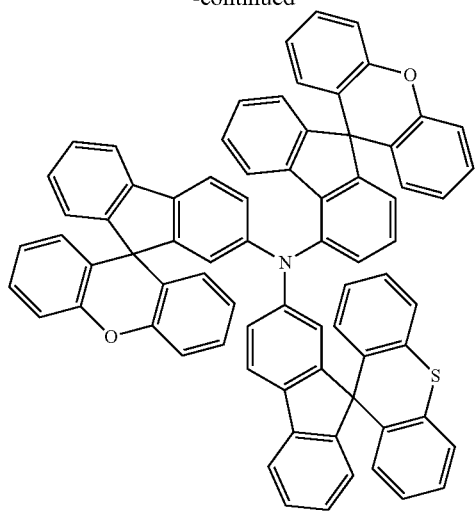
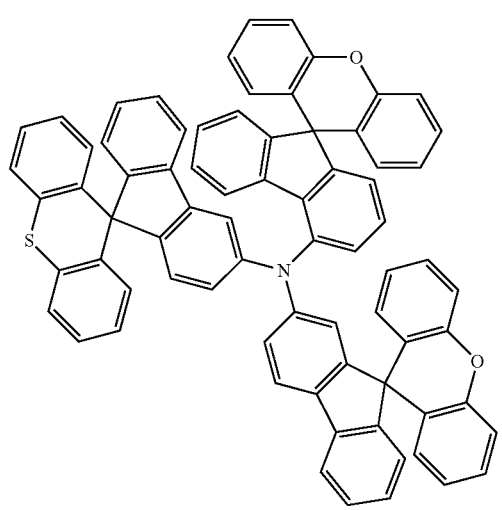
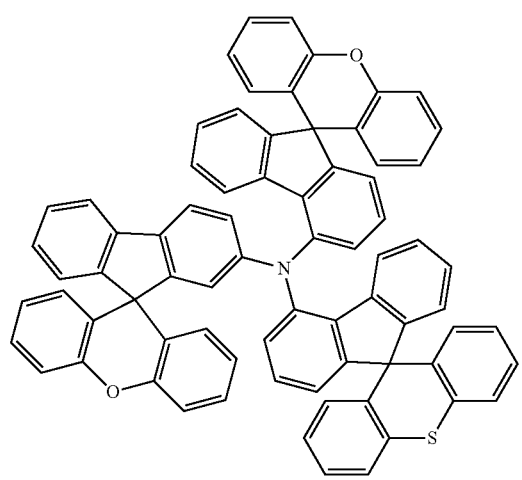
768
-continued
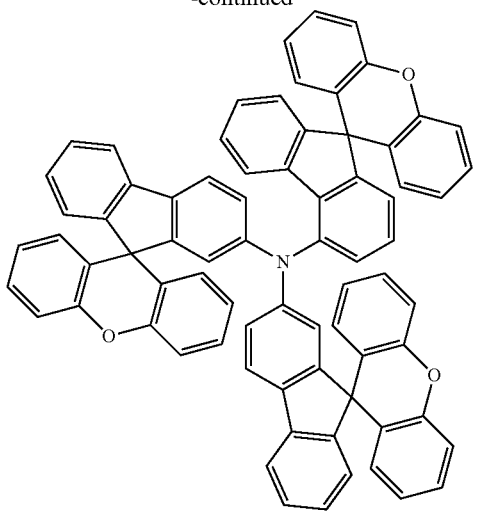
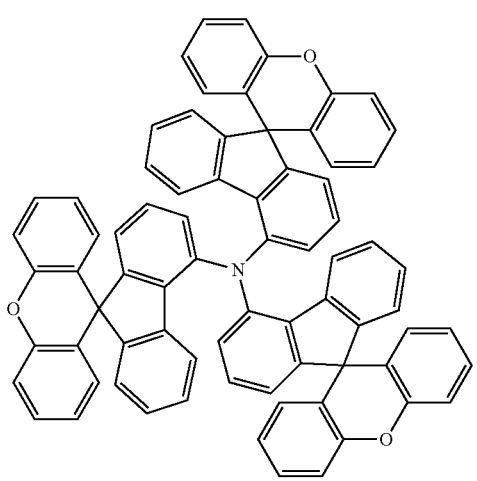
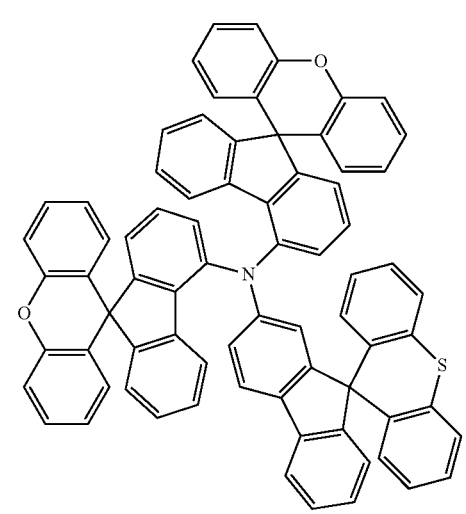

769
-continued
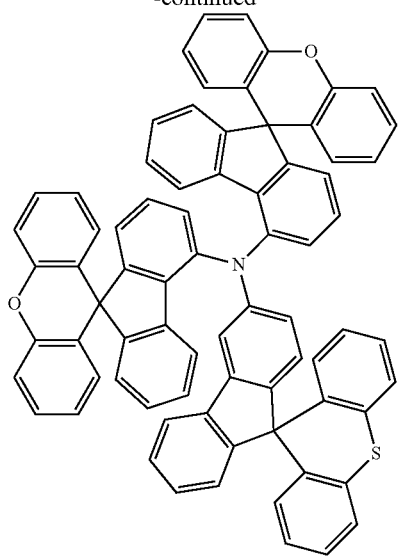
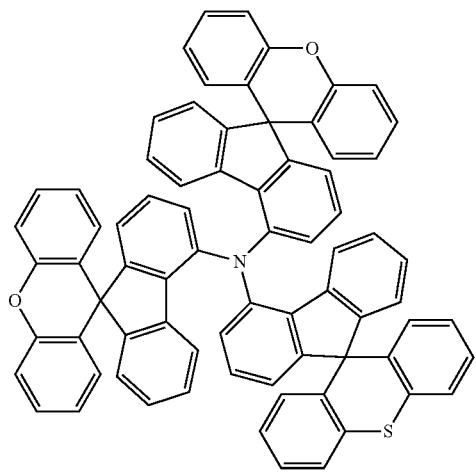
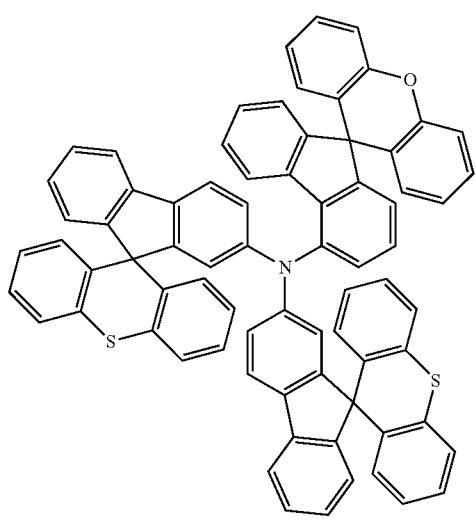
770
-continued
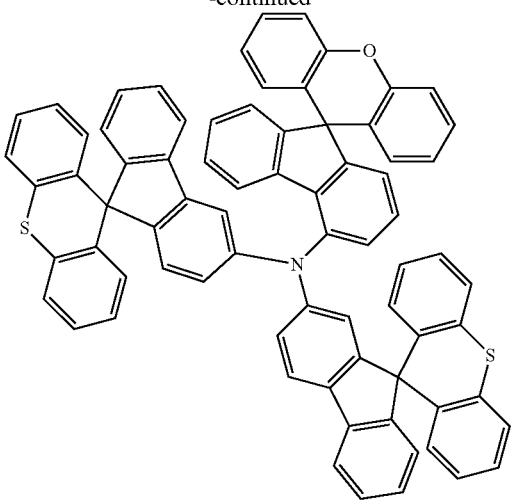
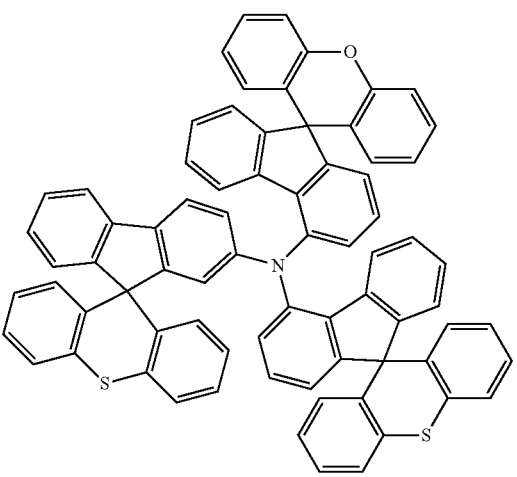
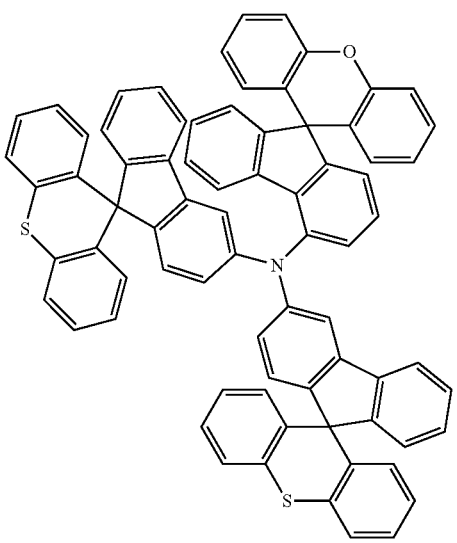

771
-continued
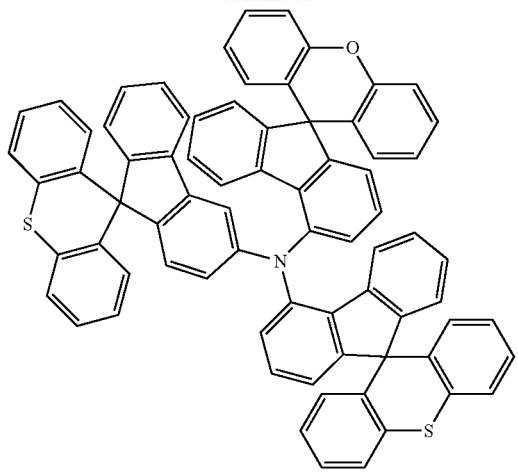
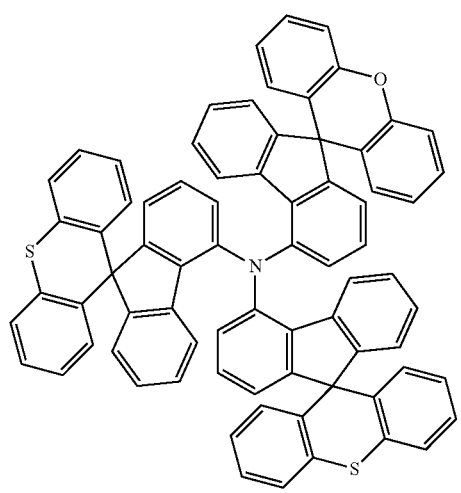
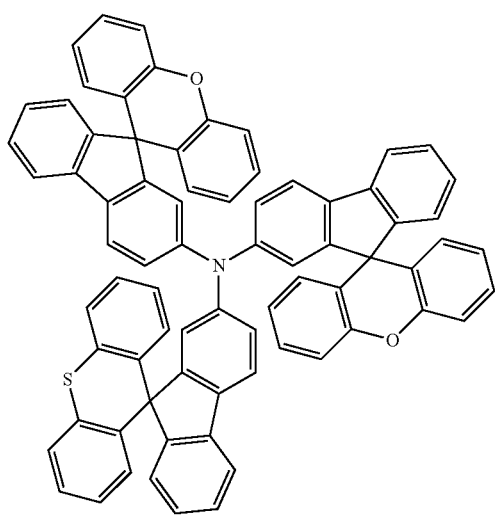
772
-continued
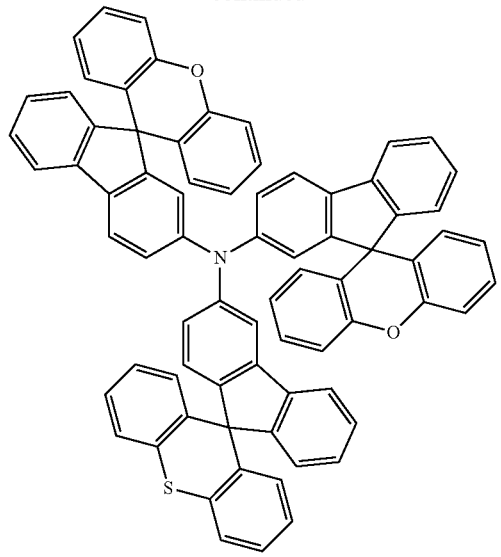
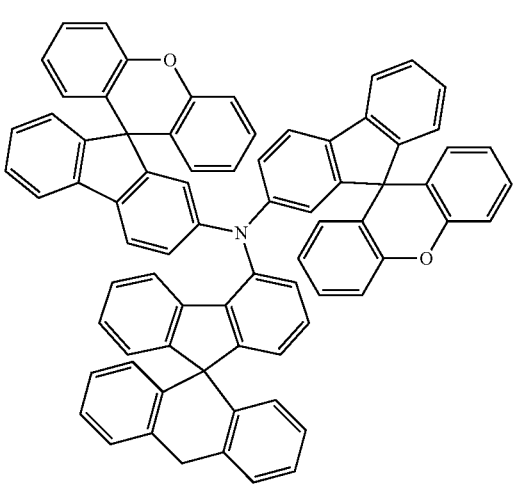
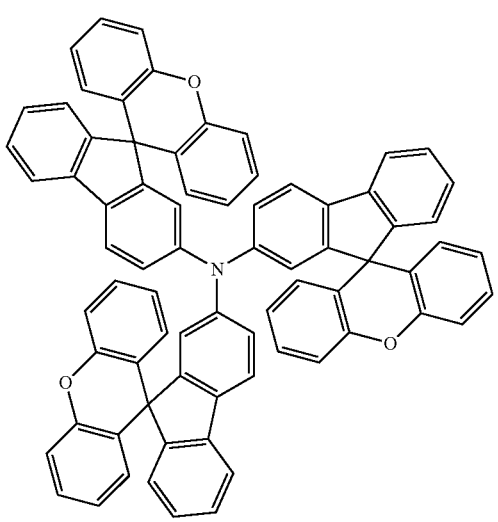

773
-continued
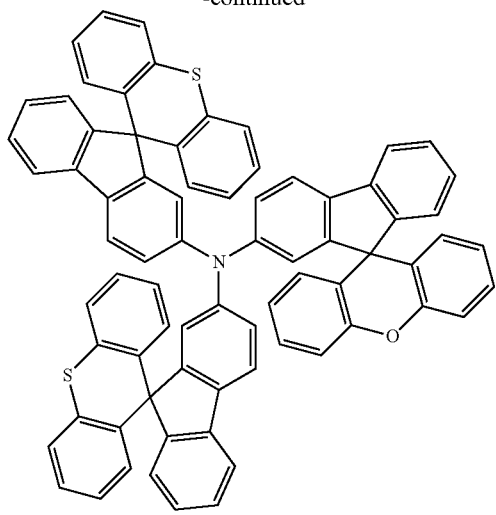
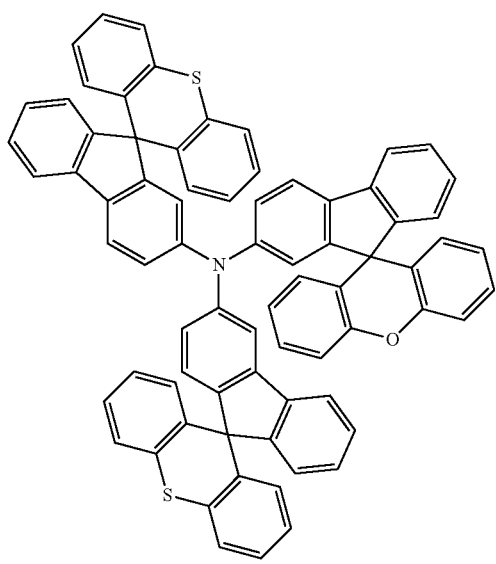
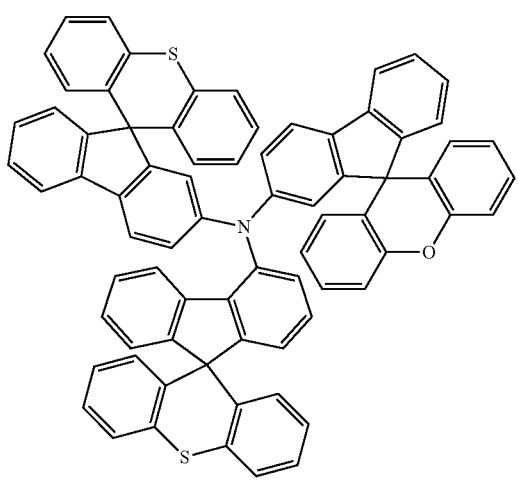
774
-continued
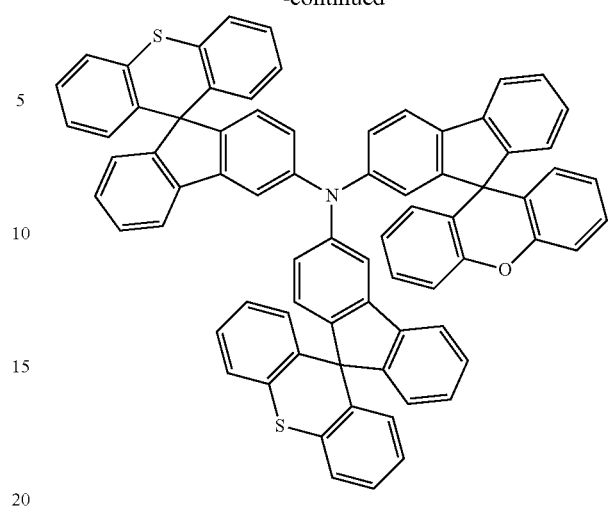
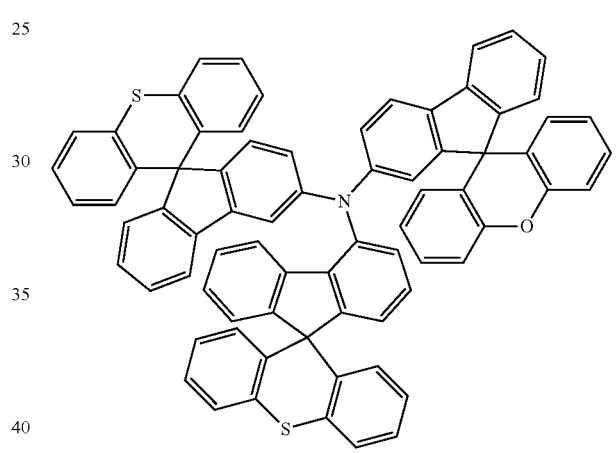
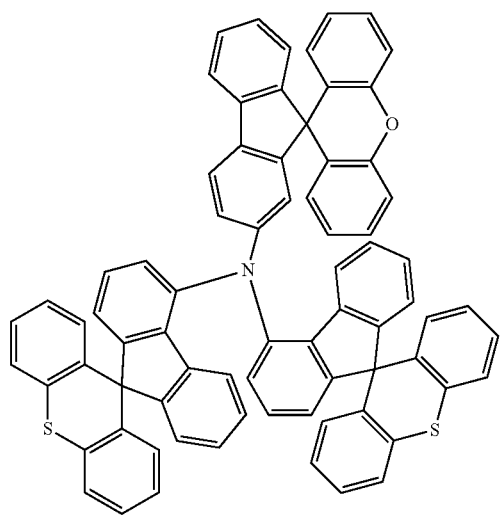

775
-continued
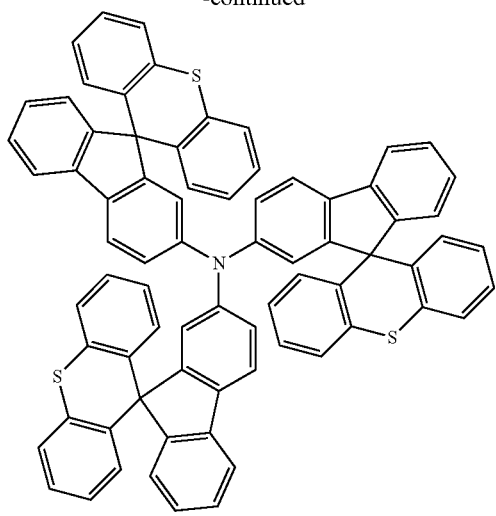
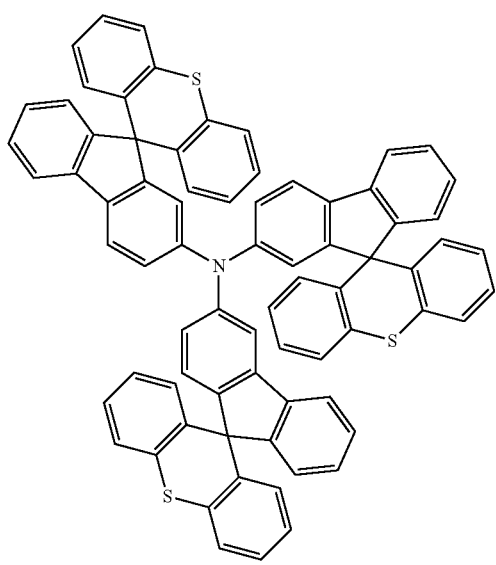
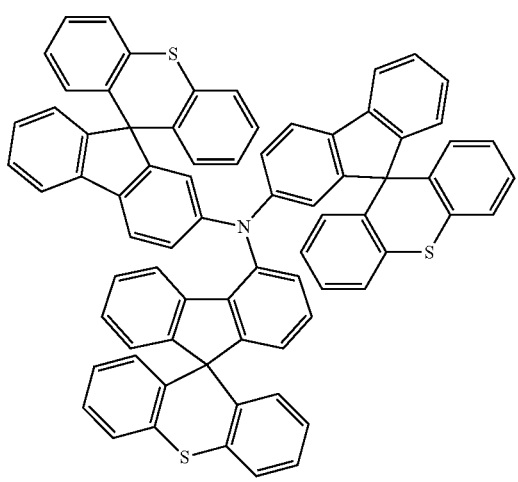
776
-continued
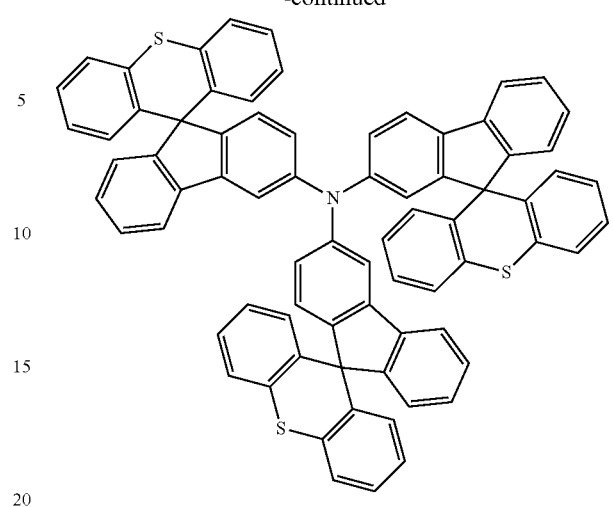
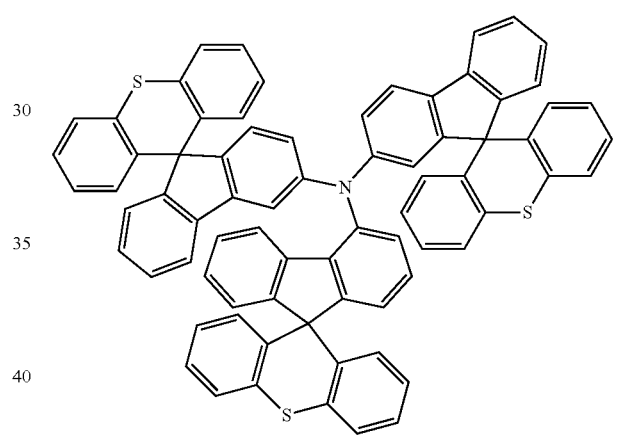
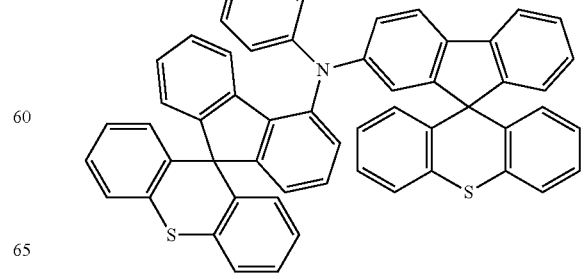

777
-continued
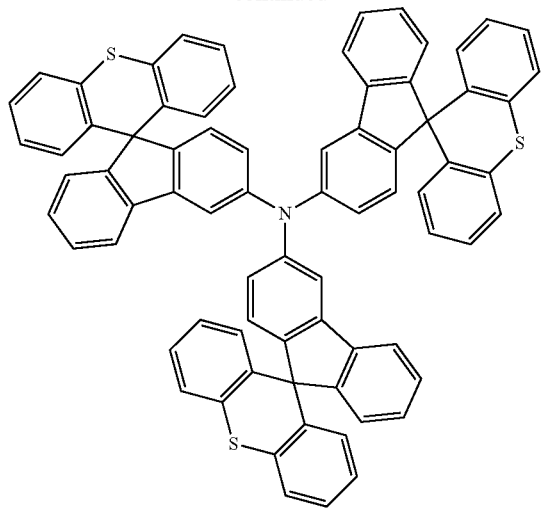
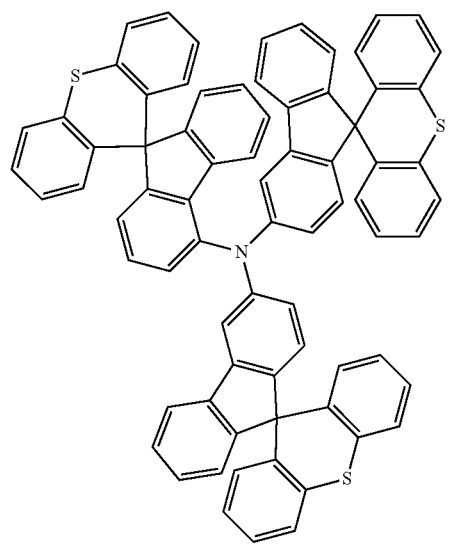
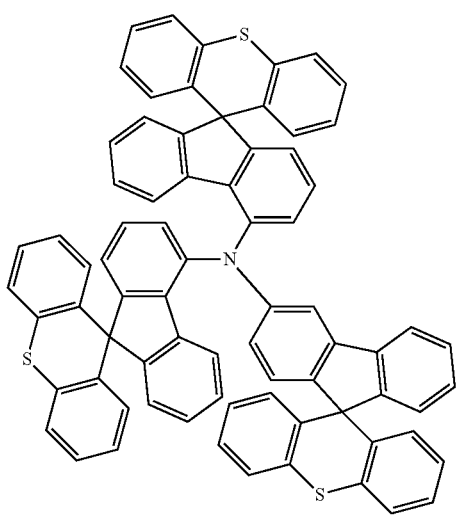
778
-continued
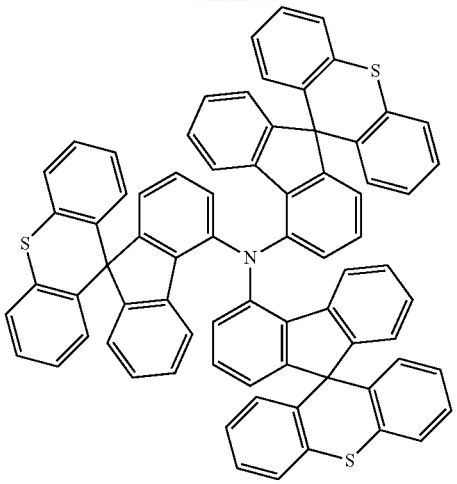
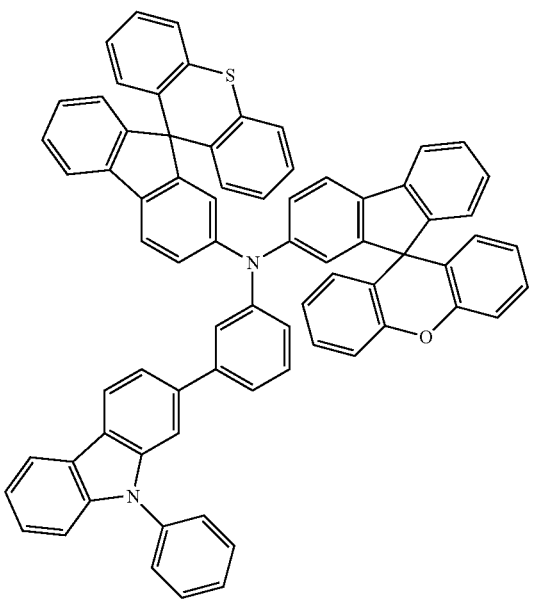
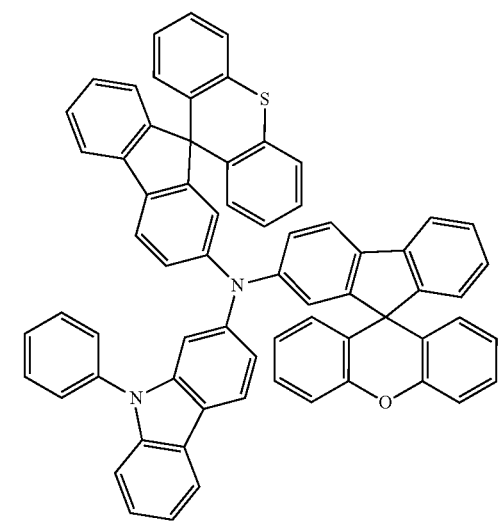

779
-continued
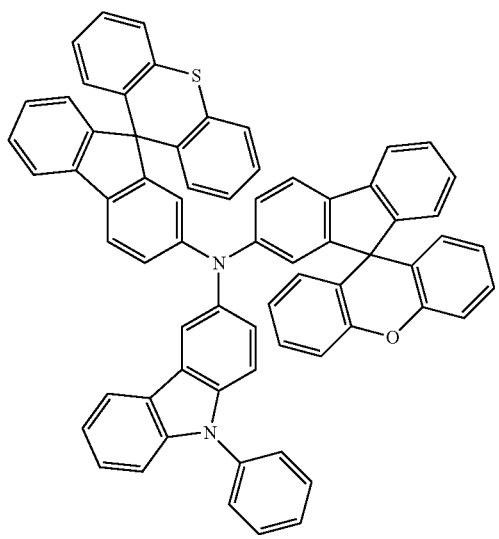
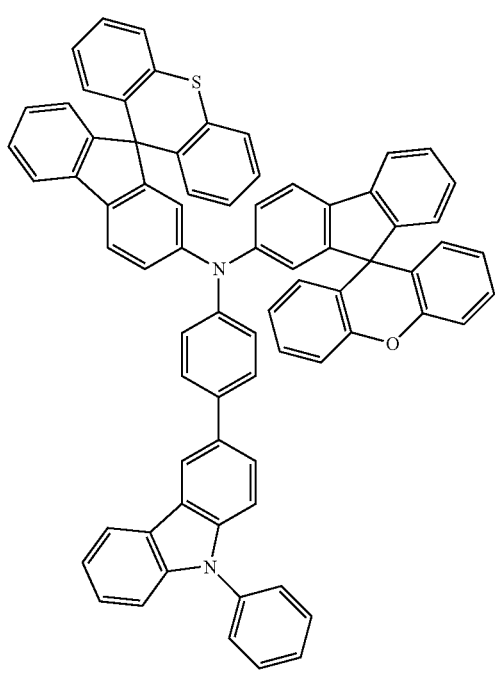
780
-continued
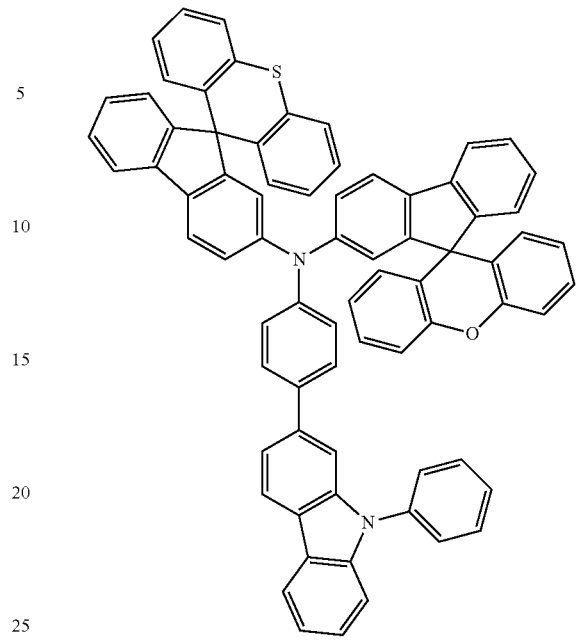
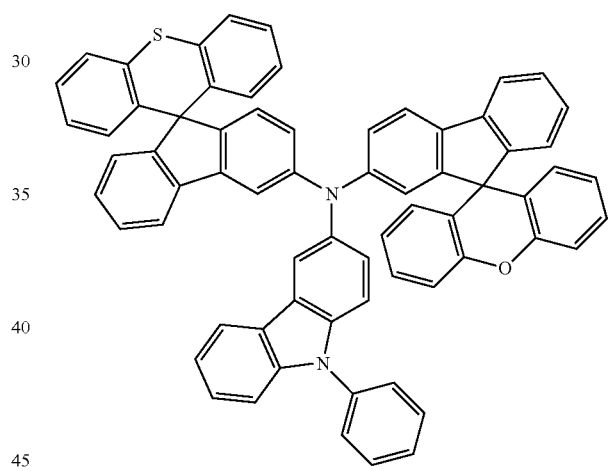
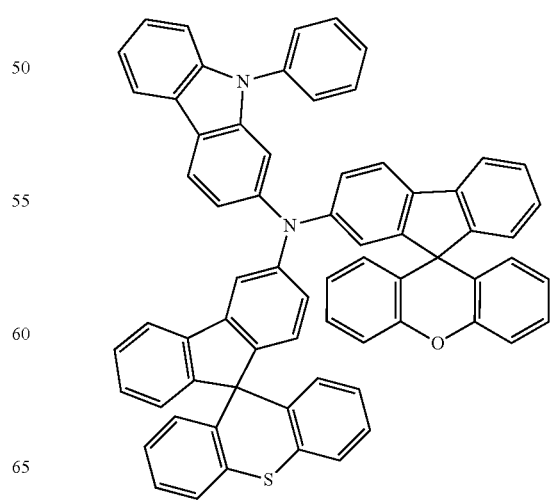

781
-continued
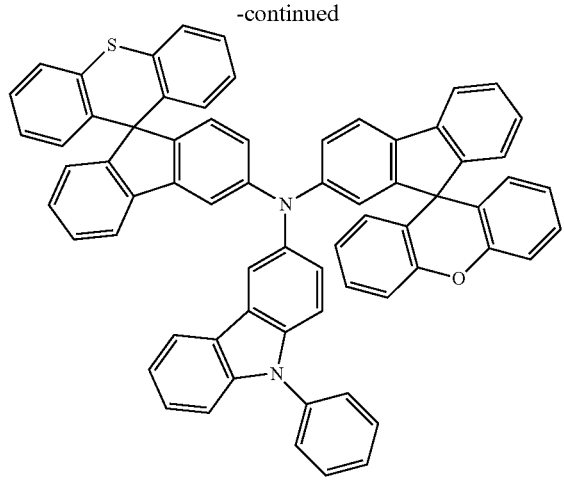
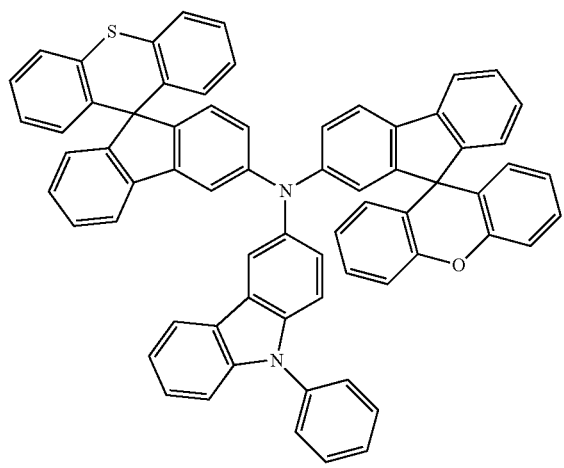
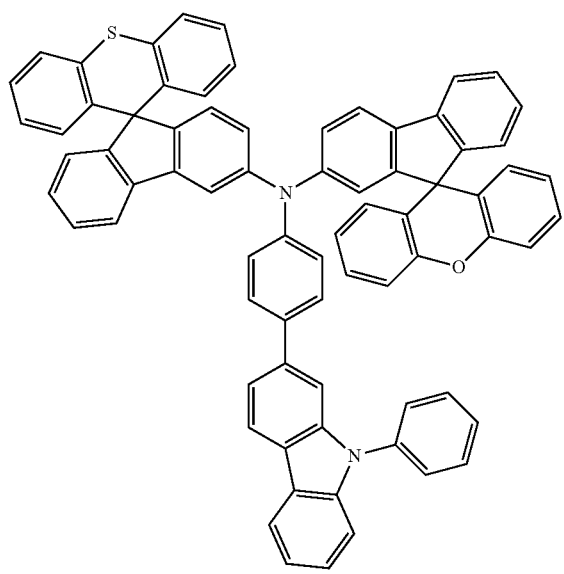
782
-continued
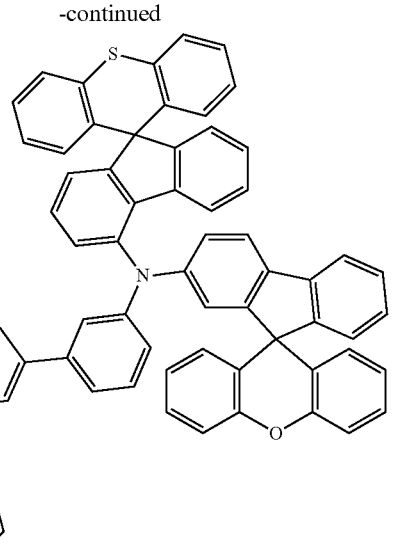
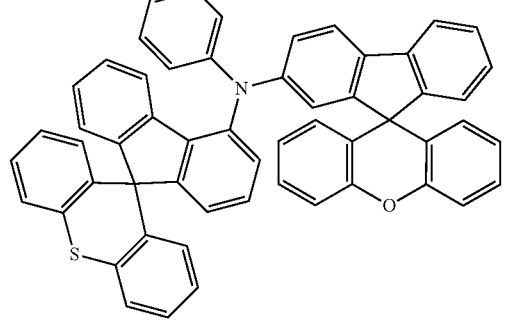
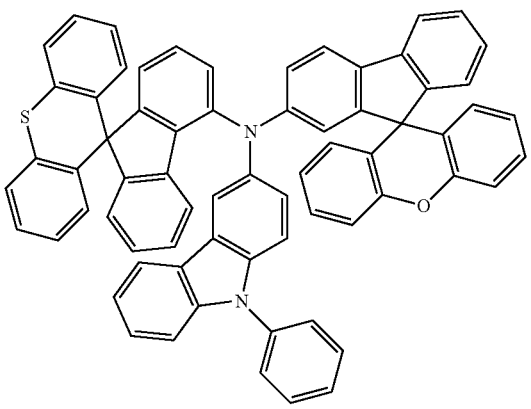

783
-continued
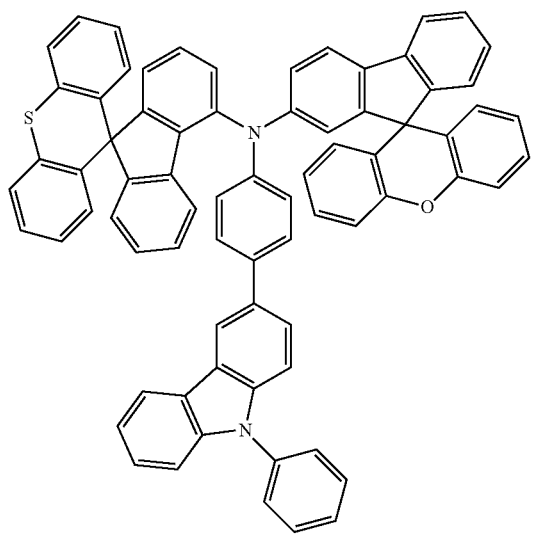
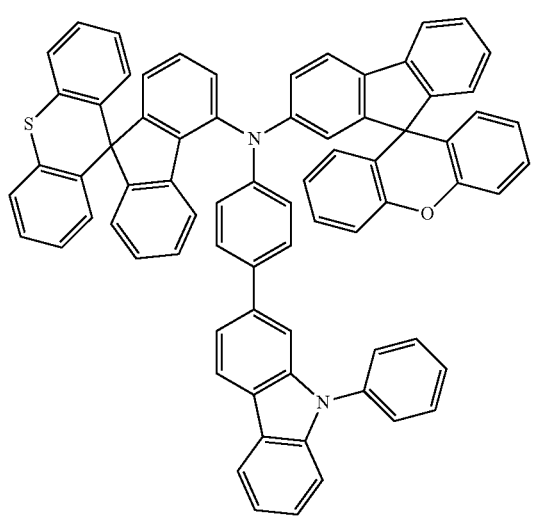
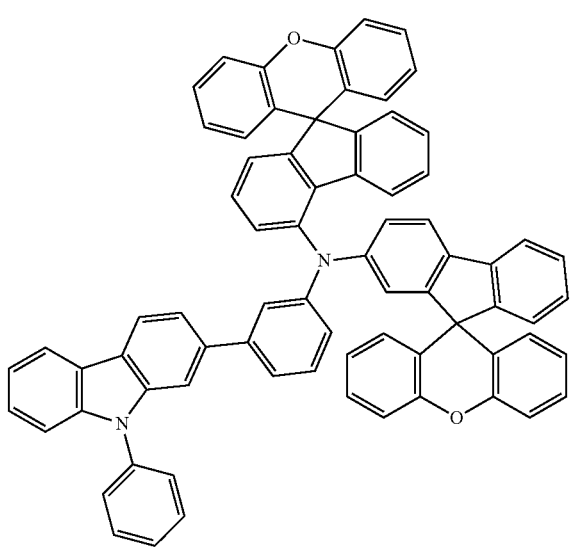
784
-continued
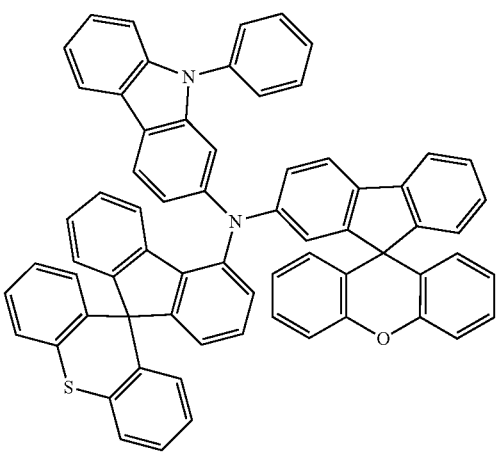
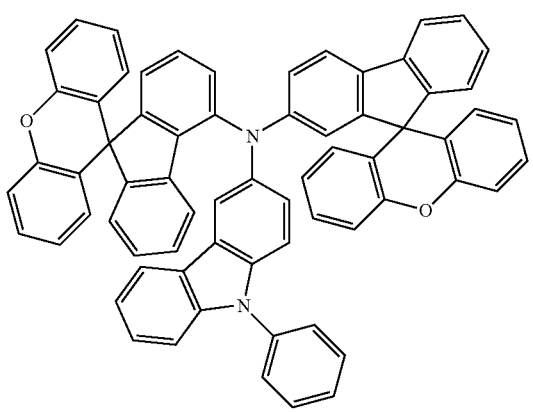
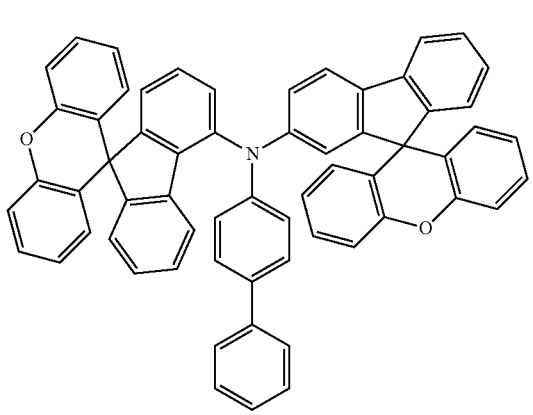

785
-continued
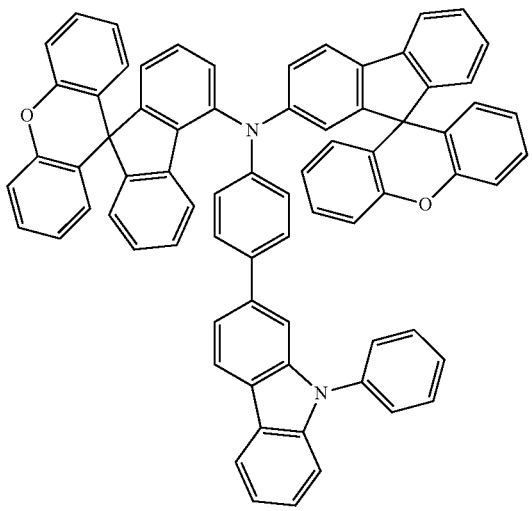
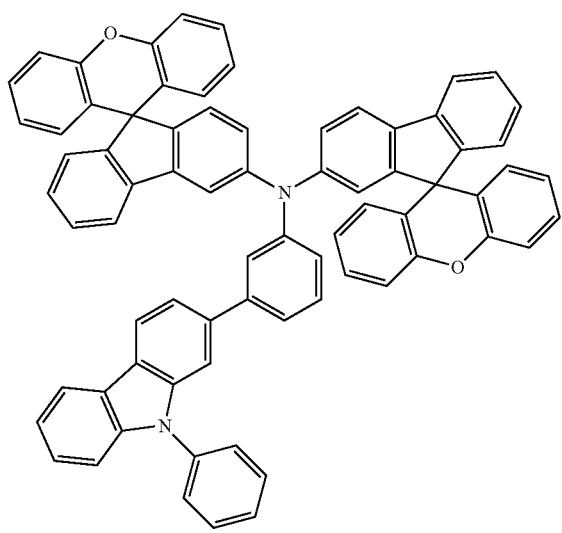
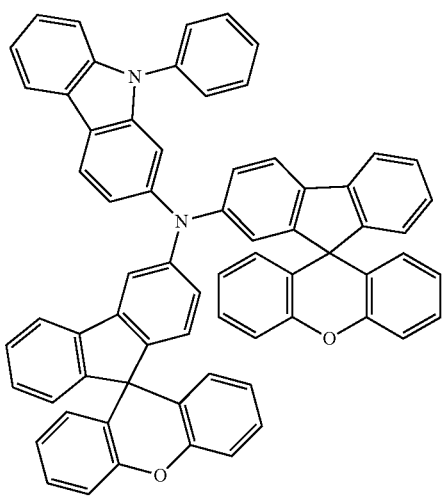
786
-continued
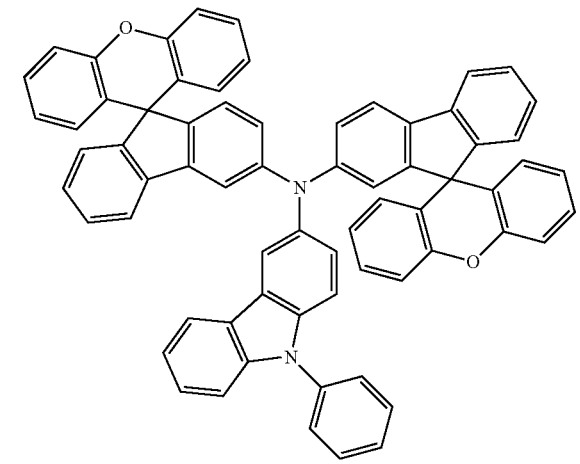
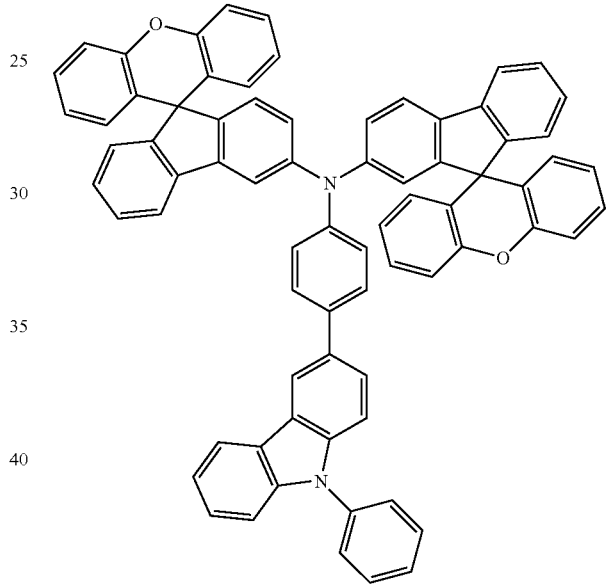
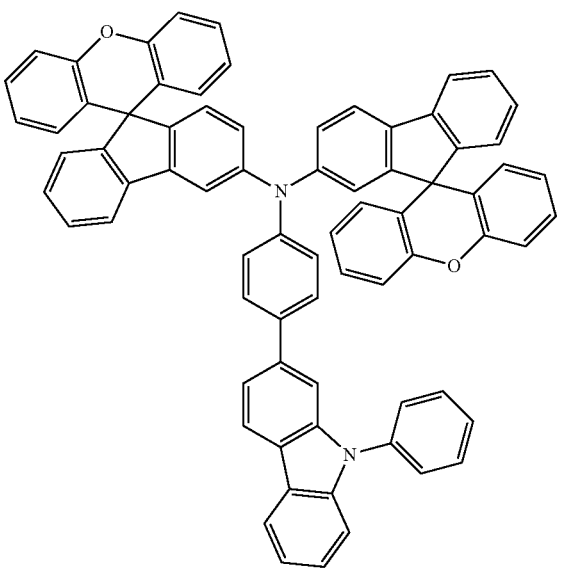

787
-continued
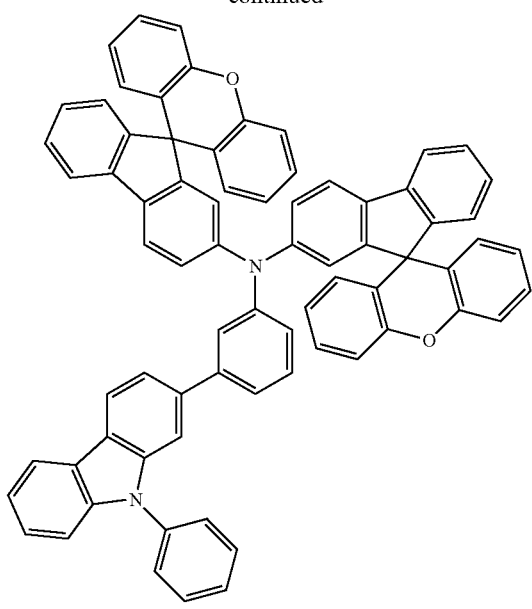
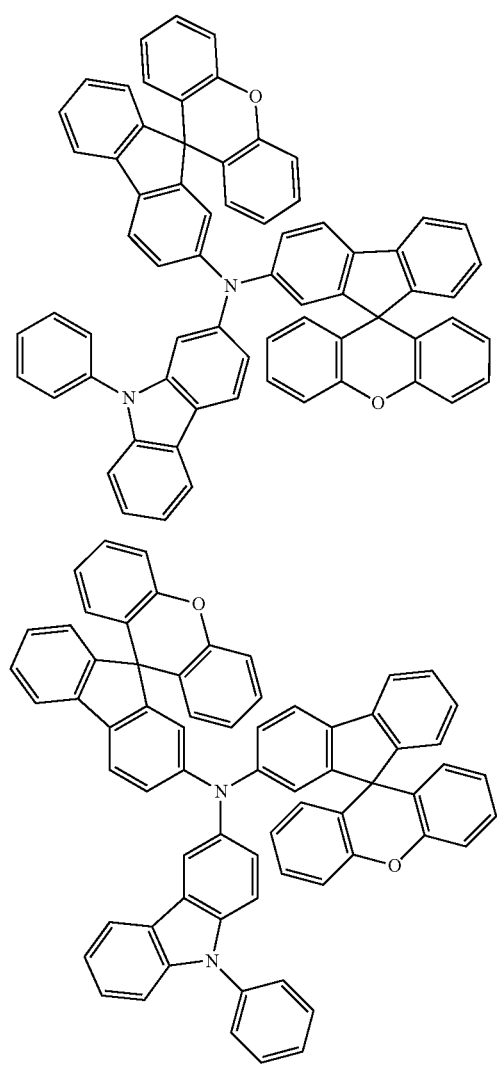
788
-continued
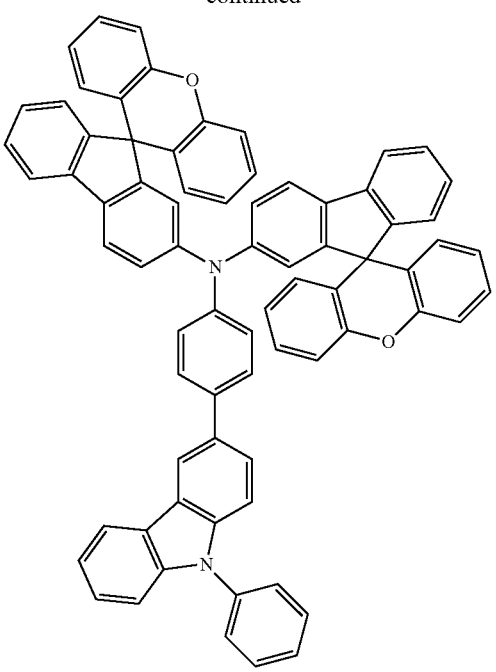
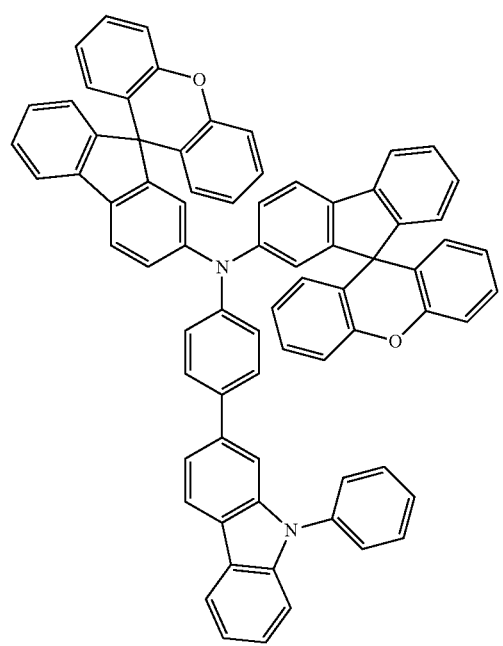

789
-continued
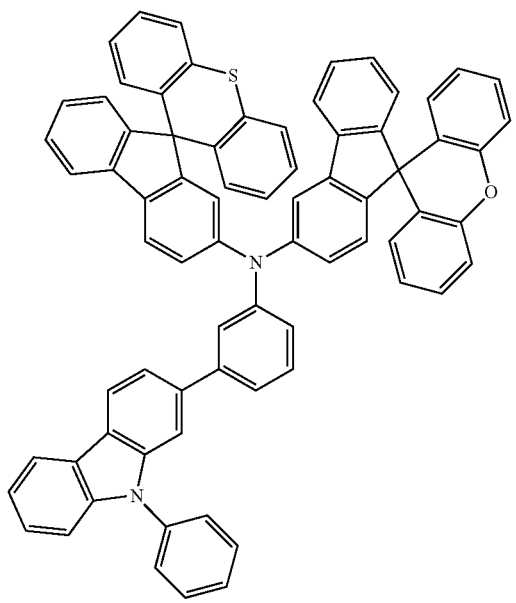
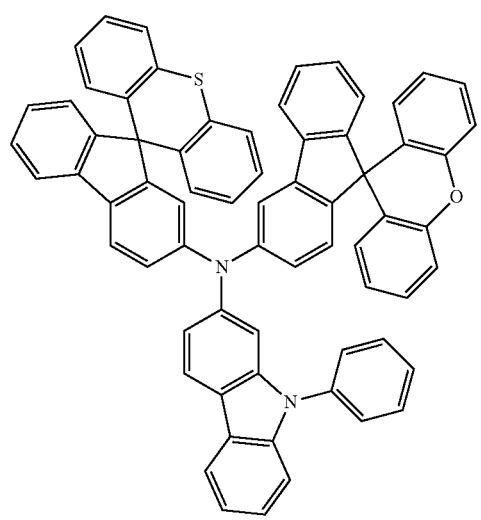
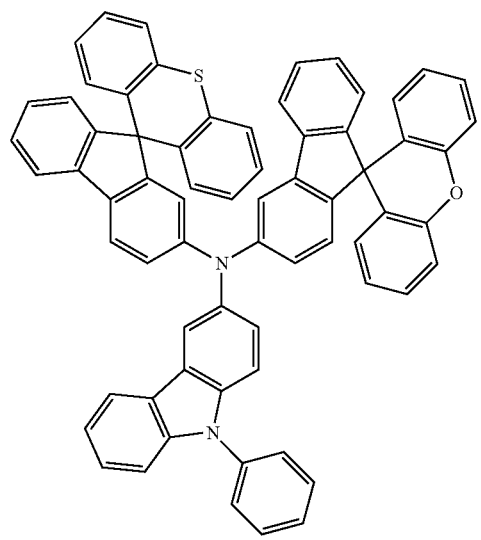
790
-continued
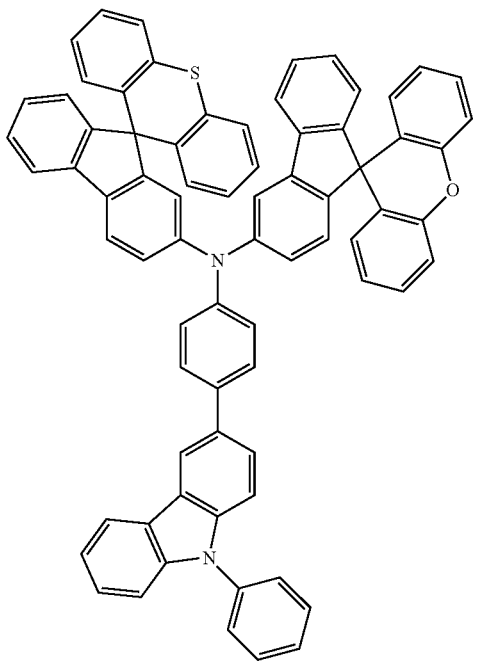
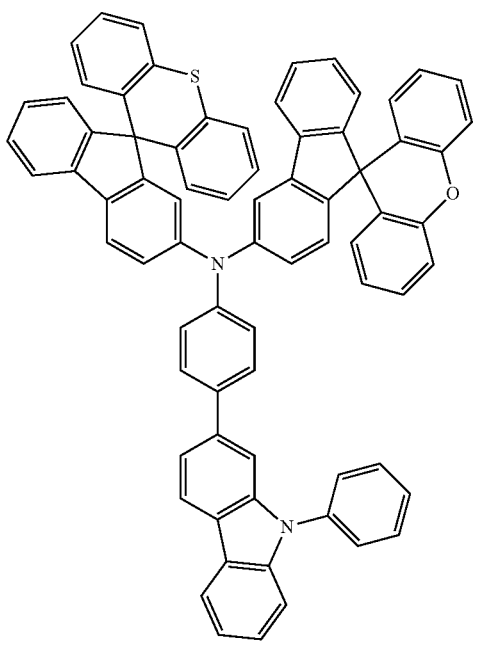

791
-continued
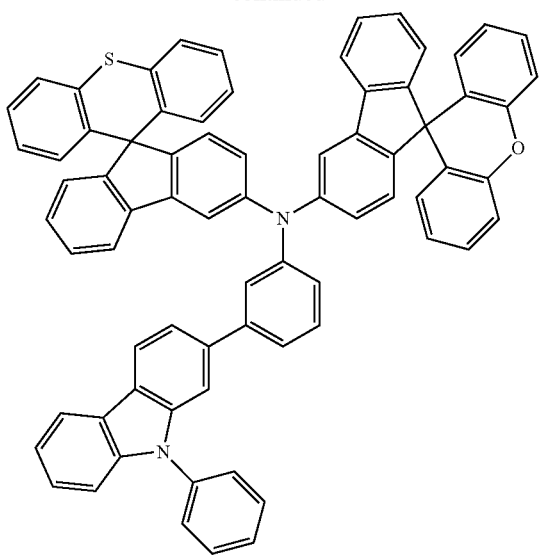
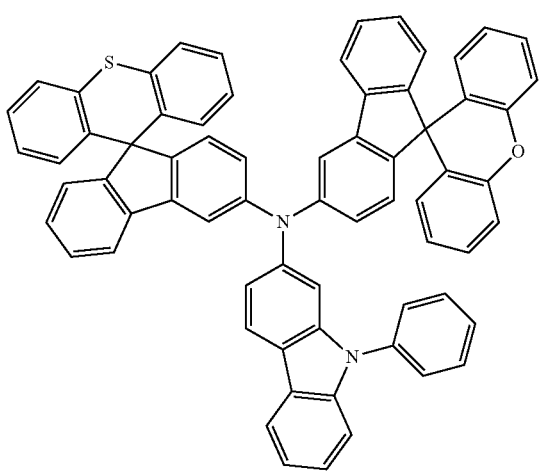
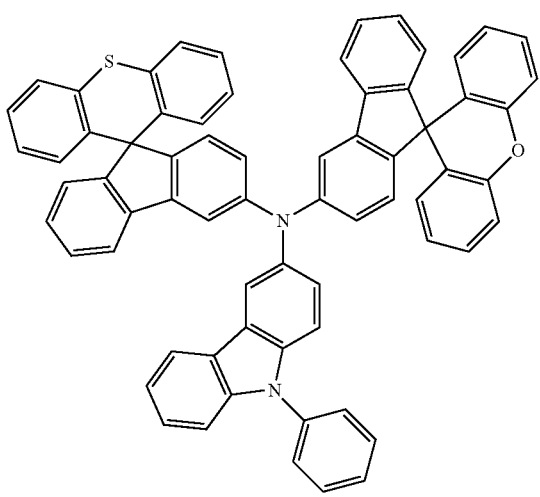
792
-continued
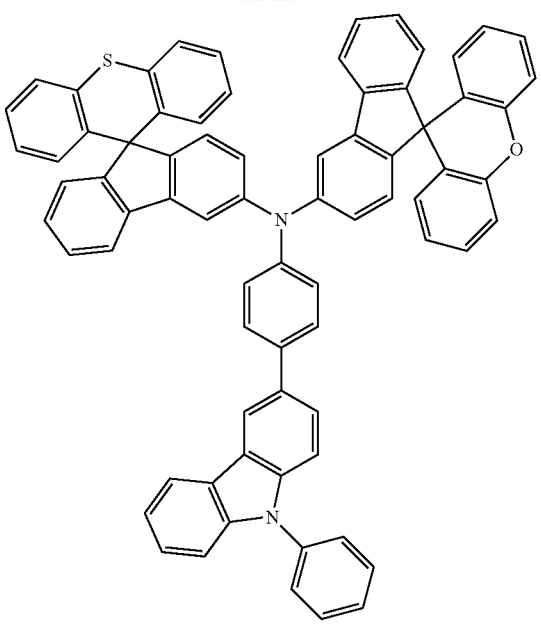
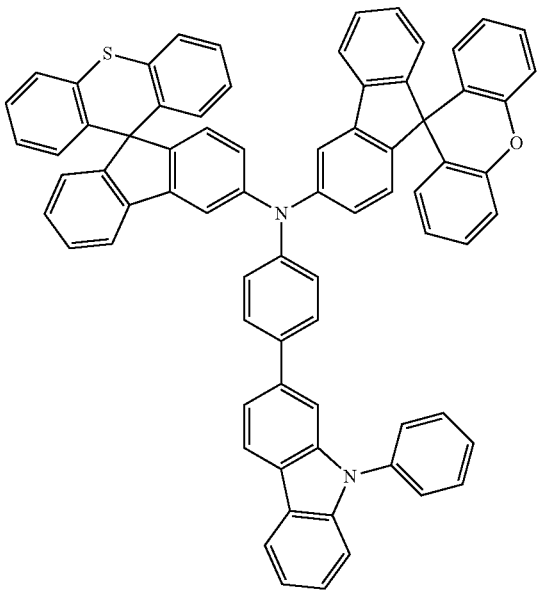 [SMILES: c1ccc(-n2c3ccccc3c3ccc(-c4ccc(N(c5ccc6c(c5)-c5ccccc5C65c6ccccc6Oc6ccccc65)c5ccc6c(c5)-c5ccccc5C65c6ccccc6Sc6ccccc65)cc4)cc32)cc1]

793
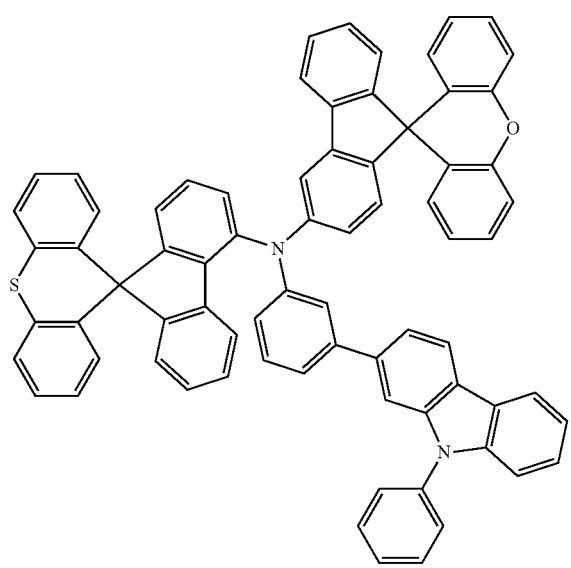
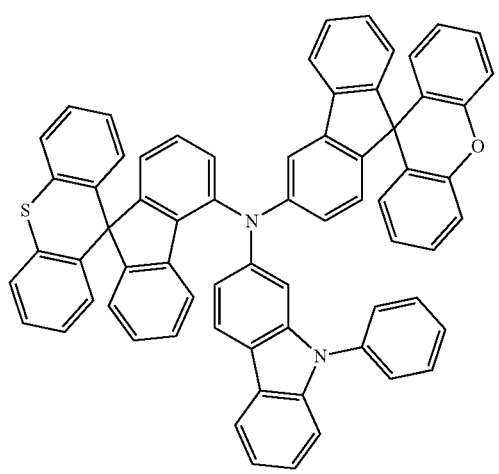
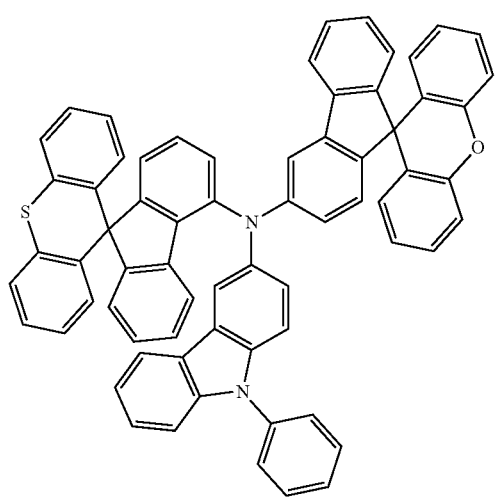
794
-continued
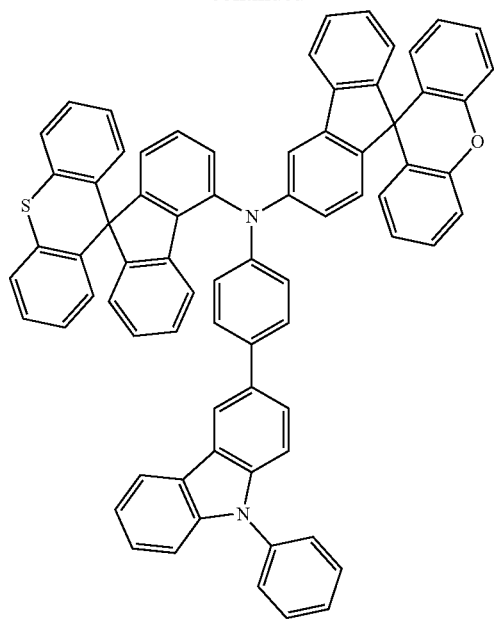
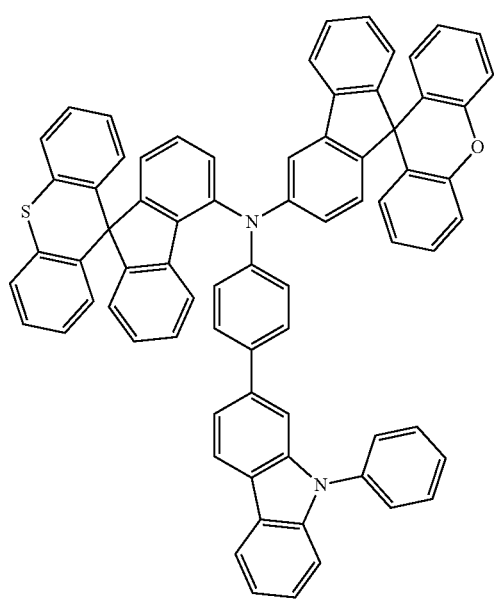

795
-continued
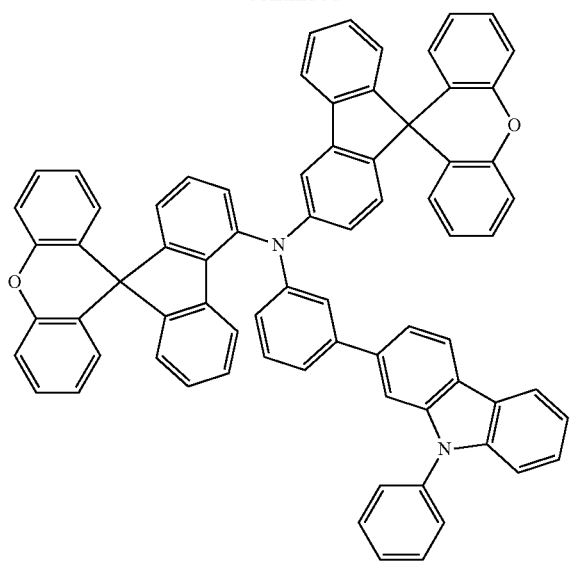
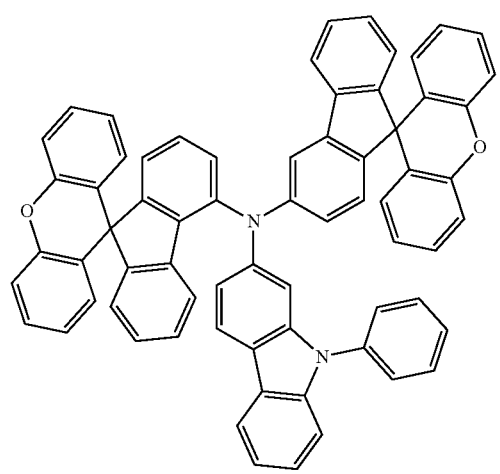
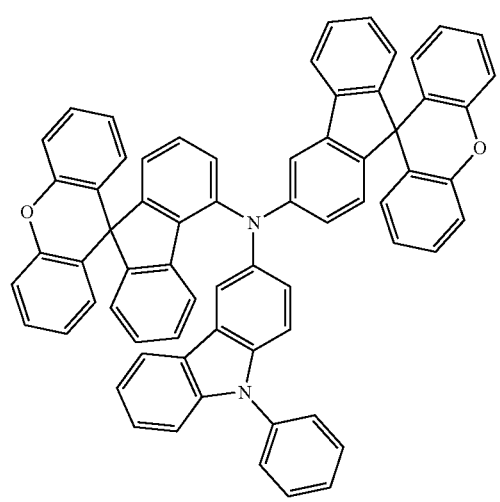
796
-continued
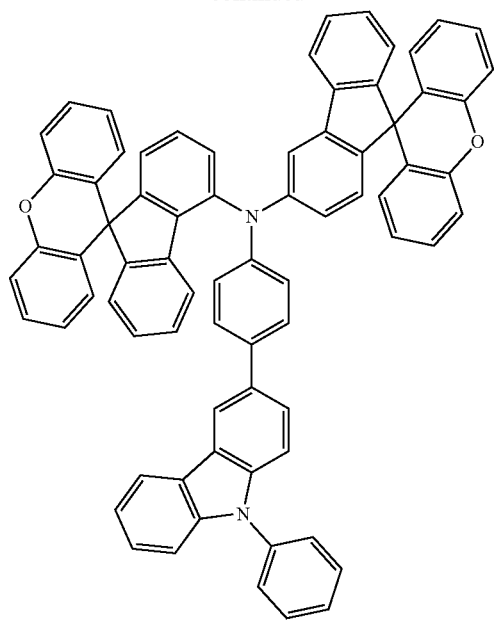
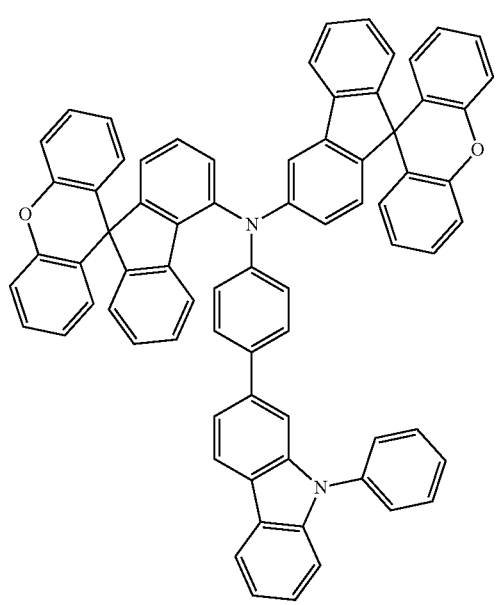 [SMILES: c1ccc(-n2c3ccccc3c3ccc(-c4ccc(N(c5ccc6c(c5)-c5ccccc5C65c6ccccc6Oc6ccccc65)c5cccc6c5-c5ccccc5C65c6ccccc6Oc6ccccc65)cc4)cc32)cc1]

797
-continued
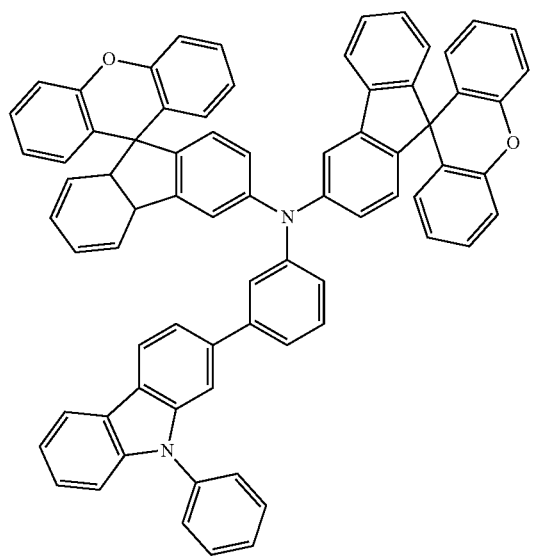
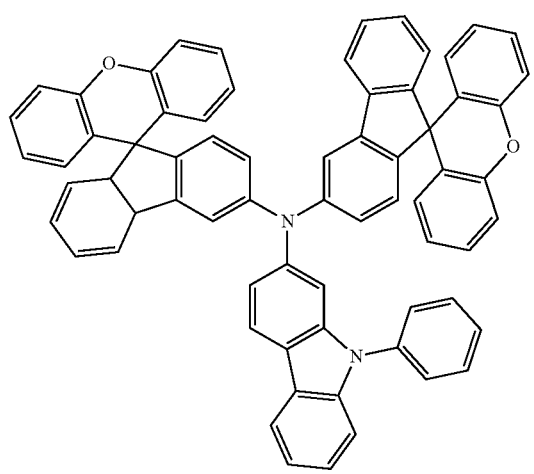
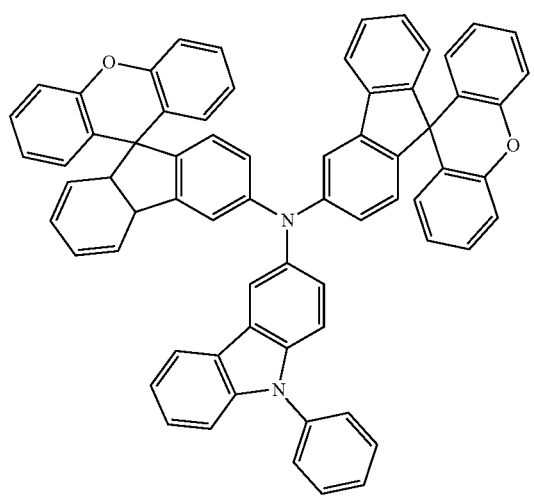
798
-continued
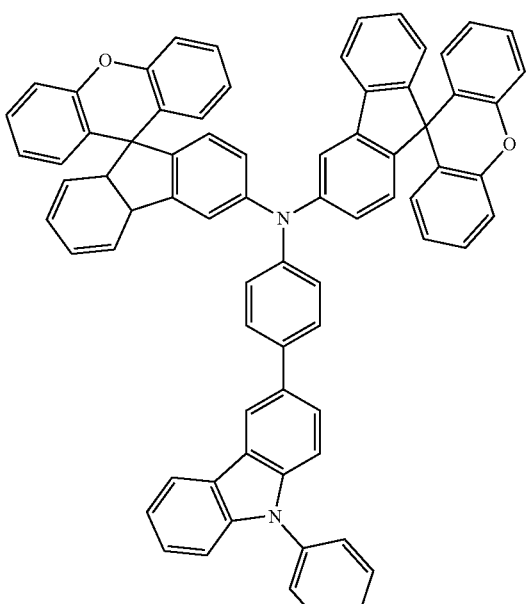
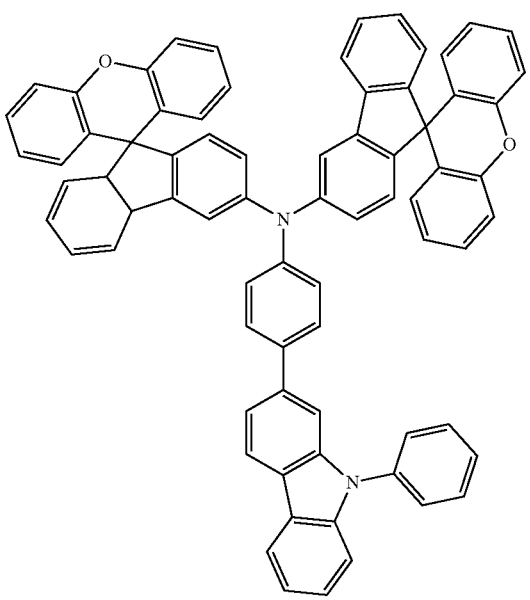
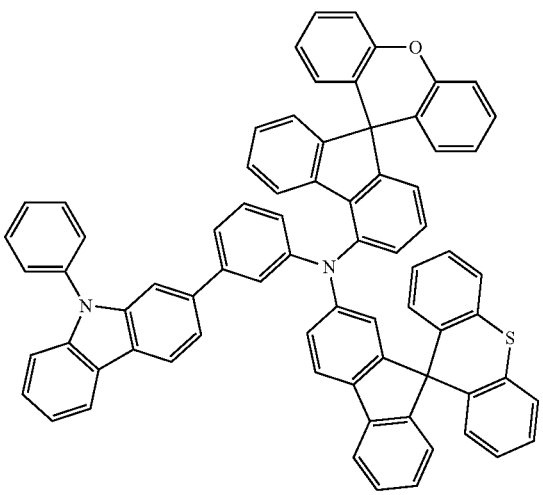

799
-continued
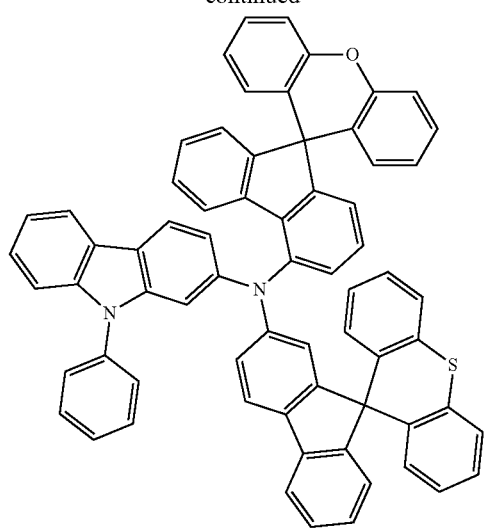
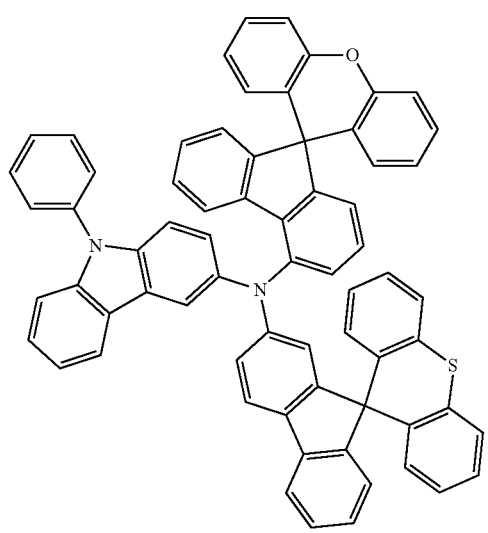
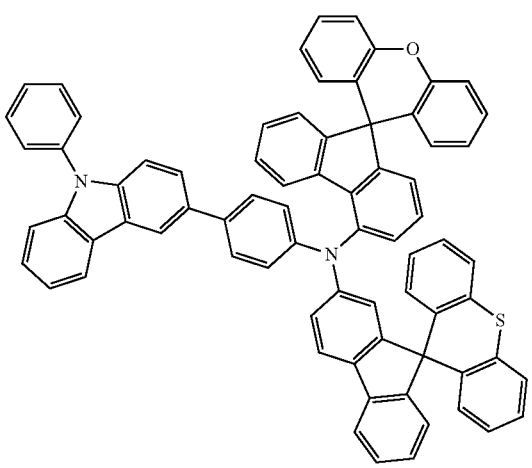
800
-continued
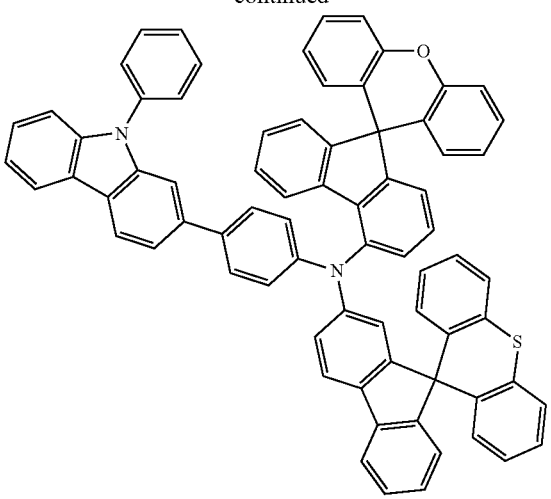
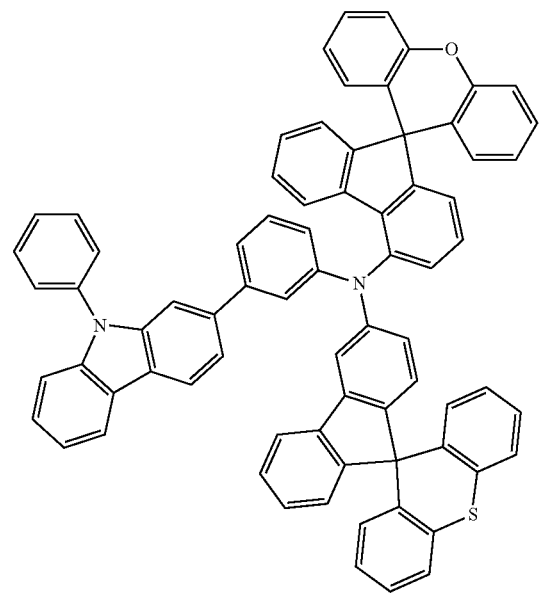
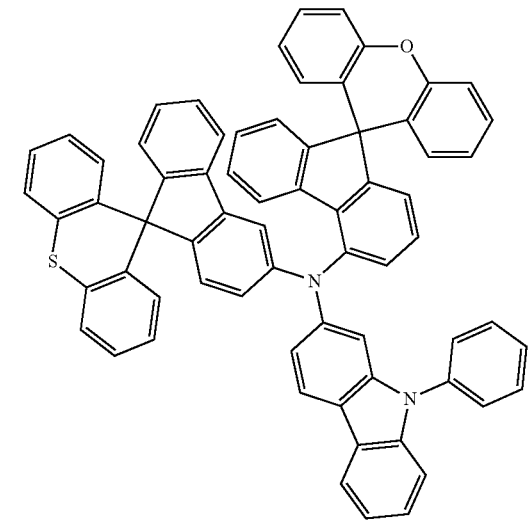

801
-continued
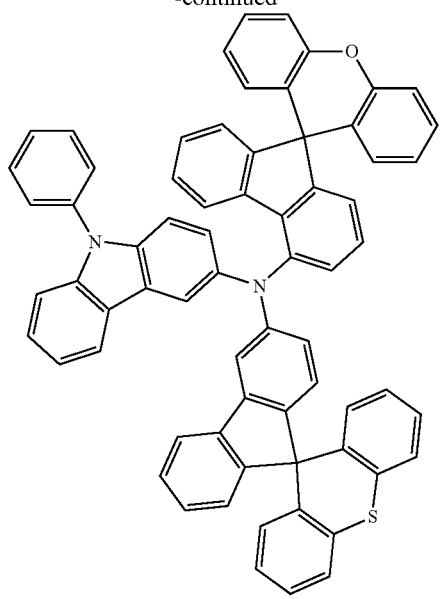
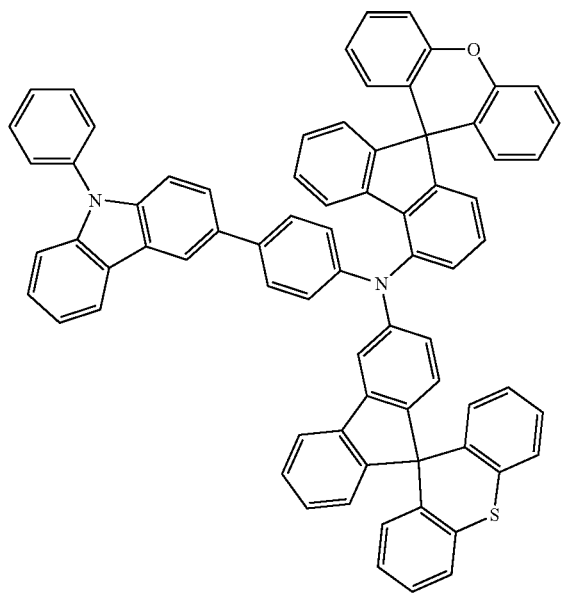
802
-continued
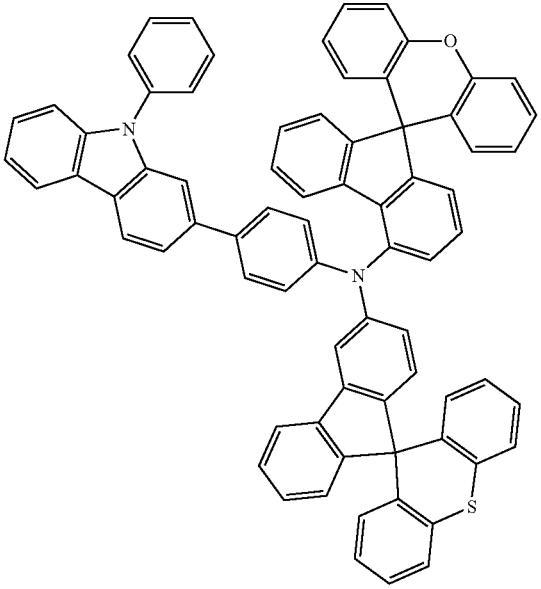
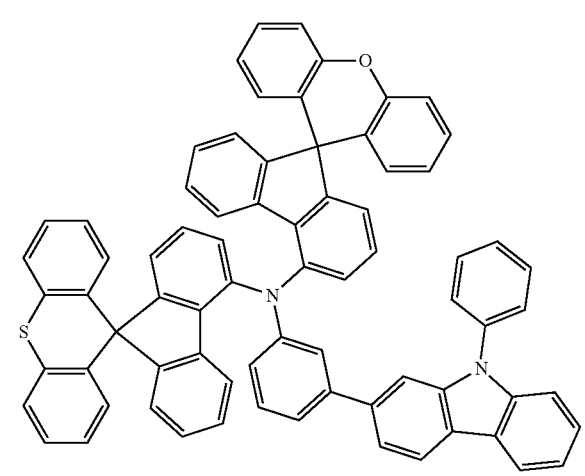
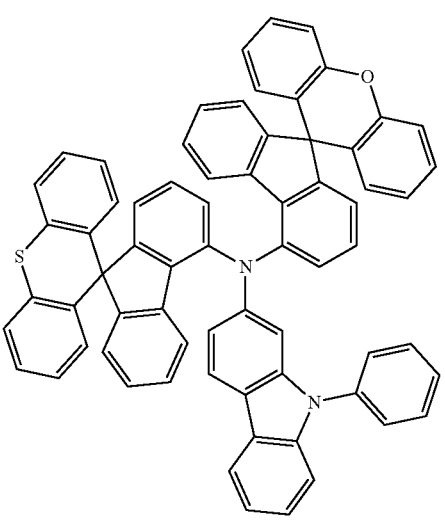

803
-continued
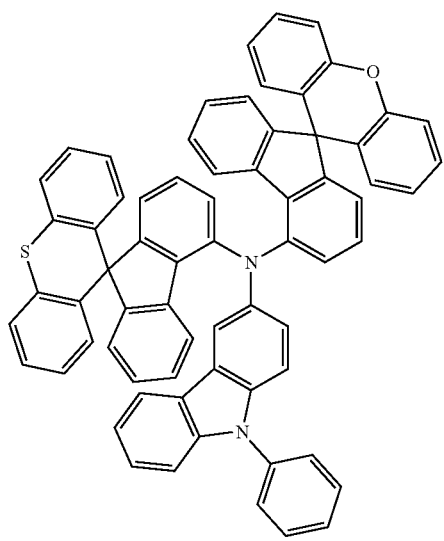
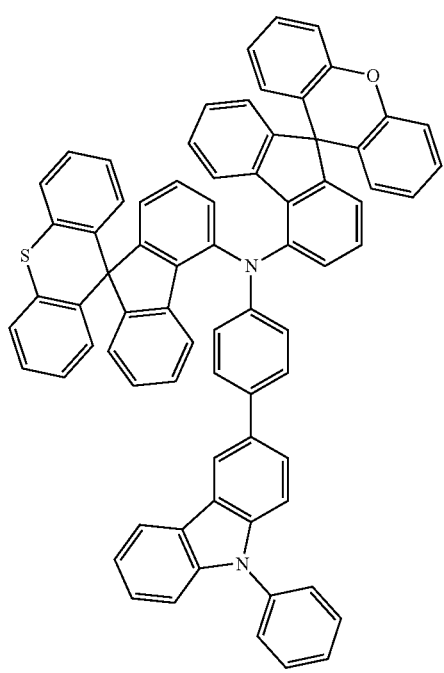
804
-continued
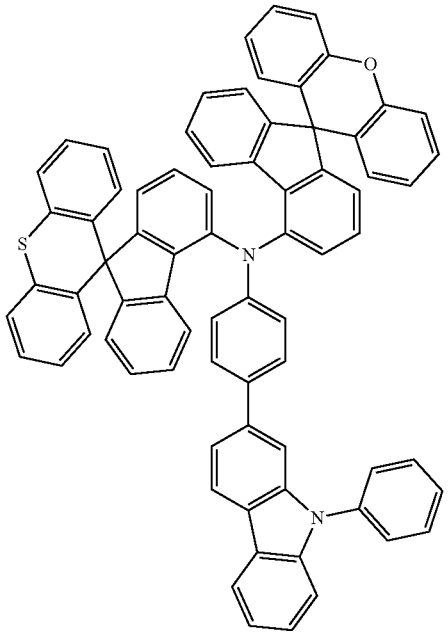
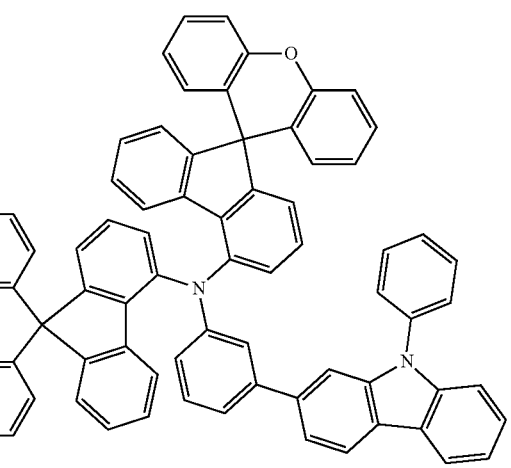
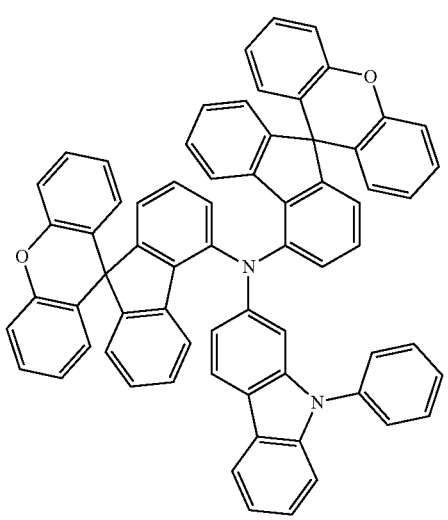

805
-continued
806
-continued
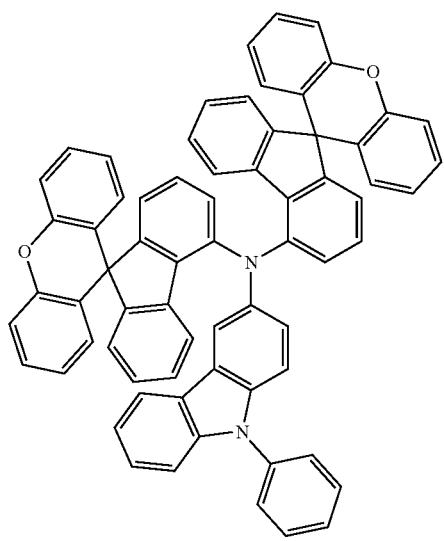
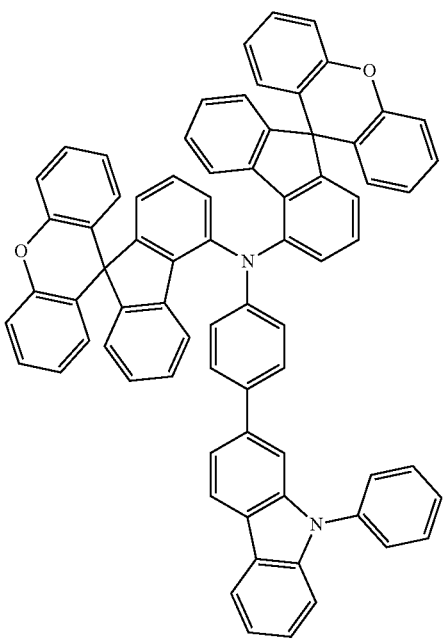
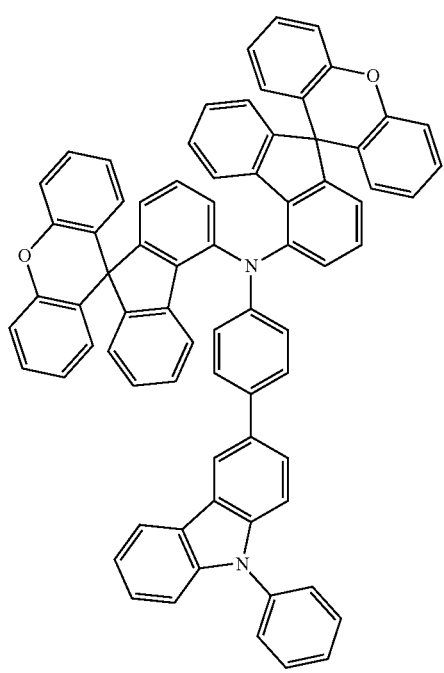
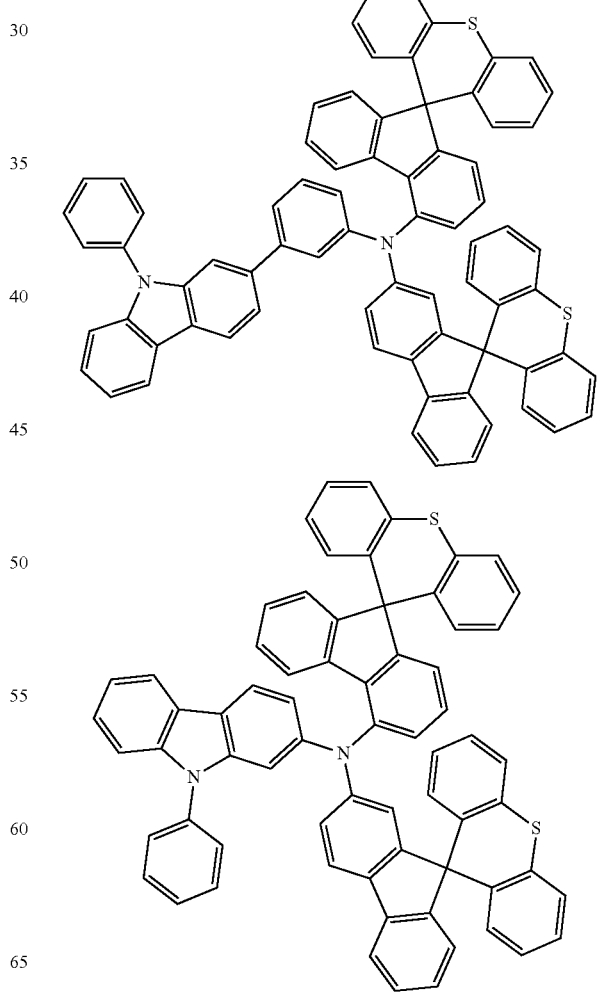

807
-continued
808
-continued
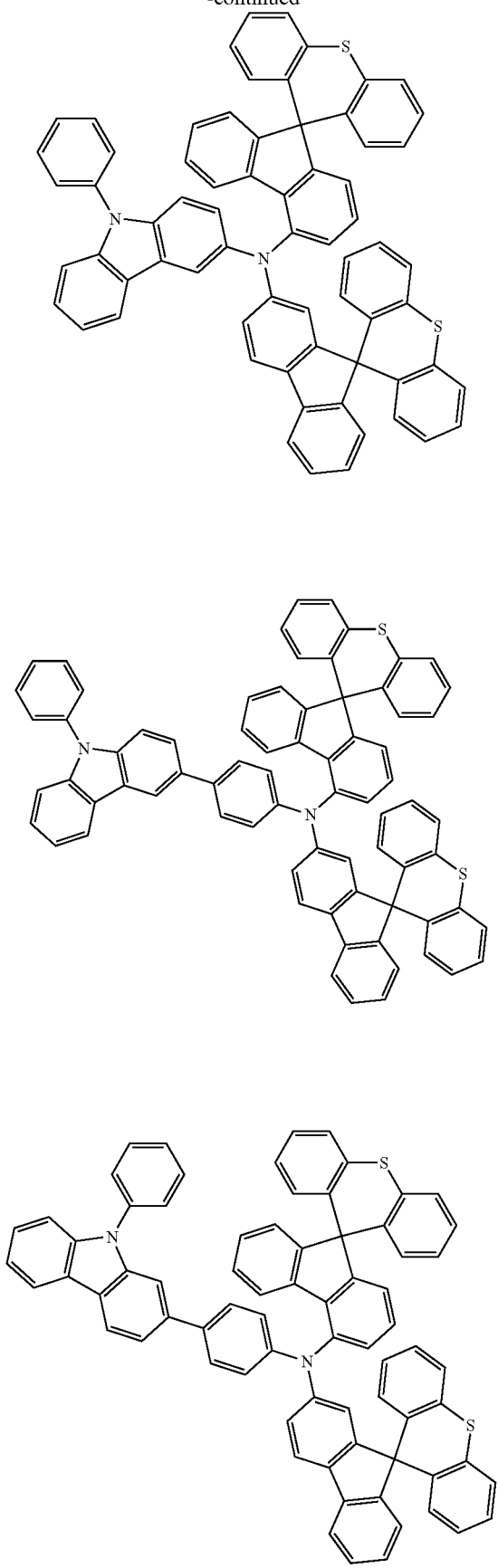
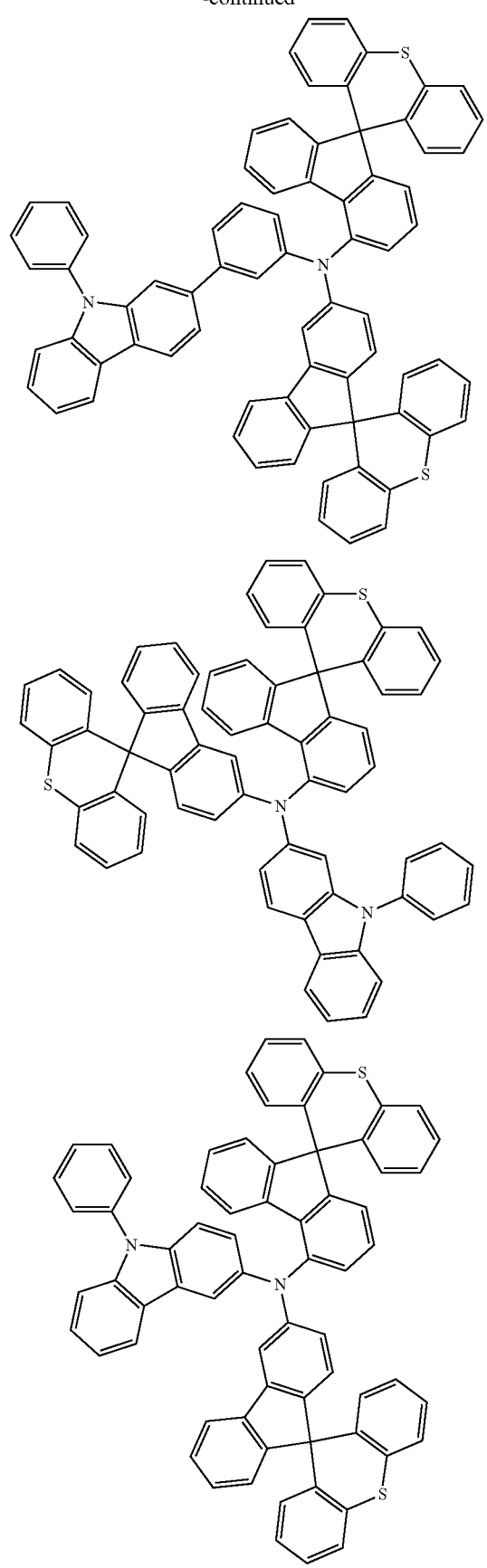

809
-continued
810
-continued
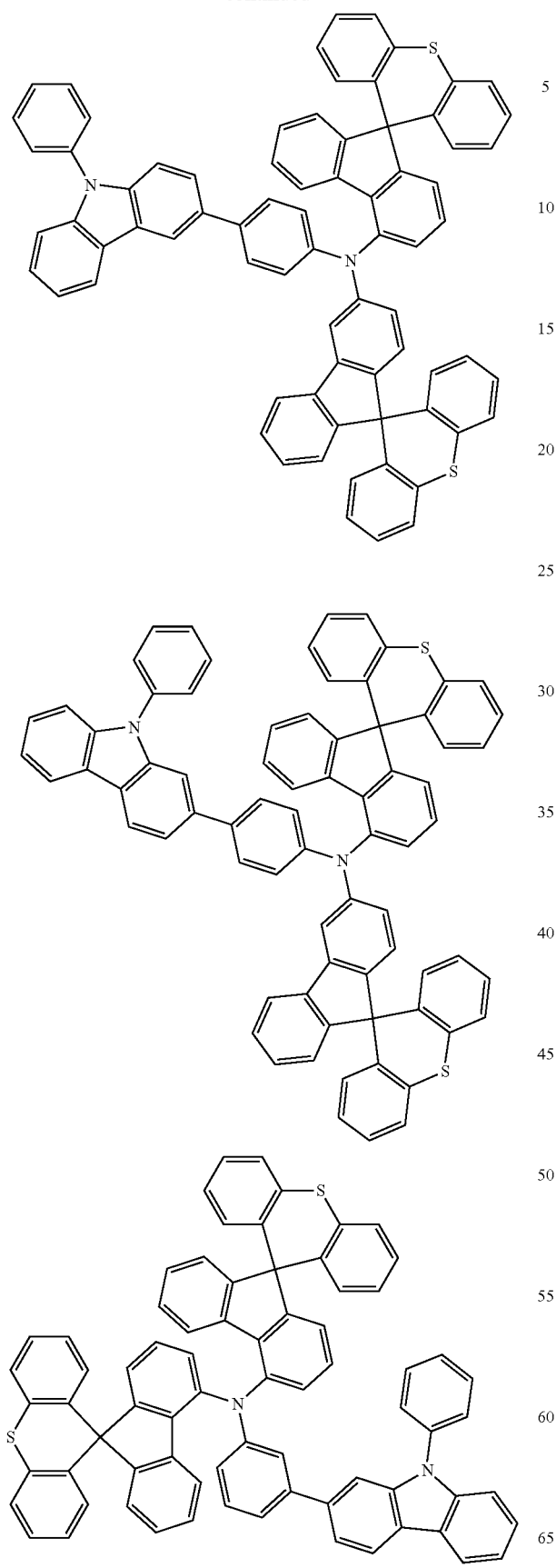
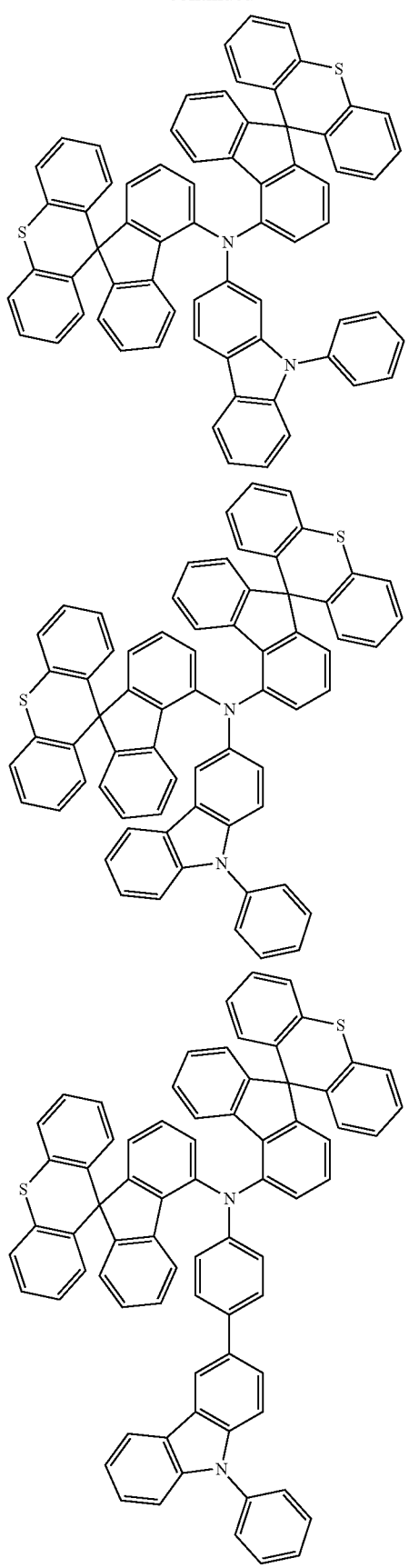

811
-continued
812
-continued
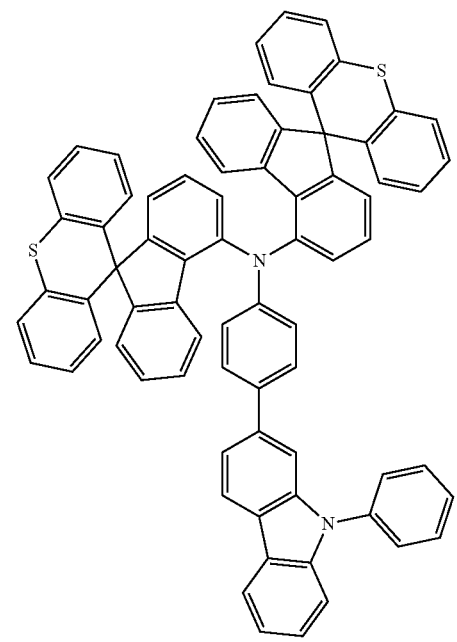
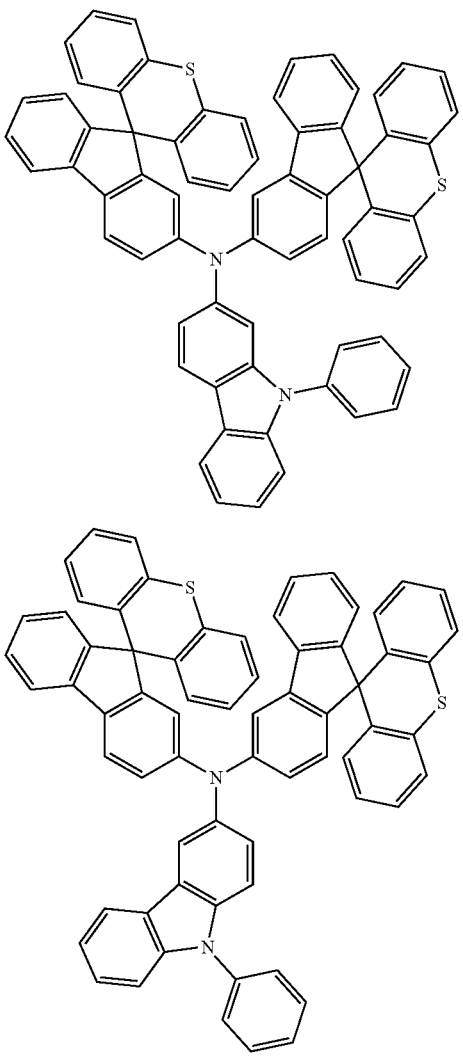
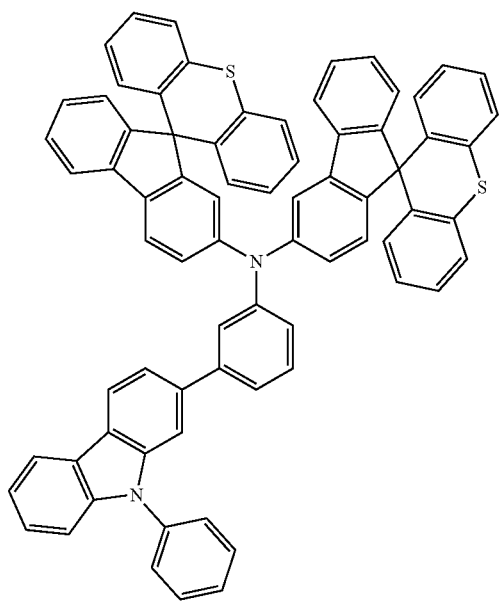
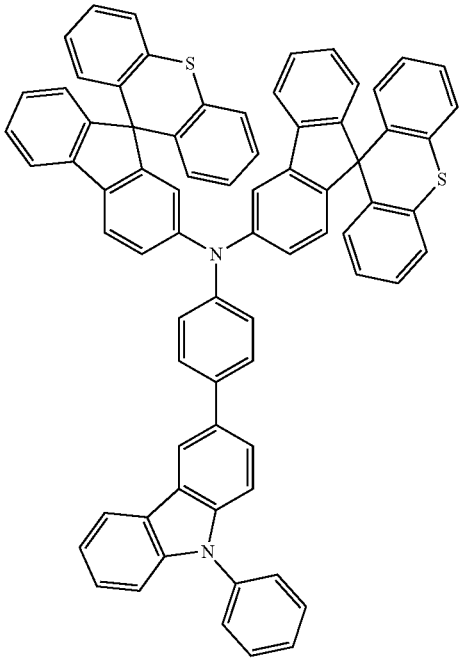

813
-continued
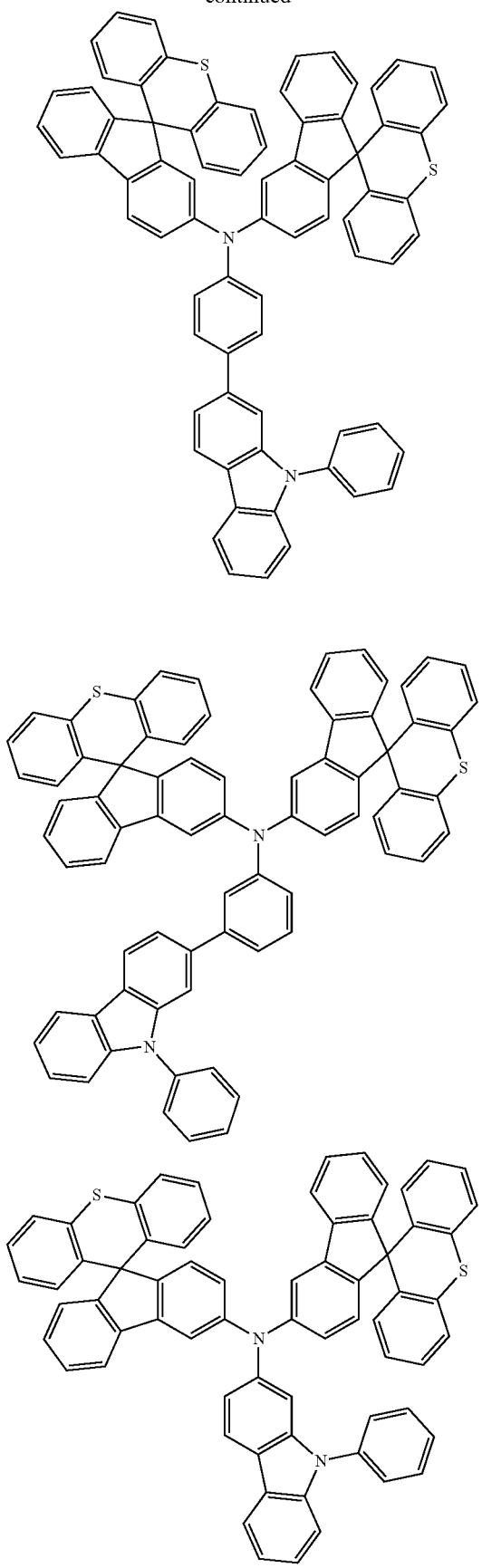
814
-continued
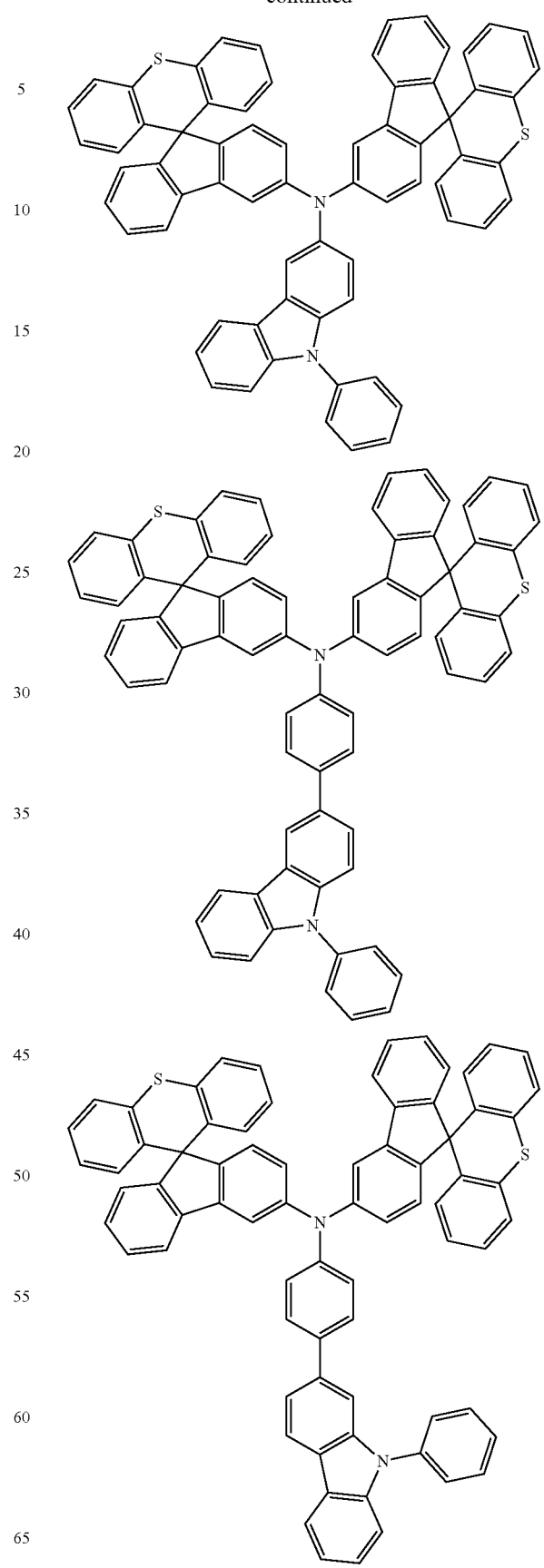

815
-continued

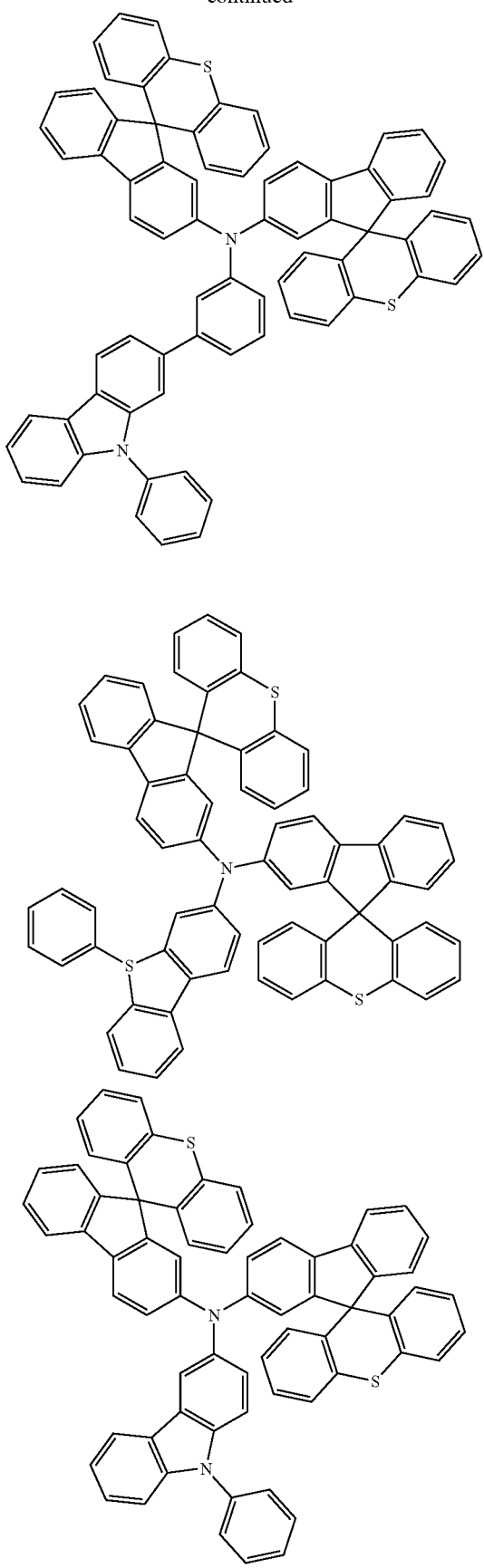

816
-continued

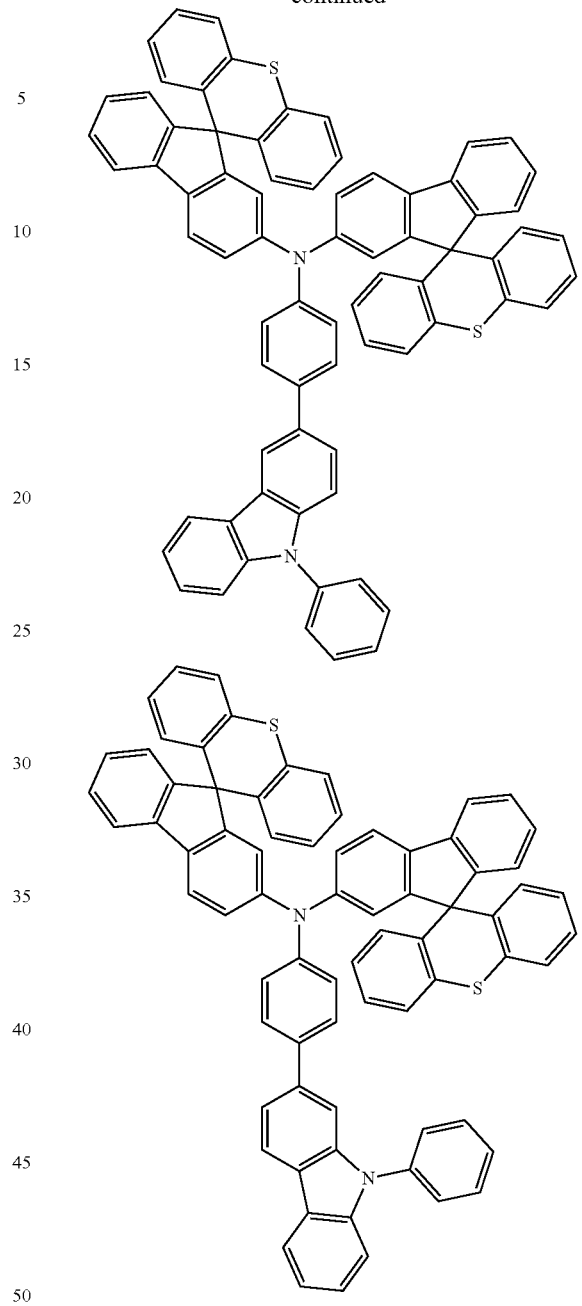

Material for Organic Electroluminescence Devices

The material for organic electroluminescence devices comprises the compound (1). The content of the compound (1) in the material for organic electroluminescence devices is, but not particularly limited, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic electroluminescences is useful for the production of an organic EL device.

Organic Electroluminescence Device

The organic EL device of the invention will be described below.

The organic EL device comprises an organic layer between a cathode and an anode. The organic layer comprises a light emitting layer and at least one layer of the organic layer comprises the compound (1).

Examples of the organic layer which comprises the compound (1) include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The compound (1) is used for the production of a fluorescent or phosphorescent EL device as a material for a hole transporting region or a light emitting layer, preferably as a material for a hole transporting region, and more preferably as a material for a hole transporting layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a laminated structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer(/Electron transporting layer/Electron injecting layer);

(b) (Hole injecting layer/)Hole transporting layer/Phosphorescent emitting layer(/Electron transporting layer/Electron injecting layer);

(c) (Hole injecting layer/)Hole transporting layer/First fluorescent emitting layer/Second fluorescent emitting layer (/Electron transporting layer/Electron injecting layer);

(d) (Hole injecting layer/)Hole transporting layer/First phosphorescent emitting layer/Second phosphorescent emitting layer(/Electron transporting layer/Electron injecting layer);

(e) (Hole injecting layer/)Hole transporting layer/Phosphorescent emitting layer/Space layer/Fluorescent emitting layer(/Electron transporting layer/Electron injecting layer);

(f) (Hole injecting layer/)Hole transporting layer/First phosphorescent emitting layer/Second phosphorescent emitting layer/Space layer/Fluorescent emitting layer(/Electron transporting layer/Electron injecting layer);

(g) (Hole injecting layer/)Hole transporting layer/First phosphorescent emitting layer/Space layer/Second phosphorescent emitting layer/Space layer/Fluorescent emitting layer(/Electron transporting layer/Electron injecting layer);

(h) (Hole injecting layer/)Hole transporting layer/Phosphorescent emitting layer/Space layer/First fluorescent emitting layer/Second fluorescent emitting layer(/Electron transporting layer/Electron injecting layer);

(i) (Hole injecting layer/)Hole transporting layer/Electron blocking layer/Fluorescent emitting layer(/Electron transporting layer/Electron injecting layer);

(j) (Hole injecting layer/)Hole transporting layer/Electron blocking layer/Phosphorescent emitting layer(/Electron transporting layer/Electron injecting layer);

(k) (Hole injecting layer/)Hole transporting layer/Exciton blocking layer/Fluorescent emitting layer(/Electron transporting layer/Electron injecting layer);

(l) (Hole injecting layer/)Hole transporting layer/Exciton blocking layer/Phosphorescent emitting layer(/Electron transporting layer/Electron injecting layer);

(m) (Hole injecting layer/)First hole transporting layer/Second hole transporting layer/Fluorescent emitting layer (/Electron transporting layer/Electron injecting layer);

(n) (Hole injecting layer/)First hole transporting layer/Second hole transporting layer/Fluorescent emitting layer(/First electron transporting layer/Second electron transporting layer/Electron injecting layer);

(o) (Hole injecting layer/)First hole transporting layer/Second hole transporting layer/Phosphorescent emitting layer (/Electron transporting layer/Electron injecting layer);

(p) (Hole injecting layer/)First hole transporting layer/Second hole transporting layer/Phosphorescent emitting layer (/First electron transporting layer/Second electron transporting layer/Electron injecting layer);

(q) (Hole injecting layer/)Hole transporting layer/Fluorescent emitting layer/Hole blocking layer(/Electron transporting layer/Electron injecting layer/Electron injecting layer);

(r) (Hole injecting layer/)Hole transporting layer/Phosphorescent emitting layer/Hole blocking layer(/Electron transporting layer/Electron injecting layer);

(s) (Hole injecting layer/)Hole transporting layer/Fluorescent emitting layer/Triplet blocking layer(/Electron transporting layer/Electron injecting layer); and (t) (Hole injecting layer/)Hole transporting layer/Phosphorescent emitting layer/Triplet blocking layer(/Electron transporting layer/Electron injecting layer).

The emission colors of two or more phosphorescent emitting layers may be different, and the emission color of the fluorescent emitting layer and that of the phosphorescent emitting layer may be different. For example, the emission unit (f) may be Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

A schematic structure of an example of the organic EL device is shown in FIG. 1, wherein the organic EL device 1 comprises a substrate 2, an anode 3, a cathode 4, and an emission unit (organic layer) 10 disposed between the anode 3 and the cathode 4. The emission unit 10 comprises a light emitting layer 5. A hole transporting region 6 (for example, a hole injecting layer or a hole transporting layer) may be disposed between the light emitting layer 5 and the anode 3, and an electron transporting region 7 (for example, an electron injecting layer or an electron transporting layer) may be disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
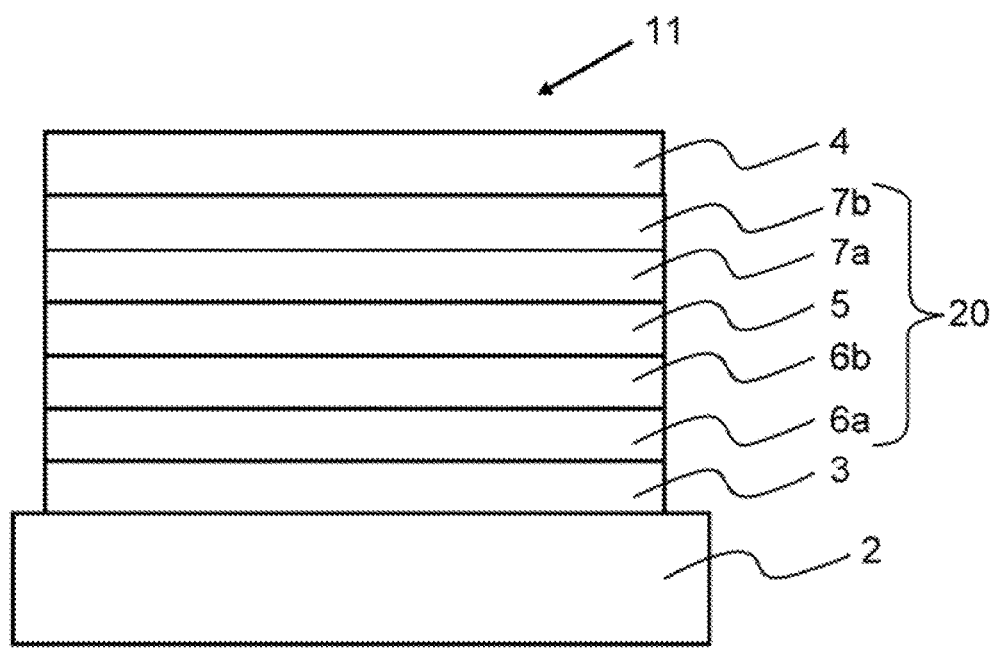
FIG. 2 is a schematic view showing the structure of an organic EL device in another embodiment of the invention.

FIG. 2 is a schematic illustration showing the structure of another example of the organic EL device, wherein the hole transporting region 6 and the electron transporting region shown in FIG. 1 are made into two-layered structure, respectively. The anode-side hole transporting region 6a may be called a first hole transporting layer and the cathode-side hole transporting region 6b may be called a second hole transporting layer. The anode-side electron transporting region 7a may be called a first electron transporting layer and the cathode-side electron transporting region 7b may be called a second electron transporting layer.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold, platinum, nickel, tungsten, chromium, molybdenum, iron, cobalt, copper, palladium, titanium, and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function, for example, an alkali metal, such as lithium and cesium, an alkaline earth metal, such as magnesium, calcium, and strontium, and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material).

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4''-tris(N,N-diphenylamino)triphenylamine (TDATA), 4,4',4''-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis [N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly [N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used:

(K)

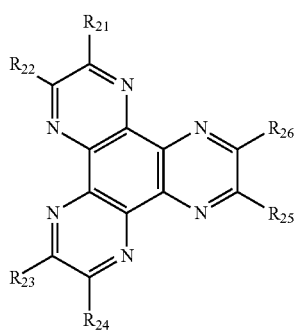

wherein:

$R_{21}$ to $R_{26}$ may be the same or different and each of $R_{21}$ to $R_{26}$ is independently a cyano group, —CONH$_2$, a carboxyl group, or —COOR$_{27}$ wherein $R_{27}$ is an alkyl group having 1 to 20 carbon atoms or a cycloalkyl group having 3 to 20 ring carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

In addition, the compound represented by formula (2-1) or (2-2) is preferably used as the hole injecting layer material:

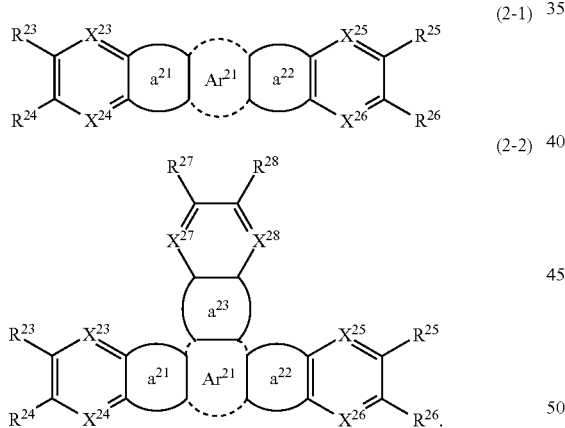

(2-1)

(2-2)

In formulae (2-1) and (2-2), $Ar^{21}$ is a substituted or unsubstituted aromatic hydrocarbon ring having 6 to 30 ring carbon atoms or a substituted or unsubstituted aromatic heterocyclic ring having 5 to 30 ring atoms. The aromatic hydrocarbon ring is preferably a benzene ring. The aromatic heterocyclic ring is preferably a ring having 6 ring atoms, such as a pyridine ring, a pyrazine ring, or a pyridazine ring.

Each of $X^{23}$ to $X^{28}$ is independently C(R) or a nitrogen atom.

Each R is independently a hydrogen atom, a halogen atom, a hydroxyl group, a cyano group, a substituted or unsubstituted alkyl group having 1 to 30 carbon atoms, a substituted or unsubstituted aryl group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, an alkoxy group having a substituted or unsubstituted alkyl group having 1 to 30 carbon atoms, an aryloxy group having a substituted or unsubstituted aryl group having 6 to 30 ring carbon atoms, a mono- or di-substituted amino group having a substituent selected from a substituted or unsubstituted alkyl group having 1 to 30 carbon atoms and a substituted or unsubstituted aryl group having 6 to 30 ring carbon atoms, an alkylthio group having a substituted or unsubstituted alkyl group having 1 to 30 carbon atoms, an arylthio group having a substituted or unsubstituted aryl group having 6 to 30 ring carbon atoms, or a substituted or unsubstituted heteroaryl group having 5 to 30 ring atoms.

The details of the alkyl group, the aryl group, and the heteroaryl group are the same as the corresponding groups mentioned above with respect to the optional groups referred to by "substituted or unsubstituted."

Each of $a^{21}$ to $a^{23}$ is a ring structure represented by formula (2b):

(2b)

wherein $X^{20}$ is represented by any of formulae (2b-1) to (2b-12):

(2b-1)

(2b-2)

(2b-3)

(2b-4)

(2b-5)

(2b-6)

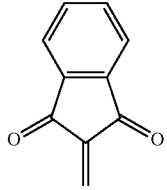

(2b-7)

-continued
(2b-8)
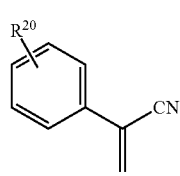
(2b-9)
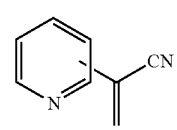
(2b-10)
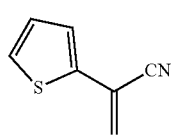
(2b-11)
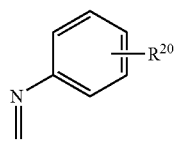
(2b-12)
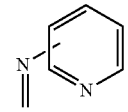
wherein $R^{20}$ has the same meaning as defined with respect to R.
Each of $R^{23}$ to $R^{28}$ independently has the same meaning as defined with respect to R.
Examples of the compound represented by formula (2-1) and (2-2) are shown below, although not limited thereto.
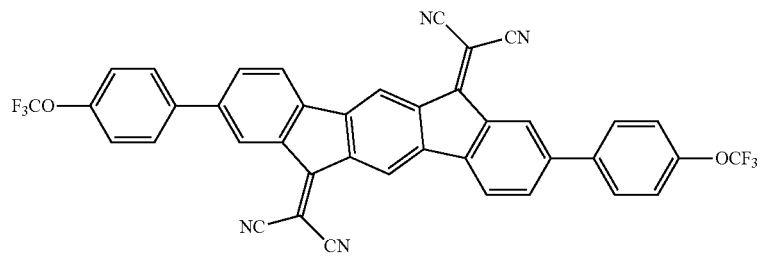
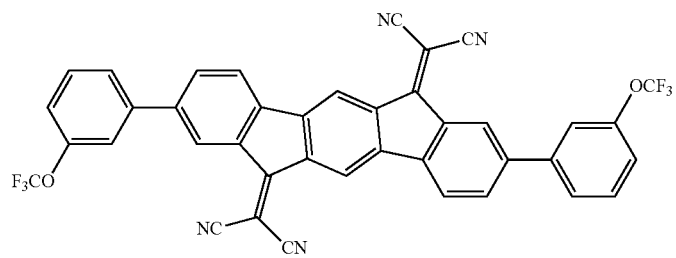
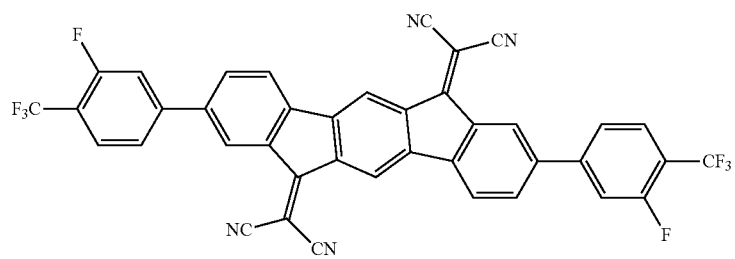
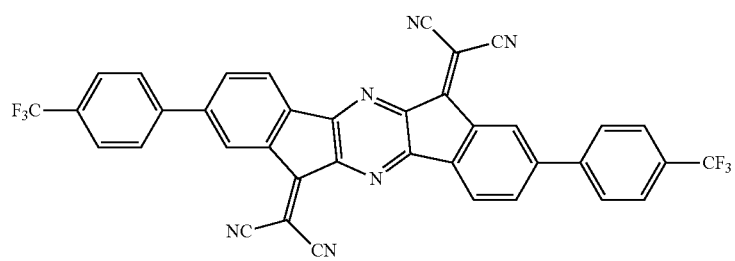

-continued
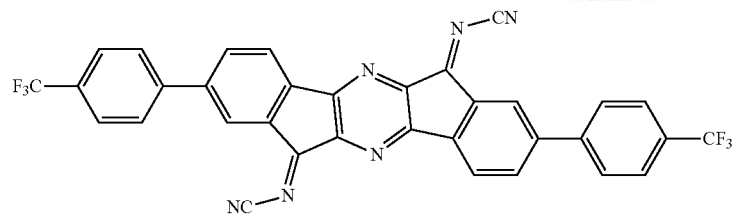
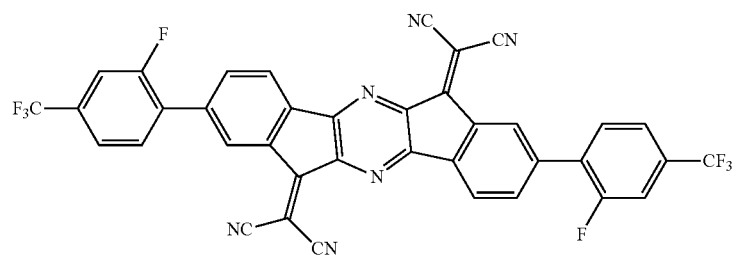
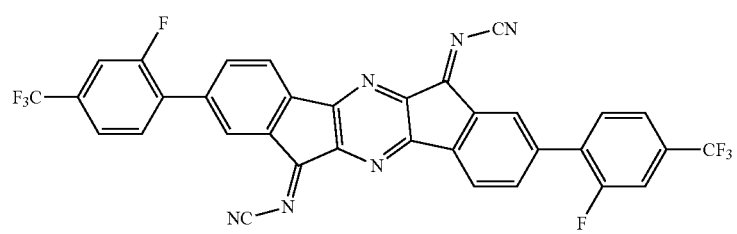
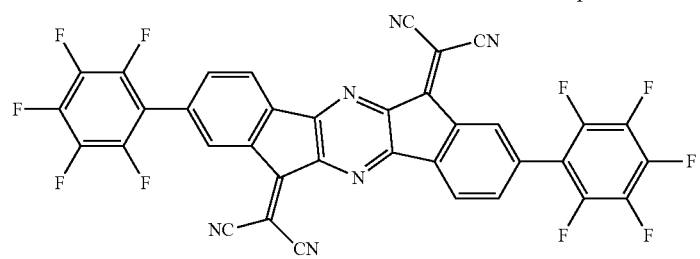
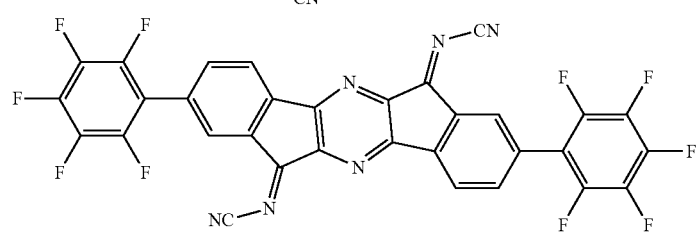
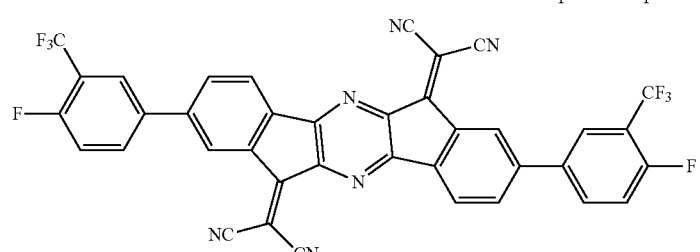
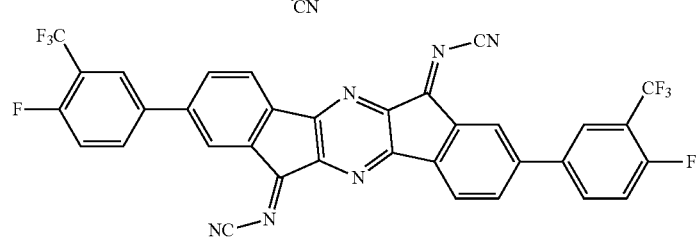

-continued
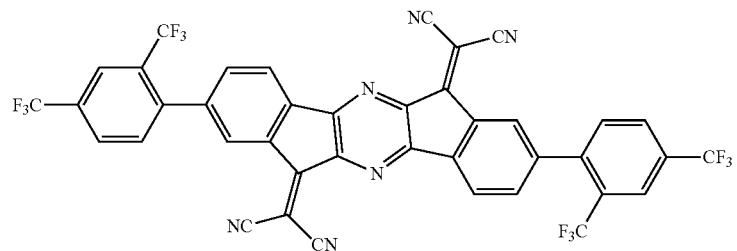
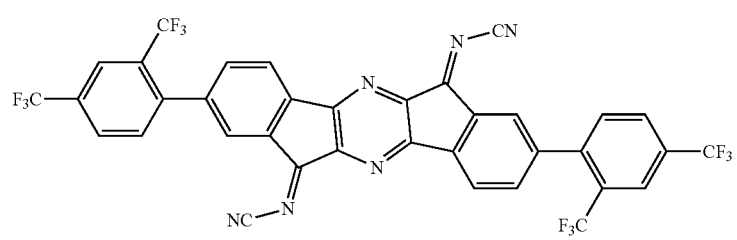
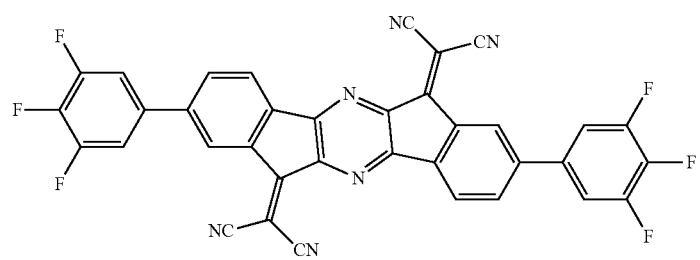
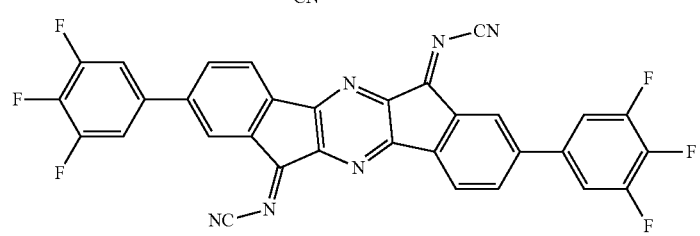
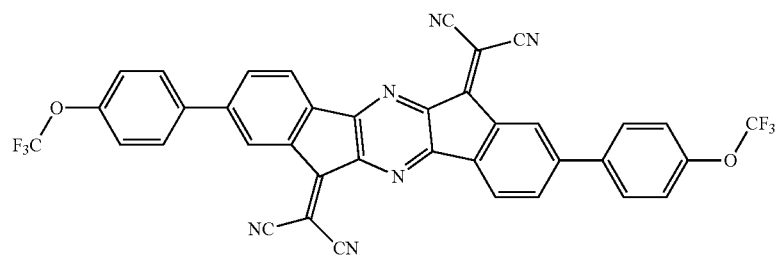
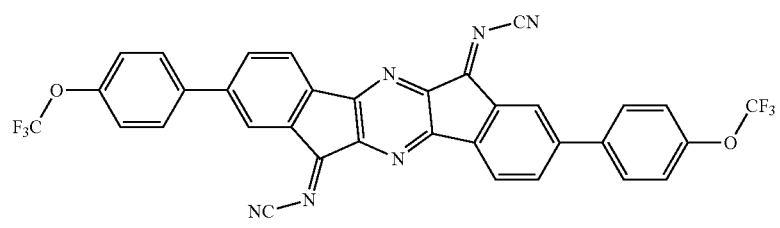
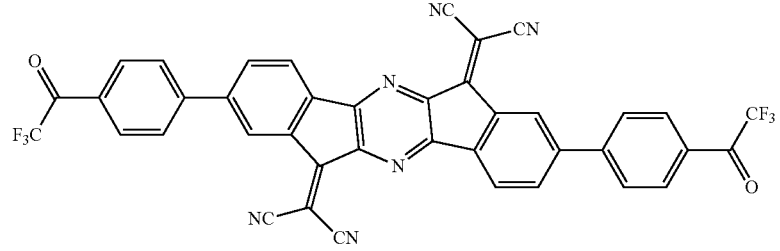

-continued
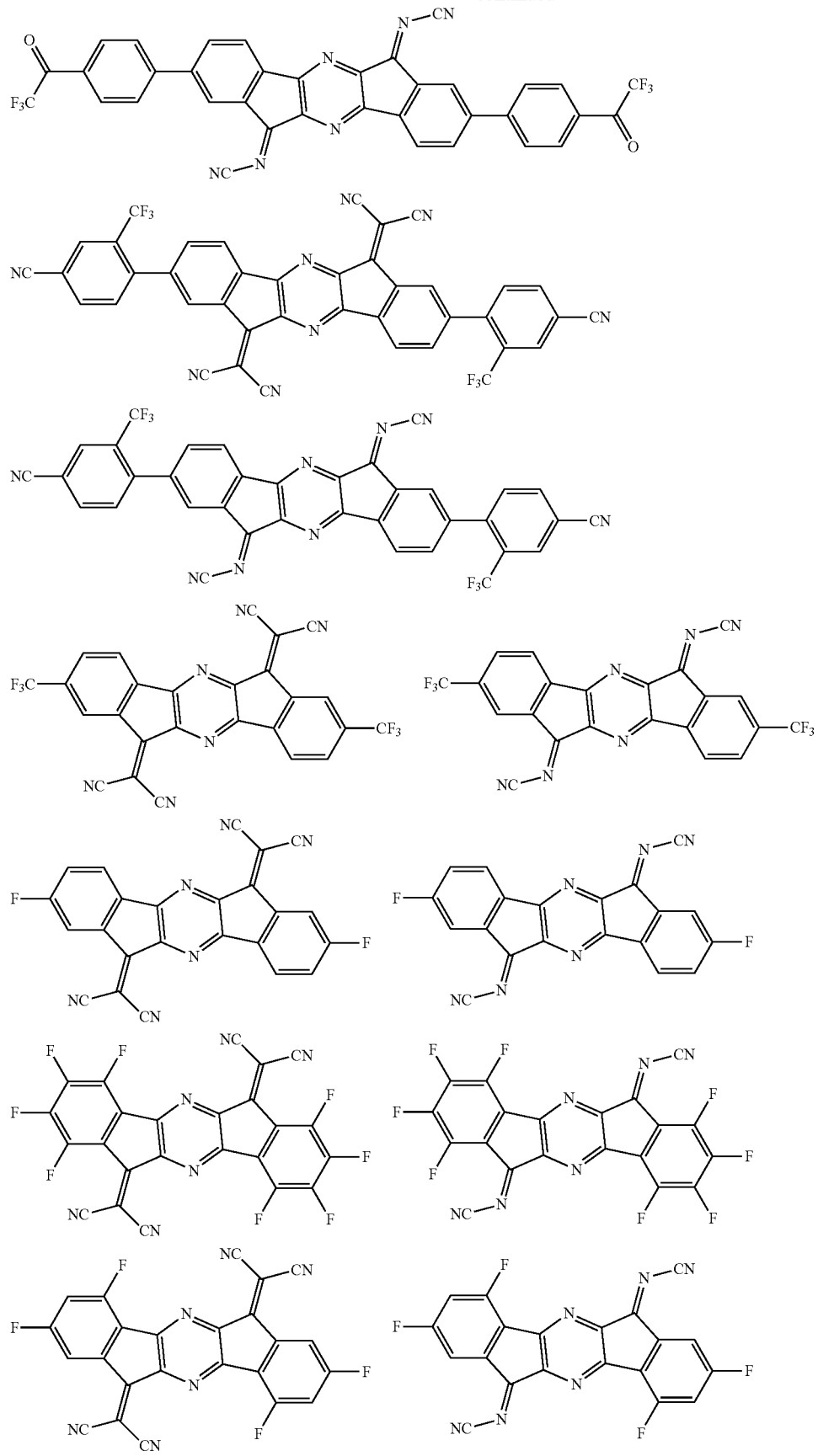

831
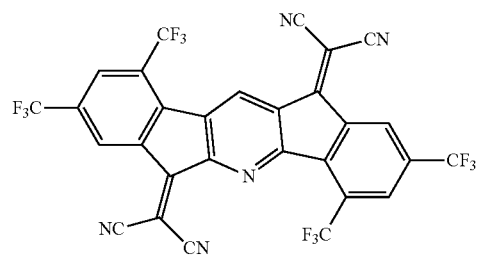
832
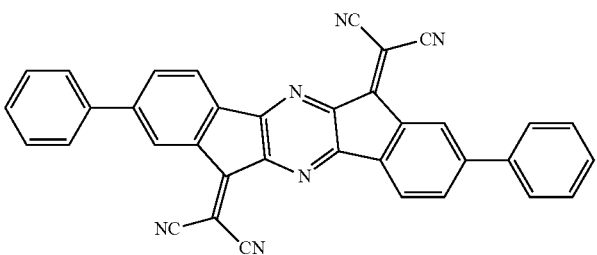
-continued
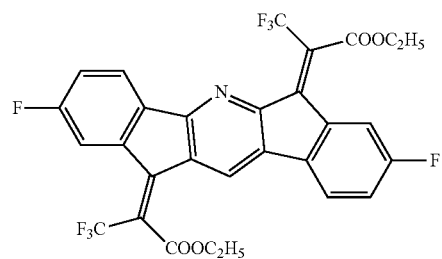
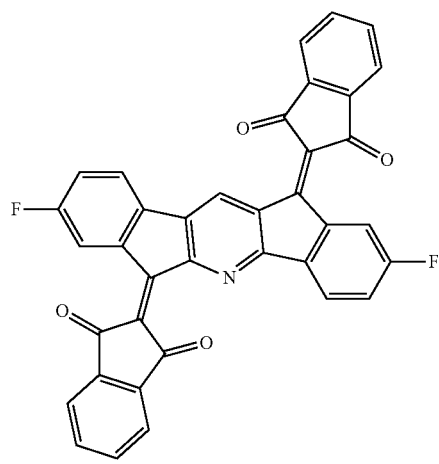
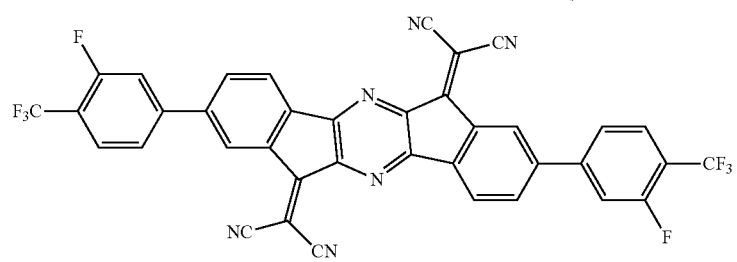
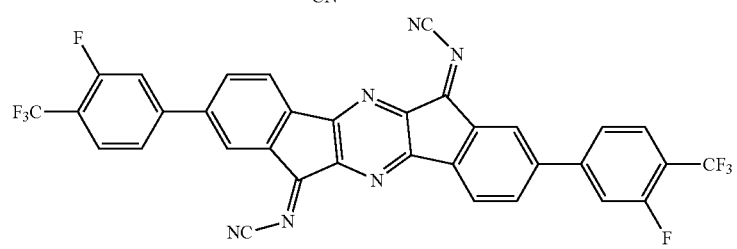
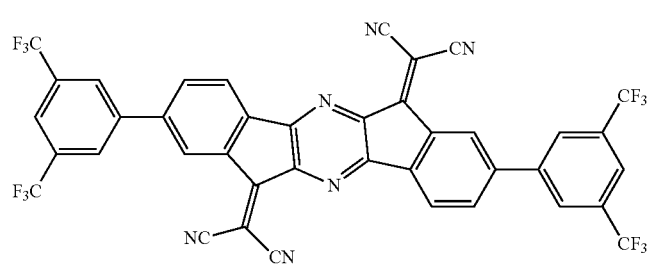
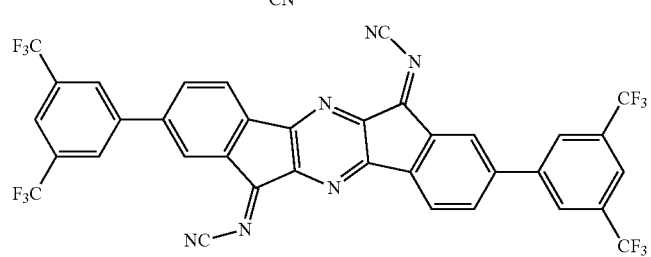

833                                                                 834
-continued
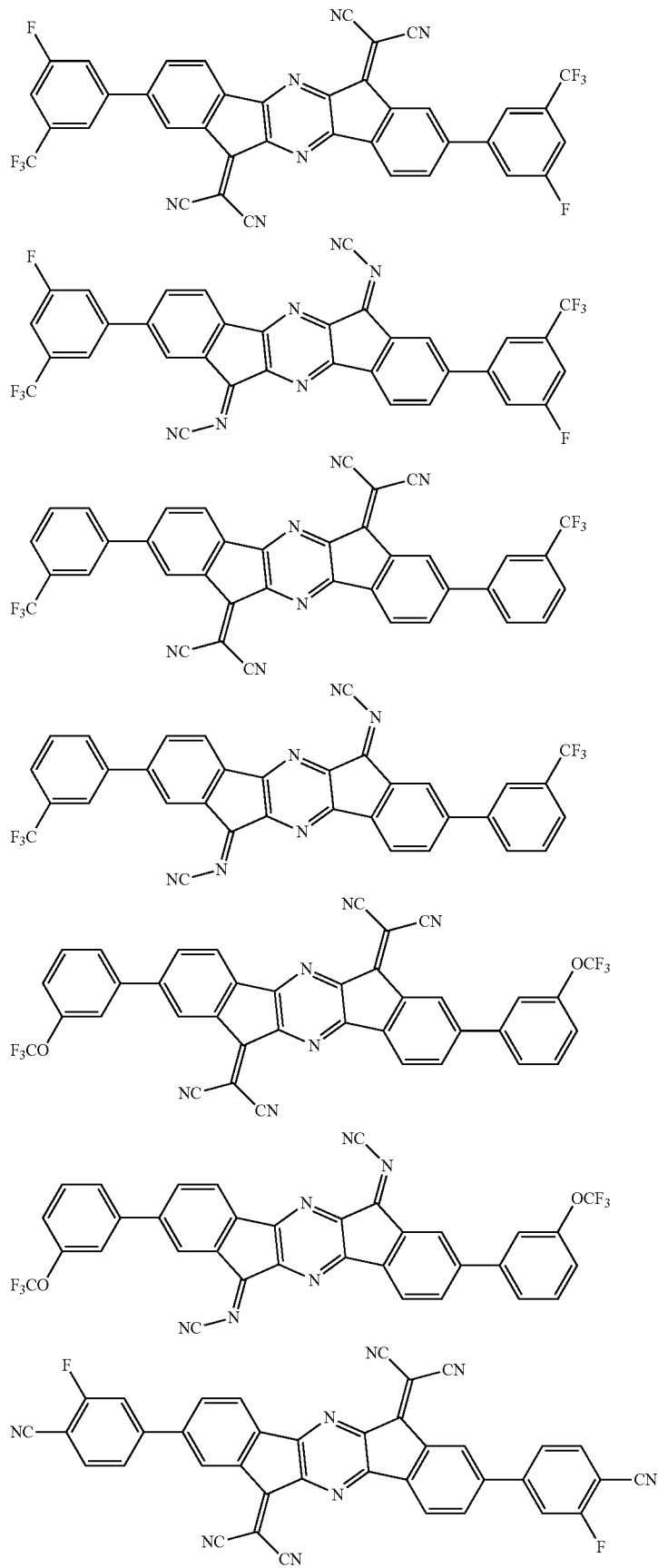

-continued
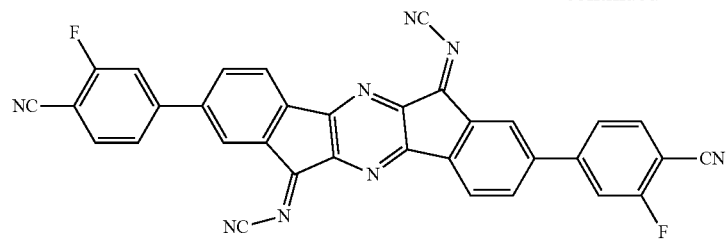
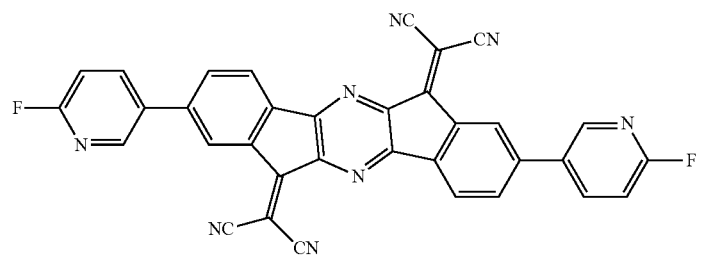
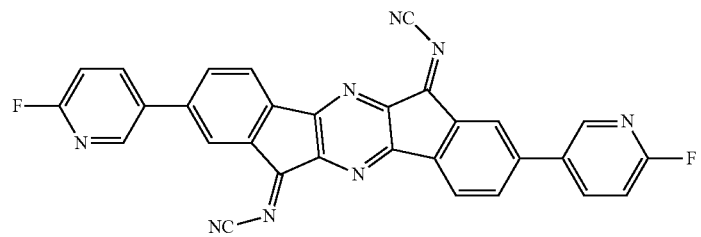
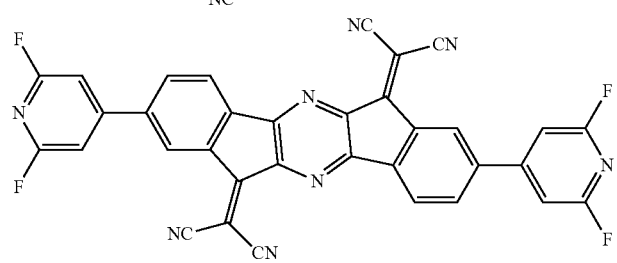
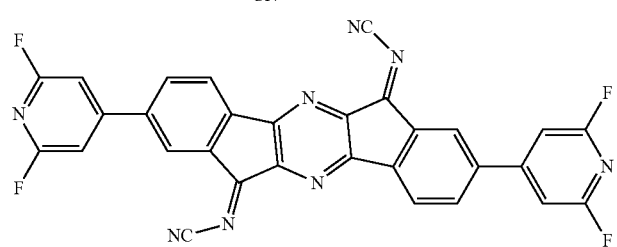
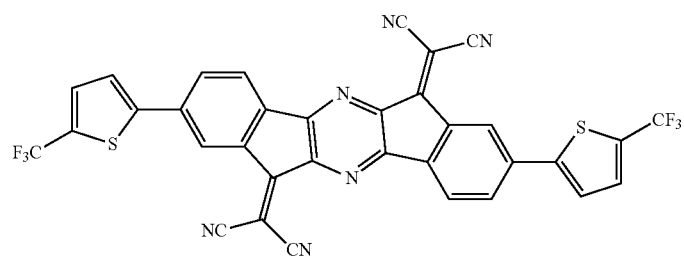
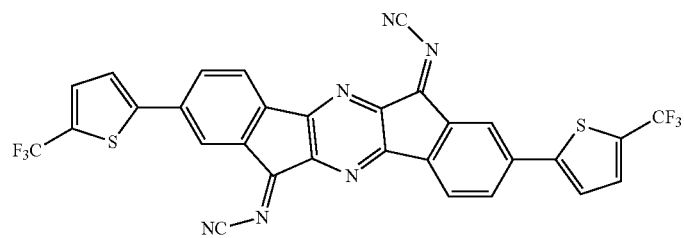

-continued
837
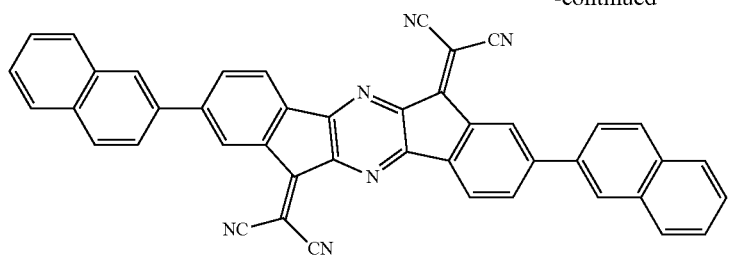
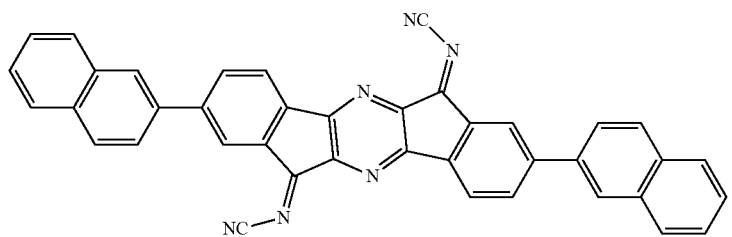
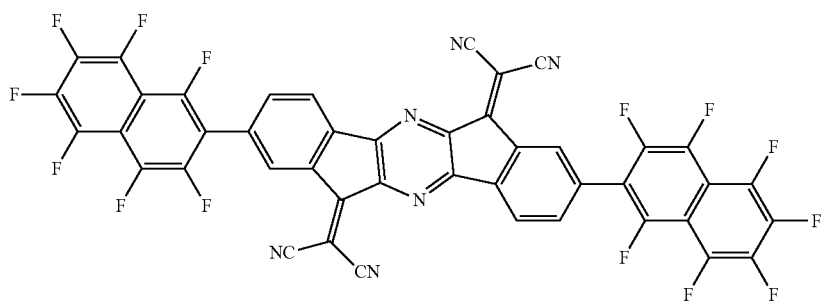
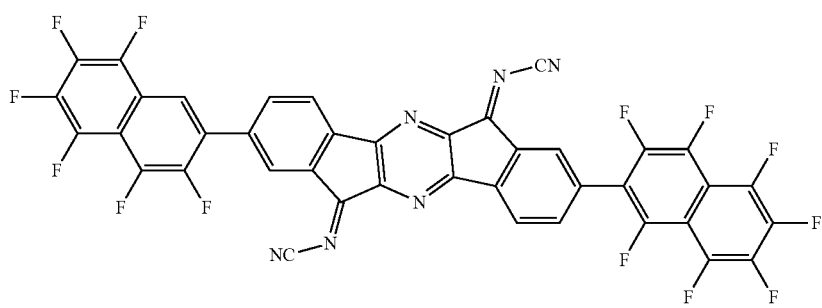
838
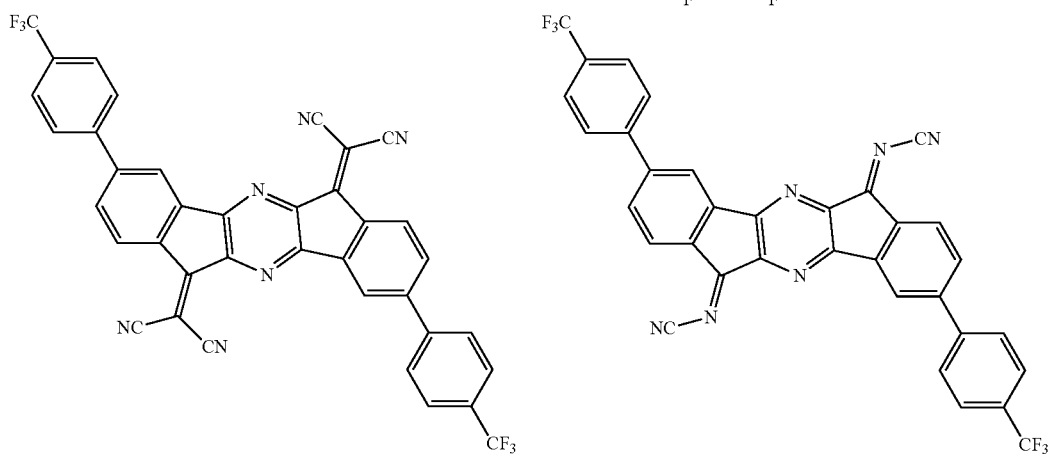

-continued
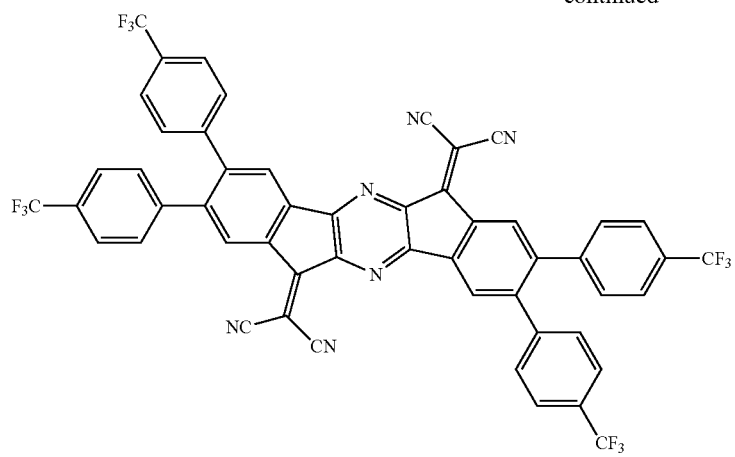
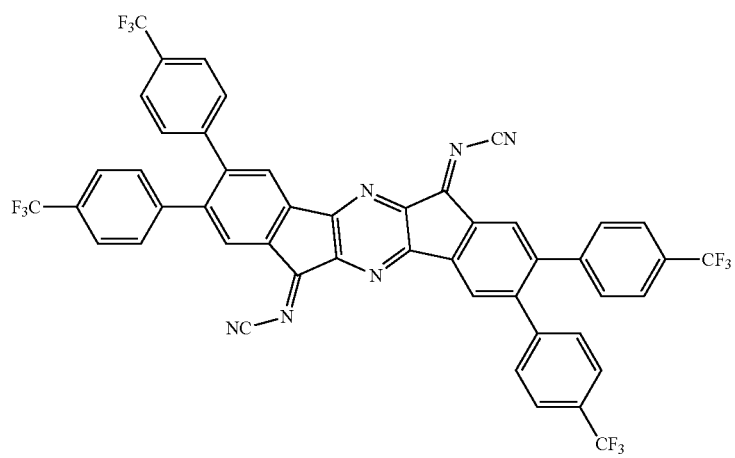
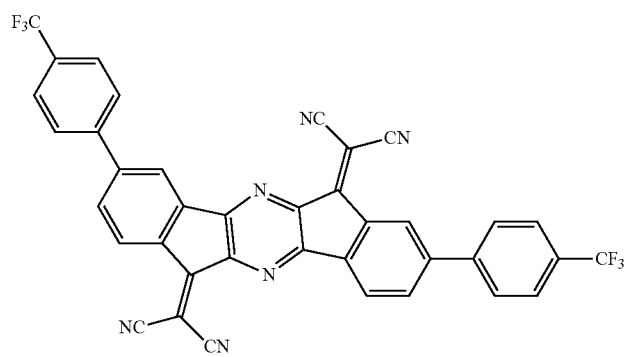
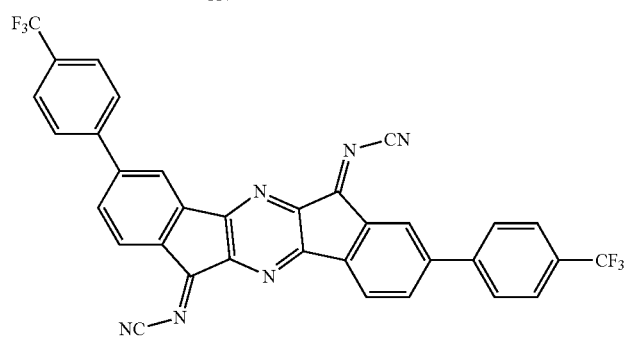

-continued
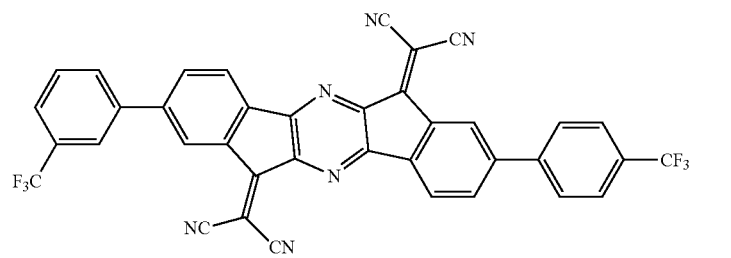
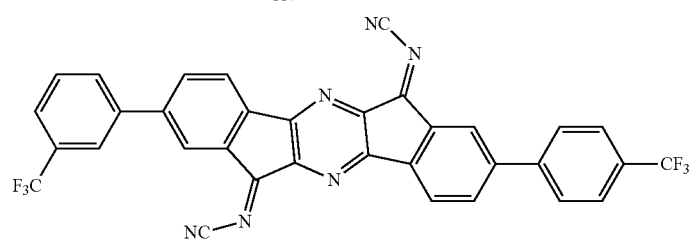
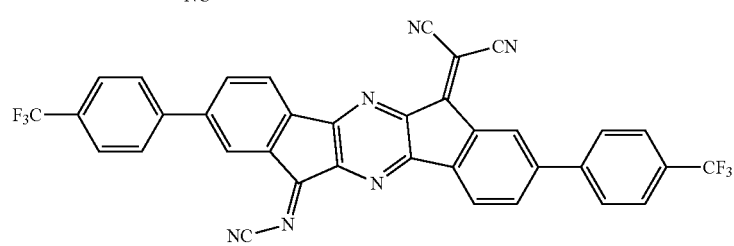
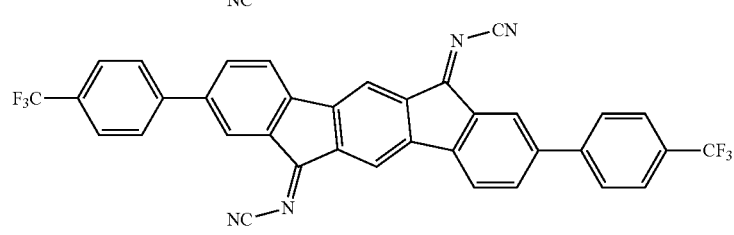
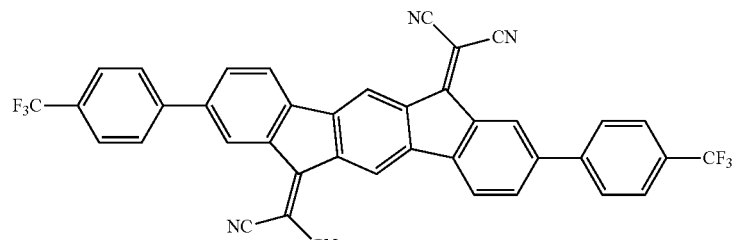
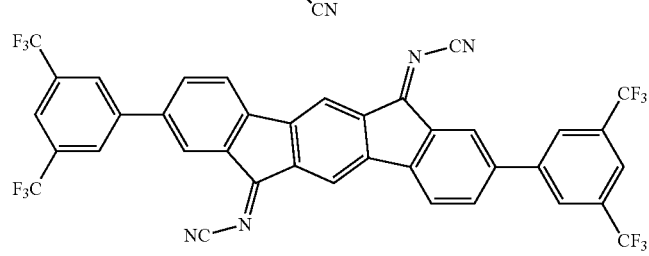
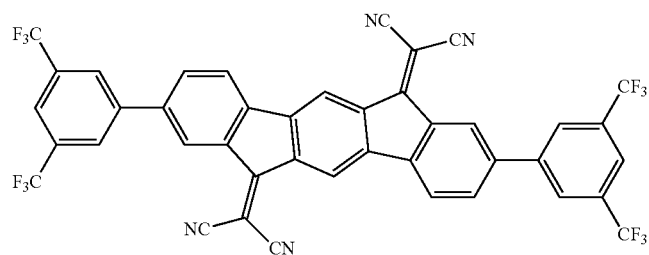

-continued
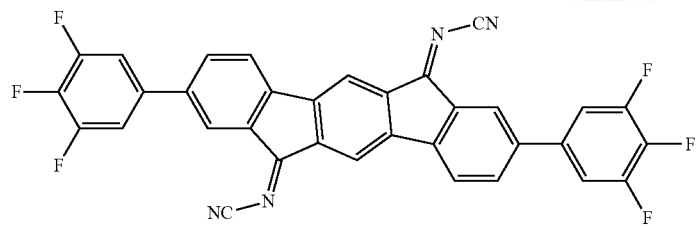
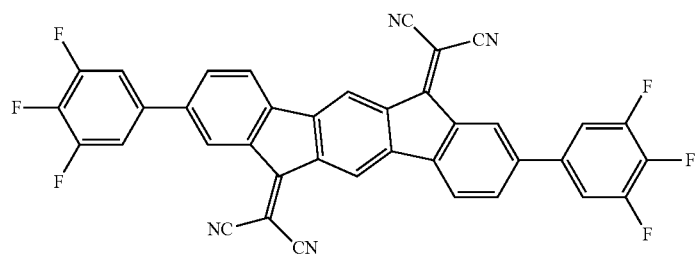
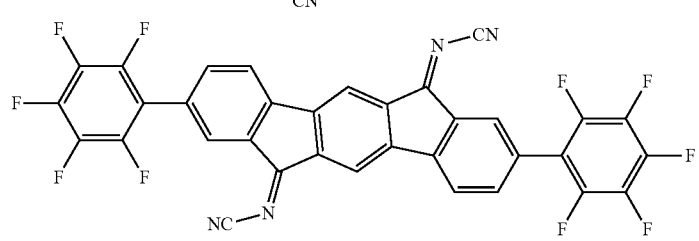
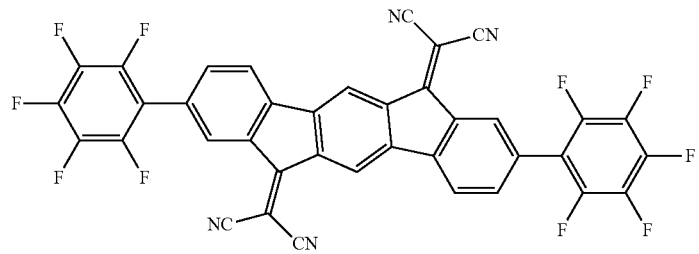
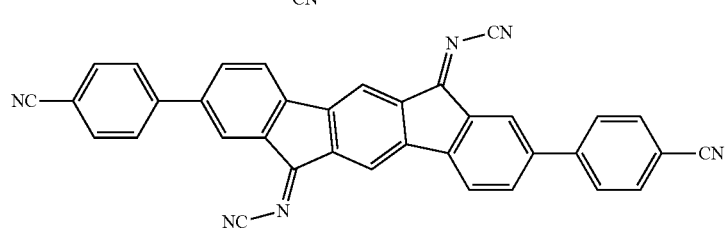
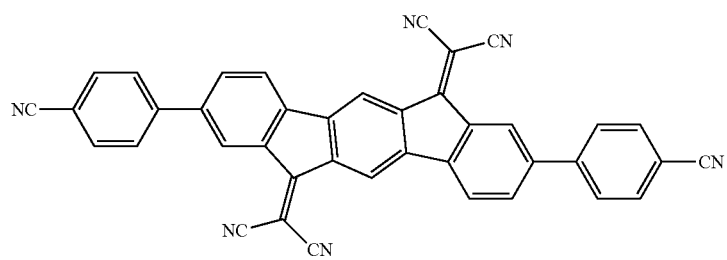
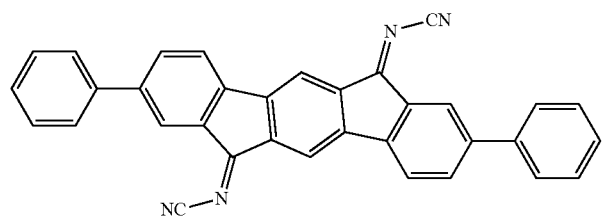

-continued
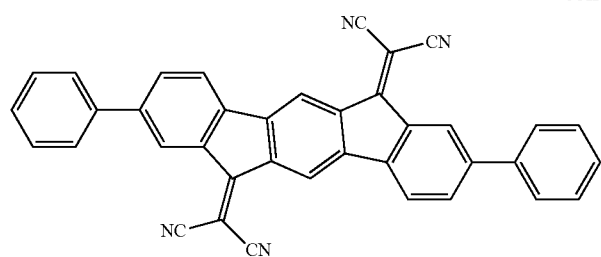
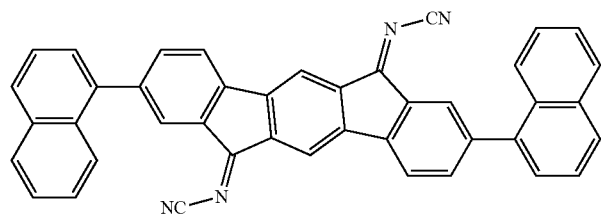
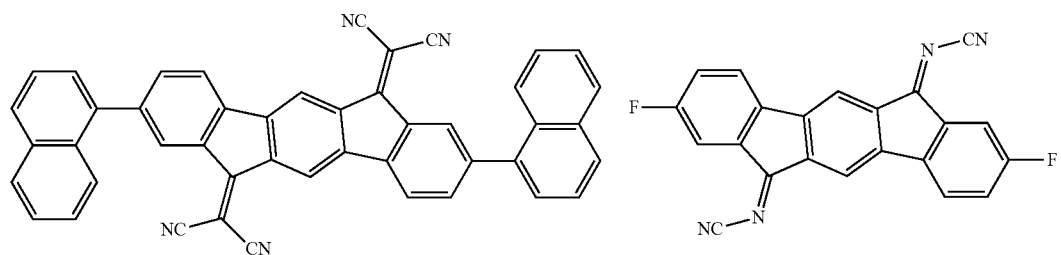
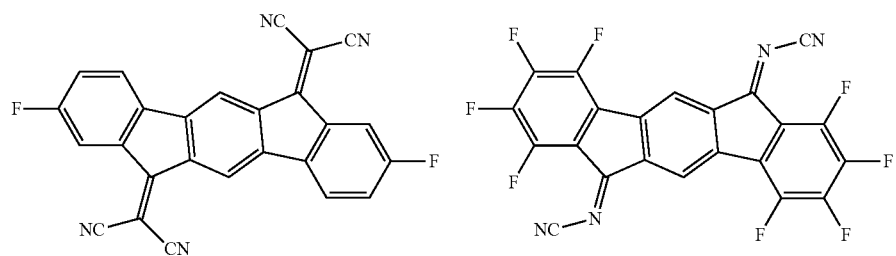
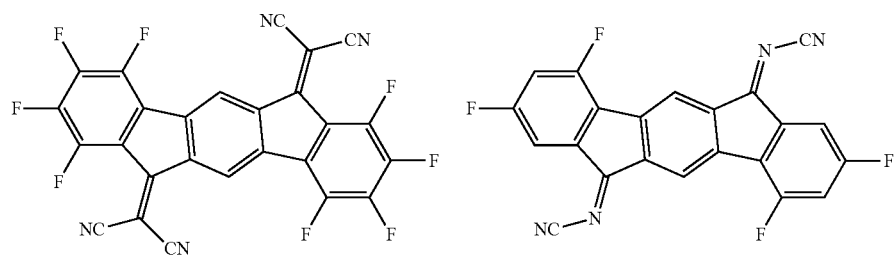
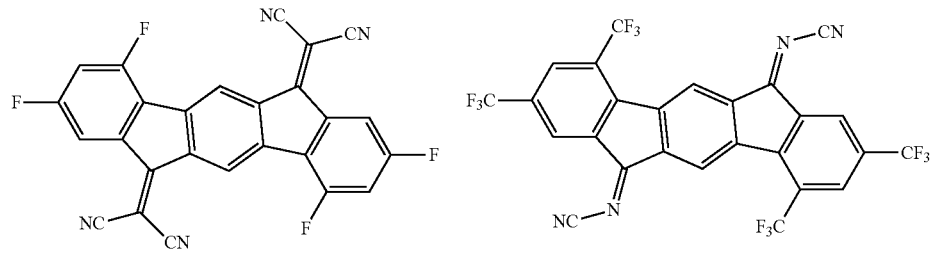

847
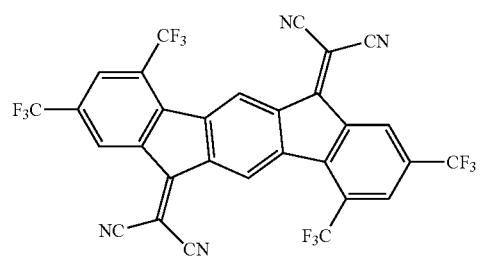
-continued
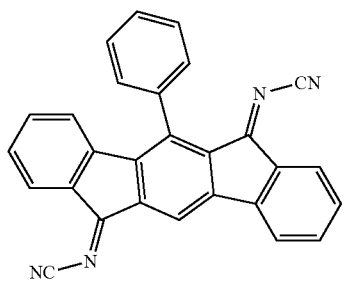
848
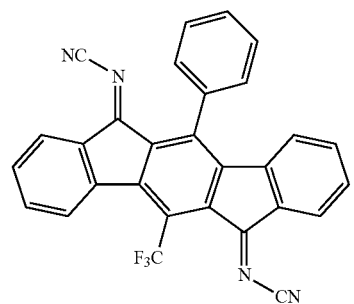
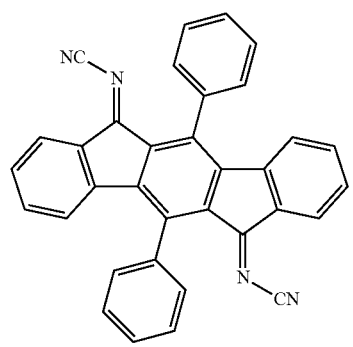
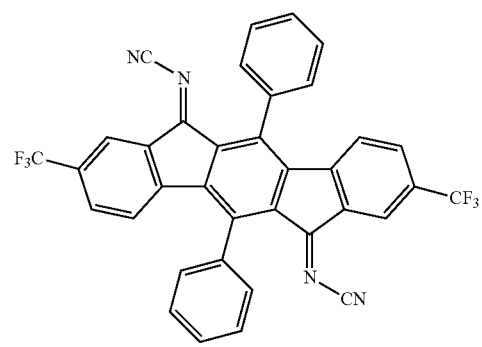
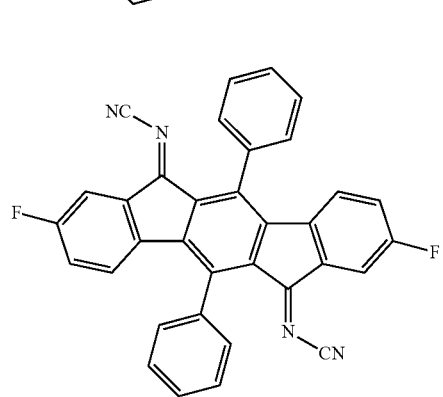
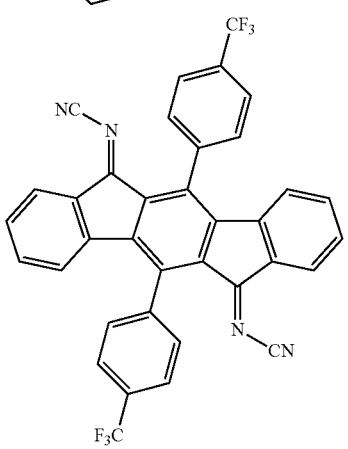
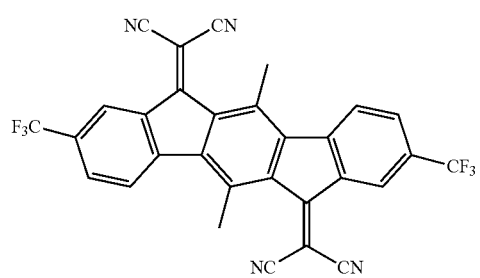
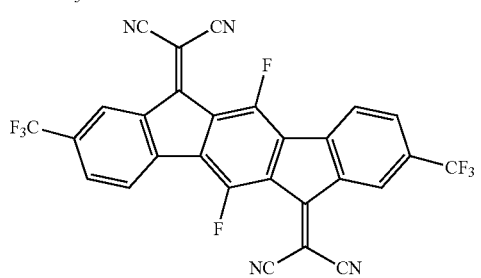
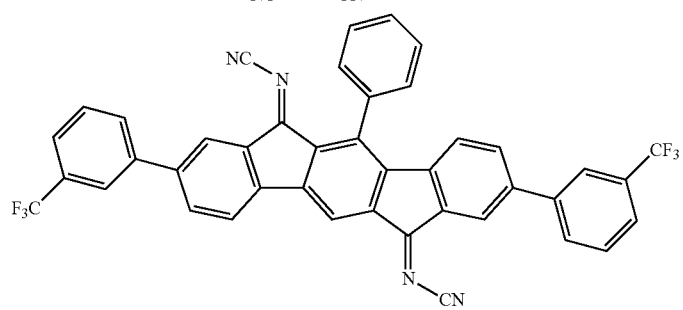

-continued
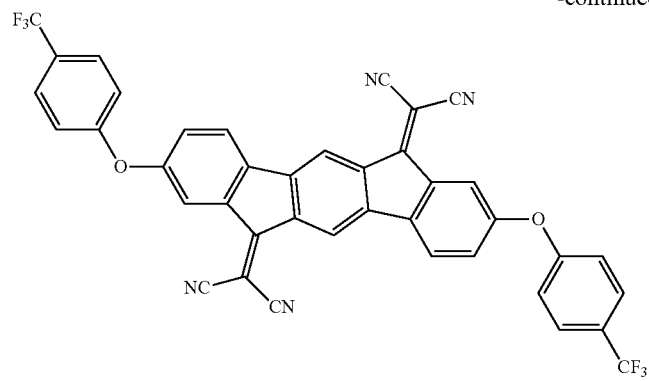
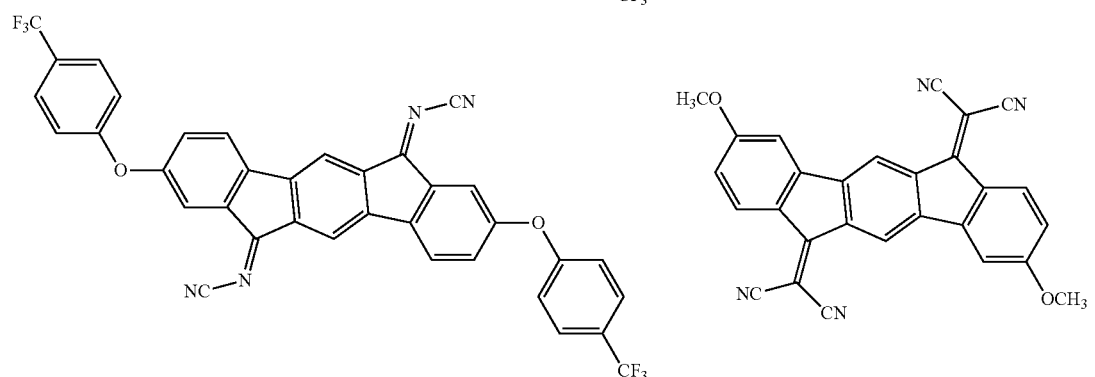
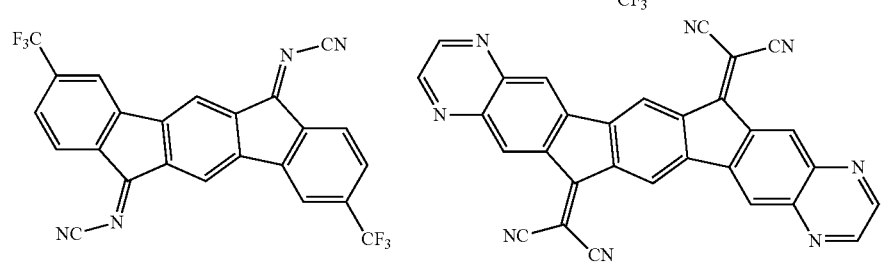
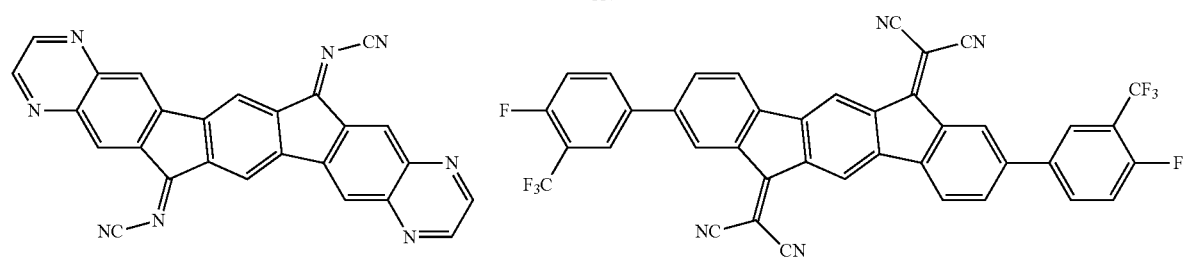 [SMILES: N#C/N=c1\c2cc3nccnc3cc2c2cc3/c(=N/C#N)c4cc5nccnc5cc4c3cc12 ; N#CC(C#N)=C1c2cc(-c3ccc(F)c(C(F)(F)F)c3)ccc2-c2cc3c(cc21)-c1ccc(-c2ccc(F)c(C(F)(F)F)c2)cc1C3=C(C#N)C#N]
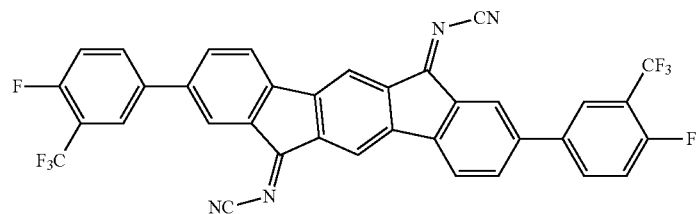
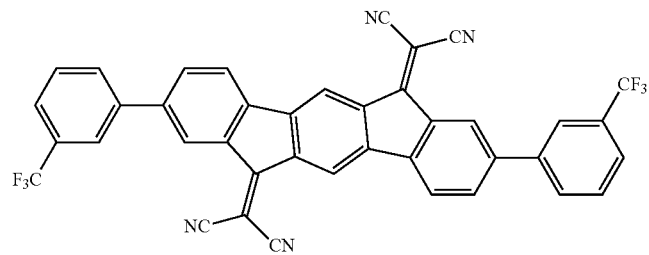

-continued
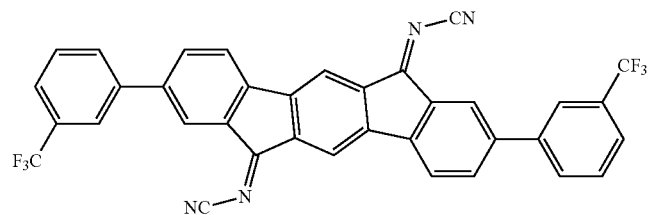
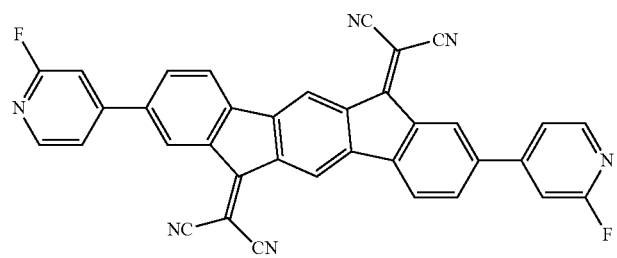
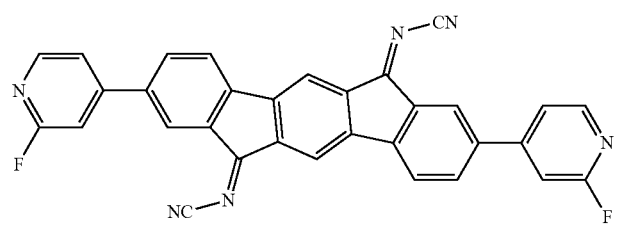
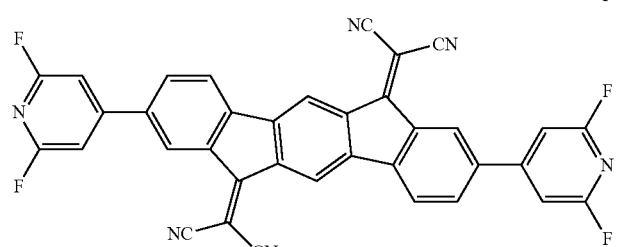
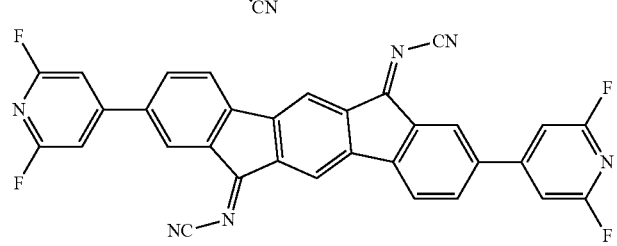
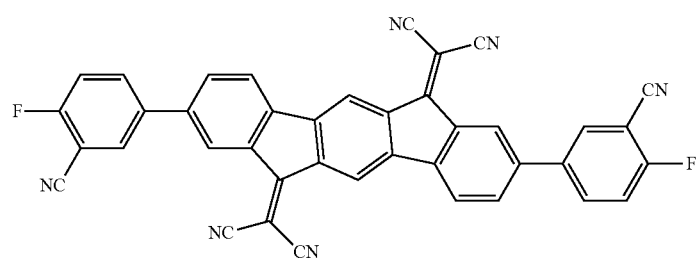
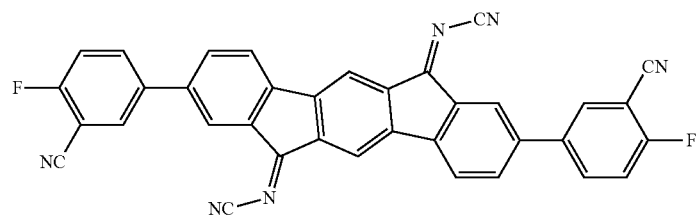

-continued
853
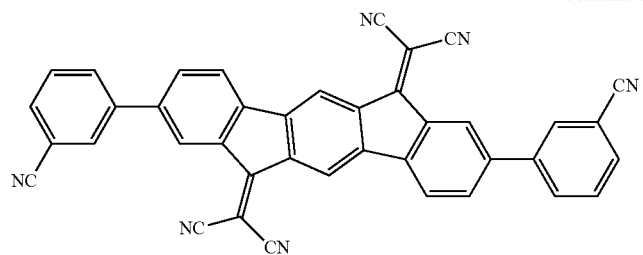
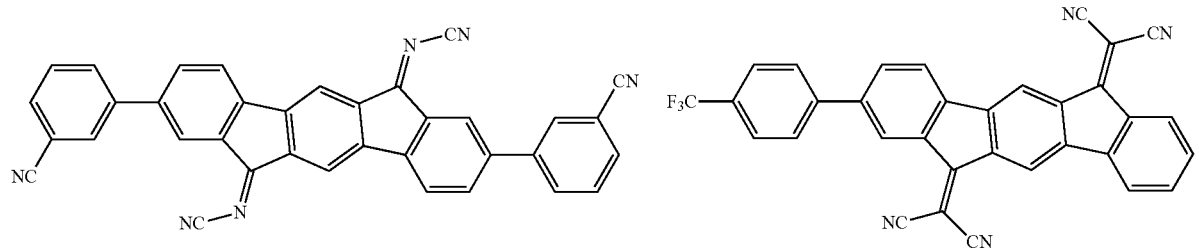
854
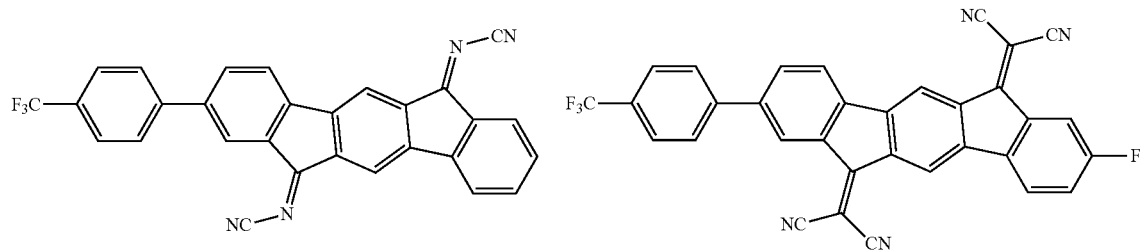
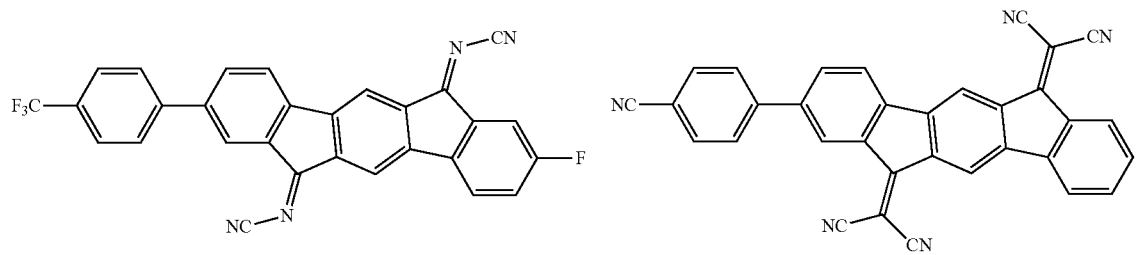
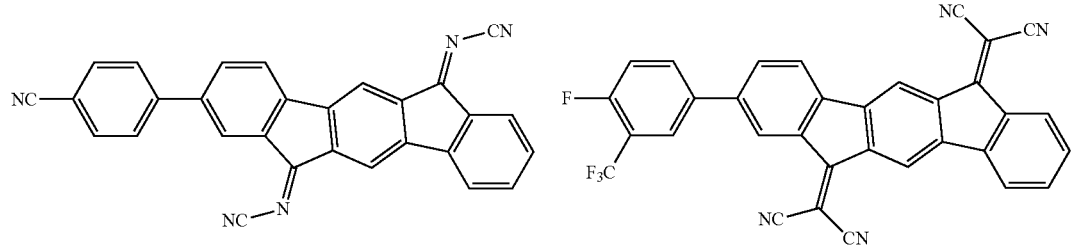
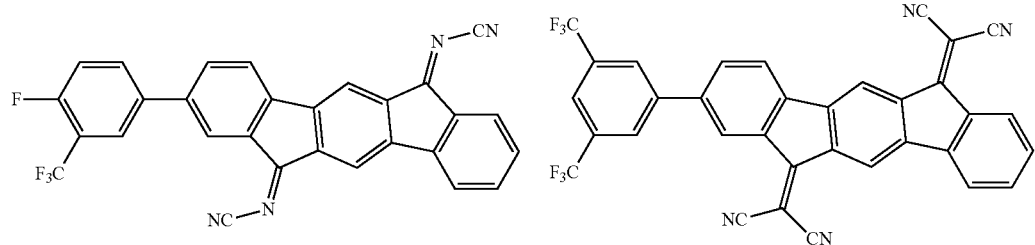

-continued
| 855 | 856 |
|---|---|
| 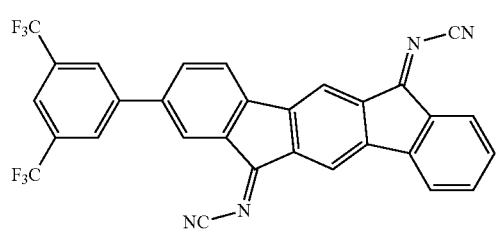 | 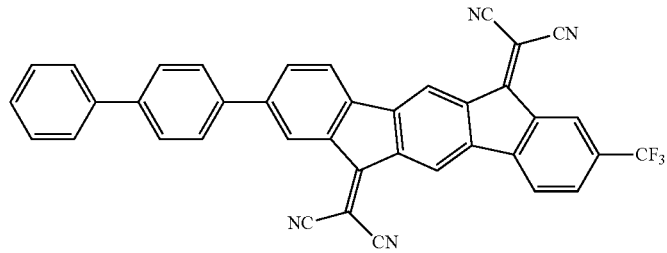 |
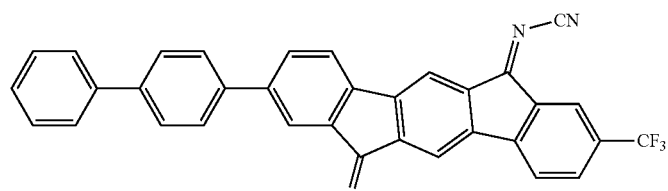
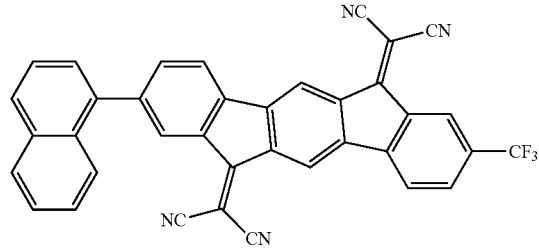
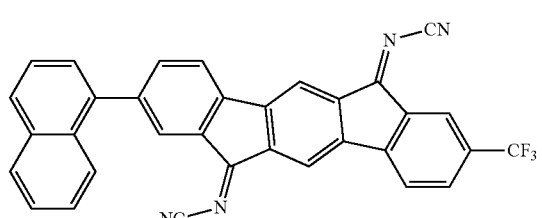
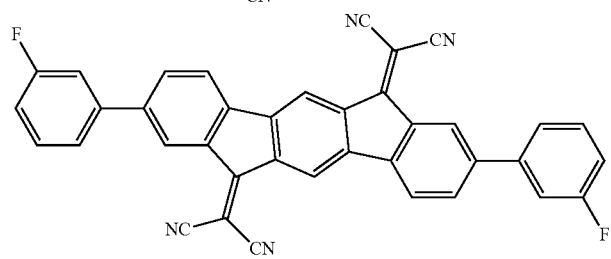
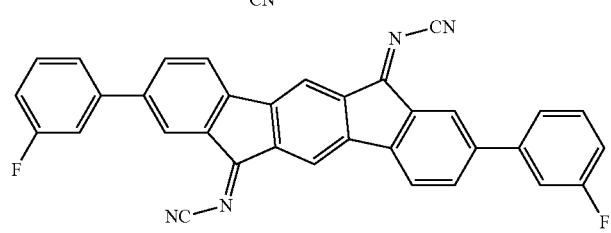
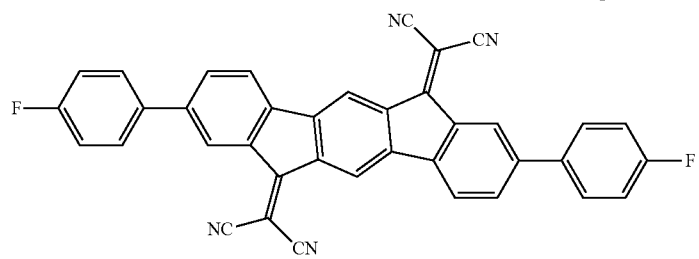
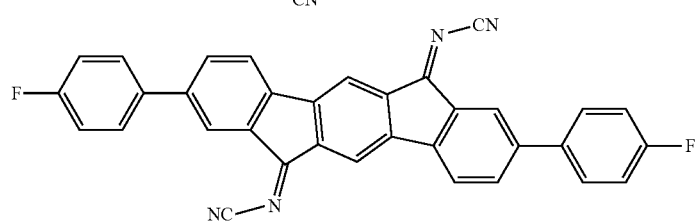

-continued
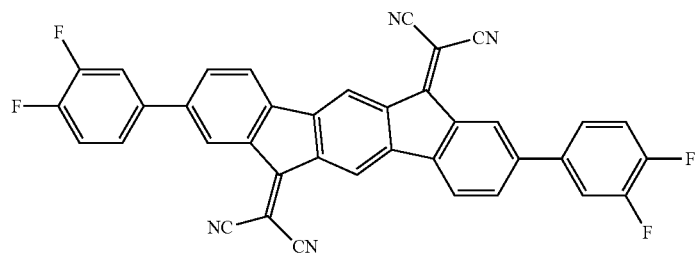
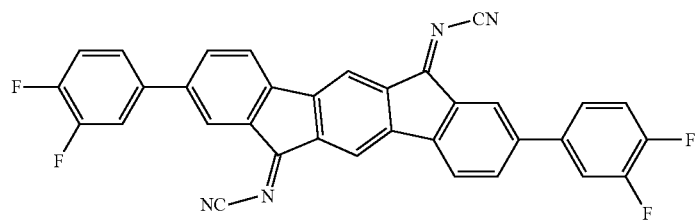
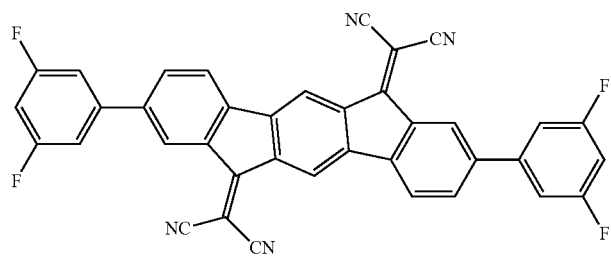
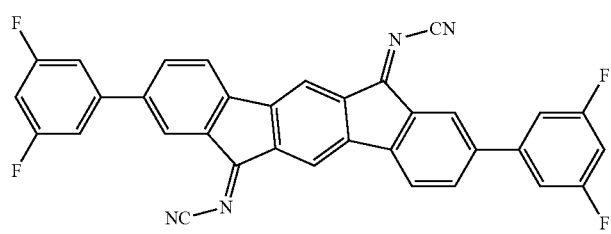
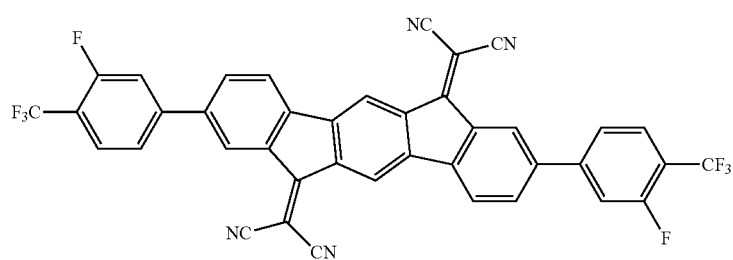
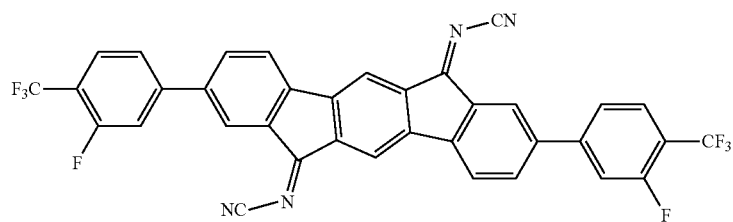
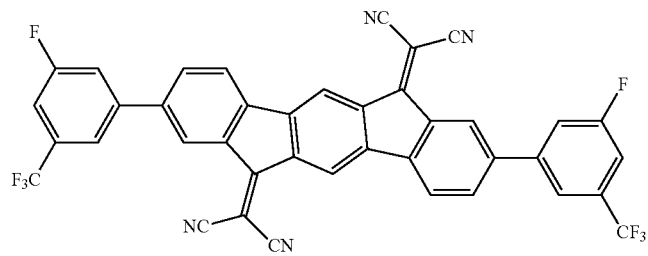

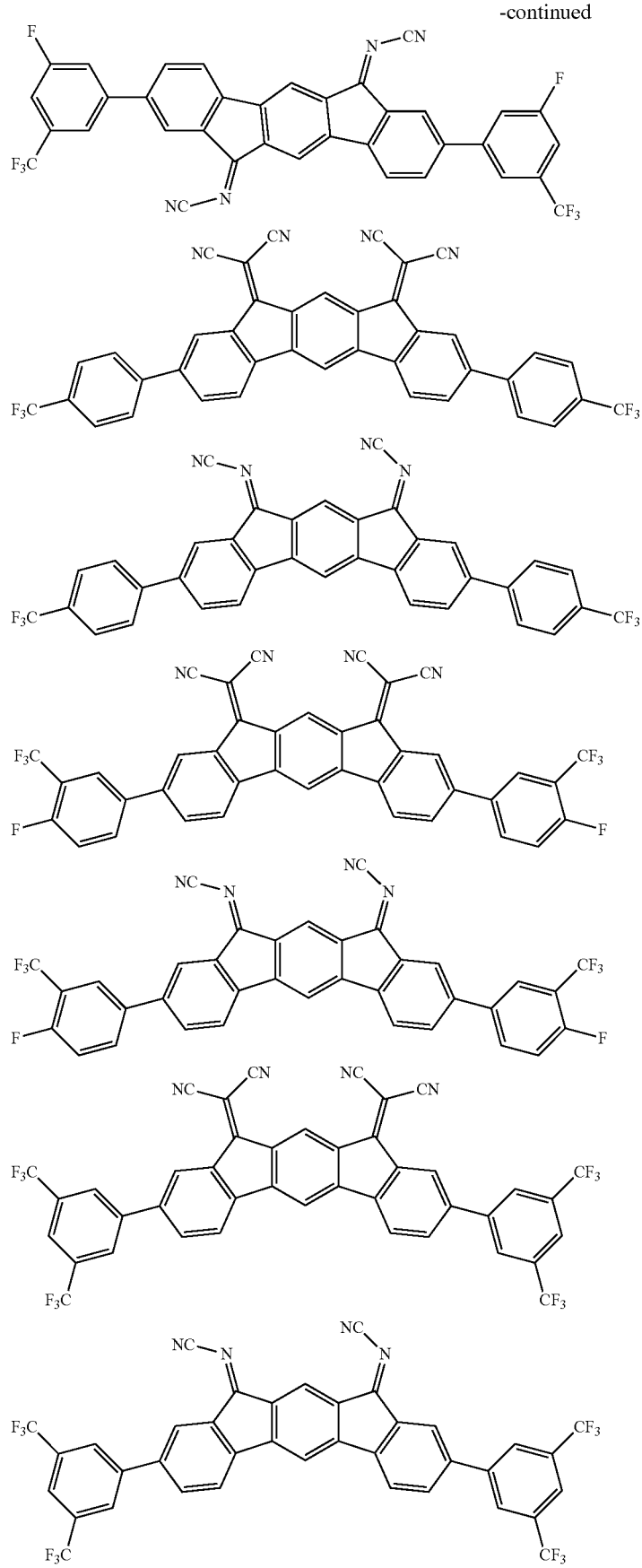

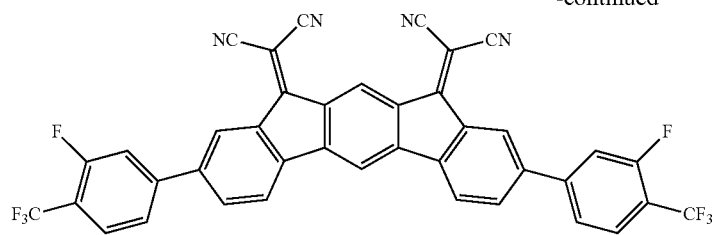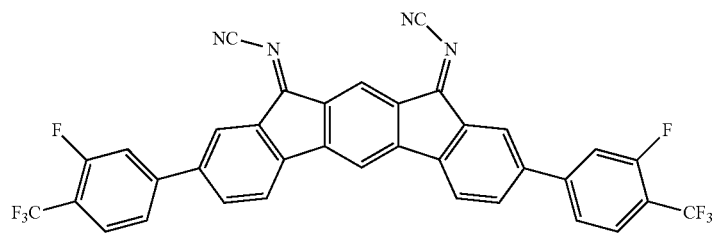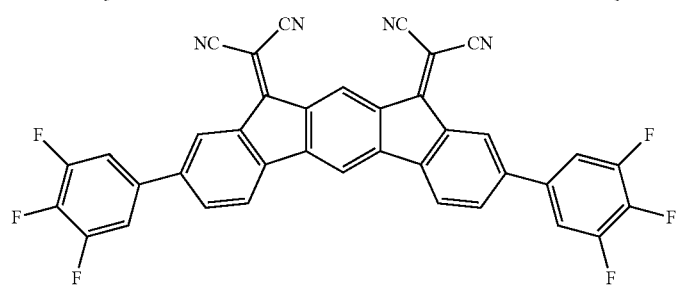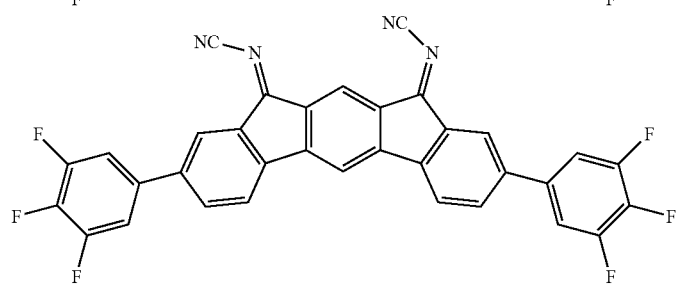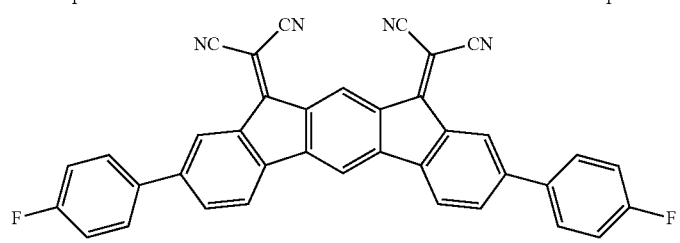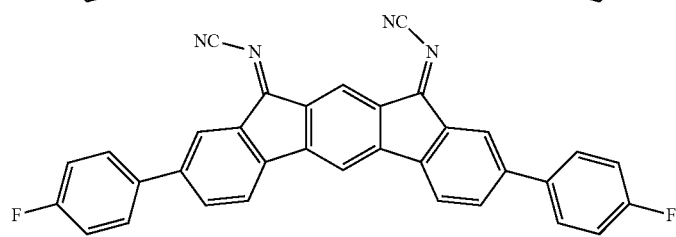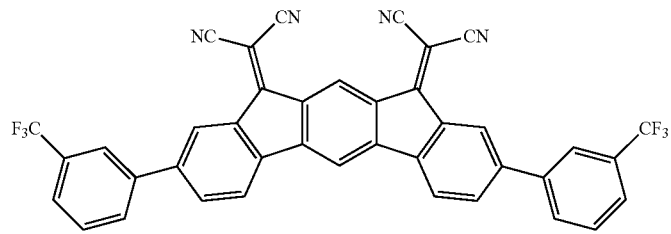

-continued
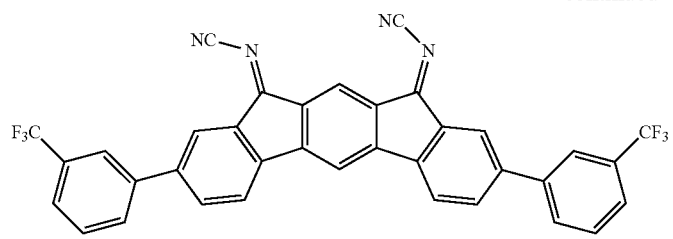
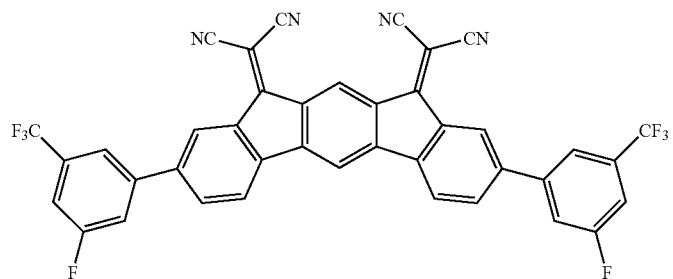
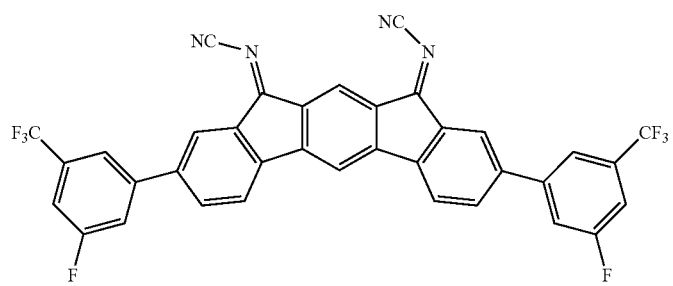
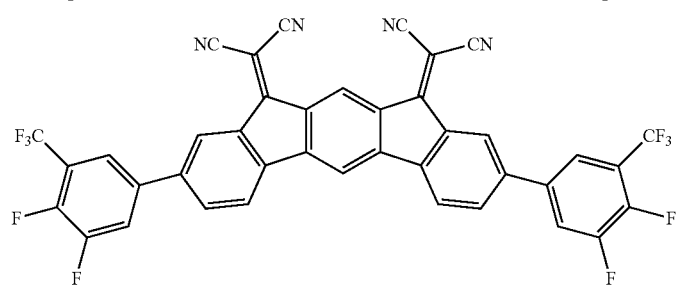
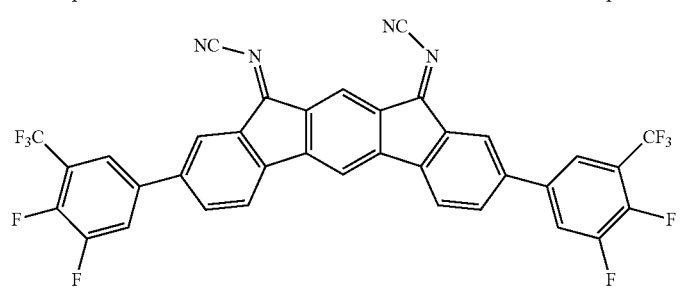
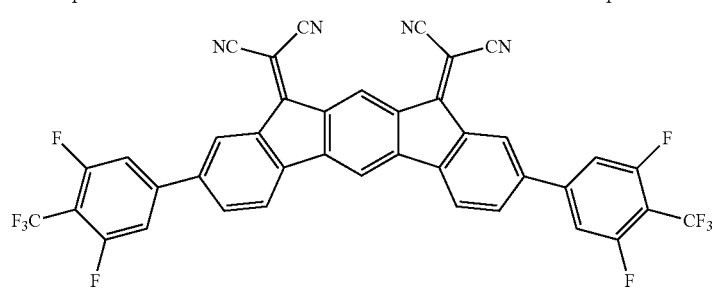

-continued
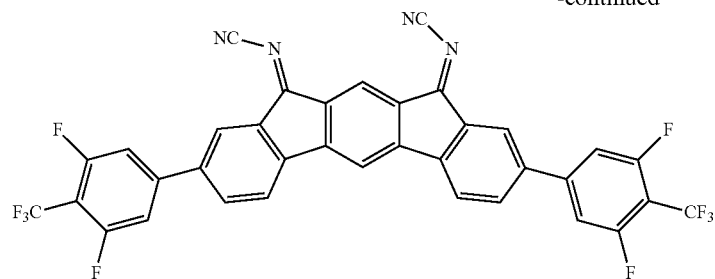
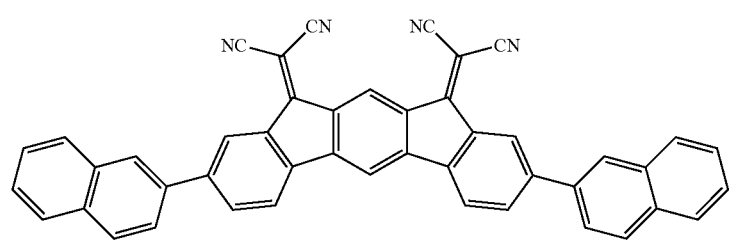
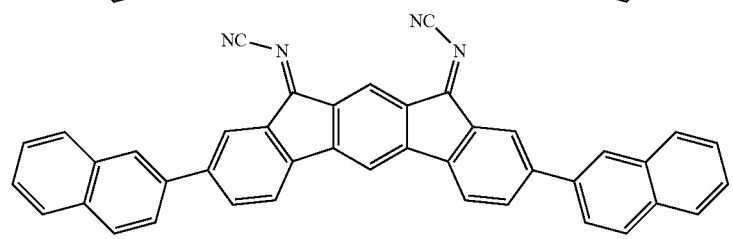
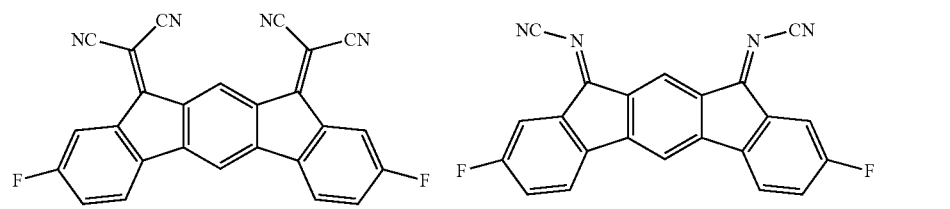
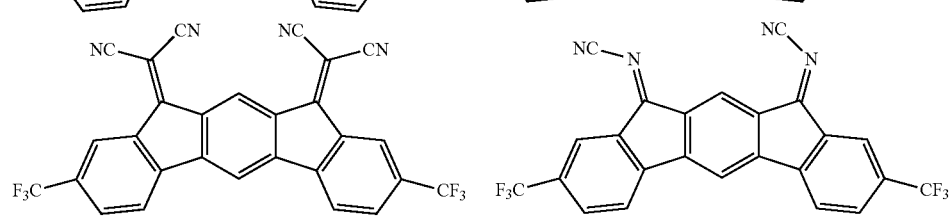
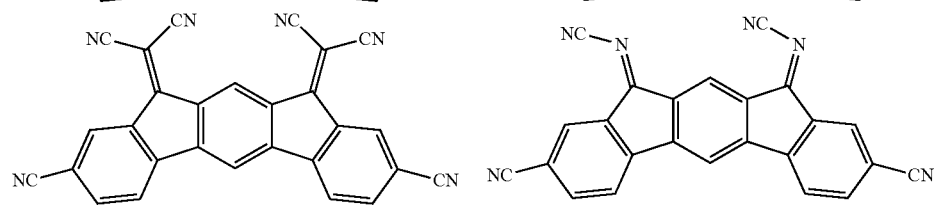
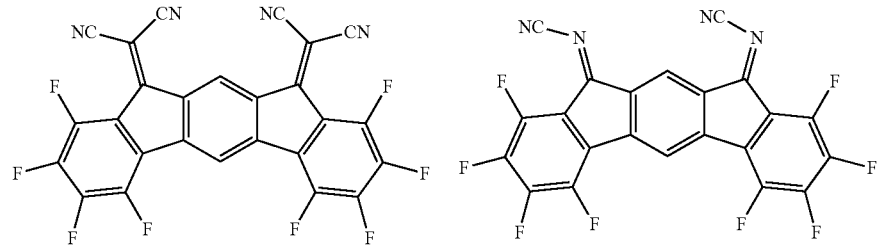

867
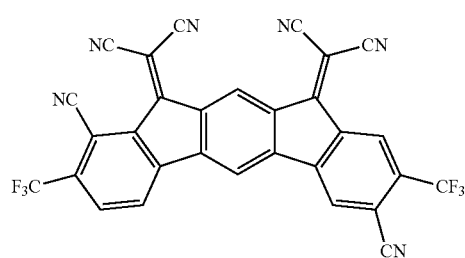
-continued
868
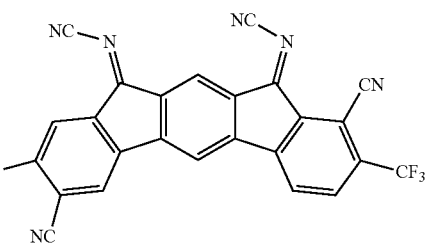
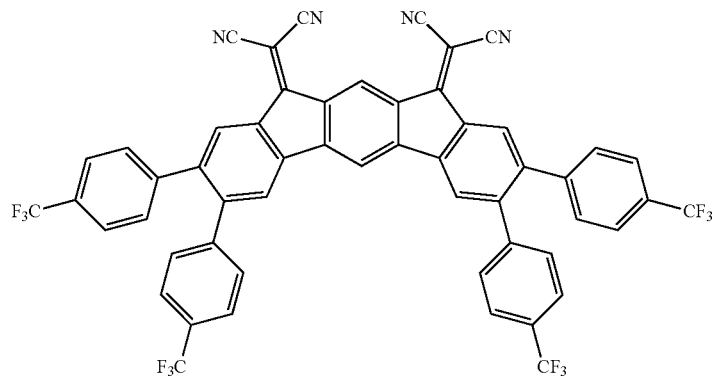
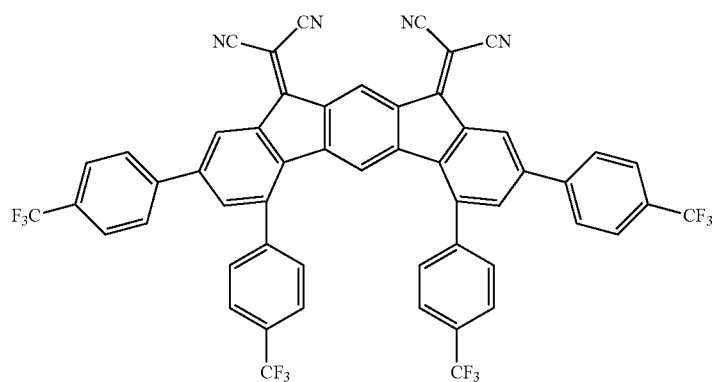
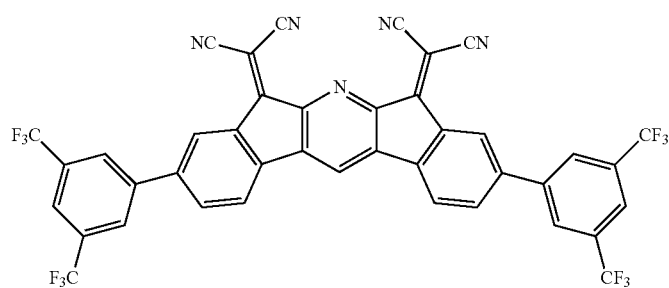
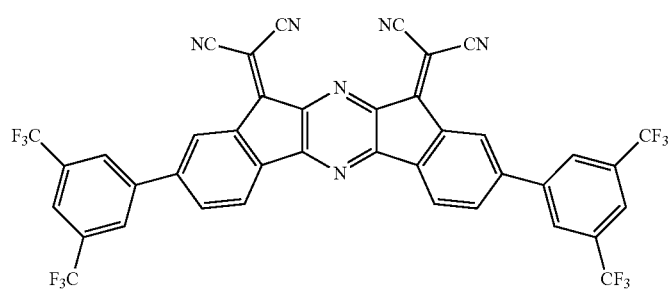

-continued
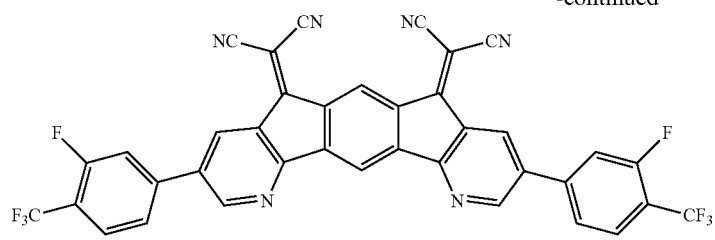
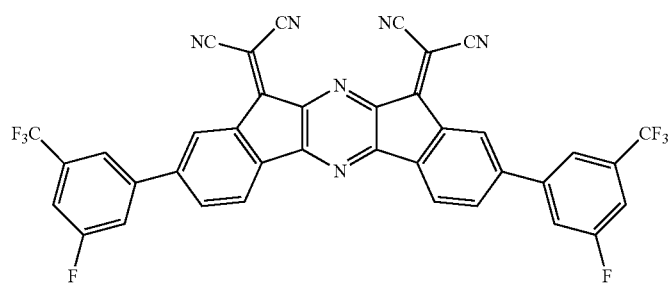
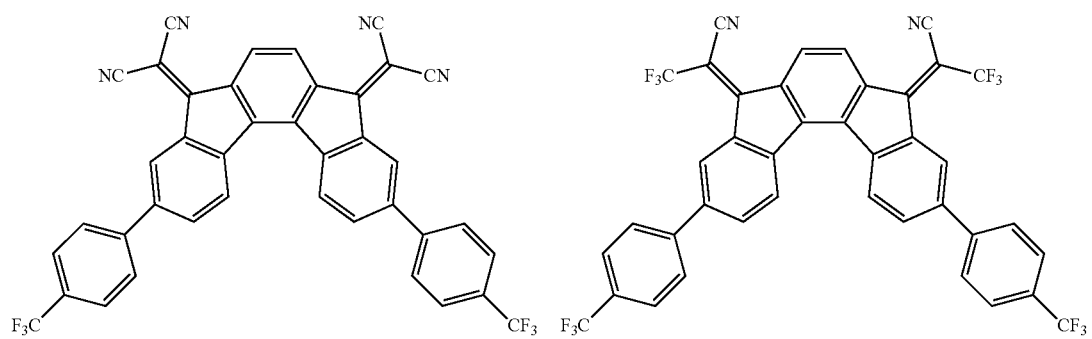
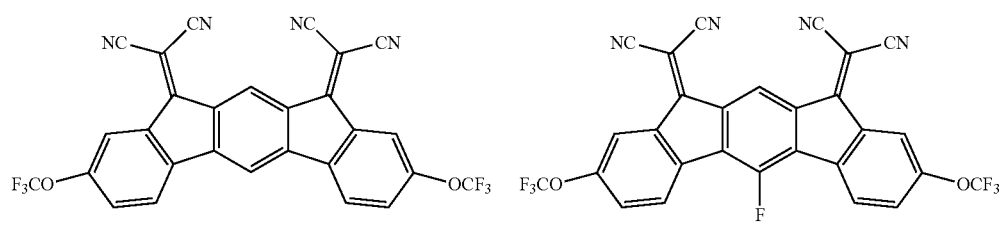
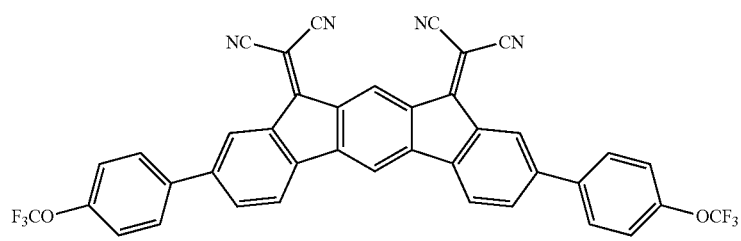
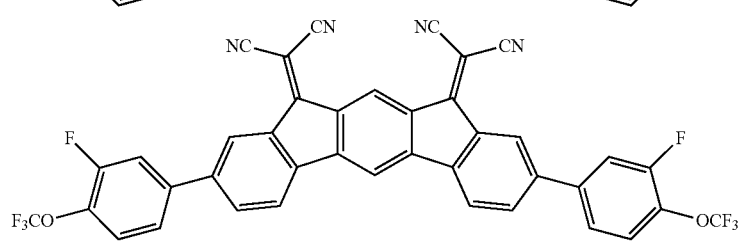

-continued
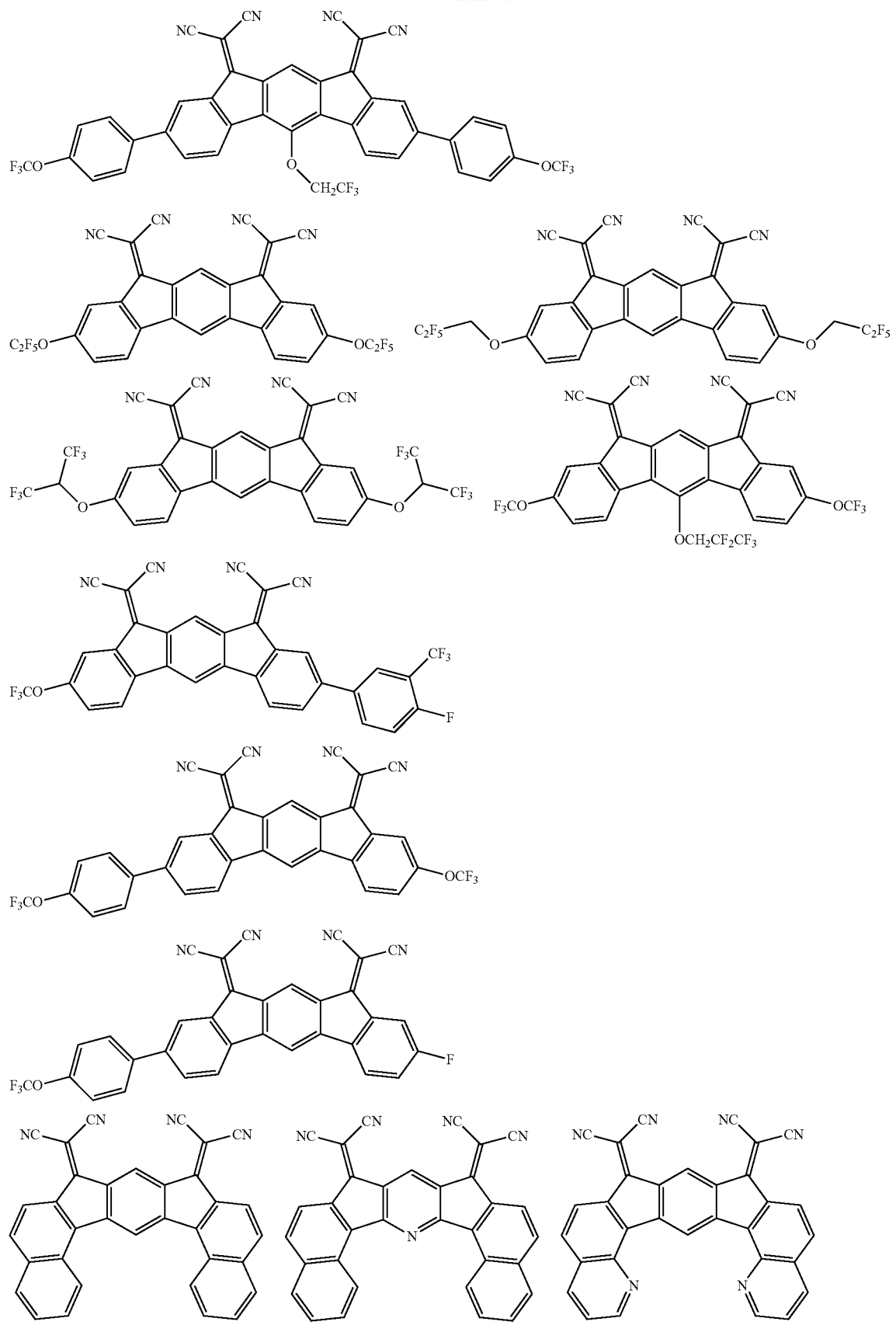

-continued
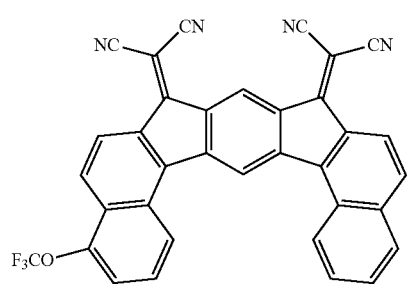
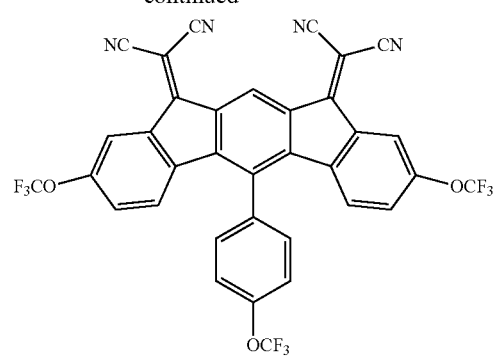
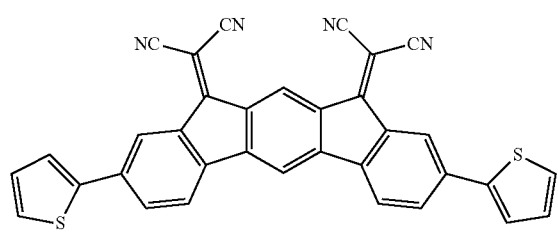
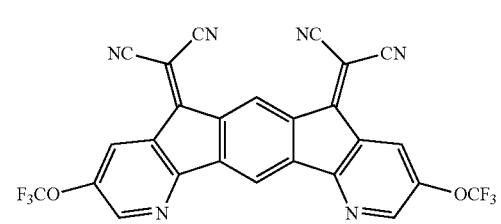
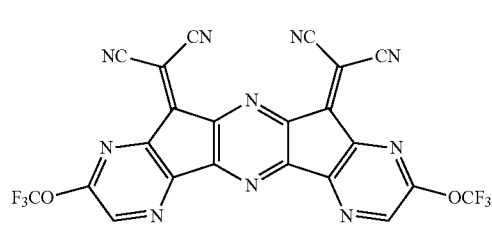
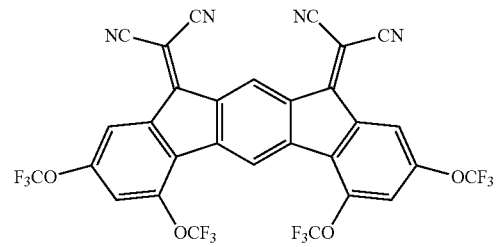
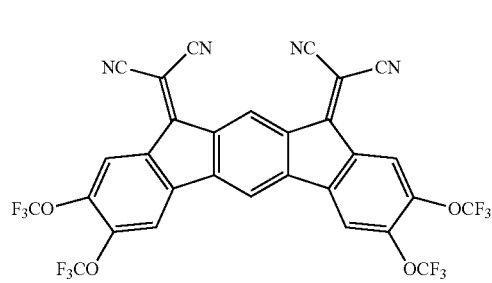
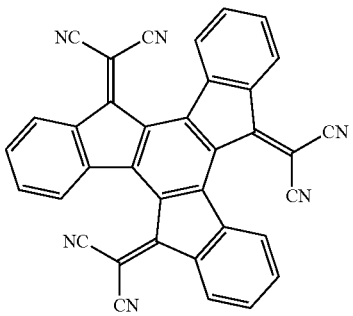
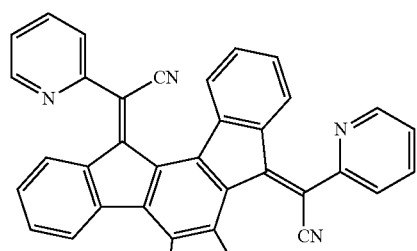
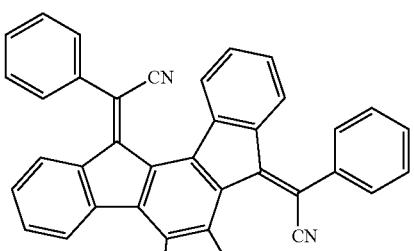

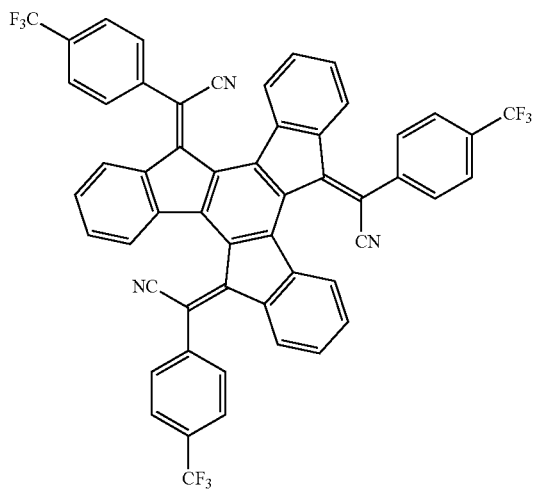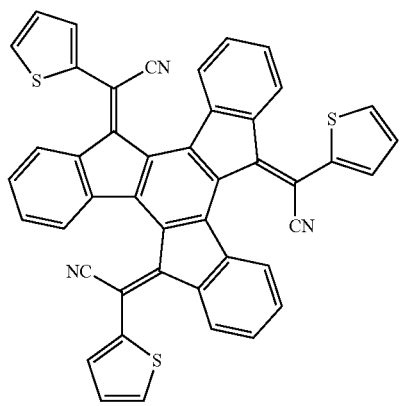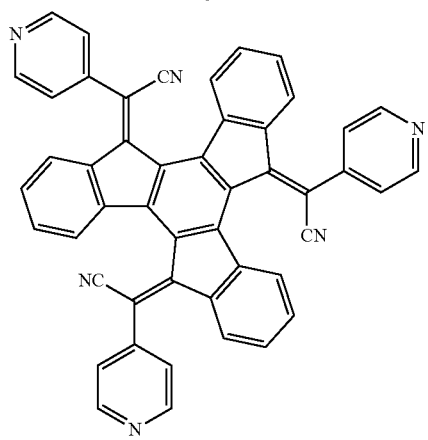 [SMILES: N#C/C(=C1/c2ccccc2-c2c1c1c(c3c2/C(=C(\C#N)c2ccncc2)c2ccccc2-3)/C(=C(\C#N)c2ccncc2)c2ccccc2-1)c1ccncc1]

Hole Transporting Layer

The hole transporting layer comprises a material having a high hole transporting ability (hole transporting material). The compound (1) of the invention is preferably used in the hole transporting layer alone or in combination with the compound mentioned below.

Examples of the hole transporting material other than the compound (1) includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ cm$^2$/Vs or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl)anthracene (t-BuDNA), 9,10-di(2-naphthyl)anthracene (DNA), and 9,10-diphenylanthracene (DPAnth).

In addition, a macromolecular compound, such as poly (N-vinylcarbazole) (PVK) and poly(4-vinyltriphenylamine) (PVTPA) are usable in the hole transporting layer.

Compounds other than those mentioned above are also usable as the hole transporting layer material, if their hole transporting ability is higher than their electron transporting ability.

The hole transporting layer may be a single layer or a laminate of two or more layers. For example, the hole transporting layer may be a two-layered structure comprising a first hole transporting layer (anode side) and a second hole transporting layer (cathode side). In such a two-layered structure, the compound (1) may be used in one of the first hole transporting layer and the second hole transporting layer, or used in both layers, wherein the compound (1) used in the first hole transporting layer is different from the compound (1) used in the second hole transporting layer. Each of two or more hole transporting layers may include a hole transporting material other than the compound (1), which is mentioned above.

In a preferred embodiment of the invention, the compound (1) is used in one of the first hole transporting layer and the second hole transporting layer. In another preferred embodiment, the compound (1) is used in only the first hole transporting layer. In still another preferred embodiment, the compound (1) is used in only the second hole transporting layer. In still another embodiment, the compound (1) is used in both the first hole transporting layer and the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl) triphenylamine (PCBAPA).

Examples of green fluorescent emitting material include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyrithnato-N,C2']irithum (III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material include an iridium complex, such as tris(2-phenylpyridinato-N,C2')iridium(III) (Ir(ppy)$_3$), bis(2-phenylpyridinato-N,C2') iridium(III) acetylacetonato (Ir(ppy)$_2$(acac)), bis(1,2-diphenyl-1H-benzimidazolato)fridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl) quinoxalinato]iridium (III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato) (monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium (III) (Eu(TTA)$_3$(Phen)), emits light from the rare earth metal ion (electron transition between different multiple states), and therefore, usable as a phosphorescent emitting material.

Host Material for Light Emitting Layer

The dopant material may be dispersed in another material (host material). The host material preferably has a lowest unoccupied molecular orbital level (LUMO level) higher than that of the dopant material and a highest occupied molecular orbital level (HOMO level) lower than that of the dopant material.

The host material may include, for example,
(1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato) aluminum(III) (BAlq), bis(8-quinolinolato)zinc(II) (Znq), bis[2-(2-benzoxazolyl)phenolato]zinc(II) (ZnPBO), and bis [2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis[N-(spiro-9,9'-bifluorene-2-yl)-N-phenylamino]biphenyl (BSPB).

The host material may be used alone or in combination of two or more.

Electron Transporting Layer

The electron transporting layer comprises a material having a high electron transporting ability (electron transporting material). Examples thereof are:
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a macromolecular compound.

Examples of the metal complex include tris(8-quinolinolato)aluminum (III) (Alq), tris(4-methyl-8-quinolinolato) aluminum (Almq$_3$), bis(10-hydroxybenzo[h]quinolinato)beryllium (BeBq$_2$), bis(2-methyl-8-quinolinato)(4-phenylphenolato)aluminum (III) (BAlq), bis(8-quinolinato) zinc(II) (Znq), bis[2-(2-benzoxazoly) phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly [(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

The above compounds have an electron mobility of $10^{-6}$ cm$^2$/Vs or more. Materials other than those mentioned above are also usable in the electron transporting layer if their electron transporting ability is higher than their hole transporting ability. The electron transporting layer may be a single layer or a laminate of two or more layers each comprising the material mentioned above. In the two-layered electron transporting layer, the anode-side layer is called a first electron transporting layer and the cathode-side layer is called a second electron transporting layer.

Electron Injecting Layer

The electron injecting layer is a layer comprising a material having a high electron injecting ability (hole injecting material), for example, an alkali metal, an alkaline earth metal, and a compound of these metals, such as lithium, cesium, calcium, lithium fluoride, cesium fluoride, calcium fluoride, and lithium oxide. In addition, an electron transporting material which is doped with an alkali metal, an alkaline earth metal or a compound thereof, for example, Alq doped with magnesium, is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an alkali metal, such as lithium and cesium, an alkaline earth metal, such as magnesium, potassium, and strontium, an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of laminated layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and a triplet blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The triplet blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples. It should be noted that the scope of the invention is not limited to the following examples.

Intermediate Synthesis 1: Synthesis of Intermediate A

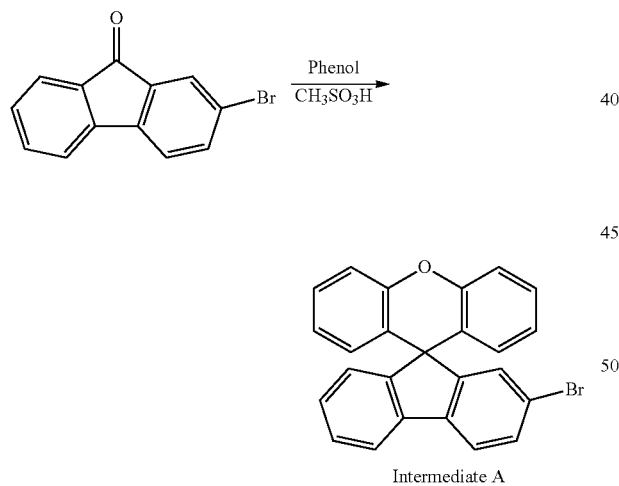

Intermediate A

Under argon atmosphere, a mixture of 2-bromo-9-fluorenone (5.0 g), phenol (17.0 mL), and methanesulfonic acid (1.85 g) was stirred under heating at 135° C. for 13 h. The reaction mixture was neutralized by a 10% aqueous solution of sodium hydroxide at room temperature and then extracted with toluene. After washing with a saturated brine, the organic layer was concentrated under reduced pressure. The residue was purified by column chromatography to obtain the intermediate A as a white solid (1.68 g, yield: 20%). The result of mass spectrometric analysis was m/e=410 to the molecular weight 410 of the intermediate A.

Intermediate Synthesis 2: Synthesis of Intermediate B

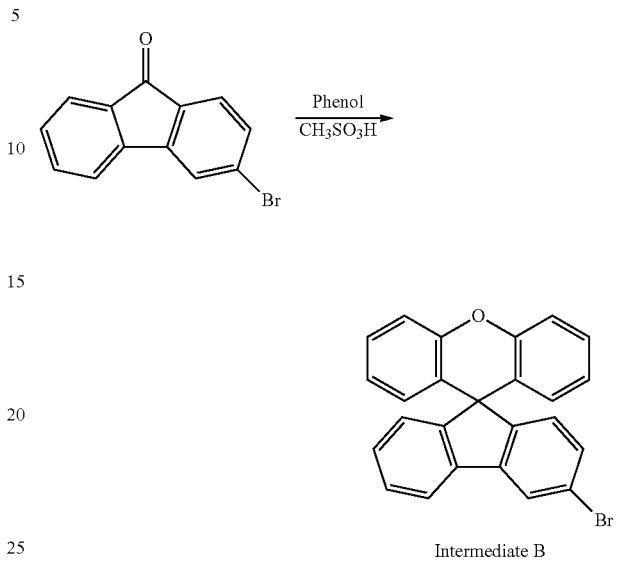

Intermediate B

The intermediate B was obtained in the same manner as in the synthesis of the intermediate A except for using 3-bromo-9-fluorenone in place of 2-bromo-9-fluorenone. The result of mass spectrometric analysis was m/e=410 to the molecular weight 410 of the intermediate B.

Intermediate Synthesis 3: Synthesis of Intermediate C

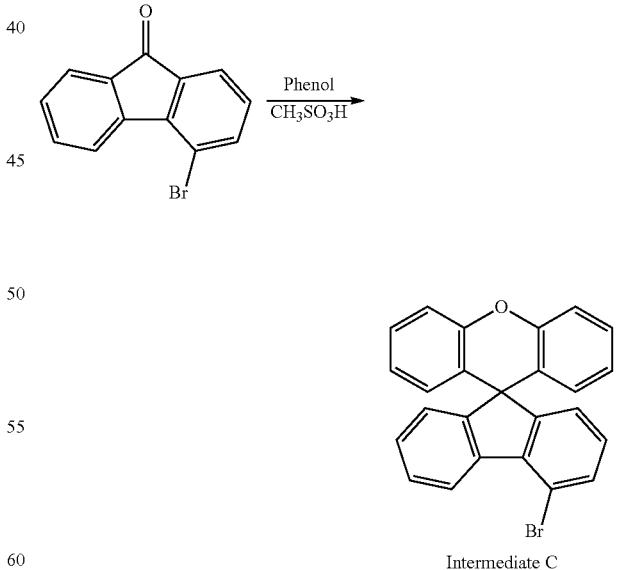

Intermediate C

The intermediate C was obtained in the same manner as in the synthesis of the intermediate A except for using 4-bromo-9-fluorenone in place of 2-bromo-9-fluorenone. The result of mass spectrometric analysis was m/e=410 to the molecular weight 410 of the intermediate C.

Intermediate Synthesis 4: Synthesis of Intermediate D

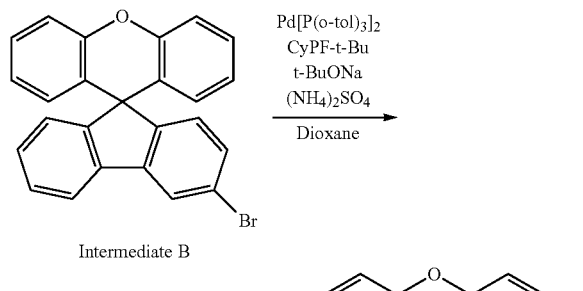

Intermediate B

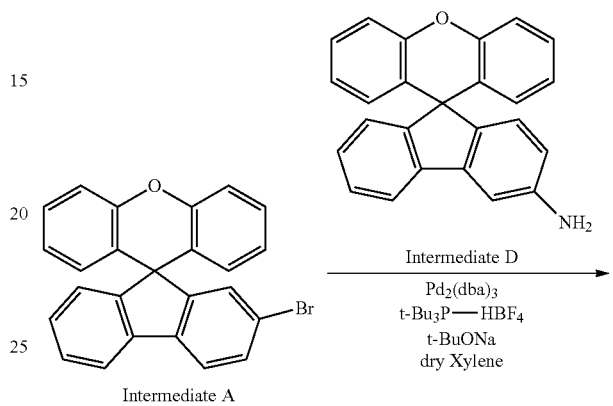

Intermediate D

Under argon atmosphere, a mixture prepared by successively mixing the intermediate B (0.41 g), bis[tris(2-methylphenyO)phosphine]palladium (1.43 mg), Josiphos ligand (CyPF-tBu, 1.11 mg), t-BuONa (0.43 g), ammonium sulfate (0.2 g), and dry dioxane (5 mL) was stirred under heating at 90° C. After 12 h, the reaction liquid was extracted with ethyl acetate. The extract was filtered through celite and the solvent was evaporated off under reduced pressure. The residue was purified by column chromatography to obtain the intermediate D (0.18 g, yield: 52%). The result of mass spectrometric analysis was m/e=347 to the molecular weight 347 of the intermediate D.

Intermediate Synthesis 5: Synthesis of Intermediate E

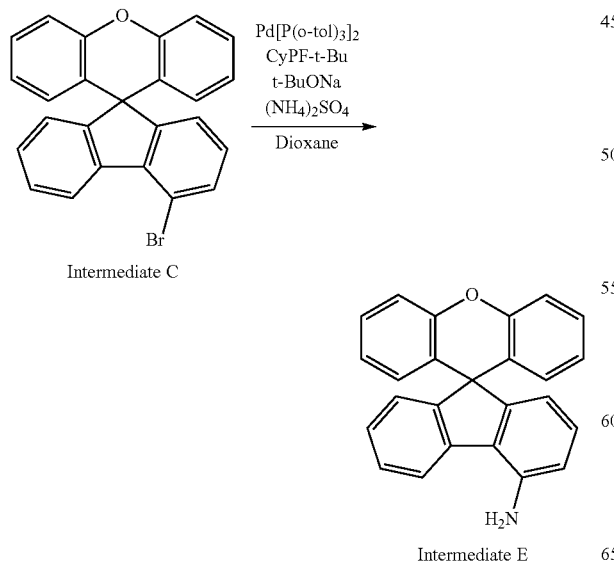

Intermediate C

Intermediate E

The intermediate E was obtained in the same manner as in the synthesis of the intermediate D except for using the intermediate C in place of the intermediate B. The result of mass spectrometric analysis was m/e=347 to the molecular weight 347 of the intermediate E.

Intermediate Synthesis 6: Synthesis of Intermediate F

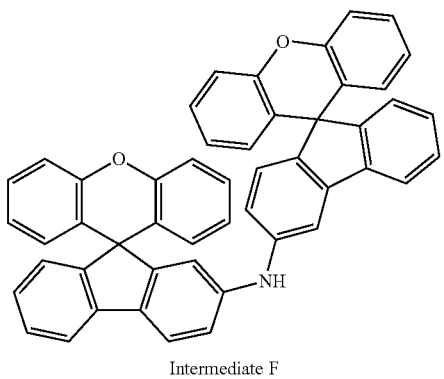

Intermediate A

Intermediate D

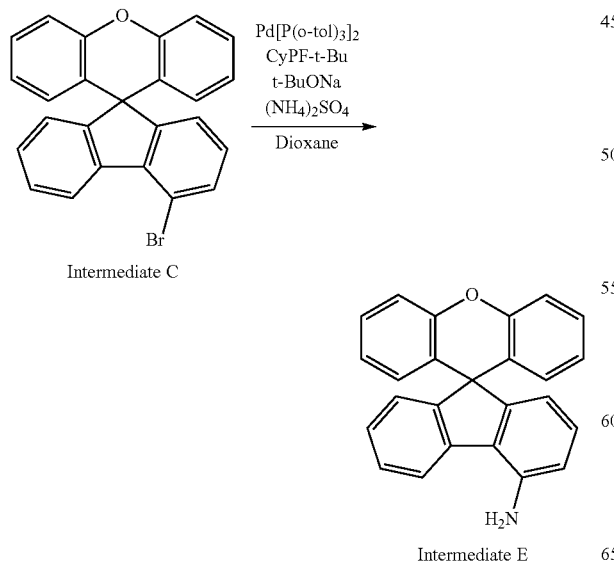

Intermediate F

Under argon atmosphere, into a mixture of the intermediate D (2.54 g), the intermediate A (3.0 g), and toluene (40 mL), tris(dibenzylideneacetone)palladium(0) (0.1 g) was added and the resultant mixture was heated to 80° C. After adding t-Bu$_3$P-HBF$_4$ (560 mg) and t-BuONa (830 mg) successively, the mixture was stirred at 100° C. for 24 h. After adding methanol and then DME at room temperature, the mixture was washed by heating to 100° C. under stirring. The obtained residue was purified by column chromatography to obtain the intermediate F (2.8 g, yield: 57%). The result of mass spectrometric analysis was m/e=677 to the molecular weight 677 of the intermediate F.

Intermediate Synthesis 7: Synthesis of Intermediate G

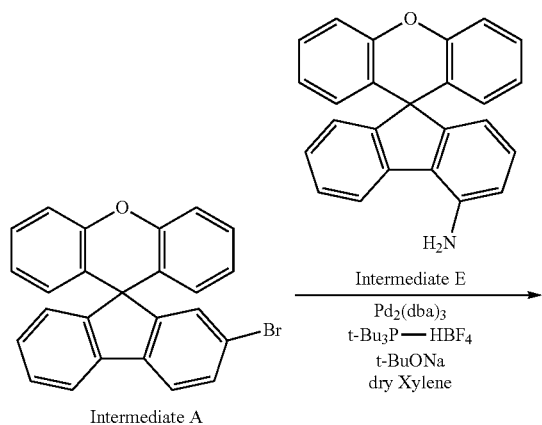

Intermediate A

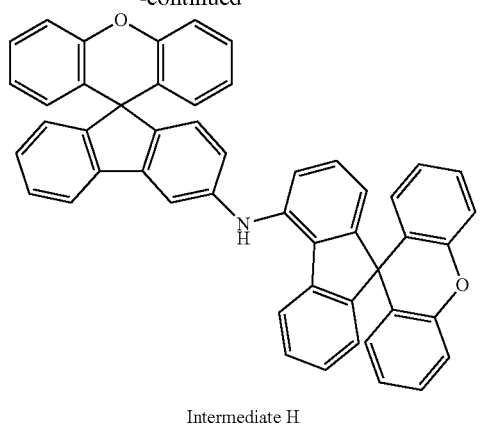

Intermediate H

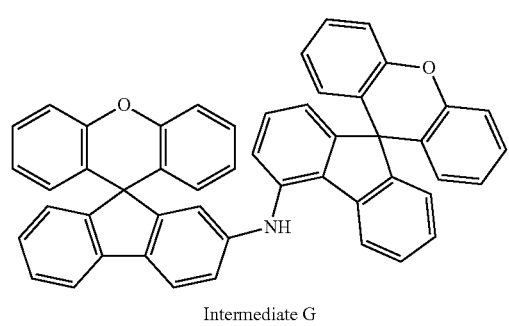

Intermediate G

The intermediate G was obtained in the same manner as in the synthesis of the intermediate F except for using the intermediate E in place of the intermediate D. The result of mass spectrometric analysis was m/e=677 to the molecular weight 677 of the intermediate G.

Intermediate Synthesis 8: Synthesis of Intermediate H

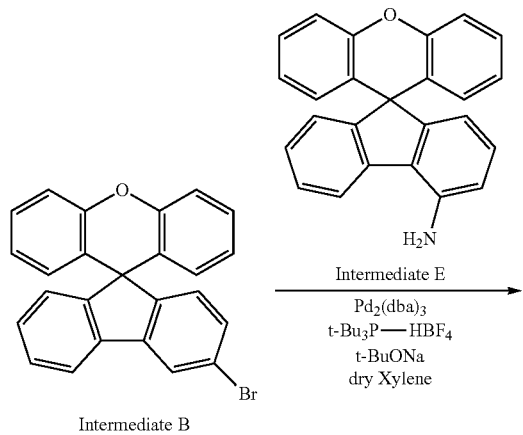

Intermediate B

The intermediate H was obtained in the same manner as in the synthesis of the intermediate G except for using the intermediate B in place of the intermediate A. The result of mass spectrometric analysis was m/e=677 to the molecular weight 677 of the intermediate H.

Synthesis Example 1: Synthesis of Compound 1

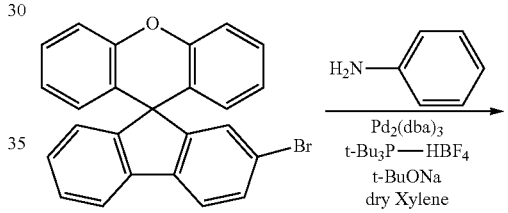

Intermediate A

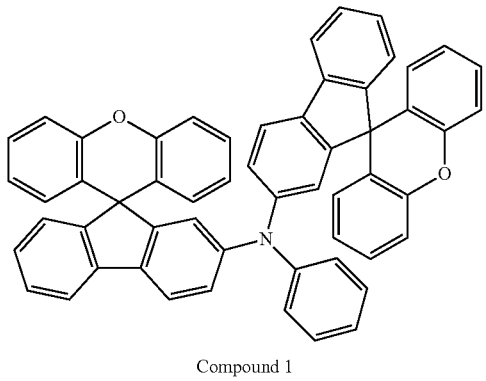

Compound 1

Under argon atmosphere, into a mixture of aniline (690 mL), the intermediate A (6.0 g), and toluene (73 mL), tris(dibenzylideneacetone)palladium(0) (0.2 g) was added and the resultant mixture was heated to 80° C. After adding t-Bu$_3$P-HBF$_4$ (0.13 g) and t-BuONa (1.67 g) successively, the mixture was stirred at 100° C. for 24 h. After adding methanol and then DME at room temperature, the mixture was washed by heating to 100° C. under stirring. The obtained residue was purified by column chromatography to obtain the compound 1 (3.6 g, yield: 65%). The result of mass spectrometric analysis was m/e=753 to the molecular weight 753 of the compound 1.

Synthesis Example 2: Synthesis of Compound 2

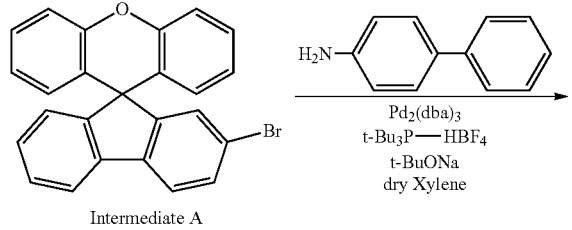
Intermediate A

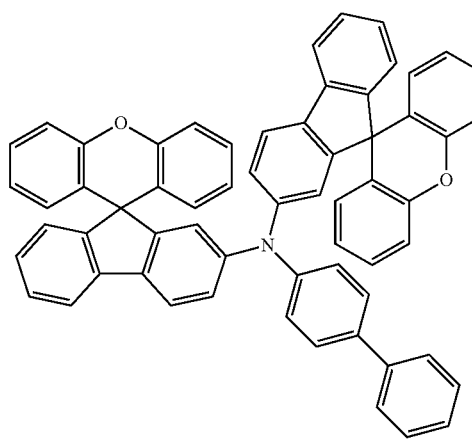
Compound 2

The compound 2 was obtained in the same manner as in the synthesis of the compound 1 except for using biphenyl-4-amine in place of aniline. The result of mass spectrometric analysis was m/e=829 to the molecular weight 829 of the compound 2.

Synthesis Example 3: Synthesis of Compound 3

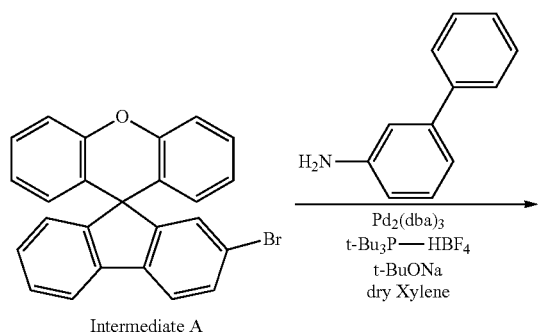
Intermediate A

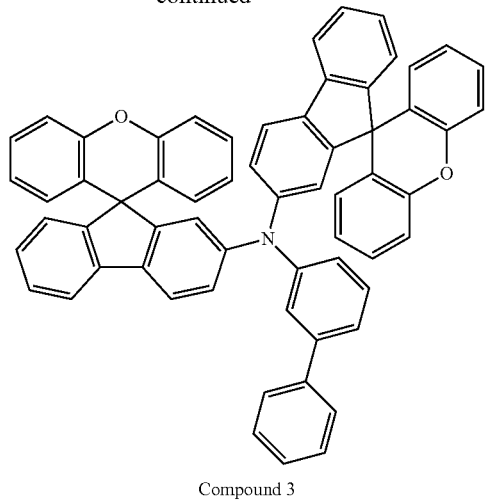
Compound 3

The compound 3 was obtained in the same manner as in the synthesis of the compound 1 except for using biphenyl-3-amine in place of aniline. The result of mass spectrometric analysis was m/e=829 to the molecular weight 829 of the compound 3.

Synthesis Example 4: Synthesis of Compound 4

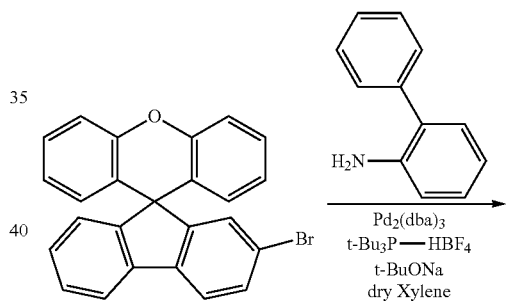
Intermediate A

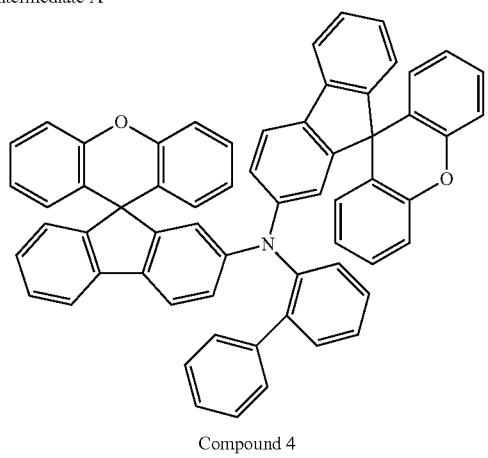
Compound 4

The compound 4 was obtained in the same manner as in the synthesis of the compound 1 except for using biphenyl-2-amine in place of aniline. The result of mass spectrometric analysis was m/e=829 to the molecular weight 829 of the compound 4.

Synthesis Example 5: Synthesis of Compound 5

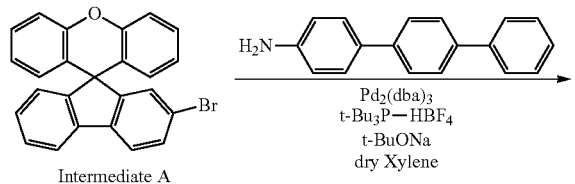

Intermediate A

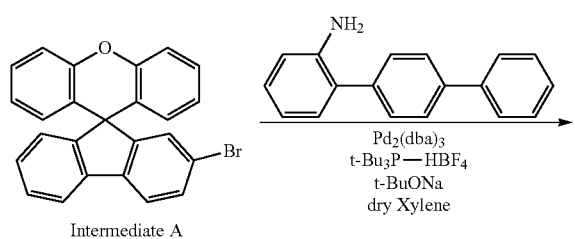

Compound 5

The compound 5 was obtained in the same manner as in the synthesis of the compound 1 except for using [1,1'4',1"-terphenyl]-4-amine in place of aniline. The result of mass spectrometric analysis was m/e=905 to the molecular weight 905 of the compound 5.

Synthesis Example 6: Synthesis of Compound 6

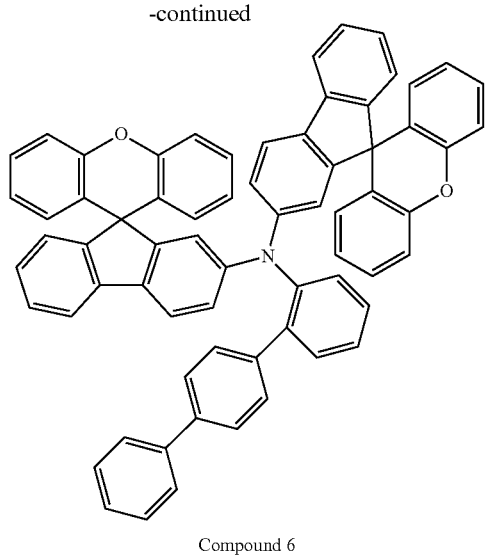

Compound 6

The compound 6 was obtained in the same manner as in the synthesis of the compound 1 except for using [1,1'4',1"-terphenyl]-2-amine in place of aniline. The result of mass spectrometric analysis was m/e=905 to the molecular weight 905 of the compound 6.

Synthesis Example 7: Synthesis of Compound 7

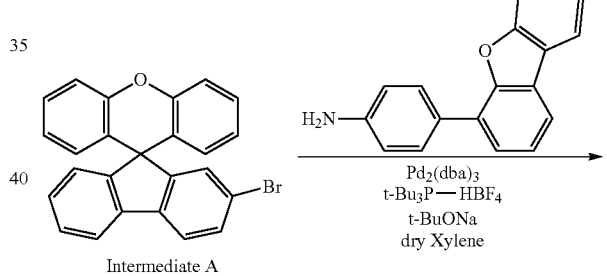

Intermediate A

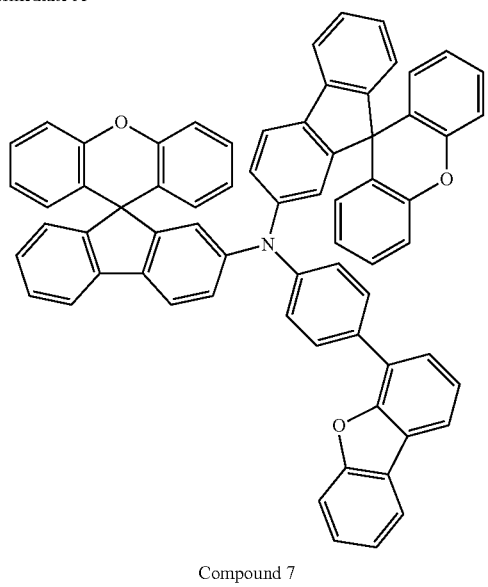

Compound 7

The compound 7 was obtained in the same manner as in the synthesis of the compound 1 except for using 4-(dibenzo[b,d]furan-4-yl)aniline in place of aniline. The result of mass spectrometric analysis was m/e=919 to the molecular weight 919 of the compound 7.

Synthesis Example 8: Synthesis of Compound 8

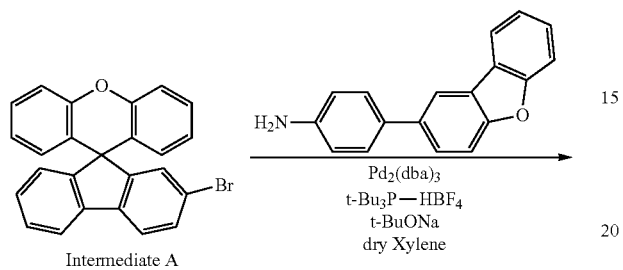

Intermediate A

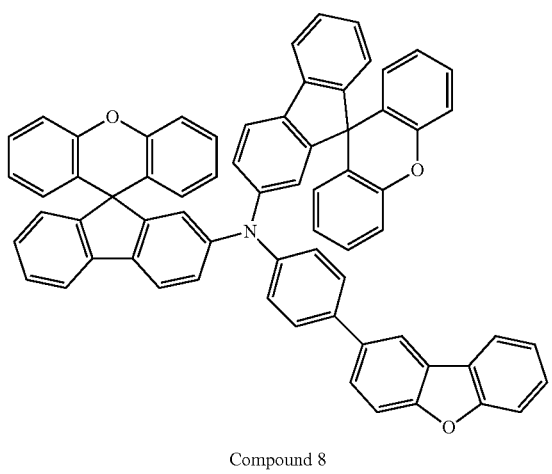

Compound 8

The compound 8 was obtained in the same manner as in the synthesis of the compound 1 except for using 4-(dibenzo[b,d]furan-2-yl)aniline in place of aniline. The result of mass spectrometric analysis was m/e=919 to the molecular weight 919 of the compound 8.

Synthesis Example 9: Synthesis of Compound 9

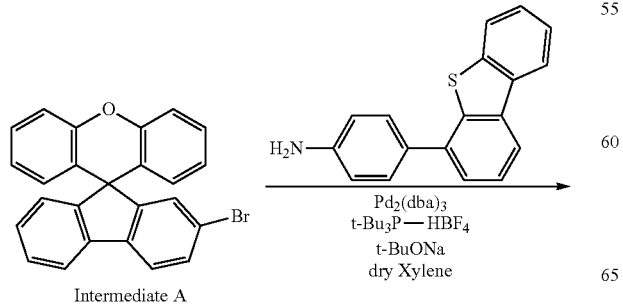

Intermediate A

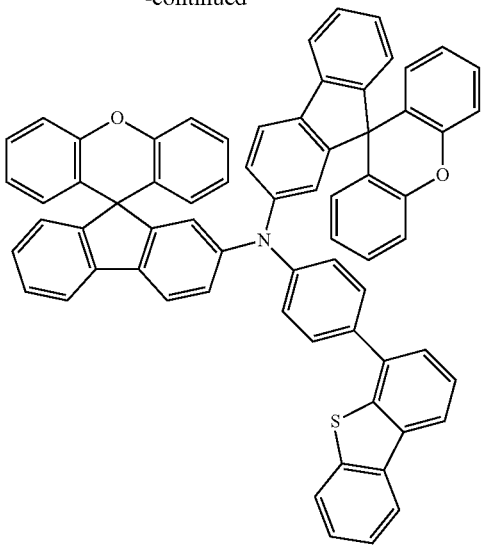

Compound 9

The compound 9 was obtained in the same manner as in the synthesis of the compound 1 except for using 4-(dibenzo[b,d]thiophene-4-yl)aniline in place of aniline. The result of mass spectrometric analysis was m/e=935 to the molecular weight 935 of the compound 9.

Synthesis Example 10: Synthesis of Compound 10

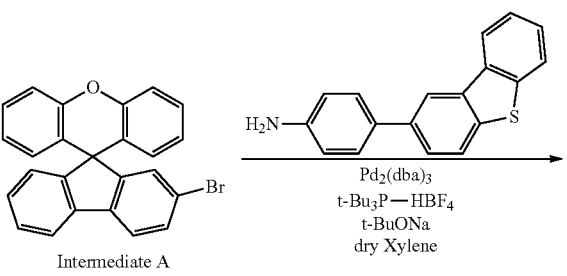

Intermediate A

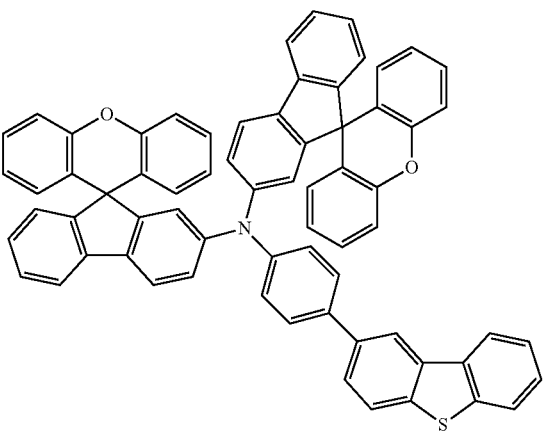

Compound 10

The compound 10 was obtained in the same manner as in the synthesis of the compound 1 except for using 4-(dibenzo[b,d]thiophene-2-yl)aniline in place of aniline. The result of mass spectrometric analysis was m/e=935 to the molecular weight 935 of the compound 10.

Synthesis Example 11: Synthesis of Compound 11

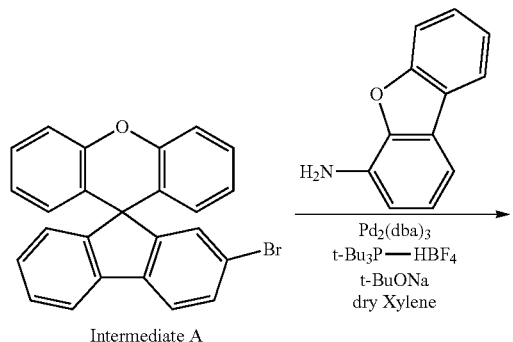

Intermediate A

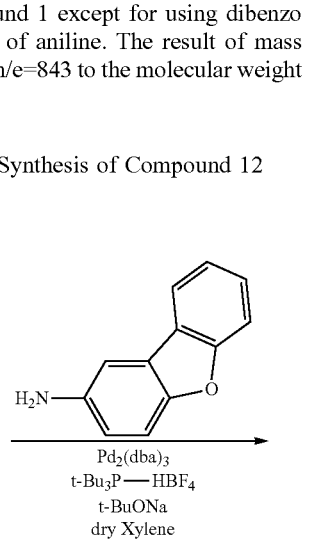

Compound 11

The compound 11 was obtained in the same manner as in the synthesis of the compound 1 except for using dibenzo[b,d]furan-4-amine in place of aniline. The result of mass spectrometric analysis was m/e=843 to the molecular weight 843 of the compound 11.

Synthesis Example 12: Synthesis of Compound 12

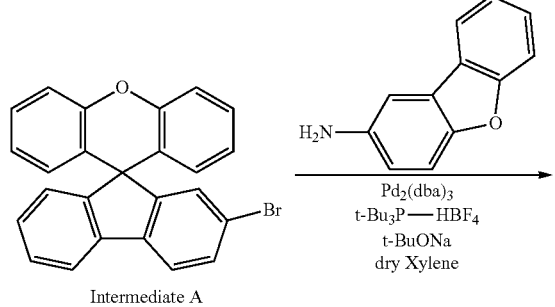

Intermediate A

-continued

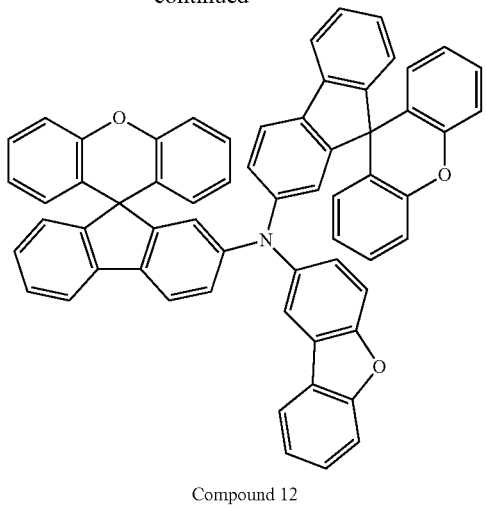

Compound 12

The compound 12 was obtained in the same manner as in the synthesis of the compound 1 except for using dibenzo[b,d]furan-2-amine in place of aniline. The result of mass spectrometric analysis was m/e=843 to the molecular weight 843 of the compound 12.

Synthesis Example 13: Synthesis of Compound 13

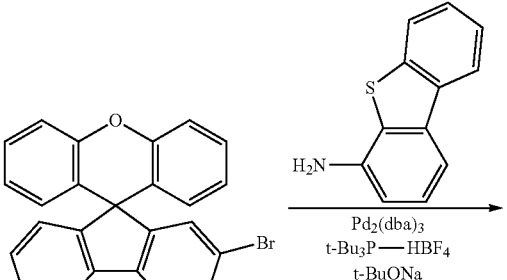

Intermediate A

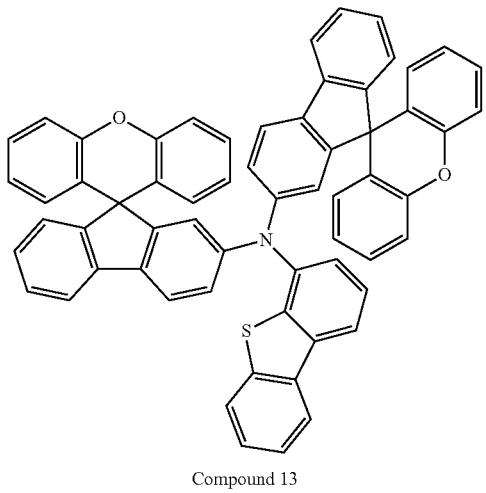

Compound 13

The compound 13 was obtained in the same manner as in the synthesis of the compound 1 except for using dibenzo[b,d]thiophene-4-amine in place of aniline. The result of mass spectrometric analysis was m/e=859 to the molecular weight 859 of the compound 13.

Synthesis Example 14: Synthesis of Compound 14

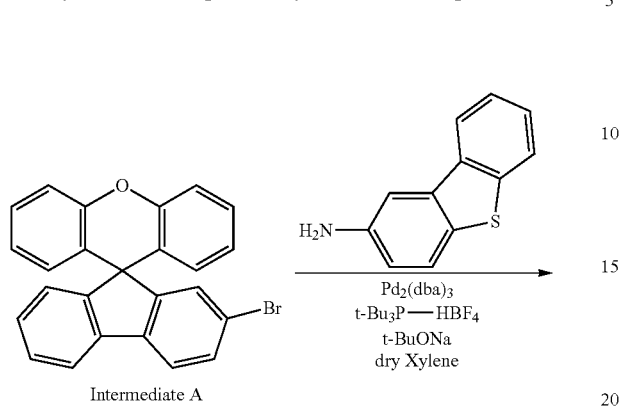

Intermediate A

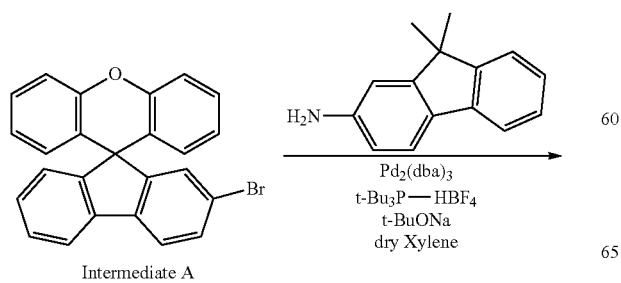

Compound 14

The compound 14 was obtained in the same manner as in the synthesis of the compound 1 except for using dibenzo[b,d]thiophene-2-amine in place of aniline. The result of mass spectrometric analysis was m/e=859 to the molecular weight 859 of the compound 14.

Synthesis Example 15: Synthesis of Compound 15

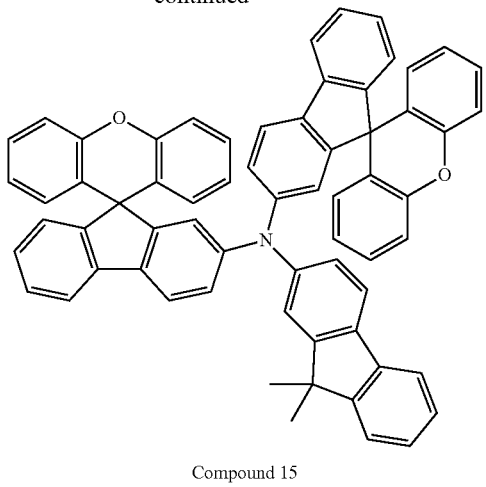

Compound 15

The compound 15 was obtained in the same manner as in the synthesis of the compound 1 except for using 9,9-dimethyl-9H-fluorene-2-amine in place of aniline. The result of mass spectrometric analysis was m/e=869 to the molecular weight 869 of the compound 15.

Synthesis Example 16: Synthesis of Compound 16

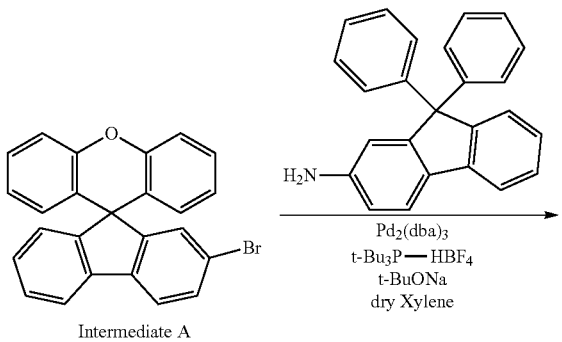

Intermediate A

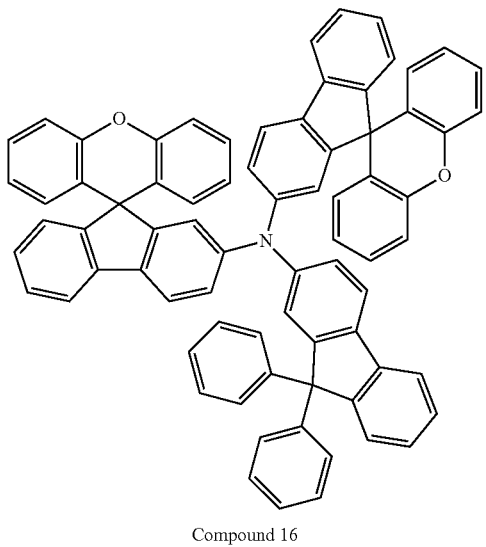

Compound 16

The compound 16 was obtained in the same manner as in the synthesis of the compound 1 except for using 9,9- diphenyl-9H-fluorene-2-amine in place of aniline. The result of mass spectrometric analysis was m/e=993 to the molecular weight 993 of the compound 16.

Synthesis Example 17: Synthesis of Compound 17

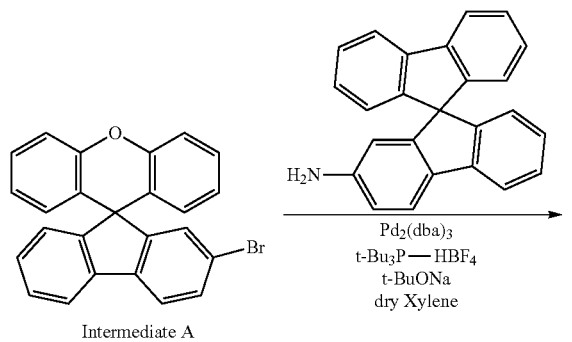

Intermediate A

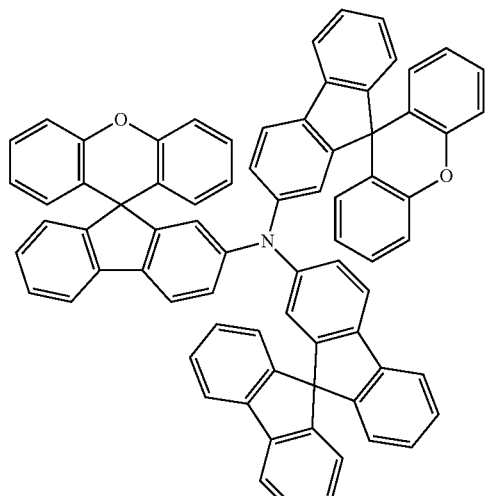

Compound 17

The compound 17 was obtained in the same manner as in the synthesis of the compound 1 except for using 9,9'-spirobi[fluorene]-2-amine in place of aniline. The result of mass spectrometric analysis was m/e=991 to the molecular weight 991 of the compound 17.

Synthesis Example 18: Synthesis of Compound 18

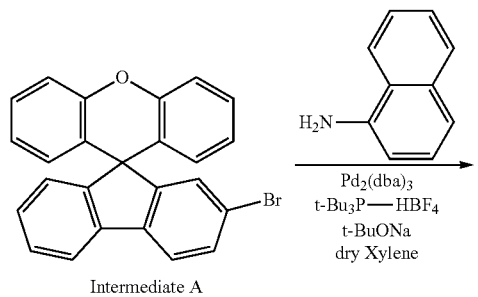

Intermediate A

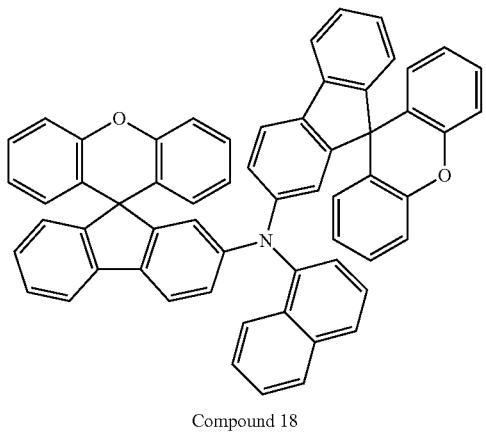

Compound 18

The compound 18 was obtained in the same manner as in the synthesis of the compound 1 except for using naphthalene-1-amine in place of aniline. The result of mass spectrometric analysis was m/e=803 to the molecular weight 803 of the compound 18.

Synthesis Example 19: Synthesis of Compound 19

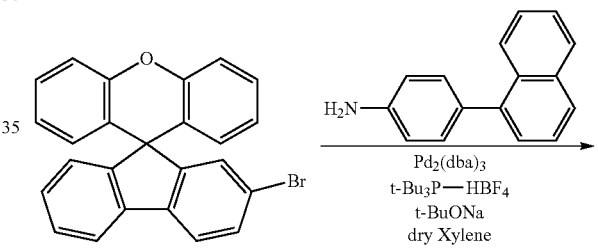

Intermediate A

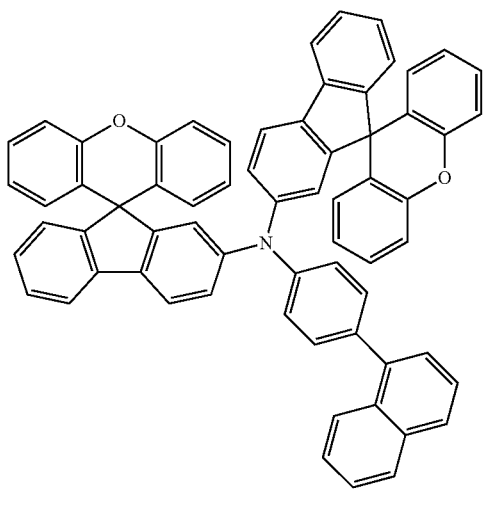

Compound 19

The compound 19 was obtained in the same manner as in the synthesis of the compound 1 except for using 4-(naphthalene-1-yl)aniline in place of aniline. The result of mass spectrometric analysis was m/e=879 to the molecular weight 879 of the compound 19.

Synthesis Example 20: Synthesis of Compound 20

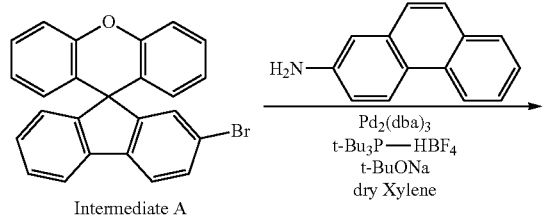

Intermediate A

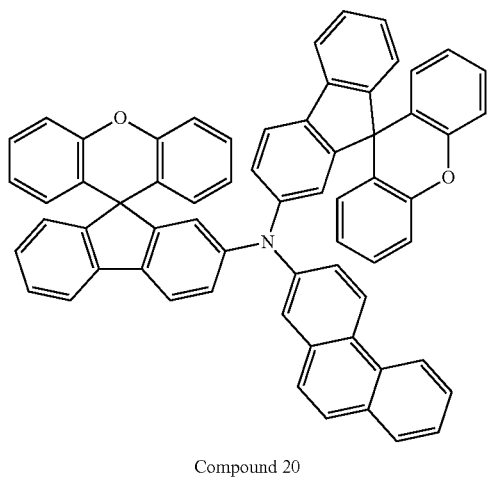

Compound 20

The compound 20 was obtained in the same manner as in the synthesis of the compound 1 except for using phenanthrene-2-amine in place of aniline. The result of mass spectrometric analysis was m/e=853 to the molecular weight 853 of the compound 20.

Synthesis Example 21: Synthesis of Compound 21

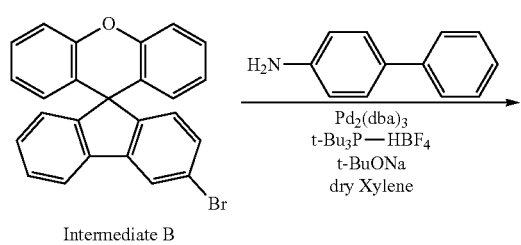

Intermediate B

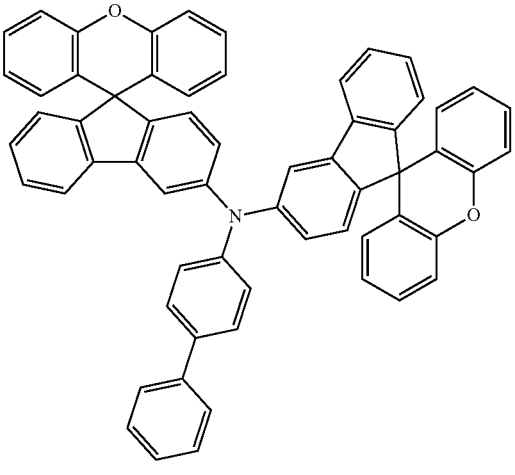

Compound 21

The compound 21 was obtained in the same manner as in the synthesis of the compound 2 except for using the intermediate B in place of the intermediate A. The result of mass spectrometric analysis was m/e=829 to the molecular weight 829 of the compound 21.

Synthesis Example 22: Synthesis of Compound 22

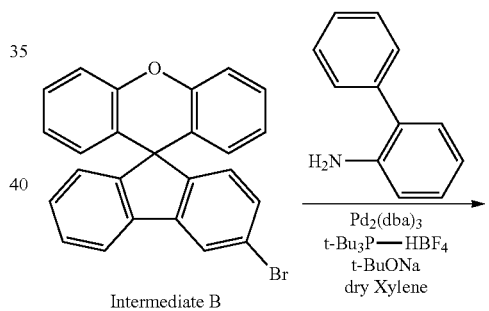

Intermediate B

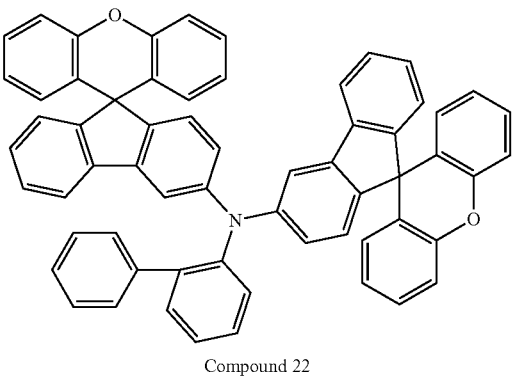

Compound 22

The compound 22 was obtained in the same manner as in the synthesis of the compound 4 except for using the intermediate B in place of the intermediate A. The result of mass spectrometric analysis was m/e=829 to the molecular weight 829 of the compound 22.

Synthesis Example 23: Synthesis of Compound 23

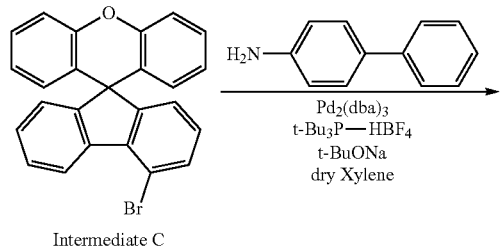

Intermediate C

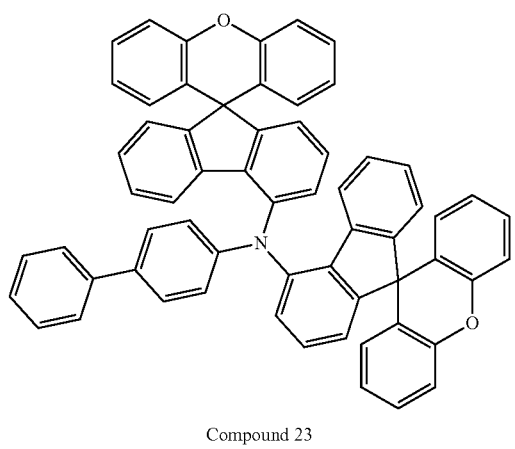

Compound 23

The compound 23 was obtained in the same manner as in the synthesis of the compound 2 except for using the intermediate C in place of the intermediate A. The result of mass spectrometric analysis was m/e=829 to the molecular weight 829 of the compound 23.

Synthesis Example 24: Synthesis of Compound 24

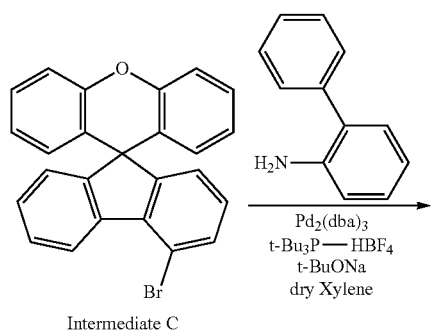

Intermediate C

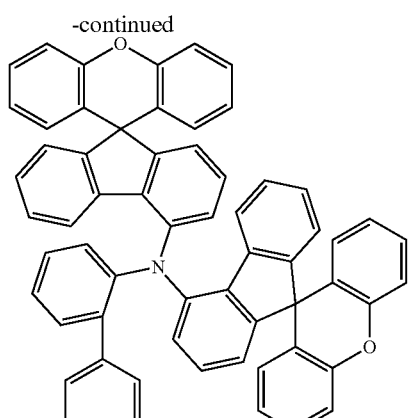

Compound 24

The compound 24 was obtained in the same manner as in the synthesis of the compound 4 except for using the intermediate C in place of the intermediate A. The result of mass spectrometric analysis was m/e=829 to the molecular weight 829 of the compound 24.

Synthesis Example 25: Synthesis of Compound 25

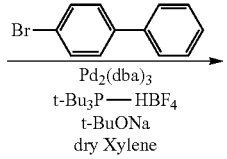

Intermediate F

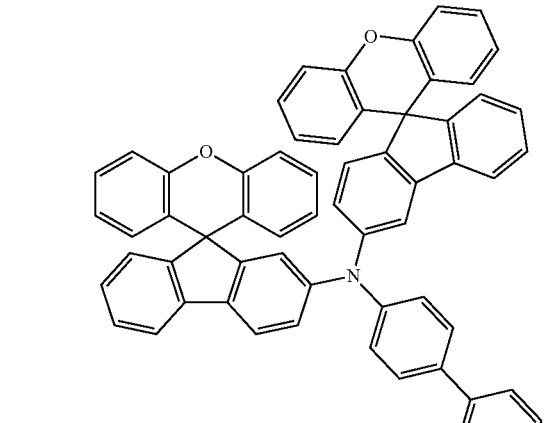

Compound 25

The compound 25 was obtained in the same manner as in the synthesis of the intermediate F except for using the intermediate F in place of the intermediate A and using 4-bromobiphenyl in place of the intermediate D. The result of mass spectrometric analysis was m/e=829 to the molecular weight 829 of the compound 25.

Synthesis Example 26: Synthesis of Compound 26

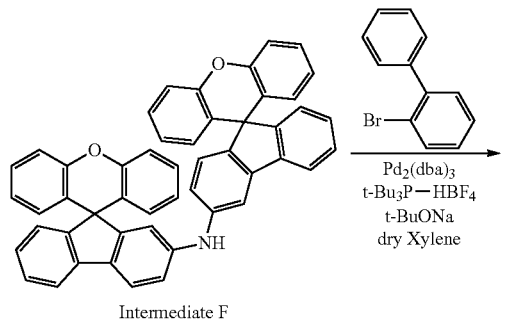

Intermediate F

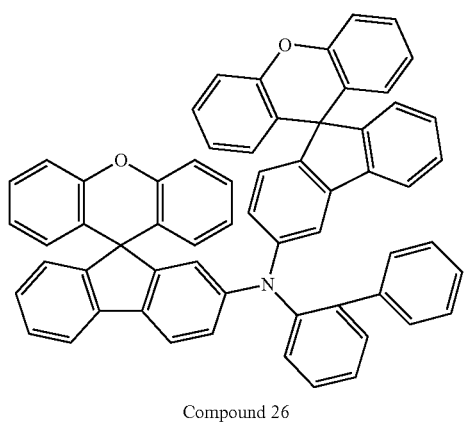

Compound 26

The compound 26 was obtained in the same manner as in the synthesis of the intermediate F except for using the intermediate F in place of the intermediate A and using 2-bromobiphenyl in place of the intermediate D. The result of mass spectrometric analysis was m/e=829 to the molecular weight 829 of the compound 26.

Synthesis Example 27: Synthesis of Compound 27

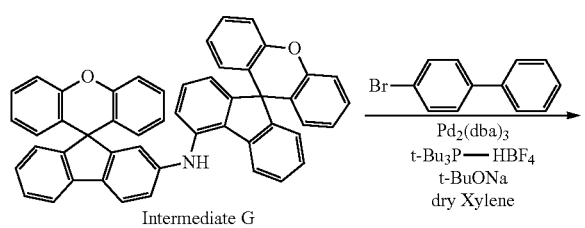

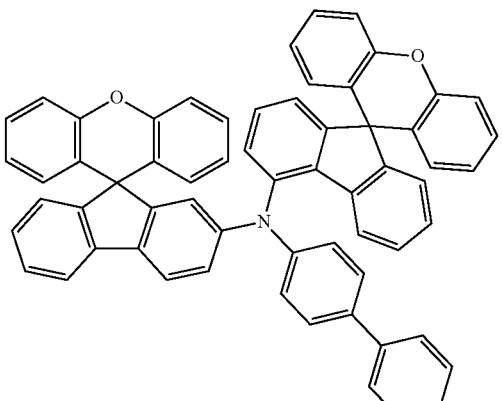

Compound 27

The compound 27 was obtained in the same manner as in the synthesis of the intermediate F except for using the intermediate G in place of the intermediate A and using 4-bromobiphenyl in place of the intermediate D. The result of mass spectrometric analysis was m/e=829 to the molecular weight 829 of the compound 27.

Synthesis Example 28: Synthesis of Compound 28

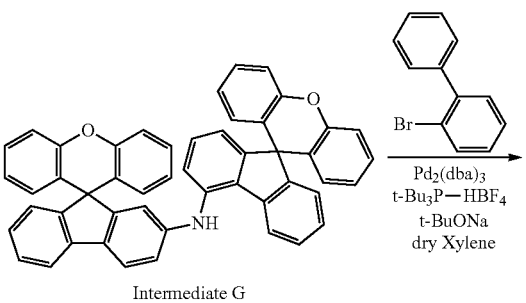

Intermediate G

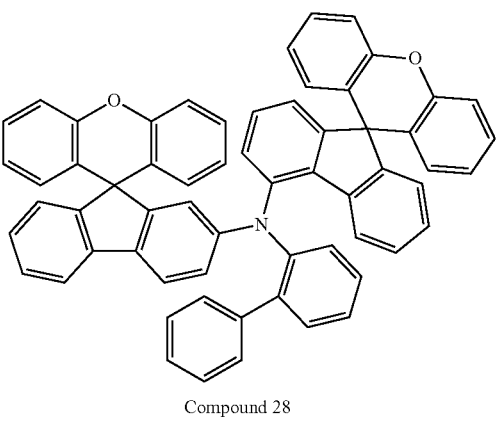

Compound 28

The compound 28 was obtained in the same manner as in the synthesis of the intermediate F except for using the intermediate G in place of the intermediate A and using 2-bromobiphenyl in place of the intermediate D. The result of mass spectrometric analysis was m/e=829 to the molecular weight 829 of the compound 28.

Synthesis Example 29: Synthesis of Compound 29

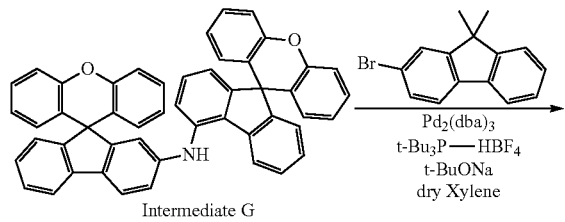

Intermediate G

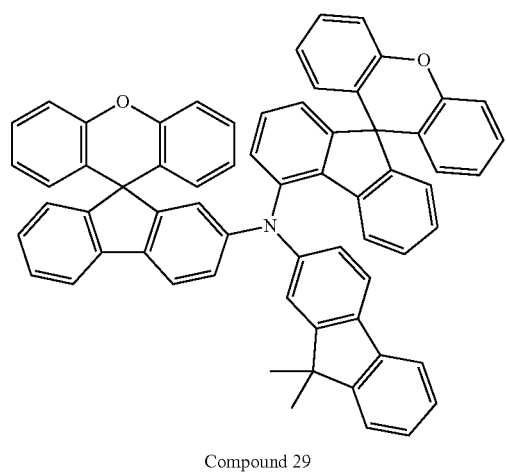

Compound 29

The compound 29 was obtained in the same manner as in the synthesis of the intermediate F except for using the intermediate G in place of the intermediate A and using 2-bromo-9,9-dimethylfluorene in place of the intermediate D. The result of mass spectrometric analysis was m/e=869 to the molecular weight 869 of the compound 29.

Synthesis Example 30: Synthesis of Compound 30

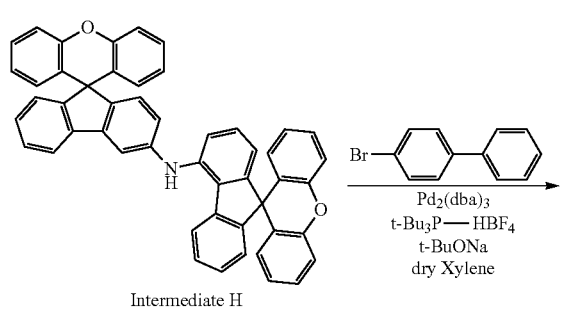

Intermediate H

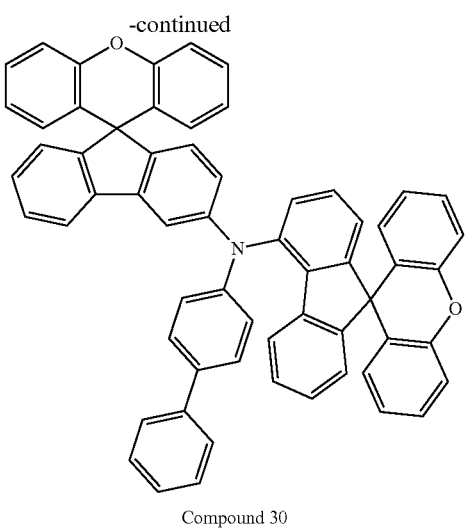

Compound 30

The compound 30 was obtained in the same manner as in the synthesis of the intermediate F except for using the intermediate H in place of the intermediate A and using 4-bromobiphenyl in place of the intermediate D. The result of mass spectrometric analysis was m/e=829 to the molecular weight 829 of the compound 30.

Synthesis Example 31: Synthesis of Compound 31

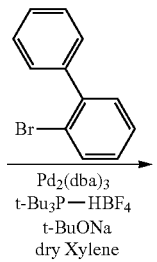

Intermediate H

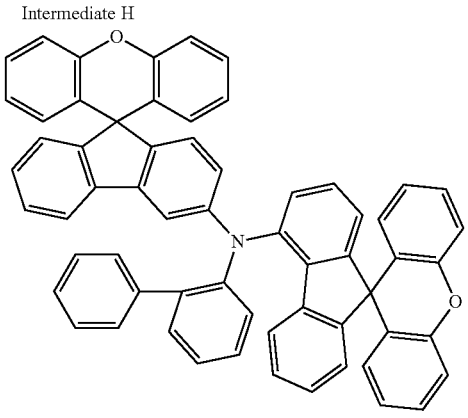

Compound 31

The compound 31 was obtained in the same manner as in the synthesis of the intermediate F except for using the intermediate H in place of the intermediate A and using 2-bromobiphenyl in place of the intermediate D. The result of mass spectrometric analysis was m/e=829 to the molecular weight 829 of the compound 31.

Synthesis Example 32: Synthesis of Compound 32

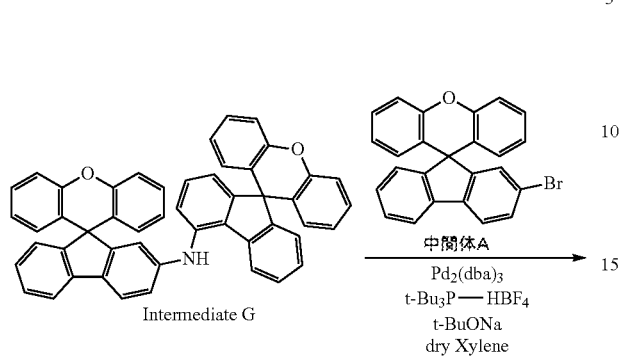

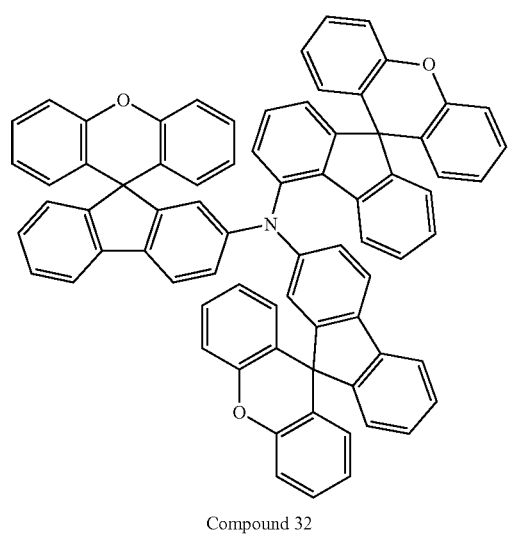

Compound 32

The compound 32 was obtained in the same manner as in the synthesis of the compound 1 except for using the intermediate G in place of the intermediate A and using the intermediate A in place of aniline. The result of mass spectrometric analysis was m/e=1007 to the molecular weight 1007 of the compound 32.

Synthesis Example 33: Synthesis of Compound 33

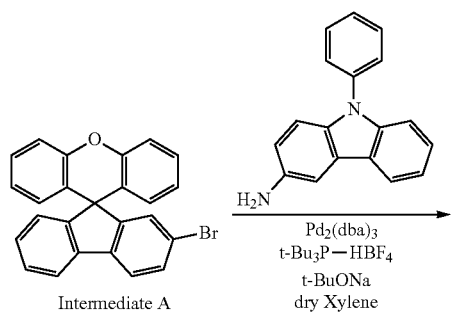

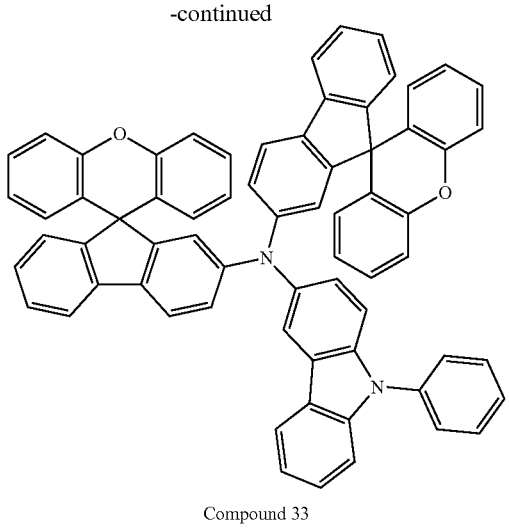

Compound 33

The compound 33 was obtained in the same manner as in the synthesis of the compound 1 except for using 9-phenyl-9H-carbazole-3-amine in place of aniline. The result of mass spectrometric analysis was m/e=918 to the molecular weight 918 of the compound 33.

Synthesis Example 34: Synthesis of Compound 34

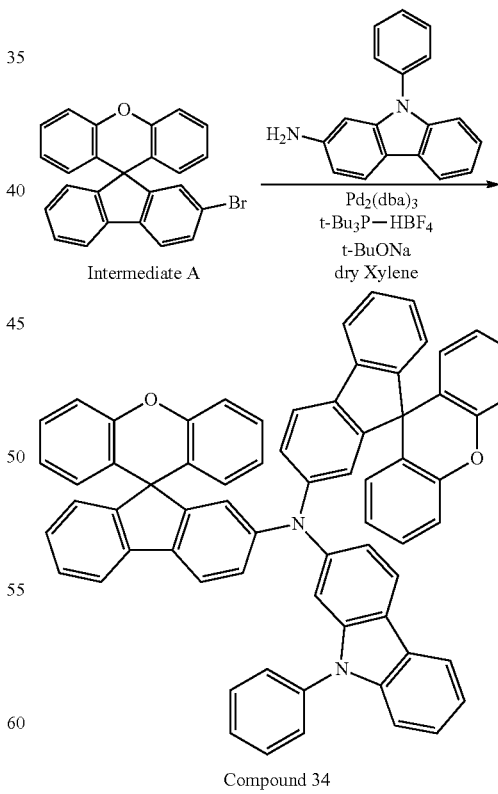

Compound 34

The compound 34 was obtained in the same manner as in the synthesis of the compound 1 except for using 9-phenyl-911-carbazole-2-amine in place of aniline. The result of mass spectrometric analysis was m/e=918 to the molecular weight 918 of the compound 34.

Example 1

Production of Organic EL Device

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO was 130 nm.

The cleaned glass substrate having a transparent electrode was mounted to a substrate holder of a vacuum vapor deposition apparatus. First, the compound HA was vapor-deposited on the surface having the transparent electrode so as to cover the transparent electrode to form a hole injecting layer with a thickness of 5 nm.

On the hole injecting layer, the compound 2 was vapor-deposited to form a first hole transporting layer with a thickness of 80 nm.

On the first hole transporting layer, the compound HT2 was vapor-deposited to form a second hole transporting layer with a thickness of 10 nm.

Then, on the second hole transporting layer, the compound BH (host material) and the compound BD (dopant material) were vapor co-deposited to form a light emitting layer with a thickness of 25 nm. The ratio of the compound BH and the compound BD in the light emitting layer was 96:4 by mass.

Successively after forming the light emitting layer, the compound ET1 was vapor-deposited to form a first electron transporting layer with a thickness of 10 nm and then the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

HA

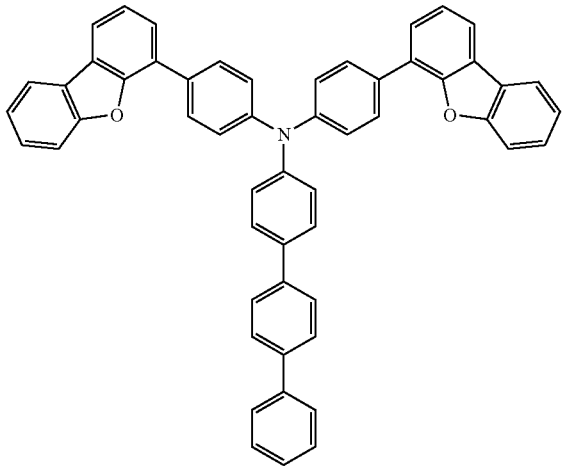

HT2

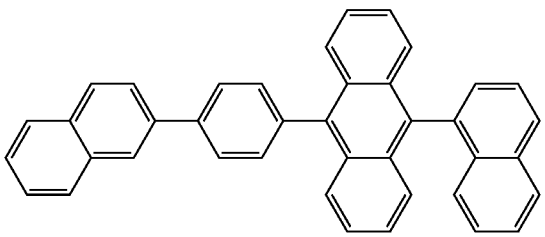

BH

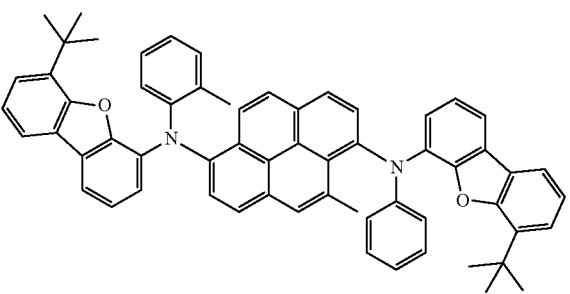

BD

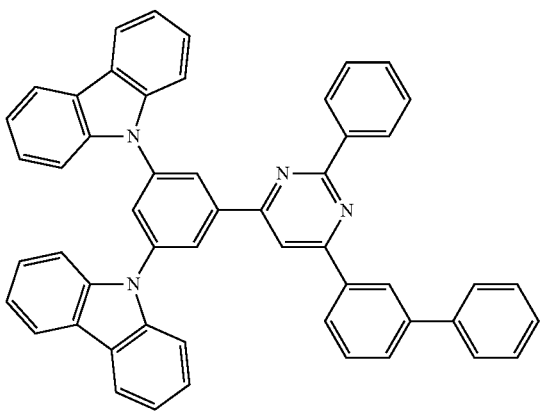

ET1

ET2

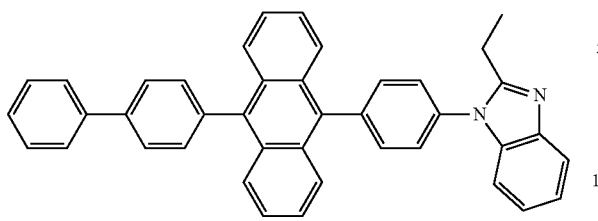

Driving Voltage

The voltage (unit: V) at a current density of 10 mA/cm² when applying a voltage to the organic EL device was measured.

External Quantum Efficiency

The organic EL device was operated at room temperature by a constant direct current at a current density of 10 mA/cm². The external quantum efficiency (%) was measured using a spectroradiometer (CS-1000 manufactured by Minolta). The result is shown in Table 1.

Example 2 and Comparative Example 1

Each organic EL device was produced in the same manner as in Example 1 except for using the compound 15 or the comparative compound 1 (compound disclosed in Patent Literature 1). Each organic EL device thus produced was measured for the driving voltage and the external quantum efficiency in the same manner as in Example 1. The results are shown in Table 1.

Compound 2

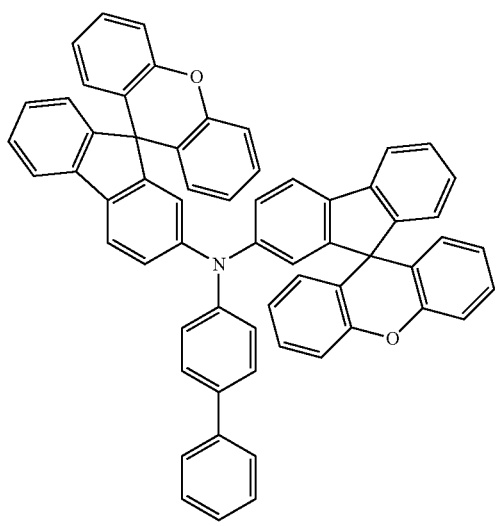

Compound 15

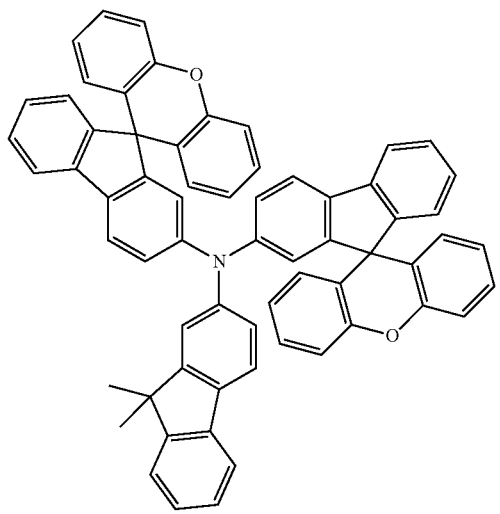

Comparative compound 1

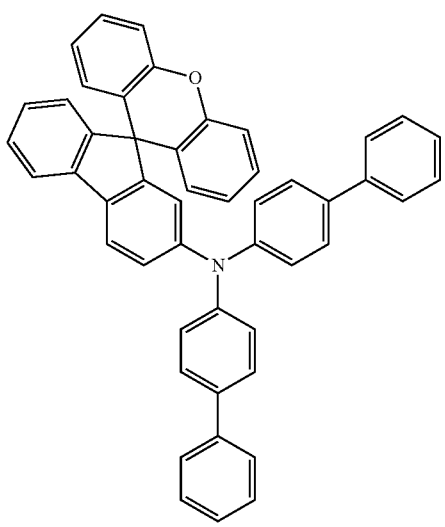

TABLE 1

|   | First hole transporting layer | Driving voltage (V) | External quantum efficiency (%) |
|---|---|---|---|
| Example 1 | Compound 2 | 3.67 | 9.0 |
| Example 2 | Compound 15 | 3.77 | 10.0 |
| Comparative Example 1 | Comparative compound 1 | 3.84 | 8.6 |

From the comparison of Examples 1 and 2 with Comparative Example 1, particularly, the comparison of Example 1 with Comparative Example 1, it can be seen that the monoamine compound having two spiro(xanthenefluorene) skeletons on the central nitrogen atom provides an organic EL device which is operated at a lower driving voltage and has a higher external quantum efficiency, as compared with the monoamine compound having only one spiro(xanthenefluorene) skeleton on the central nitrogen atom.

Example 3

Production of Organic EL Device

A 25 mm×75 mm×1.1 mm glass substrate having ITO transparent electrode (anode) (product of Geomatec Company) was ultrasonically cleaned in isopropyl alcohol for 5 min and then UV/ozone cleaned for 30 min. The thickness of ITO was 130 nm.

The cleaned glass substrate having a transparent electrode was mounted to a substrate holder of a vacuum vapor deposition apparatus. First, the compound HA was vapor-deposited on the surface having the transparent electrode so as to cover the transparent electrode to form a hole injecting layer with a thickness of 5 nm.

On the hole injecting layer, the compound HT1 was vapor deposited to form a first hole transporting layer with a thickness of 80 nm.

On the first hole transporting layer, the compound 27 was vapor-deposited to form a second hole transporting layer with a thickness of 10 nm.

Then, on the second hole transporting layer, the compound BH (host material) and the compound BD (dopant material) were vapor co-deposited to form a light emitting layer with a thickness of 25 nm. The ratio of the compound BH and the compound BD in the light emitting layer was 96:4 by mass.

Successively after forming the light emitting layer, the compound ET1 was vapor-deposited to form a first electron transporting layer with a thickness of 10 nm and then the compound ET2 was vapor-deposited to form a second electron transporting layer with a thickness of 15 nm.

On the second electron transporting layer, LiF was vapor-deposited to form an electron injecting layer with a thickness of 1 nm.

On the electron injecting layer, metallic Al was vapor-deposited to form a metallic cathode with a thickness of 80 nm, thereby producing an organic EL device.

Measurement of Device Performance

The external quantum efficiency of the obtained organic EL device were measured in the same manner as in Example 1. The results are shown in Table 2.

Comparative Example 2

An organic EL device was produced in the same manner as in Example 3 except for using the comparative compound 1 in place of the compound 27, and the external quantum efficiency thereof was measured in the same manner as in Example 1. The results are shown in Table 2.

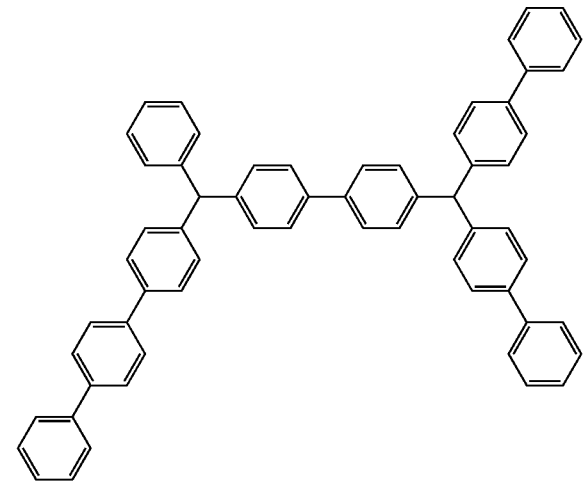

HT1

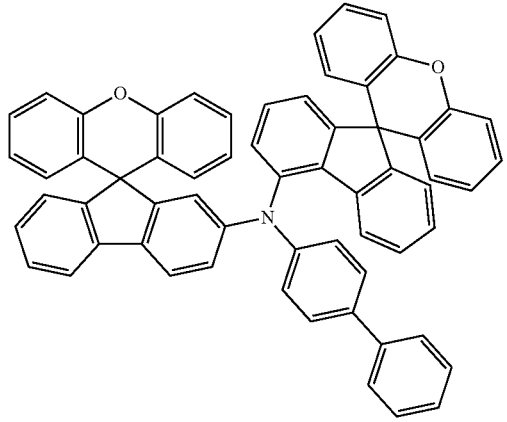

Compound 27

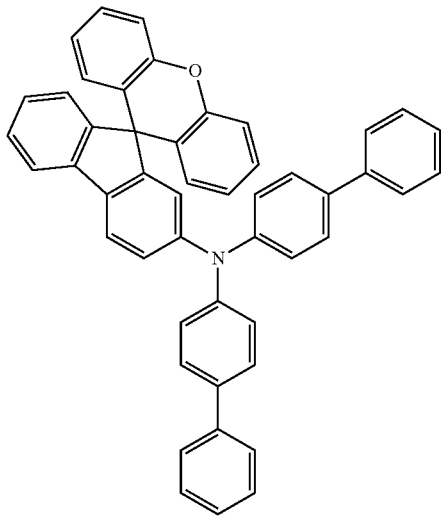

Comparative compound 1

TABLE 2

| | Second hole transporting layer | External quantum efficiency (%) |
|---|---|---|
| Example 3 | Compound 27 | 9.2 |
| Comparative Example 2 | Comparative compound 1 | 8.8 |

From the comparison of Examples 1-3 with Comparative Examples 1-2, it can be seen that the compounds of the invention having two spiro(xanthenefluorene) skeletons provide organic EL devices having a higher external quantum efficiency, as compared with the comparative compound having only one spiro(xanthenefluorene) skeleton.

This advantageous effect of the inventive compounds are attributable to lone pairs on two oxygen atoms of the spiro(xanthenefluorene) skeletons, which facilitate the carrier transport. The resultant good carrier mobility increases the amount of carrier in the light emitting layer to enhance the efficiency.

REFERENCE SIGNS LIST

1, 11: Organic EL device
2: Substrate
3: Anode
4: Cathode
5: Light emitting layer
6: Hole transporting region (hole transporting layer)
6a: First hole transporting layer
6b: Second hole transporting layer
7: Electron transporting region (electron transporting layer)
7a: First electron transporting layer
7b: Second electron transporting layer
10, 20: Emission unit

The invention claimed is:
1. A compound represented by formula (1):

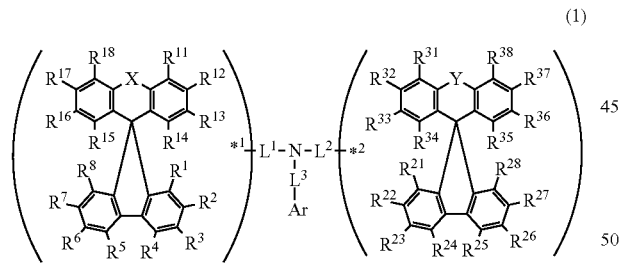

(1)

wherein:
each of $R^1$ to $R^8$, $R^{11}$ to $R^{21}$ to $R^{28}$, and $R^{31}$ to $R^{38}$ is independently a hydrogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted heteroaryl group having 5 to 30 ring atoms, a substituted or unsubstituted aralkyl group having 7 to 36 ring carbon atoms, a substituted or unsubstituted alkoxy group having 1 to 30 carbon atoms, a substituted or unsubstituted aryloxy group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, a substituted or unsubstituted haloalkyl group having 1 to 30 carbon atoms, a substituted or unsubstituted haloalkoxy group having 1 to 30 carbon atoms, a halogen atom, a cyano group, or a nitro group;

adjacent two selected from $R^1$ to $R^4$, adjacent two selected from $R^5$ to $R^8$, adjacent two selected from $R^{11}$ to $R^{14}$, adjacent two selected from $R^{15}$ to $R^{18}$, adjacent two selected from $R^{21}$ to $R^{24}$, adjacent two selected from $R^{25}$ to $R^{28}$, adjacent two selected from $R^{31}$ to $R^{34}$, and adjacent two selected from $R^{35}$ to $R^{38}$ may be bonded to each other to form a ring structure;

provided that one selected from $R^1$ to $R^8$ and $R^{11}$ to $R^{18}$ is a single bond bonded to *1, or a ring atom of the ring structure formed by adjacent two selected from $R^1$ to $R^4$, adjacent two selected from $R^5$ to $R^8$, adjacent two selected from $R^{11}$ to $R^{14}$, or adjacent two selected from $R^{15}$ to $R^{18}$ is bonded to *1;

provided that one selected from $R^{21}$ to $R^{28}$ and $R^{31}$ to $R^{38}$ is a single bond bonded to *2, or a ring atom of the ring structure formed by adjacent two selected from $R^{21}$ to $R^{24}$, adjacent two selected from $R^{25}$ to $R^{28}$, adjacent two selected from $R^{31}$ to $R^{34}$, or adjacent two selected from $R^{35}$ to $R^{38}$ is bonded to *2;

X is an oxygen atom or a sulfur atom;

Y is an oxygen atom or a sulfur atom;

each of $L^1$, $L^2$, and $L^3$ is independently a single bond, a substituted or unsubstituted arylene group having 6 to 30 ring carbon atoms, or a substituted or unsubstituted heteroarylene group having 5 to 30 ring atoms;

Ar is a substituted or unsubstituted aryl group having 6 to 30 ring carbon atoms, a substituted or unsubstituted nitrogen-comprising heteroaryl group having 5 to 30 ring atoms, a substituted or unsubstituted oxygen-comprising heteroaryl group having 5 to 30 ring atoms, or a substituted or unsubstituted sulfur-comprising heteroaryl group having 5 to 30 ring atoms; and when an optional substituent is present, the optional substituent referred to by "substituted or unsubstituted" is selected from the group consisting of an alkyl group having 1 to 30 carbon atoms, a cycloalkyl group having 3 to 30 ring carbon atoms, an aryl group having 6 to 30 ring carbon atoms, a heteroaryl group having 5 to 30 ring atoms, a substituted or unsubstituted aralkyl group having 7 to 36 ring carbon atoms, an alkoxy group having 1 to 30 carbon atoms, an aryloxy group having 6 to 30 ring carbon atoms, a mono-, di-, or tri-substituted silyl group having a substituent selected from an alkyl group having 1 to 30 carbon atoms and an aryl group having 6 to 30 ring carbon atoms, a haloalkyl group having 1 to 30 carbon atoms, a haloalkoxy group having 1 to 30 carbon atoms, a halogen atom, a cyano group, and a nitro group.

2. The compound according to claim 1, wherein one selected from $R^2$ to $R^7$ is a single bond bonded to *1.

3. The compound according to claim 1, wherein one selected from $R^{22}$ to $R^{27}$ is a single bond bonded to *2.

4. The compound according to claim 1, wherein the compound is represented by any of formulae (2) to (7):

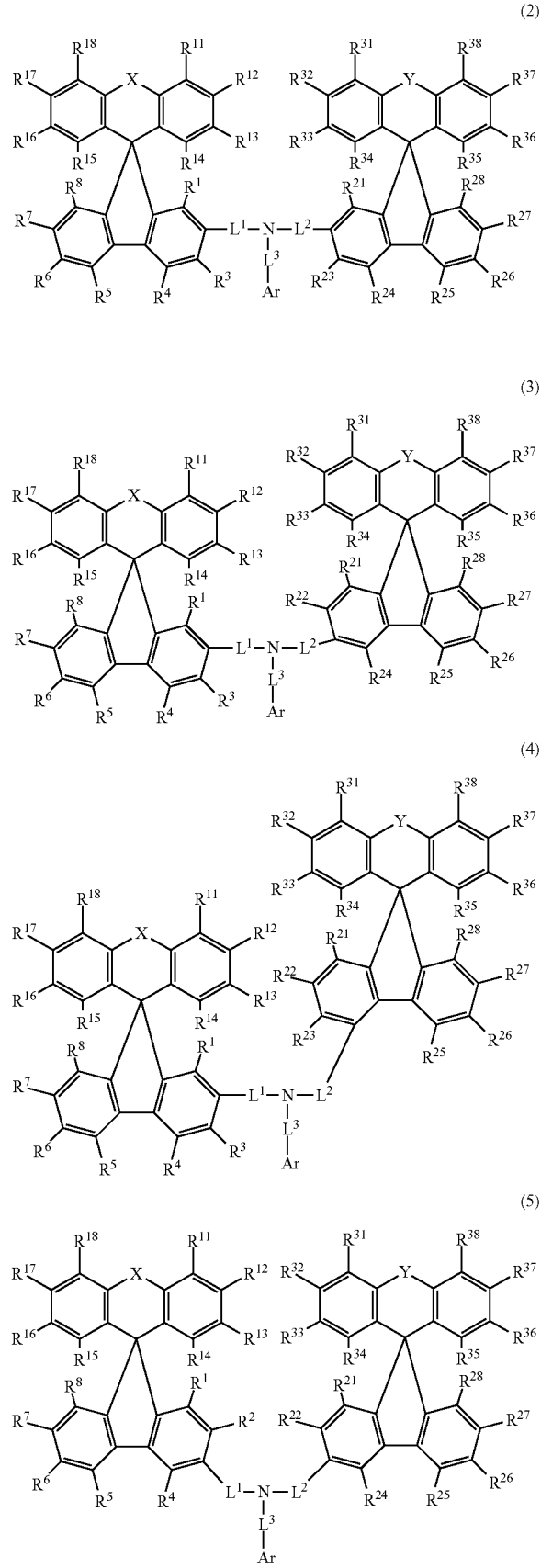

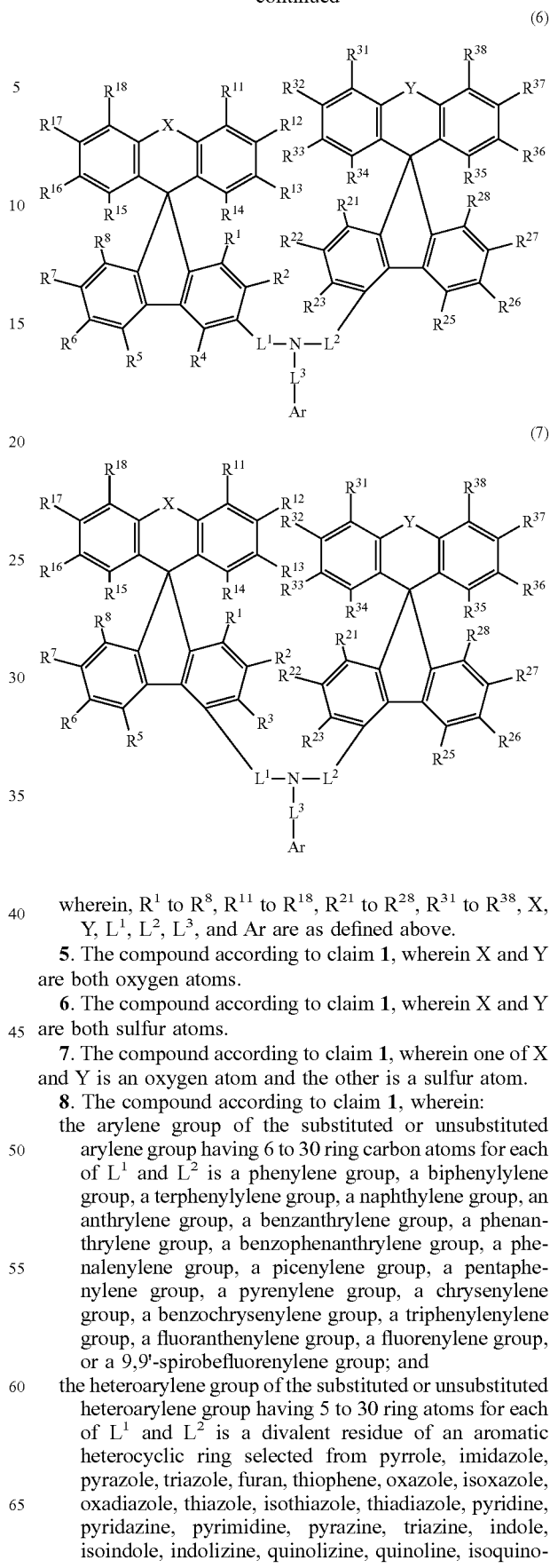

wherein, $R^1$ to $R^8$, $R^{11}$ to $R^{18}$, $R^{21}$ to $R^{28}$, $R^{31}$ to $R^{38}$, X, Y, $L^1$, $L^2$, $L^3$, and Ar are as defined above.

5. The compound according to claim 1, wherein X and Y are both oxygen atoms.

6. The compound according to claim 1, wherein X and Y are both sulfur atoms.

7. The compound according to claim 1, wherein one of X and Y is an oxygen atom and the other is a sulfur atom.

8. The compound according to claim 1, wherein:
the arylene group of the substituted or unsubstituted arylene group having 6 to 30 ring carbon atoms for each of $L^1$ and $L^2$ is a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluoranthenylene group, a fluorenylene group, or a 9,9'-spirobefluorenylene group; and
the heteroarylene group of the substituted or unsubstituted heteroarylene group having 5 to 30 ring atoms for each of $L^1$ and $L^2$ is a divalent residue of an aromatic heterocyclic ring selected from pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline, cinnoline, phthalazine, quinazoline, quinoxaline, benzimidazole, indazole, phenanthroline, phenanthridine, acridine, phenazine, carbazole, benzocarbazole, xanthene, benzofuran, isobenzofuran, dibenzofuran, naphthobenzothran, benzothiophene, dibenzothiophene, naphthobenzothiophene, benzoxazole, benzisoxazole, phenoxazine, benzothiazole, benzisothiazole, and phenothiazine.

9. The compound according to claim 1, wherein $L^1$ and $L^2$ are both single bonds.

10. The compound according to claim 1, wherein one of $L^1$ and $L^2$ is a single bond and the other is a substituted or unsubstituted arylene group having 6 to 30 ring carbon atoms, wherein the arylene group is selected from the following formulae:

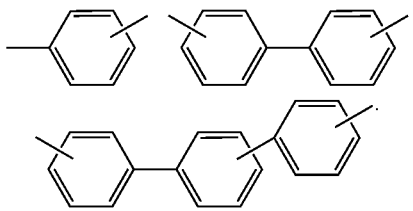

11. The compound according to claim 1, wherein each of $L^1$ and $L^2$ is a substituted or unsubstituted arylene group having 6 to 30 ring carbon atoms, wherein the arylene group is selected from the following formulae:

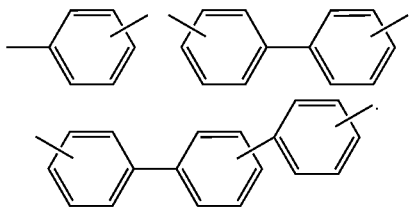

12. The compound according to claim 1, wherein:
the arylene group of the substituted or unsubstituted arylene group having 6 to 30 ring carbon atoms for $L^3$ is a phenylene group, a biphenylylene group, a terphenylylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a triphenylenylene group, a fluoranthenylene group, a fluorenylene group, or a 9,9'-spirobefluorenylene group; and
the heteroarylene group of the substituted or unsubstituted heteroarylene group having 5 to 30 ring atoms for $L^3$ is a divalent residue of an aromatic heterocyclic ring selected from pyrrole, imidazole, pyrazole, triazole, furan, thiophene, oxazole, isoxazole, oxadiazole, thiazole, isothiazole, thiadiazole, pyridine, pyridazine, pyrimidine, pyrazine, triazine, indole, isoindole, indolizine, quinolizine, quinoline, isoquinoline; cinnoline, phthalazine, quinazoline, quinoxaline, benzimidazole, indazole, phenanthroline, phenanthridine, acridine, phenazine, carbazole, benzocarbazole, xanthene, benzofuran, isobenzofuran, dibenzofuran, naphthobenzofuran, benzothiophene, dibenzothiophene, naphthobenzothiophene, benzoxazole, benzisoxazole, phenoxazine, benzothiazole, benzisothiazole, and phenothiazine.

13. The compound according to claim 1, wherein $L^3$ is a single bond.

14. The compound according to claim 1, wherein $L^3$ is a group selected from the following formulae:

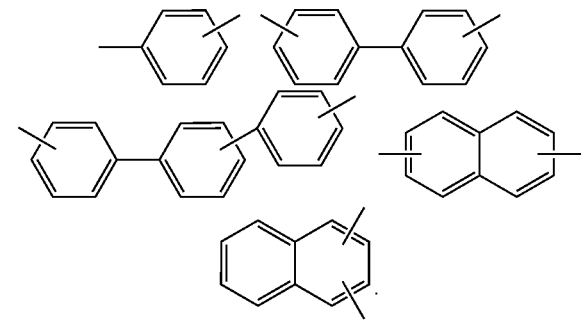

15. The compound according to claim 1, wherein:
the aryl group of the substituted or unsubstituted aryl group having 6 to 30 ring carbon atoms for Ar is selected from a phenyl group, a biphenylyl group, a terphenylyl group, a naphthyl group, an acenaphthylenyl group, a biphenylenyl group, a fluorenyl group, a s-indacenyl group, an as-indacenyl group, an anthryl group, a benzanthryl group, an aceanthryl group, a phenanthryl group, a benzophenanthryl group, a phenalenyl group, a naphthacenyl group, a fluoranthenyl group, a pyrenyl group, a chrysenyl group, a benzochrysenyl group, a triphenylenyl group, a pentacenyl group, a picenyl group, and a pentaphenyl group;
the substituted aryl group of the substituted or unsubstituted aryl group having 6 to 30 ring carbon atoms for Ar is selected from a 9,9'-spirobifluorenyl group, a 9,9-diphenylfluorenyl group, and a 9,9-dimethylfluorenyl group;
the nitrogen-comprising heteroaryl group of the substituted or unsubstituted nitrogen-comprising heteroaryl group having 5 to 30 ring atoms for Ar is selected from a pyrrolyl group, an imidazolyl group, a pyrazolyl group, a triazolyl group, an oxazolyl group, an isoxazolyl group, an oxadiazolyl group, a thiazolyl group, an isothiazolyl group, a thiadiazolyl group, a pyridyl group, a pyridazinyl group, a pyrimidinyl group, a pyrazinyl group, a triazinyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, an indazolyl group, a phenanthrolinyl group, a phenanthridinyl group, an acridinyl group, a phenazinyl group, a carbazolyl group, a benzocarbazolyl group, and a xanthenyl group;
the oxygen-comprising heteroaryl group of the substituted or unsubstituted oxygen-comprising heteroaryl group having 5 to 30 ring atoms for Ar is selected from a furyl group, an oxazolyl group, an isoxazolyl group, an oxadiazolyl group, a xanthenyl group, a benzofuranyl group, a dibenzofuranyl group, a naphthobenzofuranyl group, a benzoxazolyl group, a benzisoxazolyl group, a phenoxazinyl group, and a monovalent residue of spiro[9H-xanthene-9,9'-[9H]fluorene]; and the sulfur-comprising heteroaryl group of the substituted or unsubstituted sulfur-comprising heteroaryl group having 5 to 30 ring atoms for Ar is selected from a thienyl group, a thiazolyl group, an isothiazolyl group, a thiadiazolyl group, a benzothiophenyl group, a dibenzothiophenyl group, a naphthobenzothiophenyl group, a benzothiazolyl group, an benzisothiazolyl group, a phenothiazinyl group, and a monovalent residue of spiro[9H thioxanthene-9,9'-[9H]fluorene].

16. The compound according to claim 1, wherein $R^1$ to $R^8$ each is not a single bond bonded to *1, and each of the $R^1$ to $R^8$ that does not form the ring structure is a hydrogen atom.

17. The compound according to claim 1, wherein $R^{21}$ to $R^{28}$ each is not a single bond bonded to *2, and each of the $R^{21}$ to $R^{28}$ that does not form the ring structure is a hydrogen atom.

18. The compound according to claim 1, wherein $R^{11}$ to $R^{18}$ each is not a single bond bonded to *1, and each of the $R^{11}$ to $R^{18}$ that does not form the ring structure is a hydrogen atom.

19. The compound according to claim 1, wherein to $R^{38}$ each is not a single bond bonded to *2, and each of the $R^{31}$ to $R^{38}$ that does not form the ring structure is a hydrogen atom.

20. The compound according to claim 1, wherein $R^1$ and $R^2$; $R^2$ and $R^3$; $R^3$ and $R^4$; both of $R^2$ and $R^3$, and $R^5$ and $R^6$; both of $R^2$ and $R^3$, and $R^6$ and $R^7$; both of $R^3$ and $R^4$, and $R^5$ and $R^6$; or $R^{12}$ and $R^{13}$ form the ring structure.

21. The compound according to claim 1, wherein $R^{21}$ and $R^{22}$; $R^{22}$ and $R^{23}$; $R^{23}$ and $R^{24}$; both of $R^{22}$ and $R^{23}$, and $R^{25}$ and $R^{26}$; both of $R^{22}$ and $R^{23}$, and $R^{26}$ and $R^{27}$; both of $R^{23}$ and $R^{24}$, and $R^{25}$ and $R^{26}$; or $R^{32}$ and $R^{33}$ form the ring structure.

22. The compound according to claim 1, wherein the ring structure which is optionally formed by adjacent two selected from $R^1$ to $R^4$, adjacent two selected from $R^5$ to $R^8$, adjacent two selected from $R^{11}$ to $R^{14}$, adjacent two selected from $R^{15}$ to $R^{18}$, adjacent two selected from $R^{21}$ to $R^{24}$, adjacent two selected from $R^{25}$ to $R^{28}$, adjacent two selected from $R^{31}$ to $R^{34}$, and adjacent two selected from $R^{35}$ to $R^{38}$ is a substituted or unsubstituted aromatic hydrocarbon ring having 6 to 18 ring carbon atoms, a substituted or unsubstituted aliphatic hydrocarbon ring having 5 to 18 ring carbon atoms, a substituted or unsubstituted aromatic heterocyclic ring having 5 to 18 ring atoms, or a substituted or unsubstituted aliphatic heterocyclic ring having, 5 to 18 ring atoms.

23. An organic electroluminescence device comprising a cathode, an anode, and an organic layer disposed between the cathode and the anode, wherein the organic layer comprises a light emitting layer and at least one layer of the organic layer comprises the compound according to claim 1.

24. The organic electroluminescence device according to claim 23, wherein the organic electroluminescence device comprises a hole transporting region between the anode and the light emitting layer, and the hole transporting region comprises the compound.

25. The organic electroluminescence device according to claim 23, wherein the organic electroluminescence device comprises a hole transporting layer between the anode and the light emitting layer, and the hole transporting layer comprises the compound.

26. The organic electroluminescence device according to claim 25, wherein the hole transporting layer comprises a first hole transporting layer at anode side and a second hole transporting layer at cathode side, and one or both of the first hole transporting layer and the second hole transporting layer comprise the compound.

27. An electronic device comprising the organic electroluminescence device according to claim 23.

* * * * *

UNITED STATES PATENT AND TRADEMARK OFFICE
CERTIFICATE OF CORRECTION

PATENT NO. : 10,424,740 B2
APPLICATION NO. : 16/176762
DATED : September 24, 2019
INVENTOR(S) : Tasuku Haketa et al.

It is certified that error appears in the above-identified patent and that said Letters Patent is hereby corrected as shown below:

In the Claims

In Claim 1, Column 915, Line 54, "each of $R^1$ to $R^8$, $R^{11}$ to $R^{21}$ to $R^{28}$ and $R^{31}$ to $R^{38}$ is" should read --each of $R^1$ to $R^8$, $R^{11}$ to $R^{18}$, $R^{21}$ to $R^{28}$ and $R^{31}$ to $R^{38}$ is--

In Claim 8, Column 919, Line 5, "naphthobenzothran" should read --naphthobenzofuran--

In Claim 10, Column 919, Lines 20-25,

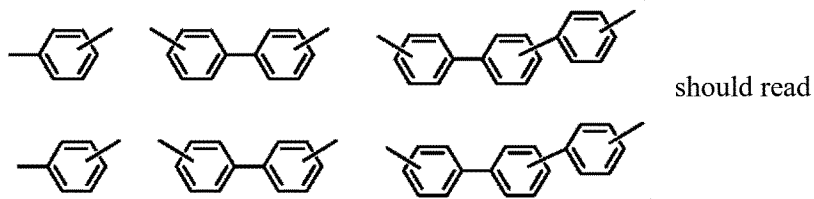

should read

In Claim 11, Column 919, Lines 35-40,

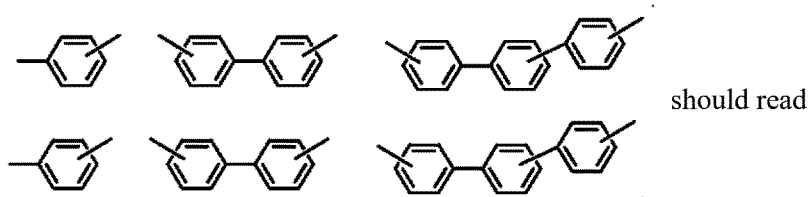

should read

In Claim 19, Column 921, Line 22, "wherein to $R^{38}$" should read --wherein $R^{31}$ to $R^{38}$--

Signed and Sealed this
Twenty-eighth Day of January, 2020

Andrei Iancu
*Director of the United States Patent and Trademark Office*